US012606541B2

(12) United States Patent
Prajapati et al.

(10) Patent No.: US 12,606,541 B2
(45) Date of Patent: Apr. 21, 2026

(54) PPARg MODULATORS AND METHODS OF USE

(71) Applicant: Eisai R&D Management Co., Ltd., Tokyo (JP)

(72) Inventors: Sudeep Prajapati, Somerville, MA (US); Hyelee Lee, Billerica, MA (US); Stephanos Ioannidis, Natick, MA (US); Kiyoyuki Omoto, Bedford, MA (US); Alan Rolfe, Medford, MA (US); Xiang Liu, Winchester, MA (US); Megan Carty, Boston, MA (US); Paul Dransfield, Arlington, MA (US); Andrew Cook, Stow, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

(21) Appl. No.: 17/521,666

(22) Filed: Nov. 8, 2021

(65) Prior Publication Data

US 2023/0062861 A1 Mar. 2, 2023

Related U.S. Application Data

(60) Provisional application No. 63/111,354, filed on Nov. 9, 2020.

(51) Int. Cl.

| | |
|---|---|
| ***C07D 401/14*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 471/04*** | (2006.01) |
| ***C07D 471/08*** | (2006.01) |
| ***C07D 487/04*** | (2006.01) |
| ***C07D 491/04*** | (2006.01) |
| ***C07D 491/10*** | (2006.01) |
| ***C07D 493/08*** | (2006.01) |
| ***C07D 498/04*** | (2006.01) |
| ***C07D 498/08*** | (2006.01) |
| ***C07F 5/02*** | (2006.01) |

(52) U.S. Cl.

CPC ......... *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 471/08* (2013.01); *C07D 487/04* (2013.01); *C07D 491/04* (2013.01); *C07D 491/10* (2013.01); *C07D 493/08* (2013.01); *C07D 498/04* (2013.01); *C07D 498/08* (2013.01); *C07F 5/025* (2013.01)

(58) Field of Classification Search

CPC .................................................... C07D 401/14

See application file for complete search history.

(56) References Cited

FOREIGN PATENT DOCUMENTS

| | | | |
|---|---|---|---|
| RU | 2448093 | C2 | 4/2012 |
| RU | 2480463 | C1 | 4/2013 |
| WO | 2017/049295 | A1 | 3/2017 |
| WO | 2019/115498 | A1 | 6/2019 |

OTHER PUBLICATIONS

STN—Chemical Database Registry entry for N-(4-Methylcyclohexyl)-1-[[5-(4-pyridinyl)-1H-pyrazol 3-yl]carbonyl]-4-piperidinecarboxamide RN 1456902-78-5, entered into STN: Oct. 11, 2013.*

Online: "https://web.archive.org/web/20130830174424/http://chemistryondemand.com/compound-library" dated, Aug. 30, 2013: accessed Dec. 5, 2022.*

STN—Chemical Database Registry for N-Cyclohexyl-1-[[5-(4-pyridinyl)-1H-pyrazol-3-yl]carbonyl]-4-piperidinecarboxamide, RN 1456914-73-0 entered into STN: Oct. 11, 2013.*

STN—Chemical Database Registry for N-Cyclohexyl-1-[[5-(4-pyridinyl)-1H-pyrazol-3-yl]carbonyl]-3-piperidinecarboxamide, RN 1239983-03-9 entered into STN: Sep. 3, 2010.*

Online: "http://web.archive.org/web/20070406205858/http://www.aurorafinechemicals.com/english/order.html" dated Apr. 6, 2007, accessed Feb. 19, 2015.*

STN—Chemical Database Registry for N-Cyclopropyl-1-[[5-(4-pyridinyl)-1H-pyrazol-3-yl]carbonyl]-4-piperidinecarboxamide, RN 1455489-41-4 entered into STN: Oct. 4, 2013.*

Moore K, Rees S: Cell-based versus isolated target screening: how lucky do you feel? J Biomol Screen 2001;6:69-74.*

Rothenberg, "Comparative Cell-Based Analysis of Various 1536Well Microplate Surfaces" SnAPPShots A brief technical report from the Corning Applications Group 2009, 1-4.*

Kuwubara "Peroxisome Proliferator-Activated Receptors (PPARs) Have Multiple Binding Points That Accommodate Ligands in Various Conformations: Phenylpropanoic Acid-Type PPAR Ligands Bind to PPAR in Different Conformations, Depending on the Subtype" J. Med. Chem. 2012, 55, 893-902.*

(Continued)

*Primary Examiner* — David K O'Dell

(74) *Attorney, Agent, or Firm* — Finnegan, Henderson, Farabow, Garrett & Dunner, LLP

(57) ABSTRACT

Disclosed herein are novel compounds of Formula (1) and pharmaceutically acceptable salts thereof, pharmaceutical compositions containing the same, and methods of using the same.

Formula (I)

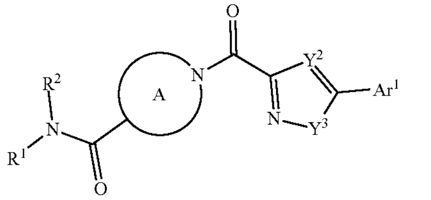

34 Claims, No Drawings

(56) References Cited

OTHER PUBLICATIONS

STN—Chemical Database Registry for N-(1,3-benzodioxol-5-ylmethyl)-1-[[5-(4-pyridinyl)-1H-pyrazol-3-yl]carbonyl-3-Piperidinecarboxamide, RN 1237756-26-1 entered into STN: Aug. 23, 2010.*
STN—Chemical Database Registry for N-(3-Fluorophenyl)-1-[[5-(4-pyridinyl)-1H-pyrazol-3-yl]carbonyl]-4-piperidinecarboxamide, RN 1455471-96-1 entered into STN: Oct. 4, 2013.*
STN—Chemical Database Registry entry for N-Cyclooctyl-1-[[5-(4-pyridinyl)-1H-pyrazol-3-yl]carbonyl]-4-Piperidinecarboxamide RN 1456902-78-5, entered into STN: Oct. 11, 2013.*
STN Chemical Database Registry entry for N-Cyclooctyl-1-[[5-(4-pyridinyl)-1H-pyrazol-3-yl]carbonyl]-4-Piperidinecarboxamide, RN 1455483-70-1, Entered STN: Oct. 4, 2013.*
Takada Ichiro et al. "Peroxisome proliferator-activated receptor agonists and antagonists: a patent review (2014-present," Expert Opinion on Therapeutic Patents, vol. 30, No. 1, Dec. 2019, pp. 1-13.
International Search Report and Written Opinion for PCT/US2021/058473 mailed Feb. 3, 2022 (16 pages).
Alekseyev (1998) "Optical isomerism and pharmacological activity of drugs", Sorovian Educational Journal, pp. 49-55.
Belikov (2007) Farmatsevticheskaya khimiya (Pharmaceutical Chemistry). Textbook. Fourth edition. M.: MEDpress-inform (4 pages).
Durnov et al. (2002) Children's Oncology, Edition Two, Moscow: Medina Publishing House (6 pages).
Dyson et al. (1959) "May's Chemistry of Synthetic Drugs", Mir Publishers, Moscow, pp. 12-19 (10 pages).
Kummerer (2010) "Pharmaceuticals in the environment", Annual Review of Environment and Resources, 35:57-75, doi: 10.1146/annurevenviron-052809-161223.
Kholodov et al. (1985) Klinicheskaya farmakokinetika (Clinical Pharmacokinetics), M., Meditsina, pp. 83-98, 134-138, 160, 378-380 (27 pages).
Malaya Meditsinskaya Entsiklopediya (Small Medical Encyclopedia) (1996) Editor-in-chief academician V.I. Pokrovskiy, Moscow, Sovetskaya entsiklopediya Publishing House, pp. 90-96 (6 pages).
Office Action and Search Report from corresponding Russian Patent Application No. 2023115101, dated Apr. 21, 2025 (38 pages).
Rukovodstavo (2014) Edition by Mironov A.N. (Manual for Pre-Clinical Studies of Drugs), Part One, M.: Grif & Co., Chapter 39 (17 pages).
Sergeev (1975) Kratkiy kurs molekulyarnoy biologii (A Concise Course in Molecular Biology), p. 10 (2 pages).
Kumar et al., (2020) "Identification of peptidomimetic compounds as potential inhibitors against MurA enzyme of *Mycobacterium tuberculosis*", Journal of Biomolecular Structure and Dynamics, vol. 38, No. 17, pp. 4997-5013.
Registry (STN) [online], Entered STN: Oct. 11, 2013 or earlier, CAS registration No. 1456930-16-7, etc. Search conducted Sep. 17, 2025, in corresponding Japanese Patent Application No. 2023-527349 (19 pages).
Registry (STN) [online], Entered STN: Oct. 11, 2013 or earlier, CAS registration No. 1456930-28-1, etc. Search conducted Sep. 17, 2025, in corresponding Japanese Patent Application No. 2023-527349 (68 pages).
CAS STNext® Structure Search in corresponding Chinese Patent Application No. 2021800893086 (34 pages). Search conducted May 26, 2025.
CAS STNext® Structure Search in corresponding Chinese Patent Application No. 2021800893086 (5 pages). Search conducted May 26, 2025.

* cited by examiner

PPARg MODULATORS AND METHODS OF USE

The present application claims the benefit of priority to U.S. Provisional Application No. 63/111,354 filed Nov. 9, 2020, the contents of which is incorporated herein by reference in its entirety.

Disclosed herein are novel compounds and pharmaceutical compositions containing such compounds. These compounds may be useful in the treatment of cancer, particularly cancers in which agents that target the RXRα and/or PPARγ pathways are known to be useful.

Muscle-invasive bladder cancer (MIBC) is an aggressive, potentially lethal disease with limited therapeutic options. Although chemotherapies and immunotherapies are approved for treatment of locally advanced or metastatic bladder cancer, the majority of patients will either not respond or present only a short duration of response (Seiler et al., 2017 *Eur Urology*; Robertson et al., 2017 *Cell*). This suggests that additional efforts are needed to identify novel therapies that can benefit those patients currently not responding to existing standard-of-care (SoC) therapies.

Recent work has revealed that not all advanced bladder cancers are created equal. Deep gene expression and genomic analysis has revealed distinct molecular subtypes of MIBC, including basal and luminal subtypes (Choi et al., 2014 *Cancer Cell*; Kardos et al., 2016 *JCI Insight*; Kamoun et al., 2020 *Eur Urology*), with unique tumor intrinsic and microenvironmental characteristics. Much like luminal breast and prostate cancers, luminal bladder cancer tends to be slower growing, less immune infiltrated, and less responsive to both chemotherapies and immunotherapies (Robertson et al., 2017 *Cell*). As only suboptimal therapies are currently available for luminal disease, a concerted effort is required to identify and exploit novel luminal lineage-specific therapeutic nodes.

Genomic alterations in the RXRα/PPARγ pathway in a large fraction of luminal bladder cancer, including recurrent mutations in RXRα at serine 427 (S427F/Y), hotspot mutations in PPARγ at threonine 475 (T475M), and amplification/overexpression of PPARγ (Guo et al., 2013 *Nature Genetics*; Van Allen et al., 2014 *Cancer Discovery*) are evident. These genomic alterations enhance PPARγ/RXRα-dependent transcription programs in MIBC (Halstead et al., 2017 *eLife*; Korpal et al., 2017 *Nat Communications*; Goldstein et al., 2017 *Cancer Research*). Additionally, only $PPAR\gamma^{active}$ luminal bladder cancer cell lines show reduced proliferation following genetic/pharmacological inhibition of PPARγ (Halstead et al., 2017 *eLife*; Goldstein et al., 2017 *Cancer Research*). Accordingly, this pathway activation is associated with dependence on RXRα/PPARγ for growth. Subsequent analysis of the functional role of PPARγ in luminal cells has revealed a critical role in promoting energy production through enhancing glucose and lipid metabolism (Liu et al., 2019 *Nat Communications*) which may contribute to the observed dependence on PPARγ in genomically altered luminal cells.

In addition to this tumor-intrinsic role played by PPARγ in PPARγ altered luminal bladder cancer, recent studies suggest that activated PPARγ/RXRα suppresses inflammatory cytokine expression and immune cell infiltration (Korpal et al., 2017 *Nat Communications*; Kardos et al., 2016 *JCI Insight*). Several clinical datasets and an in vivo tumor model indicate that $PPAR\gamma^{High}/RxR\alpha^{S427F/Y}$ impairs $CD8^+$ T cell infiltration and confers partial resistance to immune checkpoint inhibitors. Knockdown of PPARγ or RXRα and pharmacological inhibition of PPARγ significantly increases cytokine expression and may suggest therapeutic approaches to reviving immunosurveillance and sensitivity to immunotherapies (Korpal et al., 2017 *Nat Communications*). Collectively, these studies suggest PPARγ acts as a tumor cell-intrinsic "immuno-oncogene" that functions by promoting tumor cell growth, enhancing energy production, and increasing tumor cell survival through immunosuppression.

Accordingly, disclosed herein are compounds that may target the RXRα and/or PPARγ pathways.

Disclosed herein are compounds of Formula (I):

Formula (I)

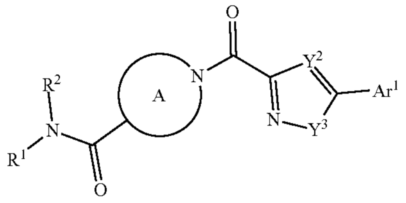

and pharmaceutically acceptable salts thereof, wherein:

$Ar^1$ is chosen from

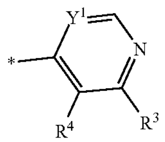 and 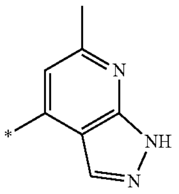

wherein $Y^1$ is chosen from N and C—$X^1$ wherein $X^1$ is chosen from hydrogen, hydroxyl, halogens, and $C_1$-$C_4$ alkyls;

$R^3$ is chosen from hydrogen, optionally substituted alkyls, optionally substituted amines, halogens, cyano, and optionally substituted alkoxys; and $R^4$ is chosen from hydrogen and optionally substituted alkyls, either $Y^2$ is chosen from C—$X^2$ and N and $Y^3$ is NH, or $Y^2$ is NH and $Y^3$ is C—$X^2$, wherein $X^2$ is chosen from hydrogen and halogens;

Ring A is chosen from saturated 6- to 9-membered cyclic rings optionally substituted with at least one substituent chosen from halogens, hydroxyl, and optionally substituted alkyls;

$R^1$ is chosen from —$(CHR^5)_k$—$(CR^6R^7)_n$—$(O)_m$-Ring B, wherein k is 0 or 1, n is 0 or 1, m is 0 or 1, $R^5$ is chosen from hydrogen and optionally substituted alkyls, $R^6$ is chosen from hydrogen and halogens, $R^7$ chosen from hydrogen and halogens, and Ring B is chosen from optionally substituted aryls, optionally substituted heteroaryls, optionally substituted cycloalkyls, optionally substituted heterocycloalkyls,
optionally substituted cycloalkenyls, and
optionally substituted heterocycloalkenyls; and $R^2$ is chosen from hydrogen and optionally substituted alkyls.

In some embodiments, $R^3$ is chosen from hydrogen, optionally substituted alkyls, optionally substituted amines, chlorine, fluorine, cyano, and optionally substituted alkoxys.

In some embodiments, $R^1$ is chosen from —$(CHR^5)_k$—$(CR^6R^7)_n$-Ring B wherein k, n, $R^5$, $R^6$, $R^7$, and Ring B are as defined in Formula (I). In some embodiments, $R^1$ is chosen from —$(CHR^5)_k$—$(CR^6R^7)_n$-Ring B wherein k, n, $R^5$, and Ring B are as defined in Formula (I) and $R^6$ and $R^7$ are fluorine.

In some embodiments, $R^2$ is chosen from hydrogen and $C_1$-$C_3$ alkyl.

In some embodiments, the compounds of Formula (I) and pharmaceutically acceptable salts thereof have a TR-FRET inverse agonist $AC_{50}$ value of less than 1000 nM. In some embodiments, the compounds of Formula (I) and pharmaceutically acceptable salts thereof have a TR-FRET inverse agonist $AC_{50}$ value of less than 500 nM. In some embodiments, the compounds of Formula (I) and pharmaceutically acceptable salts thereof have a TR-FRET inverse agonist $AC_{50}$ value of less than 250 nM. In some embodiments, the compounds of Formula (I) and pharmaceutically acceptable salts thereof have a TR-FRET inverse agonist $AC_{50}$ value ranging from 0.1 nM to 1000 nM. In some embodiments, the compounds of Formula (I) and pharmaceutically acceptable salts thereof have a TR-FRET inverse agonist $AC_{50}$ value ranging from 0.1 nM to 500 nM. In some embodiments, the compounds of Formula (I) and pharmaceutically acceptable salts thereof have a TR-FRET inverse agonist $AC_{50}$ value ranging from 0.1 nM to 250 nM.

As used herein, a "TR-FRET inverse agonist $AC_{50}$ value" refers to an $AC_{50}$ value obtained using the TR-FRET assay to measure Co—R Peptide Recruitment to PPARγ disclosed herein.

Also disclosed herein are pharmaceutical compositions comprising at least one entity chosen from compounds of Formula (I) and pharmaceutically acceptable salts thereof. In some embodiments, the pharmaceutical compositions further comprise at least one pharmaceutically acceptable carrier.

Also disclosed herein are methods of treating a subject with cancer comprising administering to the subject a therapeutically acceptable amount of at least one entity chosen from compounds of Formula (I) and/or pharmaceutically acceptable salt thereof. In some embodiments, the cancer is chosen from advanced bladder cancers, luminal breast cancer, prostate cancer, luminal bladder cancer, basal bladder cancer, and/or cancers having altered RXRα and/or PPARγ pathways. In some embodiments, the cancer is chemotherapy resistant and/or immunotherapy resistant.

Also disclosed herein is the use of at least one entity chosen from compounds of Formula (I) and pharmaceutically acceptable salts thereof in a method of therapeutic treatment, e.g., treatment for a cancer. Also disclosed herein is at least one compound chosen from compounds of Formula (I) and pharmaceutically acceptable salts thereof for use in the preparation of a medicament.

As used herein, the following definitions shall apply unless otherwise indicated.

As described herein, compounds may be substituted with one or more substituents, such as those illustrated generally herein, or as exemplified by particular classes, subclasses, and species of the disclosure. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds. The term "substituted" includes, e.g., the situation where at least one hydrogen atom is replaced by at least one non-hydrogen atom such as, for example, a halogen atom such as F, Cl, Br, and I (including, perhalogenation); a deuterium; a carbon atom in groups such as, for example, alkyl group and cyano groups; an oxygen atom in groups such as hydroxyl groups, alkoxys, and ester groups; a sulfur atom in groups such as thiol groups, thioalkyl groups, cyano groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also includes, e.g., the situation where, in any of the above groups, at least one hydrogen atom is replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

"Isomers" refers to compounds having the same number and kind of atoms; and hence the same molecular weight, but differing with respect to the arrangement or configuration of the atoms. "Stereoisomers" refers to compounds that have the same atomic connectivity but different arrangements of their atoms in space. "Diastereoisomers" or "diastereomers" refers to stereoisomers that are not enantiomers. "Enantiomers" refers to stereoisomers that are non-superimposable mirror images of one another. "Geometric isomers" refers to cis-trans isomers having different positions of groups with respect to a double bond or ring or central atom.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. In some embodiments, a stereomerically pure composition of a compound having two chiral centers will be substantially free of diastereomers, and substantially free of the opposite enantiomer, of the compound. In some embodiments, a stereomerically pure compound comprises greater than about 80% by weight of one stereoisomer of the compound and less than about 20% by weight of the other stereoisomers of the compound, such as greater than about 90% by weight of one stereoisomer of the compound and less than about 10% by weight of the other stereoisomers of the compound, further such as greater than about 95% by weight of one stereoisomer of the compound and less than about 5% by weight of the other stereoisomers of the compound, and further such as greater than about 97% by weight of one stereoisomer of the compound and less than about 3% by weight of the other stereoisomers of the compound. "R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry, Section E, Stereochemistry.

"Ar" or "aryl" refers to an aromatic carbocyclic moiety having one or more closed rings. Non-limiting examples include phenyl, naphthyl, anthracenyl, phenanthracenyl, biphenyl, and pyrenyl. In some embodiments, aryl groups contain 6 carbon atoms ("$C_6$ aryl").

"Alkyl" or "alkyl group," as used herein, includes straight-chain, branched, and cyclic hydrocarbon chains that are completely saturated. In some embodiments, alkyl groups contain 1-8 carbon atoms ("$C_1$-$C_8$ alkyl"). In some embodiments, alkyl groups contain 1-6 carbon atoms ("$C_1$-$C_6$ alkyl"). In some embodiments, alkyl groups contain 1-3 carbon atoms. In some embodiments, alkyl groups contain 2-3 carbon atoms, and, in some embodiments, alkyl groups contain 1-2 carbon atoms. In some embodiments, the term "alkyl" or "alkyl group" refers to a cycloalkyl group. In some embodiments, cycloalkyl groups contain 3-8 carbon atoms ("$C_3$-$C_8$ cycloalkyl"). In some embodiments, cycloalkyl groups contain 3-6 carbon atoms ("$C_3$-$C_6$ cycloalkyl"). Non-limiting examples of exemplary alkyl groups include methyl, ethyl, propyl, isopropyl, butyl, cyclopropyl and cyclohexyl.

"Alkenyl" or "alkenyl group," as used herein, includes straight-chain, branched, and cyclic hydrocarbon chains that contain at least one double bond (unsaturated bond).

"Alkoxy," as used herein, refers to an alkyl group, as previously defined, attached to the principal carbon chain through an oxygen ("alkoxy") atom.

"Cyclic ring" or "ring," as used herein, refers to a cyclic moiety having one or more closed rings and includes, for example, monocyclic, bicyclic, tricyclic moieties, and includes bridged and spiro moieties. The number of members in a "cyclic ring" or "ring" refers to the total number of atoms forming the one or more closed rings of the cyclic moiety. For example, 8-azabicyclo[3.2.1]octane is an 8-membered ring and 3-oxa-9-azabicyclo[3.3.1]nonane is a 9-membered ring.

"Cycloalkyl" as used herein refers to cyclic hydrocarbon chains that are completely saturated and are included within the genus of "alkyl" groups.

"Cycloalkenyl" as used herein refers to cyclic hydrocarbon chains that contain at least one double bond (unsaturated bond) and are included within the genus of "alkenyl" groups.

"Halogens" and "halo atoms" as used interchangeably herein refer to fluorine, chlorine, bromine, and iodine.

"Haloalkyl" refers to an alkyl group substituted with one or more halo atoms (F, Cl, Br, I). For example, "fluoromethyl" refers to a methyl group substituted with one or more fluoro atoms (e.g., monofluoromethyl, difluoromethyl, or trifluoromethyl).

"Heteroatom" refers to O, S, N, or P.

"Heteroalkyl" as used herein includes straight-chain, branched, and cyclic hydrocarbon chains that are completely saturated and that comprise at least one heteroatom (oxygen, nitrogen, sulfur, or phosphorus) in the chain.

"Heterocycloalkyl" as used herein refers to cyclic hydrocarbon chains that are completely saturated and comprise at least one heteroatom (oxygen, nitrogen, sulfur, or phosphorus) in the chain.

"Heterocycloalkenyl" as used herein refers to cyclic hydrocarbon chains that contain at least one double bond (unsaturated bond) and comprise at least one heteroatom (oxygen, nitrogen, sulfur, or phosphorus) in the chain.

"Heteroaryl" refers to a cyclic moiety having one or more closed rings, with one or more heteroatoms (oxygen, nitrogen, sulfur, or phosphorus) in at least one of the rings, wherein at least one of the rings is aromatic, and wherein the ring or rings may independently be fused, and/or bridged. Non-limiting examples include thiophenyl, triazolyl, pyridinyl, pyrimidinyl, pyridazinyl, and pyrazinyl.

"Heterocyclyl" or "heterocyclic," as used herein, means a monocyclic heterocycle, a bicyclic heterocycle, or a tricyclic heterocycle containing at least one heteroatom in the ring. Heterocycles may be saturated, unsaturated, aromatic (e.g., heteroaryl), or non-aromatic. In some embodiments, heterocycle groups contain 2-10 carbon atoms, 3-10 carbon atoms, 2-8 carbon atoms, 3-8 carbon atoms, 2-6 carbon atoms, 3-6 carbon atoms, 2-4 carbon atoms, 3-4 carbon atoms, or 3 carbon atoms. In some embodiments, the heterocycle may be a 3-10 membered ring, 3-8 membered ring, 3-6 membered ring, 3-4 membered ring, or 3 membered ring.

The monocyclic heterocycle is a 3-, 4-, 5-, 6-, 7, or 8-membered ring containing at least one heteroatom independently chosen from O, N, P, and S. In some embodiments, the heterocycle is a 3- or 4-membered ring containing one heteroatom chosen from O, N, P, and S. In some embodiments, the heterocycle is a 5-membered ring containing zero or one double bond and one, two or three heteroatoms chosen from O, N, P, and S. In some embodiments, the heterocycle is a 6-, 7-, or 8-membered ring containing zero, one or two double bonds and one, two or three heteroatoms chosen from O, N, P, and S. Representative examples of monocyclic heterocycle include, but are not limited to, azetidinyl, azepanyl, aziridinyl, diazepanyl, 1,3-dioxanyl, 1,3-dioxolanyl, dihydropyranyl (including 3,4-dihydro-2H-pyran-6-yl), 1,3-dithiolanyl, 1,3-dithianyl, imidazolinyl, imidazolidinyl isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl pyrrolinyl, pyrrolidinyl, tetrahydropyranyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The bicyclic heterocycles of the present disclosure are exemplified by a monocyclic heterocycle fused to an aryl group, or a monocyclic heterocycle fused to a monocyclic cycloalkyl, or a monocyclic heterocycle fused to a monocyclic cycloakenyl, or a monocyclic heterocycle fused to a monocyclic heterocycle. Representative examples of bicyclic heterocycles include, but are not limited to, 3,4-dihydro-2H-pyranyl, 1,3-benzodioxolyl, 1,3-benzodithioiyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

In some embodiments, the bicyclic heterocycle is a spiro heterocycle. As known in the art, a "spiro" heterocycle is a bicyclic moiety with rings connected through just one atom. The connecting atom is also called the spiro atom and most often is a quaternary atom such as carbon or nitrogen. Spiro compounds may be designated with the infix spiro followed by square brackets containing the number of atoms in the smaller ring and the number of atoms in the larger ring excluding the spiroatom itself; the numbers being separated by a dot. An example of such compounds includes, but is not limited to, 2,6-diazaspiro[3.3]heptane.

The tricyclic heterocycle is a bicyclic heterocycle fused to an aryl group, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycles include, but are not limited to, 2,3,4,4a,9,9a-hexahydro-1H-carbazolyl, 6,7,8,9,9a-hexahydrodibenzo[b,d]furanyl, and 5a,6,7,8,9,9a-hexahydrodibenzo[b,d]thienyl.

The heterocycle groups of the present disclosure are connected to the parent molecular moiety through any substitutable carbon atom or any substitutable nitrogen, oxygen or sulfur atom contained within the groups and may contain one or two alkylene bridges of 1, 2, 3, or 4 carbon atoms, each linking two non-adjacent carbon atoms of the groups. Examples of such "bridged" heterocycle groups include, but are not limited to, oxatricyclo[$3.3.1.1^{3,7}$]decyl (including 2-oxatricyclo[$3.3.1.1^{3,7}$]decyl), 2,4-dioxabicyclo[4.2.1]nonyl, oxabicyclo[2.2.1]heptyl (including 2-oxabicyclo[2.2.1]heptyl) and 2,5-diazabicyclo[2.2.1]heptane.

In the above heteroaryl and heterocycles the nitrogen or sulfur atoms can be optionally oxidized to various oxidation states. In a specific example, the group $S(O)_{0-2}$ refers to —S— (sulfide), —S(O)— (sulfoxide), and —$SO_2$— (sulfone) respectively. For convenience, nitrogens, particularly but not exclusively, those defined as annular aromatic nitrogens, are meant to include those corresponding N-oxide forms. Thus, for a compound of the disclosure having, for example, a pyridyl ring; the corresponding pyridyl-N-oxide is meant to be included as another compound of the disclosure.

"Treatment," "treat," or "treating" cancer refers to reversing, alleviating, and/or delaying the progression of a cancer as described herein.

"Subject", as used herein, means an animal subject, such as a mammalian subject, and particularly human beings.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al., "Commentary: Occurrence of Pharmaceutically Acceptable Anions and Cations in the Cambridge Structural Database," *J. Pharmaceutical Sciences*, vol. 94, no. 10 (2005), and Berge et al., "Pharmaceutical Salts", *J. Pharmaceutical Sciences*, vol. 66, no. 1 (1977), which are incorporated by reference herein.

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl" is attached to the rest of the molecule at the alkyl end. Further examples include methoxyethyl, where the point of attachment is at the ethyl end, and methylamino, where the point of attachment is at the amine end.

Unless indicated otherwise, where a chemical group is described by its chemical formula or structure having a terminal bond moiety indicated by "-", it will be understood that the "-" represents the point of attachment.

Disclosed herein are compounds of Formula (I):

Formula (I)

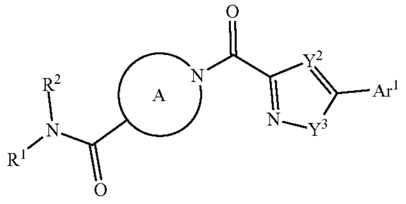

and pharmaceutically acceptable salts thereof, wherein:

$Ar^1$ is chosen from

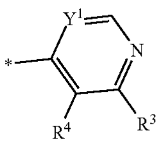

and

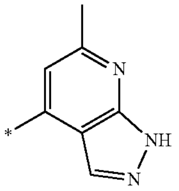

wherein $Y^1$ is chosen from N and C—$X^1$ wherein $X^1$ is chosen from hydrogen, hydroxyl, halogens, and $C_1$-$C_4$ alkyls;

$R^3$ is chosen from hydrogen, optionally substituted alkyls, optionally substituted amines, halogens, cyano, and optionally substituted alkoxys; and $R^4$ is chosen from hydrogen and optionally substituted alkyls;

either $Y^2$ is chosen from C—$X^2$ and N and $Y^3$ is NH, or $Y^2$ is NH and $Y^3$ is C—$X^2$, wherein $X^2$ is chosen from hydrogen and halogens;

Ring A is chosen from saturated 6- to 9-membered cyclic rings optionally substituted with at least one substituent chosen from halogens, hydroxyl, and optionally substituted alkyls;

$R^1$ is chosen from —$(CHR^5)_k$—$(CR^6R^7)_n$—$(O)_m$-Ring B, wherein k is 0 or 1, n is 0 or 1, m is 0 or 1, $R^5$ is chosen from hydrogen and optionally substituted alkyls, $R^6$ is chosen from hydrogen and halogens, $R^7$ chosen from hydrogen and halogens, and Ring B is chosen from optionally substituted aryls, optionally substituted heteroaryls, optionally substituted cycloalkyls, optionally substituted heterocycloalkyls, optionally substituted cycloalkenyls, and optionally substituted heterocycloalkenyls; and $R^2$ is chosen from hydrogen and optionally substituted alkyls.

In some embodiments, $R^3$ is chosen from hydrogen, optionally substituted alkyls, optionally substituted amines, chlorine, fluorine, cyano, and optionally substituted alkoxys.

In some embodiments, $R^1$ is chosen from —$(CHR^5)_k$—$(CR^6R^7)^n$-Ring B. In some embodiments, $R^1$ is chosen from —$(CHR^5)_k$—$(CR^6R^7)_n$-Ring B wherein $R^6$ and $R^7$ are fluorine.

In some embodiments, $R^2$ is chosen from hydrogen and $C_1$-$C_3$ alkyl.

In some embodiments, Ring A is chosen from piperidinyl and saturated 7- to 9-membered bicyclic rings, and Ring A is optionally substituted with at least one substituent chosen from halogens, hydroxyl, and optionally substituted alkyls.

In some embodiments, Ring A is a piperidinyl optionally substituted with at least one substituent chosen from halogens, hydroxyl, and optionally substituted alkyls. In some embodiments, Ring A is chosen from piperidinyl optionally substituted with at least one halogen. In some embodiments, Ring A is chosen from piperidinyl optionally substituted with at least one hydroxyl. In some embodiments, Ring A is chosen from piperidinyl optionally substituted with at least one optionally substituted alkyl.

In some embodiments, Ring A is chosen from saturated 7- to 9-membered bicyclic rings optionally substituted with at least one substituent chosen from halogens, hydroxyl, and optionally substituted alkyls. In some embodiments, Ring A is chosen from saturated 7- to 9-membered bicyclic rings optionally substituted with at least one halogen. In some embodiments, Ring A is chosen from saturated 7- to 9-membered bicyclic rings optionally substituted with at least one hydroxyl. In some embodiments, Ring A is chosen from saturated 7- to 9-membered bicyclic rings optionally substituted with at least one optionally substituted alkyl.

In some embodiments, Ring A is chosen from saturated 7-membered bicyclic rings optionally substituted with at least one substituent chosen from halogens, hydroxyl, and optionally substituted alkyls. In some embodiments, Ring A is chosen from saturated 8-membered bicyclic rings optionally substituted with at least one substituent chosen from halogens, hydroxyl, and optionally substituted alkyls. In some embodiments, Ring A is chosen from saturated 9-membered bicyclic rings optionally substituted with at least one substituent chosen from halogens, hydroxyl, and optionally substituted alkyls.

In some embodiments, Ring A is chosen from piperidinyl, azaspirooctane, azaspirononane, azabicyclooctane, and oxa-azabicyclononane, and Ring A is optionally substituted with at least one substituent chosen from halogens, hydroxyl, and optionally substituted alkyls.

In some embodiments, Ring A is chosen from piperidinyl optionally substituted with at least one substituent chosen from halogens, hydroxyl, and optionally substituted alkyls. In some embodiments, Ring A is chosen from azaspirooctane optionally substituted with at least one substituent chosen from halogens, hydroxyl, and optionally substituted alkyls. In some embodiments, Ring A is chosen from azaspirononane optionally substituted with at least one substituent chosen from halogens, hydroxyl, and optionally substituted alkyls. In some embodiments, Ring A is chosen from azabicyclooctane optionally substituted with at least one substituent chosen from halogens, hydroxyl, and optionally substituted alkyls. In some embodiments, Ring A is chosen from oxa-azabicyclononane optionally substituted with at least one substituent chosen from halogens, hydroxyl, and optionally substituted alkyls.

In some embodiments, Ring A is chosen from piperidinyl optionally substituted with at least one halogen. In some embodiments, Ring A is chosen from piperidinyl optionally substituted with at least one hydroxyl. In some embodiments, Ring A is chosen from piperidinyl optionally substituted with at least one optionally substituted alkyls. In some embodiments, Ring A is chosen from azaspirooctane optionally substituted with at least one halogen. In some embodiments, Ring A is chosen from azaspirooctane optionally substituted with at least one hydroxyl. In some embodiments, Ring A is chosen from azaspirooctane optionally substituted with at least one optionally substituted alkyls. In some embodiments, Ring A is chosen from azaspirononane optionally substituted with at least one halogen. In some embodiments, Ring A is chosen from azaspirononane optionally substituted with at least one hydroxyl. In some embodiments, Ring A is chosen from azaspirononane optionally substituted with at least one optionally substituted alkyls. In some embodiments, Ring A is chosen from azabicyclooctane optionally substituted with at least one halogen. In some embodiments, Ring A is chosen from azabicyclooctane optionally substituted with at least one hydroxyl. In some embodiments, Ring A is chosen from azabicyclooctane optionally substituted with at least one optionally substituted alkyls. In some embodiments, Ring A is chosen from oxa-azabicyclononane optionally substituted with at least one halogen. In some embodiments, Ring A is chosen from oxa-azabicyclononane optionally substituted with at least one hydroxyl. In some embodiments, Ring A is chosen from oxa-azabicyclononane optionally substituted with at least one optionally substituted alkyls.

In some embodiments, Ring B is chosen from optionally substituted 5- to 10-membered aryls, optionally substituted 5- to 10-membered heteroaryls, optionally substituted 3- to 10-membered cycloalkyls, optionally substituted 4- to 10-membered heterocycloalkyls, optionally substituted 6- to 10-membered cycloalkenyls, and optionally substituted 6- to 10-membered heterocycloalkenyls. In some embodiments, Ring B is chosen from optionally substituted 5- to 10-membered heteroaryls. In some embodiments, Ring B is chosen from optionally substituted 3 to 10-membered cycloalkyls. In some embodiments, Ring B is chosen from optionally substituted 4- to 10-membered heterocycloalkyls. In some embodiments, Ring B is chosen from optionally substituted 6- to 10-membered cycloalkenyls. In some embodiments, Ring B is chosen from optionally substituted 6- to 10-membered heterocycloalkenyls.

In some embodiments, Ring B is chosen from optionally substituted 5- to 6-membered monocyclic aryls, optionally substituted 10-membered bicyclic aryls, optionally substituted 5- to 6-membered monocyclic heteroaryls, optionally substituted 9- to 10-membered bicyclic heteroaryls, optionally substituted 3- to 10-membered monocyclic alkyls, optionally substituted 7- to 10-membered bridged bicyclic alkyls, optionally substituted 7- to 10-membered spirocyclic bicyclic alkyls, optionally substituted 4- to 10-membered monocyclic heterocycloalkyls, optionally substituted 7- to 10-membered bridged bicyclic heterocycloalkyls, optionally substituted 7- to 10-membered spirocyclic bicyclic heterocycloalkyls, optionally substituted 5- to 6-membered monocyclic cycloalkenyls, optionally substituted 8- to 10-membered bicyclic cycloalkenyls, optionally substituted 5- to 6-membered monocyclic heterocycloalkenyls, and optionally substituted 8- to 10-membered bicyclic heterocycloalkenyls.

In some embodiments, Ring B is chosen from optionally substituted 5- to 6-membered monocyclic aryls. In some embodiments, Ring B is chosen from optionally substituted 10-membered bicyclic aryls. In some embodiments, Ring B is chosen from optionally substituted 5- to 6-membered monocyclic heteroaryls. In some embodiments, Ring B is chosen from optionally substituted 9- to 10-membered bicyclic heteroaryls. In some embodiments, Ring B is chosen from optionally substituted 3- to 10-membered monocyclic alkyls. In some embodiments, Ring B is chosen from optionally substituted 7- to 10-membered bridged bicyclic alkyls. In some embodiments, Ring B is chosen from optionally substituted 7- to 10-membered spirocyclic bicyclic alkyls. In some embodiments, Ring B is chosen from optionally substituted 4- to 10-membered monocyclic heterocycloalkyls. In some embodiments, Ring B is chosen from optionally substituted 7- to 10-membered bridged bicyclic heterocycloalkyls. In some embodiments, Ring B is chosen from optionally substituted 7- to 10-membered spirocyclic bicyclic heterocycloalkyls. In some embodiments, Ring B is chosen from optionally substituted 5- to 6-membered monocyclic cycloalkenyls. In some embodiments, Ring B is chosen from optionally substituted 8- to 10-membered bicyclic cycloalkenyls. In some embodiments, Ring B is chosen from optionally substituted 5- to 6-membered monocyclic heterocycloalkenyls. In some embodiments, Ring B is chosen from optionally substituted 8- to 10-membered bicyclic heterocycloalkenyls.

In some embodiments, Ring B is chosen from optionally substituted 5- to 6-membered monocyclic aryls, optionally substituted 10-membered bicyclic aryls, optionally substituted 5- to 6-membered monocyclic heteroaryls having one to three ring heteroatoms chosen from oxygen and nitrogen, optionally substituted 9- to 10-membered bicyclic heteroaryls having one to three ring heteroatoms chosen from oxygen and nitrogen, optionally substituted 3- to 10-membered monocyclic alkyls, optionally substituted 7- to 10-membered bridged bicyclic alkyls, optionally substituted 7- to 10-membered spirocyclic bicyclic alkyls, optionally substituted 4- to 10-membered monocyclic heterocycloalkyls having one to three ring heteroatoms chosen from oxygen, silicon, and nitrogen, optionally substituted 7- to 10-membered bridged bicyclic heterocycloalkyls having one to three ring heteroatoms chosen from oxygen and nitrogen, optionally substituted 7- to 10-membered spirocyclic bicyclic heterocycloalkyls having one to three ring heteroatoms chosen from oxygen and nitrogen, optionally substituted 5- to 6-membered monocyclic cycloalkenyls, optionally substituted 8- to 10-membered bicyclic cycloalkenyls, optionally substituted 5- to 6-membered monocyclic heterocycloalkenyls having one to three ring heteroatoms chosen from oxygen and nitrogen, and optionally substituted 8- to 10-membered bicyclic heterocycloalkenyls having one to three ring heteroatoms chosen from oxygen and nitrogen.

In some embodiments, Ring B is chosen from optionally substituted 5- to 6-membered monocyclic aryls.

In some embodiments, Ring B is chosen from optionally substituted 10-membered bicyclic aryls.

In some embodiments, Ring B is chosen from optionally substituted 5- to 6-membered monocyclic heteroaryls having one to three ring heteroatoms chosen from oxygen and nitrogen.

In some embodiments, Ring B is chosen from optionally substituted 9- to 10-membered bicyclic heteroaryls having one to three ring heteroatoms chosen from oxygen and nitrogen.

In some embodiments, Ring B is chosen from optionally substituted 3- to 10-membered monocyclic alkyls.

In some embodiments, Ring B is chosen from optionally substituted 7- to 10-membered bridged bicyclic alkyls.

In some embodiments, Ring B is chosen from optionally substituted 7- to 10-membered spirocyclic bicyclic alkyls.

In some embodiments, Ring B is chosen from optionally substituted 4- to 10-membered monocyclic heterocycloalkyls having one to three ring heteroatoms chosen from oxygen, silicon, and nitrogen.

In some embodiments, Ring B is chosen from optionally substituted 7- to 10-membered bridged bicyclic heterocycloalkyls having one to three ring heteroatoms chosen from oxygen and nitrogen.

In some embodiments, Ring B is chosen from optionally substituted 7- to 10-membered spirocyclic bicyclic heterocycloalkyls having one to three ring heteroatoms chosen from oxygen and nitrogen.

In some embodiments, Ring B is chosen from optionally substituted 5- to 6-membered monocyclic cycloalkenyls.

In some embodiments, Ring B is chosen from optionally substituted 8- to 10-membered bicyclic cycloalkenyls.

In some embodiments, Ring B is chosen from optionally substituted 5- to 6-membered monocyclic heterocycloalkenyls having one to three ring heteroatoms chosen from oxygen and nitrogen.

In some embodiments, Ring B is chosen from optionally substituted 8- to 10-membered bicyclic heterocycloalkenyls having one to three ring heteroatoms chosen from oxygen and nitrogen.

In some embodiments, Ring A is chosen from

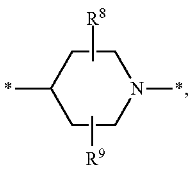, 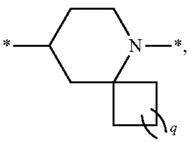,

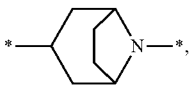, and 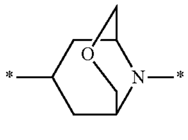

wherein q is 0 or 1, and $R^8$ and $R^9$ are each independently chosen from hydrogen; halogens, hydroxyl, optionally substituted alkoxys, and optionally substituted alkyls.

In some embodiments, at least one of $R^8$ and $R^9$ is a spiro-connected oxetane, such that Ring A is chosen from

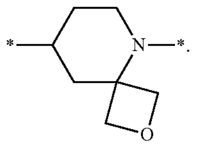

In some embodiments, disclosed herein are compounds of Formulae (II)-(V):

Formula (II)

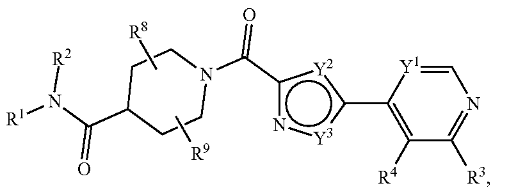

Formula (III)

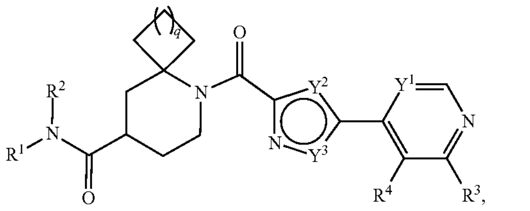

Formula (IV)

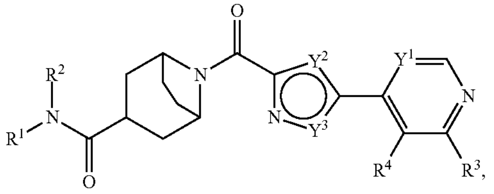

and

Formula (V)

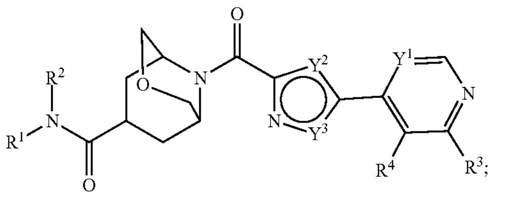

wherein $Y^1$ is chosen from N and C—$X^1$ wherein $X^1$ is chosen from hydrogen, hydroxyl, halogens, and $C_1$-$C_4$ alkyls;

either $Y^2$ is chosen from C—$X^2$ and N and $Y^3$ is NH, or $Y^2$ is NH and $Y^3$ is C—$X^2$, wherein $X^2$ is chosen from hydrogen and halogens;

q is 0 or 1;

$R^1$ is chosen from —$(CHR^5)_k$—$(CR^6R^7)_n$—$(O)_m$-Ring B, wherein k is 0 or 1, n is 0 or 1, m is 0 or 1;

$R^5$ is chosen from hydrogen and optionally substituted alkyls;

$R^6$ is chosen from hydrogen and halogens;

$R^7$ chosen from hydrogen and halogens; and

Ring B is chosen from optionally substituted 5- to 6-membered monocyclic aryls, optionally substituted 10-membered bicyclic aryls, optionally substituted 5- to 6-membered monocyclic heteroaryls having one to three ring heteroatoms chosen from oxygen and nitrogen, optionally substituted 9- to 10-membered bicyclic heteroaryls having one to three ring heteroatoms chosen from oxygen and nitrogen, optionally substituted 3- to 10-membered monocyclic alkyls, optionally substituted 7- to 10-membered bridged bicyclic alkyls, optionally substituted 7- to 10-membered spirocyclic bicyclic alkyls; optionally substituted 4- to 10-membered monocyclic heterocycloalkyls having one to three ring heteroatoms chosen from oxygen, silicon, and nitrogen, optionally substituted 7- to 10-membered bridged bicyclic heterocycloalkyls having one to three ring heteroatoms chosen from oxygen and nitrogen, optionally substituted 7- to 10-membered spirocyclic bicyclic heterocycloalkyls having one to three ring heteroatoms chosen from oxygen and nitrogen, optionally substituted 5- to 6-membered monocyclic cycloalkenyls, optionally substituted 8- to 10-membered bicyclic cycloalkenyls, optionally substituted 5- to 6-membered monocyclic heterocycloalkenyls having one to three ring heteroatoms chosen from oxygen and nitrogen, and optionally substituted 8- to 10-membered bicyclic heterocycloalkenyls having one to three ring heteroatoms chosen from oxygen and nitrogen;

$R^2$ is chosen from hydrogen and optionally substituted alkyls;

$R^3$ is chosen from hydrogen, optionally substituted alkyls, optionally substituted amines, halogens, cyano, and optionally substituted alkoxys;

$R^4$ is chosen from hydrogen and alkyl; and $R^8$ and $R^9$ are each independently chosen from hydrogen, halogens, hydroxyl, optionally substituted alkoxys, and optionally substituted alkyls.

In some embodiments, the compounds of Formula (I) and pharmaceutically acceptable salts thereof have a TR-FRET inverse agonist $AC_{50}$ value of less than 1000 nM. In some embodiments, the compounds of Formula (I) and pharmaceutically acceptable salts thereof have a TR-FRET inverse agonist $AC_{50}$ value of less than 500 nM. In some embodiments, the compounds of Formula (I) and pharmaceutically acceptable salts thereof have a TR-FRET inverse agonist $AC_{50}$ value of less than 250 nM. In some embodiments, the compounds of Formula (I) and pharmaceutically acceptable salts thereof have a TR-FRET inverse agonist $AC_{50}$ value ranging from 0.1 nM to 1000 nM. In some embodiments, the compounds of Formula (I) and pharmaceutically acceptable salts thereof have a TR-FRET inverse agonist $AC_{50}$ value ranging from 0.1 nM to 500 nM. In some embodiments, the compounds of Formula (I) and pharmaceutically acceptable salts thereof have a TR-FRET inverse agonist $AC_{50}$ value ranging from 0.1 nM to 250 nM.

In some embodiments, at least one of $R^8$ and $R^9$ is a spiro-connected oxetane.

In some embodiments, $R^3$ is chosen from hydrogen, optionally substituted alkyls, optionally substituted amines, chlorine, fluorine, cyano, and optionally substituted alkoxys.

In some embodiments, $R^1$ is chosen from —$(CHR^5)_k$—$(CR^6R^7)_n$-Ring B. In some embodiments, $R^1$ is chosen from —$(CHR^5)_k$—$(CR^6R^7)_n$-Ring B wherein $R^6$ and $R^7$ are fluorine.

In some embodiments, $R^2$ is chosen from hydrogen and $C_1$-$C_3$ alkyl.

In some embodiments, Ring B is chosen from

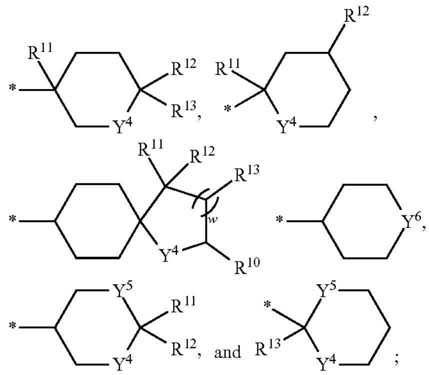

wherein w is 0 or 1;

$Y^4$ and $Y^5$ are each independently chosen from optionally substituted —($CH_2$)—, optionally substituted —(NH)—, and —O—;

$Y^6$ is chosen from optionally substituted —($CH_2$)—, optionally substituted —(NH)—, tetraalkylsilanes, and —O—;

$R^{10}$ is chosen from hydrogen, halogens, optionally substituted alkyls, and carbonyl; and $R^{11}$, $R^{12}$, and $R^{13}$ are each independently chosen from hydrogen, halogens, optionally substituted alkyls, hydroxyl, optionally substituted amines, and optionally substituted alkoxys.

In some embodiments, Ring B is chosen from

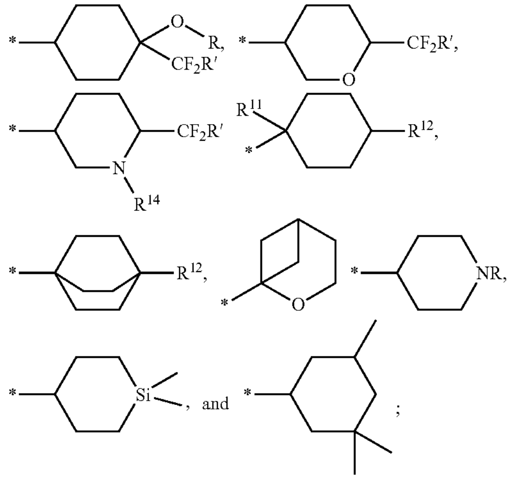

wherein $R^{11}$ and $R^{12}$ are each independently chosen from hydrogen, halogens, optionally substituted alkyls, hydroxyl, optionally substituted amines, and optionally substituted alkoxys;

$R^{14}$ is chosen from hydrogen and optionally substituted alkyls;

R is chosen from hydrogen, optionally substituted alkyls, and aryl; and

R' is chosen from hydrogen, optionally substituted alkyls, and halogens.

In some embodiments, Ring B is chosen front

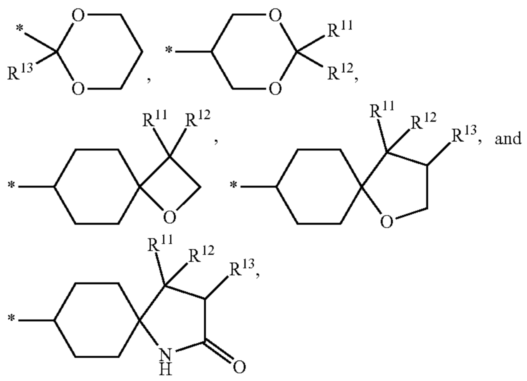

wherein $R^{11}$, $R^{12}$, and $R^{13}$ are each independently chosen from hydrogen, halogens, hydroxyl, optionally substituted alkyls, optionally substituted amines, and optionally substituted alkoxys.

In some embodiments, Ring B is chosen from

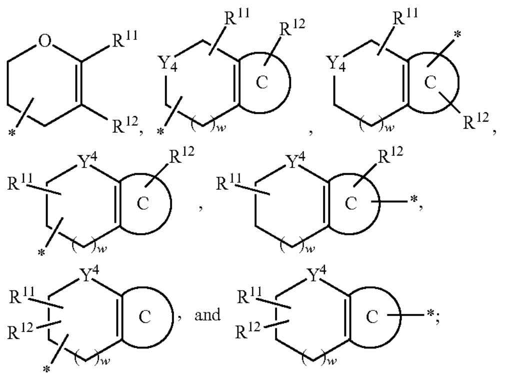

wherein w is 0 or 1;

$Y^4$ is chosen from $SO_2$, optionally substituted sulfonamides, optionally substituted amides, optionally substituted —($CH_2$)—, optionally substituted —(NH)—, and —O—;

$R^{11}$ and $R^{12}$ are each independently chosen from hydrogen, halogens, optionally substituted alkyls, hydroxyl, optionally substituted amines, and optionally substituted alkoxys; and Ring C is chosen from 5-membered aromatic rings, 5-membered heteroaromatic rings comprising 1 or 2 ring nitrogen atoms, 6-membered aromatic rings, and 6-membered heteroaromatic rings comprising 1 or 2 ring nitrogen atoms.

In some embodiments, Ring B is chosen from

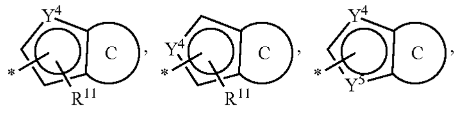

-continued

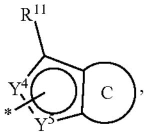 and 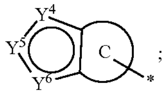

wherein $Y^4$, $Y^5$, and $Y^6$ are each independently chosen from optionally substituted —(CH)—, optionally substituted —(NH)—, and —O—;

$R^{11}$ is chosen from hydrogen, halogens, optionally substituted alkyls, hydroxyl, optionally substituted amines, and optionally substituted alkoxys; and Ring C is chosen from 5-membered aromatic rings, 5-membered heteroaromatic rings comprising 1 or 2 ring nitrogen atoms, 6-membered aromatic rings, and 6-membered heteroaromatic rings comprising 1 or 2 ring nitrogen atoms.

In some embodiments, Ring B is chosen front

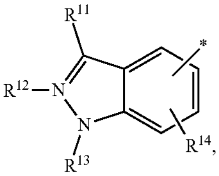 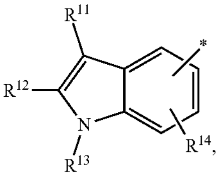

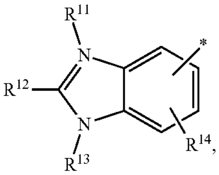 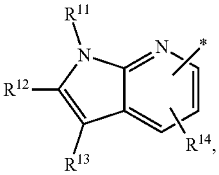

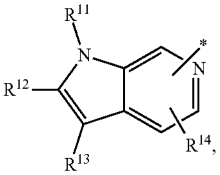 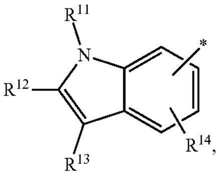

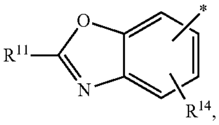 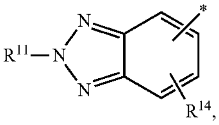 and

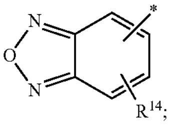

wherein when $R^{11}$ is not bonded to nitrogen, $R^{11}$ is chosen from hydrogen, halogens, optionally substituted alkyls, and hydroxyl, and $R^{11}$ is otherwise chosen from hydrogen and optionally substituted alkyls;

when $R^{12}$ is not bonded to nitrogen, $R^{12}$ is chosen from hydrogen, halogens, optionally substituted alkyls, and hydroxyl, and $R^{12}$ is otherwise chosen from hydrogen, and optionally substituted alkyls;

when $R^{13}$ is not bonded to nitrogen, $R^{13}$ is chosen from hydrogen, halogens, optionally substituted alkyls, and hydroxyl, and $R^{13}$ is otherwise chosen from hydrogen, and optionally substituted alkyls; and $R^{14}$ is chosen from hydrogen, halogens, optionally substituted alkyls, hydroxyl, optionally substituted amines, and optionally substituted alkoxys.

In some embodiments, Ring B is chosen from

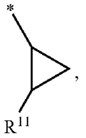 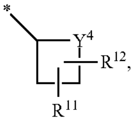 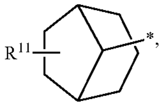

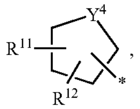 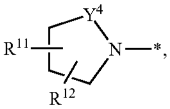 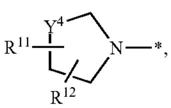

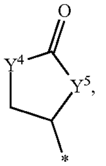 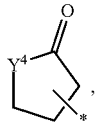 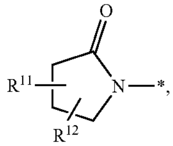 and

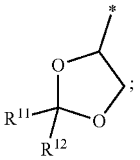

wherein $Y^4$, and $Y^5$ are each independently chosen from optionally substituted —($CH_2$)—, optionally substituted —(NH)—, and —O—; and $R^{11}$ and $R^{12}$ are independently chosen from hydrogen, cyano, halogens, optionally substituted alkyls, hydroxyl, optionally substituted amines, aryl, heteroaryl, and optionally substituted alkoxys.

In some embodiments, Ring B is chosen from

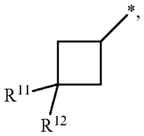 , 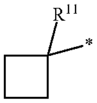 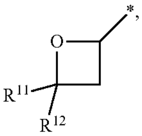

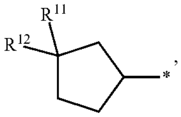 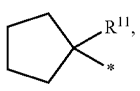 and 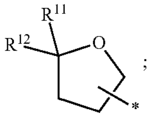

wherein $R^{11}$ and $R^{12}$ independently are chosen from hydrogen, halogens, optionally substituted alkyls, hydroxyl, optionally substituted amines, and optionally substituted alkoxys.

In some embodiments, Ring B is chosen from

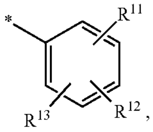 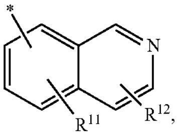 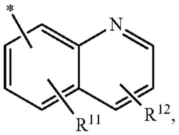

-continued

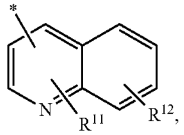

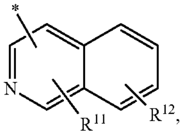

and

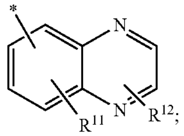

wherein $R^{11}$, $R^{12}$, and $R^{13}$ are independently chosen from hydrogen, halogens, optionally substituted alkyls, hydroxyl, optionally substituted amines, and optionally substituted alkoxys.

In some embodiments, Ring B is chosen from

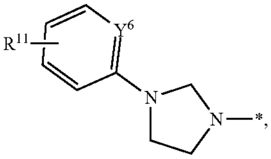

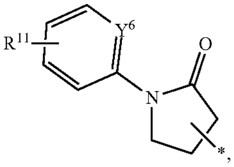

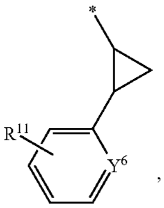

,

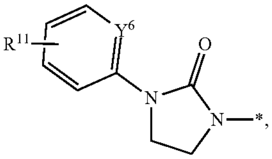

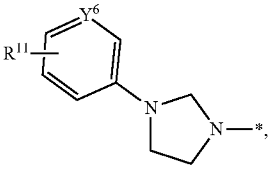

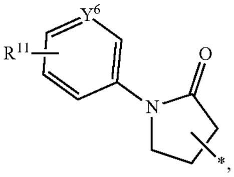

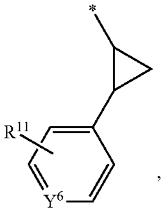

,

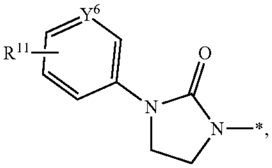

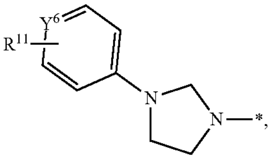

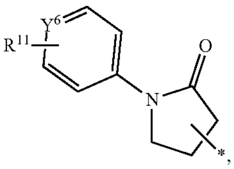

-continued

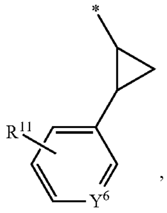

, and

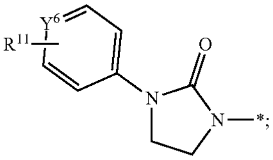

wherein $Y^6$ is chosen from optionally substituted —(CH)— and optionally substituted —(NH)—, and $R^{11}$ is chosen from hydrogen, halogens, optionally substituted alkyls, hydroxyl, optionally substituted amines, and optionally substituted alkoxys.

In some embodiments, Ring B is chosen from

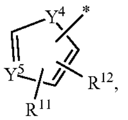

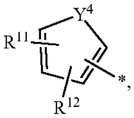

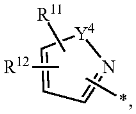

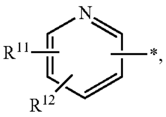

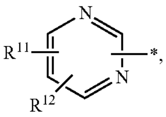

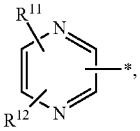

and

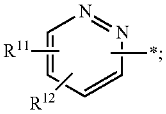

wherein $Y^4$ is chosen from optionally substituted —($CH_2$)—, optionally substituted —(NH)—, and —O—; $Y^5$ is chosen from optionally substituted —(CH)— and N; and $R^{11}$ and $R^{12}$ are chosen from hydrogen, halogens, optionally substituted alkyls, hydroxyl, optionally substituted amines, and optionally substituted alkoxys.

In some embodiments, Ring B is chosen from

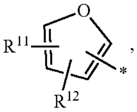

,

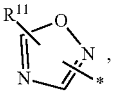

,

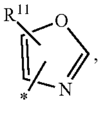

,

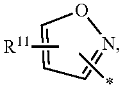

and

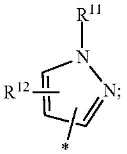

wherein $R^{11}$ and $R^{12}$ are chosen from hydrogen, halogens, optionally substituted alkyls, hydroxyl, optionally substituted amines, and optionally substituted alkoxys.

In some embodiments, Ring B is chosen from

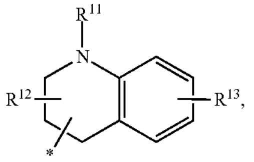
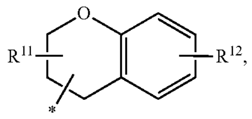
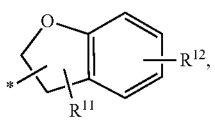
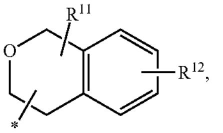
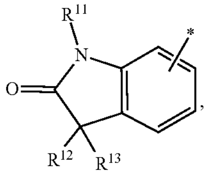
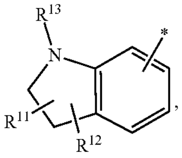
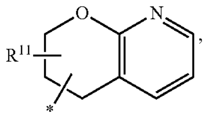
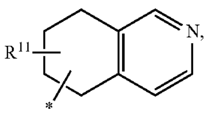
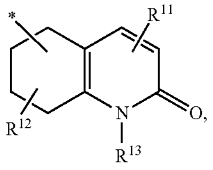
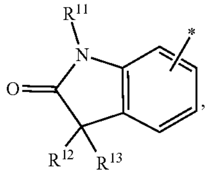
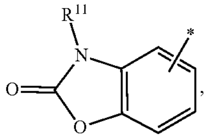
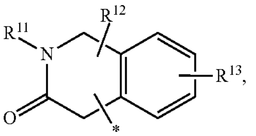
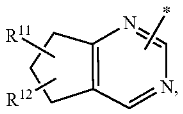
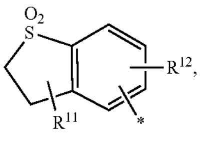
and
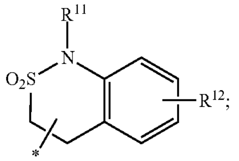

wherein $R^{11}$, $R^{12}$, and $R^{13}$ are independently chosen from hydrogen, halogens, optionally substituted alkyls, hydroxyl, optionally substituted amines, and optionally substituted alkoxys.

In some embodiments, $R^1$ is chosen from $-(CHR^5)_k-(CR^6R^7)_n-(O)_m$-Ring B wherein k is 0 or 1, n is 0 or 1, m is 0 or 1, $R^5$ is chosen from hydrogen and methyl, $R^6$ is chosen from hydrogen and halogens, $R^7$ chosen from hydrogen and halogens; and $R^2$ is chosen from hydrogen and methyl.

In some embodiments disclosed herein are compounds of the following Formulae:

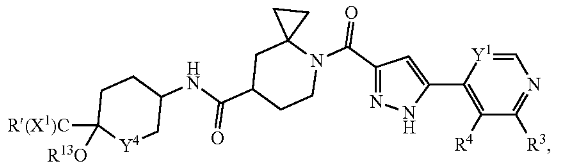
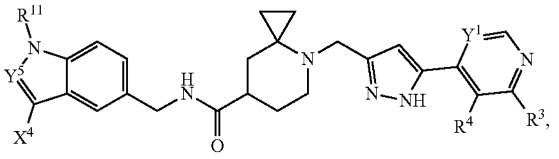
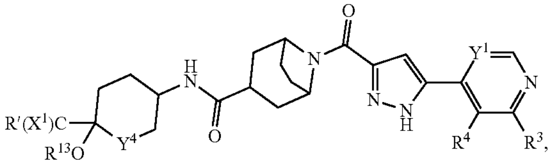
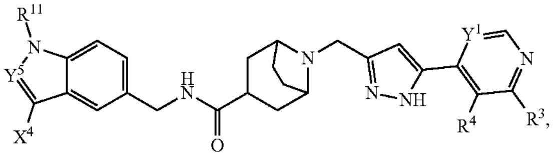
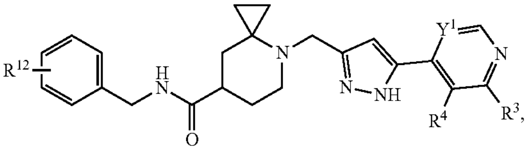
and
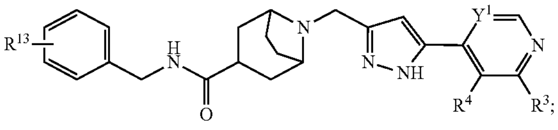

wherein $Y^1$ is chosen from N and C—$X^1$ wherein $X^1$ is chosen from hydrogen, hydroxyl, halogens, and $C_1$-$C_4$ alkyls;

$R^3$ is chosen from hydrogen, optionally substituted $C_1$-$C_3$ alkyls, halogens, cyano, and optionally substituted $C_1$-$C_3$ alkoxys; and $R^4$ is chosen from hydrogen and alkyl;

$Y^4$ is chosen from $CH_2$, O, and N—$R^{11}$;

$X^3$ is chosen from hydrogen and halogens;

R' is chosen from hydrogen and $C_1$-$C_3$ alkyls optionally substituted with at least one halogen;

$R^{11}$ is chosen from hydrogen and $C_1$-$C_3$ alkyls;

$R^{12}$ is chosen from hydrogen, halogens, and $C_1$-$C_3$ alkyls; and $R^{13}$ is chosen from hydrogen, halogens, $C_2$-$C_4$ alkoxys, and $C_1$-$C_3$ alkyls.

In some embodiments disclosed herein are compounds of the following Formulae:

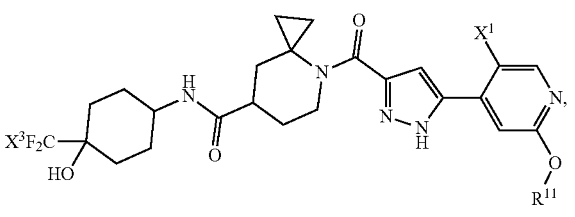

-continued

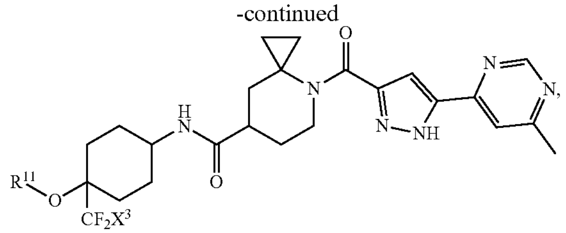

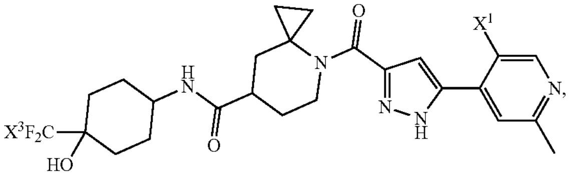

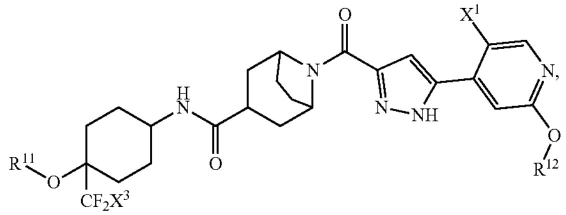

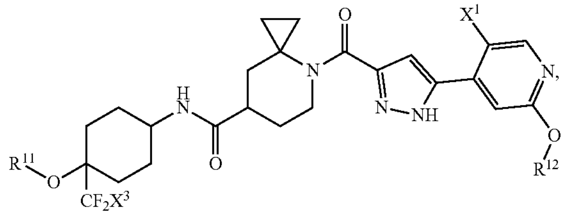

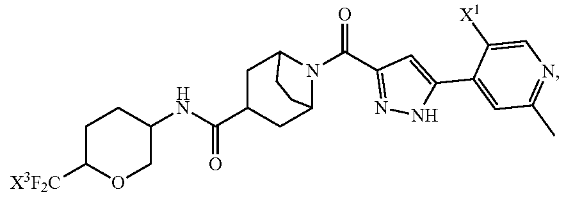

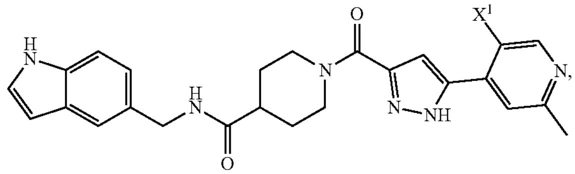

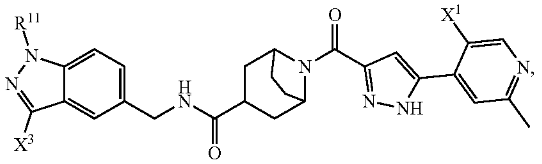

and

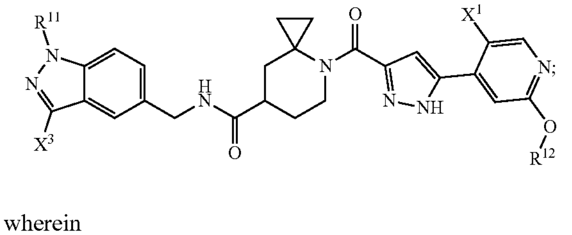

wherein $X^1$ is chosen from hydrogen, hydroxyl, halogens, and $C_1$-$C_4$ alkyls;

$X^3$ is chosen from hydrogen and halogens; and $R^{11}$ and $R^{12}$ are independently chosen from hydrogen and $C_1$-$C_3$ alkyls.

In some embodiments, substituted alkyl is chosen from haloalkyls.

In some embodiments, the haloalkyl is trifluoromethyl.

In some embodiments disclosed herein are compounds of Formula (IIB) and Formula (IIIB):

Formula (IIB)

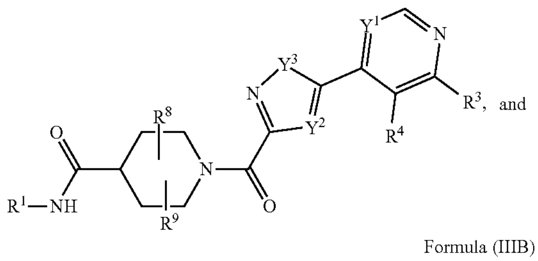

and

Formula (IIIB)

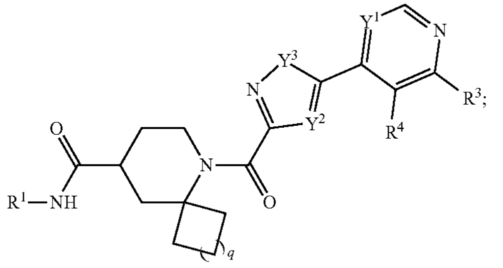

wherein q is 0 or 1; and $R^8$ and $R^9$ are each independently chosen from hydrogen, halogens, hydroxyl, optionally substituted alkoxys, and optionally substituted alkyls.

In some embodiments, provided herein are compounds of Formula (I) and pharmaceutically acceptable salts thereof having an activity of less than 40000 nM, such as less than 20000 nM, less than 10000 nM, less than 1000 nM, less than 100 nM, less than 50 nM, less than 20 nM, less than 10 nM, or less than 5 nM as measured using the TR-FRET assay disclosed herein.

Disclosed herein are pharmaceutical compositions comprising at least one entity chosen from compounds of Formula (I) and pharmaceutically acceptable salts thereof.

In some embodiments, the pharmaceutical composition further comprises at least one pharmaceutically acceptable carrier.

Disclosed herein are methods for treating and/or preventing cancer comprising administering to a subject in need thereof an effective amount of at least one entity chosen from compounds of Formula (I) and pharmaceutically acceptable salts thereof and pharmaceutical compositions comprising at least one entity chosen from compounds of Formula (I) and pharmaceutically acceptable salts thereof. In some embodiments, the cancer is chosen from bladder cancer, breast cancer, prostate cancer, and/or cancers having altered RXRα and/or PPARγ pathways. In some embodiments, the cancer is bladder cancer. In some embodiments, the bladder cancer is advanced bladder cancer, luminal bladder cancer, and/or basal bladder cancer. In some embodiments, the cancer is chemotherapy resistant and/or immunotherapy resistant cancer.

Disclosed herein are uses of at least one entity chosen from compounds of Formula (I) and pharmaceutically acceptable salts thereof and pharmaceutical compositions comprising at least one entity chosen from compounds of Formula (I) and pharmaceutically acceptable salts thereof in treating and/or preventing cancer. In some embodiments, the cancer is chosen from bladder cancers, breast cancers, prostate cancers, and cancers having altered RXRα and/or PPARγ pathways. In some embodiments, the cancer is bladder cancer. In some embodiments, the bladder cancer is chosen from advanced bladder cancers, luminal bladder cancers, and basal bladder cancers. In some embodiments, the cancer is chemotherapy resistant and/or immunotherapy resistant cancer.

The following compounds of Formula (I) are disclosed herein:

1-(5-(5-chloro-2-methoxypyridin-4-yl)-1H-pyrazole-3-carbonyl)-N-((1s,4s)-4-methylcyclohexyl)piperidine-4-carboxamide;

1-(5-(5-chloro-2-methoxypyridin-4-yl)-1H-pyrazole-3-carbonyl)-N-((1r,4r)-4-methylcyclohexyl)piperidine-4-carboxamide;

1-(4-fluoro-5-(2-methoxypyridin-4-yl)-1H-pyrazole-3-carbonyl)-N-(4-methylcyclohexyl)piperidine-4-carboxamide;

(S)-1-(5-(5-chloro-2-methoxypyridin-4-yl)-1H-pyrazole-3-carbonyl)-N-(1-(3-fluorophenyl)ethyl)piperidine-4-carboxamide;

N-((1s,4s)-4-(difluoromethyl)cyclohexyl)-1-(5-(5-fluoro-2-methoxypyridin-4-yl)-1H-pyrazole-3-carbonyl)piperidine-4-carboxamide;

N-((1r,4r)-4-(difluoromethyl)cyclohexyl)-1-(5-(5-fluoro-2-methoxypyridin-4-yl)-1H-pyrazole-3-carbonyl)piperidine-4-carboxamide;

1-(5-(2-methoxypyridin-4-yl)-1H-pyrazole-3-carbonyl)-N-(4-methylcyclohexyl)piperidine-4-carboxamide;

N-(4-methylcyclohexyl)-1-[5-(2-methylpyridin-4-yl)-1H-pyrazole-3-carbonyl]piperidine-4-carboxamide;

1-(5-(2-methoxypyridin-4-yl)-1H-pyrazole-3-carbonyl)-N-((1s,4s)-4-methylcyclohexyl)piperidine-4-carboxamide;

N-((1s,4s)-4-ethylcyclohexyl)-1-(5-(2-methoxypyridin-4-yl)-1H-pyrazole-3-carbonyl)piperidine-4-carboxamide;

N-((1r,4r)-4-ethylcyclohexyl)-1-(5-(2-methoxypyridin-4-yl)-1H-pyrazole-3-carbonyl)piperidine-4-carboxamide;

1-(5-(3-chloropyridin-4-yl)-1H-pyrazole-3-carbonyl)-N-(4-methylcyclohexyl)piperidine-4-carboxamide;

1-[4-chloro-5-(2-methoxypyridin-4-yl)-1H-pyrazole-3-carbonyl]-N-[(1s,4s)-4-methylcyclohexyl]piperidine-4-carboxamide;

1-[4-chloro-5-(2-methoxypyridin-4-yl)-1H-pyrazole-3-carbonyl]-N-[(1r,4r)-4-methylcyclohexyl]piperidine-4-carboxamide;

1-[5-(6-methoxypyrimidin-4-yl)-1H-pyrazole-3-carbonyl]-N-[(1r,4 r)-4-methylcyclohexyl]piperidine-4-carboxamide;

1-[5-(6-methoxypyrimidin-4-yl)-1H-pyrazole-3-carbonyl]-N-[(1s,4s’-4-methylcyclohexyl]piperidine-4-carboxamide;

1-[5-(5-chloro-2-methoxypyridin-4-yl)-1H-pyrazole-3-carbonyl]-N-[(3-chlorophenyl)methyl]piperidine-4-carboxamide;

N-((1s,4s)-4-(difluoromethyl)cyclohexyl)-1-(5-(2-methoxypyridin-4-yl)-1H-pyrazole-3-carbonyl)piperidine-4-carboxamide;

N-((1r,4r)-4-(difluoromethyl)cyclohexyl)-1-(5-(2-methoxypyridin-4-yl)-1H-pyrazole-3-carbonyl)piperidine-4-carboxamide;

1-(5-(5-fluoro-2-methoxypyridin-4-yl)-1H-pyrazole-3-carbonyl)-N-((1s,4s)-4-methylcyclohexyl)piperidine-4-carboxamide;

1-(5-(5-fluoro-2-methoxypyridin-4-yl)-1H-pyrazole-3-carbonyl)-N-((1r,4r)-4-methylcyclohexyl)piperidine-4-carboxamide;

(R)-1-[5-(5-chloro-2-methoxypyridin-4-yl)-1H-pyrazole-3-carbonyl]-N-[1-(3-chlorophenyl)ethyl]piperidine-4-carboxamide;

(S)-1-[5-(5-chloro-2-methoxypyridin-4-yl)-1H-pyrazole-3-carbonyl]-N-[1-(3-chlorophenyl)ethyl]piperidine-4-carboxamide;

1-[5-(5-chloro-2-methoxypyridin-4-yl)-1H-pyrazole-3-carbonyl]-N-(1-phenylpyrrolidin-3-yl)piperidine-4-carboxamide;

1-[5-(5-chloro-2-methoxypyridin-4-yl)-1H-pyrazole-3-carbonyl]-N-[(1s,4s)-4-(trifluoromethyl)cyclohexyl]piperidine-4-carboxamide;

1-[5-(5-chloro-2-methoxypyridin-4-yl)-1H-pyrazole-3-carbonyl]-N-[(1r,4r)-4-(trifluoromethyl)cyclohexyl]piperidine-4-carboxamide;

1-(5-(5-chloro-2-methoxypyridin-4-yl)-1H-pyrazole-3-carbonyl)-N-(imidazo[1,2-a]pyridin-2-yl)methyl)piperidine-4-carboxamide;

1-(5-(5-chloro-2-methoxypyridin-4-yl)-1H-pyrazole-3-carbonyl)-N-((5-chloropyridin-2-yl)methyl)piperidine-4-carboxamide;

1-[5-(5-chloro-2-methoxypyridin-4-yl)-1H-pyrazole-3-carbonyl]-N-(2-methyl-1,3-dioxan-5-yl) piperidine-4-carboxamide;

N-((1H-indol-5-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(2,3,6-trifluorobenzyl)piperidine-4-carboxamide;

1-(5-(5-chloro-2-methoxypyridin-4-yl)-1H-pyrazole-3-carbonyl)-N-((1,3-dimethyl-1H-pyrazol-4-yl)methyl)piperidine-4-carboxamide;

1-(5-(5-chloro-2-methoxypyridin-4-yl)-1H-pyrazole-3-carbonyl)-N-(2-chloro-5-fluorobenzyl)piperidine-4-carboxamide;

1-(5-(5-chloro-2-methoxypyridin-4-yl)-1H-pyrazole-3-carbonyl)-N-(1-(2,2,2-trifluoroethyl)-1H-pyrazol-4-yl)piperidine-4-carboxamide;

1-(5-(5-chloro-2-methoxypyridin-4-yl)-1H-pyrazole-3-carbonyl)-N-((5-fluoropyridin-2-yl)methyl)piperidine-4-carboxamide;

1-(5-(5-chloro-2-methoxypyridin-4-yl)-1H-pyrazole-3-carbonyl)-N-(1-cyanocyclobutyl)piperidine-4-carboxamide;

1-(5-(5-chloro-2-methoxypyridin-4-yl)-1H-pyrazole-3-carbonyl)-N-((6-(trifluoromethyl)pyridin-2-yl)methyl)piperidine-4-carboxamide;

1-(5-(5-chloro-2-methoxypyridin-4-yl)-1H-pyrazole-3-carbonyl)-N-yl)-(trifluoromethyl)pyridin-2-yl)methyl)piperidine-4-carboxamide;

1-(5-(5-chloro-2-methoxypyridin-4-yl)-1H-pyrazole-3-carbonyl)-N-((4-methylpyridin-3-yl)methyl)piperidine-4-carboxamide;

1-(5-(5-chloro-2-methoxypyridin-4-yl)-1H-pyrazole-3-carbonyl)-N-(isochroman-4-yl)piperidine-4-carboxamide;

1-(5-(5-chloro-2-ethoxypyridin-4-yl)-1H-pyrazole-3-carbonyl)-N-((1R,2S)-2-phenylcyclopropyl)piperidine-4-carboxamide;

1-(5-(5-chloro-2-methoxypyridin-4-yl)-1H-pyrazole-3-carbonyl)-N-((1-hydroxycyclohexyl)methyl)piperidine-4-carboxamide;

1-(5-(5-chloro-2-methoxypyridin-4-yl)-1H-pyrazole-3-carbonyl)-N-((4,4-dimethyloxetan-2-yl)methyl)piperidine-4-carboxamide;

1-(5-(5-chloro-2-methoxypyridin-4-yl)-1H-pyrazole-3-carbonyl)-N-((2-methyloxazol-5-yl)methyl)piperidine-4-carboxamide;
1-(5-(5-chloro-2-methoxypyridin-4-yl)-1H-pyrazole-3-carbonyl)-N-(pyrazolo[1,5-a]pyridin-7-ylmethyl)piperidine-4-carboxamide;
1-(5-(5-chloro-2-methoxypyridin-, 1-yl)-1H-pyrazole-3-carbonyl)-N-((5-chloropyrimidin-2-yl)methyl)piperidine-4-carboxamide;
1-(5-(5-chloro-2-methoxypyridin-4-yl)-1H-pyrazole-3-carbonyl)-N-((5-(trifluoromethyl)pyridin-2-yl)methyl)piperidine-4-carboxamide;
1-(5-(5-chloro-2-methoxypyridin-4-yl)-1H-pyrazole-3-carbonyl)-N-((3-chloropyridin-2-yl)methyl)piperidine-4-carboxamide;
1-(5-(5-chloro-2-methoxypyridin-4-yl)-1H-pyrazole-3-carbonyl)-N-((1,5-dimethyl-1H-pyrazol-3-yl)methyl)piperidine-4-carboxamide;
1-(5-(5-chloro-2-methoxypyridin-4-yl)-1H-pyrazole-3-carbonyl)-N-(1-(4-chlorophenoxy)propan-2-yl)piperidine-4-carboxamide;
1-(5-(5-chloro-2-methoxypyridin-4-yl)-1H-pyrazole-3-carbonyl)-N-(3,3-difluorocyclohexyl)piperidine-4-carboxamide;
1-(5-(5-chloro-2-methoxypyridin-4-yl)-1H-pyrazole-3-carbonyl)-N-(4-hydroxy-4-(trifluoromethyl)cyclohexyl)piperidine-4-carboxamide;
1-(5-(5-chloro-2-methoxypyridin-4-yl)-1H-pyrazole-3-carbonyl)-N-((3-methoxycyclobutyl)methyl)piperidine-4-carboxamide;
1-(5-(5-chloro-2-methoxypyridin-4-yl)-1H-pyrazole-3-carbonyl)-N-((3-fluoropyridin-2-yl)methyl)piperidine-4-carboxamide;
1-(5-(5-chloro-2-methoxypyridin-4-yl)-1H-pyrazole-3-carbonyl)-N-(3-(difluoromethyl)phenyl)piperidine-4-carboxamide;
1-(5-(5-chloro-2-methoxypyridin-4-yl)-1H-pyrazole-3-carbonyl)-N-((3,3-difluorocyclobutyl)methyl)piperidine-4-carboxamide;
1-(5-(5-chloro-2-methoxypyridin-4-yl)-1H-pyrazole-3-carbonyl)-N-(2,2-difluoro-2-phenylethyl)piperidine-4-carboxamide;
1-(5-(5-chloro-2-methoxypyridin-4-yl)-1H-pyrazole-3-carbonyl)-N-(3,3,5-trimethylcyclohexyl)piperidine-4-carboxamide;
1-(5-(5-chloro-2-methoxypyridin-4-yl)-1H-pyrazole-3-carbonyl)-N-(4-(difluoromethoxy)benzyl)piperidine-4-carboxamide;
N-(benzo[d]oxazol-6-ylmethyl)-1-(5-(5-chloro-2-methoxypyridin-4-yl)-1H-pyrazole-3-carbonyl)piperidine-4-carboxamide;
(R)-1-(5-(5-chloro-2-methoxypyridin-4-yl)-1H-pyrazole-3-carbonyl)-N-(1-(3-fluorophenyl)ethyl)piperidine-4-carboxamide;
N-(5-chloro-2-fluorobenzyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(2,3-difluorobenzyl)piperidine-4-carboxamide;
N-(3-chloro-2-fluorobenzyl)-1-(5-(5-chloro-2-methoxypyridin-4-yl-1H-pyrazole-3-carbonyl)piperidine-4-carboxamide;
1-(5-(5-chloro-2-methoxypyridin-4-yl)-1H-pyrazole-3-carbonyl)-N-(3-fluorobenzyl)piperidine-4-carboxamide;
1-(5-(5-chloro-2-methoxypyridin-4-yl)-1H-pyrazole-3-carbonyl)-N-((3,4-dihydro-2H-pyran-2-yl)methyl)piperidine-4-carboxamide;
N-(3-chlorobenzyl)-1-(5-(5-fluoro-2-methoxypyridin-4-yl)-1H-pyrazole-3-carbonyl)piperidine-4-carboxamide;
(1R,3s,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide;
(1R,3r,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide;
N-(3-chlorobenzyl)-1-(5-(5-fluoro-2-methoxypyridin-, 1-yl)-1H-pyrazole-3-carbonyl)-N-methylpiperidine-4-carboxamide;
1-(5-(5-chloro-2-methoxypyridin-4-yl)-1H-pyrazole-3-carbonyl)-N-(1-(trifluoromethyl)cyclopentyl)piperidine-4-carboxamide;
1-(5-(5-chloro-2-methoxypyridin-4-yl)-1H-pyrazole-3-carbonyl)-N-(1,4-dimethylcyclohexyl)piperidine-4-carboxamide;
1-(5-(5-chloro-2-methoxypyridin-4-yl)-1H-pyrazole-3-carbonyl)-N-(4-(trifluoromethoxy)benzyl)piperidine-4-carboxamide;
N-(bicyclo[3.2.1]octan-8-yl)-1-(5-(5-fluoro-2-methoxypyridin-4-yl)-1H-pyrazole-3-carbonyl)piperidine-4-carboxamide;
N-[(3-chlorophenyl)methyl]-1-[5-(5-fluoro-2-methoxypyridin-4-yl)-1H-1,2,4-triazole-3-carbonyl]piperidine-4-carboxamide;
1-(5-(5-chloro-2-methoxypyridin-4-yl)-1H-pyrazole-3-carbonyl)-N-((2-oxoindolin-5-yl)methyl)piperidine-, 1-carboxamide;
N-((1H-pyrrolo[2,3-b]pyridin-5-yl)methyl)-1-(5-(5-chloro-2-methoxypyridin-4-yl)-1H-pyrazole-3-carbonyl)piperidine-4-carboxamide;
(R)-4-(5-(5-fluoro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;
(S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;
(1R,3s,5S)-8-(5-(5-fluoro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;
(1R,3s,5S)-8-(5-(5-fluoro-2-methoxypyridin-4-yl)-1H-pyrazole-3-carbonyl)-N-((1s,4S)-4-hydroxy-4-(trifluoroethyl)cyclohexyl)-8-azabicyclo[3.2.1]octane-3-carboxamide;
1-(5-(5-chloro-2-methoxypyridin-4-yl)-1H-pyrazole-3-carbonyl)-N-(3-chlorobenzyl) hydroxypiperidine-4-carboxamide;
1-(5-(5-chloro-2-methoxypyridin-, 1-yl)-1H-pyrazole-3-carbonyl)-N-(3-chlorobenzyl)-2-methylpiperidine-4-carboxamide;
1-(5-(5-chloro-2-methoxypyridin-4-yl)-1H-pyrazole-3-carbonyl)-N-(3-chlorobenzyl)-3-methylpiperidine-4-carboxamide;
1-(5-(5-chloro-2-methoxypyridin-4-yl)-1H-pyrazole-3-carbonyl)-N-(3-chlorobenzyl) fluoropiperidine-4-carboxamide;
1-(5-(5-chloro-2-methoxypyridin-4-yl)-1H-pyrazole-3-carbonyl)-N-(3,3-difluorocyclopentyl)piperidine-4-carboxamide;
1-(5-(5-chloro-2-methoxypyridin-4-yl)-1H-pyrazole-3-carbonyl)-N-((5-methylpyridin-2-yl)methyl)piperidine-4-carboxamide;
1-(5-(5-chloro-2-methoxypyridin-4-yl)-1H-pyrazole-3-carbonyl)-N-(3-chlorobenzyl)-3-fluoropiperidine-4-carboxamide;

1-(5-(5-chloro-2-methoxypyridin-4-yl)-1H-pyrazole-3-carbonyl)-N-((6-(trifluoro-|5-methyl)pyridin-3-yl)methyl)piperidine-4-carboxamide;

1-(5-(5-chloro-2-methoxypyridin-4-yl)-1H-pyrazole-3-carbonyl)-N-((5-chloropyridin-3-yl)methyl)piperidine-4-carboxamide;

N-((1H-indazol-6-yl)methyl)-1-(5-(5-chloro-2-methoxypyridin-4-yl)-1H-pyrazole-3-carbonyl)piperidine-4-carboxamide;

N-((1H-indol-3-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(isoquinolin-6-ylmethyl)piperidine-4-carboxamide;

1-(5-(5-chloro-2-methoxypyridin-4-yl)-1H-pyrazole-3-carbonyl)-N-(5-oxo-1-phenylpyrrolidin-3-yl)piperidine-4-carboxamide;

1-(5-(5-chloro-2-methoxypyridin-4-yl)-1H-pyrazole-3-carbonyl)-N-(chroman-4-yl)piperidine-4-carboxamide;

1-(5-(5-chloro-2-methoxypyridin-4-yl)-1H-pyrazole-3-carbonyl)-N-((2,2-dimethyl-1,3-dioxolan-4-yl)methyl)piperidine-4-carboxamide;

1-(5-(5-chloro-2-methoxypyridin-4-yl)-1H-pyrazole-3-carbonyl)-N-(1-methyl-1,2,3,4-tetrahydroquinolin-4-yl)piperidine-4-carboxamide;

1-(5-(5-chloro-2-methoxypyridin-4-yl)-1H-pyrazole-3-carbonyl)-N-((1-methyl-1H-indol-3-yl)methyl)piperidine-4-carboxamide;

N-((1H-indol-6-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((5-methylfuran-2-yl)methyl)piperidine-4-carboxamide;

N-((1H-indol-4-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(5,6,7,8-tetrahydroisoquinolin-5-yl)piperidine-4-carboxamide;

N-((1H-indazol-4-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((3-chloro-5-(trifluoromethyl)pyridin-2-yl)methyl)piperidine-4-carboxamide;

N-((1H-indol-7-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(6-fluorochroman-4-yl)piperidine-4-carboxamide;

1-(5-(5-chloro-2-methoxypyridin-4-yl)-1H-pyrazole-3-carbonyl)-N-(1-phenylpiperidin-4-yl)piperidine-4-carboxamide;

N-((2H-benzo[d][1,2,3]triazol-5-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((1r,4r)-4-hydroxy-4-methylcyclohexyl)piperidine-4-carboxamide;

1-(5-(5-chloro-2-methoxypyridin-4-yl)-1H-pyrazole-3-carbonyl)-N-((1r,4r)-4-hydroxy-4-(trifluoromethyl)cyclohexyl)piperidine-4-carboxamide;

N-((3-fluoro-1H-indazol-5-yl)methyl)-1-(5-(5-fluoro-2-methoxypyridin-4-yl)-1H-pyrazole-3-carbonyl)piperidine-4-carboxamide;

N-((1H-indazol-3-yl)methyl)-1-(5-(5-chloro-2-methoxypyridin-4-yl)-1H-pyrazole-3-carbonyl)piperidine-4-carboxamide;

N-((1H-pyrrolo[2,3-b]pyridin-3-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((2-methyl-1H-indol-5-yl)methyl)piperidine-4-carboxamide;

1-[5-(5-fluoro-2-methoxypyridin-4-yl)-1H-pyrazole-3-carbonyl]-N-[(3-methyl-1H-indazol-5-yl)methyl]piperidine-4-carboxamide;

1-(5-(5-chloro-2-methoxypyridin-4-yl)-1H-pyrazole-3-carbonyl)-N-(1-isopropyl-1H-pyrazole-4-yl)piperidine-4-carboxamide;

1-(5-(5-chloro-2-methoxypyridin-4-yl)-1H-pyrazole-3-carbonyl)-N-((1-methyl-1H-indol-5-yl)methyl)piperidine-4-carboxamide;

1-(5-(5-chloro-2-methoxypyridin-4-yl)-1H-pyrazole-3-carbonyl)-N-(2-oxo-1-phenylpyrrolidin-3-yl)piperidine-4-carboxamide;

N-(5-chloro-2,3-dihydrobenzofuran-3-yl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((4-(trifluoromethyl)pyrimidin-2-yl)methyl)piperidine-4-carboxamide;

1-(5-(5-chloro-2-methoxypyridin-4-yl)-1H-pyrazole-3-carbonyl)-N-((5-methylimidazo[1,2-a]pyridin-2-yl)methyl)piperidine-4-carboxamide;

1-(5-(5-chloro-2-methoxypyridin-4-yl)-1H-pyrazole-3-carbonyl)-N-((5-(trifluoromethyl)pyrimidin-2-yl)methyl)piperidine-4-carboxamide;

N-((1H-pyrrolo[2,3-c]pyridin-5-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(5,5-dimethyltetrahydrofuran-3-yl)piperidine-4-carboxamide;

1-(5-(5-chloro-2-methoxypyridin-4-yl)-1H-pyrazole-3-carbonyl)-N-((8-fluoroimidazo[1,2-a]pyridin-2-yl)methyl)piperidine-4-carboxamide;

1-(5-(5-chloro-2-methoxypyridin-4-yl)-1H-pyrazole-3-carbonyl)-N-((2-methyl-1H-benzo[d]imidazol-5-yl)methyl)piperidine-4-carboxamide;

1-(5-(5-chloro-2-methoxypyridin-4-yl)-1H-pyrazole-3-carbonyl)-N-((2-methyl-1,3-dioxan-9-yl)methyl)piperidine-4-carboxamide;

1-(5-(5-chloro-2-methoxypyridin-4-yl)-1H-pyrazole-3-carbonyl)-N-((6-methylimidazo[1,2-a]pyridin-2-yl)methyl)piperidine-4-carboxamide;

1-(5-(5-chloro-2-methoxypyridin-4-yl)-1H-pyrazole-3-carbonyl)-N-((1-methyl-1H-indazol-3-yl)methyl)piperidine-4-carboxamide;

1-(5-(5-chloro-2-methoxypyridin-4-yl)-1H-pyrazole-3-carbonyl)-N-((6-chloroimidazo[1,2a]pyridin-2-yl)methyl)piperidine-4-carboxamide;

1-(5-(5-chloro-2-methoxypyridin-4-yl)-1H-pyrazole-3-carbonyl)-N-((4,4-difluorotetrahydrofuran-2-yl)methyl)piperidine-4-carboxamide;

1-(5-(5-chloro-2-methoxypyridin-4-yl)-1H-pyrazole-3-carbonyl)-N-((5-(trifluoromethyl)oxazol-4-yl)methyl)piperidine-4-carboxamide;

1-(5-(5-chloro-2-methoxypyridin-4-yl)-1H-pyrazole-3-carbonyl)-N-(1-(2-fluorophenyl)pyrrolidin-3-yl)piperidine-4-carboxamide;

1-(5-(5-chloro-2-methoxypyridin-4-yl)-1H-pyrazole-3-carbonyl)-N-((1-methyl-1H-benzo[d]imidazol-5-yl)methyl)piperidine-4-carboxamide;

1-(5-(5-chloro-2-methoxypyridin-4-yl)-1H-pyrazole-3-carbonyl)-N-(2-methyl-5,6, tetrahydroquinazolin-5-yl)piperidine-4-carboxamide;

1-(5-(5-chloro-2-methoxypyridin-4-yl)-1H-pyrazole-3-carbonyl)-N-((5-(difluoromethyl)isoxazol-3-yl)methyl)piperidine-4-carboxamide;

N-((1H-pyrrolo[2,3-b]pyridin-6-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(2-methyl-1,2,3,4-tetrahydroisoquinolin-4-yl)piperidine-4-carboxamide;

1-(5-(5-chloro-2-methoxypyridin-4-yl)-1H-pyrazole-3-carbonyl)-N-((3-methyl-2-oxo-2,3-dihydrobenzo[d]oxazol-5-yl)methyl)piperidine-4-carboxamide;

1-(5-(5-chloro-2-methoxypyridin-4-yl)-1H-pyrazole-3-carbonyl)-N-((1-methyl-1H-indazol-6-yl)methyl)piperidine-4-carboxamide;

N-((2-oxabicyclo[3.1.1]heptan-1-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(1-methyl-2,2-dioxido-3,4-dihydro-1H-benzo[c][1,2]thiazin-4-yl)piperidine-4-carboxamide;

1-(5-(5-chloro-2-methoxypyridin-4-yl)-1H-pyrazole-3-carbonyl)-N-((1-methyl-1H-pyrazolo[3,4-b]pyridin-5-yl)methyl)piperidine-4-carboxamide;

(S)-1-(5-(5-chloro-2-methoxypyridin-4-yl)-1H-pyrazole-3-carbonyl)-N-(6-cyanochroman-4-yl)piperidine-4-carboxamide;

1-(5-(5-chloro-2-methoxypyridin-4-yl)-1H-pyrazole-3-carbonyl)-N-(1-methyl-2-oxo-1,2,5,6,7,8-hexahydroquinolin-5-yl)piperidine-4-carboxamide;

1-(5-(5-chloro-2-methoxypyridin-4-yl)-1H-pyrazole-3-carbonyl)-N-((1-methyl-2-oxoindolin-5-yl)methyl)piperidine-4-carboxamide;

1-(5-(5-chloro-2-methoxypyridin-4-yl)-1H-pyrazole-3-carbonyl)-N-(3,4-dihydro-2H-pyrano[2,3-b]pyridin-4-yl)piperidine-4-carboxamide;

1-(5-(5-chloro-2-methoxypyridin-4-yl)-1H-pyrazole-3-carbonyl)-N-((1,1-dioxido-2,3-dihydrobenzo[b]thiophen-5-yl)methyl)piperidine-4-carboxamide;

1-(5-(5-chloro-2-methoxypyridin-4-yl)-1H-pyrazole-3-carbonyl)-N-((4-(difluoromethyl)pyrimidin-2-yl)methyl)piperidine-4-carboxamide;

1-(5-(5-chloro-2-methoxypyridin-4-yl)-1H-pyrazole-3-carbonyl)-N-((6-(difluoromethyl)pyridin-2-yl)methyl)piperidine-4-carboxamide;

1-(5-(5-chloro-2-methoxypyridin-4-yl)-1H-pyrazole-3-carbonyl)-N-(2-methyl-3-oxo-1,2,3,4-tetrahydroisoquinolin-4-yl)piperidine-4-carboxamide;

1-(5-(5-chloro-2-methoxypyridin-4-yl)-1H-pyrazole-3-carbonyl)-N-((6,7-dihydro-5H-cyclopenta[d]pyrimidin-2-yl)methyl)piperidine-4-carboxamide;

1-(5-(5-chloro-2-methoxypyridin-4-yl)-1H-pyrazole-3-carbonyl)-N-((3,3-dimethyl-2-oxoindolin-5-yl)methyl)piperidine-4-carboxamide;

1-(5-(5-chloro-2-methoxypyridin-4-yl)-1H-pyrazole-3-carbonyl)-N-((5-fluoro-1H-benzo[d]imidazol-4-yl)methyl)piperidine-4-carboxamide;

1-(5-(5-chloro-2-methoxypyridin-4-yl)-1H-pyrazole-3-carbonyl)-N-(3-oxo-1,2,3,4-tetrahydroisoquinolin-4-yl)piperidine-4-carboxamide;

(S)-4-(5-(5-chloro-2-methoxypyridin-4-yl)-1H-pyrazole-3-carbonyl)-N-(3-chlorobenzyl)-4-azaspiro[2.5]octane-7-carboxamide;

(R)-4-(5-(5-chloro-2-methoxypyridin-4-yl)-1H-pyrazole-3-carbonyl)-N-(3-chlorobenzyl)-4-azaspiro[2.5]octane-7-carboxamide;

1-(5-(5-chloro-2-methoxypyridin-4-yl)-1H-pyrazole-3-carbonyl)-N-(3-fluoro-3-methylcyclobutyl)piperidine-4-carboxamide;

1-(5-(5-chloro-2-methoxypyridin-4-yl)-1H-pyrazole-3-carbonyl)-N-(5-methyltetrahydrofuran-3-yl)piperidine-4-carboxamide;

1-(5-(5-chloro-2-methoxypyridin-4-yl)-1H-pyrazole-3-carbonyl)-N-((3R,6R)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3S,6R)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3S,6S)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3R,6S)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3S,6S)-6-(trifluoromethyl)tetrahydro-2H-pyran-3-yl)piperidine-4-carboxamide;

1-(5-(5-chloro-2-methoxypyridin-4-yl)-1H-pyrazole-3-carbonyl)-N-((3R,6R)-6-(trifluoromethyl)tetrahydro-2H-pyran-3-yl)piperidine-4-carboxamide;

1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide;

1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide;

N-((1H-indol-2-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(6-methylpyridin-2-yl)piperidine-4-carboxamide;

1-(5-(5-chloro-2-methoxypyridin-4-yl)-1H-pyrazole-3-carbonyl)-N-(3-methoxychroman-4-yl)piperidine-4-carboxamide;

1-(5-(5-chloro-2-methoxypyridin-4-yl)-1H-pyrazole-3-carbonyl)-N-(1-(4-fluorophenyl)pyrrolidin-3-yl)piperidine-4-carboxamide;

N-((1H-pyrrolo[3,2-c]pyridin-4-yl)methyl)-1-(5-(5-chloro-2-methoxypyridin-4-yl)-1H-pyrazole-3-carbonyl)piperidine-4-carboxamide;

(S)-1-(5-(5-chloro-2-methoxypyridin-4-yl)-1H-pyrazole-3-carbonyl)-N-(3-chlorobenzyl)-2,2-dimethylpiperidine-4-carboxamide;

(R)-1-(5-(5-chloro-2-methoxypyridin-4-yl)-1H-pyrazole-3-carbonyl)-N-(3-chlorobenzyl)-2,2-dimethylpiperidine-4-carboxamide;

(S)-5-(5-(5-chloro-2-methoxypyridin-4-yl)-1H-pyrazole-3-carbonyl)-N-(3-chlorobenzyl)-5-azaspiro[3.5]nonane-8-carboxamide;

(R)-5-(5-(5-chloro-2-methoxypyridin-4-yl)-1H-pyrazole-3-carbonyl)-N-(3-chlorobenzyl)-5-azaspiro[3.5]nonane-8-carboxamide;

(1R,3s,5S)-8-(5-(5-chloro-2-methoxypyridin-4-yl)-1H-pyrazole-3-carbonyl)-N-((1 OR)-4-methoxy-4-(trifluoromethyl)cyclohexyl)-8-azabicyclo[3.2.1]octane-3-carboxamide;

(1R,3s,5S)-8-(5-(5-chloro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

(1R,3S,5S)—N-[(3-fluoro-1H-indazol-5-yl)methyl]-8-[5-(5-fluoro-2-methoxypyridin-4-yl)-1H-pyrazole-3-carbonyl]-8-azabicyclo[3.2.1]octane-3-carboxamide;

(1R,3s,5S)-8-(5-(5-chloro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)-8-(5-(5-chloro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide;

1-(5-(5-chloro-2-methoxypyridin-4-yl)-1H-pyrazole-3-carbonyl)-N-(5,6-dimethylpyrazin-2-yl)piperidine-4-carboxamide;

1-(5-(5-chloro-2-methoxypyridin-4-yl)-1H-pyrazole-3-carbonyl)-N-(1H-indol-4-yl)piperidine-4-carboxamide;

1-[5-(5-chloro-2-methylpyridin-4-yl)-1H-pyrazole-3-carbonyl]-N-[(3-chlorophenyl)methyl]piperidine-4-carboxamide;

1-[5-(5-fluoro-2-methylpyridin-4-yl)-1H-pyrazole-3-carbonyl]-N-[(1r,4r)-4-hydroxy-4-(trifluoromethyl)cyclohexyl]piperidine-4-carboxamide;

1-[5-(5-fluoro-2-methylpyridin-4-yl)-1H-pyrazole-3-carbonyl]-N-[(1s,4s)-4-hydroxy-4-(trifluoromethyl)cyclohexyl]piperidine-4-carboxamide;

1-(5-(5-chloro-2-methoxypyridin-4-yl)-1H-pyrazole-3-carbonyl)-N-((1r,4r)-4-hydroxy-4-methylcyclohexyl)piperidine-4-carboxamide;

1-(5-(5-chloro-2-methoxypyridin-4-yl)-1H-pyrazole-3-carbonyl)-N-((1s,4s)-4-hydroxy-4-methylcyclohexyl)piperidine-4-carboxamide;

1-(5-(5-chloro-2-methoxypyridin-4-yl)-1H-pyrazole-3-carbonyl)-N-(2-methyl-2,3-dihydrobenzofuran-3-yl)piperidine-4-carboxamide;

(2S,5R)-1-(5-(5-chloro-2-methoxypyridin-4-yl)-1H-pyrazole-3-carbonyl)-N-(3-chlorobenzyl)-2,5-dimethylpiperidine-4-carboxamide;

(2R,5S)-1-(5-(5-chloro-2-methoxypyridin-4-yl)-1H-pyrazole-3-carbonyl)-N-(3-chlorobenzyl)-2,5-dimethylpiperidine-4-carboxamide;

(2R,5R)-1-(5-(5-chloro-2-methoxypyridin-4-yl)-1H-pyrazole-3-carbonyl)-N-(3-chlorobenzyl)-2,5-dimethylpiperidine-4-carboxamide;

(2S,5S)-1-(5-(5-chloro-2-methoxypyridin-4-yl)-1H-pyrazole-3-carbonyl)-N-(3-chlorobenzyl)-2,5-dimethylpiperidine-4-carboxamide;

N-[(3-chlorophenyl)methyl]-1-[5-(5-fluoro-2-methylpyridin-4-yl)-1H-pyrazole-3-carbonyl]piperidine-4-carboxamide;

(1R,3S,5S)—N-[(3-chlorophenyl)methyl]-8-[5-(5-fluoro-2-methylpyridin-4-yl)-1H-pyrazole-3-carbonyl]-8-azabicyclo[3.2.1]octane-3-carboxamide;

N-[(3-fluoro-1H-indazol-5-yl)methyl]-1-[5-(5-fluoro-2-methylpyridin-4-yl)-1H-pyrazole-3-carbonyl]piperidine-4-carboxamide;

1-[5-(5-chloro-2-ethylpyridin-4-yl)-1H-pyrazole-3-carbonyl]-N-[(3-chlorophenyl)methyl]piperidine-4-carboxamide;

1-[5-(5-fluoro-2-methylpyridin-4-yl)-1H-pyrazole-3-carbonyl]-N-(1H-indol-5-ylmethyl)piperidine-4-carboxamide;

N-[(2,3-dimethyl-1H-indol-5-yl)methyl]-1-[5-(5-fluoro-2-methoxypyridin-4-yl)-1H-pyrazole-3-carbonyl]piperidine-4-carboxamide;

(2R,4R)-1-(5-(5-chloro-2-methoxypyridin-4-yl)-1H-pyrazole-3-carbonyl)-N-(3-chlorobenzyl)-2-methylpiperidine-4-carboxamide;

1-(5-(5-chloro-2-methoxypyridin-4-yl)-1H-pyrazole-3-carbonyl)-N-(3-chlorobenzyl)-2,6-dimethylpiperidine-4-carboxamide;

(1R,3s,5S)-8-(5-(5-fluoro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

1-(5-(5-fluoro-2-methoxypyridin-4-yl)-1H-pyrazole-3-carbonyl)-N-(1-oxaspiro[3,5]nonan-7-yl)piperidine-4-carboxamide;

(1R,3s,5S)—N-((3-fluoro-1-methyl-1H-indazol-5-yl)methyl)-8-(5-(5-fluoro-2-methoxypyridin-4-yl)-1H-pyrazole-3-carbonyl)-8-azabicyclo[3.2.1]octane-3-carboxamide;

N-((3,3-dimethylindolin-5-yl)methyl)-1-(5-(5-fluoro-2-methoxypyridin-4-yl)-1H-pyrazole-3-carbonyl)piperidine-4-carboxamide;

(1R,3s,5S)—N-((1r,4R)-4-hydroxy-4-(trifluoromethyl)cyclohexyl)-8-(5-(6-methylpyrimidin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide;

1-(5-(5-fluoro-2-methoxypyridin-4-yl)-1H-pyrazole-3-carbonyl)-N-(1-(3-methyl-1H-indazol-5-yl)ethyl)piperidine-4-carboxamide;

9-(5-(5-fluoro-2-methoxypyridin-4-yl)-1H-pyrazole-3-carbonyl)-N-((1r,4r)-4-hydroxy-4-(trifluoromethyl)cyclohexyl)-3-oxa-9-azabicyclo[3.3.1]nonane-7-carboxamide;

(1R,3R,5S)-8-[5-(5-fluoro-2-methylpyridin-4-yl)-1H-pyrazole-3-carbonyl]-N-[(1r,4R)-4-hydroxy-4-(trifluoromethyl)cyclohexyl]-8-azabicyclo[3.2.1]octane-3-carboxamide;

(1R,3s,5S)—N-((3-fluoro-1H-indazol-5-yl)methyl)-8-(5-(5-fluoro-2-methylpyridin-4-yl)-1H-pyrazole-3-carbonyl)-8-azabicyclo[3.2.1]octane-3-carboxamide;

(1R,3R,5S)—N-[(2,3-dimethyl-1H-indol-5-yl)methyl]-8-[5-(5-fluoro-2-methoxypyridin-4-yl)-1H-pyrazole-3-carbonyl]-8-azabicyclo[3.2.1]octane-3-carboxamide;

(R)-4-(5-(5-chloro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-chloro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(R)-4-(5-(5-fluoro-2-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide;

(R)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide;

(1R,3s,5S)-8-(5-(5-fluoro-2-methylpyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((R)-1-(3-(trifluoromethyl)-1,2,4-oxadiazol-5-yl)ethyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((S)-1-(3-(trifluoromethyl)-1,2,4-oxadiazol-5-yl)ethyl)-8-azabicyclo[3.2.1]octane-3-carboxamide;

(1R,3s,5S)—N-(1,1-dimethylsilinan-4-yl)-8-(5-(5-fluoro-2-methoxypyridin-4-yl)-1H-pyrazole-3-carbonyl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

(R)-4-(5-(5-fluoro-2-methylpyridin-4-yl)-1H-pyrazole-3-carbonyl)-N-((1r,4R)-4-methoxy-4-(trifluoromethyl)cyclohexyl)-4-azaspiro[2,5]octane-7-carboxamide;

(R)-4-(5-(5-fluoro-2-methylpyridin-4-yl)-1H-pyrazole-3-carbonyl)-N-((1s,4S)-4-methoxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1r,4S)-4-methoxy-4-(trifluoromethyl)cyclohexyl)-4-azaspiro[2,5]octane-7-carboxamide;

(S)-4-(5-(5-fluoro-2-methylpyridin-4-yl)-1H-pyrazole-3-carbonyl)-N-((1s,4R)-4-methoxy-4-(trifluoromethyl)cyclohexyl)-4-azaspiro[2.5]octane-7-carboxamide;

(1R,3R,5S)-8-[5-(5-fluoro-2-methoxypyridin-4-yl)-1H-pyrazole-3-carbonyl]-N-[(1r,4r)-4-methoxy-4-(trifluoromethyl)cyclohexyl]-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1s,4s)-4-methoxy-4-(trifluoromethyl)cyclohexyl]-8-azabicyclo[3.2.1]octane-3-carboxamide;

(1R,3s,5S)-8-(5-(5-fluoro-2-methoxypyridin-4-yl)-1H-pyrazole-3-carbonyl)-N-((5R,8r)-2-oxo-1-azaspiro[4.5]decan-8-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((5S,8s)-2-oxo-1-azaspiro[4.5]decan-8-yl)-8-azabicyclo[3.2.1]octane-3-carboxamide;

4-[5-(5-fluoro-2-methoxypyridin-4-yl)-1H-pyrazole-3-carbonyl]-N—[(R)-1-(2-fluorophenyl)pyrrolidin-3-yl]-4-azaspiro[2.5]octane-7-carboxamide;

(1R,3S,5S)-8-[5-(5-fluoro-2-methoxypyridin-4-yl)-1H-pyrazole-3-carbonyl]-N-[1-oxaspiro[3.5]nonan-7-yl]-8-azabicyclo[3.2.1]octane-3-carboxamide;

(2R,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2R,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2R,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2R,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2S,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(1R,3S,5S)—N-[(3S,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3R,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(R)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide;

(S)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide;

(1R,3s,5S)-8-(5-(5-fluoro-2-methoxypyridin-4-yl)-1H-pyrazole-3-carbonyl)-N-(4-hydroxy-4-(perfluoroethyl)cyclohexyl)-8-azabicyclo[3.2]octane-3-carboxamide;

(1R,3R,5S)-8-[5-(5-fluoro-2-methoxypyridin-4-yl)-1H-pyrazole-3-carbonyl]-N-[(1r,4r)-4-(difluoromethyl)-4-methoxycyclohexyl]-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1s,4s)-4-(difluoromethyl)-4-methoxycyclohexyl]-8-azabicyclo[3.2.1]octane-3-carboxamide;

(1R,3s,5S)—N-((1r,4R)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(1R,3s,5S)—N-((1s,4S)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(1R,3S,5S)-8-[5-(5-fluoro-2-methoxypyridin-4-yl)-1H-pyrazole-3-carbonyl]-N-[(1r,4r)-4-(2-methoxyethoxy)-4-(trifluoromethyl)cyclohexyl]-8-azabicyclo[3]octane-3-carboxamide;

(1R,3S,5S)-8-[5-(5-fluoro-2-methoxypyridin-4-yl)-1H-pyrazole-3-carbonyl]-N-[(1s,4s)-4-(2-methoxyethoxy)-4-(trifluoromethyl)cyclohexyl]-8-azabicyclo[3.2.1]octane-3-carboxamide;

(1R,3S,5S)-8-[5-(5-fluoro-2-methoxypyridin-4-yl)-1H-1,2,4-triazole-3-carbonyl]-N-[(1r,4r)-4-hydroxy-4-(trifluoromethyl)cyclohexyl]-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide;

(1R,3s,5S)—N-(3,3-difluoro-1-oxaspiro[3.5]nonan-7-yl)-8-(5-(5-fluoro-2-methoxypyridin-4-yl)-1H-pyrazole-3-carbonyl)-8-azabicyclo[3.2.1]octane-3-carboxamide;

(S)—N-((1r,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1s,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1r,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1s,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1r,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1s,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide, (R)—N-((1r,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1s,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

4-(4-(5-hydroxy-2-methylpyridin-4-yl)-1H-imidazole-2-carbonyl)-N-((1r,4r)-4-hydroxy-4-(trifluoromethyl)cyclohexyl)-4-azaspiro[2.5]octane-7-carboxamide;

(1R,3s,5S)-8-(5-(5-fluoro-2-methylpyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6R)-1-methyl-6-(trifluoromethyl)piperidin-3-yl)8-azabicyclo[3.2.1]octane-3-carboxamide;

(R)—N-((1r,4S)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4R)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide;

(1R,3s,5S)-8-(5-(2,3-dimethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)—N-((1r,4R)-4-hydroxy-4-(trifluoromethyl)cyclohexyl)-8-(5-(6-methyl-1H-pyrazolo[3,4-b]pyridin-4-yl)-1H-pyrazole-3-carbonyl)-8-azabicyclo[3.2.1]octane-3-carboxamide;

(1R,3s,5S)-8-(5-(2-ethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)—N-((1r,4R)-4-hydroxy-4-(trifluoromethyl)cyclohexyl)-8-(5-(2-(hydroxymethyl)pyridin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-(3-(trifluoromethyl)-1-oxaspiro[3.5]nonan-7-yl)-8-azabicyclo[3.2.1]octane-3-carboxamide;

(1R,3s,5S)—N-(3,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide;

(1R,3s,5S)—N-(4,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide;

(S)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide;

(R)—N-((1r,4R)-4-ethoxy-4-(trifluoromethyl)cyclohexyl)-4-(5-(5-fluoro-2-methylpyridin-4-yl)-1H-pyrazole-3-carbonyl)-4-azaspiro[2.5]octane-7-carboxamide;

(S)—N-((1r,4S)-4-ethoxy-4-(trifluoromethyl)cyclohexyl)-4-(5-(5-fluoro-2-methylpyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((1r,4R)-4-methoxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-methoxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((4S,7r)-1-oxaspiro[3.5]nonan-7-yl)-4-azaspiro[2.5]octane-7-carboxamide;

(S)-4-(5-(5-fluoro-2-methoxypyridin-4-yl)-1H-pyrazole-3-carbonyl)-N-((1R,7s)-1-oxaspiro[3.5]nonan-7-yl)-4-azaspiro[2,5]octane-7-carboxamide;

(1R,3s,5S)-8-(5-(5-fluoro-2-methoxypyridin-4-yl)-1H-pyrazole-3-carbonyl)-N-((3S,6S)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-1-(2-fluoro-2-methylpropyl)-6-(trifluoromethyl)piperidin-3-yl)-8-azabicyclo[3.2.1]octane-3-carboxamide;

(R)-4-(5-(5-fluoro-2-methoxypyridin-4-yl)-1H-pyrazole-3-carbonyl)-N-((5R,8r)-1-methyl-2-oxo-1-azaspiro[4.5]decan-8-yl)-4-azaspiro[2.5]octane-7-carboxamide;

(R)-4-(5-(5-fluoro-2-methoxypyridin-4-yl)-1H-pyrazole-3-carbonyl)-N-((5S,8s)-1-methyl-2-oxo-1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-((5S,8r)-1-methyl-2-oxo-1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-((5R,8s)-1-ethyl-2-oxo-1-azaspiro[4.5]decan-8-yl)-4-azaspiro[2.5]octane-7-carboxamide;

(R)—N-((5R,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(R)—N-((5S,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-(5S,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((5R,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(2-(dimethylamino)ethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((1r,4R)-4-(2-hydroxyethoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-(2-hydroxyethoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N—(((R)-1-(2,2,2-trifluoroethyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide;

4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((3-hydroxybicyclo[1.1.1]pentan-1-yl)methyl)-4-azaspiro[2.5]octane-7-carboxamide;

(S)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(R)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide;

(R)—N-((1r,4R)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide;

(R)—N-((1r,4R)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1r,4S)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1S,4S)-4-((S)-2-methoxypropoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1R,4S)-4-((R)-2-methoxypropoxy)-4-(trifluoromethyl)cyclohexyl)-4-azaspiro[2.5]octane-7-carboxamide;

(S)-4-(3-(5-fluoro-2-methoxypyridin-4-yl)-1H-pyrazole-5-carbonyl)-N—(((R)-4,5,6,7-tetrahydro-2H-indazol-5-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-4,5,6,7-tetrahydro-2H-indazol-5-yl)methyl)-4-azaspiro[2.5]octane-7-carboxamide;

(S)-4-(3-(5-fluoro-2-methoxypyridin-4-yl)-1H-pyrazole-5-carbonyl)-N—(((R)-5,6,7,8-tetrahydroimidazo[1,5-a]pyridin-7-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-5,6,7,8-tetrahydroimidazo[1,5-a]pyridin-7-yl)methyl)-4-azaspiro[2.5]octane-7-carboxamide;

(S)-4-(5-(5-fluoro-2-methoxypyridin-4-yl)-1H-pyrazole-3-carbonyl)-N-((1-methyl-2-oxabicyclo[2.1.1]hexan-4-yl)methyl)-4-azaspiro[2.5]octane-7-carboxamide;

(R)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2,5]octane-7-carboxamide;

(S)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide;

(R)-4-(3-(5-fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—(((R)-3-methyl-5,6,7,8-tetrahydro-[1,2,4]triazolo[4,3-a]pyridin-7-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-3-methyl-5,6,7,8-tetrahydro-[1,2,4]triazolo[4,3-a]pyridin-7-yl)methyl)-4-azaspiro[2.5]octane-7-carboxamide;

(1r,4R)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1s,4S)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1r,4S)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1s,4R)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-(1-(oxetan-3-yl)-1-azaspiro[4.5]decan-8-yl)-4-azaspiro[2.5]octane-7-carboxamide;

(S)—N-((1r,4S)-4-(2-aminoethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-(1-(2,2-difluoropropyl)-1-azaspiro[4.5]decan-8-yl)-4-(5-(5-fluoro-2-methoxypyridin-4-1H-pyrazole-3-carbonyl)-4-azaspiro[2,5]octane-7-carboxamide;

(S)—N-((1S,4S)-4-((S)-2-aminopropoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide, (S)-4-(5-(5-fluoro-2-methoxypyridin-4-yl)-1H-pyrazole-3-carbonyl)-N-((1S,4S)-4-((S)-2-hydroxypropoxy)-4-(trifluoromethyl)cyclohexyl)-4-azaspiro[2.5]octane-7-carboxamide;

(7S)—N-(8-oxabicyclo[3.2.1]octan-3-yl)-4-(5-(5-fluoro-2-methoxypyridin-4-yl)-1H-pyrazole-3-carbonyl)-4-azaspiro[2.5]octane-7-carboxamide;

(S)—N-((1 S,3R)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide;

(S)—N-((1S,3S)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—(((S)-5,6,7,8-tetrahydroimidazo[1,2-a]pyridin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-5,6,7,8-tetrahydroimidazo[1,2-a]pyridin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((S)-3-(trifluoromethyl)-5,6-dihydro-8H-[1,2,4]triazolo[3,4-c][1,4]oxazin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-3-(trifluoromethyl)-5,6-dihydro-8H-[1,2,4]triazolo[3,4-c][1,4]oxazin-6-yl)methyl)-4-azaspiro[2.5]octane-7-carboxamide;

(S)—N-((3-chloropyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3-methylpyridin-2-yl)methyl)-4-azaspiro[2.5]octane-7-carboxamide;

(S)—N—((R)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((S)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-methylpyridin-2-yl)methyl)-4-azaspiro[2.5]octane-7-carboxamide;

(S)—N-((3-chloro-5-fluoropyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-(trifluoromethyl)pyridin-2-yl)methyl)-4-azaspiro[2.5]octane-7-carboxamide;

(S)—N-((3-chloro-5-(2-hydroxypropan-2-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((4-(trifluoromethyl)-2-oxabicyclo[2.1.1]hexan-1-yl)methyl)-4-azaspiro[2.5]octane-7-carboxamide;

(S)—N—((S)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide;

(S)—N—((R)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide;

(2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide;

(2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide;

(2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide;

(2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide;

(R)—N-((1r,4R)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(R)—N-((1s,4S)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(R)—N-((5S,8s)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(R)—N-((5R,8r)-4,4-difluoro-1-oxaspiro[4.5]decan-8-yl)-4-(5-(5-fluoro-2-methoxypyridin-4-yl)-1H-pyrazole-3-carbonyl)-4-azaspiro[2,5]octane-7-carboxamide;

(S)—N-((5,6-dihydro-8H-imidazo[2,1-c][1,4]oxazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(((1R,3S)-1-imino-2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1S,3S)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1S,3R)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1R,3R)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-hydroxy-4-(perfluoroethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1s,4R)-4-hydroxy-4-(perfluoroethyl)cyclohexyl)-4-azaspiro[2.5]octane-7-carboxamide;

(S)—N-((4S,7r)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4R,7s)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(1,1-difluoroethyl)-4-hydroxycyclohexyl)-4-(5-(5-fluoro-2-methoxypyridin-4-yl)-1H-pyrazole-3-carbonyl)-4-azaspiro[2,5]octane-7-carboxamide;

(S)-4-(5-(5-fluoro-2-methoxypyridin-4-yl)-1H-pyrazole-3-carbonyl)-N-((6R,8aR)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6R,8aS)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6S,8aR)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6S,8aS)-octahydroindolizin-6-yl)-4-azaspiro[2.5]octane-7-carboxamide;

(S)—N—((R)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((S)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N-((1s,3R)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide;

(S)—N-((1r,3S)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-6-methyl-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N—((S)-6-methyl-3,4-dihydro-2H-pyrano[3,2-b]pyridin-4-yl)-4-azaspiro[2.5]octane-7-carboxamide, (S)-4-(5-(5-fluoro-2-methoxypyridin-4-yl)-1H-pyrazole-3-carbonyl)-N-(5-methylpyrazolo[1,5-a]pyrimidin-3-yl)-4-azaspiro[2.5]octane-7-carboxamide;

(S)-4-(5-(5-fluoro-2-methoxypyridin-4-yl)-1H-pyrazole-3-carbonyl)-N—(((S)-3-methyl-4,5,6,7-tetrahydro-1H-indazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-3-methyl-4,5,6,7-tetrahydro-1H-indazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-7-fluoro-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N—((S)-7-fluoro-3,4-dihydro-2H-pyrano[3,2-b]pyridin-4-yl)-4-azaspiro[2.5]octane-7-carboxamide;

(1R,3s,5S)—N-((3-chloro-5-fluoropyridin-2-yl)methyl)-8-(5-(5-fluoro-2-methoxypyridin-4-yl)-1H-pyrazole-3-carbonyl)-8-azabicyclo[3.2.1]octane-3-carboxamide;

(R)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((4-methylpyridazin-3-yl)methyl)-4-azaspiro[2.5]octane-7-carboxamide;

(S)—N-((5-chloro-2-methylpyrimidin-4-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloropyrazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-methoxypyridin-2-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-1-(pyridin-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(pyridin-3-yl)pyrrolidin-3-yl)-4-azaspiro[2.5]octane-7-carboxamide;

(S)—N-((3-chloro-5-cyanopyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-(oxetan-3-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-(3-cyanoazetidin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((2-methyl-5-(trifluoromethyl)oxazol-4-yl)methyl)-4-azaspiro[2.5]octane-7-carboxamide;

(S)—N—((S)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((R)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1-(oxetan-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(oxetan-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((3-methylpyrazin-2-yl)methyl)-4-azaspiro[2.5]octane-7-carboxamide;

(S)—N-((1r,4S)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-amino-4-(trifluoromethyl)cyclohexyl)-4-(5-(5-fluoro-2-ethoxypyridin-4-yl)-1H-pyrazole-3-carbonyl)-4-azaspiro[2.5]octane-7-carboxamide;

(S)—N-((1r,4S)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((3,5-difluoropyridin-2-yl)methyl)-4-(5-(5-fluoro-2-methoxypyridin-4-yl)-1H-pyrazole-3-carbonyl)-4-azaspiro[2.5]octane-7-carboxamide;

(2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide;

(2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide;

(2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide;

(2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide;

(S)—N-((3-chloro-5-methoxypyridin-2-methyl)-4-(5-(5-fluoro-2-methoxypyridin-4-yl)-1H-pyrazole-3-carbonyl)-4-azaspiro[2.5]octane-7-carboxamide;

(2R,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide;

(2S,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide;

(2S,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide;

(2R,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide;

(S)-4-(5-(5-fluoro-2-methoxypyridin-4-yl)-1H-pyrazole-3-carbonyl)-N-((5-fluoro-3-(4-methylpiperazin-1-yl)pyridin-2-yl)methyl)-4-azaspiro[2.5]octane-7-carboxamide;

(R)—N-((5R,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(R)—N-((5S,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2,5]octane-7-carboxamide;

(S)—N-((5S,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(S)—N-((5R,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2,5]octane-7-carboxamide;

(S)-4-(5-(5-fluoro-2-methoxypyridin-4-yl)-1H-pyrazole-3-carbonyl)-N-(1-((1-fluorocyclopropyl)methyl)azetidin-3-yl)-4-azaspiro[2.5]octane-7-carboxamide;

(S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,2-dimethylpiperidine-4-carboxamide;

(R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,2-dimethylpiperidine-4-carboxamide;

(S)-4-(5-(5-fluoro-2-methoxypyridin-4-yl)-1H-pyrazole-3-carbonyl)-N-((1s,4R)-4-(hydroxymethyl)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-(hydroxymethyl)-4-(trifluoromethyl)cyclohexyl)-4-azaspiro[2,5]octane-7-carboxamide;

(7S)—N-(1-(tert-butylsulfinyl)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4S,7r)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4R,7s)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1-(4-hydroxybicyclo[2.2.2]octan-1-yl)ethyl)-4-azaspiro[2.5]octane-7-carboxamide;

(S)-4-(5-(5-fluoro-2-methoxypyridin-4-yl)-1H-pyrazole-3-carbonyl)-N—((S)-1-(4-hydroxybicyclo[2.2.2]octan-1-yl)ethyl)-4-azaspiro[2.5]octane-7-carboxamide;

(S)—N-((4,6-dimethylpyridazin-3-yl)methyl)-4-(5-(5-fluoro-2-methoxypyridin-4-yl pyrazole-3-carbonyl)-4-azaspiro[2.5]octane-7-carboxamide;

(R)—N-((5-chloropyrimidin-2-yl)methyl)-4-(5-(5-fluoro-2-methoxypyridin-4-yl)-1H-pyrazole-3-carbonyl)-4-azaspiro[2,5]octane-7-carboxamide;

(S)-4-(5-(5-fluoro-2-methoxypyridin-4-yl)-1H-pyrazole-3-carbonyl)-N-((3S,4R)-4-morpholinotetrahydrofuran-3-yl)-4-azaspiro[2.5]octane-7-carboxamide;

(S)-4-(5-(5-fluoro-2-methoxypyridin-4-yl)-1H-pyrazole-3-carbonyl)-N-((3R,4S)-4-morpholinotetrahydrofuran-3-yl)-4-azaspiro[2.5]octane-7-carboxamide;

(S)—N—((S)-1-(5,6-dihydro-8H-imidazo[2,1-c][1,4]oxazin-2-yl)ethyl)-4-(5-(5-fluoro-2 methoxypyridin-4-yl)-1H-pyrazole-3-carbonyl)-4-azaspiro[2.5]octane-7-carboxamide;

(S)—N—((R)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(pyrazolo[1,5-a]pyridin-7-ylmethyl)-4-azaspiro[2.5]octane-7-carboxamide;

(S)-4-(5-(5-fluoro-2-methoxypyridin-4-yl)-1H-pyrazole-3-carbonyl)-N-(1-(oxetan-3-yl)piperidin-4-yl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-morpholinocyclohexyl)-4-azaspiro[2.5]octane-7-carboxamide;

(S)-4-(5-(5-fluoro-2-methoxypyridin-4-yl)-1H-pyrazole-3-carbonyl)-N-((1s,4R)-4-morpholinocyclohexyl)-4-azaspiro[2.5]octane-7-carboxamide;

(S)-4-(5-(5-fluoro-2-methoxypyridin-4-yl)-1H-pyrazole-3-carbonyl)-N-((1R,5S,7r)-9-methyl-3-oxa-9-azabicyclo[3.3.1]nonan-7-yl)-4-azaspiro[2.5]octane-7-carboxamide;

(S)-4-(5-(5-fluoro-2-methoxypyridin-4-yl)-1H-pyrazole-3-carbonyl)-N-((1R,5S,7s)-9-methyl-3-oxa-9-azabicyclo[3.3.1]nonan-7-yl)-4-azaspiro[2.5]octane-7-carboxamide;

(S)-4-(5-(5-fluoro-2-methoxypyridin-4-yl)-1H-pyrazole-3-carbonyl)-N-(1-(methylsulfonyl)piperidin-4-yl)-4-azaspiro[2.5]octane-7-carboxamide;

(S)-4-(5-(5-fluoro-2-methoxypyridin-4-yl)-1H-pyrazole-3-carbonyl)-N—((S)-1-(oxetan-3-yl)piperidin-3-yl)-4-azaspiro[2.5]octane-7-carboxamide;

(S)-4-(5-(5-fluoro-2-methoxypyridin-4-yl)-1H-pyrazole-3-carbonyl)-N—(((R)-1-(oxetan-3-yl)piperidin-3-yl)-4-azaspiro[2.5]octane-7-carboxamide;

(S)—N-((3R,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide, (S)—N-((3S,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,6R)-1,6-dimethylpiperidin-3-yl)-4-(5-(5-fluoro-2-ethoxypyridin-4-1H-pyrazole-3-carbonyl)-4-azaspiro[2.5]octane-7-carboxamide;

(S)—N-((3R,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2-fluoroethyl-2,2-dimethylpiperidin-4-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-fluoroethyl)-2,2-dimethylpiperidin-4-yl)-4-azaspiro[2.5]octane-7-carboxamide;

(S)—N-((3R,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4S)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(7S)-4-(5-(5-fluoro-2-methoxypyridin-4-yl)-1H-pyrazole-3-carbonyl)-N-(3-(oxetan-3-yl)-3-azabicyclo[3.1.0]hexan-6-yl)-4-azaspiro[2.5]octane-7-carboxamide;

(S)—N-(5-chloropyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(2-methylpyrimidin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-methylpyrimidin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((3-(trifluoromethyl)pyrazin-2-yl)methyl)-4-azaspiro[2.5]octane-7-carboxamide;

(S)-4-(5-(5-fluoro-2-methoxypyridin-4-yl)-1H-pyrazole-3-carbonyl)-N-(1-((S)-tetrahydrofuran-3-yl)azetidin-3-yl)-4-azaspiro[2.5]octane-7-carboxamide;

(S)-4-(5-(5-fluoro-2-methoxypyridin-4-yl)-1H-pyrazole-3-carbonyl)-N-(1-((R)-tetrahydrofuran-3-yl)azetidin-3-yl)-4-azaspiro[2.5]octane-7-carboxamide;

(7S)—N-((3-chloro-5-(3,5-dimethylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide;

(1R,3s,5S)—N-(4-(1,1-difluoro-2-hydroxyethyl)-4-hydroxycyclohexyl)-8-(5-(5-fluoro-2-methoxypyridin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((R)-1-((1-(trifluoromethyl)cyclopropyl)methyl)pyrrolidin-3-yl)-8-azabicyclo[3.2.1]octane-3-carboxamide;

(1R,3s,5S)—N-(4-cyano-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(S)—N-((1s,4R)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((2-(2-fluoro-2-methylpropyl)-2-azabicyclo[2.1.1]hexan-4-yl)methyl)-4-azaspiro[2,5]octane-7-carboxamide;

(1R,3s,5S)—N-(4-amino-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(S)-4-(5-(5-fluoro-2-methoxypyridin-4-yl)-1H-pyrazole-3-carbonyl)-N-(2-(2-fluoro-2-methylpropyl)-2-azabicyclo[2.1.1]hexan-4-yl)-4-azaspiro[2.5]octane-7-carboxamide;

(S)-4-(5-(5-fluoro-2-methoxypyridin-4-yl)-1H-pyrazole-3-carbonyl)-N-((1-(trifluoromethyl)-2-oxabicyclo[2.1.1]hexan-4-yl)methyl)-4-azaspiro[2.5]octane-7-carboxamide, 5-(5-(5-fluoro-2-methoxypyridin-4-yl)-1H-pyrazole-3-carbonyl)-N-((1r,4r)-4-hydroxy-4-(trifluoromethyl)cyclohexyl)-2-oxa-5-azaspiro[3.5]nonane-8-carboxamide;

(S)-4-(5-(5-fluoro-2-methoxypyridin-4-yl)-1H-pyrazole-3-carbonyl)-N-(5-((R)-1-hydroxyethyl)pyrazolo[1,5-a]pyrimidin-3-yl)-4-azaspiro[2.5]octane-7-carboxamide;

(S)-4-(5-(5-fluoro-2-methoxypyridin-4-yl)-1H-pyrazole-3-carbonyl)-N-(5-((S)-1-hydroxyethyl)pyrazolo[1,5-a]pyrimidin-3-yl)-4-azaspiro[2.5]octane-7-carboxamide;

(S)—N-((3-chloro-5-(oxetan-3-yloxy)pyridin-2-yl)methyl)-4-(5-(5-fluoro-2-methoxypyridin-4-yl)-1H-pyrazole-3-carbonyl)-4-azaspiro[2,5]octane-7-carboxamide;

(7S)—N-((5-(3,5-dimethylpiperazin-1-yl)pyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)—N-(1-cyanocyclopropyl)-4-(5-(5-fluoro-2-methoxypyridin-4-yl)-1H-pyrazole-3-carbonyl)-4-azaspiro[2.5]octane-7-carboxamide;

(S)-4-(5-(2-methoxy-5-methylpyridin-4-yl)-1H-pyrazole-3-carbonyl)-N—((R)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide;

(S)—N—((S)-1-(1H-pyrazolo[3,4-b]pyridin-4-yl)pyrrolidin-3-yl)-4-(5-(5-fluoro-2-methoxypyridin-1-pyrazole-3-carbonyl)-4-azaspiro[2.5]octane-7-carboxamide;

(S)—N—((R)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3-chloro-6-methylpyrazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(6-methylpyridazin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(6-methylpyridazin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2-methylpyrimidin-5-yl)pyrrolidin-3-yl)-4-azaspiro[2,5]octane-7-carboxamide;

(S)-4-(5-(5-fluoro-2-methoxypyridin-4-yl)-1H-pyrazole-3-carbonyl)-N—((R)-1-(2-methylpyrimidin-5-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-((3-hydroxyoxetan-3-yl)methyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-((3-hydroxyoxetan-3-yl)methyl)pyrrolidin-3-yl-4-azaspiro[2.5]octane-7-carboxamide;

(S)-4-(5-(5-fluoro-2-methoxypyridin-4-yl)-1H-pyrazole-3-carbonyl)-N-((5-methoxypyrimidin-2-yl)methyl)-4-azaspiro[2.5]octane-7-carboxamide;

(S)—N-(5-cyanopyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-(trifluoromethyl)pyrimidin-2-yl)methyl)-4-azaspiro[2.5]octane-7-carboxamide;

(S)—N-(1-(3,5-dichloropyridin-2-yl)cyclopropyl)-4-(5-(5-fluoro-2-methoxypyridin-4-yl)-1H-pyrazole-3-carbonyl)-4-azaspiro[2.5]octane-7-carboxamide;

(S)—N—((S)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((1R,4S)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,4R)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide;

(S)—N—((R)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((5-((1R,4R)-2,5-diazabicyclo[2,2,1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1S,4S)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide;

(S)-4-(3-(5-fluoro-2-methoxypyridin-4-yl)-1H-pyrazole-5-carbonyl)-N-((3-hydroxyoxetan-3-yl)methyl)-4-azaspiro[2.5]octane-7-carboxamide;

(S)—N—((R)-1-((R)-1-oxaspiro[3.3]heptan-3-yl)pyrrolidin-3-yl)-4-(5-(5-fluoro-2-methoxypyridin-pyrazole-3-carbonyl)-4-azaspiro[2.5]octane-7-carboxamide;

(S)—N—((R)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide, (S)—N—((S)-1-((R)-1-oxaspiro[3,3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-(S)-1-oxaspiro[3.3]heptan-3-yl)pyrrolidin-3-yl)-4-(5-(5-fluoro-2-ethoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1,4,5-trimethyl-1H-imidazol-2-yl)methyl)-4-azaspiro[2.5]octane-7-carboxamide;

(S)—N-(5-((1S,2S)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)—N-(5-((1R,2R)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)—N-((5-((1R,4R)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1S,4S)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(R)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide;

(S)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide;

(S)—N-((5-((1S,6R)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1R,6S)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N—((R)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide;

(S)—N—((S)-4,4-difluoro-1-(1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide;

(7S)-4-(5-(5-fluoro-2-methoxypyridin-4-yl)-1H-pyrazole-3-carbonyl)-N-(pyrrolidin-3-yl)-4-azaspiro[2.5]octane-7-carboxamide;

(S)—N—((R)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1-isopropyl-3-methyl-1H-1,2,4-triazol-5-yl)methyl)-4-azaspiro[2,5]octane-7-carboxamide;

(S)—N-((1S,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(5-methyl-4,5,6,7-tetrahydropyrazolo[1,5-a]pyrazin-2-yl)ethyl)-4-azaspiro[2.5]octane-7-carboxamide;

(S)-4-(5-(5-fluoro-2-methoxypyridin-4-yl)-1H-pyrazole-3-carbonyl)-N—((R)-1-(5-methyl-4,5,6,7-tetrahydropyrazolo[1,5-a]pyrazin-2-yl)ethyl)-4-azaspiro[2.5]octane-7-carboxamide;

(S)-4-(3-(5-fluoro-2-methoxypyridin-4-yl)-1H-pyrazole-5-carbonyl)-N-((5-(trifluoromethyl)-1H-imidazol-2-yl)methyl)-4-azaspiro[2.5]octane-7-carboxamide;

4-(5-(2-acetyl-5-fluoropyridin-4-yl)-1H-pyrazole-3-carbonyl)-N-((3-chloro-5-fluoropyridin-2-yl)methyl)-4-azaspiro[2.5]octane-7-carboxamide;

(R)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-5,6,7,8-tetrahydroimidazo[1,2-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((S)-5,6,7,8-tetrahydroimidazo[1,2-a]pyridin-8-yl)-4-azaspiro[2,5]octane-7-carboxamide;

(S)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3-((1S,2S)-2-(hydroxymethyl)cyclopropyl)pyrazin-2-yl)methyl)-4-azaspiro[2.5]octane-7-carboxamide;

(S)-4-(5-(5-fluoro-2-methoxypyridin-4-yl)-1H-pyrazole-3-carbonyl)-N-((3-((1R,2R)-2-(hydroxymethyl)cyclopropyl)pyrazin-2-yl)methyl)-4-azaspiro[2.5]octane-7-carboxamide;

(S)—N-((2-((3S,5R)-3,5-dimethylpiperazin-1-yl)-5-(trifluoromethyl)oxazol-4-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide;

(S)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide;

(R)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-(trifluoromethyl)-2-((3S,5R)-3,4,5-trimethylpiperazin-1-yl)oxazol-4-yl)methyl)-4-azaspiro[2.5]octane-7-carboxamide;

(S)-5-(5-(5-fluoro-2-methoxypyridin-4-yl)-1H-pyrazole-3-carbonyl)-N-((1r,4S)-4-hydroxy-4-(trifluoromethyl)cyclohexyl)-5-azaspiro[3.5]nonane-8-carboxamide;

(R)-5-(5-(5-fluoro-2-methoxypyridin-4-yl)-1H-pyrazole-3-carbonyl)-N-((1r,4R)-4-hydroxy-4-(trifluoromethyl)cyclohexyl)-5-azaspiro[3.5]nonane-8-carboxamide;

(S)—N-(5-cyanopyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(7S)—N-(1-(6-cyanopyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3-chloro-5-isopropoxypyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-3-methyl-5,6,7,8-tetrahydro-[1,2,4]triazolo[4,3-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((R)-3-methyl-5,6,7,8-tetrahydro-[1,2,4]triazolo[4,3-a]pyridin-8-yl)-4-azaspiro[2.5]octane-7-carboxamide;

(R)-4-(5-(5-fluoro-2-methoxy-3-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-fluoro-2-methoxy-3-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)—N-(6-acetylpyrazolo[1,5-a]pyridin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(6-((S)-1-hydroxyethyl)pyrazolo[1,5-a]pyridin-3-yl)-4-azaspiro[2,5]octane-7-carboxamide;

(S)-4-(5-(5-fluoro-2-methoxypyridin-4-yl)-1H-pyrazole-3-carbonyl)-N-(6-((R)-1-hydroxyethyl)pyrazolo[1,5-a]pyridin-3-yl)-4-azaspiro[2.5]octane-7-carboxamide;

(7S)—N-(7',8'-dihydro-6'H-spiro[oxetane-3,5'-quinolin]-8'-yl)-4-(5-(5-fluoro-2-methoxypyridin-4-yl)-1H-pyrazole-3-carbonyl)-4-azaspiro[2.5]octane-7-carboxamide;

(7S)—N-(5-ethyl-2-oxa-5-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-(5,5-dimethyl-6,7-dihydro-5H-pyrazolo[5,1-b][1,3]oxazin-3-yl)-4-(5-(5-fluoro-2-methoxypyridin-4-yl)-1H-pyrazole-3-carbonyl)-4-azaspiro[2.5]octane-7-carboxamide;

(S)—N-((1-(aminomethyl)-2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((2-(trifluoromethyl)pyridin-3-yl)methyl)-4-azaspiro[2.5]octane-7-carboxamide;

(S)-4-(5-(5-fluoro-2-methoxypyridin-4-yl)-1H-pyrazole-3-carbonyl)-N-((1R,3R,4S)-3-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1S,3S,4R)-3-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N—((S)-2-(trifluoromethyl)-5,6,7,8-tetrahydroimidazo[1,2-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((R)-2-(trifluoromethyl)-5,6,7,8-tetrahydroimidazo[1,2-a]pyridin-8-yl)-4-azaspiro[2.5]octane-7-carboxamide;

(S)-4-(3-(5-fluoro-2-methoxypyridin-4-yl)-1H-pyrazole-5-carbonyl)-N-((4-(trifluoromethyl)-1H-imidazol-5-yl)methyl)-4-azaspiro[2.5]octane-7-carboxamide;

(S)—N-((1S,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)isoxazol-4-yl)methyl)-4-azaspiro[2.5]octane-7-carboxamide;

(S)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide;

(R)—N-((3-cyclopropylpyridin-2-yl)methyl)-4-(3-(5-fluoro-2-methylpyridin-4-yl)-1H-pyrazole-5-carbonyl)-4-azaspiro[2,5]octane-7-carboxamide;

(S)-4-(3-(5-fluoro-2-methoxypyridin-4-yl)-1H-pyrazole-5-carbonyl)-N-((1-methyl-4-(trifluoromethyl)-1H-pyrazol-5-yl)methyl)-4-azaspiro[2.5]octane-7-carboxamide;

(S)-4-(3-(5-fluoro-2-methoxypyridin-4-yl)-1H-pyrazole-5-carbonyl)-N-((1-methyl-5-(trifluoromethyl)-1H-1,2,3-triazol-4-yl)methyl)-4-azaspiro[2.5]octane-7-carboxamide;

(S)-4-(3-(5-fluoro-2-methoxypyridin-4-yl)-1H-pyrazole-5-carbonyl)-N-((1-methyl-3-(trifluoromethyl)-1H-pyrazol-4-yl)methyl)-4-azaspiro[2.5]octane-7-carboxamide;

(S)-4-(3-(5-fluoro-2-methoxypyridin-4-yl)-1H-pyrazole-5-carbonyl-N-((3-(trifluoromethyl)pyridin-2-yl)methyl)-4-azaspiro[2.5]octane-7-carboxamide;

(S)—N-(((S)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide;

(S)—N-(((R)-3,3-difluoropiperidin-4-yl)methyl)-4-(5-(5-fluoro-2-methoxypyridin-4-yl)-H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((5-fluoropyrimidin-2-yl)methyl)-4-azaspiro[2.5]octane-7-carboxamide;

(S)-4-(3-(5-fluoro-2-methoxypyridin-4-yl)-1H-pyrazole-5-carbonyl)-N-((2-(trifluoromethyl)pyridin-3-yl)methyl)-4-azaspiro[2.5]octane-7-carboxamide;

(S)-4-(5-(5-fluoro-2-methoxypyridin-4-yl)-1H-pyrazole-3-carbonyl)-N—((S)-5-hydroxy-4,5,6,7-tetrahydropyrazolo[1,5-a]pyridin-3-yl)-4-azaspiro[2.5]octane-7-carboxamide;

(S)-4-(5-(5-fluoro-2-methoxypyridin-4-yl)-1H-pyrazole-3-carbonyl)-N—((R)-5-hydroxy-4,5,6,7-tetrahydropyrazolo[1,5-a]pyridin-3-yl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)bicyclo[1.1.1]pentan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-(trifluoromethyl)pyridin-3-yl)methyl)-4-azaspiro[2.5]octane-7-carboxamide;

(S)-4-(3-(5-fluoro-2-methoxypyridin-4-yl)-1H-pyrazole-5-carbonyl)-N-((2-methyl-4-(trifluoromethyl)thiazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-1-(hydroxymethyl)-3-methyl-2-oxabicyclo[2.1.1]hexan-4-yl)-4-azaspiro[2.5]octane-7-carboxamide;

(S)-4-(5-(5-fluoro-2-methoxypyridin-4-yl)-1H-pyrazole-3-carbonyl)-N—((S)-1-(hydroxymethyl)-3-methyl-2-oxabicyclo[2.1.1]hexan-4-yl)-4-azaspiro[2.5]octane-7-carboxamide;

(S)-4-(3-(5-fluoro-2-methoxypyridin-4-yl)-1H-pyrazole-5-carbonyl)-N-((1-(trifluoromethyl)-1H-imidazol-2-yl)methyl)-4-azaspiro[2.5]octane-7-carboxamide;

(S)-4-(5-(5-fluoro-2-methoxypyridin-4-yl)-1H-pyrazole-3-carbonyl)-N-(1-(hydroxymethyl)-2-oxabicyclo[2.1.1]hexan-4-yl)-4-azaspiro[2.5]octane-7-carboxamide;

(S)—N-((3-chloro-5-(4-methylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((1-hydroxy-3,3-dimethyl-1,3-dihydrobenzo[c][1,2]oxaborol-6-yl)methyl)-4-azaspiro[2.5]octane-7-carboxamide;

(S)-4-(3-(5-fluoro-2-methoxypyridin-4-yl)-1H-pyrazole-5-carbonyl)-N-(1-hydroxy-1,3-dihydrobenzo[c][1,2]oxaborol-5-yl)-4-azaspiro[2.5]octane-7-carboxamide;

(S)-4-(5-(5-fluoro-2-methoxypyridin-4-yl)-1H-pyrazole-3-carbonyl)-N-((1R,3S)-3-hydroxy-3-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1S,3S)-3-hydroxy-3-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1R,3R)-3-hydroxy-3-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1S,3R)-3-hydroxy-3-(trifluoromethyl)cyclohexyl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)pyridin-4-yl)methyl)-4-azaspiro[2.5]octane-7-carboxamide;

(S)—N-((5-chloro-1-methyl-3-(trifluoromethyl)-1H-pyrazol-4-yl)methyl)-4-(3-(5-fluoro-2-methoxypyridin-4-yl)-1H-pyrazole-5-carbonyl)-4-azaspiro[2.5]octane-7-carboxamide;

(S)-4-(5-(5-fluoro-2-methoxypyridin-4-yl)-1H-pyrazole-3-carbonyl)-N-((5-methoxy-3-(trifluoromethyl)pyridin-2-yl)methyl)-4-azaspiro[2.5]octane-7-carboxamide;

(R)-4-(5-(6-cyanopyrimidin-4-yl)-1H-pyrazole-3-carbonyl)-N-((1r,4R)-4-hydroxy-4-(trifluoromethyl)cyclohexyl)-4-azaspiro[2,5]octane-7-carboxamide;

(S)-4-(5-(6-cyanopyrimidin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)-4-(5-(2-chloro-5-fluoropyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(R)-4-(5-(2-chloro-5-fluoropyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((5-methoxy-3-(trifluoromethyl)pyrazin-2-yl)methyl)-4-azaspiro[2.5]octane-7-carboxamide;

and pharmaceutically acceptable salts thereof.

Synthesis of the compounds of Formula (I) and pharmaceutically acceptable salts thereof may be performed as described herein, including the Examples, using techniques familiar to a person skilled in the art. Synthetic methods for preparing exemplary compounds described herein are described in the Examples. The methods may be used for synthesis of the compounds of Formula (I) by using appropriate reactants for preparation of the specific compound using the techniques and methods described herein, and that are routinely practiced in the art. By way of further example, Schemes 1-5 provide schematics of synthesis schemes for exemplary compounds described herein.

In general, compounds of Formula (I) can be prepared according to the following General Reaction Schemes:

Scheme 1

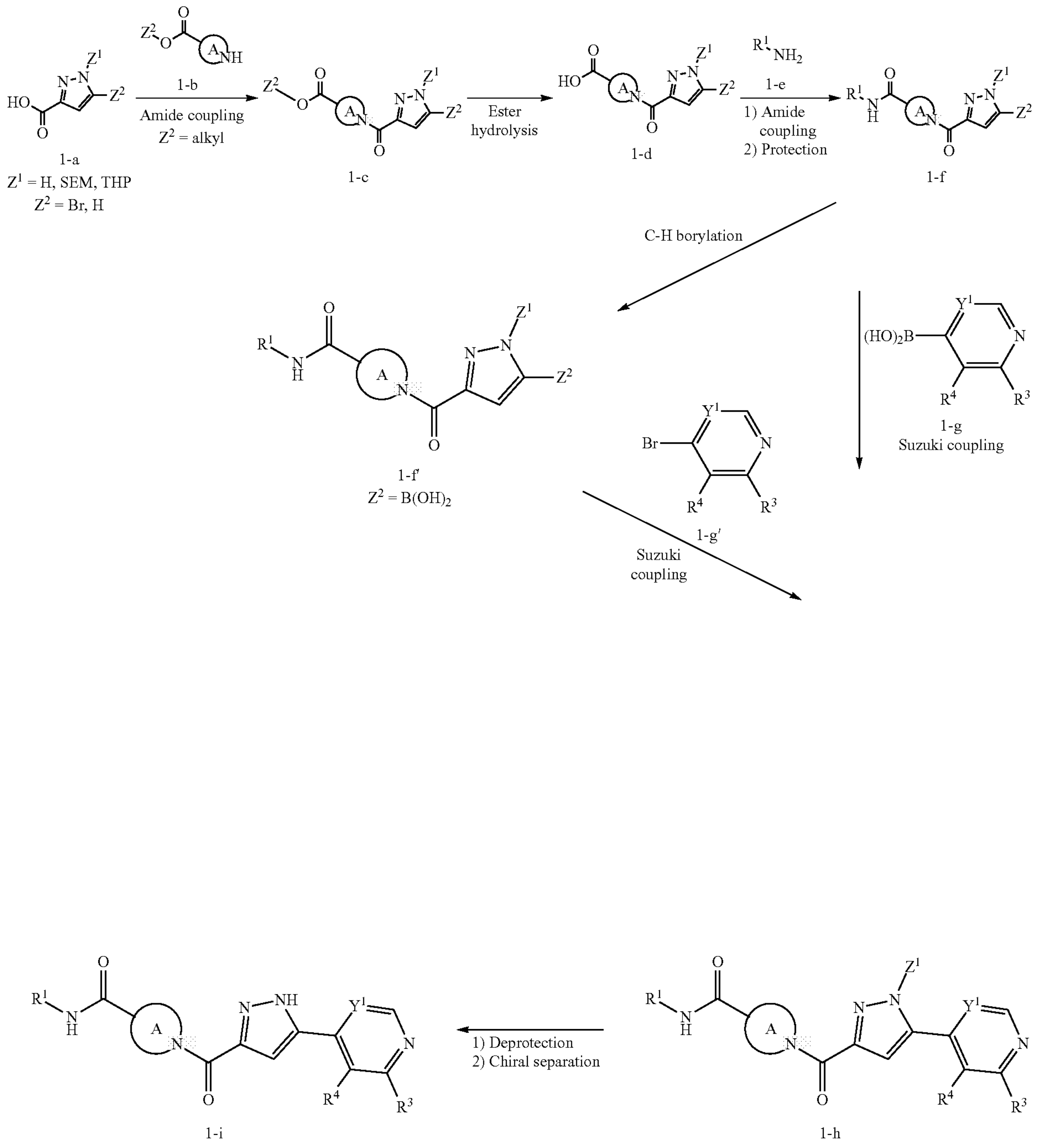

In Scheme 1 above, $R^1$, $R^3$, $R^4$, $Y^1$, and (Zing A are as described herein.

As depicted in Scheme 1 above, a pyrazole-3-carboxylic acid of Formula 1-a and a compound of formula 1-b are coupled together in a suitable solvent, such as, for example, DMF. A suitable coupling reagent, such as, for example, EDCI/HOBt, in the presence of a suitable base, such as, for example, DIPEA or TEA, promotes the reaction. The reaction may be carried out at room temperature or at an elevated temperature.

An alkyl ester of formula 1-c is converted to an acid of formula 1-d by hydrolyzing the ester group using standard conditions, such as, for example, LiOH in a mixture of water, MeOH, and THF.

A compound of formula 1-f as a mixture of enantiomers is prepared by reaction of an acid of formula 1-d with a reagent with a primary amine of formula 1-e through a coupling reaction. A coupling reagent, such as, for example, EDCI/HOBt, in the presence of a suitable base and solvents is used.

In some embodiments, a compound of formula 1-f as a mixture of enantiomers is prepared by alkylating the pyrazole product from the coupling reaction with SEM-Cl in the presence of a suitable base, such as, for example, $K_2CO_3$, in a suitable solvent, such as, for example, DMF. In some embodiments, a protected compound with formula 1-f is formed by treating with DHP in the presence of p-TsOH in THF.

In some embodiments, a pyrazole bromide of formula 1-f is reacted with aryl boronic acid 1-g under standard Suzuki coupling conditions known to one of ordinary skill in the art to form compounds of formula 1-i as enantiomeric mixtures.

In some embodiments, pyrazole bromide of formula 1-f' is first converted to pyrazole boronic acid of formula 1-f' by reacting with $B_2Pin_2$, in 1,4-dioxane in the presence of a palladium reagent, such as, for example, $Pd(dppf)Cl_2$, and KOAc at elevated temperature for a few hours.

In some embodiments, pyrazole of formula 1-f undergoes a C—H borylation process when reacted with Ir-catalyzed borylation process using Dtbpy, $[Ir(COD)OMe]_2$, $B_2Pin_2$ in MTBE, THF to synthesize compounds of formula 1-f'.

Compounds of formula 1-f' may subsequently undergo a Suzuki coupling reaction with Aryl bromide of formula 1-g' under standard conditions to produce compounds of formula 1-h.

A compound of formula 1-i as a mixture of enantiomers may be prepared by cleavage of protecting group, such as, for example, SEM or THP, using a suitable acid, such as, for example, TFA in DCM.

The enantiomers of compounds with formula 1-i may be separated using chiral purification columns, such as, for example, CHIRALPAK IF columns.

Scheme 2

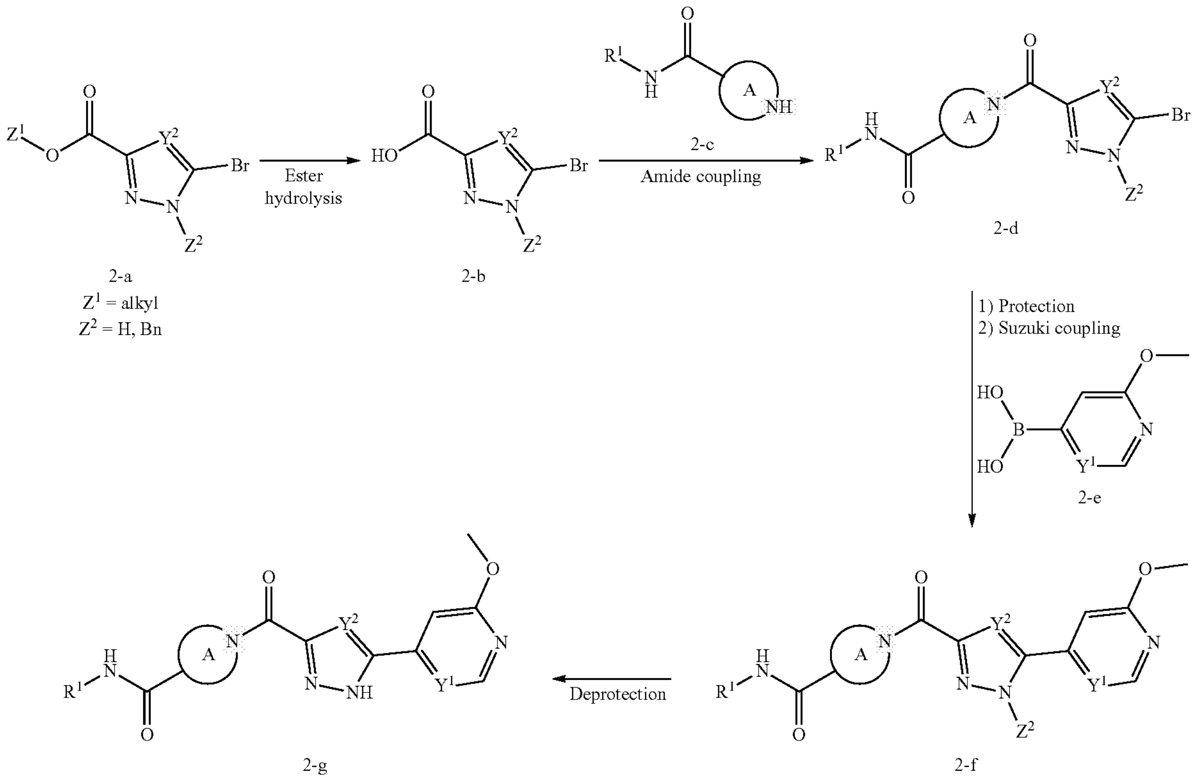

2-a
$Z^1$ = alkyl
$Z^2$ = H, Bn 2-b 2-d 2-e 2-f 2-g

In Scheme 2 above, $R^1$, $Y^1$, $Y^2$, Ring A are as described herein.

A compound of formula 2-b may be prepared by hydrolysis of either free NH or N protected pyrazole acid of formula 2-a using conditions known to one of ordinary skill in the art. Standard conditions, such as, for example, LiOH or NaOH in a mixture of MeOH, water, and THF, may be used.

A compound of formula 2-d is prepared by coupling an acid of formula 2-b with an amine of formula 2-c using a standard coupling reagent, such as, for example, HATU, in the presence of a suitable base, such as, for example, DIPEA in DMF.

In some embodiments, a compound of formula 2-d with free pyrazole NH is further protected with THP protecting groups by reacting with DHP with a suitable acid, such as, for example, p-TsOH in THF.

A compound of formula 2-f with a protected pyrazole, in some embodiments as a mixture of enantiomers, may be prepared under standard Suzuki coupling conditions by reacting an aryl boronic acid of formula 2-e with aryl bromide of formula 2-d using conditions known to one of ordinary skill in the art. A standard Suzuki condition such as, for example, $Pd(dppf)Cl_2$ in the presence of a base, such as, for example, $K_2CO_3$, in a suitable solvent, such as, for example, a mixture of 1,4-dioxane and water.

A compound of formula 2-g, as a mixture of enantiomers in some embodiments, may be prepared by cleavage of the protecting group. In some embodiments, a benzyl protecting group is removed using a catalytic amount of palladium in the presence of ammonium formate. In some embodiments, a THP protecting group is removed by using a suitable acid, such as, for example, HCl in MeOH or TFA in DCM.

In Scheme 3 above, $R^1$, $R^2$, $R^3$, and $Y^1$ are as described herein.

A compound of formula 3-c may be prepared by a coupling reaction of a commercially available acid of formula 3-a and an alkyl ester piperidine of formula 3-b using a standard coupling condition with reagents, such as, for example, HATU or EDCI/HOBt, in the presence of a suitable base, such as, for example, DIPEA in DMF. In some embodiments, compounds of formula 3-c are protected with THP or SEM protecting groups under suitable conditions known to one of ordinary skill in the art to produce aryl bromides of formula 3-d. Compounds of formula 3-d are further reacted with aryl boronic acids of formula 3-e using a Suzuki coupling reaction to produce biaryl compounds of formula 3-f.

In some embodiments, compounds of formula 3-c are protected with a THP protecting group using DHP in the presence of p-TsOH. The product may be further reacted using an Ir-catalyzed borylation process using Dtbpy, $[Ir(COD)OMe]_2$, $B_2Pin_2$ in MTBE, and THF to synthesize compounds of formula 3-d'. Compounds of formula 3-d' may be reacted with aryl boronic acids of formula 3-e' in a Suzuki coupling reaction to produce compounds of formula 3-f.

Scheme 3

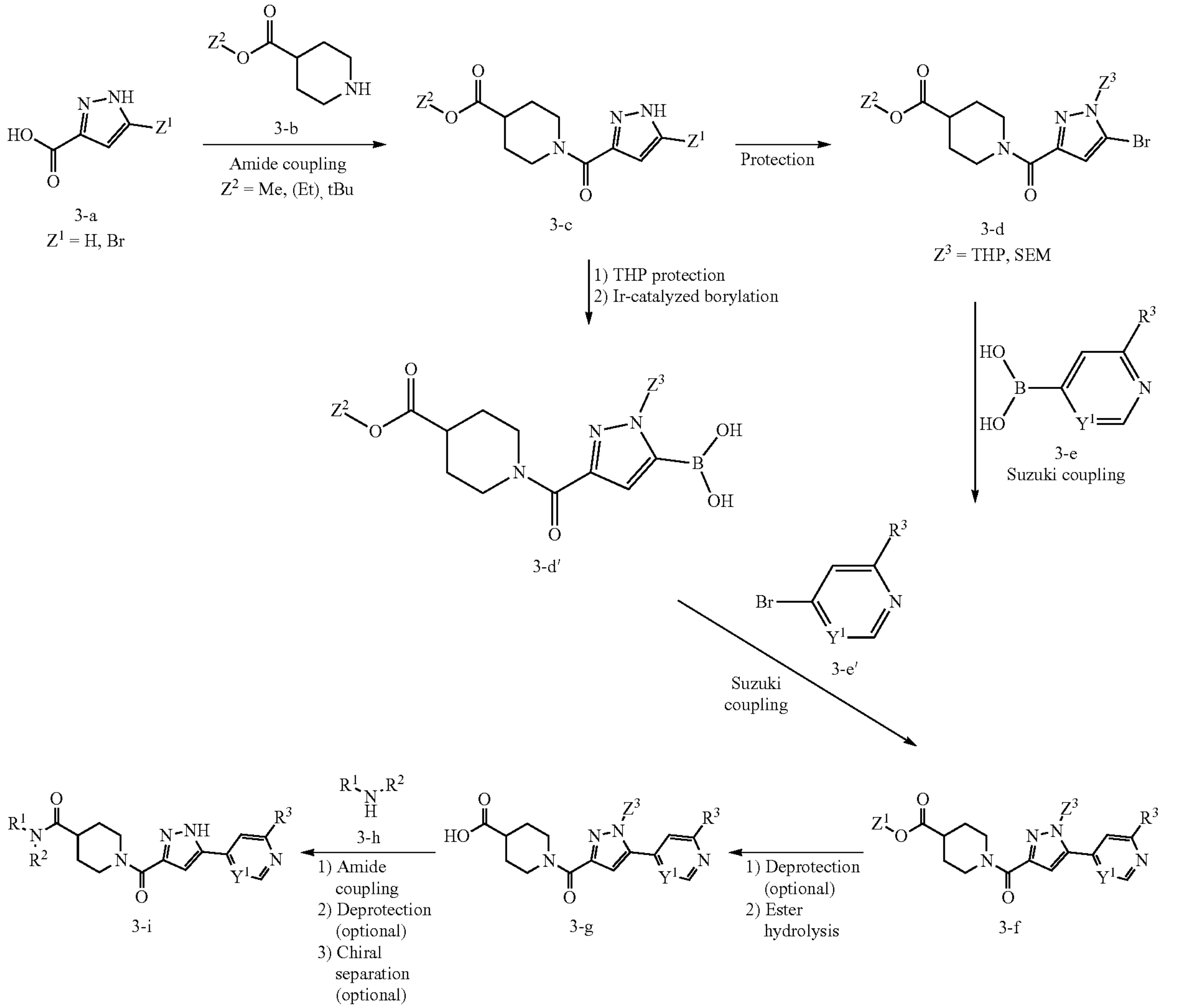

In some embodiments, compounds of formula 3-f are first treated with TFA in DCM or other suitable conditions to deprotect THP group.

In some embodiments, compounds of formula 3-g are prepared by hydrolysis of the ester in compound 3-f or deprotected 3-f using standard hydrolysis conditions. Suitable hydrolysis conditions include, for example, TFA in DCM to hydrolyze i-butyl ester and LiOH in a mixture of THE, MeOH, and water to hydrolyze methyl ester.

An acid of formula 3-g may be coupled with an amine of formula 3-h using conditions such as T3P®, HATU, or EDCI/HOBt in the presence of a suitable base, such as, for example, TFA or DIPEA, in a solvent, such as, for example, DMF. In some embodiments, an acid of formula 3-g is converted to its corresponding acyl chloride using reagents such as, for example, oxalyl chloride in DMF and DCM, followed by addition of an amine of formula 3-h with DIPEA and DMAP. The THP protecting group in the product of this coupling reaction may be cleaved using, for example, TFA in DCM, to produce compounds of formula 3-i. In some embodiments, diastereomers of compound 3-i were further separated using chiral separation.

In Scheme 4 above $R^1$, $R^3$, $Y^1$, $Y^2$, $Y^3$, and Ring A are as described herein.

As depicted in Scheme 4 above, a compound of formula 4-c may be prepared by coupling of an acid of formula 4-a with an amine of formula 4-b using coupling conditions such as, but not limited to, HATU or EDCI/HOBt, DIPEA in DMF.

Compounds of formula 4-d may be prepared by deprotection of t-Boc protecting group using suitable conditions, such as, for example, MA in DCM or HCl in 1,4-dioxane.

Compounds of formula 4-f may be prepared by adding a protecting group such as SEM or THP on compounds of formula 4-e using standard conditions known to one of ordinary skill in the art, such as, for example, SEM-$C_1$ in the presence of $K_2CO_3$ or NaH in DMF or DHP in the presence of p-TsOH in THF.

In some embodiments, a compound of formula 4-f is reacted with a boronic acid of formula 4-g using standard Suzuki coupling conditions to produce a compound of formula 4-h. Suzuki conditions may use reagents such as, for example, $Pd(dppf)Cl_2$, with a base such as, for example, $K_2CO_3$ or $K_3PO_4$ in a suitable solvent, such as, for example, Scheme 4

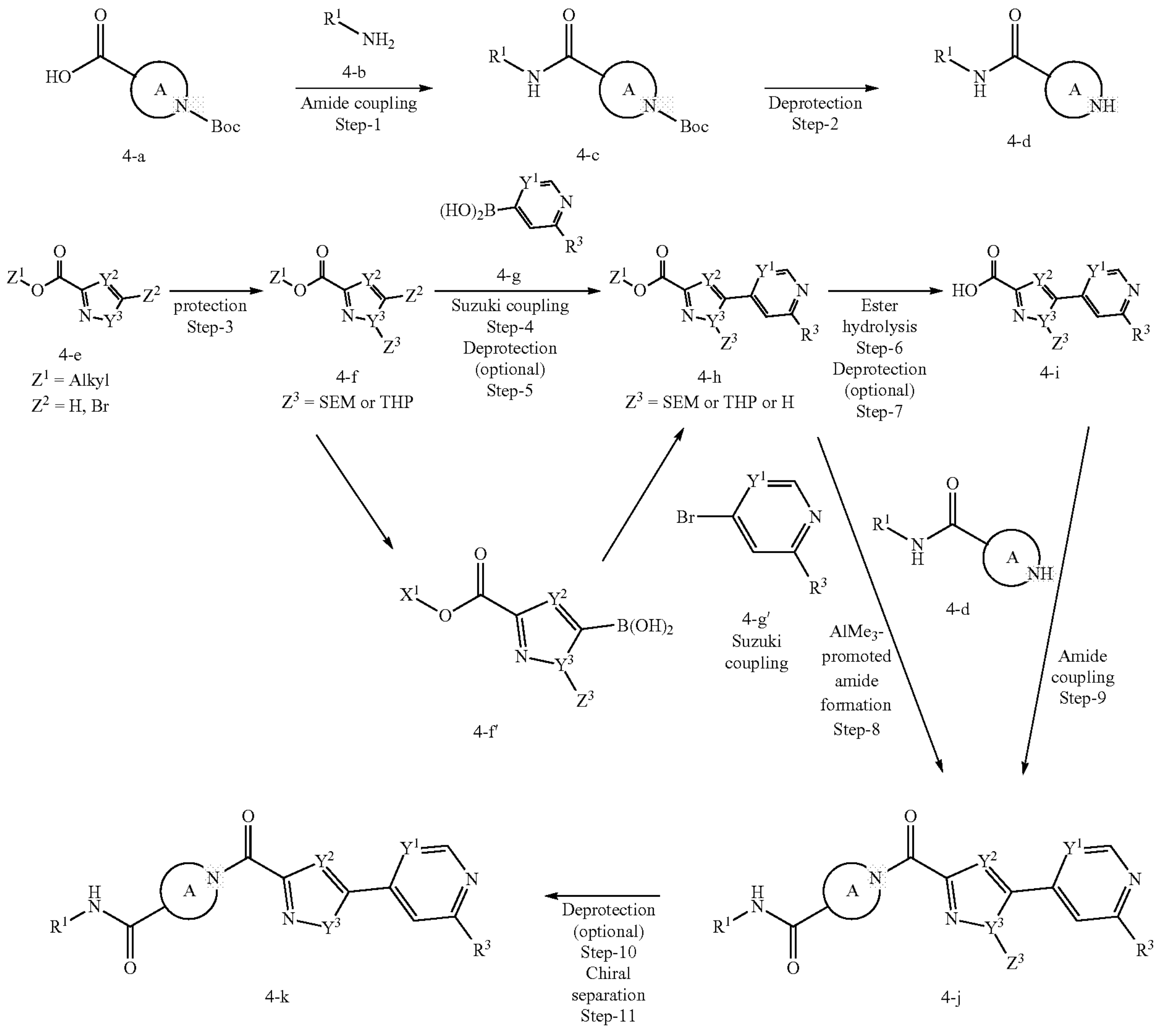

1,4-dioxane or water. In some embodiments, the product of a Suzuki coupling may undergo SEM or THP deprotection to form a product of formula 4-h.

Alternatively, in some embodiments, a compound of formula 4-f is converted to a boronic acid 4-fusing borylation conditions, such as, for example, Dtbpy, [Ir(Cod)OMe]$_2$, or $B_2pin_2$ in MTBE. Subsequently, a compound of formula 4-h directly with amines of formula 4-d promoted by reagents such as, for example, $AlMe_3$.

In some embodiments, a protecting group, such as, for example, SEM, is cleaved from a compound of formula 4-j to produce a compound of formula 4-k. In some embodiments, diastereomeric mixtures of compounds of formula 4-k are separated using a chiral separation technique.

Scheme 5

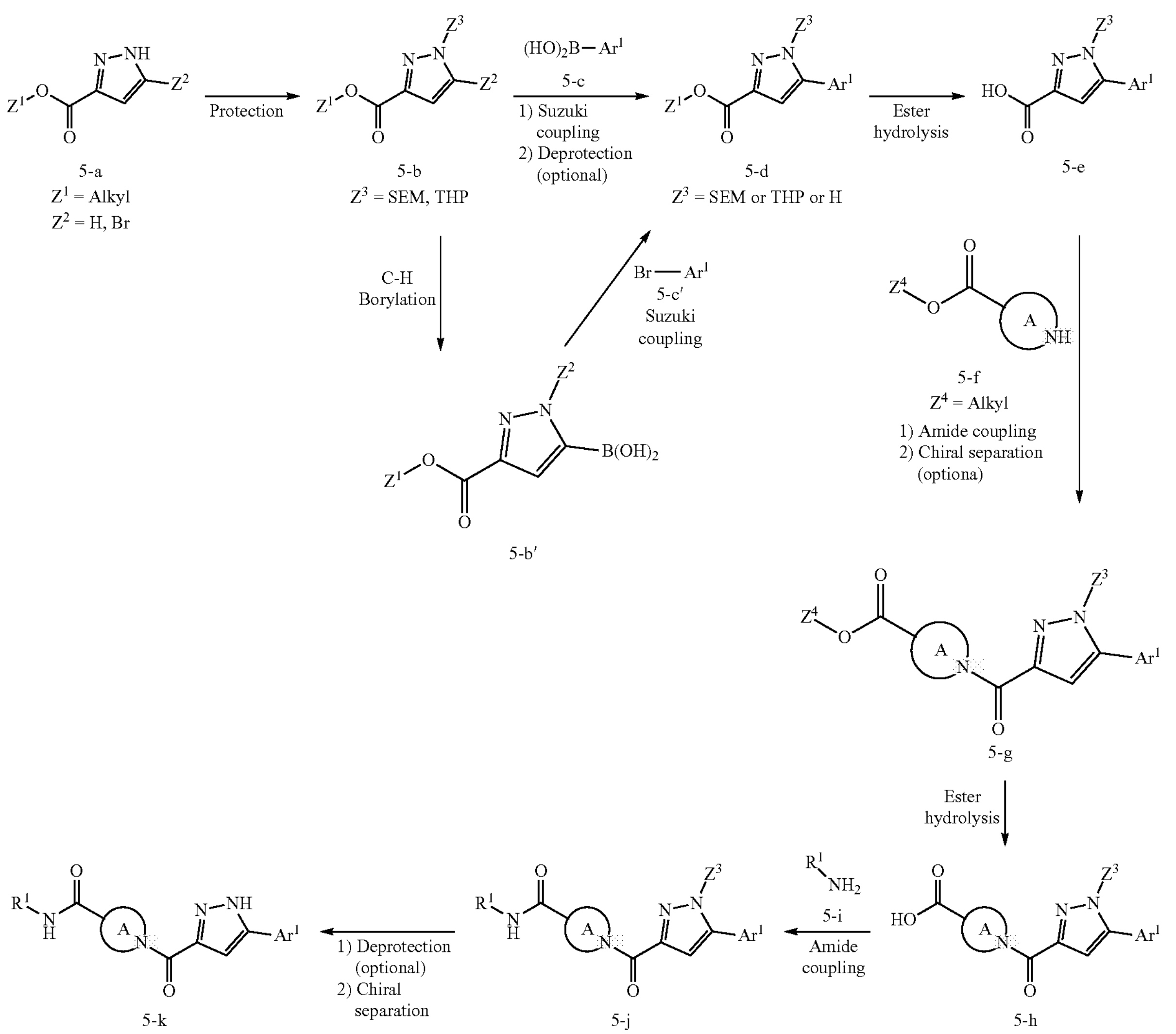

formula 4-h may be prepared using standard Suzuki coupling conditions between compounds of formula 4-f' and 4-g'.

A compound of formula 4-h may be hydrolyzed using standard conditions, such as, for example, LiOH in a mixture of water, THF, and MeOH, to deliver acids of formula 4-i. In some embodiments, the product formed by hydrolysis undergoes deprotection of a SEM or THP group to produce the unprotected compound 4-i.

Compounds of formula 4-j may be prepared by an amide coupling reaction between compounds of formulae 4-i and 4-d using conditions such as, for example, EDCI/HOBt or HAM with DIPEA in DMF. In some embodiments, compounds of formula 4-j are prepared by reacting esters of In Scheme 5 above, $R^1$, $Ar^1$, and Ring A are as described herein.

As depicted in Scheme 5 above, a compound of formula 5-a may be protected with a suitable protecting group, such as, for example, SEM or THP. In some embodiments, compounds of formula 5-b are reacted under standard Suzuki coupling conditions with an aryl boronic acid of formula 5-c. Standard Suzuki reaction conditions include, for example, a catalytic palladium source, such as, for example, $Pd(dppf)Cl_2$, in the presence of a suitable base, such as, for example, $K_2CO_3$, in a solvent, such as, for example, water or 1,4-dioxane. The reaction may be carried out at ambient temperature or at an elevated temperature.

In some embodiments, a compound of formula 5-b undergoes C—H borylation reaction using Dtbpy, [Ir(Cod)OMe]$_2$, and $B_2Pin_2$ in MTBE to form a boronic acid of formula 5-b'. Subsequently, compounds of formula 5-b' may be reacted with an aryl halide of formula 5-c' using standard Suzuki reaction conditions.

In some embodiments, a compound of formula 5-d undergoes a deprotection reaction using suitable conditions, such as, for example, TFA in DCM.

An alkyl ester of formula 5-e may be hydrolyzed using standard conditions, such as, for example, LiOH in a mixture of THF, MeOH, and water.

Acids of formula 5-f and alkyl amines of formula 5-g may be coupled together using a suitable coupling reagent, such as, for example, HATU or HOBt/EDCI, in the presence of a suitable base, such as, for example, DIPEA, that promotes the reaction. A suitable solvent, such as, for example, DMF, may be used.

In some embodiments, enantiomeric mixtures of an alkyl ester of formula 5-h are separated through chiral column purification. In some embodiments, the mixtures are used in the following step without prior separation. Compounds of formula 5-h may be hydrolyzed to acid of formula 5-i using LiOH in a mixture of THF, MeOH, and water or in case of tert-butyl ester, using HCl in 1,4-dioxane.

Acids of formula 5-i may be coupled with amines of formula 5-j using standard amide coupling conditions, such as, for example, HATU or HOBt/EDCI, DIPEA in DMF. In some embodiments, compounds of formula 5-j may be deprotected to produce compounds of formula 5-k. In some embodiments, when compounds of formula 5-k exist as diastereomeric mixtures, the diastereomers are separated by purification through a chiral column.

It will be appreciated that further synthetic manipulation may be desired to obtain certain compounds of Formula (I). Modifications to the above General Reaction Scheme I, such as varying the starting(s) material or modifying any of the reaction products are possible. Methods for these and other modifications to the above exemplary scheme are well known in the art and described in more detailed in the Examples.

It will also be appreciated by those skilled in the art that in the processes described herein the functional groups of intermediate compounds may need to be protected by suitable protecting groups, even if not specifically described. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidine include t-butoxycarbonyl, benzyloxycarbonyl, and the like. Suitable protecting groups for mercapto include C(O) R" (where R" is alkyl, aryl or arylalkyl), p methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

Analogous reactants to those described above may be identified through the indices of known chemicals prepared by the Chemical Abstract Service of the American Chemical Society, which are available in most public and university libraries, as well as through on line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Weimuth "Handbook of Pharmaceutical Salts," Verlag Helvetica Chimica Acta, Zurich, 2002.

In general, the compounds used in the reactions described herein may be made according to General Reaction Schemes 1-5 and/or organic synthesis techniques known to those of ordinary skill in this art, starting from commercially available chemicals and/or front compounds described in the chemical literature. "Commercially available chemicals" may be obtained from standard commercial sources including Acros Organics (Pittsburgh PA), Aldrich Chemical (Milwaukee WI, including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester PA), Crescent Chemical Co, (Hauppauge NY), Eastman Organic Chemicals, Eastman Kodak Company (Rochester NY), Fisher Scientific Co. (Pittsburgh PA), Fisons Chemicals (Leicestershire UK), Frontier Scientific (Logan UT), ICN Biomedicals, Inc. (Costa Mesa CA), Key Organics (Cornwall U.K.), Lancaster Synthesis (Windham NH), Maybridge Chemical Co. Ltd. (Cornwall U.K.), Parish Chemical Co. (Orem UT), Pfaltz & Bauer, Inc. (Waterbury CT), Polyorganix (Houston TX), Pierce Chemical Co. (Rockford IL), Riedel de Haen AG (Hanover, Germany), Spectrum Quality Product, Inc. (New Brunswick, NJ), Tel America (Portland OR), Trans World Chemicals, Inc. (Rockville MD), and Wako Chemicals USA, Inc. (Richmond VA).

Methods known to one of ordinary skill in the art may be identified through various reference books, articles and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3 527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN:

0-471-93022-9; Quin, L. D. et al. “A Guide to Organophosphorus Chemistry” (2000) Wiley-Interscience, ISBN: 0-471-31824-8; Solomons, T. W. G. “Organic Chemistry” 7th Edition (2000) John Wiley & Sons, ISBN: 0-471-19095-0; Stowell, J. C., “Intermediate Organic Chemistry” 2nd Edition (1993) Wiley-Interscience, ISBN: 0-471-57456-2; “Industrial Organic Chemicals: Starting Materials and Intermediates: An Ullmann’s Encyclopedia” (1999) John Wiley & Sons, ISBN: 3-527-29645-X, in 8 volumes; “Organic Reactions” (1942-2000) John Wiley & Sons, in over 55 volumes; and “Chemistry of Functional Groups” John Wiley & Sons, in 73 volumes.

Disclosed herein are compositions comprising at least one entity chosen from compounds of Formula (I) and pharmaceutically acceptable salts thereof and optionally at east one pharmaceutically acceptable carrier. The at least one pharmaceutically acceptable carrier may be chosen according to the particular route of administration for which the composition is intended.

The pharmaceutical compositions of the present disclosure may be formulated for parenteral; oral, inhalation spray, topical, rectal, nasal, buccal, vaginal and/or implanted reservoir administration, etc. The term “parenteral” as used herein includes subcutaneous, intravenous, intramuscular, intra-articular, intra-synovial, intrasternal, intrathecal, intrahepatic, intralesional and intracranial injection or infusion techniques. In some embodiments, the compositions are administered intravenously, orally, subcutaneously, or via intramuscular administration. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer’s solution and isotonic sodium chloride solution. In addition, sterile, fixed oils are conventionally employed as a solvent or suspending medium.

Any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms, may also be used for the purposes of formulation.

For oral administration, a compound (e.g., a compound of Formula (I) or pharmaceutically acceptable salt thereof) may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient is combined with an emulsifying and/or suspending agent. If desired; certain sweetening, flavoring or coloring agents may also be added.

Compounds and compositions of the present disclosure may be used to treat and/or prevent various types of cancers, including cancers that are responsive to agents that target the RXRα and/or PPARγ pathways. Accordingly, disclosed herein are methods for treating and/or preventing cancer comprising administering to a subject in need thereof an effective amount of at least one entity chosen from compounds of Formula (I) and pharmaceutically acceptable salts thereof. In some embodiments, the cancer is chosen from advanced bladder cancers, luminal breast cancer, prostate cancer, luminal bladder cancer, basal bladder cancer, chemotherapy resistant cancer; and immunotherapy resistant cancer.

In general, an appropriate dose and treatment regimen provide at least one compound of the present disclosure in an amount sufficient to provide therapeutic and/or prophylactic benefit. For both therapeutic treatment and prophylactic or preventative measures, therapeutic and/or prophylactic benefit includes, for example, an improved clinical outcome, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated with the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival, “Treatment” can include prolonging survival when compared to expected survival if a subject were not receiving treatment, Subjects in need of treatment include: (i) those who already have, e.g., cancers that are responsive to agents that target the RXRα and/or PPARγ pathways; (ii) subjects prone to have or at risk of developing such cancers; and (iii) those in which such cancers is to be prevented (i.e., decreasing the likelihood of occurrence of the disease, disorder; or condition).

In some embodiments of the methods described herein, the subject is a human. In some embodiments of the methods described herein, the subject is a non-human animal. A subject in need of treatment as described herein may exhibit at least one symptom or sequelae of such cancers or may be at risk of developing such cancers, Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, faint, and zoo animals.

The effectiveness of the compounds of the present disclosure in treating and/or preventing cancers that are responsive to agents that target the RXRα and/or PPARγ pathways can readily be determined by a person of ordinary skill in the medical and clinical arts. Determining and adjusting an appropriate dosing regimen (e.g., adjusting the amount of compound per dose and/or number of doses and frequency of dosing) can also readily be performed by a person of ordinary skill in the medical and clinical arts, One or any combination of diagnostic methods, including physical examination, assessment and monitoring of clinical symptoms, and performance of analytical tests and methods described herein, may be used for monitoring the health status of the subject.

The administration of at least one entity of the present disclosure or pharmaceutical composition comprising at least one such entity may be in conjunction with one or more other therapies, e.g., at least one additional anti-cancer agent, or at least one agent for reducing toxicities of therapy. For example, at least one palliative agent to counteract (at least in part) a side effect of a therapy may be administered. Agents (chemical or biological) that promote recovery or counteract side effects of administration of antibiotics or corticosteroids, are examples of such palliative agents.

Additional embodiments include:

1. A compound of Formula (I)

Formula (I)

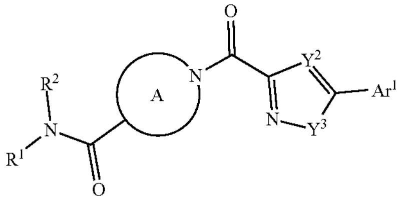

or a pharmaceutically acceptable salt thereof, wherein:

$Ar^1$ is chosen from

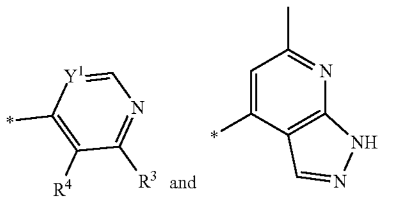

wherein $Y^1$ is chosen from N and C—$X^1$ wherein $X^1$ is chosen from hydrogen, hydroxyl, halogens, and $C_1$-$C_4$ alkyls;

$R^3$ is chosen from hydrogen, optionally substituted alkyls, optionally substituted amines, halogens, cyano, and optionally substituted alkoxys; and $R^4$ is chosen from hydrogen and alkyl;

either $Y^2$ is chosen from C—$X^2$ and N and $Y^3$ is NH, or $Y^2$ is NH and $Y^3$ is C—$X^2$, wherein $X^2$ is chosen from hydrogen and halogens;

Ring A is chosen from saturated 6- to 9-membered cyclic rings optionally substituted with at least one substituent chosen from halogens, hydroxyl, and optionally substituted alkyls;

$R^1$ is chosen from —$(CHR^5)_k$—$(CR^6R^7)_n$—$(O)_m$-Ring B, wherein k is 0 or 1, n is 0 or 1, m is 0 or 1;

$R^5$ is chosen from hydrogen and optionally substituted alkyls, $R^6$ is chosen from hydrogen and halogens, $R^7$ chosen from hydrogen and halogens, and Ring B is chosen from optionally substituted aryls,
optionally substituted heteroaryls,
optionally substituted cycloalkyls,
optionally substituted heterocycloalkyls,
optionally substituted cycloalkenyls, and
optionally substituted heterocycloalkenyls; and $R^2$ is chosen from hydrogen and optionally substituted alkyls.

2. The compound or pharmaceutically acceptable salt according to embodiment 1, wherein Ring A is chosen from piperidinyl and saturated 7- to 9-membered bicyclic rings, and Ring A is optionally substituted with at least one substituent chosen from halogens, hydroxyl, and optionally substituted alkyls.

3. The compound or pharmaceutically acceptable salt according to any one of embodiments to 2, wherein Ring A is chosen from piperidinyl, azaspirooctane, azaspirononane, azabicyclooctane, and oxa-azabicyclononane, and Ring A is optionally substituted with at least one substituent chosen from halogens, hydroxyl, and optionally substituted alkyls.

4. The compound or pharmaceutically acceptable salt according to any one of embodiments 1 to 3, wherein Ring B is chosen from optionally substituted 5- to 10-membered aryls,
optionally substituted 5- to 10-membered heteroaryls,
optionally substituted 3- to 10-membered cycloalkyls,
optionally substituted 4- to 10-membered heterocycloalkyls,
optionally substituted 6- to 10-membered cycloalkenyls, and
optionally substituted 6- to 10-membered heterocycloalkenyls.

5. The compound or pharmaceutically acceptable salt according to any one of embodiments 1 to 4, wherein Ring B is chosen from optionally substituted 5- to 6-membered monocyclic aryls, optionally substituted 10-membered bicyclic aryls, optionally substituted 5- to 6-membered monocyclic heteroaryls, optionally substituted 9- to 10-membered bicyclic heteroaryls, optionally substituted 3- to 10-membered monocyclic alkyls, optionally substituted 7- to 10-membered bridged bicyclic alkyls, optionally substituted 7- to 10-membered spirocyclic bicyclic alkyls, optionally substituted 4- to 10-membered monocyclic heterocycloalkyls, optionally substituted 7- to 10-membered bridged bicyclic heterocycloalkyls, optionally substituted 7- to 10-membered spirocyclic bicyclic heterocycloalkyls, optionally substituted 5- to 6-membered monocyclic cycloalkenyls, optionally substituted 8- to 10-membered bicyclic cycloalkenyls, optionally substituted 5- to 6-membered monocyclic heterocycloalkenyls, and optionally substituted 8- to 10-membered bicyclic heterocycloalkenyls.

6. The compound or pharmaceutically acceptable salt according to any one of embodiments 1 to 5, wherein Ring B is chosen from optionally substituted 5- to 6-membered monocyclic aryls, optionally substituted 10-membered bicyclic aryls, optionally substituted 5- to 6-membered monocyclic heteroaryls having one to three ring heteroatoms chosen from oxygen and nitrogen, optionally substituted 9- to 10-membered bicyclic heteroaryls having one to three ring heteroatoms chosen from oxygen and nitrogen, optionally substituted 3- to 10-membered monocyclic alkyls, optionally substituted 7- to 10-membered bridged bicyclic alkyls, optionally substituted 7- to 10-membered spirocyclic bicyclic alkyls, optionally substituted 4- to 10-membered monocyclic heterocycloalkyls having one to three ring heteroatoms chosen from oxygen, silicon, and nitrogen, optionally substituted 7- to 10-membered bridged bicyclic heterocycloalkyls having one to three ring heteroatoms chosen from oxygen and nitrogen, optionally substituted 7- to 10-membered spirocyclic bicyclic heterocycloalkyls having one to three ring heteroatoms chosen from oxygen and nitrogen, optionally substituted 5- to 6-membered monocyclic cycloalkenyls, optionally substituted 8- to 10-membered bicyclic cycloalkenyls, optionally substituted 5- to 6-membered monocyclic heterocycloalkenyls having one to three ring heteroatoms chosen from oxygen and nitrogen, and optionally substituted 8- to 10-membered bicyclic heterocycloalkenyls having one to three ring heteroatoms chosen from oxygen and nitrogen.

7. The compound or pharmaceutically acceptable salt according to any one of embodiments 1 to 6, wherein Ring A is chosen from

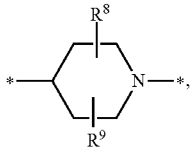
,
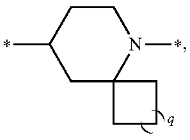
,
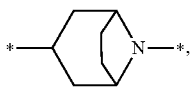
, and
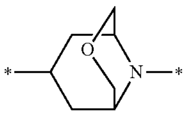

wherein q is 0 or 1, and $R^8$ and $R^9$ are each independently chosen from hydrogen, halogens, hydroxyl, optionally substituted alkoxys, and optionally substituted alkyls.

8. The compound or pharmaceutically acceptable salt thereof according to embodiment 1 chosen from compounds of Formulae (II)-(V):

Formula (II)

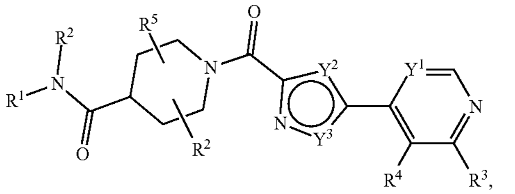
,

Formula (III)

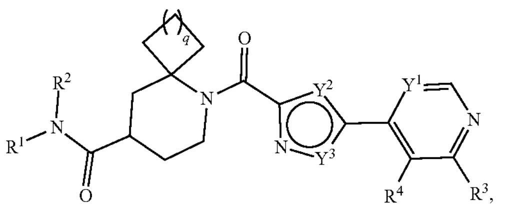
,

-continued

Formula (IV)

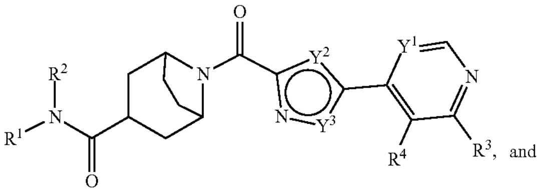
, and

Formula (V)

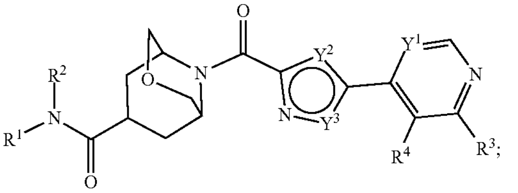
;

wherein $Y^1$ is chosen from N and C—$X^1$ wherein $X^1$ is chosen from hydrogen, hydroxyl, halogens, and $C_1$-$C_4$ alkyls;

$R^2$ is chosen from hydrogen and optionally substituted alkyls;

$R^3$ is chosen from hydrogen, optionally substituted alkyls, optionally substituted amines, halogens, cyano, and optionally substituted alkoxys;

$R^4$ is chosen from hydrogen and alkyl;

either $Y^2$ is chosen from C—$X^2$ and N and $Y^3$ is NH, or $Y^2$ is NH and $Y^3$ is C—$X^2$, wherein $X^2$ is chosen from hydrogen and halogens;

wherein q is 0 or 1;

$R^1$ is chosen from $-(CHR^5)_k-(CR^6R^7)_n-(O)_m$-Ring B, wherein k is 0 or 1, n is 0 or 1, m is 0 or 1, $R^5$ is chosen from hydrogen and optionally substituted alkyls, $R^6$ is chosen from hydrogen and halogens, $R^7$ chosen from hydrogen and halogens, and Ring B is chosen from optionally substituted 5- to 6-membered monocyclic aryls, optionally substituted 10-membered bicyclic aryls, optionally substituted 5- to 6-membered monocyclic heteroaryls having one to three ring heteroatoms chosen from oxygen and nitrogen, optionally substituted 9- to 10-membered bicyclic heteroaryls having one to three ring heteroatoms chosen from oxygen and nitrogen, optionally substituted 3- to 10-membered monocyclic alkyls, optionally substituted 7- to 10-membered bridged bicyclic alkyls, optionally substituted 7- to 10-membered spirocyclic bicyclic alkyls, optionally substituted 4- to 10-membered monocyclic heterocycloalkyls having one to three ring heteroatoms chosen from oxygen, silicon, and nitrogen, optionally substituted 7- to 10-membered bridged bicyclic heterocycloalkyls having one to three ring heteroatoms chosen from oxygen and nitrogen, optionally substituted 7- to 10-membered spirocyclic bicyclic heterocycloalkyls having one to three ring heteroatoms chosen from oxygen and nitrogen, optionally substituted 5- to 6-membered monocyclic cycloalkenyls, optionally substituted 8- to 10-membered bicyclic cycloalkenyls, optionally substituted 5- to 6-membered monocyclic heterocycloalkenyls having one to three ring heteroatoms chosen from oxygen and nitrogen, and optionally substituted 8- to 10-membered bicyclic heterocycloalkenyls having one to three ring heteroatoms chosen from oxygen and nitrogen; and $R^8$ and $R^9$ are each independently chosen from hydrogen, halogens, hydroxyl, optionally substituted alkoxys, and optionally substituted alkyls.

9. The compound or pharmaceutically acceptable salt according to any one of embodiments 1 to 8, wherein.

Ring B is chosen from

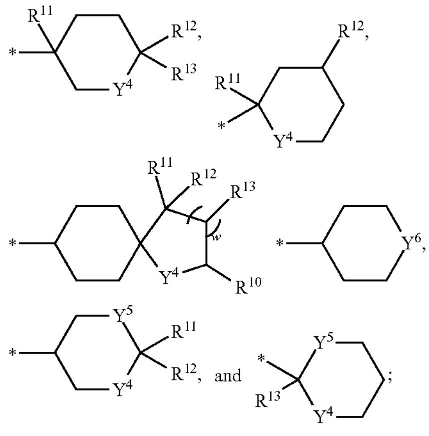
and ;

wherein:

w is 0 or 1;

$Y^1$ and $Y^5$ are each independently chosen from optionally substituted —$(CH_2)$—, optionally substituted —(NH)—, and —O—;

$Y^6$ is chosen from optionally substituted —$(CH_2)$—, optionally substituted —(NH)—, tetraalkylsilanes, and —O—;

$R^{10}$ is chosen from hydrogen, halogens, optionally substituted alkyls, and carbonyl; and $R^{11}$ and $R^{13}$ are each independently chosen from hydrogen, halogens, optionally substituted alkyls, hydroxyl, optionally substituted amines, and optionally substituted alkoxys.

10. The compound or pharmaceutically acceptable salt according to any one of embodiments 1 to 9, wherein Ring B is chosen from

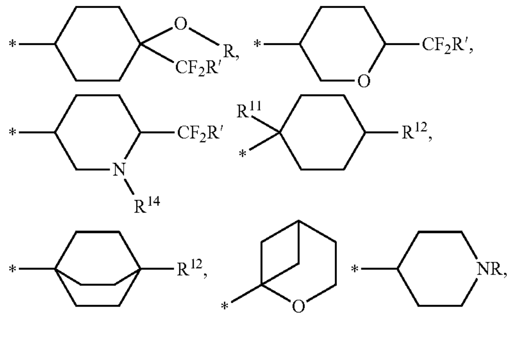

-continued

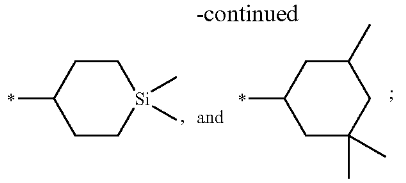
and ;

wherein $R^{11}$ and $R^{12}$ are each independently chosen from hydrogen, halogens, optionally substituted alkyls, hydroxyl, optionally substituted amines, and optionally substituted alkoxys;

$R^{14}$ is chosen from hydrogen and optionally substituted alkyls;

R is chosen from hydrogen, optionally substituted alkyls, and aryl; and

R' is chosen from hydrogen, optionally substituted alkyls, and halogens.

11. The compound or pharmaceutically acceptable salt according to any one of embodiments 1 to 9, wherein Ring B is chosen from

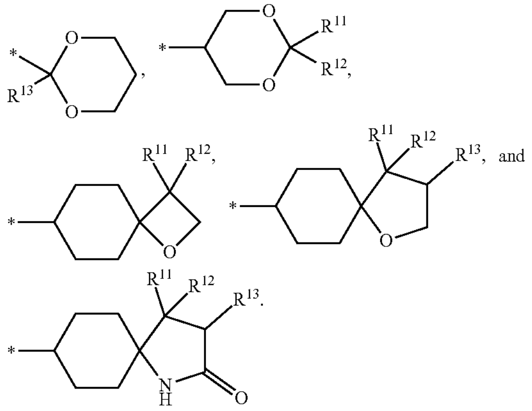
and wherein $R^{11}$, $R^{12}$, and $R^{13}$ are each independently chosen from hydrogen, halogens, hydroxyl; optionally substituted alkyls, optionally substituted amines, and optionally substituted alkoxys.

12. The compound or pharmaceutically acceptable salt according to any one of embodiments 1 to 8, wherein Ring B is chosen from

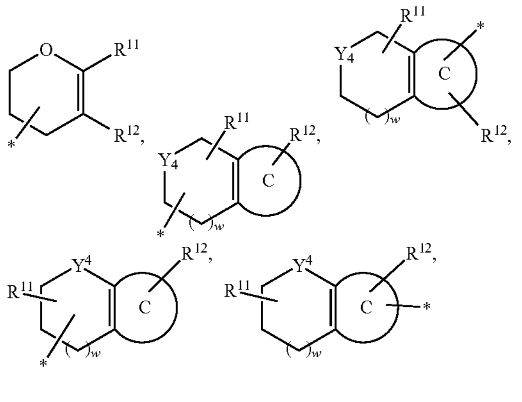

-continued

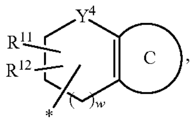

, and

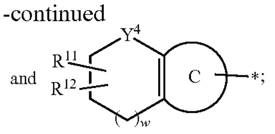

;

wherein w is 0 or 1, $Y^4$ is chosen from $SO_2$, optionally substituted sulfonamides, optionally substituted amides, optionally substituted —$(CH_2)$—; optionally substituted —(NH)—, and —O—;

$R^{11}$ and $R^{12}$ are each independently chosen from hydrogen, halogens, optionally substituted alkyls, hydroxyl, optionally substituted amines, and optionally substituted alkoxys; and Ring C is chosen from 5-membered aromatic rings, 5-membered heteroaromatic rings comprising 1 or 2 ring nitrogen atoms, 6-membered aromatic rings, and 6-membered heteroaromatic rings comprising 1 or 2 ring nitrogen atoms.

13. The compound or pharmaceutically acceptable salt according to any one of embodiments 1 to 8, wherein Ring B is chosen from

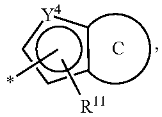

,

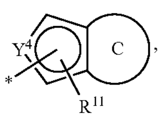

,

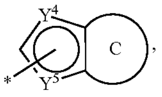

,

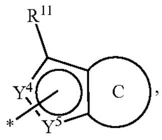

, and

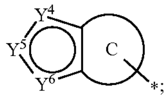

;

wherein $Y^4$, $Y^5$, and $Y^6$ are each independently chosen from optionally substituted —(CH)–, optionally substituted —(NH)—, and —O—;

$R^{11}$ is chosen from hydrogen, halogens, optionally substituted alkyls, hydroxyl, optionally substituted amines, and optionally substituted alkoxys; and Ring C is chosen from 5-membered aromatic rings; 5-membered heteroaromatic rings comprising 1 or 2 ring nitrogen atoms, 6-membered aromatic rings, and 6-membered heteroaromatic rings comprising 1 or 2 ring nitrogen atoms.

14. The compound or pharmaceutically acceptable salt according to any one of embodiments 1 to 8 and 13, wherein Ring B is chosen from

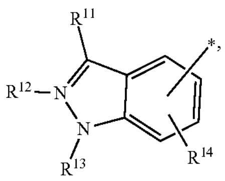

,

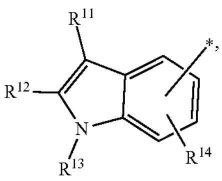

,

-continued

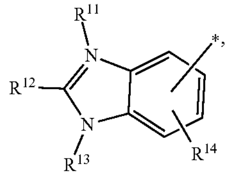

,

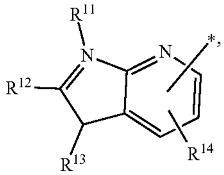

,

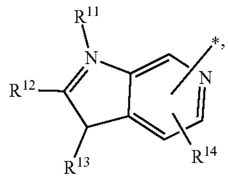

,

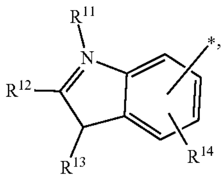

,

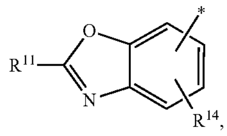

,

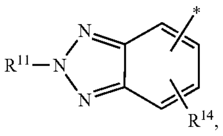

, and

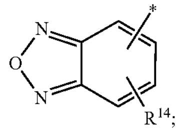

;

wherein when $R^{11}$ is not bonded to nitrogen, $R^{11}$ is chosen from hydrogen, halogens, optionally substituted alkyls, and hydroxyl, and $R^{11}$ is otherwise chosen from hydrogen and optionally substituted alkyls;

when $R^{12}$ is not bonded to nitrogen, $R^{12}$ is chosen from hydrogen, halogens, optionally substituted alkyls, and hydroxyl, and $R^{12}$ is otherwise chosen from hydrogen, and optionally substituted alkyls;

when $R^{13}$ is not bonded to nitrogen, $R^{13}$ is chosen from hydrogen, halogens, optionally substituted alkyls, and hydroxyl, and $R^{\prime 3}$ is otherwise chosen from hydrogen, and optionally substituted alkyls; and $R^{14}$ is chosen from hydrogen, halogens, optionally substituted alkyls, hydroxyl, optionally substituted amines, and optionally substituted alkoxys.

15. The compound or pharmaceutically acceptable salt according to any one of embodiments 1 to 8, wherein Ring B is chosen from

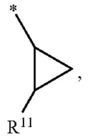

,

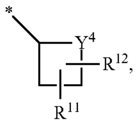

,

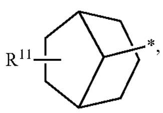

,

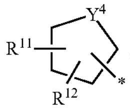

,

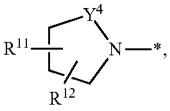

,

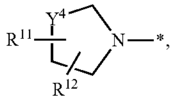

,

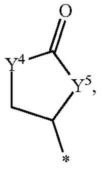

,

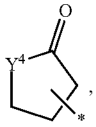

,

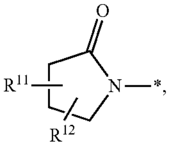

, and

-continued

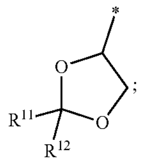

wherein $Y^4$, and $Y^5$ are each independently chosen from optionally substituted —($CH_2$)—, optionally substituted —(NH)—, and —O—; and $R^{11}$ and $R^{12}$ are independently chosen from hydrogen, cyano, halogens, optionally substituted alkyls, hydroxyl, optionally substituted amines, aryl, heteroaryl, and optionally substituted alkoxys.

16. The compound or pharmaceutically acceptable salt according to any one of embodiments 1 to 8 and 16, wherein Ring B is chosen from

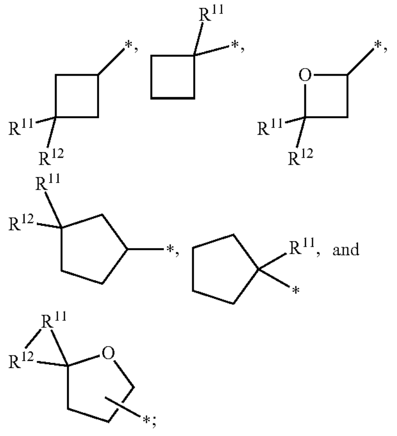

and wherein $R^{11}$ and $R^{12}$ independently are chosen from hydrogen, halogens, optionally substituted alkyls, hydroxyl, optionally substituted amines, and optionally substituted alkoxys.

17. The compound or pharmaceutically acceptable salt according to any one of embodiments 1 to 8, wherein Ring B is chosen from

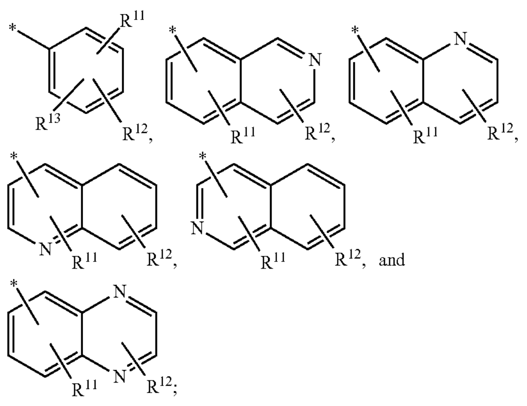

and wherein $R^{11}$, $R^{12}$, and $R^{13}$ are independently chosen from hydrogen, halogens, optionally substituted alkyls, hydroxyl, optionally substituted amines, and optionally substituted alkoxys.

18. The compound or pharmaceutically acceptable salt according to any one of embodiments 1 to 8 and 15, wherein Ring B is chosen from

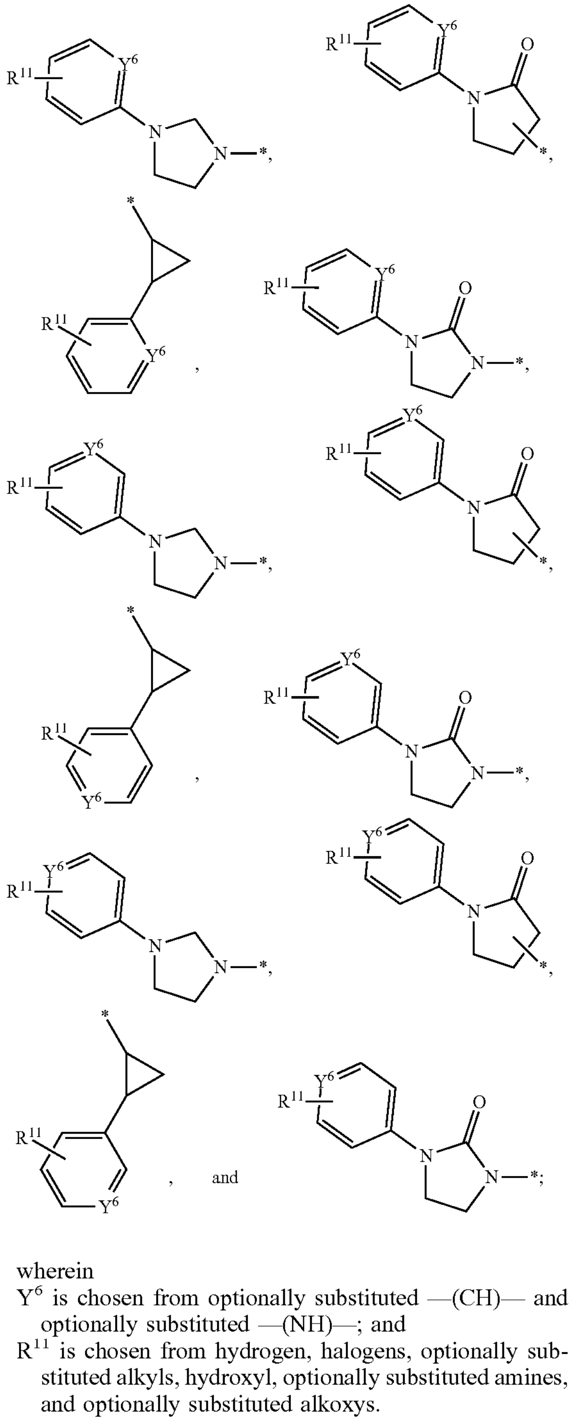

and wherein $Y^6$ is chosen from optionally substituted —(CH)— and optionally substituted —(NH)—; and $R^{11}$ is chosen from hydrogen, halogens, optionally substituted alkyls, hydroxyl, optionally substituted amines, and optionally substituted alkoxys.

19. The compound or pharmaceutically acceptable salt according to any one of embodiments 1 to 8, wherein Ring B is chosen from

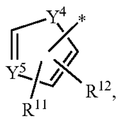 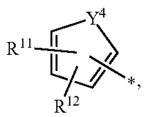 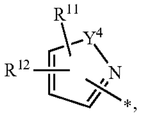

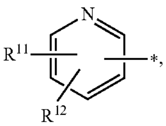 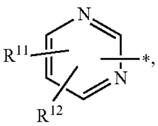 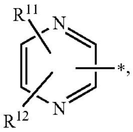 and

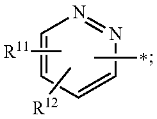

wherein $Y^4$ is chosen from optionally substituted —($CH_2$)—, optionally substituted —(NH)—, and —O—;

$Y^5$ is chosen from optionally substituted —(CH)— and N; and $R^{11}$ and $R^{12}$ are chosen from hydrogen, halogens, optionally substituted alkyls, hydroxyl, optionally substituted amities, and optionally substituted alkoxys.

20. The compound or pharmaceutically acceptable salt according to any one of embodiments 1 to 8, wherein Ring B is chosen from

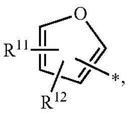 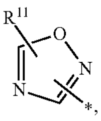 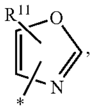 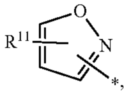 and

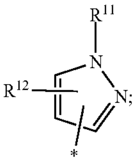

wherein $R^{11}$ and $R^{12}$ are chosen from hydrogen, halogens, optionally substituted alkyls, hydroxyl, optionally substituted amines, and optionally substituted alkoxys.

21. The compound or pharmaceutically acceptable salt according to any one of embodiments 1 to 8 and 12, wherein Ring B is chosen from

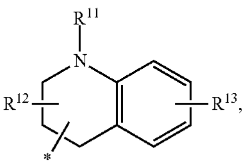 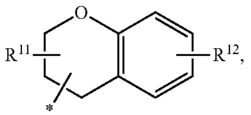

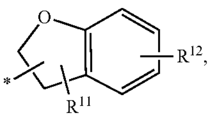 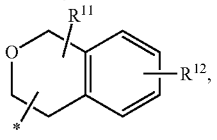

-continued

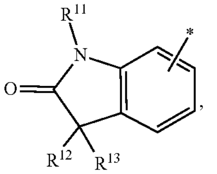 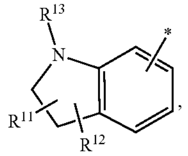

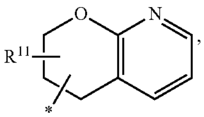 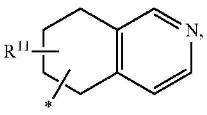

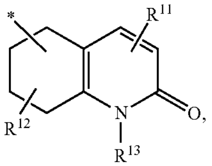 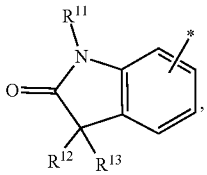

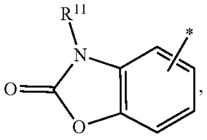 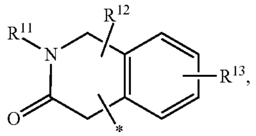

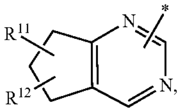 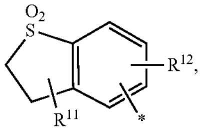 and

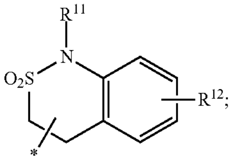

wherein $R^{11}$, $R^{12}$, and $R^{13}$ are independently chosen from hydrogen, halogens, optionally substituted alkyls, hydroxyl, optionally substituted amines, and optionally substituted alkoxys.

22. The compound or pharmaceutically acceptable salt according to any one of embodiments 1 to 21, wherein $R^1$ is chosen from —($CHR^5$)$_k$—($CR^6R^7$)$_n$—(O)$_m$-Ring B, wherein k is 0 or 1, n is 0 or 1, m is 0 or 1, $R^5$ is chosen from hydrogen and methyl, $R^6$ is chosen from hydrogen and halogens, $R^7$ chosen from hydrogen and halogens; and $R^2$ is chosen from hydrogen and methyl.

23. A compound chosen from:

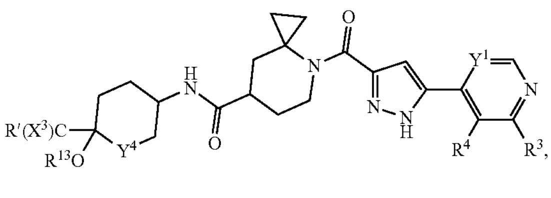

-continued

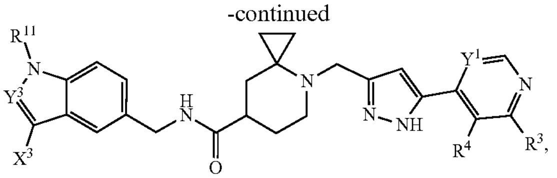
,

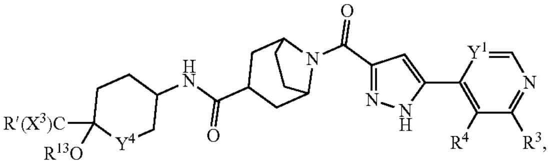
,

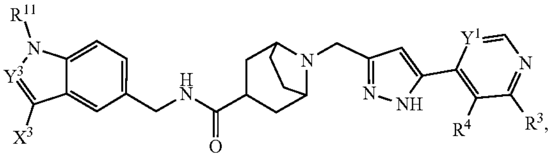
,

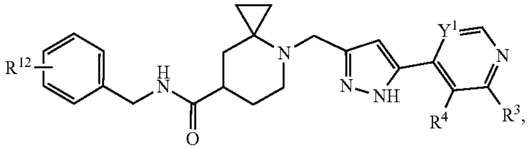
, and

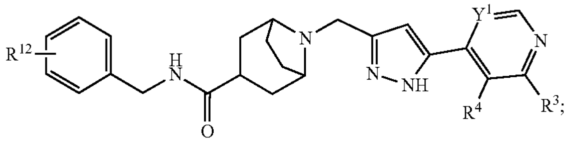
;

or pharmaceutically acceptable salt thereof, wherein $Y^1$ is chosen from N and C—$X^1$ wherein $X^1$ is chosen from hydrogen, hydroxyl, halogens, and $C_1$-$C_4$ alkyls;

$R^3$ is chosen from hydrogen, optionally substituted $C_1$-$C_3$ alkyls, halogens, cyano, and optionally substituted $C_1$-$C_3$ alkoxys; and $R^4$ is chosen from hydrogen and alkyl;

$Y^4$ is chosen from $CH_2$, O, and N—$R^{11}$;

$X^3$ is chosen from hydrogen and halogens;

R' is chosen from hydrogen and $C_1$-$C_3$ alkyls optionally substituted with at least one halogen;

$R^{11}$ is chosen from hydrogen and $C_1$-$C_3$ alkyls;

$R^{12}$ is chosen from hydrogen, halogens, and $C_1$-$C_3$ alkyls; and $R^{13}$ is chosen from hydrogen, halogens, $C_2$-$C_4$ alkoxys, and $C_1$-$C_3$ alkyls.

24. The compound or pharmaceutically acceptable salt according to embodiment 23, chosen from:

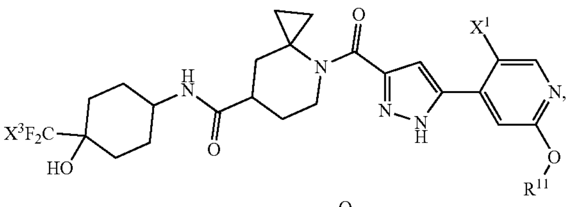
,

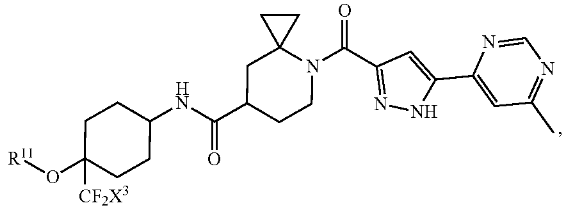
,

-continued

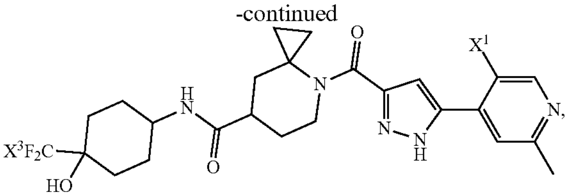
,

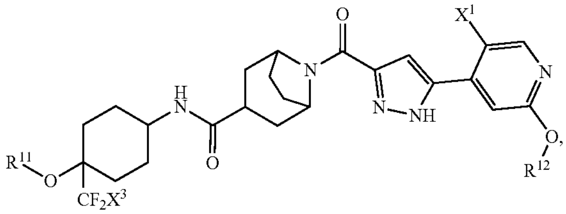
,

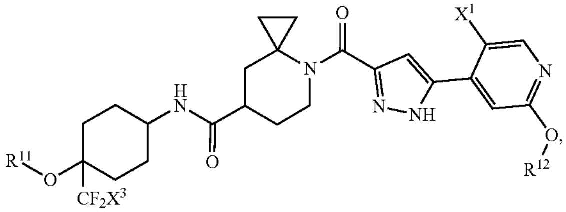
,

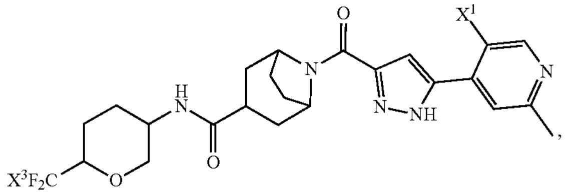
,

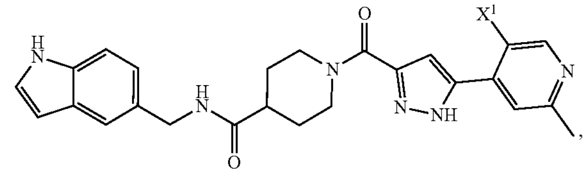
,

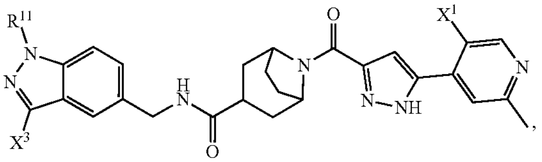
, and

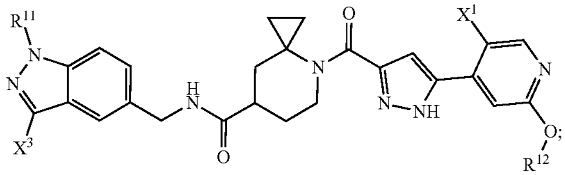
;

wherein $X^1$ is chosen from hydrogen, hydroxyl, halogens, and $C_1$-$C_4$ alkyls;

$X^3$ is chosen from hydrogen and halogens; and $R^{11}$ and $R^{12}$ are independently chosen from hydrogen and $C_1$-$C_3$ alkyls.

25. The compound or pharmaceutically acceptable salt according to any one of embodiments 1 to 24, wherein the optionally substituted alkyls are chosen from haloalkyls.

26. The compound or pharmaceutically acceptable salt according embodiment 25, wherein the haloalkyl is trifluoromethyl.

27. At least one compound chosen from:

1-(5-(5-chloro-2-methoxypyridin-4-yl)-1H-pyrazole-3-carbonyl)-N-((1s,4s)-4-methylcyclohexyl)piperidine-4-carboxamide;

1-(5-(5-chloro-2-methoxypyridin-4-yl)-1H-pyrazole-3-carbonyl)-N-((1r,4r)-4-methylcyclohexyl)piperidine-4-carboxamide;

1-(4-fluoro-5-(2-methoxypyridin-4-yl)-1H-pyrazole-3-carbonyl)-N-(4-methylcyclohexyl)piperidine-4-carboxamide;

(S)-1-(5-(5-chloro-2-methoxypyridin-4-yl)-1H-pyrazole-3-carbonyl)-N-(1-(3-fluorophenyl)ethyl)piperidine-4-carboxamide;

N-((1s,4s)-4-(difluoromethyl)cyclohexyl)-1-(5-(5-fluoro-2-methoxypyridin-4-yl)-1H-pyrazole-3-carbonyl)piperidine-4-carboxamide;

N-((1r,4r)-4-(difluoromethyl)cyclohexyl)-1-(5-(5-fluoro-2-methoxypyridin-4-yl)-1H-pyrazole-3-carbonyl)piperidine-4-carboxamide;

1-(5-(2-methoxypyridin-4-yl)-1H-pyrazole-3-carbonyl)-N-(4-methylcyclohexyl)piperidine-4-carboxamide;

N-(4-methylcyclohexyl)-1-[5-(2-methylpyridin-4-yl)-1H-pyrazole-3-carbonyl]piperidine-4-carboxamide;

1-(5-(2-methoxypyridin-4-yl)-1H-pyrazole-3-carbonyl)-N-((1s,4s)-4-methylcyclohexyl)piperidine-4-carboxamide;

N-((1s,4s)-4-ethylcyclohexyl)-1-(5-(2-methoxypyridin-4-yl)-1H-pyrazole-3-carbonyl)piperidine-4-carboxamide;

N-((1r,4r)-4-ethylcyclohexyl)-1-(5-(2-methoxypyridin-4-yl)-1H-pyrazole-3-carbonyl)piperidine-4-carboxamide;

1-(5-(3-chloropyridin-4-yl)-1H-pyrazole-3-carbonyl)-N-(4-methylcyclohexyl)piperidine-4-carboxamide;

1-[4-chloro-5-(2-methoxypyridin-4-yl)-1H-pyrazole-3-carbonyl]-N-[(1s,4s)-4-methylcyclohexyl]piperidine-4-carboxamide, 1-[4-chloro-5-(2-methoxypyridin-4-yl)-1H-pyrazole-3-carbonyl]-N-[(1r,4r)-4-methylcyclohexyl]piperidine-4-carboxamide;

1-[5-(6-methoxypyrimidin-4-yl)-1H-pyrazole-3-carbonyl]-N-[(1r,4s)-4-methylcyclohexyl]piperidine-4-carboxamide;

1-[5-(6-methoxypyrimidin-4-yl)-1H-pyrazole-3-carbonyl]-N-[(1s,4s)-4-methylcyclohexyl]piperidine-4-carboxamide;

1-[5-(5-chloro-2-methoxypyridin-4-yl)-1H-pyrazole-3-carbonyl]-N-[(3-chlorophenyl)methyl]piperidine-4-carboxamide;

N-((1s,4s)-4-(difluoromethyl)cyclohexyl)-1-(5-(2-methoxypyridin-4-yl)-1H-pyrazole-3-carbonyl)piperidine-4-carboxamide;

N-((1r,4r)-4-(difluoromethyl)cyclohexyl)-1-(5-(2-methoxypyridin-4-yl)-1H-pyrazole-3-carbonyl)piperidine-4-carboxamide;

1-(5-(5-fluoro-2-methoxypyridin-4-yl)-1H-pyrazole-3-carbonyl)-N-((1s,4s)-4-methylcyclohexyl)piperidine-4-carboxamide;

1-(5-(5-fluoro-2-methoxypyridin-4-yl)-1H-pyrazole-3-carbonyl)-N-((1r,4r)-4-methylcyclohexyl)piperidine-4-carboxamide;

(R)-1-[5-(5-chloro-2-methoxypyridin-4-yl)-1H-pyrazole-3-carbonyl]-N-[1-(3-chlorophenyl)ethyl]piperidine-4-carboxamide;

(S)-1-[5-(5-chloro-2-methoxypyridin-4-yl)-1H-pyrazole-3-carbonyl]-N-[1-(3-chlorophenyl)ethyl]piperidine-4-carboxamide;

1-[5-(5-chloro-2-methoxypyridin-4-yl)-1H-pyrazole-3-carbonyl]-N-(1-phenylpyrrolidin-3-yl)piperidine-4-carboxamide;

1-[5-(5-chloro-2-methoxypyridin-4-yl)-1H-pyrazole-3-carbonyl]-N-[(1s,4s)-4-(trifluoromethyl)cyclohexyl]piperidine-4-carboxamide;

1-[5-(5-chloro-2-methoxypyridin-4-yl)-1H-pyrazole-3-carbonyl]-N-[(1r,4r)-4-(trifluoromethyl)cyclohexyl]piperidine-4-carboxamide, 1-(5-(5-chloro-2-methoxypyridin-4-yl)-1H-pyrazole-3-carbonyl)-N-(imidazo[1,2-a]pyridin-2-ylmethyl)piperidine-4-carboxamide;

1-(5-(5-chloro-2-methoxypyridin-4-yl)-1H-pyrazole-3-carbonyl)-N-((5-chloropyridin-2-yl)methyl)piperidine-4-carboxamide;

1-[5-(5-Chloro-2-methoxypyridin-4-yl)-1H-pyrazole-3-carbonyl]-N-(2-methyl-1,3-dioxan-5-yl) piperidine-4-carboxamide;

N-((1H-indol-5-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(2,3,6-trifluorobenzyl)piperidine-4-carboxamide;

1-(5-(5-chloro-2-methoxypyridin-4-yl)-1H-pyrazole-3-carbonyl)-N-((1,3-dimethyl-1H-pyrazol-4-yl)methyl)piperidine-4-carboxamide;

1-(5-(5-chloro-2-methoxypyridin-4-yl)-1H-pyrazole-3-carbonyl)-N-(2-chloro-5-fluorobenzyl)piperidine-4-carboxamide;

1-(5-(5-chloro-2-methoxypyridin-4-yl)-1H-pyrazole-3-carbonyl)-N-(1-(2,2,2-trifluoroethyl)-1H-pyrazol-4-yl)piperidine-4-carboxamide;

1-(5-(5-chloro-2-methoxypyridin-4-yl)-1H-pyrazole-3-carbonyl)-N-((5-fluoropyridin-2-yl)methyl)piperidine-4-carboxamide;

1-(5-(5-chloro-2-methoxypyridin-4-yl)-1H-pyrazole-3-carbonyl)-N-(1-cyanocyclobutyl)piperidine-4-carboxamide;

1-(5-(5-chloro-2-methoxypyridin-4-yl)-1H-pyrazole-3-carbonyl)-N-((6-(trifluoromethyl)pyridin-2-yl)methyl)piperidine-4-carboxamide;

1-(5-(5-chloro-2-methoxypyridin-4-yl)-1H-pyrazole-3-carbonyl)-N-((3-(trifluoromethyl)pyridin-2-yl)methyl)piperidine-4-carboxamide;

1-(5-(5-chloro-2-methoxypyridin-4-yl)-1H-pyrazole-3-carbonyl)-N-((4-methylpyridin-3-yl)methyl)piperidine-4-carboxamide;

1-(5-(5-chloro-2-methoxypyridin-4-yl)-1H-pyrazole-3-carbonyl)-N-(isochroman-4-yl)piperidine-4-carboxamide;

1-(5-(5-chloro-2-methoxypyridin-4-yl)-1H-pyrazole-3-carbonyl)-N-((1R,2S)-2-phenylcyclopropyl)piperidine-4-carboxamide;

1-(5-(5-chloro-2-methoxypyridin-, 1-yl)-1H-pyrazole-3-carbonyl)-N-((hydroxycyclohexyl)methyl)piperidine-4-carboxamide;

1-(5-(5-chloro-2-methoxypyridin-4-yl)-1H-pyrazole-3-carbonyl)-N-((4,4-dimethyloxetan-2-yl)methyl)piperidine-4-carboxamide;

1-(5-(5-chloro-2-methoxypyridin-4-yl)-1H-pyrazole-3-carbonyl)-N-((2-methyloxazol-5-yl)methyl)piperidine-4-carboxamide;

1-(5-(5-chloro-2-methoxypyridin-4-yl)-1H-pyrazole-3-carbonyl)-N-(pyrazolo[1,5-a]pyridin-7-ylmethyl)piperidine-4-carboxamide;

1-(5-(5-chloro-2-methoxypyridin-4-yl)-1H-pyrazole-3-carbonyl)-N-((5-chloropyrimidin-2-yl)methyl)piperidine-4-carboxamide;

1-(5-(5-chloro-2-methoxypyridin-4-yl)-1H-pyrazole-3-carbonyl)-N-((5-(trifluoromethyl)pyridin-2-yl)methyl)piperidine-4-carboxamide;

1-(5-(5-chloro-2-methoxypyridin-4-yl)-1H-pyrazole-3-carbonyl)-N-((3-chloropyridin-2-yl)methyl)piperidine-4-carboxamide;
1-(5-(5-chloro-2-methoxypyridin-4-yl)-1H-pyrazole-3-carbonyl)-N-((1,5-dimethyl-1H-pyrazol-3-yl)methyl)piperidine-4-carboxamide;
1-(5-(5-chloro-2-methoxypyridin-4-yl)-1H-pyrazole-3-carbonyl)-N-(1-(4-chlorophenoxy)propan-2-yl)piperidine-4-carboxamide;
1-(5-(5-chloro-2-methoxypyridin-4-yl)-1H-pyrazole-3-carbonyl)-N-(3,3-difluorocyclohexyl)piperidine-4-carboxamide;
1-(5-(5-chloro-2-methoxypyridin-4-yl)-1H-pyrazole-3-carbonyl)-N-(4-hydroxy-4-(trifluoromethyl)cyclohexyl)piperidine-4-carboxamide;
1-(5-(5-chloro-2-methoxypyridin-4-yl)-1H-pyrazole-3-carbonyl)-N-((3-methoxycyclobutyl)methyl)piperidine-4-carboxamide;
1-(5-(5-chloro-2-methoxypyridin-4-yl)-1H-pyrazole-3-carbonyl)-N-((3-fluoropyridin-2-yl)methyl)piperidine-4-carboxamide;
1-(5-(5-chloro-2-methoxypyridin-4-yl)-1H-pyrazole-3-carbonyl)-N-(3-(difluoromethyl)phenyl)piperidine-4-carboxamide,
1-(5-(5-chloro-2-methoxypyridin-4-yl)-1H-pyrazole-3-carbonyl)-N-((3,3-difluorocyclobutyl)methyl)piperidine-4-carboxamide;
1-(5-(5-chloro-2-methoxypyridin-4-yl)-1H-pyrazole-3-carbonyl)-N-(2,2-difluoro-2-phenylethyl)piperidine-4-carboxamide;
1-(5-(5-chloro-2-methoxypyridin-4-yl)-1H-pyrazole-3-carbonyl)-N-(3,3,5-trimethylcyclohexyl)piperidine-4-carboxamide;
1-(5-(5-chloro-2-methoxypyridin-4-yl)-1H-pyrazole-3-carbonyl)-N-(4-(difluoromethoxy)benzyl)piperidine-4-carboxamide;
N-(benzo[d]oxazol-6-ylmethyl)-1-(5-(5-chloro-2-methoxypyridin-4-yl)-1H-pyrazole-3-carbonyl)piperidine-4-carboxamide;
(R)-1-(5-(5-chloro-2-methoxypyridin-4-yl)-1H-pyrazole-3-carbonyl)-N-(1-(3-fluorophenyl)ethyl)piperidine-4-carboxamide;
N-(5-chloro-2-fluorobenzyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(2,3-difluorobenzyl)piperidine-4-carboxamide;
N-(3-chloro-2-fluorobenzyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(3-fluorobenzyl)piperidine-4-carboxamide;
1-(5-(5-chloro-2-methoxypyridin-4-yl)-1H-pyrazole-3-carbonyl)-N-((3,4-dihydro-2H-pyran-2-yl)methyl)piperidine-4-carboxamide;
N-(3-chlorobenzyl)-1-(5-(5-fluoro-2-methoxypyridin-4-yl)-1H-pyrazole-3-carbonyl)piperidine-4-carboxamide;
(1R,3s,5S)—N-(3-chlorobenzyl)-8-(5-(5-fluoro-2-methoxypyridin-4-yl)-1H-pyrazole-3-carbonyl 8-azabicyclo[3.2.1]octane-3-carboxamide;
(1R,3r,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide;
N-(3-chlorobenzyl)-1-(5-(5-fluoro-2-methoxypyridin-4-yl)-1H-pyrazole-3-carbonyl)-N-methylpiperidine-4-carboxamide;
1-(5-(5-chloro-2-methoxypyridin-4-yl)-1H-pyrazole-3-carbonyl)-N-(1-(trifluoromethyl)cyclopentyl)piperidine-4-carboxamide;
1-(5-(5-chloro-2-methoxypyridin-4-yl)-1H-pyrazole-3-carbonyl)-N-(1,4-dimethylcyclohexyl)piperidine-4-carboxamide;
1-(5-(5-chloro-2-methoxypyridin-4-yl)-1H-pyrazole-3-carbonyl)-N-(4-(trifluoromethoxy)benzyl)piperidine-4-carboxamide;
N-(bicyclo[3.2.1]octan-8-yl)-1-(5-(5-fluoro-2-methoxypyridin-4-yl)-1H-pyrazole-3-carbonyl)piperidine-4-carboxamide;
N-[(3-chlorophenyl)methyl]-1-[5-(5-fluoro-2-methoxypyridin-4-yl)-1H-1,2,4-triazole-3-carbonyl]piperidine-4-carboxamide;
1-(5-(5-chloro-2-methoxypyridin-4-yl)-1H-pyrazole-3-carbonyl)-N-((2-oxoindolin-5-yl)methyl)piperidine-4-carboxamide;
N-((1H-pyrrolo[2,3-b]pyridin-5-yl)methyl)-1-(5-(5-chloro-2-methoxypyridin-4-yl)-1H-pyrazole-3-carbonyl)piperidine-4-carboxamide;
(R)-4-(5-(5-fluoro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;
(S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;
(1R,3s,5S)-8-(5-(5-fluoro-2-methoxypyridin-4-yl)-1H-pyrazole-3-carbonyl)-N-((1r,4R)-4-hydroxy-4-(trifluoromethyl)cyclohexyl)-8-azabicyclo[3.2.1.]octane-3-carboxamide;
(1R,3s,5S)-8-(5-(5-fluoro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide;
1-(5-(5-chloro-2-methoxypyridin-4-yl)-1H-pyrazole-3-carbonyl)-N-(3-chlorobenzyl)-4-hydroxypiperidine-4-carboxamide;
1-(5-(5-chloro-2-methoxypyridin-4-yl)-1H-pyrazole-3-carbonyl)-N-(3-chlorobenzyl)-2-methylpiperidine-4-carboxamide;
1-(5-(5-chloro-2-methoxypyridin-4-yl)-1H-pyrazole-3-carbonyl)-N-(3-chlorobenzyl)-3-methylpiperidine-4-carboxamide;
1-(5-(5-chloro-2-methoxypyridin-4-yl)-1H-pyrazole-3-carbonyl)-N-(3-chlorobenzyl)-4-fluoropiperidine-4-carboxamide;
1-(5-(5-chloro-2-methoxypyridin-4-yl)-1H-pyrazole-3-carbonyl)-N-(3,3-difluorocyclopentyl)piperidine-4-carboxamide;
1-(5-(5-chloro-2-methoxypyridin-4-yl)-1H-pyrazole-3-carbonyl)-N-((5-methylpyridin-2-yl)methyl)piperidine-4-carboxamide;
1-(5-(5-chloro-2-methoxypyridin-4-yl)-1H-pyrazole-3-carbonyl)-N-(3-chlorobenzyl)-3-fluoropiperidine-4-carboxamide;
1-(5-(5-chloro-2-methoxypyridin-4-yl)-1H-pyrazole-3-carbonyl)-N-((6-(trifluoro-15-methyl)pyridin-3-yl)methyl)piperidine-4-carboxamide;
1-(5-(5-chloro-2-methoxypyridin-4-yl)-1H-pyrazole-3-carbonyl)-N-((5-chloropyridin-3-yl)methyl)piperidine-4-carboxamide;
N-((1H-indazol-6-yl)methyl)-1-(5-(5-chloro-2-methoxypyridin-4-yl)-1H-pyrazole-3-carbonyl)piperidine-4-carboxamide;

N-((1H-indol-3-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(isoquinolin-6-ylmethyl)piperidine-4-carboxamide;
1-(5-(5-chloro-2-methoxypyridin-4-yl)-1H-pyrazole-3-carbonyl)-N-(5-oxo-1-phenylpyrrolidin-3-yl)piperidine-4-carboxamide;
1-(5-(5-chloro-2-methoxypyridin-4-yl)-1H-pyrazole-3-carbonyl)-N-(chroman-4-yl)piperidine-4-carboxamide;
1-(5-(5-chloro-2-methoxypyridin-4-yl)-1H-pyrazole-3-carbonyl)-N-((2-dimethyl-1,3-dioxolan-4-yl)methyl)piperidine-4-carboxamide;
1-(5-(5-chloro-2-methoxypyridin-4-yl)-1H-pyrazole-3-carbonyl)-N-(1-methyl-1,2,3,4-tetrahydroquinolin-4-yl)piperidine-4-carboxamide;
1-(5-(5-chloro-2-methoxypyridin-4-yl)-1H-pyrazole-3-carbonyl)-N-((1-methyl-1H-indol-3-yl)methyl)piperidine-4-carboxamide;
N-((1H-indol-6-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-((5-methylfuran-2-yl)methyl)piperidine-4-carboxamide;
N-((1H-indol-4-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(5,6,7,8-tetrahydroisoquinolin-5-yl)piperidine-4-carboxamide;
N-((1H-indazol-4-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-((3-chloro-5-(trifluoromethyl)pyridin-2-yl)methyl)piperidine-4-carboxamide;
N-((1H-indol-7-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(6-fluorochroman-4-yl)piperidine-4-carboxamide;
1-(5-(5-chloro-2-methoxypyridin-4-yl)-1H-pyrazole-3-carbonyl)-N-(1-phenylpiperidin-4-yl)piperidine-4-carboxamide;
N-((2H-benzo[d][1,2,3]triazol-5-yl)methyl)-1-(5-(5-chloro-2-methoxypyridin-4-1H-pyrazole-3-carbonyl)piperidine-4-carboxamide;
1-(5-(5-chloro-2-methoxypyridin-4-yl)-1H-pyrazole-3-carbonyl)-N-(1r,4r)-4-hydroxy-4-methylcyclohexyl)piperidine-4-carboxamide;
1-(5-(5-chloro-2-methoxypyridin-4-yl)-1H-pyrazole-3-carbonyl)-N-((1r,4r)-4-hydroxy-4-(trifluoromethyl)cyclohexyl)piperidine-4-carboxamide;
N-((3-fluoro-1H-indazol-5-yl)methyl)-1-(5-(5-fluoro-2-methoxypyridin-4-yl)-1H-pyrazole-3-carbonyl)piperidine-4-carboxamide;
N-((1H-indazol-3-yl)methyl)-1-(5-(5-chloro-2-methoxypyridin-4-yl)-1H-pyrazole-3-carbonyl)piperidine-4-carboxamide;
N-((1H-pyrrolo[2,3-b]pyridin-3-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-((2-methyl-1H-indol-5-yl)methyl)piperidine-4-carboxamide;
1-[5-(5-fluoro-2-methoxypyridin-4-yl)-1H-pyrazole-3-carbonyl]-N-[(3-methyl-1H-indazol-5-yl)methyl]piperidine-4-carboxamide;
1-(5-(5-chloro-2-methoxypyridin-4-yl)-1H-pyrazole-3-carbonyl)-N-(1-isopropyl-1H-pyrazol-4-yl)piperidine-4-carboxamide;
1-(5-(5-chloro-2-methoxypyridin-4-yl)-1H-pyrazole-3-carbonyl)-N-((1-methyl-1H-indol-5-yl)methyl)piperidine-4-carboxamide;
1-(5-(5-chloro-2-methoxypyridin-4-yl)-1H-pyrazole-3-carbonyl)-N-(2-oxo-1-phenyl)pyrrolidin-3-yl)piperidine-4-carboxamide;
N-(5-chloro-2,3-dihydrobenzofuran-3-yl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-((4-(trifluoromethyl)pyrimidin-2-yl)methyl)piperidine-4-carboxamide;
1-(5-(5-chloro-2-methoxypyridin-4-yl)-1H-pyrazole-3-carbonyl)-N-((5-methylimidazo[1,2-a]pyridin-2-yl)methyl)piperidine-4-carboxamide;
1-(5-(5-chloro-2-methoxypyridin-4-yl)-1H-pyrazole-3-carbonyl)-N-((5-(trifluoromethyl)pyrimidin-2-yl)methyl)piperidine-4-carboxamide;
N-((1H-pyrrolo[2,3-c]pyridin-5-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(5,5-dimethyltetrahydrofuran-3-yl)piperidine-4-carboxamide;
1-(5-(5-chloro-2-methoxypyridin-4-yl)-1H-pyrazole-3-carbonyl)-N-((8-fluoroimidazo[1,2-a]pyridin-2-yl)methyl)piperidine-4-carboxamide;
1-(5-(5-chloro-2-methoxypyridin-4-yl)-1H-pyrazole-3-carbonyl)-N-((2-methyl-1H-benzo[d]imidazol-5-yl)methyl)piperidine-4-carboxamide;
1-(5-(5-chloro-2-methoxypyridin-4-yl)-1H-pyrazole-3-carbonyl)-N-((2-methyl-1,3-dioxan-2-yl)methyl)piperidine-4-carboxamide;
1-(5-(5-chloro-2-methoxypyridin-4-yl)-1H-pyrazole-3-carbonyl)-N-((6-methylimidazo[1,2-a]pyridin-2-yl)methyl)piperidine-4-carboxamide;
1-(5-(5-chloro-2-methoxypyridin-4-yl)-1H-pyrazole-3-carbonyl)-N-((1-methyl-1H-indazol-3-yl)methyl)piperidine-4-carboxamide;
1-(5-(5-chloro-2-methoxypyridin-4-yl)-1H-pyrazole-3-carbonyl)-N-((6-chloroimidazo[1,2-a]pyridin-2-yl)methyl)piperidine-4-carboxamide;
1-(5-(5-chloro-2-methoxypyridin-4-yl)-1H-pyrazole-3-carbonyl)-N-((4,4-difluorotetrahydrofuran-2-yl)methyl)piperidine-4-carboxamide;
1-(5-(5-chloro-2-methoxypyridin-4-yl)-1H-pyrazole-3-carbonyl)-N-((5-(trifluoromethyl)oxazol-4-yl)methyl)piperidine-4-carboxamide;
1-(5-(5-chloro-2-methoxypyridin-4-yl)-1H-pyrazole-3-carbonyl)-N-(1-(2-fluorophenyl)pyrrolidin-3-yl)piperidine-4-carboxamide;
1-(5-(5-chloro-2-methoxypyridin-4-yl)-1H-pyrazole-3-carbonyl)-N-((1-methyl-1H-benzo[d]imidazol-5-yl)methyl)piperidine-4-carboxamide;
1-(5-(5-chloro-2-methoxypyridin-4-yl)-1H-pyrazole-3-carbonyl)-N-(2-methyl-5,6,7,8-tetrahydroquinazolin-5-yl)piperidine-4-carboxamide;

1-(5-(5-chloro-2-methoxypyridin-4-yl)-1H-pyrazole-3-carbonyl)-N-((5-(difluoromethyl)isoxazol-3-yl)methyl)piperidine-4-carboxamide;

N-((1H-pyrrolo[2,3-b]pyridin-6-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(2-methyl-1,2,3,4-tetrahydroisoquinolin-4-yl)piperidine-4-carboxamide;

1-(5-(5-chloro-2-methoxypyridin-4-yl)-1H-pyrazole-3-carbonyl)-N-((3-methyl-2-oxo-2,3-dihydrobenzo[d]oxazol-5-yl)methyl)piperidine-4-carboxamide;

1-(5-(5-chloro-2-methoxypyridin-4-yl)-1H-pyrazole-3-carbonyl)-N-((1-methyl-1H-indazol-6-yl)methyl)piperidine-4-carboxamide;

N-((2-oxabicyclo[3.1.1]heptan-1-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(1-methyl-2,2-dioxido-3,4-dihydro-1H-benzo[c][1,2]thiazin-4-yl)piperidine-4-carboxamide;

1-(5-(5-chloro-2-methoxypyridin-4-yl)-1H-pyrazole-3-carbonyl)-N-((1-methyl-1H-pyrazolo[3,4-b]pyridin-5-yl)methyl)piperidine-4-carboxamide;

(S)-1-(5-(5-chloro-2-methoxypyridin-4-yl)-1H-pyrazole-3-carbonyl)-N-(6-cyanochroman-4-yl)piperidine-4-carboxamide;

1-(5-(5-chloro-2-methoxypyridin-4-yl)-1H-pyrazole-3-carbonyl)-N-(1-methyl-2-oxo-1,2,5,6,7,8-hexahydroquinolin-5-yl)piperidine-4-carboxamide;

1-(5-(5-chloro-2-methoxypyridin-4-yl)-1H-pyrazole-3-carbonyl)-N-((1-methyl-2-oxoindolin-5-yl)methyl)piperidine-4-carboxamide;

1-(5-(5-chloro-2-methoxypyridin-4-yl)-1H-pyrazole-3-carbonyl)-N-(3,4-dihydro-2H-pyrano[2,3-b]pyridin-4-yl)piperidine-4-carboxamide;

1-(5-(5-chloro-2-methoxypyridin-4-yl)-1H-pyrazole-3-carbonyl)-N-((1,1-dioxido-2,3-dihydrobenzo[b]thiophen-5-yl)methyl)piperidine-4-carboxamide;

1-(5-(5-chloro-2-methoxypyridin-4-yl)-1H-pyrazole-3-carbonyl)-N-((4-(difluoromethyl)pyrimidin-2-yl)methyl)piperidine-4-carboxamide;

1-(5-(5-chloro-2-methoxypyridin-4-yl)-1H-pyrazole-3-carbonyl)-N-((6-(difluoromethyl)pyridin-2-yl)methyl)piperidine-4-carboxamide;

1-(5-(5-chloro-2-methoxypyridin-4-yl)-1H-pyrazole-3-carbonyl)-N-(2-methyl-3-oxo-1,2,3,4-tetrahydroisoquinolin-4-yl)piperidine-4-carboxamide;

1-(5-(5-chloro-2-methoxypyridin-4-yl)-1H-pyrazole-3-carbonyl)-N-((6,7-dihydro-5H-cyclopenta[d]pyrimidin-2-yl)methyl)piperidine-4-carboxamide;

1-(5-(5-chloro-2-methoxypyridin-4-yl)-1H-pyrazole-3-carbonyl)-N-((3,3-dimethyl-2-oxoindolin-5-yl)methyl)piperidine-4-carboxamide;

1-(5-(5-chloro-2-methoxypyridin-4-yl)-1H-pyrazole-3-carbonyl)-N-((5-fluoro-1 I-benzo[d]imidazol-4-yl)methyl)piperidine-4-carboxamide;

1-(5-(5-chloro-2-methoxypyridin-4-yl)-1H-pyrazole-3-carbonyl)-N-(3-oxo-1,2,3,4-tetrahydroisoquinolin-4-yl)piperidine-4-carboxamide;

(S)-4-(5-(5-chloro-2-methoxypyridin-4-yl)-1H-pyrazole-3-carbonyl)-N-(3-chlorobenzyl)-4-azaspiro[2.5]octane-7-carboxamide;

(R)-4-(5-(5-chloro-2-methoxypyridin-4-yl)-1H-pyrazole-3-carbonyl)-N-(3-chlorobenzyl)-4-azaspiro[2.5]octane-7-carboxamide;

1-(5-(5-chloro-2-methoxypyridin-4-yl)-1H-pyrazole-3-carbonyl)-N-(3-fluoro-3-methylcyclobutyl)piperidine-4-carboxamide;

1-(5-(5-chloro-2-methoxypyridin-4-yl)-1H-pyrazole-3-carbonyl)-N-(5-methyltetrahydrofuran-3-yl)piperidine-4-carboxamide;

1-(5-(5-chloro-2-methoxypyridin-4-yl)-1H-pyrazole-3-carbonyl)-N-((3R,6R)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3S,6R)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3S,6S)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3R,6S)-1-methyl-6-(trifluoromethyl)piperidin-3-yl)piperidine-4-carboxamide;

1-(5-(5-chloro-2-methoxypyridin-4-yl)-1H-pyrazole-3-carbonyl)-N-((3S,6S)-6-(trifluoromethyl)tetrahydro-2H-pyran-3-yl)piperidine-4-carboxamide;

1-(5-(5-chloro-2-methoxypyridin-4-yl)-1H-pyrazole-3-carbonyl)-N-((3R,6R)-6-(trifluoromethyl)tetrahydro-2H-pyran-3-yl)piperidine-4-carboxamide;

1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide;

1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide;

N-((1H-indol-2-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(6-methylpyridin-2-yl)piperidine-4-carboxamide;

1-(5-(5-chloro-2-methoxypyridin-4-yl)-1H-pyrazole-3-carbonyl)-N-(3-methoxychroman-4-yl)piperidine-4-carboxamide;

1-(5-(5-chloro-2-methoxypyridin-4-yl)-1H-pyrazole-3-carbonyl)-N-(1-(4-fluorophenyl)pyrrolidin-3-yl)piperidine-4-carboxamide;

N-((1H-pyrrolo[3,2-c]pyridin-4-yl)methyl)-1-(5-(5-chloro-2-methoxypyridin-4-yl)-1H-pyrazole-3-carbonyl)piperidine-4-carboxamide;

(S)-1-(5-(5-chloro-2-methoxypyridin-4-yl)-1H-pyrazole-3-carbonyl)-N-(3-chlorobenzyl)-2,2-dimethylpiperidine-4-carboxamide;

(R)-1-(5-(5-chloro-2-methoxypyridin-4-yl)-1H-pyrazole-3-carbonyl)-N-(3-chlorobenzyl)-2,2-dimethylpiperidine-4-carboxamide;

(S)-5-(5-(5-chloro-2-methoxypyridin-4-yl)-1H-pyrazole-3-carbonyl)-N-(3-chlorobenzyl)-5-azaspiro[3.5]nonane-8-carboxamide;

(R)-5-(5-(5-chloro-2-methoxypyridin-4-yl)-1H-pyrazole-3-carbonyl)-N-(3-chlorobenzyl)-5-azaspiro[3.5]nonane-8-carboxamide;

(1R,3s,5S)-8-(5-(5-chloro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;

(1R,3s,5S)-8-(5-(5-chloro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

(1R,3S,5S)—N-[(3-fluoro-1H-indazol-5-yl)methyl]-8-[5-(5-fluoro-2-methoxypyridin-4-yl)-1H-pyrazole-3-carbonyl]-8-azabicyclo[3.2.1]octane-3-carboxamide;

(1R,3s,5S)-8-(5-(5-chloro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)-8-(5-(5-chloro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide;

1-(5-(5-chloro-2-methoxypyridin-4-yl)-1H-pyrazole-3-carbonyl)-N-(5,6-dimethylpyrazin-2-yl)piperidine-4-carboxamide;

1-(5-(5-chloro-2-methoxypyridin-4-yl)-1H-pyrazole-3-carbonyl)-N-(1H-indol-4-yl)piperidine-4-carboxamide;

1-[5-(5-chloro-2-methylpyridin-4-yl)-1H-pyrazole-3-carbonyl]-N-[(3-chlorophenyl)methyl]piperidine-4-carboxamide;

1-[5-(5-fluoro-2-methylpyridin-4-yl)-1H-pyrazole-3-carbonyl]-N-[(1r,4r)-4-hydroxy-4-(trifluoromethyl)cyclohexyl]piperidine-4-carboxamide;

1-[5-(5-fluoro-2-methylpyridin-4-yl)-1H-pyrazole-3-carbonyl]-N-[(1s,4s)-4-hydroxy-4-(trifluoromethyl)cyclohexyl]piperidine-4-carboxamide;

1-(5-(5-chloro-2-methoxypyridin-4-yl)-1H-pyrazole-3-carbonyl)-N-((1r,4r)-4-hydroxy-4-methylcyclohexyl)piperidine-4-carboxamide;

1-(5-(5-chloro-2-methoxypyridin-4-yl)-1H-pyrazole-3-carbonyl)-N-((1s,4s)-4-hydroxy-4-methylcyclohexyl)piperidine-4-carboxamide;

1-(5-(5-chloro-2-methoxypyridin-4-yl)-1H-pyrazole-3-carbonyl)-N-(2-methyl-2,3-dihydrobenzofuran-3-yl)piperidine-4-carboxamide;

(2S,5R)-1-(5-(5-chloro-2-methoxypyridin-4-yl)-1H-pyrazole-3-carbonyl)-N-(3-chlorobenzyl)-2,5-dimethylpiperidine-4-carboxamide;

(2R,5S)-1-(5-(5-chloro-2-methoxypyridin-4-yl)-1H-pyrazole-3-carbonyl)-N-(3-chlorobenzyl)-2,5-dimethylpiperidine-4-carboxamide;

(2R,5R)-1-(5-(5-chloro-2-methoxypyridin-4-yl)-1H-pyrazole-3-carbonyl)-N-(3-chlorobenzyl)-2,5-dimethylpiperidine-4-carboxamide;

(2S,5S)-1-(5-(5-chloro-2-methoxypyridin-4-yl)-1H-pyrazole-3-carbonyl)-N-(3-chlorobenzyl)-2,5-dimethylpiperidine-4-carboxamide;

N-[(3-chlorophenyl)methyl]-1-[5-(5-fluoro-2-methylpyridin-4-yl)-1H-pyrazole-3-carbonyl]piperidine-4-carboxamide;

(1R,3S,5S)—N-[(3-chlorophenyl)methyl]-8-[5-(5-fluoro-2-methylpyridin-4-yl)-1H-pyrazole-3-carbonyl]-8-azabicyclo[3.2.1]octane-3-carboxamide;

N-[(3-fluoro-1H-indazol-5-yl)methyl]-1-[5-(5-fluoro-2-methylpyridin-4-yl)-1H-pyrazole-3-carbonyl]piperidine-4-carboxamide;

1-[5-(5-chloro-2-ethylpyridin-4-yl)-1H-pyrazole-3-carbonyl]-N-[(3-chlorophenyl)methyl]piperidine-4-carboxamide;

1-[5-(5-fluoro-2-methylpyridin-4-yl)-1H-pyrazole-3-carbonyl]-N-(1H-indol-5-ylmethyl)piperidine-4-carboxamide;

N-[(2,3-dimethyl-1H-indol-5-yl)methyl]-1-[5-(5-fluoro-2-methoxypyridin-4-yl)-1H-pyrazole-3-carbonyl]piperidine-4-carboxamide;

(2R,4R)-1-(5-(5-chloro-2-methoxypyridin-4-yl)-1H-pyrazole-3-carbonyl)-N-(3-chlorobenzyl)-2-methylpiperidine-4-carboxamide;

1-(5-(5-chloro-2-methoxypyridin-4-yl)-1H-pyrazole-3-carbonyl)-N-(3-chlorobenzyl)-2,6-dimethylpiperidine-4-carboxamide;

(1R,3s,5S)-8-(5-(5-fluoro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

1-(5-(5-fluoro-2-methoxypyridin-4-yl)-1H-pyrazole-3-carbonyl)-N-(1-oxaspiro[3.5]nonan-7-yl)piperidine-4-carboxamide;

(1R,3s,5S)—N-((3-fluoro-1-methyl-1H-indazol-5-yl)methyl)-8-(5-(5-fluoro-2-methoxypyridin-4-yl)-1H-pyrazole-3-carbonyl)-8-azabicyclo[3.2.1]octane-3-carboxamide;

N-((3,3-dimethylindolin-5-yl)methyl)-1-(5-(5-fluoro-2-methoxypyridin-4-yl)-1H-pyrazole-3-carbonyl)piperidine-4-carboxamide;

(1R,3s,5S)—N-((1r,4R)-4-hydroxy-4-(trifluoromethyl)cyclohexyl)-8-(5-(6-methylpyrimidin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide;

1-(5-(5-fluoro-2-methoxypyridin-4-yl)-1H-pyrazole-3-carbonyl)-N-(1-(3-methyl-1H-indazol-5-yl)ethyl)piperidine-4-carboxamide;

9-(5-(5-fluoro-2-methoxypyridin-4-yl)-1H-pyrazole-3-carbonyl)-N-((1r,4r)-4-hydroxy-4-(trifluoromethyl)cyclohexyl)-3-oxa-9-azabicyclo[3.3.1]nonane-7-carboxamide;

(1R,3R,5S)-8-[5-(5-fluoro-2-methylpyridin-4-yl)-1H-pyrazole-3-carbonyl]-N-[(1r,4r)-4-hydroxy-4-(trifluoromethyl)cyclohexyl]-8-azabicyclo[3.2.1]octane-3-carboxamide;

(1R,3s,5S)—N-((3-fluoro-1H-indazol-5-yl)methyl)-8-(5-(5-fluoro-2-methylpyridin-4-yl)-1H-pyrazole-3-carbonyl)-8-azabicyclo[3.2.1]octane-3-carboxamide;

(1R,3R,5S)—N-[(2,3-dimethyl-1H-indol-5-yl)methyl]-8-[5-(5-fluoro-2-methoxypyridin-4-yl)-1H-pyrazole-3-carbonyl]-8-azabicyclo[3.2.1]octane-3-carboxamide;

(R)-4-(5-(5-chloro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-chloro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(R)-4-(5-(5-fluoro-2-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide;

(R)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide;

(1R,3s,5S)-8-(5-(5-fluoro-2-methylpyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((R)-1-(3-(trifluoromethyl)-1,2,4-oxadiazol-5-yl)ethyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((S)-1-(3-(trifluoromethyl)-1,2,4-oxadiazol-5-yl)ethyl)-8-azabicyclo[3.2.1]octane-3-carboxamide;

(1R,3s,5S)—N-(1,1-dimethylsilinan-4-yl)-8-(5-(5-fluoro-2-methoxypyridin-4-yl)-1H-pyrazole-3-carbonyl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

(R)-4-(5-(5-fluoro-2-methylpyridin-4-yl)-1H-pyrazole-3-carbonyl)-N-((1r,4R)-4-methoxy-4-(trifluoromethyl)cyclohexyl)-4-azaspiro[2.5]octane-7-carboxamide;

(R)-4-(5-(5-fluoro-2-methylpyridin-4-yl)-1H-pyrazole-3-carbonyl)-N-((1s,4S)-4-methoxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1r,4S)-4-methoxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1s,4R)-4-methoxy-4-(trifluoromethyl)cyclohexyl)-4-azaspiro[2.5]octane-7-carboxamide;

(1R,3R,5S)-8-[5-(5-fluoro-2-methoxypyridin-4-yl)-1H-pyrazole-3-carbonyl]-N-[(1r,4r)-4-methoxy-4-(trifluoromethyl)cyclohexyl]-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1s,4s)-4-methoxy-4-(trifluoromethyl)cyclohexyl]-8-azabicyclo[3.2.1]octane-3-carboxamide;

(1R,3s,5S)-8-(5-(5-fluoro-2-methoxypyridin-4-yl)-1H-pyrazole-3-carbonyl)-N-((5R,8r)-2-oxo-1-azaspiro[4.5]decan-8-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((5S,8s)-2-oxo-1-azaspiro[4.5]decan-8-yl)-8-azabicyclo[3.2.1]octane-3-carboxamide;

4-[5-(5-fluoro-2-methoxypyridin-4-yl)-1H-pyrazole-3-carbonyl]-N—[(R)-1-(2-fluorophenyl)pyrrolidin-3-yl]-4-azaspiro[2.5]octane-7-carboxamide;

(1R,3S,5S)-8-[5-(5-fluoro-2-methoxypyridin-4-yl)-1H-pyrazole-3-carbonyl]-N-[1-oxaspiro[3.5]nonan-7-yl]-8-azabicyclo[3.2.1]octane-3-carboxamide;

(2R,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2R,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2R,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2R,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2S,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(1R,3S,5S)—N-[(3S,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3R,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(R)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide;

(S)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide;

(1R,3s,5S)-8-(5-(5-fluoro-2-methoxypyridin-4-yl)-1H-pyrazole-3-carbonyl)-N-(4-hydroxy-4-(perfluoroethyl)cyclohexyl)-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1r,4r)-4-(difluoromethyl)-4-methoxycyclohexyl]-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1s,4s)-4-(difluoromethyl)-4-methoxycyclohexyl]-8-azabicyclo[3.2.1]octane-3-carboxamide;

(1R,3s,5S)—N-((1r,4R)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(1R,3s,5S)—N-((1s,4S)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(1R,3S,5S)-8-[5-(5-fluoro-2-methoxypyridin-4-yl)-1H-pyrazole-3-carbonyl]-N-[(1r,4r)-4-(2-methoxyethoxy)-4-(trifluoromethyl)cyclohexyl]-8-azabicyclo[3.2.1]octane-3-carboxamide;

(1R,3S,5S)-8-[5-(5-fluoro-2-methoxypyridin-4-yl)-1H-pyrazole-3-carbonyl]-N-[(1s,4s)-4-(2-methoxyethoxy)-4-(trifluoromethyl)cyclohexyl]-8-azabicyclo[3.2.1]octane-3-carboxamide;

(1R,3S,5S)-8-[5-(5-fluoro-2-methoxypyridin-4-yl)-1H-1,2,4-triazole-3-carbonyl]-N-[(1r,4r)-4-hydroxy-4-(trifluoromethyl)cyclohexyl]-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide;

(1R,3s,5S)—N-(3,3-difluoro-1-oxaspiro[3.5]nonan-7-yl)-8-(5-(5-fluoro-2-methoxypyridin-4-yl)-1H-pyrazole-3-carbonyl)-8-azabicyclo[3.2.1]octane-3-carboxamide;

(S)—N-((1r,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1s,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1r,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1s,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1r,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1s,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1r,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1s,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

4-(4-(5-hydroxy-2-methylpyridin-4-yl)-1H-imidazole-2-carbonyl)-N-((1r,4r)-4-hydroxy-4-(trifluoromethyl)cyclohexyl)-4-azaspiro[2.5]octane-7-carboxamide;

(1R,3s,5S)-8-(5-(5-fluoro-2-methylpyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide;

(R)—N-((1r,4S)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4R)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide;

(1R,3s,5S)-8-(5-(2,3-dimethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)—N-((1r,4R)-4-hydroxy-4-(trifluoromethyl)cyclohexyl)-8-(5-(6-methyl-1H-pyrazolo[3,4-b]pyridin-4-yl)-1H-pyrazole-3-carbonyl)-8-azabicyclo[3.2.1]octane-3-carboxamide;

(1R,3s,5S)-8-(5-(2-ethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)—N-((1r,4R)-4-hydroxy-4-(trifluoromethyl)cyclohexyl)-8-(5-(2-(hydroxymethyl)pyridin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-(3-(trifluoromethyl)-1-oxaspiro[3.5]nonan-7-yl)-8-azabicyclo[3.2.1]octane-3-carboxamide;

(1R,3s,5S)—N-(3,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide;

(1R,3s,5S)—N-(4,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide;

(S)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide;

(R)—N-((1r,4R)-4-ethoxy-4-(trifluoromethyl)cyclohexyl)-4-(5-(5-fluoro-2-methylpyridin-4-yl)-1H-pyrazole-3-carbonyl)-4-azaspiro[2.5]octane-7-carboxamide;

(S)—N-((1r,4S)-4-ethoxy-4-(trifluoromethyl)cyclohexyl)-4-(5-(5-fluoro-2-methylpyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((1r,4R)-4-methoxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-methoxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((4S,7r)-1-oxaspiro[3.5]nonan-7-yl)-4-azaspiro[2.5]octane-7-carboxamide;

(S)-4-(5-(5-fluoro-2-methoxypyridin-4-yl)-1H-pyrazole-3-carbonyl)-N-((4R,7s)-1-oxaspiro[3.5]nonan-7-yl)-4-azaspiro[2.5]octane-7-carboxamide;

(1R,3s,5S)-8-(5-(5-fluoro-2-methoxypyridin-4-yl)-1H-pyrazole-3-carbonyl)-N-((3S,6S)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-1-(2-fluoro-2-methylpropyl)-6-(trifluoromethyl)piperidin-3-yl)-8-azabicyclo[3.2.1]octane-3-carboxamide;

(R)-4-(5-(5-fluoro-2-methoxypyridin-4-yl)-1H-pyrazole-3-carbonyl)-N-((5R,8r)-1-methyl-2-oxo-1-azaspiro[4.5]decan-8-yl)-4-azaspiro[2.5]octane-7-carboxamide;

(R)-4-(5-(5-fluoro-2-methoxypyridin-4-yl)-1H-pyrazole-3-carbonyl)-N-((5S,8s)-1-methyl-2-oxo-1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-((5S,8r)-1-methyl-2-oxo-1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-((5R,8s)-1-methyl-2-oxo-1-azaspiro[4.5]decan-8-yl)-4-azaspiro[2.5]octane-7-carboxamide;

(R)—N-((5R,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(R)—N-((5S,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((5S,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((5R,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(2-(dimethylamino)ethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((1r,4R)-4-(2-hydroxyethoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-(2-hydroxyethoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide;

4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((3-hydroxybicyclo[1.1.1]pentan-1-yl)methyl)-4-azaspiro[2.5]octane-7-carboxamide;

(S)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(R)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide;

(R)—N-((1r,4R)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide;

(R)—N-((1r,4R)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1r,4S)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1S,4S)-4-((S)-2-methoxypropoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1R,4S)-4-((R)-2-methoxypropoxy)-4-(trifluoromethyl)cyclohexyl)-4-azaspiro[2.5]octane-7-carboxamide;

(S)-4-(3-(5-fluoro-2-methoxypyridin-4-yl)-1 I-pyrazole-5-carbonyl)-N—(((R)-4,5,6,7-tetrahydro-2H-indazol-5-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-4,5,6,7-tetrahydro-2H-indazol-5-yl)methyl)-4-azaspiro[2.5]octane-7-carboxamide;

(S)-4-(3-(5-fluoro-2-methoxypyridin-4-yl)-1H-pyrazole-5-carbonyl)-N—(((R)-5,6,7,8-tetrahydroimidazo[1,5-a]pyridin-7-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-5,6,7,8-tetrahydroimidazo[1,5-a]pyridin-7-yl)methyl)-4-azaspiro[2.5]octane-7-carboxamide;

(S)-4-(5-(5-fluoro-2-methoxypyridin-4-yl)-1H-pyrazole-3-carbonyl)-N-((1-methyl-2-oxabicyclo[2.1.1]hexan-4-yl)methyl)-4-azaspiro[2.5]octane-7-carboxamide;

(R)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide;

(R)-4-(3-(5-fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—(((R)-3-methyl-5,6,7,8-tetrahydro-[1,2,4]triazolo[4,3-a]pyridin-7-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-3-methyl-5,6,7,8-tetrahydro-[1,2,4]triazolo[4,3-a]pyridin-7-yl)methyl)-4-azaspiro[2.5]octane-7-carboxamide;

(1r,4R)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1s,4S)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1r,4S)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1s,4R)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-(1-(oxetan-3-yl)-1-azaspiro[4.5]decan-8-yl)-4-azaspiro[2.5]octane-7-carboxamide;

(S)—N-((1r,4S)-4-(2-aminoethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-(1-(2,2-difluoropropyl)-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((1S,4S)-4-((S)-2-aminopropoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1S,4S)-4-((S)-2-hydroxypropoxy)-4-(trifluoromethyl)cyclohexyl)-4-azaspiro[2.5]octane-7-carboxamide;

(7S)—N-(8-oxabicyclo[3.2.1]octan-3-yl)-4-(5-(5-fluoro-2-methoxypyridin-4-yl)-H-pyrazole-3-carbonyl)-4-azaspiro[2.5]octane-7-carboxamide;

(S)—N-((1S,3R)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide;

(S)—N-((1S,3S)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—(((S)-5,6,7,8-tetrahydroimidazo[1,2-a]pyridin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-5,6,7,8-tetrahydroimidazo[1,2-a]pyridin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((S)-3-(trifluoromethyl)-5,6-dihydro-8H-[1,2,4]triazolo[3,4-c][1,4]oxazin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-3-(trifluoromethyl)-5,6-dihydro-8H-[1,2,4]triazolo[3,4-c][1,4]oxazin-6-yl)methyl)-4-azaspiro[2.5]octane-7-carboxamide;

(S)—N-((3-chloropyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3-methylpyridin-2-yl)methyl)-4-azaspiro[2.5]octane-7-carboxamide;

(S)—N—((R)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((S)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-methylpyridin-2-yl)methyl)-4-azaspiro[2.5]octane-7-carboxamide;

(S)—N-((3-chloro-5-fluoropyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-(trifluoromethyl)pyridin-2-yl)methyl)-4-azaspiro[2.5]octane-7-carboxamide;

(S)—N-((3-chloro-5-(2-hydroxypropan-2-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((4-(trifluoromethyl)-2-oxabicyclo[2.1.1]hexan-1-yl)methyl)-4-azaspiro[2.5]octane-7-carboxamide;

(S)—N—((S)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide;

(S)—N—((R)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide;

(2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide;

(2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide;

(2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide;

(2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide;

(R)—N-((1r,4R)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(R)—N-((1s,4S)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(R)—N-((5S,8s)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(R)—N-((5R,8r)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((5,6-dihydro-8H-imidazo[2,1-c][1,4]oxazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(((1R,3S)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1S,3S)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1S,3R)-1-imino-2,2-dimenthyl-1-oxido-tetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1R,3R)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-hydroxy-4-(perfluoroethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1s,4R)-4-hydroxy-4-(perfluoroethyl)cyclohexyl)-4-azaspiro[2.5]octane-7-carboxamide;

(S)—N-((4S,7r)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4R,7s)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((6R,8aR)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6R,8aS)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6S,8aR)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6S,8aS)-octahydroindolizin-6-yl)-4-azaspiro[2.5]octane-7-carboxamide;

(S)—N—((R)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((S)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N-((1s,3R)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide;

(S)—N-((1r,3S)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-6-methyl-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N—((S)-6-methyl-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N-(5-methylpyrazolo[1,5-a]pyrimidin-3-yl)-4-azaspiro[2.5]octane-7-carboxamide;

(S)-4-(5-(5-fluoro-2-methoxypyridin-4-yl)-1H-pyrazole-3-carbonyl)-N—(((S)-3-methyl-4,5,6,7-tetrahydro-1H-indazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-3-methyl-4,5,6,7-tetrahydro-1H-indazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-7-fluoro-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N—((S)-7-fluoro-3,4-dihydro-2H-pyrano[3,2-b]pyridin-4-yl)-4-azaspiro[2.5]octane-7-carboxamide;

(1R,3s,5S)—N-((3-chloro-5-fluoropyridin-2-yl)methyl)-8-(5-(5-fluoro-2-methoxypyridin-4-yl)-1H-pyrazole-3-carbonyl)-8-azabicyclo[3.2.1]octane-3-carboxamide;

(R)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide;

(S)—N-((3-chloro-5-fluoropyridin-2-yl))methyl)-4-(5-(5-fluoro-2-methylpyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((4-methylpyridazin-3-yl)methyl)-4-azaspiro[2.5]octane-7-carboxamide;

(S)—N-((5-chloro-2-methylpyrimidin-4-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloropyrazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-methoxypyridin-2-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-1-(pyridin-3-yl)pyrrolidin-3-yl)-4-azaspiro[2.5]octane-7-carboxamide;

(S)-4-(5-(5-fluoro-2-methoxypyridin-4-yl)-1 i-pyrazole-3-carbonyl)-N—((S)-1-(pyridin-3-yl)pyrrolidin-3-yl)-4-azaspiro[2.5]octane-7-carboxamide;

(S)—N-((3-chloro-5-cyanopyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-(oxetan-3-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-(3-cyanoazetidin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((2-methyl-5-(trifluoromethyl)oxazol-4-yl)methyl)-4-azaspiro[2.5]octane-7-carboxamide;

(S)—N—((S)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((R)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1-(oxetan-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(oxetan-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((3-methylpyrazin-2-yl)methyl)-4-azaspiro[2.5]octane-7-carboxamide;

(S)—N-((1r,4S)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((3,5-difluoropyridin-2-yl)methyl)-4-(5-(5-fluoro-2-methoxypyridin-4-yl)-1H-pyrazole-3-carbonyl)-4-azaspiro[2.5]octane-7-carboxamide;

(2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide;

(2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide;

(2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide;

(2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide;

(S)—N-((3-chloro-5-methoxypyridin-2-yl)methyl)-4-(5-(5-fluoro-2-methoxypyridin-4-yl)-1H-pyrazole-3-carbonyl)-4-azaspiro[2.5]octane-7-carboxamide;

(2R,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide;

(2S,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide;

(2S,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide;

(2R,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide;

(S)-4-(5-(5-fluoro-2-methoxypyridin-4-yl)-1H-pyrazole-3-carbonyl)-N-((5-fluoro-3-(4-methylpiperazin-1-yl)pyridin-2-yl)methyl)-4-azaspiro[2.5]octane-7-carboxamide;

(R)—N-((5R,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(R)—N-((5S,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(S)—N-((5S,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(S)—N-((5R,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(1-((1-fluorocyclopropyl)methyl)azetidin-3-yl)-4-azaspiro[2.5]octane-7-carboxamide;

(S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,2-dimethylpiperidine-4-carboxamide;

(R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,2-dimethylpiperidine-4-carboxamide;

(S)-4-(5-(5-fluoro-2-methoxypyridin-4-yl)-1H-pyrazole-3-carbonyl)-N-((1s,4R)-4-(hydroxymethyl)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-(hydroxymethyl)-4-(trifluoromethyl)cyclohexyl)-4-azaspiro[2.5]octane-7-carboxamide;

(7S)—N-(1-(tert-butylsulfinyl)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4S,7r)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4R,7s)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1-(4-hydroxybicyclo[2.2.2]octan-1-yl)ethyl)-4-azaspiro[2.5]octane-7-carboxamide;

(S)-4-(5-(5-fluoro-2-methoxypyridin-4-yl)-1H-pyrazole-3-carbonyl)-N—((S)-1-(4-hydroxybicyclo[2.2.2]octan-1-yl)ethyl)-4-azaspiro[2.5]octane-7-carboxamide;

(S)—N-((4,6-dimethylpyridazin-3-yl)methyl)-4-(5-(5-fluoro-2-methoxypyridin-4-yl)-1H-pyrazole-3-carbonyl)-4-azaspiro[2.5]octane-7-carboxamide;

(R)—N-((5-chloropyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3S,4R)-4-morpholinotetrahydrofuran-3-yl)-4-azaspiro[2.5]octane-7-carboxamide;

(S)-4-(5-(5-fluoro-2-methoxypyridin-4-yl)-1H-pyrazole-3-carbonyl)-N-((3R,4S)-4-morpholinotetrahydrofuran-3-yl)-4-azaspiro[2.5]octane-7-carboxamide;

(S)—N—((S)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((R)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(pyrazolo[1,5-a]pyridin-7-ylmethyl)-4-azaspiro[2.5]octane-7-carboxamide;

(S)-4-(5-(5-fluoro-2-methoxypyridin-4-yl)-1H-pyrazole-3-carbonyl)-N-(1-(oxetan-3-yl)piperidin-4-yl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-morpholinocyclohexyl)-4-azaspiro[2.5]octane-7-carboxamide;

(S)-4-(5-(5-fluoro-2-methoxypyridin-4-yl)-1H-pyrazole-3-carbonyl)-N-((1s,4R)-4-morpholinocyclohexyl)-4-azaspiro[2.5]octane-7-carboxamide;

(S)-4-(5-(5-fluoro-2-methoxypyridin-4-yl)-1H-pyrazole-3-carbonyl)-N-((1R,5S,7r)-9-methyl-3-oxa-9-azabicyclo[3.3.1]nonan-7-yl)-4-azaspiro[2.5]octane-7-carboxamide;

(S)-4-(5-(5-fluoro-2-methoxypyridin-4-yl)-1H-pyrazole-3-carbonyl)-N-((1R,5S,7s)-9-methyl-3-oxa-9-azabicyclo[3.3.1]nonan-7-yl)-4-azaspiro[2.5]octane-7-carboxamide;

(S)-4-(5-(5-fluoro-2-methoxypyridin-4-yl)-1H-pyrazole-3-carbonyl)-N-(1-(methylsulfonyl)piperidin-4-yl)-4-azaspiro[2.5]octane-7-carboxamide;

(S)-4-(5-(5-fluoro-2-methoxypyridin-4-yl)-1H-pyrazole-3-carbonyl)-N—((S)-1-(oxetan-3-yl)piperidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(oxetan-3-yl)piperidin-3-yl)-4-azaspiro[2.5]octane-7-carboxamide;

(S)—N-((3R,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2-fluoroethyl)-2,2-dimethylpiperidin-4-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-fluoroethyl)-2,2-dimethylpiperidin-4-yl)-4-azaspiro[2.5]octane-7-carboxamide;

(S)—N-((3R,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4S)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(7S)-4-(5-(5-fluoro-2-methoxypyridin-4-yl)-1H-pyrazole-3-carbonyl)-N-(3-(oxetan-3-yl)-3-azabicyclo[3.1.0]hexan-6-yl)-4-azaspiro[2.5]octane-7-carboxamide;

(S)—N-(5-chloropyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(2-methylpyrimidin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-methylpyrimidin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((3-(trifluoromethyl)pyrazin-2-yl)methyl)-4-azaspiro[2.5]octane-7-carboxamide;

(S)-4-(5-(5-fluoro-2-methoxypyridin-4-yl)-1H-pyrazole-3-carbonyl)-N-(1-((S)-tetrahydrofuran-3-yl)azetidin-3-yl)-4-azaspiro[2.5]octane-7-carboxamide;

(S)-4-(5-(5-fluoro-2-methoxypyridin-4-yl)-1H-pyrazole-3-carbonyl)-N-(1-((R)-tetrahydrofuran-3-yl)azetidin-3-yl)-4-azaspiro[2.5]octane-7-carboxamide;

(7S)—N-((3-chloro-5-(3,5-dimethylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-((1-(trifluoromethyl)cyclopropyl)methyl)pyrolidin-3-yl)-4-(5-(5-fluoro-2-methoxypyridin-4-yl)-1H-pyrazole-3-carbonyl)-4-azaspiro[2.5]octane-7-carboxamide;

(1R,3s,5S)—N-(4-(1,1-difluoro-2-hydroxyethyl)-4-hydroxycyclohexyl)-8-(5-(5-fluoro-2-methoxypyridin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((R)-1-((1-(trifluoromethyl)cyclopropyl)methyl)pyrrolidin-3-yl)-8-azabicyclo[3.2.1]octane-3-carboxamide;

(1R,3s,5S)—N-(4-cyano-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(S)—N-((1s,4R)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((2-(2-fluoro-2-methylpropyl)-2-azabicyclo[2.1.1]hexan-4-yl)methyl)-4-azaspiro[2.5]octane-7-carboxamide;

(1R,3s,5S)—N-(4-amino-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(S)-4-(5-(5-fluoro-2-methoxypyridin-4-yl)-1H-pyrazole-3-carbonyl)-N-(2-(2-fluoro-2-methylpropyl)-2-azabicyclo[2.1.1]hexan-4-yl)-4-azaspiro[2.5]octane-7-carboxamide;

(S)-4-(5-(5-fluoro-2-methoxypyridin-4-yl)-1H-pyrazole-3-carbonyl)-N-((1-(trifluoromethyl)-2-oxabicyclo[2.1.1]hexan-4-yl)methyl)-4-azaspiro[2.5]octane-7-carboxamide;

5-(5-(5-fluoro-2-methoxypyridin-4-yl)-1H-pyrazole-3-carbonyl)-N-((1r,4r)-4-hydroxy-4-(trifluoromethyl)cyclohexyl)-2-oxa-5-azaspiro[3.5]nonane-8-carboxamide;

(S)-4-(5-(5-fluoro-2-methoxypyridin-4-yl)-1H-pyrazole-3-carbonyl)-N-(5-((R)-1-hydroxyethyl)pyrazolo[1,5-a]pyrimidin-3-yl)-4-azaspiro[2.5]octane-7-carboxamide;

(S)-4-(5-(5-fluoro-2-methoxypyridin-4-yl)-1H-pyrazole-3-carbonyl)-N-(5-((S)-1-hydroxyethyl)pyrazolo[1,5-a]pyrimidin-3-yl)-4-azaspiro[2.5]octane-7-carboxamide;

(S)—N-((3-chloro-5-(oxetan-3-yloxy)pyridin-2-yl)methyl)-4-(5-(5-fluoro-2-methoxypyridin-4-yl)-1H-pyrazole-3-carbonyl)-4-azaspiro[2.5]octane-7-carboxamide;

(7S)—N-((5-(3,5-dimethylpiperazin-1-yl)pyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)—N-(1-cyanocyclopropyl)-4-(5-(5-fluoro-2-methoxypyridin-4-yl)-1H-pyrazole-3-carbonyl)-4-azaspiro[2.5]octane-7-carboxamide;

(S)-4-(5-(2-methoxy-5-methylpyridin-4-yl)-1H-pyrazole-3-carbonyl)-N—((R)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide;

(S)—N—((S)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3-chloro-6-methylpyrazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(6-methylpyridazin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(6-methylpyridazin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2-methylpyrimidin-5-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-methylpyrimidin-5-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-((3-hydroxyoxetan-3-yl)methyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-((3-hydroxyoxetan-3-yl)methyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((5-methoxypyrimidin-2-yl)methyl)-4-azaspiro[2.5]octane-7-carboxamide;

(S)—N-((5-cyanopyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-(trifluoromethyl)pyrimidin-2-yl)methyl)-4-azaspiro[2.5]octane-7-carboxamide;

(S)—N-(1-(3,5-dichloropyridin-2-yl)cyclopropyl)-4-(5-(5-fluoro-2-methoxypyridin-4-yl)-1H-pyrazole-3-carbonyl)-4-azaspiro[2.5]octane-7-carboxamide;

(S)—N—((S)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((1R,4S)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1 S,4R)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide;

(S)—N—((R)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((5-((I R,4R)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1S,4S)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide;

(S)-4-(3-(5-fluoro-2-methoxypyridin-4-yl)-1H-pyrazole-5-carbonyl)-N-((3-hydroxyoxetan-3-yl)methyl)-4-azaspiro[2.5]octane-7-carboxamide;

(S)—N—((R)-1-((R)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1H—((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((R)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1,4,5-trimethyl-1H-imidazol-2-yl)methyl)-4-azaspiro[2.5]octane-7-carboxamide;

(S)—N-(5-((1S,2S)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)—N-(5-((1R,2R)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)—N-((5-((1R,4R)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1S,4S)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(R)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide;

(S)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide;

(S)—N-((5-((1 S,6R)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((I R,6S)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N—((R)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide;

(S)—N—((S)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide;

(7S)-4-(5-(5-fluoro-2-methoxypyridin-4-yl)-1H-pyrazole-3-carbonyl)-N-(pyrrolidin-3-yl)-4-azaspiro[2.5]octane-7-carboxamide;

(S)—N—((R)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1-isopropyl-3-methyl-1H-1,2,4-triazol-5-yl)methyl)-4-azaspiro[2.5]octane-7-carboxamide;

(S)—N-((1S,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(5-methyl-4,5,6,7-tetrahydropyrazolo[1,5-a]pyrazin-2-yl)ethyl)-4-azaspiro[2.5]octane-7-carboxamide;

(S)-4-(5-(5-fluoro-2-methoxypyridin-4-yl)-1H-pyrazole-3-carbonyl)-N—((R)-1-(5-methyl-4,5,6,7-tetrahydropyrazolo[1,5-a]pyrazin-2-yl)ethyl)-4-azaspiro[2.5]octane-7-carboxamide;

(S)-4-(3-(5-fluoro-2-methoxypyridin-4-yl)-1H-pyrazole-5-carbonyl)-N-((5-(trifluoromethyl)-1H-imidazol-2-yl)methyl)-4-azaspiro[2.5]octane-7-carboxamide;

4-(5-(2-acetyl-5-fluoropyridin-4-yl)-1H-pyrazole-3-carbonyl)-N-((3-chloro-5-fluoropyridin-2-yl)methyl)-4-azaspiro[2.5]octane-7-carboxamide;

(R)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-5,6,7,8-tetrahydroimidazo[1,2-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((S)-5,6,7,8-tetrahydroimidazo[1,2-a]pyridin-8-yl)-4-azaspiro[2.5]octane-7-carboxamide;

(S)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3-((1S,2S)-2-(hydroxymethyl)cyclopropyl)pyrazin-2-yl)methyl)-4-azaspiro[2.5]octane-7-carboxamide;

(S)-4-(5-(5-fluoro-2-methoxypyridin-4-yl)-1H-pyrazole-3-carbonyl)-N-((3-((1R,2R)-2-(hydroxymethyl)cyclopropyl)pyrazin-2-yl)methyl)-4-azaspiro[2.5]octane-7-carboxamide;

(S)—N-((2-((3S,5R)-3,5-dimethylpiperazin-1-yl)-5-(trifluoromethyl)oxazol-4-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide;

(S)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide;

(R)—N-((3-chloro-5-methoxypyridin-2-yl)methyl)-4-(5-(5-fluoro-2-methylpyridin-4-yl)-1-1-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-(trifluoromethyl)-2-((3S,5R)-3,4,5-trimethylpiperazin-1-yl)oxazol-4-yl)methyl)-4-azaspiro[2.5]octane-7-carboxamide;

(S)-5-(5-(5-fluoro-2-methoxypyridin-4-yl)-1H-pyrazole-3-carbonyl)-N-((1r,4S)-4-hydroxy-4-(trifluoromethyl)cyclohexyl)-5-azaspiro[3.5]nonane-8-carboxamide;

(R)-5-(5-(5-fluoro-2-methoxypyridin-4-yl)-1H-pyrazole-3-carbonyl)-N-((1r,4R)-4-hydroxy-4-(trifluoromethyl)cyclohexyl)-5-azaspiro[3.5]nonane-8-carboxamide;

(S)—N-(5-cyanopyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(7S)—N-(1-(6-cyanopyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3-chloro-5-isopropoxypyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-3-methyl-5,6,7,8-tetrahydro-[1,2,4]triazolo[4,3-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((R)-3-methyl-5,6,7,8-tetrahydro-[1,2,4]triazolo[4,3-a]pyridin-8-yl)-4-azaspiro[2.5]octane-7-carboxamide;

(R)-4-(5-(5-fluoro-2-methoxy-3-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-fluoro-2-methoxy-3-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)—N-(6-acetylpyrazolo[1,5-a]pyridin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(6-((S)-1-hydroxyethyl)pyrazolo[1,5-a]pyridin-3-yl)-4-azaspiro[2.5]octane-7-carboxamide;

(S)-4-(5-(5-fluoro-2-methoxypyridin-4-yl)-1H-pyrazole-3-carbonyl)-N-(6-((R)-1-hydroxyethyl)pyrazolo[1,5-a]pyridin-3-yl)-4-azaspiro[2.5]octane-7-carboxamide;

(7S)—N-(7',8'-dihydro-6'H-spiro[oxetane-3,5'-quinolin]-8'-yl)-4-(5-(5-fluoro-2-methoxypyridin-4-yl)-1H-pyrazole-3-carbonyl)-4-azaspiro[2.5]octane-7-carboxamide;

(7S)—N-(5-ethyl-2-oxa-5-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-(5,5-dimethyl-6,7-dihydro-5H-pyrazolo[5,1-b][1,3]oxazin-3-yl)-4-(5-(5-fluoro-2-methoxypyridin-4-yl)-1H-pyrazole-3-carbonyl)-4-azaspiro[2.5]octane-7-carboxamide;

(S)—N-((1-(aminomethyl)-2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((2-(trifluoromethyl)pyridin-3-yl)methyl)-4-azaspiro[2.5]octane-7-carboxamide;

(S)-4-(5-(5-fluoro-2-methoxypyridin-4-yl)-1H-pyrazole-3-carbonyl)-N-((1R,3R,4S)-3-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1 S,3S,4R)-3-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N—((S)-2-(trifluoromethyl)-5,6,7,8-tetrahydroimidazo[1,2-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((R)-2-(trifluoromethyl)-5,6,7,8-tetrahydroimidazo[1,2-a]pyridin-8-yl)-4-azaspiro[2.5]octane-7-carboxamide;

(S)-4-(3-(5-fluoro-2-methoxypyridin-4-yl)-1H-pyrazole-5-carbonyl)-N-((4-(trifluoromethyl)-1H-imidazol-5-yl)methyl)-4-azaspiro[2.5]octane-7-carboxamide;

(S)—N-((1 S,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1S,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)isoxazol-4-yl)methyl)-4-azaspiro[2.5]octane-7-carboxamide;

(S)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide;

(R)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide;

(S)-4-(3-(5-fluoro-2-methoxypyridin-4-yl)-1H-pyrazole-5-carbonyl)-N-((1-methyl-4-(trifluoromethyl)-1H-pyrazol-5-yl)methyl)-4-azaspiro[2.5]octane-7-carboxamide;

(S)-4-(3-(5-fluoro-2-methoxypyridin-4-yl)-1H-pyrazole-5-carbonyl)-N-((1-methyl-5-(trifluoromethyl)-1H-1,2,3-triazol-4-yl)methyl)-4-azaspiro[2.5]octane-7-carboxamide;

(S)-4-(3-(5-fluoro-2-methoxypyridin-4-yl)-1H-pyrazole-5-carbonyl)-N-((1-methyl-3-(trifluoromethyl)-1H-pyrazol-4-yl)methyl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)pyridin-2-yl)methyl)-4-azaspiro[2.5]octane-7-carboxamide;

(S)—N—(((S)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide;

(S)—N—(((R)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((5-fluoropyrimidin-2-yl)methyl)-4-azaspiro[2.5]octane-7-carboxamide;

(S)-4-(3-(5-fluoro-2-methoxypyridin-4-yl)-1H-pyrazole-5-carbonyl)-N-((2-(trifluoroethyl)pyridin-3-yl)methyl)-4-azaspiro[2.5]octane-7-carboxamide;

(S)-4-(5-(5-fluoro-2-methoxypyridin-4-yl)-1H-pyrazole-3-carbonyl)-N—((S)-5-hydroxy-4,5,6,7-tetrahydropyrazolo[1,5-a]pyridin-3-yl)-4-azaspiro[2.5]octane-7-carboxamide;

(S)-4-(5-(5-fluoro-2-methoxypyridin-4-yl)-1H-pyrazole-3-carbonyl)-N—((R)-5-hydroxy-4,5,6,7-tetrahydropyrazolo[1,5-a]pyridin-3-yl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)bicyclo[1.1.1]pentan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-(trifluoromethyl)pyridin-3-yl)methyl)-4-azaspiro[2.5]octane-7-carboxamide;

(S)-4-(3-(5-fluoro-2-methoxypyridin-4-yl)-1H-pyrazole-5-carbonyl)-N-((2-methyl-4-(trifluoroethyl)thiazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-1-(hydroxymethyl)-3-methyl-2-oxabicyclo[2.1.1]hexan-4-yl)-4-azaspiro[2.5]octane-7-carboxamide;

(S)-4-(5-(5-fluoro-2-methoxypyridin-4-yl)-1H-pyrazole-3-carbonyl)-N—((S)-1-(hydroxymethyl)-3-methyl-2-oxabicyclo[2.1.1]hexan-4-yl)-4-azaspiro[2.5]octane-7-carboxamide;

(S)-4-(3-(5-fluoro-2-methoxypyridin-4-yl)-1H-pyrazole-5-carbonyl)-N-((1-(trifluoromethyl)-1H-imidazol-2-yl)methyl)-4-azaspiro[2.5]octane-7-carboxamide;

(S)-4-(5-(5-fluoro-2-methoxypyridin-4-yl)-1H-pyrazole-3-carbonyl)-N-(1-(hydroxymethyl)-2-oxabicyclo[2.1]hexan-4-yl)-4-azaspiro[2.5]octane-7-carboxamide;

(S)—N-((3-chloro-5-(4-methylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((1-hydroxy-3,3-dimethyl-1,3-dihydrobenzo[c][1,2]oxaborol-6-yl)methyl)-4-azaspiro[2.5]octane-7-carboxamide;

(S)-4-(3-(5-fluoro-2-methoxypyridin-4-yl)-1H-pyrazole-5-carbonyl)-N-(1-hydroxy-1,3-dihydrobenzo[c][1,2]oxaborol-5-yl)-4-azaspiro[2.5]octane-7-carboxamide;

(S)-4-(5-(5-fluoro-2-methoxypyridin-4-yl)-1H-pyrazole-3-carbonyl)-N-((1R,3S)-3-hydroxy-3-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1S,3S)-3-hydroxy-3-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1R,3R)-3-hydroxy-3-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1S,3R)-3-hydroxy-3-(trifluoromethyl)cyclohexyl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)pyridin-4-yl)methyl)-4-azaspiro[2.5]octane-7-carboxamide;

(S)—N-((5-chloro-1-methyl-3-(trifluoromethyl)-1H-pyrazol-4-yl)methyl)-4-(3-(5-fluoro-2-methoxypyridin-4-yl)-1H-pyrazole-5-carbonyl)-4-azaspiro[2.5]octane-7-carboxamide;

(S)-4-(5-(5-fluoro-2-methoxypyridin-4-yl)-1H-pyrazole-3-carbonyl)-N-((5-methoxy-3-(trifluoromethyl)pyridin-2-yl)methyl)-4-azaspiro[2.5]octane-7-carboxamide;

(R)-4-(5-(6-cyanopyrimidin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(6-cyanopyrimidin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)-4-(5-(2-chloro-5-fluoropyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(R)-4-(5-(2-chloro-5-fluoropyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((5-methoxy-3-(trifluoromethyl)pyrazin-2-yl)methyl)-4-azaspiro[2.5]octane-7-carboxamide;

1-(5-(5-chloro-2-methoxypyridin-4-yl)-1H-pyrazole-3-carbonyl)-N-((1-methyl-1H-indol-5-yl)methyl)piperidine-4-carboxamide;

and pharmaceutically acceptable salts thereof.

28. A pharmaceutical composition comprising at least one entity chosen from compounds and pharmaceutically acceptable salts thereof according to any one of embodiments 1 to 27.

29. The pharmaceutical composition according to embodiment 28, further comprising at least one pharmaceutically acceptable carrier.

30. A method for treating and/or preventing cancer comprising administering to a subject in need thereof an effective amount of at least one entity chosen from compounds of Formula (I) and pharmaceutically acceptable salts thereof according to any one of embodiments 1 to 27 and pharmaceutical compositions according to any one of embodiments 28 or 29.

31. The method according to embodiment 30, wherein the cancer is chosen from bladder cancer, breast cancer, prostate cancer, and/or cancers having altered RXRα and/or PPARγ pathways.

32. The method according to any one of embodiments 30 and 31, wherein the cancer is bladder cancer.

33. The method according to any one of embodiments 30 to 32, wherein the bladder cancer is advanced bladder cancer, luminal bladder cancer, and/or basal bladder cancer.

34. The method according to any one of embodiments 30 to 33, wherein the cancer is chemotherapy resistant and/or immunotherapy resistant cancer.

35. A use of at least one entity chosen from compounds of Formula (I) and pharmaceutically acceptable salts thereof according to any one of embodiments 1 to 27 and pharmaceutical compositions according to any one of embodiments 28 or 29 in treating and/or preventing cancer.

36. The use according to embodiment 35, wherein the cancer is chosen from bladder cancer, breast cancer, prostate cancer, and/or cancers having altered RXRα and/or PPARγ pathways.

37. The use according to any one of embodiments 35 and 36, wherein the cancer is bladder cancer.

38. The use according to any one of embodiments 35 to 37, wherein the bladder cancer is advanced bladder cancer, luminal bladder cancer, and/or basal bladder cancer.

39. The use according to any one of embodiments 35 to 38, wherein the cancer is chemotherapy resistant and/or immunotherapy resistant cancer.

40. The compound or pharmaceutically acceptable salt according to any one of embodiments 1 to 27, wherein the compound or the pharmaceutically acceptable salt has a TR-FRET inverse agonist $AC_{50}$ value of less than 1000 nM, less than 500 nM, or less than 250 nM.

41. The compound or pharmaceutically acceptable salt according to any one of embodiments 1 to 27, wherein the m of $R^1$ is 0.

42. The compound or pharmaceutically acceptable salt according to embodiment 8, wherein $R^8$ or $R^9$ is a spiro connected oxetane.

43. The compound or pharmaceutically acceptable salt according to any one of embodiments 1 to 27 and 40 to 42, wherein the compound is chosen from compounds of Formula (IIB) and Formula (IIIB):

Formula (IIB)

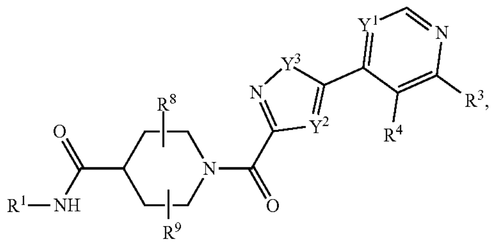

and

Formula (IIIB)

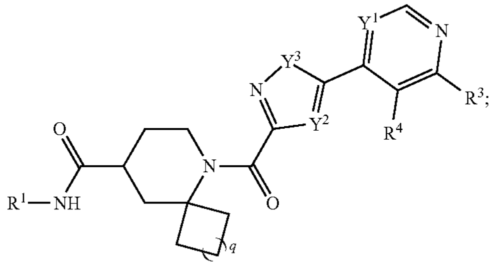

;

wherein q is 0 or 1; and $R^8$ and $R^9$ are each independently chosen from hydrogen, halogens; hydroxyl, optionally substituted alkoxys, and optionally substituted alkyls.

In order that the disclosure described herein may be more fully understood, the following examples are set forth. The reaction schemes and assays set forth below may be used to synthesize and test other embodiments of the present disclosure. It should be understood that these examples are for illustrative purposes only and are not to be construed as limiting this disclosure in any manner.

EXAMPLES

In the following illustrative examples, unless stated otherwise, (i) temperatures are given in degrees Celsius (° C.);

(ii) organic solutions were dried over anhydrous sodium sulfate or magnesium sulfate unless otherwise stated; evaporation of organic solvent was carried out using a rotary evaporator under reduced pressure (5-1000 mbar) with a bath temperature of up to 60° C.;

(iii) column chromatography means flash chromatography on silica gel or pre-packed silica gel cartridges (12, 24, 40 g, etc.); thin layer chromatography (TLC) was carried out on silica gel plates;

(iv) normal and reverse phase flash column chromatography were carried out using either Teledyne ISCO CombiFlash® systems or Biotage® Flash Columns, were used according to the manufacturers' instructions, and obtained from 4700 Superior Street, Lincoln NE 68504, USA or Biotage AB Box 8 751 03 Uppsala Sweden, respectively;

(v) Prep-TLC means preparative TLC plates used in purification;

(vi) in general, the course of reactions was followed by TLC or liquid chromatography/mass spectroscopy (LC/MS) and reaction times are given for illustration only;

(vii) final products have satisfactory proton nuclear magnetic resonance (NMR) spectra and/or mass spectra data;

(viii) preparations were repeated if more material was required;

(ix) when given, NMR data is in the form of delta values for major diagnostic protons, given in part per million (ppm) relative to tetramethylsilane (TMS, δ 0 ppm) as an internal standard;

(x) chemical symbols have their usual meanings;

(xi) in the event that the nomenclature assigned to a given compound does not correspond to the compound structure depicted herein, the structure will control;

(xii) Prep-HPLC means preparative high-performance liquid chromatography, referring to purification using reverse phase HPLC columns listed below, unless otherwise stated, and used according to the manufacturer's instructions;

Sunfire Prep C18 OBD column, 19×150 mm, 5 μm, 10 nm in MeCN/$H_2O$ with 0.1% formic acid or 0.05% TFA as mobile phase obtained from Waters, Building 13, jinlingzhidu, 1000 Jinhai Road, Pudong New Area, Shanghai (Bridge Prep OBD C18 column, 19×250 mm or 30×150 mm or 30×50 mm, 5 μm in MeCN/$H_2O$ with 10 mM $NH_4HCO_3$ as mobile phase obtained from Waters, Building 13, jinlingzhidu, 1000 Jinhai Road, Pudong New Area, Shanghai YMC-Actus Triart C18 column, 20×250 mm or 30×250 mm, 5 μm, 12 nm in MeCN/$H_2O$ with 0.1% or 1 mM formic acid or 10 mM $NH_4HCO_3$ as mobile phase obtained from YMC CO., LTD., Far East International Plaza A2404 No. 319 Xianxia Road, Shanghai 200051, P. R. China Gemini-NX C18 AXAI Packed, 21.2×150 mm, 5 μm in MeCN/$H_2O$ with 0.1% formic acid as mobile phase obtained from Phenomenex, No. 179, Southern Street West TEDA, Tianjin, 300462

XBridge Shield RP18 OBD column, 30×150 mm, 5 μm in MeCN/$H_2O$ with 10 mM $NH_4HCO_3$ as mobile phase obtained from Waters, Building 13, jinlingzhidu, 1000 Jirthai Road, Pudong New Area, Shanghai Atlantis HILIC OBD column, 19×150 mm, 5 μm, 10 nm in MeCN/$H_2O$ with 0.1% formic acid as mobile phase obtained from Waters, Building 13, jinlingzhidu, 1000 Jinhai Road, Pudong New Area, Shanghai XBridge BEH130 Prep C18 OBD Column, 130 Å, 19×150 mm, 5 μm, 13 nm in MeCN/$H_2O$ with 20 mM $NH_4HCO_3$ or 10 mM $NH_4HCO_3$ and 0.1% $NH_3H_2O$ as mobile phase obtained from Waters, Building 13, jinlingzhidu, 1000 Jinhai Road, Pudong New Area, Shanghai XSelect CSH Prep C18 OBD Column, 19×150 mm or 30×50 mm, 30×150 mm, 5 μm in MeCN/$H_2O$ with 0.1% or 0.05% formic acid or 10 mM $NH_4HCO_3$ as mobile phase obtained from Waters, Building 13, jinlingzhidu, 1000 Jinhai Road, Pudong New Area, Shanghai Xselect CSH F-Phenyl OBD column, 19×250 mm, 5 μm in MeCN/$H_2O$ with 10 mM $NH_4HCO_3$ as mobile phase obtained from Waters, Building 13, jinlingzhidu, 1000 Jirthai Road, Pudong New Area, Shanghai Ascentis Express C18 OBD Column, 50×2.1 mm in MeCN/$H_2O$ with 0.1% $NH_4HCO_3$ as mobile phase obtained from Sigma-Aldrich, 15F-18F, Building C, Qiantan World Trade Center (Phase II), No. 3, Lane 227, Dongyu Road, Pudong New Area, Shanghai, China Xbridge C18 column, 100×19 mm, 5 μm in MeCN/$H_2O$ with 0.1% $NH_4OH$ as mobile phase obtained from Waters, 34 Maple Street, Milford, MA 01757, USA CSH C18 column, 100×19 mm, 5 μm in MeCN/$H_2O$ with 0.1% formic acid as mobile phase obtained from Waters, 34 Maple Street, Milford, MA 01757, USA (xiii) Chiral-Prep-HPLC means chiral preparative high-performance liquid chromatography, referring to purification using chiral HPLC columns listed below, unless otherwise stated, and used according to the manufacturer's instructions;

*Viridis* BEH Prep OBD column, 1.9×15 cm, 5 μm in hexanes/IPA as mobile phase obtained from Waters, Building 13, jinlingzhidu, 1000 Jinhai Road, Pudong New Area, Shanghai CHIRAL ART Cellulose-SB column, 2×25 cm or 3×25 cm, 5 μm in MTBE/MeOH with 2 mM $NH_3$ in MeOH, hexanes/EtOH with 10 mM $NH_3$ in MeOH, hexanes/IPA with 10 mM $NH_3$ in MeOH, MTBE/IPA with 0.5% 2 M $NH_3$ in MeOH, MTBE/MeOH with 0.5% 2 M $NH_3$ in MeOH, or hexanes/EtOH with 8 mM $NH_3$ in MeOH as mobile phase obtained from YMC CO., LTD., Far East International Plaza A2404 No. 319 Xianxia Road, Shanghai 200051, P. R. China Gemini-NX C18 AXAI Packed column, 21.2×150 mm, 5 μm in MeCN/$H_2O$ with 0.1% formic acid as mobile phase obtained from Phenomenex, No. 149, Southern Avenue, western district, TEDA, Tianjin, China (xiv) Chiralpak® columns (e.g. type IA, IC, ID, IE, IF, IG and/or AD-H) are used according to the manufacturer's instruction and obtained from DAICEL CHIRAL TECHNOLOGIES (CHINA) CO., LTD., No. 32, XiangHe Road, WaiGaoQiao Free Trade Zone, Shanghai, 200131, P. R. China (xv) Prep-SFC refers to preparative super critical fluid chromatography, used with N-Lux 3u i-Cellulose-5 column, 0.46×10 cm, 3 μm in carbon dioxide/MeOH with 20 mM $NH_3$ as mobile phase according to the manufacturer's instruction, obtained from Phenomenex, No. 149, Southern Avenue, western district, TEDA, Tianjin, China;

(xvi) enantiomeric excess for each individual enantiomer (e.e.) are calculated using area percent at 220 nm or 254 nm unless otherwise stated;

(xvii) diastereomeric excess for each individual diastereomer (d.e.) are calculated using area percent at 220 nm or 254 nm unless otherwise stated;

(xviii) mass spectra were acquired when samples were separated using reverse-phase liquid chromatography (LC) and detected by electrospray ionization (ESI) mass spectrometry (MS) or thin-layer chromatography (TLC) and detected by atmospheric pressure chemical ionization (APCI) mass spectrometry (MS) in positive and negative ion; values for m/z are given; generally; only ions which indicate the parent mass are reported; and unless otherwise stated, the mass ion quoted is $[M+H]^+$ or $[M+Na]^+$; and (xix) The following abbreviations have been used:
AcOH: Acetic acid
$B_2Pin_2$: Bis(pinacolato)diboron
Boc: tert-butyloxycarbonyl
$Boc_2O$: Di-tert-butyl decarbonate
$Cs_2CO_3$: Cesium carbonate
DAST: (Diethylamino)sulfur trifluoride
DCE: 1,2-Dichloroethane
DCM: Dichloromethane
DEAD: Diethyl diazenedicarboxylate
DHP: Dihydropyran
DIAD: Diisopropyl azodicarboxylate
DIPEA: N,N-diisopropylethylamine, Hunig's base
DIBAL-H: Diisobutylaluminum hydride
DMF: Dimethylformamide
DMSO: Dimethylsulfoxide
DPPA: Diphenylphosphoryl azide
Dppf: 1,1'-Ferrocenediyi-bis(diphenylphosphine)
Dthpy: 4,4'-Di-tert-butyl-2,2'-dipyridyl
EDCI·HCl: N-(3-Dimethylaminopropyl)-N-ethylcarbodiimide hydrochloride
EDCI: N-(3-Dimethylaminopropyl)-N-ethylcarbodiimide
EtOH: Ethanol
EtOAc: Ethyl acetate
FA: Formic acid
h: Hours
HATU: 1-[Bis(dimethylamino)methylene]-1H-1,2,3-triazolo[4,5-b]pyridinium 3-oxide hexafluorophosphate
HCl: Hydrochloric acid
HMPA: Hexamethylphosphoramide
HOBt: Hydroxybenzotriazole
HPLC: High-performance liquid chromatography
$H_2SO_4$: Sulfuric acid
IPA: Isopropyl alcohol
$[Ir(COD)OMe]_2$: Bis(1,5-cyclooctadiene)di-μ-methoxy-diiridium(I)
$K_2CO_3$: Potassium carbonate
$K_3PO_4$: Potassium phosphate tribasic
Lawesson reagent: 2,4-Bis(4-methoxyphenyl)-2,4-dithioxo-1,3,2,4-dithiadiphosphetane
LCMS: Liquid chromatography mass spectrometry
MeCN: Acetonitrile
MeOH: Methanol
2-MeTHF: 2-Methyltetrahydrofuran
min: Minutes
MTBE: Methyl tert-butyl ether
nBuLi: n-Butyllithium
NCS: n-Chlorosuccinimide
$NH_4Cl$: Ammonium chloride
NMO: N-Methylmorpholine N-oxide
NMR: Nuclear magnetic resonance
Pd/C: Palladium (0) on carbon
$Pd_2(dba)_3$: Tris(dibenzylideneacetone)dipalladium(0)
$Pd(dppf)Cl_2$: [1,1'-Bis(diphenylphosphino)ferrocene]dichloropalladium(II)
PTSA: p-Toluenesulfonic acid
T3P®: Propylphosphonic anhydride solution
TBAF: Tetrabutylammonium fluoride
TEA: Triethylamine
TEMPO: (2,2,6,6-Tetramethylpiperidin-1-yl)oxyl
TFA: Trifluoroacetic acid
THF: Tetrahydrofuran
TLC: Thin-layer chromatography
TsOH: Tosylic acid
XPhos: 2-Dicyclohexylphosohino-2',4',6'-triisopropylbiphenyl

Intermediates

Intermediate 501. Methyl 1-(5-bromo-1H-pyrazole-3-carbonyl)piperidine-4-carboxylate

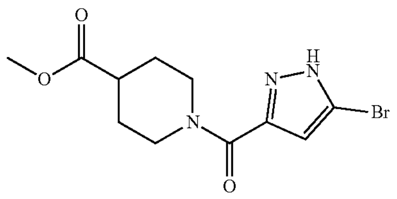 [SMILES: COC(=O)C1CCN(C(=O)c2cc(Br)[nH]n2)CC1]

EDCI (3.00 g, 15.71 mmol), HOBt (2.10 g, 15.71 mmol), and methyl piperidine-4-carboxylate (2.20 g, 15.71 mmol) were added to a stirred solution of 5-bromo-1H-pyrazole-3-carboxylic acid (2.00 g, 10.47 mmol) and DIPEA (7.28 mL, 41.89 mmol) in DMF (10.00 mL). The resulting mixture was stirred at 25° C. for 14 h. The mixture was then diluted with EtOAc, washed with water, and the organic layer was concentrated under reduced pressure. The residue was purified by silica gel column chromatography (petroleum ether/EtOAc, 1/1 v/v) to obtain the title compound (2.60 g) as an oil. LCMS (ESI): 316.0 $[M+H]^+$.

Intermediate 502. N-(4-methylcyclohexyl)piperidine-4-carboxamide

Step-1. Benzyl 4-[(4-methylcyclohexyl)carbamoyl]piperidine-1-carboxylate

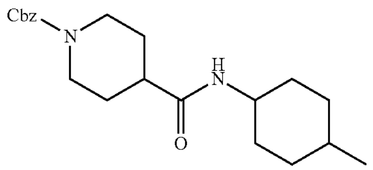 [SMILES: CC1CCC(NC(=O)C2CCN(C(=O)OCc3ccccc3)CC2)CC1]

HATU (866.5 mg, 2.28 mmol) and 4-methylcyclohexan-1-amine (258.0 mg, 2.28 mmol) were added to a stirred mixture of 1-[(benzyloxy)carbonyl]piperidine-4-carboxylic acid (500.0 mg, 1.90 mmol) and DIPEA (736.3 mg, 5.70 mmol) in DMF (5.00 mL). The resulting mixture was stirred at 25° C. for 14 h. The resulting mixture was diluted with EtOAc, washed with water, and the organics was concentrated under reduced pressure. The residue was purified by silica gel column chromatography (DCM/MeOH, 30/1 v/v) to afford the diastereomeric mixture of the title compound (300.0 mg) as an oil. LCMS (ESI): $[M+H]^+$: 359.2.

Step-2. N-(4-methylcyclohexyl)piperidine-4-carboxamide (Intermediate 502)

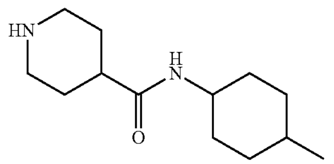 [SMILES: CC1CCC(NC(=O)C2CCNCC2)CC1]

Pd/C (90.0 mg) was added to a stirred solution of benzyl 4-[(4-methylcyclohexyl)carbamoyl]piperidine-1-carboxylate (Step-1, 300.0 mg, 0.84 mmol) in MeOH (5.00 mL). The resulting mixture was stirred at 25° C. under a $H_2$ atmosphere for 2 h, the solids were filtered out, then the resulting mixture was concentrated under reduced pressure to afford the title compound (154.0 mg) as a solid mixture of diastereomers. LCMS (ESI): $[M+H]^+$: 225.2.

Intermediate 503. 1-[5-(5-chloro-2-methoxypyridin-4-yl)-1H-pyrazole-3-carbonyl]piperidine-4-carboxylic acid Step-1. tert-butyl 1-(5-bromo-1H-pyrazole-3-carbonyl)piperidine-4-carboxylate

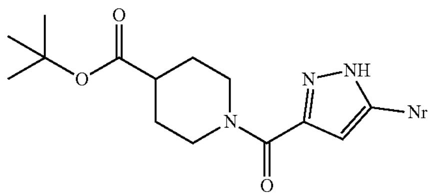

HATU (14.33 g, 37.70 mmol) and tert-butyl piperidine-4-carboxylate (8.73 g, 47.12 mmol) were added to a stirred mixture of 5-bromo-1H-pyrazole-3-carboxylic acid (6.00 g, 31.42 mmol) and DIPEA (12.18 g, 94.24 mmol) in DMF (100.00 mL). The resulting mixture was stirred at 25° C. for 2 h. The solution was then diluted with water and extracted with EtOAc. The organic layers were combined, dried over anhydrous sodium sulfate, filtered, and the solvent was evaporated. The residue was purified by silica gel column chromatography (EtOAc/petroleum ether, 1/1 v/v) to obtain the title compound (8.00 as a solid. LCMS (ESI): 358.1 $[M+H]^+$.

Step-2. tert-butyl 1-[5-bromo-1-(oxan-2-yl)pyrazole-3-carbonyl]piperidine-4-carboxylate

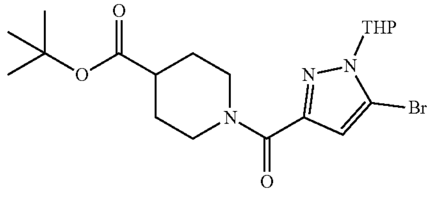

DHP (3.76 g, 44.70 mmol) and TsOH (769.1 mg, 4.47 mmol) were added to a stirred mixture of tert-butyl 1-(5-promo-1H-pyrazole-3-carbonyl)piperidine-4-carboxylate (Step-1, 8.00 g, 22.33 mmol) in THF (100.00 mL). The resulting mixture was stirred at 25° C. for 2 h. The pH value of the solution was adjusted to pH 8 with saturated solution of $NaHCO_3$. The solution was extracted with EtOAc. The organic layers were combined, then dried over anhydrous sodium sulfate, filtered, and the solvent was evaporated. The residue was purified by silica gel chromatography (EtOAc/petroleum ether, 1/4 v/v) to obtain the title compound (9.00 g) as a solid. LCMS (ESI): $[M+H]^+$: 442.1.

Step-3. tert-butyl 1-[5-(5-chloro-2-methoxypyridin-4-yl)-1-(oxan-2-yl)pyrazole-3-carbonyl]piperidine-4-carboxylate

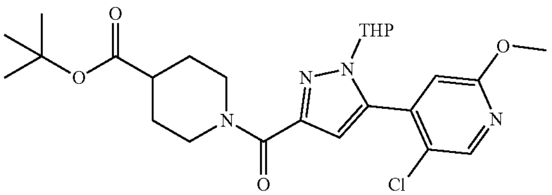

$Pd(dppf)Cl_2$ (1.65 g, 2.26 mmol) and $K_2CO_3$ (9.37 g, 67.8 mmol) were added to a stirred mixture of tert-butyl 1-[5-bromo-1-(oxan-2-yl)pyrazole-3-carbonyl]piperidine-4-carboxylate (Step-2, 10.00 g, 22.61 mmol) and 5-chloro-2-methoxypyridin-4-ylboronic acid (6.35 g, 33.91 mmol) in 1,4-dioxane (60.00 mL) and water (12.00 mL) at 25° C. The resulting solution was stirred at 80° C. for 2 h under nitrogen atmosphere. The solution was then diluted with water and extracted with EtOAc. The organic layers were combined, then dried over anhydrous sodium sulfate, filtered, and the solvent was evaporated. The residue was purified by silica gel chromatography (EtOAc/petroleum ether, 1/2 v/v) to obtain the title compound (6.00 g) as a solid. LCMS (ESI): $[M+H]^+$: 505.2.

Step-4. 1-[5-(5-chloro-2-methoxypyridin-4-yl)-1-pyrazole-3-carbonyl]piperidine-4-carboxylic acid (Intermediate 503)

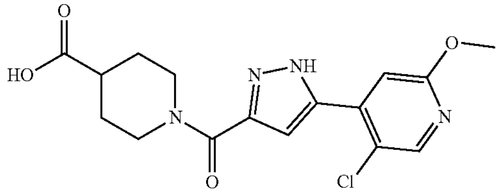 [SMILES: COc1cc(-c2cc(C(=O)N3CCC(C(=O)O)CC3)n[nH]2)c(Cl)cn1]

TFA (20.00 mL) was added to a stirred solution of tert-butyl 1-[5-(5-chloro-2-methoxypyridin-4-yl)-1-(oxan-2-yl)pyrazole-3-carbonyl]piperidine-4-carboxylate (Step-3, 6.00 g, 11.88 mmol) in DCM (20.00 mL). The resulting solution was stirred at 25° C. for 2 h. The resulting mixture was concentrated, and the resulting residue was purified by reverse phase column chromatography (using the following conditions: Column: IntelFlash-1 C18 column; Mobile Phase: MeCN/water, 1/1 v/v) to obtain the title compound (2.73 g) as a solid. LCMS (ESI): 365.1 $[M+H]^+$.

Intermediate 504. 1-[5-bromo-1-(oxan-2-yl)pyrazole-3-carbonyl]piperidine-4-carboxylate

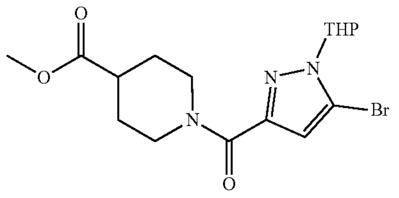

DHP (1.40 g, 16.45 mmol) and TFA (0.63 mL, 8.22 mmol) were added to a stirred mixture of methyl 1-(5-bromo-1H-pyrazole-3-carbonyl)piperidine-4-carboxylate (INTERMEDIATE 501, 2.60 g, 8.22 mmol) in THF (10.00 mL) at 25° C. The resulting mixture was stirred at 60° C. for 14 h. The solution was then concentrated under reduced pressure and purified by silica gel column chromatography (petroleum ether/EtOAc, 1/1 v/v) to obtain the title compound (1.10 g) as an oil. LCMS (ESI): 400.1 $[M+H]^+$.

Intermediate 505. 1-(5-(5-Fluoro-2-methoxypyridin-4-yl)-1-(tetrahydro-2H-pyran-2-yl)-1H-pyrazole-3-carbonyl)piperidine-4-carboxylic acid Step-1. Methyl 1-(5-(5-fluoro-2-methoxypyridin-4-yl)-1-(tetrahydro-2H-pyran-2-yl)-1H-pyrazole-3-carbonyl)piperidine-4-carboxylate

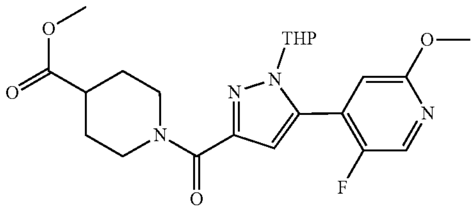

5-fluoro-2-methoxypyridin-4-ylboronic acid (514.0 mg, 3.00 mmol), Pd(dppf)$Cl_2$ (361.0 mg, 0.51 mmol) and $K_3PO_4$ (1594.0 mg, 7.52 mmol) was added to a solution of methyl 1-[5-bromo-1-(oxan-2-yl)pyrazole-3-carbonyl]piperidine-4-carboxylate (1.00 g, 2.51 mmol) in 1,4-dioxane (10.00 mL) and $H_2O$ (2.50 mL). The resulting solution was stirred at 80° C. for 2 h under nitrogen atmosphere. The resulting mixture was concentrated under vacuum, and the resulting residue was purified by a silica gel column (DCM/methanol, 10/1 v/v) to deliver 1.06 g of the title compound as an oil. LCMS (ESI): $[M+H]^+$: 447.2.

Step-2. 1-(5-(5-Fluoro-2-methoxypyridin-4-yl)-1-(tetrahydro-2H-pyran-2-yl)-1H-pyrazole-3-carbonyl)piperidine-4-carboxylic acid (Intermediate 505)

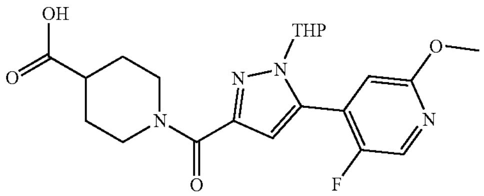

LiOH (342.0 mg, 14.26 mmol) was added to a solution of methyl 1-[5-(5-fluoro-2-methoxypyridin-4-yl)-1-(oxan-2-yl)pyrazole-3-carbonyl]piperidine-4-carboxylate (Step-1, 1.06 g, 2.38 mmol) in THF (4.00 mL)/MeOH (4.00 mL)/$H_2O$ (4.00 mL). The resulting solution was stirred at 25° C. for 1 h. The resulting solution was concentrated under vacuum and the resulting residue was diluted with dichloromethane. The pH value of the solution was adjusted to pH 6 with AcOH. The resulting mixture was concentrated under vacuum to deliver the title compound (940.0 mg) as an oil. LCMS (ESI): $[M+H]^+$: 433.2.

Intermediate 506. 5-(5-fluoro-2-methoxypyridin-4-yl)-1-((2-(trimethylsilyl)ethoxy)methyl)-1H-pyrazole-3-carboxylic acid and Intermediate 507. 5-(5-Fluoro-2-methoxypyridin-yl)-1H-pyrazole-3-carboxylic acid Step-1. Methyl 5-bromo-1-((2-(trimethylsilyl)ethoxy)methyl)-1H-pyrazole-3-carboxylate

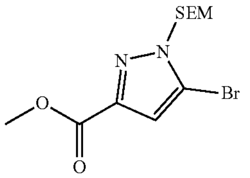 [SMILES: COC(=O)c1cc(Br)n(COCC[Si](C)(C)C)n1]

SEM-Cl (2.85 mL, 16.10 mmol) was added dropwise to a stirred solution of methyl 5-bromo-1H-pyrazole-3-carboxylate (3.00 g, 14.63 mmol) and $K_2CO_3$ (2.23 g, 16.10 mmol) in DMF (40.00 mL) at 0° C. The reaction mixture was then stirred at 25° C. for 2 h. The solution was diluted with EtOAc and water, then extracted with EtOAc. The organic layer was washed with brine, dried over anhydrous $Na_2SO_4$, filtered, and the solvent was evaporated. The residue was purified by silica gel column chromatography (EtOAc/Hexane, 0/100 to 10/90 v/v) to obtain the title compound (3.49 g) as an oil. LCMS (ESI): 337.0 $[M+H]^+$.

Step-2. Methyl 5-(5-fluoro-2-methoxypyridin-4-yl)-1-((2-(trimethylsilyl)ethoxy)methyl)-1H-pyrazole-3-carboxylate

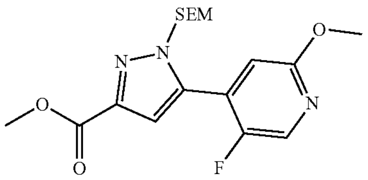

Pd(dppf) $Cl_2$ (0.44 g, 0.60 mmol) and $K_2CO_3$ (1.24 g, 8.95 mmol) were added to a stirred solution of methyl 5-bromo-1-((2-(trimethylsilyl)ethoxy)methyl)-1H-pyrazole-3-carboxylate (Step-1, 1.0 g, 2.98 mmol) and (5-fluoro-2-methoxypyridin-4-yl)boronic acid (0.61 g, 3.58 mmol) in water (2.00 mL) and 1,4-dioxane (8.00 mL). The reaction mixture was stirred at 100° C. for 15 h under nitrogen atmosphere. The reaction mixture was then cooled to 25° C. and diluted with EtOAc and water. The organic layer was washed with brine, dried over anhydrous $Na_2SO_4$, filtered, and the solvent was evaporated. The residue was purified by silica gel column chromatography (EtOAc/Hexane, 5/95 to 25/75 v/v) to obtain the title compound (765.0 mg) as an oil. LCMS (ESI): 382.2 $[M+H]^+$.

Step-3a. 5-(5-fluoro-2-methoxypyridin-4-yl)-14(2-(trimethylsilyl)ethoxy)methyl)-1H-pyrazole-3-carboxylic acid (Intermediate 506)

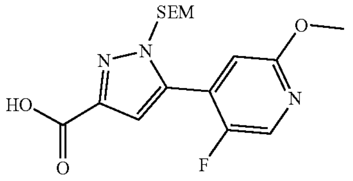 [SMILES: COc1cc(-c2cc(C(=O)O)nn2COCC[Si](C)(C)C)c(F)cn1]

1 M aqueous solution of lithium hydroxide (2.21 mL, 2.21 mmol) was added to a stirred solution of methyl 5-(5-fluoro-2-methoxypyridin-4-yl)-1-((2-(trimethylsilyl)ethoxy)methyl)-1H-pyrazole-3-carboxylate (Step-2, 281.0 mg, 0.74 mmol) in water (2.00 mL) and THF (8.00 mL). The reaction mixture was stirred at 25° C. for 7 h. The pH of the mixture was then adjusted to 1 by the addition of aqueous HCl (1 M). The solution was concentrated, and the residue was purified by silica gel column chromatography (EtOAc/Hexane, 30/70 to 50/50 v/v) to obtain the title compound (264.0 mg) as a solid. LCMS (ESI): 369.4 $[M+H]^+$.

Step-3b. Methyl 5-(5-fluoro-2-methoxypyridin-4-yl)-1H-pyrazole-3-carboxylate

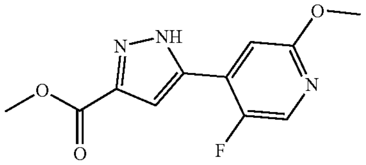

TFA (10.00 mL) was added to a stirred solution of methyl 5-(5-fluoro-2-methoxypyridin-4-yl)-1-((2-(trimethylsilyl)ethoxy)methyl)-1H-pyrazole-3-carboxylate (Step-2, 10.00 g, 26.21 mmol) in DCM (10.00 mL). The resulting mixture was stirred at 25° C. for 4 h, then the solution was concentrated under reduced pressure. The residue was purified by silica gel column chromatography (DCM/MeOH, 12/1 v/v) to obtain the title compound (7.00 g) as an oil LCMS (ESI): 252.1 $[M+H]^+$.

Step-4. 5-(5-Fluoro-2-methoxypyridin-4-yl)-1H-pyrazole-3-carboxylic acid (Intermediate 507)

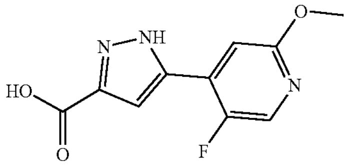 [SMILES: COc1cc(-c2cc(C(=O)O)n[nH]2)c(F)cn1]

$LiOH{\cdot}H_2O$ (1.67 g, 39.80 mmol) was added to a stirred solution of methyl 5-(5-fluoro-2-methoxypyridin-4-yl)-1H-pyrazole-3-carboxylate (Step-3b, 5.00 g, 19.90 mmol) in THF (8.00 mL), MeOH (8.00 mL) and $H_2O$ (8.00 mL). The resulting mixture was stirred at 60° C. for 14 h., then the solution was concentrated under reduced pressure. The pH of the solution was adjusted to 3 by the addition of aqueous HCl (1 M). The precipitated solids were collected by filtration and washed with water, then dried under pressure to obtain the title compound (4.50 g) as a solid. $^1H$ NMR (300 MHz, DMSO-$d_6$) δ 14.37 (s, 1H), 8.28 (s, 1H), 7.32 (s, 1H), 7.20 (s, 1H), 3.87 (s, 3H). LCMS (ESI): 238.0 $[M+H]^+$.

Alternative Method of Synthesis for Intermediate 506, 5-(5-fluoro-2-methoxypyridin-4-yl)-1-((2-(trimethylsilyl)ethoxy)methyl)-1H-pyrazole-3-carboxylic acid Step-1. Methyl 5-bromo-1-((2-(trimethylsilyl)ethoxy)methyl)-1H-pyrazole-3-carboxylate and methyl 3-bromo-1-((2-(trimethylsilyl)ethoxy)methyl)-1H-pyrazole-5-carboxylate

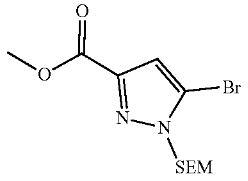

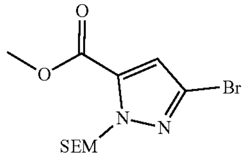

Two batches were carried out in parallel, Dichloromethane (2.50 L) was added to a 5.00 L of jacket flask equipped with overhead stirrer, addition funnel and thermometer, $N_2$ balloon at 0° C. 3. Methyl 5-bromo-1H-pyrazole-3-carboxylate (500.00 g, 2.44 mol) was added to the flask at 0° C. DIPEA (630.00 g, 4.88 mol) and SEM-Cl (610.00 kg, 3.66 mol) were added to the flask at 0° C. The resulting mixture was purged with $N_2$ for 3 times and was stirred at 0 to 20 DC for 12 h under $N_2$, Two batches were combined and the reaction mixture was poured into $H_2O$ (8.00 L), extracted with dichloromethane (4.00 L×2). The combined organic layer was washed with brine (5.00 L), dried over $Na_2SO_4$, filtered and the filtrate was concentrated in vacuum. The residue was purified by silica gel column chromatography eluting with petroleum ether/ethyl acetate (5/1 v/v) to obtain the title compounds (1.03 kg) as a solid. $^1H$ NMR (400 MHz, $CDCl_3$) 6.92 (s, 1H), 5.83 (s, 2H), 3.94 (s, 3H), 3.64 (t, 2H), 0.91-0.95 (m, 2H), 2.70-1.75 (t, 1H), 1.73-1.74 (m, 4H), 1.48-1.55 (m, 6H), 1.43 (s, 9H), 1.18-1.19 (m, 1H), 0.00 (s, 9H). LCMS: 279 $[M+H]^+$.

Step-2. Methyl 5-(5-fluoro-2-methoxypyridin-4-yl)-1-((2-(trimethylsilyl)ethoxy)methyl)-1H-pyrazole-3-carboxylate

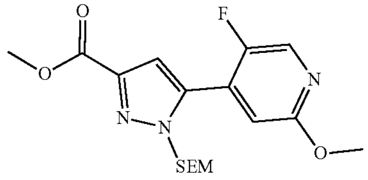

Two batches were carried out in parallel. Methanol (2.50 L) was added to a 5.00 L of jacket flask equipped with overhead stirrer, addition funnel and thermometer, $N_2$ balloon at 25 DC, Methyl 5-bromo-1-((2-(trimethylsilyl)ethoxy)methyl)-1H-pyrazole-3-carboxylate and methyl 3-bromo-1-((2-(trimethylsilyl)ethoxy)methyl)-1H-pyrazole-5-carboxylate (Step-1, 517.00 g, 1.54 mol) was added to the flask at 25° C. DIPEA (399.00 g, 3.08 mol) was added to the flask at 0° C. and (5-fluoro-2-methoxypyridin-4-yl)boronic acid (277.00 g, 1.62 mol) was added to the flask at 25° C. $P(tBu)_3PdG_2$ (39.50 g, 77.10 mmol) was added to the flask at 25° C. and the resulting mixture was purged with $N_2$ for 3 times. The reaction mixture was stirred at 65° C. for 2 h under $N_2$. Two batches were combined and the reaction mixture was poured into $H_2O$ (3.00 L), extracted with ethyl acetate (3.00 L×2). The combined organic layer was washed with brine (4.00 L), dried over $Na_2SO_4$, filtered and the filtrate was concentrated in vacuum. The residue was purified by silica gel column chromatography eluting with petroleum ether/ethyl acetate (30/1 to 5/1 v/v) to obtain the title compound (1.15 kg) as a solid. $^1$H NMR (400 MHz, $CDCl_3$) δ 8.09 (d, 1H), 7.40 (t, 2H), 5.92 (s, 2H), 3.95 (d, 6H), 3.66 (t, 2H), 0.92 (t, 2H), 0.03 (s, 9H). LCMS: 382.4 $[M+H]^+$.

Step-3. 5-(5-fluoro-2-methoxypyridin-4-yl)-1-((2-(trimethylsilyl)ethoxy)methyl)-1H pyrazole-3-carboxylic acid (Intermediate 506)

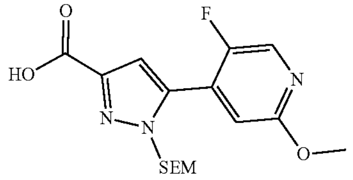 [SMILES: COc1cc(-c2cc(C(=O)O)nn2COCC[Si](C)(C)C)c(F)cn1]

Two batches were carried out in parallel. THF (1.80 L) and $H_2O$ (1.80 L) were added to a 5.00 L of jacket flask equipped with overhead stirrer, addition funnel and thermometer, $N_2$ balloon etc at 25° C. Methyl 5-(5-fluoro-2-methoxypyridin-4-yl)-1-((2-(trimethylsilyl)ethoxy)methyl)-1H-pyrazole-3-carboxylate (Step-2, 576.00 g, 1.51 mol) and $LiOH \cdot H_2O$ (127.00 g, 3.02 mol) were added to the flask at 25° C. The reaction mixture was stirred at 25° C. for 2 h under $N_7$. Two batches were combined and the reaction mixture was adjusted to pH=4, extracted with ethyl acetate (500 mL×2). The combined organic layer was washed with brine (500 mL), dried over $Na_2SO_4$, filtered and the filtrate was concentrated in vacuum. The residue was triturated with petroleum ether/ethyl acetate (10/1 v/v, 100 mL) at 25° C. for 0.5 h and concentrated to obtain the title compound (1.01 kg) as a solid. $^1$H NMR (400 MHz, MeOD) δ 8.07 (d, 1H), 7.33 (d, 1H), 7.23 (d, 1H), 6.00 (s, 2H), 3.92 (s, 3H), 3.67 (t, 2H), 0.88 (t, 2H), 0.04 (s, 9H). LCMS: 368.1 $[M+H]^+$.

Intermediate 508. (1R,3S,5S)-8-[5-(5-Fluoro-2-methoxypyridin-4-yl)-1H-pyrazole-3-carbonyl]-8-azabicyclo[3.2.1]octane-3-carboxylic acid Step-1. 3-Benzyl 8-tert-butyl (1R,3S,5S)-8-azabicyclo[3.2.1]octane-3,8-dicarboxylate

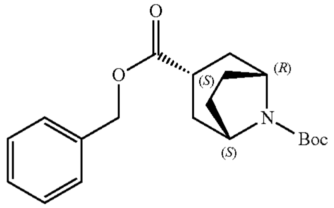

A mixture of (1R,3S,5S)-8-(tert-butoxycarbonyl)-8-azabicyclo[3.2.1]octane-3-carboxylic acid (1.00 g, 3.92 mmol), benzyl alcohol (0.47 g, 4.00 mmol), $PPh_3$ (1.54 g, 6.00 mmol) in THF (30.00 mL) was cooled to 0° C. DIAD (1.19 g, 6.00 mmol) was added dropwise to this mixture at 0° C. under nitrogen atmosphere. The resulting mixture was stirred at 25° C. for 14 h, then the mixture was concentrated under reduced pressure. The resulting residue was purified by silica gel column chromatography (petroleum ether/EtOAc, 3/1 v/v) to afford the title compound (1.30 g) as an oil. LCMS (ESI): 346.2 $[M+H]^+$ Step-2. Benzyl (1R,3S,5S)-8-azabicyclo[3.2.1]octane-3-carboxylate

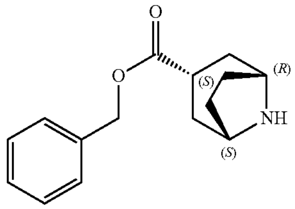

TFA (15.00 mL) was added to a mixture of 3-benzyl 8-tert-butyl (1R,3S,5S)-8-azabicyclo[3.2.1]octane-3,8-dicarboxylate (Step-1, 6.00 g, 17.37 mmol) in DCM (15.00 mL) at 0° C. and stirred at 0° C. for 30 min. The resulting mixture was concentrated under reduced pressure. The resulting residue was used in the next step directly without further purification. LCMS (ESI): $[M+H]^+$: 246.1.

Step-3. Benzyl (1R,3S,5S)-8-[5-(5-fluoro-2-methoxypyridin-4-yl)-1H-pyrazole-3-carbonyl]-8-azabicyclo[3.2.1]octane-3-carboxylate

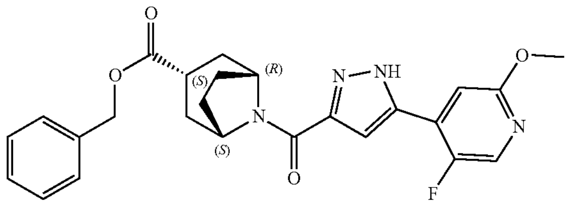

A solution of 5-(5-fluoro-2-methoxypyridin-4-yl)-1H-pyrazole-3-carboxylic acid (INTERMEDIATE 507, 4.25 g, 17.92 mmol), HOBt (3.30 g, 24.46 mmol) and EDGE (4.69 g, 24.46 mmol) in DMF (50.00 mL) was stirred at 25° C. for 30 min. Benzyl (1R,3S,5S)-8-azabicyclo[3.2.1]octane-3-carboxylate (Step-3, 4.00 g, 16.31 mmol) and DIPEA (10.54 g, 81.53 mmol) was added to the above mixture and stirred at 25° C. for 14 h. The resulting mixture was diluted with EtOAc, washed with water, then the resulting mixture was concentrated under reduced pressure. The residue was purified by silica gel column chromatography (DCM/MeOH, 19/1 v/v) to afford the title compound (3.25 g) as a solid. LCMS (ESI): $[M+H]^+$: 465.2.

Step-4. (1R,3S,5S)-8-[5-(5-Fluoro-2-methoxypyridin-4-yl)-1H-pyrazole-3-carbonyl]-8-azabicyclo[3.2.1]octane-3-carboxylic acid (Intermediate 508)

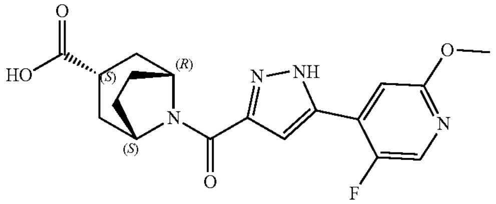

LiOH·$H_2O$ (0.59 g, 14.06 mmol) was added to a solution of benzyl (1R,3S,5S)-8-[5-(5-fluoro-2-methoxypyridin-4-yl)-1H-pyrazole-3-carbonyl]-8-azabicyclo[3.2.1]octane-3-carboxylate (Step 3, 3.25 g, 7.00 mmol) in $H_2O$ (10.00 mL), THF (10.00 mL), and MeOH (10.00 mL) and was stirred at 25° C. for 30 min. The resulting mixture was concentrated under reduced pressure to remove THF and MeOH, as much as possible. The mixture was acidified to pH 3 with aqueous HCl (1 M). The precipitates were collected by filtration, washed with water, then dried under reduced pressure, resulting in the title compound (2.10 g) as a solid. $^1H$ NMR (300 MHz, DMSO-$d_6$) δ 12.25 (s, 1H), 8.29 (s, 1H), 7.34 (d, 1H), 7.14 (s, 1H), 5.32-5.09 (m, 1H), 4.79-4.54 (m, 1H), 3.88 (s, 3H), 3.02-2.80 (m, 1H), 2.13-1.65 (m, 8H). LCMS (ESI): $[M+H]^+$: 375.1.

Intermediate 509. 1-[5-Bromo-1-(oxan-2-yl)pyrazole-3-carbonyl]piperidine-4-carboxylic acid

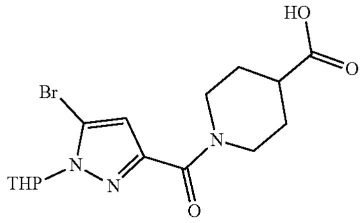

LiOH·$H_2O$ (0.69 g, 16.49 mmol) was added to a mixture of methyl 1-[5-bromo-1-(oxan-2-yl)pyrazole-3-carbonyl]piperidine-4-carboxylate (INTERMEDIATE 504, 1.10 g, 2.75 mmol) in THF (2.00 mL)/$H_2O$ (2.00 mL)/MeOH (2.00 mL). The resulting mixture was stirred at 25° C. for 14 h. The pH value of the resulting mixture was adjusted to pH 4 with HCl (1 M). The resulting solution was extracted with EtOAc, the organic layers were combined and concentrated under vacuum, resulting in 630.0 mg of the title compound as an oil. LCMS (ESI): $[M+H]^+$: 386.1.

Intermediate 510. 5-(5-chloro-2-methoxypyridin-4-yl)-1H-pyrazole-3-carboxylic acid

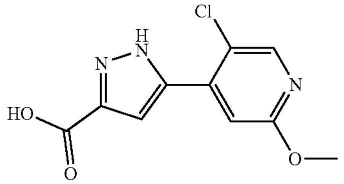 [SMILES: COc1cc(-c2cc(C(=O)O)n[nH]2)c(Cl)cn1]

The title compound was prepared using a procedure similar to the one described for the synthesis of Intermediate 507, except 5-chloro-2-methoxypyridin-4-ylboronic acid was used as starting material in Step-2, followed by conditions in Step-3b, and Step-4. The precipitated solids were collected by filtration to obtain the title compound as a white solid. (ESI): 254.0 $[M+H]^+$.

Intermediate 511. 1-[5-(5-fluoro-2-methoxypyridin-4-yl)-1H-pyrazole-3-carbonyl]piperidine-4-carboxylic acid Step-1. Ethyl 1-[5-(5-fluoro-2-methoxypyridin-4-yl)-1H-pyrazole-3-carbonyl]piperidine-4-carboxylate

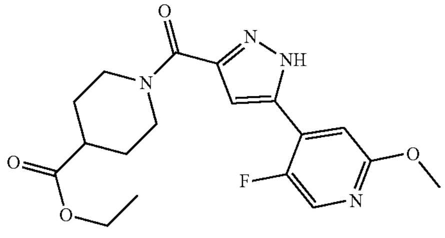 [SMILES: CCOC(=O)C1CCN(C(=O)c2cc(-c3cc(OC)ncc3F)[nH]n2)CC1]

Solution of 5-(5-fluoro-2-methoxypyridin-4-yl)-1H-pyrazole-3-carboxylic acid (1.0 g, 4.22 mmol), EDCI (1.21 g, 6.32 mmol) and HOBt (854.53 mg, 6.32 mmol) in DMF (5.00 mL) was stirred at 25° C. for 30 min. DIPEA (1.63 g, 12.65 mmol), ethyl piperidine-4-carboxylate (729.1 mg, 4.64 mmol) were added to the mixture and stirred at 25° C. for 14 h. The resulting mixture was diluted with EtOAc, washed with water, then the resulting mixture was concentrated under vacuum. The residue was purified by silica gel column chromatography (petroleum ether/EtOAc, 1/1 v/v) to afford the title compound (700.0 mg) as a solid. LCMS (ESI): 377.2 $[M+H]^+$.

Step-2. 1-[5-(5-fluoro-2-methoxypyridin-4-yl)-1H-pyrazole-3-carbonyl]piperidine-4-carboxylic acid (Intermediate 511)

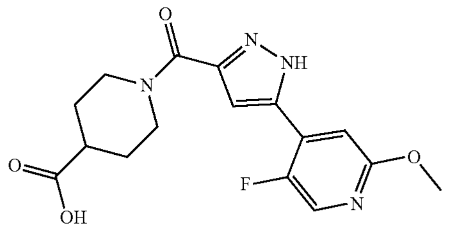 [SMILES: COc1cc(-c2cc(C(=O)N3CCC(C(=O)O)CC3)n[nH]2)c(F)cn1]

LiOH (147.3 mg, 3.50 mmol) was added to a stirred solution of ethyl 1-[5-(5-fluoro-2-methoxypyridin-4-yl)-1H-pyrazole-3-carbonyl]piperidine-4-carboxylate (Step-1, 660.0 mg, 1.75 mmol) in THF (3.00 mL), MeOH (3.00 mL) and $H_2O$ (3.00 mL). The resulting mixture was stirred at 25° C. for 30 min. The mixture was acidified to pH 3 with aqueous HCl (1 N). The aqueous layer was extracted with EtOAc and the resulting mixture was concentrated under reduced pressure to afford the title compound (550.0 mg) which was used in the next step directly without further purification. LCMS (ESI): 349.1 $[M+H]^+$.

Intermediate 512. (1R,3S,5S)-8-[5-(5-chloro-2-methoxypyridin-4-yl)-1H-pyrazole-3-carbonyl]-8-azabicyclo[3.2.1]octane-3-carboxylic acid Step-1. Methyl (1R,3S,5S)-8-[5-(5-chloro-2-methoxypyridin-4-yl)-1H-pyrazole-3-carbonyl]-8-azabicyclo[3.2.1]octane-3-carboxylate

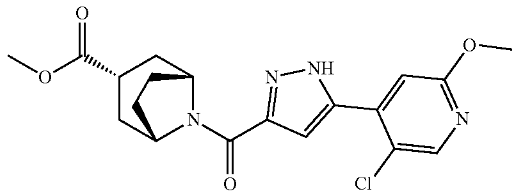

HATU (8.10 g, 21.29 mmol) and DIPEA (6.88 g, 53.23 mmol) were added to a solution of methyl (1R,3S,5S)-8-azabicyclo[3.2.1]octane-3-carboxylate (INTERMEDIATE 513, 3.60 g, 21.29 mmol) and 5-(5-chloro-2-methoxypyridin-4-yl)-1H-pyrazole-3-carboxylic acid (INTERMEDIATE 510, 4.00 g, 17.72 mmol) in DMF (15.00 mL). The solution was then stirred at 25° C. for 14 h. The solution was then diluted with water and extracted with EtOAc. The organic layers were dried over anhydrous sodium sulfate, filtered, and the solvent was evaporated. The resulting residue was purified by silica gel column chromatography (EtOAc/petroleum ether, 1/1 v/v) to yield the title compound (6.20 g) as a solid. LCMS (ESI): 405.1 $[M+H]^+$.

Step-2. (1R,3S,5S)-8-[5-(5-chloro-2-methoxypyridin-4-yl)-1H-pyrazole-3-carbonyl]-8-azabicyclo[3.2.1]octane-3-carboxylic acid (Intermediate 512)

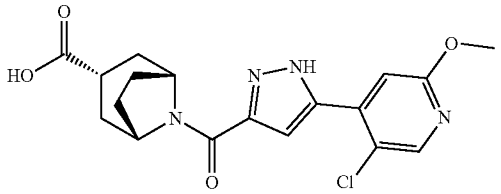 [SMILES: COc1cc(-c2cc(C(=O)N3[C@@H]4CC[C@H]3C[C@H](C(=O)O)C4)n[nH]2)c(Cl)cn1]

$LiOH \cdot H_2O$ (1.54 g, 64.46 mmol), MeOH (5.00 mL) and $H_2O$ (5.00 mL) was added sequentially into a stirred solution of benzyl (1R,3S,5S)-8-[5-(5-chloro-2-methoxypyridin-4-yl)-1H-pyrazole-3-carbonyl]-8-azabicyclo[3.2.1]octane-3-carboxylate (Step-1, 6.20 g, 12.89 mmol) in THF (5.00 mL). The resulting mixture was stirred at 60° C. for 1 h. The solution was then concentrated under reduced pressure to remove MeOH, as much as possible, then acidified to pH 6 with aqueous HCl (1 N). The precipitate was collected by filtration, washed with water, then dried in an oven under reduced pressure, to deliver the title compound (5.00 g) as a solid. $^1H$ NMR (400 MHz, DMSO-$d_6$) δ 14.06-13.93 (m, 1H), 12.22 (s, 1H), 8.38 (s, 1H), 7.31-7.23 (m, 2H), 5.25-5.17 (m, 1H), 4.70-4.50 (m, 1H), 3.90 (s, 3H), 2.95-2.86 (m, 1H), 2.01-1.80 (m, 8H). LCMS (ESI): 391.1 $[M+H]^+$.

Intermediate 513. Methyl (1R,3s,5S)-8-azabicyclo[3.2.1]octane-3-carboxylate

Step-1. 8-tert-butyl 3-methyl 8-azabicyclo[3.2.1]octane-3,8-dicarboxylate

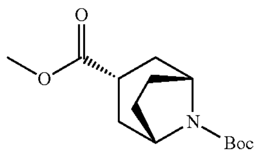 [SMILES: COC(=O)[C@@H]1C[C@H]2CC[C@@H](C1)N2C(=O)OC(C)(C)C]

Methyl iodide (3.34 g, 23.50 mmol) and $K_2CO_3$ (4.06 g, 29.38 mmol) were added to a solution of 8-(tert-butoxycarbonyl)-8-azabicyclo[3.2.1]octane-3-carboxylic acid (5.00 g, 19.58 mmol) in DMF (15.00 mL). The solution was then stirred at 25° C. for 14 h. The solution was then diluted with water and extracted with EtOAc. The organic layers were combined, then dried over anhydrous sodium sulfate, filtered, and the solvent was evaporated. The resulting residue was purified by silica gel column chromatography (EtOAc/petroleum ether, 1/1 v/v) resulting in the title compound (5.00 g) as a solid. LCMS (ESI): 270.2 $[M+H]^+$.

Step-2. methyl (1R,3s,5S)-8-azabicyclo[3.2.1]octane-3-carboxylate (Intermediate 513)

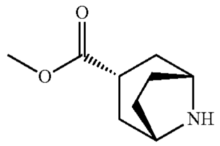

TFA (3.00 mL) were added to a solution of 8-tert-butyl 3-methyl 8-azabicyclo[3.2.1]octane-3,8-dicarboxylate (Step-1, 5.00 g, 18.56 mmol) in DCM (20.00 mL). The resulting solution was stirred for 2 h at 25° C. The solution was then concentrated under reduced pressure and the residue was purified by silica gel column chromatography (CM/Me©H, 9:1 v/v) resulting in the title compound (4.50 g) as a solid, which was used without further purification. LCMS (ESI): 170.1 $[M+H]^+$.

Intermediate 514. 1-(3-fluoro-1H-indazol-5-yl)methanamine

Step-1. Methyl 3-fluoro-1H-indazole-5-carboxylate

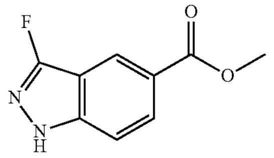

1H-indazole-5-carboxylate (1.00 g, 5.68 mmol) was added to a stirred solution of Selectfluor® (3.02 g, 8.52 mmol) in MeCN (25.00 mL) and AcOH (5.00 mL). The solution was stirred at 70° C. for 14 h, then diluted with water and extracted with EtOAc. The organic layers were combined, dried over anhydrous sodium sulfate, filtered, and the solvent was evaporated. The residue was purified by silica gel chromatography (EtOAc/petroleum ether, 1/1 v/v) to obtain the title compound (480.0 mg) as a solid. LCMS (ESI): 195.1 $[M+H]^+$.

Step-2. (3-fluoro-1H-indazol-5-yl)methanol

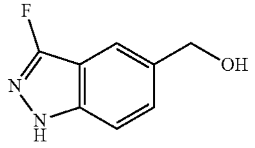 [SMILES: OCc1ccc2[nH]nc(F)c2c1]

$LiAlH_4$ (7.00 mL, 1 Min THF, 6.95 mmol) was added to a stirred solution of methyl 3-fluoro-1H-indazole-5-carboxylate (Step-1, 900.0 mg, 4.60 mmol) in THF (15.00 mL) at 0° C. The solution was stirred at 25° C. for 1 h, then diluted with water and extracted with EtOAc. The organic layers were combined, dried over anhydrous sodium sulfate, filtered, and the solvent was evaporated. The residue was purified by silica gel chromatography (EtOAc/petroleum ether, 1/2 v/v) to obtain the title compound (300.0 mg) as a solid. LCMS (ESI): 167.1 $[M+H]^+$.

Step-3. 2-[(3-fluoro-1H-indazol-5-yl)methyl]isoindole-1,3-dione

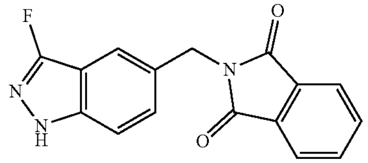 [SMILES: O=C1c2ccccc2C(=O)N1Cc1ccc2[nH]nc(F)c2c1]

$PPh_3$ (710.4 mg, 2.70 mmol) and DIAD (547.6 mg, 2.70 mmol) were added to a stirred solution of (3-fluoro-1H-indazol-5-yl)methanol (Step-2, 300.0 mg, 1.80 mmol) and phthalimide (398.5 mg, 2.70 mmol) in THF (10.00 mL). The resulting solution was stirred at 25° C. for 2 h, then diluted with water and extracted with EtOAc. The organic layers were combined, dried over anhydrous sodium sulfate, filtered, and the solvent was evaporated. The residue was purified by silica gel chromatography (EtOAc/petroleum ether, 1/2 v/v) to obtain the title compound (180.0 mg) as a solid. LCMS (ESI): 296.1 $[M+H]^+$.

Step-4. 1-(3-fluoro-1H-indazol-5-yl)methanamine (Intermediate 514)

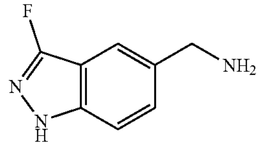 [SMILES: NCc1ccc2[nH]nc(F)c2c1]

$NH_2NH_2{\cdot}H_2O$ (0.50 mL) was added to a stirred solution of 2-[(3-fluoro-1H-indazol-5-yl)methyl]isoindole-1,3-dione (Step-3, 180.0 mg, 0.60 mmol) in EtOH (5.00 mL). The solution was stirred at 60° C. for 30 min, then the solution was concentrated to obtain the title compound (90.0 mg) as a solid, which was used in the next step without further purification. LCMS (ESI): 166.1 $[M+H]^+$.

Intermediate 515. 1-(3-Meth 1-1H-indazol-5-yl)methanamine

Step-1. 3-Methyl-1H-indazole-5-carbonitrile

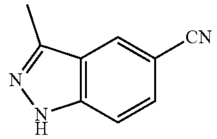

$Pd(PPh_3)_4$ (1.09 g, 0.95 mmol) and $Zn(CN)_2$ (662.0 mg, 5.64 mmol) were added to a solution of 5-bromo-3-methyl-1H-indazole (1.00 g, 4.74 mmol) in DMF (15.00 mL). The resulting solution was stirred at 100° C. for 1 h under nitrogen. The solids were then filtered out, and the solution was diluted with water, extracted with dichloromethane, and the organic layers were concentrated under vacuum. The residue was purified by silica gel chromatography (EtOAc/petroleum ether, 1/1 v/v) to obtain the title compound (700.0 mg) as an oil. LCMS (ESI): 158.1 $[M+H]^+$.

Step-2. 1-(3-Methyl-1H-indazol-5-yl)methanamine (Intermediate 515)

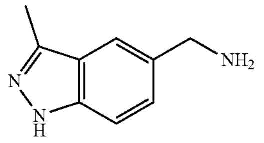

$LiAlH_4$ (762.0 mg, 20.10 mmol) was added to a solution of 3-methyl-1H-indazole-5-carbonitrile (Step-1, 700.0 mg, 4.50 mmol) in THF (14.00 mL). The solution was stirred at 0° C. for 30 min, then stirred at 70° C. for 2 h. The solution was concentrated down, then redissolved in MeOH. The solution was concentrated under vacuum and the residue was purified using silica gel column chromatography (DCM/MeOH, 10/1 v/v) to obtain the title compound (175.0 mg) as an oil. LCMS (ESI): 162.1 $[M+H]^+$.

Intermediate 516. 4-methoxy-4-(trifluoromethyl)cyclohexan-1-amine a. Step-1. Trimethyl([[8-(trifluoromethyl)-1,4-dioxaspiro[4.5]decan-8-yl]oxy])silane

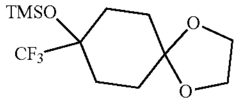

Trifluoromethyltrimethylsilane (6.83 g, 48.02 mmol) and $Cs_2CO_3$ (31.29 g, 96.04 mmol) were added to a solution of 1,4-dioxaspiro[4.5]decan-8-one (5.00 g, 32.01 mmol) in 1,2-dimethoxyethane (100.00 mL) at 25° C. The solution was stirred for 14 h and was then diluted with water and extracted with EtOAc. The organic layers were combined, then dried over anhydrous sodium sulfate, filtered, and the solvent was evaporated to obtain the title compound (6.00 g) as a solid.

Step-2. 8-(trifluoromethyl)-1,4-dioxaspiro[4.5]decan-8-ol

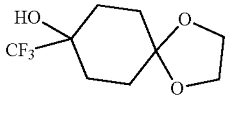 [SMILES: OC1(C(F)(F)F)CCC2(CC1)OCCO2]

TBAF in THF (20.00 mL, 1 M, 20.00 mmol) was added to a solution of trimethyl([[8-(trifluoromethyl)-1,4-dioxaspiro[4.5]decan-8-yl]oxy]) silane (Step-1, 6.00 g, 20.11 mmol) in THF (50 mL). The solution was stirred at 25° C. for 14 h and was then diluted with water and extracted with EtOAc. The organic layers were combined, then dried over anhydrous sodium sulfate, filtered, and the solvent was evaporated. The residue was purified by silica gel chromatography (DCM/MeOH, 20/1 v/v) to obtain the title compound (4.00 g) as an oil.

Step-3. 8-methoxy-8-(trifluoromethyl)-1,4-dioxaspiro[4.5]decane

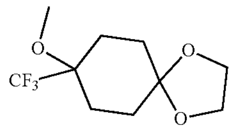 [SMILES: COC1(C(F)(F)F)CCC2(CC1)OCCO2]

NaH (424.4 mg, 17.68 mmol, 60% dispersion in mineral oil) was added to a solution of 8-(trifluoromethyl)-1,4-dioxaspiro[4.5]decan-8-ol (Step-2, 2.00 g, 8.84 mmol) in THF (10 mL) at 0° C. The solution was stirred at 0° C. for 30 min, then methyl iodide (0.72 mL, 11.49 mmol) was added. The solution was stirred at 25° C. for 14 h and was then diluted with water and extracted with EtOAc. The organic layers were combined, then dried over anhydrous sodium sulfate, filtered, and the solvent was evaporated. The residue was purified by silica gel chromatography (EtOAc/petroleum ether, 1/2 v/v) to obtain the title compound as an oil.

Step-4. 4-methoxy-4-(trifluoromethyl)cyclohexan-1-one

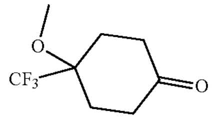

P-TsOH (186.4 mg, 1.08 mmol) was added to a solution of 8-methoxy-8-(trifluoromethyl)-1,4-dioxaspiro[4.5]decane (Step-3, 1.30 g, 5.41 mmol) in acetone (5.00 mL) and $H_2O$ (1.00 mL). The solution was stirred at 70° C. for 14 h and was then diluted with water and extracted with EtOAc. The organic layers were combined, then dried over anhydrous sodium sulfate, filtered, and the solvent was evaporated. The residue was purified by silica gel chromatography (EtOAc/petroleum ether, 1/2 v/v) to obtain the title compound (800.0 mg) as a solid.

Step-5. 4-methoxy-4-(trifluoromethyl)cyclohexan-1-amine (Intermediate 516)

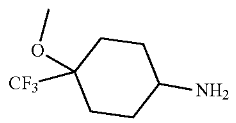

$NH_4OAc$ (943.1 mg, 12.20 mmol) was added to a solution of 4-methoxy-4-(trifluoromethyl) cyclohexan-1-one (Step-4. 400.0 mg, 2.03 mmol) in EtOH (10.00 mL). The solution was stirred at 25° C. for 30 min, then $NaBH_3CN$ (512.6 mg, 8.16 mmol) was added and the solution was stirred at 25° C.

for 28 h, then concentrated under reduced pressure. The residue was purified by silica gel column chromatography (DCM/MeOH, 6/1 v/v) to obtain the title compound (500.0 mg) as a solid mixture of diastereomers. LCMS (ESI) 198.2 $[M+H]^+$.

Intermediate 517. 1-[5-(5-chloro-2-methylpyridin-4-yl)-1H-pyrazole-3-carbonyl]piperidine-4-carboxylic acid Step-1. Methyl 1-(1H-pyrazole-3-carbonyl)piperidine-4-carboxylate

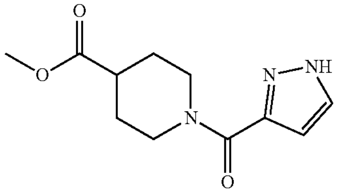 [SMILES: COC(=O)C1CCN(C(=O)c2cc[nH]n2)CC1]

1H-pyrazole-3-carboxylic acid (5.00 g, 44.61 mmol), EDCI (10.26 g, 53.53 mmol), and HOBt (7.23 g, 53.53 mmol) were dissolved in DMF (30 mL), then the reaction was stirred at 25° C. for 20 min. Methyl piperidine-4-carboxylate (6.39 g, 44.63 mmol) and DIPEA (17.30 g, 133.82 mmol). The solution was then stirred at 25° C. for 3 h. The mixture was then diluted with EtOAc and washed with water, then concentrated under reduced pressure. The residue was purified by silica gel column chromatography (DCM/MeOH, 13/1 v/v) obtain the title compound (8.9 g) as a solid. LCMS (ESI): 238.1 $[M+H]^+$.

Step-2. Methyl 1-(1-(tetrahydro-2H-pyran-2-yl)-1H-pyrazole-3-carbonyl)piperidine-4-carboxylate

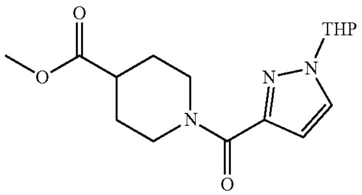

DHP (1.69 g, 20.09 mmol) and TFA (0.77 mL, 10.03 mmol) were added to a solution of methyl 1-(1H-pyrazole-3-carbonyl)piperidine-4-carboxylate (Step-1, 2.38 g, 10.03 mmol) in THF (10 mL). The resulting mixture was stirred at 60° C. for 4 h, concentrated under reduced pressure, and then the residue was purified by silica gel column chromatography (DCM/MeOH, 19/1 v/v) to obtain the title compound (3.14 as an oil. LCMS (ESI): $[M+H]^+$.

Step-3. (3-(4-(methoxycarbonyl)piperidine-1-carbonyl)-1-(tetrahydro-2H-pyran-2-yl)-1H-pyrazol-5-yl) boronic acid

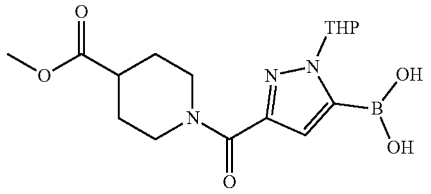

Dtbpy (194.3 mg, 0.72 mmol), $[Ir(COD)OMe]_2$ (319.9 mg, 0.48 mmol), and $B_2Pin_2$ (1348.4 mg, 5.31 mmol) were added to a stirred mixture of methyl 1-(1-(tetrahydro-2H-pyran-2-yl)-1H-pyrazole-3-carbonyl)piperidine-4-carboxylate (Step-3, 517.0 mg, 1.61 mmol) in MTBE (4.00 mL) and THF (4.00 mL). The solution was stirred at 70° C. for 14 h under nitrogen atmosphere, then quenched with MeOH. The solution was concentrated under reduced pressure, then the residue was purified by silica gel column chromatography (DCM/MeOH, 20/1 v/v) to obtain the title compound (550.0 mg) as an oil. LCMS (ESI): 366.2 $[M+H]^+$.

Step-4. Methyl 1-(5-(5-chloro-2-methylpyridin-4-yl)-1-(tetrahydro-2H-pyran-2-yl)-1H-pyrazole-3-carbonyl)piperidine-4-carboxylate

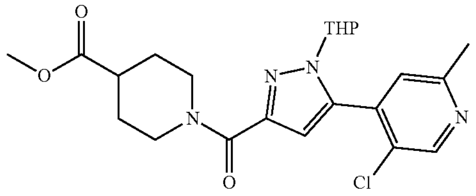

4-bromo-5-chloro-2-methylpyridine (84.0 mg, 0.41 mmol $K_3PO_4$ (116.0 mg, 0.55 mmol), and $Pd(dppf)Cl_2$ (39.0 mg, 0.05 mmol) were added to a stirred solution of (3-(4-(methoxycarbonyl)piperidine-1-carbonyl)-1-(tetrahydro-2H-pyran-2-yl)-1H-pyrazol-5-yl)boronic acid (Step-3, 100.0 mg, 0.27 mmol) in 1,4-dioxane (2.00 mL) and $H_7O$ (0.20 mL). The solution was stirred at 70° C. for 14 h under nitrogen atmosphere, then concentrated under vacuum. The residue was purified by silica gel column chromatography (DCM/MeOH, 10/1 v/v) to obtain the title compound (104.0 mg) as an oil. LCMS (ESI): 447.2 $[M+H]^+$.

Step-5. Methyl 1-[5-(5-chloro-2-methylpyridin-4-yl)-1H-pyrazole-3-carbonyl]piperidine-4-carboxylate

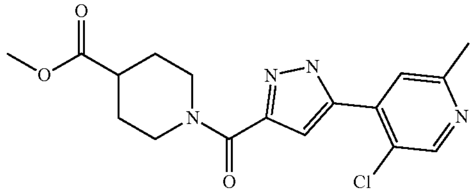

TFA (2.00 mL) was added to a stirred solution of methyl 1-(5-(5-chloro-2-methylpyridin-4-yl)-1-(tetrahydro-2H-pyran-2-yl)-1H-pyrazole-3-carbonyl)piperidine-4-carboxylate (Step-4, 104.0 mg, 0.23 mmol) in DCM (2.00 mL). The solution was stirred at 25° C. for 2 h, then concentrated under vacuum. The residue was purified by silica gel column chromatography (DCM/MeOH, 10/1 v/v) to obtain the title compound (86.0 mg) as an oil. LCMS (ESI): 363.1 [M+H]+.

Step-6. 1-[5-(5-chloro-2-methylpyridin-4-yl)-1H-pyrazole-3-carbonyl]piperidine-4-carboxylic acid (Intermediate 517)

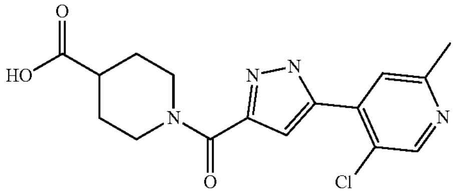 [SMILES: Cc1cc(-c2cc(C(=O)N3CCC(C(=O)O)CC3)n[nH]2)c(Cl)cn1]

LiOH·$H_2O$ (30.0 mg, 0.72 mmol) was added to a stirred solution of methyl 1-[5-(5-chloro-2-methylpyridin-4-yl)-1H-pyrazole-3-carbonyl]piperidine-4-carboxylate (Step-5, 86.0 mg, 0.24 mmol) in THF (1.00 mL), MeOH (1.00 mL), and $H_2O$ (1.00 mL). The solution was stirred at 25° C. for 14 h, then the pH value was adjusted to 5 with HCl (1 M). The solution was extracted with ethyl acetate and the organic layers were concentrated under vacuum. The residue was purified by silica gel column chromatography (DCM/MeOH, 10/1 v/v) to obtain the title compound (60.0 mg) as a solid, LCMS ESI): 349.1 [M+H]+.

Intermediate 518. 1-[5-(5-fluoro-2-methylpyridin-4-yl)-1H-pyrazole-3-carbonyl]piperidine-4-carboxylic acid

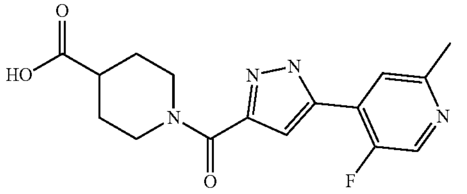 [SMILES: Cc1cc(-c2cc(C(=O)N3CCC(C(=O)O)CC3)n[nH]2)c(F)cn1]

The title compound was prepared using a procedure similar to the one described for the synthesis of Intermediate 517, except ethyl piperidine-4-carboxylate was used as a starting material in Step-1 and 4-bromo-5-fluoro-2-methylpyridine was used as a starting material in Step-4. The title compound was isolated (115.0 mg) as a solid. LCMS (ESI): 333.1 [M+H]+.

Intermediate 519, (1R,3s,5S)—N-(3-chlorobenzyl)-8-azabicyclo[3.2.1]octane-3-carboxamide Step-1. tert-butyl (1R,3s,5S)-3-[[(3-chlorophenyl)methyl]carbamoyl]-8-azabicyclo[3.2.1]octane-8-carboxylate

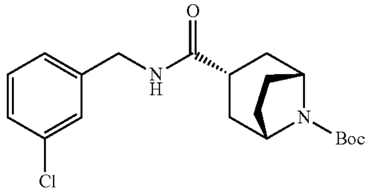

HATU (178.7 mg, 0.50 mmol), 1-(3-chlorophenyl)methanamine (66.6 mg, 0.50 mmol), and DIPEA (151.9 mg, 1.20 mmol) were added to a stirred solution of (1R,3s,5S)-8-(tert-butoxycarbonyl)-8-azabicyclo[3.2.1]octane-3-carboxylic acid (100.0 mg, 0.40 mmol) in DMF (2.00 mL). The solution was stirred at 25° C. for 2 h, then diluted with EtOAc, washed with water, and the organic layer was concentrated. The residue was purified by Prep-TLC (petroleum ether/EtOAc, 5/1 v/v) to obtain the title compound (80.0 mg) as a solid. LCMS (ESI): 379.9 [M+H]+.

Step-2. (1R,3s,5S)—N-(3-chlorobenzyl)-8-azabicyclo[3.2.1]octane-3-carboxamide (Intermediate 519)

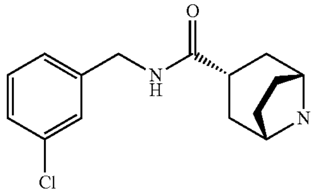

TFA (2.00 mL) was added to a stirred solution of tert-butyl (1R,3s,5S)-3-[[3-chlorophenyl)methyl]carbamoyl]-8-azabicyclo[3.2.1]octane-8-carboxylate (Step-1, 80.0 mg, 0.20 mmol) in DCM (2.00 mL) at 0° C. The solution was stirred at 25° C. for 2 h, then concentrated under reduced pressure to obtain the tide compound (90.0 mg), which was used in the next step without further purification. LCMS (ESI): 279.3 [M+H]+.

Intermediate 520. 5-(5-fluoro-2-methylpyridin-4-yl)-1H-pyrazole-3-carboxylic acid Step-1. Methyl 1-(tetrahydro-2H-pyran-2-yl)-1H-pyrazole-3-carboxylate

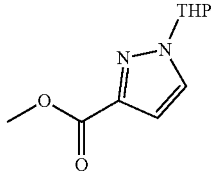

DHP (2.67 g, 31.72 mmol) and TsOH (0.68 g, 3.97 mmol) were added to a stirred solution of methyl 1H-pyrazole-3-carboxylate (2.00 g, 15.86 mmol) in THF (6.00 mL). The solution was stirred at 25° C. for 14 h, then concentrated under reduced pressure. The residue was purified by silica gel column chromatography (petroleum ether/EtOAc, 1/3 v/v) to obtain the title compound (2.30 g) as a solid. LCMS (ESI): 211.2 $[M+H]^+$.

Step-2. (3-(methoxycarbonyl)-1-(tetrahydro-2H-pyran-2-yl)-1H-pyrazol-5-yl)boronic acid

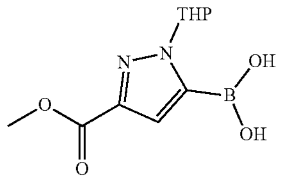

Dtbpy (255.3 mg, 0.95 mmol), $[Ir(Cod)OMe]_2$ (630.6 mg, 0.95 mmol) and $B_2Pin_2$ (1811.8 mg, 7.14 mmol) were added to a stirred solution of methyl 1-(tetrahydro-2H-pyran-2-yl)-1H-pyrazole-3-carboxylate (Step-1, 1.00 g, 4.76 mmol) in MTBE (10.00 mL). The solution was stirred at 50° C. for 3 h, then concentrated under reduced pressure. The residue was purified by silica gel column chromatography (petroleum ether/EtOAc, 1/3 v/v) to obtain the e compound (1.20 g) as a solid. LCMS (ESI): 255.0 $[M+H]^+$.

Step-3. Methyl 5-(5-fluoro-2-methylpyridin-4-yl)-1-(tetrahydro-2H-pyran-2-yl)-1H-pyrazole-3-carboxylate

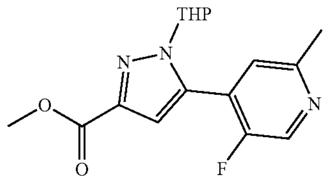

4-bromo-5-fluoro-2-methylpyridine (1.34 g, 7.09 mmol), $Pd(dppf)Cl_2$ (0.69 g, 0.95 mmol) and $K_2CO_3$ (1.30 g, 9.45 mmol) were added to a stirred solution of (3-(methoxycarbonyl)-1-(tetrahydro-2H-pyran-2-yl)-1H-pyrazol-5-yl)boronic acid (Step-2, 1.20 g, 4.72 mmol) in 1,4-dioxane (8.00 mL) and $H_2O$ (2.00 mL). The solution was stirred at 80° C. for 14 h, then the solution was then filtered, diluted with water, and extracted with EA. The organic layers were combined, then dried over anhydrous sodium sulfate, filtered, and the solvent was evaporated. The residue was purified by silica gel column chromatography (petroleum ether/EtOAc, 1/3 v/v) to obtain the title compound (255.0 mg) as a solid. LCMS (ESI): 320.3 $[M+H]^+$.

Step-4. Methyl 5-(5-fluoro-2-methylpyridin-4-yl)-1H-pyrazole-3-carboxylate

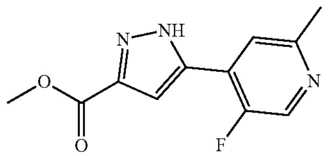

TFA (3.00 mL) was added to a stirred solution of methyl 5-(5-fluoro-2-methylpyridin-4-yl)-1-(tetrahydro-2H-pyran-2-yl)-1H-pyrazole-3-carboxylate (Step-3, 300.0 mg, 0.80 mmol) in DCM (3.00 mL). The solution was stirred at 25° C. for 1 h, then concentrated under reduced pressure. The residue was purified by silica gel column chromatography (petroleum ether/EtOAc, 1/1 v/v) to obtain the title compound (170.0 mg) as a solid. LCMS (ESI): 236.2 $[M+H]^+$.

Step-5. 5-(5-Fluoro-2-methylpyridin-4-yl)-1H-pyrazole-3-carboxylic acid (Intermediate 520)

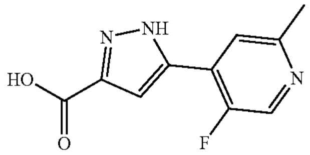 [SMILES: Cc1cc(-c2cc(C(=O)O)n[nH]2)c(F)cn1]

LiOH (86.6 mg, 3.60 mmol) was added to a stirred solution of methyl 5-(5-fluoro-2-methylpyridin-4-yl)-1H-pyrazole-3-carboxylate (170.0 mg, 0.70 mmol) in THF (2.00 mL), MeOH (2.00 mL), and $H_2O$ (2.00 The solution was stirred at 25° C. for 1 h, then acidified to pH 7 with HCl (6 M). The precipitated solids were filtered, washed with water, and then dried to obtain the title compound (0.80 g) as a solid. LCMS (ESI): 222.1 $[M+H]^+$.

Intermediate 521. 1-[5-(5-chloro-2-ethylpyridin-4-yl)-1H-pyrazole-3-carbonyl]piperidine-4-carboxylic acid

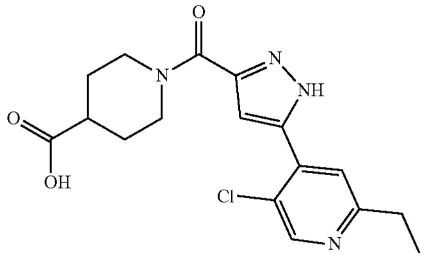 [SMILES: CCc1cc(-c2cc(C(=O)N3CCC(C(=O)O)CC3)n[nH]2)c(Cl)cn1]

The title compound was prepared using a procedure similar to the one described for the synthesis of Intel mediate 517, except ethyl piperidine-4-carboxylate was used as a starting material in Step-1 and 4-bromo-5-chloro-2-ethylpyridine was used as starting material in Step-4. The title compound was isolated (4.0 mg) as a solid. LCMS (ESI): 363.1$[M+H]^+$.

Intermediate 522. 1-(2,3-dimethyl-1H-indol-5-yl)methanamine

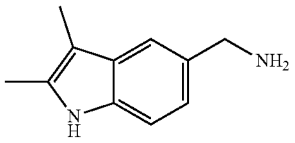

The title compound was prepared using a procedure similar to the one described for the synthesis of Intermediate 515, except 5-bromo-2,3-dimethyl-1H-indole was used as a starting material in Step-1 to obtain the title compound (90.0 mg) as a solid. LCMS (ESI): 175.2 $[M+H]^+$.

Intermediate 523. 1-Oxaspiro[3.5]nonan-7-amine

Step-1. 4-[bis[(4-methoxyphenyl)methyl]amino]cyclohexan-1-one

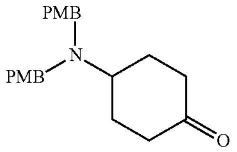

PMBCl (8.30 g, 53.00 mmol) and $K_2CO_3$ (12.21 g, 88.37 mmol) were added to a stirred mixture of 4-aminocyclohexan-1-one (2.00 g, 17.67 mmol) in DMF (15.00 mL) at 25° C. The resulting mixture was stirred at 60° C. for 14 h. The resulting mixture was diluted with EtOAc, washed with water and concentrated under reduced pressure. The residue was purified by silica gel column chromatography, (petroleum ether/EtOAc, 2/1 v/v) to afford the title compound (2.00 g) as an oil. LCMS (ESI): 354.2 $[M+H]^+$ Step-2. N,N-bis[(4-methoxyphenyl)methyl]-1-oxaspiro[3.5]nonan-7-amine

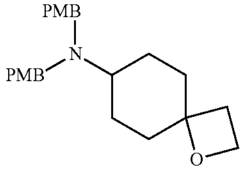

t-BuOK (6.00 g, 53.45 mmol) and trimethylsulfoxonium iodide (11.81 g, 53.19 mmol) were added to t-BuOH (25.00 mL). The resulting solution was stirred at 50° C. for 30 min, then 4-[bis[(4-methoxyphenyl)methyl]amino]cyclohexan-1-one (Step-1, 4.70 g, 13.30 mmol) was added. The resulting mixture was stirred at 50° C. for 14 h. The resulting mixture was concentrated under reduced pressure. The residue was purified by silica gel column chromatography, (petroleum ether/EtOAc, 2/1 v/v) to afford the diastereomeric mixture of the title compound (600.0 mg) as an oil. LCMS (ESI): 382.2 $[M+H]^+$ Step-3. 1-Oxaspiro[3.5]nonan-7-amine (Intermediate 523)

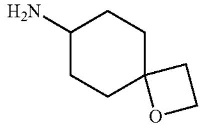

Pd/C (299.6 mg, 10% Pd) was added to a solution of N,N-bis[(4-methoxyphenyl)methyl]-1-oxaspiro[3.5]nonan-7-amine (600.0 mg, 1.57 mmol) in MeOH (5.00 mL). The resulting solution was stirred at 25° C. under a H2 for 2 days. The resulting mixture was filtered, the filter cake was washed with MeOH. The filtrate was concentrated under reduced pressure to afford the title compound (200.0 mg) as a solid mixture of diastereomers. LCMS (ESI): 142.1 $[M+H]^+$ Intermediate 524. (1R,3R,5S)-8-[5-(5-fluoro-2-methylpyridin-4-yl)-1H-pyrazole-3-carbonyl]-8-azabicyclo[3.2.1]octane-3-carboxylic acid Step-1. Benzyl (1R,3R,5S)-8-[5-(5-fluoro-2-methylpyridin-4-yl)-1H-pyrazole-3-carbonyl]-8-azabicyclo[3.2.1]octane-3-carboxylate

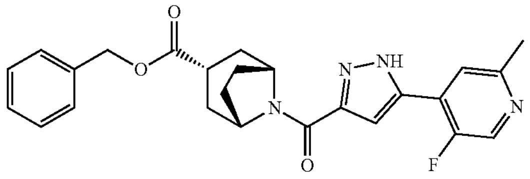 [SMILES: Cc1cc(-c2cc(C(=O)N3[C@@H]4CC[C@H]3C[C@H](C(=O)OCc3ccccc3)C4)n[nH]2)c(F)cn1]

EDCI (923.0 mg, 4.80 mmol) and HOBt (650.6 mg, 4.80 mmol) were added to a stirred solution of 5-(5-fluoro-2-methylpyridin-4-yl)-1H-pyrazole-3-carboxylic acid (INTERMEDIATE 520, 710.0 mg, 3.20 mmol) in DMF (20.00 mL). The solution was stirred at 25° C. for 30 min, then benzyl (1R,3R,5S)-8-azabicyclo[3.2.1]octane-3-carboxylate (1023.7 mg, 4.20 mmol) and DIPEA (1.68 mL, 9.6 mmol) were added. The solution was stirred at 25° C. for 2 h, then diluted with water and extracted with EtOAc. The organic layers were combined and concentrated under vacuum. The residue was purified by silica gel column chromatography (petroleum ether/EtOAc, 1/1 v/v) to obtain the title compound (750.0 mg) as a solid. LCMS (ESI): 449.2 $[M+H]^+$.

Step-2. (1R,3R,5S)-8-[5-(5-fluoro-2-methylpyridin-4-yl)-1H-pyrazole-3-carbonyl]-8-azabicyclo[3.2.1]octane-3-carboxylic acid (Intermediate 524)

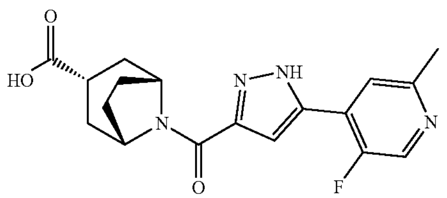 [SMILES: Cc1cc(-c2cc(C(=O)N3[C@@H]4CC[C@H]3C[C@H](C(=O)O)C4)n[nH]2)c(F)cn1]

LiOH·$H_2O$ (140.4 mg, 3.30 mmol) was added to a stirred solution of benzyl (1R,3R,5S)-8-[5-(5-fluoro-2-methylpyridin-4-yl)-1H-pyrazole-3-carbonyl]-8-azabicyclo[3.2.1]octane-3-carboxylate (Step-1, 750.0 mg, 1.70 mmol) in MeOH (2.00 mL), $H_2O$ (2.00 mL), THF (2.00 mL). The solution was stirred at 25° C. for 14 h, then concentrated under reduced pressure to remove MeOH and THF, as much as possible. The residue was acidified to pH 4 with HCl (1 M), then the precipitated solids were collected by filtration and washed with water to obtain the title compound (530.0 mg) as a white solid. LCMS (ESI): 359.1 $[M+H]^+$.

Intermediate 525. Enantiomeric mixture of Intermediate 525-A and Intermediate 525-B Intermediate 525-A. Methyl (S)-4-[5-(5-fluoro-2-methylpyridin-4-yl)-1H-pyrazole-3-carbonyl]-4-azaspiro[2.5]octane-7-carboxylate Intermediate 525-B. Methyl (R)-4-[5-(5-fluoro-2-methylpyridin-4-yl)-1H-pyrazole-3-carbonyl]-4-azaspiro[2.5]octane-7-carboxylate

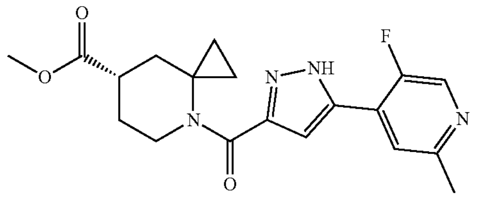

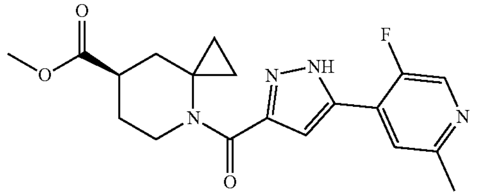

EDCI (591.5 mg, 3.10 mmol) and HOBt (416.9 mg, 3.10 mmol) were added to a stirred solution of 5-(5-fluoro-2-methylpyridin-4-yl)-1H-pyrazole-3-carboxylic acid (INTERMEDIATE 520, 455.0 mg, 2.10 mmol) in DMF (3.00 mL). The solution was stirred at 25° C. for 30 min, then methyl 4-azaspiro[2.5]octane-7-carboxylate hydrochloride (550.0 mg, 2.70 mmol, CAS #: 2253630-26-9, Enamine Ltd.) and DIPEA (1.07 mL, 6.20 mmol) were added. The solution was stirred at 25° C. for 14 h, then diluted with water and extracted with EtOAc. The organic layers were concentrated under vacuum and the residue was purified by silica gel column chromatography (DCM/MeOH, 20/1 v/v) to obtain a mixture of Methyl (S)-4-[5-(5-fluoro-2-methylpyridin-4-yl)-1H-pyrazole-3-carbonyl]-4-azaspiro[2.5]octane-7-carboxylate and methyl (R)-4-[5-(5-fluoro-2-methylpyridin-4-yl)-1H-pyrazole-3-carbonyl]-4-azaspiro[2.5]octane-7-carboxylate (500.0 mg) as a mixture of enantiomers (INTERMEDIATE 525), LCMS (ESI): 373.2 $[M+H]^+$.

The two enantiomers of the title compound were separated by CHIRAL-Prep-HPLC.

Column: CHIRALPAK IG

Column dimension: 2×25 cm, 5 μm

Gradient: Hex:DCM=3:1 (10 mM $NH_3$-MEOH)/IPA, 80/20 v/v

Flow rate:

Detection (nm): 220/254 nm

Intermediate 525-A. The first eluting compound (220.0 mg) was obtained as a solid.

The first eluting compound had a retention time of 8.41 min.

LCMS (ESI): 373.2 $[M+H]^+$.

Intermediate 525-B. The second eluting compound (220.0 mg) vas obtained as a solid The second eluting compound had a retention time of 13.45 min.

LCMS (ESI): 373.2 $[M+H]^+$.

Intermediate 526. Enantiomeric mixture of Intermediate 526-A and Intermediate 526-B Intermediate 526-A. (S)-4-[5-(5-fluoro-2-methylpyridin-4-yl)-1H-pyrazole-3-carbonyl]-4-azaspiro[2.5]octane-7-carboxylic acid Intermediate 526-B. (R)-4-[5-(5-fluoro-2-methylpyridin-4-yl)-1H-pyrazole-3-carbonyl]-4-azaspiro[2.5]octane-7-carboxylic acid

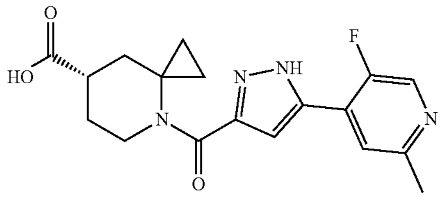

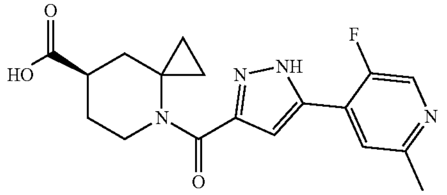

LiOH·$H_2O$ (68.0 mg, 1.62 mmol) was added to a stirred solution of an enantiomeric mixture of methyl (S)-4-[5-(5-fluoro-2-methylpyridin-4-yl)-1H-pyrazole-3-carbonyl]-4-azaspiro[2.5]octane-7-carboxylate and methyl (R)-4-[5-(5-fluoro-2-methylpyridin-4-yl)-1H-pyrazole-3-carbonyl]-4-azaspiro[2.5]octane-7-carboxylate (INTERMEDIATE 525, 300.0 mg) in THF (6.00 mL), MeOH (6.00 mL), $H_2O$ (6.00 mL). The solution was stirred at 25° C. for 2 h, then concentrated under reduced pressure to remove MeOH and THF, as much as possible, and acidified to pH 5 with HCl (1 M). The precipitated solids were collected by filtration and washed with water to obtain (S)-4-[5-(5-fluoro-2-methylpyridin-4-yl)-1H-pyrazole-3-carbonyl]-4-azaspiro[2.5]octane-7-carboxylic acid and (R)-4-[5-(5-fluoro-2-methylpyridin-4-yl)-1H-pyrazole-3-carbonyl]-4-azaspiro[2.5]octane-7-carboxylic acid as a solid mixture of enantiomers (INTERMEDIATE 526, 230.0 mg). LCMS (ESI): 359.1 $[M+H]^+$.

Separately, Methyl (S)-4-[5-(5-fluoro-2-methylpyridin-4-yl)-1H-pyrazole-3-carbonyl]-4-azaspiro[2.5]octane-7-carboxylate (INTERMEDIATE 525-A) was converted to (S)-4-[5-(5-fluoro-2-methylpyridin-4-yl)-1H-pyrazole-3-carbonyl]-4-azaspiro[2.5]octane-7-carboxylic acid (INTERMEDIATE 526-A) as a solid, LCMS (ESI): 359.1 $[M+H]^+$.

Separately, methyl (R)-4-[5-(5-fluoro-2-methylpyridin-4-yl)-1H-pyrazole-3-carbonyl]-4-azaspiro[2.5]octane-7-carboxylate (INTERMEDIATE 525-B) was also converted to (R)-4-[5-(5-fluoro-2-methylpyridin-4-yl)-1H-pyrazole-3-carbonyl]-4-azaspiro[2.5]octane-7-carboxylic acid (INTERMEDIATE 526-B, 164.0 mg) as a solid. LCMS (ESI): 359.1 $[M+H]^+$.

Intermediate 527, Enantiomeric Mixture of Intermediate 527-A and Intermediate 527-B Step-1. Methyl 4-[5-(5-fluoro-2-methoxypyridin-4-yl)-1H-pyrazole-3-carbonyl]-4-azaspiro[2.5]octane-7-carboxylate

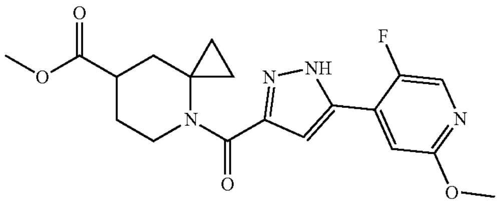

HOBt (341.8 mg, 2.53 mmol), EDCI (484.9 mg, 2.53 mmol), and methyl 4-azaspiro[2.5]octane-7-carboxylate hydrochloride (433.6 mg, 2.11 mmol, CAS #: 2253630-26-9, Enamine Ltd.) were added to a stirred solution of 5-(5-fluoro-2-methoxypyridin-4-yl)-1H-pyrazole-3-carboxylic acid (INTERMEDIATE 507, 500.0 mg, 2.11 mmol) and DIPEA (817.3 mg, 6.32 mmol) in DMF (6.00 mL). The resulting mixture was stirred at 25° C. for 14 h. The resulting mixture was diluted with EtOAc, washed with water, and concentrated. The residue was purified by silica gel column chromatography eluting with DCM/MeOH (25/1 v/v) to obtain the title compound (530.0 mg) as an oil. LCMS (ESI): $[M+H]^+$: 389.2.

Step-2. 4-[5-(5-fluoro-2-methoxypyridin-4-yl)-1H-pyrazole-3-carbonyl]-4-azaspiro[2.5]octane-7-carboxylic acid (Intermediate 527)

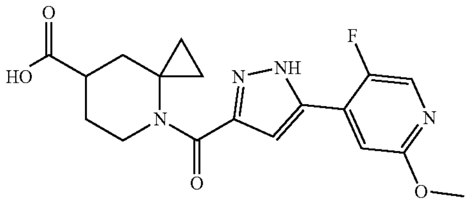 [SMILES: COc1cc(-c2cc(C(=O)N3CCC(C(=O)O)CC34CC4)n[nH]2)c(F)cn1]

LiOH·$H_2O$ (108.1 mg, 2.58 mmol) was added to a stirred mixture of methyl 4-[5-(5-fluoro-2-methoxypyridin-4-yl)-1H-pyrazole-3-carbonyl]-4-azaspiro[2.5]octane-7-carboxylate (Step-1, 500.0 mg, 1.29 mmol) in THF (2.00 mL), MeOH (2.00 mL), and $H_2O$ (2.00 mL). The resulting mixture was stirred at 25° C. for 1 h. The mixture was concentrated under reduced pressure, diluted with water, and the pH was adjusted to 5 by the addition of aqueous HCl. The aqueous layer was extracted with EtOAc. The resulting mixture was concentrated under reduced pressure. The residue was used in the next step as a mixture of enantiomers without further purification, LCMS (ESI): $[M+H]^+$: 375.1.

Intermediate 527-A. (S)-4-[5-(5-fluoro-2-methoxypyridin-4-yl)-1H-pyrazole-3-carbonyl]-4-azaspiro[2.5]octane-7-carboxylic acid Intermediate 527-B. (R)-4-(5-(5-fluoro-2-methoxypyridin-4-yl)-1H-pyrazole-3-carbonyl)-4-azaspiro[2.5]octane-7-carboxylic acid

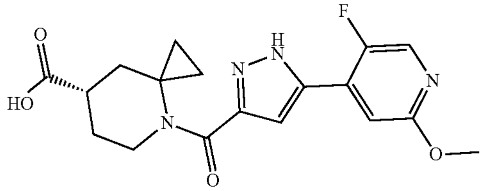

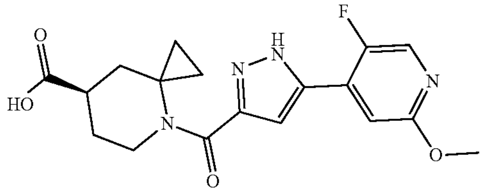

Step-1. Methyl 4-[5-(5-fluoro-2-methoxypyridin-4-yl)-1-[[2-(trimethylsilyl)ethoxy]methyl]pyrazole-3-carbonyl]-4-azaspiro[2.5]octane-7-carboxylate

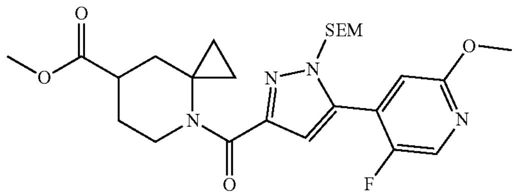

Methyl 4-azaspiro[2.5]octane-7-carboxylate hydrochloride (6.77 g, 32.9 mmol, CAS #: 2253630-26-9, Enamine Ltd.), HATU (13.66 g, 35.9 mmol) and DIPEA (11.61 g, 89.8 mmol) were added to a stirred solution of 5-(5-fluoro-2-methoxypyridin-4-yl)-1-((2-(trimethylsilyl)ethoxy)methyl)-1H-pyrazole-3-carboxylic acid (INTERMEDIATE 506, 11.0 g, 29.9 mmol) in DMF (30.00 mL). The resulting mixture was stirred at 25° C. for 1 h. The solution was diluted with EtOAc and washed with water. The organic layer was concentrated under reduced pressure to result in a residue that was purified via silica gel chromatography (EtOAc/petroleum ether, 1/3 v/v) to obtain of the title compound (14 g) as an oil. LCMS (ESI): 519.2 $[M+H]^+$ Step-2. Methyl 4-[5-(5-fluoro-2-methoxypyridin-4-yl)-1H-pyrazole-3-carbonyl]-4-azaspiro[2.5]octane-7-carboxylate

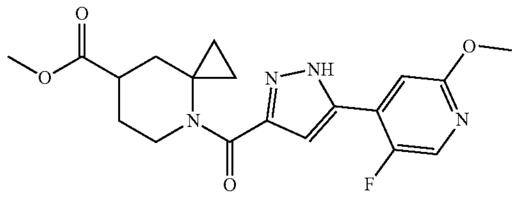

TFA (60.00 mL) was added to a stirred solution of methyl 4-[5-(5-fluoro-2-methoxypyridin-4-yl)-1-[[2-(trimethylsilyl)ethoxy]methyl]pyrazole-3-carbonyl]-4-azaspiro[2.5]octane-7-carboxylate (Step-1, 13.00 g, 25.1 mmol) in DCM (30.00 mL). The resulting mixture was stirred at 25° C. for 14 h. The solution was concentrated under reduced pressure. The residue was purified via silica gel chromatography (EtOAc/petroleum ether, 3/1 v/v) to obtain the title compound (9.65 g) as a white solid. LCMS (ESI): 389.2 [M+H]$^+$ Step-3. Methyl (S)-4-[5-(5-fluoro-ethoxypyridin-4-yl)-1H-pyrazole-3-carbonyl]-4-azaspiro[2.5]octane-7-carboxylate and methyl (R)-4-(5-(5-fluoro-2-methoxypyridin-4-yl)-1H-pyrazole-3-carbonyl)-4-azaspiro[2.5]octane-7-carboxylate

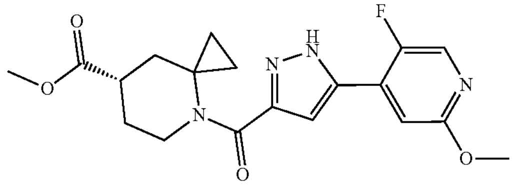

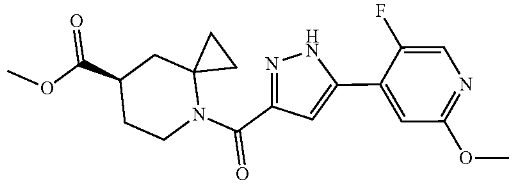

Methyl 4-[5-(5-fluoro-2-methoxypyridin-4-yl)-1H-pyrazole-3-carbonyl]-4-azaspiro[2.5]octane-7-carboxylate (Step-3, 5.54 g) was purified by Prep-SFC with the following conditions:

Column: CHIRALPAK IG column

Column dimension: 30×250 mm, 5 μm

Mobile Phase A: $CO_2$; Mobile Phase B: IPA

Flow rate: 23 mL/min

Gradient: 50% B

Detection: 220 nm;

Injection Volume: 4.8 mL;

Methyl (8)-4-[5-(5-fluoro-2-methoxypyridin-4-yl)-1H-pyrazole-3-carbonyl]-4-azaspiro[2.5]octane-7-carboxylate. The second eluting enantiomer (2.29 g) was obtained as a solid.

The second eluting enantiomer had a retention time of 14.29 min.

LCMS (ESI): 389.1 [M+H]$^+$.

Methyl (R)-4-(5-(5-fluoro-2-methoxypyridin-4-yl)-1H-pyrazole-3-carbonyl)-4-azaspiro[2.5]octane-7-carboxylate. The first eluting enantiomer (2.42 g) was obtained as a solid.

The first eluting enantiomer had a retention tune of 8.25 min.

LCMS (ESI): 389.1 [M+H]$^+$.

Step-4a. (S)-4-[5-(5-fluoro-2-methoxypyridin-4-yl)-1H-pyrazole-3-carbonyl]-4-azaspiro[2.5]octane-7-carboxylic acid (Intermediate 527-A)

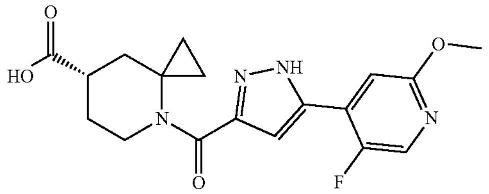 [SMILES: COc1cc(-c2cc(C(=O)N3CC[C@H](C(=O)O)CC34CC4)n[nH]2)c(F)cn1]

$LiOH \cdot H_2O$ (0.56 g, 13.4 mmol) was added to a stirred solution of methyl (S)-4-[5-(5-fluoro-2-methoxypyridin-4-yl)-1H-pyrazole-3-carbonyl]-4-azaspiro[2.5]octane-7-carboxylate (The second eluting enantiomer from Step-3, 2.6 g, 6.69 mmol, 1.00 equiv) in a mixture of THF (10.00 mL), MeOH (10.00 mL), and water (10.00 mL) at 0° C. The resulting mixture was stirred at 25° C. for 2 h. The solution was concentrated under reduced pressure to remove MeOH and THF, as much as possible, then acidified to pH 3 with HCl (1 M), then the solution was extracted with EtOAc. The organic layers were combined and concentrated under reduced pressure to obtain the title compound (2.50 g) as a solid. LCMS (ESI): 375.2 [M+H]$^+$ Step-4b. (R)-4-(5-(5-fluoro-2-methoxypyridin-4-yl)-1H-pyrazole-3-carbonyl)-4-azaspiro[2.5]octane-7-carboxylic acid (Intermediate 527-B)

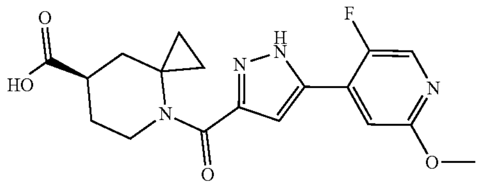 [SMILES: COc1cc(-c2cc(C(=O)N3CC[C@@H](C(=O)O)CC34CC4)n[nH]2)c(F)cn1]

$LiOH \cdot H_2O$ (497.0 mg, 11.84 mmol) was added to a stirred solution of methyl (R)-4-(5-(5-fluoro-2-methoxypyridin-4-yl)-1H-pyrazole-3-carbonyl)-4-azaspiro[2.5]octane-7-carboxylate (2.30 g, 5.92 mmol) in THF (5.00 mL), MeOH (5.00 mL), water (5.00 mL). The resulting mixture was stirred at 25° C. for 1 h. The resulting mixture was concentrated under reduced pressure to remove MeOH and THF. The mixture was acidified to pH 3 with HCl (1 M). The aqueous layer was extracted with EtOAc. The organic layers were combined and concentrated under reduced pressure to obtain the title compound (2.20 g) as a solid, LCMS (ESI): 375.1 [M+H]$^+$.

Intermediate 528-A. 1-ethyl-6-(trifluoromethyl)piperidin-3-amine

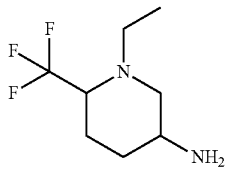

Step-1. Tert-butyl N-[6-(trifluoromethyl)pyridin-3-yl]carbamate

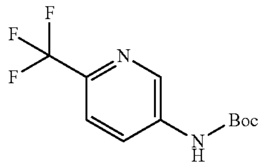 [SMILES: CC(C)(C)OC(=O)Nc1ccc(C(F)(F)F)nc1]

$Boc_2O$ (10.10 g, 46.26 mmol) was added to a stirred solution of 6-(trifluoromethyl)pyridin-3-amine (5.00 g, 30.84 mmol) and TEA (12.89 mL, 92.53 mmol) in DCM (15.00 mL). The solution was stirred at 25° C. for 2 h, then concentrated under reduced pressure. The residue was purified by silica gel column chromatography (EtOAc/petroleum ether; 1/2 v/v) to obtain the title compound (7.10 g) as a solid. LCMS (ESI): 263.2 $[M+H]^+$.

Step-2. Tert-butyl N-[6-(trifluoromethyl)piperidin-3-yl]carbamate

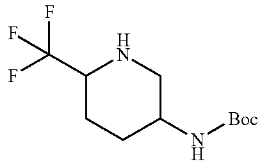 [SMILES: CC(C)(C)OC(=O)NC1CCC(C(F)(F)F)NC1]

HOAc (0.92 g, 15.32 mmol) and $Ru/Al_2O_3$ (0.31 g, 1.53 mmol) were added to a stirred solution of tert-butyl N-[6-(trifluoromethyl)pyridin-3-yl]carbamate (Step-1, 4.00 g, 15.25 mmol) in MeOH (10.00 mL). The solution was stirred at 50° C. for 14 h under hydrogen (50 atm), then the solution was filtered, and the filter cake was washed with MeOH. The filtrate was concentrated under reduced pressure and the residue was purified by silica gel column chromatography (EtOAc/petroleum ether, 1/1 v/v) to obtain the title compound (3.40 g) as a solid. LCMS (ESI): 269.3 $[M+H]^+$.

Step-3. Tert-butyl N-[1-ethyl-6-(trifluoromethyl)piperidin-3-yl]carbamate

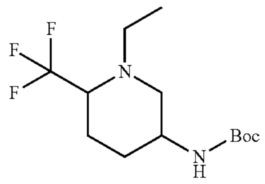 [SMILES: CCN1CC(NC(=O)OC(C)(C)C)CCC1C(F)(F)F]

Acetaldehyde (246.3 mg, 5.60 mmol) and AcOH (0.50 ml) were added to a solution of tert-butyl N-[6-(trifluoromethyl)piperidin-3-yl]carbamate (Step-2, 500.0 mg, 1.90 mmol) in MeOH (5.00 mL). The solution was stirred at 25° C. for 30 min, then $NaBH_3CN$ (351.4 mg, 5.60 mmol) was added. The solution was stirred at 25° C. for 14 h, then concentrated under vacuum. The residue was purified by silica gel column chromatography (EtOAc/petroleum ether, 1/1 v/v) to obtain the title compound (410.0 mg) as a solid. LCMS (ESI): 297.3 $[M+H]^+$.

Step-4. 1-ethyl-6-(trifluoromethyl)piperidin-3-amine (INTERMEDIATE 528-A)

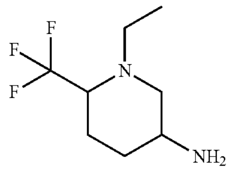

TFA 0.32 mL, 4.15 mmol) was added to a stirred solution of tert-butyl N-[1-ethyl-6-(trifluoromethyl)piperidin-3-yl] carbamate (Step-3, 410.0 mg, 1.38 mmol) in DCM (5.00 mL). The solution was stirred at 25° C. for 1 h, then concentrated under reduced pressure. The residue was purified by silica gel column chromatography (DCM/MeOH, 10/1 v/v) to obtain the title compound (250.0 mg) as a solid. LCMS (ESI): 197.2 $[M+H]^+$.

Intermediate 528-B. 1-methyl-6-(trifluoromethyl)piperidin-3-amine

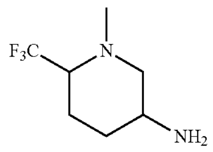

The title compound was prepared using a procedure similar to the one described for the synthesis of Intel mediate 528-A, except formaldehyde was used as starting material in Step-3. The title compound was collected (290.0 mg) as a solid. LCMS (ESI): 391.1 $[M+H]^+$.

Intermediate 529. (1R,3S,5S)-8-[5-(5-fluoro-2-methoxypyridin-4-yl)-1-[[2-(trimethylsilyl)ethoxy]methyl]pyrazole-3-carbonyl]-8-azabicyclo[3.2.1]octane-3-carboxylic acid

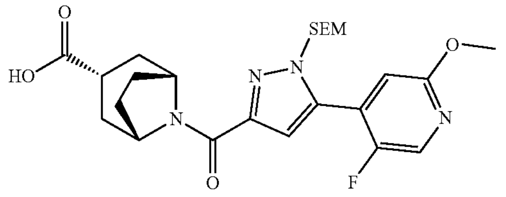 [SMILES: COc1cc(-c2cc(C(=O)N3[C@@H]4CC[C@H]3C[C@H](C(=O)O)C4)nn2COCC[Si](C)(C)C)c(F)cn1]

The title compound was prepared using a procedure similar to the one described for the synthesis of Intermediate 508, except 5-(5-fluoro-2-methoxypyridin-4-yl)-1-((2-(trimethylsilyl)ethoxy)methyl)-1H-pyrazole-3-carboxylic acid (INTERMEDIATE 506) was used as a starting material in Step-3. The resulting solid was dried in an oven under reduced pressure to obtain the title compound (450.0 mg) as a solid. LCMS (ESI): 505.1 $[M+H]^+$.

Intermediate 530. 4-(difluoromethyl)-4-methoxycyclohexan-1-amine

Step-1. 4-(dibenzylamino)cyclohexan-1-one

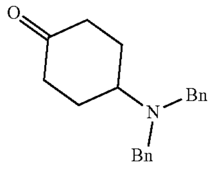 [SMILES: O=C1CCC(N(Cc2ccccc2)Cc2ccccc2)CC1]

Benzyl bromide (1.50 g, 8.84 mmol) and DIPEA (1.50 mL, 8.84 mmol) were added to a stirred solution of 4-aminocyclohexan-1-one (0.50 g, 4.42 mmol) in MeCN (8.00 mL). The solution was stirred at 25° C. for 14 h, then concentrated under reduced pressure. The residue was purified by silica gel column chromatography (petroleum ether/EtOAc, 5/1 v/v) to obtain the title compound (600.0 mg) as an oil. LCMS (ESI): 294.2 $[M+H]^+$.

Step-2. 4-(dibenzylamino)-1-(difluoromethyl)cyclohexan-1-ol

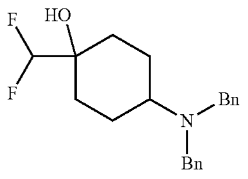 [SMILES: OC1(C(F)F)CCC(N(Cc2ccccc2)Cc2ccccc2)CC1]

HMPA (4.58 g, 25.56 mmol), CsF (0.23 g, 1.53 mmol), and $TMSCF_2H$ (1.27 g, 10.23 mmol) were added to a solution of 4-(dibenzylamino)cyclohexan-1-one (Step-1, 1.50 g, 5.11 mmol) in THE (10.00 mL). The solution was stirred at 70° C. for 14 h, then concentrated under reduced pressure. The residue was purified by silica gel column chromatography (petroleum ether/EtOAc, 5/1 v/v) to obtain the title compound (550.0 mg) as a solid. LCMS (ESI): 346.2 $[M+H]^+$.

Step-3. N,N-dibenzyl-4-(difluoromethyl)-4-methoxycyclohexan-1-amine

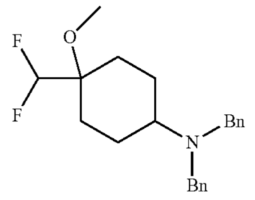 [SMILES: COC1(C(F)F)CCC(N(Cc2ccccc2)Cc2ccccc2)CC1]

NaH (61.1 mg, 2.50 mmol) was added to a solution of 4-(dibenzylamino)-1-(difluoromethyl)cyclohexan-1-ol (Step-2, 440.0 mg, 1.30 mmol) in THF (5.00 mL) at 0° C. The solution was stirred at 25° C. for 1 h, then MeOH (0.40 mL, 6.40 mmol) was added. The solution was stirred at 25° C. for 14 h, then the reaction was quenched with MeOH. The solution was concentrated under reduced pressure and the residue was purified by silica gel column chromatography (petroleum ether/EtOAc, 1/1 v/v) to obtain the title compound (350.0 mg) as an oil. LCMS (ESI): 360.2 $[M+H]^+$.

Step-4. 4-(difluoromethyl)-4-methoxycyclohexan-1-amine (Intermediate 530)

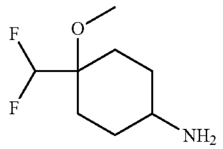

Pd/C (104.7 mg) was added to a stirred solution of N,N-dibenzyl-4-(difluoromethyl)-4-methoxycyclohexan-1-amine (Step-3, 350.0 mg, 0.97 mmol) in MeOH (2.00 mL). The solution was stirred at 25° C. for 14 h under hydrogen atmosphere, then filtered and the filter cake was washed with MeOH. The filtrate was concentrated under reduced pressure to obtain the title compound (130.0 mg) as an oil. LCMS (ESI): 180.1 $[M+H]^+$.

Intermediate 531. 4-(2-methoxyethoxy)-4-(trifluoromethyl)cyclohexan-1-amine

Step-1. 8-(2-methoxyethoxy)-8-(trifluoromethyl)-1,4-dioxaspiro[4.5]decane

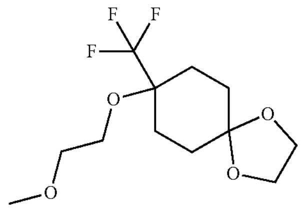 [SMILES: COCCOC1(C(F)(F)F)CCC2(CC1)OCCO2]

NaH (170.0 mg, 7.10 mmol, 60% dispersion in mineral oil) was added to a stirred mixture of 8-(trifluoromethyl)-1,4-dioxaspiro[4.5]decan-8-ol (INTERMEDIATE 516, Step-2, 800.0 mg, 3.50 mmol) in THF (10.00 mL) at 0° C. The solution was stirred at 25° C. for 1 h, then 2-bromoethyl methyl ether (2.46 g, 17.69 mmol) was added. The solution was stirred at 80° C. for 14 h, then quenched by the addition of MeOH. The solution was concentrated, then the residue was purified by silica gel column chromatography (EtOAc/petroleum ether, 1/3 v/v) to obtain the title compound (300.0 mg) as an oil. LCMS (ESI): 285.1 $[M+H]^+$.

Step-2. 4-(2-methoxyethoxy)-4-(trifluoromethyl) cyclohexan-1-one

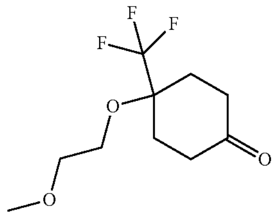 [SMILES: COCCOC1(C(F)(F)F)CCC(=O)CC1]

Para-toluene sulfonic acid (36.0 mg, 0.20 mmol) was added to a stirred solution of 8-(2-methoxyethoxy)-8-(trifluoromethyl)-1,4-dioxaspiro[4.5]decane (Step-1, 300.0 mg, 1.10 mmol) in acetone (4.00 mL) and $H_2O$ (2.00 mL). The solution was stirred at 80° C. for 14 h, then concentrated under reduced pressure. The residue was purified by silica gel column chromatography (DCM/MeOH, 10/1 v/v) to obtain the title compound (120.0 mg) as a solid. LCMS (ESI): 241.1 $[M+H]^+$.

Step-3. N-benzyl-4-(2-methoxyethoxy)-4-(trifluoromethyl)cyclohexan-1-amine

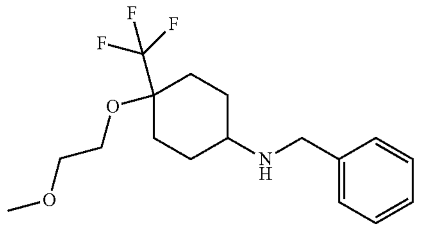 [SMILES: COCCOC1(C(F)(F)F)CCC(NCc2ccccc2)CC1]

Benzylamine (107.0 mg, 1.00 mmol) was added to a stirred solution of 4-(2-methoxyethoxy)-4-(trifluoromethyl) cyclohexan-1-one (Step-2, 120.0 mg, 0.50 mmol) in MeOH (3.00 mL) and AcOH (0.20 mL). The solution was stirred at 25° C. for 30 min, then sodium triacetoxyborohydride (317.0 mg, 1.50 mmol) was added. The solution was stirred at 25° C. for 14 h, then concentrated under reduced pressure. The residue was purified by silica gel column chromatography (DCM/MeOH, 10/1 v/v) to obtain the title compound (100.0 mg) as a solid. LCMS (EST): 332.2 $[M+H]^+$.

Step-4. 4-(2-methoxyethoxy)-4-(trifluoromethyl) cyclohexan-1-amine (Intermediate 531)

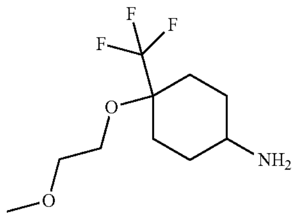 [SMILES: COCCOC1(C(F)(F)F)CCC(N)CC1]

Pd/C (30.0 mg) was added to a stirred solution of N-benzyl-4-(2-methoxyethoxy)-4-(trifluoromethyl)cyclohexan-1-amine (Step-3, 100.0 mg, 0.30 mmol) in MeOH (4.00 mL). The solution was stirred at 25° C. for 14 h under hydrogen atmosphere, and then was filtered. The filtrate was concentrated under reduced pressure and the residue was purified by silica gel column chromatography (DCM/MeOH, 10/1 v/v) to obtain the title compound (55.0 mg) as a solid. LCMS (EST): 242.1 $[M+H]^+$.

Intermediate 532. 6-(trifluoromethyl)oxan-3-amine

Step-1. Benzyl 2-(hydroxymethyl)prop-2-enoate

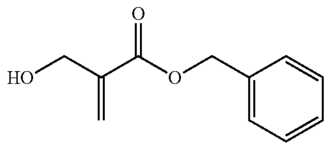

HCHO (9.26 g, 308.40 mmol) and 1,4-diazabicyclo [2.2.2]octane (34.57 g, 308.19 mmol) were added to a stirred solution of benzyl prop-2-enoate (50.00 g, 308.28 mmol) in 1,4-dioxane (100.00 mL) and $H_2O$ (100.00 mL). The solution was stirred at 25° C. for 14 h, then concentrated under vacuum. The residue was diluted with ethyl acetate and washed with water. The organic layer was concentrated under reduced pressure and the residue was purified by silica gel column chromatography (EtOAc/petroleum ether, 1/3 v/v) to obtain the title compound (10.17 g) as an oil.

Step-2. Benzyl 2-(bromomethyl)prop-2-enoate

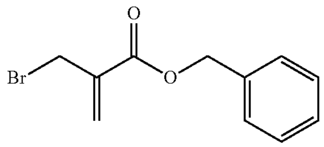

Phosphorus tribromide (15.62 g, 57.71 mmol) was added in portions to a stirred solution of benzyl 2-(hydroxymethyl) prop-2-enoate (Step-1, 10.10 g, 52.55 mmol) in diethyl ether (150.00 mL) at 0° C. The solution was stirred at 0 CC for 30 min, then concentrated under vacuum. The residue was purified by silica gel column chromatography (EtOAc/petroleum ether, 1/10 v/v) to obtain the title compound (9.63 as an oil.

Step-3. Benzyl 2-[[(1,1,1-trifluoropent-4-en-2-yl)oxy]methyl]prop-2-enoate

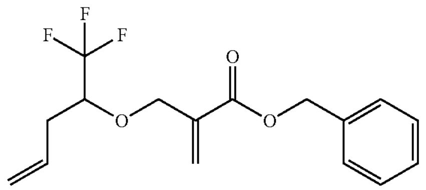 [SMILES: C=CCC(OCC(=C)C(=O)OCc1ccccc1)C(F)(F)F]

NaH (661.2 mg, 27.60 mmol, 60% dispersion in mineral oil) was added to a stirred solution of 1,1,1-trifluoropent-4-en-2-ol (1.93 g, 13.78 mmol) in DMF (15.00 mL) at 0° C. The solution was stirred at 0° C. for 30 min, then benzyl 2-(bromomethyl)prop-2-enoate (Step-2, 3.87 g, 15.15 mmol) was added. The solution was warmed slowly to 25° C. and stirred for 2 h, then diluted with ethyl acetate and washed with water. The organic layer was concentrated under reduced pressure and the residue was purified by silica gel column chromatography (EtOAc/petroleum ether, 1/10 v/v) to obtain the title compound (2.51 g) as a liquid.

Step-4. Benzyl 6-(trifluoromethyl)-5,6-dihydro-2H-pyran-3-carboxylate

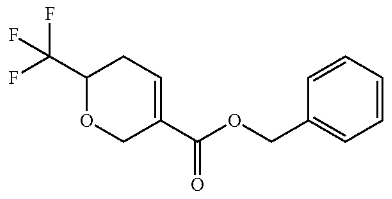 [SMILES: O=C(OCc1ccccc1)C1=CCC(C(F)(F)F)OC1]

Grubbs Catalyst (2$^{nd}$ gen, 676.0 mg, 0.80 mmol) was added to a stirred solution of benzyl 2-[[(1,1,1-trifluoropent-4-en-2-yl)oxy]methyl]prop-2-enoate (Step-3, 2.51 g, 7.95 mmol) in DCM (1250.00 mL). The solution was stirred at 25° C. for 30 min, then diluted with water. The organic layer was concentrated under reduced pressure and the residue was purified by silica gel column chromatography (EtOAc/petroleum ether, 1/10 v/v) to obtain the title compound (1.98 g) as an oil.

Step-5. 6-(trifluoromethyl)oxane-3-carboxylic acid

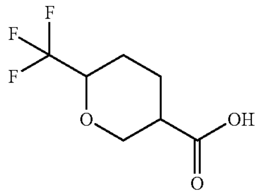 [SMILES: O=C(O)C1CCC(C(F)(F)F)OC1]

$Pd(OH)_2/C$ (990.8 mg) was added to a stirred solution of benzyl 6-(trifluoromethyl)-5,6-dihydro-2H-pyran-3-carboxylate (Step-4, 1.98 g, 6.90 mmol) in THF (50.00 mL). The solution was stirred at 25° C. for 20 h under atmosphere of $H_2$. The solids were filtered out and the filtrate was concentrated under vacuum to obtain the title compound (1.25 g) as a solid.

Step-6. Benzyl N-[6-(trifluoromethyl)oxan-3-yl]carbamate

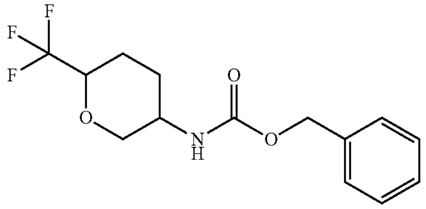 [SMILES: O=C(NC1CCC(C(F)(F)F)OC1)OCc1ccccc1]

Benzyl alcohol (982.0 mg, 9.10 mmol), DPPA (2.50 g, 9.10 mmol) and DIPEA (4.2 mL, 24.22 mmol) were added to a stirred solution of 6-(trifluoromethyl)oxane-3-carboxylic acid (Step-5, 1.20 g, 6.06 mmol) in toluene (20.00 mL). The solution was stirred at 110° C. for 13 h, then concentrated under vacuum. The residue was purified by silica gel column chromatography (EtOAc/petroleum ether, 1/4 v/v) to obtain the title compound (1.60 g) as an oil. LCMS (ESI): 304.1 $[M+H]^+$.

Step-7. 6-(trifluoromethyl)oxan-3-amine (Intermediate 532)

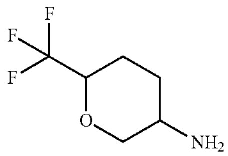 [SMILES: NC1CCC(C(F)(F)F)OC1]

Pd/C (300.0 mg) was added to a stirred solution of benzyl N-[6-(trifluoromethyl)oxan-3-yl]carbamate (Step-6, 600.0 mg, 1.90 mmol) in MeOH (10.00 mL) and EtOAc (10.00 mL). The solution was stirred at 25° C. for 1 h under atmosphere of $H_2$. The solids were filtered out and the filtrate was concentrated under vacuum to obtain the title compound (340.0 mg) as an oil. LCMS (ESI): 170.1 $[M+H]^+$.

Intermediate 533. 1-[5-(5-chloro-2-methoxypyridin-4-yl)-1H-pyrazole-3-carbonyl]-2,5-dimethylpiperidine-4-carboxylic acid Step-1. Methyl 2,5-dimethylpyridine-4-carboxylate

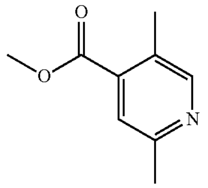

$Pd(dppf)Cl_2$ (393.3 mg, 0.54 mmol) and TEA (2.25 mL, 16.13 mmol) were added to a solution of 4-bromo-2,5- dimethylpyridine (1.00 g, 5.38 mmol) in MeOH (20.00 mL). The solution was stirred at 70° C. for 14 h under a CO atmosphere. The solution was then diluted with water and extracted with EA. The organic layers were combined, dried over anhydrous sodium sulfate, filtered, and the solvent was evaporated. The residue was purified by silica gel column chromatography (EtOAc/petroleum ether, 1/4 v/v) to obtain the title compound (600.0 mg) as an oil. LCMS (ESI): 166.1 $[M+H]^+$.

Step-2. Methyl 2,5-dimethylpiperidine-4-carboxylate

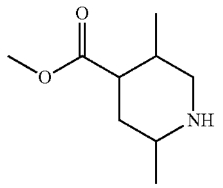

$Rh/Al_2O_3$ (20%, 120.0 mg) was added to a solution of methyl 2,5-dimethylpyridine-4-carboxylate (Step-1, 600.0 mg, 3.60 mmol) in MeOH (10.00 mL). The solution was stirred at 50° C. for 14 h under a $H_2$ atmosphere (50 atm). The solids were filtered out, and the resulting solution was concentrated under reduced pressure to obtain the title compound (500.0 mg) as a solid. LCMS (ESI): 172.1 $[M+H]^+$.

Step-3. 1-[5-(5-chloro-2-methoxypyridin-4-yl)-1H-pyrazole-3-carbonyl]-2,5-dimethylpiperidine-4-carboxylate

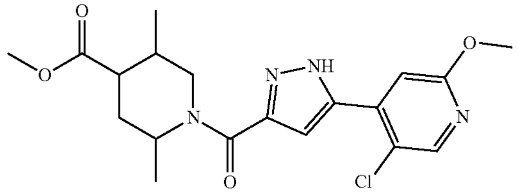

Methyl 2,5-dimethylpiperidine-4-carboxylate (Step-2, 50.0 mg, 0.30 mmol) and 5-(5-chloro-2-meth-oxypyridin-4-yl)-1H-pyrazole-3-carboxylic acid (INTERMEDIATE 510, 74.1 mg, 0.30 mmol) were added to a solution of HOBt (51.3 mg, 0.40 mmol), EDCI (72.8 mg, 0.40 mmol) and DIPEA (0.15 mL, 0.90 mmol) in DMF (3.00 mL). The solution was stirred at 25° C. for 14 h, then diluted with water and extracted with EA. The organic layers were combined, dried over anhydrous sodium sulfate, filtered, and the solvent was evaporated. The residue was purified by silica gel column chromatography (DCM/MeOH, 20/1 v/v) to obtain the title compound (100.0 mg) as a solid. LCMS (ESI): 407.2 $[M+H]^+$.

Step-4. 1-[5-(5-chloro-2-methoxypyridin-4-yl)-1H-pyrazole-3-carbonyl]-2,5-dimethylpiperidine-4-carboxylic acid (Intermediate 533)

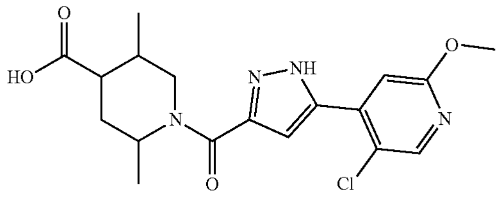 [SMILES: COc1cc(-c2cc(C(=O)N3CC(C)C(C(=O)O)CC3C)n[nH]2)c(Cl)cn1]

LiOH (29.3 mg, 1.20 mmol) was added to a solution of methyl 1-[5-(5-chloro-2-methoxypyridin-4-yl)-1H-pyrazole-3-carbonyl]-2,5-dimethyl-piperidine-4-carboxylate (Step-3, 100.0 mg, 0.20 mmol) in THF (1.00 mL), MeOH (1.00 mL), and $H_2O$ (1.00 mL). The solution was stirred at 25° C. for 1 h, then the pH was adjusted to 5 by HCl (6 M). The solution was then diluted with water and extracted with EA. The organic layers were combined, dried over anhydrous sodium sulfate, filtered, and the solvent was evaporated to obtain the title compound (70.0 mg) as a solid. LCMS (ESI): 393.1 $[M+H]^+$.

Intermediate 534. 4-[5-(5-chloro-2-methoxypyridin-4-yl)-1H-pyrazole-3-carbonyl]-4-azaspiro[2.5]octane-7-carboxylic acid

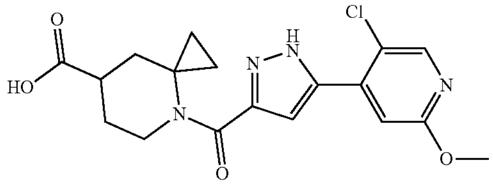 [SMILES: COc1cc(-c2cc(C(=O)N3CCC(C(=O)O)CC34CC4)n[nH]2)c(Cl)cn1]

The title compound was prepared using a procedure similar to the one described for the synthesis of Intermediate 527, except 5-(5-chloro-2-methoxypyridin-4-yl)-1H-pyrazole-3-carboxylic acid (INTERMEDIATE 510) was used as starting material in Step-1. The title compound was collected (290.0 mg) as a solid. LCMS (ESI): 391.1$[M+H]^+$.

Intermediate 535-A. 4-ethoxy-4-(trifluoromethyl)cyclohexan-1-amine

Step-1. 4-(dibenzylamino)cyclohexan-1-one

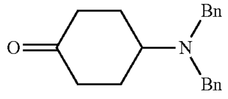 [SMILES: O=C1CCC(N(Cc2ccccc2)Cc2ccccc2)CC1]

Benzyl bromide (17.50 g, 100.25=top and potassium carbonate (13.80 g, 100.25 mmol) were added to a stirred mixture of 4-aminocyclohexan-1-one hydrochloride (5.00 g, 33.42 mmol) in MeCN (30.00 mL). The resulting mixture was stirred at 25° C. for 5 h. The resulting mixture was concentrated under reduced pressure. The residue was purified by silica gel column chromatography eluting with petroleum ether/EtOAc (5/1 v/v) to obtain the title compound (8.30 g) as a solid. LCMS (ESI): $[M+H]^+$: 294.2.

Step-2. N,N-dibenzyl-4-(trifluoromethyl)-4-[(trimethylsilyl)oxy]cyclohexan-1-amine

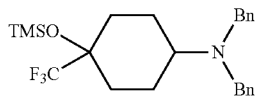

CsF (621.0 mg, 4.10 mmol), $TMSCF_3$ (3.80 g, 27.27 mmol) and HMPA (12.00 g, 68.16 mmol) were added to a stirred mixture of 4-(dibenzylamino)cyclohexan-1-one (Step-1, 4.00 g, 13.63 mmol) in THE (20.00 mL) at 25° C. The resulting mixture was stirred at 70° C. for 14 h. The resulting mixture was concentrated under reduced pressure. The residue was purified by silica gel column chromatography eluting with petroleum ether/EtOAc (5/1 v/v) to obtain the title compound (4.50 g) as a solid. LCMS (ESI): $[M+H]^+$: 436.2.

Step-3. 4-(dibenzylamino)-1-(trifluoromethyl)cyclohexan-1-ol

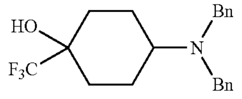 [SMILES: OC1(C(F)(F)F)CCC(N(Cc2ccccc2)Cc2ccccc2)CC1]

Tetrabutylammonium fluoride trihydrate (3.20 g, 10.33 mmol) was added to a stirred mixture of N,N-dibenzyl-4-(trifluoromethyl)-4-[(trimethylsilyl)oxy]cyclohexan-1-amine (Step-2, 4.50 g, 10.33 mmol) in THE (30.00 mL). The resulting mixture was stirred at 25° C. for 3 h. The resulting mixture was concentrated under reduced pressure. The residue was purified by silica gel column chromatography eluting with petroleum ether/EtOAc (10 v/v) to obtain the title compound (3.70 g) as a solid. LCMS (ESI): $[M+H]^+$: 364.2.

Step-4. N,N-dibenzyl-4-ethoxy-4-(trifluoromethyl) cyclohexan-1-amine

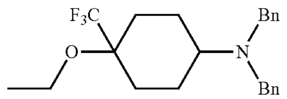 [SMILES: CCOC1(C(F)(F)F)CCC(N(Cc2ccccc2)Cc2ccccc2)CC1]

NaH (220.0 mg, 5.50 mmol, 60% dispersion in mineral oil) was added to a stirred mixture of 4-(dibenzylamino)-1-(trifluoromethyl)cyclohexan-1-ol (Step-3, 1.00 g, 2.75 mmol) in DMF (10.00 mL). The resulting mixture was stirred at 25° C. for 1 h. Ethyl iodide (2.10 g, 13.76 mmol) was added to the reaction mixture. The resulting mixture was stirred at 60° C. for 4 h. The solution was diluted with EtOAc and washed with water. The organic layer was concentrated under vacuum. The residue was purified by silica gel column chromatography eluting with petroleum ether/EtOAc (10/1 v/v) to obtain the title compound (920.0 mg) as a solid. LCMS (ESI): $[M+H]^+$: 392.2.

Step-5. 4-ethoxy-4-(trifluoromethyl)cyclohexan-1-amine (Intermediate 535-A)

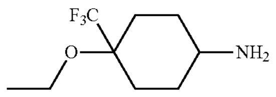

Pd/C (450.0 mg, 4.20 mmol) was added to a stirred mixture of N,N-dibenzyl-4-ethoxy-4-(trifluoromethyl)cyclohexan-1-amine (Step-4, 920.0 mg, 2.45 mmol) in MeOH (5.00 mL)/THF (2.00 mL). The resulting mixture was stirred at 25° C. for 14 h under hydrogen atmosphere. The resulting mixture was filtered. The filter cake was washed with MeOH. The filtrate was concentrated under reduced pressure to obtain the title compound (475.0 mg) as an oil. LCMS (ESI): $[M+H]^+$: 212.1.

Intermediate 535-B. (1r,4r)-4-ethoxy-4-(trifluoromethyl)cyclohexan-1-amine

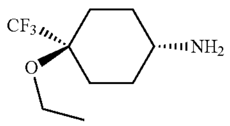

The title compound was prepared using a procedure similar to the one described for the synthesis of Intermediate 535-A, except (1r,4r)-4-(dibenzylamino)-1-(trifluoromethyl)cyclohexan-1-ol was used as starting material in Step-3. The title compound was collected (70 mg) as an oil. LCMS (ESI): 212.1 $[M+H]^+$.

Intermediate 536. (1R,3S,5S)—N-[(1r,4r)-4-hydroxy-4-(trifluoromethyl)cyclohexyl]-8-azabicyclo [3.2.1]octane-3-carboxamide Step-1. Tert-butyl (1R,3S,5S)-3-[[(1r,4r)-4-hydroxy-4-(trifluoromethyl)cyclohexyl]carbamoyl]-8-azabicyclo[3.2.1]octane-8-carboxylate

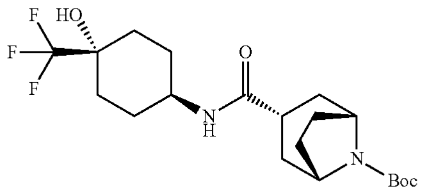 [SMILES: CC(C)(C)OC(=O)N1[C@@H]2CC[C@H]1C[C@H](C(=O)N[C@H]1CC[C@@](O)(C(F)(F)F)CC1)C2]

(1r,4r)-4-amino-1-(trifluoromethyl)cyclohexan-1-ol (100.0 mg, 0.50 mmol, CAS #: 1408075-09-1, Enamine Ltd.), HATU (228.3 mg, 0.60 mmol), and DIPEA (0.29 mL, 1.60 mmol) were added to a stirred solution of (1R,3S,5S)-8-(tert-butoxycarbonyl)-8-azabicyclo[3.2.1]octane-3-carboxylic acid (139.4 mg, 0.50 mmol) in DMF (3.00 mL). The solution was stirred at 25° C. for 14 h, then diluted with EtOAc and washed with water. The organic layer was concentrated under reduced pressure, and the residue was purified by silica gel column chromatography (DCM/

MeOH, 10/1 v/v) to obtain the title compound (220.0 mg) as a solid. LCMS (ESI): 421.2 $[M+H]^+$.

Step-2. (1R,3S,5S)—N-[(1r,4r)-4-hydroxy-4-(trifluoromethyl)cyclohexyl]-8-azabicyclo[3.2.1]octane-3-carboxamide (Intermediate 536)

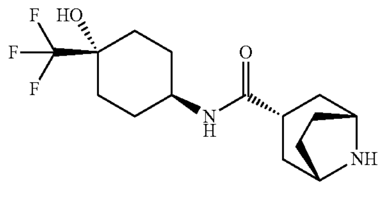 [SMILES: O=C(N[C@H]1CC[C@@](O)(C(F)(F)F)CC1)[C@@H]1C[C@H]2CC[C@@H](C1)N2]

TFA (2.00 mL) was added to a stirred solution of tert-butyl (1R,3S,5S)-3-[[(1r,4r)-4-hydroxy-4-(trifluoromethyl)cyclohexyl]carbamoyl]-8-azabicyclo[3.2.1]octane-8-carboxylate (Step-1, 100.0 mg, 0.20 mmol) in DCM (2.00 mL). The solution was stirred at 25° C. for 30 min, then concentrated under reduced pressure. The residue was purified by silica gel column chromatography (DCM/MeOH, 10/1 v/v) to obtain the title compound (53.0 mg) as a solid. LCMS (ESI): 321.2 $[M+H]^+$.

Intermediate 537. 3,3-difluoro-1-oxaspiro[3.5]nonan-7-amine 2,2,2-trifluoroacetate Step-1. Ethyl 2,2-difluoro-2-(8-hydroxy-1,4-dioxaspiro[4.5]decan-8-yl)acetate

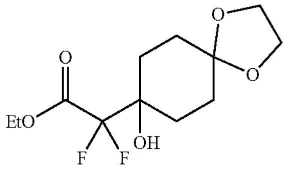 [SMILES: CCOC(=O)C(F)(F)C1(O)CCC2(CC1)OCCO2]

TMSCl (0.15 mL, 1.15 mmol) was added to a stirred solution of zinc (1.00 g, 15.40 mmol) in THF (20.00 mL) at 22° C. The resulting mixture was stirred for 20 min at 65° C., before ethyl 2-bromo-2,2-difluoroacetate (0.49 mL, 3.84 mmol) was added and stirring was continued for 30 min. 1,4-dioxaspiro[4.5]decan-8-one (500.0 mg, 3.20 mmol) was then added as a solution in THF (10.00 mL) and the resulting mixture was stirred for 2 h. The solution was then cooled to 22° C., quenched with AcOH (2.34 mL), diluted with water and extracted with EtOAc. The organic layers were combined, washed with brine, dried over anhydrous sodium sulfate, filtered, and the solvent was evaporated to obtain the title compound (605.0 mg) as an oil. $^1H$ NMR (400 MHz, $CDCl_3$) δ 4.36 (q, 2H), 3.98-3.92 (m, 4H), 1.96-1.91 (m, 3H), 1.83-1.76 (m, 2H), 1.70-1.64 (m, 2H), 1.36 (t, 3H).

Step-2. 8-(1,1-difluoro-2-hydroxyethyl)-1,4-dioxaspiro[4.5]decan-8-ol

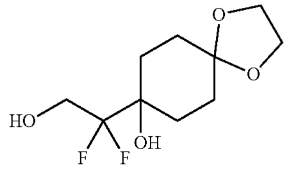 [SMILES: OCC(F)(F)C1(O)CCC2(CC1)OCCO2]

$NaBH_4$ (245.0 mg, 6.48 mmol) was added to a stirred solution of ethyl 2,2-difluoro-2-(8-hydroxy-1,4-dioxaspiro[4.5]decan-8-yl)acetate (Step-1, 605.0 mg, 2.16 mmol) in MeOH (13.10 mL) at 0° C. The resulting mixture was stirred for 2 h before additional $NaBH_4$ (245 mg, 6.48 mmol) was added and the resulting mixture was stirred at 22° C. for 16 h. The solution was quenched with water and concentrated under reduced pressure. The residue was dissolved in EtOAc, washed with brine, then dried over anhydrous sodium sulfate, filtered; and the solvent was evaporated. The residue was purified by silica gel column chromatography eluting with cyclohexane/EtOAc (1/1 v/v to 1/4 v/v) to obtain the title compound (160.0 mg) as an oil. $^1H$ NMR (400 MHz, $CDCl_3$) δ 4.04-3.90 (m, 6H) 2.19 (t, 1H), 2.01-1.87 (m, 5H), 1.83-1.77 (m, 2H), 1.70-1.63 (m, 2H).

Step-3. 2,2-difluoro-2-(8-hydroxy-1,4-dioxaspiro[4.5]decan-8-yl)ethyl 4-methylbenzenesulfonate

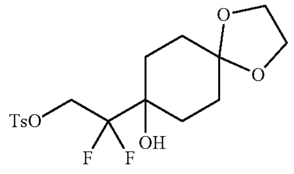 [SMILES: Cc1ccc(S(=O)(=O)OCC(F)(F)C2(O)CCC3(CC2)OCCO3)cc1]

TEA (0.19 mL, 1.34 mmol) and TsCl (154.0 mg, 0.81 mmol) were added to a stirred solution of 8-(1,1-difluoro-2-hydroxyethyl)-1,4-dioxaspiro[4.5]decan-8-ol (Step-2, 160.0 mg, 0.67 mmol) in DCM (5.60 mL). The resulting mixture was stirred at 22° C. for 16 h. The solution was then diluted with water and extracted with EtOAc. The organic layers were combined, washed with water and brine, then dried over anhydrous sodium sulfate, filtered, and the solvent was evaporated to obtain the title compound (217.0 mg) as an oil. TLC-MS (APCI): $[M+H]^+$: 392.7.

Step-4. 3,3-difluoro-1,8,11-trioxadispiro[3.2.47.24]tridecane

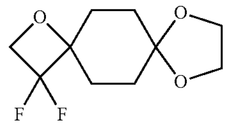 [SMILES: FC1(F)COC12CCC1(CC2)OCCO1]

NaH (30.0 mg, 0.76 mmol, 60% dispersion in mineral oil) was added to a stirred solution of 2,2-difluoro-2-(8-hydroxy-1,4-dioxaspiro[4.5]decan-8-yl)ethyl 4-methylbenzenesulfonate (Step-3, 198.0 mg, 0.51 mmol) in THF (50.00 mL)

at 0° C. The resulting mixture was warmed to 22° C. and stirred for 6 h. The solution was then diluted with water and extracted with $Et_2O$. The organic layers were combined, washed with brine, then dried over anhydrous sodium sulfate, filtered, and the solvent was evaporated. The residue was purified by silica gel column chromatography eluting with cyclohexane/EtOAc (95/5 v/v to 1/1.5 v/v) to obtain the title compound (101.0 mg) as an oil. NMR (400 MHz, $CDCl_3$) δ 4.64 (t, 2H), 3.99-3.90 (m, 4H), 2.02 (t, 4H), 1.87-1.77 (m, 2H), 1.76-1.67 (m, 2H).

Step-5. 3,3-difluoro-1-oxaspiro[3.5]nonan-7-one

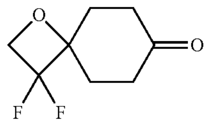 [SMILES: O=C1CCC2(CC1)OCC2(F)F]

TFA (1.90 mL, 0.23 mmol) was added to a stirred solution of 3,3-difluoro-1,8,11-trioxadispiro[3.2.47.24]tridecane (Step-4, 50.0 mg, 0.23 mmol) in DCM (0.50 mL). The resulting mixture was stirred at 22° C. for 16 h. The solution was concentrated under reduced pressure and the resulting residue was dissolved in DCM, washed with aqueous saturated solution of $NaHCO_3$ and brine, then dried over anhydrous sodium sulfate, filtered, and the solvent was evaporated to afford the title compound (20.0 mg) as an oil. $^1H$ NMR (400 MHz, $CDCl_3$) δ 4.76 (t, 2H), 2.60 (ddd, 2H), 2.42 (dt, 2H), 2.37-2.25 (m, 2H), 2.23-2.12 (m, 2H).

Step-6. 3,3-difluoro-1-oxaspiro[3.5]nonan-7-one oxime

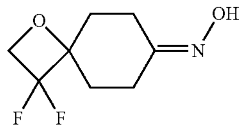 [SMILES: ON=C1CCC2(CC1)OCC2(F)F]

A solution of 3,3-difluoro-1-oxaspiro[3.5]nonan-7-one (Step-5, 380.0 mg, 1.90 mmol) in MeOH (1.00 mL) was added to a stirred solution of hydroxylamine hydrochloride (0.15 g, 2.10 mmol) and sodium acetate (0.19 g, 2.30 mmol) in MeOH (4.00 mL) at 22° C. The resulting mixture was stirred at 60° C. for 16 h. The solution was then diluted with EtOAc and the organic layer was washed with water and brine. The organic layer was dried over anhydrous sodium sulfate, filtered, and the solvent was evaporated. The residue was purified by silica gel chromatography eluting with cyclohexane/EtOAc (4/1 v/v to 1.5/1 v/v) to obtain the title compound (310.0 mg) as a solid. $^1H$ NMR (400 MHz, $CDCl_3$) δ 6.94 (s, 1H), 4.69 (t, 2H), 2.81 (dt, 1H), 2.55 (ddd, 1.14), 2.45 (ddd, 1H), 2.34 (dt, 1H), 2.13-1.93 (m, 4H).

Step-7. tert-butyl (3,3-difluoro-1-oxaspiro[3.5]nonan-7-yl)carbamate

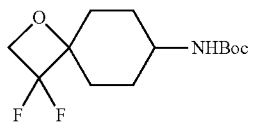 [SMILES: CC(C)(C)OC(=O)NC1CCC2(CC1)OCC2(F)F]

$NaBH_4$ (79.0 mg, 2.10 mmol) was added to a stirred solution of 3,3-difluoro-1-oxaspiro[3.5]nonan-7-one oxime (Step-6, 50.0 mg, 0.26 mmol) and nickel(II) chloride hexahydrate (81.0 mg, 0.34 mmol) in MeOH (5.20 mL) at −78° C. The resulting mixture was warmed to 0° C. for 4.5 h. $Boc_2O$ (86.0 mg, 0.39 mmol) was added and the reaction mixture was stirred at 22° C. for 16 h. The solution was cooled to 0° C., quenched with brine, and then concentrated under reduced pressure. The aqueous layer was extracted with $Et_2O$. The organic layers were combined, washed with brine, dried over anhydrous sodium sulfate, filtered, and the solvent was evaporated. The residue was purified by silica gel column chromatography eluting with cyclohexane/EtOAc (4/1 v/v to 2/1 v/v) to obtain the title compound (47.0 mg) as a solid. $^1H$ NMR (400 MHz, $CDCl_3$) δ 4.62 (td, 2H), 4.41 (s, 1H), 3.49 (s, 1H), 2.23 (d, 2H), 2.07 (d, 2H), 1.91 (d, 2H), 1.73-1.60 (m, 2H), 1.54 (s, 9H).

Step-8. 3,3-difluoro-1-oxaspiro[3.5]nonan-7-amine 2,2,2-trifluoroacetate (Intermediate 537)

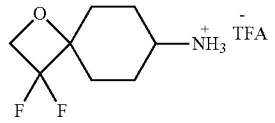 [SMILES: NC1CCC2(CC1)OCC2(F)F]

TFA (0.13 mL, 1.60 mmol) was added to a stirred solution of tert-butyl (3,3-difluoro-1-oxaspiro[3.5]nonan-7-yl)carbamate (Step-7, 45.0 mg, 0.16 mmol) in DCM (0.30 mL) at 0° C. The resulting mixture was stirred at 22° C. for 4.5 h. The resulting mixture was then concentrated under reduced pressure to obtain the title compound (47.0 mg) as an oil. TLC-MS (APCI): $[M+H]^+$: 178.2.

Intermediate 538. 5-(6-methylpyrimidin-4-yl)-1H-pyrazole-3-carboxylic acid

Step-1. Ethyl 1-(tetrahydro-2H-pyran-2-yl)-1H-pyrazole-3-carboxylate

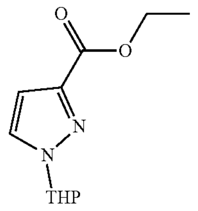

DHP (11.90 g, 141.47 mmol) and TFA (8.10 g, 112.34 mmol) were added to a stirred mixture of ethyl 1H-pyrazole-3-carboxylate (10.00 g, 71.36 mmol) in THF (100.00 mL). The resulting mixture was stirred at 60° C. for 14 h. The solution was then concentrated under reduced pressure and the residue was purified by silica gel column chromatography eluting with DCM/MeOH (10/1 v/v) to obtain the title compound (15.00 g) as an oil. LCMS (ESI): $[M+H]^+$: 225.1.

Step-2. (3-(ethoxycarbonyl)-1-(tetrahydro-2H-pyran-2-yl)-1H-pyrazol-5-yl)boronic acid

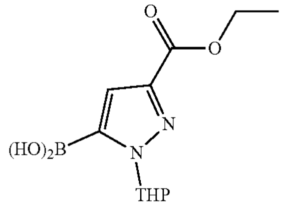

$B_2pin_2$ (8.20 g, 32.28 mmol), 4,4'-di-tert-butyl-2,2'-dipyridyl (1.80 g, 6.76 mmol) and $[Ir(COD)OMe]_2$ (2.20 g, 3.32 mmol) were added to a stirred mixture of ethyl 1-(oxan-2-yl)pyrazole-3-carboxylate (Step-1, 5.00 g, 22.30 mmol) in MTBE (100.00 mL). The resulting mixture was stirred at 80° C. for 14 h under nitrogen atmosphere. The solution was then concentrated under reduced pressure and the residue was purified by silica gel column chromatography eluting with DCM/MeOH (10/1 v/v) to obtain the title compound (5.50 g) as an oil. LCMS (ESI): $[M+H]^+$: 269.1.

Step-3. Ethyl 5-(6-methylpyrimidin-4-yl)-1-(oxan-2-yl)pyrazole-3-carboxylate

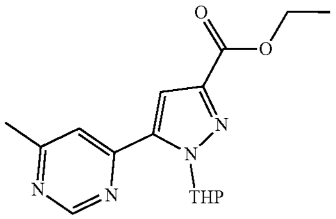

4-chloro-6-methylpyrimidine (172.0 mg, 1.34 mmol), $K_3PO_4$ (474.0 mg, 2.23 mmol) and $Pd(dppf)Cl_2$ (163.0 mg, 0.22 trump were added to a stirred solution of (3-(ethoxycarbonyl)-1-(tetrahydro-2H-pyran-2-yl)-1H-pyrazol-5-yl) boronic acid (Step-2, 300.0 mg, 1.12 mmol) in 1,4-dioxane (10.00 mL) and 1-120 (1.00 mL). The resulting solution was stirred at 70° C. for 14 h. The resulting solution was diluted with EtOAc, washed with water. The organic layer was concentrated under reduced pressure and the residue was purified by silica gel column chromatography eluting with EtOAc/petroleum ether (1/1 v/v) to obtain the title compound (260.0 mg) as a solid. LCMS (ESI): $[M+H]^+$: 317.2.

Step-4. Ethyl 5-(6-methylpyrimidin-4-yl)-1H-pyrazole-3-carboxylate

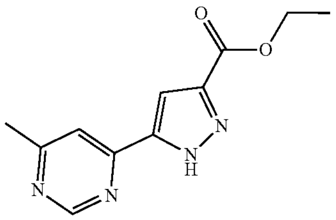 [SMILES: CCOC(=O)c1cc(-c2cc(C)ncn2)[nH]n1]

TFA (4.00 mL) was added to a stirred solution of ethyl 5-(6-methylpyrimidin-4-yl)-1-(oxan-2-yl)pyrazole-3-carboxylate (Step-3, 260.0 mg, 0.82 mmol) in DCM (4.00 mL). The resulting solution was stirred at 25° C. for 1 h. The resulting mixture was concentrated under vacuum and the residue was purified by silica gel column chromatography eluting with DCM/MeOH (10/1 v/v) to obtain the title compound (170.0 mg) as a solid. LCMS (ESI): $[M+H]^+$: 233.1.

Step-5. 5-(6-methylpyrimidin-4-yl)-1H-pyrazole-3-carboxylic acid (Intermediate 538)

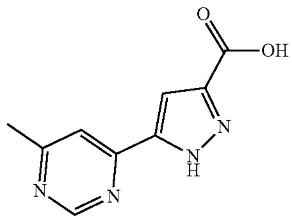

$LiOH \cdot H_2O$ (124.0 mg, 2.96 mmol) was added to a stirred solution of ethyl 5-(6-methylpyrimidin-4-yl)-1H-pyrazole-3-carboxylate (Step-4, 170.0 mg, 0.73 mmol) in THF (4.00 mL), MeOH (4.00 mL), and $H_2O$ (4.00 mL). The resulting solution was stirred at 60° C. for 14 h. The pH value of the solution was adjusted to 5 with HCl (1 M). The resulting mixture was extracted with EtOAc. The organic layers were concentrated under reduced pressure and the residue was purified by silica gel column chromatography eluting with (10/1 v/v) to obtain the title compound (135.0 mg) as an oil. LCMS (ESI): $[M+H]^+$: 205.1.

Intermediate 539. 1-(3-chlorophenyl)ethanamine

Step-1. (E)-N-(3-chlorobenzylidene)-2-methylpropane-2-sulfinamide

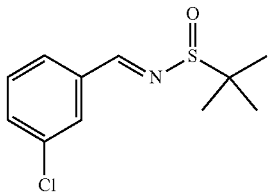

tert-butanesulfinamide (1.00 g, 8.25 mmol), $MgSO_4$ (3.00 g, 24.76 mmol), and PTSA (1.00 g, 5.81 mmol) were added to a solution of M-chlorobenzaldehyde (1.00 g, 8.20 mmol) in DCM (2.0 mL). The solution was stirred at 25° C. for 14 h. The magnesium sulfate was then filtered out, and the filtrate was concentrated under vacuum to obtain the title compound (1.9 g) as a solid. LCMS (ESI): 244.1 $[M+H]^+$.

Step-2. N-[1-(3-chlorophenyl)ethyl]-2-methylpropane-2-sulfinamide

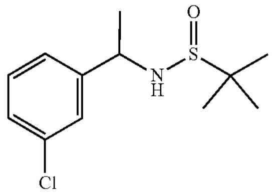 [SMILES: CC(NS(=O)C(C)(C)C)c1cccc(Cl)c1]

Bromo(methyl)magnesium (23.4 mL, 1 M, 23.4 mmol) was added dropwise to a solution of (E)-N-(3-chlorobenzylidene)-2-methylpropane-2-sulfinamide (Step-2, 2.00 g, 7.79 mmol) in THF (8 mL) at 0° C. The solution was stirred at 25° C. for 14 h. The resulting solution was quenched with water, then the pH of the solution was adjusted to pH 6 with HCl (1 M). The solution was then extracted with EtOAc, the organic layers were combined, and then concentrated under vacuum to obtain the title compound (1.57 g) as a solid. LCMS (ESI): 260.1 $[M+H]^+$.

Step-3. 1-(3-chlorophenyl)ethanamine (Intermediate 539)

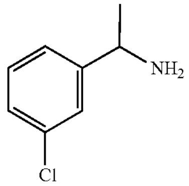

A mixture of N-[1-(3-chlorophenyl)ethyl]-2-methylpropane-2-sulfinamide (Step-2, 1.57 g, 6.04 mmol) in HCl in 1,4-dioxane (1 M, 10 mL) was stirred at 25° C. for 2 h. The solution was concentrated under vacuum, then the residue was purified by silica gel column chromatography (petroleum ether/EtOAc, 2/1 v/v) to obtain the title compound (700 mg) as a solid. LCMS (ESI): 156.1 $[M+H]^+$.

Intermediate 540. Tert-butyl (4,4-difluoro-1-oxaspiro[4.5]decan-8-yl)carbamate

Step-1. 8-(oxiran-2-yl)-1,4-dioxaspiro[4.5]decan-8-ol

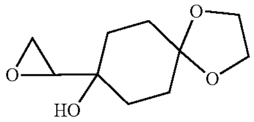 [SMILES: OC1(C2CO2)CCC2(CC1)OCCO2]

mCPBA (75 wt %, 7.07 g, 30.7 mmol) was added to a stirred solution of 8-vinyl-1,4-dioxaspiro[4.5]decan-8-ol (which was prepared according to WO 2017044877 but in one step, and which is also commercially available) (4.72 g, 25.6 mmol) in DCM (51.00 mL) at 0° C. The resulting mixture was stirred at 22° C. for 16 h. The solution was then diluted with DCM and quenched with sodium bisulfate solution (40% aq.). The aqueous layer was extracted with DCM, and the combined organic layers were washed with aqueous saturated solution of $NaHCO_3$, water, and brine. The organic layers were combined, then dried over anhydrous sodium sulfate, filtered, and the solvent was evaporated to obtain the title compound (3.69 as a solid mixture of diastereomers. $^1H$ NMR (400 MHz, $CDCl_3$) δ 4.02-3.90 (m, 4H), 2.93 (dd, 1H), 2.84 (dd, 1H), 2.72 (dd, 1H), 2.01-1.91 (m, 2H), 1.83 (td, 1H), 1.76 (ddd, 2H), 1.71-1.60 (m, 3H), 1.44 (d, 1H).

Step-2. 1,4,9-trioxadispiro[4.2.48.25]tetradecan-12-ol

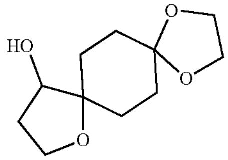 [SMILES: OC1CCOC12CCC1(CC2)OCCO1]

nBuLi (1.6 M, 34.6 mL, 55.3 mmol) was added to a stirred solution of trimethylsulfoxonium iodide (12.2 g, 55.3 mmol) in THF (500.00 mL) at −78° C. The resulting mixture was stirred and warmed to 0° C. for 30 min before being cooled to −78° C. and adding a solution of 8-(oxiran-2-yl)-1,4-dioxaspiro[4.5]decan-8-ol (Step-1, 3.69 g, 18.4 mmol) in THF (50.00 mL) over 10 min. The reaction mixture was warmed to 22° C. and then refluxed for 4.5 h. The resulting mixture was cooled to 22° C. and diluted with water and extracted with EtOAc. The organic layers were combined, washed with brine, dried over anhydrous sodium sulfate, filtered, and the solvent was evaporated. The residue was purified by silica gel column chromatography eluting with cyclohexane/EtOAc (2/3 v/v to 1/4 v/v) to obtain the title compound (1.34 g) as a solid mixture of diastereomers. $^1H$ NMR (400 MHz, $CDCl_3$) δ 4.04-3.91 (m, 6H), 3.82 (td, 1H), 2.31 (dddd, 1H), 1.98-1.61 (m, 8H), 1.59 (s, 1H), 1.54 (d, 1H).

Step-3. 1,4,9-trioxadispiro[4.2.48.25]tetradecan-12-one

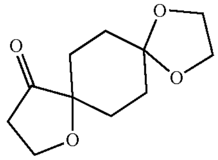 [SMILES: O=C1CCOC12CCC1(CC2)OCCO1]

DMSO (0.89 mL, 12.50 mmol) was added to a stirred solution of oxalyl chloride (0.82 mL, 9.38 mmol) in DCM (6.50 mL) at −78° C. The resulting mixture was stirred at −78° C. for 45 min. A solution of 1,4,9-trioxadispiro[4.2.48.25]tetradecan-12-ol (Step-2, 1.34 g, 6.25 mmol) in DCM (12.50 mL) was then added dropwise and the resulting mixture was stirred for 45 min. TEA (4.30 mL, 31.3 mmol) was added, and the reaction mixture was stirred at −78° C. for 30 min and warmed up to 22° C. over 45 min. The reaction mixture was quenched with water and extracted with DCM. The organic layers were combined, washed with water, brine, dried over anhydrous sodium sulfate, filtered, and the solvent was evaporated. The residue was purified by silica gel chromatography eluting with cyclohexane/EtOAc (3/2 v/v to 2/3 v/v) to obtain the title compound (1.13 g) as a solid. $^1$H NMR (400 MHz, $CDCl_3$) δ 4.14 (t, 2H), 4.00-3.90 (m, 4H), 2.55 (t, 2H), 1.89-1.63 (m, 8H).

Step-4. 12,12-difluoro-1,4,9-trioxadispiro[4.2.48.25]tetradecane

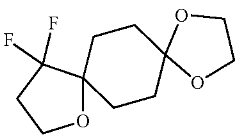 [SMILES: FC1(F)CCOC12CCC1(CC2)OCCO1]

DAST (1.87 mL, 14.10 mmol) was added to a stirred solution of 1,4,9-trioxadispiro[4.2.48.25]tetradecan-12-one (Step-3, 300.0 mg, 1.41 mmol) in DCM (7.07 mL). The resulting mixture was stirred at 22° C. for 4 days. The reaction mixture was then added dropwise to a stirred solution of aqueous saturated $NaHCO_3$. The aqueous layer was further extracted with DCM. The organic layers were combined, then dried over anhydrous sodium sulfate, filtered, and the solvent was evaporated. The residue was purified by silica gel column chromatography eluting with cyclohexane/EtOAc (9/1 v/v to 4/1 v/v) to obtain the title compound (93.0 mg) as a solid. $^1$H NMR (400 MHz, $CDCl_3$) δ 4.01-3.88 (m, 6H), 2.42 (tt, 2H), 1.89-1.66 (m, 8H).

Step-5. Synthesis of 4-difluoro-1-oxaspirol[4.5]decan-8-one

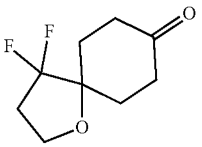 [SMILES: O=C1CCC2(CC1)OCCC2(F)F]

TFA (0.44 g, 0.30 mL, 3.80 mmol) was added to a stirred solution of 12,12-difluoro-1,4,9-trioxadispiro[4.2.48.25]tetradecane (Step-4, 90.0 mg, 0.38 mmol) in DCM (3.80 mL). The resulting mixture was stirred at 22° C. for 16 h. The reaction mixture was concentrated under reduced pressure and the resulting residue was dissolved in DCM, washed with aqueous saturated solution of $NaHCO_3$ and brine, then dried over anhydrous sodium sulfate, filtered, and the solvent was evaporated to obtain the title compound (58.0 mg) as an oil. $^1$H NMR (400 MHz, $CDCl_3$) δ 4.05 (t, 2H), 2.64 (td, 2H), 2.51 (m, 2H), 2.42-2.30 (m, 2H), 2.10-2.01 (m, 2H), 1.94 (td, 2H).

Step-6. 4,4-difluoro-1-oxaspiro[4.5]decan-8-one oxime

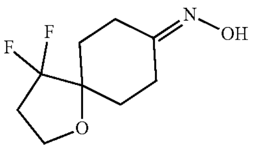 [SMILES: ON=C1CCC2(CC1)OCCC2(F)F]

A solution of 4,4-difluoro-1-oxaspiro[4.5]decan-8-one (Step-5, 58.0 mg, 0.30 mmol) in MeOH (0.40 mL) was added to a stirred solution of hydroxylamine hydrochloride (23.0 mg, 0.34 mmol) and sodium acetate (30.0 mg, 0.37 mmol) in MeOH (0.40 mL) at 22° C. The resulting mixture was stirred at 60° C. for 16 h. The solution was then diluted with EtOAc and the organic layer was washed with water and brine. The organic layer was dried over anhydrous sodium sulfate, filtered, and the solvent was evaporated. The residue was purified by silica gel chromatography eluting with cyclohexane/EtOAc (3/1 v/v to 3/2 v/v) to obtain the title compound (30.0 mg) as a solid. $^1$H NMR (400 MHz, $CDCl_3$) δ 6.73 (s, 1H), 4.00 (t, 2H), 3.18 (dt, 1H), 2.62-2.29 (m, 4H), 2.21-2.11 (m, 1H), 1.95-1.80 (m, 2H), 1.77-1.63 (m, 2H).

Step-7. tert-butyl (4,4-difluoro-1-oxaspiro[4.5]decan-8-yl)carbamate (Intermediate 540)

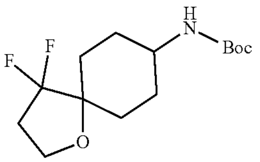 [SMILES: CC(C)(C)OC(=O)NC1CCC2(CC1)OCCC2(F)F]

$NaBH_4$ (44.0 mg, 1.20 mmol) was added to a stirred solution of 4,4-difluoro-1-oxaspiro[4.5]decan-8-one oxime (Step-6, 30.0 mg, 0.15 mmol) and nickel(II) chloride hexahydrate (45.0 mg, 0.19 mmol) in MeOH (2.90 mL) at −78° C. The resulting mixture was warmed to 0° C. for 4.5 h. $Boc_2O$ (48.0 mg, 0.22 mmol) was added and the resulting mixture was stirred at 22° C. for 16 h. The solution was cooled to 0° C., quenched with brine, and then concentrated under reduced pressure. The aqueous layer was extracted with $Et_2O$. The organic layers were combined, washed with brine, dried over anhydrous sodium sulfate, filtered, and the solvent was evaporated to obtain the title compound (30.0 mg) as a solid mixture of diastereomers. $^1$H NMR (400 MHz, $CDCl_3$) δ 4.56-4.37 (m, 1H), 3.93 (td, 214), 3.68-3.47 (m, 114), 2.49-2.33 (m, 2H), 1.97-1.85 (m, 2H), 1.85-1.70 (m, 2H), 1.61-1.54 (m, 4H), 1.44 (s, 9H).

Intermediate 541. 4-(5-(5-fluoro-2-methoxypyridin-4-yl)-1-(2-(trimethylsilyl)ethoxy)methyl)-1H-pyrazole-3-carbonyl)-4-azaspiro[2.5]octane-7-carboxylic acid Step-1. methyl 5-bromo-1-{[2-(trimethylsilyl)ethoxy]methyl}pyrazole-3-carboxylate

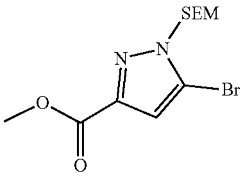 [SMILES: COC(=O)c1cc(Br)n(COCC[Si](C)(C)C)n1]

SEMCl (24.40 g, 146.33 mmol) was added dropwise to a stirred solution of methyl 5-bromo-1H-pyrazole-3-carboxylate (20.00 g, 97.56 mmol) and $K_2CO_3$ (26.97 g, 195.11 mmol) in DMF (70.00 mL) at 0° C. The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (5/1 v/v) to obtain the title compound (29.57 g) as an oil. LCMS (ESI): 335.0 $[M+H]^+$.

Step-2. methyl 5-(5-fluoro-2-methoxypyridin-4-yl)-1-{[2-(trimethylsilyl)ethoxy]methyl}pyrazole-3-carboxylate

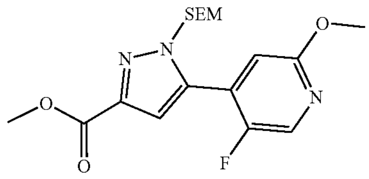

5-fluoro-2-methoxypyridin-4-ylboronic acid (15.77 g, 92.28 mmol), $K_3PO_4$ (30.14 g, 141.97 mmol) and Pd(dppf) $Cl_2$ (10.39 g, 14.20 mmol) were added to a stirred solution of methyl 5-bromo-1-{[2-(trimethylsilyl)ethoxy] methyl}pyrazole-3-carboxylate (Step-1, 23.80 g, 70.99 mmol) in 1,4-dioxane (150.00 mL)/$H_2O$ (15.00 mL). The resulting mixture was stirred at 90° C. for 14 h under the atmosphere of nitrogen. The resulting mixture was concentrated under reduced pressure. The residue was purified by silica gel column chromatography eluting with petroleum ether/EtOAc (3/1 v/v) to obtain the title compound (26.00 g) as an oil. LCMS (ESI): 382.1 $[M+H]^+$.

Step-3. 5-(5-fluoro-2-methoxypyridin-4-yl-1-{[2-(trimethylsilyl)ethoxy]methyl}pyrazole-3-carboxylic acid

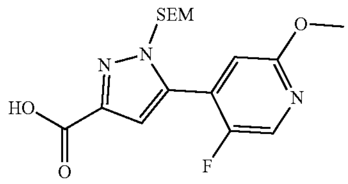 [SMILES: COc1cc(-c2cc(C(=O)O)nn2COCC[Si](C)(C)C)c(F)cn1]

LiOH·$H_2O$ (8.94 g, 213.12 mmol) was added to a stirred solution of methyl 5-(5-fluoro-2-methoxypyridin-4-yl)-1-{[2-(trimethylsilyl)ethoxy]methyl}pyrazole-3-carboxylate (Step-2, 27.1 g, 71.04 mmol) in THF (30.00 mL)/MeOH (30.00 mL)/$H_2O$ (30.00 mL). The resulting mixture was stirred at 70° C. for 14 h. The resulting mixture was concentrated under reduced pressure. Then the mixture was acidified to pH 3 with HCl (1 M). The aqueous layer was extracted with EtOAc. The organic layers were combined, dried over anhydrous $Na_2SO_4$, filtered, and concentrated under reduced pressure to obtain the title compound (23.50 g) as a solid. LCMS (ESI): 368.1 $[M+H]^+$.

Step-4. methyl 4-[5-(5-fluoro-2-methoxypyridin-4-yl)-1-{[2-(trimethylsilyl)ethoxy]methyl}pyrazole-3-carbonyl]-4-azaspiro[2.5]octane-7-carboxylate

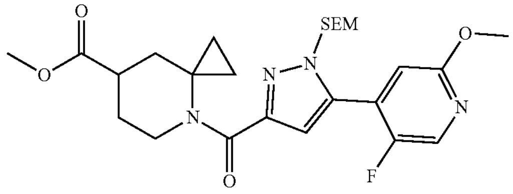

Methyl 4-azaspiro[2.5]octane-7-carboxylate (10.82 g, 63.95 mmol) and HATU (26.75 g, 70.359 mmol) were added to a stirred solution of 5-(5-fluoro-2-methoxypyridin-4-yl)-1-{[2-(trimethylsilyl)ethoxy]methyl}pyrazole-3-carboxylic acid (Step-3, 23.5 g, 63.954 mmol, 1.00 equiv) and DIPEA (24.80 g, 191.86 mmol) in DMF (50.00 mL). The resulting mixture was stirred at 25° C. for 14 h. The resulting mixture was diluted with EtOAc and washed with water. The organic layers were combined, dried over anhydrous $Na_2SO_4$, filtered; and concentrated under reduced pressure. The residue was purified by silica gel column chromatography eluting with petroleum ether/EtOAc (2/1 v/v) to obtain the title compound (25.85 g) as an oil. LCMS (ESI): 519.4 $[M+H]^+$.

Step-5. 4-(5-(5-fluoro-2-methoxypyridin-4-yl)-1-((2-(trimethylsilyl)ethoxy)methyl)-1H-pyrazole-3-carbonyl)-4-azaspiro[2.5]octane-7-carboxylic acid

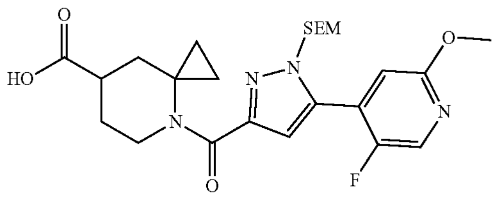 [SMILES: COc1cc(-c2cc(C(=O)N3CCC(C(=O)O)CC34CC4)nn2COCC[Si](C)(C)C)c(F)cn1]

LiOH·$H_2O$ (56.63 mg, 1.35 mmol) was added to a stirred solution of methyl 4-[5-(5-fluoro-2-methoxypyridin-4-yl)-1-[2-(trimethylsilyl)ethoxy]methyl) pyrazole-3-carbonyl]-4-azaspiro[2.5]octane-7-carboxylate (Step-4, 350.0 mg, 0.68 mmol) in MeOH (2.00 mL)/$H_2O$ (2.00 mL)/THF (2.00 The resulting mixture was stirred at 25° C. for 14 h. The resulting mixture was concentrated under reduced pressure. The mixture was acidified to pH 3 with HCl (1 M). The aqueous layer was extracted with EtOAc. The organic layers were combined, dried over anhydrous $Na_2SO_4$, filtered, and concentrated under reduced pressure to obtain the title compound (300.0 mg) as a solid. LCMS (ESI): 505.2 $[M+H]^+$.

EXAMPLES

Example 101. A diastereomeric mixture of 1-(5-(5-chloro-2-methoxypyridin-4-yl)-1H-pyrazole-3-carbonyl)-N-((1s,4s)-4-methylcyclohexyl)piperidine-4-carboxamide and 1-(5-(5-chloro-2-methoxypyridin-4-yl)-1H-pyrazole-3-carbonyl)-N-((1r,4r)-4-methylcyclohexyl)piperidine-4-carboxamide

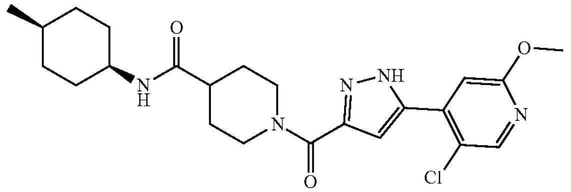

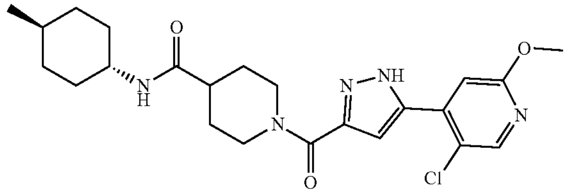

Step-1. Ethyl 1-(5-bromo-1H-pyrazole-3-carbonyl) piperidine-4-carboxylate

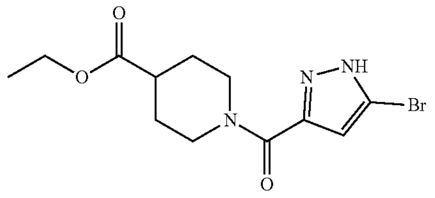 [SMILES: CCOC(=O)C1CCN(C(=O)c2cc(Br)[nH]n2)CC1]

EDCI (6.13 g, 31.99 mmol), HOBt (4.32 g, 31.99 mmol), and ethyl piperidine-4-carboxylate (4.24 g, 27.07 mmol) were added to a stirred solution of 5-bromo-1H-pyrazole-3-carboxylic acid (4.7 g, 24.61 mmol) and DIPEA (12.9 mL, 73.83 mmol) in DMF (40 mL). The resulting mixture was stirred at 25° C. for 14 h, then diluted with EtOAc and washed with water. The resulting mixture was concentrated under vacuum. The residue was purified by silica gel column chromatography (petroleum ether/EtOAc, 1/1 v/v) to obtain the title compound (7.7 g) as a solid. LCMS (ESI): 330.1 $[M+H]^+$.

Step-2. 1-(5-bromo-1H-pyrazole-3-carbonyl)piperidine-4-carboxylic acid

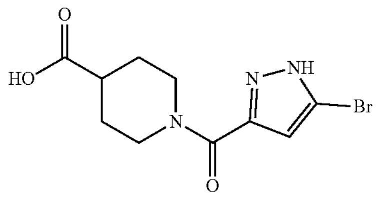 [SMILES: O=C(O)C1CCN(C(=O)c2cc(Br)[nH]n2)CC1]

LiOH (160.0 mg, 6.66 mmol) was added to a stirred solution of ethyl 1-(5-bromo-1H-pyrazole-3-carbonyl)piperidine-4-carboxylate (Step-1, 1.1 g, 3.33 mmol) in THF (4.00 mL), MeOH (4.00 mL), and $H_2O$ (4.00 mL). The resulting mixture was stirred at 25° C. for 2 h. The mixture was acidified to pH 4 with aqueous HCl (1 M). The aqueous layer was extracted with EtOAc and concentrated under reduced pressure to obtain the title compound (950 mg) as a solid. LCMS (ESI): 302.1 $[M+H]^+$.

Step-3. 1-(5-bromo-1H-pyrazole-3-carbonyl)-N-(4-methylcyclohexyl)piperidine-4-carboxamide

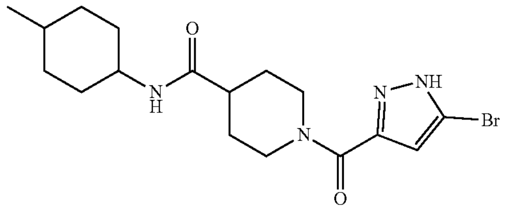 [SMILES: CC1CCC(NC(=O)C2CCN(C(=O)c3cc(Br)[nH]n3)CC2)CC1]

EDCI (3.56 g, 22.93 mmol), HOBt (2.52 g, 18.65 mmol), 4-methylcyclohexan-1-amine (2.11 g, 18.64 mmol) were added to a stirred solution of 1-(5-bromo-1H-pyrazole-3-carbonyl)piperidine-4-carboxylic acid (Step-2, 3.75 g, 12.46 mmol) and DIPEA (8.41 mL, 48.28 mmol) in DMF (40 mL). The solution was then stirred at 25° C. for 14 h. The resulting mixture was diluted with EtOAc and washed with water, then the organic layer was concentrated under vacuum. The residue was purified by silica gel column chromatography (DCM/MeOH, 95/5 v/v) to obtain the title compound (2.02 g) as a solid. $^1H$ NMR (300 MHz, DMSO-$d_6$) δ 13.75 (s, 1H), 7.66-7.58 (m, 1H), 6.72-6.65 (m, 1H), 4.43-4.25 (m, 1H), 4.12-3.85 (m, 1H), 3.75-3.34 (m, 1H), 3.25-2.96 (m, 1H), 2.91-2.65 (m, 1H), 2.44-2.20 (m, 1H), 1.75-1.65 (m, 4H), 1.53-1.35 (m, 6H), 1.33-1.16 (m, 2H), 1.16-1.03 (m, 1H), 1.01-0.79 (m, 3H). LCMS (ESI): 397.1 $[M+H]^+$.

Step-4. 1-(5-bromo-1-[[2-(trimethylsilyl)ethoxy] methyl]pyrazole-3-carbonyl)-N-(4-methylcyclohexyl)piperidine-4-carboxamide

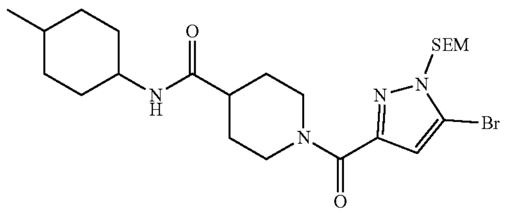 [SMILES: CC1CCC(NC(=O)C2CCN(C(=O)c3cc(Br)n(COCC[Si](C)(C)C)n3)CC2)CC1]

SEM-Cl (251.8 mg, 1.5 mmol) was added to a stirred solution of 1-(5-bromo-1H-pyrazole-3-carbonyl)-N-(4-methylcyclohexyl)piperidine-4-carboxamide (Step-3, 200.0 mg, 0.50 mmol) and $K_2CO_3$ (208.7 mg, 1.50 mmol) in DMF (3.00 mL) at 0° C. The resulting mixture was stirred at 25° C. for 14 h. The resulting mixture was diluted with EtOAc, washed with water, and the organic layer was concentrated under reduced pressure. The residue was purified by Prep-TLC (DCM/MeOH, 20/1 v/v) to obtain the title compound (200.0 mg) as an oil. LCMS (ESI): 527.3 $[M+H]^+$.

Step-5. 1-(5-(5-chloro-2-methoxypyridin-4-yl)-1-((2-(trimethylsilyl)ethoxy)methyl)-1H-pyrazole-3-carbonyl)-N-(4-methylcyclohexyl)piperidine-4-carboxamide

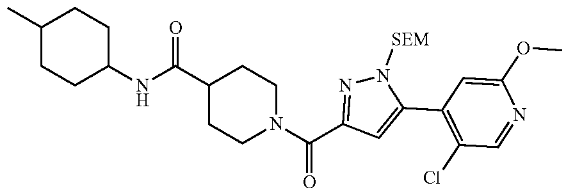

Pd(dppf)$Cl_2$ (61.0 mg, 0.10 mmol) and $K_3PO_4$ (17.1 mg, 0.80 mmol) were added to a stirred mixture of 1-(5-bromo-1-[[2-(trimethylsilyl)ethoxy]methyl]pyrazole-3-carbonyl)-N-(4-methylcyclohexyl)piperidine-4-carboxamide (Step-4, 200.00 mg, 0.40 mmol) and 5-chloro-2-methoxypyridin-4-ylboronic acid (233.0 mg, 1.20 mmol) in 1,4-dioxane (3.00 mL) and water (0.60 mL) at 25° C. The resulting mixture was stirred at 80° C. for 14 h under nitrogen atmosphere. After completion, the solution was concentrated under vacuum, then the residue was purified by Prep-TLC (DCM/MeOH, 20/1 v/v) to obtain the title compound (210.0 mg) as an oil. LCMS (ESI): 590.3 $[M+H]^+$.

Step-6. 1-(5-(5-chloro-2-methoxypyridin-4-yl)-1H-pyrazole-3-carbonyl)-N-((1s,4s)-4-methylcyclohexyl)piperidine-4-carboxamide and 1-(5-(5-chloro-2-methoxypyridin-4-yl)-1H-pyrazole-3-carbonyl)-N-((1r,4r)-4-methylcyclohexyl)piperidine-4-carboxamide

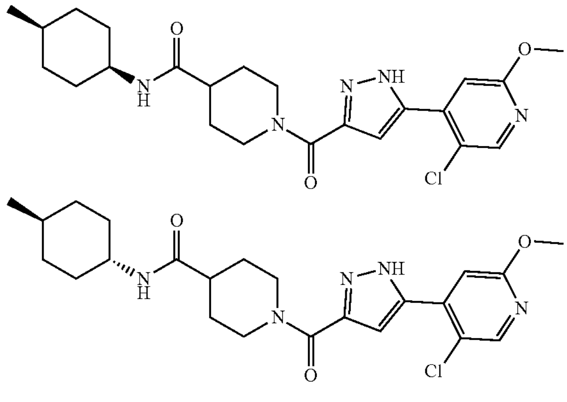

TFA (1.5 mL) was added to a stirred solution of 1-(5-(5-chloro-2-methoxypyridin-4-yl)-1-((2-(trimethylsilyl)ethoxy)methyl)-1H-pyrazole-3-carbonyl)-N-(4-methylcyclohexyl)piperidine-4-carboxamide (Step-5, 210 mg, 0.4 mmol) in DCM (1.5 mL). The resulting mixture was stirred at 25° C. for 2 h, then the solution was concentrated under vacuum. The residue was purified by Prep-HPLC (Column: XBridge Prep OBD C18 Column, 30×150 mm, 5 μm; Mobile Phase: Water (10 mM $NH_4HCO_3$)/MeCN (68/32 to 38/62 v/v); Flow rate: 60 mL/min; Detection (nm): 254 nm) and yielded 1-(5-(5-chloro-2-methoxypyridin-4-yl)-1H-pyrazole-3-carbonyl)-N-((1s,4s)-4-methylcyclohexyl)piperidine-4-carboxamide and 1-(5-(5-chloro-2-methoxypyridin-4-yl)-1H-pyrazole-3-carbonyl)-N-((1r,4r)-4-methylcyclohexyl)piperidine-4-carboxamide (13.9 mg) as a solid mixture of diastereomers (Example 101), $^1$H NMR (300 MHz, $CD_3OD$-d4) δ 8.24 (s, 1H), 7.14 (dHz, 1H), 4.63 (s, 2H), 3.94 (s, 3H), 3.83 (s, 1H), 3.55 (m, 1H), 3.45-3.26 (m, 1H), 2.93 (s, 1H), 2.72-2.36 (m, 1H), 1.87-1.55 (m, 9H), 1.37-1.34 (m, 3H), 1.11-0.91 (m, 4H). LCMS (ESI): 460.2 $[M+H]^+$.

This mixture of two diastereomers was separated using Chiral Prep-HPLC.

Column: CHIRALPAK IF

Column dimensions: 2*25 cm, 5 μm

Mobile Phase: MTBE (0.1% FA):EtOH (80/20 v/v)

Flow rate: 14 mL/min

Detection (nm): 220/254 nm.

Example 101-A. The first eluting diastereomer (4.9 mg) was obtained as a solid.

The first eluting diastereomer had a retention time of 14.07 min.

$^1$H NMR (300 MHz, DMSO-$d_6$) δ 13.96 (m, 1H), 8.38-8.32 (m, 1H), 7.64 (d, 1H), 7.25-7.21 (m, 1H), 7.13 (s, 1H), 4.64-4.08 (m, 2H), 3.89 (s, 3H), 3.51-3.37 (m, 1H), 3.19-3.14 (m, 1H), 2.90-2.73 (m, 1H), 2.51-2.49 (m, 1H), 1.76-1.72 (s, 1.15-1.25 (m, 9H), 1.15 (s, 2H), 0.89 (d, 3H). LCMS (ESI): 460.2 $[M+H]^+$.

Example 101-B. The second eluting diastereomer (14.5 mg) was obtained as a solid.

The second eluting diastereomer had a retention time of 22.53 min.

$^1$H NMR (300 MHz, DMSO-$d_6$) δ 13.96 (s, 1H), 8.35 (s, 1H), 7.64 (d, 1H), 7.23 (s, 1H), 7.13 (s, 1H), 4.63-4.10 (m, 2H), 3.89 (s, 3H), 3.51-3.37 (m, 1H), 3.14-3.05 (m, 1H), 2.82-2.71 (m, 1H), 2.42-2.35 (m, 1H), 1.77-1.48 (m, 7H), 1.42-1.06 (m, 4H), 0.96-0.85 (m, 5H). LCMS (ESI): 460.2 $[M+H]^+$.

Example 102. 1-(4-fluoro-5-(2-methoxypyridin-1-yl)-1H-pyrazole-3-carbonyl)-N-(4-methylcyclohexyl)piperidine-4-carboxamide

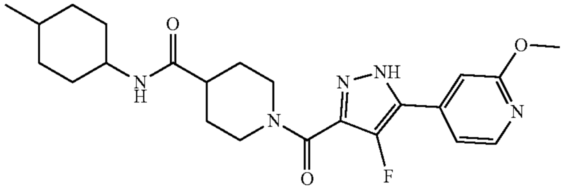

Step-1. Methyl 1-benzyl-5-bromo-1H-pyrazole-3-carboxylate

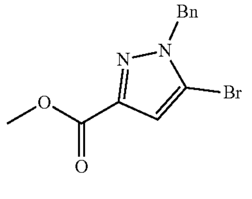 [SMILES: COC(=O)c1cc(Br)n(Cc2ccccc2)n1]

NaH (210.7 mg, 8.8 mmol, 60% dispersion in mineral oil) was added to a stirred solution of methyl 5-bromo-1H- pyrazole-3-carboxylate (600.0 mg, 2.9 mmol) in THF (10.0 mL) at 0° C. Benzyl bromide (1501.7 mg, 8.8 mmol) was then added to the mixture. The resulting mixture was stirred at 25° C. for 14 h. The solution was then diluted with water and extracted with EtOAc. The organic layers were combined, dried over anhydrous sodium sulfate, filtered, and the solvent was evaporated. The residue was purified by silica gel column chromatography (EtOAc/petroleum ether, 1/3 v/v) to obtain the title compound (460.0 mg) as a solid. LCMS (ESI): 295.1 $[M+H]^+$.

Step-2. Methyl 1-benzyl-5-bromo-4-fluoro-1H-pyrazole-3-carboxylate

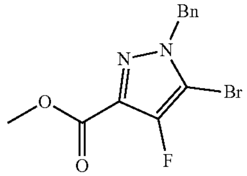 [SMILES: COC(=O)c1nn(Cc2ccccc2)c(Br)c1F]

Selectfluor® (1.65 g, 4.68 mmol) was added to a stirred solution of methyl 1-benzyl-5-bromopyrazole-3-carboxylate (Step-1, 60.0 mg, 1.56 mmol) in MeCN (10.00 mL) at 25 CC. The resulting mixture was stirred at 80° C. for 14 h. The mixture was concentrated and purified by silica gel column chromatography (EtOAc/petroleum ether, 1/3 v/v) to obtain the title compound (130.0 mg) as a solid. LCMS (ESE): 313.1 $[M+H]^+$.

Step-3. 1-benzyl-5-bromo-4-fluoro-1H-pyrazole-3-carboxylic acid

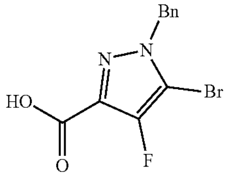 [SMILES: O=C(O)c1nn(Cc2ccccc2)c(Br)c1F]

LiOH·$H_2O$ (174.2 mg, 4.15 mmol) was added to a stirred solution of methyl 1-benzyl-5-bromo-4-fluoro-1H-pyrazole-3-carboxylate (Step-2, 30.0 mg, 0.42 mmol) in MeOH (1.0 mL) and water (1.0 mL) at 25 CC. The resulting mixture was stirred at 40 CC for 14 h. The pH of the solution was adjusted to 5 using aqueous HCl (6 M), then the solution was then diluted with water and extracted with EtOAc. The organic layers were combined, dried over anhydrous sodium sulfate, filtered, and the solvent was evaporated. The residue was purified by reverse phase column chromatography (MeCN/water, 5/95 to 95/5 v/v) to obtain the title compound (80.0 mg) as a solid. LCMS (ESI): $[M+H]^+$: 279.1.

Step-4. 1-(1-benzyl-5-bromo-4-fluoro-1H-pyrazole-3-carbonyl)-N-(4-methylcyclohexyl)piperidine-4-carboxamide

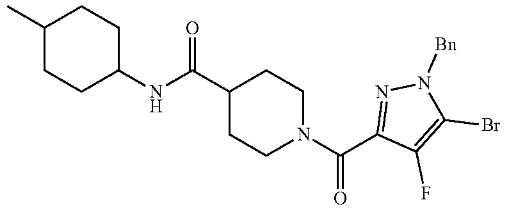 [SMILES: CC1CCC(NC(=O)C2CCN(C(=O)c3nn(Cc4ccccc4)c(Br)c3F)CC2)CC1]

HATU (61.0 mg, 0.16 mmol) and N-(4-methylcyclohexyl)piperidine-4-carboxamide (INTERMEDIATE 502, 36.0 mg, 0.16 mmol) were added to a stirred solution of 1-benzyl-5-bromo-4-fluoro-1H-pyrazole-3-carboxylic acid (Step-3, 40.0 mg, 0.13 mmol) and DIPEA (70 μL, 0.40 mmol) in DMF (5.0 mL). The resulting mixture was stirred at 25° C. for 2 h. The solution was then diluted with water and extracted with EtOAc. The organic layers were combined, dried over anhydrous sodium sulfate, filtered, and the solvent was evaporated. The residue was purified by silica gel column chromatography (EtOAc/petroleum ether, 1/1 v/v) to obtain the title compound (60.0 mg) as a solid mixture of diastereomers. LCMS (ESI): $[M+H]^+$: 505.2.

Step-5. 1-(1-benzyl-4-fluoro-5-(2-methoxypyridin-4-yl)-1H-pyrazole-3-carbonyl)-N-(4-methylcyclohexyl)piperidine-4-carboxamide

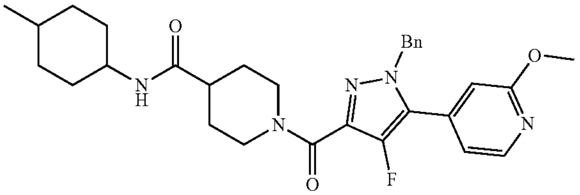

Pd(dppf)$Cl_2$ (11.6 mg, 0.02 mmol) and $K_2CO_3$ (65.6 mg, 0.48 mmol) were added to a stirred mixture of 1-(1-benzyl-5-bromo-4-fluoro-1H-pyrazole-3-carbonyl)-N-(4-methylcyclohexyl)piperidine-4-carboxamide (Step-4, 80.0 mg, 0.16 mmol) and 2-methoxypyridin-4-ylboronic acid (24.2 mg, 0.16 mmol) in 1,4-dioxane (2.5 mL) and water (0.5 mL) at 25° C. The resulting mixture was stirred at 80° C. for 2 h under nitrogen atmosphere. The solution was then diluted with water and extracted with EtOAc. The organic layers were combined, dried over anhydrous sodium sulfate, filtered, and then the solvent was evaporated. The residue was purified by silica gel column chromatography (EtOAc/petroleum ether, 1/1 v/v) to obtain the title compound (50.0 mg) as a mixture of diastereomers. LCMS (ESI): $[M+H]^+$: 534.3.

Step-6. 1-(4-fluoro-5-(2-methoxypyridin-4-yl)-1H-pyrazole-3-carbonyl)-N-(4-methylcyclohexyl)piperidine-4-carboxamide

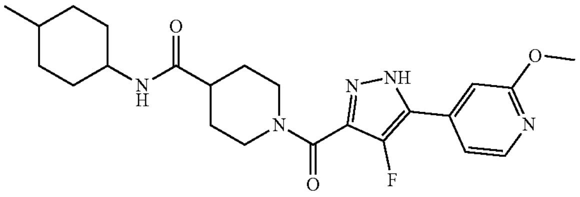

$NH_4HCO_2$ (586.1 mg, 7.39 mmol) and $Pd(OH)_2$ (10.5 mg, 0.08 mmol) were added to a stirred solution of 1-(1-benzyl-4-fluoro-5-(2-methoxypyridin-4-yl)-1H-pyrazole-3-carbonyl)-N-(4-methylcyclohexyl)piperidine-4-carboxamide (Step-5, 40.0 mg, 0.08 mmol) in $HCO_2H$ (10.0 mL) at 25° C. The resulting mixture was stirred at 70° C. for 14 h. The mixture was concentrated and purified by reverse phase column chromatography (MeCN/water, 5/95 to 95/5 v/v) to obtain the title compound (4.6 mg) as a solid mixture of diastereomers. $^1H$ NMR (300 MHz, $CD_3OD$) δ 8.22 (s, 1H), 7.84-7.50 (m, 1H), 7.37-7.05 (m, 2H), 4.70-4.60 (m, 1H), 3.98 (s, 3H), 3.88-3.60 (m, 1H), 3.25-3.20 (m, 1H), 3.00-2.85 (m, 1H), 2.70-2.45 (m, 1H), 1.98-1.50 (m, 9H), 1.35-1.12 (m, 3H), 1.10-0.85 (m, 4H). LCMS (ESI): $[M+H]^+$: 444.2.

Example 103. (8)-1-(5-(5-chloro-2-methoxypyridin-4-yl)-1H-pyrazole-3-carbonyl)-N-(1-(3-fluorophenyl)ethyl)piperidine-4-carboxamide

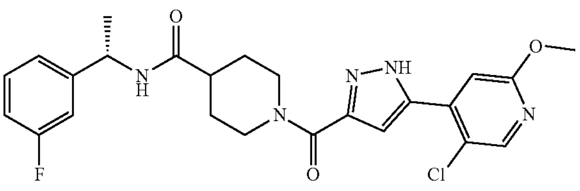 [SMILES: COc1cc(-c2cc(C(=O)N3CCC(C(=O)N[C@@H](C)c4cccc(F)c4)CC3)n[nH]2)c(Cl)cn1]

T3P® (50% in DMF, 64 uL, 0.11 mmol) and (S)-1-(3-fluorophenyl)ethan-1-amine (10.4 uL, 0.08 mmol) were added to a stirred solution of 1-[5-(5-chloro-2-methoxypyridin-4-yl)-1H-pyrazole-3-carbonyl]piperidine-4-carboxylic acid (INTERMEDIATE 503, 20.0 mg, 0.06 mmol) and TEA (23 μL, 0.16 mmol) in DMF (0.55 mL, 0.06 mmol). The resulting mixture was stirred at 25° C. for 4 h. The reaction mixture was dried down in a Genevac (HT12 system), then purified (using the following conditions: Column: Waters CSH C18, 100×19 mm, 5 μm; Mobile Phase: A: 0.1% formic acid in water; Mobile Phase: B: 0.1% formic acid in MeCN, Flow rate: 30 mL/min; Gradient: 20% B to 95% B over 8.5 min) to obtain the title compound (3.4 mg) as a solid. LCMS (ESI): $[M+H]^+$: 468.18.

Example 104. A diastereomeric mixture of N-((1s,4s)-4-(difluoromethyl)cyclohexyl)-1-(5-(5-fluoro-2-methoxypyridin-4-yl)-1H-pyrazole-3-carbonyl)piperidine-4-carboxamide and N-((1r,4r)-4-(difluoromethyl)cyclohexyl)-1-(5-(5-fluoro-2-methoxypyridin-4-yl)-1H-pyrazole-3-carbonyl)piperidine-4-carboxamide

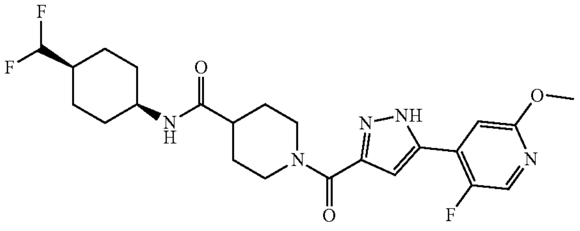

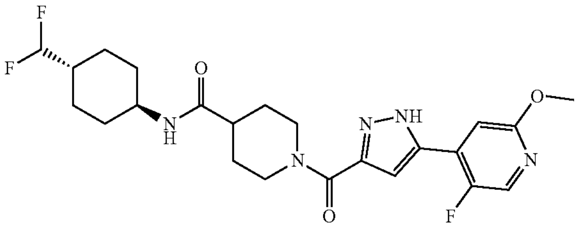

Step-1. N-[4-(difluoromethyl)cyclohexyl]-1-[5-(5-fluoro-2-methoxypyridin-4-yl)-1-(oxan-2-yl)pyrazole-3-carbonyl]piperidine-4-carboxamide

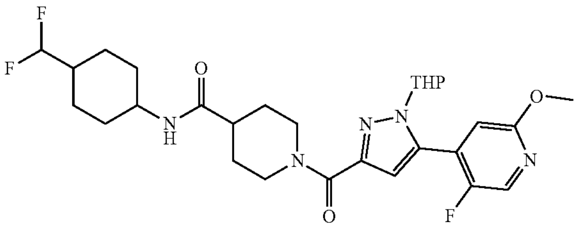

HATU (221.57 mg, 0.58 mmol) and 4-(difluoromethyl)cyclohexan-1-amine (86.93 mg, 0.58 mmol) were added to a stirred solution of 1-(5-(5-fluoro-2-methoxypyridin-4-yl)-1-(tetrahydro-2H-pyran-2-yl)-1H-pyrazole-3-carbonyl)piperidine-4-carboxylic acid (INTERMEDIATE 505, 210 mg, 0.49=top and DIPEA. (0.25 mL, 1.46 mmol) in DMF (2 mL). The resulting mixture was stirred at 25° C. for 2 h. The solution was then diluted with EtOAc, washed with water, and concentrated under reduced pressure. The residue was purified by Prep-TLC (DCM/MeOH, 15/1 v/v) to obtain the title compound (140 mg) as a mixture of diastereomers. LCMS (ESI): $[M+H]^+$: 564.3.

Step-2. N-((1s,4s)-4-(difluoromethyl)cyclohexyl)-1-(5-(5-fluoro-2-methoxypyridin-4-yl)-1H-pyrazole-3-carbonyl)piperidine-4-carboxamide and N-((1r,4r)-4-(difluoromethyl)cyclohexyl)-1-(5-(5-fluoro-2-methoxypyridin-4-yl)-1H-pyrazole-3-carbonyl)piperidine-4-carboxamide

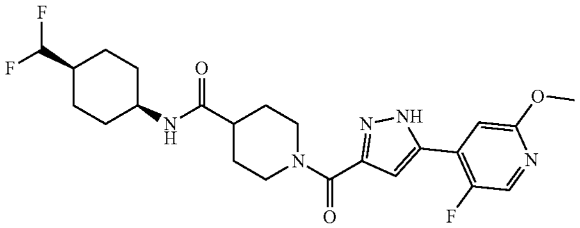

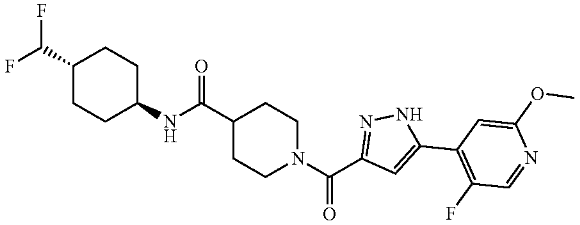

TFA (1.0 mL) was added to a stirred solution of N-[4-(difluoromethyl)cyclohexyl]-1-[5-(5-fluoro-2-methoxypyridin-4-yl)-1-(oxan-2-yl)pyrazole-3-carbonyl]piperidine-4-carboxamide (Step-3, 140 mg, 0.25 mmol) in DCM (1 mL). The resulting mixture was stirred at 25° C. for 30 min. The solution was then concentrated under reduced pressure and purified by reverse phase column chromatography (Water (0.1% $NH_4HCO_3$)/MeCN, 65/35 to 40/60 v/v) to obtain N-((1s,4s)-4-(difluoromethyl)cyclohexyl)-1-(5-(5-fluoro-2-methoxypyridin-4-yl)-1H-pyrazole-3-carbonyl)piperidine-4-carboxamide and N-((1r,4r)-4-(difluoromethyl)cyclohexyl)-1-(5-(5-fluoro-2-methoxypyridin-4-yl)-1H-pyrazole-3-carbonyl)piperidine-4-carboxamide (60 mg), as a solid mixture of diastereomers (Example 104).

This solid mixture of diastereomers was separated using Chiral-HPLC.

Column: CHIRALPAK IF

Column dimensions: 2×25 cm, 5 μm

Mobile Phase: Hex:DCM (1:1, 10 mM $NH_3$·MeOH): MeOH=50:50

Flow rate: 15 mL/min

Detection (nm): 220/254 nm

Example 104-A. The first eluting diastereomer (10.4 mg) was obtained as a solid.

The first eluting diastereomer had a retention time of 8.67 min.

$^1$H NMR (300 MHz, DMSO-$d_6$) δ 14.08-13.91 (m, 1H), 8.28 (d, 1H), 7.75 (d, 1H), 7.36-7.29 (m, 1H), 7.04 (d, 1H), 6.12-5.52 (m, 1H), 4.50-4.43 (m, 1H), 3.87 (s, 3H), 3.60-3.29 (m, 2H), 3.25-3.02 (m, 1H), 2.82-2.76 (m, 1H), 2.38 (d, 1H), 1.85-1.40 (m, 9H), 1.27-1.09 (m, 4H). LCMS (ESI): $[M+H]^+$: 480.2.

Example 104-B. The second eluting diastereomer (10.6 mg) was obtained as a solid.

The second eluting diastereomer had a retention time of 15.25 min.

$^1$H NMR (300 MHz, DMSO-$d_6$) δ 14.51-13.41 (m, 1H), 8.28 (d, 1H), 7.94-7.59 (m, 1H), 7.43-7.20 (m, 1H), 7.14-6.94 (m, 1H), 6.19-5.59 (m, 1H), 4.78-4.38 (m, 1H), 4.24-4.01 (m, 1H), 3.87 (s, 3H), 3.85-3.78 (m, 1H), 3.45-3.01 (m, 1H), 2.94-2.67 (m, 1H), 2.63-2.45 (m, 2H), 1.91-1.58 (m, 6H), 1.58-1.32 (m, 6H). LCMS (ESI): $[M+H]^+$: 480.2.

Example 105. 1-(5-(2-methoxypyridin-4-yl)-1H-pyrazole-3-carbonyl)-N-(4-methylcyclohexyl)piperidine-4-carboxamide

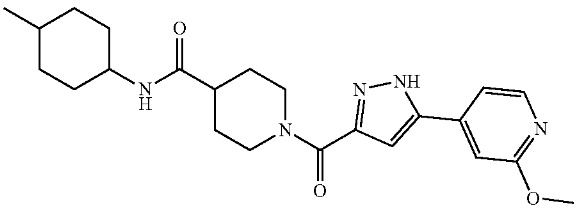

A mixture of 1-(5-bromo-1H-pyrazole-3-carbonyl)-N-(4-methylcyclohexyl)piperidine-4-carboxamide (Example 101, Step-3, 180.0 mg, 0.45 mmol), Pd(dppf)$Cl_2$ (66.3 mg, 0.09 mmol), $K_3PO_4$ (192.3 mg, 0.91 mmol) and 2-methoxypyridin-4-ylboronic acid (83.2 mg, 0.54 mmol) in $H_2O$ (0.30 mL) and 1,4-dioxane (3.00 mL) was stirred at 100° C. for 3 h under $N_2$ atmosphere. The resulting mixture was diluted with EtOAc, washed with water, and the organic layer was concentrated under reduced pressure. The residue was purified via Prep-HPLC (using the following conditions: Column: XBridge Shield RP18 OBD, 30×150 mm, 5 μm; Mobile Phase A: Water (10 mM $NH_4HCO_3$); Mobile Phase B: MeCN; Flow rate: 60 mL/min; Gradient: 28% B to 58% B in 7 min; Detection: 220 nm) to obtain the title compound (8 mg) as a solid mixture of diastereomers, $^1$H NMR (300 MHz, $CD_3OD$) δ 8.20-8.19 (s, 1H), 7.34 (bs, 1H), 7.20-7.18 (bs, 1H), 7.10 (s, 1H), 4.67 (bs, 2H), 3.97 (s, 3H), 3.85-3.84 (m, 1H), 3.29-3.24 (m, 1H), 2.93 (m, 1H), 2.63-2.61 (m, 1H), 1.86-1.56 (m, 10H), 1.38-1.30 (m, 3H), 0.98-0.91 (m, 3H). LCMS (ESI): $[M+H]^+$: 426.2.

Example 106. N-(1-methylcyclohexyl)-1-[5-(2-methylpyridin-4-yl)-1H-pyrazole-3-carbonyl]piperidine-4-carboxamide

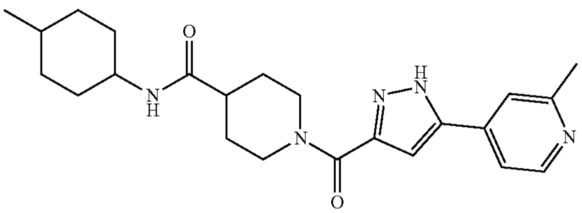

The title compound was prepared using a procedure similar to the one described for the synthesis of Example 105, except 2-methylpyridin-4-yl boronic acid was used as the starting material. The resulting product was purified (using the following conditions: Column: XBridge Prep C18 OBD, 19×150 mm, 5 μm; Mobile Phase A: Water (10 mM $NH_4HCO_3$); Mobile Phase B: MeCN; Flow rate: 25 mL/min; Gradient: 22% B to 44% B in 7 min; Detection: 10/254 nm) obtain the title compound (28.7 mg) as a solid mixture of diastereomers. $^1$H NMR (300 MHz, $CD_3OD$) δ 8.47 (d, 1H), 7.76-7.70 (m, 1H), 7.67-7.61 (m, 1H), 7.18-

7.11 (m, 1H), 4.70-4.64 (m, 2H), 3.89-3.47 (m, 1H), 3.41-3.17 (m, 1H), 2.98-2.92 (m, 1H), 2.61 (s, 3H), 2.55-2.49 (m, 1H), 1.99-1.72 (m, 6H), 1.70-1.50 (m, 3H), 1.47-1.16 (m, 3H), 1.14-0.89 (m, 4H). LCMS (ESI): 410.3 $[M+H]^+$.

Example 107. 1-(5-(2-methoxypyridin-4-yl)-1H-pyrazole-3-carbonyl)-N-((1s,4s)-4-methylcyclohexyl)piperidine-4-carboxamide

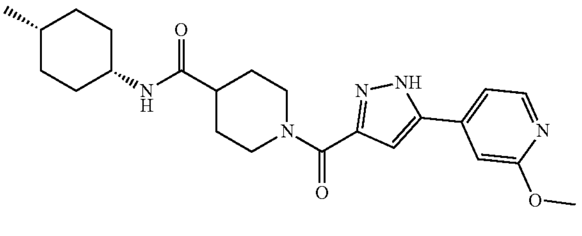

Step-1. 1-(5-bromo-1H-pyrazole-3-carbonyl)-N-[(1s,4s)-4-methylcyclohexyl]piperidine-4-carboxamide

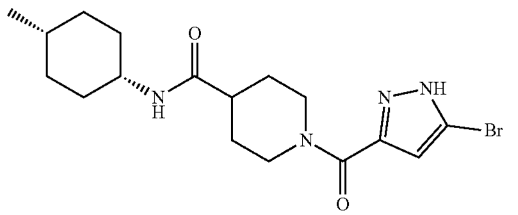 [SMILES: C[C@H]1CC[C@@H](NC(=O)C2CCN(C(=O)c3cc(Br)[nH]n3)CC2)CC1]

(1s,4s)-4-methylcyclohexan-1-amine (374 mg, 3.31 mmol), HOBT (670 mg, 4.97 mmol), EDCI (951.8 mg, 4.97 mmol), and DIPEA (1.6 mL, 9.90 mmol) were added to a stirred mixture of 1-(5-bromo-1H-pyrazole-3-carbonyl) piperidine-4-carboxylic acid (1.00 g, 3.31 mmol, Example 101-Step-2) in DMF (5 nil). The resulting mixture was stirred at 25° C. for 14 h. The reaction was then quenched with water, the aqueous layer was extracted with EtOAc, and the organic layer was concentrated. The residue was purified by Prep-TLC (DCM/MeOH, 20/1 v/v) to obtain the title compound (1.1 g) as a solid. LCMS (ESI): 397.3 $[M+H]^+$.

Step-2. 1-[5-(2-methoxypyridin-4-yl)-1H-pyrazole-3-carbonyl]-N-[(1s,4s)-4-methylcyclohexyl]piperidine-4-carboxamide

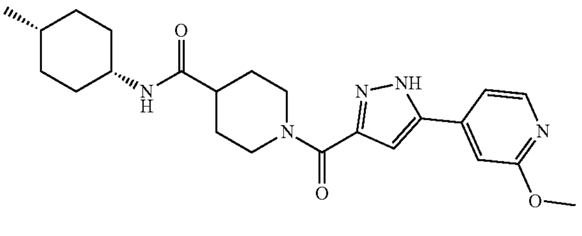

2-methoxypyridin-4-ylboronic acid (76 mg, 0.5 mmol), $K_3PO_4$ (160 mg, 0.75 mmol), and Pd(dppf)$Cl_2$ (36 mg, 0.05 mmol) were added to a stirred mixture of 1-(5-bromo-1H-pyrazole-3-carbonyl)-N-[(1s,4s)-4-methylcyclohexyl]piperidine-4-carboxamide (Step-1, 100 mg, 0.25 mmol) in 1,4-dioxane (2 mL) and $H_2O$ (0.2 mL). The resulting mixture was stirred at 110° C. for 14 h, then concentrated. The residue was purified with Prep-TLC (DCM/MeOH, 15/1 v/v), then with Prep-HPLC (using the following conditions: Column: XBridge Shield RP18 OBD Column, 30*150 mm, 5 um; Mobile Phase A: Water (10 mM $NH_4HCO_3$); Mobile Phase B: MeCN, Flow rate: 60 mL/min, Gradient: 25% B to 41% B in 7 min; Detection: 254/220 nm) to obtain the title compound (18 mg) as a solid. $^1H$ NMR (300 MHz, $CD_3OD$) δ 8.20-8.18 (d, 1H), 7.36-7.34 (m, 1H), 7.20 (s, 1H), 7.09 (s, 1H), 4.68-4.61 (m, 2H), 3.99-3.94 (s, 3H), 3.86-3.85 (m, 1H), 2.94 (m, 1H), 2.67-2.57 (m, 1H), 1.98-1.71 (m, 5H), 1.69-1.51 (m, 6H), 1.40-1.29 (m, 1H) 0.98 (d, 3H). LCMS (ESI): 426.2 $[M+H]^+$.

Example 108. A diastereomeric mixture of Example 108-A and 108-B

Example 108-A. N-((1s,4s)-4-ethylcyclohexyl)-1-(5-(2-methoxypyridin-4-yl)-1H-pyrazole-3-carbonyl)piperidine-4-carboxamide and

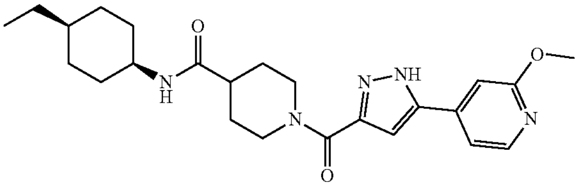 [SMILES: CC[C@H]1CC[C@@H](NC(=O)C2CCN(C(=O)c3cc(-c4ccnc(OC)c4)[nH]n3)CC2)CC1]

Example 108-B, N-((1r,4r)-4-ethylcyclohexyl)-1-(5-(2-methoxypyridin-4-yl)-1H-pyrazole-3-carbonyl)piperidine-4-carboxamide

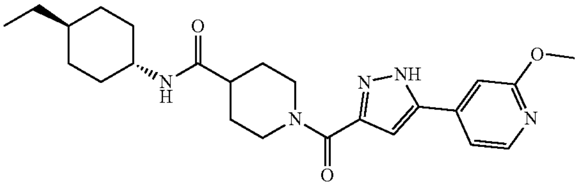 [SMILES: CC[C@H]1CC[C@H](NC(=O)C2CCN(C(=O)c3cc(-c4ccnc(OC)c4)[nH]n3)CC2)CC1]

N-(4-ethylcyclohexyl)-1-(5-(2-methoxypyridin-4-yl)-1H-pyrazole-3-carbonyl)piperidine-4-carboxamide was prepared using a procedure similar to the one described for the synthesis of Example 107, except 4-ethylcyclohexane-1-amine was used as a starting material. The resulting product was purified by silica gel chromatography (12:1 DCM:MeOH) and yielded N-((1s,4s)-4-ethylcyclohexyl)-1-(5-(2-methoxypyridin-4-yl)-1H-pyrazole-3-carbonyl)piperidine-4-carboxamide and N-((1r,4r)-4-ethylcyclohexyl)-1-(5-(2-methoxypyridin-4-yl)-1H-pyrazole-3-carbonyl)piperidine-4-carboxamide (90 mg), as a solid mixture of diastereomers (Example 108). $^1H$ NMR (300 MHz, DMSO-d6) δ 13.88-13.72 (m, 1H), 8.21-8.15 (m, 1H), 7.65-7.59 (m, 1H), 7.47-7.35 (m, 1H), 7.27-7.17 (m, 2H), 4.52-4.02 (m, 2H), 3.77-3.71 (m, 1H), 3.46-3.40 (m, 1H), 3.29 (s, 3H), 3.14-3.08 (m, 1H), 2.81-2.75 (m, 1H), 1.81-1.61 (m, 4H), 1.60-1.35 (m, 5H), 1.33-0.97 (m, 5H), 0.96-0.76 (m, 4H). LCMS (ESI): 440.2 $[M+H]^+$.

The two diastereomers of the title compound were separated using Chiral Prep-HPLC.

Column: CHIRAL-PAK. IC

Column dimensions: 2×25 cm, 5 μm

Mobile Phase: Hex:DCM (1:1, 10 mM $NH_3$·MeOH=50:50

Flow rate: 18 mL/min

Detection (nm): 220/254 nm

Example 108-A. The first eluting diastereomer N-((1s,4s)-4-ethylcyclohexyl)-1-(5-(2-methoxypyridin-4-yl)-1H-pyrazole-3-carbonyl)piperidine-4-carboxamide (17.0 mg) was obtained as a solid and had a retention time of 10.8 min.

$^1$H NMR (300 MHz, DMSO-d6) δ 13.89-13.67 (m, 1H), 8.19 (dd, 1H), 7.67-7.56 (m, 1H), 7.41 (dd, 1H), 7.27-7.16 (m, 2H), 4.54-4.43 (m, 2H), 4.19-4.13 (m, 1H), 3.87 (s, 3H), 3.74 (s, 1H), 3.12 (d, 1H), 2.78 (d, 1H), 1.73 (d, 3H), 1.59-1.40 (m, 7H), 1.35-1.16 (m, 5H), 0.84 (t, 3H). LCMS (ESI): 440.2 $[M+H]^+$.

Example 108-B. The second eluting diastereomer N-((1r,4 r)-4-ethylcyclohexyl)-1-(5-(2-methoxypyridin-4-yl)-1H-pyrazole-3-carbonyl)piperidine-4-carboxamide (40.0 mg) was obtained as a solid and had a retention time of 14.7 min.

Example 108-B was also synthesized following the procedure below (Steps-1 to -3 shown below), then the retention time of the sample was compared to the racemic sample of N-(4-ethylcyclohexyl)-1-(5-(2-methoxypyridin-4-yl)-1H-pyrazole-3-carbonyl)piperidine-4-carboxamide (using the following conditions: Column: CHIRALPAK IC-3, 4.6×50 mm, 3 μm; Mobile Phase: (Hex:DCM=1:1)(0.1% DEA)/MeOH, 1/1 v/v; Flow rate: 1 mL/min) to determine the compound chirality. Example 108-A had a retention time of 1.47 min and Example 108-B had a retention time of 2.01 min.

Step-1. Methyl 1-[5-(2-methoxypyridin-4-yl)-1H-pyrazole-3-carbonyl]piperidine-4-carboxylate

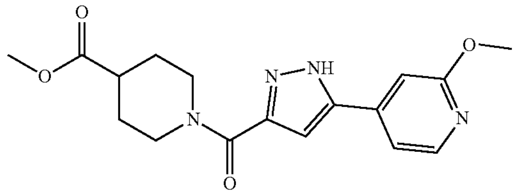

2-methoxypyridin-4-ylboronic acid (1.45 g, 9.5 mmol), $K_3PO_4$ (2.66 g, 12.5 mmol), and Pd(dppf)$Cl_2$ (918.0 mg, 1.2 mmol) were added to a stirred solution of methyl 1-(5-bromo-1H-pyrazole-3-carbonyl)piperidine-4-carboxylase (INTERMEDIATE 501, 2 g, 6.3 mmol) in 1,4-dioxane (20.0 mL) and $H_2O$ (2.0 mL). The solution was stirred at 110° C. for 14 h under nitrogen atmosphere, then concentrated under vacuum. The residue was purified by silica gel column chromatography (DCM/MeOH, 97/3 v/v) to obtain the title compound (1.4 g) as a solid. LCMS (ESI): 345.1 $[M+H]^+$.

Step-2. 1-[5-(2-methoxypyridin-4-yl)-1H-pyrazole-3-carbonyl]piperidine-4-carboxylic acid

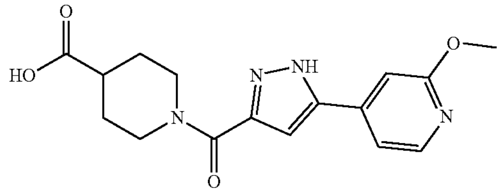 [SMILES: COc1cc(-c2cc(C(=O)N3CCC(C(=O)O)CC3)n[nH]2)ccn1]

LiOH (293.0 mg, 12.2 mmol) to a stirred mixture of methyl 1-[5-(2-methoxypyridin-4-yl)-1H-pyrazole-3-carbonyl]piperidine-4-carboxylate (Step-2, 1.40 g, 4.1 mmol) in THF (3.0 mL), MeOH (3.0 mL) and $H_2O$ (3.0 mL). The solution was stirred at 25° C. for 14 h under nitrogen atmosphere, then extracted with EtOAc. The combined organic layers were washed with water, dried over anhydrous $Na_2SO_4$, filtered, and the solvent was concentrated under reduced pressure to obtain the title compound (1.0 g) as a solid. $^1$H NMR (300 MHz, DMSO-$d_6$) δ 8.20 (d, 1H), 7.42 (m, 1H), 7.25-7.21 (m, 2H), 4.29 (s, 2H), 3.88 (s, 3H), 3.27 (s, 1H), 2.96 (s, 1H), 2.58 (m, 1H), 1.89-1.86 (m, 2H), 1.54 (s, 2H). LCMS (ESI): 331.1 $[M+H]^+$.

Step-3. N-((1r,4r)-4-ethylcyclohexyl)-1-(5-(2-methoxypyridin-4-yl)-1H-pyrazole-3-carbonyl)piperidine-4-carboxamide (Example 108-B)

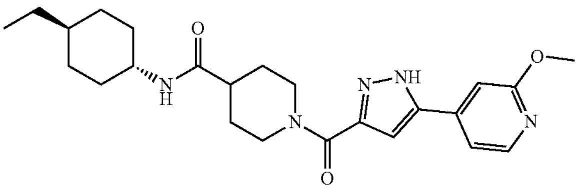 [SMILES: CC[C@H]1CC[C@H](NC(=O)C2CCN(C(=O)c3cc(-c4ccnc(OC)c4)[nH]n3)CC2)CC1]

EDCI (86.2 mg, 0.5 mmol), HOBt (60.7 mg, 0.5 mmol), and (1r,4r)-4-ethylcyclohexane-1-amine hydrochloride (58.9 mg, 0.4 mmol) were added to a solution of 1-[5-(2-methoxypyridin-4-yl)-1H-pyrazole-3-carbonyl]piperidine-4-carboxylic acid (Step-3, 99.0 mg, 0.3 mmol) and DIPEA (0.16 mL, 0.9 mmol) in DMF (1.50 mL). The solution was stirred at 25° C. for 14 h. The precipitate was collected by filtration, washed with EtOAc, and dried under reduced pressure to obtain the title compound (40 mg) as a solid. $^1$H NMR (300 MHz, DMSO-d6) δ 13.84 (s, 1H), 8.21 (s, 1H), 7.65 (d, 1H), 7.43 (s, 1H), 7.28-7.18 (m, 2H), 4.51-4.06 (m, 2H), 3.88 (s, 3H), 3.49-3.38 (m, 1H), 3.23-2.99 (m, 1H), 2.90-2.70 (m, 1H), 2.42-2.32 (m, 1H), 1.86-1.65 (m, 6H), 1.62-1.38 (m, 2H), 1.29-1.00 (m, 5H), 0.99-0.77 (m, 5H). LCMS (ESI): 440.2 $[M+H]^+$.

Example 109. 1-(5-(3-chloropyridin-4-yl)-1H-pyrazole-3-carbonyl)-N-(4-methylcyclohexyl)piperidine-4-carboxamide

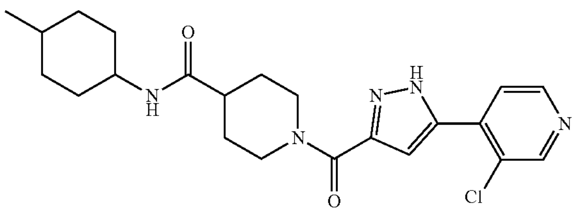 [SMILES: CC1CCC(NC(=O)C2CCN(C(=O)c3cc(-c4ccncc4Cl)[nH]n3)CC2)CC1]

The title compound was prepared using a procedure similar to the one described for the synthesis of Example 101, except 3-chloropyridin-4-yl boronic acid was used as a starting material in Step-5. The resulting residue was purified via Prep-HPLC (using the following conditions: Column: XBridge Shield RP18 OBD, 30×150 mm, 5 μm; Mobile Phase A: Water (10 mM $NH_4HCO_3$); Mobile Phase B: MeCN; Flow rate: 60 mL/min; Gradient: 27% B to 57% B in 7 min; Detection: 254 nm) to obtain the title compound (10.2 mg) as a solid mixture of diastereomers. $^1H$ NMR (400 MHz, DMSO-d6) δ 13.93 (s, 1H), 8.74 (s, 1H), 8.58 (d, 1H), 7.84 (d, 1H), 7.73-7.50 (m, 1H), 7.17 (d, 1H), 4.45 (s, 2H), 3.89-3.36 (m, 1H), 3.30 (s, 1H), 2.96-2.61 (m, 1H), 2.61-2.29 (m, 1H), 1.83-1.60 (m, 4H), 1.61-1.38 (m, 6H), 1.34-1.06 (m, 4H), 1.02-0.80 (m, 4H). LCMS (ESI): 429.2 $[M+H]^+$.

Example 110. A diastereomeric mixture of 1-[4-chloro-5-(2-methoxypyridin-4-yl)-1H-pyrazole-3-carbonyl]-N-[(1s,4s)-4-methylcyclohexyl]piperidine-4-carboxamide and 1-[4-chloro-5-(2-methoxypyridin-4-yl)-1H-pyrazole-3-carbonyl]-N-[(1r,4r)-4-methylcyclohexyl]piperidine-4-carboxamide

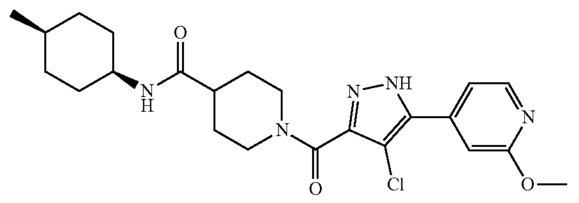

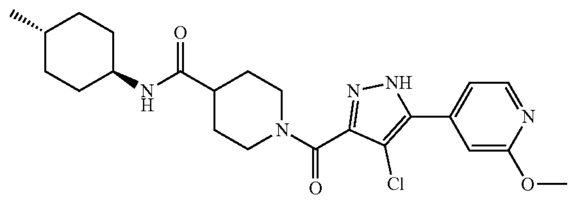

Step-1. Methyl 5-bromo-4-chloro-1H-pyrazole-3-carboxylate

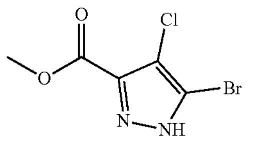

NCS (195.4 mg, 1.46 mmol) was added to a solution of methyl 5-bromo-1H-pyrazole-3-carboxylate (250.0 mg, 1.22 mmol) in MeCN (5.0 mL). The resulting mixture was stirred at 70° C. for 14 h, then the mixture was concentrated. The residue was purified by silica gel column chromatography (EtOAc/petroleum ether, 1/1 v/v) to obtain the title compound (270 mg) as a solid. LCMS (ESI): 239.0 $[M+H]^1$.

Step-2. 5-bromo-4-chloro-1H-pyrazole-3-carboxylic acid

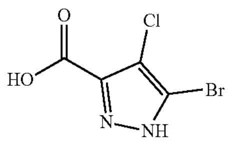

NaOH (225.5 mg, 5.64 mmol) was added to a solution of methyl 5-bromo-4-chloro-1H-pyrazole-3-carboxylate (Step-2, 270.0 mg, 1.13 mmol) in THF (1.0 mL), MeOH (1.0 mL) and $H_2O$ (1.0 mL). The resulting mixture was stirred at 25° C. for 1 h, then the pH of the solution was adjusted to pH 3 with HCl (6 M). The solids were collected by filtration to obtain the title compound (200 mg) as a solid. LCMS (ESI): 225.0 $[M+H]^+$.

Step-3. 1-(5-bromo-4-chloro-1H-pyrazole-3-carbonyl)-N-(4-methylcyclohexyl)piperidine-4-carboxamide

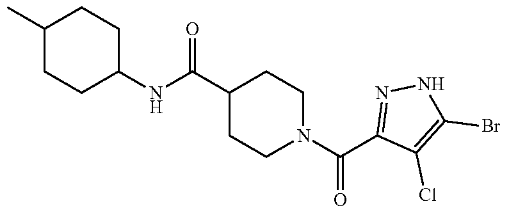 [SMILES: CC1CCC(NC(=O)C2CCN(C(=O)c3n[nH]c(Br)c3Cl)CC2)CC1]

HATU (506.0 mg, 1.33 mmol), N-(4-methylcyclohexyl) piperidine-4-carboxamide (INTERMEDIATE 502, 238.9 mg, 1.07 mmol) and DIPEA (343.9 mg, 2.66 mmol) were added to a solution of 5-bromo-4-chloro-1H-pyrazole-3-carboxylic acid (Step-2, 200.0 mg, 0.89 mmol) in DMF (5.0 mL). The resulting solution was stirred at 25° C. for 1 h, then quenched with water (5 mL). The solution was then extracted with EtOAc, and then organic layer was concentrated. The residue was purified by silica gel column chromatography (EtOAc/petroleum ether, 1/1 v/v) to obtain the title compound (200 mg) as a solid mixture of diastereomers. LCMS (ESI): 431.1 $[M+H]^+$.

Step-4. 1-[5-bromo-4-chloro-1-(oxan-2-yl)pyrazole-3-carbonyl]-N-(4-methylcyclohexyl)piperidine-4-carboxamide

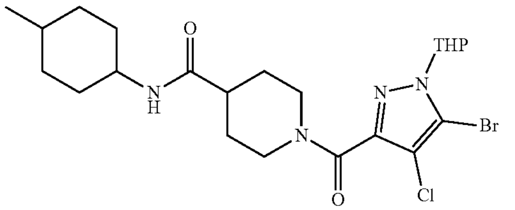

DHP (116.9 mg, 1.39 mmol) and TsOH (15.9 mg, 0.09 mmol) were added to a solution of 1-(5-bromo-4-chloro-1H-pyrazole-3-carbonyl)-N-(4-methylcyclohexyl)piperidine-4-carboxamide (Step-3, 400.0 mg, 0.93 mmol) in THF (10.0 mL). The resulting solution was stirred at 25° C. for 14 It, then the solution was concentrated. The residue was purified by silica gel column chromatography (EtOAc/petroleum ether, 1/1 v/v) to obtain the title compound (380 mg) as a solid mixture of diastereomers, LCMS (ESI): 426.2 $[M+H]^+$.

Step-5. 1-[4-Chloro-5-(2-methoxypyridin-4-yl)-1-oxan-2-yl)pyrazole-3-carbonyl]-N-(4-methylcyclohexyl)piperidine-4-carboxamide

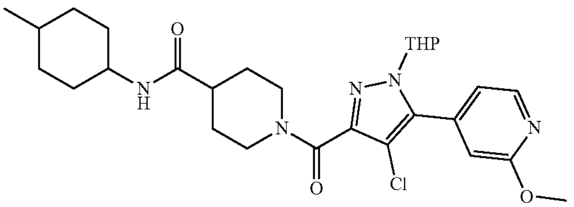

2-methoxypyridin-4-ylboronic acid (36.6 mg 0.24 mmol), $Pd(dppf)Cl_2$ (7.3 mg, 0.01 mmol) and $K_2CO_3$ (82.6 mg, 0.6=top were added to a solution of 1-[5-bromo-4-chloro-1-(oxan-2-yl)pyrazole-3-carbonyl]-N-cyclohexylpiperidine-4-carboxamide (Step-4, 100.0 mg, 0.2 mmol) in 1,4-dioxane (2.0 mL) and $H_2O$ (0.4 mL). The resulting mixture was stirred at 80° C. for 2 h, then the solution was concentrated. The residue was purified by silica gel column chromatography (EtOAc/petroleum ether, 1/1 v/v) to obtain the title compound (80 mg) as a solid mixture of diastereomers. LCMS (ESI): 544.3 $[M+H]^+$.

Step-6. 1-[4-chloro-5-(2-methoxypyridin-4-yl)-1H-pyrazole-3-carbonyl]-N-[1(1s,4s)-4-methylcyclohexyl]piperidine-4-carboxamide, and 1-[4-chloro-5-(2-methoxypyridin-4-yl)-1H-pyrazole-3-carbonyl]-N-[1r,4r)-4-methylcyclohexyl]piperidine-4-carboxamide

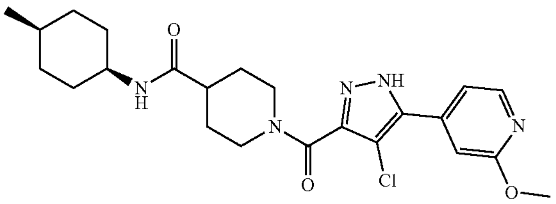

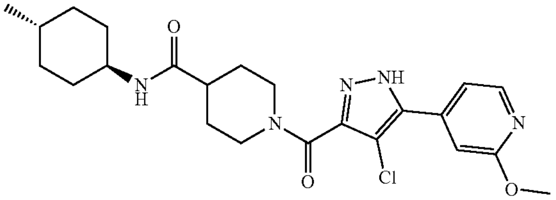

HCl (6 M, 1.0 mL) was added to a solution of 1-[4-chloro-5-(2-methoxypyridin-4-yl)-1-(oxan-2-yl)pyrazole-3-carbonyl]-N-cyclohexylpiperidine-4-carboxamide (Step-5, 80.0 mg, 0.15 mmol) in MeOH (1 mL). The resulting mixture was stirred at 50° C. for 1 h, then the solution was concentrated. The residue was purified by reverse phase column chromatography (Water (10 mM $NH_4CO_3$):MeCN, 80/20 to 40/60 v/v) to obtain 1-[4-chloro-5-(2-methoxypyridin-4-yl)-1H-pyrazole-3-carbonyl]-N-[(1s,4s)-4-methylcyclohexyl]piperidine-4-carboxamide, and 1-[4-chloro-5-(2-methoxypyridin-4-yl)-1H-pyrazole-3-carbonyl]-N-[(1r,4r)-4-methylcyclohexyl]piperidine-4-carboxamide (3.2 mg) as a solid mixture of diastereomers (Example 110). $^1H$ NMR (300 MHz, $CD_3OD$) δ 8.28-8.26 (m, 1H), 7.45-7.40 (m, 1H), 7.28-7.26 (m, 1H), 4.72-4.60 (m, 1H), 3.98 (s, 3H), 3.97-3.80 (m, 1H), 3.62-3.51 (m, 1H), 3.28-3.16 (m, 1H), 3.05-2.90 (m, 1H), 2.70-2.45 (m, 1H), 2.01-1.83 (m, 2H), 1.83-1.70 (m, 4H), 1.69-1.50 (m, 4H), 1.45-1.17 (m, 2H), 1.15-1.01 (m, 1H), 1.01-0.84 (m, 3H). LCMS (ESI) 460.31 $[M+H]^+$.

The two diastereomers of the title compound were separated using Achiral Prep-HPLC.

Column: XBridge Prep OBD C18 Column

Column dimensions: 19×250 mm, 5 μm

Mobile Phase: Water (10 mM $NH_4HCO_3$):MeCN

Gradient: 37% MeCN to 45% MeCN

Flow rate: 25 mL/min

Detection (nm): 220/254 nm

Example 110-A. The first eluting diastereomer (6.2 mg) was obtained as a solid.

The first eluting diastereomer had a retention time of 10.5 min.

$^1H$ NMR (300 MHz, $CD_3OD$) δ 8.28-8.26 (m, 1H), 7.45-7.40 (m, 1H), 7.28-7.26 (m, 1H), 4.70-4.60 (m, 1H), 3.99 (s, 3H), 3.97-3.80 (m, 1H), 3.61-3.52 (m, 1H), 3.28-3.15 (m, 1H), 3.05-2.90 (m, 1H), 2.50-2.42 (m, 1H), 1.99-1.84 (m, 2H), 1.83-1.68 (m, 4H), 1.66-1.49 (m, 1H), 1.46-1.17 (m, 4H), 1.16-0.98 (m, 2H), 0.93 (d, 3H). LCMS (ESI): 460.31 $[M+H]^+$.

Example 110-B. The second eluting diastereomer (6.3 mg) was obtained as a solid.

The second eluting diastereomer had a retention time of 10.8 min.

$^1H$ NMR (300 MHz, $CD_3OD$) δ 8.28-8.26 (m, 1H), 7.45-7.40 (m, 1H), 7.28-7.26 (m, 1H), 4.74-4.65 (m, 1H), 3.99 (s, 3H), 3.98-3.80 (m, 2H), 3.28-3.15 (m, 1H), 3.05-2.90 (m, 1H), 2.50-2.42 (m, 1H), 1.99-1.86 (m, 1H), 1.84-1.72 (m, 3H), 1.72-1.50 (m, 6H), 1.44-1.22 (m, 3H), 0.98 (d, 3H). LCMS (ESI): 460.31 $[M+H]^+$.

Example 111. A diastereomeric mixture of 1-[5-(6-methoxypyrimidin-4-yl)-1H-pyrazole-3-carbonyl]-N-[(1r,4r)-4-methylcyclohexyl]piperidine-4-carboxamide and 1-[5-(6-methoxypyrimidin-4-yl)-1H-pyrazole-3-carbonyl]-N-[(1s,4s)-4-methylcyclohexyl]piperidine-4-carboxamide

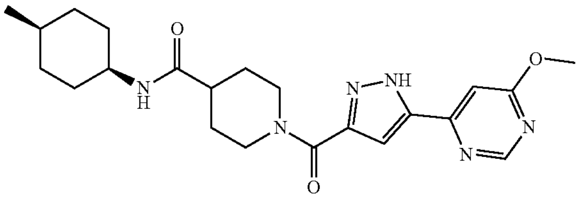

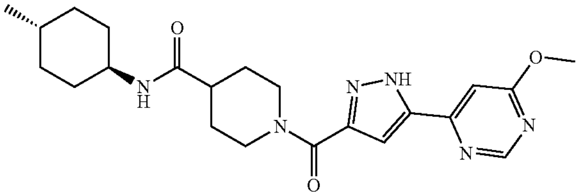

Step-1: 1-(1-(tetrahydro-2H-pyran-2-yl)-1H-pyrazole-3-carbonyl)piperidine-4-carboxylic acid

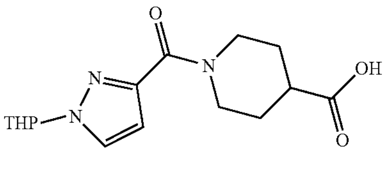

LiOH (821.70 mg, 19.56 mmol) was added portion wise to a stirred solution of methyl 1-(1-(tetrahydro-2H-pyran-2-yl)-1H-pyrazole-3-carbonyl)piperidine-4-carboxylate (INTERMEDIATE 517, Step-2, 3.14 g, 9.77 mmol) and $H_2O$ (10.00 mL) in THF (10 mL) at 0° C. The resulting mixture was stirred at 24° C. for 1 h. The mixture was acidified to pH 6 with HCl (6 M). The aqueous layer was extracted with EtOAc. The resulting mixture was concentrated under reduced pressure to deliver the title compound (2.6 g) as an oil. LCMS (ESI): $[M+H]^+$: 308.1.

Step-2. N-(4-methylcyclohexyl)-1-[1-(oxan-2-yl)pyrazole-3-carbonyl]piperidine-4-carboxamide

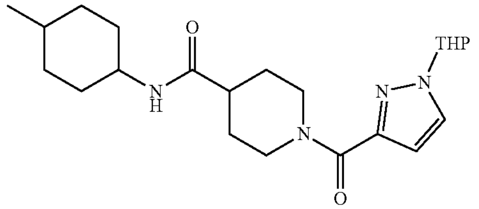

HATU (3.86 g, 10.15 mmol), 4-methylcyclohexan-1-amine (1.15 g, 10.16 mmol), and DIPEA (3.28 g, 25.38 mmol) were added to a stirred solution of 1-(1-(tetrahydro-2H-pyran-2-yl)-1H-pyrazole-3-carbonyl)piperidine-4-carboxylic acid (Step-1, 2.60 g, 8.46 mmol) in DMF (20 mL). The solution was stirred at 25° C. for 1 h. then diluted with EtOAc and washed with water. The organic layer was concentrated under reduced pressure and the residue was purified by reverse phase column chromatography (MeCN/$H_2O$ (0.5% $NH_4HCO_3$), 10/90 to 60/40 v/v) to obtain the title compound (2.1 g) as a solid mixture of diastereomers. LCMS (ESI): 403.3 $[M+H]^+$.

Step-3. 5-[4-[(4-methylcyclohexyl)carbamoyl]piperidine-1-carbonyl]-2-(oxan-2-yl)pyrazol-3-yl boronic acid

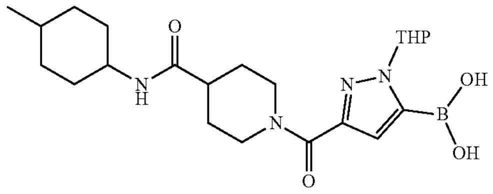

Dtbpy (53.6 mg, 0.2 mmol), $[Ir(COD)OMe]_2$ (66.2 mg, 0.1 mmol), and $B_2Pin_2$ (253.7 mg, 0.1 mmol) were added to a stirred solution of N-(4-methylcyclohexyl)-1-[1-(oxan-2-yl)pyrazole-3-carbonyl]piperidine-4-carboxamide (Step-2, 402.0 mg, 0.99 mmol) in MTBE (8 mL). The resulting mixture was stirred at 70° C. under nitrogen atmosphere for 14 h, then concentrated under reduced pressure to obtain the title compound as a diastereomeric mixtures, which was used in the next step without further purification. LCMS (ESI): 447.3 $[M+H]^+$.

Step-4. 1-[5-(6-methoxypyrimidin-4-yl)-1-(oxan-2-yl)pyrazole-3-carbonyl]-N-(4-methylcyclohexyl)piperidine-4-carboxamide

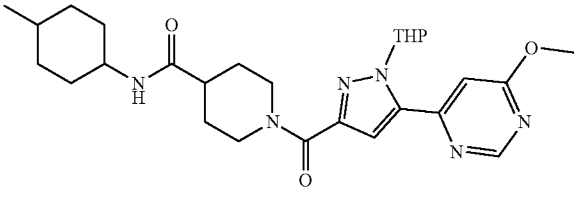

4-chloro-6-methoxypyrimidine (34 mg, 0.24 mmol), $Pd(dppf)Cl_2$ (28 mg, 0.04 mmol), and $K_3PO_4$ (126 mg, 0.59 mmol) were added to a mixture of 5-[4-[(4-methylcyclohexyl)carbamoyl]piperidine-1-carbonyl]-2-(oxan-2-yl)pyrazol-3-ylboronic acid (used directly from Step-3) in 1,4-dioxane (2 mL) and $H_2O$ (0.2 mL). The solution was stirred at 70° C. for 3 h under nitrogen atmosphere, then diluted with ethyl acetate and washed with water. The organic layer was concentrated under reduced pressure and the residue was purified by Prep-TLC (DCM/MeOH, 15/1 v/v) to obtain the title compound (90 mg) as a solid mixture of diastereomers. LCMS (ESI): 511.3 $[M+H]^+$.

Step-5. 1-[5-(6-methoxypyrimidin-4-yl)-1H-pyrazole-3-carbonyl]-N-[(1r,4r)-4-methylcyclohexyl]piperidine-4-carboxamide and 1-[5-(6-methoxypyrimidin-4-yl)-1H-pyrazole-3-carbonyl]-N-[(1s,4s)-4-methylcyclohexyl]piperidine-4-carboxamide

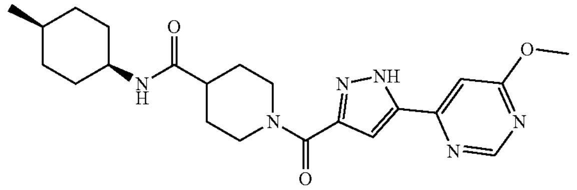

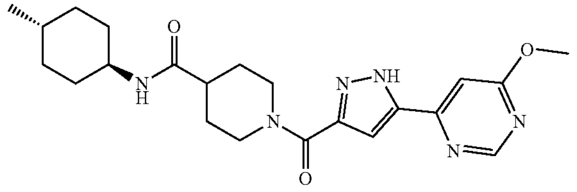

TFA (2 mL) was added to a mixture of 1-[5-(6-methoxypyrimidin-4-yl)-1-(oxan-2-yl)pyrazole-3-carbonyl]-N-(4-methylcyclohexyl)piperidine-4-carboxamide (Step-4, 90 mg, 0.18 mmol) in DCM (2 mL). The resulting mixture was stirred at 25° C. for 1 h, then the solution was concentrated under reduced pressure to obtain 1-[5-(6-methoxypyrimidin-4-yl)-1H-pyrazole-3-carbonyl]-N-[(1r,4r)-4-methylcyclohexyl]piperidine-4-carboxamide and 1-[5-(6-methoxypyrimidin-4-yl)-1H-pyrazole-3-carbonyl]-N-[(1s,4s)-4-methylcyclohexyl]piperidine-4-carboxamide as a mixture of diastereomers (Example 111).

The two diastereomers of the title compound were separated using Chiral Prep-HPLC.

Column: CHIRALPAK IC

Column dimensions: 2x25 cm, 5 μm

Mobile Phase: MTBE (0.1% FA)/MeOH, 1/1 v/v

Flow rate: 20 mL/min

Detection (nm): 220/254 nm

Example 111-A. The first eluting diastereomer (9.3 mg) was obtained as a solid.

The first eluting diastereomer had a retention time of 11.36 min.

$^1H$ NMR (400 MHz, DMSO-$d_6$) δ 8.83 (s, 1H), 8.38 (s, 1H), 7.66-7.58 (m, 1H), 7.41 (s, 1H), 7.25 (s, 1H), 4.44 (s, 2H), 3.97 (s, 3H), 3.53-3.37 (m, 1H), 3.23-3.15 (m, 1H), 2.80 (s, 2.43-2.28 (m, 1H), 1.77-1.69 (m, 3H), 1.66-1.63 (m, 2H), 1.53 (s, 2H), 1.25-1.23 (m, 2H), 1.17-1.07 (m, 2H), 1.00-0.90 (m, 2H), 0.85 (d, 3H). LCMS (ESI): 427.4 $[M+H]^+$.

Example 111-B. The second eluting diastereomer (11.4 mg) was obtained as a solid. The second eluting diastereomer had a retention time of 16.17 min.

$^1H$ NMR (400 MHz, DMSO-$d_6$) δ 8.83 (s, 1H), 8.38 (s, 1H), 7.62 (d, 1H), 7.41 (s, 1H), 7.26 (s, 1H), 4.46 (s, 2H), 3.97 (s, 3H), 3.74 (s, 1H), 3.02-3.15 (m, 1H), 2.92-2.73 (m, 1H), 2.42-2.33 (m, 1H), 1.72 (s, 2H), 1.51 (s, 4H), 1.47-1.40 (m, 4H), 1.25-1.23 (m, 3H), 0.89 (d, 3H). LCMS (ESI): 427.4 $[M+H]^+$.

Example 112. 1-[5-(5-chloro-2-methoxypyridin-4-yl)-1H-pyrazole-3-carbonyl]-N-[(3-chlorophenyl)methyl]piperidine-4-carboxamide

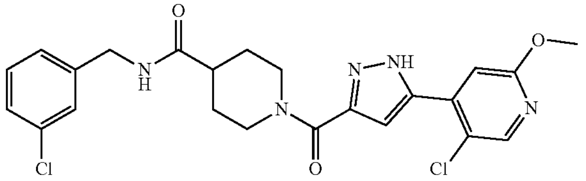

Step-1. 1-[5-bromo-1-(oxan-2-yl)pyrazole-3-carbonyl]piperidine-4-carboxylic acid

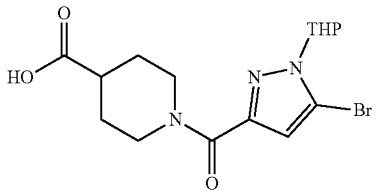

Lithium hydroxide (1.00 g, 41.75 mmol) was added to a solution of methyl 1-[5-bromo-1-(oxan-2-yl)pyrazole-3-carbonyl]piperidine-4-carboxylate (INTERMEDIATE 504, 1.60 g, 4.0 mmol) in THF (5.0 mL), MeOH (5.0 mL), and $H_2O$ (5.0 mL). The resulting solution was stirred at 25° C. for 1 h, then the solution was concentrated under vacuum. The pH of the solution was adjusted to 5 with HCl (1 M), then the solution was extracted with ethyl acetate. The organic layer was concentrated under vacuum to obtain the title compound (1.3 g) as a solid. LCMS (ESI): 386.1 $[M+H]^+$.

Step-2. 1-[5-bromo-1-(oxan-2-yl)pyrazole-3-carbanyl]-N-[(3-chlorophenyl)methyl]piperidine-4-carboxamide

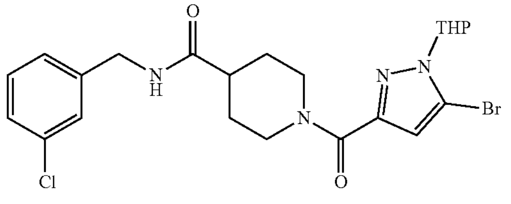

1-(3-chlorophenyl) methanamine (88.0 mg, 0.6 mmol), HMV (237.0 mg, 0.6 mmol), and DIPEA (0.27 mL, 1.6 mmol) were added to a solution of 1-[5-bromo-1-(oxan-2-yl)pyrazole-3-carbonyl]piperidine-4-carboxylic acid (Step-1, 200.0 mg, 0.52 mmol) in DMF (4.0 mL). The solution was stirred at 25° C. for 1 h, then diluted with water and extracted with dichloromethane. The organic layers were combined, dried over anhydrous sodium sulfate, and concentrated under vacuum. The residue was purified by silica gel column chromatography (DCM/MeOH, 10/1 v/v) to obtain the title compound (200 mg) as an oil. LCMS (ESI): 509.1 $[M+H]^+$.

Step-3. 1-[5-(5-chloro-2-methoxypyridin-4-yl)-1-(oxan-2-yl)pyrazole-3-carbonyl 1(3-chlorophenyl) methyl]piperidine-4-carboxamide

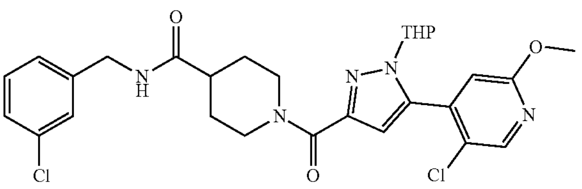

5-chloro-2-methoxypyridin-4-ylboronic acid (213.0 mg, 1.16 $Pd(dppf)Cl_2$ (85 mg, 0.12 mmol) and $K_3PO_4$ (369.0 mg, 1.27 mmol) were added to a solution of 1-[5-bromo-1-(oxan-2-yl)pyrazole-3-carbonyl]-N-[(3-chlorophenyl) methyl]piperidine-4-carboxamide (Step-3, 295.0 mg, 0.58 mmol) in 1,4-dioxane (4.0 mL) and $H_2O$ (1.0 mL). The resulting solution was stirred at 80° C. for 4 h under nitrogen, then concentrated under vacuum. The residue was purified by silica gel column chromatography (DCM/MeOH, 10/1 v/v) to obtain the title compound (150 mg) as an oil. LCMS (ESI): 572.2 $[M+H]^+$.

Step-4. 1-[5-(5-chloro-2-methoxypyridin-4-yl)-1-pyrazole-3-carbonyl]-N-[(3-chlorophenyl)methyl] piperidine-4-carboxamide

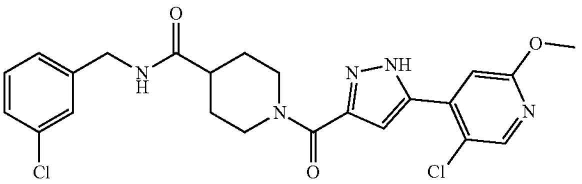 [SMILES: COc1cc(-c2cc(C(=O)N3CCC(C(=O)NCc4cccc(Cl)c4)CC3)n[nH]2)c(Cl)cn1]

TFA (2.0 mL) was added to a solution of 1-[5-(5-chloro-2-methoxypyridin-4-yl)-1-(oxan-2-yl)pyrazole-3-carbonyl]-N-[(3-chlorophenethyl]piperidine-4-carboxamide (Step-3, 150.0 mg, 0.26 mmol) in DCM (2.0 mL). The solution was stirred at 25° C. for 1 h, then the pH value of the solution was adjusted to 8 with a saturated aqueous solution of $NaHCO_3$. The solution was then extracted with DCM and the organic layers were concentrated under vacuum. The residue was purified by Prep-HPLC (using the following conditions: Column: Atlantis HILIC OBD, 19×150 mm, 5 μm, 10 nm; Mobile Phase A: Water (0.1% FA); Mobile Phase B: MeCN; Gradient: 31% B to 60% B in 8 min; Detector: UV 220/254 nm) to obtain the title compound (54.9 mg) as a solid. $^1H$ NMR (300 MHz, DMSO-$d_6$) δ 13.90 (s, 1H), 8.47-8.39 (m, 1H), 8.35 (s, 1H), 7.39-7.29 (m, 3H), 7.29-7.20 (m, 2H), 7.16 (s, 1H), 4.45 (bs, 2H), 4.27 (d, 2H), 3.90 (s, 3H), 3.22 (s, 1H), 2.91-2.86 (m, 1H), 2.55 (d, 1H), 1.90-1.81 (m, 2H), 1.70-1.58 (m, 2H). LCMS (ESI): 488.1 $[M+H]^+$.

Example 113. A Diastereomeric Mixture of N-((1s,4s)-4-(difluoromethyl)cyclohexyl)-1-(5-(2-methoxypyridin-4-yl)-1H-pyrazole-3-carbonyl)piperidine-41-carboxamide and N-((1r,4r)-4-(difluoromethyl) cyclohexyl)-1-(5-(2-methoxypyridin-4-yl)-1H-pyrazole-3-carbonyl)piperidine-4-carboxamide

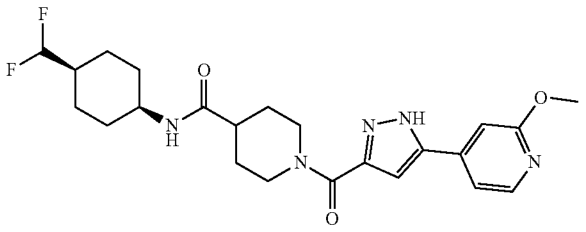

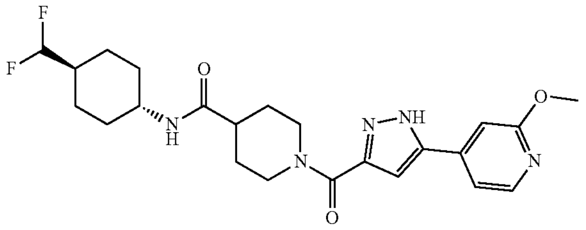

Step-1. Methyl 1-[5-(2-methoxypyridin-4-yl)-1H-pyrazole-3-carbonyl]piperidine-4-carboxylate

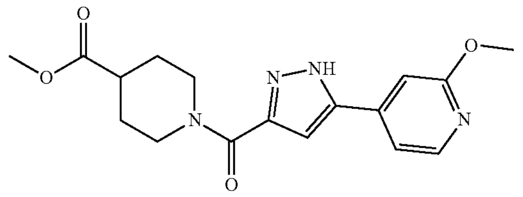

2-methoxypyridin-4-ylboronic acid (1.45 g, 9.5 ram $K_3PO_4$ (2.66 g, 12.53 mmol) and $Pd(dppf)Cl_2$ (918 mg, 1.2 mmol) were added to a stirred mixture of methyl 1-(5-bromo-1H-pyrazole-3-carbonyl)piperidine-4-carboxylate (INTERMEDIATE 501, 2.00 g, 6.3 mmol) and 1,4-dioxane (20 mL) and $H_2O$ (2 mL). The resulting solution was stirred at 110° C. for 14 h under nitrogen atmosphere, then the solution was concentrated under vacuum. The residue was purified by silica gel column chromatography (DCM/MeOH, 97/3 v/v) to obtain the title compound (1.4 g) as a solid. LCMS (ESI): 345.1 $[M+H]^+$.

Step-2. 1-[5-(2-ethoxypyridin-4-yl)-1H-pyrazole-3-carbonyl]piperidine-4-carboxylic acid

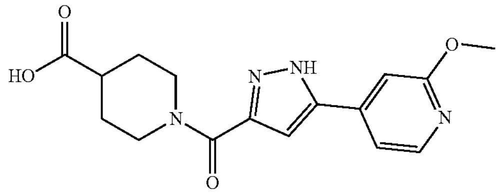 [SMILES: COc1cc(-c2cc(C(=O)N3CCC(C(=O)O)CC3)n[nH]2)ccn1]

LiOH (293 mg, 12.2 mmol) was added to a stirred mixture of methyl 1-[5-(2-methoxypyridin-4-yl)-1H-pyrazole-3-carbonyl]piperidine-4-carboxylate (1.40 g, 4.07 mmol) in THF (3 mL), MeOH (3 mL), and $H_2O$ (3 mL). The resulting mixture was stirred at 25° C. for 14 h under nitrogen atmosphere. The solution was then extracted with EtOAc then the combined organic layers were washed with water, dried over anhydrous $Na_2SO_4$, filtered, and concentrated under reduced pressure to obtain the title compound (1.0 g) as a solid. $^1H$ NMR (300 MHz, DMSO-$d_6$) δ 8.20 (d, 1H), 7.42 (m, 1H), 7.25-7.21 (m, 2H), 4.29 (s, 2H), 3.88 (s, 3H), 3.27 (s, 1H), 2.96 (s, 1H), 2.58 (m, 1H), 1.89-1.86 (m, 1.54 (s, 2H). LCMS (ESI): 331.1 $[M+H]^+$.

Step-3. N-((1s,4s)-4-(difluoromethyl)cyclohexyl)-1-(5-(2-methoxypyridin-4-yl)-1H-pyrazole-3-carbonyl)piperidine-4-carboxamide and N-((1r,4r)-4-(difluoromethyl)cyclohexyl)-1-(5-(2-methoxypyridin-4-yl)-1H-pyrazole-3-carbonyl)piperidine-4-carboxamide

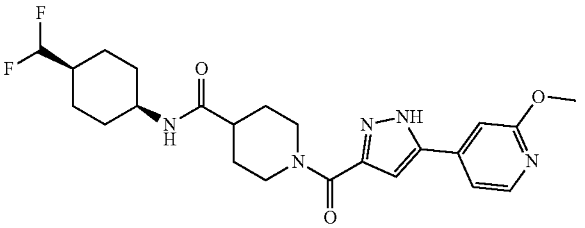

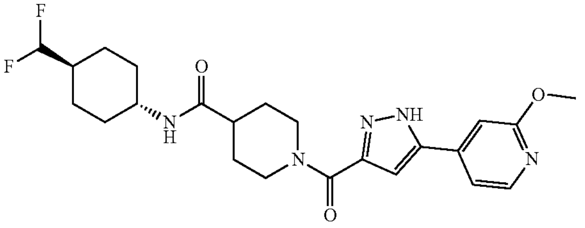

4-(difluoromethyl)cyclohexan-1-amine hydrochloride (14.6 mg, 0.08 mmol) was added to a solution of 1-[5-(2-methoxypyridin-4-yl)-1H-pyrazole-3-carbonyl]piperidine-4-carboxylic acid (20.0 mg, 0.06 mmol) and triethylamine (25 μL, 0.18 mmol) in THF (0.6 mL). The solution was stirred at 25° C. under nitrogen atmosphere for 15 min, then T3P® (50% in DMF, 53 μL, 0.1 mmol) was added. The solution was stirred for an additional 2 h, then diluted with water and EtOAc. The organic layer was isolated, washed with water, dried over anhydrous sodium sulfate, filtered, and then concentrated under reduced pressure. The residue was purified first by silica gel column chromatography (EtOAc/Hex, 0/100 to 100/0 v/v) to obtain a diastereomeric mixture of N-((1s,4s)-4-(difluoromethyl)cyclohexyl)-1-(5-(2-methoxypyridin-4-yl)-1H-pyrazole-3-carbonyl)piperidine-4-carboxamide and N-((1r,4r)-4-(difluoromethyl)cyclohexyl)-1-(5-(2-methoxypyridin-4-yl pyrazole-3-carbonyl)piperidine-4-carboxamide (Example 113).

The mixture of the title compounds was separated using Prep-HPLC.

Column: Waters CSH C18

Column dimensions: 150×19 mm, 5 μm

Gradient: Water (0.1% FA)/MeCN (0.1% FA), 75/25 to 5/95 v/v

Flow rate: 30 mL/min

Detection (nm): 254 nm

Example 113-A. The first eluting diastereomer (1.7 mg) was obtained as a solid.

The first eluting diastereomer has a retention time of 1.45 min in the QC conditions below.

LCMS (ESE): 462.7 $[M+H]^+$.

Example 113-B. The second eluting diastereomer (2.0 mg) was obtained as a solid.

The second eluting diastereomer has a retention time of 1.47 min in the QC conditions below.

$^1H$ NMR (400 MHz, $CDCl_3$) δ 8.23 (d, 1H), 7.29 (br s, 1H), 7.11 (s, 1H), 6.87 (s, 1H), 5.87-5.50 (m, 2H), 4.73-4.46 (m, 2H), 4.12 (br s, 1H), 3.99 (s, 3H), 3.43-3.13 (m, 1H), 3.13-2.88 (m, 2.44 (br s, 1H), 2.06-1.92 (m, 2H), 1.91-1.69 (m, 9H), 1.67-1.59 (m, 2H), 1.50-1.37 (m, 3H). LCMS (ESI): 462.7 $[M+H]^+$.

QC Conditions:

Column: Waters Acquity UPLC CSH $C_{18}$

Column dimensions: 50×2.1 trim, 1.8 μm

Gradient: MeCN (0.1% FA)/Water (0.1% FA), 5/95 to 100/0

Flow rate: 0.8 mL/min

Example 114. A diastereomeric mixture of Example 114-A and 114-B. 1-(5-(5-fluoro-2-methoxypyridin-4-yl)-1H-pyrazole-3-carbonyl)-N-((1s,4s)-4-methylcyclohexyl)piperidine-4-carboxamide and 1-(5-(5-fluoro-2-methoxypyridin-4-yl)-1H-pyrazole-3-carbonyl)-N-((1r,4r)-4-methylcyclohexyl)piperidine-4-carboxamide

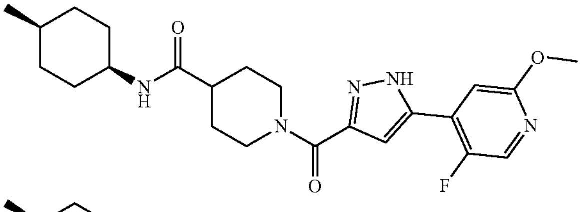

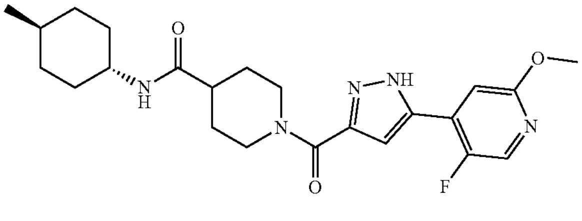

Step-1. 1-[5-bromo-1-(oxan-2-yl)pyrazole-3-carbonyl]-N-(4-methylcyclohexyl)piperidine-4-carboxamide

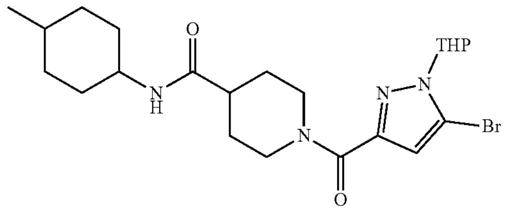

DHP (158.8 mg, 1.89 mmol) and TsOH (10.8 mg, 0.06 mmol) were added to a solution of 1-(5-bromo-1H-pyrazole-3-carbonyl)-N-(4-methylcyclohexyl)piperidine-4-carboxamide (250.0 mg, 0.63 mmol, Example 101, Steps 1-3) in THF (10.0 mL). The solution was stirred at 25° C. for 2 h, then the solution was concentrated. The residue was purified by silica gel column chromatography (EtOAc/petroleum ether, 1/1 v/v) to obtain the title compound (230.0 mg) as a solid mixture of diastereomers. LCMS (ESE): 481.2 $[M+H]^+$.

Step-2. 1-[5-(5-fluoro-2-methoxypyridin-4-yl)-1-(oxan-2-yl)pyrazole-3-carbonyl]-N-(4-methylcyclohexyl)piperidine-4-carboxamide

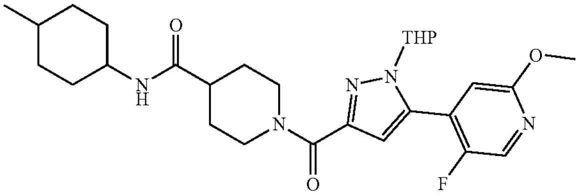

5-fluoro-2-methoxypyridin-4-ylboronic acid (142.0 mg, 0.83 mmol), $Pd(dppf)Cl_2$ (60.8 mg, 0.08 mmol) and $K_3PO_4$ (176.4 mg, 0.83 mmol) were added to a solution of 1-[5-bromo-1-(oxan-2-yl)pyrazole-3-carbonyl]-N-(4-methylcyclohexyl)piperidine-4-carboxamide (Step-1, 200.0 mg, 0.42 mmol), in 1,4-dioxane (5.0 mL) and $H_2O$ (0.5 mL). The solution was stirred at 70° C. under nitrogen atmosphere for 14 h, then diluted with ethyl acetate and washed with water. The organic layer was then concentrated under reduced pressure, and the residue was purified by Prep-TLC ($CH_2Cl_2$/MeOH, 20/1 v/v) to obtain the title compound (212 mg) as a solid mixture of diastereomers. LCMS (ESI): 528.3 $[M+H]^+$.

Step-3. 1-(5-(5-fluoro-2-methoxypyridin-4-yl)-1(1-pyrazole-3-carbonyl)-N-((1s,4s)-4-methylcyclohexyl)piperidine-4-carboxamide and 1-(5-(5-fluoro-2-methoxypyridin-4-yl)-1H-pyrazole-3-carbonyl)-N-((1r,4r)-4-methylcyclohexyl)piperidine-4-carboxamide

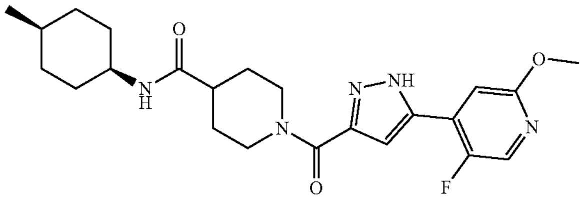

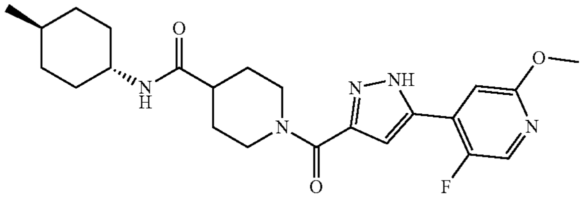

TFA (2.0 mL) was added to a stirred solution of 1-[5-(5-fluoro-2-methoxypyridin-4-yl)-1-(oxan-2-yl)pyrazole-3-carbonyl]-N-(4-methylcyclohexyl)piperidine-4-carboxamide (Step-2, 236.0 mg, 0.45 mmol) in DCM (2.0 mL). The solution was stirred at 25° C., for 30 min, then concentrated under reduced pressure. The residue was purified by reverse phase column chromatography (using the following conditions: C18 column; Mobile Phase A: Water (10 mM $NH_4HCO_3$), Mobile Phase B: MeCN; Flow rate: 30 mL/min; Gradient: 30% B to 60% B in 30 min; Detector, UV 220/254 nm) to obtain 1-(5-(5-fluoro-2-methoxypyridin-4-yl)-1H-pyrazole-3-carbonyl)-N-((1s,4s)-4-methylcyclohexyl)piperidine-4-carboxamide and 1-(5-(5-fluoro-2-methoxypyridin-4-yl)-1H-pyrazole-3-carbonyl)-N-((1r,4r)-4-methylcyclohexyl)piperidine-4-carboxamide (72.0 mg) as a mixture of diastereomers (Example 114). $^1H$ NMR (300 MHz, $CD_3OD$) δ 8.12 (d, 1H), 7.24 (d, 1H), 7.07 (d, 1H), 4.71-4.42 (m, 2H), 3.92 (s, 3H), 3.87-3.46 (m, 1H), 3.32-3.20 (m, 1H), 2.96-2.90 (m, 1H), 2.69-2.38 (m, 1H), 1.86-1.44 (m, 10H), 1.41-1.10 (m, 3H), 1.08-0.86 (m, 3H). LCMS (ESI): 444.4 $[M+H]^+$.

The two diastereomers of the title compound were separated using Chiral Prep-HPLC.

Column: CHIRALPAK IF

Column dimensions: 2×25 cm, 5 μm

Mobile Phase: (Hex/DCM, 1/1 v/v, 10 mM $NH_3$·MeOH)/EtOH (1/1 v/v)

Flow rate: 20 mL/min

Detection (nm): 220/254 nm

Example 114-A. The first eluting diastereomer (4.4 mg) was obtained as a solid.

The first eluting diastereomer had a retention time of 14.3 min.

$^1H$ NMR (300 MHz, DMSO-d6) δ 13.94 (s, 1H), 8.27 (d, 1H), 7.64 (d, 1H), 7.32 (d, 1H), 7.03 (d, 4.61-4.14 (m, 2H), 3.87 (s, 3H), 3.54-3.34 (m, 1H), 3.25-3.06 (m, 1H), 2.94-2.64 (m, 1H), 2.46-2.29 (m, 1H), 1.83-1.41 (m, 8H), 1.39-0.96 (m, 5H), 0.91-0.84 (m, 3H). LCMS (ESI): 444.2 $[M+H]^+$.

Example 114-B. The second eluting diastereomer (42.6 mg) was obtained as a solid.

The second eluting diastereomer had a retention time of 24.8 min.

$^1$H NMR (300 MHz, DMSO-d6) δ 13.97 (s, 1H), 8.27 (d, 1H), 7.63 (d, 1H), 7.32 (d, 1H), 7.03 (d, 1H), 4.59-4.29 (m, 2H), 3.87 (s, 3H), 3.78-3.71 (m, 1H), 3.25-3.06 (m, 1H), 2.92-2.69 (m, 1H), 2.69-2.38 (m, 1H), 1.75-1.69 (m, 2H), 1.63-1.15 (m, 11H), 0.94-0.85 (m, 3H). LCMS (ESI): 444.2 $[M+H]^+$.

Example 115. Enantiomeric mixture of (R)-1-[5-(5-chloro-2-methoxypyridin-4-yl)-1H-pyrazole-3-carbonyl]-N-[1-(3-chlorophenyl)ethyl]piperidine-4-carboxamide and (S)-1-[5-(5-chloro-2-methoxypyridin-4-yl)-1H-pyrazole-3-carbonyl]-N-[1-(3-chlorophenyl)ethyl]piperidine-4-carboxamide

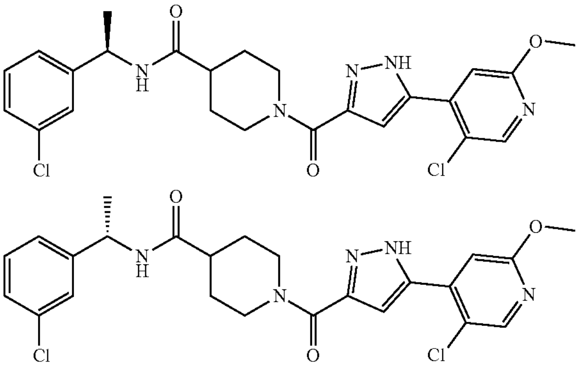

Step-1. 1-[5-Bromo-1-(oxan-2-yl)pyrazole-3-carbonyl]-N-[1-(3-chlorophenyl)ethyl]piperidine-4-carboxamide

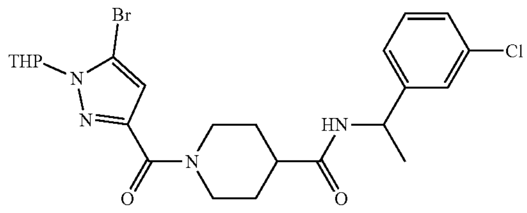

1-(3-chlorophenyl)ethan-1-amine (INTERMEDIATE 539, 112 mg, 0.72 mmol), DIPEA (187 mg, 1.45 mmol), and HATU (220 mg, 0.58 mmol) were added to a solution of 1-[5-bromo-1-(oxan-2-yl)pyrazole-3-carbonyl]piperidine-4-carboxylic acid (INTERMEDIATE 509, 186 mg, 0.48 mmol) in DMF (2 mL). The resulting solution was stirred at 25° C. for 1 h. The resulting solution was diluted with water, then organics was extracted with DCM. The organic layers were concentrated under vacuum. The residue was purified by silica gel column chromatography (DCM/MeOH, 10/1 v/v) to obtain the title compound (240 mg) as a solid. LCMS (ESI): $[M+H]^+$: 523.1.

Step-2. 1-[5-(5-Chloro-2-methoxypyridin-4-yl)-1-(oxan-2-yl)pyrazole-3-carbonyl]-N-[1-(3-chlorophenyl)ethyl]piperidine-4-carboxamide

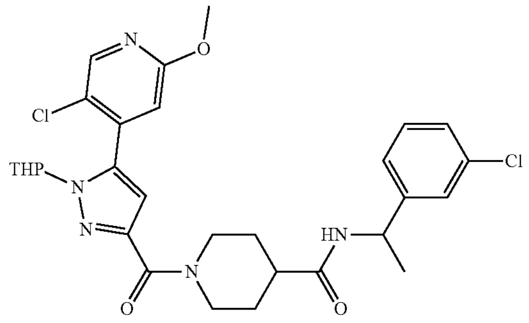

$Pd(dppf)Cl_2$ (78 mg, 0.11 mmol), $K_3PO_4$ (340 mg, 1.60 mmol and 5-chloro-2-methoxypyridin-4-ylboronic acid (200 mg 1.07 mmol) was added to a solution of 1-[5-bromo-1-(oxan-2-yl)pyrazole-3-carbonyl]-N-[1-(3-chlorophenyl)ethyl]piperidine-4-carboxamide (Step-1, 280 mg, 0.53 mmol) in dioxane (4.00 mL), $H_2O$ (1 mL). The resulting solution was stirred at 80° C. for 12 h under $N_2$ atmosphere. The resulting solution was diluted with water and the organics was extracted with DCM. The organic layers were concentrated under vacuum and the resulting residue was purified by silica gel column chromatography (petroleum ether/EtOAC, 1/1 v/v) to obtain the title compound (120 mg) as a solid. LCMS (ESI): $[M+H]^+$: 586.2.

Step-3. (R)-1-[5-(5-chloro-2-methoxypyridin-4-yl)-1H-pyrazole-3-carbonyl]-N-[1-(3-chlorophenyl)ethyl]piperidine-4-carboxamide and (S)-1-[5-(5-chloro-2-methoxypyridin-4-yl)-1H-pyrazole-3-carbonyl]-N-[1-(3-chlorophenyl)ethyl]piperidine-4-carboxamide

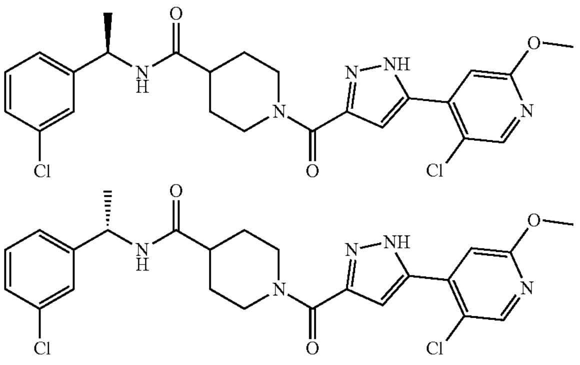

TFA (2 mL) was added to a solution of 1-[5-(5-chloro-2-methoxypyridin-4-yl)-1-(oxan-2-yl)pyrazole-3-carbonyl]-N-[1-(3-chlorophenyl)ethyl]piperidine-4-carboxamide (Step-2, 120 mg, 0.21 mmol, 1.00 equiv) in DCM (2 mL). The resulting solution was stirred at 25° C. for 3 h. The pH of the mixture was adjusted to pH 8 with addition of DIPEA. The resulting solution was concentrated under vacuum. The resulting residue was purified by Prep-HPLC (using the following conditions: Column: Atlantis HILIC OBD, 19×150 mm, 5 μm, 10 nm; Mobile Phase A: Water (0.1%

FA); Mobile Phase B: MeCN; Gradient: 42% B to 57% B in 7 min; Detector: UV 220/254) to obtain (R)-1-[5-(5-chloro-2-methoxypyridin-4-yl)-1H-pyrazole-3-carbonyl]-N-[1-(3-chlorophenyl)ethyl]piperidine-4-carboxamide and (S)-1-[5-(5-chloro-2-methoxypyridin-4-yl)-1H-pyrazole-3-carbonyl]-N-[1-(3-chlorophenyl)ethyl]piperidine-4-carboxamide (27.2 mg) as a solid mixture of enantiomers (Example 115). $^1$H NMR (300 MHz, DMSO-d6) δ 13.92 (s, 1H), 8.31 (d, 2H), 7.38-7.17 (m, 5H), 7.11 (s, 1H), 4.96-4.80 (m, 1H), 4.44 (s, 2H), 3.87 (s, 3H), 3.18 (s, 1H), 2.82 (s, 1H), 2.52 (s, 1H), 1.77 (s, 2H), 1.53 (s, 2H), 1.32 (d, 3H). LCMS (ESI): 502.1 $[M+H]^+$.

This solid mixture of enantiomers was separated using Chiral Prep-HPLC.

Column: CHIRALPAK IC

Column dimensions: 3×25 cm, 5 μm

Mobile Phase: MTBE (10 mM $NH_3$·MeOH)/MeOH, 4/1 v/v

Flow rate: 50 mL/min

Detector (nm): 220/254 nm

Example 115-A. The first eluting enantiomer (7.1 mg) was obtained as a solid.

The first eluting enantiomer had a retention time of 7.3 min.

$^1$H NMR (300 MHz, DMSO-d6) δ 14.14-13.72 (m, 1H), 8.47-8.16 (m, 2H), 7.38-7.30 (m, 2H), 7.30-7.17 (m, 3H), 7.16-7.07 (m, 1H), 4.97-4.71 (m, 1H), 4.70-3.99 (m, 2H), 3.89 (d, 3H), 3.28-3.07 (m, 1H), 2.73 (s, 1H), 2.50 (s, 1H), 1.77 (s, 2H), 1.53 (s, 2H), 1.33 (d, 3H). LCMS (ESI): 502.1 $[M+H]^+$.

Example 115-B. The second eluting enantiomer (8.2 mg) was obtained as a solid.

$^1$H NMR (300 MHz, DMSO-d6) δ 14.14-13.61 (m, 1H), 8.35 (d, 2H), 7.40-7.29 (m, 2H), 7.30-7.16 (m, 3H), 7.13 (s, 1H), 4.99-4.71 (m, 1H), 4.73-3.96 (m, 2H), 3.89 (d, 3H), 3.19 (s, 1H), 2.76 (s, 1H), 2.50 (s, 1H), 1.78 (s, 2H), 1.53 (s, 2H), 1.33 (d, 3H). LCMS (ESI): 502.1 $[M+H]^+$.

Example 117. 1-[5-(5-chloro-2-methoxypyridin-4-yl)-1H-pyrazole-3-carbonyl]-N-(1-phenylpyrrolidin-3-yl)piperidine-4-carboxamide

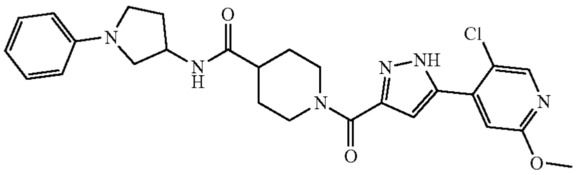 [SMILES: COc1cc(-c2cc(C(=O)N3CCC(C(=O)NC4CCN(c5ccccc5)C4)CC3)n[nH]2)c(Cl)cn1]

Step-1. tert-butyl 3-[1-[5-bromo-1-(oxan-2-yl)pyrazole-3-carbonyl]piperidine-4-amido]pyrrolidine-1-carboxylate

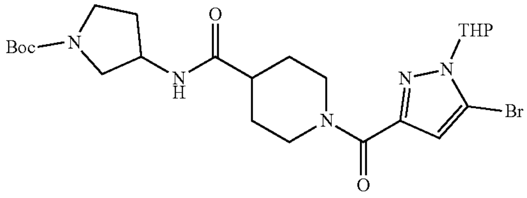

EDCI (469 mg, 2.45 mmol) and HOBT (330 mg, 2.45 mmol) were added to a solution of 1-[5-bromo-1-(oxan-2-yl)pyrazole-3-carbonyl]piperidine-4-carboxylic acid (INTERMEDIATE 509, 630 mg, 1.63 mmol) in DMF (5 mL). The solution was stirred at 25° C. for 30 min, then tert-butyl 3-aminopyrrolidine-1-carboxylate (364 mg, 1.96 mmol) and DIPEA (843 mg, 6.52=top were added. The solution was stirred at 25° C. for 3 h, then diluted with EtOAc and washed with water. The organic layer was concentrated under reduced pressure, then the residue was purified by silica gel column chromatography (DCM/MeOH, 20/1 v/v) to obtain the enantiomeric mixtures of the title compound (600 mg) as an oil. LCMS (ESI): 554.2 $[M+H]^+$.

Step-2. tert-butyl 3-(1-(5-(5-chloro-2-methoxypyridin-4-yl)-1-(oxan-2-yl)-1H-pyrazole-3-carbonyl)piperidine-4-carboxamido)pyrrolidine-1-carboxylate

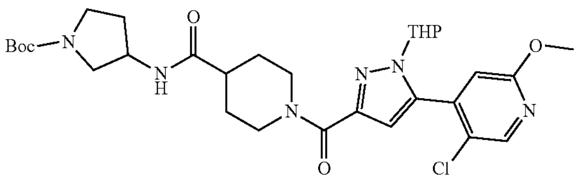

5-chloro-2-methoxypyridin-4-ylboronic acid (Step-1, 392 mg, 2.1 mmol), Pd(dppf)$Cl_2$ (153 mg, 0.2 mmol) and $K_3PO_4$ (666 mg, 3.1 mmol) were added to a solution of tert-butyl 3-[1-[5-bromo-1-(oxan-2-yl)pyrazole-3-carbonyl]piperidine-4-amido]pyrrolidine-1-carboxylate (580 mg, 1.0 mmol) in 1,4-dioxane (10 mL) and $H_2O$ (2.5 mL). The solution was stirred at 80° C. for under nitrogen atmosphere, then diluted with ethyl acetate and washed with water. The organic layer was concentrated under reduced pressure, and the residue was purified by silica gel column chromatography (DCM/MeOH, 20/1 v/v) to obtain the title compound (430 mg) as a solid mixture of enantiomers. LCMS (ESI): 617.3 $[M+H]^+$.

Step-3. 1-[5-(5-chloro-2-methoxypyridin-4-yl)-1H-pyrazole-3-carbonyl]-N-(pyrrolidin-3-yl)piperidine-4-carboxamide

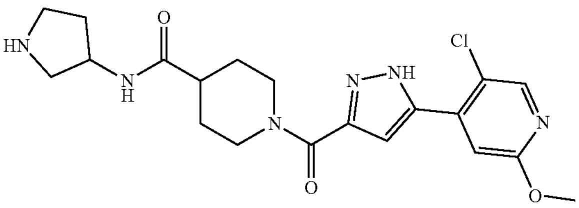 [SMILES: COc1cc(-c2cc(C(=O)N3CCC(C(=O)NC4CCNC4)CC3)n[nH]2)c(Cl)cn1]

TFA (2.00 mL) was added to a solution of tert-butyl 3-[1-[5-(5-chloro-2-methoxypyridin-4-yl)-1-(oxan-2-yl)pyrazole-3-carbonyl]piperidine-4-amido]pyrrolidine-1-carboxylate (Step-2, 430.0 mg, 0.70 mmol) in DCM (2.00 mL). The solution was stirred at 25° C. for 1 h, then concentrated under reduced pressure. The residue was purified by C18 reverse phase column chromatography (MeCN/$H_2O$ 1/1 v/v) to obtain the enantiomeric mixtures of the title compound (200.0 mg) as an oil. LCMS (ESI): 433.2 $[M+H]^+$ Step-4. 1-[5-(5-chloro-2-methoxypyridin-4-yl)-1H-pyrazole-3-carbonyl]-N-(1-phenylpyrrolidin-3-yl)piperidine-4-carboxamide

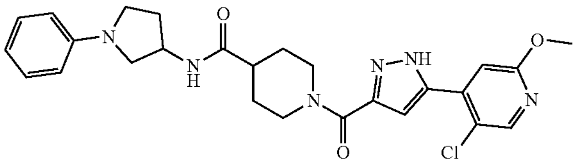 [SMILES: COc1cc(-c2cc(C(=O)N3CCC(C(=O)NC4CCN(c5ccccc5)C4)CC3)n[nH]2)c(Cl)cn1]

Bromobenzene (81 mg, 0.5 mmol), $Pd_2(dba)_3$ (31 mg, 0.03 mmol), XPhos (33 mg, 0.07 mmol) and $K_3PO_4$ (220 mg, 1.04 mmol) were added to a mixture of 1-[5-(5-chloro-2-methoxypyridin-4-yl)-1H-pyrazole-3-carbonyl]-N-(pyrrolidin-3-yl)piperidine-4-carboxamide (Step-3, 150 mg, 0.35 mmol) in DMSO (3.0 mL). The solution was stirred at 120° C. for 3 h under nitrogen atmosphere, then diluted with ethyl acetate and washed with water. The organic layer was concentrated under reduced pressure, then the residue was purified by Prep-HPLC (using the following conditions: Column: XBridge Shield RP18 OBD, 30×150 mm, 5 μm; Mobile Phase A: Water (10 mM $NH_4HCO_3$); Mobile Phase B: MeCN; Gradient: 38% B to 55% B in 8 min; Detection: 220/254 nm) to obtain the title compound (15.7 mg) as a solid mixture of diastereomers. $^1H$ NMR (300 MHz, DMSO-$d_6$) δ 13.80 (s, 1H), 8.35 (s, 1H), 8.15 (d, 1H), 7.24 (s, 1H), 7.20-7.10 (m, 3H), 6.63-6.55 (m, 1H), 6.54-6.48 (m, 2H), 4.53-4.30 (m, 3H), 3.90 (s, 3H), 3.53-3.41 (m, 1H), 3.36 (s, 1H), 3.30-3.18 (m, 2H), 3.08-2.96 (m, 1H), 2.77 (s, 1H), 2.45 (s, 1H), 2.27-2.07 (m, 1H), 1.95-1.82 (m, 1H), 1.75 (s, 2H), 1.56 (s, 2H). LCMS (ESI): 509.3 $[M+H]^+$.

Example 118. A diastereomeric mixtures of 1-[5-(5-chloro-2-methoxypyridin-4-yl)-1H-pyrazole-3-carbonyl]-N-[(1s,4s)-4-(trifluoromethyl)cyclohexyl]piperidine-4-carboxamide and 1-[5-(5-chloro-2-methoxypyridin-4-yl)-1H-pyrazole-3-carbonyl]-N-[(1r,4r)-4-(trifluoromethyl)cyclohexyl]piperidine-4-carboxamide

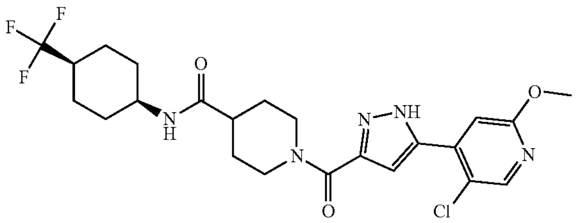

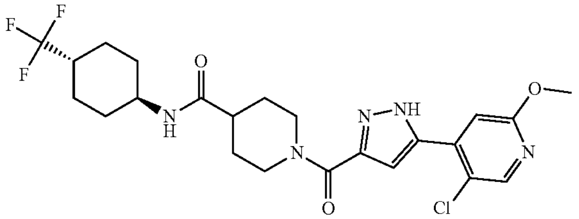

Step-1. 1-[5-bromo-1-(oxan-2-yl)pyrazole-3-carbonyl]-N-[4-(trifluoromethyl)cyclohexyl]piperidine-4-carboxamide

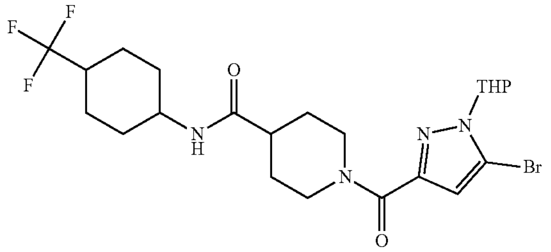

4-(trifluoromethyl)cyclohexan-1-amine (103.9 mg, 0.6 mmol) and DIPEA (200.8 mg, 1.6 mmol) were added to a stirred solution of 1-[5-bromo-1-(oxan-2-yl)pyrazole-3-carbonyl]piperidine-4-carboxylic acid (INTERMEDIATE 509, 200.0 mg, 0.5 mmol) and HATU (236.3 mg 0.6 mmol) in DMF (3.0 mL). The solution was stirred at 25° C. for 2 h, then diluted with ethyl acetate and washed with water. The organic layer was concentrated under reduced pressure, then the residue was purified by silica gel column chromatography (petroleum ether/EtOAc, 2/1 v/v) to obtain the title compound (290 mg) as a solid mixture of diastereomers. LCMS (ESI): 535.2 $[M+H]^+$.

Step-2. 1-[5-(5-chloro-2-methoxypyridin-4-yl)-1-(oxan-2-yl)pyrazole-3-carbonyl]-N-[4-(trifluoromethyl)cyclohexyl]piperidine-4-carboxamide

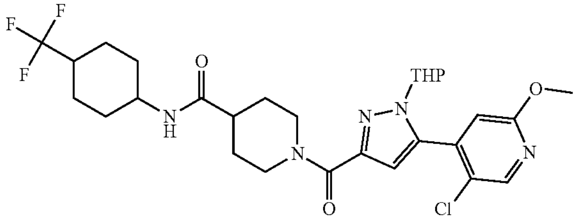

5-chloro-2-methoxypyridin-4-ylboronic acid (98.7 mg, 0.50 mmol), $Pd(dppf)Cl_2$ (64.2 mg, 0.10 mmol) and $K_3PO_4$ (186.3 mg, 0.90 mmol) were added to a stirred solution of 1-[5-bromo-1-(oxan-2-yl)pyrazole-3-carbonyl]-N-[4-(trifluoromethyl)cyclohexyl]piperidine-4-carboxamide (Step-1, 235.0 mg, 0.40 mmol) in $H_2O$ (0.40 mL) and 1,4-dioxane (4.00 mL) were added. The solution was stirred at 70° C. for 14 h under $N_2$ atmosphere, then concentrated under reduced pressure. The residue was purified by silica gel column chromatography (100% EtOAc) to obtain the title compound (180 mg) as a solid mixture of diastereomers. LCMS (ESI): 598.2 $[M+H]^+$.

Step-3. 1-[5-(5-chloro-2-methoxypyridin-4-yl)-1H-pyrazole-3-carbonyl]-N-[(1s,4s)-4-(trifluoromethyl)cyclohexyl]piperidine-4-carboxamide and 1-[5-(5-chloro-2-methoxypyridin-4-yl)-1H-pyrazole-3-carbonyl]-N-[(1r,4r)-4-(trifluoromethyl)cyclohexyl]piperidine-4-carboxamide

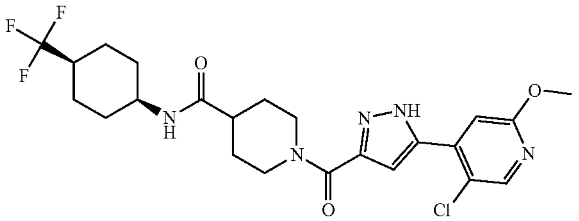

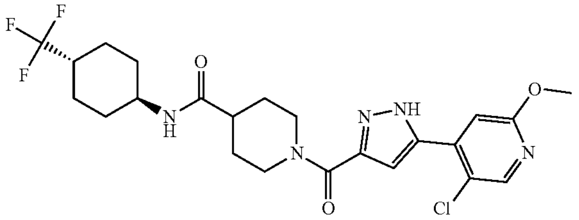

TFA (3.0 mL) was added to a solution of 1-[5-(5-chloro-2-methoxypyridin-4-yl)-1-(oxan-2-yl)pyrazole-3-carbonyl]-N-[4-(trifluoromethyl)cyclohexyl]piperidine-4-carboxamide (Step-2, 198.0 mg, 0.3 mmol) in DCM (3.0 mL). The solution was stirred at 25 CC for 1 h, then concentrated under reduced pressure. The residue was purified by Prep-HPLC (using the following conditions: Column: XBridge Shield RP18 OBD, 30×150 mm, 5 μm; Mobile Phase A: Water (10 mM $NH_4HCO_3$); Mobile Phase B: MeCN, Flow rate: 60 mL/min; Gradient: 36% B to 54% B in 7 min; Detection: 220/254 nm) to obtain 1-[5-(5-chloro-2-methoxypyridin-4-yl)-1H-pyrazole-3-carbonyl]-N-[(1s,4s)-4-(trifluoromethyl)cyclohexyl]piperidine-4-carboxamide and 1-[5-(5-chloro-2-methoxypyridin-4-yl)-1H-pyrazole-3-carbonyl]-N-[(1r,4r)-4-(trifluoromethyl)cyclohexyl]piperidine-4-carboxamide (51.6 mg) as a solid mixture of diastereomers (Example 118). $^1$H NMR (300 MHz, DMSO-$d_6$) δ 8.33 (s, 1H), 7.83-7.71 (m, 1H), 7.22 (s, 1H), 7.15-7.08 (m, 1H), 4.47-4.41 (m, 2H), 3.88 (s, 3H), 3.86-3.81 (m, 1H), 3.19-3.13 (m, 1H), 2.84-2.78 (m, 1H), 2.37-2.09 (m, 1H), 1.90-1.79 (m, 1H), 1.78-1.64 (m, 4H), 1.64-1.42 (m, 7H). LCMS (ESI): 514.2 $[M+H]^+$.

This solid mixture of diastereomers was separated using Chiral Prep-HPLC.

Column: CHIRAL ART Cellulose-SB

Column dimensions: 2×25 cm, 5 μm

Mobile Phase: MTBE (2 mM $NH_3$·MEOH)/MeOH, 9/1 v/v

Flow rate: 20 mL/min

Detection (nm): 220/254 nm

Example 118-A. The first eluting diastereomer (22.6 mg) was obtained as a solid.

The first eluting diastereomer had a retention time of 7.14 min.

$^1$H NMR (300 MHz, $CD_3OD$) δ 8.25 (s, 1H), 7.14 (s, 2H), 4.68-4.62 (m, 2H), 3.94 (s, 3H), 3.40-3.15 (m, 1H), 2.96-2.90 (m, 2H), 2.73-2.60 (m, 1H), 2.23-2.17 (m, 1H), 1.95-1.71 (m, 7H), 1.69-1.55 (m, 5H). LCMS (ESI): 514.2 $[M+H]^+$.

Example 118-B. The second eluting diastereomer (5.1 mg) was obtained as a solid.

The second eluting diastereomer had a retention time of 9.65 min.

$^1$H NMR (300 MHz, $CD_3OD$) 8.25 (s, 1H), 7.14 (s, 2H), 4.77-4.50 (m, 2H), 3.94 (s, 3H), 3.64-3.58 (m, 1H), 3.40-2.80 (m, 2H), 2.53-2.47 (m, 2.20-2.05 (m, 2H), 2.04-1.92 (m, 2H), 1.88-1.61 (m, 5H), 1.51-1.13 (m, 4H). LCMS (ESI): 514.2 $[M+H]^+$.

Example 119. 1-(5-(5-chloro-2-methoxypyridin-4-yl)-1H-pyrazole-3-carbonyl)-N-(imidazo[1,2-a]pyridin-2-ylmethyl)piperidine-4-carboxamide

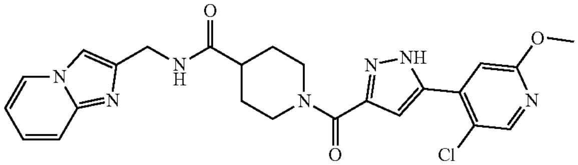 [SMILES: COc1cc(-c2cc(C(=O)N3CCC(C(=O)NCc4cn5ccccc5n4)CC3)n[nH]2)c(Cl)cn1]

HATU (25.0 mg, 0.07 mmol) and imidazo[1,2-a]pyridin-2-ylmethanamine (9.7 mg, 0.07 mmol) were added to a stirred solution of 1-[5-(5-chloro-2-methoxypyridin-4-yl)-1H-pyrazole-3-carbonyl]piperidine-4-carboxylic acid (INTERMEDIATE 503, 20.0 mg, 0.06 mmol) and DIPEA (21.0 mg, 0.17 mmol) in DMF (2.00 mL). The resulting mixture was stirred at 25° C. for 14 h. The resulting residue was filtered. The filtrate was purified by Prep-HPLC (using the following conditions: Column: XBridge BEH130 Prep C18 OBD Column, 130 Å, 19×150 mm 5 μm 13 nm; Mobile phase A: Water (20 mM $NH_4HCO_3$), mobile phase B: MeCN; Detector, UV 254/210 nm) to obtain the title compound (19.8 mg) as a solid. $^1$H NMR (400 MHz, $CD_3OD$): δ 8.41-8.19 (m, 2H), 7.71 (s, 1H), 7.48 (m, 1H), 7.32-7.23 (m, 2H), 7.15 (s, 2H), 6.92-6.87 (m, 1H), 4.55 (m, 3H), 3.94 (m, 4H), 2.61 (m, 1H), 2.00-1.73 (m, 4H), 1.29 (s, 1H). LCMS (ESI): $[M+H]^+$: 494.3.

Example 120. 1-(5-(5-chloro-2-methoxypyridin-4-yl)-1H-pyrazole-3-carbonyl)-N-((5-chloropyridin-2-yl)methyl)piperidine-4-carboxamide

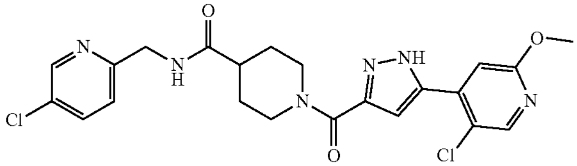 [SMILES: COc1cc(-c2cc(C(=O)N3CCC(C(=O)NCc4ccc(Cl)cn4)CC3)n[nH]2)c(Cl)cn1]

The title compound was prepared using a procedure similar to the one described for the synthesis of Example 119, except (5-chloropyridin-2-yl)methanamine was used as a starting material. The title compound was obtained as a solid (21.7 mg). $^1$H NMR (300 MHz, DMSO-$d_6$) δ 13.94 (m, 1H), 8.59-8.46 (m, 2H), 8.36 (m, 1H), 7.95-7.84 (m, 1H), 7.36-7.20 (m, 2H), 7.18-7.11 (m, 1H), 4.76-4.42 (m, 1H), 4.36 (m, 2H), 4.14 (s, 1H), 3.99-3.80 (m, 3H), 3.28-3.10 (m, 1H), 3.02-2.78 (m, 1H), 2.78-2.56 (m, 1H), 2.00-1.69 (m, 2H), 1.69-1.42 (m, 2H). LCMS (ESI): $[M+H]^+$: 489.35.

Example 121. 1-[5-(5-Chloro-2-methoxypyridin-4-yl)-1H-pyrazole-3-carbonyl]-N-(2-methyl-1,3-dioxan-5-yl) piperidine-4-carboxamide

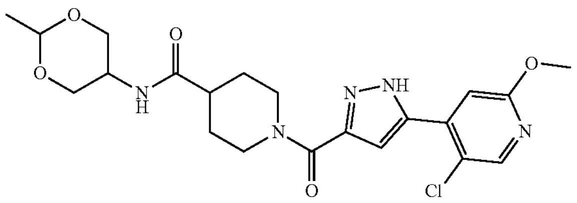

EDCI (35.5 mg, 0.19 mmol), HOBT (25.0 mg, 0.19 mmol), and 2-methyl-1,3-dioxin-5-amine (21.7 mg, 0.19 mmol) were added to a stirred solution of 1-[5-(5-chloro-2-methoxypyridin-4-yl)-1H-pyrazole-3-carbonyl]piperidine-4-carboxylic acid (INTERMEDIATE 503, 45.0 mg, 0.12 mmol) and DIPEA (31.9 mg, 0.25 mmol) in DMF (2.00 mL). The resulting mixture was stirred at 25° C. for 14 h. The resulting mixture was diluted with water and extracted with EtOAc. The organic layers were combined and dried over anhydrous sodium sulfate, filtered, and the solvent was evaporated. The residue was purified by reverse phase column chromatography (C18 column; mobile phase: MeCN in water, 10% to 95% gradient in 20 min; detector: UV 254 nm) to obtain the title compound (20.9 mg) as a solid mixture of diastereomers. $^1$H NMR (300 MHz, DMSO-$d_6$) δ 13.92 (s, 1H), 8.36 (s, 1H), 7.24 (d, 1H), 7.14 (d, 1H), 4.72 (q, 1H), 4.47 (s, 2H), 3.90-3.86 (m, 5H), 3.79-3.75 (m, 2H), 3.57 (d, 1H), 3.18-3.14 (m, 1H), 2.83-2.75 (m, 2H), 1.76-1.72 (m, 2H), 1.65-1.60 (m, 2H), 1.21 (s, 3H). LCMS (ESI): $[M+H]^+$: 464.1.

Examples 122. N-((1H-indol-5-yl)methyl)-1-(5-(5-chloro-2-methoxypyridin-4-yl)-1H-pyrazole-3-carbonyl)piperidine-4-carboxamide

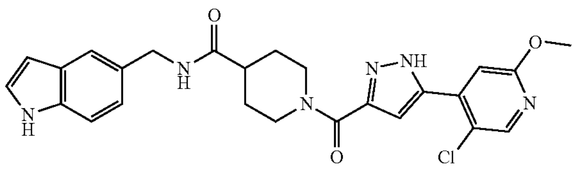 [SMILES: COc1cc(-c2cc(C(=O)N3CCC(C(=O)NCc4ccc5[nH]ccc5c4)CC3)n[nH]2)c(Cl)cn1]

The title compound was prepared using a procedure similar to the one described for the synthesis of Example 119, except (1H-indol-5-yl)methanamine was used as a starting material. The title compound was obtained as a solid (17.0 mg). $^1$H NMR (300 MHz, $CD_3OD$) δ 8.26 (s, 1H), 7.47 (d, 1H), 7.34 (d, 1H), 7.22 (d, 1H), 7.15 (s, 2H), 7.09-7.00 (m, 1H), 6.40 (dd, 1H), 4.74-4.52 (m, 2H), 4.44 (s, 2H), 3.95 (s, 3H), 3.39-3.18 (m, lii), 2.97-2.91 (m, 1H), 2.66-2.53 (m, 1H), 1.98-1.63 (m, 4H). LCMS (ESI): $[M+H]^+$: 493.3.

Example 123. 1-(5-(5-chloro-2-methoxypyridin-4-yl)-1H-pyrazole-3-carbonyl)-N-(2,3,6-trifluorobenzyl)piperidine-4-carboxamide

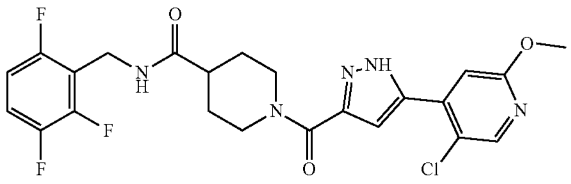 [SMILES: COc1cc(-c2cc(C(=O)N3CCC(C(=O)NCc4c(F)ccc(F)c4F)CC3)n[nH]2)c(Cl)cn1]

The title compound was prepared using a procedure similar to the one described for the synthesis of Example 119, except (2,3,6-trifluorophenyl)methanamine was used as a starting material. The title compound was obtained as a solid (16.2 mg). $^1$H NMR (300 MHz, $CD_3OD$) δ 8.27 (s, 1H), 7.35-7.18 (m, 1H), 7.15 (s, 2H), 7.06-6.92 (m, 1H), 4.66-4.60 (m, 2H), 4.50 (s, 2H), 3.96 (s, 3H), 3.31-3.25 (m, 1H), 2.97-2.91 (m, 1H), 2.64-2.49 (m, 1H), 1.95-1.61 (m, 4H). LCMS (ESI): $[M+H]^+$: 508.35.

Example 124. 1-(5-(5-chloro-2-methoxypyridin-4-yl)-1H-pyrazole-3-carbonyl)-N-((1,3-dimethyl-1H-pyrazol-4-yl)methyl)piperidine-4-carboxamide

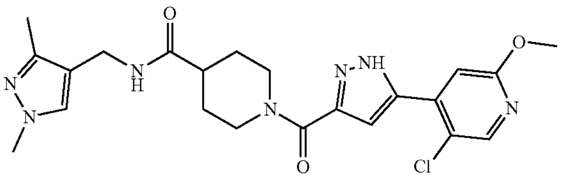 [SMILES: COc1cc(-c2cc(C(=O)N3CCC(C(=O)NCc4cn(C)nc4C)CC3)n[nH]2)c(Cl)cn1]

The title compound was prepared using a procedure similar to the one described for the synthesis of Example 119, except (1,3-dimethyl-1H-pyrazol-4-yl)methanamine was used as a starting material. The title compound was obtained as a solid (13.2 mg). $^1$H NMR (300 MHz, $CD_3OD$) δ 8.26 (s, 1H), 7.42 (s, 1H), 7.15 (s, 2H), 4.62 (s, 2H), 4.18 (5, 2H), 3.95 (s, 3H), 3.77 (s, 3H), 2.93 (5, 1H), 2.52 (m, 1H), 2.19 (s, 3H), 1.93-1.64 (m, 5H). LCMS (ESI): $[M+H]^+$: 472.4.

Example 125. 1-(5-(5-chloro-2-methoxypyridin-4-yl)-1H-pyrazole-3-carbonyl)-N-(2-chloro-5-fluorobenzyl)piperidine-4-carboxamide

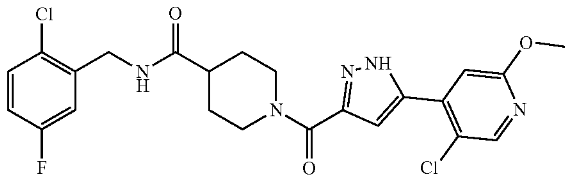 [SMILES: COc1cc(-c2cc(C(=O)N3CCC(C(=O)NCc4cc(F)ccc4Cl)CC3)n[nH]2)c(Cl)cn1]

The title compound was prepared using a procedure similar to the one described for the synthesis of Example 119, except (2-chloro-5-fluorophenyl)methanamine was used as a starting material. The title compound was obtained as a solid (15.9 mg). $^1$H NMR (300 MHz, $CD_3OD$) 8.26 (s, 1H), 7.56-7.35 (m, 1H), 7.21-6.96 (m, 4H), 4.64 (s, 3H), 4.45 (s, 1H), 3.95 (s, 3H), 2.97-2.87 (m, 1H), 2.74-2.56 (m, 1H), 1.98-1.64 (m, 4H), 1.32 (m, 1H). LCMS (ESI): $[M+H]^+$; 506.3.

Example 126. 1-(5-(5-chloro-2-methoxypyridin-4-yl)-1H-pyrazole-3-carbonyl)-N-(1-(2,2,2-trifluoro-ethyl)-1H-pyrazol-4-yl)piperidine-4-carboxamide

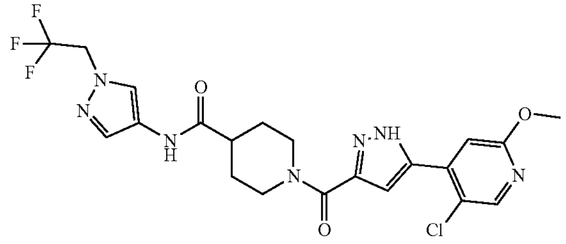 [SMILES: COc1cc(-c2cc(C(=O)N3CCC(C(=O)Nc4cnn(CC(F)(F)F)c4)CC3)n[nH]2)c(Cl)cn1]

The title compound was prepared using a procedure similar to the one described for the synthesis of Example 119, except 1-(2,2,2-trifluoroethyl)-1H-pyrazol-4-amine was used as a starting material. The title compound was obtained as a solid (21.7 mg). $^1H$ NMR (400 MHz, $CD_3OD$) δ 8.26 (s, 1H), 8.06 (s, 1H), 7.59 (m, 1H), 7.16 (s, 1H), 7.14 (s, 1H), 4.94-4.88 (m, 2H), 4.86-4.81 (m, 1H), 4.68 (s, 2H), 3.94 (s, 3H), 3.01-2.96 (m, 1H), 2.75-2.63 (m, 1H), 1.98-1.94 (m, 2H), 1.85-1.77 (m, 2H). LCMS (ESI): $[M+H]^+$: 512.1.

Example 127. 1-(5-(5-chloro-2-methoxypyridin-4-yl)-1H-pyrazole-3-carbonyl)-N-((5-fluoropyridin-2-yl)methyl)piperidine-4-carboxamide

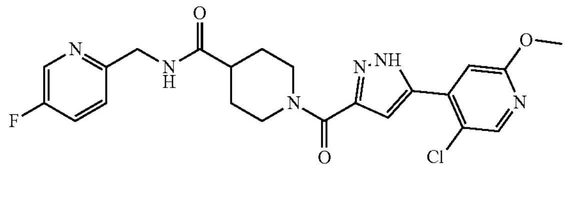 [SMILES: COc1cc(-c2cc(C(=O)N3CCC(C(=O)NCc4ccc(F)cn4)CC3)n[nH]2)c(Cl)cn1]

The title compound was prepared using a procedure similar to the one described for the synthesis of Example 119, except (5-fluoropyridin-2-yl)methanamine was used as a starting material. The title compound was obtained as a solid (21.3 mg). $^1H$ NMR (400 MHz, $CD_3OD$) δ 8.39 (m, 1H), 8.25 (s, 1H), 7.63-7.54 (m, 1H), 7.42-7.34 (m, 1H), 7.14 (s, 2H), 4.64 (s, 2H), 4.47 (s, 2H), 3.94 (s, 3H), 2.96 (s, 1H), 2.65 (s, 1H), 1.94 (s, 2H), 1.76 (m, 2H), 1.31 (m, 1H). LCMS (ESI): $[M+H]^+$: 473.35.

Example 128. 1-(5-(5-chloro-2-methoxypyridin-4-yl)-1H-pyrazole-3-carbonyl)-N-(1-cyanocyclobutyl) piperidine-4-carboxamide

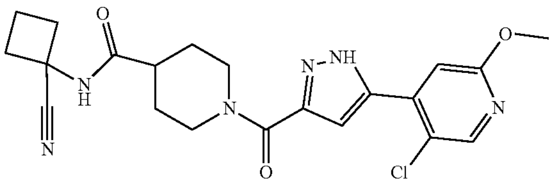 [SMILES: COc1cc(-c2cc(C(=O)N3CCC(C(=O)NC4(C#N)CCC4)CC3)n[nH]2)c(Cl)cn1]

The title compound was prepared using a procedure similar to the one described for the synthesis of Example 119, except 1-aminocyclobutane-1-carbonitrile hydrochloride was used as a starting material. The title compound was obtained as a solid (17.7 mg). $^1H$ NMR (300 MHz, $CD_3OD$) δ 8.26 (s, 1H), 7.15 (s, 2H), 4.63 (s, 2H), 3.95 (s, 3H), 3.44-2.85 (m, 3H), 2.76-1.70 (m, 10H). LCMS (ESI): $[M+H]^+$443.3.

Example 129. 1-(5-(5-chloro-2-methoxypyridin-4-yl)-1H-pyrazole-3-carbonyl)-N-((6 (trifluoromethyl) pyridin-2-yl)methyl)piperidine-4-carboxamide

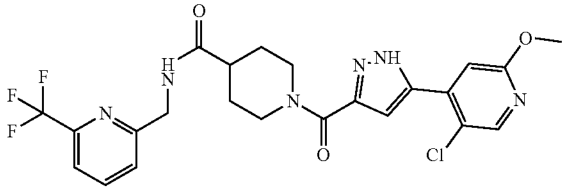 [SMILES: COc1cc(-c2cc(C(=O)N3CCC(C(=O)NCc4cccc(C(F)(F)F)n4)CC3)n[nH]2)c(Cl)cn1]

The title compound was prepared using a procedure similar to the one described for the synthesis of Example 119, except (6-(trifluoromethyl)pyridin-2-yl)methanamine hydrochloride was used as a starting material. The title compound was obtained as a solid (14.6 mg). $^1H$ NMR (400 MHz, $CD_3OD$) δ 8.25 (s, 1H), 8.02-7.94 (m, 1H), 7.71-7.62 (m, 1H), 7.56 (m, 1H), 7.14 (m, 2H), 4.55 (s, 1H), 4.45 (s, 3H), 3.94 (s, 3H), 2.99 (s, 1H), 2.74-2.48 (m, 1H), 2.08-1.67 (m, 4H), 1.30 (m, 1H). LCMS (ESI): $[M+H]^+$: 523.3.

Example 130. 1-(5-(5-chloro-2-methoxypyridin-4-yl)-1H-pyrazole-3-carbonyl)-N-((3-(trifluoromethyl) pyridin-2-yl)methyl)piperidine-4-carboxamide

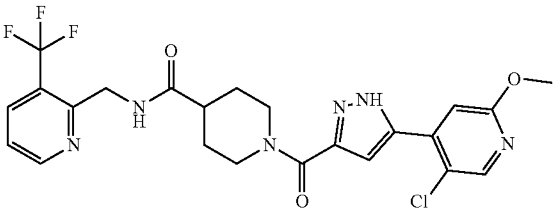 [SMILES: COc1cc(-c2cc(C(=O)N3CCC(C(=O)NCc4ncccc4C(F)(F)F)CC3)n[nH]2)c(Cl)cn1]

The title compound was prepared using a procedure similar to the one described for the synthesis of Example 119, except (3-(trifluoromethyl)pyridin-2-yl)methanamine hydrochloride was used as a starting material. The title compound was obtained as a solid (8.4 mg). $^1$H NMR (400 MHz, $CD_3OD$) δ 8.82-8.73 (m, 1H), 8.25 (s, 8.15-8.08 (m, 1H), 7.53-7.45 (m, 7.15 (s, 2H), 4.68 (s, 2H), 4.64 (s, 2H), 3.94 (s, 3H), 2.99 (s, 1H), 2.77-2.65 (m, 1H), 1.97 (s, 2H), 1.81 (d, 1H), 1.75 (d, 1H), 1.31 (m, 1H), LCMS (ESI): $[M+H]^+$: 523.40.

Example 131. 1-(5-(5-chloro-2-methoxypyridin-4-yl)-1H-pyrazole-3-carbonyl)-N-((4-methylpyridin-3-yl)methyl)piperidine-4-carboxamide

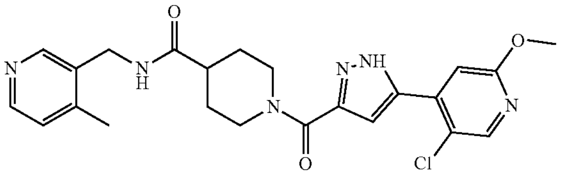 [SMILES: COc1cc(-c2cc(C(=O)N3CCC(C(=O)NCc4cnccc4C)CC3)n[nH]2)c(Cl)cn1]

The title compound was prepared using a procedure similar to the one described for the synthesis of Example 119, except (4-methylpyridin-3-yl)methanamine was used as a starting material. The title compound was obtained as a solid (11.5 mg) NMR (400 MHz, $CD_3OD$) δ 8.35 (s, 1H), 8.33-8.22 (m, 2H), 7.26 (m, 1H), 7.14 (s, 2H), 4.64 (s, 1H), 4.57 (s, 1H), 4.43 (s, 2H), 3.94 (s, 3H), 2.94 (s, 2H), 2.65-2.55 (m, 1H), 2.39 (s, 3H), 2.02-1.63 (m, 4H). LCMS (ESI): $[M+H]^+$: 469.40.

Example 132. 1-(5-(5-chloro-2-methoxypyridin-4-yl)-1H-pyrazole-3-carbonyl)-N-(isochroman-4-yl) piperidine-4-carboxamide

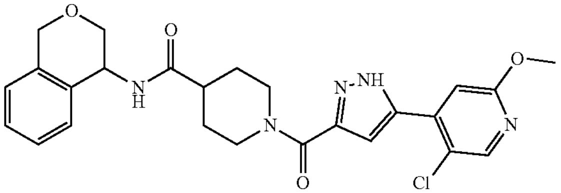 [SMILES: COc1cc(-c2cc(C(=O)N3CCC(C(=O)NC4COCc5ccccc54)CC3)n[nH]2)c(Cl)cn1]

The title compound was prepared using a procedure similar to the one described for the synthesis of Example 119, except isochroman-4-amine was used as a starting material. The title compound was obtained as a solid mixture of enantiomers (18.0 mg). $^1$H NMR (300 MHz, $CD_3OD$) δ 8.28 (s, 1H), 7.33-7.22 (m, 3H), 7.17 (s, 2H), 7.13-7.05 (m, 114), 5.07-4.98 (m, 1H), 4.90-4.79 (m, 1H), 4.79-4.68 (m, 1H), 4.65 (s, 2H), 3.97 (s, 3H), 4.01-3.83 (m, 2H), 3.39-3.18 (m, 1H), 2.94 (s, 1H), 2.67-2.53 (m, 1H), 2.00-1.63 (m, 4H). LCMS (ESI): $[M+H]^+$: 496.40.

Example 133. 1-(5-(5-chloro-2-methoxypyridin-4-yl)-1H-pyrazole-3-carbonyl)-N-((1R,2S)-2-phenylcyclopropyl)piperidine-4-carboxamide

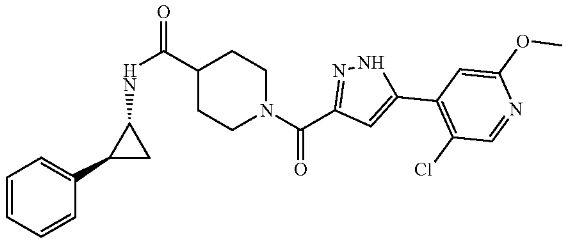 [SMILES: COc1cc(-c2cc(C(=O)N3CCC(C(=O)N[C@@H]4C[C@H]4c4ccccc4)CC3)n[nH]2)c(Cl)cn1]

The title compound was prepared using a procedure similar to the one described for the synthesis of Example 119, except (1R,2S)-2-phenylcyclopropane-1-amine was used as a starting material. The title compound was obtained as a solid (17.3 mg). $^1$H NMR (300 MHz, $CD_3OD$) δ 8.28 (s, 1H), 7.35-7.10 (m, 7H), 4.64 (s, 2H), 3.97 (s, 3H), 3.29-3.07 (m, 1H), 3.14-2.77 (m, 2H), 2.61-2.46 (m, 1H), 2.10-1.98 (m, 1H), 1.97-1.66 (m, 4H), 1.34-1.12 (m, LCMS (ESI): $[M+H]^+$: 480.3.

Example 134. 1-(5-(5-chloro-2-methoxypyridin-4-yl)-1H-pyrazole-3-carbonyl)-N-((1-hydroxycyclohexyl)methyl)piperidine-4-carboxamide

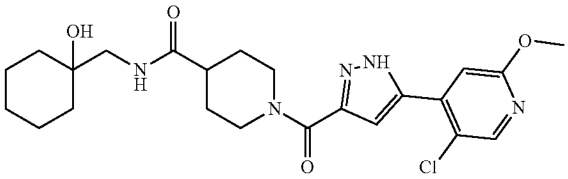 [SMILES: COc1cc(-c2cc(C(=O)N3CCC(C(=O)NCC4(O)CCCCC4)CC3)n[nH]2)c(Cl)cn1]

The title compound was prepared using a procedure similar to the one described for the synthesis of Example 119, except 1-(aminomethyl)cyclohexan-1-ol was used as a starting material. The title compound was obtained as a solid (18.9 mg). $^1$H NMR, (400 MHz, $CD_3OD$) δ 8.25 (s, 1H), 7.14 (s, 2H), 4.66-4.62 (m, 2H), 3.94 (s, 3H), 3.34-3.30 (m, 1H), 3.23-3.18 (m, 2H), 2.96-2.92 (m, 1H), 2.68-2.55 (m, 1H), 2.02-1.27 (m, 14H). LCMS (ESI): $[M+H]^+$: 476.45.

Example 135. 1-(5-(5-chloro-2-methoxypyridin-4-yl)-1H-pyrazole-3-carbonyl)-N-((4,4-dimethyloxetan-2-yl)methyl)piperidine-4-carboxamide

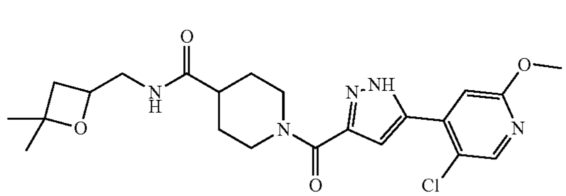

The title compound was prepared using a procedure similar to the one described for the synthesis of Example 119, except (4,4-dimethyloxetan-2-yl)methanamine was used as a starting material. The title compound was obtained as a solid mixture of enantiomers (19.2 mg), NMR (300 MHz, $CD_3OD$) δ 8.26 (s, 1H), 7.15 (s, 2H), 4.73-4.58 (m, 2H), 3.95 (s, 3H), 3.51-3.33 (m, 2H), 2.95 (s, 1H), 2.67-2.52 (m, 1H), 2.47-2.34 (m, 1H), 2.26-2.14 (m, 1H), 2.03-1.64 (m, 6H), 1.46 (s, 3H), 1.40 (s, 3H). LCMS (ESI): $[M+H]^+$: 462.4.

Example 136. 1-(5-(5-chloro-2-methoxypyridin-4-yl)-1H-pyrazole-3-carbonyl)-N-((2-methyloxazol-5-yl)methyl)piperidine-4-carboxamide

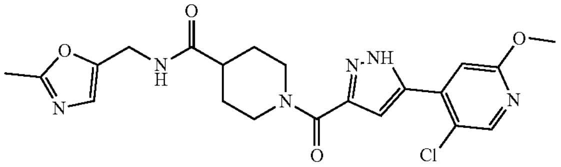

The title compound was prepared using a procedure similar to the one described for the synthesis of Example 119, except (2-methyloxazol-5-yl)methanamine was used as a starting material. The title compound was obtained as a solid (18.7 mg), $^1$H NMR (400 MHz, $CD_3OD$) δ 8.25 (s, 1H), 7.14 (s, 1H), 7.13 (s, 1H), 6.84 (d, 1H), 4.63 (s, 2H), 4.38 (d, 2H), 3.94 (s, 3H), 3.00-2.87 (m, 1H), 2.62-2.51 (m, H), 2.41 (s, 3H), 2.03-1.57 (m, 4H). LCMS (ESI): $[M+H]^+$: 459.40.

Example 137. 1-(5-(5-chloro-2-methoxypyridin-4-yl)-1H-pyrazole-3-carbonyl)-N-(pyrazolo[1,5-a]pyridin-7-ylmethyl)piperidine-4-carboxamide

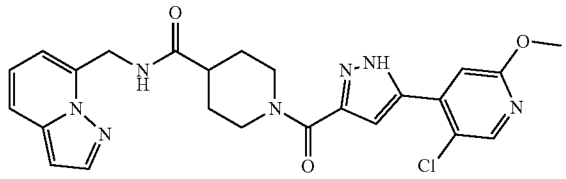 [SMILES: COc1cc(-c2cc(C(=O)N3CCC(C(=O)NCc4cccc5ccnn45)CC3)n[nH]2)c(Cl)cn1]

The title compound was prepared using a procedure similar to the one described for the synthesis of Example 119, except pyrazolo[1,5-a]pyridin-7-ylmethanamine was used as a starting material. The title compound was obtained as a solid (22.6 mg). $^1$H NMR (400 MHz, $CD_3OD$): δ 8.25 (s, 1H), 8.00 (d, 1H), 7.61 (d, 1H), 7.23-7.03 (m, 3H), 6.78 (d, 1H), 6.65 (d, 1H), 4.83 (s, 2H), 4.66 (s, 2H), 3.94 (s, 3H), 2.97 (s, 1H), 2.75-2.62 (m, 1H), 2.09-1.86 (m, 2H), 1.83-1.73 (m, 2H). LCMS (ESI): $[M+H]^+$: 494.3.

Example 138. 1-(5-(5-chloro-2-methoxypyridin-4-yl)-1H-pyrazole-3-carbonyl)-N-((5-chloropyrimidin-2-yl)methyl)piperidine-4-carboxamide

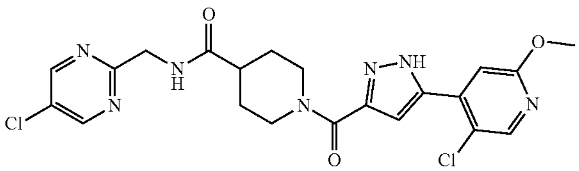 [SMILES: COc1cc(-c2cc(C(=O)N3CCC(C(=O)NCc4ncc(Cl)cn4)CC3)n[nH]2)c(Cl)cn1]

The title compound was prepared using a procedure similar to the one described for the synthesis of Example 119, except (5-chloropyrimidin-2-yl)methanamine hydrochloride was used as a starting material. The title compound was obtained as a solid (17.4 mg). $^1$H NMR (400 MHz, $CD_3OD$): δ 8.76 (s, 2H) 8.25 (s, 1H), 7.15 (s, 2H), 4.65 (s, 2H), 4.58 (s, 2H), 3.94 (s, 3H), 3.00 (s, 2H), 2.74-2.63 (m, 1H), 1.97 (s, 2H), 1.86-1.69 (m, 2H). LCMS (ESI): $[M+H]^+$: 490.3.

Example 139, 1-(5-(5-chloro-2-methoxypyridin-4-yl)-1H-pyrazole-3-carbonyl)-N-((5-(trifluoromethyl)pyridin-2-yl)methyl)piperidine-4-carboxamide

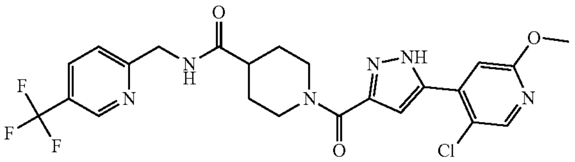 [SMILES: COc1cc(-c2cc(C(=O)N3CCC(C(=O)NCc4ccc(C(F)(F)F)cn4)CC3)n[nH]2)c(Cl)cn1]

The title compound was prepared using a procedure similar to the one described for the synthesis of Example 119, except (5-(trifluoromethyl)pyridin-2-yl)methanamine hydrochloride was used as a starting material. The title compound was obtained as a solid (13.0 mg). $^1$H NMR (400 MHz, $CD_3OD$): δ 8.81 (s, 1H), 8.25 (s, 1H), 8.11-8.07 (m, 1H), 7.52 (m, 1H), 7.15 (s, 2H), 4.68 (s, 2H), 4.57 (s, 2H), 3.94 (s, 3H), 2.98 (s, 1H), 2.70 (d, 2H), 1.95 (d, 1H), 1.77 (d, 2H), 1.31 (d, 1H). LCMS (ESI): $[M+H]^+$: 523.3.

Example 140. 1-(5-(5-chloro-2-methoxypyridin-4-yl)-1H-pyrazole-3-carbonyl)-N-((3-chloropyridin-2-yl)methyl)piperidine-4-carboxamide

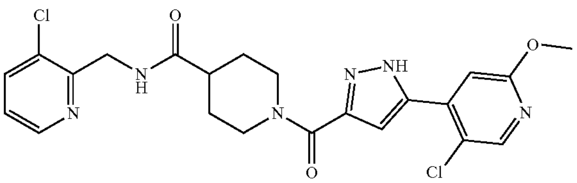 [SMILES: COc1cc(-c2cc(C(=O)N3CCC(C(=O)NCc4ncccc4Cl)CC3)n[nH]2)c(Cl)cn1]

The title compound was prepared using a procedure similar to the one described for the synthesis of Example 119, except (3-chloropyridin-2-yl)methanamine was used as a starting material. The title compound was obtained as a solid (20.8 mg). NMR (400 MHz, $CD_3OD$) δ 8.51-8.40 (m, 1H), 8.25 (s, 1H), 7.90-7.76 (m, 1H), 7.43-7.27 (m, 2H), 7.15 (s, 1H), 4.61 (s, 2H), 3.94 (s, 3H), 3.37-3.23 (m, 3H), 2.98 (s, 1H), 2.70 (s, 1H), 1.96 (s, 2H), 1.84-1.69 (m, 2H). LCMS (ESI): $[M+H]^+$: 489.3.

Example 141. 1-(5-(5-chloro-2-methoxypyridin-4-yl)-1H-pyrazole-3-carbonyl)-N-((1,5-dimethyl-1H-pyrazol-3-yl)methyl)piperidine-4-carboxamide

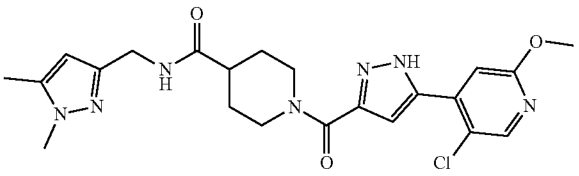

The title compound was prepared using a procedure similar to the one described for the synthesis of Example 119, except (1,5-dimethyl-1H-pyrazol-3-yl)methanamine was used as a starting material. The title compound was obtained as a solid (18.1 mg). $^1$H NMR (300 MHz, $CD_3OD$) δ 8.28 (s, 1H), 7.16 (s, 2H), 5.98 (d, 1H), 4.65 (s, 2H), 4.28 (s, 2H), 3.97 (s, 3H), 3.73 (s, 3H), 3.32 (s, 1H), 2.96 (s, 1H), 2.59 (m, 1H), 2.27 (d, 3H), 2.08-1.64 (m, 4H). LCMS (ESI): $[M+H]^+$: 472.3.

Example 142. 1-(5-(5-chloro-2-methoxypyridin-4-yl)-1H-pyrazole-3-carbonyl)-N-(1-(4-chlorophenoxy)propan-2-yl)piperidine-4-carboxamide

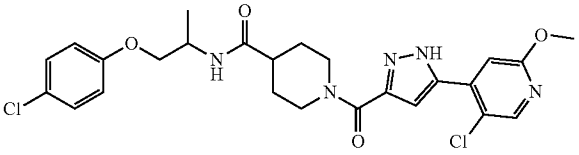 [SMILES: COc1cc(-c2cc(C(=O)N3CCC(C(=O)NC(C)COc4ccc(Cl)cc4)CC3)n[nH]2)c(Cl)cn1]

The title compound was prepared using a procedure similar to the one described for the synthesis of Example 119, except 1-(4-chlorophenoxy)propan-2-amine was used as a starting material. The title compound was obtained as a solid (22.1 mg). $^1$H NMR (300 MHz, $CD_3OD$) δ 8.28 (s, 1H), 7.32-7.21 (m, 2H), 7.16 (s, 2H), 7.00-6.88 (m, 2H), 4.66-4.60 (m, 2H), 4.36-4.19 (m, 1H), 3.97 (s, 3H), 4.02-3.86 (m, 2H), 3.40-3.17 (m, 1H), 2.98-2.92 (m, 1H), 2.66-2.50 (m, 1H), 2.03-1.61 (m, 4H), 1.28 (d, 3H). LCMS (ESI): $[M+H]^+$: 532.35.

Example 143. 1-(5-(5-chloro-2-methoxypyridin-4-yl)-1H-pyrazole-3-carbonyl)-N-(3,3-difluorocyclohexyl)piperidine-4-carboxamide

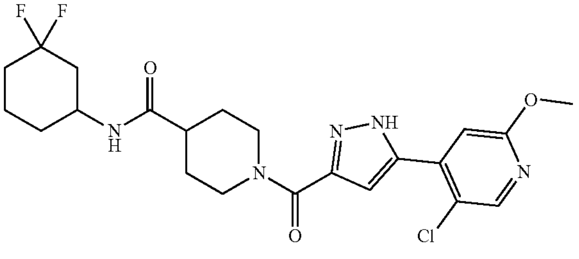 [SMILES: COc1cc(-c2cc(C(=O)N3CCC(C(=O)NC4CCCC(F)(F)C4)CC3)n[nH]2)c(Cl)cn1]

The title compound was prepared using a procedure similar to the one described for the synthesis of Example 119, except 3,3-difluorocyclohexan-1-amine hydrochloride was used as a starting material. The title compound was obtained as a solid (19.7 mg). $^1$H NMR (400 MHz, $CD_3OD$) δ 8.25 (s, 1H), 7.14 (s, 2H), 4.67-4.62 (m, 2H), 3.97-3.86 (m, 4H), 2.93 (s, 1H), 2.57-2.45 (m, 1H), 2.25 (s, 1H), 2.05-1.48 (m, 10H), 1.35-1.16 (m, 2H). LCMS (ESI): $[M+H]^+$: 482.40.

Example 144. 1-(5-(5-chloro-2-methoxypyridin-4-yl)-1H-pyrazole-3-carbonyl)-N-(4-hydroxy-4-(trifluoromethyl)cyclohexyl)piperidine-4-carboxamide

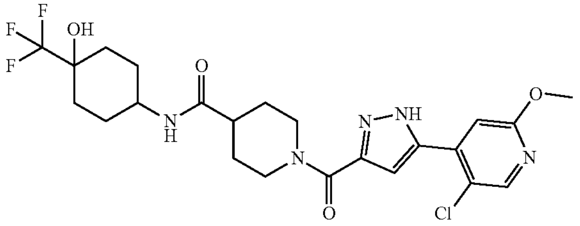 [SMILES: COc1cc(-c2cc(C(=O)N3CCC(C(=O)NC4CCC(O)(C(F)(F)F)CC4)CC3)n[nH]2)c(Cl)cn1]

The title compound was prepared using a procedure similar to the one described for the synthesis of Example 119, except 4-amino-1-(trifluoromethyl)cyclohexan-1-ol hydrochloride was used as a starting material. The title compound was obtained as a solid mixture of diastereomers (11.8 mg). $^1$H NMR (400 MHz, $CD_3OD$): δ 8.25 (s, 1H), 7.17-7.12 (m, 2H), 4.65 (s, 2H), 3.94 (s, 3H), 3.70-3.60 (m, 1H), 2.92 (s, 1H), 2.75-2.42 (m, 1H), 1.98-1.57 (m, 12H), 1.41-1.20 (m, 1H). LCMS (ESI): $[M+H]^+$; 530.4.

Example 145. 1-(5-(5-chloro-2-methoxypyridin-4-yl)-1H-pyrazole-3-carbonyl)-N-((3-methoxycyclobutyl)methyl)piperidine-4-carboxamide

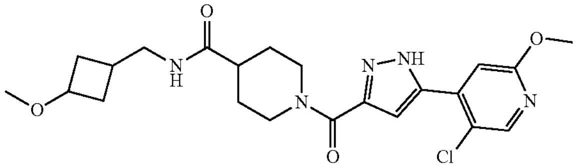

The title compound was prepared using a procedure similar to the one described for the synthesis of Example 119, except (3-methoxycyclobutyl)methanamine was used as a starting material. The title compound was obtained as a solid mixture of diastereomers (17.2 mg). $^1$H NMR (300 MHz, $CD_3OD$) δ 8.26 (s, 1H), 7.15 (s, 2H), 4.64 (s, 2H), 3.95 (s, 3H), 3.84-3.67 (m, 1H), 3.31-3.27 (m, 1H) 3.26 (s, 3H), 3.21 (d, 2H), 3.06-2.88 (m, 1H), 2.67-2.47 (m, 1H), 2.43-2.26 (m, 2H), 2.15-1.99 (m, 1H), 1.96-1.69 (m, 4H), 1.69-1.49 (m, 2H). LCMS (ESI): $[M+H]^+$: 462.3.

Example 146. 1-(5-(5-chloro-2-methoxypyridin-4-yl)-1H-pyrazole-3-carbonyl)-N-((3-fluoropyridin-2-yl)methyl)piperidine-4-carboxamide

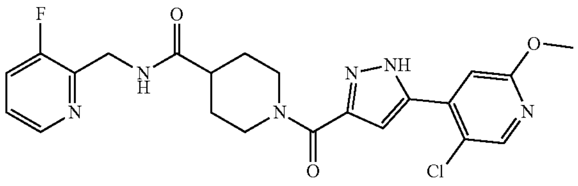 [SMILES: COc1cc(-c2cc(C(=O)N3CCC(C(=O)NCc4ncccc4F)CC3)n[nH]2)c(Cl)cn1]

The title compound was prepared using a procedure similar to the one described for the synthesis of Example 119, except (3-fluoropyridin-2-yl)methanamine hydrochloride was used as a starting material. The title compound was obtained as a solid (15.0 mg). $^1$H NMR (300 MHz, $CD_3OD$) δ 8.41-8.33 (m, 1H), 8.26 (s, 1H), 7.64-7.54 (m, 1H), 7.43-7.34 (m, 1H), 7.15 (s, 2H), 4.59 (m, 4H), 3.96 (s, 3H), 3.67 (s, 1H), 3.14-2.85 (m, 1H), 2.77-2.55 (m, 1H), 1.93 (s, 2H), 1.87-1.63 (m, 2H). LCMS (ESI): $[M+H]^+$: 473.35.

Example 147. 1-(5-(5-chloro-2-methoxypyridin-4-yl)-1H-pyrazole-3-carbonyl)-N-(3-(difluoromethyl)phenyl)piperidine-4-carboxamide

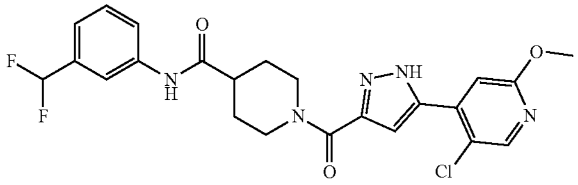 [SMILES: COc1cc(-c2cc(C(=O)N3CCC(C(=O)Nc4cccc(C(F)F)c4)CC3)n[nH]2)c(Cl)cn1]

The title compound was prepared using a procedure similar to the one described for the synthesis of Example 119, except 3-(difluoromethyl)aniline was used as a starting material. The title compound was obtained as a solid (17.6 mg). $^1$H NMR (400 MHz, $CD_3OD$) δ 8.26 (s, 1H), 7.84 (s, 1H), 7.70-7.63 (m, 1H), 7.46-7.38 (m, 1H), 7.29-7.22 (m, 1H), 7.16 (s, 1H), 7.14 (s, 1H), 4.69 (s, 2H), 3.94 (s, 3H), 3.00 (s, 1H), 2.80-2.68 (m, 2H), 1.99 (s, 2H), 1.83 (m, 3H). LCMS (ESI): $[M+H]^+$: 490.40.

Example 148. 1-(5-(5-chloro-2-methoxypyridin-4-yl)-1H-pyrazole-3-carbonyl)-N-((3,3-difluorocyclobutyl)methyl)piperidine-4-carboxamide

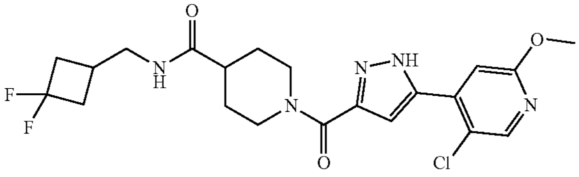 [SMILES: COc1cc(-c2cc(C(=O)N3CCC(C(=O)NCC4CC(F)(F)C4)CC3)n[nH]2)c(Cl)cn1]

The title compound was prepared using a procedure similar to the one described for the synthesis of Example 119, except (3,3-difluorocyclobutyl)methanamine hydrochloride was used as a starting material. The title compound was obtained as a solid (23.3 mg). $^1$H NMR (400 MHz, $CD_3OD$) δ 8.26 (s, 1H), 7.14 (s, 2H), 4.64 (s, 2H), 3.94 (s, 3H), 3.28 (s, 1H), 2.93 (s, 1H), 2.66-2.49 (m, 4H), 2.34-2.24 (m, 4H), 2.01-1.69 (m, 2H), 1.31 (m, 2H). LCMS (ESI): $[M+H]^+$: 468.35.

Example 149. 1-(5-(5-chloro-2-methoxypyridin-4-yl)-1H-pyrazole-3-carbonyl)-N-(2,2-difluoro-2-phenylethyl)piperidine-4-carboxamide

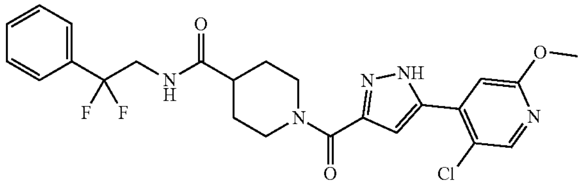 [SMILES: COc1cc(-c2cc(C(=O)N3CCC(C(=O)NCC(F)(F)c4ccccc4)CC3)n[nH]2)c(Cl)cn1]

The title compound was prepared using a procedure similar to the one described for the synthesis of Example 119, except 2,2-difluoro-2-phenylethan-1-amine was used as a starting material. The title compound was obtained as a solid (20.8 mg). NMR (400 MHz, $CD_3OD$) δ 8.25 (s, 1H), 7.57-7.38 (m, 5H), 7.12 (s, 2H), 4.59-4.54 (m, 2H), 3.96-3.82 (m, 5H), 3.26-3.22 (m, 1H), 2.94-2.89 (m, 1H), 2.60-2.48 (m, 1H), 1.85-1.54 (m, 4H). LCMS (ESI): $[M+H]^+$: 504.3.

Example 150. 1-(5-(5-chloro-2-methoxypyridin-4-yl)-1H-pyrazole-3-carbonyl)-N-(3,3,5-trimethylcyclohexyl)piperidine-4-carboxamide

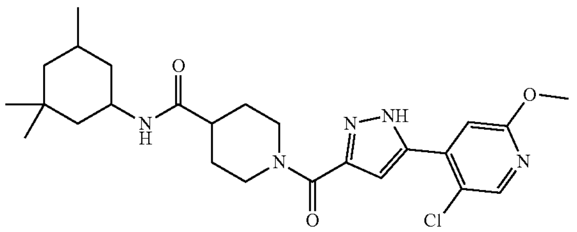

The title compound was prepared using a procedure similar to the one described for the synthesis of Example 119, except 3,3,5-trimethylcyclohexan-1-amine was used as a starting material. The title compound was obtained as a solid mixture of diastereomers (21.7 mg). $^1$H NMR (300 MHz, $CD_3OD$) δ 8.26 (s, 1H), 7.15 (s, 2H), 4.66-4.60 (m, 2H), 4.04-3.92 (m, 4H), 3.43-3.17 (m, 1H), 2.96-2.90 (m, 1H), 2.62-2.56 (m, 1H), 2.10-0.60 (m, 20H). LCMS (ESI): $[M+H]^+$: 488.4.

Example 151. 1-(5-(5-chloro-2-methoxypyridin-4-yl)-1H-pyrazole-3-carbonyl)-N-(4-(difluoromethoxy)benzyl)piperidine-4-carboxamide

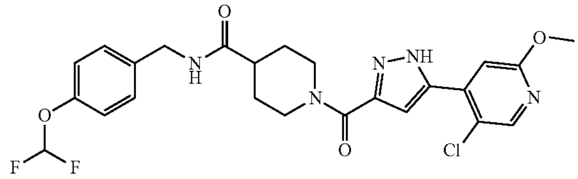 [SMILES: COc1cc(-c2cc(C(=O)N3CCC(C(=O)NCc4ccc(OC(F)F)cc4)CC3)n[nH]2)c(Cl)cn1]

The title compound was prepared using a procedure similar to the one described for the synthesis of Example 119, except (4-(difluoromethoxy)phenyl)methanamine was used as a starting material. The title compound was obtained as a solid (5.8 mg). $^1$H NMR (400 MHz, $CD_3OD$) δ 8.25 (s, 1H), 7.35-7.26 (m, 2H), 7.18-7.00 (m, 4H), 6.99-6.55 (m, 1H), 4.65 (s, 2H), 4.35 (s, 2H), 3.94 (s, 3H), 3.35-3.20 (m, 1H), 2.94 (s, 1H), 2.65-2.53 (m, 1H), 2.00-1.71 (m, 4H). LCMS (ESI): $[M+H]^+$: 520.4.

Example 152. N-(benzo[d]oxazol-6-ylmethyl)-1-(5-(5-chloro-2-methoxypyridin-4-1H-pyrazole-3-carbonyl)piperidine-4-carboxamide

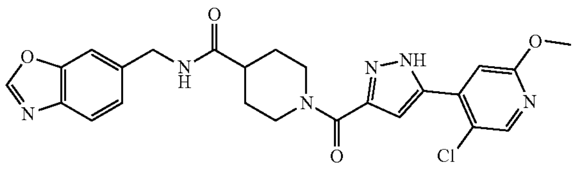 [SMILES: COc1cc(-c2cc(C(=O)N3CCC(C(=O)NCc4ccc5ncoc5c4)CC3)n[nH]2)c(Cl)cn1]

The title compound was prepared using a procedure similar to the one described for the synthesis of Example 119, except benzo[d]oxazol-6-ylmethanamine hydrochloride was used as a starting material. The title compound was obtained as a solid (8.1 mg). $^1$H NMR (300 MHz, $CD_3OD$) δ 8.45 (s, 1H), 8.30-8.24 (m, 1H), 7.71 (m, 1H), 7.65-7.57 (m, 1H), 7.41-7.33 (m, 1H), 7.15 (s, 2H), 4.69 (s, 2H), 4.53 (s, 2H), 4.29 (s, 1H), 3.96 (s, 3H), 2.96 (s, 1H), 2.75-2.52 (m, 1H), 2.05-1.63 (m, 4H). LCMS (ESI): $[M+H]^+$: 495.40.

Example 153. (R)-1-(5-(5-chloro-2-methoxypyridin-4-yl)-1H-pyrazole-3-carbonyl)-N-(1-(3-fluorophenyl)ethyl)piperidine-4-carboxamide

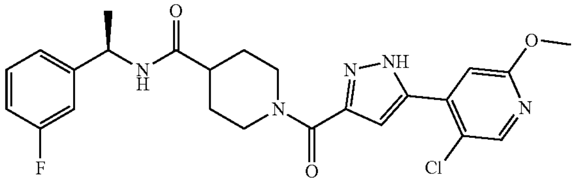 [SMILES: COc1cc(-c2cc(C(=O)N3CCC(C(=O)N[C@H](C)c4cccc(F)c4)CC3)n[nH]2)c(Cl)cn1]

The title compound was prepared using a procedure similar to the one described for the synthesis of Example 103, except (R)-1-(3-fluorophenyl)ethan-1-amine was used as the starting material. The resulting product was purified (using the following conditions: Column: Waters CSH C18, 100×19 mm, 5 μm; Mobile Phase: A: 0.1% formic acid in water; Mobile Phase: B: 0.1% formic acid in MeCN; Flow rate: 30 mL/min; Gradient: 20% B to 95% B over 8.5 min) to obtain the title compound (4.6 mg) as a solid. $^1$H NMR (400 MHz, $CD_3OD$) δ 8.25 (s, 1H), 7.36-7.27 (m, 1H), 7.13 (s, 2H), 7.11 (br s, 1H), 7.04 (br d, 1H), 6.98-6.92 (m, 1H), 5.01-4.93 (m, 1H), 4.71-4.47 (m, 2H), 3.94 (s, 3H), 3.05-2.81 (m, 1H), 2.66-2.55 (m, 1H), 1.98-1.82 (m, 2H), 1.81-1.65 (m, 2H), 1.44 (d, 3H). LCMS (ESI): 486.18 $[M+H]^+$.

Example 154. N-(5-chloro-2-fluorobenzyl)-1-(5-(5-chloro-2-methoxypyridin-4-yl)-1H-pyrazole-3-carbonyl)piperidine-4-carboxamide

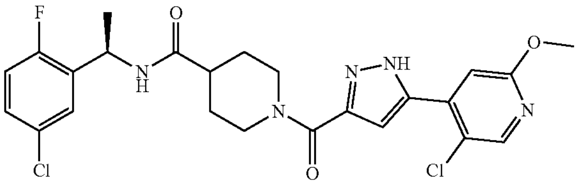 [SMILES: COc1cc(-c2cc(C(=O)N3CCC(C(=O)N[C@H](C)c4cc(Cl)ccc4F)CC3)n[nH]2)c(Cl)cn1]

The title compound was prepared using a procedure similar to the one described for the synthesis of Example 103, except (5-chloro-2-fluorophenyl)methanamine was used as the starting material to obtain the title compound (4.5 mg) as a solid. $^1$H NMR (400 MHz, $CD_3OD$) δ 8.25 (s, 1H), 7.34-7.25 (m, 2H), 7.18-7.06 (m, 3H), 4.70-4.54 (m, 2H), 4.39 (s, 2H), 3.94 (s, 3H), 3.78 (s, 1H), 3.02-2.83 (m, 1H), 2.60 (s, 1H), 1.98-1.83 (m, 2H), 1.81-1.67 (m, 2H). LCMS (ESI): 506.10 $[M+H]^+$.

Example 155. 1-(5-(5-chloro-2-methoxypyridin-4-yl)-1H-pyrazole-3-carbonyl)-N-(2,3-difluorobenzyl)piperidine-4-carboxamide

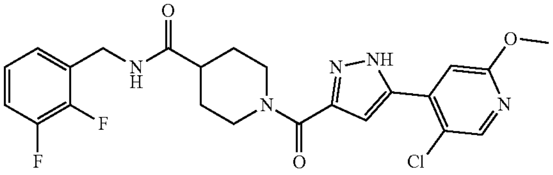 [SMILES: COc1cc(-c2cc(C(=O)N3CCC(C(=O)NCc4cccc(F)c4F)CC3)n[nH]2)c(Cl)cn1]

The title compound was prepared using a procedure similar to the one described for the synthesis of Example 103, except (2,3-difluorophenyl)methanamine was used as the starting material to obtain the title compound (5.4 mg) as a solid. LCMS (ESI): 490.14 $[M+H]^+$.

Example 156. N-(3-chloro-2-fluorobenzyl)-1-(5-(5-chloro-2-methoxypyridin-4-yl)-1H-pyrazole-3-carbonyl)piperidine-4-carboxamide

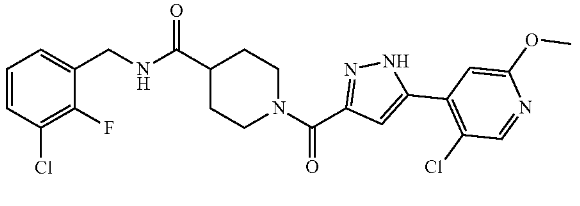 [SMILES: COc1cc(-c2cc(C(=O)N3CCC(C(=O)NCc4cccc(Cl)c4F)CC3)n[nH]2)c(Cl)cn1]

The title compound was prepared using a procedure similar to the one described for the synthesis of Example 103, except (3-chloro-2-fluorophenyl)methanamine was used as the starting material to obtain the title compound (6.6 mg) as a solid. $^1$H NMR (400 MHz, $CD_3OD$) δ 8.26 (s, 1H), 7.39 (t, 1H), 7.28 (t, 1H), 7.18-7.10 (m, 3H), 4.65 (br s, 2H), 4.45 (s, 2H), 3.96 (s, 3H), 3.03-2.86 (m, 1H), 2.67-2.57 (m, 1H), 1.97-1.84 (m, 2H), 1.76 (br d, 2H) LCMS (ESI): 506.10 $[M+H]^+$.

Example 157. 1-(5-(5-chloro-2-methoxypyridin-4-yl)-1H-pyrazole-3-carbonyl)-N-(3-fluorobenzyl)piperidine-4-carboxamide

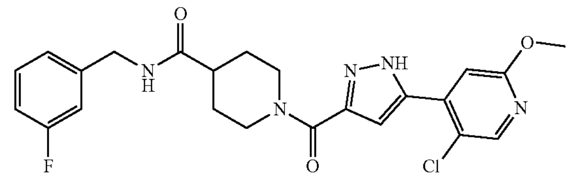 [SMILES: COc1cc(-c2cc(C(=O)N3CCC(C(=O)NCc4cccc(F)c4)CC3)n[nH]2)c(Cl)cn1]

The title compound was prepared using a procedure similar to the one described for the synthesis of Example 103, except (3-fluorophenyl)methanamine was used as the starting material to obtain the title compound (6.4 mg) as a solid. $^1$H NMR (400 MHz, $CD_3OD$) δ 8.25 (s, 1H), 7.35-7.28 (m, 1H), 7.14 (s, 2H), 7.09 (d, 1H), 7.03-6.94 (m, 2H), 4.75-4.53 (m, 2H), 4.37 (s, 2H), 3.94 (s, 3H), 3.02-2.83 (m, 1H), 2.60 (br s, 1H), 1.98-1.84 (m, 2H), 1.84-1.69 (m, 2H). LCMS (ESI): 472.19 $[M+H]^+$.

Example 158. 1-(5-(5-chloro-2-methoxypyridin-4-yl)-1H-pyrazole-3-carbonyl)-N-((3,4-dihydro-2H-pyran-2-yl)methyl)piperidine-4-carboxamide

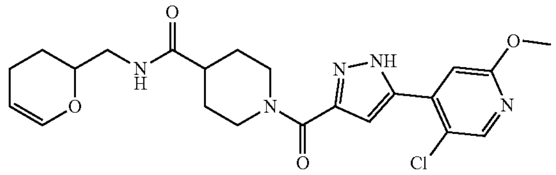 [SMILES: COc1cc(-c2cc(C(=O)N3CCC(C(=O)NCC4CCC=CO4)CC3)n[nH]2)c(Cl)cn1]

The title compound was prepared using a procedure similar to the one described for the synthesis of Example 103, except (3,4-dihydro-2H-pyran-2-yl)methanamine was used as the starting material to obtain the title compound (4.0 mg) as a solid of enantiomers. LCMS (ESI): 460.19 $[M+H]^+$.

Example 159. N-(3-chlorobenzyl)-1-(5-(5-fluoro-2-methoxypyridin-4-yl)-1H-pyrazole-3-carbonyl)piperidine-4-carboxamide

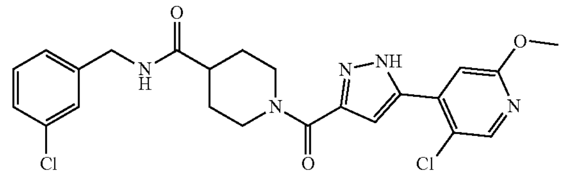 [SMILES: COc1cc(-c2cc(C(=O)N3CCC(C(=O)NCc4cccc(Cl)c4)CC3)n[nH]2)c(Cl)cn1]

Step-1. Methyl 1-[5-(5-fluoro-2-methoxypyridin-4-yl)-1-oxan-2-yl)pyrazole-3-carbonyl]piperidine-4-carboxylate

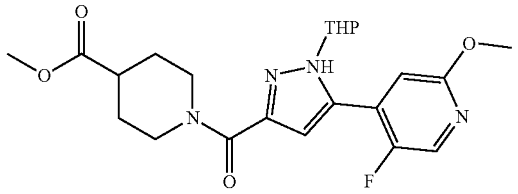

5-fluoro-2-methoxypyridin-4-ylboronic acid (514.0 mg, 3.0 mmol), Pd(dppf)$Cl_2$ (361.0 mg, 0.5 mmol), and $K_3PO_4$ (1.59 g, 7.5 mmol) were added to a solution of methyl1-[5-bromo-1-(oxan-2-yl)pyrazole-3-carbonyl]piperidine-4-carboxylate (INTERMEDIATE 504, 1.0 g, 2.5 mmol) in 1,4-dioxane (10.0 mL) and $H_2O$ (2.5 mL). The solution was stirred at 80° C. for 2 h under $N_2$ atmosphere. The solution was then concentrated under vacuum, and the residue was purified by silica gel column chromatography (DCM/MeOH, 10/1 v/v) to obtain the title compound (1.06 g) as an oil. LCMS (ESI): 447.2 $[M+H]^+$.

Step-2. 1-[5-(5-fluoro-2-methoxypyridin-4-yl)-1-(oxan-2-yl)pyrazole-3-carbonyl]piperidine-4-carboxylic acid

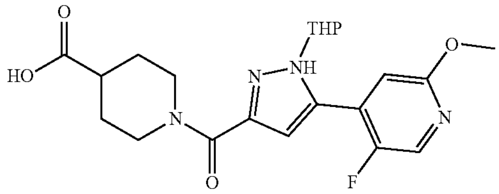

LiOH (342.0 mg, 14.3 mmol) was added to a solution of methyl 1-[5-(5-fluoro-2-methoxypyridin-4-yl)-1-(oxan-2-yl)pyrazole-3-carbonyl]piperidine-4-carboxylate (Step-1, 1.06 g, 2.4 mmol) in THF (4.0 mL), MeOH (4.0 mL), and $H_2O$ (4.0 mL). The solution was stirred at 25° C. for 1 h, then concentrated under vacuum. The residue was diluted with DCM, then the pH of the solution was adjusted to pH 6 with AcOH. The resulting mixture was concentrated under vacuum to afford the title compound (940 mg) as a yellow oil. LCMS (ESI): $[M+H]^+$: 433.2.

Step-3. N-[(3-chlorophenyl)methyl]-1-[5-(5-fluoro-2-methoxypyridin-4-yl)-1-(oxan-2-yl)pyrazole-3-carbonyl]piperidine-4-carboxamide

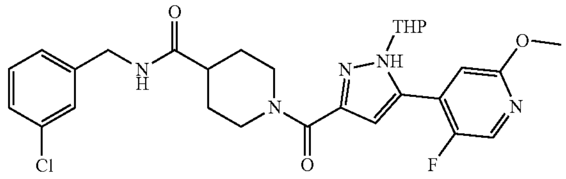

1-(3-chlorophenyl)methanamine (49.1 mg, 0.3 mmol), HAM (131.9 mg, 0.3 mmol) and DIPEA (89.7 mg, 0.7 mmol) were added to a solution of 1-[5-(5-fluoro-2-methoxypyridin-4-yl)-1-(oxan-2-yl)pyrazole-3-carbonyl]piperidine-4-carboxylic acid (Step-2, 100.0 mg, 0.2 mmol) in DMF (1.0 mL). The solution was stirred at 25° C. for 4 h, then diluted with EtOAc and washed with water. The organic layer was concentrated under vacuum, and then the residue was purified by silica gel column chromatography (DCM/MeOH, 10/1 v/v) to obtain the title compound (55 mg) as an oil. LCMS (ESI): 556.2 $[M+H]^+$.

Step-4. N-(3-chlorobenzyl)-1-(5-(5-fluoro-2-methoxypyridin-4-yl)-1H-pyrazole-3-carbonyl)piperidine-4-carboxamide

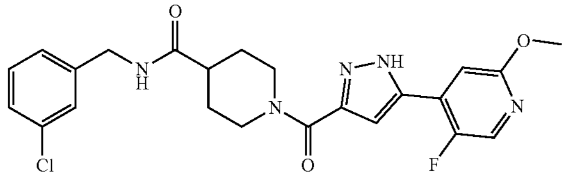 [SMILES: COc1cc(-c2cc(C(=O)N3CCC(C(=O)NCc4cccc(Cl)c4)CC3)n[nH]2)c(F)cn1]

TFA (2.0 mL) was added to a solution of N-[(3-chlorophenyl)methyl]-1-[5-(5-fluoro-2-methoxypyridin-4-yl)-1-(oxan-2-yl)pyrazole-3-carbonyl]piperidine-4-carboxamide (Step-3, 55.0 mg, 0.1 mmol) in DCM (2.0 mL). The solution was stirred at 25° C. for 1 h, then concentrated under vacuum. The residue was diluted with DOM, and then the pH of the solution was adjusted to pH 8 with DIPEA. The solution was then concentrated under vacuum and the residue was purified by Prep-HPLC (using the following conditions: Column: XBridge Shield RP18 OBD, 30×150 mm, μm; Mobile Phase A: Water (10 mM $NH_4HCO_3$); Mobile Phase B: MeCN; Gradient: 33% B up to 50% B in 7 min; Detection: 220/254 nm) to obtain the title compound (2.9 mg) as a solid. $^1H$ NMR (300 MHz, DMSO-$d_6$) δ 14.09-13.90 (m, 1H), 8.54-8.37 (m, 1H), 8.27 (d, 1H), 7.39-7.25 (m, 4H), 7.22-7.17 (m, 1H), 7.04 (d, 1H), 4.46 (s, 2H), 4.27 (d, 2H), 3.87 (s, 3H), 2.93-2.68 (m, 1H), 2.51 (d, 1H), 1.81 (s, 2H), 1.56 (s, 2H), 1.23 (s, 1H). LCMS (ESI): 472.2 $[M+H]^+$.

Example 160. A Diastereomeric Mixture of (1R,3s,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide and (1R,3r,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide

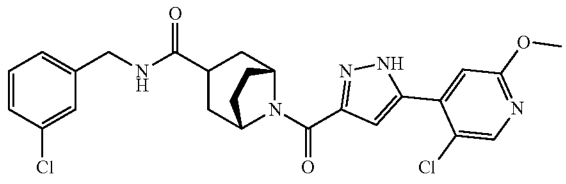

-continued

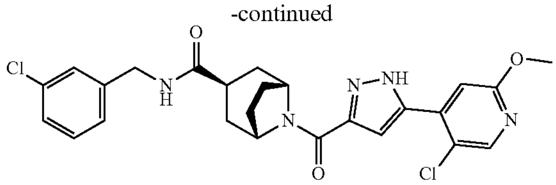

Step-1. tert-butyl 3-((3-chlorobenzyl)carbamoyl)-8-azabicyclo[3.2.1]octane-8-carboxylate

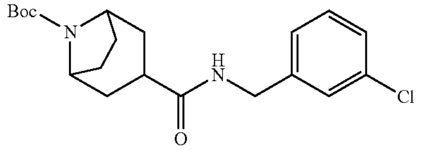 [SMILES: CC(C)(C)OC(=O)N1C2CCC1CC(C(=O)NCc1cccc(Cl)c1)C2]

HATU (536.1 mg, 1.41 mmol) and 8-(tert-butoxycarbonyl)-8-azabicyclo[3.2.1]octane-3-carboxylic acid (300.0 mg, 1.18 mmol) were added to a stirred solution of 1-(3-chlorophenyl)methanamine (183.0 mg, 1.29 mmol) and DIPEA (455.6 mg, 3.53 mmol) in DMF (5.00 mL). The resulting mixture was stirred at 25° C. for 2 h. The resulting mixture was diluted with EtOAc and washed with water. The organic layers were dried over anhydrous $Na_2SO_4$. After filtration, the filtrate was concentrated under reduced pressure. The residue was purified by silica gel column chromatography (EtOAc/petroleum ether, 1/1 v/v) to obtain the title compound (440.0 mg) as a solid mixture of diastereomers. LCMS: ESI $[M+H]^+$: 379.2.

Step-2. N-(3-chlorobenzyl)-8-azabicyclo[3.2.1]octane-3-carboxamide

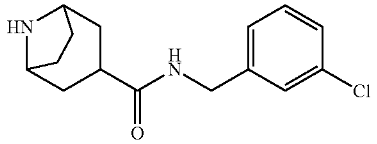 [SMILES: O=C(NCc1cccc(Cl)c1)C1CC2CCC(C1)N2]

TFA (1.00 mL) was added to a stirred solution of tert-butyl 3-[[(3-chlorophenyl)methyl]carbamoyl]-8-azabicyclo[3,2,1]octane-8-carboxylate (Step-1, 440.0 mg, 1.16 mmol) in DCM (5.00 mL). The resulting mixture was stirred at 25° C. for 1 h. The resulting mixture was concentrated under reduced pressure to obtain the title compound (300.0 mg) as a solid mixture of diastereomers. LCMS: ESI $[M+H]^+$: 279.1.

Step-3. 8-(5-bromo-1H-pyrazole-3-carbonyl)-N-(3-chlorobenzyl)-8-azabicyclo[3.2.1]octane-3-carboxamide

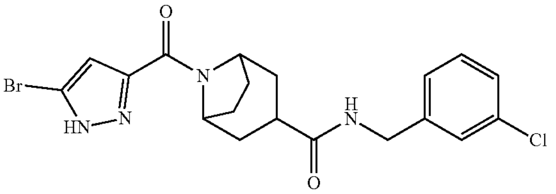 [SMILES: O=C(NCc1cccc(Cl)c1)C1CC2CCC(C1)N2C(=O)c1cc(Br)[nH]n1]

HATU (491.0 mg, 1.29 mmol) and 5-bromo-1H-pyrazole-3-carboxylic acid (205.5 mg, 1.08 mmol) were added to a stirred solution of N-[(3-chlorophenyl)methyl]-8-azabicyclo[3.2.1]octane-3-carboxamide (Step-2, 300.0 mg, 1.08 mmol) and DIPEA (417.2 mg, 3.23 mmol) in DMF (5.00 mL). The resulting mixture was stirred at 25° C. for 2 h. The resulting mixture was diluted with EtOAc and washed with water. The organic layers were dried over anhydrous $Na_2SO_4$. After filtration, the filtrate was concentrated under reduced pressure. The residue was purified by silica gel column chromatography (EtOAc/petroleum ether, 1/1 v/v) to obtain the title compound (350.0 mg) as a solid mixture of diastereomers. ESI $[M+H]^+$: 451.2

Step-4. 8-(5-bromo-1-(tetrahydro-2H-pyran-2-yl)-1H-pyrazole-3-carbonyl)-N-(3-chlorobenzyl)-8-azabicyclo[3.2.1]octane-3-carboxamide

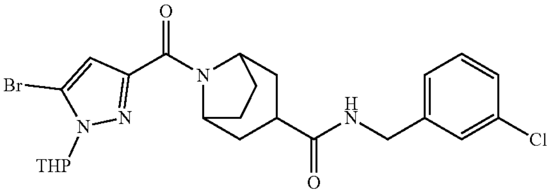

DHP (130.3 mg, 1.55 mmol) was added to a stirred solution of 8-(5-bromo-1H-pyrazole-3-carbonyl)-N-[(3-chlorophenyl)methyl]-8-azabicyclo[3.2.1]octane-3-carboxamide (Step-3, 350.0 mg, 0.78 mmol) in THF (5.00 mL). The resulting mixture was stirred at 25 for 1 h. The resulting mixture was concentrated under reduced pressure. The residue was purified by silica gel column chromatography (EtOAc/petroleum ether, 1/1 v/v) to obtain the title compound (240.0 mg) as a solid mixture of diastereomers. LCMS: ESI $[M+H]^+$: 535.3.

Step-5. N-(3-chlorobenzyl)-8-(5-(5-fluoro-2-methoxypyridin-4-yl)-1-(tetrahydro-2H-pyran-2-yl)-1H-pyrazole-3-carbonyl)-8-azabicyclo[3.2.1]octane-3-carboxamide

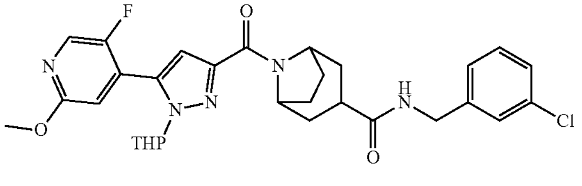

$K_2CO_3$ (185.7 mg, 1.34 mmol) and $Pd(dppf)Cl_2$ (32.8 mg, 0.05 mmol) were added to a mixture of 8-[5-bromo-1-(oxan-2-yl)pyrazole-3-carbonyl]-N-[(3-chlorophenyl)methy 1]-8-azabicyclo[3.2.1]octane-3-carboxamide (Step-4, 240.0 mg, 0.45 mmol) and 5-fluoro-2-methoxypyridin-4-ylboronic acid (114.8 mg, 0.67 mmol) in 1,4-dioxane (5.00 mL) and $H_2O$ (1.00 mL). The resulting mixture was stirred at 90° C. for 2 h. The resulting mixture was concentrated under reduced pressure. The residue was purified by silica gel column chromatography (EtOAc/petroleum ether, 1/1 v/v) to obtain the title compound (200.0 mg) as a solid mixture of diastereomers. LCMS: ESI $[M+H]^+$: 582.1.

Step-6. Diastereomeric mixture of (1R,3s,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide and (1R,3r,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide

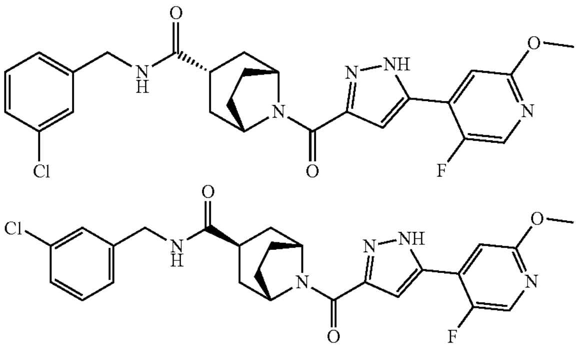

TFA (1.00 mL) was added to a stirred solution of N-[(3-chlorophenyl)methyl]-8-[5-(5-fluoro-2-methoxypyridin-4-yl)-1-(oxan-2-yl)pyrazole-3-carbonyl]-8-azabicyclo[3.2.1]octane-3-carboxamide (Step-5, 180.0 mg, 0.31 mmol) in DCM (5.00 mL). The resulting mixture was stirred at 25° C. for 1 h. The resulting mixture was concentrated under reduced pressure. The residue was purified by Prep-HPLC (using the following conditions: Column: XSelect CSH Prep C18 OBD Column, 5 μm, 19×150 mm; Mobile Phase A: Water (0.05% FA), Mobile Phase B: MeCN; Flow rate: 25 mL/min; Gradient: 37 B to 48 B in 8 mitt; Detector, UV 254 nm) to obtain the title compound (48.5 mg) as a solid mixtures of two diastereomers (Example 160). $^1H$ NMR (400 MHz, DMSO-$d_6$) δ 8.44-8.36 (m, 1H), 8.29-8.27 (m, 1H), 7.39-7.25 (m, 4H), 7.22-7.16 (m, 2H), 5.01-4.92 (m, 1H), 4.72 (s, 1H), 4.25 (d, 2H), 3.88 (s, 3H), 2.97-2.86 (m, 1H), 2.04-1.65 (m, 9H). LCMS (ESI): $[M+H]^+$: 498.1.

Example 160-A. (1R,3s,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide

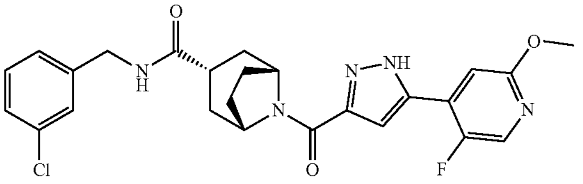 [SMILES: COc1cc(-c2cc(C(=O)N3[C@@H]4CC[C@H]3C[C@H](C(=O)NCc3cccc(Cl)c3)C4)n[nH]2)c(F)cn1]

A solution of 5-(5-fluoro-2-methoxypyridin-4-yl)-1H-pyrazole-3-carboxylic acid (INTERMEDIATE 507, 59.8 mg, 0.3 mmol), EDI (48.3 mg, 0.3 mmol), and HOBt (34.1 mg, 0.3 mmol) in DMF (2.0 mL) was stirred at 25° C. for 40 min, then (1R,3s,5S)—N-(3-chlorobenzyl)-8-azabicyclo[3.2.1]octane-3-carboxamide (INTERMEDIATE 519, 58.5 mg, 0.2 mmol) and DIPEA (0.18 mL, 1.1 mmol). The solution was stirred at 25° C. for 14 h, then diluted with EtOAc, washed with water, and the organic layer was concentrated. The residue was purified by Prep-HPLC (using the following conditions: Column: Xselect CSH OBD, 30×150 mm, 5 μm; Mobile Phase A: Water (10 mM $NH_4HCO_3$); Mobile Phase B: MeCN; Flow rate: 60 ml/min; Gradient: 36% B to 55% B in 8 min; Detection: 220/254 nm) to obtain the title compound (20 mg) as a solid. $^1$H NMR (400 MHz, $CD_3OD$) δ 8.14 (d, 1H), 7.43-7.06 (m, 6H), 5.51-4.92 (m, 2H), 4.35 (s, 2H), 3.94 (s, 3H), 3.08-2.94 (m, 1H), 2.24-1.99 (m, 4H), 1.97-1.75 (m, 4H). LCMS (ESI): 498.20 $[M+H]^+$.

Example 160-B. (1R,3r,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide

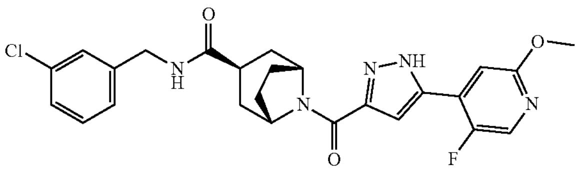 [SMILES: COc1cc(-c2cc(C(=O)N3[C@@H]4CC[C@H]3C[C@@H](C(=O)NCc3cccc(Cl)c3)C4)n[nH]2)c(F)cn1]

The title compound was prepared using a procedure similar to the one described for the synthesis of Example 160-A, except (1R,3r,5S)-8-(tert-butoxycarbonyl)-8-azabicyclo[3.2.1]octane-3-carboxylic acid was used as starting in Step-1. The title compound was obtained as a solid (4.7 mg). $^1$H NMR (300 MHz, DMSO-$d_6$) δ 14.03 (s, 1H), 8.40 (t, 1H), 8.28 (d, 7.41-7.26 (m, 4H), 7.26-7.18 (m, 1H), 7.13 (d, 1H), 4.89 (s, 1H), 4.61 (s, 1H), 4.30 (d, 2H), 3.87 (s, 3H), 2.61 (s, 1H), 2.25-2.04 (m, 4H), 1.83 (s, 2H), 1.75 (s, 2H). LCMS (ESI): $[M+H]^+$: 498.3.

Example 161. N-(3-chlorobenzyl)-1-(5-(5-fluoro-2-methoxypyridin-4-yl)-1H-pyrazole-3-carbonyl)-N-methylpiperidine-4-carboxamide

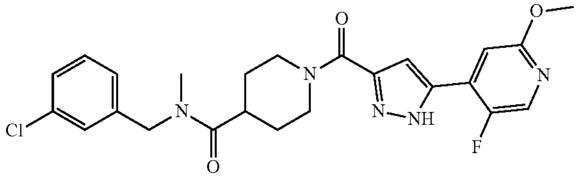 [SMILES: COc1cc(-c2cc(C(=O)N3CCC(C(=O)N(C)Cc4cccc(Cl)c4)CC3)n[nH]2)c(F)cn1]

The title compound was prepared using a procedure similar to the one described for the synthesis of Example 104, except 1-(3-chlorophenyl)-N-methylmethanamine was used as starting material in Step-3. The resulting residue was purified by Prep-HPLC (using the following conditions: Column: XBridge Shield RP18 OBD Column, 30×150 mm, 5 μm; mobile phase A: Water (10 mM $NH_4HCO_3$), mobile phase B: MeCN; Gradient: 37% B to 50% B in 7 min; Detector, UV 254/220 nm) to obtain the title compound (8.2 mg) as a solid. $^1$H NMR (300 MHz, DMSO-$d_6$) δ 14.12-13.87 (m, 1H), 8.28 (d, 1H), 7.50-7.22 (m, 4H), 7.15 (d, 1H), 7.11-6.96 (m, 1H), 4.70 (s, 1H), 4.51 (s, 3H), 4.11 (s, 1H), 3.87 (s, 3H), 3.02 (s, 3H), 2.79 (s, 1H), 2.73 (s, 1H), 1.90-1.42 (m, 4H). LCMS (ESI): $[M+H]^+$: 486.3.

Example 162. 1-(5-(5-chloro-2-methoxypyridin-4-yl)-1H-pyrazole-3-carbonyl)-N-(1-(trifluoromethyl)cyclopentyl)piperidine-4-carboxamide

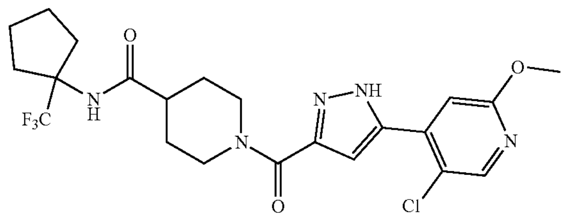 [SMILES: COc1cc(-c2cc(C(=O)N3CCC(C(=O)NC4(C(F)(F)F)CCCC4)CC3)n[nH]2)c(Cl)cn1]

Oxalyl dichloride (41 mg, 0.33 mmol) and DMF (1 drop) were added to a stirred solution of 1-[5-(5-chloro-2-methoxypyridin-4-yl)-1H-pyrazole-3-carbonyl]piperidine-4-carboxylic acid (INTERMEDIATE 503, 20.0 mg, 0.06 mmol) in DCM (2.0 mL). The resulting mixture was stirred at 30° C. for 3 h. The resulting mixture was concentrated under vacuum. The residue was dissolved in chloroform (1.0 mL). A solution of 1-(trifluoromethyl)cyclopentan-1-amine hydrochloride (21 mg, 0.11 mmol), DIPEA (29.0 μL, 0.17 mmol) and DMAP (6.7 mg, 0.06 mmol) in chloroform (1.0 mL) was added to the reaction mixture above. The resulting mixture was stirred at 50° C. for 24 h. The resulting mixture was concentrated under vacuum and the residue was dissolved in DMF (1.0 mL), filtered. Purification by Prep-HPLC (using the following conditions: Column: XBridge BEH130 Prep C18 OBD Column, 130 Å, 19×150 mm 5 μm 13 nm; Mobile phase A: Water (20 mM $NH_4HCO_3$), mobile phase MeCN; Detector, UV 254/210 nm) yielded the title compound (1.6 mg) as a solid. LCMS (ESI): $[M+H]^+$: 500.51.

Example 163. 1-(5-(5-chloro-2-methoxypyridin-4-yl)-1H-pyrazole-3-carbonyl)-N (1,4-dimethylcyclohexyl)piperidine-4-carboxamide

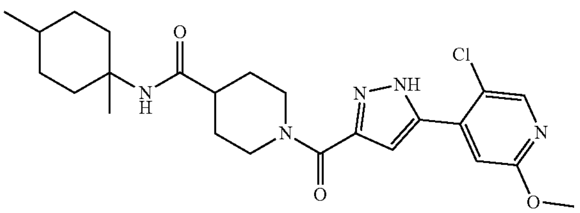

HATU (10.4 mg, 0.03 mmol) and 1,4-dimethylcyclohexan-1-amine (17.4 mg, 0.14 mmol) were added to a stirred solution of 1-[5-(5-chloro-2-methoxypyridin-4-yl)-1H-pyrazole-3-carbonyl]piperidine-4-carboxylic acid (INTERMEDIATE 503, 10.0 mg, 0.03 mmol) and DIPEA (10.6 mg, 0.08 mmol) in DMF (274 μl). The resulting mixture was stirred at 25° C. for 18 h. The resulting mixture was diluted with EtOAc and washed with water. The organic layers were dried over anhydrous $Na_2SO_4$. After filtration, the filtrate was concentrated under reduced pressure. The residue was purified by Prep-HPLC (using the following conditions: Column: Waters CSH C18 column, 19×100 mm, 5 μm; Mobile phase A: water (0.1% formic acid), Mobile phase B: MeCN (0.1% formic acid); Detector: Waters 2489 dual wavelength UV detector; Flow rate: 30 mL/min) to obtain the title compound (9.6 mg) as a solid mixture of diastereomers. $^1$H NMR (400 MHz, $CD_3OD$) δ 8.26 (s, 1H), 7.14 (s, 3H), 4.62-4.71 (m, 1H) 3.95 (s, 3H); 3.18-3.28 (m, 1H), 2.78-3.04 (m, 1H), 2.46-2.68 (m, 1H), 2.26 (br d, 2H), 1.64-1.96 (m, 5H), 1.51 (br d, 2H), 1.20-1.38 (m, 7H), 1.12 (br t, 2H), 0.90 (br d, 3H). LCMS (ESI): $[M+H]^+$: 474.3.

Example 164. 1-(5-(5-chloro-2-methoxypyridin-4-yl)-1H-pyrazole-3-carbonyl)-N-(4-(trifluoromethoxy)benzyl)piperidine-4-carboxamide

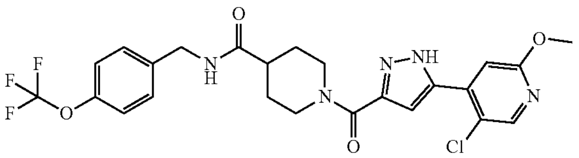 [SMILES: COc1cc(-c2cc(C(=O)N3CCC(C(=O)NCc4ccc(OC(F)(F)F)cc4)CC3)n[nH]2)c(Cl)cn1]

The title compound was prepared using a procedure similar to the one described for the synthesis of Example 103, except (4-(trifluoromethoxy)phenyl)methanamine was used as starting material. The solution was diluted with water and EtOAc, then the organic layer was dried over anhydrous sodium sulfate, filtered, and the solvent was evaporated. The resulting residue was purified by silica gel column chromatography (DCM/MeOH, 10/1 v/v) obtain the title compound (8.4 mg) as a solid. $^1$H NMR (400 MHz, $CD_3OD$) δ 8.27 (s, 1H), 7.38 (d, 2H), 7.24 (d, 2H), 7.15 (s, 2H), 4.61-4.73 (m, 1H), 4.40 (s, 2H), 3.96 (s, 3H), 3.33-3.37 (m, 2H), 2.88-3.03 (m, 1H), 2.61 (s, 1H), 1.84-2.00 (m, 2H), 1.69-1.83 (m, 2H). LCMS (ESI): 538.15 $[M+H]^+$.

Example 165. N-(bicyclo[3.2.1]octan-8-yl)-1-(5-(5-fluoro-2-methoxypyridin-4-yl)-1H-pyrazole-3-carbonyl)piperidine-4-carboxamide

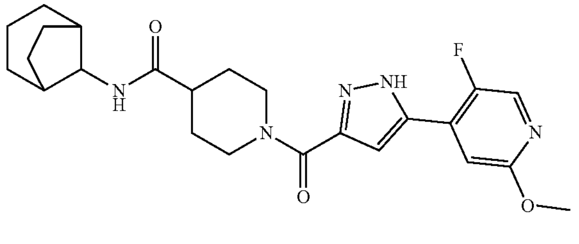 [SMILES: COc1cc(-c2cc(C(=O)N3CCC(C(=O)NC4C5CCCC4CC5)CC3)n[nH]2)c(F)cn1]

The title compound was prepared using a procedure similar to the one described for the synthesis of Example 104, except bicyclo[3.2.1]octan-8-amine was used as starting material in Step-3. The resulting residue was purified by Prep-HPLC (using the following conditions: Column: YMC-Actus Triart C18, 20×250 mm, 5 μm 12 nm; mobile phase A: Water (10 mM $NR_4HCO_3$), mobile phase B: MeCN; Gradient: 44% B to 74% B in 7 min; Detector, UV 254/220 nm) to obtain the title compound (10.3 mg) as a solid mixture of diastereomers, NMR (400 MHz, $CD_3OD$) δ 8.15 (d, 1H), 7.33-7.24 (m, 1H), 7.11 (d, 1H), 4.76-4.47 (m, 3H), 3.95 (s, 3H), 3.79-3.75 (m, 1H), 2.96 (s, 1H), 2.84-2.69 (m, 1H), 2.16 (s, 2H), 1.99-1.55 (m, 12H), 1.50-1.41 (m, 1H), 1.36-1.23 (m, 2H). LCMS (ESI): $[M+H]^+$: 456.2.

Example 166. N-[(3-chlorophenyl)methyl]-1-[5-(5-fluoro-2-methoxypyridin-4-yl)-1H-1,2,4-triazole-3-carbonyl]piperidine-4-carboxamide

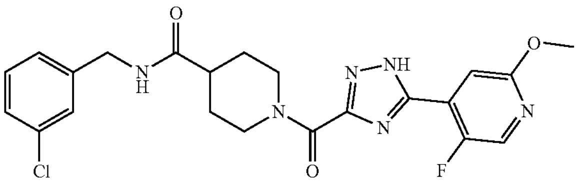

Step-1. Ethyl 1-(5-bromo-1H-1,2,4-triazole-3-carbonyl)piperidine-4-carboxylate

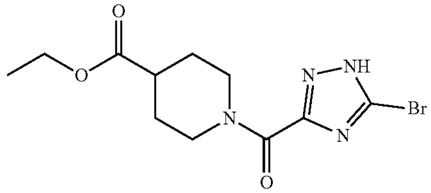 [SMILES: CCOC(=O)C1CCN(C(=O)c2n[nH]c(Br)n2)CC1]

EDCI (460.2 mg, 2.4 mmol) and HOBt (324.3 mg, 2.4 mmol) were added to a solution of 5-bromo-1H-1,2,4-triazole-3-carboxylic acid (384.0 mg, 2.0 mmol) in DMF (2.0 mL), then the solution was stirred at 25° C. for 20 min. Ethyl piperidine-4-carboxylate (377.4 mg, 2.4 mmol) and DIPEA (1.05 mL, 6.0 mmol) were then added, and the solution was stirred at 25° C. for 14 h. The solution was concentrated, then the residue was purified by Prep-HPLC (conditions??) to obtain the title compound (400 mg) as an oil. LCMS (ESI): 331.0 $[M+H]^+$.

Step-2. 1-(5-bromo-1-[[2-(trimethylsilyl)ethoxy]methyl]-1,2,4-triazole-3-carbonyl)piperidine-4-carboxylate

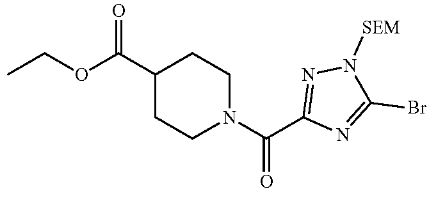 [SMILES: CCOC(=O)C1CCN(C(=O)c2nc(Br)n(COCC[Si](C)(C)C)n2)CC1]

SEMCl (184.3 mg, 1.1 mmol) and $K_2CO_3$ (152.7 mg, 1.1 mmol) were added to a stirred solution of ethyl 1-(5-bromo-1H-1,2,4-triazole-3-carbonyl)piperidine-4-carboxylate (Step-1, 305.0 mg, 0.9 mmol) in DMF (2.0 mL) at 0° C. The solution was stirred at 0° C. for 3 h, then diluted with EtOAc, washed with water, and concentrated to obtain the title compound (250 mg), which was used in the next step without further purification. LCMS (ESI): 461.1 $[M+H]^+$.

Step-3. 1-[5-(5-fluoro-2-methoxypyridin-4-yl)-1-[[2-(trimetliyisilyl)ethoxy]methyl]-1,2,4-triazole-3-carbonyl]piperidine-4-carboxylate

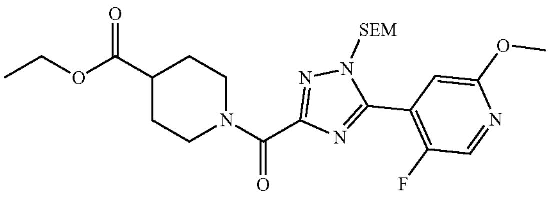 [SMILES: CCOC(=O)C1CCN(C(=O)c2nc(-c3cc(OC)ncc3F)n(COCC[Si](C)(C)C)n2)CC1]

5-fluoro-2-methoxypyridin-4-ylboronic acid (170.4 mg, 0.99 mmol), $Pd(dppf)Cl_2$ (72.9 mg, 0.1 mmol), and $K_3PO_4$ (211.61 mg, 0.997 mmol) were added to a solution of ethyl 1-(5-bromo-1-[[2-(trimethylsilyl)ethoxy]methyl]-1,2,4-triazole-3-carbonyl)piperidine-4-carboxylate (used directly from Step-2) in 1,4-dioxane (5.00 mL) and $H_2O$ (0.50 mL). The solution was stirred at 80° C. under $N_2$ atmosphere for 4 h, then concentrated under reduced pressure. The residue was purified by silica gel column chromatography (petroleum ether/EtOAc, 4/1 v/v) to obtain the title compound (110 mg) as a solid. LCMS (ESI): 508.2 $[M+H]^+$.

Step-4. 1-[1-(5-fluoro-2-methoxypyridin-4-yl)-1-[[2-(trimethylsilyl)ethoxy]methyl]-1,2,4-triazole-3-carbonyl]piperidine-4-carboxylic acid

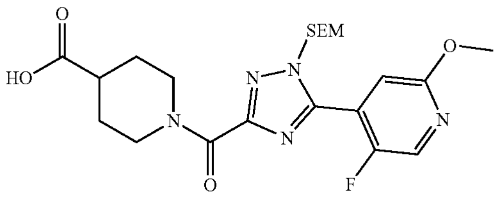 [SMILES: COc1cc(-c2nc(C(=O)N3CCC(C(=O)O)CC3)nn2COCC[Si](C)(C)C)c(F)cn1]

LiOH (18.2 mg, 0.4 mmol) was added to a stirred solution of ethyl 1-[5-(5-fluoro-2-methoxypyridin-4-yl)-1-[[2-(trimethylsilyl)ethoxy]methyl]-1,2,4-triazole-3-carbonyl]piperidine-4-carboxylate (Step-4, 110.0 mg, 0.2 mmol) in THF (1.5 mL), $H_2O$ (1.5 mL) and MeOH (1.5 mL). The solution was stirred at 25° C. for 30 min, then the pH was adjusted to pH 3 with HCl (6 M). The aqueous layer was extracted with EtOAc, then the organic layer was concentrated to obtain the title compound (100 mg), which was used in the next step without further purification. LCMS (ESI): 480.2 $[M+H]^+$.

Step-5. N-[(3-chlorophenyl)methyl]-1-[5-(5-fluoro-2-methoxypyridin-4-yl)-1-[[2-(trimethylsilyl)ethoxy]methyl]-1,2,4-triazole-3-carbonyl]piperidine-4-carboxamide

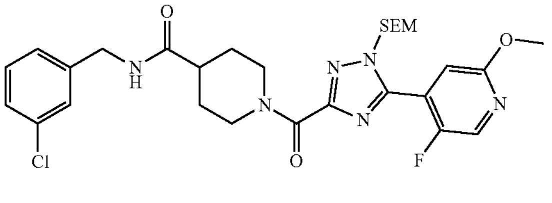 [SMILES: COc1cc(-c2nc(C(=O)N3CCC(C(=O)NCc4cccc(Cl)c4)CC3)nn2COCC[Si](C)(C)C)c(F)cn1]

HATU (95.1 mg, 0.3 mmol) 1-(3-chlorophenyl)methanamine (35.4 mg, 0.3 mmol) and DIPEA (80.9 mg, 0.6 mmol) were added to a stirred solution of 1-[5-(5-fluoro-2-methoxypyridin-4-yl)-1-[[2-(trimethylsilyl)ethoxy]methyl]-1,2,4-triazole-3-carbonyl]piperidine-4-carboxylic acid (used directly from Step-4) in DMF (1.0 mL). The solution was stirred at 25° C. for 14 h, then diluted with EtOAc, washed with water, and concentrated to obtain the title compound (120 mg), which was used in the next step without further purification. LCMS (ESI): 603.2 $[M+H]^+$.

Step-6. N-[(3-chlorophenyl)methyl]-1-[5-(5-fluoro-2-methoxypyridin-4-yl)-1H-1,2,4-triazole-3-carbonyl]piperidine-4-carboxamide

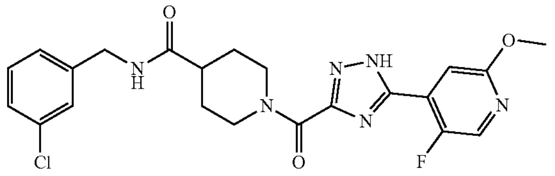 [SMILES: COc1cc(-c2nc(C(=O)N3CCC(C(=O)NCc4cccc(Cl)c4)CC3)n[nH]2)c(F)cn1]

TFA (1.0 mL) was added to a stirred solution of N-[(3-chlorophenyl)methyl]-1-[5-(5-fluoro-2-methoxypyridin-4-yl)-1-[[2-(trimethylsilyl)ethoxy]methyl]-1,2,4-triazole-3-carbonyl]piperidine-4-carboxamide (used directly from Step-5) in DCM (1.0 mL). The solution was stirred at 25° C. for 2 h, then concentrated under reduced pressure. The residue was purified by Prep-HPLC (using the following conditions: Column: XBridge Prep C18 OBD, 30×50 mm, 5 μm, 13 nm; Mobile Phase A: Water (10 mM $NH_4HCO_3$); Mobile Phase B: MeOH; Flow rate: 25 mL/min; Gradient: 46% B to 69% B in 7 min; Detection: 254 nm) to obtain the title compound (32.8 mg) as a solid. $^1H$ NMR (300 MHz, $CD_3OD$) δ 8.23-8.16 (m, 1H), 7.41 (d, 1H), 7.37-7.27 (m, 2H), 7.33-7.18 (m, 2H), 4.95-4.85 (m, 1H), 4.70 (d, 1H), 4.37 (s, 2H), 3.95 (s, 3H), 3.37-3.25 (m, 1H), 3.00 (t, 1H), 2.76-2.51 (m, 1H), 2.05-1.66 (m, 4H). LCMS (ESI): 473.1 $[M+H]^+$.

Example 167. 1-(5-(5-chloro-2-methoxypyridin-4-yl)-1H-pyrazole-3-carbonyl)-N-((2-oxoindolin-5-yl)methyl)piperidine-4-carboxamide

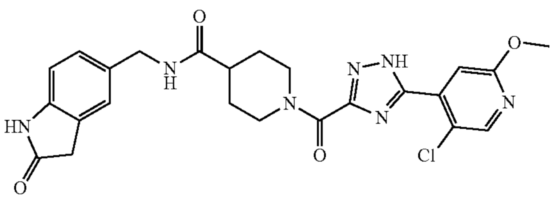 [SMILES: COc1cc(-c2nc(C(=O)N3CCC(C(=O)NCc4ccc5c(c4)CC(=O)N5)CC3)n[nH]2)c(Cl)cn1]

The title compound was prepared using a procedure similar to the one described for the synthesis of Example 163, except 5-(aminomethyl)indolin-2-one was used as starting material. The resulting residue was purified by Prep-HPLC (using the following conditions: Column: XBridge BEH130 Prep C18 OBD Column, 130 Å, 19×150 mm; 5 μm 13 nm; Mobile phase A: Water (20 mM $NH_4HCO_3$), mobile phase B: MeCN; Detector, UV 210/254 nm) to obtain the title compound (8.2 mg) as a solid. $^1H$ NMR (300 MHz, $CD_3OD$) δ 8.28 (s, 1H), 7.24-7.11 (m, 4H), 6.95-6.81 (m, 1H), 4.66-4.60 (m, 2H), 4.39-4.30 (m, 2H), 3.97 (s, 3H), 3.65-3.35 (m, 2H), 3.03-2.97 (m, 2H), 2.63-2.57 (m, 1H), 1.93-1.54 (m, 4H). LCMS (ESI): $[M+H]^+$: 509.3.

Example 168. N-((1H-pyrrolo[2,3-b]pyridin-5-yl)methyl)-1-(5-(5-chloro-2-methoxypyridin-4-yl)-1H-pyrazole-3-carbonyl)piperidine-4-carboxamide

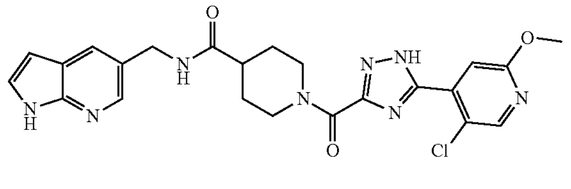 [SMILES: COc1cc(-c2nc(C(=O)N3CCC(C(=O)NCc4cnc5[nH]ccc5c4)CC3)n[nH]2)c(Cl)cn1]

The title compound was prepared using a procedure similar to the one described for the synthesis of Example 167, except 1H-pyrrolo[2,3-b]pyridin-5-yl)methanamine was used as starting material. The title compound was obtained as a solid (12.1 mg). $^1H$ NMR (300 MHz, $CD_3OD$) δ 8.27 (s, 1H), 8.17 (d, 1H), 7.95 (d, 1H), 7.40 (d, 1H), 7.16 (s, 2H), 6.48 (d, 1H), 4.66 (s, 2H), 4.49 (s, 2H), 3.96 (s, 3H), 3.24 (s, 1H), 3.00 (s, 1H), 2.68-2.52 (m, 1H), 1.98-1.78 (m, 4H). LCMS (ESI): 494.3 $[M+H]^+$.

Example 169. A diastereomeric mixture of Example 169-A and Example 169-B

Example 169-A. (R)-4-(5-(5-fluoro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide

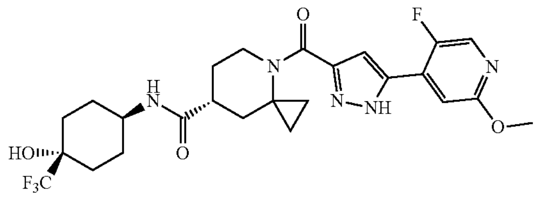 [SMILES: COc1cc(-c2cc(C(=O)N3CC[C@@H](C(=O)N[C@H]4CC[C@@](O)(C(F)(F)F)CC4)CC34CC4)n[nH]2)c(F)cn1]

Example 169-B. (S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide

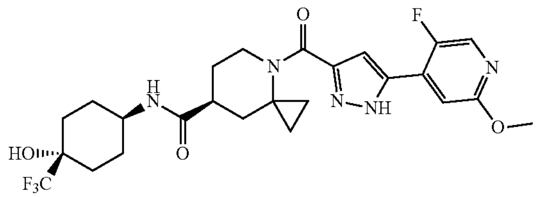 [SMILES: COc1cc(-c2cc(C(=O)N3CC[C@H](C(=O)N[C@H]4CC[C@@](O)(C(F)(F)F)CC4)CC34CC4)n[nH]2)c(F)cn1]

Step-1. tert-butyl 7-(((1r,4r)-4-hydroxy-4-(trifluoromethyl)cyclohexyl)carbamoyl)-4-azaspiro[2.5]octane-4-carboxylate

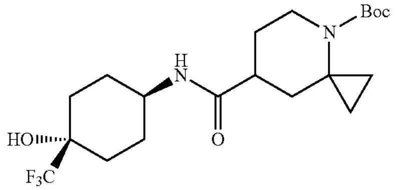 [SMILES: CC(C)(C)OC(=O)N1CCC(C(=O)N[C@H]2CC[C@@](O)(C(F)(F)F)CC2)CC12CC2]

HATU (447.0 mg, 1.18 mmol) and (1r,4r)-4-amino-1-(trifluoromethyl)cyclohexan-1-ol (226.0 mg, 1.23 mmol, CAS #: 1408075-09-1, Enamine Ltd.) were added to a stirred mixture of 4-(tert-butoxycarbonyl)-4-azaspiro[2.5]octane-7-carboxylic acid (300.0 mg, 1.18 mmol) and DIPEA (0.62 mL, 3.53 mmol) in DMF (6.00 mL) at 0° C. The resulting mixture was stirred at 25° C. for 1 h. The reaction mixture was diluted with EtOAc, water, then extracted with EtOAc. The organic layer was washed with brine, dried over anhydrous $Na_2SO_4$, filtered, and the solvent was evaporated. The residue was purified by silica gel column chromatography eluting with 60-100% EtOAc/hexanes to afford the diastereomeric mixtures of the title compound (494.0 mg) as an oil, containing residual solvent. LCMS (ESI): $[M+Na]^+$: 443.4.

Step-2. N-((1r,4r)-4-hydroxy-4-(trifluoromethyl)cyclohexyl)-4-azaspiro[2.5]octane-7-carboxamide

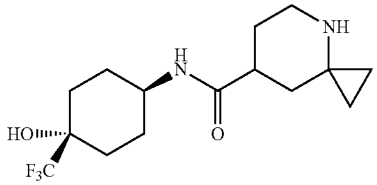 [SMILES: O=C(N[C@H]1CC[C@@](O)(C(F)(F)F)CC1)C1CCNC2(CC2)C1]

TFA (3.00 mL) was added to a solution of tert-butyl 7-(((1r,4r)-4-hydroxy-4-(trifluoromethyl)cyclohexyl)carbamoyl)-4-azaspiro[2.5]octane-4-carboxylate (Step-1, 494.0 mg, 1.18 mmol) in DCM (5.00 mL). The reaction mixture was stirred at 25° C. for 8 h. The reaction mixture was concentrated under reduced pressure and purified by reverse phase column chromatography (using the following conditions: C18 Column, 0-20% MeCN/water (0.1% formic acid)) to obtain the title compound (534.0 mg) as a solid mixture of diastereomers, containing residual solvent. LCMS (ESI): $[M+H]^+$: 322.3.

Step-3. 4-(5-(5-fluoro-2-methoxypyridin-4-yl)-1-((2-(trimethylsilyl)ethoxy)methyl)-1H-pyrazole-3-carbonyl)-N-((1r,4r)-4-hydroxy-4-(trifluoromethyl)cyclohexyl)-4-azaspiro[2.5]octane-7-carboxamide

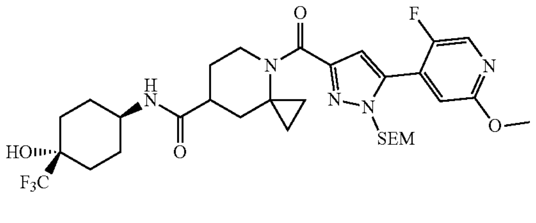 [SMILES: COc1cc(-c2cc(C(=O)N3CCC(C(=O)N[C@H]4CC[C@@](O)(C(F)(F)F)CC4)CC34CC4)nn2COCC[Si](C)(C)C)c(F)cn1]

HATU (103.0 mg, 0.27 mmol) and N-((1r,4r)-4-hydroxy-4-(trifluoromethyl)cyclohexyl)-4-azaspiro[2.5]octane-7-carboxamide (Step-2, 164.0 mg, 0.36 mmol) were added to a stirred solution of 5-(5-fluoro-2-methoxypyridin-4-yl)-1-((2-(trimethylsilyl)ethoxy)methyl)-1H-pyrazole-3-carboxylic acid (INTERMEDIATE 506, 100.0 mg, 0.27 mmol) and DIPEA (0.19 mL, 1.09 mmol) in DMF (6.00 mL). The resulting mixture was stirred at 25° C. for 16 h. The reaction mixture was diluted with EtOAc and water, then extracted with EtOAc. The organic layer was washed with brine, dried over anhydrous $Na_2SO_4$, filtered, and the solvent was evaporated. The residue was purified by silica gel column chromatography eluting with 70-100% EtOAc/hexanes to afford the title compound (153.0 mg) as a solid mixture of diastereomers. LCMS (ESI): $[M+H]^+$: 670.6.

Step-4. (R)-4-(5-(5-fluoro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide

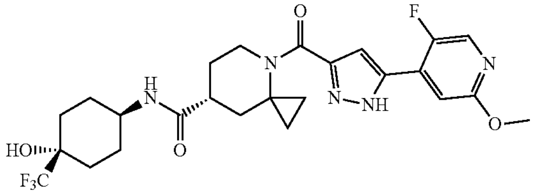

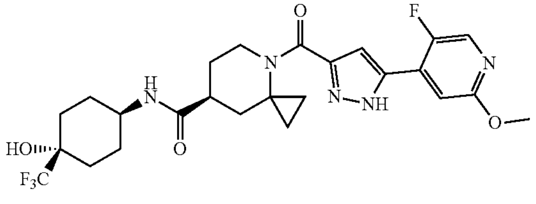

TFA (3.00 mL) was added to a stirred solution of 4-(5-(5-fluoro-2-methoxypyridin-4-yl)-1-((2-(trimethylsilyl)ethoxy)methyl)-1H-pyrazole-3-carbonyl)-N-((1r,4r)-4-hydroxy-4-trifluoromethyl)cyclohexyl)-4-azaspiro[2.5]octane-7-carboxamide (Step-4, 89.0 mg, 0.13 mmol) in DCM (3.00 mL). The resulting mixture was stirred at 25° C. for 1 h. The reaction mixture was concentrated and purified by silica gel column chromatography eluting with 0-10% MeOH/DCM to obtain (R)-4-(5-(5-fluoro-2-methoxypyridin-4-yl)-1H-pyrazole-3-carbonyl)-N-((1r,4r)-4-hydroxy-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide (62.0 mg) as a solid mixture of diastereomers (Example 169). $^1$H NMR (400 MHz, $CD_3OD$) δ 8.12 (d, 1H), 7.27 (br d, 1H), 7.10 (br s, 1H), 4.89-4.95 (m, 1H), 4.39-4.71 (m, 1H), 3.93 (s, 4H), 2.91 (br d, 1H), 2.21-2.61 (m, 1H), 1.56-2.01 (m, 10H), 1.14-1.40 (m, 2H), 0.81-1.10 (m, 2H), 0.73 (br s, 2H). LCMS (ESI): $[M+H]^+$: 540.2.

The solid mixture of diastereomers (80.0 mg) was separated using Chiral-Prep-HPLC.

Column: CHIRALPAK IA column

Column dimension: 2×25 cm, 5 μm

Mobile Phase: hexanes (8 mM $NH_3$·MeOH):EtOH=50:50 hold for 15 min

Flow rate: 18 mL/min

Detection: 220/254 nm

Example 169-A. The first eluting diastereomer (26.3 mg) was obtained as a solid.

The first eluting diastereomer had a retention time of 4.59 min.

$^1$H NMR (300 MHz, DMSO-$d_6$) δ 14.09-13.85 (m, 1H), 8.29-8.23 (m, 1H), 7.82 (s, 1H), 7.32 (d, 1H), 7.04 (s, 1H), 5.70 (s, 1H), 4.56-4.49 (m, 1H), 3.91-3.76 (m, 4H), 2.86-2.70 (m, 2H), 2.22-2.16 (m, 1H), 1.83-1.72 (m, 5H), 1.56-1.46 (m, 1.30-0.43 (m, 5H). LCMS (ESI): $[M+H]^+$: 540.2.

Example 169-B. The second eluting diastereomer (28.3 mg) was obtained as a solid.

The second eluting diastereomer had a retention time of 8.06 min.

$^1$H NMR (300 MHz, DMSO-$d_6$) δ 14.00 (s, 1H), 8.27 (d, 1H), 7.82 (d, 1H), 7.33 (d, 1H), 7.03 (d, 1H), 5.71 (s, 1H), 4.44 (br s, 1H), 3.91-3.80 (m, 4H), 3.38-3.33 (m, 1H), 2.90-2.76 (m, 1H), 2.21 (s, 1H), 1.83-1.71 (m, 5H), 1.56-1.46 (m, 5H), 1.29-1.00 (m, 1H), 0.99-0.80 (m, 2H), 0.78-0.61 (m, 2H), LCMS (ESI): $[M+H]^+$: 540.2,

Alternative Method of Synthesis for Example 169-B. (S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide

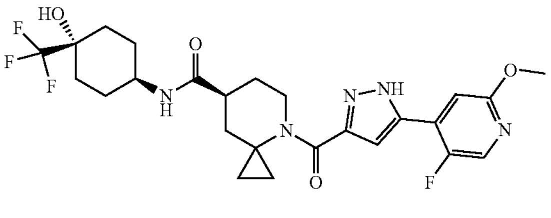 [SMILES: COc1cc(-c2cc(C(=O)N3CC[C@H](C(=O)N[C@H]4CC[C@@](O)(C(F)(F)F)CC4)CC34CC4)n[nH]2)c(F)cn1]

HOBt (2.44 g, 18.03 mmol) and EDCI (3.46 g, 18.00 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (Intel mediate 527-A, 4.50 g, 12.02 mmol) in DMF (20.00 mL). The resulting mixture was stirred at 25° C. for 30 min. Then (1r,4r)-4-amino-1-(trifluoromethyl)cyclohexan-1-ol hydrochloride (3.17 g, 14.42 mmol, CAS #: 2137056-98-3, Enamine Ltd.) and DIPEA (7.77 g, 60.10 mmol) were added to the resulting mixture. The resulting mixture was stirred at 25° C. for 14 h. The solution was diluted with EtOAc and washed with water. The organic layer was concentrated under reduced pressure. The residue was purified by reverse phase column chromatography (using the following conditions: Column: C18 column; Mobile Phase A: Water (10 mM $NH_4HCO_3$), Mobile Phase B: MeCN; Gradient: 5% B to 40% B in 30 min; Flow rate: 40 mL/min; Detector, UV 220/254 nm) to obtain the title compound (4.91 g). $^1$H NMR (400 MHz, DMSO-$d_6$) δ 14.18-13.81 (m, 1H), 8.23 (d, 1H), 7.81 (d, 1H), 7.30 (d, 1H), 7.02 (br s, 1H), 5.69 (s, 1H), 4.64-4.32 (m, 1H), 3.87-3.84 (m, 4H), 3.36-3.34 (m, 1H), 2.90-2.75 (m, 1H), 2.27-2.08 (m, 1H), 1.79-1.70 (m, 5H), 1.56-1.45 (m, 5H), 1.25-0.80 (m, 2H), 0.68-0.44 (m, 3H). LCMS (ESI): 540.45 $[M+H]^+$.

Alternative Method of Synthesis for Example 169-B. (S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide Step-1. 4-benzyl-7-(((tert-butyldiphenylsilyl)oxy) methyl)-4-azaspiro[2.5]octane

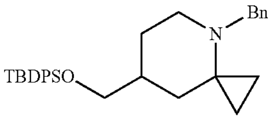

THF (30.00 L) was added to a 50.0 L of the flask equipped with stirrer, addition funnel and thermometer, $N_2$ protection at 5° C. (4-Benzyl-4-azaspiro[2.5]octan-7-yl)methanol (3.00 kg, 12.90 mol) was added to the flask at 5° C., imidazole (2.21 kg, 32.40 mol) was added to the flask at 5° C. Tert-butyl-chloro-diphenyl-silane (4.28 kg, 15.60 mol) was added to the flask at 5° C. The reaction mixture was stirred at 5 to 25° C. for 12 h under $N_2$. The reaction mixture was poured into $H_2O$ (10.00 L), extracted with ethyl acetate (10.00 L×2). The combined organic layer was washed with brine (10.00 L), dried over $Na_2SO_4$, filtered and the filtrate was concentrated in vacuum. The residue was purified by silica gel column chromatography eluting with petroleum ether/ethyl acetate (10/1 v/v) to obtain the title compound (5.50 kg) as an oil and which was directly used to next step.

Step-2. tert-butyl 7-(((tert-butyldiphenylsilyl)oxy) methyl)-4-azaspiro[2.5]octane-4-carboxylate

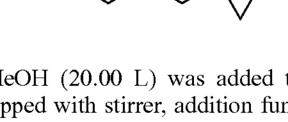

MeOH (20.00 L) was added to a 50.0 L of the flask equipped with stirrer, addition funnel and thermometer, $N_2$ protection at 20 to 30° C. 4-Benzyl-7-(((tert-butyldiphenylsilyl)oxy)methyl)-4-azaspiro[2.5]octane (Step-1, 1.00 kg, 2.13 mol) was added to the flask at 20 to 30° C. in one portion and Pd/C (100.00 g, 213.00 mmol, 10.0% purity) was added to the flask at 20 to 30° C. in several portions under $N_2$. HCOOH (1.02 kg, 21.30 mol) was added to the flask at 20 to 30° C. under $N_2$. The mixture was stirred at 50 to 55° C. for 1 h. The mixture was filtered through Celite and the filtrated cake was washed with MeOH (5.00 L×2). The mixture was adjusted the pH to 7 to 8 with $NaHCO_3$ solution (10.00 L) and extracted with ethyl acetate (10.0 L×2), the combined organic layers were washed with brine (10.0 L×2), and dried over $Na_2SO_4$, filtered and concentrated under reduced pressure to give a residue of 1.30 kg. THF (6.50 L) and $H_2O$ (3.90 L) were added to a 50.0 L of jacket flask with overhead stirrer, addition funnel and thermometer, $N_2$ balloon etc at 20 to 30° C. The residue (1.30 kg) was added to the flask at 20 to 30° C. in one portion and $NaHCO_3$ (447.00 g, 5.32 mol) was added to the flask at 20 to 30° C. $Boc_2O$ (697.00 g, 3.19 mot) was added to the flask dropwise at 10 to 20° C. The mixture was stirred at 20 to 30° C. for 1.5 h. $H_2O$ (10.0 L) was added to the reaction mixture and extracted with MTBE (10.0 L×2), the combined organic layers were washed with brine (10.0 L×2), and dried over $Na_2SO_4$, filtered and concentrated under reduced pressure to give a residue. The residue was purified by silica gel column chromatography eluting with petroleum ether/ethyl acetate (1/1 v/v) to obtain the title compound (810.00 g) as a solid. $^1$H NMR (400 MHz, $CDCl_3$) δ 7.66 (d, 4H), 7.29-7.45 (m, 6H), 4.03 (d, 3.51 (d, 2H), 2.90 (t, 1H), 1.98-2.07 (m, 1H), 1.72-1.75 (m, 2H), 1.48 (s, 9H), 1.26-1.29 (m, 2H), 1.08 (s, 9H), 1.00-1.06 (m, 1H), 0.83-0.99 (m, 1H), 0.50-0.52 (m, 1H), 0.39-0.40 (m, 1H). LCMS: 380.1 $[M+H]^+$.

Step-3. tert-butyl 7-(hydroxymethyl)-4-azaspiro[2.5] octane-4-carboxylate

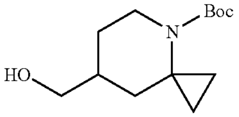 [SMILES: CC(C)(C)OC(=O)N1CCC(CO)CC12CC2]

THF (24.00 L) was added to a 50.0 L of the flask with stirrer, addition funnel and thermometer, $N_2$ protection at 20° C. Tert-butyl 7-(((tert-butyldiphenylsilyl)oxy)methyl)-4-azaspiro[2,5]octane-4-carboxylate (Step-2, 3.10 kg, 6.46 mol) was added to the flask at 20° C. at one portion. TBAF (1.00 M, 6.46 L) was added to the flask at 20° C. and the resulting mixture was stirred at 20° C. for 2 h. The mixture was poured into $H_2O$ (10.00 L), extracted with ethyl acetate (10.00 L×2). The combined organic layer was washed with brine (5.00 L), dried over $Na_2SO_4$, filtered and the filtrate was concentrate in vacuum. The residue was purified by silica gel column chromatography eluting with petroleum ether/ethyl acetate (3/1 v/v) to obtain the title compound (1.45 kg) as an oil. $^1$H NMR (400 MHz, DMSO-$d_6$) (54.43 (t, 1H), 3.83-3.86 (m, 1H), 3.21-3.24 (m, 2H), 1.75-1.99 (m, 1H), 1.65-1.70 (m, 1H), 1.39 (t, 1H), 1.18 (s, 9H), 1.00-1.06 (m, 1H), 0.99-1.04 (m, 2H), 0.76-0.78 (m, 1H), 0.37-0.38 (m, 1H), 0.33-0.35 (m, 1H).

Step-4. 4-(tert-butoxycarbonyl)-4-azaspiro[2.5]octane-7-carboxylic acid

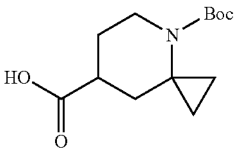 [SMILES: CC(C)(C)OC(=O)N1CCC(C(=O)O)CC12CC2]

Five batches were carried out in parallel. MeCN (1.10 L) and $H_2O$ (1.10 L) were added to a 5.00 L of jacket flask with overhead stirrer, addition funnel and thermometer, $N_2$ balloon at 10° C. Tert-butyl 7-(hydroxymethyl)-4-azaspiro[2.5] octane-4-carboxylate (Step-3, 284.00 g, 1.18 mol) was added to the flask at 10 DC, TEMPO (74.00 g, 470.00 mmol) was added to the flask at 10° C. in one portion and $PhI(OAc)_2$ (947.00 g, 2.94 mol) was slowly added to the reaction at 10° C. in ten portions under $N_2$. The mixture was stirred at 25° C. for 12 h under $N_2$. Five batches were combined and the reaction mixture was slowly added to saturated $Na_2SO_3$ solution (8.00 L) and stirred at 20° C. for 0.5 h. Then saturated $K_2CO_3$ solution was added and adjusted to pH=11. The mixture was extracted with petroleum ether (3.00 L×2) and 1N HCl 20.0 L) was added to the aqueous solution and adjusted to pH=3. The mixture was extracted with DCM (5.00 L×3) and the combined organic layer was concentrated in vacuum. The residue was crystallized from (heptanes, 2.00 L, 20° C.) and the mixture was filtered and the filtrate cake was washed with heptanes (300 mL×2). The residue was collected and concentrated in vacuum to obtain the title compound (1.40 kg, 4.47 mol) as a solid. $^1H$ NMR (400 MHz, DMSO-$d_6$) 12.2 (brs, 1H), 3.81 (d, 1H), 2.91 (t, 1H), 2.60 (t, 1H), 1.75-1.78 (m, 2H), 1.23-1.26 (m, 10H), 0.81-0.82 (m, 1H), 0.51-0.79 (m, 1H), 0.47-0.49 (m, 2H). LCMS: 156.6 $[M-100]^+$.

Step-5. tert-butyl 7-(((1r,4r)-4-hydroxy-4-(trifluoromethyl)cyclohexyl)carbamoyl)-4-azaspiro[2.5] octane-4-carboxylate

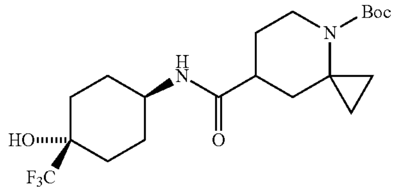 [SMILES: CC(C)(C)OC(=O)N1CCC(C(=O)N[C@H]2CC[C@@](O)(C(F)(F)F)CC2)CC12CC2]

Four batches were carried out in parallel, DCM (3.20 L) was added to a 5.00 L of jacket flask equipped with overhead stirrer, addition funnel and thermometer, $N_2$, balloon. 4-(tert-butoxycarbonyl)-4-azaspiro[2.5]octane-7-carboxylic acid (Step-4, 317.00 g, 1.24 mol) was added to the flask at 0° C. DIPEA (321.00 g, 2.48 mol), EDCI (297.00 g, 1.55 mol), and HOBt (209.00 g, 1.55 mol) were added to the flask at 0° C. (1r,4r)-4-amino-1-(trifluoromethyl)cyclohexan-1-ol (239.00 g, 1.30 mol) was added to the flask at 0° C. and the resulting mixture was purged with $N_2$ for 3 times. The reaction mixture was stirred at 0 to 25° C. for 2 h under $N_2$. Four batches were combined and the reaction was poured into $H_2O$ (10.00 L), extracted with ethyl acetate (10.0 L×2). The combined organic layer was washed with brine (10.00 L), dried over $Na_2SO_4$, filtered and the filtrate was concentrated in vacuum. The residue was purified by silica gel column chromatography eluting with petroleum ether/ethyl acetate (1/2 v/v) to obtain the title compound (1.55 kg) as a solid. $^1H$ NMR (400 MHz, DMSO-$d_6$) δ 7.74 (d, 1H), 5.77 (s, 1H), 3.80-3.88 (m, 2H), 2.78-2.88 (m, 1H), 2.70-2.70 (m, 1H), 2.70-1.75 (t, 1H), 1.73-1.74 (m, 4H), 1.48-1.55 (m, 6H), 1.43 (s, 9H), 1.18-1.19 (m, 1H), 0.80-0.81 (m, 1H), 0.79-0.81 (m, 1H), 0.46-0.48 (m, 2H).

Step-6. N-((1r,4r)-4-hydroxy-4-(trifluoromethyl) cyclohexyl)-4-azaspiro[2.5]octane-7-carboxamide hydrochloride

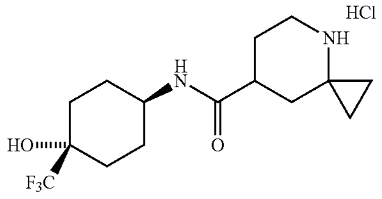 [SMILES: Cl ; O=C(N[C@H]1CC[C@@](O)(C(F)(F)F)CC1)C1CCNC2(CC2)C1]

Ethyl acetate (10.00 L) was added to a 30.0 L flask equipped with stirrer, addition funnel and thermometer, $N_2$ protection. Tert-butyl 7-(((1r,4r)-4-hydroxy-4-(trifluoromethyl)cyclohexyl)carbamoyl)-4-azaspiro[2,5]octane-4-carboxylate (Step-5, 1.50 kg, 3.57 mol) was added to the flask at 0° C. The reaction mixture was purged with $N_2$ for 3 times. HCl/dioxane (4.00 M, 2.50 L) was added to the flask at 0° C. The reaction was stirred at 0 to 20° C. for 1 h under $N_2$. The reaction mixture was concentrated under vacuum to obtain the title compound (1.40 kg) as a solid and was directly used to next step. $^1H$ NMR (400 MHz, DMSO-$d_6$) δ 9.43 (s, 2H), 7.94 (d, 1H), 5.37 (brs, 1H), 3.81 (s, 1H), 3.42-3.44 (m, 1H), 2.80-2.90 (m, 1H), 2.51-2.64 (m, 1H), 2.10-2.13 (m, 1H), 1.78-1.83 (s, 6H), 1.74-1.78 (m, 4H), 1.49 (d, 1H), 1.03-1.05 (m, 2H), 0.70-0.73 (m, 2H).

Step-7. 4-(5-(5-fluoro-2-methoxypyridin-4-yl)-1-((2-(trimethylsilyl)ethoxy)methyl)-1H-pyrazole-3-carbonyl)-N-((1r,4r)-4-hydroxy-4-(trifluoromethyl)cyclohexyl)-4-azaspiro[2.5]octane-7-carboxamide

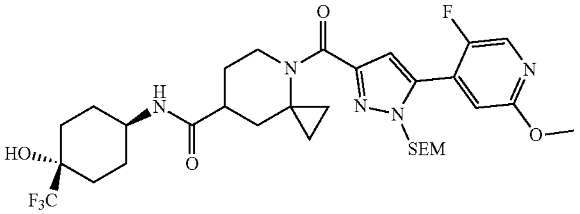 [SMILES: COc1cc(-c2cc(C(=O)N3CCC(C(=O)N[C@H]4CC[C@@](O)(C(F)(F)F)CC4)CC34CC4)nn2COCC[Si](C)(C)C)c(F)cn1]

Four batches were carried out in parallel. DMF (3.00 L) was added a 5.00 L of jacket flask equipped with overhead stirrer, addition funnel and thermometer, $N_2$ balloon at 0° C. N-((1r,4r)-4-hydroxy-4-(trifluoromethyl)cyclohexyl)-4-azaspiro[2.5]octane-7-carboxamide hydrochloride (Step-6, 317.00 g, 863.00 mmol) was added to the flask at 0° C. DIPEA (502.00 g, 3.88 mol), EDCI (298.00 g, 1.55 mol), and HOBt (209.00 g, 1.55 mol) were added to the flask at 0° C. The reaction mixture was stirred at 0° C. and purged with $N_2$. 5-(5-fluoro-2-methoxypyridin-4-yl)-1-((2-(trimethylsilyl)ethoxy)methyl)-1H-pyrazole-3-carboxylic acid (Intermediate 506, 370.00 g, 1.04 mol) was added to the flask at 0° C. and the resulting mixture was stirred at 0 to 30° C. for 12 h under $N_2$. Four batches were combined and the reaction mixture was poured into $H_2O$ (10.00 L), extracted with ethyl acetate (10.00 L×2). The combined organic layer was washed with brine (10.00 L), dried over $Na_2SO_4$, filtered and the filtrate was concentrated in vacuum. The residue was purified by silica gel column chromatography eluting with petroleum ether/ethyl acetate (1/2 v/v) to obtain the title compound (1.50 kg) as an oil, $^1$H NMR (400 MHz, DMSO-$d_6$) δ 8.31 (d, 1H), 7.86 (s, 1H), 7.33 (d, 1H), 7.08 (s, 1H), 5.81-5.80 (m, 1H), 5.49 (d, 1H), 3.93 (s, 3H), 3.92-3.89 (m, 1H), 3.63-3.61 (m, 2H), 2.98-2.96 (m, 1H), 2.06-2.02 (m, 1H), 1.85-1.25 (m, 11H), 1.23 (t, 3H), 1.23-0.64 (m, 6H), 0.00 (s, 9H), LCMS: 670.2 $[M+H]^+$.

Step-8. 4-(5-(5-fluoro-2-methoxypyridin-4-yl)-1H-pyrazole-3-carbonyl)-N-((1r,4r)-4-hydroxy-4-(trifluoromethyl)cyclohexyl)-4-azaspiro[2.5]octane-7-carboxamide

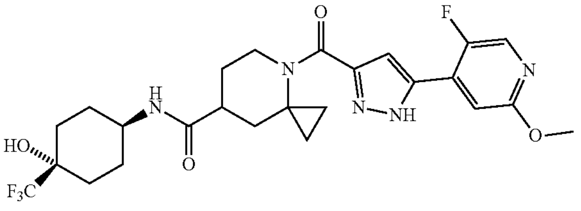 [SMILES: COc1cc(-c2cc(C(=O)N3CCC(C(=O)N[C@H]4CC[C@@](O)(C(F)(F)F)CC4)CC34CC4)n[nH]2)c(F)cn1]

Three batches were carried out in parallel. DCM (500.00 mL) was added to a 10 L of the flask equipped with stirrer, addition funnel and thermometer, $N_2$ protection at 20° C. 4-(5-(5-fluoro-2-methoxypyridin-4-yl)-1-((2-(trimethylsilyl)ethoxy)methyl)-1H-pyrazole-3-carbonyl)-N-((1r,4r)-4-hydroxy-4-(trifluoromethyl)cyclohexyl)-4-azaspiro[2.5]octane-7-carboxamide (Step-7, 500 g, 747 mmol, 1.00 eq) was added to the flask at 20° C. under $N_2$. TFA (1.28 kg, 11.20 mol) was added to the flask at 20° C. The reaction mixture was stirred at 20 to 25° C. for 2 h under $N_2$. Three batches were combined and the reaction mixture was poured into $NaHCO_3$ (10.00 L), extracted with ethyl acetate (10.0 L×2). The combined organic layer was concentrated under vacuum. The resulting 1.20 kg of residue was dissolved into methanol (3.00 L) and $NH_3{\cdot}H_2O$ (1.00 L) was slowly added dropwise at 5 to 10° C. and the mixture was stirred for 1 h. The mixture was poured into sat, NaCl (2.00 L) solution, extracted with ethyl acetate (4.00 L×2), the combined organic layer was dried over $Na_2SO_4$, filtered and the filtrate was concentrated under vacuum. The residue was crystallized from (MTBE, 2.00 L, 25° C.), the mixture was filtered and the filtrate cake was washed with MTBE (300 mL×2). The filtrate cake was collected and concentrated under vacuum to obtain the title compound (970.00 g) as a solid. $^1$H NMR (400 MHz, DMSO-d6) δ 14.0 (brs, 1H), 8.27 (s, 1H), 7.81 (d, 1H), 7.32 (d, 1H), 7.03 (s, 1H), 4.37-4.34 (m, 1H), 3.88 (s, 3H), 3.83 (s, 1H) 2.79 (s, 1H), 2.20-2.10 (m, 1.79-1.50 (m, 1H), 1.08-0.98 (m, 3H), 0.89-0.65 (m, 2H). LCMS: 540.1 $[M+H]^+$.

Step-9. (S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide (Example 169-B)

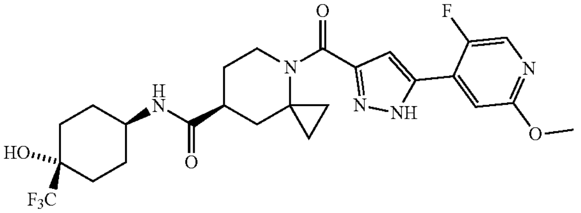 [SMILES: COc1cc(-c2cc(C(=O)N3CC[C@H](C(=O)N[C@H]4CC[C@@](O)(C(F)(F)F)CC4)CC34CC4)n[nH]2)c(F)cn1]

4-(5-(5-fluoro-2-methoxypyridin-4-yl)-1H-pyrazole-3-carbonyl)-N-((1r,4 r)-4-hydroxy-4-(trifluoromethyl)cyclohexyl)-4-azaspiro[2.5]octane-7-carboxamide (Step-8, 1.15 kg, 2.13 mol) was separated using Prep-SFC.

Instrument: Waters SFC prep 350

Column: DAICEL CHIRALPAK IG (250 mm×50 mm, 10 μm)

Mobile phase A: $CO_2$

Mobile phase B: EtOH

Gradient: B 55%

Flow rate: 200 mL/min

Back pressure: 100 bar

Column temperature: 35° C.

Wavelength: 220 nm

Cycle time: ~12.2 min

Sample preparation: 1150 g compound was dissolved in 4700 ml ethanol

Injection: 15 mL per injection

Example 169-B. The title compound (411.00 g) was obtained as a solid. It had a retention time of 21.69 min.

$^1$H NMR (400 MHz, DMSO-$d_6$) δ 14.0 (brs, 1H), 8.26 (s, 1H), 7.82 (d, 1H), 7.32 (d, 1H) 7.03 (s, 1H), 5.68 (s, 1H), 4.47-4.34 (m, 1H), 3.87 (s, 3H), 3.83 (s, 1H) 2.79 (s, 1H), 2.20-2.10 (m, 1H), 1.78-1.50 (m, 11H), 1.08-0.98 (m, 3H), 0.89-0.65 (m, 2H). LCMS: 540.1 $[M+H]^+$.

Example 170-A. (1R,3S,5S)-8-(5-(5-fluoro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide

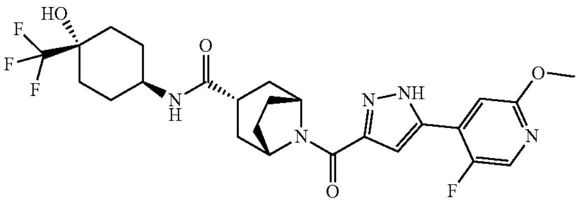 [SMILES: COc1cc(-c2cc(C(=O)N3[C@@H]4CC[C@H]3C[C@H](C(=O)N[C@H]3CC[C@@](O)(C(F)(F)F)CC3)C4)n[nH]2)c(F)cn1]

HOBt (151.6 mg, 1.12 mmol), EDCI (215.1 mg, 1.12 mmol), and (1r,4r)-4-amino-1-(trifluoromethyl)cyclohexan-1-ol (164.4 mg, 0.90 mmol) were added to a stirred solution of (1R,3S,5S)-8-[5-(5-fluoro-2-methoxypyridin-4-yl)-1H-pyrazole-3-carbonyl]-8-azabicyclo[3.2.1]octane-3-carboxylicacid (INTERMEDIATE 508, 280.0 mg, 0.75 mmol) and DIPEA (483.3 mg, 3.74 mmol) in DMF (5.00 mL). The resulting solution was stirred at 25° C. for 14 h. The resulting mixture was diluted with EtOAc and washed with water. The mixture was concentrated under reduced pressure. The residue was purified by reverse phase column chromatography (using the following conditions: C18 column; Mobile Phase A: Water (10 mM $NH_4HCO_3$), Mobile Phase B: MeCN; Flow rate: 40 mL/min; Gradient: 25 B to 35 B in 20 mitt; Detector, UV 220/254 nm) to obtain the title compound (242.0 mg) as a solid. $^1$H NMR (300 MHz, DMSO-$d_6$) δ 13.97 (s, 1H), 8.28 (d, 1H), 7.76 (d, 1H), 7.33 (d, 1H), 7.13 (d, 1H), 5.70 (s, 1H), 5.00-4.54 (m, 2H), 3.88

(s, 3H), 3.84-3.77 (m, 1H), 3.00-2.86 (m, 1H), 2.10-1.41 (m, 16H). LCMS (ESI): $[M+H]^+$: 540.2.

Alternative Method: A Diastereomeric Mixture of Example 170-A and Example 170-B. (1R,3s,5S)-8-(5-(5-fluoro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide

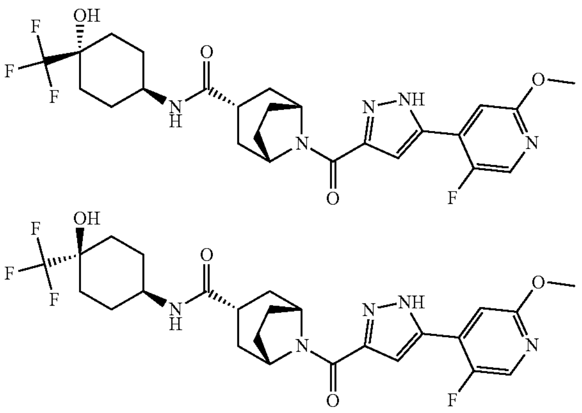

The title compound was prepared using a procedure similar to the one described for the synthesis of Example 170-A, except 4-amino-1-(trifluoromethyl)cyclohexan-1-ol was used as a starting material in Step-5.

The two diastereomers of the title compounds were separated using Prep-HPLC.

Column: XBridge Prep OBD C18 column

Column dimension: 30×150 mm, 5 μm

Mobile Phase: Water (10 mM $NH_4HCO_3$):MeCN=81:19 to 51:49 for 7 min

Flow rate: 60 mL/min

Detection: 254 nm

Example 170-B. (1R,3s,5S)-8-(5-(5-fluoro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide The first eluting diastereomer (10.9 was obtained as a solid.

The first eluting diastereomer had a retention time of 8.15 min.

$^1$H NMR (400 MHz, DMSO-$d_6$) δ 14.02 (s, 1H), 8.28 (s, 1H), 7.77 (d, 1H), 7.32 (d, 1H), 7.13 (s, 1H), 5.74 (s, 1H), 5.40-5.02 (m, 1H), 4.71-4.65 (m, 1H), 3.87 (s, 3H), 3.57-3.34 (m, 1H), 2.83-2.71 (m, 1H), 2.12-1.37 (m, 16H). LCMS (ESI): $[M+H]^+$: 540.3.

Example 170-A. (1R,3S,5S)-8-(5-(5-fluoro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide The second eluting diastereomer (11.4 mg) was obtained as a solid.

The second eluting diastereomer had a retention time of 9.73 min.

$^1$H NMR (400 MHz, DMSO-$d_6$) δ 13.97 (s, 1H), 8.28 (d, 1H), 7.76 (d, 1H), 7.33 (d, 1H), 7.13 (d, 1H), 5.70 (s, 1H), 5.00-4.54 (m, 2H), 3.88 (s, 3H), 3.84-3.77 (m, 1H), 3.00-2.86 (m, 1H), 2.14-1.97 (m, 2H), 1.95-1.72 (m, 8H), 1.71-1.58 (m, 2H), 1.58-1.35 (m, 4H). LCMS (ESI): $[M+H]^+$: 540.3.

Example 171. 1-(5-(5-chloro-2-methoxypyridin-4-yl)-1H-pyrazole-3-carbonyl)-N-(3-chlorobenzyl)-4-hydroxypiperidine-4-carboxamide

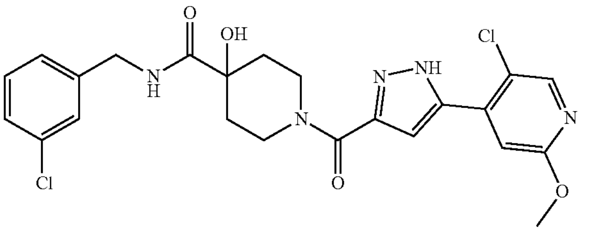 [SMILES: COc1cc(-c2cc(C(=O)N3CCC(O)(C(=O)NCc4cccc(Cl)c4)CC3)n[nH]2)c(Cl)cn1]

Step-1. Methyl 1-(5-(5-chloro-2-methoxypyridin-4-yl)-1H-pyrazole-3-carbonyl)-4-hydroxypiperidine-4-carboxylate

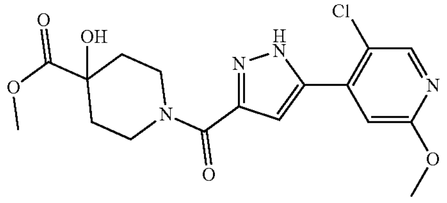 [SMILES: COC(=O)C1(O)CCN(C(=O)c2cc(-c3cc(OC)ncc3Cl)[nH]n2)CC1]

HATU (38.0 mg, 0.10 mmol) and methyl 4-hydroxypiperidine-4-carboxylate (12.7 mg, 0.08 mmol) were added to a stirred solution of 5-(5-chloro-2-methoxypyridin-4-yl)-1H-pyrazole-3-carboxylic acid (INTERMEDIATE 510, 20.0 mg, 0.08 mmol) and DIPEA (31.0 mg, 0.24 mmol) in DCM (2.00 mL). The resulting mixture was stirred at 25° C. for 14 h. The resulting mixture was concentrated under vacuum to obtain the title compound and used in the next step without further purification.

Step-2. 1-(5-(5-chloro-2-methoxypyridin-4-yl)-1H-pyrazole-3-carbonyl)-4-hydroxypiperidine-4-carboxylic acid

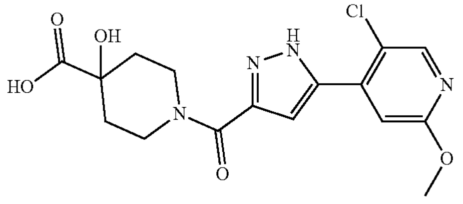 [SMILES: COc1cc(-c2cc(C(=O)N3CCC(O)(C(=O)O)CC3)n[nH]2)c(Cl)cn1]

A solution of LiOH (9.6 mg, 0.40 mmol) in water (0.50 mL) was added to a stirred solution of methyl 1-(5-(5-chloro-2-methoxypyridin-4-yl)-1H-pyrazole-3-carbonyl)-4- hydroxypiperidine-4-carboxylate as is from Step-1 in MeOH (1.00 mL). The resulting mixture was stirred at 25° C. for 14 h. The resulting mixture was concentrated under vacuum to obtain the title compound and used in the next step without further purification.

Step-3. 1-(5-(5-chloro-2-methoxypyridin-4-yl)-1H-pyrazole-3-carbonyl)-N-(3-chlorobenzyl)-4-hydroxypiperidine-4-carboxamide

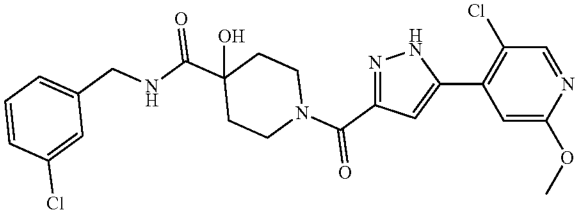 [SMILES: COc1cc(-c2cc(C(=O)N3CCC(O)(C(=O)NCc4cccc(Cl)c4)CC3)n[nH]2)c(Cl)cn1]

HATU (38.0 mg, 0.10 mmol) and (3-chlorophenyl)methanamine (15.0 mg, 0.10 mmol) were added to a stirred solution of 1-(5-(5-chloro-2-methoxypyridin-4-yl)-1H-pyrazole-3-carbonyl)-4-hydroxypiperidine-4-carboxylic acid as is from Step-2 and DIPEA (31.0 mg, 0.24 mmol) in DMF (1.00 mL). The resulting mixture was stirred at 25° C. for 14 h. The resulting mixture was filtered. The filtrate was then purified by Prep-HPLC (using the following conditions: Column: Sunfire Prep C18 OBD Column, 19×150 Mill 5 μm 10 nm; Mobile phase A: Water (0.1% FA), mobile phase B: MeCN; Detector, UV 210/254 nm) to obtain the title compound (21.6 mg) as a solid. $^1$H NMR (400 MHz, $CD_3OD$) δ 8.27 (s, 1H), 7.34-7.00 (m, 6H), 4.58-4.53 (m, 2H), 4.38 (s, 2H), 3.94 (s, 3H), 3.59-3.55 (m, 1H), 3.26-3.21 (m, 1H), 2.15-2.11 (m, 2H), 1.81-1.54 (m, 2H). LCMS (ESI): $[M+H]^+$: 504.3.

Example 172. 1-(5-(5-chloro-2-methoxypyridin-4-yl)-1H-pyrazole-3-carbonyl)-N-(3-chlorobenzyl)-2-methylpiperidine-4-carboxamide

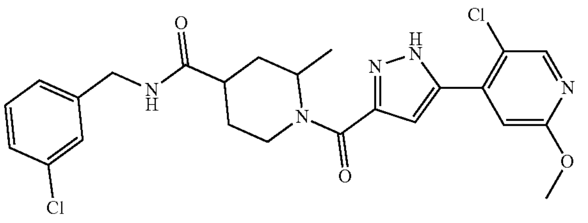 [SMILES: COc1cc(-c2cc(C(=O)N3CCC(C(=O)NCc4cccc(Cl)c4)CC3C)n[nH]2)c(Cl)cn1]

The title compound was prepared using a procedure similar to the one described for the synthesis of Example 171, except methyl 2-methylpiperidine-4-carboxylate hydrochloride was used as starting material in Step-1. The title compound was obtained as a solid mixture of diastereomers (9.0 mg). $^1$H NMR (400 MHz, $CD_3OD$) δ 8.29-8.25 (m, 1H), 7.34-7.24 (m, 2H), 7.28-7.18 (m, 2H), 7.14 (s, 1H), 7.07 (s, 1H), 4.57-4.52 (m, 1H), 4.45-4.29 (m, 2H), 4.16-4.01 (m, 1H), 3.94 (s, 3H), 3.41-3.37 (m, 1H), 2.59-2.52 (m, 1H), 2.04-1.74 (m, 4H), 1.29 (d, 3H). LCMS (ESI): $[M+H]^+$: 502.4.

Example 173, 1-(5-(5-chloro-2-methoxypyridin-4-yl)-1H-pyrazole-3-carbonyl)-N-(3-chlorobenzyl)-3-methylpiperidine-4-carboxamide

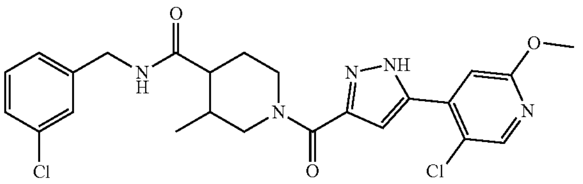 [SMILES: COc1cc(-c2cc(C(=O)N3CCC(C(=O)NCc4cccc(Cl)c4)C(C)C3)n[nH]2)c(Cl)cn1]

The title compound was prepared using a procedure similar to the one described for the synthesis of Example 171, except tert-butyl 3-methylpiperidine-4-carboxylate hydrochloride was used as starting material in Step-1 and 4 M HCl in 1,4-dioxane was substituted as the reagent in Step-2. The title compound was obtained as a solid mixture of diastereomers (10.9 mg). $^1$H NMR (400 MHz, $CD_3OD$) δ 8.35-8.20 (m, 1H), 7.34-7.19 (m, 4H), 7.13 (s, 1H), 7.07 (s, 1H), 4.43-4.28 (m, 3H), 4.26-4.22 (m, 1H), 3.94 (s, 3H), 3.72-3.35 (m, 1H), 2.75-2.69 (m, 1H), 2.29-2.14 (m, 1H), 2.11-1.89 (m, 1H), 1.80-1.71 (m, 1H), 0.99-0.93 (m, 2H), 0.90-0.84 (m, 2H). LCMS (ESI): $[M+H]^+$: 502.3.

Example 174. 1-(5-(5-chloro-2-methoxypyridin-4-yl)-1H-pyrazole-3-carbonyl)-N-(3-chlorobenzyl)-4-fluoropiperidine-4-carboxamide

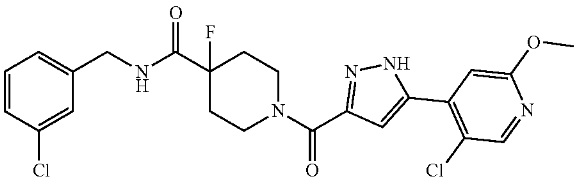 [SMILES: COc1cc(-c2cc(C(=O)N3CCC(F)(C(=O)NCc4cccc(Cl)c4)CC3)n[nH]2)c(Cl)cn1]

Step-1. tert-butyl 4-((3-chlorobenzyl)carbamoyl)-4-fluoropiperidine-1-carboxylate

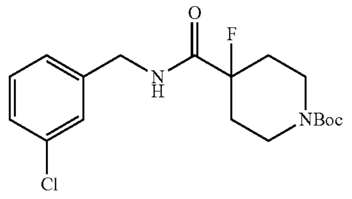 [SMILES: CC(C)(C)OC(=O)N1CCC(F)(C(=O)NCc2cccc(Cl)c2)CC1]

HATU (64.6 mg, 0.17 mmol) and (3-chlorophenyl)methanamine (20.0 mg, 0.14 mmol) were added to a stirred solution of potassium 1-(tert-butoxycarbonyl)-4-fluoropiperidine-4-carboxylate (40.0 mg, 0.14 mmol) and DIPEA (54.3 mg, 0.42 mmol) in DCM (2.00 mL). The resulting mixture was stirred at 25° C. for 14 h. The resulting mixture was concentrated under vacuum to obtain the title compound and used in the next step without further purification.

Step-2. N-(3-chlorobenzyl)-4-fluoropiperidine-4-carboxamide

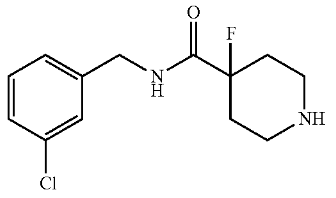 [SMILES: O=C(NCc1cccc(Cl)c1)C1(F)CCNCC1]

A solution of 4 M HCl in 1,4-dioxane (1.00 mL) was added to tert-butyl 4-chlorobenzyl)carbamoyl)-4-fluoropiperidine-1-carboxylate as is from Step-1 and the resulting mixture was stirred at 25° C. for 14 h. The resulting mixture was concentrated under vacuum to obtain the title compound and used in the next step without further purification.

Step-3. 1-(5-(5-chloro-2-methoxypyridin-4-yl)-1H-pyrazole-3-carbonyl)-N-(3-chlorobenzyl)-4-fluoropiperidine-4-carboxamide

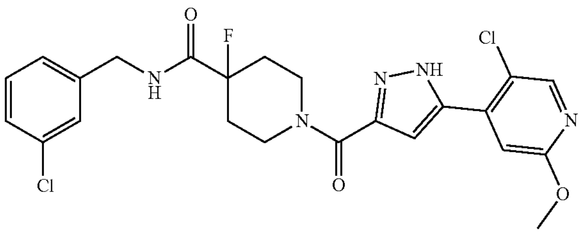 [SMILES: COc1cc(-c2cc(C(=O)N3CCC(F)(C(=O)NCc4cccc(Cl)c4)CC3)n[nH]2)c(Cl)cn1]

HATU (64.6 mg, 0.17 mmol) and N-(3-chlorobenzyl)-4-fluoropiperidine-4-carboxamide as is from Step-2 were added to a solution of 5-(5-chloro-2-methoxypyridin-4-yl)-1H-pyrazole-3-carboxylic acid (INTERMEDIATE 510, 30.0 mg, 0.11 mmol) and DIPEA (90.5 mg, 0.70 mmol) in DMF (1.00 mL). The resulting mixture was stirred at 25° C. for 14 h. The resulting mixture was filtered. The filtrate was then purified by Prep-HPLC (using the following conditions: Column: Sunfire Prep C18 OBD Column, 19×150 mm 5 μm 10 nm; Mobile phase A: Water (0.1% FA), mobile phase B: MeCN; Detector, UV 210/254 nm) to obtain the title compound (7.3 mg) as a solid. $^1$H NMR (400 MHz, $CD_3OD$) δ 8.26 (s, 2H), 7.35-7.28 (m, 1H), 7.32-7.16 (m, 3H) 7.10 (s, 1H), 4.79 (s, 1H), 4.63 (s, 1H), 4.39 (s, 2H), 3.94 (s, 3H), 3.53 (s, 1H), 3.20 (s, 1H), 2.27 (s, 1H), 2.17 (s, 1H), 1.99 (s, 2H). LCMS (ESI): $[M+H]^+$: 506.3.

Example 175. 1-(5-(5-chloro-2-methoxypyridin-4-yl)-1H-pyrazole-3-carbonyl)-N-(3,3-difluorocyclopentyl)piperidine-4-carboxamide

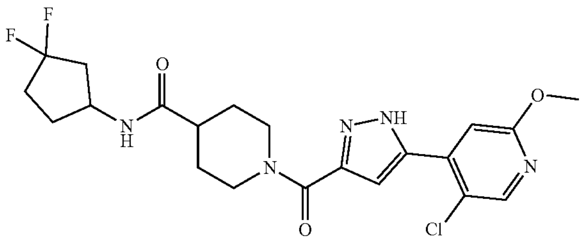 [SMILES: COc1cc(-c2cc(C(=O)N3CCC(C(=O)NC4CCC(F)(F)C4)CC3)n[nH]2)c(Cl)cn1]

The title compound was prepared using a procedure similar to the one described for the synthesis of Example 167, except 3,3-difluorocyclopentan-1-amine hydrochloride was used as starting material. The title compound was obtained as a solid mixture of enantiomers (24.1 mg). $^1$H NMR (300 MHz, $CD_3OD$) δ 8.27 (s, 1H), 7.25-7.14 (s, 2H), 4.81-4.18 (m, 3H), 3.95 (s, 3H), 3.14-2.83 (m, 1H), 2.62-2.40 (m, 2H), 2.39-1.48 (m, 10H). LCMS (ESI): $[M+H]^+$: 468.3.

Example 176. 1-(5-(5-chloro-2-methoxypyridin-4-yl)-1H-pyrazole-3-carbonyl)-N-((5-methylpyridin-2-yl)methyl)piperidine-4-carboxamide

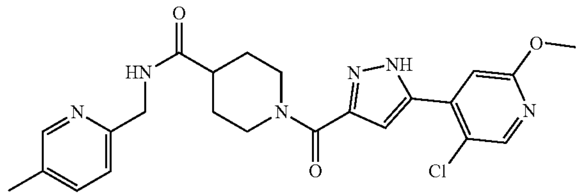

The title compound was prepared using a procedure similar to the one described for the synthesis of Example 167, except (5-methylpyridin-2-yl)methanamine was used as starting material. The title compound was obtained as a solid (4.0 mg). $^1$H NMR (300 MHz, $CD_3OD$) δ 8.44-8.36 (m, 1H), 8.28 (s, 1H), 7.82 (d, 1H), 7.40 (d, 1H), 7.17 (s, 2H), 4.80-4.57 (m, 2H), 4.51 (s, 2H), 3.97 (s, 3H), 3.79-3.47 (m, 1H), 3.18-2.79 (m, 1H), 2.78-2.56 (m, 1H), 2.40 (s, 3H), 1.96 (s, 2H), 1.87-1.64 (m, 2H). LCMS (ESI): $[M+H]^+$: 469.15.

Example 177. 1-(5-(5-chloro-2-methoxypyridin-4-yl)-1H-pyrazole-3-carbonyl)-N-(3-chlorobenzyl)-3-fluoropiperidine-4-carboxamide

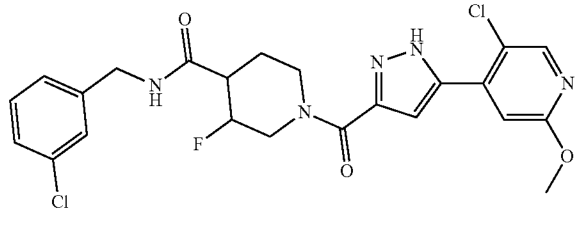 [SMILES: COc1cc(-c2cc(C(=O)N3CCC(C(=O)NCc4cccc(Cl)c4)C(F)C3)n[nH]2)c(Cl)cn1]

The title compound was prepared using a procedure similar to the one described for the synthesis of Example 171, except methyl 3-fluoropiperidine-4-carboxylase hydrochloride was used as starting material in Step-1. The title compound was obtained as a solid mixture of diastereomers (4.6 mg). $^1$H NMR (400 MHz, $CD_3OD$) δ 8.30-8.17 (m, 1H), 7.32-7.02 (m, 6H), 5.27-4.96 (m, 2H), 4.80-4.47 (m, 1H), 4.40 (s, 2H), 3.94 (s, 3H), 3.65-3.44 (m, 1H), 3.21-2.74 (m, 2H), 2.24-2.04 (m, 1H), 1.94-1.86 (m, 1H). LCMS (ESI): 506.3.

Example 178. 1-(5-(5-chloro-2-methoxypyridin-4-yl)-1H-pyrazole-3-carbonyl)-N-((6-(trifluoro-15-methyl)pyridin-3-yl)methyl)piperidine-4-carboxamide

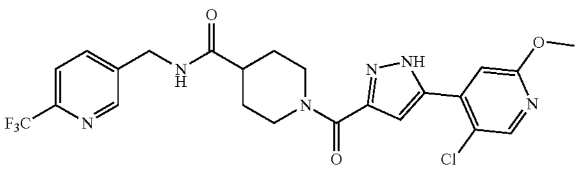 [SMILES: COc1cc(-c2cc(C(=O)N3CCC(C(=O)NCc4ccc(C(F)(F)F)nc4)CC3)n[nH]2)c(Cl)cn1]

The title compound was prepared using a procedure similar to the one described for the synthesis of Example 163, except (6-(trifluoro-15-methyl)pyridin-3-yl)methanamine was used as starting material. The resulting residue was purified by Prep-HPLC (using the following conditions: Column: Sunfire Prep C18 OBD Column, 19×150 mm 5 μm 10 nm; Mobile phase A: Water (0.1% FA), mobile phase B: MeCN; Detector, UV 210/254 nm) to obtain the title compound (24.8 mg) as a solid. $^1$H NMR (300 MHz, $CD_3OD$) δ 10.06 (s, 1H), 9.68 (d, 1H), 9.36 (m, 1H), 9.26-9.16 (m, 1H), 8.57 (d, 2H), 5.91 (s, 2H), 5.37 (d, 3H), 4.73 (m, 4H), 4.03 (m, 1H), 3.60-2.89 (m, 4H). LCMS (ESI): $[M+H]^+$: 523.3.

Example 179. 1-(5-(5-chloro-2-methoxypyridin-4-yl)-1H-pyrazole-3-carbonyl)-N-((5-chloropyridin-3-yl)methyl)piperidine-4-carboxamide

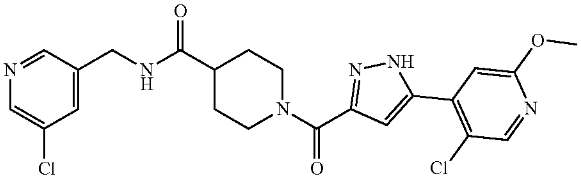 [SMILES: COc1cc(-c2cc(C(=O)N3CCC(C(=O)NCc4cncc(Cl)c4)CC3)n[nH]2)c(Cl)cn1]

The title compound was prepared using a procedure similar to the one described for the synthesis of Example 167, except (5-chloropyridin-3-yl)methanamine was used as starting material. The title compound was obtained as a solid (14.3 mg). $^1$H NMR (400 MHz, $CD_3OD$) δ 8.48-8.39 (m, 2H), 8.25 (s, 1H), 7.82-7.77 (m, 2H), 7.14 (s, 1H), 4.66-4.62 (m, 2H), 4.42-4.38 (m, 2H), 3.94 (s, 3H), 2.97-2.92 (m, 1H), 2.66-2.54 (m, 2H), 1.93-1.89 (m, 2H), 1.78-1.70 (m, 2H). LCMS (ESI): $[M+H]^+$: 489.3.

Example 180. N-((1H-indazol-6-yl)methyl)-1-(5-(5-chloro-2-methoxypyridin-4-yl)-1H-pyrazole-3-carbonyl)piperidine-4-carboxamide

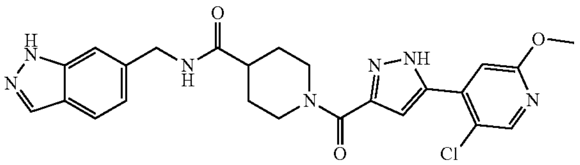 [SMILES: COc1cc(-c2cc(C(=O)N3CCC(C(=O)NCc4ccc5cn[nH]c5c4)CC3)n[nH]2)c(Cl)cn1]

The title compound was prepared using a procedure similar to the one described for the synthesis of Example 179, except (1H-indazol-6-yl)methanamine was used as starting material. The title compound was obtained as a solid (4.8 mg). $^1$H NMR (400 MHz, $CD_3OD$) δ 8.54 (s, 8.26 (s, 1H), 7.99 (d, 1H), 7.76-7.69 (m, 1H), 7.43 (s, 1H), 7.20-7.03 (m, 2H), 4.63-4.58 (m, 2H), 4.53-4.48 (m, 2H), 3.94 (s, 3H), 2.97-2.93 (m, 1H), 2.67-2.57 (m, 1H), 2.06-1.64 (m, 4H), 1.47-0.99 (m, 1H). LCMS (ESI): $[M+H]^+$: 494.3.

Example 181. N-((1H-indol-3-yl)methyl)-1-(5-(5-chloro-2-methoxypyridin-4-yl)-1H-pyrazole-3-carbonyl)piperidine-4-carboxamide

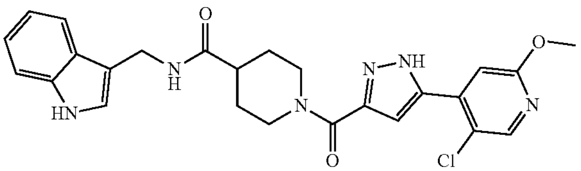 [SMILES: COc1cc(-c2cc(C(=O)N3CCC(C(=O)NCc4c[nH]c5ccccc45)CC3)n[nH]2)c(Cl)cn1]

The title compound was prepared using a procedure similar to the one described for the synthesis of Example 167, except (1H-indol-3-yl)methanamine was used as starting material. The title compound was obtained as a solid (17.5 mg). $^1$H NMR (400 MHz, $CD_3OD$) δ 8.25 (s, 1H), 7.58-7.51 (m, 1H), 7.37-7.30 (m, 1H), 7.20 (s, 1H), 7.16-7.06 (m, 3H), 7.05-6.96 (m, 1H), 4.66-4.62 (m, 1H), 4.54 (s, 2H), 3.94 (s, 3H), 3.25-3.21 (m, 2H), 2.91-2.87 (m, 1H), 2.60-2.48 (m, 1H), 1.98-1.73 (m, 4H). LCMS (ESI): $[M+H]^+$: 493.3.

Example 182. 1-(5-(5-chloro-2-methoxypyridin-4-yl)-1H-pyrazole-3-carbonyl)-N (isoquinolin-6-ylmethyl)piperidine-4-carboxamide

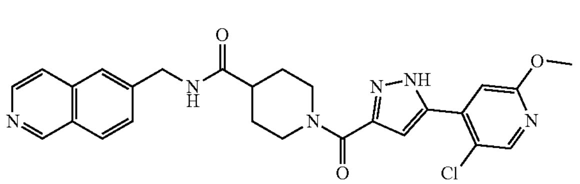 [SMILES: COc1cc(-c2cc(C(=O)N3CCC(C(=O)NCc4ccc5cnccc5c4)CC3)n[nH]2)c(Cl)cn1]

The title compound was prepared using a procedure similar to the one described for the synthesis of Example 167, except isoquinolin-6-ylmethanamine hydrochloride was used as starting material. The title compound was obtained as a solid (12.9 mg), $^1$H NMR (300 MHz, $CD_3OD$)

δ 9.21 (s, 1H), 8.44-8.42 (m, 1H), 8.27 (s, 1H), 8.11-8.09 (m, 1H), 7.83-7.81 (m, 2H), 7.66-7.63 (m, 1H), 7.20-7.10 (m, 2H), 4.80-4.55 (m, 4H), 3.99 (s, 3H), 3.33-3.19 (m, 1H), 3.17-2.92 (m, 1H), 2.77-2.56 (m, 1H), 2.10-1.73 (m, 4H). LCMS (ESI): $[M+H]^+$: 505.40.

Example 183. 1-(5-(5-chloro-2-methoxypyridin-4-yl)-1H-pyrazole-3-carbonyl)-N-(5-oxo-1-phenylpyrrolidin-3-yl)piperidine-4-carboxamide

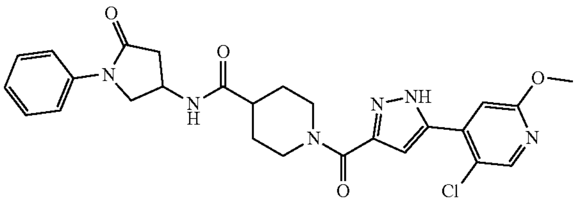 [SMILES: COc1cc(-c2cc(C(=O)N3CCC(C(=O)NC4CC(=O)N(c5ccccc5)C4)CC3)n[nH]2)c(Cl)cn1]

The title compound was prepared using a procedure similar to the one described for the synthesis of Example 167, except 4-amino-1-phenylpyrrolidin-2-one was used as starting material. The title compound was obtained as a solid (24.3 mg). $^1$H NMR (300 MHz, $CD_3OD$) δ 8.25 (s, 1H), 7.66-7.54 (m, 2H), 7.45-7.33 (m, 2H), 7.24-7.07 (m, 3H), 4.79-4.37 (m, 3H), 4.35-4.14 (m, 1H), 3.94 (s, 3H), 3.78-3.50 (m, 1H), 3.22-2.77 (m, 3H), 2.72-2.42 (m, 2H), 2.01-1.57 (m, 4H). LCMS (ESI): $[M+H]^+$: 523.45.

Example 184. 1-(5-(5-chloro-2-methoxypyridin-4-yl)-1H-pyrazole-3-carbonyl)-N (chroman-4-yl)piperidine-4-carboxamide

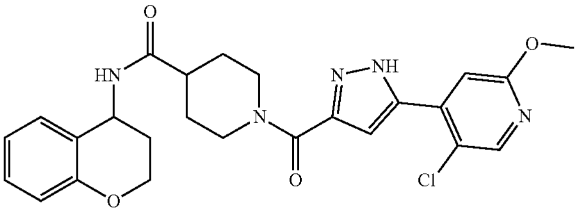 [SMILES: COc1cc(-c2cc(C(=O)N3CCC(C(=O)NC4CCOc5ccccc54)CC3)n[nH]2)c(Cl)cn1]

The title compound was prepared using a procedure similar to the one described for the synthesis of Example 167, except chroman-4-amine hydrochloride was used as starting material. The title compound was obtained as a solid of enantiomers (11.1 mg). $^1$H NMR (400 MHz, $CD_3OD$) δ 8.26 (s, 1H), 7.17-7.09 (m, 4H), 6.91-6.83 (m, 1H), 6.81-6.74 (m, 1H), 5.10-5.02 (m, 1H), 4.65 (s, 2H), 4.28-4.13 (m, 2H), 3.94 (s, 3H), 2.94 (d, 1H), 2.64-2.51 (m, 1H), 2.19-2.07 (m, 1H), 2.04-1.91 (m, 2H), 1.81 (d, 2H), 1.43-1.08 (m, 2H). LCMS (ESI): $[M+H]^+$496.40.

Example 185. 1-(5-(5-chloro-2-methoxypyridin-4-yl)-1H-pyrazole-3-carbonyl)-N-((2,2-dimethyl-1,3-dioxolan-4-yl)methyl)piperidine-4-carboxamide

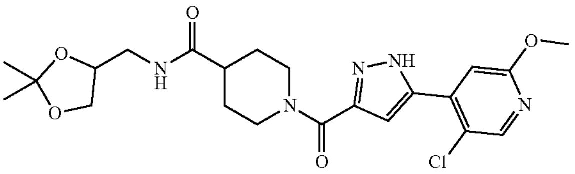

The title compound was prepared using a procedure similar to the one described for the synthesis of Example 167, except (2,2-dimethyl-1,3-dioxolan-4-yl)methanamine hydrochloride was used as starting material. The title compound was obtained as a solid mixture of enantiomers (19.4 mg). $^1$H NMR (400 MHz, $CD_3OD$): δ 8.25 (s, 1H), 7.14 (s, 2H), 4.64 (s, 2H), 4.22-4.11 (m, 1H), 4.06-3.98 (m, 1H), 3.94 (s, 3H), 3.68-3.59 (m, 1H), 3.40-3.35 (m, 3H), 2.96 (s, 1H), 2.64-2.51 (m, 1H), 1.98-1.63 (m, 4H), 1.39 (s, 3H), 1.31 (s, 3H). LCMS (ESI): $[M+H]^+$: 478.3.

Example 186. 1-(5-(5-chloro-2-methoxypyridin-4-yl)-1H-pyrazole-3-carbonyl)-N-(1-methyl-1,2,3,4-tetrahydroquinolin-4-yl)piperidine-4-carboxamide

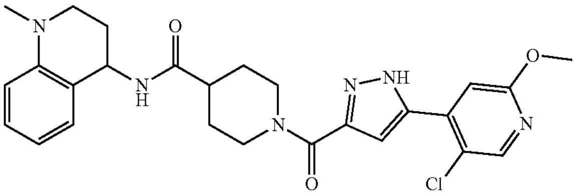 [SMILES: COc1cc(-c2cc(C(=O)N3CCC(C(=O)NC4CCN(C)c5ccccc54)CC3)n[nH]2)c(Cl)cn1]

The title compound was prepared using a procedure similar to the one described for the synthesis of Example 167, except 1-methyl-1,2,3,4-tetrahydroquinolin-4-amine was used as starting material. The title compound was obtained as a solid mixture of enantiomers (7.4 mg). $^1$H NMR (300 MHz, $CD_3OD$) δ 8.26 (s, 1H), 7.15 (s, 2H), 7.16-7.06 (m, 1H), 7.06-6.98 (m, 1H), 6.72-6.57 (m, 2H), 5.04-4.94 (m, 1H), 4.76-4.44 (m, 2H), 3.96 (s, 3H), 3.28-3.18 (m, 2H), 2.94-2.88 (m, 5H), 2.65-2.51 (m, 1H), 2.16-1.76 (m, 6H). LCMS (ESI): $[M+H]^+$: 509.4.

Example 187. 1-(5-(5-chloro-2-methoxypyridin-4-yl)-1H-pyrazole-3-carbonyl)-N-((1-methyl-1H-indol-3-yl)methyl)piperidine-4-carboxamide

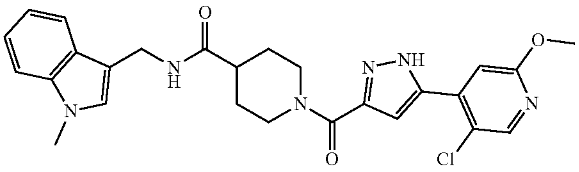 [SMILES: COc1cc(-c2cc(C(=O)N3CCC(C(=O)NCc4cn(C)c5ccccc45)CC3)n[nH]2)c(Cl)cn1]

The title compound was prepared using a procedure similar to the one described for the synthesis of Example 167, except (1-methyl-1H-indol-3-yl)methanamine was used as starting material. The title compound was obtained as a solid (14.0 mg). $^1$H NMR (400 MHz, $CD_3OD$): δ 8.25 (s, 1H), 7.56 (m, 1H), 7.33 (d, 1H), 7.21-7.10 (m, 3H), 7.07-7.01 (m, 1H), 4.52 (m, 4H), 3.94 (s, 3H), 3.76 (s, 3H), 3.01-2.82 (m, 2H), 2.60-2.48 (m, 1H), 1.88-1.72 (m, 4H). LCMS (ESI): $[M+H]^+$: 507.4.

Example 188. N-((1H-indol-6-yl)methyl)-1-(5-(5-chloro-2-methoxypyridin-4-yl)-1H-pyrazole-3-carbonyl)piperidine-4-carboxamide

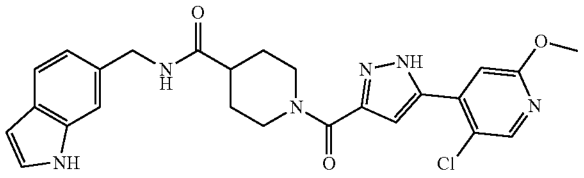 [SMILES: COc1cc(-c2cc(C(=O)N3CCC(C(=O)NCc4ccc5cc[nH]c5c4)CC3)n[nH]2)c(Cl)cn1]

The title compound was prepared using a procedure similar to the one described for the synthesis of Example 167, except (1H-indol-6-yl)methanamine was used as starting material. The title compound was obtained as a solid (8.4 mg). $^1$H NMR (300 MHz, $CD_3OD$) δ 8.28 (s, 1H), 7.24-7.11 (m, 4H), 6.95-6.81 (m, 2H), 4.63 (s, 2H), 4.35 (m, 2H), 3.97 (s, 3H), 3.00 (s, 2H), 2.60 (s, 1H), 1.90 (s, 2H), 1.77 (m, 2H), 1.31 (s, 1H), 0.92 (s, 1H). LCMS (ESI): $[M+H]^+$: 493.3.

Example 189. 1-(5-(5-chloro-2-methoxypyridin-4-yl)-1H-pyrazole-3-carbonyl)-N-((5-methylfuran-2-yl)methyl)piperidine-4-carboxamide

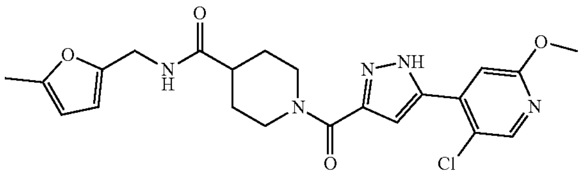

The title compound was prepared using a procedure similar to the one described for the synthesis of Example 167, except (5-methylfuran-2-yl)methanamine was used as starting material. The title compound was obtained as a solid (13.0 mg). $^1$H NMR (400 MHz, $CD_3OD$): δ 8.25 (s, 1H), 7.14 (s, 2H), 6.09 (d, 1H), 5.92-5.88 (m, 1H), 4.65 (s, 2H), 4.28 (s, 2H), 3.94 (s, 3H), 2.96 (d, 1H), 2.62-2.49 (m, 1H), 2.23 (d, 3H), 1.95-1.65 (m, 5H). LCMS (ESI): $[M+H]^+$: 458.3.

Example 190. N-((1H-indol-4-yl)methyl)-1-(5-(5-chloro-2-methoxypyridin-4-yl)-1H-pyrazole-3-carbonyl)piperidine-4-carboxamide

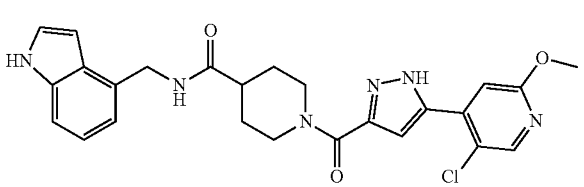 [SMILES: COc1cc(-c2cc(C(=O)N3CCC(C(=O)NCc4cccc5[nH]ccc45)CC3)n[nH]2)c(Cl)cn1]

The title compound was prepared using a procedure similar to the one described for the synthesis of Example 167, except (1H-indol-4-yl)methanamine was used as starting material. The title compound was obtained as a solid (5.7 mg). $^1$H NMR (300 MHz, $CD_3OD$) δ 8.25 (s, 1H), 7.36-7.28 (m, 1H), 7.23 (d, 1H), 7.14 (s, 2H), 7.09-7.01 (m, 1H), 6.97-6.90 (m, 1H), 6.54-6.47 (m, 1H), 4.64 (s, 3H), 3.94 (s, 3H), 3.30-3.03 (m, 2H), 3.02-2.83 (m, 1H), 2.67-2.52 (m, 1H), 2.08-1.60 (m, 4H). LCMS (ESI): $[M+H]^+$: 493.40.

Example 191. 1-(5-(5-chloro-2-methoxypyridin-4-yl)-1H-pyrazole-3-carbonyl)-N-(5,6,7,8-tetrahydroisoquinolin-5-yl)piperidine-4-carboxamide

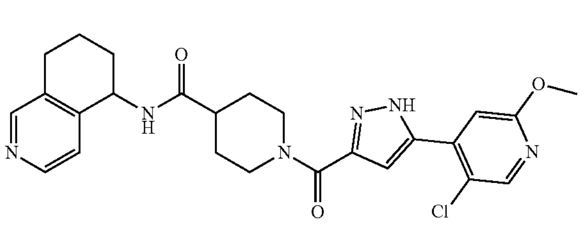 [SMILES: COc1cc(-c2cc(C(=O)N3CCC(C(=O)NC4CCCc5cnccc54)CC3)n[nH]2)c(Cl)cn1]

The title compound was prepared using a procedure similar to the one described for the synthesis of Example 167, except 5,6,7,8-tetrahydroisoquinolin-5-amine hydrochloride was used as starting material. The title compound was obtained as a solid mixture of enantiomers (20.5 mg). $^1$H NMR (300 MHz, $CD_3OD$) δ 8.35-8.25 (m, 3H), 7.24 (m, 1H), 7.18 (s, 1H), 7.17 (s, 1H), 5.15-5.05 (m, 1H), 4.69 (s, 3H), 3.97 (s, 3H), 2.99 (m, 2H), 2.90-2.80 (m, 2H), 2.71-2.55 (m, 2H), 2.16-1.91 (m, 3H), 1.95-1.71 (m, 3H). LCMS (ESI): $[M+H]^+$: 495.3.

Example 192, N-((1H-indazol-4-yl)methyl)-1-(5-(5-chloro-2-methoxypyridin-4-yl)-1H-pyrazole-3-carbonyl)piperidine-4-carboxamide

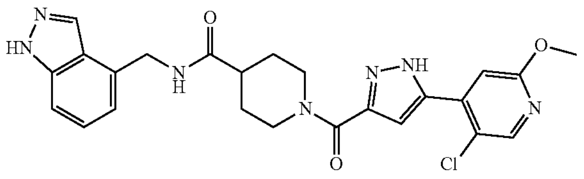 [SMILES: COc1cc(-c2cc(C(=O)N3CCC(C(=O)NCc4cccc5[nH]ncc45)CC3)n[nH]2)c(Cl)cn1]

The title compound was prepared using a procedure similar to the one described for the synthesis of Example 167, except (1H-indazol-4-yl)methanamine was used as starting material. The title compound was obtained as a solid (14.5 mg). $^1$H NMR (400 MHz, $CD_3OD$) δ 8.25 (s, 1H), 8.13 (d, 1H), 7.46 (d, 1H), 7.39-7.28 (m, 1H), 7.14 (s, 2H), 7.08-7.01 (m, 1H), 4.71 (s, 2H), 4.65 (s, 2H), 3.94 (s, 3H), 3.00-2.85 (m, 2H), 2.67-2.50 (m, 1H), 1.97-1.59 (m, 4H). LCMS (ESI): $[M+H]^+$: 494.3.

Example 193. 1-(5-(5-chloro-2-methoxypyridin-4-yl)-1H-pyrazole-3-carbonyl)-N-((3-chloro-5-(trifluoromethyl)pyridin-2-yl)methyl)piperidine-4-carboxamide

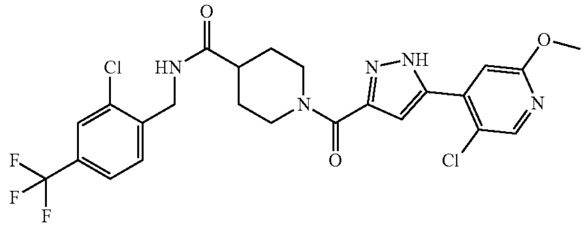 [SMILES: COc1cc(-c2cc(C(=O)N3CCC(C(=O)NCc4ccc(C(F)(F)F)cc4Cl)CC3)n[nH]2)c(Cl)cn1]

The title compound was prepared using a procedure similar to the one described for the synthesis of Example 167, except (3-chloro-5-(trifluoromethyl)pyridin-2-yl)methanamine hydrochloride was used as starting material. The title compound was obtained as a solid (13.7 mg). $^{1}$H NMR (400 MHz, $CD_3OD$) δ 8.79 (d, 1H), 8.36-8.16 (m, 2H), 7.31-6.74 (m, 2H), 4.68 (s, 2H), 3.94 (d, 3H), 3.54-3.43 (m, 1H), 3.17-3.08 (m, 1H), 3.06-2.94 (m, 1H), 2.79-2.67 (m, 2H), 2.10-1.57 (m, 4H). LCMS (ESI): $[M+H]^+$: 557.3.

Example 194. N-((1H-indol-7-yl)methyl)-1-(5-(5-chloro-2-methoxypyridin-4-yl)-1H-pyrazole-3-carbonyl)piperidine-4-carboxamide

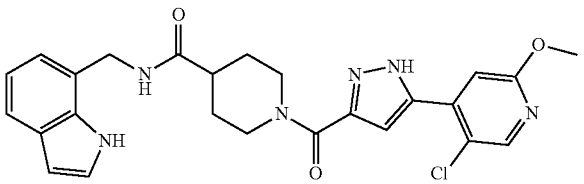 [SMILES: COc1cc(-c2cc(C(=O)N3CCC(C(=O)NCc4cccc5cc[nH]c45)CC3)n[nH]2)c(Cl)cn1]

The title compound was prepared using a procedure similar to the one described for the synthesis of Example 179, except (1H-indol-7-yl)methanamine was used as starting material. The title compound was obtained as a solid (7.4 mg). $^{1}$H NMR (300 MHz, $CD_3OD$) δ 8.29 (s, 1H), 7.55-7.46 (m, 1H), 7.26 (d, 1H), 7.24-6.95 (m, 4H), 6.48 (d, 1H), 4.70 (s, 1H), 4.64 (s, 3H), 3.97 (s, 3H), 3.25 (s, 1H), 2.93 (s, 1H), 2.69-2.52 (m, 1H), 1.93-1.73 (m, 4H). LCMS (ESI): $[M+H]^+$: 493.3.

Example 195. 1-(5-(5-chloro-2-methoxypyridin-4-yl)-1H-pyrazole-3-carbonyl)-N-(6-fluorochroman-4-yl)piperidine-4-carboxamide

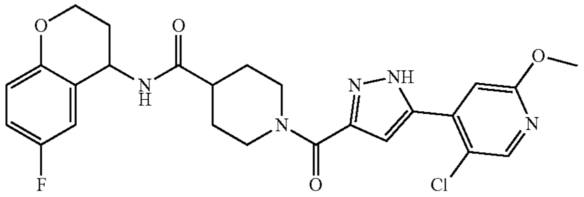 [SMILES: COc1cc(-c2cc(C(=O)N3CCC(C(=O)NC4CCOc5ccc(F)cc54)CC3)n[nH]2)c(Cl)cn1]

The title compound was prepared using a procedure similar to the one described for the synthesis of Example 167, except 6-fluorochroman-4-amine was used as starting material. The title compound was obtained as a solid mixture of enantiomers (17.6 mg). $^{1}$H NMR (300 MHz, $CD_3OD$) δ 8.28 (s, 1H), 7.17 (s, 2H), 6.98-6.86 (m, 2H), 6.84-6.73 (m, 1H), 5.14-5.05 (m, 1H), 4.68 (s, 2H), 4.28-4.14 (m, 2H), 3.97 (s, 3H), 3.17-2.84 (m, 1H), 2.71-2.43 (m, 1H), 2.32-2.08 (m, 1H), 2.04-1.68 (m, 6H). LCMS (ESI): $[M+H]^+$: 514.10.

Example 196. 1-(5-(5-chloro-2-methoxypyridin-4-yl)-1H-pyrazole-3-carbonyl)-N-(1-phenylpiperidin-4-yl)piperidine-4-carboxamide

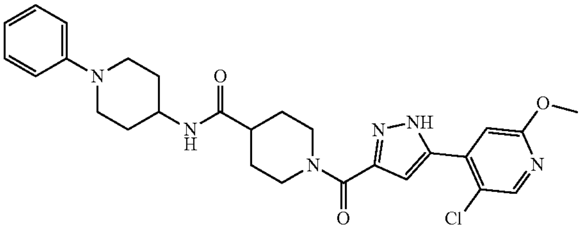 [SMILES: COc1cc(-c2cc(C(=O)N3CCC(C(=O)NC4CCN(c5ccccc5)CC4)CC3)n[nH]2)c(Cl)cn1]

The title compound was prepared using a procedure similar to the one described for the synthesis of Example 167, except 1-phenylpiperidin-4-amine was used as starting material. The title compound was obtained as a solid (15.5 mg). $^{1}$H NMR (300 MHz, $CD_3OD$) δ 8.28 (s, 1H), 7.30-7.14 (m, 4H), 7.05-6.96 (m, 2H), 6.90-6.79 (m, 1H), 4.66 (s, 2H), 3.97 (s, 3H), 3.88-3.75 (m, 1H), 3.66 (d, 2H), 2.96 (s, 1H), 2.90-2.76 (m, 2H), 2.70-2.23 (m, 1H), 2.13-1.57 (m, 9H). LCMS (ESI): $[M+H]^+$; 523.4.

Example 197. N-((2H-benzo[d][1,2,3]triazol-5-yl)methyl)-1-(5-(5-chloro-2-methoxypyridin-4-yl)-1H-pyrazole-3-carbonyl)piperidine-4-carboxamide

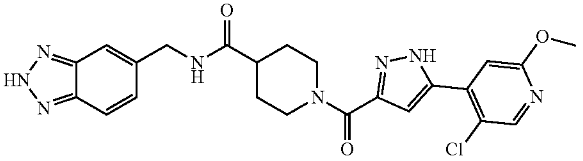 [SMILES: COc1cc(-c2cc(C(=O)N3CCC(C(=O)NCc4ccc5n[nH]nc5c4)CC3)n[nH]2)c(Cl)cn1]

The title compound was prepared using a procedure similar to the one described for the synthesis of Example 103, except (2H-benzo[d][1,2,3]triazol-5-yl)methanamine was used as starting material to obtain the title compound (2.4 mg) as a solid. LCMS (ESI): 495.42 $[M+H]^+$.

Example 198. 1-(5-(5-chloro-2-methoxypyridin-4-yl)-1H-pyrazole-3-carbonyl)-N-((1r,4r)-4-hydroxy-4-methylcyclohexyl)piperidine-4-carboxamide

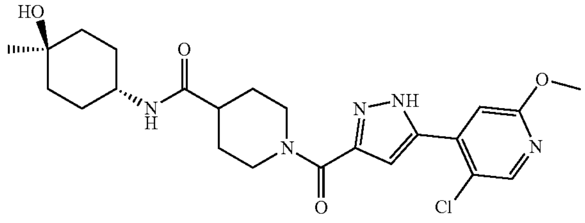

The title compound was prepared using a procedure similar to the one described for the synthesis of Example 103, except (1r,4r)-4-amino-1-methylcyclohexan-1-ol was used as starting material to obtain the title compound (7.3 mg) as a solid. LCMS (ESI): 476.52 $[M+H]^+$.

Example 199. 1-(5-(5-chloro-2-methoxypyridin-4-yl)-1H-pyrazole-3-carbonyl)-N-((1r,4r)-4-hydroxy-4-(trifluoromethyl)cyclohexyl)piperidine-4-carboxamide

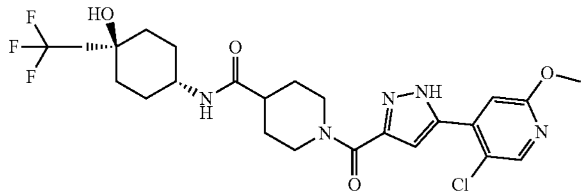 [SMILES: COc1cc(-c2cc(C(=O)N3CCC(C(=O)N[C@H]4CC[C@@](O)(CC(F)(F)F)CC4)CC3)n[nH]2)c(Cl)cn1]

The title compound was prepared using a procedure similar to the one described for the synthesis of Example 103, except (1r,4r)-4-amino-1-(trifluoromethyl)cyclohexan-1-ol was used as starting material to obtain the title compound (18.1 mg) as a solid. $^1$H NMR (400 MHz, $CD_3OD$) δ 8.26 (s, 1H), 7.14 (s, 2H), 4.59 (s, 1H), 3.95 (s, 3H), 3.79 (s, 1H), 2.83-2.98 (m, 1H), 2.61-2.69 (m, 1H), 1.83-1.93 (m, 6H), 1.69-1.81 (m, 6H), 1.62-1.67 (m, 2H). LCMS (ESI): 530.95 $[M+H]^+$.

Example 200. N-((3-fluoro-1H-indazol-5-yl)methyl)-1-(5-(5-fluoro-2-methoxypyridin-4-yl)-1H-pyrazole-3-carbonyl)piperidine-4-carboxamide

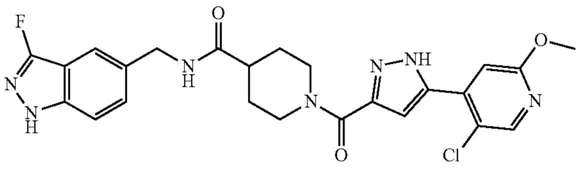 [SMILES: COc1cc(-c2cc(C(=O)N3CCC(C(=O)NCc4ccc5[nH]nc(F)c5c4)CC3)n[nH]2)c(Cl)cn1]

1-(3-fluoro-1H-indazol-5-yl)methanamine (INTERMEDIATE 514, 56.0 mg, 0.3 mmol) was added to a stirred solution of 1-[5-(5-fluoro-2-methoxypyridin-4-yl)-1H-pyrazole-3-carbonyl]piperidine-4-carboxylic acid (INTERMEDIATE 511, 118.1 mg, 0.3 mmol) HATU (193.4 mg, 0.5 mmol) and DIPEA (0.18 mL, 1.0 mmol) in DMF (5.0 mL). The solution was stirred at 25° C. for TIME, then diluted with water and extracted with EtOAc. The organic layers were combined, dried over anhydrous sodium sulfate, filtered, and the solvent was evaporated. The residue was purified by Flash-Prep-HPLC (using the following conditions: Column: XSelect CSH Prep C18 OBD, 19×150 mm, 5 μm; Mobile Phase A: Water (0.1% FA); Mobile Phase B: MeCN; Flow rate: 25 mL/min; Gradient: 33% B to 33% B in 6 min; Detection: 254 nm) to obtain the title compound (41.5 mg) as a solid. $^1$H NMR (400 MHz, DMSO-d6) δ 14.00 (m, 1H), 12.50 (s, 1H), 8.41 (s, 1H), 8.25 (s, 1H), 7.52 (s, 1H), 7.45-7.42 (m, 2H), 7.33-7.30 (m, 1H), 7.04-7.02 (m, 1H), 4.52-4.31 (m, 4H), 3.88 (s, 3H), 3.20-3.16 (m, 1H), 2.90-2.80 (m, 1H), 2.55-2.50 (m, 1H), 1.88-1.76 (m, 2H), 1.74-1.50 (m, 2H). LCMS (ESI): 496.2 $[M+H]^+$.

Example 201. N-((1H-indazol-3-yl)methyl)-1-(5-(5-chloro-2-methoxypyridin-4-yl)-1H-pyrazole-3-carbonyl)piperidine-4-carboxamide

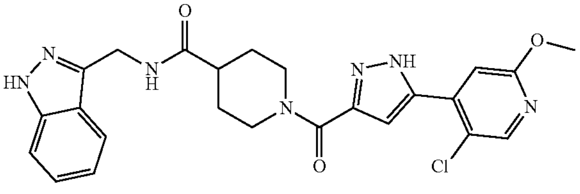 [SMILES: COc1cc(-c2cc(C(=O)N3CCC(C(=O)NCc4n[nH]c5ccccc45)CC3)n[nH]2)c(Cl)cn1]

The title compound was prepared using a procedure similar to the one described for the synthesis of Example 167, except (1H-indazol-3-yl)methanamine was used as starting material. The title compound was obtained as a solid (23.0 mg). $^1$H NMR (400 MHz, $CD_3OD$) δ 8.25 (s, 1H), 7.80-7.73 (m, 1H), 7.53-7.44 (m, 1H), 7.44-7.33 (m, 1H), 7.23-7.08 (m, 3H), 4.75 (s, 2H), 4.62 (s, 2H), 3.94 (s, 3H), 2.91 (s, 2H), 2.65-2.53 (m, 1H), 1.85-1.73 (m, 4H). LCMS (ESI): $[M+H]^+$: 494.4.

Example 202. N-((1H-pyrrolo[2,3-b]pyridin-3-yl)methyl)-1-(5-(5-chloro-2-methoxypyridin-4-yl)-1H-pyrazole-3-carbonyl)piperidine-4-carboxamide

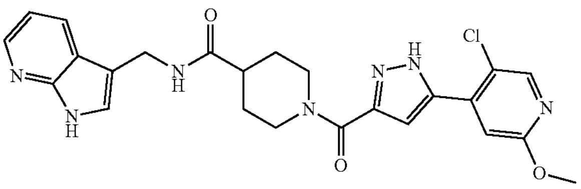 [SMILES: COc1cc(-c2cc(C(=O)N3CCC(C(=O)NCc4c[nH]c5ncccc45)CC3)n[nH]2)c(Cl)cn1]

The title compound was prepared using a procedure similar to the one described for the synthesis of Example 167, except (1H-pyrrolo[2,3-b]pyridin-3-yl)methanamine dihydrochloride was used as starting material. The title compound was obtained as a solid (21.6 mg). $^1$H NMR (300 MHz, DMSO-$d_6$) δ 13.94 (s, 1H), 11.44 (s, 1H), 8.36 (s, 1H), 8.25-8.16 (m, 2H), 7.99-7.90 (m, 1H), 7.39-7.32 (m, 1H), 7.24 (s, 1H), 7.14 (s, 1H), 7.10-7.00 (m, 1H), 4.55-4.30 (m, 4H), 3.90 (s, 3H), 3.17 (s, 1H), 2.82 (s, 1H), 2.59-2.41 (m, 1H), 1.78-1.72 (m, 2H), 1.63-1.57 (m, 2H). LCMS (ESI): $[M+H]^+$: 494.3.

Example 203. 1-(5-(5-chloro-2-methoxypyridin-4-yl)-1H-pyrazole-3-carbonyl)-N-((2-methyl-1H-indol-5-yl)methyl)piperidine-4-carboxamide

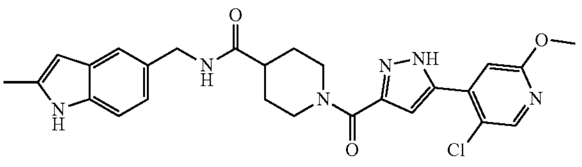

The title compound was prepared using a procedure similar to the one described for the synthesis of Example 167, except (2-methyl-1H-indol-5-yl)methanamine was used as starting material. The title compound was obtained as a solid (4.8 mg). LCMS (ESI): 507.53 $[M+H]^+$.

Example 204. 1-[5-(5-fluoro-2-methoxypyridin-4-yl)-1H-pyrazole-3-carbonyl]-N-[(3-methyl-1H-indazol-5-yl)methyl]piperidine-4-carboxamide

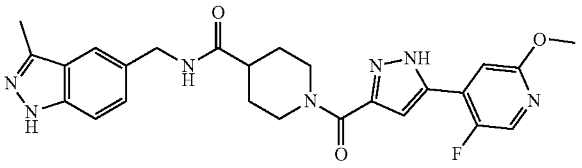 [SMILES: COc1cc(-c2cc(C(=O)N3CCC(C(=O)NCc4ccc5[nH]nc(C)c5c4)CC3)n[nH]2)c(F)cn1]

Step-1. 1-(5-(5-fluoro-2-methoxypyridin-4-yl)-1-(tetrahydro-2H-pyran-2-yl)-1H-pyrazole-3-carbonyl)-N-((3-methyl-1H-indazol-5-yl)methyl)piperidine-4-carboxamide

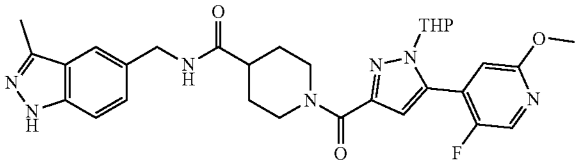

HOBt (47.0 mg, 0.3 mmol), EDCI (67.0 mg, 0.3 mmol), 1-(3-methyl-1H-indazol-5-yl)methanamine (INTERMEDIATE 515, 56.0 mg, 0.3 mmol), and DIPEA (90.0 mg, 0.7 mmol) were added to a solution of 1-(5-(5-fluoro-2-methoxypyridin-4-yl)-1-(tetrahydro-2H-pyran-2-yl)-1H-pyrazole-3-carbonyl)piperidine-4-carboxylic acid (INTERMEDIATE 505, 100.0 mg, 0.2 mmol) in DMF (2.0 mL). The solution was stirred at 25° C. for 2 h, then diluted with water and extracted with dichloromethane. The organic layers were concentrated under vacuum and the residue was purified by silica gel column chromatography (DCM/MeOH, 10/1 v/v) to obtain the title compound (90 mg) as an oil. LCMS (ESI): 576.3 $[M+H]^+$.

Step-2. 1-[5-(5-fluoro-2-methoxypyridin-4-yl)-1H-pyrazole-3-carbonyl]-N-[(3-methyl-1H-indazol-5-yl)methyl]piperidine-4-carboxamide

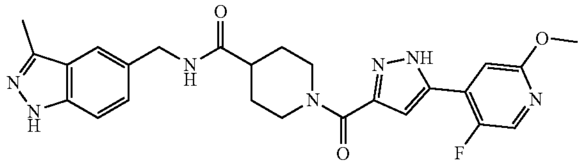 [SMILES: COc1cc(-c2cc(C(=O)N3CCC(C(=O)NCc4ccc5[nH]nc(C)c5c4)CC3)n[nH]2)c(F)cn1]

TFA (2.0 mL) was added to a solution of 1-(5-(5-fluoro-2-methoxypyridin-4-yl)-1-(tetrahydro-2H-pyran-2-yl)-1H-pyrazole-3-carbonyl)-N-((3-methyl-1H-indazol-5-yl)methyl)piperidine-4-carboxamide (Step-2, 90.0 mg, 0.16 mmol) in DCM (2.00 mL). The solution was stirred at 25° C. for 1 h, then concentrated under vacuum. The residue was diluted with DCM then the pH of the solution was adjusted to pH 8 with DIPEA. The solution was concentrated under vacuum, and the residue was purified by Prep-HPLC (using the following conditions: Column: Xselect CSH OBD, 30×150 mm, 5 μm; Mobile Phase A: Water (10 mM $NH_4HCO_3$); Mobile Phase B: MeCN; Gradient: 20% B to 40% B in 8 min; Detection: 220/254 nm) to obtain the title compound (9.4 mg) as a solid. $^1H$ NMR (300 MHz, DMSO-d6) δ 13.98 (s, 1H), 12.56 (s, 1H), 8.42-8.34 (m, 1H), 8.28 (s, 1H), 7.52 (s, 1H), 7.43-7.36 (m, 1H), 7.32 (d, 1H), 7.25-7.18 (m, 1H), 7.04 (s, 1H), 4.47 (s, 1H), 4.35 (d, 3H), 3.87 (s, 3H), 3.20 (s, 2H), 2.85 (s, 1H), 2.46 (s, 3H), 1.70 (m, 4H). LCMS (ESI): 492.2 $[M+H]^+$.

Example 205. 1-(5-(5-chloro-2-methoxypyridin-4-yl)-1H-pyrazole-3-carbonyl)-N-(1-isopropyl-1H-pyrazol-4-yl)piperidine-4-carboxamide

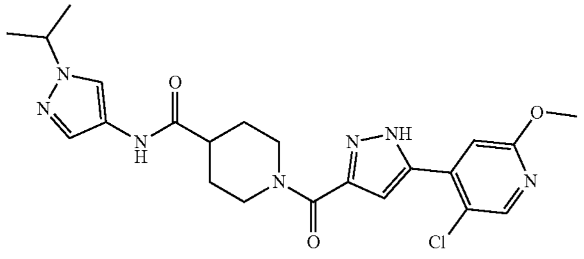 [SMILES: COc1cc(-c2cc(C(=O)N3CCC(C(=O)Nc4cnn(C(C)C)c4)CC3)n[nH]2)c(Cl)cn1]

The title compound was prepared using a procedure similar to the one described for the synthesis of Example 167, except 1-isopropyl-1H-pyrazol-4-amine was used as starting material. The title compound was obtained as a solid (12.2 mg). $^1H$ NMR (300 MHz, $CD_3OD$) δ 8.27 (s, 1H), 7.92 (d, 1H), 7.49 (d, 1H), 7.19-7.13 (m, 2H), 4.97-4.58 (m, 3H), 4.55-4.40 (m, 1H), 3.96 (s, 3H), 3.03-2.97 (m, 1H), 2.76-2.62 (m, 1H), 2.09-1.77 (m, 4H), 1.51-1.43 (m, 6H). LCMS (ESI): $[M+H]^+$: 472.4.

Example 206. 1-(5-(5-chloro-2-methoxypyridin-4-yl)-1H-pyrazole-3-carbonyl)-N-((1-methyl-1H-indol-5-yl)methyl)piperidine-4-carboxamide

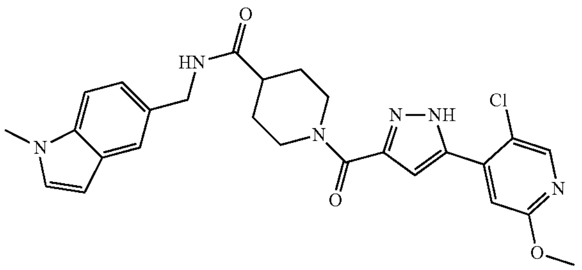

HATU (31.3 mg, 0.08 mmol) and (1-methyl-1H-indol-5-yl)methanamine (26.4 mg, 0.16 mmol) were added to a stirred solution of 1-[5-(5-chloro-2-methoxypyridin-4-yl)-1H-pyrazole-3-carbonyl]piperidine-4-carboxylic acid (INTERMEDIATE 503, 30.0 mg, 0.08 mmol) and DIPEA (31.9 mg, 0.25 mmol) in DMF (1.00 mL). The resulting mixture was stirred at 25° C. for 3 h. The resulting mixture was diluted with EtOAc and washed with water. The organic layers were dried over anhydrous $Na_2SO_4$. After filtration, the filtrate was concentrated under reduced pressure. The residue was purified silica gel column chromatography with 100% EtOAc to obtain the title compound (35.3 mg) as a solid. $^1H$ NMR (400 MHz, $CD_3OD$) δ 8.26 (s, 1H), 7.46 (s, 1H), 7.32 (d, 1H), 7.18-7.26 (m, 1H), 7.10-7.19 (m, 3H), 6.38 (d, 1H), 4.52-4.71 (m, 3H), 4.44 (s, 2H), 3.95 (s, 3H), 3.78 (s, 3H), 3.19-3.28 (m, 1H), 2.87-3.07 (m, 1H), 2.51-2.67 (m, 1H), 1.72-1.96 (m, 4H). LCMS (ESI): $[M+H]^+$: 507.3.

Example 207. 1-(5-(5-chloro-2-methoxypyridin-4-yl)-1H-pyrazole-3-carbonyl)-N-(2-oxo-1-phenylpyrrolidin-3-yl)piperidine-4-carboxamide

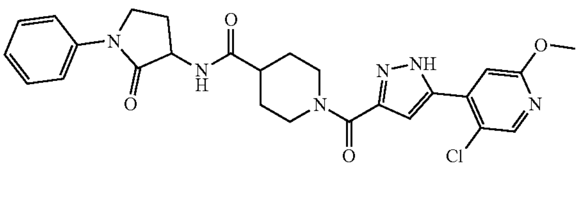 [SMILES: COc1cc(-c2cc(C(=O)N3CCC(C(=O)NC4CCN(c5ccccc5)C4=O)CC3)n[nH]2)c(Cl)cn1]

The title compound was prepared using a procedure similar to the one described for the synthesis of Example 167, except 3-amino-1-phenylpyrrolidin-2-one was used as starting material. The title compound was obtained as a solid mixture of enantiomers (12.2 mg). $^1H$ NMR (400 MHz, $CD_3OD$) δ 8.26 (s, 1H), 7.66-7.60 (m, 2H), 7.43-7.35 (m, 2H), 7.23-7.07 (m, 3H), 4.75-4.48 (m, 2H), 3.94 (s, 3H), 3.93-3.81 (m, 2H), 3.17-2.87 (m, 2H), 2.73-2.47 (m, 2H), 2.24-1.68 (m, 5H), 1.35-1.26 (m, 1H). LCMS (ESI): $[M+H]^+$: 523.45.

Example 208. N-(5-chloro-2,3-dihydrobenzofuran-3-yl)-1-(5-(5-chloro-2-methoxypyridin-4-yl)-1H-pyrazole-3-carbonyl)piperidine-4-carboxamide

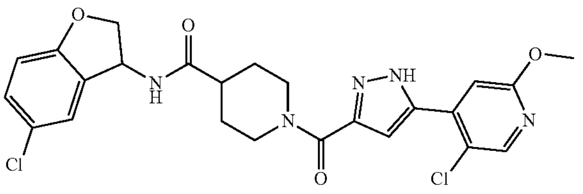 [SMILES: COc1cc(-c2cc(C(=O)N3CCC(C(=O)NC4COc5ccc(Cl)cc54)CC3)n[nH]2)c(Cl)cn1]

The title compound was prepared using a procedure similar to the one described for the synthesis of Example 167, except 5-chloro-2,3-dihydrobenzofuran-3-amine hydrochloride was used as starting material. The title compound was obtained as a solid (20.1 mg). $^1H$ NMR (300 MHz, $CD_3OD$) δ 8.28 (s, 1H), 7.33 (s, 2H), 7.22 (m, 1H), 7.17 (s, 1H), 6.81 (m, 1H), 5.56 (m, 1H), 4.73 (m, 1H), 4.65 (s, 2H), 4.33 (m, 1H), 3.97 (s, 3H), 2.95 (s, 2H), 2.56 (m, 1H), 1.98-1.70 (m, 4H). LCMS (ESI): $[M+H]^+$: 516.3.

Example 209. 1-(5-(5-chloro-2-methoxypyridin-4-yl)-1H-pyrazole-3-carbonyl)-N-((4-(trifluoromethyl)pyrimidin-2-yl)methyl)piperidine-4-carboxamide

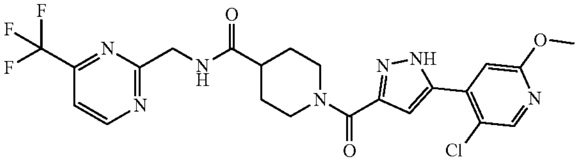 [SMILES: COc1cc(-c2cc(C(=O)N3CCC(C(=O)NCc4nccc(C(F)(F)F)n4)CC3)n[nH]2)c(Cl)cn1]

The title compound was prepared using a procedure similar to the one described for the synthesis of Example 167, except (4-(trifluoromethyl)pyrimidin-2-yl)methanamine was used as starting material. The title compound was obtained as a solid (18.5 mg). $^1H$ NMR (400 MHz, $CD_3OD$): δ 9.04 (d, 1H), 8.25 (s, 1H), 7.73 (d, 1H), 7.14 (s, 2H), 4.67 (s, 3H), 4.61 (s, 1H), 3.94 (s, 3H), 3.35 (s, 1H), 3.14-2.95 (m, 1H), 2.77-2.66 (m, 1H), 2.05-1.88 (m, 2H), 1.87-1.71 (m, 2H). LCMS (ESI): $[M+H]^+$: 524.3.

Example 210. 1-(5-(5-chloro-2-methoxypyridin-4-yl)-1H-pyrazole-3-carbonyl)-N-((5-methylimidazo[1,2-a]pyridin-2-yl)methyl)piperidine-4-carboxamide

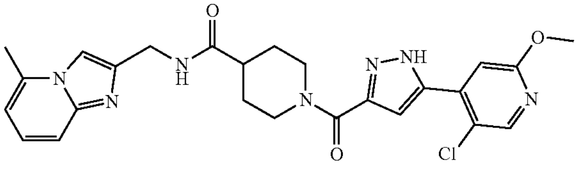 [SMILES: COc1cc(-c2cc(C(=O)N3CCC(C(=O)NCc4cn5c(C)cccc5n4)CC3)n[nH]2)c(Cl)cn1]

The title compound was prepared using a procedure similar to the one described for the synthesis of Example 179, except (5-methylimidazo[1,2-a]pyridin-2-yl)methanamine dihydrochloride was used as starting material. The title compound was obtained as a solid (5.4 mg). $^1H$ NMR (300 MHz, $CD_3OD$) δ 8.26 (s, 2H), 7.67 (s, 1H), 7.48-7.39 (m, 1H), 7.39-7.27 (m, 1H), 7.15 (s, 1H), 6.83 (d, 1H), 4.76-4.53 (m, 4H), 3.96 (s, 3H), 3.13-2.86 (m, 3H), 2.67-2.61 (m, 3H), 1.98-1.67 (m, 4H). LCMS (ESI): $[M+H]^+$: 508.4.

Example 211. 1-(5-(5-chloro-2-methoxypyridin-4-yl)-1H-pyrazole-3-carbonyl)-N-((5-(trifluoromethyl)pyrimidin-2-yl)methyl)piperidine-4-carboxamide

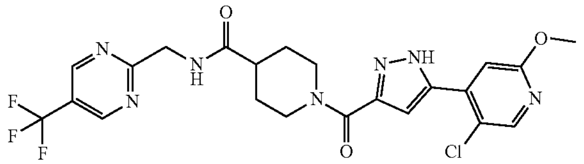 [SMILES: COc1cc(-c2cc(C(=O)N3CCC(C(=O)NCc4ncc(C(F)(F)F)cn4)CC3)n[nH]2)c(Cl)cn1]

The title compound was prepared using a procedure similar to the one described for the synthesis of Example 167, except (5-(trifluoromethyl)pyrimidin-2-yl)methanamine hydrochloride was used as starting material. The title compound was obtained as a solid (20.3 mg). $^1H$ NMR (300 MHz, $CD_3OD$) δ 9.10 (d, 2H), 8.28 (s, 1H), 7.17 (s, 2H), 4.71 (s, 3H), 4.65 (s, 1H), 3.97 (s, 3H), 3.34 (s, 1H), 3.17-2.94 (m, 1H), 2.82-2.68 (m, 1H), 2.00 (s, 2H), 1.89-1.66 (m, 2H). LCMS (ESI): $[M+H]^+$: 524.10.

Example 212. N-((1H-pyrrolo[2,3-c]pyridin-5-yl)methyl)-1-(5-(5-chloro-2-methoxypyridin-4-yl)-1H-pyrazole-3-carbonyl)piperidine-4-carboxamide

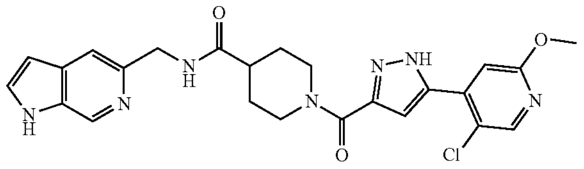 [SMILES: COc1cc(-c2cc(C(=O)N3CCC(C(=O)NCc4cc5cc[nH]c5cn4)CC3)n[nH]2)c(Cl)cn1]

The title compound was prepared using a procedure similar to the one described for the synthesis of Example 179, except (1H-pyrrolo[2,3-c]pyridin-5-yl)methanamine dihydrochloride was used as starting material. The title compound was obtained as a solid (11.7 mg). $^1H$ NMR (400 $CD_3OD$): δ 8.72 (d, 1H), 8.28 (d, 2H), 7.76-7.65 (m, 2H), 7.14 (s, 2H), 6.67-6.63 (m, 1H), 4.68 (s, 1H), 4.59 (s, 3H), 3.94 (s, 3H), 2.96 (s, 1H), 2.71-2.61 (m, 1H), 1.95 (s, 2H), 1.78 (d, 2H). LCMS (ESI): $[M+H]^+$: 494.3.

Example 213. 1-(5-(5-chloro-2-methoxypyridin-4-yl)-1H-pyrazole-3-carbonyl)-N (5,5-dimethyltetrahydrofuran-3-yl)piperidine-4-carboxamide

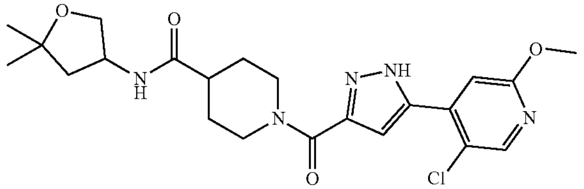

The title compound was prepared using a procedure similar to the one described for the synthesis of Example 167, except 5,5-dimethyltetrahydrofuran-3-amine was used as starting material. The title compound was obtained as a solid mixture of enantiomers (19.3 mg). $^1H$ NMR (300 MHz, $CD_3OD$) δ 8.25 (s, 1H), 7.14 (s, 2H), 4.64 (s, 2H), 4.48-4.35 (m, 1H), 4.11-3.99 (m, 1H), 3.94 (s, 3H), 3.71-3.49 (m, 1H), 3.29 (s, 1H), 3.11-2.79 (m, 1H), 2.69-2.46 (m, 1H), 2.23-2.07 (m, 1H), 1.97-1.58 (m, 5H), 1.33 (s, 3H), 1.23 (s, 3H). LCMS (ESI): $[M+H]^+$: 462.15.

Example 214. 1-(5-(5-chloro-2-methoxypyridin-4-yl)-1H-pyrazole-3-carbonyl)-N-((8-fluoroimidazo[1,2-a]pyridin-2-yl)methyl)piperidine-4-carboxamide

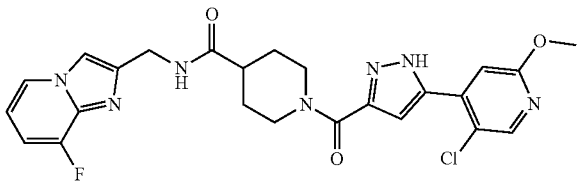 [SMILES: COc1cc(-c2cc(C(=O)N3CCC(C(=O)NCc4cn5cccc(F)c5n4)CC3)n[nH]2)c(Cl)cn1]

The title compound was prepared using a procedure similar to the one described for the synthesis of Example 167, except (8-fluoroimidazo[1,2-a]pyridin-2-yl)methanamine was used as starting material. The title compound was obtained as a solid (22.8 mg), $^1H$ NMR (300 MHz, DMSO-$d_6$) δ 13.94 (d, 1H), 8.52-8.28 (m, 3H), 7.87 (d, 1H), 7.32-7.20 (m, 1H), 7.18-7.06 (m, 2H), 6.92-6.78 (m, 1H), 4.80-4.44 (m, 1H), 4.39 (d, 2H), 4.14 (s, 1H), 3.99-3.79 (m, 3H), 3.31 (s, 2H), 3.07-2.76 (m, 1H), 1.82 (s, 2H), 1.71-1.46 (m, 2H). LCMS (ESI): $[M+H]^+$: 512.45.

Example 215. 1-(5-(5-chloro-2-methoxypyridin-4-yl)-1H-pyrazole-3-carbonyl)-N-((2-methyl-1H-benzo[d]imidazol-5-yl)methyl)piperidine-4-carboxamide

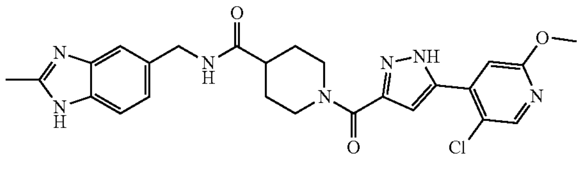

The title compound was prepared using a procedure similar to the one described for the synthesis of Example 167, except (2-methyl-1H-benzo[d]imidazol-5-yl)methanamine was used as starting material. The title compound was obtained as a solid (19.0 mg). $^1H$ NMR (300 MHz, DMSO-$d_6$) δ 13.95 (s, 1H), 12.09 (s, 1H), 8.37 (d, 2H), 7.54-7.18 (m, 3H), 7.15 (s, 1H), 7.00 (d, 1H), 4.58-4.27 (m, 4H), 3.90 (s, 3H), 3.31-3.22 (m, 2H), 2.86 (s, 1H), 2.46 (s, 3H), 1.80 (s, 2H), 1.61 (s, 2H). LCMS (ESI): $[M+H]^+$: 508.4.

Example 216. 1-(5-(5-chloro-2-methoxypyridin-4-yl)-1H-pyrazole-3-carbonyl)-N-((2-methyl-1,3-dioxan-2-yl)methyl)piperidine-, 1-carboxamide

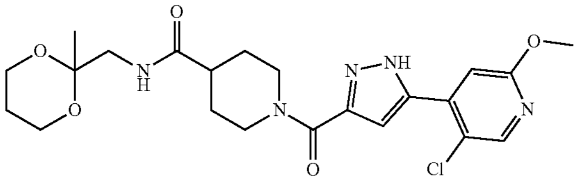 [SMILES: COc1cc(-c2cc(C(=O)N3CCC(C(=O)NCC4(C)OCCCO4)CC3)n[nH]2)c(Cl)cn1]

The title compound was prepared using a procedure similar to the one described for the synthesis of Example 167, except (2-methyl-1,3-dioxan-2-yl)methanamine was used as starting material. The title compound was obtained as a solid (19.5 mg). $^1$H NMR (300 MHz, $CD_3OD$) δ 8.26 (s, 1H), 7.15 (s, 2H), 4.65 (s, 2H), 4.03-3.70 (m, 7H), 3.42 (s, 3H), 3.02 (m, 1H), 2.80-1.66 (m, 6H), 1.59 (m, 1H), 1.36 (s, 3H). LCMS (ESI): $[M+H]^+$: 478.4.

Example 217. 1-(5-(5-chloro-2-methoxypyridin-4-yl)-1H-pyrazole-3-carbonyl)-N-((6-methylimidazo[1,2-a]pyridin-2-yl)methyl)piperidine-4-carboxamide

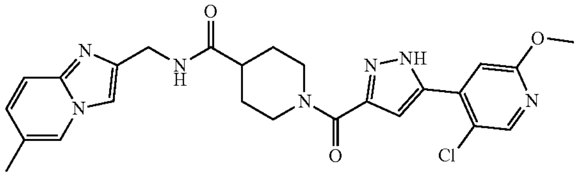 [SMILES: COc1cc(-c2cc(C(=O)N3CCC(C(=O)NCc4cn5cc(C)ccc5n4)CC3)n[nH]2)c(Cl)cn1]

The title compound was prepared using a procedure similar to the one described for the synthesis of Example 167, except (6-methylimidazo[1,2-a]pyridin-2-yl)methanamine dihydrochloride was used as starting material. The title compound was obtained as a solid (16.4 mg). $^1$H NMR (400 MHz, $CD_3OD$) δ 8.25 (s, 1H), 8.17 (s, 1H), 7.61 (s, 2H), 7.38 (m, 1H), 7.16 (m, 2H), 4.82 (s, 1H), 4.48 (s, 3H), 3.94 (s, 3H), 2.81 (s, 2H), 2.31 (s, 3H), 1.99-1.77 (m, 5H). LCMS (ESI): $[M+H]^+$: 508.3.

Example 218. 1-(5-(5-chloro-2-methoxypyridin-4-yl)-1H-pyrazole-3-carbonyl)-N-((1-methyl-1H-indazol-3-yl)methyl)piperidine-4-carboxamide

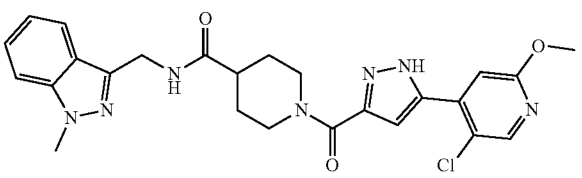 [SMILES: COc1cc(-c2cc(C(=O)N3CCC(C(=O)NCc4nn(C)c5ccccc45)CC3)n[nH]2)c(Cl)cn1]

The title compound was prepared using a procedure similar to the one described for the synthesis of Example 167, except (1-methyl-1H-indazol-3-yl)methanamine was used as starting material. The title compound was obtained as a solid (20.2 mg). $^1$H NMR (400 MHz, $CD_3OD$) δ 8.25 (s, 1H), 7.85-7.64 (m, 1H), 7.53-7.46 (m, 1H), 7.43-7.37 (m, 1H), 7.21-7.06 (m, 3H), 4.72 (s, 2H), 4.65 (s, 2H), 4.02 (s, 3H), 3.94 (s, 3H), 3.25 (s, 1H), 2.91 (s, 1H), 2.64-2.47 (m, 1H), 2.01-1.54 (m, 4H). LCMS (ESI): $[M+H]^+$: 508.4.

Example 219. 1-(5-(5-chloro-2-methoxypyridin-4-yl)-1H-pyrazole-3-carbonyl)-N-((6-chloroimidazo[1,2-a]pyridin-2-yl)methyl)piperidine-4-carboxamide

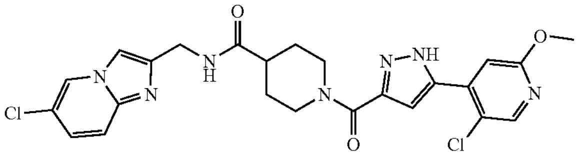 [SMILES: COc1cc(-c2cc(C(=O)N3CCC(C(=O)NCc4cn5cc(Cl)ccc5n4)CC3)n[nH]2)c(Cl)cn1]

The title compound was prepared using a procedure similar to the one described for the synthesis of Example 167, except (6-chloroimidazo[1,2-a]pyridin-2-yl)methanamine was used as starting material. The title compound was obtained as a solid (21.9 mg). $^1$H NMR (300 MHz, DMSO-$d_6$) δ 8.84-8.77 (m, 1H), 8.48-8.38 (m, 1H), 8.36 (s, 1H), 7.73 (s, 1H), 7.58-7.48 (m, 1H), 7.31-7.21 (m, 2H), 7.15 (s, 1H), 4.37 (m, 2H), 3.90 (s, 3H) 3.22 (s, 2H), 2.94-2.53 (m, 2H), 1.71 (m, 4H). LCMS (ESI): $[M+H]^+$: 528.4.

Example 220. 1-(5-(5-chloro-2-methoxypyridin-4-yl)-1H-pyrazole-3-carbonyl)-N-((4,4-difluorotetrahydrofuran-2-yl)methyl)piperidine-4-carboxamide

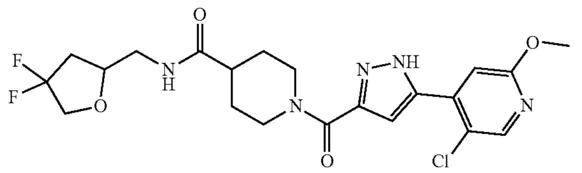 [SMILES: COc1cc(-c2cc(C(=O)N3CCC(C(=O)NCC4CC(F)(F)CO4)CC3)n[nH]2)c(Cl)cn1]

The title compound was prepared using a procedure similar to the one described for the synthesis of Example 167, except (4,4-difluorotetrahydrofuran-2-yl)methanamine hydrochloride was used as starting material. The title compound was obtained as a solid mixture of enantiomers (18.9 mg). $^1$H NMR (300 MHz, $CD_3OD$) δ 8.25 (s, 7.14 (s, 2H), 4.65 (s, 2H), 4.36-4.14 (m, 1H), 4.13-3.98 (m, 1H), 3.94 (s, 3H), 3.90-3.74 (m, 1H), 3.73-3.60 (m, 1H), 3.54-3.37 (m, 2H), 3.14-2.84 (m, 1H), 2.74-2.51 (m, 1H), 2.50-2.33 (m, 1H) 2.23-2.01 (m, 1H), 2.01-1.63 (m, 4H). LCMS (ESI): $[M+H]^+$: 484.40.

Example 221. 1-(5-(5-chloro-2-methoxypyridin-4-yl)-1H-pyrazole-3-carbonyl)-N-((5-(trifluoromethyl)oxazol-4-yl)methyl)piperidine-4-carboxamide

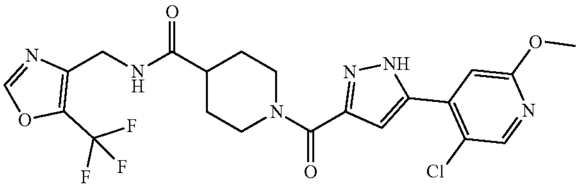 [SMILES: COc1cc(-c2cc(C(=O)N3CCC(C(=O)NCc4ncoc4C(F)(F)F)CC3)n[nH]2)c(Cl)cn1]

The title compound was prepared using a procedure similar to the one described for the synthesis of Example 167, except (5-(trifluoromethyl)oxazol-4-yl)methanamine hydrochloride was used as starting material. The title compound was obtained as a solid (9.7 mg). $^1$H NMR (300 MHz, $CD_3OD$) δ 8.36 (s, 1H), 8.28 (s, 1H), 7.16 (s, 2H), 4.64 (s, 2H), 4.50-4.42 (m, 2H), 3.97 (s, 3H), 3.83-3.50 (m, 1H), 3.15-2.85 (m, 1H), 2.72-2.51 (m, 1H), 1.91 (s, 2H), 1.83-1.65 (m, 2H). LCMS (ESI): $[M+H]^+$: 513.05.

Example 222. 1-(5-(5-chloro-2-methoxypyridin-4-yl)-1H-pyrazole-3-carbonyl)-N-(1-(2-fluorophenyl)pyrrolidin-3-yl)piperidine-4-carboxamide

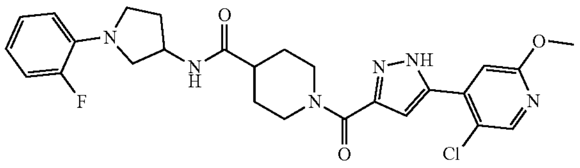 [SMILES: COc1cc(-c2cc(C(=O)N3CCC(C(=O)NC4CCN(c5ccccc5F)C4)CC3)n[nH]2)c(Cl)cn1]

The title compound was prepared using a procedure similar to the one described for the synthesis of Example 167, except 1-(2-fluorophenyl)pyrrolidin-3-amine was used as starting material. The title compound was obtained as a solid mixture of enantiomers (20.8 mg). $^1$H NMR (300 MHz, $CD_3OD$) δ 8.28 (s, 1H), 7.16 (s, 1H), 7.12 (s, 1H), 7.07-6.96 (m, 1H), 7.02-6.91 (m, 1H), 6.82-6.65 (m, 2H), 4.70 (s, 2H), 4.51-4.38 (m, 1H), 3.97 (s, 3H), 3.69-3.49 (m, 2H), 3.45-3.33 (m, 1H), 3.33-3.23 (m, 1H), 2.94 (s, 1H), 2.66-2.51 (m, 1H), 2.37-2.19 (m, 1H), 2.03-1.76 (m, 6H). LCMS (ESI): $[M+H]^+$: 527.4.

Example 223. 1-(5-(5-chloro-2-methoxypyridin-4-yl)-1H-pyrazole-3-carbonyl)-N-((1-methyl-1H-benzo[d]imidazol-5-yl)methyl)piperidine-4-carboxamide

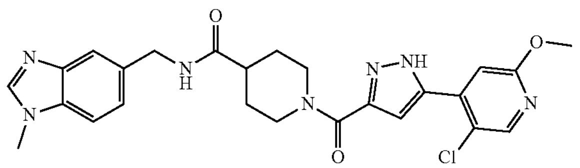 [SMILES: COc1cc(-c2cc(C(=O)N3CCC(C(=O)NCc4ccc5c(c4)ncn5C)CC3)n[nH]2)c(Cl)cn1]

The title compound was prepared using a procedure similar to the one described for the synthesis of Example 167, except (1-methyl-1H-benzo[d]imidazol-5-yl)methanamine was used as starting material. The title compound was obtained as a solid (12.0 mg). $^1$H NMR (300 MHz, DMSO-$d_6$) δ 13.95 (m, 1H), 8.48-8.29 (m, 2H), 8.15 (s, 1H), 7.56-7.43 (m, 2H), 7.32-7.05 (m, 3H), 4.76-4.43 (m, 2H), 4.38 (m, 2H), 4.23-3.98 (m, 1H), 3.96-3.86 (m, 3H), 3.82 (s, 3H), 3.26-3.09 (m, 1H), 2.99-2.56 (m, 1H), 1.94-1.71 (m, 2H), 1.71-1.38 (m, 2H), LCMS (ESI): $[M+H]^+$: 508.4.

Example 224. 1-(5-(5-chloro-2-methoxypyridin-4-yl)-1H-pyrazole-3-carbonyl)-N-(2-methyl-5,6,7,8-tetrahydroquinazolin-5-yl)piperidine-4-carboxamide

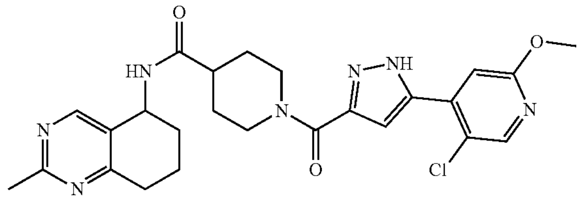

The title compound was prepared using a procedure similar to the one described for the synthesis of Example 167, except 2-methyl-5,6,7,8-tetrahydroquinazolin-5-amine was used as starting material. The title compound was obtained as a solid mixture of enantiomers (12.5 mg). $^1$H NMR (300 MHz, $CD_3OD$) δ 8.45 (s, 1H), 8.27 (s, 1H), 7.16 (s, 2H), 5.24-5.06 (m, 1H), 4.68 (s, 1H), 3.96 (s, 3H), 3.79-3.45 (m, 1H), 3.16-2.74 (m, 2H), 2.63 (s, 3H), 2.04 (s, 3H), 1.99-1.63 (m, 8H). LCMS (ESI): 510.5.

Example 225. 1-(5-(5-chloro-2-methoxypyridin-4-yl)-1H-pyrazole-3-carbonyl)-N-((5-(difluoromethyl)isoxazol-3-yl)methyl)piperidine-4-carboxamide

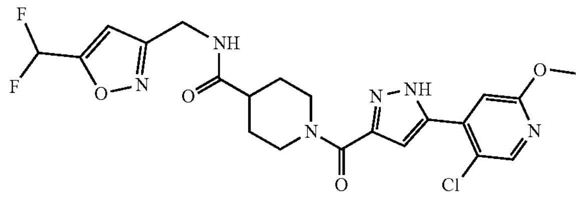 [SMILES: COc1cc(-c2cc(C(=O)N3CCC(C(=O)NCc4cc(C(F)F)on4)CC3)n[nH]2)c(Cl)cn1]

The title compound was prepared using a procedure similar to the one described for the synthesis of Example 167, except (5-(difluoromethyl)isoxazol-3-yl)methanamine was used as starting material. The title compound was obtained as a solid (21.1 mg). $^1$H NMR (300 MHz, $CD_3OD$) δ 8.29 (s, 1H), 7.32-7.05 (m, 2H), 6.91 (d, 1H), 6.75-6.68 (m, 1H), 4.71 (s, 2H), 4.49 (s, 2H), 3.97 (s, 3H), 3.32 (s, 1H), 2.97 (s, 1H), 2.71-2.55 (m, 1H), 2.03-1.61 (m, 4H). LCMS (ESI): $[M+H]^+$: 495.3.

Example 226. N-((1H-pyrrolo[2,3-b]pyridin-6-yl)methyl)-1-(5-(5-chloro-2-methoxypyridin-4-yl)-1H-pyrazole-3-carbonyl)piperidine-4-carboxamide

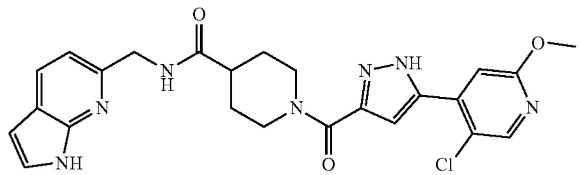 [SMILES: COc1cc(-c2cc(C(=O)N3CCC(C(=O)NCc4ccc5cc[nH]c5n4)CC3)n[nH]2)c(Cl)cn1]

The title compound was prepared using a procedure similar to the one described for the synthesis of Example 167, except (1H-pyrrolo[2,3-b]pyridin-6-yl)methanamine was used as starting material. The title compound was obtained as a solid (21.1 mg). $^1$H NMR (400 MHz, $CD_3OD$) δ 8.25 (d, 1H), 7.94 (d, 1H), 7.33 (d, 1H), 7.15 (s, 1H), 7.10-7.01 (m, 2H), 6.45 (d, 1H), 4.77-4.65 (m, 1H), 4.55 (s, 2H), 3.94 (s, 3H), 3.30 (d, 2H), 3.03-2.89 (m, 1H), 2.72-2.57 (m, 1H), 1.99-1.73 (m, 4H). LCMS (ESI): $[M+H]^+$: 494.3.

Example 227. 1-(5-(5-chloro-2-methoxypyridin-4-yl)-1H-pyrazole-3-carbonyl)-N-(2-methyl-1,2,3,4-tetrahydroisoquinolin-4-yl)piperidine-4-carboxamide

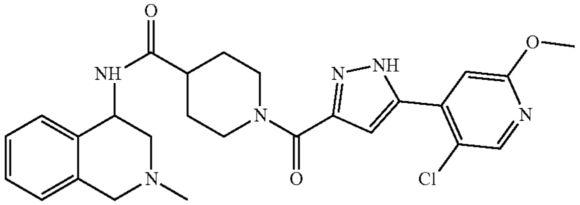 [SMILES: COc1cc(-c2cc(C(=O)N3CCC(C(=O)NC4CN(C)Cc5ccccc54)CC3)n[nH]2)c(Cl)cn1]

The title compound was prepared using a procedure similar to the one described for the synthesis of Example 167, except 2-methyl-1,2,3,4-tetrahydroisoquinolin-4-amine was used as starting material. The title compound was obtained as a solid mixture of enantiomers (21.3 mg). $^1$H NMR (400 MHz, $CD_3OD$) δ 8.26 (s, 1H), 7.41-6.94 (m, 6H), 5.27-5.19 (m, 2H), 4.76-4.48 (m, 2H), 3.94 (s, 3H), 3.76-3.45 (m, 3H), 2.93-2.84 (m, 1H), 2.64-2.52 (m, 2H), 2.46 (s, 3H), 2.06-1.65 (m, 4H). LCMS (ESI): $[M+H]^+$: 509.4.

Example 228. 1-(5-(5-chloro-2-methoxypyridin-4-yl)-1H-pyrazole-3-carbonyl)-N-((3-methyl-2-oxo-2,3-dihydrobenzo[d]oxazol-5-yl)methyl)piperidine-4-carboxamide

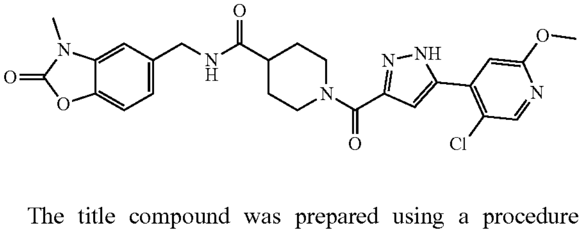

The title compound was prepared using a procedure similar to the one described for the synthesis of Example 167, except 5-(aminomethyl)-3-methylbenzo[d]oxazol-2(3H)-one was used as starting material. The title compound was obtained as a solid (22.4 mg), $^1$H NMR (400 MHz, DMSO-$d_6$) δ 8.44-8.37 (m, 1H), 8.34 (s, 1H), 7.29-7.18 (m, 1H), 7.12 (s, 1H), 7.09 (d, 1H), 7.01-6.94 (m, 1H), 4.45 (s, 2H), 4.29 (d, 2H), 3.88 (s, 3H), 3.16 (d, 1H), 2.85 (d, 1H), 2.58-2.47 (4H), 1.80 (s, 2H), 1.57 (s, 2H). LCMS (ESI): $[M+H]^+$: 525.3.

Example 229. 1-(5-(5-chloro-2-methoxypyridin-4-yl)-1H-pyrazole-3-carbonyl)-N-((1-methyl-1H-indazol-6-yl)methyl)piperidine-4-carboxamide

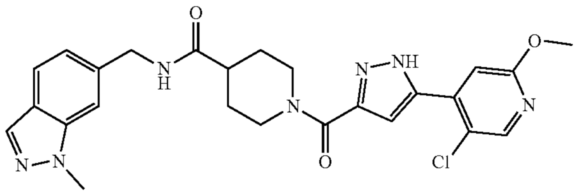 [SMILES: COc1cc(-c2cc(C(=O)N3CCC(C(=O)NCc4ccc5cnn(C)c5c4)CC3)n[nH]2)c(Cl)cn1]

The title compound was prepared using a procedure similar to the one described for the synthesis of Example 167, except (1-methyl-1H-indazol-6-yl)methanamine was used as starting material. The title compound was obtained as a solid (22.8 mg). $^1$H NMR (400 MHz, $CD_3OD$) δ 8.26 (s, 1H), 7.87 (s, 1H), 7.62 (d, 1H), 7.23 (s, 1H), 7.14 (s, 1H), 7.09 (s, 1H), 6.92 (d, 1H), 4.79-4.58 (m, 2H), 4.36-4.31 (m, 2H), 3.94 (s, 3H), 3.54-3.49 (m, 1H), 3.20 (s, 3H), 2.96-2.91 (m, 1H), 2.63-2.52 (m, 1H), 2.01-1.84 (m, 2H), 1.78-1.74 (m, 2H). LCMS (ESI): $[M+H]^+$: 508.4.

Example 230. N-((2-oxabicyclo[3.1.1]heptan-1-yl)methyl)-1-(5-(5-chloro-2-methoxypyridin-4-yl)-1H-pyrazole-3-carbonyl)piperidine-1-carboxamide

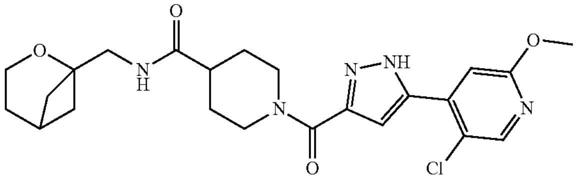 [SMILES: COc1cc(-c2cc(C(=O)N3CCC(C(=O)NCC45CC(CCO4)C5)CC3)n[nH]2)c(Cl)cn1]

The title compound was prepared using a procedure similar to the one described for the synthesis of Example 167, except (2-oxabicyclo[3.1.1]heptan-1-yl)methanamine was used as starting material. The title compound was obtained as a solid (19.6 mg). $^1$H NMR (400 MHz, $CD_3OD$) δ 8.25 (d, 1H), 7.38-6.75 (m, 2H), 4.78-4.58 (m, 2H), 4.25 (s, 1H), 4.15-4.03 (m, 2H), 3.94 (d, 3H), 3.27-3.21 (m, 3H), 3.19 (s, 2H), 2.98-2.88 (m, 1H), 2.66-2.55 (m, 1H), 2.53-2.45 (m, 1H), 2.10-2.02 (m, 2H), 2.01-1.93 (m, 2H), 1.82-1.67 (m, 3H). LCMS (ESI): $[M+H]^+$: 474.3.

Example 231. 1-(5-(5-chloro-2-methoxypyridin-4-yl)-1H-pyrazole-3-carbonyl)-N-(1-methyl-2,2-dioxido-3,4-dihydro-1H-benzo[c][1,2]thiazin-4-yl)piperidine-4-carboxamide

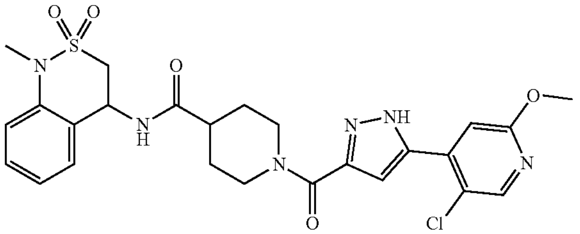 [SMILES: COc1cc(-c2cc(C(=O)N3CCC(C(=O)NC4CS(=O)(=O)N(C)c5ccccc54)CC3)n[nH]2)c(Cl)cn1]

The title compound was prepared using a procedure similar to the one described for the synthesis of Example 167, except 4-amino-1-methyl-3,4-dihydro-1H-benzo[c][1,2]thiazine 2,2-dioxide was used as starting material. The title compound was obtained as a solid mixture of enantiomers (11.4 mg). $^1$H NMR (400 MHz, $CD_3OD$) δ 8.26 (s, 1H), 7.42-7.29 (m, 2H), 7.21-7.12 (m, 4H), 5.67-5.59 (m, 1H), 4.68-4.64 (m, 2H), 3.94 (s, 3H), 3.76-3.66 (m, 1H), 3.54-3.42 (m, 1H), 3.32-3.29 (m, 3H), 2.97-2.93 (m, 1H), 2.81 (s, 1H), 2.69-2.57 (m, 1H), 2.06-1.68 (m, 4H). LCMS (ESI): $[M+H]^+$: 559.3.

Example 232. 1-(5-(5-chloro-2-methoxypyridin-4-yl)-1H-pyrazole-3-carbonyl)-N-((1-methyl-1H-pyrazolo[3,4-b]pyridin-5-yl)methyl)piperidine-4-carboxamide

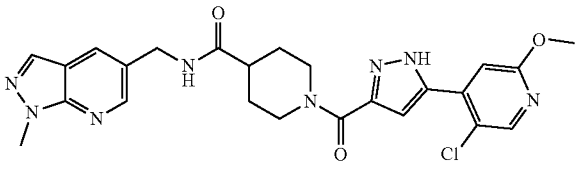 [SMILES: COc1cc(-c2cc(C(=O)N3CCC(C(=O)NCc4cnc5c(cnn5C)c4)CC3)n[nH]2)c(Cl)cn1]

The title compound was prepared using a procedure similar to the one described for the synthesis of Example 167, except (1-methyl-1H-pyrazolo[3,4-b]pyridin-5-yl) methanamine was used as starting material. The title compound was obtained as a solid (19.6 mg). $^1$H NMR (400 MHz, $CD_3OD$) δ 8.53 (d, 1H), 8.25 (s, 1H), 8.13 (d, 1H), 8.05 (s, 1H), 7.14 (s, 2H), 4.78-4.56 (m, 2H), 4.53-4.49 (m, 2H), 4.10 (s, 3H), 3.94 (s, 3H), 3.35-3.30 (m, 1H), 3.02-2.84 (m, 1H), 2.64-2.53 (m, 1H), 1.93-1.88 (m, 2H), 1.79-1.71 (m, 2H). LCMS (ESI): $[M+H]^+$: 509.4.

Example 233. (S)-1-(5-(5-chloro-2-methoxypyridin-4-yl)-1H-pyrazole-3-carbonyl)-N-(6-cyanochroman-4-yl)piperidine-4-carboxamide

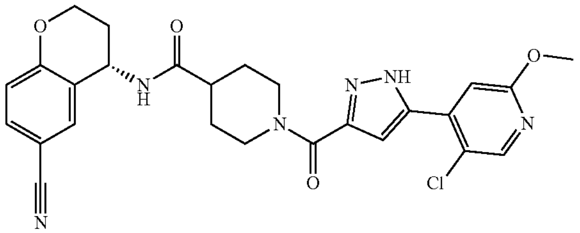 [SMILES: COc1cc(-c2cc(C(=O)N3CCC(C(=O)N[C@H]4CCOc5ccc(C#N)cc54)CC3)n[nH]2)c(Cl)cn1]

The title compound was prepared using a procedure similar to the one described for the synthesis of Example 179, except (S)-4-aminochromane-6-carbonitrile was used as starting material. The title compound was obtained as a solid (15.8 mg). $^1$H NMR (300 MHz, $CD_3OD$) δ 8.30 (s, 1H), 7.60-7.48 (m, 2H), 7.18 (s, 1H), 7.10 (s, 1H), 6.96 (d, 1H), 5.17-5.07 (m, 2H), 4.77-4.71 (m, 2H), 4.38-4.32 (m, 2H), 4.00-3.94 (m, 4H), 2.72-2.51 (m, 1H), 2.20-2.14 (m, 1.89-1.83 (m, 5H). LCMS (ESI): $[M+H]^+$: 521.4.

Example 234. 1-(5-(5-chloro-2-methoxypyridin-4-yl)-1H-pyrazole-3-carbonyl)-N-(1-methyl-2-oxo-1,2,5,6,7,8-hexahydroquinolin-5-yl)piperidine-4-carboxamide

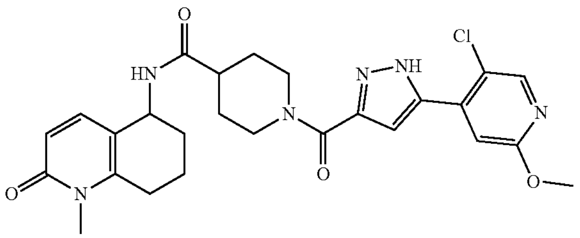 [SMILES: COc1cc(-c2cc(C(=O)N3CCC(C(=O)NC4CCCc5c4ccc(=O)n5C)CC3)n[nH]2)c(Cl)cn1]

The title compound was prepared using a procedure similar to the one described for the synthesis of Example 167, except 5-amino-1-methyl-5,6,7,8-tetrahydroquinolin-2(1H)-one was used as starting material. The title compound was obtained as a solid mixture of enantiomers (19.8 mg). $^1$H NMR (400 MHz, $CD_3OD$): δ 8.26 (s, 1H), 7.34 (d, 1H), 7.14 (s, 2H), 6.46 (d, 1H), 4.66 (s, 2H), 3.94 (s, 3H), 3.53 (s, 3H), 2.98-2.66 (m, 3H), 2.60-2.50 (m, 1H), 2.13-1.25 (m, 10H). LCMS (ESI): $[M+H]^+$: 525.4.

Example 235. 1-(5-(5-chloro-2-methoxypyridin-4-yl)-1H-pyrazole-3-carbonyl)-N-((1-methyl-2-oxoindolin-5-yl)methyl)piperidine-4-carboxamide

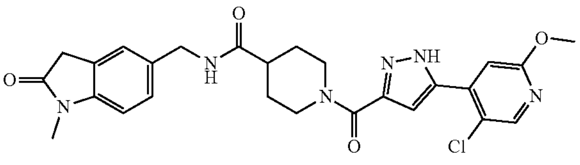 [SMILES: COc1cc(-c2cc(C(=O)N3CCC(C(=O)NCc4ccc5c(c4)CC(=O)N5C)CC3)n[nH]2)c(Cl)cn1]

The title compound was prepared using a procedure similar to the one described for the synthesis of Example 167, except 5-(aminomethyl)-1-methylindolin-2-one hydrochloride was used as starting material. The title compound was obtained as a solid (18.9 mg), $^1$H NMR (400 MHz, $CD_3OD$) δ 8.26 (s, 1H), 7.23 (m, 1H), 7.14 (s, 1H), 6.92 (m, 1H), 4.79-4.58 (m, 2H), 4.36-4.31 (m, 2H), 3.94 (s, 3H), 3.54-3.49 (m, 1H), 3.20 (s, 3H), 2.96-2.91 (m, 1H), 2.63-2.52 (m, 1H), 2.01-1.84 (m, 4H), 1.78-1.74 (m, 2H), 1.40-1.13 (m, 2H). LCMS (ESI): $[M+H]^+$: 523.4.

Example 236. 1-(5-(5-chloro-2-methoxypyridin-4-yl)-1H-pyrazole-3-carbonyl)-N (3,4-dihydro-2H-pyrano[2,3-b]pyridin-4-yl)piperidine-4-carboxamide

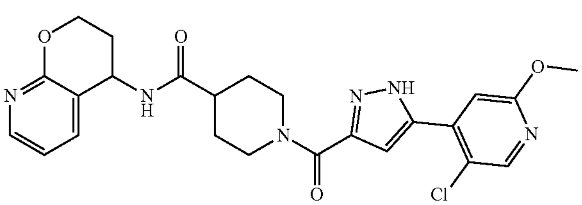 [SMILES: COc1cc(-c2cc(C(=O)N3CCC(C(=O)NC4CCOc5ncccc54)CC3)n[nH]2)c(Cl)cn1]

The title compound was prepared using a procedure similar to the one described for the synthesis of Example 167, except 3,4-dihydro-2H-pyrano[2,3-b]pyridin-4-amine dihydrochloride was used as starting material. The title compound was obtained as a solid mixture of enantiomers (13.1 mg). $^1$H NMR (300 MHz, $CD_3OD$) δ 8.28 (s, 1H), 8.07 (d, 1H), 7.70 (d, 1H), 7.20-7.14 (m, 2H), 7.04 (d, 1H), 5.23-5.13 (m, 1H), 4.71-4.65 (m, 3H), 4.48-4.38 (m, 2H), 3.97 (s, 3H), 2.99-2.93 (m, 1H), 2.68-2.53 (m, 1H), 2.28-1.98 (m, 1H) 1.96-1.78 (m, 5H). LCMS (ESI): $[M+H]^+$: 497.3.

Example 237. 1-(5-(5-chloro-2-methoxypyridin-4-yl)-1H-pyrazole-3-carbonyl)-N-((1,1-dioxido-2,3-dihydrobenzo[b]thiophen-5-yl)methyl)piperidine-4-carboxamide

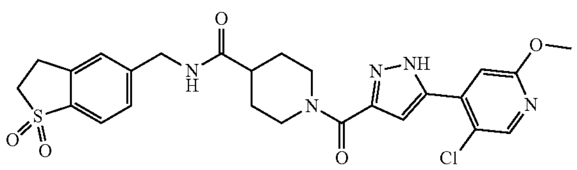 [SMILES: COc1cc(-c2cc(C(=O)N3CCC(C(=O)NCc4ccc5c(c4)CCS5(=O)=O)CC3)n[nH]2)c(Cl)cn1]

The title compound was prepared using a procedure similar to the one described for the synthesis of Example 167, except 5-(aminomethyl)-2,3-dihydrobenzo[b]thiophene 1,1-dioxide hydrochloride was used as starting material. The title compound was obtained as a solid (21.0 mg). $^1$H NMR (400 MHz, $CD_3OD$) δ 8.27 (s, 1H), 7.65 (d, 1H), 7.51-7.33 (m, 2H), 7.33-7.11 (m, 1H), 7.11-6.94 (m, 1H), 4.80-4.56 (m, 1H), 4.51-4.39 (m, 2H), 3.94 (s, 3H), 3.73-3.33 (m, 4H), 2.01-1.68 (m, 4H), 1.56-1.22 (m, 3H), 0.94-0.85 (m, 1H) LCMS (ESI): $[M+H]^+$: 544.3.

Example 238. 1-(5-(5-chloro-2-methoxypyridin-4-yl)-1H-pyrazole-3-carbonyl)-N-((4-(difluoromethyl)pyrimidin-2-yl)methyl)piperidine-4-carboxamide

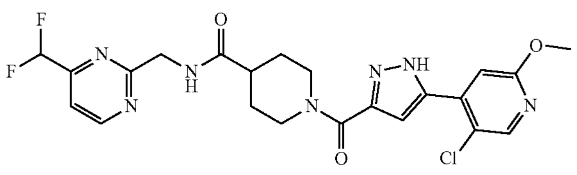 [SMILES: COc1cc(-c2cc(C(=O)N3CCC(C(=O)NCc4nccc(C(F)F)n4)CC3)n[nH]2)c(Cl)cn1]

The title compound was prepared using a procedure similar to the one described for the synthesis of Example 167, except (4-(difluoromethyl)pyrimidin-2-yl)methanamine hydrochloride was used as starting material. The title compound was obtained as a solid (17.6 mg). $^1$H NMR (400 MHz, $CD_3OD$) δ 8.93 (d, 1H), 8.25 (s, 1H), 7.60 (d, 1H), 7.14 (d, 2H), 6.89-6.51 (m, 1H), 4.64 (s, 5H), 3.94 (s, 3H), 3.02 (s, 1H), 2.81-2.61 (m, 1H), 1.98 (s, 2H), 1.88-1.62 (m, 2H). LCMS (ESI): $[M+H]^+$; 506.3.

Example 239. 1-(5-(5-chloro-2-methoxypyridin-4-yl)-1H-pyrazole-3-carbonyl)-N-((6-(difluoromethyl)pyridin-2-yl)methyl)piperidine-4-carboxamide

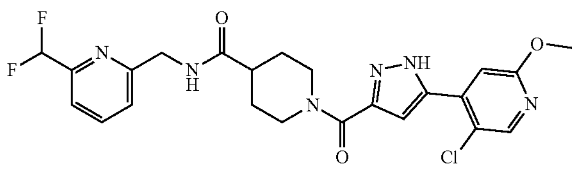 [SMILES: COc1cc(-c2cc(C(=O)N3CCC(C(=O)NCc4cccc(C(F)F)n4)CC3)n[nH]2)c(Cl)cn1]

The title compound was prepared using a procedure similar to the one described for the synthesis of Example 167, except (6-(difluoromethyl)pyridin-2-yl)methanamine was used as starting material. The title compound was obtained as a solid (24.1 mg). $^1$H NMR (400 MHz, $CD_3OD$) δ 8.25 (s, 1H), 7.97-7.88 (m, 1H), 7.56 (d, 1H), 7.45 (dd, 1H), 7.15 (s, 2H), 6.90-6.49 (m, 1H), 4.66 (s, 2H), 4.52 (s, 2H), 3.94 (s, 3H), 3.32 (s, 1H), 3.18-2.89 (m, 1H), 2.76-2.58 (m, 1H), 1.96 (s, 2H), 1.86-1.67 (m, 2H). LCMS (ESI): $[M+H]^+$: 505.3.

Example 240. 1-(5-(5-chloro-2-methoxypyridin-4-yl)-1H-pyrazole-3-carbonyl)-N-(2-methyl-3-oxo-1,2,3,4-tetrahydroisoquinolin-4-yl)piperidine-4-carboxamide

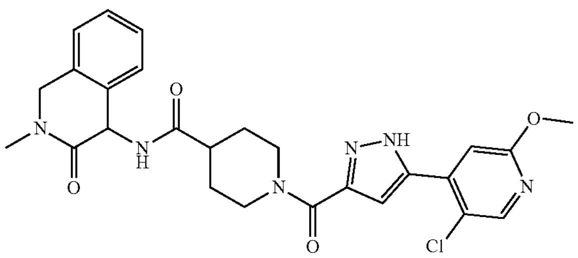

The title compound was prepared using a procedure similar to the one described for the synthesis of Example 167, except 4-amino-2-methyl-1,4-dihydroisoquinolin-3(2H)-one hydrochloride was used as starting material. The title compound was obtained as a solid mixture of enantiomers (19.2 mg). $^1$H NMR (400 MHz, $CD_3OD$) δ 8.25 (d, 1H), 7.38-7.27 (m, 3H), 7.23 (s, 1H), 7.16 (s, 1H), 7.08 (s, 1H) 5.49 (s, 1H), 4.73 (d, 1H), 4.69 (d, 1H), 4.49 (d, 1H), 4.45 (d, 1H), 3.95 (s, 2H), 3.13 (s, 3H), 3.09-2.91 (m, 2H), 2.88-2.75 (m, 2.03 (d, 2H) 1.93-1.76 (m, 2H). LCMS (ESI): $[M+H]^+$: 523.4.

Example 241. 1-(5-(5-chloro-2-methoxypyridin-4-yl)-1H-pyrazole-3-carbonyl)-N-((6,7-dihydro-5H-cyclopenta[d]pyrimidin-2-yl)methyl)piperidine-4-carboxamide

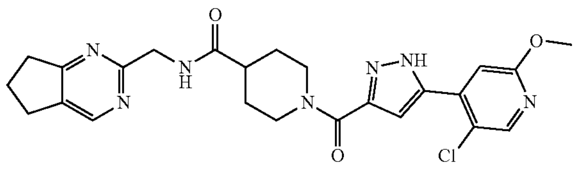 [SMILES: COc1cc(-c2cc(C(=O)N3CCC(C(=O)NCc4ncc5c(n4)CCC5)CC3)n[nH]2)c(Cl)cn1]

The title compound was prepared using a procedure similar to the one described for the synthesis of Example 167, except (6,7-dihydro-5H-cyclopenta[d]pyrimidin-2-yl) methanamine dihydrochloride was used as starting material. The title compound was obtained as a solid (20.7 mg). $^1$H NMR (400 MHz, $CD_3OD$): δ 8.49 (d, 1H), 8.25 (s, 1H), 7.14 (s, 2H), 4.63 (d, 2H), 4.54 (s, 2H), 3.94 (s, 3H), 3.08-2.91 (m, 3H), 2.75-2.64 (m, 2H), 2.24-2.10 (m, 3H), 2.06-1.65 (m, 5H). LCMS (ESI): $[M+H]^+$: 496.4.

Example 242. 1-(5-(5-chloro-2-methoxypyridin-4-yl)-1H-pyrazole-3-carbonyl)-N-((3,3-dimethyl-2-oxoindolin-5-yl)methyl)piperidine-4-carboxamide

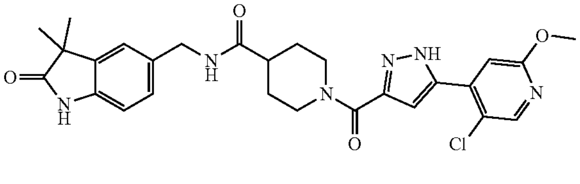 [SMILES: COc1cc(-c2cc(C(=O)N3CCC(C(=O)NCc4ccc5c(c4)C(C)(C)C(=O)N5)CC3)n[nH]2)c(Cl)cn1]

The title compound was prepared using a procedure similar to the one described for the synthesis of Example 167, except 5-(aminomethyl)-3,3-dimethylindolin-2-one hydrochloride was used as starting material. The title compound was obtained as a solid (22.1 mg). $^1$H NMR (400 MHz, $CD_3OD$) δ 8.25 (s, 1H), 7.19 (d, 1H), 7.13 (d, 3H) 6.87 (d, 1H), 4.67-4.63 (m, 2H), 4.35-4.30 (m, 2H), 3.94 (s, 3H), 2.96-2.91 (m, 2H), 2.64-2.52 (m, 1H), 1.87-1.82 (m, 2H), 1.79-1.72 (m, 2H), 1.35-1.30 (m, 6H). LCMS (ESI): 537.4.

Example 243. 1-(5-(5-chloro-2-methoxypyridin-4-yl)-1H-pyrazole-3-carbonyl)-N-((5-fluoro-1H-benzo[d]imidazol-4-yl)methyl)piperidine-4-carboxamide

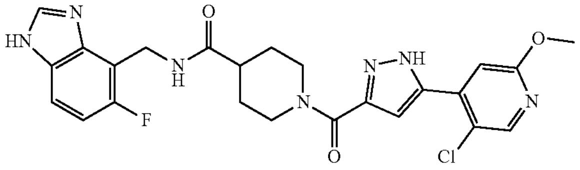 [SMILES: COc1cc(-c2cc(C(=O)N3CCC(C(=O)NCc4c(F)ccc5[nH]cnc45)CC3)n[nH]2)c(Cl)cn1]

The title compound was prepared using a procedure similar to the one described for the synthesis of Example 167, except (5-fluoro-1H-benzo[d]imidazol-4-yl)methanamine dihydrochloride was used as starting material. The title compound was obtained as a solid (9.0 mg). $^1$H NMR (400 MHz, $CD_3OD$) δ 8.27 (s, 1H), 8.21 (s, 1H), 7.60-7.48 (m, 1H), 7.13 (s, 1H), 7.09-7.03 (m, 2H), 4.72 (s, 2H), 4.63 (d, 1H), 3.94 (d, 3H), 3.30-3.07 (m, 2H), 2.96-2.83 (m, 1H), 2.61-2.45 (m, 1H) 1.97-1.59 (m, 4H). LCMS (ESI): $[M+H]^+$: 512.3.

Example 244. 1-(5-(5-chloro-2-methoxypyridin-4-yl)-1H-pyrazole-3-carbonyl)-N-(3-oxo-1,2,3,4-tetrahydroisoquinolin-4-yl)piperidine-4-carboxamide

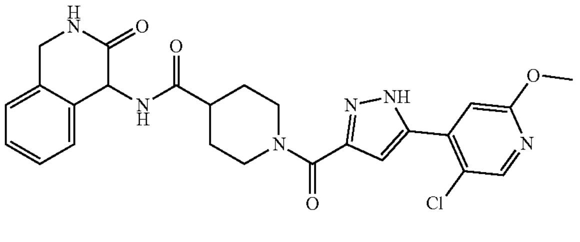 [SMILES: COc1cc(-c2cc(C(=O)N3CCC(C(=O)NC4C(=O)NCc5ccccc54)CC3)n[nH]2)c(Cl)cn1]

The title compound was prepared using a procedure similar to the one described for the synthesis of Example 167, except 4-amino-1,4-dihydroisoquinolin-3(2H)-one dihydrobromide was used as starting material. The title compound was obtained as a solid mixture of enantiomers (22.4 mg). $^1$H NMR (300 MHz, $CD_3OD$) δ 8.28 (s, 1H), 7.44-7.22 (m, 5H), 7.19 (s, 1H), 5.56 (s, 1H), 4.70 (s, 2H), 4.58 (d, 1H), 4.41 (d, 1H), 3.97 (s, 3H), 3.23-2.65 (m, 3H), 2.09 (s, 2H), 1.89 (s, 2H). LCMS (ESI): $[M+H]^+$: 509.4.

Example 245. Enantiomeric Mixture of Example 245-A and Example 245-B

Example 245-A. (S)-4-(5-(5-chloro-2-methoxypyridin-4-yl)-1H-pyrazole-3-carbonyl)-N-(3-chlorobenzyl)-4-azaspiro[2.5]octane-7-carboxamide

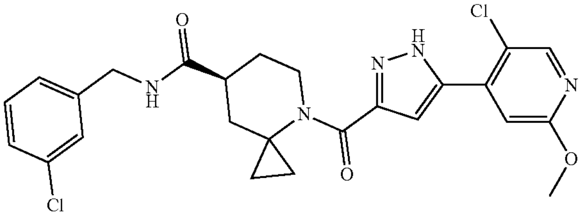 [SMILES: COc1cc(-c2cc(C(=O)N3CC[C@H](C(=O)NCc4cccc(Cl)c4)CC34CC4)n[nH]2)c(Cl)cn1]

Example 245-B. (R)-4-(5-(5-chloro-2-methoxypyridin-4-yl)-1H-pyrazole-3-carbonyl)-N-(3-chlorobenzyl)-4-azaspiro[2.5]octane-7-carboxamide

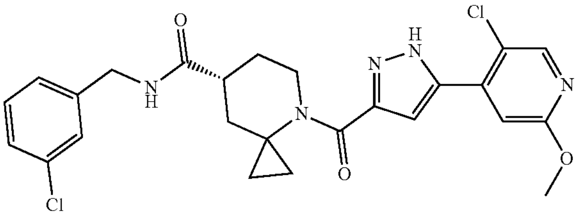

The title compound was prepared using a procedure similar to the one described for the synthesis of Example 174, except 4-(tert-butoxycarbonyl)-4-azaspiro[2.5]octane-7-carboxylic acid was used as starting material in Step-1. (S)-4-(5-(5-chloro-2-methoxypyridin-4-yl)-1H-pyrazole-3-carbonyl)-N-(3-chlorobenzyl)-4-azaspiro[2.5]

octane-7-carboxamide and (R)-4-(5-(5-chloro-2-methoxypyridin-4-yl)-1H-pyrazole-3-carbonyl)-N-(3-chlorobenzyl)-4-azaspiro[2.5]octane-7-carboxamide were obtained as a solid mixture of enantiomers (5.5 mg, Example 245). LCMS (ESI): 514.4 $[M+H]^+$.

The two enantiomers of the title compounds were separated using Chiral-Prep-HPLC.

Column: CHIRALPAK IC column

Column dimension: 2×25 cm, 5 μm

Mobile Phase: MTBE (10 mM $NH_3$·MeOH):EtOH:=50:50 hold for 15 min

Flow rate: 20 mL/min

Detection: 220/254 nm

Example 245-A. The first eluting compound (2.5 mg) was obtained as a solid.

The first eluting compound had a retention time of 7.24 min.

LCMS (ESI): 514.4 $[M+H]^+$.

Example 245-B. The second eluting compound (1.9 mg) was obtained as a solid.

The second eluting compound had a retention time of 9.88 min.

LCMS (ESI): 514.4 $[M+H]^+$.

Example 246. 1-(5-(5-chloro-2-methoxypyridin-4-yl)-1H-pyrazole-3-carbonyl)-N-(3-fluoro-3-methylcyclobutyl)piperidine-4-carboxamide

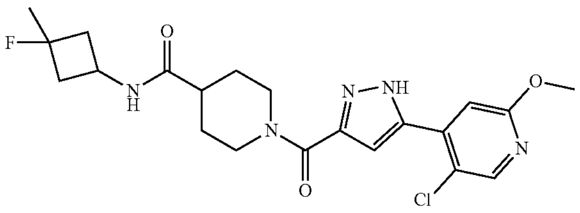 [SMILES: COc1cc(-c2cc(C(=O)N3CCC(C(=O)NC4CC(C)(F)C4)CC3)n[nH]2)c(Cl)cn1]

The title compound was prepared using a procedure similar to the one described for the synthesis of Example 167, except 3-fluoro-3-methylcyclobutan-1-amine hydrochloride was used as starting material. The title compound was obtained as a solid mixture of diastereomers (17.0 g), $^1H$ NMR (300 MHz, $CD_3OD$) δ 8.29 (s, 1H), 7.19-7.13 (m, 2H), 4.74-4.68 (m, 2H), 4.46-4.30 (m, 1H), 3.97 (s, 3H), 2.94 (s, 1H), 2.74-2.45 (m, 2H), 2.22-2.01 (m, 1H), 1.91-1.85 (m, 2H), 1.83-1.68 (m, 4H), 1.55-1.40 (m, 4H), LCMS (ESI): $[M+H]^+$: 450.3, Example 247. 1-(5-(5-chloro-2-methoxypyridin-4-yl)-1H-pyrazole-3-carbonyl)-N-(5-methyltetrahydrofuran-3-yl)piperidine-4-carboxamide

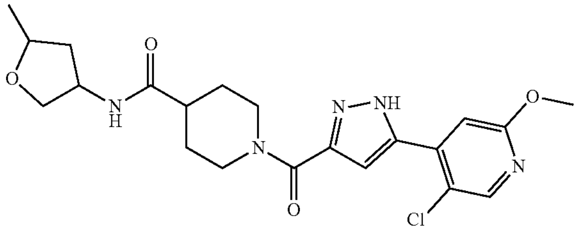

The title compound was prepared using a procedure similar to the one described for the synthesis of Example 167, except 5-methyltetrahydrofuran-3-amine hydrochloride was used as starting material. The title compound was obtained as a solid mixture of diastereomers (16.8 mg). $^1H$ NMR (400 MHz, $CD_3OD$): δ 8.25 (m, 1H), 7.10 (m, 2H), 4.76-4.64 (m, 1H), 4.40-4.32 (m, 1H), 4.18-4.06 (m, 1H), 3.98-3.89 (m, 4H), 3.86-3.79 (m, 1H), 3.68-3.46 (m, 1H), 2.97-2.85 (m, 1H), 2.60-2.49 (m, 1H), 2.46-2.36 (m, 1H), 2.00-1.62 (m, 5H) 1.42-1.20 (m, 4H). LCMS (ESI): $[M+H]^+$: 448.3.

Example 248. A diastereomeric mixture of 1-(5-(5-chloro-2-methoxypyridin-4-yl)-1H-pyrazole-3-carbonyl)-N-((3R,6R)-1-methyl-6-(trifluoromethyl)piperidin-3-yl)piperidine-4-carboxamide and 1-(5-(5-chloro-2-methoxypyridin-4-yl)-1H-pyrazole-3-carbonyl)-N-((3S,6R)-1-methyl-6-(trifluoromethyl)piperidin-3-yl)piperidine-4-carboxamide and 1(5-(5-chloro-2-methoxypyridin-4-yl)-1H-pyrazole-3-carbonyl)-N-((3S,6S)-1-methyl-6-(trifluoromethyl)piperidin-3-yl)piperidine-4-carboxamide and 1-(5-(5-chloro-2-methoxypyridin-4-yl)-1H-pyrazole-3-carbonyl)-N-((3R,6S)-1-methyl-6-(trifluoromethyl)piperidin-3-yl)piperidine-4-carboxamide

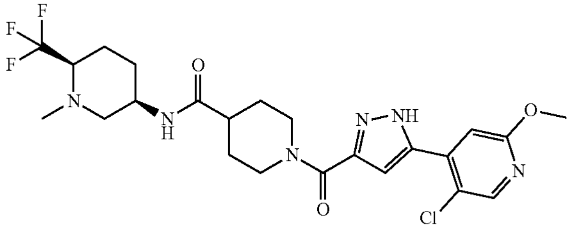

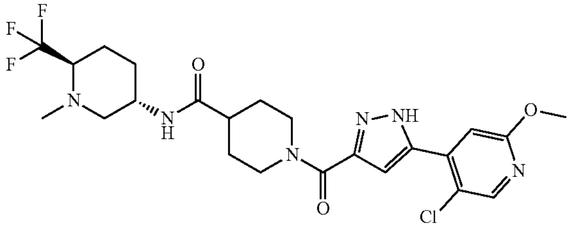

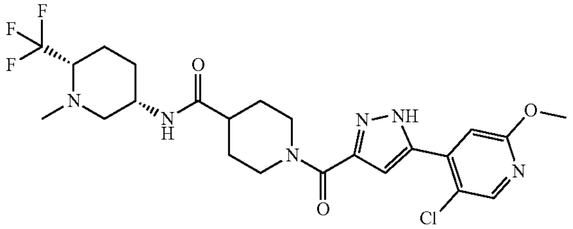

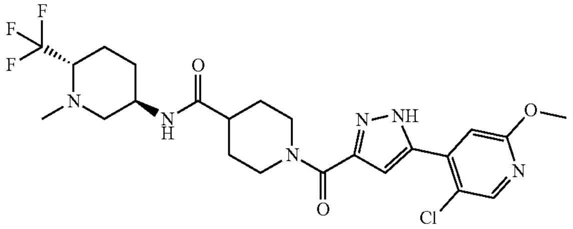

The title compound was prepared using a procedure similar to the one described for the synthesis of Example 179, except 1-methyl-6-(trifluoromethyl)piperidin-3-amine dihydrochloride was used as starting material. 1-(5-(5-chloro-2-methoxypyridin-4-yl)-1H-pyrazole-3-carbonyl)-N-((3R,6R)-1-methyl-6-(trifluoromethyl)piperidin-3-yl)piperidine-4-carboxamide and 1-(5-(5-chloro-2-methoxypyridin-4-yl)-1H-pyrazole-3-carbonyl)-N-((3S,6S)-1-methyl-6-(trifluoromethyl)piperidin-3-yl)piperidine-4-carboxamide and 1-(5-(5-chloro-2-methoxypyridin-4-yl)-1H-pyrazole-3-carbonyl)-N-((3S,6S)-1-methyl-6-(trifluoromethyl)piperidin-3-yl)piperidine-4-carboxamide and 1-(5-(5-chloro-2-methoxypyridin-4-yl)-1H-pyrazole-3-carbonyl)-N-((3R,6S)-1-methyl-6-(trifluoromethyl)piperidin-3-yl)piperidine-4-carboxamide were obtained as a solid mixture of diastereomers (18.4 mg, Example 248). LCMS (ESI): $[M+H]^+$: 530.4.

The four diastereomers of the title compounds were separated using Chiral-Prep-HPLC to yield two fractions, each containing two diastereomers.

Column: CHIRALPAK IC column

Column dimension: 2×25 cm, 5 μm

Mobile Phase: hexanes (8 mM $NH_3$·MeOH):EtOH:=50:50 hold for 25 min

Flow rate: 18 mL min

Detection: 220/254 nm

Example 248-A. The first eluting peak (5.2 mg) was obtained as a solid.

The first eluting peak had a retention time of 17.03 min.

$^1$H NMR (400 MHz, $CD_3OD$): δ 8.25 (d, 1H), 7.14 (s, 2H), 4.68 (d, 1H), 3.94 (s, 3H), 3.92 (s, 1H), 3.08-2.98 (m, 1H), 2.72-2.66 (m, 2H), 2.61-2.48 (m, 4H), 1.90-1.64 (m, 9H), 1.37-1.26 (m, 2H). LCMS (ESI): $[M+H]^+$: 529.4.

Example 248-B. The second eluting peak (5.3 mg) was obtained as a solid.

The second eluting peak had a retention time of 21.87 min.

$^1$H NMR (400 MHz, $CD_3OD$) δ 8.26 (s, 1H), 7.30-7.06 (m, 2H), 4.78-4.58 (m, 3H), 3.97-3.90 (m, 4H), 3.08-2.97 (m, 1H), 2.94-2.90 (m, 1H), 2.75-2.66 (m, 2H), 2.62-2.48 (m, 4H), 1.95-1.53 (m, 8H). LCMS (ESI): $[M+H]^+$: 529.4.

Example 249. A Diastereomeric Mixture of 1-(5-(5-chloro-2-methoxypyridin-4-yl)-1H-pyrazole-3-carbonyl)-N-((3S,6S)-6-(trifluoromethyl)tetrahydro-2H-pyran-3-yl)piperidine-4-carboxamide and 1-(5-(5-chloro-2-methoxypyridin-4-yl)-1H-pyrazole-3-carbonyl)-N-((3R,6R)-6-(trifluoromethyl)tetrahydro-2H-pyran-3-yl)piperidine-4-carboxamide and 1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide and 1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide

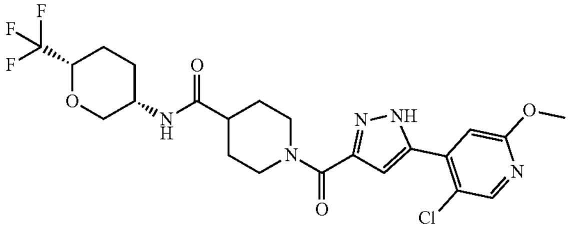

-continued

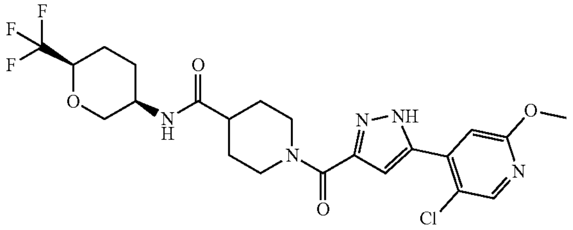

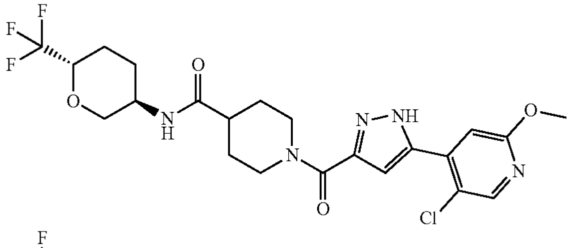

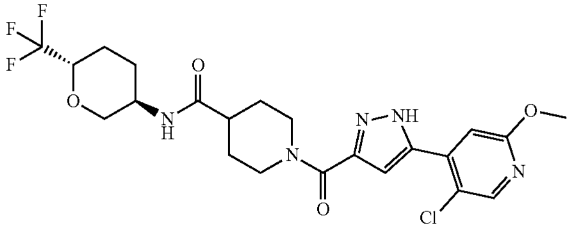

6-(trifluoromethyl)oxan-3-amine (INTERMEDIATE 532, 55.0 mg, 0.33 mmol), HATU (156.4 mg, 0.41 mmol) and DIPEA (106.3 mg, 0.82 mmol) were added to a solution of 1-[5-(5-chloro-2-methoxypyridin-4-yl)-1H-pyrazole-3-carbonyl]piperidine-4-carboxylic acid (INTERMEDIATE 503, 100.0 mg, 0.27 mmol in DMF (2.00 mL). The solution was stirred at 25° C. for 2 h, then diluted with EtOAc, washed with water, and the organic layer was concentrated. The residue was purified by silica gel column chromatography (DCM/MeOH, 12/1 v/v) and further purified by Prep-HPLC (using the following conditions: Column: YMC-Actus Triart C18, 30×250 mm, 5 μm; Mobile Phase A: Water (10 mM $NH_4HCO_3$), Mobile Phase B: MeCN/MeOH; Flow rate: 60 mL/min; Gradient: 50 B to 66 B in 7 min; 220 nm) to obtain 1-(5-(5-chloro-2-methoxypyridin-4-yl)-1H-pyrazole-3-carbonyl)-N-((3S,6S)-6-(trifluoromethyl)tetrahydro-2H-pyran-3-yl)piperidine-4-carboxamide and 1-(5-(5-chloro-2-methoxypyridin-4-yl)-1H-pyrazole-3-carbonyl)-N-((3R,6R)-6-(trifluoromethyl)tetrahydro-2H-pyran-3-yl)piperidine-4-carboxamide and 1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide and 1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide as a solid mixture of diastereomers (12.0 mg, Example 249). $^1$H NMR (300 MHz, $CD_3OD$) δ 8.27 (s, 1H), 7.16 (s, 2H), 4.69-4.63 (m, 2H), 4.04-3.60 (m, 8H), 2.99-2.92 (m, 1H), 2.78-2.62 (m, 1H), 2.03-1.51 (m, 8H). LCMS (ESI): 516.2 $[M+H]^+$.

The four diastereomers of the title compounds were separated using Chiral Prep-HPLC to yield two fractions, each containing two diastereomers.

Column: Reg-AD

Column dimensions: 3×25 cm, 5 μm

Mobile Phase: Hex (8 mM $NH_3$·MeOH)/EtOH, 65/35 v/v

Flow rate: 45 mL/min

Detection (nm): 220/254 nm

Example 249-A. The first eluting peak (67.5 mg) was obtained as a solid.

The first eluting peak had a retention time of 12.5 min.

$^1$H NMR (300 MHz, $CD_3OD$) δ 8.28 (s, 1H), 7.17 (s, 2H), 4.72 (s, 2H), 4.08-3.80 (m, 7H), 3.74 (d, 1H), 3.10 (s, 1H), 2.72 (s, 1H), 2.11-1.62 (m, 8H). LCMS (ESI): 516.2 $[M+H]^+$.

Example 249-B. The second eluting peak (66.0 mg) was obtained as a solid.

The second eluting peak had a retention time on 19.0 min.

$^1$H NMR (300 MHz, $CD_3OD$) δ 8.28 (s, 1H), 7.17 (s, 2H), 4.85-4.47 (m, 2H), 4.12-3.54 (m, 8H), 2.96 (s, 1H), 2.80-2.48 (m, 1H), 2.16-1.42 (m, 8H). LCMS (ESI): 516.2 $[M+H]^+$.

Example 250. N-((1H-indol-2-yl)methyl)-1-(5-(5-chloro-2-methoxypyridin-4-yl)-1H-pyrazole-3-carbonyl)piperidine-4-carboxamide

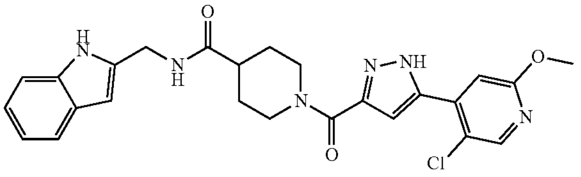

The title compound was prepared using a procedure similar to the one described for the synthesis of Example 167, except (1H-indol-2-yl)methanamine was used as starting material. The title compound was obtained as a solid (20.1 mg). $^1$H NMR (300 MHz, $CD_3OD$) δ 8.33-8.18 (m, 1H), 7.48-7.43 (m, 1H), 7.34-7.29 (m, 1H), 7.25 (s, 1H), 7.15 (s, 1H), 7.11-7.01 (m, 1H), 7.01-6.94 (m, 1H), 6.31 (m, 1H), 4.81-4.61 (m, 2H), 4.52 (s, 2H), 3.95 (s, 3H), 3.31 (s, 1H), 3.14-2.83 (m, 1H), 2.77-2.50 (m, 1H), 2.02-1.69 (m, 4H). LCMS (ESI): $[M+H]^+$: 493.3.

Example 251. 1-(5-(5-chloro-2-methoxypyridin-4-yl)-1H-pyrazole-3-carbonyl)-N-(6-methylpyridin-2-yl)piperidine-4-carboxamide

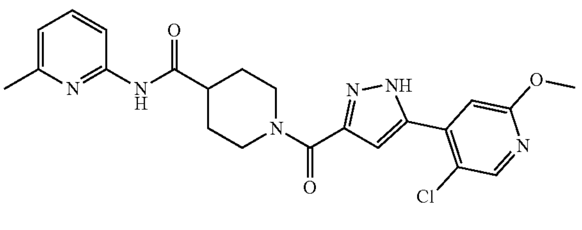

The title compound was prepared using a procedure similar to the one described for the synthesis of Example 167, except 6-methylpyridin-2-amine was used as starting material. The title compound was obtained as a solid (6.9 mg). $^1$H NMR (300 MHz, $CD_3OD$) δ 8.28 (s, 1H), 7.89 (d, 1H), 7.71-7.60 (m, 1H), 7.18 (s, 2H), 6.99 (d, 1H), 4.69 (s, 2H), 3.97 (s, 3H), 3.03 (s, 1H), 2.90-2.76 (m, 1H), 2.46 (s, 3H), 2.02 (s, 2H), 1.94-1.78 (m, 2H), 1.33 (d, 1H). LCMS (ESI): $[M+H]^+$: 455.3.

Example 252. 1-(5-(5-chloro-2-methoxypyridin-4-yl)-1H-pyrazole-3-carbonyl)-N-(3-methoxychroman-4-yl)piperidine-4-carboxamide

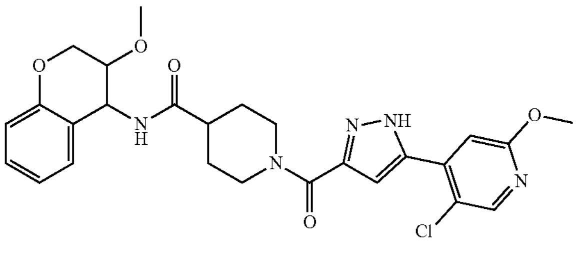 [SMILES: COc1cc(-c2cc(C(=O)N3CCC(C(=O)NC4c5ccccc5OCC4OC)CC3)n[nH]2)c(Cl)cn1]

The title compound was prepared using a procedure similar to the one described for the synthesis of Example 167, except 3-methoxychroman-4-amine was used as starting material. The title compound was obtained as a solid mixture of diastereomers (13.4 mg). $^1$H NMR (300 MHz, $CD_3OD$) δ 8.27 (s, 1H), 7.16 (m, 4H), 6.99-6.86 (m, 1H), 6.82 (m, 1H), 5.09-4.92 (m, 1H), 4.67 (s, 2H), 4.40-4.21 (m, 1H), 4.20-4.05 (m, 1H), 3.96 (s, 3H), 3.70-3.55 (m, 1H), 3.58 (s, 1H), 3.49 (s, 3H), 3.09-2.79 (m, 1H), 2.68-2.42 (m, 1H), 2.10-1.65 (m, 4H). LCMS (ESI): $[M+H]^+$: 526.4.

Example 253. 1-(5-(5-chloro-2-methoxypyridin-4-yl)-1H-pyrazole-3-carbonyl)-N-(1-(4-fluorophenyl)pyrrolidin-3-yl)piperidine-4-carboxamide

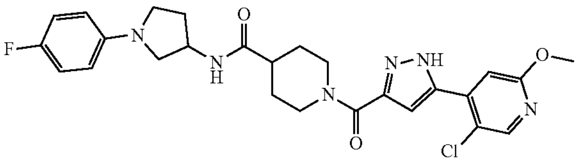 [SMILES: COc1cc(-c2cc(C(=O)N3CCC(C(=O)NC4CCN(c5ccc(F)cc5)C4)CC3)n[nH]2)c(Cl)cn1]

The title compound was prepared using a procedure similar to the one described for the synthesis of Example 179, except 1-(4-fluorophenyl)pyrrolidin-3-amine was used as starting material. The title compound was obtained as a solid mixture of enantiomers (9.3 mg). $^1$H NMR (400 MHz, $CD_3OD$) δ 8.25 (s, 1H), 7.14 (s, 2H), 7.01-6.78 (m, 2H), 6.63-6.41 (m, 2H), 4.77-4.34 (m, 4H), 3.94 (s, 3H), 3.62-3.35 (m, 2H), 3.17-3.04 (m, 1H), 2.91 (s, 1H), 2.67-2.46 (m, 1H), 2.36-2.24 (m, 1H), 2.08-1.57 (m, 6H). LCMS (ESI): $[M+H]^+$: 527.5.

Example 254. N-((1H-pyrrolo[3,2-c]pyridin-4-yl)methyl)-1-(5-(5-chloro-2-methoxypyridin-4-yl)-1H-pyrazole-3-carbonyl)piperidine-4-carboxamide

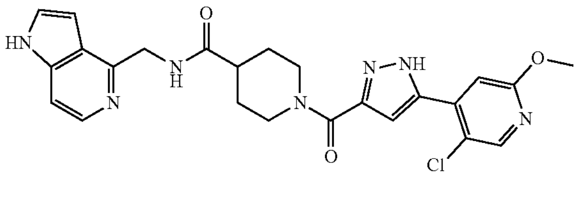 [SMILES: COc1cc(-c2cc(C(=O)N3CCC(C(=O)NCc4nccc5[nH]ccc45)CC3)n[nH]2)c(Cl)cn1]

The title compound was prepared using a procedure similar to the one described for the synthesis of Example 167, except (1H-pyrrolo[3,2-c]pyridin-4-yl)methanamine dihydrochloride was used as starting material. The title compound was obtained as a solid (18.8 mg). $^1$H NMR (400 MHz, DMSO-$d_6$) δ 8.42-8.35 (m, 1H), 8.33 (s, 1H), 8.05 (d, 1H), 7.45-7.37 (m, 1H), 7.34-7.26 (m, 1H), 7.22 (s, 1H), 7.12 (s, 1H), 6.61-6.51 (m, 1H), 4.61 (d, 2H), 4.44 (s, 2H), 3.29 (s, 1H), 3.18 (s, 2H), 3.03 (s, 1H), 2.80 (s, 1H), 1.67 (d, 4H). LCMS (ESI): $[M+H]^+$: 494.2.

Example 255. Enantiomeric Mixture of Example 255-A and Example 255-B

Example 255-A. (S)-1-(5-(5-chloro-2-methoxypyridin-4-yl)-1H-pyrazole-3-carbonyl)-N-(3-chlorobenzyl)-2,2-dimethylpiperidine-4-carboxamide

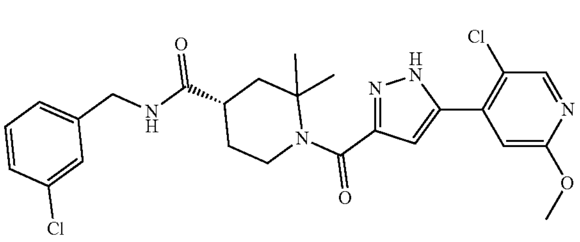

Example 255-B. (R)-1-(5-(5-chloro-2-methoxypyridin-4-yl)-1H-pyrazole-3-carbonyl)-N-(3-chlorobenzyl)-2,2-dimethylpiperidine-4-carboxamide

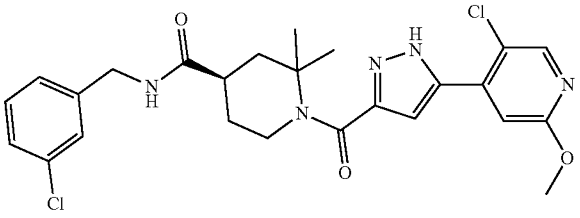

The title compound was prepared using a procedure similar to the one described for the synthesis of Example 171, except methyl 2,2-dimethylpiperidine-4-carboxylate was used as starting material in Step-1. (S)-1-(5-(5-chloro-2-methoxypyridin-4-yl)-1H-pyrazole-3-carbonyl)-N-(3-chlorobenzyl)-2,2-dimethylpiperidine-4-carboxamide and (R)-1-(5-(5-chloro-2-methoxypyridin-4-yl)-1H-pyrazole-3-carbonyl)-N-(3-chlorobenzyl)-2,2-dimethylpiperidine-4-carboxamide were obtained as a solid mixture of enantiomers (6.5 mg, Example 255). LCMS (ESI): $[M+H]^+$: 516.5.

The two enantiomers of the title compounds were separated using Chiral-Prep-HPLC.

Column: CHIRALPAK IC column

Column dimension: 2×25 cm, 5 μm

Mobile Phase: 3/1 hexanes/DCM (10 mM $NH_3$·MeOH): IPA=80:20 hold for 18 min

Flow rate: 20 mL/min

Detection: 220/254 nm

Example 255-A. The first eluting compound (1.1 mg) was obtained as a solid.

The first eluting compound had a retention time of 7.02 min.

LCMS (ESI): $[M+H]^+$: 516.5.

Example 255-B. The second eluting compound (0.7 mg) was obtained as a solid.

The second eluting compound had a retention time of 14.32 min.

LCMS (ESI): 516.4 $[M+H]^+$.

Example 256. Enantiomeric mixture of Example 256-A and Example 256-9

Example 256-A. (S)-5-(5-(5-chloro-2-methoxypyridin-4-yl)-1H-pyrazole-3-carbonyl)-N-(3-chlorobenzyl)-5-azaspiro[3.5]nonane-8-carboxamide

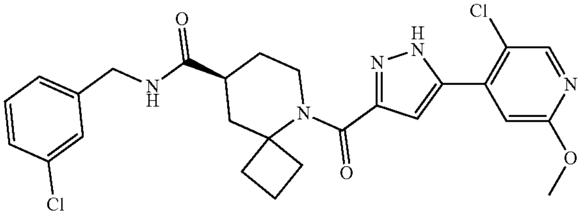

Example 256-B. (R)-5-(5-(5-chloro-2-methoxypyridin-4-yl)-1H-pyrazole-3-carbonyl)-N-(3-chlorobenzyl)-5-azaspiro[3.5]nonane-8-carboxamide

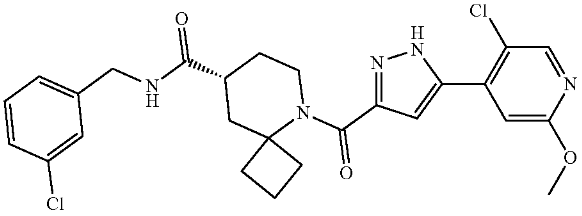

The title compound was prepared using a procedure similar to the one described for the synthesis of Example 174, except 5-(tert-butoxycarbonyl)-5-azaspiro[3.5]nonane-8-carboxylic acid was used as starting material in Step-1. (S)-5-(5-(5-chloro-2-methoxypyridin-4-yl)-1H-pyrazole-3-carbonyl)-N-(3-chlorobenzyl)-5-azaspiro[3.5]nonane-8-carboxamide and (R)-5-(5-(5-chloro-2-methoxypyridin-4-yl)-1H-pyrazole-3-carbonyl)-N-(3-chlorobenzyl)-5-azaspiro[3.5]nonane-8-carboxamide were obtained as a solid mixture of enantiomers (4.3 mg, Example 256). LCMS (ESI): $[M+H]^+$: 528.5.

The two enantiomers of the title compounds were separated using Chiral-Prep-HPLC.

Column: CHIRALPAK. ID column

Column dimension: 2×25 cm, 5 μm

Mobile Phase: 3/1 hexanes/DCM (10 mM $NH_3$·MeOH): EtOH=80:20 hold for 20 min

Flow rate: 20 mL/min

Detection: 220/254 nm

Example 256-A. The first eluting compound (1.5 mg) was obtained as a solid.

The first eluting compound had a retention time of 9.52 min.

LCMS (ESI): $[M+H]^+$: 528.5.

Example 256-B. The second eluting compound (1.6 mg) was obtained as a solid.

The second eluting compound had a retention time of 17.13 min.

LCMS (ESI): $[M+H]^+$: 528.4.

Example 257. (1R,3s,5S)-8-(5-(5-chloro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide and (1R,3s,5S)-8-(5-(5-chloro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide

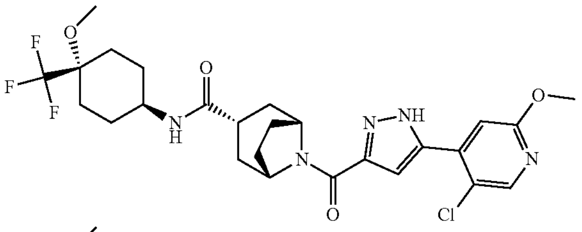

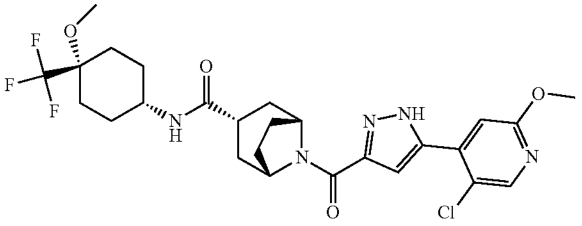

(1R,3s,5S)-8-[5-(5-chloro-2-methoxypyridin-4-yl)-1H-pyrazole-3-carbonyl]-8-azabicyclo[3.2.1]octane-3-carboxylic acid (INTERMEDIATE 512, 297.3 mg, 0.76 mmol) and 4-methoxy-4-(trifluoromethyl)cyclohexan-1-amine (150.0 mg, 0.76 mmol) were added to a mixture of HOBt (133.6 mg, 0.99 mmol), EDCI (189.6 mg, 0.99 mmol) and DIPEA (0.39 mL, 2.28 mmol) in DMF (10 mL). The solution was stirred at 25° C. for 14 h, and then diluted with water and extracted with EtOAc. The organic layers were combined, then dried over anhydrous sodium sulfate, filtered, and the solvent was evaporated. The residue was purified by silica gel chromatography (DCM/MeOH, 20/1 v/v) to obtain a diastereomeric mixture of (1R,3s,5S)-8-(5-(5-chloro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide and (1R,3s,5S)-8-(5-(5-chloro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide (300 mg) as a solid (Example 257). LCMS (ESI) 570.4 $[M+H]^+$.

The two diastereomers were separated by Chiral Prep-HPLC.

Column: CHIRALART Cellulose-SB

Column dimensions: 2×25 cm, 5 μm

Gradient: Hex (10 mM $NH_3$·MeOH)/EtOH, 90/10 v/v

Flow rate: 20 mL/min

Detection (nm): 220/254 nm

Example 257-A. The first eluting diastereomer (41.3 mg) was obtained as a solid. The first eluting diastereomer had a retention time of 6.63 min.

$^1$H NMR (300 MHz, $CD_3OD$) δ 8.29 (s, 1H), 7.27 (s, 1H), 7.10 (s, 1H), 5.39 (s, 1H), 4.85-4.80 (m, 1H), 3.97 (s, 4H), 3.41 (s, 3H), 3.13-3.05 (m, 1H), 2.20-1.90 (m, 6H), 1.88-1.60 (m, 10H). LCMS (ESI): 570.4 $[M+H]^+$.

Example 257-B. The second eluting diastereomer 125.2 mg) was obtained as a solid.

The second eluting diastereomer had a retention time of 8.45 min.

$^1$H NMR (300 MHz, $CD_3OD$) δ 8.30-8.26 (m, 1H), 7.30-7.20 (m, 1H), 7.10 (s, 1H), 5.39 (s, 1H), 4.85-4.80 (m, 1H), 3.97 (s, 3H), 3.71-3.57 (m, 1H), 3.42 (s, 3H), 2.98-2.85 (m, 1H), 2.20-1.85 (m, 8H), 1.82-1.70 (m, 4H), 1.68-1.55 (m, 2H), 1.54-1.40 (m, 2H). LCMS (ESI): 570.4 $[M+H]^+$.

Example 258. (1R,3S,5S)—N-[(3-fluoro-1H-indazol-5-yl)methyl]-8-[5-(5-fluoro-2-methoxypyridin-4-yl)-1H-pyrazole-3-carbonyl]-8-azabicyclo[3.2.1]octane-3-carboxamide

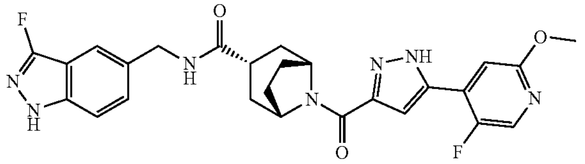 [SMILES: COc1cc(-c2cc(C(=O)N3[C@@H]4CC[C@H]3C[C@H](C(=O)NCc3ccc5[nH]nc(F)c5c3)C4)n[nH]2)c(F)cn1]

Step-1. Tert-butyl (1R,3S,5S)-3-[[(3-fluoro-1H-indazol-5-yl)methyl]carbamoyl]-8-azabicyclo[3.2.1]octane-8-carboxylate

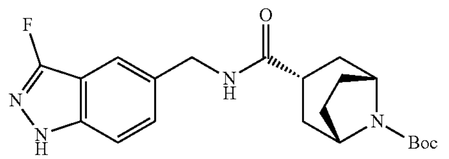 [SMILES: CC(C)(C)OC(=O)N1[C@@H]2CC[C@H]1C[C@H](C(=O)NCc1ccc3[nH]nc(F)c3c1)C2]

1-(3-fluoro-1H-indazol-5-yl)methanamine (155.0 mg, 0.94 mmol) was added to a solution of (1R,3S,5S)-8-(tert-butoxycarbonyl)-8-azabicyclo[3.2.1]octane-3-carboxylic acid (239.0 mg, 0.94 mmol), HOBt (139.0 mg, 1.03 mmol), EDCI (198.0 mg, 1.03 mmol) and DIPEA (0.49 mL, 2.8 mmol) in DMF (4.00 mL). The solution was stirred at 25° C. for 14 h, then diluted with $H_2O$ and extracted with ethyl acetate. The organic layers were concentrated under vacuum and the residue was purified by silica gel column chromatography (DCM/MeOH, 20/1 v/v) to obtain the title compound (60 mg) as an oil. LCMS (ESI): 403.2 $[M+H]^+$.

Step-2. (1R,3S,5S)—N-[(3-fluoro-1H-indazol-5-yl)methyl]-8-azabicyclo[3.2.1]octane-3-carboxamide

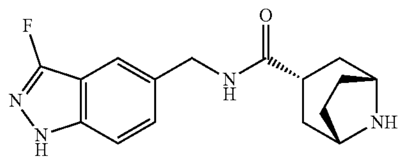 [SMILES: O=C(NCc1ccc2[nH]nc(F)c2c1)[C@@H]1C[C@H]2CC[C@@H](C1)N2]

TFA (1.00 mL) was added to a solution of tert-butyl (1R,3S,5S)-3-[[(3-fluoro-1H-indazol-5-yl)methyl]carbamoyl]-8-azabicyclo[3.2.1]octane-8-carboxylate (Step-1, 60.0 mg, 0.15 mmol) in DCM (2.0 mL). The solution was stirred at 25° C. for 1 h, then concentrated under vacuum. The residue was diluted with DCM and the pH value of the solution was adjusted to 8 with DIPEA. The solution was concentrated under vacuum and the residue was purified by silica gel column chromatography (DCM/MeOH, 10/1 v/v) to obtain the title compound (40 mg) as an oil. LCMS (ESI): 303.2 [M+H]+.

Step-3. (1R,3S,5S)—N-[(3-fluoro-1H-indazol-5-yl)methyl]-8-[5-(5-fluoro-2-methoxypyridin-4-yl)-1H-pyrazole-3-carbonyl]-8-azabicyclo[3.2.1]octane-3-carboxamide

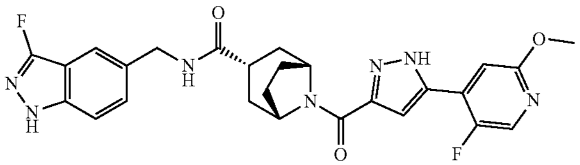 [SMILES: COc1cc(-c2cc(C(=O)N3[C@@H]4CC[C@H]3C[C@H](C(=O)NCc3ccc5[nH]nc(F)c5c3)C4)n[nH]2)c(F)cn1]

5-(5-fluoro-2-methoxypyridin-4-yl)-1H-pyrazole-3-carboxylic acid (INTERMEDIATE 507, 19.0 mg, 0.08 mmol), HATU (18.0 mg, 0.05 mmol), and DIPEA (33 μL, 0.19 mmol) were added to a solution of (1R,3S,5S)—N-[(3-fluoro-1H-indazol-5-yl)methyl]-8-azabicyclo[3.2.1]octane-3-carboxamide (Step-2, 20.0 mg, 0.07 mmol) in DMF (2.0 mL). The solution was stirred at 25° C. for 2 h, then concentrated under vacuum. The residue was purified by silica gel column chromatography (EtOAc/petroleum ether, 2/1 v/v), then by Prep-HPLC (using the following conditions: Column: YMC-Actus Triart C18, 20×250 mm, 5 μm, 12 nm; Mobile Phase A: Water (10 mM $NH_4HCO_3$); Mobile Phase B: MeCN, Gradient: 31% B to 42% B in 8 min, Detection: 220/254 nm) to obtain the title compound (1.4 mg) as a solid. $^1$H NMR (400 MHz, $CD_3OD$) δ 8.14 (d, 1H), 7.56 (s, 1H), 7.44-7.36 (m, 2H), 7.28-7.18 (m, 2H), 5.15 (s, 1H), 4.45 (s, 2H), 3.94 (s, 3H), 3.32 (s, 1H), 3.08-2.94 (m, 1H), 2.29-1.99 (m, 4H), 1.99-1.76 (m, 4H). LCMS (ESI): 522.3 [M+H]+.

Example 259. A Diastereomeric Mixture of (1R,3s,5S)-8-(5-(5-chloro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide and (1R,3s,5S)-8-(5-(5-chloro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide

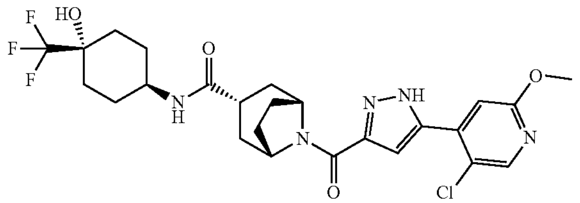

-continued

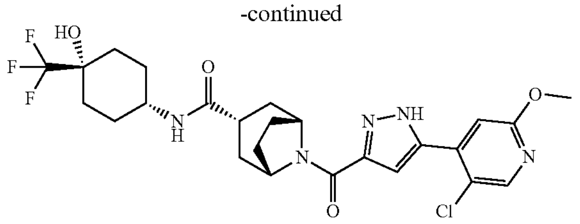

The title compound was prepared using a procedure similar to the one described for the synthesis of Example 257-A and 257-B, except (1R,3S,5S)-8-[5-(5-chloro-2-methoxypyridin-4-yl)-1H-pyrazole-3-carbonyl]-8-azabicyclo[3.2.1]octane-3-carboxylic acid (INTERMEDIATE 512) was used as the starting material. The residue was purified by silica gel column chromatography (DCM/MeOH, 20/1 v/v) to obtain a diastereomeric mixture of (1R,3s,5S)-8-(5-(5-chloro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide and (1R,3s,5S)-8-(5-(5-chloro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide (200.0 mg) as a solid (Example 259).

The two diastereomers were separated by Chiral Prep-HPLC.

Column: CHIRALPAK IE

Column dimensions: 2×25 cm, 5 μm

Gradient: Hex (10 mM $NH_3$·MeOH)/EtOH, 70/30 v/v

Flow rate: 20 mL/min

Detection (nm): 225/260 nm

Example 259-A. The first eluting diastereomer (65.0 mg) was obtained as a solid.

The first eluting diastereomer had a retention time of 17.6 min.

$^1$H NMR (300 MHz, $CD_3OD$) δ 8.28 (s, 1H), 7.27 (s, 1H), 7.15 (s, 1H), 5.20-5.10 (m, 1H), 4.87-4.85 (m, 1H), 3.97 (s, 3H), 3.69-3.60 (m, 1H), 2.94-2.90 (m, 1H), 2.20-1.90 (m, 4H), 2.24-1.97 (m, 4H), 1.98-1.83 (m, 4H), 1.82-1.71 (m, 4H), 1.70-1.54 (m, 4H). LCMS (ESI): 556.4 [M+H]+.

Example 259-B. The second eluting diastereomer (60.0 mg) was obtained as a solid. The second eluting diastereomer had a retention time of 22.5 min.

$^1$H NMR (300 MHz, $CD_3OD$) δ 8.28 (s, 1H), 7.27 (s, 1H) 7.09 (s, 1H), 5.39 (s, 1H), 4.69 (s, 1H), 3.96 (s, 4H), 3.12-2.98 (s, 1H), 2.24-1.99 (m, 4H), 1.99-1.83 (m, 6H), 1.82-1.59 (m, 6H). LCMS (ESI): 556.4 [M+H]+.

Example 260. 1-(5-(5-chloro-2-methoxypyridin-4-yl)-1H-pyrazole-3-carbonyl)-N-(5,6-dimethylpyrazin-2-yl)piperidine-4-carboxamide

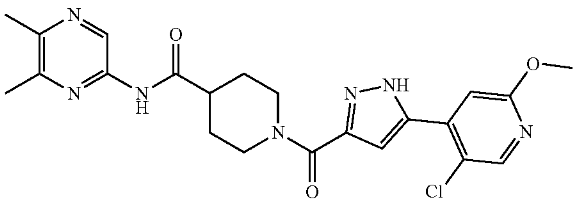

The title compound was prepared using a procedure similar to the one described for the synthesis of Example 167, except 5,6-dimethylpyrazin-2-amine was used as starting material. The title compound was obtained as a solid (6.0 mg). $^1$H NMR (300 MHz, $CD_3OD$) δ 9.03 (s, 1H), 8.26 (s, 1H), 7.16 (s, 2H), 4.66 (s, 2H) 3.94 (s, 3H), 3.78-3.33 (m, 1H), 3.17-2.92 (m, 1H), 2.90-2.73 (m, 1H), 2.58-2.41 (m, 6H), 1.99 (s, 2H), 1.90-1.67 (m, 2H). LCMS (ESI): $[M+H]^+$: 470.2.

Example 261. 1-(5-(5-chloro-2-methoxypyridin-4-yl)-1H-pyrazole-3-carbonyl)-N-(1H-indol-4-yl)piperidine-4-carboxamide

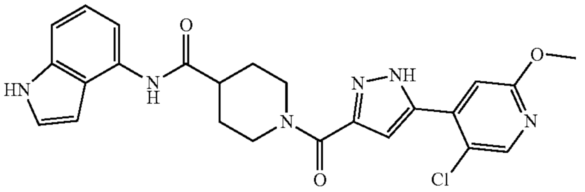 [SMILES: COc1cc(-c2cc(C(=O)N3CCC(C(=O)Nc4cccc5[nH]ccc45)CC3)n[nH]2)c(Cl)cn1]

The title compound was prepared using a procedure similar to the one described for the synthesis of Example 103, except 1H-indol-4-amine was used as a starting material to obtain the title compound (4.2 mg) as a solid. LCMS (ESI): 479.3 $[M+H]^+$.

Example 262. 1-[5-(5-chloro-2-methylpyridin-4-yl)-1H-pyrazole-3-carbonyl]-N-[(3-chlorophenyl)methyl]piperidine-4-carboxamide

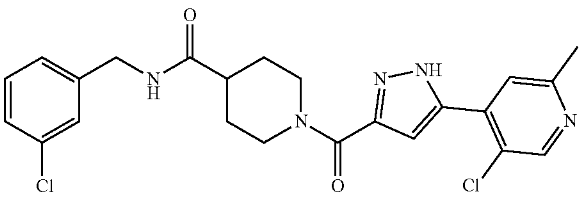 [SMILES: Cc1cc(-c2cc(C(=O)N3CCC(C(=O)NCc4cccc(Cl)c4)CC3)n[nH]2)c(Cl)cn1]

1-(3-chlorophenyl)methanamine (29.0 mg, 0.2 mmol), HATU (98.0 mg, 0.3 mmol), and DIPEA (89 μL, 0.5 mmol) were added to a stirred solution of 1-[5-(5-chloro-2-methylpyridin-4-yl)-1H-pyrazole-3-carbonyl]piperidine-4-carboxylic acid (INTERMEDIATE 517, 60.0 mg, 0.2 mmol) in DMF (2.0 mL). The solution was stirred at 25° C. for 14 h, then diluted with ethyl acetate and washed with water. The organic layer was concentrated under reduced pressure, then the residue was purified by reverse phase column chromatography (using the following conditions: Column, C18; Mobile Phase A: Water (10 mM $NH_4HCO_3$); Mobile Phase B: MeCN; Gradient: 25% B to 35% B in 15 min; Detection: 220/254 nm) to obtain the title compound (5 mg) as a solid. $^1$H NMR (400 MHz, $CD_3OD$) δ 8.55 (s, 1H), 7.69 (s, 1H), 7.36-7.19 (m, 5H), 4.69-4.65 (m, 2H), 4.37 (s, 2H), 2.99-2.95 (m, 1H), 2.68-2.60 (m, 2H), 2.59 (s, 3H), 2.05-1.85 (m, 2H), 1.82-1.74 (m, 2H). LCMS (ESI): 472.1 $[M+H]^+$.

Example 263. A Diastereomeric Mixture of 1-[5-(5-fluoro-2-methylpyridin-4-yl)-1H-pyrazole-3-carbonyl]-N-[(1r,4r)-4-hydroxy-1-(trifluoromethyl)cyclohexyl]piperidine-4-carboxamide and 1-[5-(5-fluoro-2-methylpyridin-4-yl)-1H-pyrazole-3-carbonyl]-N-[(1s,4s)-4-hydroxy-4-(trifluoromethyl)cyclohexyl]piperidine-4-carboxamide

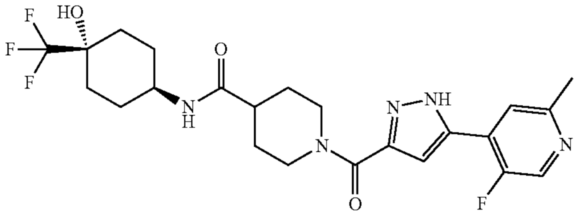

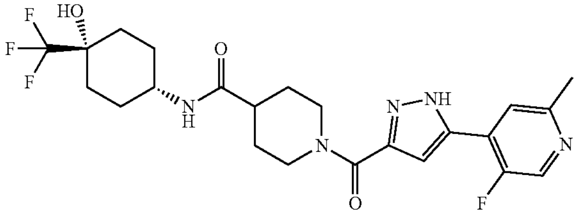

HOBt (67 mg, 0.5 mmol) and EDCI (95 mg, 0.5 mmol) were added to a stirred solution of 1-[5-(5-fluoro-2-methylpyridin-4-yl)-1H-pyrazole-3-carbonyl]piperidine-4-carboxylic acid (INTERMEDIATE 518, 110 mg, 0.3 mmol) in DMF (3 mL). The solution was stirred at 25° C. for 30 min, then 4-amino-1-trifluoromethyl)cyclohexan-1-ol hydrochloride (87 mg, 0.4 mmol) and DIPEA (0.17 mL, 0.9 mmol) were added. The solution was stirred at 25° C. for 6 h, then diluted with ethyl acetate and washed with water. The organic layer was concentrated under reduced pressure, and the residue was purified by silica gel column chromatography (DCM/MeOH, 20/1 v/v) to obtain a diastereomeric mixture of 1-[5-(5-fluoro-2-methylpyridin-4-yl)-1H-pyrazole-3-carbonyl]-N-[(1r,4r)-4-hydroxy-4-(trifluoromethyl)cyclohexyl]piperidine-4-carboxamide and 1-[5-(5-fluoro-2-methylpyridin-4-yl)-1H-pyrazole-3-carbonyl]-N-[(1s,4s)-4-hydroxy-4-(trifluoromethyl)cyclohexyl]piperidine-4-carboxamide (100 mg) as a solid (Example 263).

The two diastereomers were separated by Chiral Prep-HPLC.

Column: CHIRALPAK IG

Column dimensions: 20×250 mm, 5 μm

Mobile Phase: Hex:DCM:=3:1 (10 mM $NH_3$·MeOH)/MeOH 51/49 to 21/79 v/v

Flow Rate: 20 mL/min

Detection (nm): 220/254 nm

Example 263-A. The first eluting diastereomer (9.7 mg) was obtained as a solid.

The first eluting diastereomer had a retention time of 5.04 min.

$^1$H NMR (400 MHz, DMSO-d6) δ 13.99 (s, 1H), 8.53 (s, 1H), 7.86 (d, 1H), 7.80 (d, 1H), 7.03 (s, 1H), 5.70 (s, 1H), 4.51-4.47 (m, 1H), 4.35-4.00 (m, 1H), 3.88-3.81 (m, 1H), 3.33 (s, 3H), 3.21-3.16 (m, 1H), 2.84-2.80 (m, 1H), 2.61-2.51 (m, 1.81-1.74 (m, 6H), 1.58-1.48 (m, 6H). LCMS (ESI): 498.3 $[M+H]^+$.

Example 263-B. Second eluting diastereomer (6.7 mg) was obtained as a solid.

The second eluting diastereomer had a retention time of 7.46 min.

$^1$H NMR (400 MHz, DMSO-$d_6$) δ 14.03 (s, 1H), 8.53 (s, 1H), 7.92-7.66 (m, 2H), 7.03 (s, 1H), 5.74 (s, 1H), 4.75-4.35 (m, 2H), 4.11 (s, 1H), 3.60-3.45 (m, 1H), 3.28-3.09 (m, 1H), 2.95-2.68 (m, 1H) 2.46-2.30 (m, 1.86-1.67 (m, 5H), 1.67-1.43 (m, 9H). LCMS (ESI): 498.3 $[M+H]^+$.

Example 264. A Diastereomeric Mixture of 1-(5-(5-chloro-2-methoxypyridin-4-yl)-1H-pyrazole-3-carbonyl)-N-((1r,4r)-4-hydroxy-4-methylcyclohexyl) piperidine-4-carboxamide and 1-(5-(5-chloro-2-methoxypyridin-4-yl)-1H-pyrazole-3-carbonyl)-N-((1s,4s)-4-hydroxy-4-methylcyclohexyl)piperidine-4-carboxamide

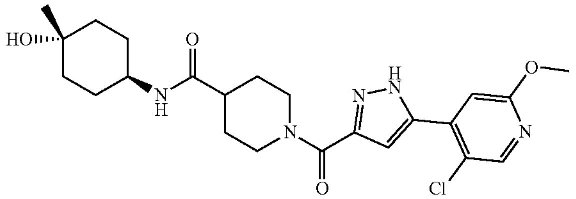

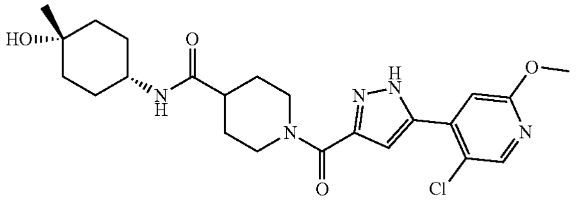

The title compound was prepared using a procedure similar to the one described for the synthesis of Example 167, except 4-amino-1-methylcyclohexan-1-ol was used as starting material. 1-(5-(5-chloro-2-methoxypyridin-4-yl)-1H-pyrazole-3-carbonyl)-N-((1r,4r)-4-hydroxy-4-methylcyclohexyl)piperidine-4-carboxamide and 1-(5-(5-chloro-2-methoxypyridin-4-yl)-pyrazole-3-carbonyl)-N-((1s,4s)-4-hydroxy-4-methylcyclohexyl)piperidine-4-carboxamide isolated as the mixture of diastereomers (Example 264) were separated using Prep-HPLC.

Column: XBridge BEH130 Prep C18 OBD column

Column dimension: 19×150 mm, 5 μm

Mobile Phase: Water (10 mM $NH_4HCO_3$+0.1% $NH_3H_2O$):MeCN

Detection: 210/254 inn

Example 264-A. The first eluting diastereomer (4.6 mg) was obtained as a solid.

$^1$H NMR (400 MHz, $CD_3OD$) δ 8.25 (s, 1H), 7.14 (s, 2H), 4.90-4.38 (m, 2H), 3.94 (s, 3H), 3.76-3.65 (m, 1H), 3.33-3.19 (m, 1H), 2.92 (s, 1H), 2.59-2.47 (m, 1H), 1.88-1.32 (12H), 1.23 (s, 3H). LCMS (ESI): $[M+H]^+$: 476.5.

Example 264-B. The second eluting diastereomer (6.9 mg) was obtained as a solid.

$^1$H NMR (300 MHz, $CD_3OD$) δ 8.27 (d, 1H), 7.13 (d, 2H), 4.82-4.51 (m, 1H), 4.42-4.10 (m, 1H), 3.97 (s, 3H), 3.70-3.45 (m, 1H), 3.32-3.09 (m, 1H), 3.07-2.77 (m, 1H), 2.62-2.35 (m, 1H), 2.03-1.33 (m, 13H), 1.21 (s, 3H). LCMS (ESI): $[M+H]^+$: 476.4.

Example 265. 1-(5-(5-chloro-2-methoxypyridin-4-yl)-1H-pyrazole-3-carbonyl)-N-(2-methyl-2,3-dihydrobenzofuran-3-yl)piperidine-4-carboxamide

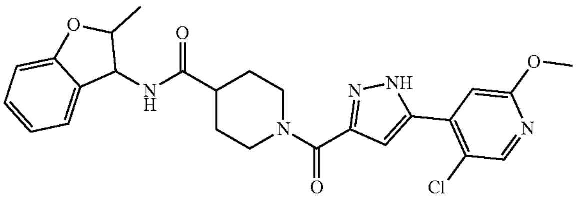 [SMILES: COc1cc(-c2cc(C(=O)N3CCC(C(=O)NC4c5ccccc5OC4C)CC3)n[nH]2)c(Cl)cn1]

The title compound was prepared using a procedure similar to the one described for the synthesis of Example 167, except 2-methyl-2,3-dihydrobenzofuran-3-amine hydrochloride was used as starting material. The title compound was obtained as a solid (7.0 mg). $^1$H NMR (300 MHz, $CD_3OD$) δ 8.28 (s, 1H), 7.32-7.14 (m, 4H), 6.97-6.86 (m, 1H), 6.79 (m, 1H), 5.17 (m, 1H), 4.67 (s, 1H), 4.60-4.46 (m, 1H), 3.97 (s, 3H), 2.94 (s, 1H), 2.65-2.50 (m, 1H), 1.93-1.79 (m, 4H), 1.77 (s, 1H), 1.45 (m, 3H), 1.40-1.28 (m, 1H). LCMS (ESI): $[M+H]^+$: 496.3.

Example 266. A Diastereomeric Mixture of (2S,5R)-1-(5-(5-chloro-2-methoxypyridin-4-yl)-1H-pyrazole-3-carbonyl)-N-(3-chlorobenzyl)-2,5-dimethylpiperidine-4-carboxamide and (2R,5S)-1-(5-(5-chloro-2-methoxypyridin-4-yl)-1H-pyrazole-3-carbonyl)-N-(3-chlorobenzyl)-2,5-dimethylpiperidine-4-carboxamide and (2R,5R)-1-(5-(5-chloro-2-methoxypyridin-4-yl)-1H-pyrazole-3-carbonyl)-N-(3-chlorobenzyl)-2,5-dimethylpiperidine-4-carboxamide and (2S,5S)-1-(5-(5-chloro-2-methoxypyridin-4-yl)-1H-pyrazole-3-carbonyl)-N-(3-chlorobenzyl)-2,5-dimethylpiperidine-4-carboxamide

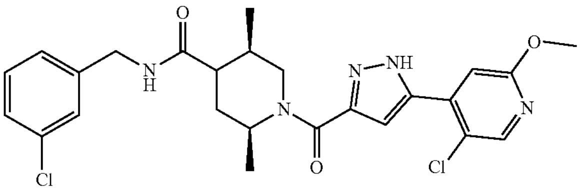

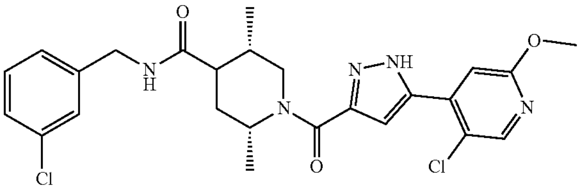

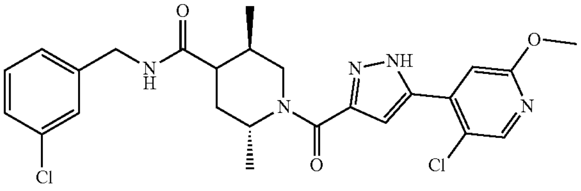

-continued

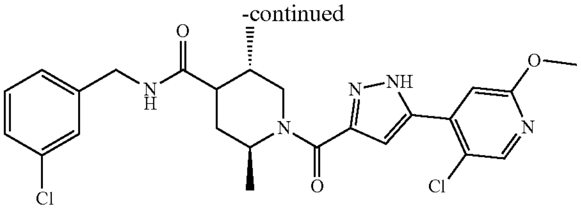

1-[5-(5-chloro-2-methoxypyridin-4-yl)-1H-pyrazole-3-carbonyl]-2,5-dimethylpiperidine-4-carboxylic acid (INTERMEDIATE 533, 50.0 mg, 0.1 mmol) and 1-(3-chlorophenyl)methanamine (18. mg, 0.1 mmol) were added to a solution of EDCI (31.9 mg, 0.17 mmol) and HOBt (22.4 mg, 0.16 mmol) and DIPEA (67 μL, 0.4 mmol) in DMF (3 mL). The solution was stirred at 25° C. for 14 h, then diluted with water and extracted with EtOAc. The organic layers were combined, then dried over anhydrous sodium sulfate, filtered, and the solvent was evaporated to obtain (2S,5R)-1-(5-(5-chloro-2-methoxypyridin-4-yl)-1H-pyrazole-3-carbonyl)-N-(3-chlorobenzyl)-2,5-dimethylpiperidine-4-carboxamide and (2R,5S)-1-(5-(5-chloro-2-methoxypyridin-4-yl)-1H-pyrazole-3-carbonyl)-N-(3-chlorobenzyl)-2,5-dimethylpiperidine-4-carboxamide and (2R,5R)-1-(5-(5-chloro-2-methoxypyridin-4-yl)-1H-pyrazole-3-carbonyl)-N-(3-chlorobenzyl)-2,5-dimethylpiperidine-4-carboxamide and (2S,5S)-1-(5-(5-chloro-2-methoxypyridin-4-yl)-1H-pyrazole-3-carbonyl)-N-(3-chlorobenzyl)-2,5-dimethylpiperidine-4-carboxamide as a diastereomeric mixture (Example 266).

The four diastereomers were separated using Chiral Prep-HPLC to yield two fractions, each containing two diastereomers.

Column: Gemini-NX C18 AXAI Packed

Column dimensions: 21.2×150 mm, 5 μm

Gradient: Water (0.1% FA)/MeCN, 57/43 to 54/46 v/v

Flow Rate: 25 mL/min

Detection (nm): 220/254

Example 266-A. The first eluting peak (2.2 mg) was obtained as a solid.

The first eluting peak had a retention time of 10.5 min.

$^{1}$H NMR (400 MHz, DMSO-$d_6$) δ 13.95 (s, 1H), 8.57 (d, 1H), 8.36 (s, 1H), 7.37-7.15 (m, 5H), 7.13 (s, 1H), 4.91-4.68 (m, 1H), 4.38-4.20 (m, 3H), 3.90 (s, 3H), 2.93-2.60 (m, 1H), 2.40 (m, 1H), 1.76-1.50 (m, 3H), 1.29-1.22 (m, 3H), 0.87-0.78 (m, 3H). LCMS (ESI): 516.3 $[M+H]^+$.

Example 266-B. The second eluting peak (2.1 mg) was obtained as a solid.

The second eluting peak had a retention time of 11.5 min.

$^{1}$H NMR (300 MHz, DMSO-d6) δ 13.95 (s, 1H), 8.57 (d, 1H), 8.36 (s, 1H), 7.37-7.15 (m, 5H), 7.13 (s, 1H), 4.35-4.32 (m, 1H), 4.25-4.20 (m, 3H), 3.90 (s, 3H), 2.93-2.60 (m, 1H), 2.40 (m, 1H), 1.90-1.80 (m, 1H), 1.70-1.58 (m, 1H), 1.23 (d, 3H), 0.81 (d, 3H). LCMS (ESI): 516.3 $[M+H]^+$.

Example 267. N-[(3-chlorophenyl)methyl]-1-[5-(5-fluoro-2-methylpyridin-4-yl)-1H-pyrazole-3-carbonyl]piperidine-4-carboxamide

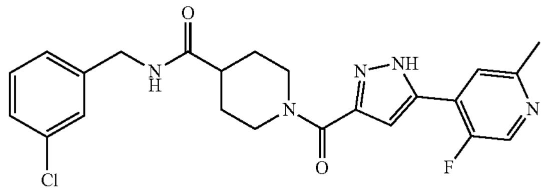 [SMILES: Cc1cc(-c2cc(C(=O)N3CCC(C(=O)NCc4cccc(Cl)c4)CC3)n[nH]2)c(F)cn1]

The title compound was prepared using a procedure similar to the one described for the synthesis of Example 262, except 1-[5-(5-fluoro-2-methylpyridin-4-yl)-1H-pyrazole-3-carbonyl]piperidine-4-carboxylic acid INTERMEDIATE 518 was used as a starting material. The residue was purified by reverse phase column chromatography (using the following conditions: Column, C18; Mobile Phase A: Water (10 mM $NH_4HCO_3$), Mobile Phase B: MeCN; Gradient: 20% B to 30% B in 12 min; Detection: 220/254 nm) to obtain the title compound (2 mg) as a solid. $^{1}$H NMR (400 MHz, $CD_3OD$) δ 8.44 (s, 1H), 7.82 (s, 1H), 7.36-7.28 (m, 2H), 7.26 (d, Hz, 1H), 7.23 (m, 1H), 7.16 (s, 1H), 4.70 (s, 2H), 4.37 (s, 2H), 2.97-2.58 (s, 5H), 1.94 (s, 2H), 1.77 (m, 2H). LCMS (ESI): 456.2 $[M+H]^+$.

Example 268. (1R,3S,5S)—N-[(3-chlorophenyl)methyl]-8-[5-(5-fluoro-2-methylpyridin-4-yl)-1H-pyrazole-3-carbonyl]-8-azabicyclo[3.2.1]octane-3-carboxamide

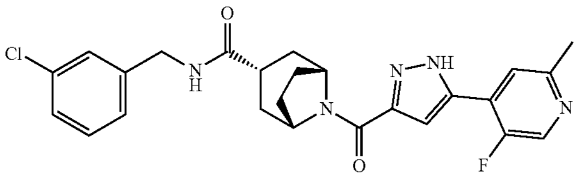 [SMILES: Cc1cc(-c2cc(C(=O)N3[C@@H]4CC[C@H]3C[C@H](C(=O)NCc3cccc(Cl)c3)C4)n[nH]2)c(F)cn1]

HATU (128.9 mg, 0.3 mmol), DIPEA (0.12 mL, 0.7 mmol) and (1R,3S,5S)—N-[(3-chlorophenyl)methyl]-8-azabicyclo[3.2.1]octane-3-carboxamide (INTERMEDIATE 519, 63.0 mg, 0.2 mmol) were added to a stirred solution of 5-(5-fluoro-2-methylpyridin-4-yl)-1H-pyrazole-3-carboxylic acid (INTERMEDIATE 520, 50.0 mg, 0.2 mmol) in DMF (5 mL). The solution was stirred at 25° C. for 14 h, then diluted with water and extracted with EtOAc. The organic layers were combined, then dried over anhydrous sodium sulfate, filtered, and the solvent was evaporated. The residue was purified by reverse phase column chromatography (MeCN/water, 95/5 to 5/95 v/v) to obtain the title compound (19.5 mg) as a solid. $^{1}$H NMR (300 MHz, $CD_3OD$) δ 8.64 (d, 1H), 8.07 (d, 1H), 7.38-7.22 (m, 4H), 7.26-7.17 (m, 1H), 5.04 (s, 1H), 4.89-4.87 (m, 1H), 4.36 (s, 2H), 3.07-2.95 (m, 1H), 2.67 (s, 3H), 2.20-2.03 (m, 4H), 1.98-1.80 (m, 4H). LCMS (ESI): 482.1 $[M+H]^+$.

Example 269. N-[(3-fluoro-1H-indazol-5-yl)methyl]-1-[5-(5-fluoro-2-methylpyridin-4-yl)-1H-pyrazole-3-carbonyl]piperidine-4-carboxamide

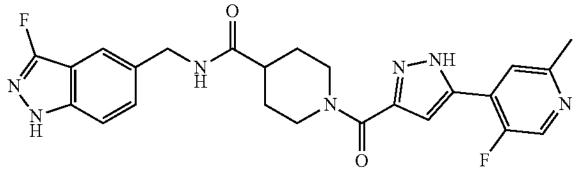 [SMILES: Cc1cc(-c2cc(C(=O)N3CCC(C(=O)NCc4ccc5[nH]nc(F)c5c4)CC3)n[nH]2)c(F)cn1]

The title compound was prepared using a procedure similar to the one described for the synthesis of Example 262, except 1-[5-(5-fluoro-2-methylpyridin-4-yl)-1H-pyrazole-3-carbonyl]piperidine-4-carboxylic acid (INTERMEDIATE 518) and 1-(3-fluoro-1H-indazol-5-yl)methanamine (INTERMEDIATE 514) were used as the starting materials. The residue was purified first by silica gel column chromatography (DCM/MeOH, 10/1 v/v), then by Prep-HPLC (using the following conditions: Column: Xselect CSH OBD, 30×150 mm, 5 μm; Mobile Phase A: Water (10 mM $NH_4HCO_3$); Mobile Phase B: MeCN; Gradient: 20% B to 35% B in 8 min; Detection: 220/254 nm) to obtain the title compound (2.6 mg) as a solid. $^1H$ NMR (400 MHz, DMSO-$d_6$) δ 14.01 (s, 1H), 12.49 (s, 1H), 8.52 (s, 1H), 8.43 (d, 1H), 7.79 (d, 1H), 7.51 (s, 1H), 7.47-7.41 (m, 1H), 7.34 (s, 1H), 7.03 (s, 1H), 4.57-4.40 (m, 2H), 4.39-4.26 (m, 2H), 2.85 (s, 1H), 2.52-2.36 (m, 5H), 1.81 (s, 2H), 1.58 (s, 2H). LCMS (ESI): 480.2 $[M+H]^+$.

Example 270. 1-[5-(5-chloro-2-ethylpyridin-4-yl)-1H-pyrazole-3-carbonyl]-N-[(3-chlorophenyl)methyl]piperidine-4-carboxamide

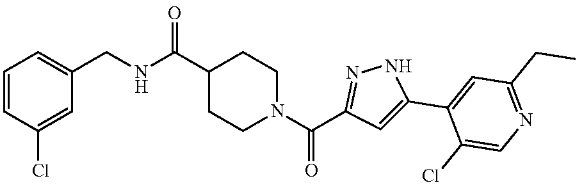 [SMILES: CCc1cc(-c2cc(C(=O)N3CCC(C(=O)NCc4cccc(Cl)c4)CC3)n[nH]2)c(Cl)cn1]

HOBt (11.6 mg, 0.09 mmol) and EDCI (16.5 mg, 0.09 mmol) were added to a stirred solution of 1-[5-(5-chloro-2-ethylpyridin-4-yl)-1H-pyrazole-3-carbonyl]piperidine-4-carboxylic acid (INTERMEDIATE 521, 24.0 mg, 0.07 mmol) in DMF (1.0 mL). The solution was stirred at 25° C. for 30 min, then 1-(3-chlorophenyl)methanamine (11.2 mg, 0.08 mmol) and DIPEA (35 μL, 0.2 mmol) were added. The solution was stirred at 25° C. for 14 h, then diluted with EtOAc, washed with water, and the organic layer was concentrated under reduced pressure. The residue was first purified by silica gel column chromatography (DCM/MeOH, 20/1 v/v), then Prep-HPLC (using the following conditions: Column: Xselect CSH OBD, 30×50 mm, 5 μm; Mobile Phase A: Water (10 mM $NH_4HCO_3$); Mobile Phase B: MeCN; Gradient: 35% B to 52% B in 7 min; Detection: 220/254 nm) to obtain the title compound (2.1 mg) as a solid. $^1H$ NMR (300 MHz, $CD_3OD$) δ 8.57 (s, 1H), 7.69 (s, 1H), 7.39-7.17 (m, 5H), 4.81-4.49 (m, 2H), 4.37 (s, 2H), 3.13-2.78 (m, 3H), 2.63 (s, 1H), 2.03-1.72 (m, 4H), 1.48-1.21 (a), 4H). LCMS (ESI): 486.1 $[M+H]^+$.

Example 271. 1-[5-(5-fluoro-2-methylpyridin-4-yl)-1H-pyrazole-3-carbonyl]-N-(1H-indol-5-ylmethyl)piperidine-4-carboxamide

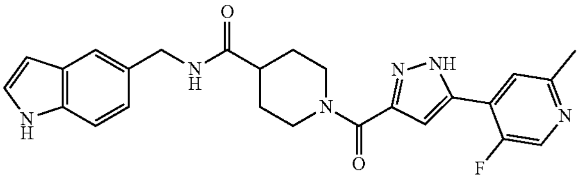 [SMILES: Cc1cc(-c2cc(C(=O)N3CCC(C(=O)NCc4ccc5[nH]ccc5c4)CC3)n[nH]2)c(F)cn1]

The title compound was prepared using a procedure similar to the one described for the synthesis of Example 267, except 1-(H-indol-5-yl)methanamine was used as a starting material. The residue was purified by Prep-HPLC (using the following conditions: Column: XselectCSH OBD, 30×150 mm, 5 μm; Mobile Phase A: Water (0.1% FA); Mobile Phase B: MeCN; Flow rate: 60 mL/min; Gradient: 20% B to 33% B in 8 min; Detection: 220/254 nm) to obtain the title compound (9.6 mg) as a solid. $^1H$ NMR (400 MHz, DMSO-$d_6$) δ 14.00 (s, 1H); 11.01 (s, 1H); 8.52 (s, 8.35-8.28 (m, 1H), 7.80 (s, 1H), 7.42-7.37 (m, 1H), 7.36-7.28 (m, 2H), 7.03 (s, 1H), 7.01-6.94 (m, 1H), 6.40-6.34 (m, 1H); 4.51-4.46 (m, 1H), 4.32 (d, 2H), 4.15-4.11 (m, 1H); 3.31 (s, 3H), 3.28-3.11 (m, 1H), 3.18 (s, 1H), 2.86-2.81 (m, 1H), 1.83-1.78 (m, 2H), 1.62-1.57 (m, 2H). LCMS (ESI): 461.4 $[M+H]^+$;

Example 272. N-[(2,3-dimethyl-1H-indol-5-yl)methyl]-1-[5-(5-fluoro-2-methoxypyridin-4-yl)-1H-pyrazole-3-carbonyl]piperidine-4-carboxamide

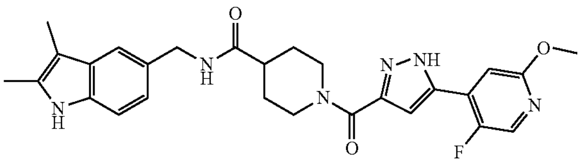

The title compound was prepared using a procedure similar to the one described for the synthesis of Example 270, except 1-[5-(5-fluoro-2-methoxypyridin-4-yl)-1H-pyrazole-3-carbonyl]piperidine-4-carboxylic acid (INTERMEDIATE 511) and 1-(2,3-dimethyl-1H-indol-5-yl)methanamine (INTERMEDIATE 522) were used as starting materials. The residue was first purified by silica gel column chromatography (DCM/MeOH, 10/1 v/v), then by Prep-HPLC (using the following conditions: Column: YMC-Actus Triart C18, 30×250 mm, 5 μm; Mobile Phase A: Water (10 mM $NH_4HCO_3$); Mobile Phase MeCN, Gradient: 34% B to 50% B in 7 min; Detection: 220/254 nm) to obtain the title compound (31.1 mg) as a solid. $^1H$ NMR (300 MHz, $CD_3OD$) δ 8.14 (d, 1H), 7.35-7.29 (m, 1H), 7.27 (s, 1H), 7.23-7.14 (m, 1H), 7.10 (d, 1H), 7.01-6.91 (m, 1H), 4.66 (s, 2H), 4.44 (s, 2H), 3.95 (s, 3H), 3.18-3.03 (m, 1H), 2.95 (s, 1H), 2.67-2.52 (m, 1H), 2.34 (s, 3H), 2.20 (d, 3H), 2.08-1.60 (m, 4H). LCMS (ESI): 505.2 $[M+H]^+$.

Example 273. (2R,4R)-1-(5-(5-chloro-2-methoxypyridin-4-yl)-1H-pyrazole-3-carbonyl)-N-(3-chlorobenzyl)-2-methylpiperidine-4-carboxamide

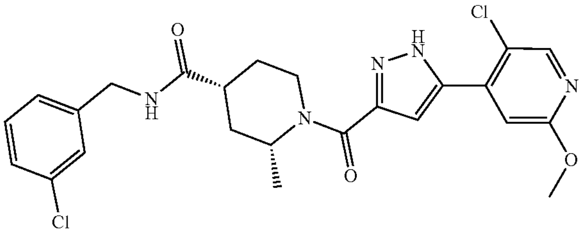 [SMILES: COc1cc(-c2cc(C(=O)N3CC[C@@H](C(=O)NCc4cccc(Cl)c4)C[C@H]3C)n[nH]2)c(Cl)cn1]

The title compound was prepared using a procedure similar to the one described for the synthesis of Example 174, except (2R,4R)-1-(tert-butoxycarbonyl)-2-methylpiperidine-4-carboxylic acid was used as starting material in Step-1 The title compound was obtained as a solid (2.0 mg). LCMS (ESI): $[M+H]^+$: 504.3.

Example 274. 1-(5-(5-chloro-2-methoxypyridin-4-yl)-1H-pyrazole-3-carbonyl)-N-(3-chlorobenzyl)-2,6-dimethylpiperidine-4-carboxamide

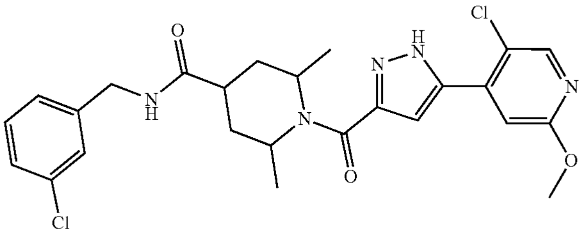 [SMILES: COc1cc(-c2cc(C(=O)N3C(C)CC(C(=O)NCc4cccc(Cl)c4)CC3C)n[nH]2)c(Cl)cn1]

Step-1. Methyl 1-(5-(5-chloro-2-methoxypyridin-4-yl)-1H-pyrazole-3-carbonyl)-2,6-dimethylpiperidine-4-carboxylate

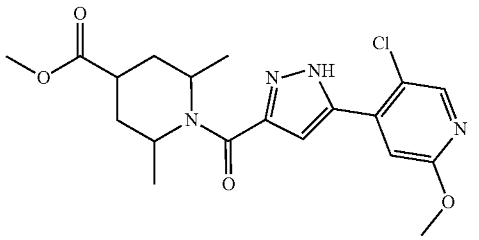 [SMILES: COC(=O)C1CC(C)N(C(=O)c2cc(-c3cc(OC)ncc3Cl)[nH]n2)C(C)C1]

$SOCl_2$ (1.00 mL) was added to 5-(5-chloro-2-methoxypyridin-4-yl)-1H-pyrazole-3-carboxylic acid (INTERMEDIATE 510, 90.0 mg, 0.35 mmol) and the resulting mixture was stirred at 70° C. for 5 h. The resulting mixture was concentrated under vacuum and the residue was dissolved in THF (2.00 mL). A solution of methyl 2,6-dimethylpiperidine-4-carboxylate (60.0 mg, 0.35 mmol) and NaH (28.0 mg, 0.70 mmol, 60% dispersion in mineral oil) in THF (1.00 mL) and DIPEA (274.0 mg, 2.13 mmol) were added to the reaction mixture. The resulting mixture was stirred at 80° C. for 24 h and concentrated under vacuum upon completion. The residue was used in the next step without further purification.

Step-2. 1-(5-(5-chloro-2-methoxypyridin-4-yl)-1H-pyrazole-3-carbonyl)-2,6-dimethylpiperidine-4-carboxylic acid

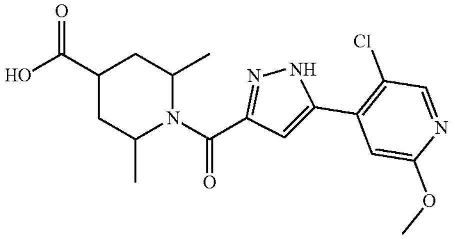 [SMILES: COc1cc(-c2cc(C(=O)N3C(C)CC(C(=O)O)CC3C)n[nH]2)c(Cl)cn1]

A solution of LiOH (44.0 mg, 1.05 mmol) in water (0.50 mL) was added to a stirred solution of methyl 1-(5-(5-chloro-2-methoxypyridin-4-yl)-1H-pyrazole-3-carbonyl)-2,6-dimethylpiperidine-4-carboxylate (Step-1) in MeOH (1.00 mL). The resulting mixture was stirred at 30° C. for 5 h. The resulting mixture was concentrated under vacuum to obtain the title compound and used in the next step without further purification.

Step-3. 1-(5-(5-chloro-2-methoxypyridin-4-yl)-1H-pyrazole-3-carbonyl)-N-(3-chlorobenzyl)-2,6-dimethylpiperidine-4-carboxamide

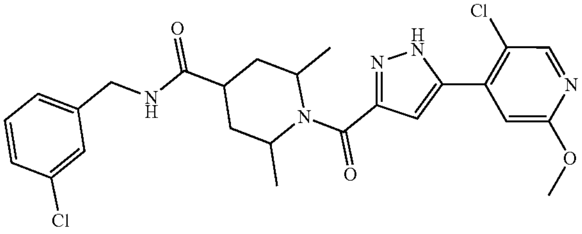 [SMILES: COc1cc(-c2cc(C(=O)N3C(C)CC(C(=O)NCc4cccc(Cl)c4)CC3C)n[nH]2)c(Cl)cn1]

HATU (199.0 mg, 0.53 mmol) and (3-chlorophenyl)methanamine (50.0 mg, 0.35 mmol) were added to a stirred solution of 1-(5-(5-chloro-2-methoxypyridin-4-yl)-1H-pyrazole-3-carbonyl)-2,6-dimethylpiperidine-4-carboxylic acid (Step-2) and DIPEA (137.0 mg, 1.05 mmol) in DMF (1.00 mL). The resulting mixture was stirred at 30° C. for 14 h. The resulting mixture was filtered. The filtrate was then purified by Prep-HPLC (using the following conditions: Column: Sunfire Prep C18 OBD Column, 19×150 mm 5 μm 10 nm; Mobile phase A: Water (0.1% FA), mobile phase B: MeCN; Detector, UV 210/254 nm) to obtain the title compound (3.6 mg) as a solid mixture of diastereomers. $^1H$ NMR (400 MHz, $CD_3OD$): δ 8.27 (s, 1H), 7.49-6.70 (m, 6H), 4.64 (d, 1H), 4.35 (s, 2H), 3.94 (s, 3H), 2.53-2.42 (m, 1H), 2.26-2.14 (m, 2H), 1.89-1.74 (m, 2H), 1.43 (d, 6H), 1.31 (d, 1H). LCMS (ESI): $[M+H]^+$: 518.1.

Example 275. A diastereomeric mixture of (1R,3s,5S)-8-(5-(5-fluoro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide

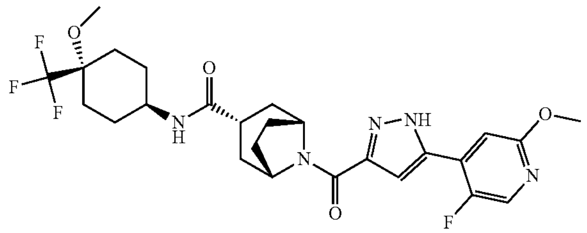

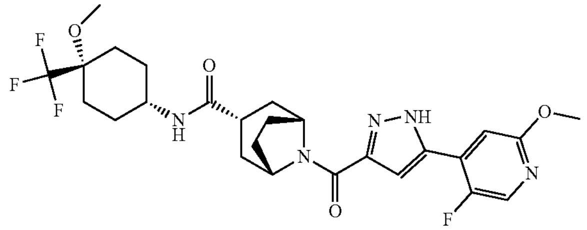

The title compound was prepared using a procedure similar to the one described for the synthesis of Example 170-A, except methoxy-4-(trifluoromethyl)cyclohexan-1-amine was used as starting material in Step-5. Purification by silica gel column chromatography eluting with DCM/MeOH (10:1 v/v) yielded diastereomeric mixture of (1R,3s,5S)-8-(5-(5-fluoro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide as a solid (210.0 mg, Example 275). LCMS (ESI): $[M+H]^+$: 554.4.

The two diastereomers of the title compounds were separated using Chiral-Prep-HPLC.

Column: CHIRAL ART Cellulose-SB column

Column dimension: 2×25 cm, 5 μm

Mobile Phase: hexanes (10 mM $NH_3$·MeOH):IPA=70:30 hold for 19 min

Flow rate: 20 mL/min

Detection: 210/260 nm

Example 275-A. The first eluting diastereomer (35.4 mg) was obtained as a solid.

The first eluting diastereomer had a retention time of 9.10 min.

$^1H$ NMR (400 MHz, $CD_3OD$) δ 8.16-8.06 (m, 1H), 7.38-7.08 (m, 2H), 5.37 (s, 1H), 4.80-4.78 (m, 1H), 3.95 (s, 3H), 3.94 (s, 1H), 3.31 (s, 3H), 3.15-3.05 (m, 1H), 2.21-1.65 (m, 16H). LCMS (ESI): $[M+H]^+$: 554.4.

Example 275-B. The second eluting diastereomer (128.1 mg) was obtained as a solid.

The second eluting diastereomer had a retention time of 12.40 min.

$^1H$ NMR (400 MHz, $CD_3OD$) δ 8.20-7.90 (m, 1H), 7.38-7.08 (m, 2H), 5.37 (s, 1H) 4.80-4.78 (m, 1H), 3.95 (s, 3H), 3.70-3.60 (m, 1H), 3.35 (s, 3H), 3.15-3.05 (m, 1H), 2.21-1.65 (m, 16H). LCMS (ESI): $[M+H]^+$: 554.4.

Example 276. 1-(5-(5-fluoro-2-methoxypyridin-4-yl)-1H-pyrazole-3-carbonyl)-N-(1-oxaspiro[3.5]nonan-7-yl)piperidine-4-carboxamide

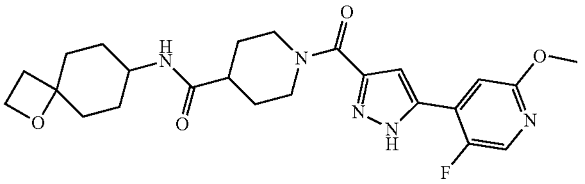 [SMILES: COc1cc(-c2cc(C(=O)N3CCC(C(=O)NC4CCC5(CCO5)CC4)CC3)n[nH]2)c(F)cn1]

EDCI (165.1 mg, 0.86 mmol), HOBt (116.4 mg, 0.86 mmol), and 1-oxaspiro[3.5]nonan-7-amine (INTERMEDIATE 523, 202.7 mg, 1.44 mmol) were added to a stirred solution of 1-[5-(5-fluoro-2-methoxypyridin-4-yl)-1H-pyrazole-3-carbonyl]piperidine-4-carboxylic acid (INTERMEDIATE 511, 200.0 mg, 0.57 mmol) and DIPEA (222.6 mg, 1.72 mmol) in DMF (4.00 mL). The resulting mixture was stirred at 25° C. for 14 h. The resulting mixture was diluted with EtOAc, washed with water. The resulting mixture was concentrated under reduced pressure. The residue was purified by reverse phase column chromatography (using the following conditions: C18 column, Mobile Phase A: Water (0.1% $NH_4HCO_3$), Mobile Phase B: MeCN; Flow rate: 30 mL/min; Gradient: 20 B to 50 B in 20 min; 220/254 nm) to obtain the title compound (162.0 mg) as a solid mixtures of diastereomers. $^1H$ NMR (300 MHz, DMSO-$d_6$) δ 14.01 (s, 1H), 8.29 (s, 1H), 7.69 (d, 1H), 7.33 (d, 1H), 7.05 (s, 1H), 4.73-4.03 (m, 4H), 3.88 (s, 3H), 3.55-3.49 (m, 1H), 3.18-3.12 (m, 1H), 2.85-2.78 (m, 1H), 2.45-2.38 (m, 1H), 2.33-2.21 (m, 2H), 2.03-1.93 (m, 2H), 1.76-1.69 (m, 2H), 1.58-1.37 (m, 8H). LCMS (ESE): $[M+H]^+$: 472.3.

Example 277. (1R,3s,5S)—N-((3-fluoro-1-methyl-1H-indazol-5-yl)methyl)-8-(5-(5-fluoro-2-methoxypyridin-4-yl)-1H-pyrazole-3-carbonyl)-8-azabicyclo[3.2.1]octane-3-carboxamide

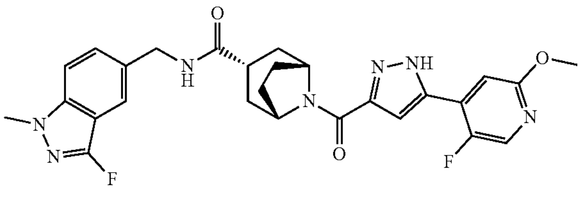

Step-1. 3-fluoro-1-methylindazole-5-carbonitrile

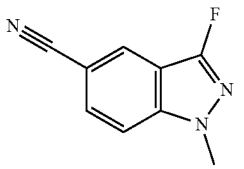

Selectfluor® (4.51 g, 12.73 mmol) and AcOH (1.00 mL) were added to a stirred solution of 1-methylindazole-5-carbonitrile (1.00 g, 6.36 mmol) in MeCN (10.00 mL). The resulting solution was stirred at 70° C. for 14 h. The resulting mixture was concentrated under vacuum. The residue was purified by silica gel column chromatography eluting with EtOAc/petroleum ether (1/5 v/v) to obtain the title compound (623.0 mg) as a solid. LCMS (ESI): $[M+H]^+$: 176.1.

Step-2. 1-(3-fluoro-1-methylindazol-5-yl)methanamine

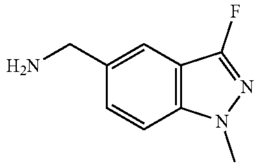

Pd/C (300.0 mg, 2.82 mmol) was added to a stirred solution of 3-fluoro-1-methylindazole-5-carbonitrile (Step-1, 600.0 mg, 3.43 mmol) in MeOH (10.00 mL) and AcOH (5.00 mL), The resulting solution was stirred at 25° C. for 1 h under hydrogen atmosphere. The solid was filtered out. The filtrate was concentrated under vacuum, and the residue was purified by silica gel column chromatography eluting with DCM/MeOH (10/1 v/v) to obtain the title compound (648.0 mg) as a solid. LCMS (ESI): $[M+H]^+$: 180.1.

Step-3. tert-butyl (1R, 3S, 5S)-3-[[(3-fluoro-1-methylindazol-5-yl)methyl]carbamoyl]-8-azabicyclo[3.2.1]octane-8-carboxylate

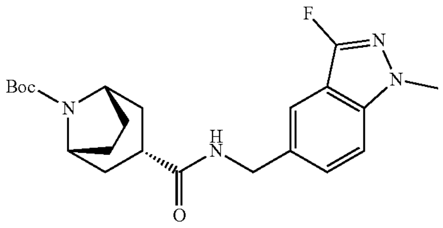 [SMILES: Cn1nc(F)c2cc(CNC(=O)[C@@H]3C[C@H]4CC[C@@H](C3)N4C(=O)OC(C)(C)C)ccc21]

HOBt (135.7 mg, 1.00 mmol), EDCI (192.6 mg, 1.00 mmol), and 1-(3-fluoro-1-methylindazol-5-yl)methanamine (150.0 mg, 0.84 mmol) were added to a stirred solution of (1R,3S,5S)-8-(tert-butoxycarbonyl)-8-azabicyclo[3.2.1]octane-3-carboxylic acid (256.5 mg, 1.00 mmol) and DIPEA. (324.5 mg, 2.51 mmol) in DMF (5.00 mL). The resulting solution was stirred at 25° C. for 1 h. The resulting mixture was diluted with EtOAc and washed with water. The organic layer was concentrated under vacuum, and the residue was purified by silica gel column chromatography eluting with DCM/MeOH (20/1 v/v) to obtain the title compound (249.0 mg) as a solid. LCMS (ESI): $[M+H]^+$: 417.2.

Step-4. (1R, 3S, 5S)—N-[(3-fluoro-1-methylindazol-5-yl)methyl]-8-azabicyclo[3.2.1]octane-3-carboxamide

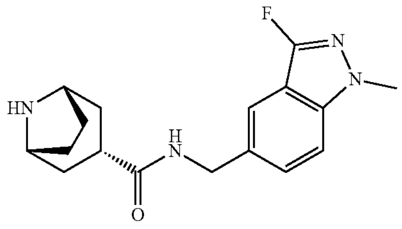 [SMILES: Cn1nc(F)c2cc(CNC(=O)[C@@H]3C[C@H]4CC[C@@H](C3)N4)ccc21]

TFA (2.00 mL) was added to a stirred solution of tert-butyl (1R,3S,5S)-3-[[(3-fluoro-1-methylindazol-5-yl)methyl]carbamoyl]-8-azabicyclo[3.2.1]octane-8-carboxylate (249.0 mg, 0.60 mmol) in DCM (2.00 mL). The resulting solution was stirred at 25° C. for 30 min. The resulting mixture was concentrated under vacuum, and the residue was purified by silica gel column chromatography eluting with DCM/MeOH (10/1 v/v) to obtain the title compound (185.0 mg) as an oil. LCMS (ESI): $[M+H]^+$: 317.2.

Step-5. (1R, 3S, 5S)—N-[(3-fluoro-1-methylindazol-5-yl)methyl]-8-[5-(5-fluoro-2-methoxypyridin-4-yl)-1H-pyrazole-3-carbonyl]-8-azabicyclo[3.2.1]octane-3-carboxamide

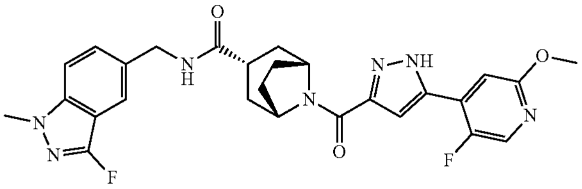

HOBt (44.4 mg, 0.33 mmol), EDCI (63.0 mg, 0.33 mmol), and (1R,3S,5S)—N-[(3-fluoro-1-methylindazol-5-yl)methyl]-8-azabicyclo[3.2.1]octane-3-carboxamide (96.0 mg, 0.30 mmol) were added to a stirred solution of 5-(5-fluoro-2-methoxypyridin-4-yl)-1H-pyrazole-3-carboxylic acid (INTERMEDIATE 513, 60.0 mg, 0.25 mmol) and DIPEA (98.1 mg, 0.76 mmol) in DMF (4.00 mL). The resulting solution was stirred at 25° C. for 14 h. The resulting mixture was diluted with EtOAc and washed with water. The organic layer was concentrated under vacuum. The residue was purified by Prep-HPLC (using the following conditions: Column: Xselect CSH F-Phenyl OBD column, 19×250 mm, 5 μm, mobile phase A: Water (10 mM $NH_4HCO_3$), mobile phase B: MeOH, Gradient: 61% B to 71% B in 10 min; Detector, UV 220 nm) to obtain the title compound (42.1 mg) as a solid. $^1H$ NMR (300 MHz, $CD_3OD$) δ 8.16 (s, 1H), 7.60-7.05 (m, 5H), 5.38 (s, 1H), 4.60 (s, 1H), 4.46 (s, 2H), 4.15-3.70 (m, 6H), 3.10-2.93 (m, 1H), 2.28-1.67 (m, 8H). LCMS (ESI): $[M+H]^+$: 536.2.

Example 278. N-((3,3-dimethylindolin-5-yl) methyl)-1-(5-(5-fluoro-2-methoxypyridin-4-yl)-1H-pyrazole-3-carbonyl)piperidine-4-carboxamide

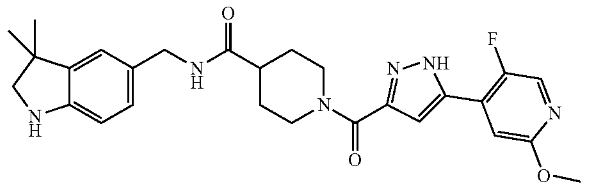

Step-1. 5-bromo-3,3-dimethylindoline

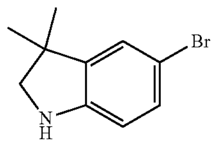

$BH_3$ in THF (1 M, 21.00 mL) was added to a stirred solution of 5-bromo-3,3-dimethyl-1H-indol-2-one (1.00 g, 4.17 mmol) in THF (5.00 mL) at 25° C. The resulting mixture was stirred at 70° C. for 4 h. The solution was then concentrated under reduced pressure and the residue was purified by silica gel column chromatography eluting with petroleum ether/EtOAc (15/1 v/v) to obtain the title compound (660.0 mg) as a solid. LCMS (ESI): $[M+H]^+$: 226.0.

Step-2. tert-butyl 5-bromo-3,3-dimethylindoline-1-carboxylate

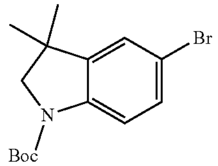 [SMILES: CC(C)(C)OC(=O)N1CC(C)(C)c2cc(Br)ccc21]

Di-tert-butyl dicarbonate (2.55 g, 11.68 mmol) and DMAP (36.0 mg, 0.29 mmol) were added to a stirred mixture of 5-bromo-3,3-dimethylindoline (Step-1, 660.0 mg, 2.92 mmol) in THF (50.00 mL). The resulting mixture was stirred at 80° C. for 3 h. The solution was then concentrated under reduced pressure and the residue was purified by silica gel column chromatography eluting with petroleum ether/EtOAc (20/1 v/v) to obtain the title compound (510.0 mg) as an oil. LCMS (ESI): $[M+H]^+$: 326.1.

Step-3. tert-butyl 5-cyano-3,3-dimethylindoline-1-carboxylate

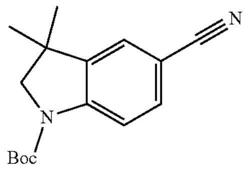 [SMILES: CC(C)(C)OC(=O)N1CC(C)(C)c2cc(C#N)ccc21]

$Zn(CN)_2$ (220.0 mg, 1.88 mmol) and $Pd(PPh_3)_4$ (3.61 g, 3.13 mmol) were added to a stirred mixture of tert-butyl 5-bromo-33-dimethyl-2H-indole-1-carboxylate (Step-2, 510.0 mg, 1.56 mmol) in DMF (5.00 mL). The resulting mixture was stirred at 80° C. for 3 h under nitrogen atmosphere. The resulting mixture was diluted with EtOAc and washed with water. The solution was then concentrated under reduced pressure and the residue was purified by silica gel column chromatography eluting with petroleum ether/EtOAc (3/1 v/v) to obtain the title compound (244.0 mg) as a solid. LCMS (ESI): $[M+H]^+$: 273.2.

Step-4. tert-butyl 5-(aminomethyl)-3,3-dimethylindoline-1-carboxylate

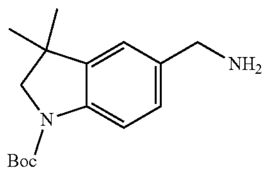 [SMILES: CC(C)(C)OC(=O)N1CC(C)(C)c2cc(CN)ccc21]

Pd/C (60.0 mg) and AcOH (2.00 mL) were added to a stirred mixture of tert-butyl 5-cyano-3,3-dimethyl-2H-indole-1-carboxylate (Step-3, 200.0 mg, 0.73 mmol) in MeOH (4.00 mL). The resulting mixture was stirred at 25° C. for 3 h under hydrogen atmosphere. The solid was filtered out. The solution was then concentrated under reduced pressure to obtain the title compound (150.0 mg) as a solid. LCMS (ESI): $[M+H]^+$: 277.2.

Step-5. Synthesis of tert-butyl 5-[([1-[5-(5-fluoro-2-methoxypyridin-4-yl)-1H-pyrazole-3-carbonyl]piperidin-4-yl]formamido)methyl]-3,3-dimethyl-2H-indole-1-carboxylate

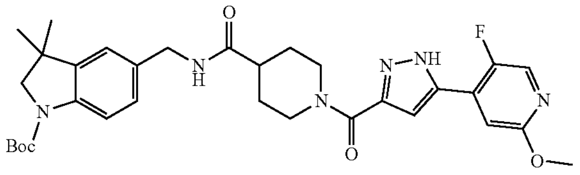

HATU (85.9 mg, 0.23 mmol) and tert-butyl 5-(aminomethyl)-3,3-dimethyl-2H-indole-1-carboxylate (Step-4, 52.0 mg, 0.19 mmol) were added to a stirred solution of 1-[5-(5-fluoro-2-methoxypyridin-4-yl)-1H-pyrazole-3-carbonyl]piperidine-4-carboxylic acid (78.7 mg, 0.23 mmol) and DIPEA (74.3 mg, 0.57 mmol) in DMF (5.00 mL). The solution was stirred at 25° C. for 14 h. The resulting mixture was diluted with EtOAc and washed with water. The resulting mixture was concentrated under vacuum. The residue was purified by silica gel column chromatography eluting with petroleum ether/EtOAc (2/1 v/v) to obtain the title compound (110.0 mg) as a solid. LCMS (ESI): $[M+H]^+$: 607.3.

Step-6. N-((3,3-dimethylindolin-5-yl)methyl)-1-(5-(5-fluoro-2-methoxypyridin-4-yl)-1H-pyrazole-3-carbonyl)piperidine-4-carboxamide

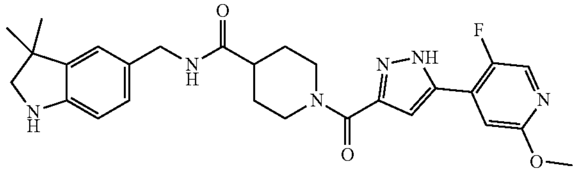

TFA (2.00 mL) was added to a stirred solution of tert-butyl 5-[([1-[5-(5-fluoro-2-methoxypyridin-4-yl)-1H-pyrazole-3-carbonyl]piperidin-4-yl]formamido)methyl]-3,3-dimethyl-2H-indole-1-carboxylate (Step-5, 150.0 mg, 0.25 mmol) in DCM (2.00 mL). The solution was stirred at 25° C. for 1 h. The resulting mixture was concentrated under reduced pressure. The residue was purified by silica gel column chromatography eluting with DCM/MeOH (10/1 v/v). The resulting residue was purified by Prep-HPLC (using the following conditions: SHIMADZU (HPLC-01): Column, YMC-Actus Triart C18, 30×250 mm, 5 µm, mobile phase, Water (10 mM $NH_4HCO_3$) and MeCN (25% to 55% in 7 min); Detector, UV 220/254 nm) to obtain the title compound (33.7 mg) as a solid. $^1$H NMR (400 MHz, $CD_3OD$) δ 8.14 (s, 1H), 7.26 (s, 1H), 7.09 (s, 1H), 6.98 (s, 1H), 6.94 (d, 1H), 6.62 (d, 1H), 4.65 (s, 2H), 4.27 (s, 2H), 3.94 (s, 3H), 3.24 (s, 3H), 2.95 (s, 1H), 2.63-2.53 (m, 1H), 2.00-1.64 (m, 4H), 1.29 (s, 6H). LCMS (ESI): $[M+H]^+$: 507.2.

Example 279. (1R,3s,5S)—N-((1r,4R)-4-hydroxy-4-(trifluoromethyl)cyclohexyl)-8-(5-(6-methylpyrimidin-4-yl)-1H-pyrazole-3-carbonyl)-8-azabicyclo[3.2.1]octane-3-carboxamide

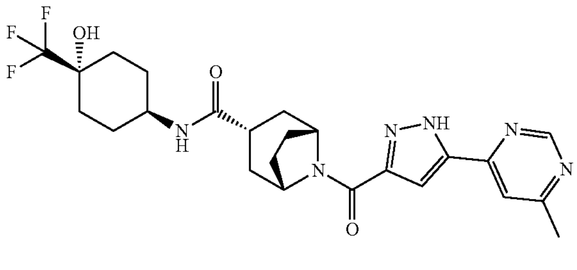 [SMILES: Cc1cc(-c2cc(C(=O)N3[C@@H]4CC[C@H]3C[C@H](C(=O)N[C@H]3CC[C@@](O)(C(F)(F)F)CC3)C4)n[nH]2)ncn1]

Step-1. Synthesis of benzyl (1R,3R,5S)-8-[5-(6-methylpyrimidin-4-yl)-1H-pyrazole-3-carbonyl]-8-azabicyclo[3.2.1]octane-3-carboxylate

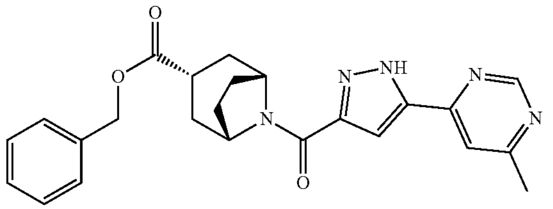 [SMILES: Cc1cc(-c2cc(C(=O)N3[C@@H]4CC[C@H]3C[C@H](C(=O)OCc3ccccc3)C4)n[nH]2)ncn1]

EDCI (185.0 mg, 0.97 mmol), HOBt (130.0 mg, 0.96=top, and benzyl (1R,3R,5S)-8-azabicyclo[3.2.1]octane-3-carboxylate (190.0 mg, 0.77 mmol) were added to a stirred solution of 5-(6-methylpyrimidin-4-yl)-1H-pyrazole-3-carboxylic acid (INTERMEDIATE 538, 130.0 mg, 0.64 mmol) and DIPEA (490.0 mg, 3.79 mmol) in DMF (4.00 mL). The resulting solution was stirred at 25° C. for 14 h. The resulting solution was diluted with EtOAc, washed with water. The organic layer was concentrated under reduced pressure and the residue was purified by silica gel column chromatography eluting with DCM/MeOH (10/1 v/v) to obtain the title compound (150.0 mg) as a solid. LCMS (ESI): $[M+H]^+$: 432.2.

Step-2. (1R,3R,5S)-8-[5-(6-methylpyrimidin-4-yl)-1H-pyrazole-3-carbonyl]-8-azabicyclo[3.2.1]octane-3-carboxylic acid

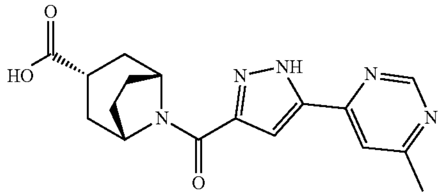 [SMILES: Cc1cc(-c2cc(C(=O)N3[C@@H]4CC[C@H]3C[C@H](C(=O)O)C4)n[nH]2)ncn1]

$LiOH·H_2O$ (29.0 mg, 0.69 mmol, 1.99 equiv) was added to a stirred solution of benzyl (1R,3R,5S)-8-[5-(6-methylpyrimidin-4-yl)-1H-pyrazole-3-carbonyl]-8-azabicyclo[3.2.1]octane-3-carboxylate (Step-5, 150.0 mg, 0.35 mmol) in THF (2.00 mL), MeOH (2.00 mL), and $H_2O$ (2.00 mL). The resulting solution was stirred at 25° C. for 14 h. The solution was then concentrated under reduced pressure and dissolved in water, and pH was adjusted to 5 with HCl (1 M). The resulting mixture was extracted with EtOAc. The organic layers were concentrated under reduced pressure and the residue was purified by silica gel column chromatography eluting with DCM/MeOH (10/1 v/v) to obtain the title compound (100.0 mg) as an oil. LCMS (ESI): $[M+H]^+$: 342.1

Step-3. (1R,3R,5S)-8-[5-(6-methylpyrimidin-4-yl)-1H-pyrazole-3-carbonyl]-N-[(1r,4r)-4-hydroxy-4-(trifluoromethyl)cyclohexyl]-8-azabicyclo[3.2.1]octane-3-carboxamide

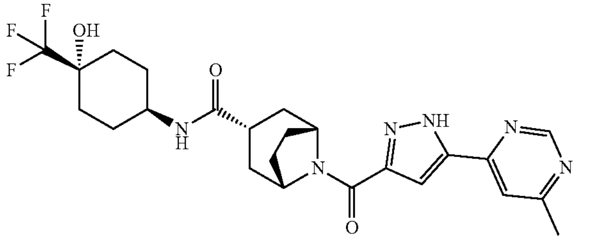 [SMILES: Cc1cc(-c2cc(C(=O)N3[C@@H]4CC[C@H]3C[C@H](C(=O)N[C@H]3CC[C@@](O)(C(F)(F)F)CC3)C4)n[nH]2)ncn1]

EDCI (89.0 mg, 0.46 mmol), HOBt (62.0 mg, 0.46 mmol), and (1r,4r)-4-amino-1-(trifluoromethyl)cyclohexan-1-ol (68.0 mg, 0.37 mmol) were added to a stirred solution of 1H-pyrazole-3-carbonyl]-8-azabicyclo[3.2.1]octane-3-carboxylic acid (Step-7, 105.0 mg, 0.31 mmol) and DIPEA (119.0 mg, 0.92 mmol) in DMF (2.00 mL). The resulting solution was stirred at 25° C. for 14 h. The resulting solution was diluted with EtOAc, washed with water. The organic layer was concentrated under reduced pressure and the residue was purified by silica gel column chromatography eluting with DCM/MeOH (10/1 v/v). The resulting residue was further purified by Prep-HPLC (using the following conditions: Column: Ascentis Express C18 OBD Column, 50×2.1 mm; mobile phase A: Water (0.1% $NH_4HCO_3$), Mobile Phase B: MeCN; Gradient: 20% B to 50% B in 20 min; Detector, UV 220/254 nm) to obtain the title compound (66.0 mg) as a solid. $^1$H NMR (400 MHz, DMSO-$d_6$) δ 14.17 (s, 1H), 9.07 (s, 1H), 7.93 (s, 1H), 7.75 (d, 1H), 7.43 (s, 1H), 5.68 (s, 1H), 5.23 (s, 1H), 4.69 (d, 1H), 3.80 (s, 1H), 2.92 (s, 1H), 2.52 (s, 3H), 2.02 (s, 1H), 1.78 (m, 9H), 1.62 (d, 2H), 1.51 (m, 4H). LCMS (ESI): [M+H]$^+$: 507.2.

Example 280. A diastereomeric mixtures of (1R,3s,5S)-8-(5-(5-fluoro-2-methoxypyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide

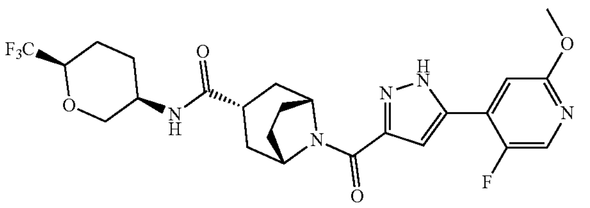

-continued

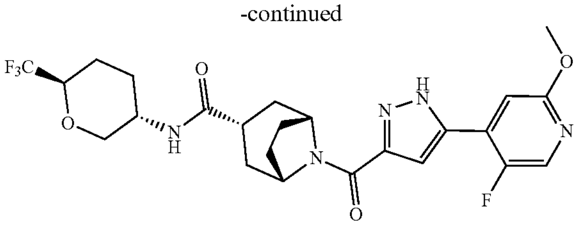

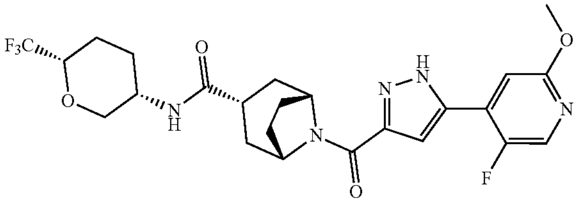

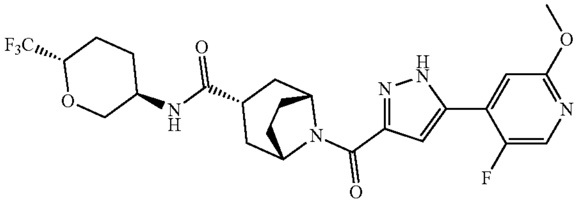

The title compound was prepared using a procedure similar to the one described for the synthesis of Example 170-A, except 6-(trifluoromethyl)oxan-3-amine (INTERMEDIATE 532) was used as a starting material in Step-5.

The mixture of four diastereomers (Example 280) of (1r,3s,5S)-8-(5-(5-fluoro-2-methoxypyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide were separated using Chiral-Prep-HPLC.

Column: CHIRAL ART Cellulose-SB column
Column dimension: 2×25 cm, 5 μm
Mobile Phase: hexanes (8 mM $NH_3$·MeOH):EtOH=80:20 hold for 21 min
Flow rate: 20 mL/min
Detection: 220/254 nm Example 280-A. The first eluting diastereomer (4.2 mg) was obtained as a solid.

The first eluting diastereomer had a retention time of 9.81 min.

LCMS (ESI): [M+H]$^+$: 526.2.

Example 280-B. The second eluting diastereomer (18.8 mg) was obtained as a solid.

The second eluting diastereomer had a retention time of 14.25 min.

$^1$H NMR (400 MHz, $CD_3OD$) δ 8.14 (s, 1H), 7.22 (s, 2H), 5.35 (s, 1H), 4.57 (s, 1H), 3.94 (s, 5H), 3.83 (s, 1H), 3.72 (d, 1H), 3.14 (s, 1H), 2.27-1.86 (m, 9H), 1.86-1.64 (m, 2H), 1.55 (s, 1H). LCMS (ESI): [M+H]$^+$: 526.2.

Example 280-C. Third eluting diastereomer (1.6 mg) was obtained as a solid.

The third eluting diastereomer had a retention time of 16.53 min.

LCMS (ESI): $[M+H]^+$: 526.2.

Example 280-D. Fourth eluting diastereomer (10.9 mg) was obtained as a solid.

The fourth eluting diastereomer had a retention time of 17.57 min.

$^1H$ NMR (400 MHz, $CD_3OD$) δ 8.16 (s, 1H), 7.45-6.98 (m, 2H), 5.36 (s, 1H), 4.57 (s, 1H), 3.94 (s, 5H), 3.83 (s, 1H), 3.72 (d, 1H), 3.14 (s, 1H), 3.12 (s, 9H), 2.50-1.85 (m, 2H), 1.88-1.67 (m, 1H), LCMS (ESI): $[M+H]^+$: 526.2.

Example 281. 1-(5-(5-fluoro-2-methoxypyridin-4-yl)-1H-pyrazole-3-carbonyl)-N-(1-(3-methyl-1H-indazol-5-yl)ethyl)piperidine-4-carboxamide

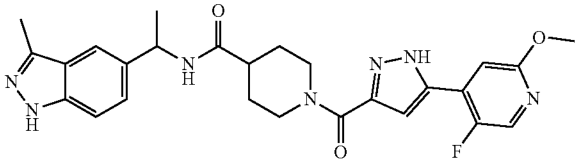 [SMILES: COc1cc(-c2cc(C(=O)N3CCC(C(=O)NC(C)c4ccc5[nH]nc(C)c5c4)CC3)n[nH]2)c(F)cn1]

Step-1. 5-bromo-1-(4-methoxybenzyl)-3-methyl-1H-indazole

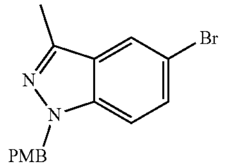

PMBCl (0.96 g, 6.16 mmol) and $K_2CO_3$ (1.96 g, 14.21 mmol) were added to a stirred solution of 5-bromo-3-methyl-1H-indazole (1.00 g, 4.74 mmol) in DMF (20.00 mL). The resulting mixture was stirred at 25° C. for 14 h. The solution was diluted with water and extracted with EtOAc. The organic layers were combined, then dried over anhydrous sodium sulfate, filtered, and the solvent was evaporated. The residue was purified by silica gel column chromatography eluting with EtOAc/petroleum ether (1/2 v/v) to obtain the title compound (1.20 g) as a solid. LCMS (ESI): $[M+H]^+$: 331.2.

Step-2. 1-(1-(4-methoxybenzyl)-3-methyl-1H-indazol-5-yl)ethan-1-one

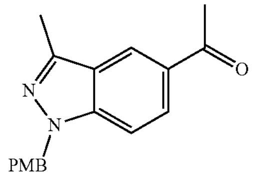

$Pd(PPh_3)_4$ (349.0 mg, 0.30 mmol) and tributyl(1-ethoxyethenyl)stannane (1.63 g, 4.53 mmol) were added to a stirred solution of 5-bromo-1-[(4-methoxyphenyl)methyl]-3-methylindazole (Step-1, 500.0 mg, 1.51 mmol) in DMF (20.00 mL) at 25° C. The resulting mixture was stirred at 80° C. for 4 h. The solution was diluted with water and extracted with EtOAc. The organic layers were combined, then dried over anhydrous sodium sulfate, filtered, and the solvent was evaporated. The residue was purified by silica gel column chromatography eluting with EtOAc/petroleum ether (1/1 v/v) to obtain the title compound (200.0 mg) as a solid. LCMS (ESI): $[M+H]^+$: 295.1.

Step-3. 1-(1-(4-methoxybenzyl)-3-methyl-1H-indazol-5-yl)ethan-1-amine

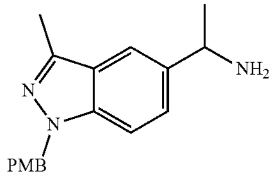

$NH_4OAc$ (196.0 mg, 2.55 mmol) was added to a stirred solution of 1-[1-[(4-methoxyphenyl)methyl]-3-methylindazol-5-yl]ethanone (Step-2, 150.0 mg, 0.51 mmol) in EtOH (4.00 mL). The resulting mixture was stirred at 25° C. for 30 min. Then $NaBH_3CN$ (160.0 mg, 2.55 mmol) was added to the reaction mixture. The resulting mixture was stirred at 25° C. for 14 h. The mixture was concentrated under reduced pressure. The residue was purified by silica gel column chromatography eluting with DCM/MeOH (10/1 v/v) to obtain the title compound (90.0 mg) as a solid mixture of enantiomers. LCMS (ESI): $[M+H]^+$: 296.3.

Step-4. 1-[5-(5-fluoro-2-methoxypyridin-4-yl)-1H-pyrazole-3-carbonyl]-N-(1-[(1[(4-methoxyphenyl) methyl]-3-methylindazol-5-yl]ethyl)piperidine-4-carboxamide

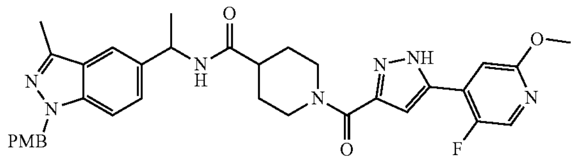

EDCI (23.1 mg, 0.26 mmol), HOBt (35.7 mg, 0.26 mmol) and 1-[1-[(4-methoxyphenyl)methyl]-3-methylindazol-5-yl] ethanamine (Step-3, 60.0 mg, 0.20 mmol) were added to a stirred solution of 1-[5-(5-fluoro-2-methoxypyridin-4-yl)-1H-pyrazole-3-carbonyl]piperidine-4-carboxylic acid (70.8 mg, 0.20 mmol) and DIPEA (78.8 mg, 0.61 mmol) in DMF (5.00 mL). The resulting mixture was stirred at 25° C. for 2 h. The solution was then diluted with water and extracted with EtOAc. The organic layers were combined, then dried over anhydrous sodium sulfate, filtered, and the solvent was evaporated. The residue was purified by silica gel chromatography eluting with DCM/MeOH (15/1 v/v) to obtain the title compound (90.0 mg) as a solid mixture of enantiomers, LCMS (ESI): $[M+H]^+$: 626.1.

Step-5. 1-(5-(5-fluoro-2-methoxypyridin-4-yl)-1H-pyrazole-3-carbonyl)-N-(1-(3-methyl-1H-indazol-5-yl)ethyl)piperidine-4-carboxamide

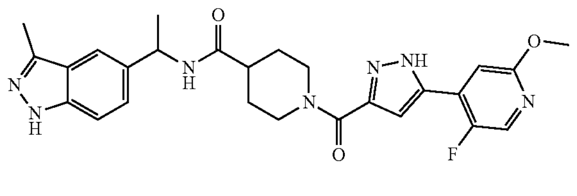 [SMILES: COc1cc(-c2cc(C(=O)N3CCC(C(=O)NC(C)c4ccc5[nH]nc(C)c5c4)CC3)n[nH]2)c(F)cn1]

TfOH (1.50 mL) was added to a stirred solution of 1-[5-(5-fluoro-2-methoxypyridin-4-yl)-1H-pyrazole-3-carbonyl]-N-(1-[1-[(4-methoxyphenyl)methyl]-3-methylindazol-5-yl]ethyl)piperidine-4-carboxamide (Step-4, 60.0 mg) in TFA (3.00 mL) at 25° C. The resulting mixture was stirred at 80° C. for 4 h. The solution was then diluted with water and extracted with EtOAc. The organic layers were combined, then dried over anhydrous sodium sulfate, filtered, and the solvent was evaporated. The resulting mixture was purified by reverse phase column chromatography (using the following conditions: C18 column; mobile phase, MeCN in water, 10% to 95% gradient in 20 min; detector UV 254 nm) to obtain the title compound (17.4 mg) as a solid mixture of enantiomers. $^1H$ NMR (300 MHz, DMSO-$d_6$) δ 14.00 (s, 1H), 12.55 (s, 1H), 8.35-8.25 (m, 2H), 7.57 (s, 1H), 7.40 (d, 1H), 7.36-7.25 (m, 2H), 7.04 (s, 1H), 5.07-4.97 (m, 1H), 4.47-4.25 (m, 2H), 3.88 (s, 3H), 3.25-3.10 (m, 2H), 2.90-2.70 (m, 1H), 2.50-2.40 (m, 3H), 1.82-1.70 (m, 2H), 1.65-1.42 (m, 2H), 1.40 (d, 3H). LCMS (ESI): $[M+H]^+$: 506.1.

Example 282. 9-(5-(5-fluoro-2-methoxypyridin-4-yl)-1H-pyrazole-3-carbonyl)-N-((1r,4r)-4-hydroxy-4-(trifluoromethyl)cyclohexyl)-3-oxa-9-azabicyclo[3.3.1]nonane-7-carboxamide

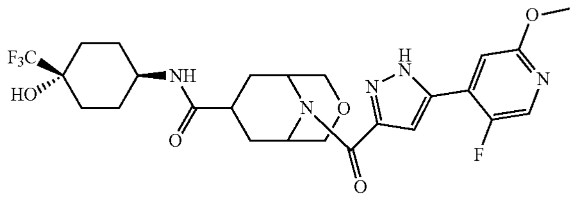 [SMILES: COc1cc(-c2cc(C(=O)N3C4COCC3CC(C(=O)N[C@H]3CC[C@@](O)(C(F)(F)F)CC3)C4)n[nH]2)c(F)cn1]

Step-1. Methyl 9-(5-(5-fluoro-2-methoxypyridin-4-yl)-1-((2-(trimethylsilyl)ethoxy)methyl)-1H-pyrazole-3-carbonyl)-3-oxa-9-azabicyclo[3.3.1]nonane-7-carboxylate

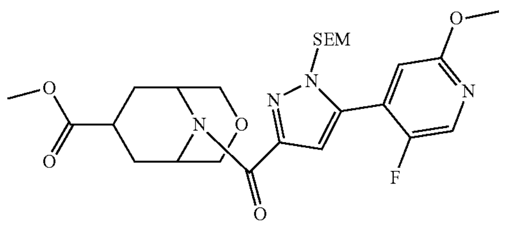

HATU (55.1 mg, 0.15 mmol) and methyl 3-oxa-9-azabicyclo[3.3.1]nonane-7-carboxylate (28.2 mg, 0.15 mmol) were added to a stirred solution of 5-(5-fluoro-2-methoxypyridin-4-yl)-1-((2-(trimethylsilyl)ethoxy)methyl)-1H-pyrazole-3-carboxylic acid (INTERMEDIATE 506, 53.2 mg, 0.15 mmol) and DIPEA (76.0 μL, 0.43 mmol) in DMF (2.00 mL). The resulting mixture was stirred at 23° C. for 18 h. The solution was then diluted with water and extracted with EtOAc. The organic layers were combined, then dried over anhydrous sodium sulfate, filtered, and the solvent was evaporated. The residue was purified by silica gel column chromatography eluting with 30-50% EtOAc/hexanes to obtain the title compound (51.0 mg) as a solid. LCMS (ESI): $[M+H]^+$: 535.5.

Step-2. 9-(5-(5-fluoro-2-methoxypyridin-4-yl)-1-((2-(trimethylsilyl)ethoxy)methyl)-1H-pyrazole-3-carbonyl)-3-oxa-9-azabicyclo[3.3.1]nonane-7-carboxylic acid

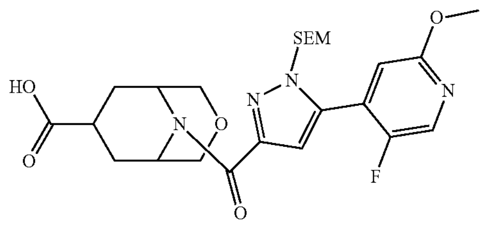 [SMILES: COc1cc(-c2cc(C(=O)N3C4COCC3CC(C(=O)O)C4)nn2COCC[Si](C)(C)C)c(F)cn1]

A solution of 1 M LiOH (292.5 μL, 0.30 mmol) was added to a stirred solution of methyl 9-(5-(5-fluoro-2-methoxypyridin-4-yl)-1-((2-(trimethylsilyl)ethoxy)methyl)-1H-pyrazole-3-carbonyl)-3-oxa-9-azabicyclo[3.3.1]nonane-7-carboxylate (Step-1, 52.0 mg, 0.10 mmol) in THF (1.00 ml) and water (1.00 ml). The resulting mixture was stirred at 23° C. for 18 h. The pH was adjusted to pH 5 by adding acetic acid. The resulting mixture was concentrated and used in the next step without further purification. LCMS (ESI): $[M+H]^+$: 521.3.

Step-3. 9-(5-(5-fluoro-2-methoxypyridin-4-yl)-1-((2-(trimethylsilyl)ethoxy)methyl)-1H-pyrazole-3-carbonyl)-N-((1r,4r)-4-hydroxy-4-(trifluoromethyl)cyclohexyl)-3-oxa-9-azabicyclo[3.3.1]nonane-7-carboxamide

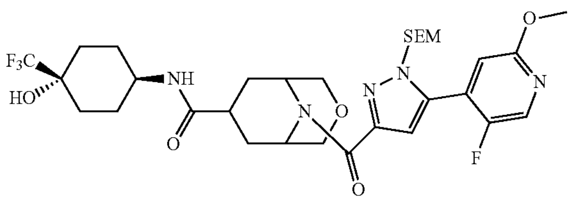 [SMILES: COc1cc(-c2cc(C(=O)N3C4COCC3CC(C(=O)N[C@H]3CC[C@@](O)(C(F)(F)F)CC3)C4)nn2COCC[Si](C)(C)C)c(F)cn1]

HATU (40.6 mg, 0.11 mmol) and (1r,4r)-4-amino-1-(trifluoromethyl)cyclohexan-1-ol (19.5 mg, 0.11 mmol) were added to a stirred solution of 9-(5-(5-fluoro-2-methoxypyridin-4-yl)-1-((2-(trimethylsilyl)ethoxy)methyl)-1H-pyrazole-3-carbonyl)-3-oxa-9-azabicyclo[3.3.1]nonane-7-carboxylic acid (Step-3, 50.5 mg, 0.10 mmol) and DIPEA (50.8 μL, 0.29 mmol) in DMF (3.00 mL). The resulting mixture was stirred at 23° C. for 22 h. The solution was then diluted with water and extracted with EtOAc. The organic layers were combined, then dried over anhydrous sodium sulfate, filtered, and the solvent was evaporated. The residue was purified by silica gel column chromatography eluting with 70-100% EtOAc/hexanes to obtain the title compound (64.0 mg) as a solid. LCMS (ESI): $[M+H]^+$: 686.5.

Step-4. 9-(5-(5-fluoro-2-methoxypyridin-4-yl)-1H-pyrazole-3-carbonyl)-N-((1r,4r)-4-hydroxy-4-(trifluoromethyl)cyclohexyl)-3-oxa-9-azabicyclo[3.3.1]nonane-7-carboxamide

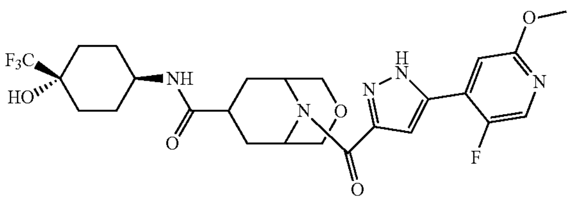 [SMILES: COc1cc(-c2cc(C(=O)N3C4COCC3CC(C(=O)N[C@H]3CC[C@@](O)(C(F)(F)F)CC3)C4)n[nH]2)c(F)cn1]

TFA (3.00 mL) was added to a stirred solution of 9-(5-(5-fluoro-2-methoxypyridin-4-yl)-1-((2-(trimethylsilyl)ethoxy)methyl)-1H-pyrazole-3-carbonyl)-N-((1r,4r)-4-hydroxy-4-(trifluoromethyl)cyclohexyl)-3-oxa-9-azabicyclo[3.3.1]nonane-7-carboxamide (Step-3, 64.0 mg, 0.09 mmol) in DCM (23.00 mL). The resulting mixture was stirred at 23° C. for 15 h. The solution was then diluted with water and extracted with EtOAc. The organic layers were combined, then dried over anhydrous sodium sulfate, filtered, and the solvent was evaporated. The residue was purified by silica gel column chromatography eluting with 5-15% MeOH/DCM to obtain the title compound (45.0 mg) as a solid, $^1$H NMR (400 MHz, $CD_3OD$) δ 7.95-8.31 (m, 2H), 6.93-7.39 (m, 2H), 4.93-5.13 (m, 1H), 4.53-4.73 (m, 1H), 4.18-4.33 (m, 1H), 4.01-4.12 (m, 1H), 3.75-3.99 (m, 8H), 3.35 (s, 1H), 1.82-2.22 (m, 8H), 1.59-1.77 (m, 4H), LCMS (ESI): $[M+H]^+$: 556.3.

Example 283. (1R,3R,5S)-8-[5-(5-fluoro-2-methylpyridin-4-yl)-1H-pyrazole-3-carbonyl]-N-[(1r,4r)-4-hydroxy-4-(trifluoromethyl)cyclohexyl]-8-azabicyclo[3.2.1]octane-3-carboxamide

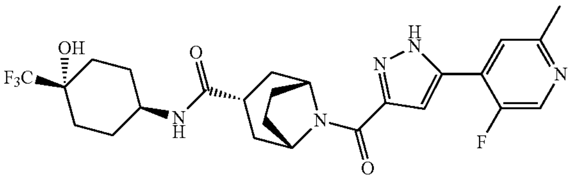 [SMILES: Cc1cc(-c2cc(C(=O)N3[C@@H]4CC[C@H]3C[C@H](C(=O)N[C@H]3CC[C@@](O)(C(F)(F)F)CC3)C4)n[nH]2)c(F)cn1]

HOBt (57.0 mg, 0.42 mmol), EDCI (80.0 mg, 0.42 mmol), and (1r,4r)-4-amino-1-(trifluoromethyl)cyclohexan-1-ol (74.0 mg, 0.40 mmol) were added to a solution of (1R,3R,5S)-8-[5-(5-fluoro-2-methylpyridin-4-yl)-1H-pyrazole-3-carbonyl]-8-azabicyclo[3.2.1]octane-3-carboxylic acid (INTERMEDIATE 524, 100.0 mg, 0.28 mmol) and DIPEA (108.0 mg, 0.84 mmol) in DMF (20.00 mL). The resulting solution was stirred at 25° C. for 14 h. The resulting solution was diluted with water and extracted with EtOAc. The organic layers were combined and concentrated under vacuum, then the residue was purified by silica gel column chromatography eluting with DCM/MeOH (10/1 v/v) to obtain the resulting residue. The resulting residue was then further purified by Prep-HPLC (using the following conditions: Column: YMC-Actus Triart C18, 30×250 mm, 5 μm; Mobile Phase A: Water (10 mM $NH_4HCO_3$); Mobile Phase B: MeCN; Gradient: 26% B to 38% B in 8 min; Detector, UV 220/254 nm) to obtain the title compound (56.8 mg) as a solid. $^1$H NMR (300 MHz, DMSO-$d_6$) δ 8.53 (d, 1H), 7.84-7.70 (m, 2H), 7.12 (d, 1H), 5.70 (s, 1H), 4.69 (d, 1H), 3.81 (d, 1H), 3.01-2.83 (m, 1H), 2.50 (d, 3H), 2.15-1.41 (m, 17H). LCMS (ESI): $[M+H]^+$: 524.3.

Example 284. (1R,3s,5S)—N-((3-fluoro-1H-indazol-5-yl)methyl)-8-(5-(5-fluoro-2-methylpyridin-4-yl)-1H-pyrazole-3-carbonyl)-8-azabicyclo[3.2.1]octane-3-carboxamide

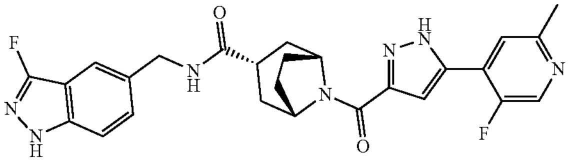 [SMILES: Cc1cc(-c2cc(C(=O)N3[C@@H]4CC[C@H]3C[C@H](C(=O)NCc3ccc5[nH]nc(F)c5c3)C4)n[nH]2)c(F)cn1]

EDCI (80.2 mg, 0.42 mmol), HOBt (56.5 mg, 0.42 mmol), and 1-(3-fluoro-1H-indazol-5-yl)methanamine (INTERMEDIATE 514, 69.1 mg, 0.42 mmol) were added to a stirred solution of (1R,3R,5S)-8-[5-(5-fluoro-2-methylpyridin-4-yl)-1H-pyrazole-3-carbonyl]-8-azabicyclo[3.2.1]octane-3-carboxylic acid (INTERMEDIATE 524, 100.0 mg, 0.28 mmol) and DIPEA (108.0 mg, 0.84 mmol) in DMF (2.00 mL). The resulting solution was stirred at 25° C. for 14 h. The resulting mixture was dilute with EtOAc and washed with water. The organic layer was concentrated under vacuum. The residue was purified by Chiral-Prep-HPLC (using the following conditions: Column: YMC-Actus Triart C18, 30×250 mm, 5 μm; Mobile Phase A: Water (10 mM $NH_4HCO_3$), Mobile Phase B: MeCN; Gradient: 25% B to 37% B in 8 min; Detector, UV 220/254 nm) to obtain the title compound (30.7 mg) as a solid. $^1$H NMR (400 MHz, DMSO-$d_6$) δ 14.01 (s, 1H), 12.49 (s, 1H), 8.54 (s, 1H), 8.41-8.29 (m, 1H), 7.81 (d, 1H), 7.51 (s, 1H), 7.48-7.41 (m, 1H), 7.36-7.30 (m, 1H), 7.13 (s, 1H), 5.54-4.45 (m, 2H), 4.34 (d, 2H), 3.01-2.85 (m, 1H), 2.52 (s, 3H), 2.04 (s, 1H), 1.97-1.62 (m, 7H). LCMS (ESI): $[M+H]+^+$: 506.2.

Example 285. (1R,3R,5S)—N-[(2,3-dimethyl-1H-indol-5-yl)methyl]-8-[5-(5-fluoro-2-methoxypyridin-4-yl)-1H-pyrazole-3-carbonyl]-8-azabicyclo[3.2.1]octane-3-carboxamide

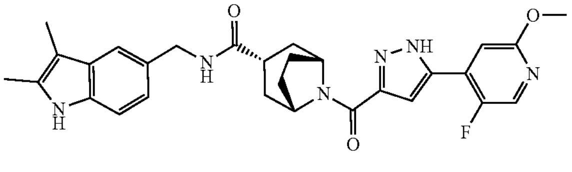

The title compound was prepared using a procedure similar to the one described for the synthesis of Example 266, except (1R,3s,5S)-8-(5-(5-fluoro-2-methoxypyridin-4-yl)-1H-pyrazole-3-carbonyl)-8-azabicyclo[3.2.1]octane-3- carboxylic acid (INTERMEDIATE 508) and 1-(2,3-dimethyl-1H-indol-5-yl)methanamine (INTERMEDIATE 522) were used as starting materials. The residue was purified by Prep-HPLC (using the following conditions: Column: YMC-Actus Triart C18, 30×250 mm, 5 μm; Mobile Phase A: Water (10 mM $NH_4HCO_3$); Mobile Phase B: MeCN; Gradient: 38% B to 52% B in 7 min; Detection: 220/254 nm) to obtain the title compound (9.1 mg) as a solid. $^1$H NMR (400 MHz, $CD_3OD$) δ 8.14 (d, 1H), 7.31-7.22 (m, 2H), 7.22-7.14 (m, 2H), 6.97-6.90 (m, 1H), 5.28 (s, 1H), 4.41 (s, 2H), 3.95 (s, 3H), 3.06-2.92 (m, 1H), 2.36-2.31 (m, 3H), 2.19-2.02 (m, 8H), 1.97-1.85 (m, 2H), 1.81 (d, 2H). LCMS (ESI): 531.2 $[M+H]^+$.

Example 286-A. (R)-4-(5-(5-chloro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide

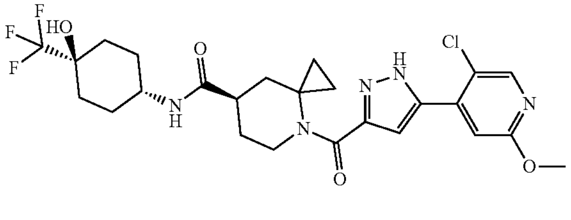 [SMILES: COc1cc(-c2cc(C(=O)N3CC[C@@H](C(=O)N[C@H]4CC[C@@](O)(C(F)(F)F)CC4)CC34CC4)n[nH]2)c(Cl)cn1]

Example 286-B, (S)-4-(5-(5-chloro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide

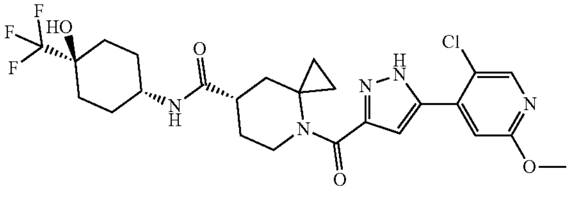 [SMILES: COc1cc(-c2cc(C(=O)N3CC[C@H](C(=O)N[C@H]4CC[C@@](O)(C(F)(F)F)CC4)CC34CC4)n[nH]2)c(Cl)cn1]

HOBt (140.0 mg, 1.04 mmol), EDCI (198.7 mg, 1.04 mmol), and (1r, 4r)-4-amino-1-(trifluoromethyl)cyclohexan-1-ol hydrochloride (227.6 mg, 1.04 mmol) were added to a stirred solution of 4-[5-(5-chloro-2-methoxypyridin-4-yl)-1H-pyrazole-3-carbonyl]-4-azaspiro[2.5]octane-7-carboxylic acid (INTERMEDIATE 534, 270.0 mg, 0.69 mmol) and DIPEA (267.9 mg, 2.07 mmol) in DMF (6.00 mL). The resulting solution was stirred at 25° C. for 14 h. The resulting mixture was diluted with EtOAc and washed with water. The organic layer was concentrated under vacuum. The residue was purified by silica gel column chromatography eluting with DCM/MeOH (10/1 v/v) yielded (R)-4-(5-(5-chloro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(5-chloro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide as a solid mixture of diastereomers.

The two diastereomers of the title compounds were separated using Chiral-Prep-HPLC.

Column: CHIRALPAK IA column
Column dimension: 2×25 cm, 5 μm
Mobile Phase: hexanes (8 mM $NH_3$·MeOH):EtOH=70:30 hold for 14 min
Flow rate: 20 mL/min
Detection: 220/254 nm Example 286-A. The first eluting diastereomer (34.7 mg) was obtained as a solid.

The first eluting diastereomer had a retention time of 5.75 min.

$^1$H NMR (300 MHz, $CD_3OD$) δ 8.27 (s, 1H), 7.39-7.00 (m, 2H), 4.60 (s, 1H), 3.97 (s, 3H), 3.05-2.73 (m, 1H), 2.53 (s, 1H), 2.01-1.80 (m, 5H), 1.81-1.60 (m, 5H), 1.31 (s, 2H), 1.17-0.91 (m, 2H), 0.76 (s, 3H). LCMS (ESI): $[M+H]^+$: 556.3.

Example 286-B. The second eluting diastereomer (41.8 mg) was obtained as a solid.

The second eluting diastereomer had a retention time of 5.75 min.

$^1$H NMR (300 MHz, $CD_3OD$) δ 8.26 (s, 1H), 7.20 (s, 2H), 4.51 (s, 1H), 3.90 (s, 3H), 3.83 (s, 1H), 3.07-2.68 (m, 1H), 2.42 (s, 1H), 2.15-1.36 (m, 11H), 1.36-0.50 (m, 6H). LCMS (ESI): $[M+H]^+$: 556.1.

Example 287-A. (S)-4-(5-(5-fluoro-2-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide

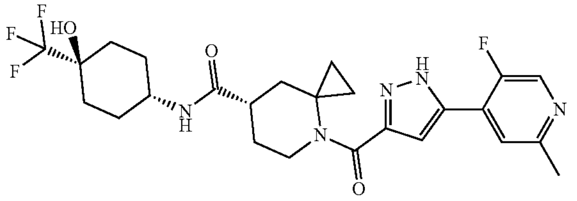 [SMILES: Cc1cc(-c2cc(C(=O)N3CC[C@H](C(=O)N[C@H]4CC[C@@](O)(C(F)(F)F)CC4)CC34CC4)n[nH]2)c(F)cn1]

Example 287-B. (R)-4-(5-(5-fluoro-2-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide

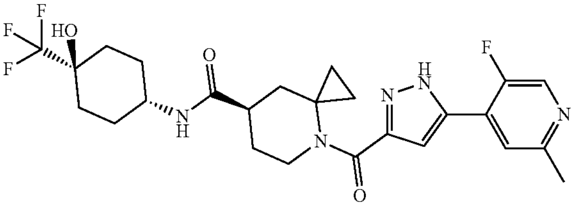 [SMILES: Cc1cc(-c2cc(C(=O)N3CC[C@@H](C(=O)N[C@H]4CC[C@@](O)(C(F)(F)F)CC4)CC34CC4)n[nH]2)c(F)cn1]

The title compound was prepared using a procedure similar to the one described for the synthesis of Example 283, except a mixture of (S)-4-[5-(5-fluoro-2-methylpyridin-4-yl)-1H-pyrazole-3-carbonyl]-4-azaspiro[2.5]octane-7-carboxylic acid and (R)-4-[5-(5-fluoro-2-methylpyridin-4-yl)-1H-pyrazole-3-carbonyl]-4-azaspiro[2.5]octane-7-carboxylic acid (INTERMEDIATE 526) was used as starting material. The resulting residue was purified by silica gel column chromatography (DCM/MeOH, 10/1 v/v) to obtain the diastereomeric mixtures of (S)-4-(5-(5-fluoro-2-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide and (R)-4-(5-(5-fluoro-2-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide as a solid.

The two diastereomers of the title compounds were separated using Chiral-Prep-HPLC.

Column: CHIRAL ART Cellulose-SB column

Column dimension: 2×25 cm, 5 μm

Mobile Phase: hexanes (8 mM $NH_3$·MeOH):EtOH=80:20 hold for 14 min

Flow rate: 20 mL/min

Detection: 220/254 nm

Example 287-A. The first eluting diastereomer (41.5 mg) was obtained as a solid.

The first eluting diastereomer had a retention time of 8.35 min.

$^1$H NMR (400 MHz, $CD_3OD$) δ 8.42 (d, 1H), 7.83 (s, 1H), 7.14 (s, 1H), 4.87-4.41 (m, 1H), 3.95 (s, 1H), 2.93 (s, 1H), 2.58 (s, 3H), 2.32-2.51 (m, 1H), 2.04-1.77 (m, 5H), 1.80-1.59 (m, 5H), 1.52-1.42 (m, 1H), 1.28 (m, 1H), 1.04-0.83 (m, 2H), 0.75 (s, 2H). LCMS (ESI): $[M+H]^+$: 524.3.

Example 287-B. The second eluting diastereomer (39.4 mg) was obtained as a solid.

The second eluting diastereomer had a retention time of 10.16 min.

$^1$H NMR (400 MHz, $CD_3OD$) δ 8.44-8.39 (m, 1H), 7.83 (s, 1H), 7.14 (s, 1H), 4.60 (s, 1H), 3.95 (s, 1H), 2.92 (s, 1H), 2.58 (s, 3H), 2.51-2.32 (m, 1H), 2.03-1.57 (m, 12H), 1.52-1.13 (m, 4H). LCMS (ESI): $[M+H]^+$: 524.3.

Example 288-A. (S)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide

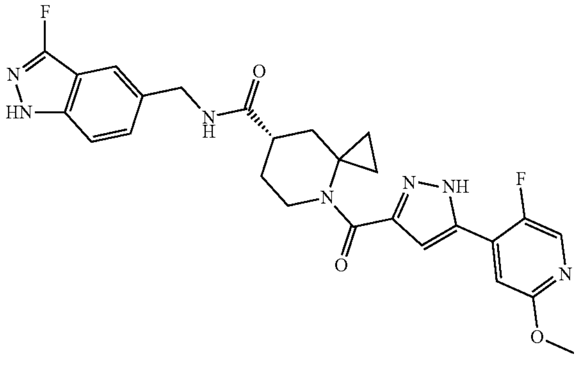 [SMILES: COc1cc(-c2cc(C(=O)N3CC[C@H](C(=O)NCc4ccc5[nH]nc(F)c5c4)CC34CC4)n[nH]2)c(F)cn1]

Example 288-B. (R)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide

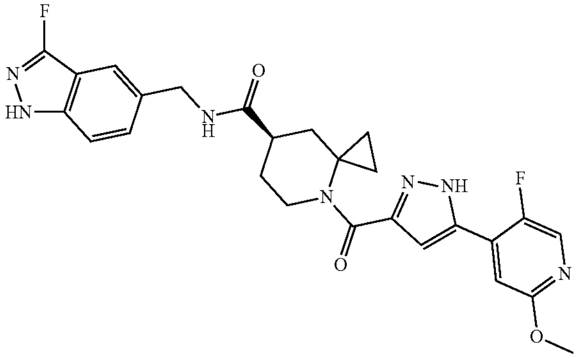 [SMILES: COc1cc(-c2cc(C(=O)N3CC[C@@H](C(=O)NCc4ccc5[nH]nc(F)c5c4)CC34CC4)n[nH]2)c(F)cn1]

EDCI (92.2 mg, 0.48 mmol), HOBt (65.0 mg, 0.48 mmol), and 1-(3-fluoro-1H-indazol-5-yl)methanamine (INTERMEDIATE 514, 72.8 mg, 0.44 mmol) were added to a stirred solution of 4-[5-(5-fluoro-2-methoxypyridin-4-yl)-1H-pyrazole-3-carbonyl]-4-azaspiro[2.5]octane-7-carboxylic acid (INTERMEDIATE 527, 150.0 mg, 0.40 mmol) and DIPEA (155.4 mg, 1.20 mmol) in DMF (3.00 mL). The resulting mixture was stirred at 25° C. for 14 h. The resulting mixture was diluted with EtOAc, washed with water. The residue was purified by reverse phase column chromatography (using the following conditions: C18 column, Mobile Phase A: water (10 mM $NH_4HCO_3$), Mobile Phase B: MeCN; Flow rate: 30 mL/min; Gradient: 35 B to 60 B in 20 min; Detector, UV 220/254 nm) to obtain enantiomeric mixtures of (S)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide and (R)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide as a solid (50 mg). LCMS (ESI): $[M+H]^+$: 522.2.

The two enantiomers of the title compounds were separated using Chiral-Prep-HPLC.

Column: CHIRALPAK IE column

Column dimension: 2×25 cm, 5 μm

Mobile Phase: hexanes (0.5% 2 M $NH_3$·MeOH):EtOH=50:50 hold for 30 min

Flow rate: 15 mL/min

Detection: 220/254 nm

Example 288-A. The first eluting enantiomer (10.6 mg) was obtained as a solid.

The first eluting enantiomer had a retention time of 14.62 min.

$^1$H NMR (300 MHz, $CD_3OD$) δ 8.14 (s, 1H), 7.57 (s, 1H), 7.44-7.38 (m, 2H), 7.28 (s, 1H), 7.11 (s, 1H), 4.48 (s, 2H), 3.95 (s, 3H), 3.65-3.36 (m, 1H), 2.86 (s, 1H), 2.50-2.44 (m, 1H), 1.91 (s, 2H), 1.34-1.28 (m, 2H), 1.05-0.99 (m, 2H), 0.73 (s, 2H). LCMS (ESI): $[M+H]^+$: 551.2.

Example 288-B. The second eluting enantiomer (10.1 mg) was obtained as a solid.

The second eluting enantiomer had a retention time of 21.53 min.

$^1$H NMR (300 MHz, $CD_3OD$) δ 8.14 (d, 1H), 7.57 (s, 1H), 7.44-7.38 (m, 2H), 7.20 (s, 1H), 7.12 (s, 1H), 4.48 (s, 2H), 3.95 (s, 3H), 3.56 (s, 1H), 2.87 (s, 1H), 2.44 (s, 1H), 1.91 (s, 2H), 1.31 (s, 2H), 1.04 (s, 2H), 0.74 (s, 2H). LCMS (ESI): $[M+H]^+$: 551.2.

Example 289. Diastereomeric Mixtures of (1R,3s,5S)-8-(5-(5-fluoro-2-methylpyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide

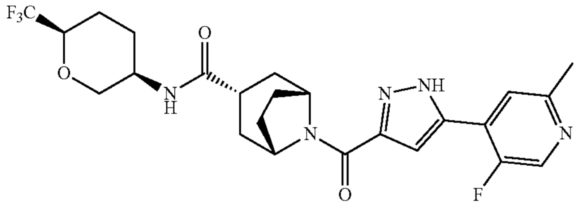

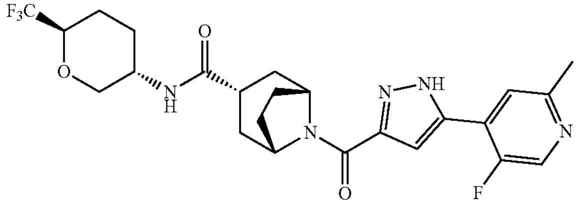

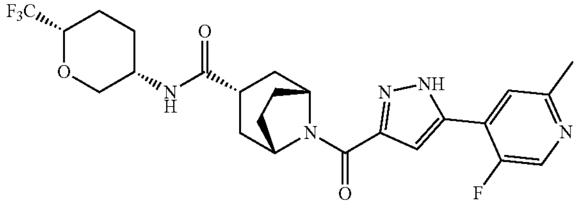

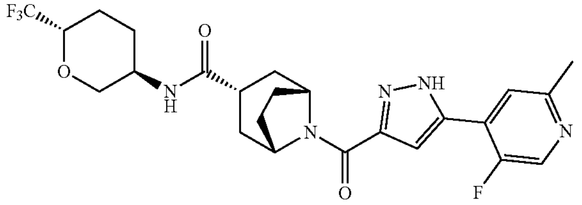

The title compound was prepared using a procedure similar to the one described for the synthesis of Example 283, except 6-(trifluoromethyl)tetrahydro-2H-pyran-3-amine (INTERMEDIATE 532) was used as starting material. The resulting residue was purified by silica gel column chromatography with DCM/MeOH (10/1 v/v) to obtain (1R,3s,5S)-8-(5-(5-fluoro-2-methylpyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide as a solid mixture of diastereomers (Example 289).

The four diastereomers of the title compounds were separated using Chiral-Prep-HPLC.

Column: CHIRAL ART Cellulose-SB column

Column dimension: 2×25 cm, 5 μm

Mobile Phase: hexanes (8 mM $NH_3$·MeOH):EtOH:=80:20 hold for 2 min

Flow rate: 50 mL/min

Detection: 220/254 nm

Example 289-A. The first eluting diastereomer (1.0 mg) was obtained as a solid.

The first eluting diastereomer had a retention time of 9.75 min.

LCMS (ESI): $[M+H]^+$: 510.2.

Example 289-B. The second eluting diastereomer (15.9 mg) was obtained as a solid.

The second eluting diastereomer had a retention time of 12.83 min.

$^1$H NMR (300 MHz, $CD_3OD$) δ 8.49-8.37 (m, 1H), 7.79 (s, 1H), 7.24 (s, 1H), 5.30 (s, 1H), 4.04-3.79 (m, 3H), 3.79-3.65 (m, 1H), 3.22-3.05 (m, 1H), 2.59 (d, 3H), 2.26-1.66 (m, 13H). LCMS (ESI): $[M+H]^+$: 510.2.

Example 289-C. The third eluting diastereomer (16.0 mg) was obtained as a solid.

The third eluting diastereomer had a retention time of 15.40

$^1$H NMR (300 MHz, $CD_3OD$) δ 8.44 (d, 1H), 7.80 (s, 1H), 7.24 (s, 1H), 5.21 (s, 1H), 4.04-3.78 (m, 3H), 3.78-3.67 (m, 3.22-3.06 (m, 1H), 2.59 (d, 3H), 2.23-1.63 (m, 13H). LCMS (ESI): $[M+H]^+$: 510.2.

Example 289-D. The fourth eluting diastereomer (3.0 mg) was obtained as a solid.

The fourth eluting diastereomer had a retention time of 17.80 min.

LCMS (ESI): $[M+H]^+$: 510.2.

Example 290. A Diastereomeric Mixture of (1R,3s,5S)-8-(5-(5-fluoro-2-methoxypyridin-4-yl)-1H-pyrazole-3-carbonyl)-N—((R)-1-(3-(trifluoromethyl)-1,2,4-oxadiazol-5-yl)ethyl)-8-azabicyclo[3.2.1]octane-3-carboxamide and (1R,3s,5S)-8-(5-(5-fluoro-2-methoxypyridin-4-yl)-1H-pyrazole-3-carbonyl)-N—(S)-1-(3-(trifluoromethyl)-1,2,4-oxadiazol-5-yl)ethyl)-8-azabicyclo[3.2.1]octane-3-carboxamide

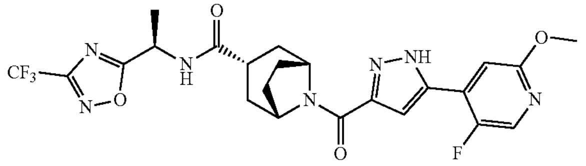

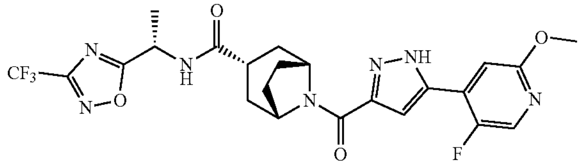

HATU (112.0 mg, 0.29 mmol) and 1-[3-(trifluoromethyl)-1,2,4-oxadiazol-5-yl]ethanamine (48.0 mg, 0.27 mmol) were added to a stirred solution of (1R,3R,5S)-8-[5-(5-fluoro-2-methoxypyridin-4-yl)-1H-pyrazole-3-carbonyl]-8-azabicyclo[3.2.1]octane-3-carboxylic acid (INTERMEDIATE 508, 100.0 mg, 0.27 mmol) and DIPEA (104.0 mg, 0.80 mmol) in DMF (5.00 mL). The resulting mixture was stirred at 25° C. for 14 h. The resulting mixture was diluted with EtOAc and washed with water. The resulting mixture was concentrated under reduced pressure. The residue was purified by reverse phase column chromatography (using the following conditions: C18 column, Mobile Phase A: water (10 mM $NH_4HCO_3$), Mobile Phase B: MeCN; Flow rate: 30 mL/min; Gradient: 20 B to 50 B in 20 min; Detector, UV 220/254 nm) to obtain (1R,3s,5S)-8-(5-(5-fluoro-2-methoxypyridin-4-yl)-1H-pyrazole-3-carbonyl)-N—((R)-1-(3-(trifluoromethyl)-1,2,4-oxadiazol-5-yl)ethyl)-8-azabicyclo[3.2.1]octane-3-carboxamide and (1R,3s,5S)-8-(5-(5-fluoro-2-methoxypyridin-4-yl)-1H-pyrazole-3-carbonyl)-N—((S)-1-(3-(trifluoromethyl)-1,2,4-oxadiazol-5-yl)ethyl)-8-azabicyclo[3.2.1]octane-3-carboxamide as a solid mixture of diastereomers (125.8 mg, Example 290). $^1H$ NMR (300 MHz, $CD_3OD$) δ 8.15 (d, 1H), 7.29-7.17 (m, 2H), 5.42-5.00 (m, 3H), 3.95 (s, 3H), 3.12-2.96 (m, 1H), 2.26-1.90 (m, 8H), 1.65 (d, 3H). LCMS (ESI): $[M+H]^+$: 538.3.

The two diastereomers of the title compounds were separated using Chiral-Prep-HPLC.

Column: CHIRALPAK IG column

Column dimension: 2×25 cm, 5 μm

Mobile Phase: 3/1 hexanes/DCM (10 mM $NH_3$·MeOH): EtOH=90:10 hold for 22 min

Flow rate: 20 mL/min

Detection: 220/254 nm

Example 290-A. The first eluting diastereomer (46.4 mg) was obtained as a solid.

The first eluting diastereomer had a retention time of 13.43 min.

$^1H$ NMR (300 MHz, $CD_3OD$) δ 8.15 (s, 1H), 7.29-7.17 (m, 2H), 5.42-3.82 (m, 3H), 3.95 (s, 3H), 3.12-2.96 (m, 1H), 2.26-1.90 (m, 8H), 1.65 (d, 3H). LCMS (ESI): $[M+H]^+$: 538.2.

Example 290-B. The second eluting diastereomer (45.5 mg) was obtained as a solid.

The second eluting diastereomer had a retention time of 18.50

$^1H$ NMR (300 MHz, $CD_3OD$) δ 8.16 (s, 1H), 7.29-7.17 (m, 2H), 5.42-3.85 (m, 3H), 3.95 (s, 3H), 3.12-2.96 (m, 1H), 2.26-1.90 (m, 8H), 1.65 (d, 3H). LCMS (ESI): $[M+H]^+$: 538.2.

Example 291. (1R,3s,5S)—N-(1,1-dimethylsilinan-4-yl)-8-(5-(5-fluoro-2-methoxypyridin-4-yl)-1H-pyrazole-3-carbonyl)-8-azabicyclo[3.2.1]octane-3-carboxamide

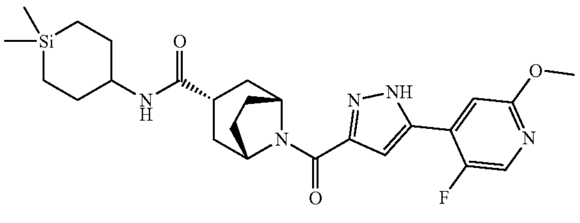

HATU (45.6 mg, 0.12 mmol) and 1,1-dimethylsilinan-4-amine hydrochloride (21.6 mg, 0.12 mmol) were added to a stirred solution of (1R,3R,5S)-8-[5-(5-fluoro-2-methoxypyridin-4-yl)-1H-pyrazole-3-carbonyl]-8-azabicyclo[3.2.1]octane-3-carboxylic acid (INTERMEDIATE 508, 29.9 mg, 0.08 mmol) and DIPEA (31.0 mg, 0.24 mmol) in DMF (2.00 mL). The resulting mixture was stirred at 30° C. for 14 h. The resulting mixture was filtered. The filtrate was then purified by Prep-HPLC (using the following conditions: Column: XBridge BEH130 Prep C18 OBD column, 130 Å, 19×150 mm 5 μm 13 nm; Mobile phase A: Water (20 mM, $NH_4HCO_3$), mobile phase B: MeCN, Detector, UV 210/254 nm) to obtain the title compound (20.4 mg) as a solid. $^1H$ NMR (400 MHz, $CD_3OD$) δ 8.13 (m, 1H), 7.24 (s, 1H), 7.18 (s, 1H), 5.22-5.18 (m, 1H), 4.86-4.82 (m, 1H), 3.93 (s, 3H), 3.56-3.48 (m, 1H), 3.00-2.79 (m, 1H), 2.25-1.80 (m, 6H), 1.77-1.69 (m, 2H), 1.56-1.42 (m, 2H), 1.32-1.26 (m, 2H), 0.86-0.69 (m, 2H), 0.67-0.55 (m, 2H), 0.07 (s, 3H), 0.01 (s, 3H). LCMS (ESI): $[M+H]^+$: 500.4.

Example 292. A diastereomeric mixture of (1R,3s,5S)-8-(5-(5-fluoro-2-methylpyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide and (1R,3s,5S)-8-(5-(5-fluoro-2-methylpyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide

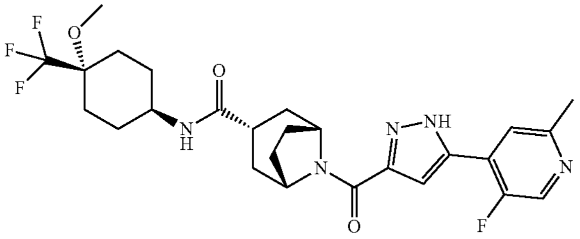

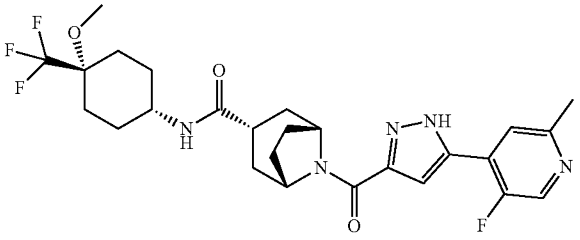

The title compound was prepared using a procedure similar to the one described for the synthesis of Example 276, except (1R,3R,5S)-8-[5-(5-fluoro-2-methylpyridin-4-yl)-1H-pyrazole-3-carbonyl]-8-azabicyclo[3.2.1]octane-3-carboxylic acid (INTERMEDIATE 524) and 4-methoxy-4-(trifluoromethyl)cyclohexan-1-amine (INTERMEDIATE 516) were used as the starting materials. The residue was purified by Prep-TLC (DCM/MeOH, 10/1 v/v) to obtain a diastereomeric mixture of (1R,3s,5S)-8-(5-(5-fluoro-2-methylpyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide and (1R,3s,5S)-8-(5-(5-fluoro-2-methylpyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide (150 mg, Example 292) solid. LCMS (ESI): 538.2 $[M+H]^+$.

The two diastereomers were separated by Chiral Prep-HPLC.

Column: CHIRALPAK IA

Column dimensions: 2×25 cm, 5 μm

Gradient: Hex:DCM=3:1 (10 mM $NH_3$·MEOH)/EtOH, 80/20 v/v

Flow rate: 17 mL/min

Detection (nm): 220/254 nm.

Example 292-A. The first eluting diastereomer (69.5 mg) was obtained as a solid.

The first eluting diastereomer had a retention time of 5.64 min, $^1$H NMR (300 MHz, DMSO-d6) δ 14.00 (s, 1H), 8.52 (s, 1H), 7.90-7.65 (m, 2H), 7.11 (s, 1H), 4.67 (s, 2H), 3.69-3.38 (m, 1H), 3.31 (s, 3H), 2.85-2.67 (m, 1H), 2.50-2.47 (m, 3H), 2.11-1.42 (m, 14H), 1.44-1.06 (m, 2H). LCMS (ESI): 538.2 $[M+H]^+$.

Example 292-B. The second eluting diastereomer (15.7 mg) was obtained as a solid. The second eluting diastereomer had a retention time of 8.02 min.

$^1$H NMR (300 MHz, DMSO-d6) δ 14.00 (s, 1H) 8.51 (s, 1H) 7.81 (d, 2H), 7.11 (s, 1H), 4.94 (m, 2H), 3.91-3.55 (m, 1H), 3.30 (s, 3H), 2.97-2.75 (m, 1H), 2.49-2.48 (m, 3H), 2.33-1.66 (m, 10H), 1.59 (m, 6H). LCMS (ESI): 538.2 $[M+H]^+$.

Example 293-A. (R)-4-(5-(5-fluoro-2-methylpyridin-4-yl)-1H-pyrazole-3-carbonyl)-N-((1r,4R)-4-methoxy-4-(trifluoromethyl)cyclohexyl)-4-azaspiro[2.5]octane-7-carboxamide

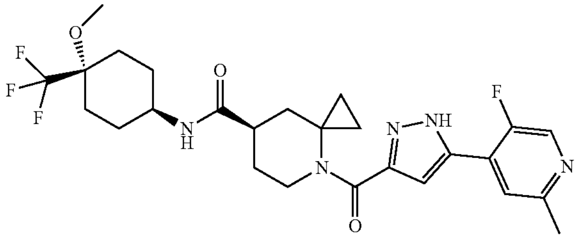 [SMILES: CO[C@]1(C(F)(F)F)CC[C@@H](NC(=O)[C@@H]2CCN(C(=O)c3cc(-c4cc(C)ncc4F)[nH]n3)C3(CC3)C2)CC1]

Example 293-B. (R)-4-(5-(5-fluoro-2-methylpyridin-4-yl)-1H-pyrazole-3-carbonyl)-N-((1s,4S)-4-methoxy-4-(trifluoromethyl)cyclohexyl)-4-azaspiro[2.5]octane-7-carboxamide

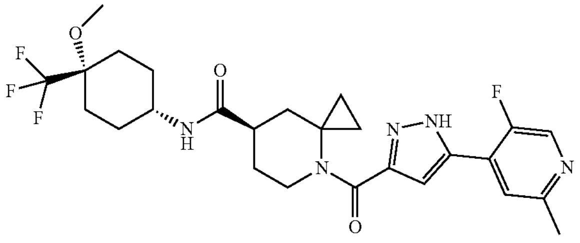 [SMILES: CO[C@]1(C(F)(F)F)CC[C@H](NC(=O)[C@@H]2CCN(C(=O)c3cc(-c4cc(C)ncc4F)[nH]n3)C3(CC3)C2)CC1]

Example 293-C. (S)-4-(5-(5-fluoro-2-methylpyridin-4-yl)-1H-pyrazole-3-carbonyl)-N-((1r,4R)-4-methoxy-4-(trifluoromethyl)cyclohexyl)-4-azaspiro[2.5]octane-7-carboxamide

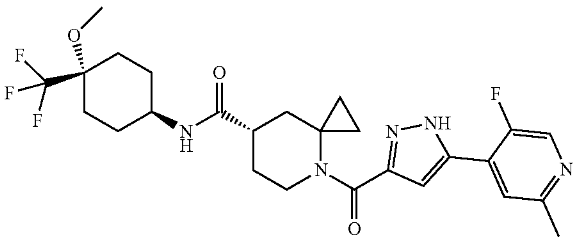 [SMILES: CO[C@]1(C(F)(F)F)CC[C@@H](NC(=O)[C@H]2CCN(C(=O)c3cc(-c4cc(C)ncc4F)[nH]n3)C3(CC3)C2)CC1]

Example 293-D. (S)-4-(5-(5-fluoro-2-methylpyridin-4-yl)-1H-pyrazole-3-carbonyl)-N-((1s,4R)-4-methoxy-4-(trifluoromethyl)cyclohexyl)-4-azaspiro[2.5]octane-7-carboxamide

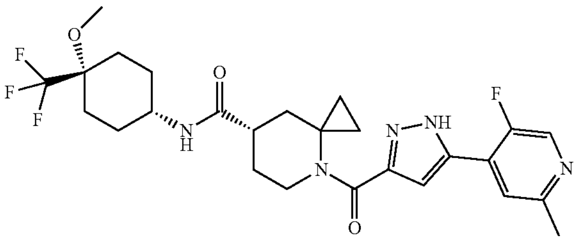 [SMILES: CO[C@]1(C(F)(F)F)CC[C@H](NC(=O)[C@H]2CCN(C(=O)c3cc(-c4cc(C)ncc4F)[nH]n3)C3(CC3)C2)CC1]

HATU (127.3 mg, 0.34 mmol), 4-methoxy-4-(trifluoromethyl)cyclohexan-1-amine (INTERMEDIATE 516, 88.0 mg, 0.45 mmol) and DIPEA (86.6 mg, 0.67 mmol) were added to a stirred solution of (R)-4-[5-(5-fluoro-2-methylpyridin-4-yl)-1H-pyrazole-3-carbonyl]-4-azaspiro[2.5]octane-7-carboxylic acid (INTERMEDIATE 526-B, 80.0 mg, 0.22 mmol) in DMF (3.0 0 mL). The resulting mixture was stirred at 25° C. for 14 h. The resulting mixture was diluted with water and extracted with EtOAc. The organic layers were concentrated under vacuum and the residue was purified by Prep-TLC (DCM/MeOH, 20/1 v/v) to obtain a mixture of (R)-4-(5-(5-fluoro-2-methylpyridin-4-yl)-1H-pyrazole-3-carbonyl)-N-((1r,4R)-4-methoxy-4-(trifluoromethyl)cyclohexyl)-4-azaspiro[2.5]octane-7-carboxamide and (R)-4-(5-(5-fluoro-2-methylpyridin-4-yl)-1H-pyrazole-3-carbonyl)-N-((1s,4R)-4-methoxy-4-(trifluoromethyl)cyclohexyl)-4-azaspiro[2.5]octane-7-carboxamide (80.0 mg) as a solid. LCMS (ESI): 538.2 $[M+H]^+$.

The two diastereomers of (R)-4-(5-(5-fluoro-2-methylpyridin-4-yl)-1H-pyrazole-3-carbonyl)-N-((1r,4R)-4-methoxy-4-(trifluoromethyl)cyclohexyl)-4-azaspiro[2.5]octane-7-carboxamide and (R)-4-(5-(5-fluoro-2-methylpyridin-4-yl)-1H-pyrazole-3-carbonyl)-N-((1s,4S)-4-methoxy-4-(trifluoromethyl)cyclohexyl)-4-azaspiro[2,5]octane-7-carboxamide (80.0 mg) were purified by CHIRAL-Prep-HPLC.

Column: CHIRALPAK IA,

Column dimensions: 2×25 cm, 5 μm

Gradient: Hex:DCM=3:1 (10 mM $NH_3$·MeOH)/EtOH, 90/10 v/v

Flow rate: 20 mL/min

Detection (nm): 220/254 nm

Example 293-A. The first eluting diastereomer (6.7 mg) was obtained as a solid.

The first eluting diastereomer had a retention time of 10.88 min.

$^1$H NMR (300 MHz, $CD_3OD$) δ 8.42 (d, 1H), 8.07-7.72 (m, 1H), 7.19-7.02 (m, 1H), 4.56 (s, 1H), 3.94 (s, 1H), 3.42-3.34 (m, 3H), 3.10-2.81 (m, 1H), 2.57 (d, 3H), 2.40 (m, 1H), 2.14-1.35 (m, 10H), 1.29 (s, 2H), 1.10-0.79 (m, 2H), 0.74 (s, 2H). LCMS (ESI): 538.2 $[M+H]^+$.

Example 293-B. The second eluting diastereomer (28.3 mg) was obtained as a solid.

The second eluting diastereomer had a retention time of 13.05 min.

$^1$H NMR (300 MHz, $CD_3OD$) δ 8.41 (d, 1H), 7.89 (s, 1H), 7.13 (d, 1H), 4.55 (s, 3.81-3.50 (m, 1H), 3.40 (d, 3H), 2.76 (s, 1H), 2.57 (d, 3H) 2.39 (m), 2.14-1.93 (m, 2H), 1.92-1.68 (m, 4H), 1.65-1.53 (m, 2H), 1.53-1.40 (m, 2H), 1.40-1.15 (m, 2H), 1.04 (s, 2H), 0.73 (d, 2H). LCMS (ESI): 538.2 $[M+H]^+$.

Separately, in a similar reaction, a mixture of (S)-4-[5-(5-fluoro-2-methylpyridin-4-yl)-1H-pyrazole-3-carbonyl]-4-azaspiro[2.5]octane-7-carboxylic acid (INTERMEDIATE 526-A) was reacted with 4-methoxy-4-(trifluoromethyl)cyclohexan-1-amine (INTERMEDIATE 516) to obtain a mixture of (S)-4-(5-(5-fluoro-2-methylpyridin-4-yl)-1H-pyrazole-3-carbonyl)-N-((1r,4S)-4-methoxy-4-(trifluoromethyl) cyclohexyl)-4-azaspiro[2.5]octane-7-carboxamide and 5-(5-fluoro-2-methylpyridin-4-yl)-1H-pyrazole-3-carbonyl)-N-((1s,4R)-4-methoxy-4-(trifluoromethyl)cyclohexyl)-4-azaspiro[2.5]octane-7-carboxamide (xx mg).

The two diastereomers of (S)-4-(5-(5-fluoro-2-methylpyridin-4-yl)-1H-pyrazole-3-carbonyl)-N-((1r,4S)-4-methoxy-4-(trifluoromethyl)cyclohexyl)-4-azaspiro[2.5]octane-7-carboxamide and (S)-4-(5-(5-fluoro-2-methylpyridin-4-yl)-1H-pyrazole-3-carbonyl)-N-((1s,4R)-4-methoxy-4-(trifluoromethyl)cyclohexyl)-4-azaspiro[2.5] octane-7-carboxamide were purified by Chiral-HPLC.

Column: CHIRALPAK IA,

Column dimensions: 2×25 cm, 5 μm

Gradient: Hex:DCM=3:1 (10 mM $NH_3$·MeOH)/EtOH, 90/10 v/v

Flow rate: 20 mL/min

Detection (nm) 220/254 nm

Example 293-C. The first eluting diastereomer (5.1 mg) was obtained as a solid. The first eluting diastereomer had a retention time of 13.03 min.

$^1$H NMR (300 MHz, $CD_3OD$) δ 8.43 (d, 1H), 7.85 (s, 1H), 7.15 (s, 1H), 4.59 (s, 1H), 3.96 (s, 1H), 3.50-3.34 (m, 3H), 3.01-2.82 (m, 2.68-2.48 (m, 3H), 2.52-2.13 (m, 1H), 1.98-1.50 (m, 10H), 1.43-1.15 (m, 2H), 1.13-0.82 (m, 2H), 0.75 (s, 2H). LCMS (ESI): 538.2 $[M+H]^+$.

Example 293-D. The second eluting diastereomer (28.6 mg) was obtained as a solid. The second eluting diastereomer had a retention time of 15.32 min.

$^1$H NMR (300 MHz, $CD_3OD$) 8.41 (d, 1H), 7.85 (s, 1H), 7.15 (s, 1H), 4.60 (s, 1H), 3.65 (s, 1H), 3.50-3.34 (m, 3H), 2.82-2.70 (m, 1H), 2.60 (s, 3H), 2.40 (s, 1H), 2.17-1.97 (m, 2H), 1.95-1.73 (m, 4H), 1.72-1.57 (m, 2H), 1.55-1.39 (m, 2H) 1.38-1.14 (m, 2H), 1.13-0.83 (m, 2H), 0.82-0.61 (m, 2H). LCMS (ESI): 538.2 $[M+H]^+$.

Example 294. A Diastereomeric Mixture of (1R,3R,5S)-8-[5-(5-fluoro-2-methoxypyridin-4-yl)-1H-pyrazole-3-carbonyl]-N-[(1r,4r)-4-methoxy-4-(trifluoromethyl)cyclohexyl]-8-azabicyclo[3.2.1]octane-3-carboxamide and (1R,3R,5S)-8-[5-(5-fluoro-2-methoxypyridin-4-yl)-1H-pyrazole-3-carbonyl]-N-[(1s,4s)-4-methoxy-4-(trifluoromethyl)cyclohexyl]-8-azabicyclo[3.2.1]octane-3-carboxamide

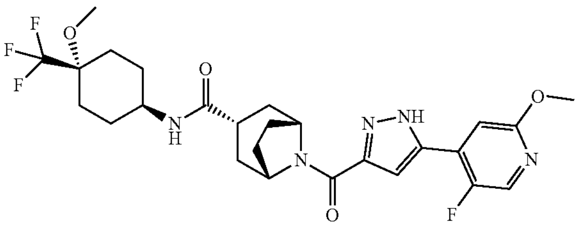

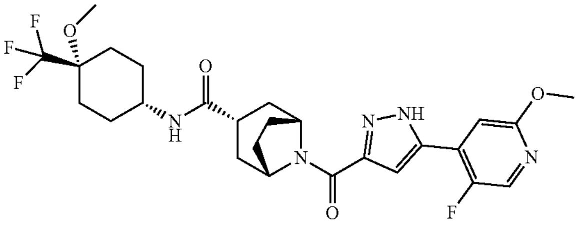

The title compounds were prepared using a procedure similar to the one described for the synthesis of Example 267, except 4-methoxy-4-(trifluoromethyl)cyclohexan-1-amine (INTERMEDIATE 516) and (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508) were used as the starting material. The residue was purified by silica gel column chromatography (DCM/MeOH, 15/1 v/v) to obtain a diastereomeric mixture of (1R,3R,5S)-8-[5-(5-fluoro-2-methoxypyridin-4-yl)-1H-pyrazole-3-carbonyl]-N-[(1r,4r)-4-methoxy-4-(trifluoromethyl)cyclohexyl]-8-azabicyclo[3.2.1]octane-3-carboxamide and (1R,3R,5S)-8-[5-(5-fluoro-2-methoxypyridin-4-1H-pyrazole-3-carbonyl]-N-[(1s,4s)-4-methoxy-4-(trifluoromethyl)cyclohexyl]-8-azabicyclo [3.2.1]octane-3-carboxamide (140 mg, Example 294) as a solid. LCMS (ESI): 554.2 $[M+H]^+$.

The diastereomers of the title compound were separated by Chiral Prep-HPLC.

Column: CHIRALPAK IA,

Column dimensions: 2×25 cm, 5 μm

Gradient: Hex:DCM=3:1 (10 mM $NH_3$·MeOH)/EtOH, 80/20 v/v

Flow rate: 17 mL/min

Detection (nm): 220/254 nm

Example 294-A. The first eluting diastereomer (71.5 mg) was obtained as a solid.

The first eluting diastereomer had a retention time of 6.32 min.

$^1$H NMR (400 MHz, $CD_3OD$) δ 8.14 (s, 1H), 7.23-7.18 (m, 2H), 5.37-4.90 (m, 2H), 3.98-3.91 (m, 4H), 3.43-3.39 (m, 3H), 3.15-3.01 (m, 1H), 2.24-1.98 (m, 4H), 1.99-1.90 (m, 2H), 1.89-1.81 (m, 5H), 1.81-1.62 (m, 5H). LCMS (ESI): 554.2 $[M+H]^+$.

Example 294-B. The second eluting diastereomer (3.2 mg) was obtained as a solid.

The second eluting diastereomer had a retention time of 8.56 min.

$^1H$ NMR (300 MHz, $CD_3OD$) δ 8.33-8.01 (m, 1H), 7.51-6.89 (m, 2H), 5.37 (s, 2H), 3.95 (s, 3H), 3.78-3.55 (m, 1H), 3.42 (s, 3H), 2.92 (s, 1H), 2.26-1.95 (m, 5H), 1.94-1.86 (m, 2H), 1.86-1.73 (m, 4H), 1.71-1.39 (m, 5H). LCMS (ESI): 554.2 $[M+H]^+$.

Example 295. A Diastereomeric Mixture of (1R,3s,5S)-8-(5-(5-fluoro-2-methoxypyridin-4-yl)-1H-pyrazole-3-carbonyl)-N-((5R,8r)-2-oxo-1-azaspiro[4.5]decan-8-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((5S,8s)-2-oxo-1-azaspiro[4.5]decan-8-yl)-8-azabicyclo[3.2.1]octane-3-carboxamide

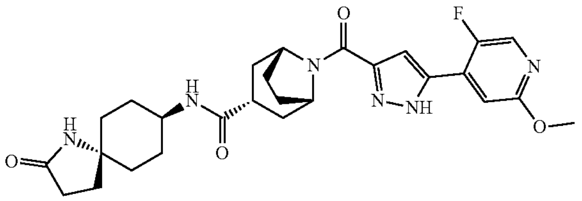

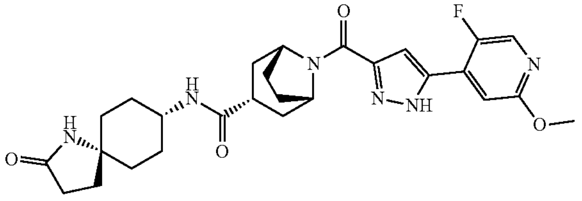

The title compound was prepared using a procedure similar to the one described for the synthesis of Example 301, except 8-amino-1-azaspiro[4.5]decan-2-one hydrochloride was used as a starting material.

The diastereomeric mixture (Example 295) of the (1R,3s,5S)-8-(5-(5-fluoro-2-methoxypyridin-4-yl)-1H-pyrazole-3-carbonyl)-N-((5R,8r)-2-oxo-1-azaspiro[4.5]decan-8-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((5S,8s)-2-oxo-1-azaspiro[4.5]decan-8-yl)-8-azabicyclo[3.2.1]octane-3-carboxamide were separated using Prep-HPLC.

Column: XBridge BEH130 Prep C18 OBD column

Column dimension: 19×150 mm, 5 μm

Mobile Phase: Water (10 mM $NH_4HCO_3$, 0.1% $NH_3H_2O$):MeCN

Detection: 210/254 nm

Example 295-A. The first eluting diastereomer (1.9 mg) was obtained as a solid.

LCMS (ESI): 525.5 $[M+H]^+$.

Example 295-B. The second eluting diastereomer (10.2 mg) was obtained as a solid.

$^1H$ NMR (400 MHz, $CD_3OD$): δ 8.12 (m, 1H), 7.39-7.05 (m, 2H), 5.35 (s, 1H), 3.93 (s, 3H), 3.76-3.45 (m, 1H), 3.22-2.75 (m, 1H), 2.42-2.32 (m, 2H), 2.20-1.52 (m, 17H), 1.47-1.31 (m, 2H). LCMS (ESI): $[M+H]^+$: 525.4.

Example 296. 4-[5-(5-fluoro-2-methoxypyridin-4-yl)-1H-pyrazole-3-carbonyl]-N—[(R)-1-(2-fluorophenyl)pyrrolidin-3-yl]-4-azaspiro[2.5]octane-7-carboxamide

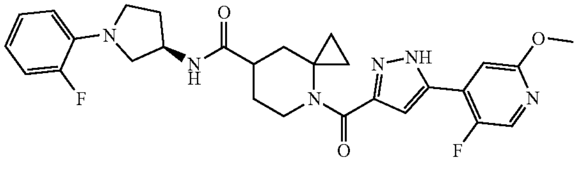 [SMILES: COc1cc(-c2cc(C(=O)N3CCC(C(=O)N[C@@H]4CCN(c5ccccc5F)C4)CC34CC4)n[nH]2)c(F)cn1]

Step-1. tert-butyl (R)-3-[4-[5-(5-fluoro-2-methoxypyridin-4-yl)-1H-pyrazole-3-carbonyl]-4-azaspiro[2.5]octane-7-amido]pyrrolidine-1-carboxylate

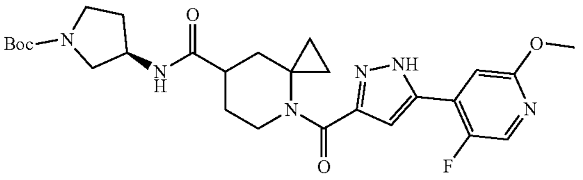 [SMILES: COc1cc(-c2cc(C(=O)N3CCC(C(=O)N[C@@H]4CCN(C(=O)OC(C)(C)C)C4)CC34CC4)n[nH]2)c(F)cn1]

EDCI (217.6 mg, 1.1 mmol) and HOBt (153.4 mg, 1.1 mmol) were added to a solution of 4-[5-(5-fluoro-2-methoxypyridin-4-yl)-1H-pyrazole-3-carbonyl]-4-azaspiro[2.5]octane-7-carboxylic acid (INTERMEDIATE 527, 170.0 mg, 0.45 mmol) in DMF (6.00 mL). The solution was stirred at 25° C. for 30 min, then tert-butyl (3R)-3-aminopyrrolidine-1-carboxylate (101.5 mg, 0.54 mmol) and DIPEA (0.40 mL, 2.3 mmol) were added. The solution was then stirred at 25° C. for 14 h, then diluted with EtOAc, washed with water, and the organic layer was concentrated. The residue was purified by silica gel column chromatography (DCM/MeOH, 15/1 v/v) to obtain the title compound (270.0 mg) as a solid. LCMS (ESI): 543.3 $[M+H]^+$.

Step-2. 4-[5-(5-fluoro-2-methoxypyridin-4-yl)-1H-pyrazole-3-carbonyl]-N—[(R)-pyrrolidin-3-yl]-4-azaspiro[2.5]octane-7-carboxamide

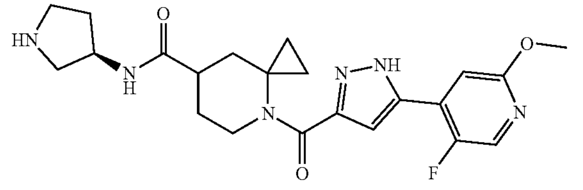 [SMILES: COc1cc(-c2cc(C(=O)N3CCC(C(=O)N[C@@H]4CCNC4)CC34CC4)n[nH]2)c(F)cn1]

TFA (2.00 mL) was added to a solution of tert-butyl (R)-3-[4-[5-(5-fluoro-2-methoxypyridin-4-yl)-1H-pyrazole-3-carbonyl]-4-azaspiro[2.5]octane-7-amido]pyrrolidine-1-carboxylate (Step-1, 270.0 mg, 0.5 mmol) in DCM (2.00 mL). The solution was then stirred at 25° C. for 1 h, then concentrated under reduced pressure. The residue was purified by silica gel column chromatography (DCM/MeOH, 5/1 v/v) to obtain the title compound (170.0 mg) as a solid. LCMS (EST): 443.3 $[M+H]^+$.

Step-3. 4-[5-(5-fluoro-2-methoxypyridin-4-yl)-1H-pyrazole-3-carbonyl]-N—[(R)-1-(2-fluorophenyl)pyrrolidin-3-yl]-4-azaspiro[2.5]octane-7-carboxamide

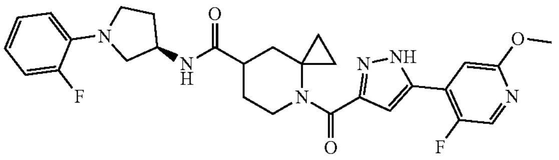 [SMILES: COc1cc(-c2cc(C(=O)N3CCC(C(=O)N[C@@H]4CCN(c5ccccc5F)C4)CC34CC4)n[nH]2)c(F)cn1]

1-bromo-2-fluorobenzene (94.9 mg, 0.5 mmol), RuPhos (37.9 mg, 0.08 mmol), RuPhos Palladacycle G3 (68.0 mg, 0.08 mmol), and $Cs_2CO_3$ (265.1 mg, 0.8 mmol) were added to a stirred solution of 4-[5-(5-fluoro-2-methoxypyridin-4-yl)-1H-pyrazole-3-carbonyl]-N—[(R)-pyrrolidin-3-yl]-4-azaspiro[2.5]octane-7-carboxamide (Step-2, 120.0 mg, 0.3 mmol) in DMF (5 mL). The solution was stirred at 110° C. for 14 h under nitrogen atmosphere, then diluted with EtOAc and washed with water. The solution was then concentrated under reduced pressure and the residue was purified first by silica gel column chromatography (DCM/MeOH, 25/1 v/v), then by reverse phase column chromatography (using the following conditions: C18 column; Mobile Phase A: Water (10 mM $NH_4HCO_3$), Mobile Phase B: MeCN; Flow rate: 30 mL/min; Gradient: 10% B to 50% B in 30 min; Detector, UV 220/254 nm) to obtain the title compound (0.5 mg) as a solid. LCMS (ESI): 537.2 $[M+H]^+$.

Example 297. (1R,3S,5S)-8-[5-(5-fluoro-2-methoxypyridin-4-yl)-1H-pyrazole-3-carbonyl]-N-[1-oxaspiro[3.5]nonan-7-yl]-8-azabicyclo[3.2.1]octane-3-carboxamide

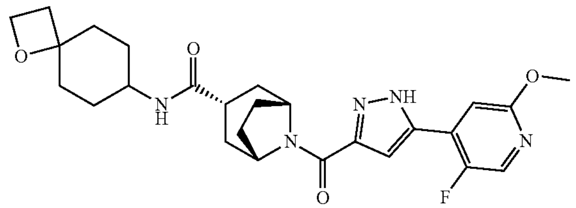 [SMILES: COc1cc(-c2cc(C(=O)N3[C@@H]4CC[C@H]3C[C@H](C(=O)NC3CCC5(CCO5)CC3)C4)n[nH]2)c(F)cn1]

The title compound was prepared using a procedure similar to the one described for the synthesis of Example 276, except 1-oxaspiro[3.5]nonan-7-amine (INTERMEDIATE 523) and ((1R,3S,5S)-8-[5-(5-fluoro-2-methoxypyridin-4-yl)-1H-pyrazole-3-carbonyl]-8-azabicyclo[3.2.1]octane-3-carboxylic acid (INTERMEDIATE 508) were used as starting materials. The residue was purified by Chiral-Prep-HPLC (using the following conditions: Column: CHIRAL ART Cellulose-SB, 2×25 cm, 5 μm; Mobile Phase A: MTBE (10 mM $NH_3$·MEOH); Mobile Phase B: EtOH; Flow rate: 20 mL/min; Gradient: 20% B to 20% B in 11 min; Detection: 220/254 nm) to obtain the title compound as a solid mixture of diastereomers. $^1H$ NMR (300 MHz, DMSO-$d_6$) δ 14.14-13.91 (m, 1H), 8.35-8.23 (m, 1H), 7.67 (d, 1H), 7.34 (d, 1H), 7.18-7.12 (m, 1H), 5.24-4.51 (m, 2H), 4.33 (t, 2H), 3.88 (s, 3H), 3.55-3.45 (m, 1H), 2.83-2.77 (m, 1H), 2.27 (t, 2H), 2.12-1.87 (m, 4H), 1.84-1.68 (m, 4H), 1.67-1.45 (m, 6H), 1.44-1.17 (m, 2H). LCMS (ESI): 498.3 $[M+H]^+$;

Example 298. A diastereomeric mixture of (2R,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2S,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2R,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide and (2R,4S,5R)-1-(5-(5-fluoro-2-methoxypyridin-4-yl)-1H-pyrazole-3-carbonyl)-N-((1r,4S)-4-hydroxy-, 1-(trifluoromethyl)cyclohexyl)-2,5-dimethylpiperidine-4-carboxamide and (2S,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2S,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide and (2R,4R,5R)-1-(5-(5-fluoro-2-methoxypyridin-, 1-yl)-1H-pyrazole-3-carbonyl)-N-((1r,4R)-4-hydroxy-4-(trifluoromethyl)cyclohexyl)-2,5-dimethylpiperidine-4-carboxamide and (2S,4R,5R)-1-(5-(5-fluoro-2-methoxypyridin-4-yl)-1H-pyrazole-3-carbonyl)-N-((1r,4R)-4-hydroxy-1-(trifluoromethyl)cyclohexyl)-2,5-dimethylpiperidine-4-carboxamide

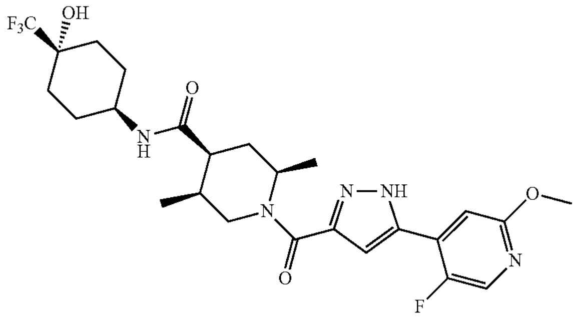

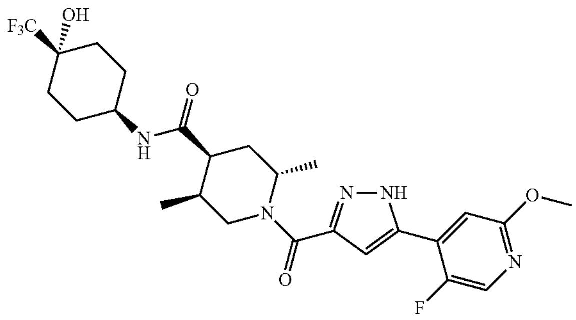

-continued

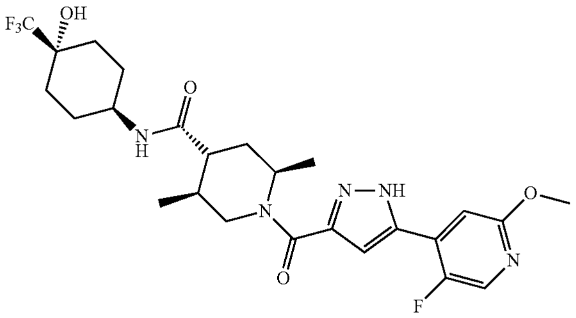

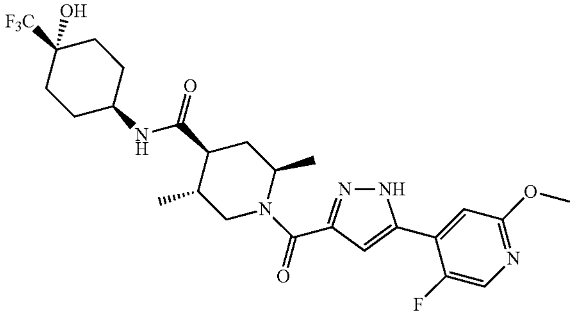

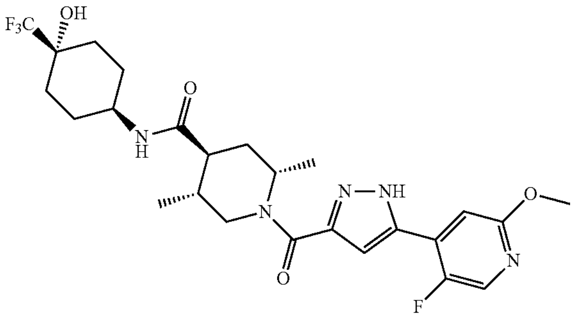

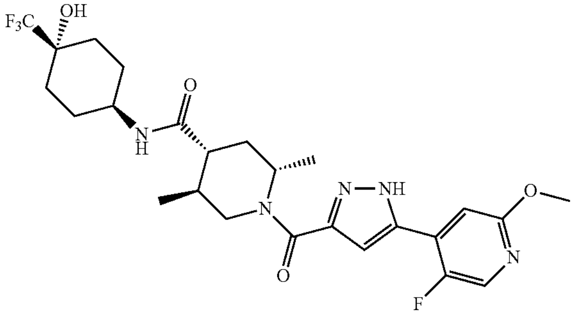

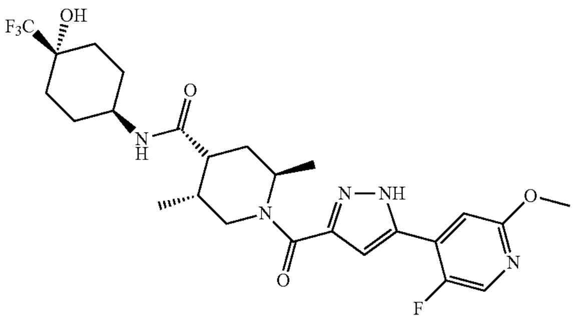

-continued

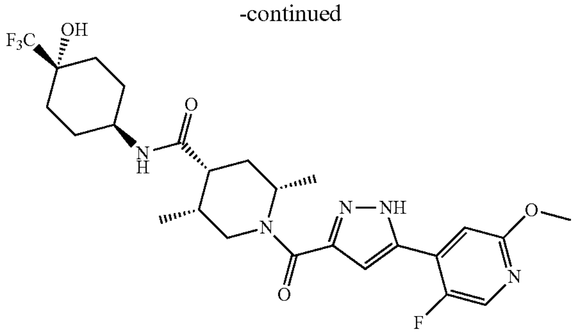

Step-1. Methyl 1-[5-(5-chloro-2-methoxypyridin-4-yl)-1-[[2-(trimethylsilyl)ethoxy]methyl]pyrazole-3-carbonyl]-2,5-dimethylpiperidine-4-carboxylate

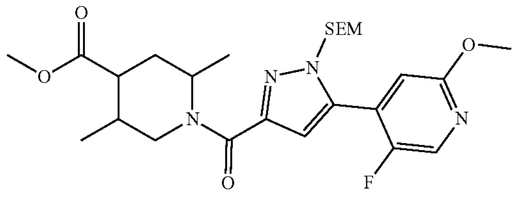

EDCI (671.7 mg, 3.50 mmol), HOBt: (473.8 mg, 3.50 mmol), and methyl 2,5-dimethylpiperidine-4-carboxylate (200.0 mg, 1.17 mmol) were added to a stirred solution of 5-(5-fluoro-2-methoxypyridin-4-yl)-1-((2-(trimethylsilyl)ethoxy)methyl)-1H-pyrazole-3-carboxylic acid (INTERMEDIATE 506, 448.4 mg, 1.17 mmol) and DIPEA (452.9 mg, 3.50 mmol) in DMF (5.00 mL). The resulting mixture was stirred at 25° C. for 14 h. The solution was then diluted with water and extracted with EtOAc. The organic layers were combined, dried over anhydrous sodium sulfate, filtered, and the solvent was evaporated. The residue was purified by silica gel column chromatography eluting with EtOAc/petroleum ether (1/1 v/v) to obtain the title compound (420.0 mg) as a solid. LCMS (ESI): $[M+H]^+$: 521.7.

Step-2. 1-[5-(5-fluoro-2-methoxypyridin-4-yl)-1-[[2-(trimethylsilyl)ethoxy]methyl]pyrazole-3-carbonyl]-2,5-dimethylpiperidine-4-carboxylic acid

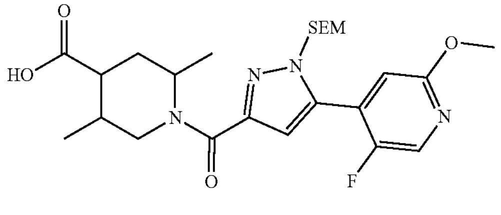 [SMILES: COc1cc(-c2cc(C(=O)N3CC(C)C(C(=O)O)CC3C)nn2COCC[Si](C)(C)C)c(F)cn1]

$LiOH \cdot H_2O$ (96.6 mg, 4.03 mmol) was added to a stirred solution of methyl 1-[5-(5-fluoro-2-methoxypyridin-4-yl)-1-[[2-(trimethylsilyl)ethoxy]methyl]pyrazole-3-carbonyl]-2,5-dimethylpiperidine-4-carboxylate (Step-1, 420.0 mg, 0.81 mmol) in MeOH (2.00 mL), $H_2O$ (2.00 mL) and THF (2.00 mL). The resulting mixture was stirred at 25° C. for 1 h. The solution was then concentrated under reduced pressure, diluted with water, then the pH was adjusted to 6 by the addition of aqueous HCl. The precipitated solids were collected by filtration and washed with water. The resulting solid was dried in an oven under reduced pressure to obtain the title compound (350.0 mg) as a solid. LCMS (ESI): $[M+H]^+$: 521.7.

Step-3. 1-[5-(5-fluoro-2-methoxypyridin-4-yl)-1-[[2-(trimethylsilyl)ethoxy]methyl]pyrazole-3-carbonyl]-2,5-dimethyl-N-[(1r,4r)-4-hydroxy-4-(trifluoromethyl)cyclohexyl]piperidine-4-carboxamide

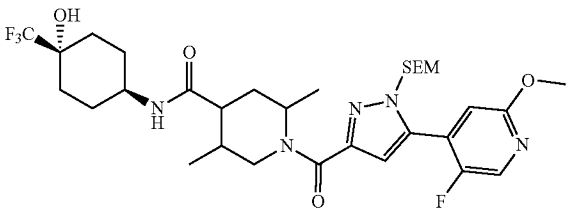 [SMILES: COc1cc(-c2cc(C(=O)N3CC(C)C(C(=O)N[C@H]4CC[C@@](O)(C(F)(F)F)CC4)CC3C)nn2COCC[Si](C)(C)C)c(F)cn1]

HATU (394.0 mg, 1.04 mmol) and (1r,4r)-4-amino-1-(trifluoromethyl)cyclohexan-1-ol (151.9 mg, 0.83 mmol) were added to a stirred solution of 1-[5-(5-fluoro-2-methoxypyridin-4-yl)-1-[[2-(trimethylsilyl)ethoxy]methyl]pyrazole-3-carbonyl]-2,5-dimethylpiperidine-4-carboxylic acid (Step-2, 350.0 mg, 0.69 mmol) and DIPEA (267.9 mg, 2.07 mmol) in DMF (5.00 mL). The resulting mixture was stirred for at 25° C. for 1 h. The solution was then diluted with water and extracted with EtOAc. The organic layers were combined, dried over anhydrous sodium sulfate, filtered, and the solvent was evaporated. The residue was purified by silica gel column chromatography eluting with EtOAc/petroleum ether (1/1 v/v) to obtain the title compound (420.0 mg) as a solid. LCMS (ESI): $[M+H]^+$: 672.8.

Step-4. (2R,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2S,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2R,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide and (2R,4S,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide and (2S,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2S,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide and (2R,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide and (2S,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide

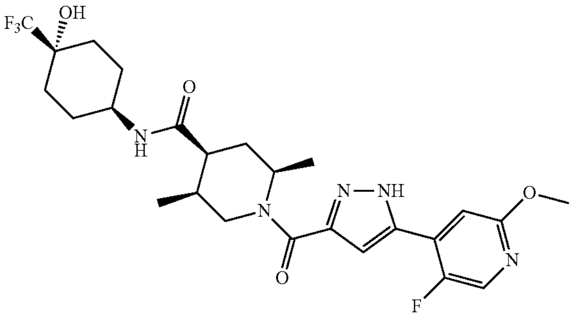

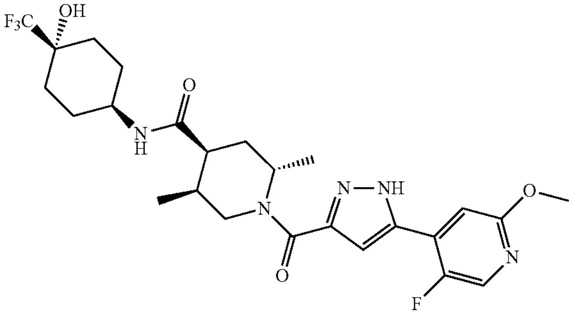

-continued

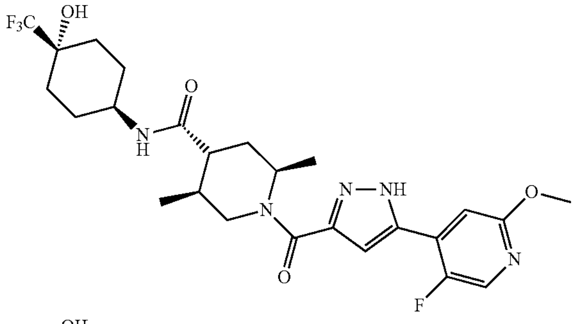

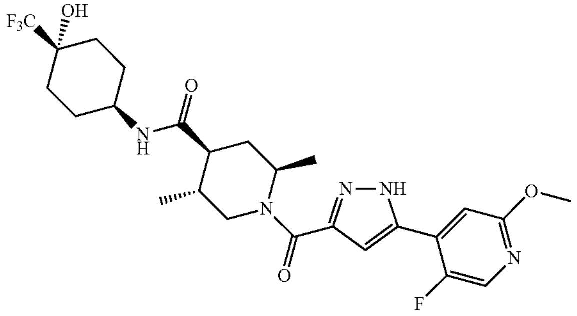

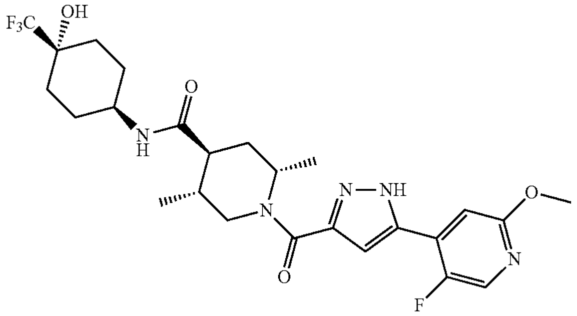

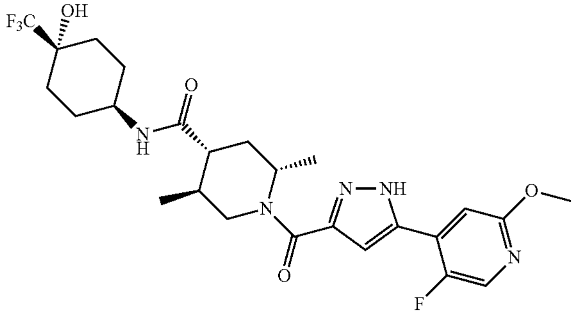

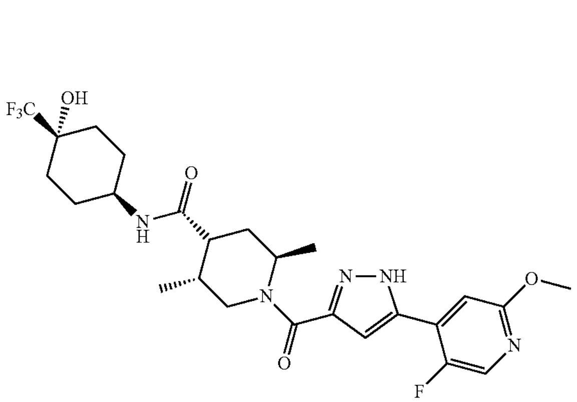

-continued

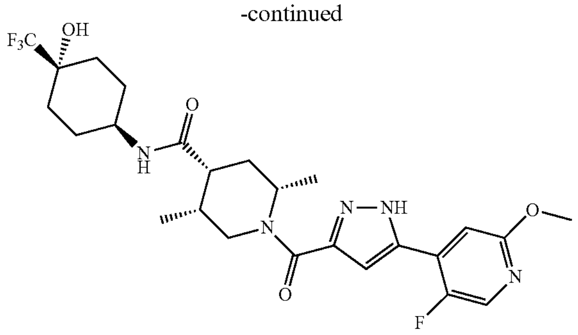

TFA (0.14 mL, 1.88 mmol) was added to a stirred mixture of (1-[5-(5-fluoro-2-methoxypyridin-4-yl)-1-[[2-(trimethylsilyl)ethoxy]methyl]pyrazole-3-carbonyl]-2,5-dimethyl-N-[(1r,4r)-4-hydroxy-4-(trifluoromethyl)cyclohexyl]piperidine-4-carboxamide (Step-3, 420.0 mg, 0.63 mmol) in DCM (4.00 mL). The resulting mixture was stirred at 25° C. for 1 h. The solution was then concentrated under reduced pressure and the residue was purified by silica gel column chromatography eluting with DCM/MeOH (3/1 v/v) to obtain the title compound (310.0 mg, Example 298) as a solid mixture of diastereomers of (2R,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2S,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2R,4S,5S)-1-(5-(5-fluoro-2-methoxypyridin-4-yl)-pyrazole-3-carbonyl)-N-((1r,4R)-4-hydroxy-4-(trifluoromethyl)cyclohexyl)-2,5-dimethylpiperidine-4-carboxamide and (2R,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2S,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide and (2S,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide and (2R,4R,5R)-1-(5-(5-fluoro-2-methoxypyridin-4-yl pyrazole-3-carbonyl)-N-((1r,4R)-4-hydroxy-4-(trifluoromethyl)cyclohexyl)-2,5-dimethylpiperidine-4-carboxamide and (2S,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide (380.0 mg). LCMS (ESI): $[M+H]^+$: 542.5.

The eight diastereomers of the title compounds were separated using Prep-HPLC to yield two fractions, each containing four diastereomers.

Column: Sunfire Prep C18 OBD column

Column dimension: 19×150 mm, 5 μm

Mobile phase: water (0.05% TFA):MeCN

Detection: 220/254 nm

The first eluting peak (15.0 mg) had a retention time of 11.13 min.

The second eluting peak (200.0 mg) had a retention time of 12.32 min.

The first fraction (15.0 mg) from Prep-HPLC containing four diastereomers of the title compounds was separated using Chiral-Prep-HPLC to yield two fractions, each containing two diastereomers.

Column: Viridis BEH Prep OBD column.
Column dimension: 1.9×15 cm, 5 μm
Mobile phase: hexanes:IPA=85:15 hold for 19.5 min
Flow rate: 15 mL/min
Detection: 220/254 nm Example 298-A. The first eluting peak (2.8 mg) was obtained as a solid.

The first eluting peak had a retention time of 11.25 min.

$^1$H NMR (300 MHz, CD SOD) δ 8.14 (d, 1H), 7.44-7.03 (m, 2H), 4.56 (s, 1H), 4.48-4.24 (m, 1H), 4.05-3.90 (m, 4H), 3.70-3.45 (m, 1H), 2.25 (m, 2H), 2.18-1.80 (m, 6H), 1.80-1.58 (m, 5H), 1.37-1.28 (m, 3H), 0.98 (d, 3H). LCMS (ESI): $[M+H]^+$: 542.5.

Example 298-B. The second eluting peak (2.0 mg) was obtained as a solid.

The second eluting peak had a retention time of 16.56 min.

$^1$H NMR (300 MHz, $CD_3OD$) δ 8.14 (d, 1H), 7.44-7.03 (m, 2H), 4.56 (s, 1H), 4.48-4.24 (m, 1H), 4.05-3.90 (m, 4H), 3.70-3.45 (m, 1H), 2.25 (m, 2H), 2.18-1.80 (m, 6H), 1.80-1.58 (m, 5H), 1.37-1.28 (m, 3H), 0.98 (d, 3H). LCMS (ESI): $[M+H]^+$: 542.5.

The second fraction (200.0 mg) from Prep-HPLC containing four diastereomers of the title compounds was separated using Chiral-Prep-HPLC to yield two fractions, each containing two diastereomers.

Column: Chiralpak IC column
Column dimension: 2×25 cm, 5 μm
Mobile phase: hexanes (10 mM $NH_3$·MeOH): EtOH
Detection: 215/260 nm The first eluting peak (150.0 mg) had a retention time of 10.89 min.

The second eluting peak (30.0 mg) had a retention time of 21.56 min.

The first fraction (150.0 mg) from Chiral-Prep-HPLC containing two diastereomers of the title compounds was separated using Prep-SFC.

Column: N-Lux 3u i-Cellulose-5 column
Column dimension: 0.46×10 cm, 3 μm
Mobile phase: EtOH (10% to 50% for 4.0 min, 50% hold for 2 min)
Flow rate: 2 mL/min
Detection: 220/254 nm
Outlet pressure: 100 bar Example 298-C. The first eluting compound (36.5 mg) was obtained as a solid.

The first eluting compound had a retention time of 2.40 min.

$^1$H NMR (300 MHz, $CD_3OD$) δ 8.14 (m, 1H), 7.44-7.03 (m, 2H), 4.56 (s, 1H), 4.48-4.24 (m, 1H), 4.05-3.90 (m, 4H), 3.70-3.45 (m, 1H), 2.25 (m, 2H), 2.18-1.80 (m, 6H), 1.80-1.58 (m, 5H), 1.37-1.28 (m, 3H), 0.98 (d, 3H). LCMS (ESI): $[M+H]^+$: 542.1.

Example 298-D. The second eluting compound (33.0 mg) was obtained as a solid.

The second eluting compound had a retention time of 2.69

$^1$H NMR (300 MHz, $CD_3OD$) δ 8.14 (m, 1H), 7.44-7.03 (m, 2H), 4.56 (s, 1H), 4.48-4.24 (m, 1H), 4.05-3.90 (m, 4H), 3.70-3.45 (m, 1H), 2.25 (m, 2H), 2.18-1.80 (m, 6H), 1.80-1.58 (m, 5H), 1.37-1.28 (m, 3H), 0.98 (d, 3H). LCMS (ESI): $[M+H]^+$: 542.1.

The second fraction (30.0 mg) from Chiral-Prep-HPLC containing two diastereomers of the title compounds was separated using Chiral-Prep-HPLC.

Column: Chiralpak IC-3 column
Column dimension: 0.46×5 cm, 3 μm
Mobile phase: hexanes (0.1% DEA):EtOH=70:30
Detection: 220/254 nm Example 298-E. The first eluting compound (7.8 mg) was obtained as a solid.

The first eluting compound had a retention time of 2.36 min.

$^1$H NMR (300 MHz, $CD_3OD$) δ 8.14 (m, 1H), 7.44-7.03 (m, 2H), 4.56 (s, 1H), 4.48-4.24 (m, 1H), 4.05-3.90 (m, 4H), 3.70-3.45 (m, 1H), 2.25 (m, 2H), 2.18-1.80 (m, 6H), 1.80-1.58 (m, 5H), 1.37-1.28 (m, 3H), 0.98 (d, 3H). LCMS (ESI): $[M+H]^+$: 542.3.

Example 298-F. The second eluting compound (7.5 mg) was obtained as a solid.

The second eluting compound had a retention time of 4.65 rain.

$^1$H NMR (300 MHz, $CD_3OD$) δ 8.14 (m, 1H), 7.44-7.03 (m, 2H), 4.56 (s, 1H), 4.48-4.24 (m, 1H), 4.05-3.90 (m, 4H), 3.70-3.45 (m, 1H), 2.25 (m, 2H), 2.18-1.80 (m, 6H), 1.80-1.58 (m, 5H), 1.37-1.28 (m, 3H), 0.98 (d, 3H). LCMS (ESE): $[M+H]^+$: 542.3.

Example 299. A Diastereomeric Mixture of (1R,3S,5S)—N-[(3S,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide and (1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide and (1R,3S,5S)—N-[(3R,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide and (1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide

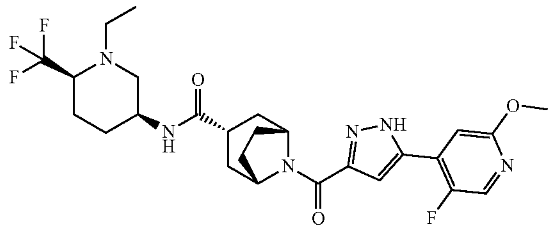

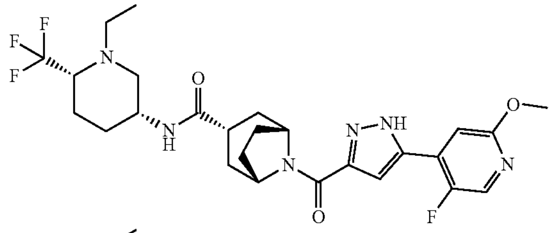

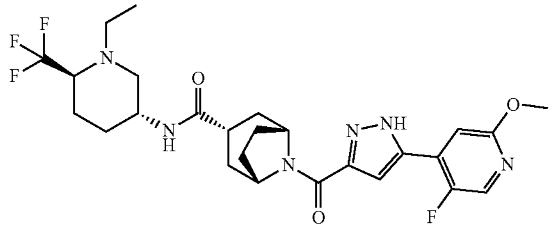

-continued

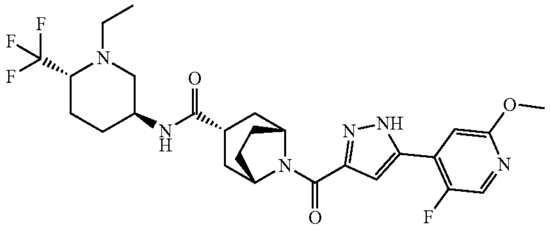

Step-1. (1R,3S,5S)—N-[1-ethyl-6-(trifluoromethyl)piperidin-3-yl]-8-[5-(5-fluoro-2-methoxypyridin-4-yl)-1-[[2-(trimethylsilyl)ethoxyl]methyl]pyrazole-3-carbonyl]-8-azabicyclo[3.2. 1]octane-3-carboxamide

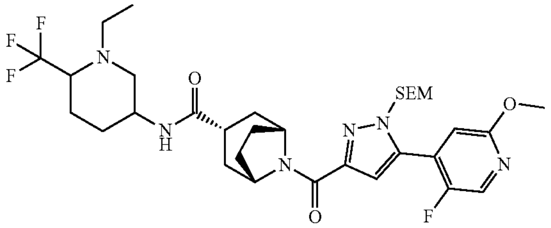 [SMILES: CCN1CC(NC(=O)[C@@H]2C[C@H]3CC[C@@H](C2)N3C(=O)c2cc(-c3cc(OC)ncc3F)n(COCC[Si](C)(C)C)n2)CCC1C(F)(F)F]

1-ethyl-6-(trifluoromethyl)piperidin-3-amine (INTERMEDIATE 528-A, 139.9 mg, 0.7 mmol) was added to a solution of (1R,3S,5S)-8-[5-(5-fluoro-2-methoxypyridin-4-yl)-1-[[2-(trimethylsilyl)ethoxy]methyl]pyrazole-3-carbonyl]-8-azabicyclo[3.2.1]octane-3-carboxylic acid (INTERMEDIATE 529, 300.0 mg, 0.6 mmol), EDCI (191.7 mg, 1.8 mmol), HOBt (240.9 mg, 1.8 mmol) and DIPEA (0.31 mL). The solution was stirred at 25° C. for 14 h, then diluted with water and extracted with EtOAc. The organic layers were combined, then dried over anhydrous sodium sulfate, filtered, and the solvent was evaporated. The residue was purified by silica gel column chromatography (EtOAc/petroleum ether; 1/1 v/v) to obtain the title compound (220 mg) as a solid. LCMS (ESI): 683.3 $[M+H]^+$.

Step-2. (1R,3S,5S)—N-[(3S,6S)-1-Ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide and (1R,3S,5S)—N-[(3S,6R)-1-ethyl-6-(trifluoromethyl)piperidin-3-yl]-8-[5-(5-fluoro-2-methoxypyridin-, 1-yl)-1H-pyrazole-3-carbonyl]-8-azabicyclo[3.2.1]octane-3-carboxamide and (1R,3S,5S)—N-[(3R,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide and (1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide

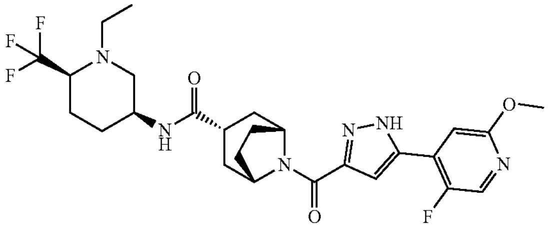

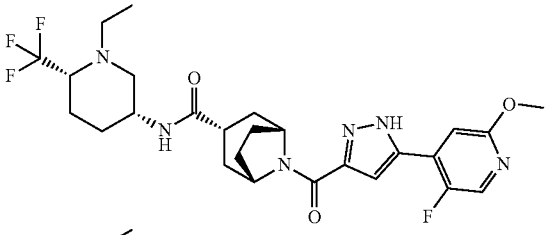

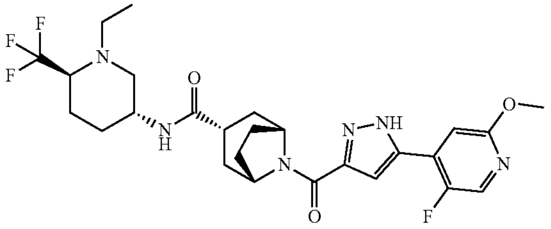

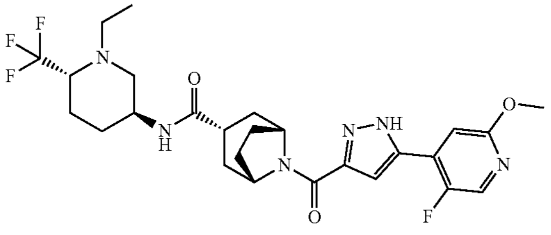

TFA (74 μL, 0.97 mmol) was added to a stirred mixture of (1R,3S,5S)—N-[1-ethyl-6-(trifluoromethyl)piperidin-3-yl]-8-[5-(5-fluoro-2-methoxypyridin-4-yl)-1-[[2-(trimethylsilyl)ethoxy]methyl]pyrazole-3-carbonyl]-8-azabicyclo[3.2.1]octane-3-carboxamide (Step-1, 220.0 mg, 0.32 mmol) in DCM (4.00 mL). The solution was stirred at 25° C. for 1 h, then concentrated under reduced pressure. The residue was purified by silica gel column chromatography (DCM/MeOH, 10/1 v/v) to obtain a diastereomeric mixture of (1R,3S,5S)—N-[(3S,6S)-1-Ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide and (1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide and (1R,3S,5S)—N-[(3R,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1.]octane-3-carboxamide and (1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide (130 mg, Example 299) as a solid.

The title compounds were purified by Prep-HPLC to yield two fractions, each containing two diastereomers.

Column: YMC-Actus Triart $C_{18}$

Column dimensions: 20×250 mm, 5 μm

Gradient: Water (1 mM FA)/MeCN, 90/10 to 35/65 v/v

Flow rate: 25 mL/min

Detection (nm): 254 nm

Example 299-A. The first eluting peak (30 mg) was obtained as a solid mixture of diastereomers.

$^1$H NMR (300 MHz, $CD_3OD$) δ 8.20-8.09 (m, 1H), 7.51-6.82 (m, 2H), 5.36 (s, 1H), 3.95 (s, 3H), 3.93-3.83 (m, 1H), 3.40-3.34 (m, 1H), 3.25-3.12 (m, 1H), 3.08-2.98 (m, 2H), 2.85-2.74 (m, 2H), 2.45-2.33 (m, 1H), 2.21-1.96 (m, 6H), 1.95-1.86 (m, 2H), 1.85-1.60 (m, 3H), 1.52-1.35 (m, 1H), 1.07 (t, 3H). LCMS (ESI): 553.2 $[M+H]^+$.

Example 299-B. The second eluting peak (65.0 mg) was obtained as a solid mixture of diastereomers.

$^1$H NMR (300 MHz, $CD_3OD$) δ 8.15 (s, 1H), 7.22 (s, 2H), 5.36 (s, 1H), 3.95 (s, 3H), 3.86 (dt, 5.5 Hz, 1H), 3.43-3.36 (m, 2H), 3.02-2.71 (m, 4H), 2.60 (t, 1H), 2.17-1.86 (m, 8H), 1.86-1.69 (m, 3H), 1.57 (d, 1H), 1.09 (t, 3H). LCMS (ESI): 553.2 $[M+H]^+$.

The first eluting peak (Example 299-A) was further purified using Chiral Prep-HPLC to separate the two diastereomers.

Column: CHIRALPAK IA

Column dimensions: 2×25 cm, 5 μm

Gradient: Hex (10 mM $NH_3$·MeOH)/EtOH, 80/40 v/v

Flow rate: 28 mL/min

Detection (nm): 220/254 nm

Example 299-C. The first eluting diastereomer (6.8 mg) was obtained as a solid.

The first eluting diastereomer had a retention time of 6.08 min.

$^1$H NMR (300 MHz, $CD_3OD$) δ 8.15 (d, 1H), 7.29-7.17 (m, 2H), 5.20-5.14 (m, 1H), 4.05-3.97 (m, 1H), 3.95 (s, 3H), 3.74-3.68 (m, 1H), 3.08-2.90 (m, 5H), 2.66-2.56 (m, 1H), 2.27-2.12 (m, 2H), 2.12-1.95 (m, 5H), 1.94-1.73 (m, 4H), 1.68-1.40 (m, 1H), (t, 3H). LCMS (ESI): 553.1 $[M+H]^+$.

Example 299-D. The second eluting diastereomer (6.9 was obtained as a solid.

The first eluting diastereomer had a retention time of 11.17 min, $^1$H NMR (300 MHz, $CD_3OD$) δ 8.15 (d, 1H) 7.29-7.17 (m, 2H), 5.17 (s, 1H), 4.04-3.97 (m, 1H), 3.95 (s, 3H), 3.69-3.63 (m, 1H), 3.22-2.92 (m, 5H), 2.68-2.58 (m, 1H), 2.27-2.11 (m, 2H), 2.12-1.96 (m, 5H), 1.95-1.87 (m, 1H), 1.86-1.72 (m, 3H), 1.63-1.50 (m, 1.21 (t, 3H). LCMS (ESI): 553.1 $[M+H]^+$.

The second eluting peak (Example 299-B) was further purified using Chiral Prep-HPLC to separate the two diastereomers.

Column: CHIRAL ART Cellulose-SB

Column dimensions: 2×25 cm, 5 μm

Gradient: Hex (10 mM $NH_3$·MeOH)/IPA, 70/30 v/v

Flow rate: 20 ML/min

Detection (nm): 220/254 nm

Example 299-E. The first eluting diastereomer (16.9 mg) was obtained as a solid.

The first eluting diastereomer had a retention time of 7.98 min.

$^1$H NMR (300 MHz, $CD_3OD$) δ 8.17 (s, 1H), 7.28-7.16 (m, 2H), 5.36 (s, 1H), 4.86-4.62 (m, 1H), 3.98-3.92 (m, 3H), 3.86 (dt, 1H), 3.41-3.35 (m, 1H), 3.02-2.69 (m, 4H), 2.60 (t, 1H), 2.22-1.86 (m, 8H), 1.86-1.67 (m, 3H), 1.67-1.48 (m, 1H), 1.09 (t, 3H). LCMS (ESI): 553.1 $[M+H]^+$.

Example 299-F. The second eluting diastereomer (18.0 mg) was obtained as a solid.

The second eluting diastereomer had a retention time of 10.11 min.

$^1$H NMR (300 MHz, $CD_3OD$) δ 8.20-8.14 (m, 1H), 7.47-6.85 (m, 2H), 5.40-5.34 (m, 1H), 4.82-4.54 (m, 1H), 3.95 (s, 3H), 3.92-3.80 (m, 1H), 3.44-3.27 (m, 1H), 3.03-2.72 (m, 4H), 2.67-2.53 (m, 1H), 2.27-1.99 (m, 4H), 1.99-1.86 (m, 4H), 1.86-1.68 (m, 3H), 1.68-1.48 (m, 1H), 1.09 (t, 3H). LCMS (ESI): 553.1 $[M+H]^+$.

Example 300-A. (R)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide

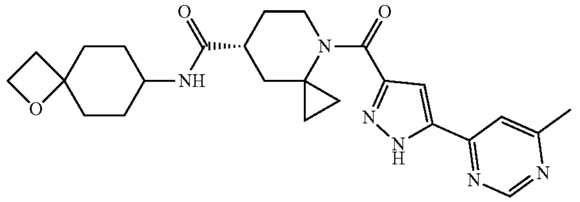 [SMILES: Cc1cc(-c2cc(C(=O)N3CC[C@@H](C(=O)NC4CCC5(CCO5)CC4)CC34CC4)n[nH]2)ncn1]

HATU (134.0 mg, 0.35 mmol) and 1-oxaspiro[3.5]nonan-7-amine (66.0 mg, 0.47 mmol) were added to a stirred solution of (7R)-4-(5-(6-methylpyrimidin-4-yl)-1H-pyrazole-3-carbonyl)-4-azaspiro[2.5]octane-7-carboxylic acid (Example 308, Step-3b, 80.0 mg, 0.23 mmol) and DIPEA (91.0 mg, 0.70 mmol) in DMF (5.00 mL). The resulting mixture was stirred at 25° C. for 14 h. The resulting mixture was diluted with EtOAc, washed with water and concentrated. The residue was purified by silica gel column chromatography eluting with DCM/MeOH (10/1 v/v) and further purified by reverse phase column chromatography (using the following conditions: C18 column, Mobile Phase A: Water (0.1% $NH_4HCO_3$), Mobile Phase B: MeCN; Flow rate: 30 mL/min; Gradient: 15 B to 50 B in 20 min; 220/254 nm) to obtain the title compound (5.0 mg) as a solid mixture of diastereomers, $^1$H NMR (300 MHz, DMSO-$d_6$) δ 14.20 (s, 1H), 9.05 (d, 1H), 7.91 (d, 1H), 7.67 (d, 1H), 7.23 (s, 1H), 4.62-4.28 (m, 3H), 3.56-3.27 (m, 2H), 2.68-2.61 (m, 2H), 2.33-2.22 (m, 3H), 2.03-1.93 (m, 2H), 1.80-0.55 (m, 15H). LCMS (ESI): $[M+H]^+$: 465.2.

Example 300-B. (S)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide

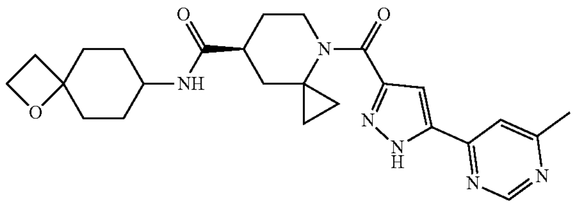 [SMILES: Cc1cc(-c2cc(C(=O)N3CC[C@H](C(=O)NC4CCC5(CCO5)CC4)CC34CC4)n[nH]2)ncn1]

The title compound was prepared using a procedure similar to the one described for the synthesis of Example 119, except (7S)-4-(5-(6-methylpyrimidin-4-yl)-1H-pyrazole-3-carbonyl)-4-azaspiro[2.5]octane-7-carboxylic acid (Example 308, Step-3a) was used as a starting material. The title compound was obtained as a solid (6.0 mg). $^{1}$H NMR (300 MHz, DMSO-$d_6$) δ 13.52 (s, 1H), 9.05 (d, 1H), 7.91 (d, 1H), 7.67 (d, 1H), 7.23 (s, 1H), 4.61-4.28 (m, 3H), 3.56-3.27 (m, 2H), 2.68-2.61 (m, 2H), 2.33-2.22 (m, 3H), 2.03-1.93 (m, 2H), 1.80-0.52 (m, 15H). LCMS (ESI): $[M+H]^+$: 465.2.

Example 301. (1R,3s,5S)-8-(5-(5-fluoro-2-methoxy-pyridin-, 1-yl)-1H-pyrazole-3-carbonyl)-N-(4-hydroxy-4-(perfluoroethyl)cyclohexyl)-8-azabicyclo[3.2.1]octane-3-carboxamide

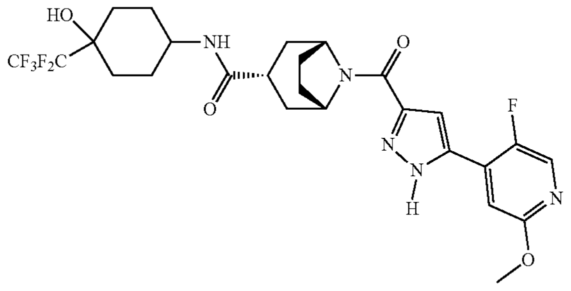

Step-1. tert-butyl (4-hydroxy-4-(perfluoroethyl)cyclohexyl)carbamate

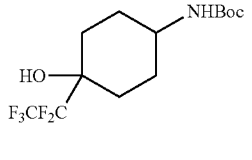

Trimethyl(perfluoroethyl)silane (1.10 g, 5.74 mmol) and TBAF (1.53 g, 5.85 mmol) were added to a stirred solution of tert-butyl (4-oxocyclohexyl)carbamate (600.0 mg, 2.81 mmol) in THF (10.00 mL) at 0° C. The resulting mixture was stirred at 22° C. for 16 h. The solution was then quenched with aqueous saturated solution of $NH_4Cl$. The reaction was then concentrated under reduced pressure, dissolved in DCM, and extracted with water. The aqueous layer was further extracted with DCM and the organic layers were combined, then dried over anhydrous sodium sulfate, filtered, and the solvent was evaporated. The residue was purified by silica gel column chromatography eluting with cyclohexane/EtOAc (4/1 v/v to 1.5/1 v/v) to obtain the diasteromeric mixture of the title compound (40.0 mg) as an oil. $^{1}$H NMR (400 MHz, $CDCl_3$) δ 4.42 (s, 1H), 3.44 (s, 1H), 1.95-1.73 (m, 8H), 1.69 (s, 1H), 1.57-1.51 (m, 2H), 1.45 (s, 9H).

Step-2. 4-amino-1-(perfluoroethyl)cyclohexan-1-ol hydrochloride

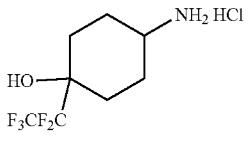

HCl (4 M in 1,4-dioxane, 88.0 mg, 2.40 mmol) was added to a stirred solution of ten-butyl (4-hydroxy-4-(perfluoroethyl)cyclohexyl)carbamate (Step-1, 40.0 mg, 0.12 mmol) in 1,4-dioxane (0.60 mL) at 22° C. The resulting mixture was stirred for 48 h. The solution was then concentrated under reduced pressure to obtain the title compound (32.0 mg) as a solid mixture of diastereomers. TLC-MS (APCI): $[M+H]^+$: 234.1.

Step-3. (1R,3s,5S)-8-(5-(5-fluoro-1-ethoxypyridin-4-yl)-1H-pyrazole-3-carbonyl)-N-(4-hydroxy-4-(perfluoroethyl)cyclohexyl)-8-azabicyclo[3.2.1]octane-3-carboxamide

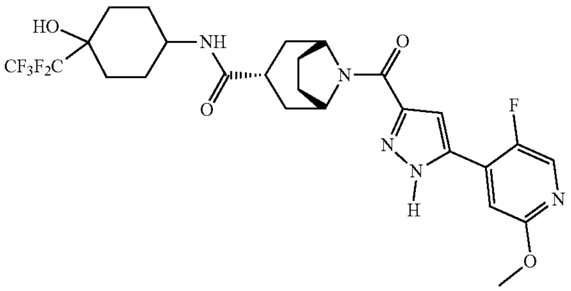

HOBt (22.0 mg, 0.14 mmol), EDCI (28.0 mg, 0.14 mmol), and 4-amino-1-(perfluoroethyl)cyclohexan-1-01 hydrochloride (Step-2, 31.0 mg, 0.12 mmol) were added to a stirred solution of (1R,3s,5S)-8-(5-(5-fluoro-2-methoxy-pyridin-4-yl)-1H-pyrazole-3-carbonyl)-8-azabicyclo[3.2.1]octane-3-carboxylic acid (INTERMEDIATE 508, 36.0 mg, 96.0 μmol) and DIPEA (0.08 mL, 0.48 trump in DMF (1.60 mL). The resulting mixture was stirred at 22° C. for 16 h. The reaction mixture was concentrated under reduced pressure and diluted with EtOAc/water (1/1 v/v) and washed with water and brine, and then dried over anhydrous sodium sulfate, filtered, and the solvent was evaporated. The residue was purified by reverse phase column chromatography (using the following conditions: C18 column, 10% to 95% MeOH/Water (0.1% HCOOH)) to obtain the title compound (32.0 mg) as a solid mixture of diastereomers. $^{1}$H NMR (400 MHz, DMSO-$d_6$) δ 14.03 (s, 1H), 8.29 (s, 1H), 7.77 (d, 1H), 7.33 (d, 1H), 7.13 (d, 1H), 5.84 (s, 1H), 4.68 (s, 1H), 3.88

(s, 3H), 3.50 (s, 1H), 2.84-2.72 (m, 1H), 2.11-1.43 (m, 16H). LCMS (ESI): $[M+H]^+$: 590.1.

Example 302. A Diastereomeric Mixture of (1R,3R,5S)-8-[5-(5-fluoro-2-methoxypyridin-4-yl)-1H-pyrazole-3-carbonyl]-N-[(1r,4r)-4-(difluoromethyl)-4-methoxycyclohexyl]-8-azabicyclo[3.2.1]octane-3-carboxamide and (1R,3R,5S)-8-[5-(5-fluoro-2-methoxypyridin-1-yl)-1H-pyrazole-3-carbonyl]-N-[(1s,4s)-4-(difluoromethyl)-4-methoxycyclohexyl]-8-azabicyclo[3.2.1]octane-3-carboxamide

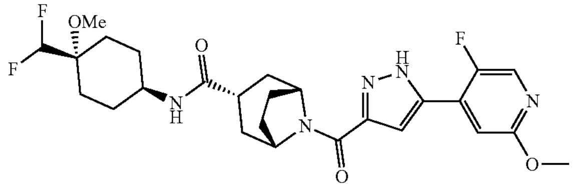

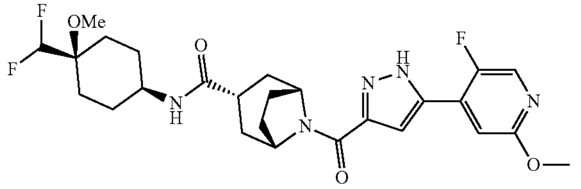

HOBt (81.2 mg, 0.60 mmol), EDCI (115.2 mg, 0.60 mmol), and 4-(difluoromethyl)-4-methoxycyclohexan-1-amine (INTERMEDIATE 530, 79.0 mg, 0.44 mmol) were added to a solution of (1R,3S,5S)-8-[5-(5-fluoro-2-methoxypyridin-4-yl)-1H-pyrazole-3-carbonyl]-8-azabicyclo[3.2.1]octane-3-carboxylic acid (INTERMEDIATE 508, 150.0 mg, 0.40 mmol) and DIPEA (258.9 mg, 2.00 mmol) in DMF (5.00 mL). The resulting solution was stirred at 25° C. for 14 h. The resulting mixture was diluted with EtOAc and water. The organic layer was concentrated under reduced pressure and the residue was purified by Prep-TLC (DCM/MeOH, 15/1 v/v) to obtain a diastereomeric mixture of (1R,3R,5S)-8-[5-(5-fluoro-2-methoxypyridin-4-yl)-1H-pyrazole-3-carbonyl]-N-[(1r,4r)-4-(difluoromethyl)-4-methoxycyclohexyl]-8-azabicyclo[3.2.1]octane-3-carboxamide and (1R,3R,5S)-8-[5-(5-fluoro-2-methoxypyridin-4-yl)-1H-pyrazole-3-carbonyl]-N-[(1s,4s)-4-(difluoromethyl)-4-methoxycyclohexyl]-8-azabicyclo[3.2.1]octane-3-carboxamide (150.0 mg, Example 302) as a solid. LCMS (ESI): 536.2 $[M+H]^+$.

The diastereomers of the title compound were separated by Chiral Prep-HPLC.

Column: CHIRAL ART Cellulose-SB

Column dimensions: 2×25 cm, 5 μm

Gradient: MTBE (0.5% 2 M $NH_3$·MeOH)/MeOH, 90/10 v/v

Flow Rate: 20 mL/min

Detection (nm): 220/254 nm

Example 302-A. The first eluting diastereomer (42.7 mg) was obtained as a solid.

The first eluting diastereomer had a retention time of 8.81 min.

$^1$H NMR (300 MHz, DMSO-$d_6$) δ 14.04 (m, 1H), 8.29 (d, 1H), 7.74 (s, 1H), 7.34 (d, 1H), 7.13 (d, 1H), 6.26-5.61 (m, 1H), 5.21 (s, 1H) 4.65 (d, 1H), 3.88 (s, 3H), 3.79 (s, 1H), 3.25 (s, 3H), 2.94-2.88 (m, 1H), 2.14-1.73 (m, 7H), 1.70-1.55 (m, 7H), 1.54-1.40 (m, 2H). LCMS (ESI): 536.2 $[M+H]^+$.

Example 302-B. The second eluting diastereomer (43.9 mg) was obtained as a solid. The second eluting diastereomer had a retention time of 10.68 min.

$^1$H NMR (300 MHz, DMSO-$d_6$) δ 14.02 (s, 1H), 8.29 (s, 1H), 7.74 (d, 1H), 7.34 (d, 1H), 7.14 (s, 1H), 6.24-5.63 (m, 1H), 5.45-5.00 (m, 1H), 4.71-4.65 (m, 1H), 3.88 (s, 3H), 3.50-3.44 (m, 1H), 3.27 (s, 3H), 2.91-2.65 (m, 1H), 2.12-1.96 (m, 1H), 1.95-1.70 (m, 6H), 1.70-1.54 (m, 4H), 1.47-1.15 (m, 5H). LCMS (ESI): 536.2 $[M+H]^+$.

Example 303. A Diastereomeric Mixture of (1R,3s,5S)—N-((1r,4R)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide and (1R,3s,5S)—N-((1s,4S)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide

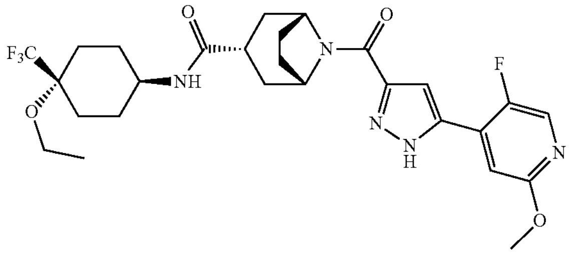

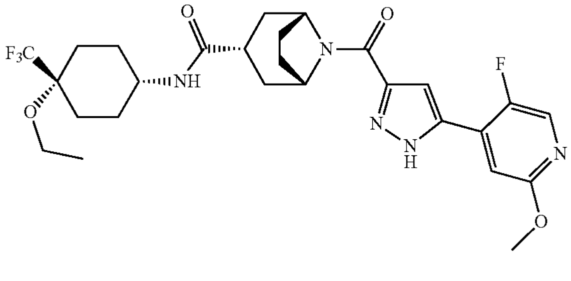

EDCI (10.0 mg, 0.06 mmol), HOBt (7.00 mg, 0.06 mmol), and 4-ethoxy-4-(trifluoromethyl)cyclohexan-1-amine (INTERMEDIATE 535-A, 9.0 mg, 0.05 mmol) were added to a stirred mixture of (1R,3S,5S)-8-[5-(5-fluoro-2-methoxypyridin-4-yl)-1H-pyrazole-3-carbonyl]-8-azabicyclo[3.2.1]octane-3-carboxylic acid (INTERMEDIATE 508, 14.0 mg, 0.04 mmol) and DIPEA (14.0 mg, 0.11 mmol) in DMF (1.00 mL). The resulting mixture was stirred at 25° C. for 3 h. The residue was purified by reverse phase column chromatography (using the following conditions: C18 column; Mobile Phase A: Water (10 mM $NH_4HCO_3$), Mobile Phase B: MeCN, Gradient: 20% B to 30% B in 12 min; Detector, UV 220/254 nm) to obtain the title compounds as a solid mixture of diastereomers (2.6 mg, Example 303). $^1$H NMR (300 MHz, DMSO-$d_6$) δ 13.99 (s, 1H), 8.27 (d, 1H), 7.80 (d, 1H), 7.31 (d, 1H), 7.11 (d, 1H), 4.67 (s, 1H), 3.86 (s, 3H), 3.83-3.76 (m, 1H), 3.60-3.44 (m, 2H), 3.28 (s, 1H), 3.00-2.80 (m, 1H), 2.10-1.68 (m, 10H), 1.60 (d, 6H) 1.16-1.05 (m, 3H). LCMS (ESI): $[M+H]^+$: 568.2.

The two diastereomers of the title compounds (100.0 mg) were separated using Chiral-Prep-HPLC, Column: CHIRAL ART Cellulose-SB column Column dimension: 2×25 cm, 5 μm Mobile Phase: MTBE (0.5% 2 M $NH_3$·MeOH): MeOH=90:10 hold for 13 min Flow rate: 20 mL/min Example 303-A. The first eluting diastereomer (84.0 mg) was obtained as a solid.

The first eluting diastereomer had a retention time of 7.04 min.

$^1$H NMR (300 MHz, DMSO-$d_6$) δ 14.02 (s, 1H), 8.30 (s, 1H), 7.80 (d, 1H), 7.33 (d, 1H), 7.14 (s, 1H), 5.30-4.59 (m, 2H), 3.88 (s, 3H), 3.83 (d, 1H), 3.59-3.48 (m, 2H), 3.00-2.79 (m, 1H), 2.13-1.44 (m, 16H), 1.19-1.02 (m, 3H). LCMS (ESI): [M+H]$^+$: 568.3.

Example 303-B. The second eluting diastereomer (2.7 mg) was obtained as a solid.

The second eluting diastereomer had a retention time of 9.74 min.

LCMS (ESI): [M+H]$^+$: 568.3.

Example 304. A Diastereomeric Mixture of (1R,3S,5S)-8-[5-(5-fluoro-2-methoxypyridin-4-yl)-1H-pyrazole-3-carbonyl]-N-[(1r,4r)-4-(2-methoxyethoxy)-4-(trifluoromethyl)cyclohexyl]-8-azabicyclo[3.2.1]octane-3-carboxamide and (1R,3S,5S)-8-[5-(5-fluoro-2-methoxypyridin-4-yl)-1H-pyrazole-3-carbonyl]-N-[(1s,4s)-4-(2-methoxyethoxy)-4-(trifluoromethyl)cyclohexyl]-8-azabicyclo[3.2.1]octane-3-carboxamide

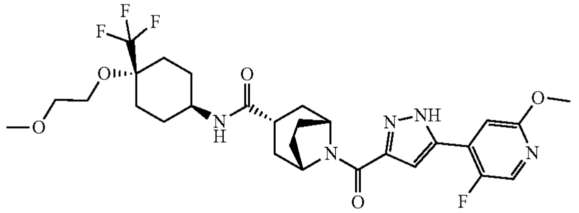

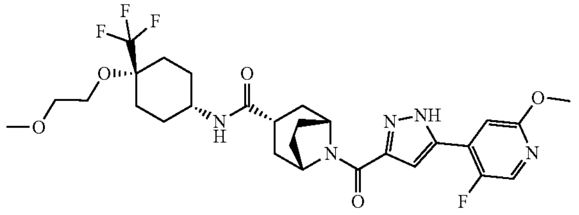

EDCI (60.0 mg, 0.31 mmol), HOBt (42.0 mg, 0.31 mmol), and 4-(2-methoxyethoxy)-4-(trifluoromethyl)cyclohexan-1-amine (INTERMEDIATE 531, 50.0 mg, 0.21 mmol) were added to a stirred solution of (1R,3S,5S)-8-[5-(5-fluoro-2-methoxypyridin-4-yl)-1H-pyrazole-3-carbonyl]-8-azabicyclo[3.2.1]octane-3-carboxylic acid (INTERMEDIATE 508, 78.00 mg, 0.21 mmol) and DIPEA (81.0 mg, 0.63 mmol) in DMF (2.00 mL). The resulting solution was stirred at 25° C. for 14 h. The resulting mixture was dilute with EtOAc and washed with water. The organic layer was concentrated under reduced pressure and the residue was purified by reverse phase column chromatography (using the following conditions: Column: C18; Mobile Phase A: Water (10 mM $NH_4HCO_3$), Mobile Phase B: MeCN; Gradient: 30% B to 40% B in 12 min; Detection: 220/254 nm) to obtain a diastereomeric mixture of (1R,3S,5S)-8-[5-(5-fluoro-2-methoxypyridin-4-yl)-1H-pyrazole-3-carbonyl]-N-[(1r,4r)-4-(2-methoxyethoxy)-4-(trifluoromethyl)cyclohexyl]-8-azabicyclo[3.2.1]octane-3-carboxamide and (1R,3S,5S)-8-[5-(5-fluoro-2-methoxypyridin-4-yl)-1H-pyrazole-3-carbonyl]-N-[(1s,4s)-4-(2-methoxyethoxy)-4-(trifluoromethyl)cyclohexyl]-8-azabicyclo[3.2.1]octane-3-carboxamide (62 mg, Example 304) as a solid. $^1$H NMR (400 MHz, $CD_3OD$) δ 8.14 (d, 1H), 7.22 (d, 2H), 5.29 (s, 1H), 4.58 (s, 1H), 3.95 (s, 3H), 3.76-3.69 (m, 2H), 3.69-3.52 (m, 3H) 3.39 (d, 3H), 2.98-2.86 (m, 1H), 2.25-1.97 (m, 6H) 1.96-1.82 (m, 3H), 1.82-1.72 (m, 3H), 1.72-1.46 (m, 4H). LCMS (ESI): 598.2 [M+H]$^+$.

The two diastereomers were purified by Chiral Prep-HPLC.

Column: CHIRAL ART Cellulose-SB

Column dimensions: 2×25 cm, 5 μm

Gradient: MTBE (0.5% 2 M $NH_3$·MeOH)/IPA

Flow Rate: 20 mL/min

Detection (nm): 220/254

Example 304-A. The first eluting diastereomer (2.4 mg) was obtained as a solid.

The first eluting diastereomer had a retention time of 6.52 min.

$^1$H NMR (400 MHz, $CD_3OD$) δ 8.15 (s, 1H), 7.28 (s, 2H), 5.41 (s, 1H) 4.59 (s, 1H), 3.95 (s, 3H), 3.74-3.69 (m, 2H), 3.58-3.53 (m, 3H), 3.38 (s, 3H), 3.16-2.97 (m, 1H), 2.28-2.11 (m, 2H), 2.11-1.98 (m, 3H), 1.97-1.90 (m, 2H), 1.90-1.80 (m, 5H), 1.81-1.62 (m, 4H). LCMS (ESI): 598.3 [M+H]$^+$.

Example 304-B. The second eluting diastereomer (5.4 mg) was obtained as a solid.

The second eluting diastereomer had a retention time of 7.76 min.

$^1$H NMR (400 MHz, $CD_3OD$) δ 8.16 (s, 1H), 7.40-6.93 (m, 2H), 5.36 (s, 1H), 4.68 (s, 1H), 3.95 (s, 3H), 3.75-3.68 (m, 2H), 3.62-3.54 (m, 3H), 3.40 (s, 3H), 2.93 (d, 1H), 2.23-1.97 (m, 6H), 1.95-1.84 (m, 2H), 1.83-1.71 (m, 4H), 1.70-1.61 (m, 2H), 1.60-1.46 (m, 2H). LCMS (ESI): 598.3 [M+H]$^+$.

Example 305. (1R,3S,5S)-8-[5-(5-fluoro-2-methoxypyridin-4-yl)-1H-1,2,4-triazole-3-carbonyl]-N-[(1r,4r)-4-hydroxy-4-(trifluoromethyl)cyclohexyl]-8-azabicyclo[3.2.1]octane-3-carboxamide

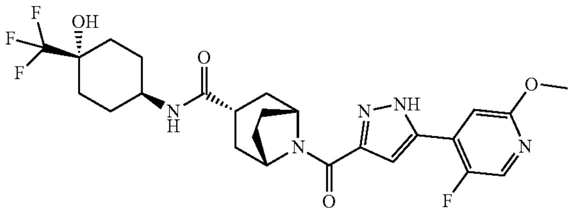 [SMILES: COc1cc(-c2cc(C(=O)N3[C@@H]4CC[C@H]3C[C@H](C(=O)N[C@H]3CC[C@@](O)(C(F)(F)F)CC3)C4)n[nH]2)c(F)cn1]

Step-1. Methyl 5-bromo-1-[[2-(trimethylsilyl)ethoxy]methyl]-1,2,4-triazole-3-carboxylate

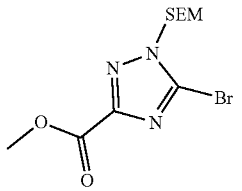 [SMILES: COC(=O)c1nc(Br)n(COCC[Si](C)(C)C)n1]

NaH (209.0 mg, 5.2 mmol, 60% dispersion in mineral oil) was added to a solution of methyl 5-bromo-1H-1,2,4-triazole-3-carboxylate (900.0 mg, 4.4 mmol) in DMF (5.0 mL) at 0° C. The solution was stirred at 0° C. for 1 h, then SEMCl (0.93 mL, 5.2 mmol) was added. The solution was stirred at 0° C. for 3 h, then diluted with EtOAc and washed with water. The organic layer was concentrated under vacuum and the residue was purified by silica gel column chromatography (petroleum ether/EtOAc, 5/1 v/v) to obtain the title compound (830 mg) as an oil. LCMS (ESI): 336.0 [M+H]+.

Step-2. Methyl 5-(5-fluoro-2-methoxypyridin-4-yl)-1-[[2-(trimethylsilyl)ethoxy]methyl]-1,2,4-triazole-3-carboxylate

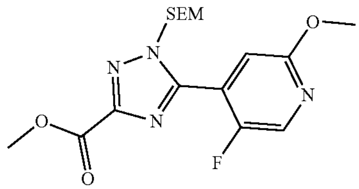

5-fluoro-2-methoxypyridin-4-ylboronic acid (640.0 mg, 3.7 mmol), Pd(dppf)$Cl_2$ (365.0 mg, 0.5 mmol), and $K_3PO_4$ (1.0 g, 5.0 mmol) were added to a solution of methyl 5-bromo-1-[[2-(trimethylsilyl)ethoxy]methyl]-1,2,4-triazole-3-carboxylate (Step-1, 840 mg, 2.5 mmol) in 1,4-dioxane (10.00 mL) and $H_2O$ (1.00 mL). The solution was stirred at 70° C. for 4 h under nitrogen atmosphere, then concentrated under reduced pressure. The residue was purified by silica gel column chromatography (petroleum ether/EtOAc, 10/1 v/v) to obtain the title compound (450.0 mg) as a solid. LCMS (ESI): 383.1 [M+H]+.

Step-3. (1R,3S,5S)-8-[5-(5-fluoro-2-methoxypyridin-, 1-yl)-1H-1,2,4-triazole-3-carbonyl]-N-[(1r,4r)-4-hydroxy-4-(trifluoromethyl)cyclohexyl]-8-azabicyclo[3.2.1]octane-3-carboxamide

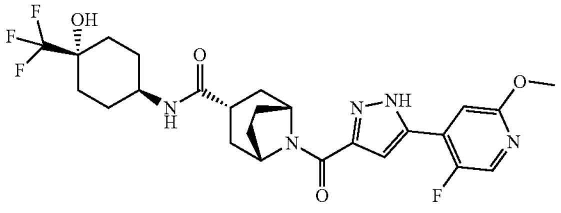 [SMILES: COc1cc(-c2cc(C(=O)N3[C@@H]4CC[C@H]3C[C@H](C(=O)N[C@H]3CC[C@@](O)(C(F)(F)F)CC3)C4)n[nH]2)c(F)cn1]

$AlMe_3$ (1 M, 1.30 mL, 1.30 mmol) was added dropwise to a mixture of (1R,3S,5S)—N-[(1r,4r)-4-hydroxy-4-(trifluoromethyl)cyclohexyl]-8-azabicyclo[3.2.1]octane-3-carboxamide (INTERMEDIATE 536, 251 mg, 0.8 mmol) in toluene (3 mL) under nitrogen atmosphere. The solution was stirred 25° C. for 1 h under nitrogen atmosphere, then methyl 5-(5-fluoro-2-methoxypyridin-4-yl)-1-[[2-(trimethylsilyl)ethoxy]methyl]-1,2,4-triazole-3-carboxy late (Step-2, 200 mg, 0.5 mmol) was added. The solution was stirred at 80° C. for 14 h under nitrogen atmosphere, then $AlMe_3$ (1 M, 2 mL, 2.1 mmol) was added. The solution was stirred at 80° C. for 14 h under nitrogen atmosphere, then MeOH was added and then solution was concentrated under reduced pressure. The resulting solution was diluted with EtOAc and washed with water, then the organic layer was concentrated under vacuum. The residue was purified by reverse phase column chromatography (using the following conditions: Column: C18; Mobile Phase A: Water (10 mM $NH_4HCO_3$); Mobile Phase B: MeCN; Gradient: 35% B to 47% B in 12 min; Detection: 220/254 nm) to obtain the title compound (9 mg) as a solid. $^1H$ NMR (400 MHz, $CD_3OD$) δ 8.12 (s, 1H), 7.36 (d, 1H), 5.46 (s, 1H), 4.59 (s, 1H), 3.93 (s, 4H), 3.17-3.00 (m, 1H), 2.26-2.13 (m, 1H), 2.13-1.99 (m, 3H), 1.99-1.83 (m, 6H), 1.78 (s, 2H), 1.68 (d, 4H). LCMS (ESI): 541.3 [M+H]+.

Example 306. A Diastereomeric Mixture (1R,3s,5S)-8-(5-(5-fluoro-2-methoxypyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide

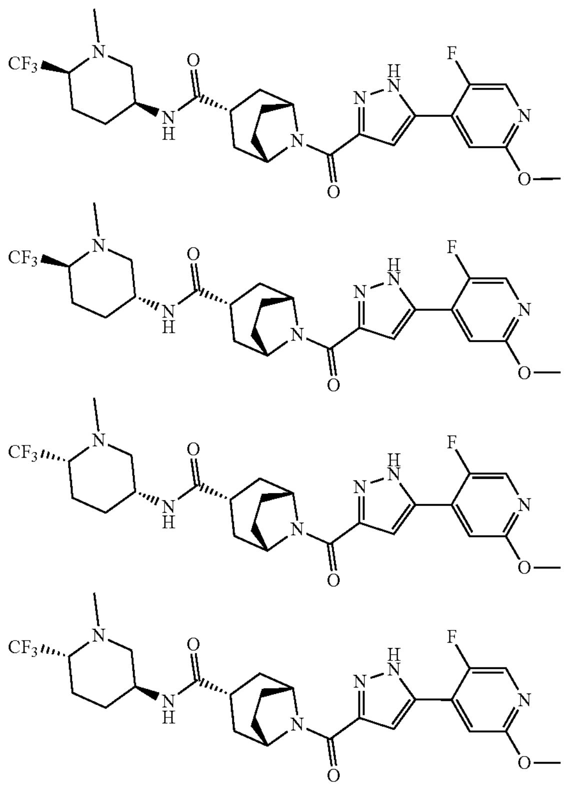

HATU (690.0 mg, 1.80 mmol) and 1-methyl-6-(trifluoromethyl)piperidin-3-amine (INTERMEDIATE 528-B, 200.0 mg, 1.20 mmol) were added to a stirred solution of (1R,3R,5S)-8-[5-(5-fluoro-2-methoxypyridin-4-yl)-1H- pyrazole-3-carbonyl]-8-azabicyclo[3.2.1]octane-3-carboxylicacid (INTERMEDIATE 508, 500.0 mg, 1.32 mmol) and DIPEA (1.40 g, 10.80 mmol) in DMF (3.00 mL). The resulting mixture was stirred at 25° C. for 14 h. The resulting mixture was diluted with EtOAc, washed with water and concentrated. The residue was purified by Prep-TLC eluting with DCM/MeOH (20/1 v/v) to obtain the diastereomeric mixture (Example 306) of (1R,3s,5S)-8-(5-(5-fluoro-2-methoxypyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide, (1R,3s,5S)-8-(5-(5-fluoro-2-methoxypyridin-4-yl)-1H-pyrazole-3-carbonyl)-N-((3R,6S)-1-meth 6-(trifluoromethyl)piperidin-3-yl)-8-azabicyclo[3.2.1]octane-3-carboxamide, (1R,3s,5S)-8-(5-(5-fluoro-2-methoxypyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide, and (1R,3s,5S)-8-(5-(5-fluoro-2-methoxypyridin-4-yl)-1H-pyrazole-3-carbonyl)-N-((4S,6R)-1-methyl-6-(trifluoromethyl)piperidin-3-yl)-8-azabicyclo[3.2.1]octane-3-carboxamide in two fractions, each containing two diastereomers.

Example 306-A. The first eluting spot (240.0 mg) was obtained as a solid.

$^1$H NMR (300 MHz, $CD_3OD$) δ 8.14 (d, 1H), 7.32-7.15 (m, 2H), 5.16-4.52 (m, 2H), 4.06-3.76 (m, 4H), 3.14-2.86 (m, 2H), 2.77-2.64 (m, 1H), 2.51 (s, 3H), 2.08-1.55 (m, 13H). LCMS (ESI): $[M+H]^+$: 539.4.

Example 306-B. The second eluting spot (55.0 mg) was obtained as a solid.

$^1$H NMR (300 MHz, $CD_3OD$) δ 8.15 (d, 1H), 7.30-7.17 (m, 2H), 5.54-4.53 (m, 2H), 4.06-3.75 (m, 4H), 3.07-2.86 (m, 2H), 2.82-2.66 (m, 1H), 2.43 (s, 3H), 2.20-1.23 (m, 13H). LCMS (ESI): $[M+H]^+$: 538.9.

The first eluting spot (240 mg) from Prep-TLC containing two diastereomers of the title compounds was separated using Chiral-Prep-HPLC, Column: CHIRALPAK IG column Column dimension: 2×25 cm, 5 μm Mobile Phase: 3/1 hexanes/DCM (0.5% 2 M $NH_3$·MeOH):EtOH=50:50 hold for 30 min Flow rate: 17 mL/min Detection: 220/254 nm Example 306-C. The first eluting diastereomer (14.3 mg) was obtained as a solid.

The first eluting diastereomer had a retention time of 9.97 min.

$^1$H NMR (300 MHz, $CD_3OD$) δ 8.15 (d, 1H), 7.32-7.15 (m, 2H), 5.16-4.52 (m, 2H), 4.07-3.76 (m, 4H), 3.14-2.86 (m, 2H), 2.77-2.64 (m, 1H), 2.51 (s, 3H), 2.08-1.55 (m, 13H). LCMS (ESI): $[M+H]^+$: 539.3.

Example 306-D. The second eluting diastereomer (14.7 mg) was obtained as a solid.

The second eluting diastereomer had a retention time of 25.54 min.

$^1$H NMR (300 MHz, $CD_3OD$) δ 8.14 (d, 1H), 7.32-7.15 (m, 2H), 5.40-4.52 (m, 2H), 4.06-3.76 (m, 4H), 3.14-2.86 (m, 2H), 2.77-2.64 (m, 1H), 2.51 (s, 3H), 2.08-1.55 (m, 13H). LCMS (ESI): $[M+H]^+$: 539.4.

The second eluting spot (55 mg) from Prep-TLC containing two diastereomers of the title compounds was separated using Chiral-Prep-HPLC.

Column: CHIRALPAK IE column

Column dimension: 2×25 cm, 5 μm

Mobile Phase: 3/1 hexanes/DCM (0.5% 2M $NH_3$·MeOH):EtOH=70:30 hold for 15 min

Flow rate: 20 mL/min

Detection: 220/254 nm

Example 306-E. The first eluting diastereomer (18.1 mg) was obtained as a solid.

The first eluting diastereomer had a retention time of 8.36 min.

$^1$H NMR (300 MHz, $CD_3OD$) δ 8.27-8.05 (m, 1H), 7.52-6.98 (m, 2H), 5.28 (s, 1H), 4.82-4.62 (m, 1H), 4.11-3.62 (m, 4H), 3.13-2.84 (m, 2H), 2.84-2.64 (m, 1H), 2.53-2.26 (m, 3H), 2.19-1.85 (m, 9H), 1.83-1.48 (m, 3H), 1.45-1.27 (m, 1H). LCMS (ESI): $[M+H]^+$: 539.3.

Example 306-F. The second eluting diastereomer (16.5 mg) was obtained as a solid.

The second eluting diastereomer had a retention time of 10.74 min.

$^1$H NMR (300 MHz, $CD_3OD$) δ 8.32-8.00 (m, 1H), 7.45-6.91 (m, 2H), 5.37 (s, 1H), 4.82-4.61 (m, 1H), 4.04-3.78 (m, 4H), 3.15-2.89 (m, 2H), 2.84-2.61 (m, 1H), 2.46-2.32 (m, 3H), 2.20-1.86 (m, 11H), 1.85-1.55 (m, 1H), 1.47-1.23 (m, 1H). LCMS (ESI): $[M+H]^+$: 538.9.

Example 307. (1R,3s,5S)—N-(3,3-difluoro-1-oxaspiro[3.5]nonan-7-yl)-8-(5-(5-fluoro-2-methoxypyridin-4-yl)-1H-pyrazole-3-carbonyl)-8-azabicyclo[3.2.1]octane-3-carboxamide

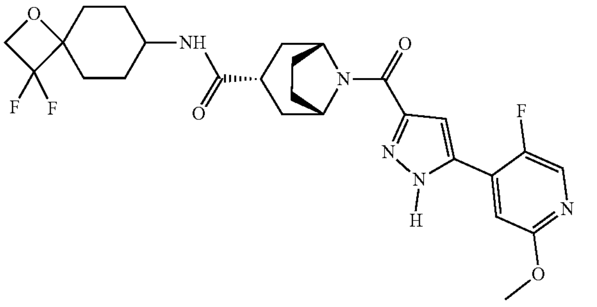 [SMILES: COc1cc(-c2cc(C(=O)N3[C@@H]4CC[C@H]3C[C@H](C(=O)NC3CCC5(CC3)OCC5(F)F)C4)n[nH]2)c(F)cn1]

HATU (45.0 mg, 0.12 mmol) and 3,3-difluoro-1-oxaspiro[3,5]nonan-7-amine 2,2,2-trifluoroacetate (INTERMEDIATE 537, 48.0 mg, 0.17 mmol) were added to a stirred solution of (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 40.0 mg, 0.11 mmol) and DIPEA (94.0 μL, 0.54 mmol) in DMF (0.46 mL) at 22° C. for 16 h. The reaction mixture was concentrated under reduced pressure and diluted with EtOAc/water (1/1 v/v) and washed with water and brine, and then dried over anhydrous sodium sulfate, filtered, and the solvent was evaporated. The residue was purified by reverse phase column chromatography (C18 column, 10% to 95% MeOH/Water (0.1% HCOOH)) to obtain the title compound (44.0 mg) as a solid mixture of diastereomers.

Example 308-A. A diastereomeric mixture of Example 308-C and Example 308-D

Example 308-B. A Diastereomeric Mixture of Example 308-E and Example 308-F

Example 308-C. (S)—N-((1r,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

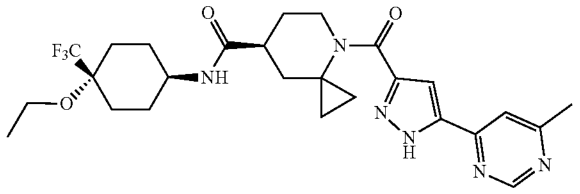 [SMILES: CCO[C@]1(C(F)(F)F)CC[C@@H](NC(=O)[C@H]2CCN(C(=O)c3cc(-c4cc(C)ncn4)[nH]n3)C3(CC3)C2)CC1]

Example 308-D. (S)—N-((1s,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

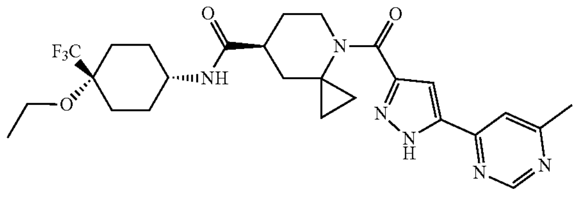 [SMILES: CCO[C@]1(C(F)(F)F)CC[C@H](NC(=O)[C@H]2CCN(C(=O)c3cc(-c4cc(C)ncn4)[nH]n3)C3(CC3)C2)CC1]

Example 308-E. (R)—N-((1r,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

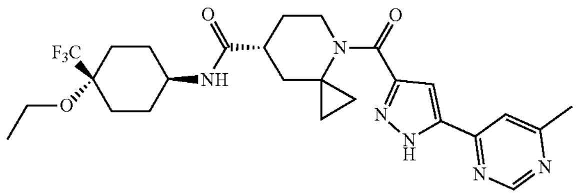

Example 308-F. (R)—N-((1s,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

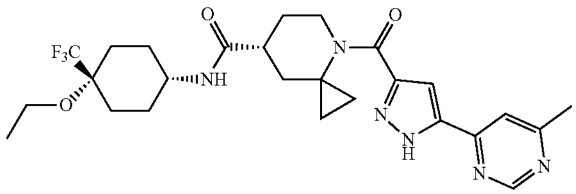 [SMILES: CCO[C@]1(C(F)(F)F)CC[C@H](NC(=O)[C@@H]2CCN(C(=O)c3cc(-c4cc(C)ncn4)[nH]n3)C3(CC3)C2)CC1]

Step-1. Methyl 4-[5-(6-methylpyrimidin-4-yl)-1H-pyrazole-3-carbonyl]-4-azaspiro[2.5]octane-7-carboxylate

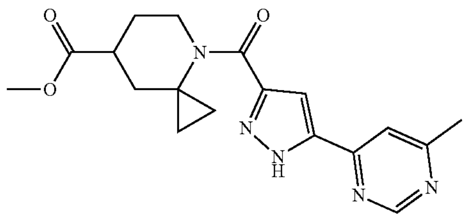

HOBt (496.3 mg, 3.67 mmol), EDCI (704.1 mg, 3.67 mmol), and methyl 4-azaspiro[2.5]octane-7-carboxylate hydrochloride (554.0 mg, 2.69 mmol, CAS #: 2253630-26-9, Enamine Ltd.) were added to a solution of 5-(6-methylpyrimidin-4-yl)-1H-pyrazole-3-carboxylic acid (INTERMEDIATE 538, 500.0 mg, 2.45 mmol) and DIPEA (1.58 g, 12.24 mmol) in DMF (5.00 mL). The resulting mixture was stirred at 25° C. for 14 h. The resulting mixture was diluted with EtOAc and water. The resulting mixture was concentrated under reduced pressure. The residue was purified by reverse phase column chromatography (using the following conditions: C18 column; Mobile Phase A: $NH_3HCO_3$ in water, Mobile Phase B: MeCN; 20 to 30% B gradient in 10 min; detector, UV 220/254 nm) to obtain the title compound (400.0 mg) as a solid. LCMS (ESI): $[M+H]^+$: 356.2.

Step-2. Methyl (7S)-4-[5-(6-methylpyrimidin-4-yl)-1H-pyrazole-3-carbonyl]-4-azaspiro[2.5]octane-7-carboxylate and methyl (7R)-4-[5-(6-methylpyrimidin-4-yl)-1H-pyrazole-3-carbonyl]-4-azaspiro[2.5]octane-7-carboxylate

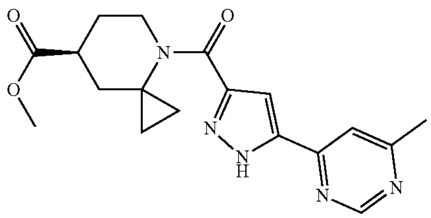

-continued

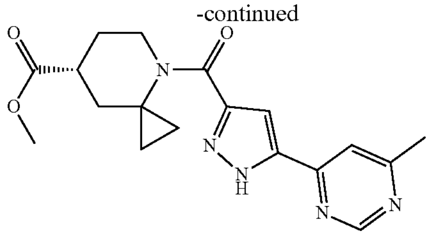

The two enantiomers of methyl 4-[5-(6-methylpyrimidin-4-yl)-1H-pyrazole-3-carbonyl]-4-azaspiro[2.5]octane-7-carboxylate (Step-1, 600.0 mg, 1.69 mmol) were separated by Chiral-Prep-HPLC (using the following conditions: Column: CHIRALPAK IE, 3×25 cm, 5 nm; Mobile Phase A: MTBE (0.5% 2 M $NH_3$·MeOH), Mobile Phase B: EtOH; Flow rate: 32 mL/min; Gradient: 50 B to 50 B in 30 min; Detector, UV 220/254 nm). The first eluting compound ((7S)-4-[5-(6-methylpyrimidin-4-yl)-1H-pyrazole-3-carbonyl]-4-azaspiro[2.5]octane-7-carboxylic acid) was obtained as a solid (300.0 mg) and had a retention time of 12.26 min. The second eluting compound ((7R)-4-[5-(6-methylpyrimidin-4-yl)-1H-pyrazole-3-carbonyl]-4-azaspiro[2,5]octane-7-carboxylic acid) was obtained as a solid (270.0 and had a retention time of 23.81 min. LCMS (ESI): $[M+H]^+$: 356.2.

Step-3a. (7S)-4-[5-(6-methylpyrimidin-4-yl)-1H-pyrazole-3-carbonyl]-4-azaspiro[2.5]octane-7-carboxylic acid

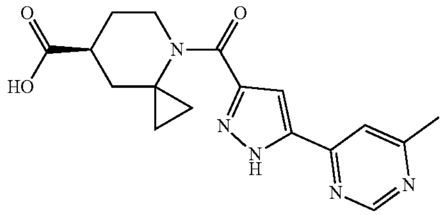 [SMILES: Cc1cc(-c2cc(C(=O)N3CC[C@H](C(=O)O)CC34CC4)n[nH]2)ncn1]

LiOH·$H_2O$ (46.1 mg, 1.10 mmol) was added to a stirred solution of methyl (7S)-4-[5-(6-methylpyrimidin-4-yl)-1H-pyrazole-3-carbonyl]-4-azaspiro[2.5]octane-7-carboxylate (Step-2, 150.0 mg, 0.42 mmol) in $H_2O$ (1.00 mL), THF (1.00 mL) and MeOH (1.00 mL). The resulting mixture was stirred at 25° C. for 2 h. The resulting mixture was concentrated under reduced pressure. The pH was adjusted to 3 by the addition of aqueous HCl. The aqueous layer was extracted with EtOAc. The resulting mixture was concentrated under reduced pressure to obtain the title compound (120.0 mg) as a solid. LCMS (ESI): $[M+H]^+$: 342.2.

Step-3b. (7R)-4-[5-(6-methylpyrimidin-4-yl)-1H-pyrazole-3-carbonyl]-4-azaspiro[2.5]octane-7-carboxylic acid

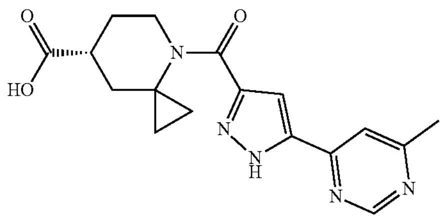 [SMILES: Cc1cc(-c2cc(C(=O)N3CC[C@@H](C(=O)O)CC34CC4)n[nH]2)ncn1]

LiOH·$H_2O$ (53.1 mg, 1.27 mmol) was added to a stirred solution of methyl (7R)-4-[5-(6-methylpyrimidin-4-yl)-1H-pyrazole-3-carbonyl]-4-azaspiro[2.5]octane-7-carboxylate (Step-2, 150.0 mg, 0.42 mmol) in $H_2O$ (1.00 mL), THF (1.00 mL) and MeOH (1.00 mL). The resulting mixture was stirred at 25° C. for 2 h. The resulting mixture was concentrated under reduced pressure. The pH was adjusted to 3 by the addition of aqueous HCl. The aqueous layer was extracted with EtOAc. The resulting mixture was concentrated under reduced pressure to obtain the title compound (140.0 mg) as a solid. LCMS (ESI): $[M+H]^+$: 342.2.

Step-4a. (S)—N-(4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

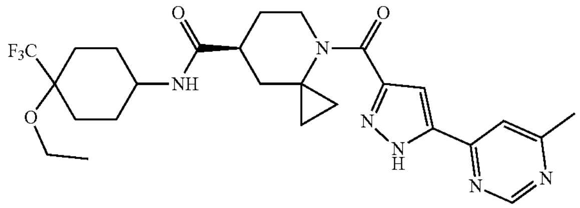 [SMILES: CCOC1(C(F)(F)F)CCC(NC(=O)[C@H]2CCN(C(=O)c3cc(-c4cc(C)ncn4)[nH]n3)C3(CC3)C2)CC1]

HOBt (77.2 mg, 0.57 mmol), EDGE (109.5 mg, 0.57 mmol), and 4-ethoxy-4-(trifluoromethyl)cyclohexan-1-amine (88.5 mg, 0.42 mmol) were added to a stirred solution of (7S)-4-[5-(6-methylpyrimidin-4-yl)-1H-pyrazole-3-carbonyl]-4-azaspiro[2.5]octane-7-carboxylic acid (Step-3a, 130.0 mg, 0.38 mmol) and DIPEA (246.1 mg, 1.90 mmol) in DMF (3.00 mL). The resulting mixture was stirred at 25° C. for 14 h. The resulting mixture was diluted with EtOAc and water. The resulting mixture was concentrated under reduced pressure. The residue was purified by silica gel column chromatography eluting with DCM/MeOH (25/1 v/v) to obtain the title compound (110.0 mg) as a solid mixture of diastereomers (Example 308-A).

$^1$H NMR (300 MHz, $CD_3OD$) δ 9.03 (d, 1H), 7.90 (s, 1H), 7.34 (s, 1H), 4.61 (s, 1H), 3.97 (s, 1H), 3.70-3.57 (m, 2H), 2.93 (s, 1H), 2.63-2.34 (m, 4H), 2.12-1.60 (m, 9H), 1.42-0.63 (m, 1H). LCMS (ESI): $[M+H]^+$: 535.3.

Step-4b. (R)—N-(4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

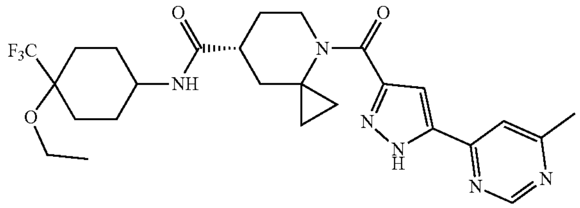 [SMILES: CCOC1(C(F)(F)F)CCC(NC(=O)[C@@H]2CCN(C(=O)c3cc(-c4cc(C)ncn4)[nH]n3)C3(CC3)C2)CC1]

HOBt (89.1 mg, 0.66 mmol), EDCI (126.4 mg, 0.66 mmol), and 4-ethoxy-4-(trifluoromethyl)cyclohexan-1-amine (102.1 mg, 0.48 mmol) were added to a stirred solution of (7R)-4-[5-(6-methylpyrimidin-4-yl)-1H-pyrazole-3-carbonyl]-4-azaspiro[2.5]octane-7-carboxylic acid (Step-3b, 150.0 mg, 0.44 mmol) and DIPEA (284.0 mg, 2.20 mmol) in DMF (3.00 mL). The resulting mixture was stirred at 25° C. for 14 h. The resulting mixture was diluted with EtOAc and water. The resulting mixture was concentrated under reduced pressure. The residue was purified by silica gel column chromatography eluting with DCM/MeOH (25/1 v/v) to obtain the title compound (120.0 mg) as a solid mixture of diastereomers (Example 308-B). $^1$H NMR (300 MHz, $CD_3OD$) δ 9.03 (s, 1H), 7.92-7.86 (m, 7.34 (s, 1H), 4.75-4.45 (m, 1H), 3.97 (s, 1H), 3.70-3.57 (m, 2H), 2.93 (s, 1H), 2.63-2.24 (m, 2.01-1.53 (m, 10H), 1.44-1.14 (m, 5H), 1.14-0.93 (m, 1H), 0.78-0.72 (m, 3H). LCMS (ESI): $[M+H]^+$: 535.2.

Step-5a. (S)—N-((1r,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide and (S)—N-((1s,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

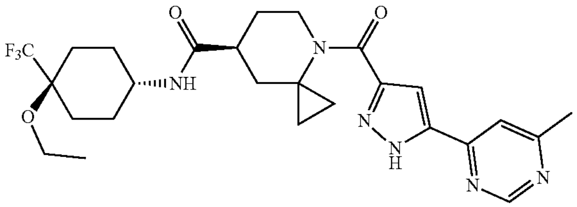

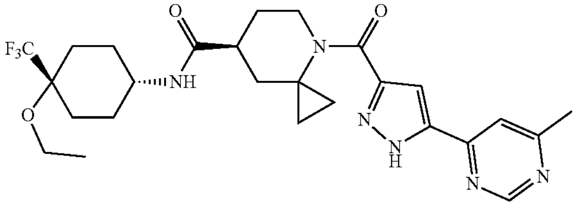

The mixture of two diastereomers from Example 308-A (Step-4a, 120.0 mg) was separated using Chiral-Prep-HPLC.

Column: CHIRAL ART Cellulose-SB column

Column dimension: 3×25 cm, 5 μm

Mobile Phase: MTBE (0.5% 2M $NH_3$·MeOH): MeOH=90:10 hold for 42 min

Flow rate: 20 mL/min

Detection: 220/254 nm

Example 308-C. The first eluting diastereomer ((S)—N-((1r,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide) (47.9 mg) was obtained as a solid.

The first eluting diastereomer had a retention time of 16.33 min.

$^1$H NMR (400 MHz, CD SOD) δ 9.02 (s, 1H), 8.11-7.71 (m, 1H), 7.35 (s, 1H), 4.80-4.39 (m, 1H), 3.96 (s, 1H), 3.68-3.58 (m, 2H), 2.95-2.91 (m, 1H), 2.60 (s, 3H), 2.44 (s, 1H), 2.03-1.58 (m, 11H), 1.39-0.97 (m, 6H), 0.87-0.60 (m, 2H). LCMS (ESI): $[M+H]^+$: 535.3.

Example 308-D. The second eluting diastereomer ((S)—N-((1s,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide) (0.7 mg) was obtained as a solid.

The first eluting diastereomer had a retention time of 20.14 min.

LCMS (ESI): $[M+H]^+$: 535.1.

Step-5b. (R)—N-((1s,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide and (R)—N-((1r,1R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide

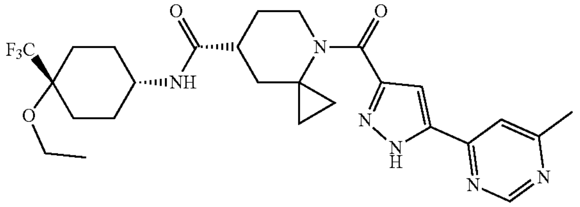

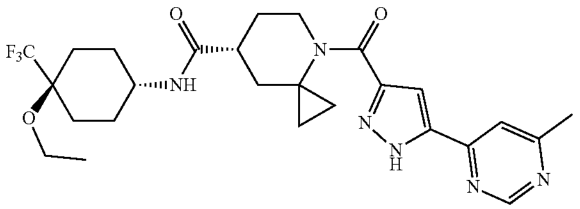

The mixture of two diastereomers from Example 308-B (Step-4b, 110.0 mg) was separated using Chiral-Prep-HPLC.

Column: CHIRAL ART Cellulose-SB column

Column dimension: 3×25 cm, 5 μm

Mobile Phase: MTBE (0.5% 2 M $NH_3$·MeOH): MeOH=80:20 hold for 17 min

Flow rate: 20 mL/min

Detection: 220/254 nm

Example 308-E. The first eluting diastereomer ((R)—N-((1s,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide) (36.4 mg) was obtained as a solid.

The first eluting diastereomer had a retention time of 10.89 min.

$^1$H NMR (400 MHz, $CD_3OD$) δ 9.02 (s, 1H), 7.90 (s, 1H), 7.34 (s, 1H), 4.64-4.60 (m, 1H), 3.96 (s, 1H), 3.68-3.58 (m, 2H), 2.95-2.91 (m, 1H), 2.60 (s, 3H), 2.44 (s, 1H), 1.99-1.59 (m, 10H), 1.42-1.14 (m, 5H), 1.14-0.88 (m, 2H), 0.77-0.73 (m, 2H). LCMS (ESI): $[M+H]^+$535.3.

Example 308-F. The second eluting diastereomer ((R)—N-((1r,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide) (0.6 mg) was obtained as a solid.

The second eluting diastereomer had a retention time of 13.44 min.

LCMS (ESI): $[M+H]^+$: 535.1.

Example 309-A. (S)—N-((1r,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

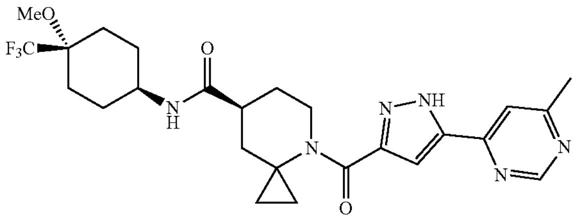 [SMILES: CO[C@]1(C(F)(F)F)CC[C@@H](NC(=O)[C@H]2CCN(C(=O)c3cc(-c4cc(C)ncn4)[nH]n3)C3(CC3)C2)CC1]

Example 309-B. (S)—N-((1s,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

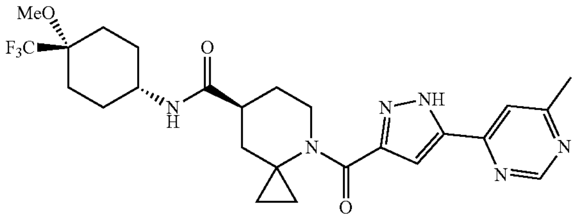 [SMILES: CO[C@]1(C(F)(F)F)CC[C@H](NC(=O)[C@H]2CCN(C(=O)c3cc(-c4cc(C)ncn4)[nH]n3)C3(CC3)C2)CC1]

Example 309-C. (R)—N-((1r,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

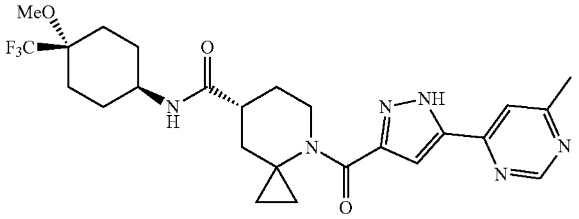 [SMILES: CO[C@]1(C(F)(F)F)CC[C@@H](NC(=O)[C@@H]2CCN(C(=O)c3cc(-c4cc(C)ncn4)[nH]n3)C3(CC3)C2)CC1]

Example 309-D. (R)—N-((1s,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

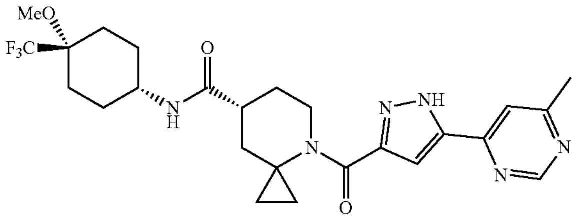 [SMILES: CO[C@]1(C(F)(F)F)CC[C@H](NC(=O)[C@@H]2CCN(C(=O)c3cc(-c4cc(C)ncn4)[nH]n3)C3(CC3)C2)CC1]

Step-1a. (S)—N-(4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

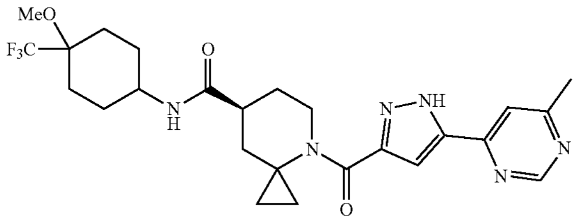 [SMILES: COC1(C(F)(F)F)CCC(NC(=O)[C@H]2CCN(C(=O)c3cc(-c4cc(C)ncn4)[nH]n3)C3(CC3)C2)CC1]

HOBt (48.0 mg, 0.35 mmol), EDCI (67.0 mg, 0.35 mmol), and 4-methoxy-4-(trifluoromethyl)cyclohexan-1-amine (139.0 mg, 0.70 mmol) were added to a stirred solution of (7S)-4-[5-(6-methylpyrimidin-4-yl)-1H-pyrazole-3-carbonyl]-4-azaspiro[2.5]octane-7-carboxylic acid (Example 308, Step-3a, 80.0 mg, 0.23 mmol) and DIPEA (151.0 mg, 1.17 mmol) in DMF (5.00 mL). The resulting mixture was stirred at 25° C. for 14 h. The resulting mixture was diluted with EtOAc, washed with water and concentrated. The residue was purified by silica gel column chromatography eluting with DCM/MeOH (15/1 v/v) to obtain the title compounds (100.0 mg) as a solid mixture of diastereomers. LCMS (ESI): $[M+H]^+$: 521.2.

Step-1b. (R)—N-(4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

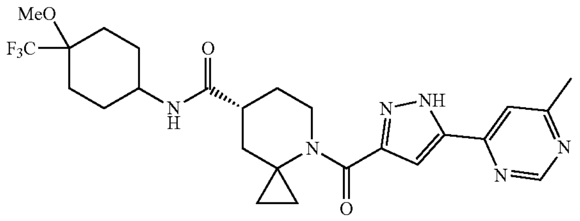 [SMILES: COC1(C(F)(F)F)CCC(NC(=O)[C@@H]2CCN(C(=O)c3cc(-c4cc(C)ncn4)[nH]n3)C3(CC3)C2)CC1]

HOBt (59.0 mg, 0.44 mmol), EDCI (84.0 mg, 0.44 mmol), and 4-methoxy-4-(trifluoromethyl)cyclohexan-1-amine (58.0 mg, 0.29 mmol) were added to a stirred solution of (7R)-4-[5-(6-methylpyrimidin-4-yl)-1H-pyrazole-3-carbonyl]-4-azaspiro[2,5]octane-7-carboxylic acid (Example 308, Step-3b, 100.0 mg, 0.29 mmol) and DIPEA (189.0 mg, 1.47 mmol) in DMF (5.00 mL). The resulting mixture was stirred at 25° C. for 14 h. The resulting mixture was diluted with EtOAc, washed with water and concentrated. The residue was purified by silica gel column chromatography eluting with DCM/MeOH (15/1 v/v) to obtain the title compounds (100.0 mg) as a solid mixture of diastereomers. LCMS (ESI): $[M+H]^+$: 521.3.

Step-2a. (S)—N-((1r,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide and (S)—N-((1s,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

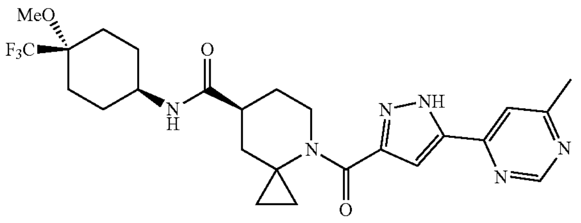

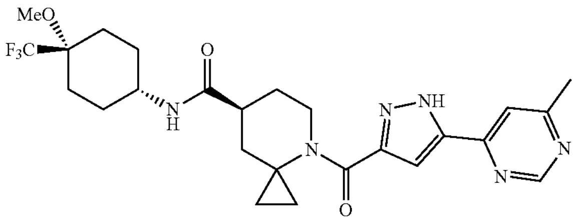

The two diastereomers of the title compounds from Step-1a were separated using Chiral-Prep-HPLC.

Column: CHIRALPAK ID column

Column dimension: 2×25 cm, 5 μm

Mobile Phase: MTBE (0.5% 2 M $NH_3$·MeOH): MeOH=50:50 hold for 10 min

Flow rate: 18 mL/min

Detection: 2201254 nm

Example 309-A. The first eluting diastereomer ((S)—N-((1r,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide) (18.2 mg) was obtained as a solid.

The first eluting diastereomer had a retention time of 3.27 min.

$^1$H NMR (300 MHz, $CD_3OD$) δ 9.01 (s, 1H), 8.02-7.71 (m, 1H), 7.35-7.28 (m, 1H), 4.75-4.51 (m, 1H), 3.98-3.91 (m, 1H), 3.39 (d, 3H), 2.94-2.88 (m, 1H), 2.61-2.26 (m, 4H), 1.99-1.58 (m, 1H) 1.32-0.90 (m, 3H), 0.76-0.69 (m, 2H). LCMS (ESI): $[M+H]^+$: 521.3.

Example 309-B. The second eluting diastereomer ((S)—N-((1s,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide) (27.7 mg) was obtained as a solid.

The first eluting diastereomer had a retention time of 8.65 min.

$^1$H NMR (300 MHz, $CD_3OD$) δ 9.04-8.98 (m, 1H), 8.09-7.69 (m, 1H), 7.35-7.29 (m, 1H), 4.64-4.57 (m, 1H), 3.68-3.61 (m, 1H), 3.40 (s, 3H), 2.79-2.72 (m, 1H), 2.61-2.25 (m, 4H), 2.03 (m, 2H), 1.90-0.50 (m, 14H). LCMS (ESI): $[M+H]^+$: 521.3.

Step-2b. (R)—N-((1r,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide and (R)—N-((1s,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide

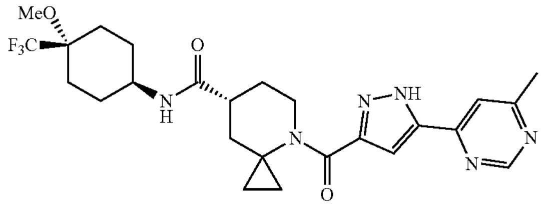

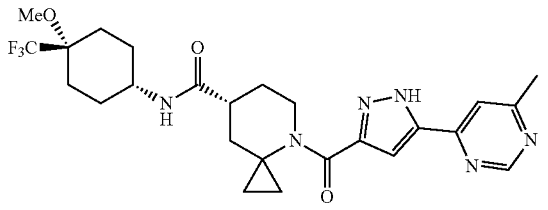

The two diastereomers of the title compounds from Step-1b were separated using Chiral-Prep-HPLC.

Column: CHIRAL ART Cellulose-SB column

Column dimension: 2×25 cm, 5 μm

Mobile Phase: MTBE (0.5% 2 M $NH_3$·MeOH): MeOH=80:20 hold for 21 min

Flow rate: 20 mL/min

Detection: 220/254 nm

Example 309-C. The first eluting diastereomer ((R)—N-((1r,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxam) (9.5 mg) was obtained as a solid The first eluting diastereomer had a retention time of 14.43 min.

$^1$H NMR (300 MHz, $CD_3OD$) δ 9.04 (s, 1H), 8.04-7.69 (m, 1H), 7.38-7.31 (m, 1H), 4.64-4.57 (m, 1H), 3.97 (s, 1H), 3.42 (s, 3H), 2.97-2.90 (m, 1H), 2.60 (s, 3H), 2.48-2.41 (m, 1H), 1.93-0.62 (m, 16H). LCMS (ESI): $[M+H]^+$: 521.0.

Example 309-D. The second eluting diastereomer ((R)—N-((1s,4S)-4-methoxy-4-(trifluoromethyl)cyclohexyl)-4-(5-(6-methylpyrimidin-4-yl)-1H-pyrazole-3-carbonyl)-4-azaspiro[2,5]octane-7-carboxamide) (23.9 mg) was obtained as a solid.

The first eluting diastereomer had a retention time of 18.37 min.

$^1$H NMR (300 MHz, $CD_3OD$) δ 9.03 (s, 1H), 8.03-7.66 (m, 1H), 7.34 (s, 1H), 4.60 (s, 1H), 3.74-3.60 (m, 1H), 3.42 (s, 3H), 2.78 (s, 1H), 2.64-2.25 (m, 4H), 2.12-1.99 (m, 2H), 1.92-0.57 (m, 14H). LCMS (ESI): $[M+H]^+$: 521.0.

Example 310. 4-(4-(5-hydroxy-2-methylpyridin-4-yl)-1H-imidazole-2-carbonyl)-N-((1r,4r)-4-hydroxy-4-(trifluoromethyl)cyclohexyl)-4-azaspiro[2.5]octane-7-carboxamide

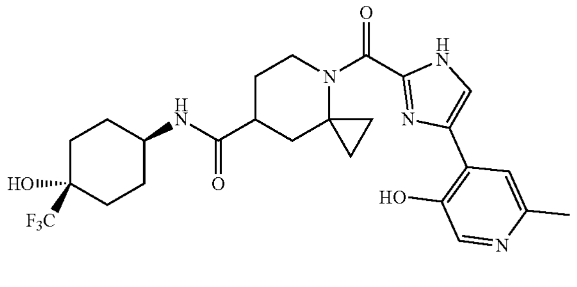 [SMILES: Cc1cc(-c2c[nH]c(C(=O)N3CCC(C(=O)N[C@H]4CC[C@@](O)(C(F)(F)F)CC4)CC34CC4)n2)c(O)cn1]

Step-1. Ethyl 4-bromo-1-((2-(trimethylsilyl)ethoxy) methyl)-1H-imidazole-2-carboxylate and ethyl 5-bromo-1-((2-(trimethylsilyl)ethoxy)methyl)-1H-imidazole-2-carboxylate

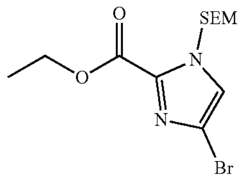

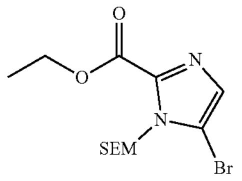

SEMCl (0.49 mL, 2.74 mmol) was added to a stirred solution of ethyl 4-bromo-1H-imidazole-2-carboxylate (500.0 mg, 2.28 mmol) and $K_2CO_3$ (379.0 mg, 2.74 mmol) in DMF (40.00 ml) at 0° C. The resulting mixture was stirred at 25° C. for 5 h. The reaction mixture was diluted with EtOAc, water, washed with brine. Concentrated residue was purified by silica gel column chromatography eluting with 10-20% EtOAc/hexanes to obtain ethyl 4-bromo-1-((2-(trimethylsilyl)ethoxy)methyl)-1H-imidazol-2-carboxylate (416.0 mg) as an oil (LCMS (ESI): $[M+H]^+$: 349.5) and ethyl 5-bromo-1-((2-(trimethylsilyl)ethoxy)methyl)-1H-imidazole-2-carboxylate (169.0 mg) as an oil (LCMS (ESI): $[M+H]^+$: 349.5).

Step-2. Ethyl 4-(5-hydroxy-2-methylpyridin-4-yl)-1-((2-(trimethylsilyl)ethoxy)methyl)-1H-imidazole-2-carboxylate

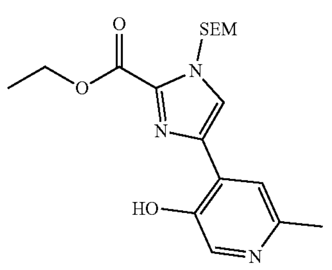 [SMILES: CCOC(=O)c1nc(-c2cc(C)ncc2O)cn1COCC[Si](C)(C)C]

$Pd(dppf)Cl_2$ (105.0 mg, 0.13 mmol), $K_2CO_3$ (119.0 mg, 0.86 mmol), and KOAc (63.0 mg, 0.64 mmol) were added to a stirred solution of ethyl 4-bromo-1-((2-(trimethylsilyl) ethoxy)methyl)-1H-imidazole-2-carboxylate (Step-1, 150.0 mg, 0.43 mmol), 4-bromo-6-methylpyridin-3-ol (120.0 mg, 0.64 mmol), and 1,4,4,4',4',5,5,5',5'-octamethyl-2,2'-bi(1,3,2-dioxaborolane) (164.0 mg, 0.64 mmol) in 1,4-dioxane (2.00 mL). Nitrogen was sparged through the reaction mixture for 5 min. Then, the reaction mixture was stirred at 85° C. for 1 h, Degassed water (0.4 mL) was added to the reaction mixture and the resulting mixture was stirred at 85 DC for 16 h. The reaction mixture was diluted with EtOAc, water, washed with brine. Concentrated residue was purified by silica gel column chromatography eluting with 20-100% EtOAc/hexanes to obtain the title compound (49.0 mg) as an oil. LCMS (ESI): $[M+H]^+$: 378.5.

Step-3. 4-(5-hydroxy-2-methylpyridin-4-yl)-1-((2-(trimethylsilyl)ethoxy)methyl)-1H-imidazole-2-carboxylic acid

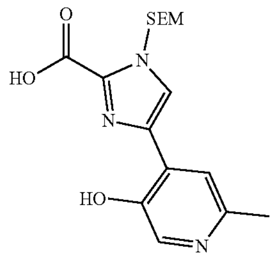 [SMILES: Cc1cc(-c2cn(COCC[Si](C)(C)C)c(C(=O)O)n2)c(O)cn1]

LiOH (1 M in water, 46.0 mL, 0.05 mmol) was added to a stirred solution of ethyl 4-(5-hydroxy-2-methylpyridin-4-yl)-1-((2-(trimethylsilyl)ethoxy)methyl)-1H-imidazole-2-carboxylate (Step-2, 5.80 mg, 0.02 mmol) in MeOH (1.00 mL). The reaction mixture was stirred at 60° C. for 1 h. The pH was adjusted to 2 by the addition of aqueous HCl (1 M). The reaction mixture was concentrated and the residue was purified by silica gel column chromatography eluting with 20-30% MeOH/DCM to obtain the title compound (2.4 mg) as an oil, LCMS (ESI): $[M+H]^+$: 350.5.

Step-4. 4-(4-(5-hydroxy-2-methylpyridin-4-yl)-1H-imidazole-2-carbonyl)-N-((1r,4r)-4-hydroxy-4-(trifluoromethyl)cyclohexyl)-4-azaspiro[2.5]octane-7-carboxamide

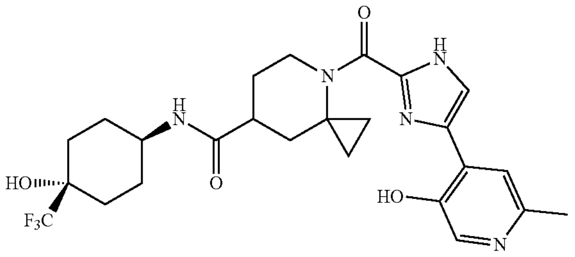 [SMILES: Cc1cc(-c2c[nH]c(C(=O)N3CCC(C(=O)N[C@H]4CC[C@@](O)(C(F)(F)F)CC4)CC34CC4)n2)c(O)cn1]

HATU (3.9 mg, 10.3 μmol) and N-((1r,4r)-4-hydroxy-4-(trifluoromethyl)cyclohexyl)-4-azaspiro[2,5]octane-7-carboxamide (3.3 mg, 10.3 μmol) were added to a stirred solution of 4-(5-hydroxy-2-methylpyridin-4-yl)-1-((2-(trimethylsilyl)ethoxy)methyl)-1H-imidazole-2-carboxylic acid (Step-3, 2.4 mg, 6.9 μmol) and DIPEA (3.60 μL, 0.02 mmol)

in DMF (0.50 mL). The resulting mixture was stirred at 60° C. for 4 h. The reaction mixture was diluted with EtOAc and water. The organic layer was washed with brine, dried over $Na_2SO_4$, filtered, and concentrated. DCM (1.00 mL) and TFA (1.00 mL) were added to the concentrated residue and the resulting mixture was stirred for at 23° C. for 30 min. The residue was purified by reverse phase column chromatography (C18 column) eluting with 0-40% water/MeCN (0.1% formic acid) to obtain the title compound (2.3 mg) as a solid. $^1$H NMR (400 MHz, $CD_3OD$) δ 8.16-8.28 (m, 1H), 7.95-8.16 (m, 3H), 7.60-7.83 (m, 1H), 5.15-5.44 (m, 1H), 4.55-4.81 (m, 1H), 3.84-4.09 (m, 1H), 2.85-3.05 (m, 1H), 2.48 (s, 3H), 2.23-2.42 (m, 1H), 1.90-1.66 (m, 11H), 1.19-1.45 (m, 2H), 0.90-1.19 (m, 2H), 0.57-0.85 (m, 2H). LCMS (ESI): $[M+H]^+$:522.6.

Example 311. A diastereomeric mixture of (1R,3s,5S)-8-(5-(5-fluoro-2-methylpyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-(3R,6S)-1-methyl-6-(trifluoromethyl)piperidin-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide

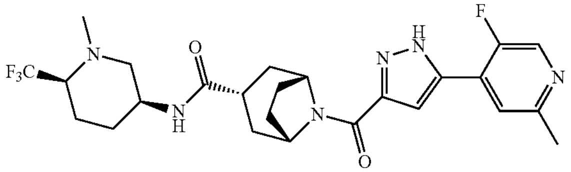

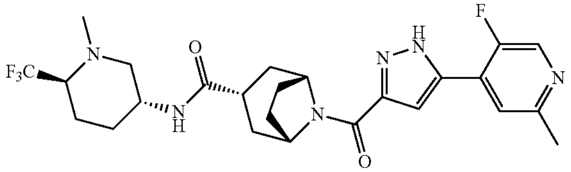

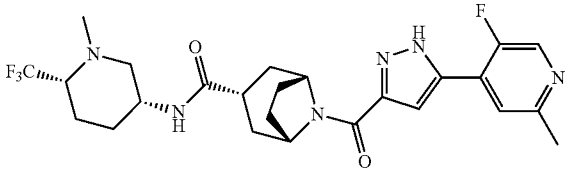

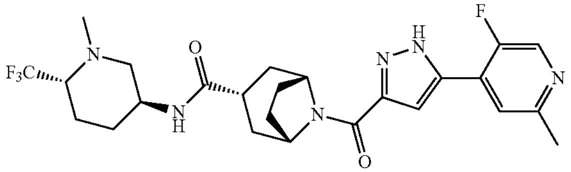

EDCI (160.5 mg, 0.84 mmol), HOBt (113.1 mg, 0.84 mmol), 1-methyl-6-(trifluoromethyl)piperidin-3-amine (INTERMEDIATE 528-B, 305.0 mg, 1.67 mmol) were added to a stirred solution of (1R,3R,5S)-8-[5-(5-fluoro-2-methylpyridin-4-yl)-1H-pyrazole-3-carbonyl]-8-azabicyclo[3.2.1]octane-3-carboxylic acid (INTERMEDIATE 524, 200.0 mg, 0.56 mmol) and DIPEA (432.8 mg, 3.35 mmol) in DMF (4.00 mL). The resulting mixture was stirred at 25° C. for 14 h. The mixture was diluted with EtOAc and water. The organic layers were combined and concentrated under vacuum. The residue was purified by Prep-TLC (DCM/MeOH 10/1 v/v) to obtain the diastereomeric mixtures (Example 311) of (1R,3s,5S)-8-(5-(5-fluoro-2-methylpyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide and (1R,3s,5S)-8-(5-(5-fluoro-2-methylpyridin-4-yl)-1-pyrazole-3-carbonyl)-N-((3R,6R)-1-methyl-6-(trifluoromethyl)piperidin-3-yl)-8-azabicyclo[3.2.1]octane-3-carboxamide and (1R,3s,5S)-8-(5-(5-fluoro-2-methylpyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide in two fractions, each containing two diastereomers. The first fraction (263.0 mg) was obtained as a solid (LCMS (ESI): $[M+H]^+$: 523.2) and the second fraction (93.0 mg) was obtained as a solid (LCMS $[M+H]^+$: 523.2).

The first fraction (263.0 mg) from Prep-TLC containing two diastereomers of the title compounds was separated using Chiral-Prep-HPLC.

Column: CHIRALPAK IG column

Column dimension: 2×25 cm, 5 μm

Mobile Phase: 3/1 hexanes/DCM (0.5% 2 M $NH_3$·MeOH):EtOH=70:30 hold for 33 min

Flow rate: 20 mL/min

Detection: 220/254 nm

Example 311-A. The first eluting diastereomer (43.9 mg) was obtained as a solid.

The first eluting diastereomer had a retention time of 7.64 min.

$^1$H NMR (400 MHz, DMSO-$d_6$) δ 14.19-13.74 (m, 1H), 8.65-8.27 (m, 1H), 7.90-7.57 (m, 1H), 7.27-6.90 (m, 1H), 5.44-4.44 (m, 2H), 3.95-3.50 (m, 1H), 3.19 (s, 1H) 2.84 (s, 1H), 2.51 (s, 3H), 2.44 (s, 3H), 2.19-1.91 (m, 1H), 1.91 (d, 2H), 1.78 (s, 7H), 1.63 (s, 3H), 1.42 (m, 1H). LCMS (ESI): $[M+H]^+$: 523.2.

Example 311-B. The second eluting diastereomer (44.6 mg) was obtained as a solid.

The second eluting diastereomer had a retention time of 15.92

$^1$H NMR (400 MHz, DMSO-$d_6$) δ 14.19-13.74 (m, 1H), 8.65-8.27 (m, 1H), 7.90-7.57 (m, 1H), 7.27-6.90 (m, 1H), 5.39-4.41 (m, 2H), 3.92-3.59 (m, 1H), 3.26-3.03 (m, 1H), 2.84 (s, 1H), 2.62-2.47 (m, 3H), 2.44 (s, 3H), 2.19-1.91 (m, 1H), 1.91 (s, 2H), 1.81-1.66 (m, 7H), 1.66-1.50 (m, 3H), 1.41 (m, 1H). LCMS (ESI): $[M+H]^+$: 523.2.

The second fraction (93.0 mg) from Prep-TLC containing two diastereomers of the title compounds was separated using Chiral-Prep-HPLC.

Column: CHIRALPAK IF column

Column dimension: 2×25 cm, 5 μm

Mobile Phase: MBTE (0.5% 2 M $NH_3$·MeOH):EtOH=70:30 hold for 38 min

Flow rate: 13 mL/min

Detection: 220/254 nm

Example 311-C. The first eluting diastereomer (4.5 mg) was obtained as a solid.

The first eluting diastereomer had a retention time of 16.05 min.

$^1$H NMR (300 MHz, DMSO-$d_6$) δ 14.01 (s, 1H), 8.53 (s, 1H), 7.78 (s, 2H), 7.12 (s, 1H), 4.95 (m, 2H), 3.64 (s, 1H), 3.50 (s, 1H), 2.77 (m, 3H), 2.30 (m, 4H), 2.25-2.11 (m, 1H), 2.10-1.93 (m, 2H), 1.77 (s, 7H), 1.65 (s, 2H), 1.23 (m, 2H). LCMS (ESI): [M+H]$^+$: 523.2.

Example 311-D. The second eluting diastereomer (3.5 mg) was obtained as a solid.

The second eluting diastereomer had a retention time of 29.13 min.

$^1$H NMR (300 MHz, DMSO-$d_6$) δ 14.00 (s, 1H), 8.65-8.27 (m, 1H), 7.90-7.57 (m, 2H), 7.27-6.90 (m, 1H), 5.38-4.47 (m, 2H), 3.72 (s, 1H), 3.28 (s, 1H), 2.77 (m, 1H), 2.49 (d, 3H), 2.42 (s, 3H), 1.89 (s, 2H), 1.88-1.65 (m, 10H), 1.43 (m, 1H), 1.20 (m, 1H). LCMS (ESI): [M+H]$^+$: 523.2.

Example 312-A. (R)—N-((1r,4S)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

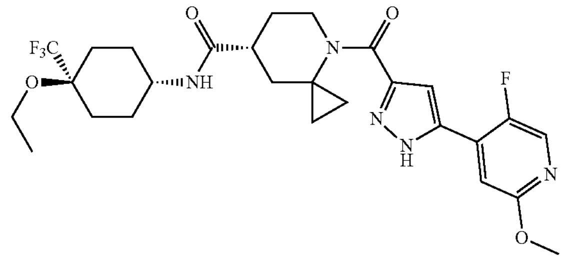 [SMILES: CCO[C@]1(C(F)(F)F)CC[C@@H](NC(=O)[C@@H]2CCN(C(=O)c3cc(-c4cc(OC)ncc4F)[nH]n3)C3(CC3)C2)CC1]

Example 312-B. (S)—N-((1r,4R)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

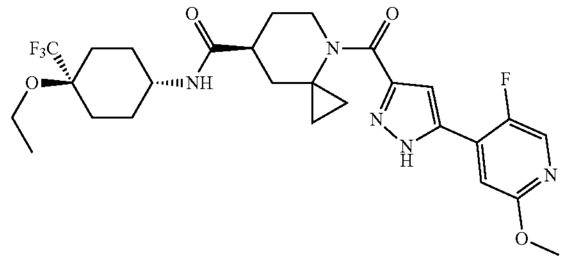 [SMILES: CCO[C@]1(C(F)(F)F)CC[C@@H](NC(=O)[C@H]2CCN(C(=O)c3cc(-c4cc(OC)ncc4F)[nH]n3)C3(CC3)C2)CC1]

HATU (270.0 mg, 0.71 mmol) and (1r,4r)-4-ethoxy-4-(trifluoromethyl)cyclohexan-1-amine (INTERMEDIATE 535-B, 100.0 mg, 0.47 mmol) were added to a stirred solution of 4-[5-(5-fluoro-2-methoxypyridin-4-yl)-1H-pyrazole-3-carbonyl]-4-azaspiro[2.5]octane-7-carboxylic acid (INTERMEDIATE 527, 177.0 mg, 0.47 mmol) and DIPEA (184.0 mg, 1.42 mmol) in DMF (5.00 mL). The resulting mixture was stirred at 25° C. for 14 h. The resulting solution was diluted with EtOAc and washed with water. The organic layers were concentrated under vacuum. The residue was purified by silica gel column chromatography eluting with DCM/MeOH (15/1 v/v) to obtain the diastereomeric mixtures of (R—N-((1r,4S)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1r,4R)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide as a solid (190.0 mg). LCMS (ESI): [M+H]$^+$: 568.3.

The two diastereomers of the title compounds were separated using Chiral-Prep-HPLC.

Column: CHIRALPAK IA column

Column dimension: 2×25 cm, 5 μm

Mobile Phase: hexanes (0.5% 2 M $NH_3$·MeOH): EtOH=50:50 hold for 14 min

Flow rate: 17 mL/min

Detection: 220/254 nm

Example 312-A. The first eluting compound (32.9 mg) was obtained as a Solid.

The first eluting compound had a retention time of 5.71 min, $^1$H NMR (300 MHz, DMSO-$d_6$) δ 14.00 (s, 1H), 8.27 (d, 1H), 7.87 (d, 1H), 7.33 (d, 1H), 7.03 (d, 1H), 4.45 (s, 1H), 3.91-3.81 (m, 4H), 3.62-3.48 (m, 2H) 2.83-2.76 (m, 1H), 2.25-2.18 (m, 1H), 1.84-1.42 (m, 11H), 1.19-1.08 (m, 4H), 1.03-0.77 (m, 2H), 0.68-0.62 (m, 2H). LCMS (ESI): [M+H]$^+$568.3.

Example 312-B. The second eluting compound (35.2 mg) was obtained as a solid.

The second eluting compound had a retention time of 10.23 min.

$^1$H NMR (300 MHz, DMSO-$d_6$) δ 14.00 (m, 1H), 8.27 (m, 1H), 7.87 (d, 1H), 7.33 (d, 1H), 7.03 (d, 1H), 4.45 (s, 1H), 3.91-3.81 (m, 4H), 3.62-3.48 (m, 2H), 2.83-2.76 (m, 1H), 2.25-2.18 (m, 1H), 1.84-1.42 (m, 11H), 1.19-1.08 (m, 4H), 1.03-0.77 (m, 2H), 0.68-0.62 (m, 2H). LCMS (ESI): [M+H]$^+$: 568.3.

Example 313-A. (R)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide

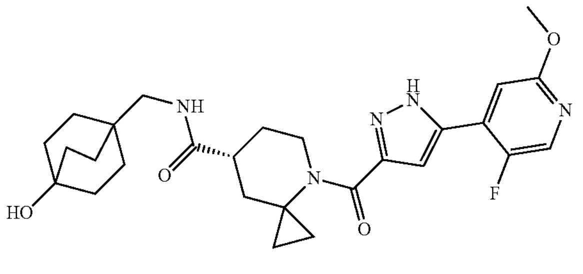 [SMILES: COc1cc(-c2cc(C(=O)N3CC[C@@H](C(=O)NCC45CCC(O)(CC4)CC5)CC34CC4)n[nH]2)c(F)cn1]

Example 313-B. (S)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide

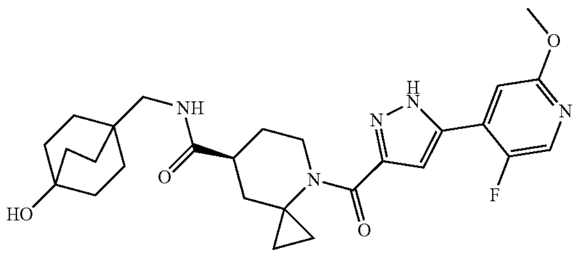 [SMILES: COc1cc(-c2cc(C(=O)N3CC[C@H](C(=O)NCC45CCC(O)(CC4)CC5)CC34CC4)n[nH]2)c(F)cn1]

The title compound was prepared using a procedure similar to the one described for the synthesis of Example 288, except 4-(aminomethyl)bicyclo[2.2.2]octan-1-ol was used as starting material. The resulting residue was purified by silica gel column chromatography eluting with DCM/MeOH (10/1 v/v) yielded (S)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide and (R)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide as a solid mixture of enantiomers (120.0 mg). LCMS (ESI): 512.3.

The two enantiomers of the title compounds were separated using Prep-Chiral-HPLC.

Column: CHIRALPAK IA column

Column dimension: 2×25 cm, 5 μm

Mobile Phase: hexanes (0.5% 2 M $NH_3$·MeOH):IPA=70:30 hold for 25 min

Flow rate: 20 mL/min

Detection: 220/254 nm

Example 313-A. The First Eluting Compound (35.2 mg) was obtained as a solid.

The first eluting compound had a retention time of 7.12 min.

$^1$H NMR (400 MHz, DMSO-$d_6$) δ 14.12-13.84 (m, 1H), 8.27-8.21 (m, 1H), 7.61 (s, 1H), 7.31 (d, 1H), 7.03 (s, 1H), 4.55-4.26 (m, 1H), 4.16 (s, 1H), 3.87 (s, 3H), 2.80-2.74 (m, 3H), 2.32-2.04 (m, 1H), 1.76-1.71 (m, 1H), 1.57-0.76 (m, 15H), 0.69-0.47 (m, 4H). LCMS (ESI): $[M+H]^+$: 512.3.

Example 313-B. The second eluting compound (38.6 mg) was obtained as a solid.

The second eluting compound had a retention time of 17.65 min.

$^1$H NMR (400 MHz, DMSO-$d_6$) δ 14.14-13.84 (m, 1H), 8.27-8.21 (m, 1H), 7.61 (s, 1H), 7.31 (d, 1H), 7.03 (s, 1H), 4.58-4.26 (m, 1H), 4.16 (s, 1H), 3.87 (s, 3H), 2.80-2.75 (m, 3H), 2.32-2.04 (m, 1H), 1.76-1.71 (m, 1H), 1.57-0.76 (m, 15H), 0.69-0.47 (m, 4H). LCMS (ESI): $[M+H]^+$: 512.2.

Example 314. (1R,3s,5S)-8-(5-(2,3-dimethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide

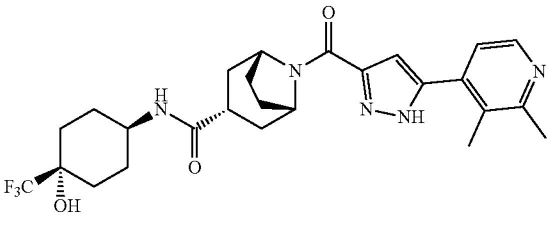 [SMILES: Cc1nccc(-c2cc(C(=O)N3[C@@H]4CC[C@H]3C[C@H](C(=O)N[C@H]3CC[C@@](O)(C(F)(F)F)CC3)C4)n[nH]2)c1C]

Step-1. 5-bromo-1-((2-(trimethylsilyl)ethoxy)methyl/1-pyrazole-3-carboxylic acid

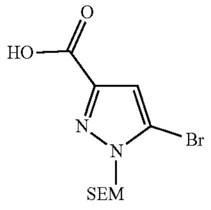 [SMILES: C[Si](C)(C)CCOCn1nc(C(=O)O)cc1Br]

LiOH·$H_2O$ (0.63 g, 14.91 mmol) was added to a stirred solution of methyl 5-bromo-1-((2-(trimethylsilyl)ethoxy)methyl)-1H-pyrazole-3-carboxylate (INTERMEDIATE 506, Step-1, 2.50 g, 7.46 mmol) in THF (12.00 mL), MeOH (12.00 mL), and $H_2O$ (12.00 mL). The resulting mixture was stirred at 25° C. for 1 h. The solution was then concentrated under reduced pressure, then the pH was adjusted to 5 by the addition of aqueous HCl (1 M). The solid was collected by filtration and concentrated under vacuum to obtain the title compound (300.0 mg) as a solid. LCMS (ESI): $[M+H]^+$: 321.0.

Step-2. Benzyl (1R,3s,5S)-8-(5-bromo-1-((2-(trimethylsilyl)ethoxy)methyl)-1H-pyrazole-3-carbonyl)-8-azabicyclo[3.2.1]octane-3-carboxylate

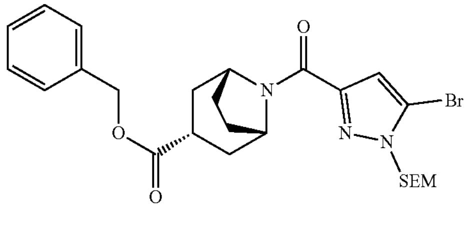 [SMILES: C[Si](C)(C)CCOCn1nc(C(=O)N2[C@@H]3CC[C@H]2C[C@H](C(=O)OCc2ccccc2)C3)cc1Br]

HOBt (1.41 g, 10.41 mmol), EDC (2.00 g, 10.41 mmol), and benzyl (1R,3R,5S)-8-azabicyclo[3.2.1]octane-3-carboxylate (1.70 g, 6.94 mmol) were added to a stirred mixture of 5-bromo-1-[[2-(trimethylsilyl)ethoxy]methyl]pyrazole-3-carboxylic acid (Step-1, 2.23 g, 6.94 mmol) and DIPEA (2.69 g, 20.83 mmol) in DMF (4.00 mL). The resulting solution was stirred at 25° C. for 2 h. The resulting mixture was diluted with water and extracted with EtOAc. The organic layers were combined and concentrated under vacuum. The residue was purified by silica gel column chromatography eluting with EtOAc/petroleum ether (1/4 v/v) to obtain the title compound (2.00 g) as a solid. LCMS (ESI): $[M+H]^+$: 548.2.

Step-3. (1R,3s,5S)-8-(5-bromo-1-((2-(trimethylsilyl)ethoxy)methyl)-1H-pyrazole-3-carbonyl)-8-azabicyclo[3.2.1]octane-3-carboxylic acid

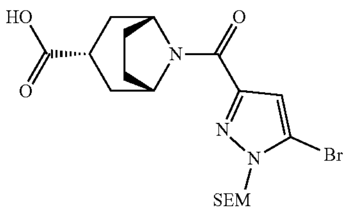 [SMILES: C[Si](C)(C)CCOCn1nc(C(=O)N2[C@@H]3CC[C@H]2C[C@H](C(=O)O)C3)cc1Br]

$LiOH·H_2O$ (0.31 g, 7.29 mmol) was added to a stirred solution of benzyl (1R,3s,5S)-8-(5-bromo-1-((2-(trimethylsilyl)ethoxy)methyl)-1H-pyrazole-3-carbonyl)-8-azabicyclo[3.2.1]octane-3-carboxylate (Step-2, 2.00 g, 3.65 mmol) in THF (5.00 mL), MeOH (5.00 mL), and $H_2O$ (5.00 mL). The resulting mixture was stirred at 25° C. for 1 h. The solution was then concentrated under reduced pressure, then the pH was adjusted to 5 by the addition of aqueous HCl (1 M). The solid was collected by filtration and concentrated under vacuum to obtain the title compound (1.60 g) as a solid. LCMS (ESI): $[M+H]^+$: 458.1.

Step-4. (1R,3s,5S)-8-(5-bromo-1-((2-(trimethylsilyl)ethoxy)methyl)-1H-pyrazole-3-carbonyl)-N-((1r,4R)-4-hydroxy-4-(trifluoromethyl)cyclohexyl)-8-azabicyclo[3.2.1]octane-3-carboxamide

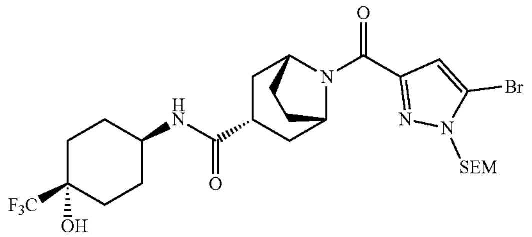 [SMILES: C[Si](C)(C)CCOCn1nc(C(=O)N2[C@@H]3CC[C@H]2C[C@H](C(=O)N[C@H]2CC[C@@](O)(C(F)(F)F)CC2)C3)cc1Br]

HOBt (884.0 mg, 6.54 mmol), EDCI (1.25 g, 6.54 mmol), and (1r,4r)-4-amino-1-(trifluoromethyl)cyclohexan-1-ol (919.0 mg, 5.02 mmol) were added to a stirred mixture of (1R,3R,5S)-8-(5-bromo-1-[[2-(trimethylsilyl)ethoxy]methyl]pyrazole-3-carbonyl)-8-azabicyclo[3.2.1]octane-3-carboxylic acid (Step-3, 1.60 g, 4.36 mmol) and DIPEA (2.81 g, 21.81 mmol) in DMF (4.00 mL). The resulting solution was stirred at 25° C. for 2 h. The resulting mixture was diluted with water and extracted with EtOAc. The organic layers were combined and concentrated under vacuum. The residue was purified by silica gel column chromatography eluting with EtOAc/petroleum ether (1/4 v/v) to obtain the title compound (1.60 g) as a white solid. $^1H$ NMR (300 MHz, DMSO-$d_6$) δ 7.72 (d, 1H), 6.83 (s, 1H), 5.67 (s, 1H), 5.49 (s, 2H), 5.04 (d, 1H), 4.63 (s, 1H), 3.78 (s, 1H), 3.68-3.52 (m, 2H), 2.98-2.80 (m, 1H), 2.16-1.54 (m, 10H), 1.64-1.42 (m, 6H), 0.93-0.78 (m, 2H), 0.07 (s, 9H). LCMS (ESI): $[M+H]^+$: 625.2.

Step-5. (3-((1R,3s,5S)-3-4(1r,4R)-4-hydroxy-4-(trifluoromethyl)cyclohexyl)carbamoyl)-8-azabicyclo[(3.2.1]octane-8-carbonyl)-1-((2-(trimethylsilyl)ethoxy)methyl)-1H-pyrazol-5-yl)boronic acid

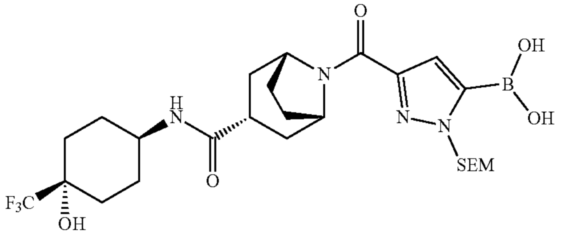 [SMILES: C[Si](C)(C)CCOCn1nc(C(=O)N2[C@@H]3CC[C@H]2C[C@H](C(=O)N[C@H]2CC[C@@](O)(C(F)(F)F)CC2)C3)cc1B(O)O]

$Pd(dppf)Cl_2$ (168.0 mg, 0.20 mmol) and KOAc (303.0 mg, 3.09 mmol) were added to a stirred solution of (1R,3s,5S)-8-(5-bromo-1-((2-(trimethylsilyl)ethoxy)methyl)-1H-pyrazole-3-carbonyl)-N-((1r,4R)-4-hydroxy-4-(trifluoromethyl)cyclohexyl)-8-azabicyclo[3.2.1]octane-3-carboxamide (Step-4, 640.0 mg, 1.03 mmol) and $B_2Pin_2$ (523.0 mg, 2.06 mmol) in 1,4-dioxane (32.00 mL) under nitrogen atmosphere. The resulting mixture was stirred at 100° C. for 5 h. This resulting residue was used directly in the next step as a solution.

Step-6. (1R,3s,5S)-8-(5-(2,3-dimethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide

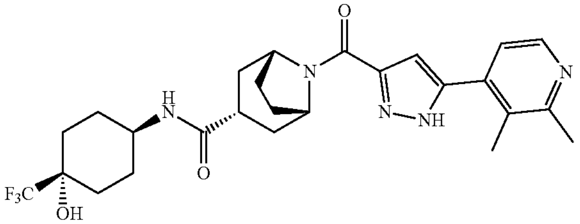 [SMILES: Cc1nccc(-c2cc(C(=O)N3[C@@H]4CC[C@H]3C[C@H](C(=O)N[C@H]3CC[C@@](O)(C(F)(F)F)CC3)C4)n[nH]2)c1C]

$Pd(dppf)Cl_2$ (11.0 mg, 0.01 mmol) and $K_3PO_4$ (41.0 mg, 0.19 mmol) were added to a stirred solution of (3-((1R,3s,5S)-3-(((1r,4R)-4-hydroxy-4-(trifluoromethyl)cyclohexyl)carbamoyl)-8-azabicyclo[3.2.1]octane-8-carbonyl)-1-((2-(trimethylsilyl)ethoxy)methyl)-1H-pyrazol-5-yl)boronic acid (Step-5, 1.0 mL in 1,4-dioxane, 0.06 mmol) and 4-bromo-2,3-dimethylpyridine (24.2 mg, 0.13 mmol) in 1,4-dioxane (1 mL) and $H_2O$ (0.50 mL) under nitrogen atmosphere. The resulting mixture was stirred at 100° C. for 14 h. The resulting mixture was filtered. The filtrate was then purified by reverse phase column chromatography (using the following conditions: Column: welFlash C18-I, 20-40 μm, 120 g; Mobile Phase A: Water (0.1% $NH_4HCO_3$), Mobile Phase B: MeCN; Flow rate: 60 mL/min; Gradient: 40% B to 85% B in 15 min; 220/254 nm). Two drops of concentrated HCl was added to a stirred solution of the purified residue in MeOH (2.00 mL), The resulting mixture was stirred at 60° C. for 4 h. The resulting mixture was filtered. The filtrate was purified by Prep-HPLC (using the following conditions: Column: XBridge BEH130 Prep C18 OBD Column, 130 Å, 19×150 mm 5 μm 13 nm; Mobile phase A: Water (20 mM $NH_4HCO_3$), mobile phase B: MeCN; Detector; UV 210/254 nm) to obtain the title compound (6.5 mg) as a solid. $^1$H NMR (400 MHz, $CD_3OD$) δ 8.29 (d, 1H), 7.32 (s, 1H), 6.92 (s, 1H), 5.38 (s, 1H), 3.91 (d, 1H), 3.14-3.01 (m, 1H), 2.59 (s; 3H), 2.39 (s, 3H), 2.19-1.78 (m, 11H), 1.78-1.60 (m, 6H). LCMS (ESI): $[M+H]^+$: 520.5.

Example 315. (1R,3s,5S)—N-((1r,4R)-4-hydroxy-4-(trifluoromethyl)cyclohexyl)-8-(5-(6-methyl-1H-pyrazolo[3,4-b]pyridin-4-yl)-1H-pyrazole-3-carbonyl)-8-azabicyclo[3.2.1]octane-3-carboxamide

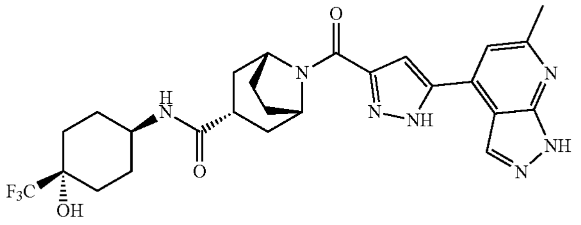 [SMILES: Cc1cc(-c2cc(C(=O)N3[C@@H]4CC[C@H]3C[C@H](C(=O)N[C@H]3CC[C@@](O)(C(F)(F)F)CC3)C4)n[nH]2)c2cn[nH]c2n1]

The title compound was prepared using a procedure similar to the one described for the synthesis of Example 314, except 4-bromo-6-methyl-1H-pyrazolo[3,4-b]pyridine was used as a starting material in Step-6. The title compound was obtained as a solid (6.8 mg). $^1$H NMR (400 MHz, $CD_3OD$) δ 8.51 (d, 1H), 7.51 (s, 1H), 7.38 (s, 1H), 3.99-3.86 (m, 1H), 3.52-3.45 (m, 1H), 3.14-3.11 (m, 1H), 3.11-3.03 (m, 1H), 2.70 (s, 3H), 2.29-1.55 (m, 16H). LCMS (ESI): $[M+H]^+$: 546.3.

Example 316. (1R,3s,5S)-8-(5-(2-ethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide

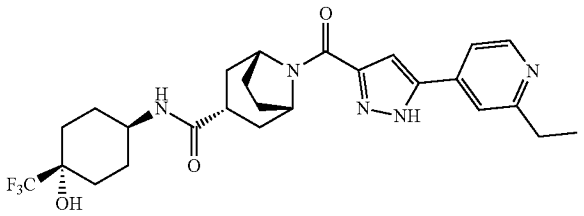 [SMILES: CCc1cc(-c2cc(C(=O)N3[C@@H]4CC[C@H]3C[C@H](C(=O)N[C@H]3CC[C@@](O)(C(F)(F)F)CC3)C4)n[nH]2)ccn1]

The title compound was prepared using a procedure similar to the one described for the synthesis of Example 314, except 4-bromo-2-ethylpyridine was used as a starting material in Step-6. The title compound was obtained as a solid (9.7 mg). $^1$H NMR (400 MHz, $CD_3OD$) δ 8.48 (d, 1H), 7.72 (s, 1H), 7.62 (s, 1H), 7.23 (s, 1H), 5.32-5.27 (m, 1H), 4.86-3.80 (m, 1H), 3.95-3.89 (m, 1H), 3.13-3.00 (m, 1H), 2.92-2.81 (m, 2H), 2.24-1.80 (m, 10H), 1.80-1.56 (m, 6H), 1.38-1.26 (m, 3H). LCMS (ESI): $[M+H]^+$: 520.4.

Example 317. (1R,3s,5S)—N-((1r,4R)-4-hydroxy-4-(trifluoromethyl)cyclohexyl)-8-(5-(2-(hydroxymethyl)pyridin-4-yl)-1H-pyrazole-3-carbonyl)-8-azabicyclo[3.2]octane-3-carboxamide

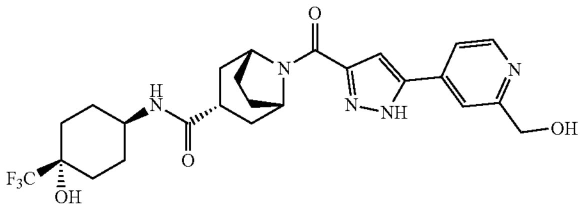 [SMILES: O=C(N[C@H]1CC[C@@](O)(C(F)(F)F)CC1)[C@@H]1C[C@H]2CC[C@@H](C1)N2C(=O)c1cc(-c2ccnc(CO)c2)[nH]n1]

The title compound was prepared using a procedure similar to the one described for the synthesis of Example 314, except (4-bromopyridin-2-yl)methanol was used as a starting material in Step-6. The title compound was obtained as a solid (9.9 mg). $^1$H NMR (400 MHz, $CD_3OD$) δ 8.52 (d, 1H), 7.95 (s, 1H), 7.69 (s, 1H), 7.23 (s, 1H), 5.15-5.10 (m, 2H), 4.79-4.66 (m, 2H), 3.94-3.89 (m, 1H), 3.12-3.02 (m, 1H), 2.27-1.43 (m, 16H). LCMS (ESI): $[M+H]^+$: 522.4.

Example 318. (1R,3s,5S)-8-(5-(5-fluoro-2-methoxypyridin-1-yl)-1H-pyrazole-3-carbonyl)-N-(3-(trifluoromethyl)-1-oxaspiro[3.5]nonan-7-yl)-8-azabicyclo[3.2.1]octane-3-carboxamide

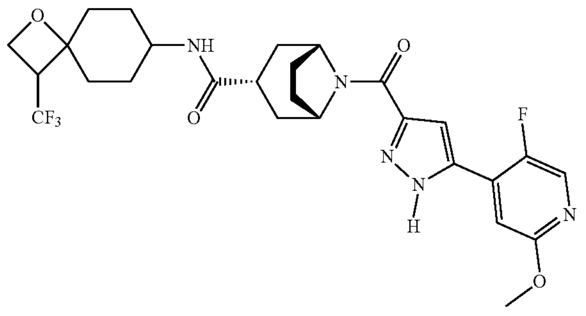

Step-1. Tert-butyl (3-oxo-1-oxaspiro[3.5]nonan-7-yl)carbamate

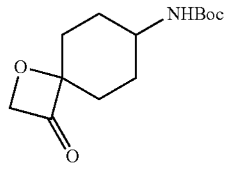 [SMILES: CC(C)(C)OC(=O)NC1CCC2(CC1)OCC2=O]

Methanesulfonic acid (98.1 μL, 1.51 mmol) was added to a stirred solution of tert-butyl (4-ethynyl-4-hydroxycyclohexyl)carbamate (which was prepared according to WO 2004002992, and which is also commercially available) (241.0 mg, 1.01 mmol), BrettPhos $AuNTf_2$ (51.0 mg, 50.4 μmol) and 8-ethylquinoline 1-oxide (349.0 mg, 2.01 mmol) in DCE (4.00 mL) at 0° C. The resulting mixture was stirred for 15 min before being warmed up to 22° C. and stirred for 3 h. The resulting solution was then diluted with water and extracted kith DCM. The organic layers were combined, then dried over anhydrous sodium sulfate, filtered, and the solvent was evaporated. The residue was purified by silica gel column chromatography eluting with EtOAc/cyclohexane (1/4 v/v to 3/7 v/v) to obtain the diastereomeric mixture of the title compound (170.0 mg) as an oil. $^1$H NMR (400 MHz, $CDCl_3$) δ 5.19 (s, 2H), 4.43 (s, 1H), 3.49 (s, 1H), 2.08 (d, 2H), 1.98-1.91 (m, 2H), 1.79-1.71 (m, 2H), 1.54-1.48 (m, 2H), 1.44 (s, 9H).

Step-2. Tert-butyl (3-hydroxy-3-(trifluoromethyl)-1-oxaspiro[3.5]nonan-7-yl)carbamate

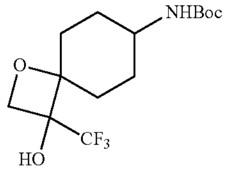 [SMILES: CC(C)(C)OC(=O)NC1CCC2(CC1)OCC2(O)C(F)(F)F]

Trimethyl(trifluoromethyl)silane (504.0 μL, 3.41 mmol) and CsF (526.0 mg, 3.46 mmol) were added to a stirred solution of tert-butyl (3-oxo-1-oxaspiro[3.5]nonan-7-yl)carbamate (Step-1, 145.0 mg, 0.57 mmol) in THF (0.50 mL) at 0° C. The resulting mixture was stirred for 16 h. The solution was then diluted with aqueous saturated solution of $NH_4Cl$, stirred for 30 min and extracted with EtOAc. The organic layers were combined, then dried over anhydrous sodium sulfate, filtered, and the solvent was evaporated. The residue was purified by silica gel column chromatography eluting with EtOAc/cyclohexane (3/7 v/v to 1/3 v/v) to obtain the diastereomeric mixture of the title compound (110.0 mg) as an oil. $^1$H NMR (400 MHz, $CDCl_3$) δ 4.59 (d, 1H), 4.42-4.32 (m, 2H), 3.45 (s, 1H), 2.63 (s, 1H), 2.46-2.19 (m, 4H), 1.99-1.92 (m, 1H), 1.91-1.83 (m, 1H), 1.49-1.39 (m, 11H).

Step-3. Tert-butyl (3-(((methylthio)carbonothioyl)oxy)-3-(trifluoromethyl)-1-oxaspiro[3.5]nonan-7-yl)carbamate

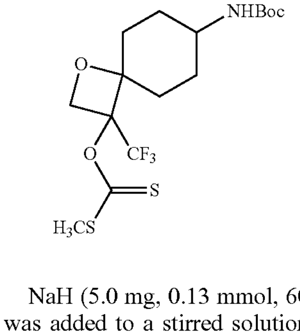

NaH (5.0 mg, 0.13 mmol, 60% dispersion in mineral oil) was added to a stirred solution of tert-butyl (3-hydroxy-3-(trifluoromethyl)-1-oxaspiro[3.5]nonan-7-yl)carbamate (Step-2, 37.0 mg, 0.11 mmol) in THF (1.10 mL) at 0° C. The resulting mixture was stirred at 0° C. for 20 min. $CS_2$ (0.01 mL, 0.17 mmol) was added to the reaction mixture. The resulting mixture was stirred at 0° C. for 30 min, then MeI (0.02 mL, 0.34 mmol) was added. The reaction mixture was stirred at 22° C. for 4 h. The solution was then diluted with water and extracted with EtOAc. The organic layers were combined, washed with aqueous saturated $NaHCO_3$, then dried over anhydrous sodium sulfate, filtered, and the solvent was evaporated to obtain the diastereomeric mixture of the title compound (26.0 mg) as an oil, which was used without further purification. TLC-MS (APCI): $[M+H]^+$: 416.1.

Step-4. Tert-butyl-3-(trifluoromethyl)-1-oxaspiro[3.5]nonan-7-yl)carbamate

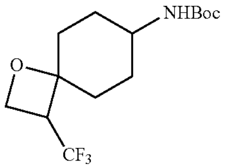 [SMILES: CC(C)(C)OC(=O)NC1CCC2(CC1)OCC2C(F)(F)F]

1,1,1,3,3,3-hexamethyl-2-(trimethylsilyl)trisilane (45.0 mg, 0.18 mmol) and AIBN (2.0 mg, 0.01 mmol) were added to a stirred solution of tert-butyl (3-(((methylthio)carbonothioyl)oxy)-3-(trifluoromethyl)-1-oxaspiro[3.5]nonan-7-yl) carbamate (Step-3, 50.0 mg, 0.12 mmol) in toluene (1.70 mL) at 22° C. The resulting mixture was stirred at 110° C. for 18 h. The resulting mixture was concentrated and was directly purified by silica gel column chromatography eluting with EtOAc/cyclohexane (1/9 v/v to 3/7 v/v) to obtain the diastereomeric mixture of the title compound (13.0 mg) as an oil. $^1$H NMR (400 MHz, $CDCl_3$) δ 4.58-4.47 (m, 2H), 4.35 (s, 1H), 3.45 (s, 1H), 3.26-3.14 (m, 1H), 2.40-2.31 (m, 1H), 2.20-2.11 (m, 1H), 1.91-1.81 (m, 2H), 1.69-1.56 (m, 3H), 1.51-1.27 (m, 10H).

Step-5. 2,2,2-trifluoro-1-((3-(trifluoromethyl)-1-oxaspiro[3.5]nonan-7-yl)-15-azaneyl)ethan-1-one

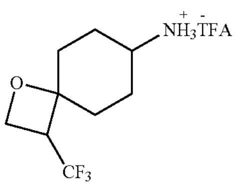

TFA (32.0 μL, 0.42 mmol) was added to a stirred solution of tert-butyl (3-(trifluoromethyl)-1-oxaspiro[3.5]nonan-7-yl)carbamate (Step-4, 13.0 mg, 0.04 mmol) in DCM (0.11 mL) at 0° C. The resulting mixture was stirred at 22° C. for 4.5 h. The reaction mixture was then concentrated and further dried under high vacuum. The resulting residue (14.0 mg) containing the diastereomeric mixture of the title compound was used directly in the next step without further purification. TLC-MS (APCI): $[M+H]^+$: 210.1.

Step-6. (1R,3s,5S)-8-(5-(5-fluoro-2-methoxypyridin-4-yl)-1H-pyrazole-3-carbonyl)-N-(3-(trifluoromethyl)-1-oxaspiro[3.5]nonan-7-yl)-8-azabicyclo[3.2.1]octane-3-carboxamide

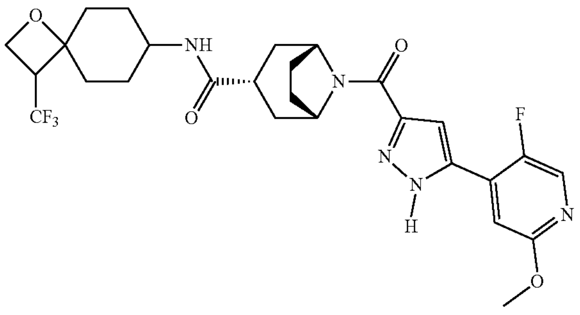 [SMILES: COc1cc(-c2cc(C(=O)N3[C@@H]4CC[C@H]3C[C@H](C(=O)NC3CCC5(CC3)OCC5C(F)(F)F)C4)n[nH]2)c(F)cn1]

HATU (12.0 mg, 0.03 mmol) and 3-(trifluoromethyl)-1-oxaspiro[3.5]nonan-7-amine 2,2,2-trifluoroacetate (Step-5, 15.0 mg, 0.05 mmol) were added to a stirred solution of (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 11.0 mg, 0.03 mmol) and DIPEA (26.0 μL, 0.15 mmol) in DMF (0.10 mL). The resulting mixture was stirred at 22° C. for 16 h. The reaction mixture was concentrated and diluted with EtOAc and water. The organic layer was washed with water and brine, dried over anhydrous sodium sulfate, filtered, and the solvent was evaporated. The residue was purified by reverse phase column chromatography (C18 column, 10% to 95% MeOH/Water (0.1% HCOOH)), after which the resulting residue was dissolved in DCM and subjected to Prep-TLC eluting with 2.5% MeOH/DCM, and finally reverse phase column chromatography (C18 column, 10% to 95% MeOH/Water (0.1% HCOOH)) to obtain the title compound (3.3 mg) as a solid mixture of diastereomers. H NMR (400 MHz, $CD_3OD$) δ 8.13 (s, 1H), 7.21 (s, 2H), 5.34 (s, 1H), 4.65-4.56 (m, 1H), 4.50-4.41 (m, 1H), 3.93 (s, 3H), 3.65-3.54 (m, 1H), 3.49-3.38 (m, 1H), 2.95-2.84 (m, 1H), 2.36-2.26 (m, 1H), 2.26-2.19 (m, 1H), 2.15-1.24 (m, 15H). LCMS (EST): $[M+H]^+$: 566.2.

Example 319. (1R,3s,5S)—N-(3,41-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide

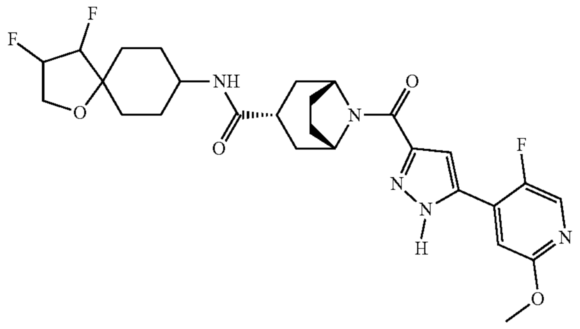 [SMILES: COc1cc(-c2cc(C(=O)N3[C@@H]4CC[C@H]3C[C@H](C(=O)NC3CCC5(CC3)OCC(F)C5F)C4)n[nH]2)c(F)cn1]

Step-1. 11-fluoro-1,4,9-trioxadispiro[4.2.48.25]tetradecan-12-one

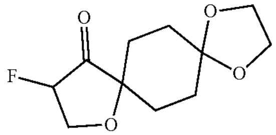 [SMILES: O=C1C(F)COC12CCC1(CC2)OCCO1]

A solution of 1,4,9-trioxadispiro[4.2.48.25]tetradecan-12-one (370.0 mg, 1.74 mmol) in THF (3.00 mL) was added to a stirred solution of LiHMDS (1 M, 1.59 mL, 1.59 mmol) in THF (14.30 mL) at −78° C. The resulting mixture was stirred for 40 min before NEST (500.0 mg, 1.59 mmol) was added as a solution in THE (3.00 mL). The resulting mixture was stirred at 22° C. for 16 h. The solution was quenched with aqueous saturated solution of $NH_4Cl$ and extracted with EtOAc. The combined organic layers were washed with water and brine, dried over anhydrous sodium sulfate, filtered, and the solvent was evaporated. The residue was purified by silica gel column chromatography eluting with DCM/EtOAc (0/1 v/v to 4/1 v/v) to obtain the title compound (234.0 mg) as a solid mixture of diastereomers, NMR (400 MHz, $CDCl_3$) δ 5.06 (dt, 1H), 4.38 (ddd, 1H), 4.07-3.90 (m, 5H), 1.92-1.66 (m, 8H).

Step-2. 11-fluoro-1,4,9-trioxadispiro[4.2.48.25]tetradecan-12-ol

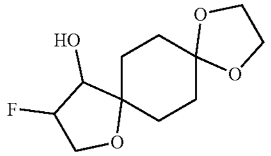 [SMILES: OC1C(F)COC12CCC1(CC2)OCCO1]

$NaBH_4$ (46.1 mg, 1.22 mmol) was added to a stirred solution of 11-fluoro-1,4,9-trioxadispiro[4.2.48.25]tetradecan-12-one (Step-1, 234.0 mg, 1.02 mmol) in MeOH (5.08 mL) at 0° C. The resulting mixture was stirred at 0° C. for 5 h. The reaction mixture was quenched with aqueous saturated solution of $NH_4C_1$ and extracted with EtOAc. The combined organic layers were washed with water and brine, dried over anhydrous sodium sulfate, filtered, and the solvent was evaporated. The residue was purified by silica gel column chromatography eluting with DCM/EtOAc (9/1 v/v to 4/1 v/v) to obtain diastereomeric mixture of the title compound (191.0 mg) as an oil. $^1H$ NMR (400 MHz, $CDCl_3$) δ 5.17-4.98 (m, 1H), 4.16-3.90 (m, 5H), 3.83 (ddd, 1H), 2.16 (dd, 1H), 1.97-1.54 (m, 8H).

Step-3. 11,12-difluoro-1,4,9-trioxadispiro[4.2.48.25]tetradecane

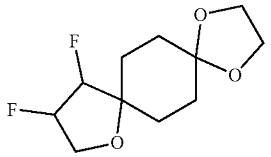 [SMILES: FC1COC2(CCC3(CC2)OCCO3)C1F]

DAST (0.19 mL, 1.46 mmol) was added to a stirred solution of 11-fluoro-1,4,9-trioxadispiro[4.2.48.25]tetradecan-12-ol (Step-2, 170.0 mg, 0.73 mmol) in DCM (7.32 mL). The resulting mixture was stirred at 22° C. for 16 h. The reaction mixture was then added dropwise to a stirred solution of aqueous saturated $NaHCO_3$. The aqueous layer was further extracted with DCM. The organic layers were combined, then dried over anhydrous sodium sulfate, filtered, and the solvent was evaporated. The residue was purified by silica gel column chromatography eluting with DCM/EtOAc (I/O v/v to 9/1 v/v) to obtain diastereomeric mixture of the title compound (23 mg) as an oil. $^1$H NMR (400 MHz, $CDCl_3$) δ 5.29-5.10 (m, 1H), 4.92-4.74 (m, 1H), 4.22-4.07 (m, 1H), 4.06-3.87 (m, 5H), 1.96-1.62 (m, 8H).

Step-4. 3,4-difluoro-1-oxaspiro[4.5]decan-8-one

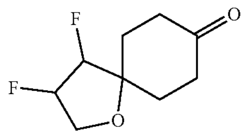

TFA (0.13 mL, 15.0 μmol) was added to a stirred solution of 11,12-difluoro-1,4,9-trioxadispiro[4.2.48.25]tetradecane (Step-3, 30.0 mg, 0.13 mmol) in DCM (0.26 mL) at 0° C. The resulting mixture was stirred at 22° C. for 16 h. The reaction mixture was concentrated under reduced pressure to obtain the diastereomeric mixture of the title compound (24.0 mg) as an oil. $^1$H NMR (400 MHz, $CDCl_3$) δ 5.37-5.17 (m, 1H), 5.00-4.81 (m, 1H), 4.32-4.17 (m, 1H), 4.17-4.05 (m, 1H), 2.68 (qd, 2H), 2.43-2.24 (m, 2H), 2.24-2.06 (m, 2H), 2.00-1.82 (m, 2H).

Step-5. 3,4-difluoro-1-oxaspiro[4.5]decan-8-one oxime

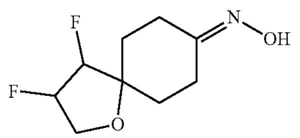 [SMILES: ON=C1CCC2(CC1)OCC(F)C2F]

3,4-difluoro-1-oxaspiro[4.5]decan-8-one (Step-4, 24.0 mg, 0.13 mmol) was added as a solution in MeOH (0.20 mL) to a stirred solution of hydroxylamine hydrochloride (9.6 mg, 0.14 mmol) and sodium acetate (13.0 mg, 0.16 mmol) in MeOH (0.20 mL) at 22° C. The resulting mixture was stirred at 60° C. for 16 h. The resulting solution was diluted with EtOAc and the organic layer was washed with water and brine. The organic layer was dried over anhydrous sodium sulfate, filtered, and the solvent was evaporated. The residue was purified by silica gel column chromatography eluting with cyclohexane/EtOAc (3/1 v/v to 3/2 v/v) to obtain the diastereomeric mixture of the title compound (7.0 mg) as an oil. TLC-MS (APCI): $[M+H]^+$: 206.0.

Step-6. tert-butyl (3,4-difluoro-1-oxaspiro[4.5]decan-8-yl)carbamate

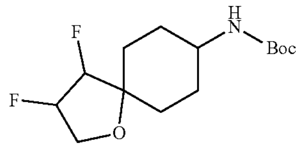 [SMILES: CC(C)(C)OC(=O)NC1CCC2(CC1)OCC(F)C2F]

$NaBH_4$ (10.3 mg, 0.27 mmol) was added to a stirred solution of 3,4-difluoro-1-oxaspiro[4.5]decan-8-one oxime (Step-5, 7.0 mg, 0.03 mmol) and nickel (II) chloride hexahydrate (10.5 mg, 0.04 mmol) in MeOH (0.68 mL) at −78° C. The resulting mixture was warmed to 0° C. for 4.5 h. $Boc_2O$ (11.2 mg, 0.05 mmol) was added and the reaction mixture was stirred at 22° C. for 16 h. The resulting solution was cooled to 0° C., quenched with brine, and then concentrated under reduced pressure. The aqueous was extracted with $Et_2O$. The organic layers were combined, washed with brine, dried over anhydrous sodium sulfate, filtered, and the solvent was evaporated to obtain the title compound (10.0 mg) as a solid mixture of diastereomers. $^1$H NMR (400 MHz, $CDCl_3$) δ 5.31-5.07 (m, 1H), 5.00-4.66 (m, 1H), 4.43 (s, 1H), 4.21-4.06 (m, 1H), 4.01-3.93 (m, 1H), 3.48 (s, 1H), 1.98-1.76 (m, 4H), 1.74-1.58 (m, 2H) 1.52-1.46 (m, 2H), 1.44 (s, 9H).

Step-7. 2,2,2-trifluoroacetaldehyde-(3,4-difluoro-1-oxaspiro[4.5]decan-8-yl)-14-azane

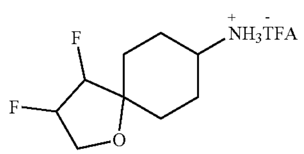

TFA (26.0 μL, 0.34 mmol) was added to a stirred solution of tert-butyl (3,4-difluoro-1-oxaspiro[4.5]decan-8-yl)carbamate (Step-6, 10.0 mg, 34.3 μmol) in DCM (0.21 mL) at 0° C. The resulting mixture was stirred at 22° C. for 4.5 h and then concentrated under reduced pressure to obtain the diastereomeric mixture of the title compound (10.5 mg) as an oil. TLC-MS (APCI): $[M+H]^+$: 192.1.

Step-8. (1R,3s,5S)—N-(3,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide

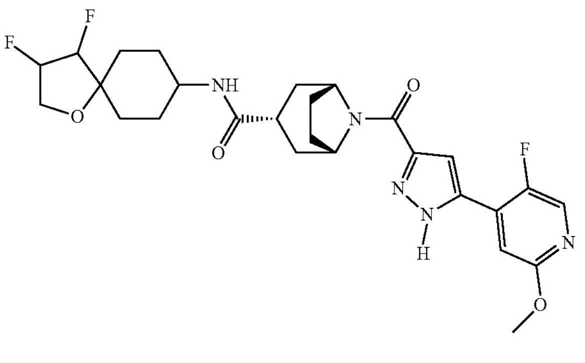 [SMILES: COc1cc(-c2cc(C(=O)N3[C@@H]4CC[C@H]3C[C@H](C(=O)NC3CCC5(CC3)OCC(F)C5F)C4)n[nH]2)c(F)cn1]

HATU (11.2 mg 29.4 μmol) and 2,2,2-trifluoroacetaldehyde-(3,4-difluoro-1-oxaspiro[4.5]decan-8-yl)-14-azane (Step-7, 10.6 mg, 34.73 μmol) were added to a stirred solution of (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 10.0 mg, 26.7 μmol) and DIPEA (23.0 μL, 0.13 mmol) in DMF (0.20 mL). The resulting solution was stirred at 22° C. for 16 h. The reaction mixture was concentrated and diluted with EtOAc and water, washed with water and brine, and then dried over anhydrous sodium sulfate, filtered, and the solvent was evaporated. The residue was purified by reverse phase column chromatography (C18 column, 10% to 95% MeOH/Water (0.1% HCOOH)) to obtain the title compound (6.0 mg) as a solid mixture of diastereomers. $^1$H NMR (400 MHz, DMSO-$d_6$) δ 14.00 (s, 1H), 8.28 (d, 1H), 7.76-7.63 (m, 1H), 7.33 (d, 1H), 7.12 (d, 1H), 5.45-5.26 (m, 1H), 5.17-4.88 (m, 1H), 4.69 (s, 1H), 4.19-3.78 (m, 5H), 3.71-3.58 (m, 1H), 3.58-3.44 (m, 1H), 2.88-2.70 (m, 1H), 2.11-0.99 (m, 16H). LCMS (ESI): $[M+H]^+$: 548.2.

Example 320. (1R,3s,5S)—N-(4,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide

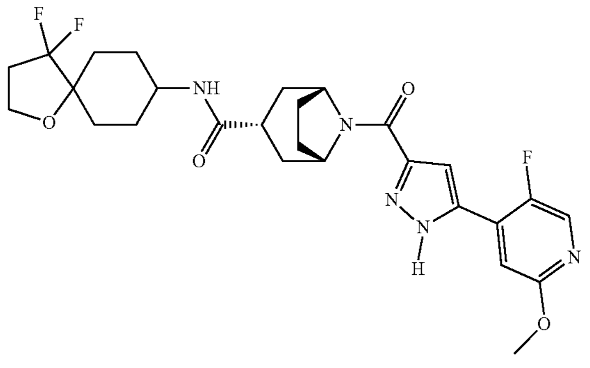 [SMILES: COc1cc(-c2cc(C(=O)N3[C@@H]4CC[C@H]3C[C@H](C(=O)NC3CCC5(CC3)OCCC5(F)F)C4)n[nH]2)c(F)cn1]

Step-1. 2,2,2-trifluoroacetaldehyde, 4,4-difluoro-1-oxaspiro[4.5]decan-8-aminium Salt

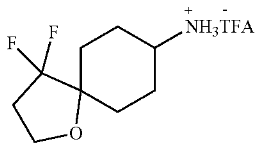

TFA (0.08 mL, 1.00 mmol) was added to a stirred solution of tert-butyl (4,4-difluoro-1-oxaspiro[4.5]decan-8-yl)carbamate (INTERMEDIATE 540, 30.0 mg, 0.10 mmol) in DCM (0.21 mL) at 0° C. The resulting mixture was stirred at 22° C. for 4.5 h. The reaction mixture was concentrated under reduced pressure to obtain the diastereomeric mixture of the title compound (31.0 mg) as an oil. TLC-MS (APCI): $[M+H]^+$: 192.1.

Step-2. (1R,3s,5S)—N-(4,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide

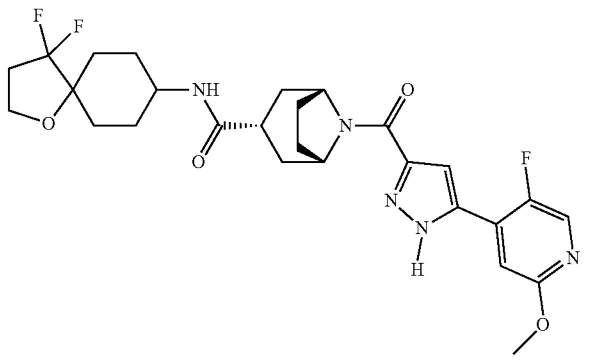 [SMILES: COc1cc(-c2cc(C(=O)N3[C@@H]4CC[C@H]3C[C@H](C(=O)NC3CCC5(CC3)OCCC5(F)F)C4)n[nH]2)c(F)cn1]

HATU (28.0 mg, 0.07 mmol) and 4,4-difluoro-1-oxaspiro[4.5]decan-8-amine 2,2,2-trifluoroacetate (Step-1, 32.0 mg, 0.10 mmol) were added to a stirred solution of (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 25.0 mg, 0.07 mmol) and DIPEA (0.06 mL, 0.33 mmol) in DMF (0.2 mL). The resulting solution was stirred at 22° C. for 16 h. The reaction was concentrated and diluted with EtOAc and water, washed with water and brine, and then dried over anhydrous sodium sulfate, filtered, and the solvent was evaporated. The residue was purified by reverse phase column chromatography (C18 column, 10% to 95% MeOH/Water (0.1% HCOOH)) to obtain the title compound (19.0 mg) as a solid mixture of diastereomers. $^1$H NMR (400 MHz, DMSO-$d_6$) δ 14.01 (s, 1H), 8.28 (s, 1H), 7.74 (dd, 1H), 7.33 (d, 1H), 7.13 (s, 1H), 4.68 (s, 1H), 3.99-3.77 (m, 5H), 3.78-3.73 (m, 0.5H), 3.51-3.47 (m, 0.5H), 2.90-2.85 (m, 0.5H), 2.80-2.75 (m, 0.5H), 2.46-2.39 (m, 2H), 2.05-1.22 (m, 17H). LCMS (ESI): $[M+H]^+$:548.1.

Example 321. A Diastereomeric Mixture of (8)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide and (S)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide and (S)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide and (S)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide

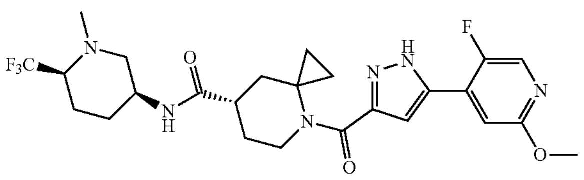

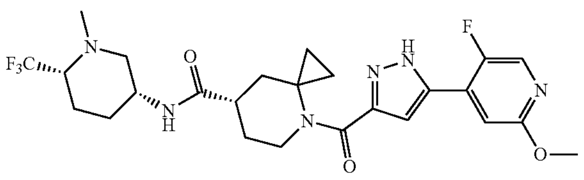

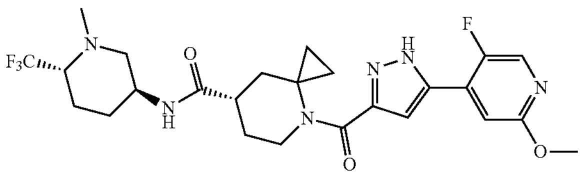

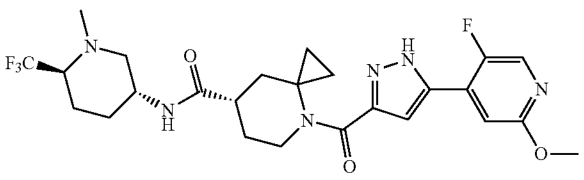

The title compound was prepared using a procedure similar to the one described for the synthesis of Example 311, except (S)-4-[5-(5-fluoro-2-methoxypyridin-4-yl)-1H-pyrazole-3-carbonyl]-4-azaspiro[2.5]octane-7-carboxylic acid (INTERMEDIATE 527-A) was used as starting material. The resulting residue was purified by Prep-TLC (DCM/MeOH, 20/1 v/v) to obtain the diastereomeric mixtures (Example 321) of (S)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide and (S)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide and (S)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide and (S)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide in two fractions, each containing two diastereomers. The first fraction (90.0 mg) was obtained as an oil (LCMS (ESI): $[M+H]^+$: 539.2) and the second fraction (23.0 mg) was obtained as an oil (LCMS (ESI): $[M+H]^+$: 539.2).

The first fraction (90.0 mg) from Prep-TLC containing two diastereomers of the title compounds was separated using Chiral Prep-HPLC.

Column: CHIRALPAK ID column

Column dimension: 2×25 cm, 5 μm

Mobile Phase: MTBE (0.5% 2M $NH_3$·MeOH):MeOH-80:20 hold for 27 min

Flow rate: 16 mL/min

Detection: 220/254 nm

Example 321-A. The first eluting diastereomer (28.1 mg) was obtained as a solid.

The first eluting diastereomer had a retention time of 14.53 min.

$^1$H NMR (300 MHz, DMSO-$d_6$) δ 13.97 (s, 1H), 8.25 (s, 1H), 7.75 (d, 1H), 7.30 (d, 1H), 7.01 (s, 1H), 4.47-4.41 (m, 1H), 3.86 (s, 3H), 3.78-3.72 (m, 1H), 3.25-3.05 (m, 1H), 2.69-2.63 (m, 3H), 2.48-2.40 (m, 3H), 2.17-2.11 (m, 1H), 1.90-1.57 (m, 5H), 1.54-1.38 (m, 2H), 1.20-1.14 (m, 1H) 0.97-0.91 (m, 2H), 0.64-0.58 (m, 2H). LCMS (ESI): 539.3

Example 321-B. The second eluting diastereomer (24.6 mg) was obtained as a solid.

The second eluting diastereomer had a retention time of 20.09 min.

$^1$H NMR (300 MHz, DMSO-$d_6$) δ 13.97 (s, 1H), 8.25 (s, 1H), 7.75 (d, 1H), 7.30 (d, 1H), 7.01 (s, 1H), 4.47-4.41 (m, 1H), 3.86 (s, 3H), 3.78-3.72 (m, 1H), 3.25-3.05 (m, 1H), 2.69-2.63 (m, 3H), 2.48-2.40 (m, 3H), 2.17-2.10 (m, 1H), 1.90-1.55 (m, 5H), 1.54-1.36 (m, 2H), 1.20-1.14 (m, 1H), 0.97-0.91 (m, 2H), 0.64-0.58 (m, 2H). LCMS (ESI): 539.3 $[M+H]^+$.

The second fraction (23.0 mg) from Prep-TLC containing two diastereomers of the title compounds was separated using Chiral Prep-HPLC.

Column: CHIRALPAK IE column

Column dimension: 2×25 cm, 5 μm

Mobile Phase: 3/1 hexanes/DCM (0.5% 2M $NH_3$·MeOH):EtOH=70:30 hold for 13 min

Flow rate: 20 mL/min

Detection: 220/254 nm

Example 321-C. The first eluting diastereomer (3.1 mg) was obtained as a solid.

The first eluting diastereomer had a retention time of 8.40 min.

LCMS (ESI): 539.25 $[M+H]^+$.

Example 321-D. The second eluting diastereomer (4.0 mg) was obtained as a solid.

The second eluting diastereomer had a retention time of 11.30 min.

LCMS (ESI): 539.25 $[M+H]^+$.

Example 322. A Diastereomeric Mixture of (R)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide and (R)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide and (R)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide and (R)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide

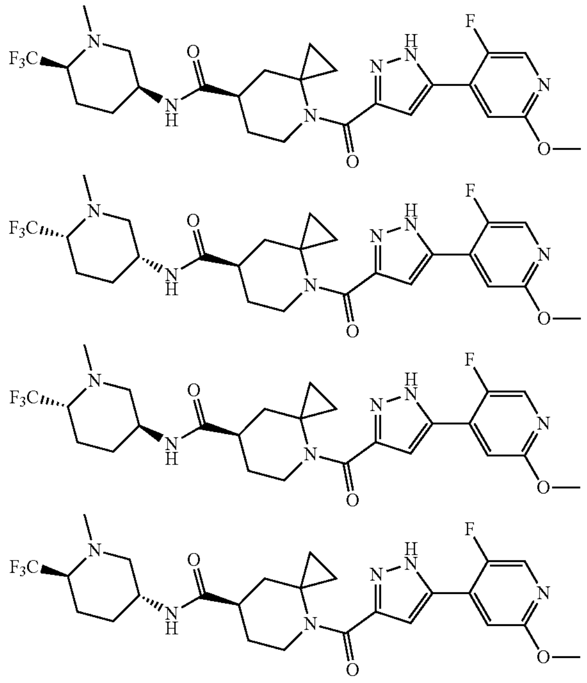

The title compound was prepared using a procedure similar to the one described for the synthesis of Example 311, except (R)-4-(3-(5-fluoro-2-methoxypyridin-4-yl)-1H-pyrazole-5-carbonyl)-4-azaspiro[2.5]octane-7-carboxylic acid (INTERMEDIATE 527-B) was used as starting material. The resulting residue was purified by Prep-TLC (DCM/MeOH, 10/1 \TN) to obtain the diastereomeric mixtures (Example 322) of (R)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2,5]octane-7-carboxamide and (R)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide and (R)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide and (R)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide in two fractions, each containing two diastereomers. The first fraction (90.0 mg) was obtained as an oil (LCMS (ESI): 539.2 $[M+H]^+$) and the second fraction (1.0 mg) was obtained as a solid mixture of diastereomers (Example 322-C). LCMS (ESI): 539.2 $[M+H]^+$.

The first fraction (90.0 mg) from Prep-TLC containing two diastereomers of the title compounds was separated using Chiral Prep-HPLC.

Column: CHIRALPAK IA column

Column dimension: 2×25 cm, 5 μm

Mobile Phase: MTBE (0.5% 2 M $NH_3$·MeOH): MeOH=95:5 hold for 13 min

Flow rate: 20 mL/min

Detection: 220/254 nm

Example 322-A. The first eluting diastereomer (20.1 mg) was obtained as a solid.

The first eluting diastereomer had a retention time of 8.93 min.

1H NMR (300 MHz, DMSO-$d_6$) δ 13.99 (s, 1H), 8.26 (s, 1H), 7.75 (d, 1H), 7.31 (d, 1H), 7.02 (s, 1H), 4.83-4.08 (m, 1H) 3.87 (s, 3H), 3.76 (s, 1H), 3.28-2.99 (m, 1H), 2.76-2.53 (m, 3H), 2.49-2.41 (m, 3H), 2.11 (d, 1H), 2.01-1.57 (m, 5H), 1.57-1.29 (m, 2H), 1.23 (s, 1H), 1.09-0.74 (m, 2H) 0.64 (s, 2H). LCMS (ESI): 539.3 $[M+H]^+$.

Example 322-B. The second eluting diastereomer (17.6 mg) was obtained as a solid.

The second eluting diastereomer had a retention time of 10.71 min.

1H NMR (300 MHz, DMSO-d6) δ 13.94 (s, 1H), 8.26 (d, 1H), 7.74 (d, 1H), 7.31 (d, 1H), 7.02 (d, 1H), 4.42 (s, 1H), 3.87 (s, 3H), 3.83-3.64 (m, 1H), 3.26-3.03 (m, 1H), 2.81-2.54 (m, 3H), 2.47-2.43 (m, 3H), 2.27-2.03 (m, 1H), 1.96-1.56 (m, 3H), 1.56-1.36 (m, 2H), 1.34-0.99 (m, 3H), 1.03-0.76 (m, 2H), 0.63 (s, 2H). LCMS (ESI): 539.3 $[M+H]^+$.

Example 323. A diastereomeric mixture of (R)—N-((1r,4R)-4-ethoxy-4-(trifluoromethyl)cyclohexyl)-4-(5-(5-fluoro-2-methylpyridin-, 1-yl)-1H-pyrazole-3-carbonyl)-4-azaspiro[2.5]octane-7-carboxamide and (S)—N-(1r,4S)-4-ethoxy-4-(trifluoromethyl)cyclohexyl)-4-(5-(5-fluoro-2-methylpyridin-4-yl)-1H-pyrazole-3-carbonyl)-4-azaspiro[2.5]octane-7-carboxamide

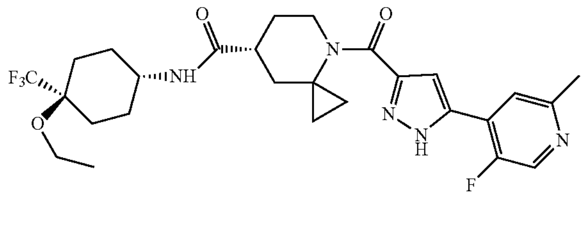

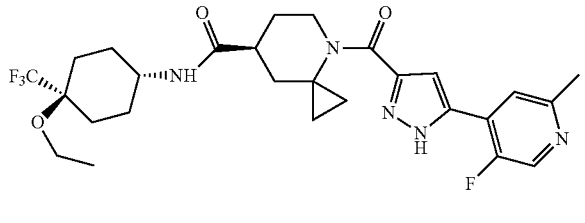

Step-1. (1r,4r)-4-(dibenzylamino)-1-(trifluoromethyl)cyclohexan-1-ol

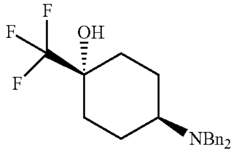

$K_2CO_3$ (6.00 g, 43.67 mmol) was added to a mixture of (1r,4r)-4-amino-1-(trifluoromethyl)cyclohexan-1-ol (2.00 g, 10.92 mmol) and benzyl bromide (4.30 g, 25.11 mmol) in MeCN (10.00 mL). The resulting mixture was stirred at 25° C. for 14 h. The resulting mixture was concentrated under reduced pressure. The residue was purified by silica gel column chromatography (petroleum ether/EtOAc, 3/1 v/v) to obtain the title compound (3.60 g) as a solid. LCMS (ESI): 364.2 $[M+H]^+$.

Step-2. (1r,4r)-N,N-dibenzyl-4-ethoxy-4-(trifluoromethyl)cyclohexan-1-amine

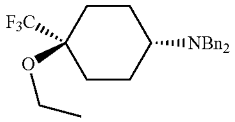

NaH (39.6 mg, 1.65 mmol) was added to a stirred solution of (1r,4r)-4-(dibenzylamino)-1-(trifluoromethyl)cyclohexan-1-ol (Step-1, 300.0 mg, 0.86 mmol) in DMF (5.00 mL). The resulting mixture was stirred at 25° C. for 1 h. Iodoethane (643.7 mg, 4.13 mmol) was added to the resulting mixture. The resulting mixture was stirred at 25° C. for 14 h. The reaction mixture was diluted with water and EtOAc. The organic layers were combined, dried over anhydrous $Na_2SO_4$, filtered, and concentrated under reduced pressure. The residue was purified by silica gel column chromatography (EtOAc/petroleum ether, 1/10 v/v) to obtain the title compound (130.0 mg) as a solid. LCMS (ESI): 392.2 $[M+H]^+$.

Step-3. (1r,4r)-4-ethoxy-4-(trifluoromethyl)cyclohexan-1-amine

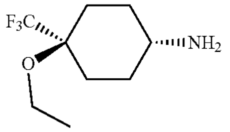

Pd/C (50.0 mg) was added to a stirred solution of (1r,4r)-N,N-dibenzyl-4-ethoxy-4-(trifluoromethyl)cyclohexan-1-amine (Step-2, 130.0 mg, 0.33 mmol) in MeOH (3.00 mL), The resulting mixture was stirred at 25° C. under a $H_2$ atmosphere for 14 h. The solid was filtered out. The organic layer was concentrated under reduced pressure to obtain the title compound (70.0 mg) as an oil. LCMS (ESI): 212.1 $[M+H]^+$.

Step-4. (7R)-4-[5-(5-fluoro-2-methylpyridin-4-yl)-1H-pyrazole-3-carbonyl]-N-[(1r,4r)-4-ethoxy-4-(trifluoromethyl)cyclohexyl]-4-azaspiro[2.5]octane-7-carboxamide and (7S)-4-[5-(5-fluoro-2-methylpyridin-4-yl)-1H-pyrazole-3-carbonyl]-N-[(1r,4r)-4-ethoxy-4-(trifluoromethyl)cyclohexyl]-4-azaspiro[2.5]octane-7-carboxamide

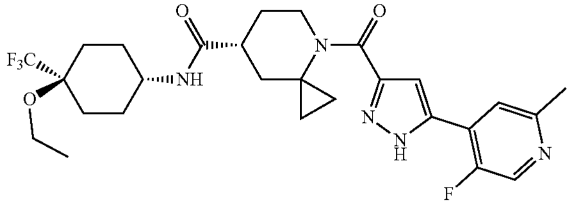

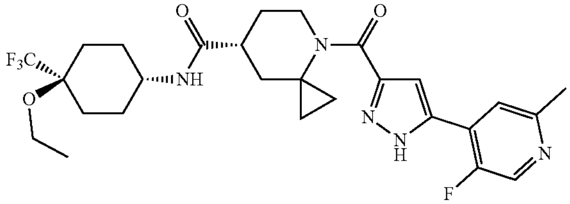

HOBt (56.4 mg, 0.42 mmol), EDCI (80.0 mg, 0.42 mmol), and (1r,4r)-4-ethoxy-4-(trifluoromethyl)cyclohexan-1-amine (Step-3, 76.4 mg, 0.362 mmol) were added to a stirred solution of 4-[5-(5-fluoro-2-methylpyridin-4-yl)-1H-pyrazole-3-carbonyl]-4-azaspiro[2.5]octane-7-carboxylic acid (INTERMEDIATE 526, 99.7 mg, 0.28 mmol) and DIPEA (143.8 mg, 1.11 mmol) in DMF (3.00 mL). The resulting mixture was stirred at 25° C. for 1 h. The resulting mixture was diluted with EtOAc and water. The organic layers were combined, dried over anhydrous $Na_2SO_4$, filtered, and concentrated under reduced pressure. The residue was purified by silica gel column chromatography (DCM/MeOH, 10/1 v/v) to obtain (7R)-4-[5-(5-fluoro-2-methylpyridin-4-yl)-1H-pyrazole-3-carbonyl]-N-[(1r,4r)-4-ethoxy-4-(trifluoromethyl)cyclohexyl]-4-azaspiro[2.5]octane-7-carboxamide and (7S)-4-[5-(5-fluoro-2-methylpyridin-4-yl)-1H-pyrazole-3-carbonyl]-N-[(1r,4r)-4-ethoxy-4-(trifluoromethyl)cyclohexyl]-4-azaspiro[2.5]octane-7-carboxamide (57.0 mg) as an oil mixture of diastereomers. LCMS (ESI): 552.3 $[M+H]^+$.

This mixture of two diastereomers (57.0 mg) was separated using Chiral Prep-HPLC.

Column: CHIRALPAK IA column

Column dimension: 2×25 cm, 5 μm

Mobile Phase: 3/1 hexanes/DCM (0.5% 2 M $NH_3$·MeOH):EtOH=90:10 hold for 12 min

Flow rate: 17 mL/min

Detection: 220/254 nm

Example 323-A. The first eluting diastereomer (5.7 mg) was obtained as a solid.

The first eluting diastereomer had a retention time of 6.35 min, $^1$H NMR (300 MHz, DMSO-$d_6$) δ 14.01 (s, 1H), 8.49 (s, 1H), 7.82 (s, 2H), 7.25-6.89 (m, 1H), 4.49 (s, 1H), 3.85 (s, 1H), 3.67-3.47 (m, 2H), 2.97-2.65 (m, 2H), 2.05-1.32 (m, 12H), 1.31-1.07 (m, 5H), 1.06-0.74 (m, 2H), 0.67 (s, 3H). LCMS (ESI): 552.25 $[M+H]^+$.

Example 323-B. The second eluting diastereomer (10.9 mg) was obtained as a solid.

The second eluting diastereomer had a retention time of 9.91 min.

$^1$H NMR (400 MHz, DMSO-$d_6$) δ 14.24-13.77 (m, 1H), 8.52 (s, 1H), 8.03-7.71 (m, 2H), 7.03 (s, 1H), 4.51 (s, 1H), 3.93-3.79 (m, 1H), 3.63-3.48 (m, 2H), 3.20-2.62 (m, 2H), 2.42-2.04 (m, 1H), 2.01-1.35 (m, 11H), 1.33-0.77 (m, 7H), 0.66 (s, 3H). LCMS (ESI): 552.25 $[M+H]^+$.

Example 324. A Diastereomeric Mixture of (R)-4-(5-(5-fluoro-2-methoxypyridin-4-yl)-1H-pyrazole-3-carbonyl)-N-((1r,4R)-4-methoxy-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-methoxy-4-(trifluoromethyl)cyclohexyl)-4-azaspiro[2.5]octane-7-carboxamide

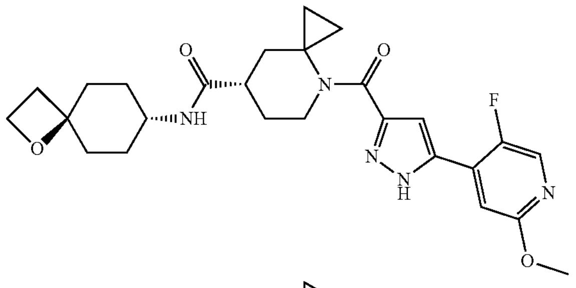

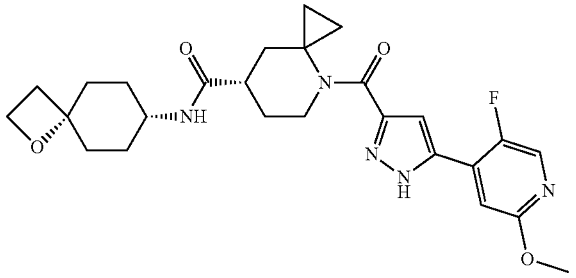

The title compound was prepared using a procedure similar to the one described for the synthesis of Example 323, except iodomethane was used as a starting material in Step-2 and 4-[5-(5-fluoro-2-methoxypyridin-4-yl)-1H-pyrazole-3-carbonyl]-4-azaspiro[2.5]octane-7-carboxylic acid (INTERMEDIATE 527) was used as a starting material in Step-4. The resulting residue was purified by silica gel column chromatography (DCM/MeOH, 10/1 v/v) to obtain (R)-4-(5-(5-fluoro-2-methoxypyridin-4-yl)-1H-pyrazole-3-carbonyl)-N-((1r,4R)-4-methoxy-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-methoxy-4-(trifluoromethyl)cyclohexyl)-4-azaspiro[2.5]octane-7-carboxamide as a solid mixture of diastereomers.

This mixture of two diastereomers was separated using Chiral Prep-HPLC.

Column: CHIRALPAK ID column

Column dimension: 2×25 cm, 5 μm

Mobile Phase: 3/1 hexanes/DCM (0.5% 2 M $NH_3$·MeOH):EtOH=90:10 hold for 21 min

Flow rate: 20 mL/min

Detection: 220/254 nm

Example 324-A. The first eluting diastereomer (51.8 mg) was obtained as a solid.

The first eluting diastereomer had a retention time of 9.80 min.

$^1$H NMR (400 MHz, DMSO-$d_6$) δ 13.95 (d, 1H), 8.25 (d, 1H), 7.84 (s, 1H), 7.29 (d, 1H), 7.02 (s, 1H), 4.51 (s, 1H), 3.86-3.80 (m, 4H), 3.28 (s, 3H), 2.77 (s, 1H), 2.18 (s, 1H), 1.91-1.66 (m, 5H), 1.60 (m, 5H), 1.27-1.04 (m, 2H), 0.92-0.79 (m, 2H), 0.70-0.52 (m, 2H). LCMS (ESI): 554.25 $[M+H]^+$.

Example 324-B. The second eluting diastereomer (45.3 mg) was obtained as a solid.

The second eluting diastereomer had a retention time of 15.55 min.

$^1$H NMR (400 MHz, DMSO-$d_6$) δ 13.95 (d, 1H), 8.26 (d, 1H), 7.85 (d, 1H), 7.29 (d, 7.02 (s, 1H), 4.51 (s, 1H), 3.86-3.80 (m, 4H), 3.28 (s, 3H), 2.77 (s, 1H), 2.17 (s, 1H), 1.72 (s, 5H), 1.64-1.50 (m, 5H), 1.22 (s, 1H), 1.13 (s, 1H), 0.95 (s, 2H), 0.66 (s, 1H), 0.57 (s, 1H). LCMS (ESI): 554.25 $[M+H]^+$.

Example 325. A diastereomeric mixture of (S)-4-(5-(5-fluoro-2-methoxypyridin-4-yl)-1H-pyrazole-3-carbonyl)-N-((4S,7r)-1-oxaspiro[3.5]nonan-7-yl)-4-azaspiro[2.5]octane-7-carboxamide and (8)-4-(5-(5-fluoro-2-methoxypyridin-4-yl)-1H-pyrazole-3-carbonyl)-N-((4R,7s)-1-oxaspiro[3.5]nonan-7-yl)-4-azaspiro[2.5]octane-7-carboxamide

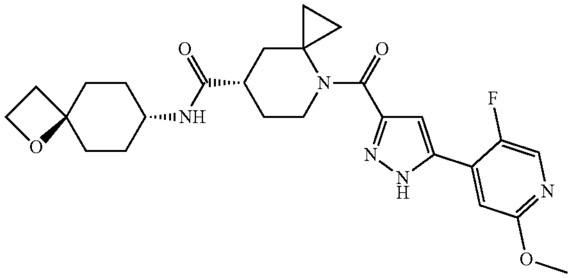

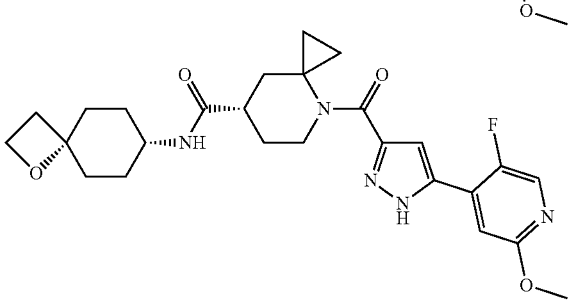

The title compound was prepared using a procedure similar to the one described for the synthesis of Example 276, except (S)-4-[5-(5-fluoro-2-methoxypyridin-4-yl)-1H-pyrazole-3-carbonyl]-4-azaspiro[2.5]octane-7-carboxylic acid (INTERMEDIATE 527-A) was used as a starting material. The resulting residue was purified by silica gel column chromatography (DCM/MeOH, 15/1 v/v) to obtain (S)-4-(5-(5-fluoro-2-methoxypyridin-4-yl)-1H-pyrazole-3-carbonyl)-N-((4S,7r)-1-oxaspiro[3.5]nonan-7-yl)-4-azaspiro[2.5]octane-7-carboxamide and (S)-4-(5-(5-fluoro-2-methoxypyridin-4-yl)-1H-pyrazole-3-carbonyl)-N-((4R,7s)-1-oxaspiro[3.5]nonan-7-yl)-4-azaspiro[2.5]octane-7-carboxamide as a solid mixture of diastereomers (60.0 mg), LCMS (ESI): 498.5 $[M+H]^+$.

The two diastereomers of the title compound were separated using Chiral Prep-HPLC.

Column: CHIRALPAK ART Cellulose-SC column

Column dimension: 2×25 cm, 5 μm

Mobile Phase: 3/1 hexanes/DCM (0.5% 2 M $NH_3$·MeOH):EtOH=50:50 hold for 14 min

Flow rate: 20 mL/min

Detection: 220/254 nm

Example 325-A. The first eluting diastereomer (3.7 mg) was obtained as a solid.

The first eluting diastereomer had a retention time of 7.38 min,

1H NMR (300 MHz, $CD_3OD$) δ 8.14 (s, 1H), 7.42-7.08 (m, 2H), 4.52 (t, 2H), 3.95 (s, 3H), 3.69-3.57 (m, 1H), 2.82-2.76 (m, 1H), 2.47-2.35 (m, 3H), 2.25-2.06 (m, 3H), 1.97-1.41 (m, 8H), 1.34-1.20 (m, 2H), 1.08-1.02 (m, 2H), 0.73 (s, 2H). LCMS (ESI): 498.45 $[M+H]^+$.

Example 325-B. The second eluting diastereomer (0.9 mg) as obtained as a solid.

The second eluting diastereomer had a retention time of 7.95 min.

$^1$H NMR (300 MHz, $CD_3OD$) δ 8.14 (s, 1H), 7.54-7.08 (m, 2H), 4.54 (t, 2H), 3.95 (s, 3H), 3.67-3.61 (m, 1H), 2.80-2.74 (m, 1H), 2.52-2.08 (m, 6H), 1.92-1.72 (m, 4H), 1.70-1.55 (m, 2H), 1.41-1.23 (m, 4H), 1.08-0.86 (m, 2H), 0.76-0.70 (m, 2H). LCMS (ESI): 498.50 $[M+H]^+$.

Example 326. A Diastereomeric Mixture of (1R,3s,5S)-8-(5-(5-fluoro-2-methoxypyridin-4-yl)-1H-pyrazole-3-carbonyl)-N-((3S,6S)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6S)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6R)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6R)-1-(2-fluoro-2-methylpropyl)-6-(trifluoromethyl)piperidin-3-yl)-8-azabicyclo[3.2.1]octane-3-carboxamide Step-1. Tert-butyl N-[6-(trifluoromethyl)piperidin-3-yl]carbamate

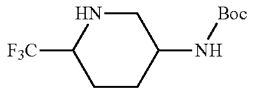

$Rh/Al_2O_3$ (0.14 g, 1.34 mmol) and HOAc (4.00 mL) were added to a stirred solution of tert-butyl N-[6-(trifluoromethyl)pyridin-3-yl]carbamate (3.50 g, 13.35 mmol) in MeOH (30.00 mL). The resulting mixture was stirred at 50° C. under 50 atm $H_2$ atmosphere for 14 h. The solution was filtered and the solvent was evaporated. The residue was purified by silica gel column chromatography (petroleum ether/EtOAc, 1/1 v/v) to obtain the title compound (2.50 g) as a solid. LCMS (ESI): 269.3$[M+H]^+$.

Step-2. Tert-butyl N-[1-(2-hydroxy-2-methylpropyl)-6-(trifluoromethyl)piperidin-3-yl]carbamate

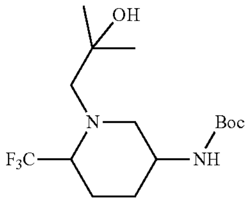 [SMILES: CC(C)(O)CN1CC(NC(=O)OC(C)(C)C)CCC1C(F)(F)F]

2,2-Dimethyloxirane (0.60 g, 8.39 mmol) and $K_2CO_3$ (2.32 g, 16.78 mmol) were added to a stirred solution of tert-butyl N-[(3S,6S)-6-(trifluoromethyl)piperidin-3-yl]carbamate (Step-1, 1.50 g, 5.59 mmol) in EtOH (8.00 mL) and $H_2O$ (2.00 mL). The resulting mixture was stirred at 110° C. for 14 h. The solution was filtered, and the solvent was evaporated. The residue was purified by silica gel column

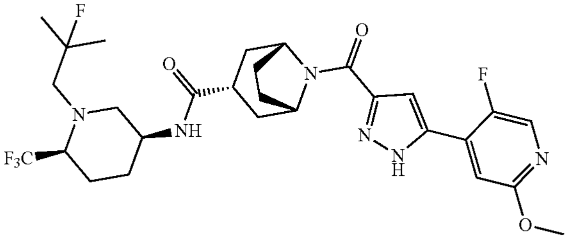

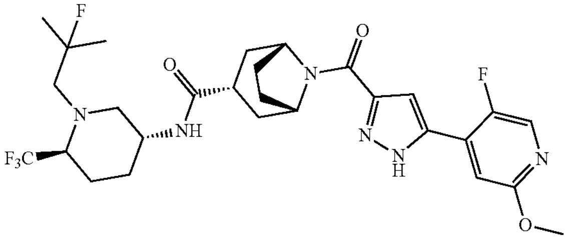

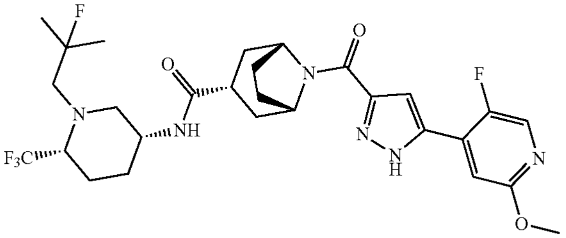

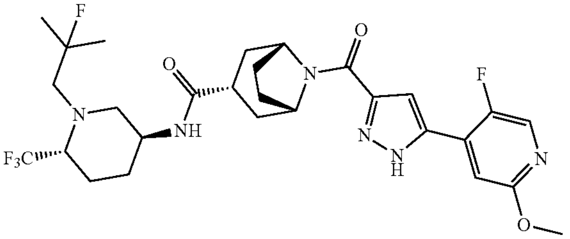

chromatography (petroleum ether/EtOAc, 2/1 v/v) to obtain the title compound (750.0 mg) as a solid. LCMS (ESI): 341.4 [M+H]+.

Step-3. Tert-butyl N-[1-(2-fluoro-2-methylpropyl)-6-(trifluoromethyl)piperidin-3-yl]carbamate

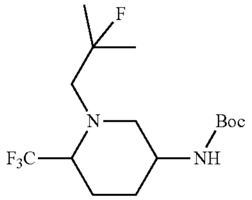 [SMILES: CC(C)(F)CN1CC(NC(=O)OC(C)(C)C)CCC1C(F)(F)F]

$Et_2NSF_3$ (461.2 mg, 2.87 mmol) was added to a stirred solution of tert-butyl N-[1-(2-hydroxy-2-methylpropyl)-6-(trifluoromethyl)piperidin-3-yl]carbamate (Step-2, 750.0 mg, 2.20 mmol) in DCM (6.00 mL). The resulting mixture was stirred at 25° C. for 2 h. The solution was diluted with water and DCM. The organic layers were combined, dried over anhydrous sodium sulfate, filtered, and the solvent was evaporated. The residue was purified by silica gel column chromatography (petroleum ether/EtOAc, 3/1 v/v) to obtain the title compound (700.0 mg) as a solid. LCMS (ESI): 343.4 [M+H]+.

Step-4. 1-(2-Fluoro-2-methylpropyl)-6-(trifluoromethyl)piperidin-3-amine

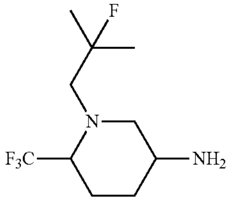 [SMILES: CC(C)(F)CN1CC(N)CCC1C(F)(F)F]

TFA (3.00 mL) was added to a stirred solution of tert-butyl N-[1-(2-fluoro-2-methylpropyl)-6-(trifluoromethyl)piperidin-3-yl]carbamate (Step-3, 700.0 mg, 2.05 mmol) DCM (3.00 mL). The resulting mixture was stirred at 25° C. for 1 h. The resulting mixture was concentrated under reduced pressure. The residue was purified by silica gel chromatography (DCM/MeOH, 10/1 v/v) to obtain the title compound (400.0 mg) as a solid. LCMS (ESI): 243.2 [M+H]+.

Step-5. (1R,3s,5S)-8-(5-(5-fluoro-2-methoxypyridin-4-yl)-1-((2-(trimethylsilyl)ethoxy)methyl)-1H-pyrazole-3-carbonyl)-N-(1-(2-fluoro-2-methylpropyl)-6-(trifluoromethyl)piperidin-3-yl)-8-azabicyclo[3.2.1]octane-3-carboxamide

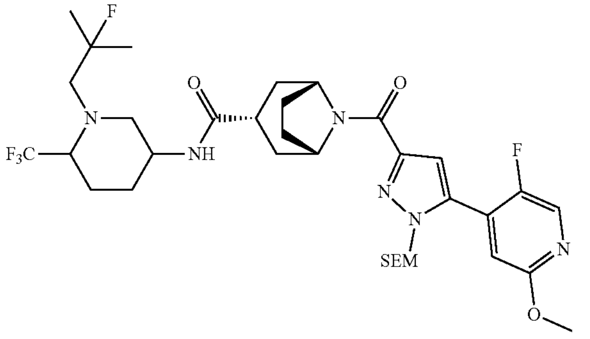 [SMILES: COc1cc(-c2cc(C(=O)N3[C@@H]4CC[C@H]3C[C@H](C(=O)NC3CCC(C(F)(F)F)N(CC(C)(C)F)C3)C4)nn2COCC[Si](C)(C)C)c(F)cn1]

EDCI (411.5 mg, 2.15 mmol), HOBt (290.0 mg, 2.15 mmol), and 1-(2-fluoro-2-triethylpropyl)-6-(trifluoromethyl)piperidin-3-amine (Step-4, 400.0 mg, 1.65 mmol) were added to a stirred solution of (1R,3S,5S)-8-[5-(5-Fluoro-2-methoxypyridin-4-yl)-1-[[2-(trimethylsilyl)ethoxy]methyl]pyrazole-3-carbonyl]-8-azabicyclo[3.2.1]octane-3-carboxylic acid (INTERMEDIATE 529, 833.2 mg, 1.65 mmol) and DIPEA (640.2 mg, 4.95 mmol) in DMF (6.00 ml). The resulting mixture was stirred at 25° C. for 14 h. The solution was diluted with water and extracted with EtOAc. The organic layers were combined, then dried over anhydrous sodium sulfate, filtered, and the solvent was evaporated. The residue was purified by silica gel chromatography (DCM/MeOH, 20/1 v/v) to obtain the title compound (750.0 mg) as a solid. LCMS (ESI): 729.9 [M+H]+.

Step-6. (1R,3s,5S)-8-(5-(5-fluoro-2-methoxypyridin-4-yl)-1H-pyrazole-3-carbonyl)-N-((3S,6S)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6S)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6R)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6R)-1-(2-fluoro-2-methylpropyl)-6-(trifluoromethyl)piperidin-3-yl)-8-azabicyclo[3.2.1]octane-3-carboxamide This mixture of four diastereomers (400.0 mg) was separated using Chiral Prep-HPLC, Column: CHIRALPAK ID column Column dimension: 2×25 cm, 5 μm Mobile Phase: MTBE (0.5% 2 M $NH_3$·MeOH): MeOH=85:15 hold for 23 min Flow rate: 18 mL/min Detection: 220/254 nm Example 326-A and Example 326-B. The first eluting peak (180.0 mg) was Obtained as a Solid Mixture of Two Diasteromers.

The first eluting peak had a retention time of 9.13 min

Example 326-C. The second eluting diastereomer (111.6 mg) was obtained as a solid.

The second eluting diastereomer had a retention time of 11.83 min,

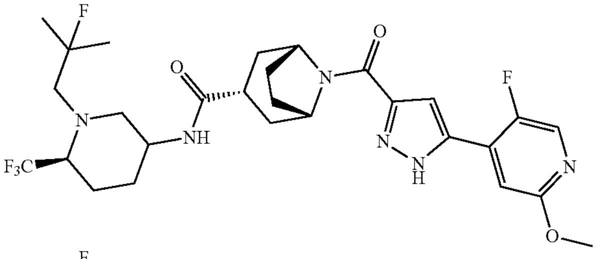

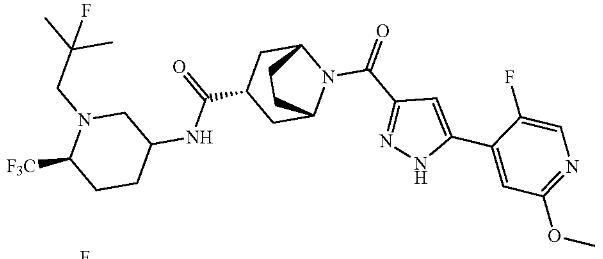

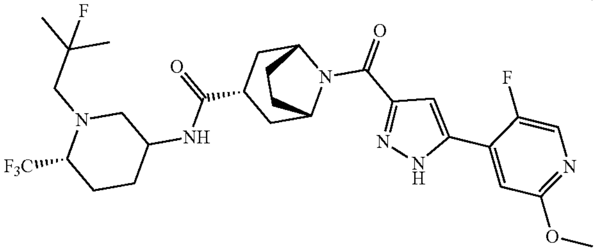

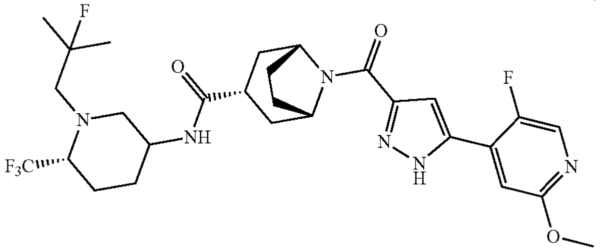

TFA (3.00 mL) was added to a stirred solution of (1R,3S,5S)-8-[5-(5-fluoro-2-methoxypyridin-4-yl)-1-[[2-(trimethylsilyl)ethoxy]methyl]pyrazole-3-carbonyl]-N-[(3S,6S)-1-(2-fluoro-2-methylpropyl)-6-(trifluoromethyl)piperidin-3-yl]-8-azabicyclo[3.2.1]octane-3-carboxamide (Step-5, 750.0 mg, 1.028 mmol) in DCM (3.00 mL). The resulting mixture was stirred at 25° C. for 1 h. The resulting mixture was concentrated under reduced pressure. The residue was purified by reverse flash column chromatography (using the following conditions: C18 column; mobile phase A: Water (0.5% $NH_4HCO_3$), mobile phase B: MeCN; gradient: 5% B to 60% B in 40 min; Detector, 220/254 nm) to obtain (1R,3s,5S)-8-(5-(5-fluoro-2-methoxypyridin-4-yl)-1H-pyrazole-3-carbonyl)-N-((3S,6S)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6S)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3R,6R)-1-(2-fluoro-2-methylpropyl)-6-(trifluoromethyl)piperidin-3-yl)-8-azabicyclo[3.2.1]octane-3-carboxamide and (1R,3s,5S)-8-(5-(5-fluoro-2-methoxypyridin-4-yl)-1H-pyrazole-3-carbonyl)-N-((3S,6R)-1-(2-fluoro-2-methylpropyl)-6-(trifluoromethyl)piperidin-3-yl)-8-azabicyclo[3.2.1]octane-3-carboxamide (500.0 mg) as a solid mixture of diastereomers. LCMS (ESI): 599.4 $[M+H]^+$.

$^1H$ NMR (400 MHz, $CD_3OD$) δ 8.14 (s, 1H), 7.44-6.98 (m, 2H), 5.34 (s, 1H), 3.94 (s, 3H), 3.90-3.79 (m, 1H), 3.42-3.32 (m, 2H), 2.99-2.86 (m, 4H), 2.82-2.68 (m, 1H), 2.18-1.92 (m, 6H), 1.87-1.84 (m, 3H), 1.79-1.71 (m, 2H), 1.60-1.47 (m, 1H), 1.37-1.25 (m, LCMS (ESI): 599.1 $[M+H]^+$.

Example 326-D. The third eluting diastereomer (16.0 mg) was obtained as a solid.

The third eluting diastereomer had a retention time of 18.93 min.

$^1H$ NMR (400 MHz, $CD_3OD$) δ 8.16 (s, 1H), 7.42-7.02 (m, 2H), 5.39 (s, 1H), 3.94 (s, 3H), 3.92-3.85 (m, 1H), 3.43-3.33 (m, 2H), 3.18 (d, 1H), 3.06-2.93 (m, 1H), 2.89-2.72 (m, 3H), 2.20-1.99 (m, 5H), 1.95-1.72 (m, 6H), 1.67-1.58 (m, 1H), 1.41-1.24 (m, 6H). LCMS (ESI): 599.1 $[M+H]^+$.

The first eluting peak (180.0 mg) containing two diastereomers of the title compounds was separated using Chiral Prep-HPLC.

Column: CHIRALPAK IE column

Column dimension: 2×25 cm, 5 μm

Mobile Phase: 3/1 hexanes/DCM (0.5% 2 M $NH_3$·MeOH): EtOH=80:20 hold for 17 min Flow rate: 20 mL/min Detection: 220/254 nm Example 326-A. The first eluting diastereomer (76.8 mg) was obtained as a solid.

The first eluting diastereomer had a retention time of 10.37 min.

$^{1}H$ NMR (400 MHz, $CD_3OD$) δ 8.13 (s, 1H), 7.40-7.03 (m, 2H), 5.34 (s, 1H), 3.93 (s, 3H), 3.91-3.80 (m, 1H), 3.42-3.32 (m, 2H), 2.99-2.86 (m, 3H), 2.89-2.78 (m, 1H), 2.78-2.68 (m, 1H), 2.21-1.93 (m, 5H), 1.92-1.67 (m, 6H), 1.60-1.47 (m, 1H), 1.33 (d, 3H), 1.28 (d, 3H). LCMS (ESI): 599.1 $[M+H]^+$.

Example 326-B. The second eluting diastereomer (9.0 mg) was obtained as a solid.

The second eluting diastereomer had a retention time of 14.75 min.

$^{1}H$ NMR (400 MHz, $CD_3OD$) δ 8.14 (s, 1H), 7.24-7.19 (m, 2H), 5.36 (s, 1H), 3.94 (s, 3H), 3.91-3.85 (m, 1H), 3.42-3.33 (m, 2H), 3.21-3.14 (m, 1H), 3.07-2.93 (m, 1H), 2.86 (s, 1H), 2.84-2.73 (m, 2H), 2.24-1.96 (m, 5H), 1.95-1.74 (m, 6H) 1.67-1.58 (m, 1H), 1.43-1.23 (m, 6H). LCMS (ESI): 599.1 $[M+H]^+$.

Example 327. A Diastereomeric Mixture of (R)-4-(5-(5-fluoro-2-methoxypyridin-4-yl)-1H-pyrazole-3-carbonyl)-N-((5R,8r)-1-methyl-2-oxo-1-azaspiro[4.5]decan-8-yl)-4-azaspiro[2.5]octane-7-carboxamide and (R)-4-(5-(5-fluoro-2-methoxypyridin-4-yl)-1H-pyrazole-3-carbonyl)-N-((5S,8s)-1-methyl-2-oxo-1-azaspiro[4.5]decan-8-yl)-4-azaspiro[2.5]octane-7-carboxamide and (S)-4-(5-(5-fluoro-2-methoxypyridin-4-yl)-1H-pyrazole-3-carbonyl)-N-((5S,8r)-1-methyl-2-oxo-1-azaspiro[4.5]decan-8-yl)-4-azaspiro[2.5]octane-7-carboxamide and (S)-4-(5-(5-fluoro-2-methoxypyridin-4-yl)-1H-pyrazole-3-carbonyl)-N-(5R,8s)-1-methyl-2-oxo-1-azaspiro[4.5]decan-8-yl)-4-azaspiro[2.5]octane-7-carboxamide Step-1. 8-(dibenzylamino)-1-azaspiro[4.5]decan-2-one

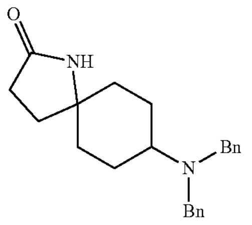 [SMILES: O=C1CCC2(CCC(N(Cc3ccccc3)Cc3ccccc3)CC2)N1]

Sodium triacetoxyborohydride (2.54 g, 11.96 mmol) was added to a mixture of 1-azaspiro[4.5]decane-2,8-dione (1.00 g, 5.98 mmol), dibenzyl amine (1.30 g, 6.59 mmol) in AcOH (0.10 mL) and DCE (6.00 mL). The resulting mixture was stirred at 25° C. for 14 h. The resulting mixture was diluted with DCM, washed with water. The resulting mixture was concentrated under vacuum. The residue was purified by silica gel column chromatography (DCM/MeOH, 19/1 v/v) to obtain the title compound (1.50 g) as a solid. LCMS (ESI): 349.2 $[M+H]^+$.

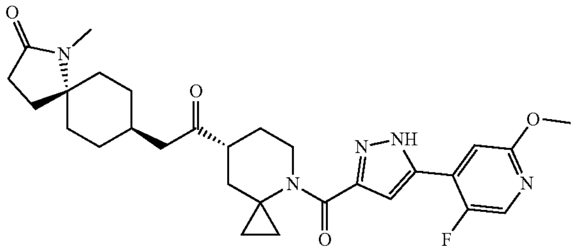

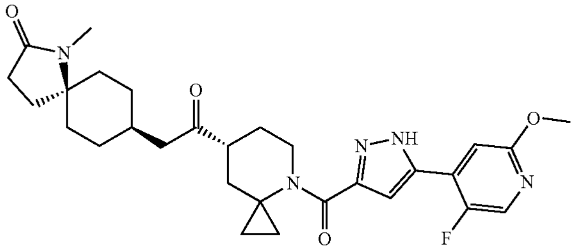

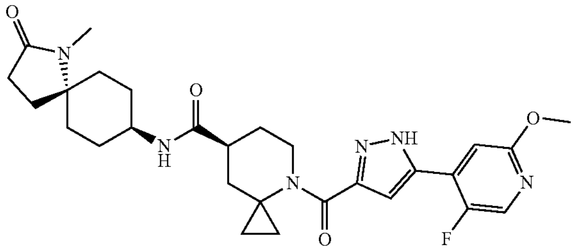

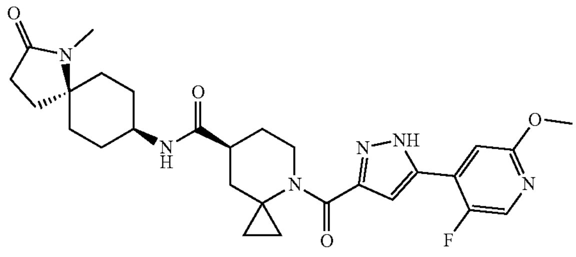

Step-2. 8-(dibenzylamino)-1-methyl-1-azaspiro[4.5]decan-2-one

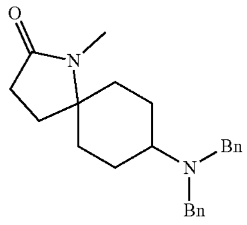 [SMILES: CN1C(=O)CCC12CCC(N(Cc1ccccc1)Cc1ccccc1)CC2]

NaH (110.2 mg, 2.76 mmol, 60% dispersion in mineral oil) was added to a stirred solution of 8-(dibenzylamino)-1-azaspiro[4.5]decan-2-one (Step-1, 800.0 mg, 2.30 mmol) in DMF (6.00 mL) at 0° C. The resulting mixture was stirred at 0° C. for 30 min. MeI (391.0 mg, 2.76 mmol) was added to the resulting mixture at 0° C. The resulting mixture was stirred at 25° C. for 14 h. The resulting mixture was diluted with EtOAc, washed with water. The organic layers were combined, dried over anhydrous $Na_7SO_4$, filtered, and concentrated under reduced pressure. The residue was purified by silica gel column chromatography (DCM/MeOH, 30/1 v/v) to obtain the title compound (810.0 mg) as a liquid. LCMS (ESI): 363.2 $[M+H]^+$.

Step-3. 8-amino-1-methyl-1-azaspiro[4.5]decan-2-one

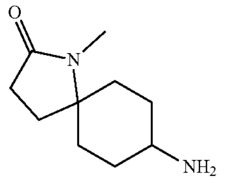

Pd/C (160.0 mg) was added to a stirred solution of 8-(dibenzylamino)-1-methyl-1-azaspiro[4.5]decan-2-one (Step-2, 800.0 mg, 2.21 mmol) in MeOH (6.00 mL) at 0° C. The resulting mixture was stirred at 25° C. under a $H_2$ atmosphere for 14 h. The resulting mixture was filtered, washed with MeOH. The filtrate was concentrated to obtain the title compound (360.0 mg) as an oil, which was used in the next step without further purification. LCMS (ESI): 183.1 $[M+H]^+$.

Step-4. (R)-4-(5-(5-fluoro-2-methoxypyridin-4-yl)-1H-pyrazole-3-carbonyl)-N-((5R,8r)-1-methyl-2-oxo-1-azaspiro[4.5]decan-8-yl)-4-azaspiro[2.5]octane-7-carboxamide and (R)-4-(5-(5-fluoro-2-methoxypyridin-4-yl)-1H-pyrazole-3-carbonyl)-N-((5S,8s)-1-methyl-2-oxo-1-azaspiro[4.5]decan-8-yl)-4-azaspiro[2.5]octane-7-carboxamide and (S)-4-(5-(5-fluoro-2-methoxypyridin-4-yl)-1H-pyrazole-3-carbonyl)-N-((5S,8r)-1-methyl-2-oxo-1-azaspiro[4.5]decan-8-yl)-4-azaspiro[2.5]octane-7-carboxamide and (S)-4-(5-(5-fluoro-2-methoxypyridin-4-yl)-1H-pyrazole-3-carbonyl)-N-((5R,8s)-1-methyl-2-oxo-1-azaspiro[4.5]decan-8-yl)-4-azaspiro[2.5]octane-7-carboxamide

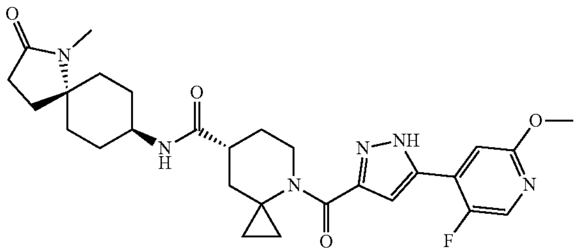

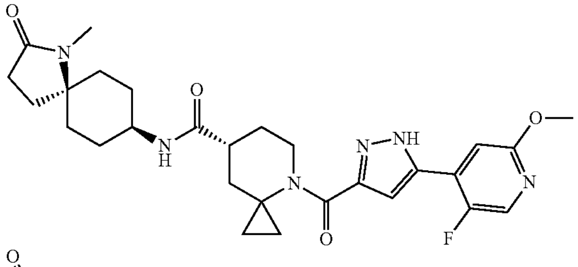

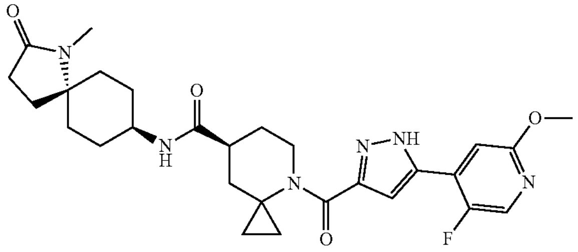

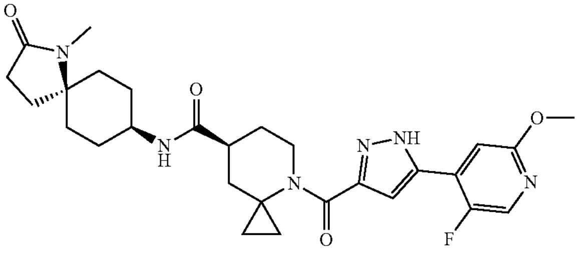

EDCI (122.9 mg, 0.64 mmol), HOBt (86.6 mg, 0.64 mmol), and 8-amino-1-methyl-1-azaspiro[4.5]decan-2-one (Step-3, 194.7 mg, 1.07 mmol) were added to a stirred solution of 4-[5-(5-fluoro-2-methoxypyridin-4-yl)-1H-pyrazole-3-carbonyl]-4-azaspiro[2.5]octane-7-carboxylic acid (INTERMEDIATE 527, 200.0 mg, 0.53 mmol) and DIPEA (207.1 mg, 1.60 mmol) in DMF (5.00 mL). The resulting mixture was stirred at 25° C. for 14 h. The resulting mixture was diluted with EtOAc, washed with water. The organic layers were combined, dried over anhydrous $Na_2SO_1$, filtered, and concentrated under reduced pressure. The residue was purified by silica gel column chromatography (DCM/MeOH, 10/1 v/v) to obtain (R)-4-(5-(5-fluoro-2-methoxy-pyridin-4-yl)-1H-pyrazole-3-carbonyl)-N-((5R,8r)-1-methyl-2-oxo-1-azaspiro[4.5]decan-8-yl)-4-azaspiro[2.5]octane-7-carboxamide and (R)-4-(5-(5-fluoro-2-methoxypyridin-4-yl)-1H-pyrazole-3-carbonyl)-N-((5S,8s)-1-methyl-2-oxo-1-azaspiro[4.5]decan-8-yl)-4-azaspiro[2.5]octane-7-carboxamide and (S)-4-(5-(5-fluoro-2-methoxypyridin-4-yl)-1H-pyrazole-3-carbonyl)-N-((5S,8r)-1-methyl-2-oxo-1-azaspiro[4.5]decan-8-yl)-4-azaspiro[2,5]octane-7-carboxamide and (S)-4-(5-(5-fluoro-2-methoxypyridin-4-yl)-1H-pyrazole-3-carbonyl)-N-((5R,8s)-1-methyl-2-oxo-1-azaspiro[4.5]decan-8-yl)-4-azaspiro[2.5]octane-7-carboxamide (300.0 mg) as a solid mixture of diastereomers. LCMS (ESI): 539.3 $[M+H]^+$ This mixture of four diastereomers (300.0 mg) was separated using Chiral Prep-HPLC.

Column: CHIRAL ART Cellulose-SB column

Column dimension: 2×25 cm, 5 μm

Mobile Phase: MTBE (0.5% 2 M $NH_3$·MeOH): MeOH=70:30 hold for 15 min

Flow rate: 20 mL/min

Detection: 220/254 nm

Example 327-A. The first eluting diastereomer (91.5 mg) was obtained as a solid.

The first eluting diastereomer had a retention time of 5.01 min.

$^1$H NMR (400 MHz, DMSO-$d_6$) δ 14.04-14.00 (m, 1H), 8.25-8.20 (m, 1H), 7.83-7.77 (m, 1H), 7.32-7.26 (m, 1H), 7.02 (s, 1H), 4.45-4.40 (m, 1H), 3.88-3.80 (m, 4H), 2.65-2.62 (m, 4H), 2.18 (t, 3H), 1.90-1.86 (m, 3H), 1.90-1.72 (m, 2H), 1.66-1.61 (m, 4H), 1.55-1.50 (m, 1H), 1.24-1.08 (m, 4H), 0.98-0.93 (m, 2H), 0.70-0.65 (m, 1H), 0.60-0.56 (m, 1H). LCMS (ESI): 539.3 $[M+H]^+$.

Example 327-B and Example 327-C. The second eluting peak (140.0 mg) was obtained as a solid mixture of two diasteromers.

The second eluting peak had a retention time of 6.51 min.

Example 327-D. The third eluting diastereomer (26.8 mg) was obtained as a solid.

The third eluting diastereomer had a retention time of 11.45 min.

$^1$H NMR (400 MHz, DMSO-$d_6$) δ 13.99-13.95 (m, 1H), 8.25 (s, 1H), 7.71-7.65 (m, 1H), 7.30 (d, 1H), 7.01 (s, 1H), 4.50-4.46 (m, 1H), 3.86 (s, 3H), 3.52-3.29 (m, 1H), 2.59-2.56 (m, 4H), 2.19 (t, 3H), 1.88-1.63 (m, 7H), 1.53-1.49 (m, 1H), 1.37-1.22 (m, 2H), 1.44-1.07 (m, 4H), 0.95 (s, 2H), 0.62 (s, 2H). LCMS (ESI): 539.4 $[M+H]^+$.

The second eluting peak (140.0 mg) containing two diastereomers of the title compounds was separated using Chiral Prep-HPLC.

Column: CHIRALPAK IA column

Column dimension: 2×25 cm, 5 μm

Mobile Phase: MTBE (0.5% 2 M $NH_3$·MeOH):1/1 MeOH/DCM=50:50 hold for 12 min

Flow rate: 20 mL/min

Detection: 220/254 nm

Example 327-B. The first eluting diastereomer (52.6 mg) was obtained as a solid.

The first eluting diastereomer had a retention time of 3.87 min.

$^1$H NMR (400 MHz, DMSO-$d_6$) δ 14.15-13.71 (m, 1H), 8.29-8.20 (m, 1H), 7.83-7.76 (m, 1H), 7.32-7.26 (m, 1H), 7.02 (s, 1H), 4.54-4.45 (m, 1H), 3.88-3.80 (m, 4H), 2.84-2.79 (m, 1H), 2.65 (s, 3H), 2.18 (t, 3H), 1.93-1.74 (m, 5H), 1.66-1.46 (m, 6H), 1.17 (d, 3H), 0.98-0.94 (m, 2H), 0.70-0.66 (m, 1H), 0.61-0.56 (m, 1H). LCMS (ESI): 539.1 $[M+H]^+$.

Example 327-C. The second eluting diastereomer (21.5 mg) was obtained as a solid.

The second eluting diastereomer had a retention time of 7.50 min.

$^1$H NMR (400 MHz, DMSO-$d_6$) δ 14.19-13.62 (m, 1H), 8.29-8.21 (m, 1H), 7.72-7.65 (m, 1H), 7.32-7.28 (m, 1H), 7.04-6.99 (m, 1H), 4.52-4.48 (m, 1H), 3.86 (s, 3H), 3.55-3.45 (m, 1H), 2.59-2.54 (m, 4H), 2.19 (t, 3H), 1.86-1.63 (m, 7H), 1.54-1.50 (m, 1H), 1.37-1.26 (m, 4H), 1.25-1.04 (m, 2H), 0.97-0.87 (m, 2H), 0.69-0.46 (m, 2H). LCMS (ESI): 539.1 $[M+H]^+$.

Example 328. A diastereomeric mixture of (R)—N-((5R,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide and (R)—N-((5S,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7 carboxamide and (S)—N-((5S,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide and (S)—N-((5R,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide

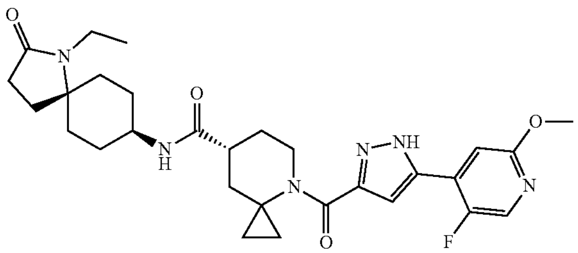

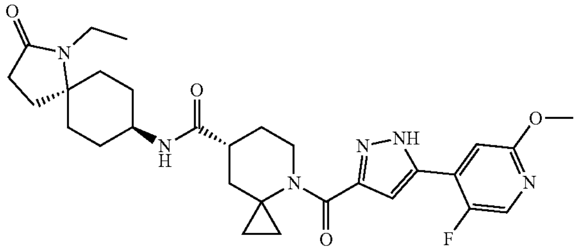

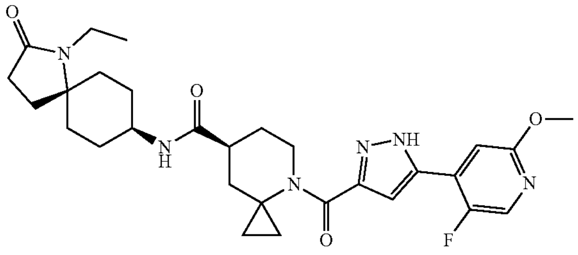

-continued

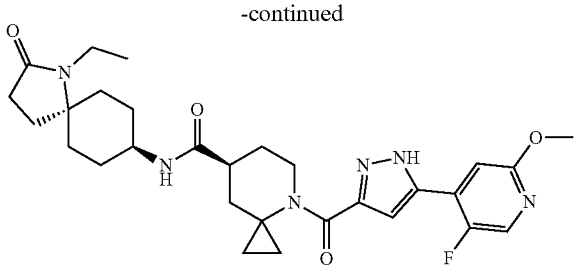

The title compound was prepared using a procedure similar to the one described for the synthesis of Example 327, except iodoethane was used as a starting material in Step-2. The resulting residue was purified by silica gel column chromatography (DCM/MeOH, 10/1 v/v) to obtain the diastereomeric mixture (Example 328) of (R)—N-((5R,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide and (R)—N-((5S,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide and (S)—N-((5S,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide and (S)—N-((5R,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2,5]octane-7-carboxamide as a solid (200.0 mg). LCMS (ESI): 553.3 $[M+H]^+$.

The four diastereomers of the title compound were separated using Chiral Prep-HPLC.

Column: CHIRAL ART Cellulose-SB column

Column dimension: 2×25 cm, 5 μm

Mobile Phase: MTBE (0.5% 2 M $NH_3$·MeOH): MeOH=70:30 hold for 18 min

Flow rate: 20 mL/min

Example 328-A. The first eluting diastereomer (28.7 mg) was obtained as a solid.

The first eluting diastereomer had a retention time of 7.00 min, $^1$H NMR (400 MHz, DMSO-$d_6$) δ 8.27 (d, 1H), 7.84 (d, 1H), 7.32 (d, 1H), 7.03 (d, 1H), 4.44 (s, 1H), 3.90-3.82 (m, 4H), 3.21-3.12 (m, 2H), 2.85-2.81 (m, 1H), 2.56-2.52 (m, 3H), 2.22-2.14 (m, 2H), 1.92-1.73 (m, 5H), 1.66-1.41 (m, 5H), 1.27-1.19 (m, 3H), 1.10-1.02 (m, 3H), 0.93-0.88 (m, 1H), 0.69-0.65 (m, 2H). LCMS (ESI): 553.1 $[M+H]^+$.

Example 328-B and Example 328-C. The second eluting peak was obtained as a solid mixture of two diasteromers.

The second eluting peak had a retention time of 8.29 min.

Example 328-D. The third eluting diastereomer (11.4 mg) was obtained as a solid.

The third eluting diastereomer had a retention time of 15.44 min.

$^1$H NMR (400 MHz, DMSO-$d_6$) δ 8.27 (d, 1H), 7.69 (d, 1H), 7.32 (d, 1H), 7.06-7.00 (m, 1H), 4.46-4.41 (m, 1H), 3.88 (s, 3H), 3.63-3.48 (m, 1H), 3.14-3.05 (m, 2H), 2.67-2.62 (m, 4H), 2.24-2.16 (m, 2H), 1.88-1.79 (m, 2H), 1.78-1.66 (m, 5H), 1.56-1.51 (m, 1H), 1.45-1.36 (m, 2H), 1.35-1.11 (m, 3H), 1.05-0.8 (m, 4H), 0.65-0.60 (m, 2H). LCMS (ESI): 553.1 $[M+H]^+$.

The second eluting peak containing two diastereomers of the title compounds was separated using Chiral Prep-HPLC.

Column: CHIRALPAK IH column

Column dimension: 2×25 cm, 5 μm

Mobile Phase: MTBE (0.5% 2 M $NH_3$·MeOH):1/1 MeOH/DCM=80:20 hold for 14 min

Flow rate: 20 mL/min

Detection: 220/254 nm

Example 328-B. The first eluting diastereomer (10.2 mg) was obtained as a solid.

The first eluting diastereomer had a retention time of 6.62 min.

$^1$H NMR (400 MHz, DMSO-$d_6$) δ 8.43-8.17 (m, 1H), 7.70 (d, 1H), 7.34-7.28 (m, 1H), 7.03 (s, 1H), 4.56-4.48 (m, 1H), 3.88 (s, 3H), 3.56-3.49 (m, 1H), 3.14-3.04 (m, 2H), 2.56-2.52 (m, 4H), 2.24-2.15 (m, 2H), 1.87-1.79 (m, 2H), 1.78-1.66 (m, 5H), 1.61-1.21 (m, 6H), 1.05-0.83 (m, 4H), 0.68-0.64 (m, 1H), 0.58-0.54 (m, 1H), LCMS (ESI): 553.4 $[M+H]^+$.

Example 328-C. The second eluting diastereomer (32.1 mg) was obtained as a solid.

The second eluting diastereomer had a retention time of 10.94 min:

$^1$H NMR (400 MHz, DMSO-$d_6$) δ 8.29-8.24 (m, 1H), 7.84 (d, 1H), 7.32 (d, 1H), 7.04 (s, 1H), 4.50-4.46 (m, 1H), 3.90-3.85 (m, 4H), 3.21-3.12 (m, 2H), 2.85-2.81 (m, 1H), 2.56-2.52 (m, 3H), 2.22-2.14 (m, 3H), 1.88-1.80 (m, 5H), 1.66-1.62 (m, 5H), 1.27-1.19 (m, 3H), 1.10-0.87 (m, 3H), 0.69-0.64 (m, 2H). LCMS (ESI): 553.1 $[M+H]^+$.

Example 329-A. (S)—N-((1r,4S)-4-(2-(dimethylamino)ethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

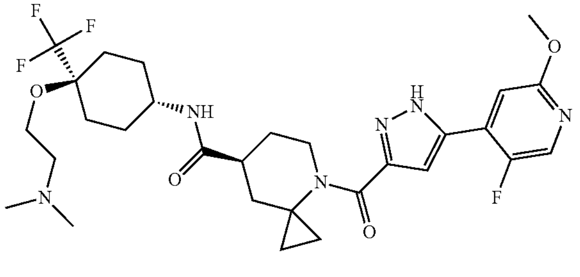 [SMILES: COc1cc(-c2cc(C(=O)N3CC[C@H](C(=O)N[C@H]4CC[C@@](OCCN(C)C)(C(F)(F)F)CC4)CC34CC4)n[nH]2)c(F)cn1]

The title compound was prepared using a procedure similar to the one described for the synthesis of Example 323, except (2-bromoethyl)dimethylamine was used as a starting material in Step-2 and (S)-4-[5-(5-fluoro-2-methoxypyridin-4-yl)-1H-pyrazole-3-carbonyl]-4-azaspiro[2.5]octane-7-carboxylic acid (INTERMEDIATE 527-A) was used as a starting material in Step-4. The resulting residue was purified by reverse phase column chromatography (using the following conditions: column: C18 column; mobile phase A: Water (10 mM $NH_4HCO_3$), mobile phase B: MeCN; Gradient: 20% B up to 40% B in 20 min; Detector, UV 254/220 nm) to obtain the title compound (49.9 mg) as a solid. $^1$H NMR (300 MHz, DMSO-$d_6$) δ 13.96 (s, 1H), 8.25 (d, 1H), 7.84 (d, 1H), 7.30 (d, 1H), 7.01 (d, 1H), 4.41 (s, 1H), 3.86-3.82 (m, 4H), 3.60-3.42 (m, 2H), 2.87-2.64 (m, 1H), 2.32-2.11 (m, 8H), 2.01-1.32 (m, 11H), 1.32-0.99 (m, 2H), 0.87 (d, 2H), 0.63 (s, 2H). LCMS (ESI): 611.3 $[M+H]^+$.

Example 329-B. (R)—N-((1r,4R)-4-(2-(dimethylamino)ethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

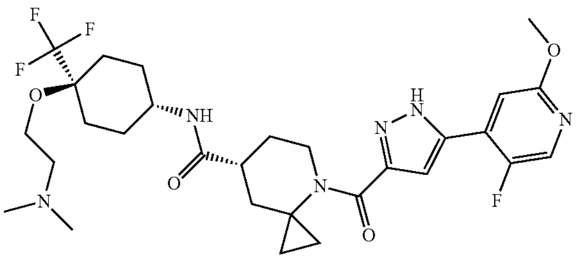 [SMILES: COc1cc(-c2cc(C(=O)N3CC[C@@H](C(=O)N[C@H]4CC[C@@](OCCN(C)C)(C(F)(F)F)CC4)CC34CC4)n[nH]2)c(F)cn1]

The title compound was prepared using a procedure similar to the one described for the synthesis of Example 323, except (2-bromoethyl)dimethylamine was used as a starting material in Step-2 and (R)-4-(3-(5-fluoro-2-methoxypyridin-4-yl)-1H-pyrazole-5-carbonyl)-4-azaspiro[2,5]octane-7-carboxylic acid (INTERMEDIATE 527-B) was used as a starting material in Step-4. The resulting residue was purified by reverse phase column chromatography (using the following conditions: column: C18 column; mobile phase A: Water (10 mM $NH_4HCO_3$), mobile phase B: MeCN, Gradient: 20% B up to 40% B in 20 min; Detector, UV 254/220 nm) to obtain the title compound (12.6 mg) as a solid. $^1$H NMR (300 MHz, DMSO-$d_6$) δ 8.42-8.04 (m, 2H), 7.84 (d, 1H), 7.39-7.15 (m, 1H), 7.02 (d, 1H), 4.42 (s, 1H), 3.87 (d, 4H), 3.64-3.48 (m, 2H), 2.92-2.59 (m, 1H), 2.47-2.36 (m, 1H), 2.34-1.92 (m, 7H), 1.88-1.34 (m, 12H), 1.15 (s, 1H), 0.90 (s, 2H), 0.64 (s, 2H). LCMS (ESI): 611.4 $[M+H]^+$.

Example 330. A Diastereomeric Mixture of (R)-4-(5-(5-fluoro-2-methoxypyridin-4-yl)-1H-pyrazole-3-carbonyl)-N-((1r,4R)-4-(2-hydroxyethoxy)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-(2-hydroxyethoxy)-4-(trifluoromethyl)cyclohexyl)-4-azaspiro[2.5]octane-7-carboxamide

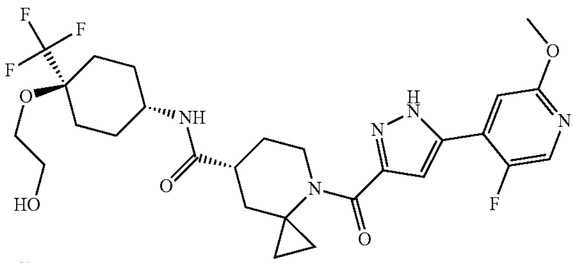

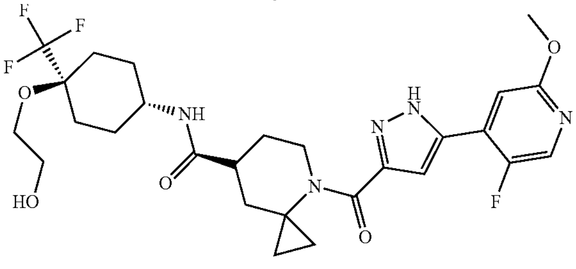

Step-1. (1r,4r)-N,N-dibenzyl-4-(2-methoxyethoxy)-4-(trifluoromethyl)cyclohexan-1-amine

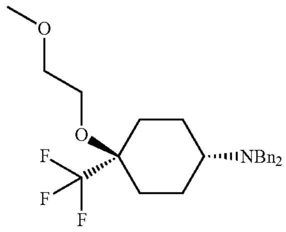

NaH (79.2 mg, 3.30 mmol) was added to a solution of (1r,4r)-4-(dibenzylamino)-1-(trifluoromethyl)cyclohexan-1-ol (600.0 mg, 1.65 mmol) in DMF (5.00 mL). The resulting solution was stirred at 25° C. for 1 h. Then 2-bromoethyl methyl ether (1.15 g, 8.26 mmol) was added to the resulting mixture. The resulting solution was stirred at 80° C. for 14 h. The resulting mixture was diluted with EtOAc, washed with water. The organic layers were combined, dried over anhydrous $Na_2SO_4$, filtered, and concentrated under reduced pressure. The residue was purified by silica gel column chromatography eluting with EtOAc/petroleum ether (1/1 v/v) to obtain the title compound (394.0 mg) as a solid. LCMS (ESI): 422.2 $[M+H]^+$.

Step-2. 2-(((1r,4r)-4-(dibenzylamino)-1-(trifluoromethyl)cyclohexyl)oxy)ethan-1-ol

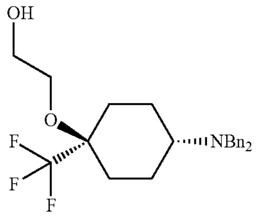

$BBr_3$ in DCM (1 M, 0.69 mL) was added to a stirred mixture of (1r,4r)-N,N-dibenzyl-4-(2-methoxyethoxy)-4-(trifluoromethyl)cyclohexan-1-amine (Step-1, 145.0 mg, 0.34 mmol) in DCM (4.00 mL) at 0° C. The resulting solution was stirred at 25° C. for 14 h. The reaction mixture was then quenched with the addition of MeOH. The solution was concentrated under reduced pressure and the residue was purified by silica gel column chromatography eluting with DCM/MeOH to obtain the title compound (90.0 mg) as a solid. LCMS (ESI): 408.2 $[M+H]^+$.

Step-3. 2-(((1r,4r)-4-amino-1-(trifluoromethyl)cyclohexyl)oxy)ethan-1-ol

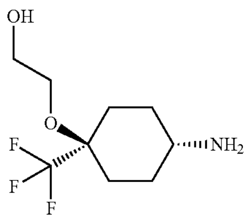 [SMILES: N[C@H]1CC[C@@](OCCO)(C(F)(F)F)CC1]

Pd/C (18.0 mg) was added to a stirred mixture of 2-(((1r, 4r)-4-(dibenzylamino)-1-(trifluoromethyl)cyclohexyl)oxy) ethan-1-ol (Step-2, 90.0 mg, 0.22 mmol) in MeOH (4.00 mL). The resulting solution was stirred at 25° C. for 14 h under a $H_2$ atmosphere. Then Pd/C was filtered out. The filtrate was concentrated under reduced pressure to obtain the title compound (40.0 mg) as an oil. LCMS (ESI): 228. 1[M+H]+.

Step-4. (R)-4-(5-(5-fluoro-2-methoxypyridin-4-yl)-1H-pyrazole-3-carbonyl)-N-((1r,4R)-4-(2-hydroxyethoxy)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-(2-hydroxyethoxy)-4-(trifluoromethyl)cyclohexyl)-4-azaspiro[2.5]octane-7-carboxamide

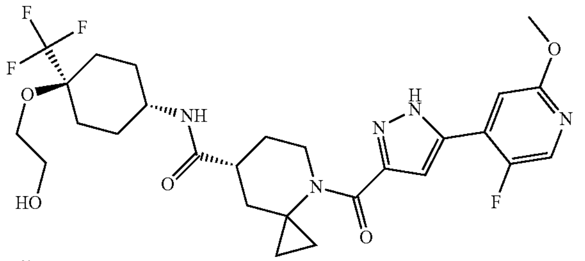

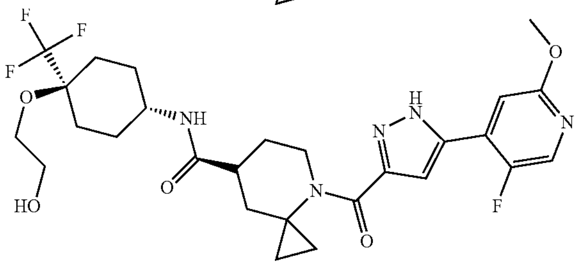

HOBt (29.2 mg, 0.22 mmol), EDCI (41.5 mg, 0.22 mmol), and 2-[[(1r,4r)-4-amino-1-(trifluoromethyl)cyclohexyl]oxy]ethanol. (Step-3, 32.8 mg, 0.14 mmol) were added to a stirred mixture of 4-[5-(5-fluoro-2-methoxypyridin-4-yl)-1H-pyrazole-3-carbonyl]-4-azaspiro[2.5]octane-7-carboxylic acid (INTERMEDIATE 527, 54.0 mg, 0.14 mmol) and DIPEA (74.6 mg, 0.58 mmol) in DMF (4.00 mL). The resulting solution was stirred at 25° C. for 14 h. The solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (1)-4-(5-(5-fluoro-2-methoxypyridin-4-yl)-1H-pyrazole-3-carbonyl)-N-((1r,4R)-4-(2-hydroxyethoxy)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-(2-hydroxyethoxy)-4-(trifluoromethyl)cyclohexyl)-4-azaspiro[2.5]octane-7-carboxamide (45.0 mg) as a solid mixture of diastereomers. LCMS (ESI): 584.2 [M+H]+.

This mixture of two diastereomers (45.0 mg) was separated using Chiral Prep-HPLC.

Column: CHIRALPAK IA column

Column dimension: 2×25 cm, 5 μm

Mobile Phase: 3/1 hexanes/DCM (0.5% 2 M $NH_3$·MeOH):EtOH=80:20 hold for 22 min

Flow rate: 16 mL/min

Detection: 220/254 nm

Example 330-A. The first eluting diastereomer (4.0 mg) was obtained as a solid.

The first eluting diastereomer had a retention time of 6.24 min.

LCMS (ESI): 584.3 [M+H]+.

Example 330-B. The second eluting diastereomer (3.6 mg) was obtained as a solid.

The second eluting diastereomer had a retention time of 17.96 min.

LCMS (ESI): 584.3 [M+H]+.

Example 331. A Diastereomeric Mixture of (S)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide and (R)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide

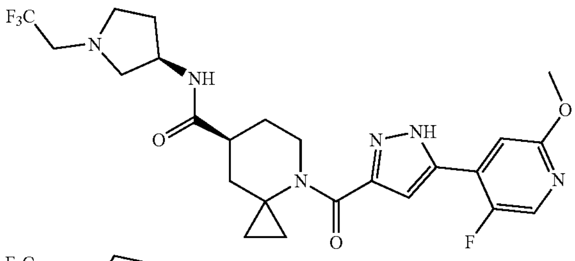

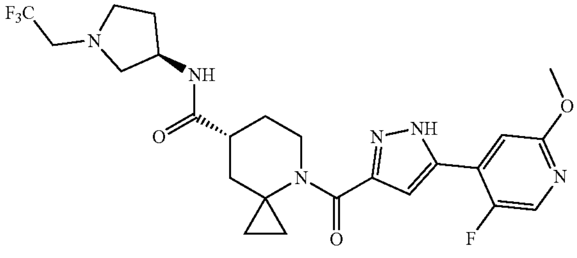

Step-1. Tert-butyl-(3R)-3-(dibenzylamino)pyrrolidine-1-carboxylate

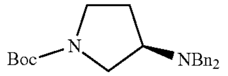

$K_2CO_3$ (6.68 g, 48.32 mmol) and benzyl bromide (4.59 g, 26.85 mmol) were added to a stirred mixture of tert-butyl (3R)-3-aminopyrrolidine-1-carboxylate (1.00 g, 5.37 mmol) in MeCN (23.00 mL) at 0° C. The resulting mixture was stirred at 60° C. for 14 h. The resulting mixture was concentrated under reduced pressure. The residue was purified by silica gel column chromatography eluting with petroleum ether/EtOA (10/1 v/v) to obtain the title compound (1.70 g) as a solid, LCMS (ESI): 367.2 [M+H]+.

Step-2. (3R)—N,N-dibenzylpyrrolidin-3-amine

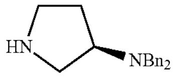

TFA (5.00 mL) was added to a stirred mixture of tert-butyl (3R)-3-(dibenzylamino)pyrrolidine-1-carboxylate (Step-1, 1.00 g, 2.73 mmol) in DCM (5.00 mL) at 0° C. The resulting mixture was stirred at 25° C. for 1 h. The resulting mixture was concentrated under reduced pressure. The residue was purified by silica gel column chromatography eluting with DCM/MeOH (15/1 v/v) to obtain the title compound (650.0 mg) as a solid. LCMS (ESI): 267.2 [M+H]$^+$.

Step-3. 1-[(3R)-3-(dibenzylamino)pyrrolidin-1-yl]-2,2,2-trifluoroethanone

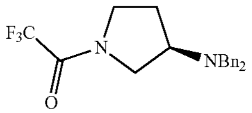

TEA (3.42 g, 33.79 mmol) was added to a stirred mixture of (3R)—N,N-dibenzylpyrrolidin-3-amine (Step-2, 3.00 g, 11.26 mmol) in DCM (15.00 mL). The resulting mixture was stirred at 25° C. for 5 min. Then trifluoroacetic anhydride (3.55 g, 16.89 mmol) was added at 0° C. The resulting mixture was stirred at 0° C. for 30 min and then 25° C. for 1 h. The resulting mixture was concentrated under reduced pressure. The residue was purified by silica gel column chromatography eluting with petroleum ether/EtOAc (2/1 v/v) to obtain the title compound (3.00 g) as a solid. LCMS (ESI): 363.2 [M+H]$^+$.

Step-4. (3R)—N,N-dibenzyl-1-(2,2,2-trifluoroethyl) pyrrolidin-3-amine

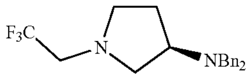

$BH_3$-THF (13.25 mL, 13.25 mmol) was added to a stirred mixture of 1-[(3R)-3-(dibenzylamino)pyrrolidin-1-yl]-2,2,2-trifluoroethanone (Step-3, 3.00 g, 8.28 mmol) in dry THF (15.00 mL) at 0° C. The resulting mixture was stirred at 80° C. for 2 h under nitrogen atmosphere. The reaction mixture was quenched with MeOH at 25° C. The resulting mixture was concentrated under reduced pressure. The residue was purified by silica gel column chromatography eluting with petroleum ether/EtOAc (1/1 v/v) to obtain the title compound (1.50 g) as a solid. LCMS (ESI): 349.2 [M+H]$^+$.

Step-5. (3R)-1-(2,2,2-trifluoromethyl)pyrrolidin-3-amine

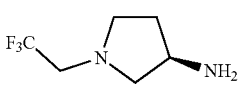 [SMILES: N[C@@H]1CCN(CC(F)(F)F)C1]

Pd/C (450.0 mg) was added to a stirred mixture of (3R)—N,N-dibenzyl-1-(2,2,2-trifluoroethyl)pyrrolidin-3-amine (Step-4, 1.50 g, 4.31 mmol) in MeOH (10.00 mL) at 0° C. The resulting mixture was stirred at 25° C. for 14 h under a 1-12 atmosphere. The resulting mixture was filtered, the filter cake was washed with MeOH. The filtrate was concentrated under reduced pressure to obtain the title compound (300.0 mg) as a solid. The resulting residue was used in the next step directly without further purification. LCMS (ESI): 169.1 [M+H]$^+$.

Step-6. (S)-4-(5-(5-fluoro-2-methoxypyridin-4-yl)-1H-pyrazole-3-carbonyl)-N—((R)-1-(2,2,2-trifluoromethyl)pyrrolidin-3-yl)-4-azaspiro[2.5]octane-7-carboxamide and (R)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide

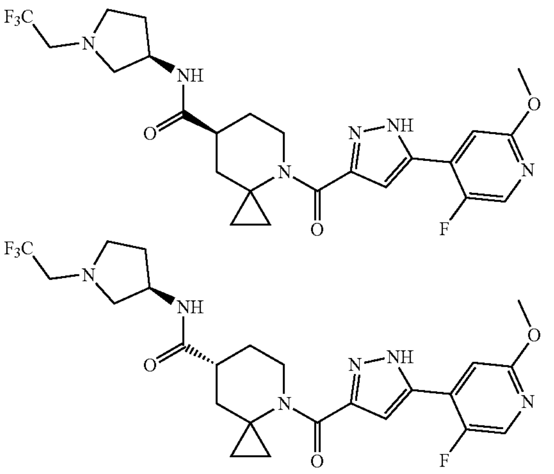

HOBt (216.6 mg, 1.60 mmol), EDCI (307.2 mg, 1.60 mmol), and (3R)-1-(2,2,2-trifluoroethyl)pyrrolidin-3-amine (Step-5, 161.7 mg, 0.96 mmol) were added to a stirred mixture of 4-[5-(5-fluoro-2-methoxypyridin-4-yl)-1H-pyrazole-3-carbonyl]-4-azaspiro[2.5]octane-7-carboxylic acid (INTERMEDIATE 527, 300.0 mg, 0.80 mmol) and DIPEA (517.8 mg, 4.00 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (EtOAc) to obtain (S)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide and (R)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide (200.0 mg) as a solid mixture of diastereomers. LCMS (ESI): 525.2 [M+H]$^+$.

This mixture of two diastereomers (200.0 was separated using Chiral Prep-HPLC.

Column: CHIRALPAK IC column

Column dimension: 2×25 cm, 5 μm

Mobile Phase: MTBE (0.5% 2 M $NH_3$·MeOH): MeOH=50:50 hold for 11 min

Flow rate: 20 mL/min

Detection: 220/254 nm

Example 331-A. The first eluting diastereomer (49.6 mg) was obtained as a solid.

The first eluting diastereomer had a retention time of 6.43 min.

$^1$H NMR (300 MHz, $CD_3OD$) δ 8.11 (d, 1H), 7.29-7.23 (m, 1H), 7.08 (d, 1H), 4.55 (s, 1H), 4.32-4.26 (m, 1H), 3.92 (s, 3H), 3.24-3.08 (m, 2H), 3.02-2.86 (m, 2H), 2.82-2.76 (m, 1H), 2.72-2.58 (m, 2H), 2.43-2.37 (m, 1H), 2.31-2.13 (m, 1H), 1.98-1.52 (m, 3H), 1.31-1.20 (m, 1H), 1.01-0.93 (m, 3H), 0.76-0.67 (m, 2H). LCMS (ESI): 525.2 $[M+H]^+$.

Example 331-B. The second eluting diastereomer (49.8 mg) was obtained as a solid.

The second eluting diastereomer had a retention time of 8.94 min.

$^1$H NMR (300 MHz, $CD_3OD$) δ 8.11 (d, 1H), 7.26 (s, 1H), 7.09 (d, 1H), 4.58-4.52 (m, 1H), 4.33-4.24 (m, 1H), 3.92 (s, 3H), 3.24-3.05 (m, 2H), 3.02-2.86 (m, 2H), 2.81-2.75 (m, 1H), 2.72-2.59 (m, 2H), 2.42-2.36 (m, 1H), 2.31-2.13 (m, 1H), 1.95-1.54 (m, 3H), 1.41-0.82 (m, 3H), 0.82-0.56 (m, 3H). LCMS (ESI): 525.3 $[M+H]^+$.

Example 332. A Diastereomeric Mixture of (8)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide and (R)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide

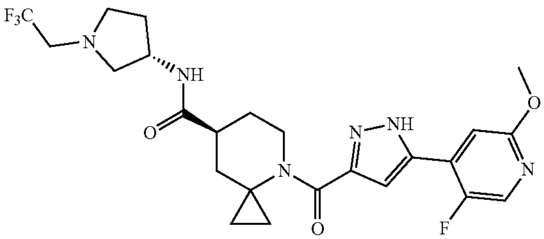

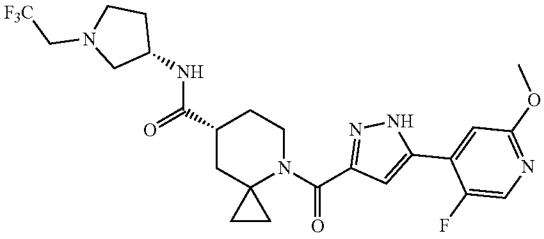

The title compound was prepared using a procedure similar to the one described for the synthesis of Example 331, except tert-butyl (3S)-3-aminopyrrolidine-1-carboxylate was used as a starting material in Step-1. The resulting residue was purified by Prep-TLC (EtOAc) to obtain (S)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide and (R)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide (45.0 mg) as a solid mixture of diastereomers.

This mixture of two diastereomers was separated using Chiral Prep-HPLC.

Column: CHIRAL ART Cellulose-SC column

Column dimension: 2×25 cm, 5 μm

Mobile Phase: MTBE (0.5% 2 M $NH_3$·MeOH): MeOH=50:50 hold for 15 min

Flow rate: 20 mL/min

Detection: 220/254 nm

Example 332-A. The first eluting diastereomer (7.8 mg) was obtained as a solid.

The first eluting diastereomer had a retention time of 7.07 min.

$^1$H NMR (300 MHz, DMSO-$d_6$) δ 14.00 (s, 1H), 8.27 (s, 1H), 8.00 (d, 1H), 7.32 (d, 1H), 7.03 (s, 1H), 4.58-4.42 (m, 1H), 4.18-4.09 (m, 1H), 3.88 (s, 3H), 3.33-3.14 (m, 3H), 2.93-2.75 (m, 3H), 2.68-2.57 (m, 2H), 2.16-1.98 (m, 2H), 1.76-1.70 (m, 1H), 1.67-1.52 (m, 2H), 1.35-1.06 (m, 2H), 0.99-0.93 (m, 1H), 0.67-0.61 (m, 2H). LCMS (ESI): 525.1 $[M+H]^+$.

Example 332-B. The second eluting diastereomer (11.2 mg) was obtained as a solid.

The second eluting diastereomer had a retention time of 11.74 min.

$^1$H NMR (400 MHz, $CD_3OD$) δ 8.13 (d, 1H), 7.28 (s, 1H), 7.13-7.08 (m, 1H), 4.61-4.56 (m, 1H), 4.35-4.28 (m, 1H), 3.94 (s, 3H), 3.25-3.11 (m, 2H), 3.01-2.90 (m, 2H), 2.83-2.78 (m, 1H), 2.72-2.62 (m, 2H), 2.42-2.37 (m, 1H), 2.30-2.17 (m, 1H), 1.98-1.59 (m, 3H), 1.30-1.25 (m, 1H), 1.14-0.84 (n, 3H) 0.82-0.57 (m, 2H). LCMS (ESI): 525.1 $[M+H]^+$.

Example 333. A Enantiomeric Mixture of (R)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide and (S)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide

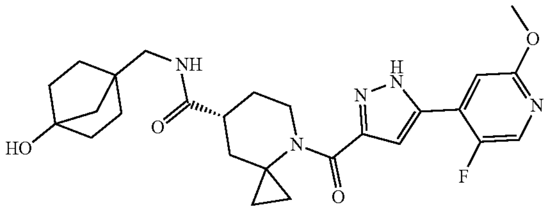

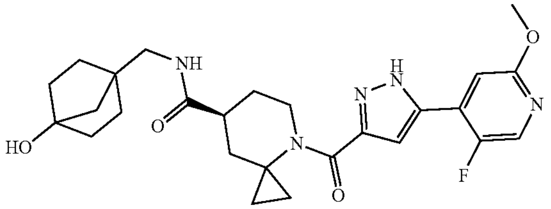

Step-1. N-benzyl-4-hydroxybicyclo[2.2.1]heptane-1-carboxamide

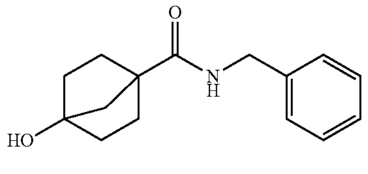 [SMILES: O=C(NCc1ccccc1)C12CCC(O)(CC1)C2]

EDCI (921.0 mg, 4.80 mmol), HOBt (649.0 mg, 4.80 mmol), and benzylamine (343.0 mg, 3.20 mmol) were added to a mixture of 4-hydroxybicyclo[2.2.1]heptane-1-carboxylic acid (500.0 mg, 3.20 mmol) and DIPEA (2.10 g, 16.01 mmol) in DMF (5.00 mL). The resulting mixture was stirred at 25° C. for 14 h. The resulting mixture was diluted with EtOAc, washed with water. The organic layers were combined, dried over anhydrous $Na_2SO_4$, filtered, and concentrated under reduced pressure. The residue was purified by silica gel column chromatography eluting with DCM/MeOH (20/1 v/v) to obtain the title compound (630.0 mg) as a solid. LCMS (ESI): 246.2 $[M+14]^+$.

Step-2. 4[(benzylamino)methyl]bicyclo[2.2.1]heptan-1-ol

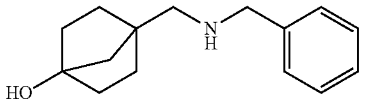 [SMILES: OC12CCC(CNCc3ccccc3)(CC1)C2]

$LiAlH_4$ (472.0 mg, 12.43=top were added to a stirred solution of N-benzyl-4-hydroxybicyclo[2.2.1]heptane-1-carboxamide (Step-1, 610.0 mg, 2.49 mmol) in THF (5.00 mL). The resulting mixture was stirred at 70° C. for 14 h. The resulting mixture was concentrated under reduced pressure. The residue was purified by silica gel column chromatography by eluting with DCM/MeOH (20/1 v/v) to obtain the title compound (390.0 mg) as an oil. LCMS (ESI): 232.2 $[M+H]^+$.

Step-3. 4-(aminomethyl)bicyclo[2.2.1]heptan-1-ol

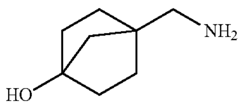

Pd/C (39.0 mg) was added to a mixture of 4-[(benzylamino)methyl]bicyclo[2.2.1]heptan-1-ol (Step-2, 390.0 mg, 1.69 mmol) in MeOH (5.00 mL). The resulting mixture was stirred at 25° C. for 2 h under a $H_2$ atmosphere. The resulting mixture was filtered, the filter cake was washed with MeOH. The filtrate was concentrated under reduced pressure to obtain the title compound (120.0 mg) as an oil. LCMS (ESI): 142.1 $[M+H]^+$.

Step-4. 4-[5-(5-fluoro-2-methoxypyridin-4-yl)-1-[[2-(trimethylsilyl)ethoxy]methyl]pyrazole-3-carbonyl]-4-azaspiro[2.5]octane-7-carboxylic acid

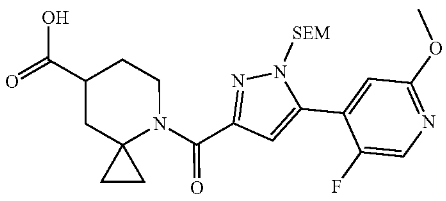 [SMILES: COc1cc(-c2cc(C(=O)N3CCC(C(=O)O)CC34CC4)nn2COCC[Si](C)(C)C)c(F)cn1]

$LiOH{\cdot}H_2O$ (162.0 mg, 3.86 mmol) was added to a mixture of methyl 4-[5-(5-fluoro-2-methoxypyridin-4-yl)-1-[[2-(trimethylsilyl)ethoxy]methyl]pyrazole-3-carbonyl]-4-azaspiro[2.5]octane-7-carboxylate (Step-1 from synthesis of INTERMEDIATE 527-A, 1.00 g, 1.93 mmol) in THE (3.00 mL), MeOH (3.00 mL) and $H_2O$ (3.00 mL). The resulting mixture was stirred at 25° C. for 2 h. The resulting mixture was concentrated under reduced pressure. The mixture was acidified to pH 3 with HCl (1 M). The aqueous layer was extracted with EtOAc. The organic layers were combined, dried over anhydrous $Na_2SO_4$, filtered, and concentrated under reduced pressure to obtain the title compound (950.0 mg) as a solid, LCMS (ESI): 505.4 $[M+H]^+$.

Step-5. 4-[5-(5-fluoro-2-methoxypyridin-4-yl)-1-[[2-(trimethylsilyl)ethoxy]methyl]pyrazole-3-carbonyl]-N-([4-hydroxybicyclo[2.2.1]heptan-1-yl]methyl)-4-azaspiro[2.5]octane-7-carboxamide

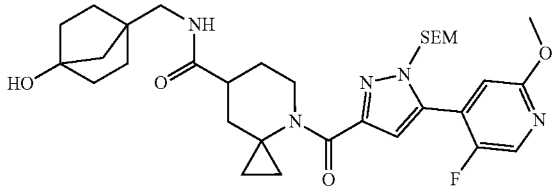 [SMILES: COc1cc(-c2cc(C(=O)N3CCC(C(=O)NCC45CCC(O)(CC4)C5)CC34CC4)nn2COCC[Si](C)(C)C)c(F)cn1]

HOBt (215.0 mg, 1.59 mmol), EDGE (305.0 mg, 1.59 mmol), and 4-(aminomethyl)bicyclo[2.2.1]heptan-1-ol (Step-3, 150.0 mg, 1.06 mmol) were added to a mixture of 4-[5-(5-fluoro-2-methoxypyridin-4-yl)-1-[[2-(trimethylsilyl)ethoxy]methyl]pyrazole-3-carbonyl]-4-azaspiro[2.5]octane-7-carboxylic acid (Step-4, 536.0 mg, 1.06 mmol) and DIPEA (686.0 mg, 5.31 mmol) in DMF (5.00 mL). The resulting mixture was stirred at 25° C. for 14 h. The resulting mixture was diluted with EtOAc, washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (600.0 mg) as a solid. LCMS (ESI): 628.3 $[M+H]^+$.

Step-6. (R)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide and (S)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide

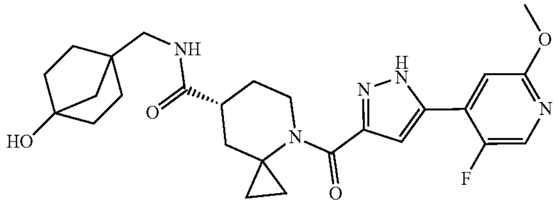

-continued

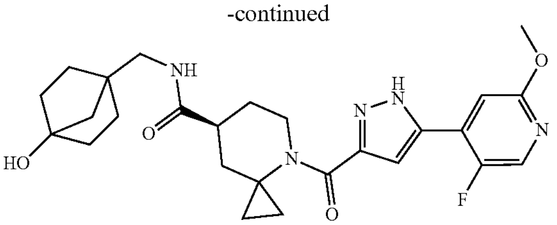

TFA (3.00 mL) was added to a mixture of 4-[5-(5-fluoro-2-methoxypyridin-4-yl)-1-[[2-(trimethylsilyl)ethoxy]methyl]pyrazole-3-carbonyl]-N-([4-hydroxybicyclo[2.2.1]heptan-1-yl]methyl)-4-azaspiro[2.5]octane-7-carboxamide (Step-5, 300.0 mg, 0.48 mmol) in DCM (3.00 mL). The resulting mixture was stirred at 25° C. for 1 h. The resulting mixture was concentrated under reduced pressure. The residue was purified by silica gel column chromatography eluting with DCM/MeOH (10/1 v/v) to obtain (R)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide and (S)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide (220.0 mg) as a solid mixture of enantiomers, LCMS (ESI): 498.6 $[M+H]^+$.

This mixture of two enantiomers (220.0 mg) was separated using Chiral Prep-HPLC.

Column: CHIRALPAK IE column

Column dimension: 2×25 cm, 5 μm

Mobile Phase: 3/1 hexanes/DCM (0.5% 2 M $NH_3$·MeOH):EtOH=50:50 hold for 16 min

Flow rate: 16 mL/min

Detection: 220/254 nm

Example 333-A. The first eluting enantiomer (60.1 mg) was obtained as a solid.

The first eluting enantiomer had a retention time of 11.81 min.

$^1$H NMR (300 MHz, DMSO-$d_6$) δ 14.07-13.88 (m, 1H), 8.34-8.23 (m, 1H), 7.74 (s, 1H), 7.33 (s, 1H), 7.04 (s, 1H), 4.77 (s, 1H), 4.54-4.48 (m, 1H), 3.88 (s, 3H), 3.32-3.29 (m, 1H), 3.12-3.04 (m, 2H), 2.22-2.16 (m, 1H), 1.74 (s, 1H), 1.64-1.39 (m, 7H), 1.30-1.19 (m, 6H), 1.01-0.95 (m, 2H), 0.70-0.50 (m, 2H). LCMS (ESI): 498.45 $[M+H]^+$.

Example 333-B. The second eluting enantiomer (64.0 mg) was obtained as a solid.

The first eluting enantiomer had a retention time of 19.40 min.

$^1$H NMR (300 MHz, DMSO-$d_6$) δ 14.07-13.86 (m, 1H), 8.34-8.23 (m, 1H), 7.74 (s, 7.33 (s, 1H), 7.04 (s, 1H), 4.77 (s, 1H), 4.55-4.49 (m, 1H), 3.88 (s, 3H), 3.31-3.29 (m, 1H), 3.12-3.04 (m, 2H), 2.22-2.16 (m, 1H), 1.80-1.71 (m, 1H), 1.49 (d, 7H), 1.24 (d, 6H), 1.01-0.95 (m, 2H), 0.76-0.50 (m, 2H). LCMS (ESI): 498.45 $[M+H]^+$.

Example 334. (S)-4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide

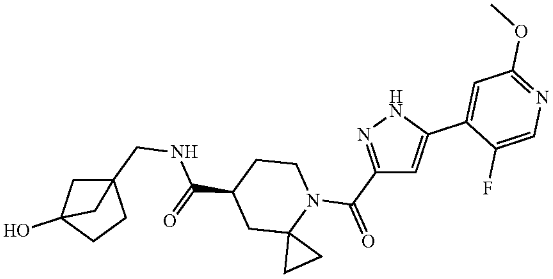 [SMILES: COc1cc(-c2cc(C(=O)N3CC[C@H](C(=O)NCC45CCC(O)(C4)C5)CC34CC4)n[nH]2)c(F)cn1]

Step-1. Tert-butyl N-[4-(dibenzylcarbamoyl)bicyclo[2.1.1]hexan-1-yl]carbamate

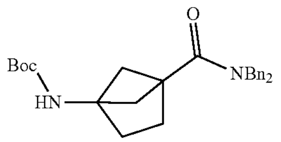

EDCI (1.59 g, 0.01 mol), HOBt (1.12 g, 0.01 mmol), and dibenzyl amine (0.98 g, 5.00 mmol) were added to a stirred mixture of 4-[(tert-butoxycarbonyl)amino]bicyclo[2.1.1]hexane-1-carboxylic acid (1.00 g, 4.14 mmol) and DIPEA (2.68 g, 21.00 mmol) in DMF (15.00 mL). The resulting mixture was stirred at 25° C. for 14 h. The resulting mixture was diluted with EtOAc, and washed with water. The organic layers were combined, dried over anhydrous $Na_2SO_4$, filtered, and concentrated under reduced pressure. The residue was purified by silica gel column chromatography eluting with petroleum ether/EtOAc (2/1 v/v) to obtain the title compound (1.90 g) as a solid. LCMS (ESI): 421.2 $[M+H]^+$.

Step-2. 4-Amino-N,N-dibenzylbicyclo[2.1.1]hexane-1-carboxamide

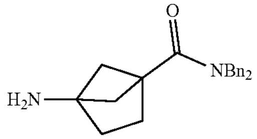

TFA (8.00 mL) was added to a stirred mixture of tert-butyl N-[4-(dibenzylcarbamoyl)bicyclo[2.1.1]hexan-1-yl]carbamate (Step-1, 1.90 g, 4.52 mmol) in DCM (8.00 mL) at 0° C. The resulting mixture was stirred at 25° C. for 3 h. The resulting mixture was concentrated under vacuum. The residue was purified by silica gel column chromatography eluting with DCM/MeOH (9/1 v/v) to obtain the title compound (1.50 g) as a solid. LCMS (ESI 321.2 $[M+H]^+$.

Step-3. N,N-dibenzyl-4-hydroxybicyclo[2.1.1]hexane-1-carboxamide

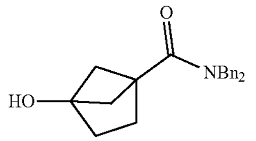

$NaNO_2$ (516.8 mg, 7.49 mmol) was added to a stirred mixture of 4-amino-N,N-dibenzylbicyclo[2.1.1]hexane-1-carboxamide (Step-2, 800.0 mg, 2.50 mmol) in AcOH (0.50 mL) and $H_2O$ (5.00 mL). The resulting mixture was stirred at 65° C. for 14 h. The mixture was allowed to cool down to 25° C. Then KOH (1.12 g, 19.98 mmol) in MeOH (3.00 mL) was added to the reaction mixture. The resulting mixture was stirred at 65° C. for 3 h. The resulting mixture was concentrated under reduced pressure. The residue was purified by Prep-TLC (petroleum ether/EtOAc 2/1 v/v) to obtain the title compound (200.0 mg) as a solid. LCMS (ESI): 322.2 $[M+H]^+$.

Step-4. 4-[(dibenzylamino)methyl]bicyclo[2.1.1]hexan-1-ol

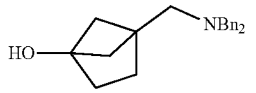

$BH_3$-THF (3.11 mL, 3.11 mmol) was added to a stirred mixture of N,N-dibenzyl-4-hydroxybicyclo[2.1.1]hexane-1-carboxamide (Step-3, 100.0 mg, 0.31 mmol) in THF (1.00 mL). The resulting mixture was stirred at 60° C. for 14 h. The reaction mixture was quenched with MeOH. The resulting mixture was concentrated under reduced pressure. The residue was purified by Prep-TLC (petroleum ether/EtOAc 1/1 v/v) to obtain the title compound (30.0 mg) as a solid. LCMS (ESI): 308.2 $[M+H]^+$.

Step-5. 4-(aminomethyl)bicyclo[2.1.1]hexan-1-ol

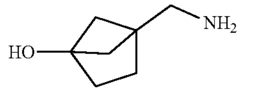

Pd/C (24.0 mg) was added to stirred a mixture of 4-[(dibenzylamino)methyl]bicyclo[2.1.1]hexan-1-ol (Step-4, 30.0 mg, 0.10 mmol) in MeOH (2.00 mL) at 0° C. The resulting mixture was stirred at 25° C. for 14 h under a $H_2$ atmosphere. The resulting mixture was filtered, the filter cake was washed with MeOH. The filtrate was concentrated under reduced pressure to obtain the title compound (11.0 mg) as a solid. LCMS (ESI): 128.1 $[M+H]^+$.

Step-6. (S)-4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide

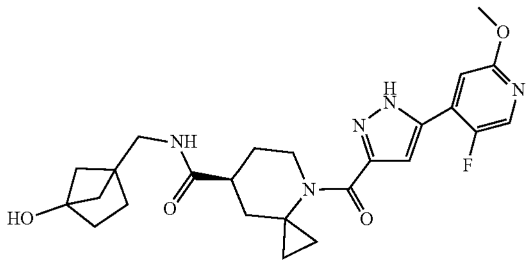

HOBt (25.5 mg, 0.19 mmol), EDGE (36.2 mg, 0.19 mmol), and 4-(aminomethyl)bicyclo[2.1.1]hexan-1-ol (Step-5, 12.0 mg, 0.09 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 38.9 mg, 0.10 mmol) and DIPEA (61.0 mg, 0.47 mmol) in DMF (1.50 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-HPLC (using the following conditions: Column: XSelect CSH Fluoro Phenyl, 30×150 mm, 5 μm; Mobile Phase A: Water (10 mM $NH_4HCO_3$), Mobile Phase B: MeOH, Flow rate: 60 mL/min; Gradient: 45% B to 55% B in 7 min; Detection: 254/220 nm) to obtain the title compound (4.3 mg) as a solid.

$^1H$ NMR (400 MHz, $CD_3OD$) δ 8.11 (s, 1H), 7.30 (s, 1H), 7.09 (s, 1H), 5.39-5.29 (m, 1H), 3.92 (s, 3H), 2.85-2.80 (m, 1H), 2.23-2.15 (m, 2H), 2.06-2.00 (m, 1H), 1.70-1.62 (m, 2H), 1.62-1.58 (m, 2H), 1.56-1.47 (m, 2H), 1.41-1.31 (m, 6H), 0.93-0.85 (m, 2H), 0.81-0.60 (m, 2H). LCMS (ESI): 484.20 $[M+H]^+$.

Example 335. 4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide

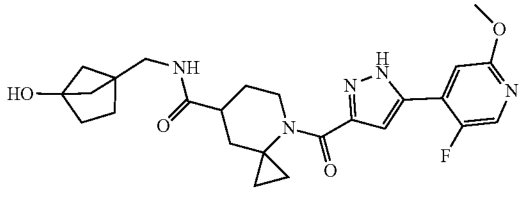

Step-1. 4-[5-(5-fluoro-2-methoxypyridin-4-yl)-1-[[2-(trimethylsilyl)ethoxy]methyl]pyrazole-3-carbonyl]-N-([4-hydroxybicyclo[2.1.1]hexan-1-yl]methyl)-4-azaspiro[2.5]octane-7-carboxamide

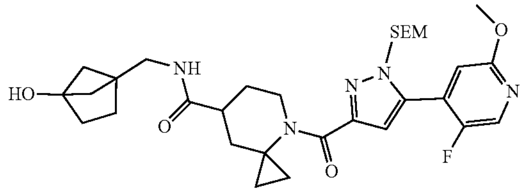 [SMILES: COc1cc(-c2cc(C(=O)N3CCC(C(=O)NCC45CCC(O)(C4)C5)CC34CC4)nn2COCC[Si](C)(C)C)c(F)cn1]

HOBt (31.9 mg, 0.24 mmol), EDGE (45.2 mg, 0.24 mmol), and 4-(aminomethyl)bicyclo[2.1.1]hexan-1-ol (Step-5 from synthesis of Example 334, 15.0 mg, 0.12 mmol) were added to a stirred mixture of 4-[5-(5-fluoro-2-methoxypyridin-4-yl)-1-[[2-(trimethylsilyl)ethoxy]methyl]pyrazole-3-carbonyl]-4-azaspiro[2.5]octane-7-carboxylic acid (Step-4 from synthesis of Example 333, 71.4 mg, 0.14 mmol) and DIPEA (76.2 mg, 0.59 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (1/5 v/v) to obtain the title compound (15.0 mg) as a solid. LCMS (ESI): 614.3 $[M+H]^+$.

Step-2. 4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide

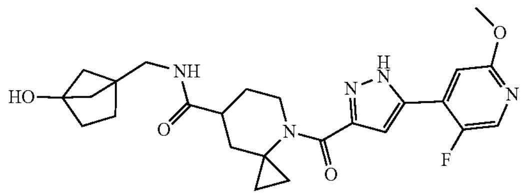

TFA (0.50 mL) was added to a stirred mixture of 4-[5-(5-fluoro-2-methoxypyridin-4-yl)-1-[[2-(trimethylsilyl)ethoxy]methyl]pyrazole-3-carbonyl]-N-([4-hydroxybicyclo[2.1.1]hexan-1-yl]methyl)-4-azaspiro[2.5]octane-7-carboxamide (Step-1, 20.0 mg, 0.03 mmol) in DCM (0.50 mL). The resulting mixture was stirred at 25° C. for 1 h. The resulting mixture was concentrated under reduced pressure. The residue was purified by silica gel column chromatography eluting with DCM/MeOH (20/1 v/v) to obtain the title compound (2.2 mg) as a solid. LCMS (ESI): 484.2 $[M+H]^+$.

Example 336. (S)-4-(5-(5-fluoro-2-methoxypyridin-4-yl)-1H-pyrazole-3-carbonyl)-N-((3-hydroxybicyclo[1.1.1]pentan-1-yl)methyl)-4-azaspiro[2.5]octane-7-carboxamide

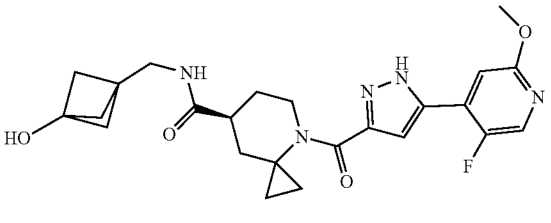

The title compound was prepared using a procedure similar to the one described for the synthesis of Example 325, except 3-(aminomethyl)bicyclo[1.1.1]pentan-1-ol hydrochloride was used as a starting material. The residue was purified by reverse phase column chromatography (using the following conditions: column, C18 column; Mobile Phase A: Water (10 mM $NH_4HCO_3$), Mobile Phase MeCN; Flow rate: 20 mL/min; Gradient: 45% B to 55% B in 7 min; Detection: 254/220 nm) to obtain the title compound (14.1 mg) as a solid.

$^1$H NMR (400 MHz, DMSO-$d_6$) δ 14.01 (s, 1H), 8.25 (s, 1H), 7.75 (s, 1H), 7.30 (d, 1H), 7.02 (s, 1H), 6.03 (s, 1H), 4.51-4.46 (m, 1H), 3.85 (s, 3H), 3.22-3.16 (m, 3H), 2.17-2.13 (m, 1H), 1.74-1.38 (m, 9H), 1.29-0.81 (m, 3H), 0.65-0.60 (m, 2H). LCMS (ESI): 470 $[M+H]^+$.

Example 337. A Enantiomeric Mixture of (S)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide and (R)—N-((2-oxabicyclo[2.1.1]hexan-4-yl)methyl)-4-(5-(5-fluoro-2-methoxypyridin-4-yl)-lit-pyrazole-3-carbonyl)-4-azaspiro[2.5]octane-7-carboxamide

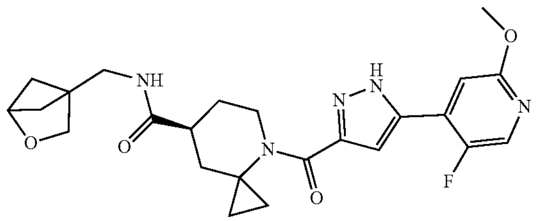

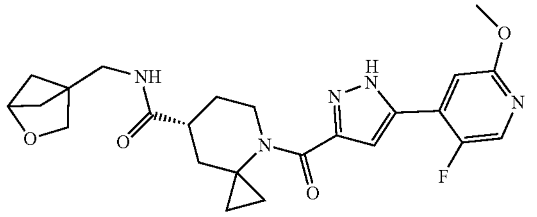

The title compound was prepared using a procedure similar to the one described for the synthesis of Example 288, except (2-oxabicyclo[2.1.1]hexan-4-yl)methanamine hydrogen chloride was used as a starting material. The residue was purified by silica gel column chromatography eluting with DCM/MeOH (15/1 v/v) to obtain (S)—N-((2-oxabicyclo[2.1.1]hexan-4-yl)methyl)-4-(5-(5-fluoro-2- methoxypyridin-4-yl)-1H-pyrazole-3-carbonyl)-4-azaspiro[2.5]octane-7-carboxamide and (R)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide (65.0 mg) as a solid mixture of enantiomers.

This mixture of two enantiomers was separated using Chiral Prep-HPLC.

Column: CHIRAL ART Cellulose-SB column

Column dimension: 2×25 cm, 5 μm

Mobile Phase: 3/1 hexanes/DCM (0.5% 2 M $NH_3$·MeOH):EtOH=90:10 hold for 11 min

Flow rate: 20 mL/min

Detection: 220/254 nm

Example 337-A. The first eluting enantiomer (14.3 was obtained as a solid.

The first eluting enantiomer had a retention time of 6.72 min.

$^1$H NMR (300 MHz, DMSO-$d_6$) δ 14.06-13.85 (m, 1H), 8.34-8.22 (m, 1H), 7.96 (s 1H), 7.32 (s, 1H), 7.04 (s, 1H), 4.64-4.38 (m, 2H), 3.88 (s, 3H), 3.44-3.35 (m, 5H), 2.33-2.11 (m, 1H), 1.79-1.46 (m, 4H), 1.38-1.08 (m, 4H) 1.01-0.81 (m, 2H), 0.70-0.49 (m, 2H). LCMS (ESI): 470.4 $[M+H]^+$.

Example 337-B. The second eluting enantiomer (11.2 mg) was obtained as a solid.

The second eluting enantiomer had a retention time of 7.83 min.

$^1$H NMR (300 MHz, DMSO-$d_6$) δ 14.06-13.85 (m, 1H), 8.34-8.22 (m, 1H), 7.96 (s, 1H), 7.35-7.28 (m, 1H), 7.04 (s, 1H), 4.65-4.38 (m, 2H), 3.88 (s, 3H), 3.49-3.37 (m, 5H), 2.23-2.17 (m, 1H), 1.79-1.44 (m, 4H), 1.38-1.06 (m, 4H), 1.01-0.78 (m, 2H), 0.70-0.49 (m, 2H). LCMS (ESI): 470.4 $[M+H]^+$.

Example 338. A Diastereomeric Mixture of (S)—N-((1r,4S)-4-hydroxy-4-)trifluoromethyl)cyclohexyl)-4-(5-(6-methoxypyrimidin-4-yl)-1H-pyrazole-3-carbonyl)-4-azaspiro[2.5]octane-7-carboxamide and (R)—N-((1r,4R)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide

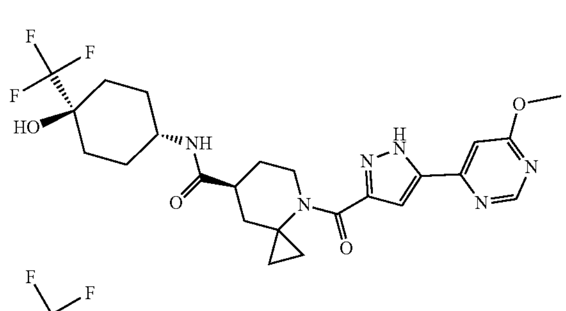

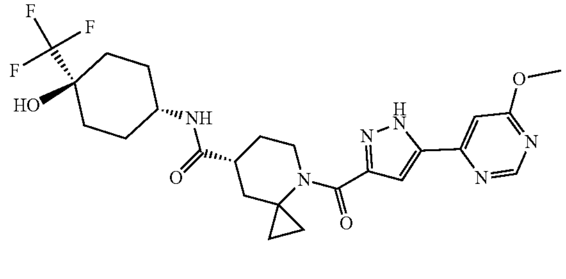

Step-1. Ethyl 5-(6-methoxypyrimidin-4-yl)-1-(tetrahydro-2H-pyran-2-yl)-1H-pyrazole-3-carboxylate

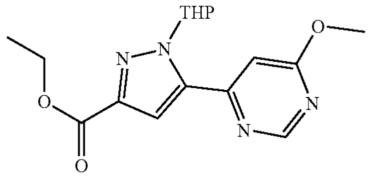

4-chloro-6-methoxypyrimidine (388.3 mg, 2.69 mmol), $K_3PO_4$ (1425.2 mg, 6.71 mmol) and Pd(dppf)$Cl_2$ (327.5 mg, 0.448 mmol) were added to a stirred mixture of 5-(ethoxycarbonyl)-2-(oxan-2-yl)pyrazol-3-ylboronic acid (600.0 mg, 2.24 mmol) in 1,4-dioxane (5.00 mL) and $H_2O$ (0.50 mL). The resulting mixture was stirred at 70° C. for 3 h under nitrogen atmosphere. The resulting mixture was concentrated under reduced pressure and the residue was purified by silica gel column chromatography eluting with DCM/MeOH (10/1 v/v) to obtain the title compound (450.0 mg) as a solid. LCMS (ESI): 333.2 $[M+H]^+$.

Step-2. Ethyl 5-(6-methoxypyrimidin-4-yl)-1H-pyrazole-3-carboxylate

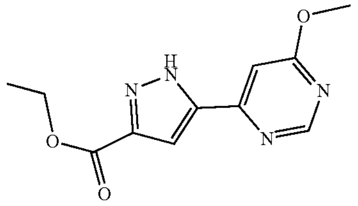

Trifluoroacetic acid (6.00 mL) was added to a stirred solution of ethyl 6-methoxypyrimidin-4-yl)-1-(oxan-2-yl)pyrazole-3-carboxylate (Step-1, 450.0 mg, 1.35 mmol) in DCM (6.00 mL). The resulting solution was stirred at 25° C. for 1 h. The solution was then concentrated under reduced pressure to obtain the title compound (300.0 mg) as an oil. LCMS (ESI): 249.1 $[M+H]^+$.

Step-3. 5-(6-methoxypyrimidin-4-yl)-1H-pyrazole-3-carboxylic acid

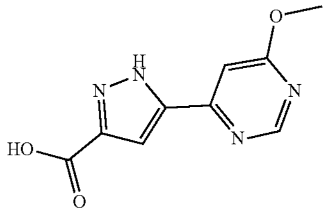

LiOH·$H_2O$ (152.1 rug, 3.62 mmol) was added to a stirred solution of ethyl 5-(6-methoxypyrimidin-4-yl)-1H-pyrazole-3-carboxylate (Step-2, 300.0 mg, 1.21 mmol) in THF (2.00 mL), MeOH (2.00 mL), and $H_2O$ (2.00 mL). The resulting mixture was stirred at 60° C. for 14 h. The solution was concentrated under reduced pressure. The mixture was acidified to pH 4 with aqueous HCl (1 M). The solids were collected by filtration and concentrated under vacuum to obtain the title compound (180.0 mg) as a solid. LCMS (ESI): 221.1 $[M+H]^+$.

Step-4. Methyl 4-(5-(6-methoxypyrimidin-4-yl)-1H-pyrazole-3-carbonyl)-4-azaspiro[2.5]octane-7-carboxylate

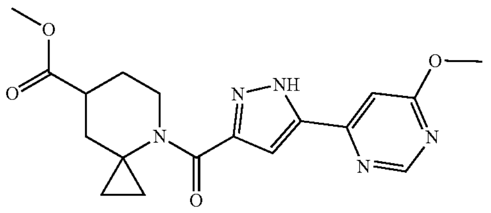 [SMILES: COC(=O)C1CCN(C(=O)c2cc(-c3cc(OC)ncn3)[nH]n2)C2(CC2)C1]

HOBt (174.9 mg, 1.29 mmol), EDCI (248.1 mg, 1.29 mmol), and methyl 4-azaspiro[2.5]octane-7-carboxylate (230.0 mg, 1.12 mmol) were added to a stirred mixture of 5-(6-methoxypyrimidin-4-yl)-1H-pyrazole-3-carboxylic acid (Step-3, 190.0 mg, 0.86 mmol) and DIPEA (446.1 mg, 3.45 mmol) in DMF (4.00 mL). The resulting solution was stirred at 25° C. for 14 h. The resulting mixture was diluted with EtOAc and washed with water. The organic layers were combined, dried over anhydrous $Na_7SO_4$, filtered, and concentrated under reduced pressure. The residue was purified by silica gel column chromatography eluting with DCM/MeOH (10/1 v/v) to obtain the title compound (260.0 mg) as a solid. LCMS (EST: 372.2 $[M+H]^+$.

Step-5. 4-(5-(6-methoxypyrimidin-4-yl)-1H-pyrazole-3-carbonyl)-4-azaspiro[2.5]octane-7-carboxylic acid

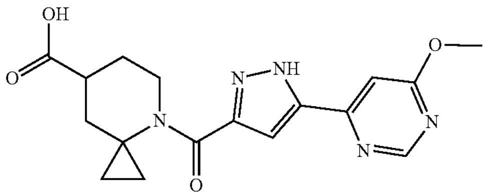 [SMILES: COc1cc(-c2cc(C(=O)N3CCC(C(=O)O)CC34CC4)n[nH]2)ncn1]

$LiOH \cdot H_2O$ (117.5 mg, 2.80 mmol) was added to a stirred solution of methyl 4-[5-(6-methoxypyrimidin-4-yl)-1H-pyrazole-3-carbonyl]-4-azaspiro[2.5]octane-7-carboxylate (Step-4, 260.0 mg, 0.70 mmol) in THF (1.50 mL), MeOH (1.50 mL), and $H_2O$ (1.50 mL). The resulting mixture was stirred at 25° C. for 1 h. The solution was concentrated under reduced pressure. The mixture was acidified to pH 3 with aqueous HCl (1 M). The mixture was then extracted with EtOAc. The organic layers were combined, dried over anhydrous $Na_2SO_4$, filtered, and concentrated under reduced pressure to obtain the title compound (140.0 mg) as a solid. LCMS (EST): 358.1 $[M+14]^+$.

Step-6. (S)—N-((1r,4S)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide and (R)—N-((1r,4R)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide

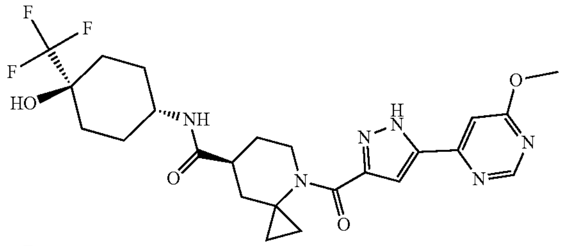

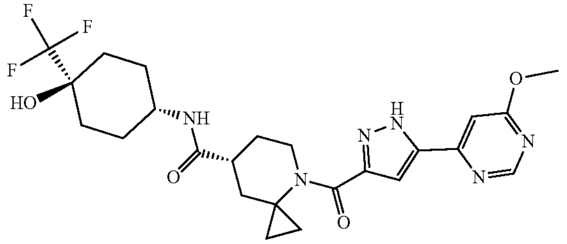

HOBt (79.4 mg, 0.59 mmol), EDCI (112.7 mg, 0.59 mmol), methyl (1r,4r)-4-amino-1-(trifluoromethyl)cyclohexan-1-ol (106.4 mg, 0.51 mmol) were added to a stirred solution of 4-[5-(6-methoxypyrimidin-4-yl)-1H-pyrazole-3-carbonyl]-4-azaspiro[2.5]octane-7-carboxylic acid (Step-5, 140.0 mg, 0.39 mmol) and DIPEA (202.5 mg, 1.57 mmol) in DMF (2.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (20/1 v/v) to obtain the title compound (150.0 mg) as a solid. LCMS (ESI): 523.2 $[M+H]^+$.

This mixture of two diastereomers (50.0 mg) was separated using Chiral Prep-HPLC.

Column: CHIRALPAK IE column

Column dimension: 2×25 cm, 5 μm

Mobile Phase: 3/1 hexanes/DCM (0.5% 2 M $NH_3 \cdot MeOH$):EtOH=70:30 hold for 15 min Flow rate: 20 mL/min Detection: 220/254 nm Example 338-A. The first eluting diastereomer (22.5 mg) was obtained as a solid.

The first eluting diastereomer had a retention time of 9.74 min.

$^1H$ NMR (400 MHz, DMSO-$d_6$) δ 13.99 (s, 1H), 8.81 (s, 1H), 7.78 (s, 1H), 7.53-7.10 (m, 2H), 5.67 (s, 1H), 4.51 (s, 1H), 3.96 (s, 3H), 3.81 (s, 1H), 2.76 (s, 1H), 2.39-1.92 (m, 1H), 1.83-1.37 (m, 1H), 1.22 (s, 2H), 1.11 (d, 1H), 0.96 (s, 1H), 0.90-0.76 (m, 1H), 0.60 (s, 2H). LCMS (ESI): 523.20 $[M+H]^+$.

Example 338-B. The second eluting diastereomer (20.8 mg) was obtained as a solid.

The second eluting diastereomer had a retention time of 12.66 min, $^1H$ NMR (400 MHz, DMSO-$d_6$) δ 13.99 (s, 1H), 8.81 (s, 1H), 7.78 (d, 1H), 7.38 (s, 2H), 5.67 (s, 1H), 4.48 (s, 1H), 3.95 (s, 3H), 3.80 (d, 1H), 2.76 (s, 1H), 2.34-2.04 (m, 1H), 1.83-1.65 (m, 5H), 1.65-1.39 (m, 6H), 1.22 (s, 1H), 1.19-1.10 (m, 1H), 1.03 (d, 1H) 0.91 (d, 1H), 0.85-0.72 (m, 1H), 0.60 (s, 2H). LCMS (ESI): 523.3 $[M+H]^+$.

Example 339. A Diastereomeric Mixture of (R)—N-((1r,4R)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide and (S)—N-((1r,4S)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide

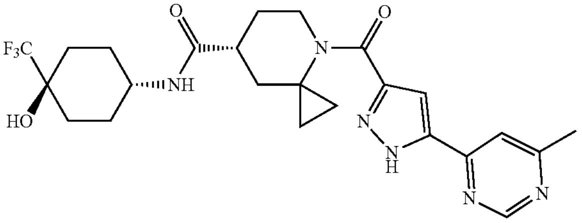

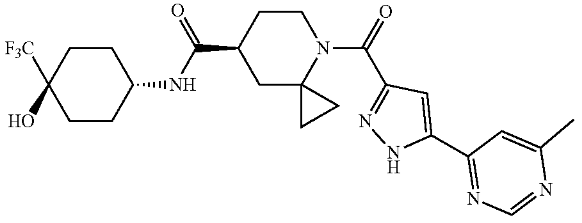

Step-1. 4-[5-(6-methylpyrimidin-4-yl)-1H-pyrazole-3-carbonyl]-4-azaspiro[2.5]octane-7-carboxylic acid

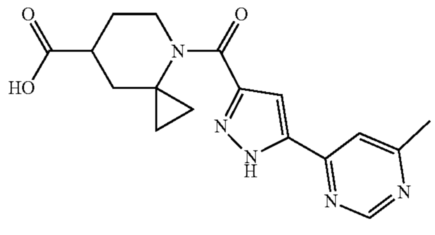

LiOH·$H_2O$ (59.0 mg, 1.41 mmol) was added to a stirred solution of methyl 4-[5-(6-methylpyrimidin-4-yl)-1H-pyrazole-3-carbonyl]-4-azaspiro[2.5]octane-7-carboxylate (Step-1 from synthesis of Example 308, 250.0 mg, 0.70 mmol) in THF (2.00 mL), MeOH (2.00 mL) and $H_2O$ (2.00 mL). The resulting mixture was stirred at 25° C. for 14 h. The solution was concentrated under reduced pressure. The mixture was acidified to pH 4 with aqueous HCl (1 M). The resulting solution was extracted with EtOAc. The organic layers were combined, dried over anhydrous $Na_2SO_4$, filtered, and concentrated under reduced pressure to obtain the title compound (200.0 mg) as a solid. LCMS (ESI): 342.2 $[M+H]^+$.

Step-2. (R)—N-((1r,4R)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide and (S)—N-((1r,4S)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide

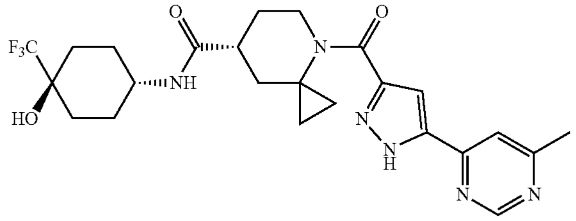

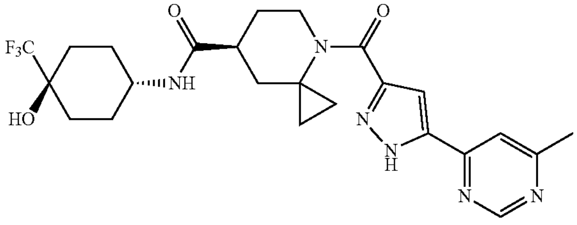

HOBt (89.1 mg, 0.66 mmol), EDCI (126.4 mg, 0.66 mmol), and (1r,4r)-4-amino-1-(trifluoromethyl)cyclohexan-1-ol hydrochloride (125.5 mg, 0.57 mmol) were added to a stirred mixture of 4-[5-(6-methylpyrimidin-4-yl)-1H-pyrazole-3-carbonyl]-4-azaspiro[2.5]octane-7-carboxylic acid (Step-1, 150.0 mg, 0.44 mmol) and DIPEA (284.0 mg, 2.20 mmol) in DMF (4.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (18/1 v/v) to obtain (R)—N-((1r,4R)-4-hydroxy-4-(trifluoromethyl)cyclohexyl)-4-(5-(6-methylpyrimidin-4-yl)-1H-pyrazole-3-carbonyl)-4-azaspiro[2,5]octane-7-carboxamide and (S)—N-((1r,4S)-4-hydroxy-4-(trifluoromethyl)cyclohexyl)-4-(5-(6-methylpyrimidin-4-yl)-1H-pyrazole-3-carbonyl)-4-azaspiro[2,5]octane-7-carboxamide (180.0 mg) as a solid mixture of diastereomers. LCMS (ESI): 507.2 $[M+H]^+$.

This mixture of two diastereomers (180.0 mg) was separated using Chiral Prep-HPLC.

Column: CHIRALPAK IA column

Column dimension: 2×25 cm, 5 μm

Mobile Phase: MTBE (0.5% 2 M $NH_3$·MeOH):EtOH=70:30 hold for 20 min

Flow rate: 16 mL/min

Detection: 220/254 nm

Example 339-A. The first eluting diastereomer (34.1 mg) was obtained as a solid.

The first eluting diastereomer had a retention time of 9.47 min, $^1H$ NMR (400 MHz, DMSO-$d_6$) δ 13.82 (d, 1H), 9.03 (d, 1H), 7.89 (d, 1H), 7.78 (s, 1H), 7.21 (s, 1H), 5.67 (s, 1H), 4.45 (s, 1H), 3.84-3.78 (m, 1H), 3.00-2.95 (m, 1H), 2.79-2.75 (m, 1H), 2.48 (d, 3H), 2.24-2.20 (m, 1H), 1.88-1.63 (m, 5H), 1.57-1.46 (m, 5H), 1.19-1.11 (m, 1H), 1.00-0.69 (m, 2H), 0.65-0.56 (m, 2H), LCMS (ESI): 507.1 $[M+H]^+$.

Example 339-B. The second eluting diastereomer (46.6 mg) was obtained as a solid.

The first eluting diastereomer had a retention time of 15.61 min.

$^1$H NMR (300 MHz, DMSO-$d_6$) δ 14.02 (d, 1H), 9.05 (s, 1H), 7.91 (s, 1H), 7.81 (d, 1H), 7.21 (s, 1H), 5.69 (s, 1H), 4.56-4.50 (m, 1H), 3.87-3.81 (m, 1H), 3.30-3.01 (m, 1H), 2.82-2.76 (m, 1H), 2.51-2.48 (m, 3H), 2.24-2.18 (m, 1H), 1.83-1.72 (m, 5H), 1.57-1.47 (m, 5H), 1.01-0.95 (m, 3H), 0.67-0.61 (m, 2H). LCMS (ESI): 507.1 $[M+H]^+$.

Example 340. A Diastereomeric Mixture of (S)-4-(5-(5-fluoro-2-methoxypyridin-4-yl)-1H-pyrazole-3-carbonyl)-N-((1S,4S)-4-((S)-2-methoxypropoxy)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1R,4S)-4-((R)-2-methoxypropoxy)-4-(trifluoromethyl)cyclohexyl)-4-azaspiro[2.5]octane-7-carboxamide

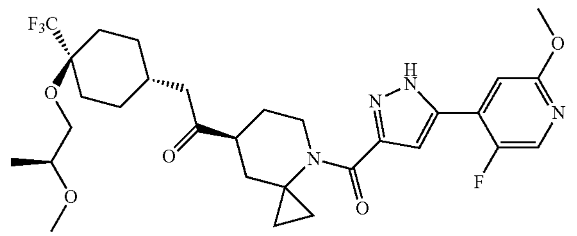

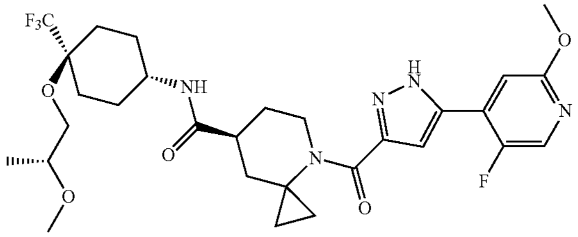

Step-1. 2-Methoxypropyl trifluoromethanesulfonate

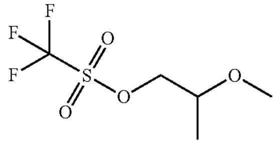

$Tf_2O$ (25.04 g, 88.75 mmol) and TEA (8.98 g, 88.77 mmol) were added to a mixture of 2-methoxypropanol (4.00 g, 44.38 mmol) in DCM (10.00 mL) at 0° C. The resulting mixture was stirred at 25° C. for 5 h. The resulting mixture was concentrated under reduced pressure. The residue was purified by silica gel column chromatography eluting with petroleum ether/EtOAc (9/1 v/v) to obtain the title compound (660.0 mg) as a liquid.

Step-2. (1r,4r)-N,N-dibenzyl-4-(2-methoxypropoxy)-4-(trifluoromethyl)cyclohexan-1-amine

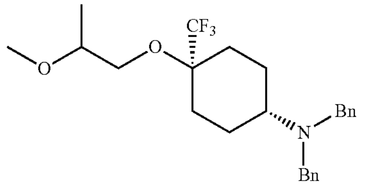 [SMILES: COC(C)CO[C@]1(C(F)(F)F)CC[C@@H](N(Cc2ccccc2)Cc2ccccc2)CC1]

NaH (61.7 mg, 1.54 mmol, 60% dispersion in mineral oil) was added to a stirred mixture of (1r,4r)-4-(dibenzylamino)-1-(trifluoromethyl)cyclohexan-1-ol (Step-1 from synthesis of Example 323, 280.0 mg, 0.77 mmol) in THF (4.00 mL) at 0° C. The resulting mixture was stirred at 25° C. for 30 min. Then 2-methoxypropyl trifluoromethanesulfonate (Step-1, 660.0 mg, 1.62 mmol) was added to the reaction mixture. The resulting mixture was stirred at 25° C. for 14 h. The reaction mixture was quenched with MeOH and concentrated under reduced pressure. The residue was purified by silica gel column chromatography eluting with petroleum ether/EtOAc (9/1 v/v) to obtain the title compound (250.0 mg) as a solid. LCMS (ESI): 436.2 $[M+H]^+$.

Step-3. (1r,4r)-4-(2-methoxypropoxy)-4-(trifluoromethyl)cyclohexan-1-amine

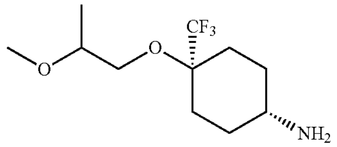 [SMILES: COC(C)CO[C@]1(C(F)(F)F)CC[C@@H](N)CC1]

Pd/C (125.0 mg) was added to a stirred mixture of (1r,4r)-N,N-dibenzyl-4-(2-methoxypropoxy)-4-(trifluoromethyl)cyclohexan-1-amine (Step-3, 250.0 mg, 0.58 mmol) in MeOH (3.00 mL) at 0° C. The resulting mixture was stirred at 25° C. for 14 h under a $H_2$ atmosphere. The resulting mixture was filtered, the filter cake was washed with MeOH. The filtrate was concentrated under reduced pressure to obtain the title compound as a solid (100.0 mg). LCMS (ESI): 256.2 $[M+H]^+$.

Step-4. (S)-4-(5-(5-fluoro-2-methoxypyridin-4-yl)-1H-pyrazole-3-carbonyl)-N-((1S,4S)-4-((S)-2-methoxypropoxy)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1R,4S)-4-((R)-2-methoxypropoxy)-4-(trifluoromethyl)cyclohexyl)-4-azaspiro[2.5]octane-7-carboxamide

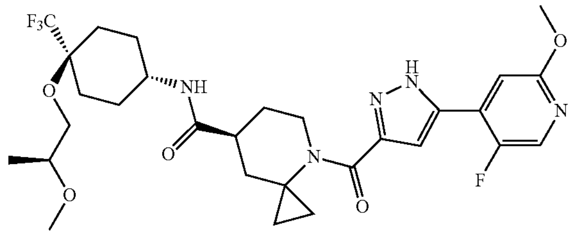

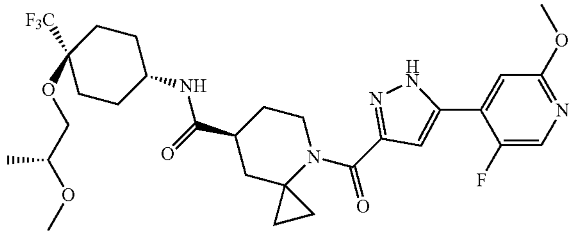

HOBt (84.7 mg, 0.63 mmol), EDCI (120.2 mg, 0.63 mmol), and (1r,4r)-4-(2-methoxypropoxy)-4-(trifluoromethyl)cyclohexan-1-amine (Step-3, 80.0 mg, 0.31 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 129.1 mg, 0.35 mmol) and DIPEA (202.5 mg, 1.57 mmol) in DMF (4.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC eluting with petroleum ether/EtOAc (1/20 v/v) to obtain (S)-4-(5-(5-fluoro-2-methoxypyridin-4-yl)-1H-pyrazole-3-carbonyl)-N-((1S,4S)-4-((S)-2-methoxypropoxy)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1R,4S)-4-((R)-2-methoxypropoxy)-4-(trifluoromethyl)cyclohexyl)-4-azaspiro[2.5]octane-7-carboxamide (120.0 mg) as a solid mixture of diastereomers. LCMS (ESI): 612.3 $[M+H]^+$.

This mixture of two diastereomers (80.0 mg) was separated using Chiral Prep-HPLC.

Column: CHIRALPAK IA column

Column dimension: 2×25 cm, 5 μm

Mobile Phase: 3/1 hexanes/DCM (0.5% 2 M $NH_3$·MeOH):EtOH=95:5 hold for 29 min

Flow rate: 20 mL/min

Detection: 220/254 nm

Example 340-A. The first eluting diastereomer (1.9 mg) was obtained as a solid.

The first eluting diastereomer had a retention time of 21.48 min.

LCMS (ESI): 612.0 $[M+H]^+$.

Example 340-B. The second eluting diastereomer 3.4 mg) was obtained as a solid.

The second eluting diastereomer had a retention time of 24.89 min.

LCMS (ESI): 612.0 $[M+H]^+$.

Example 341. A Diastereomeric Mixture of (S)-4-(3-(5-fluoro-2-methoxypyridin-4-yl)-1H-pyrazole-5-carbonyl)-N—(((R)-4,5,6,7-tetrahydro-2H-indazol-5-yl)methyl)-4-azaspiro[2.5]octane-7-carboxamide and (S)-4-(3-(5-fluoro-2-methoxypyridin-4-yl)-1H-pyrazole-5-carbonyl)-N—(((S)-4,5,6,7-tetrahydro-2H-indazol-5-yl)methyl)-4-azaspiro[2.5]octane-7-carboxamide

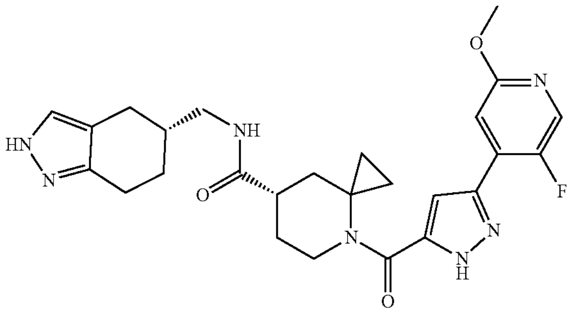

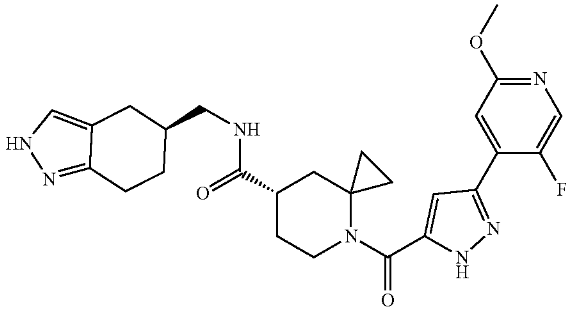

Step-1. N-benzyl-4,5,6,7-tetrahydro-1H-indazole-5-carboxamide

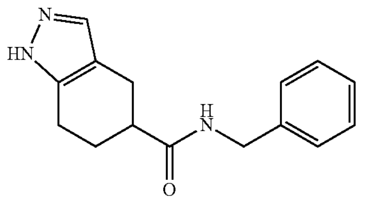 [SMILES: O=C(NCc1ccccc1)C1CCc2[nH]ncc2C1]

EDCI (865.2 mg, 4.51 mmol), HOBt (609.8 mg, 4.51 mmol), and benzylamine (386.9 mg, 3.61 mmol) were added to a solution of 4,5,6,7-tetrahydro-1H-indazole-5-carboxylic acid (500.0 mg, 3.01 mmol) and DIPEA (1944.33 mg, 15.044 mmol) in DMF (3.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (15/1 v/v) to obtain the title compound (300.0 mg) as a solid. LCMS (ESI): 256.1 $[M+H]^+$.

Step-2. benzyl(4,5,6,7-tetrahydro-1H-indazol-5-ylmethyl)amine

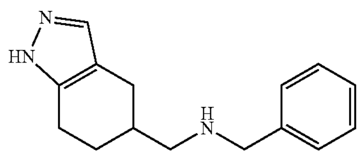 [SMILES: c1ccc(CNCC2CCc3[nH]ncc3C2)cc1]

$BH_3$-THF (7.80 mL, 7.83 mmol) was added to a stirred mixture of N-benzyl-4,5,6,7-tetrahydro-1H-indazole-5-carboxamide (Step-1, 200.0 mg, 0.78 mmol) in THF (2.00 mL) at 0° C. The resulting mixture was stirred at 70° C. for 5 h. MeOH (6.00 mL) was added to the resulting mixture and the resulting mixture was stirred at 70° C. for 1 h. The resulting mixture was concentrated under reduced pressure. The residue was purified by silica gel column chromatography eluting with DCM/MeOH (15/1 v/v) to obtain the title compound (90.0 mg) as a solid. LCMS (ESI): 242.2 $[M+H]^+$.

Step-3. 1-(4,5,6,7-tetrahydro-1H-indazol-5-yl)methanamine

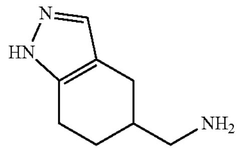 [SMILES: NCC1CCc2[nH]ncc2C1]

Pd/C (25.0 mg) was added to a stirred mixture of benzyl (4,5,6,7-tetrahydro-1H-indazol-5-ylmethyl)amine (Step-2, 70.0 mg, 0.29 mmol) in MeOH (3.00 mL) at 0° C. The resulting mixture was stirred at 25° C. for 14 h under a $H_2$ atmosphere. The solids were filtered and washed with MeOH. The filtrate was concentrated to obtain the title compound (40.0 mg) as a solid. LCMS (ESI): 152.1 $[M+H]^+$.

Step-4. (S)-4-(3-(5-fluoro-2-methoxypyridin-4-yl)-1H-pyrazole-5-carbonyl)-N—((R)-4,5,6,7-tetrahydro-2H-indazol-5-yl)methyl)-4-azaspiro[2.5]octane-7-carboxamide and (S)-4-(3-(5-fluoro-2-methoxypyridin-4-yl)-1H-pyrazole-5-carbonyl)-N—(((S)-4,5,6,7-tetrahydro-2H-indazol-5-yl)methyl)-4-azaspiro[2.5]octane-7-carboxamide

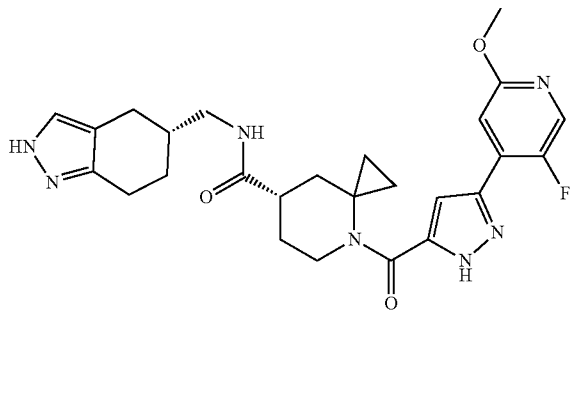

-continued

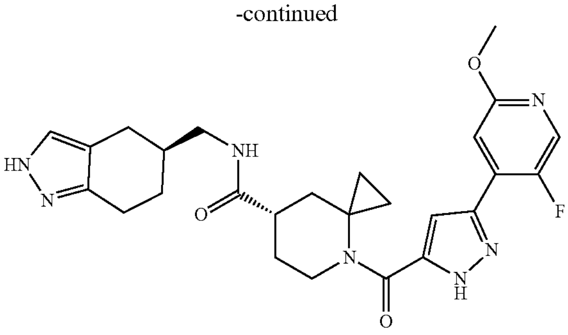

EDCI (76.8 mg, 0.40 mmol), HOBt (54.0 mg, 0.40 mmol), and 1-(4,5,6,7-tetrahydro-1H-indazol-5-yl)methanamine (Step-3, 40.0 mg, 0.27 mmol) were added to a solution of (S)-4-[5-(5-fluoro-2-methoxypyridin-4-yl)-1H-pyrazole-3-carbonyl]-4-azaspiro[2,5]octane-7-carboxylic acid (INTERMEDIATE 527-A, 100.0 mg, 0.27 mmol) and DIPEA (170.0 mg, 1.34 mmol) in DMF (2.00 mL). The resulting solution was stirred at 25° C. for 14 h. The resulting mixture was dilute with EtOAc, washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)-4-(3-(5-fluoro-2-methoxypyridin-4-yl)-1H-pyrazole-5-carbonyl)-N—(((R)-4,5,6,7-tetrahydro-2H-indazol-5-yl)methyl)-4-azaspiro[2.5]octane-7-carboxamide and (S)-4-(3-(5-fluoro-2-methoxypyridin-4-yl)-1H-pyrazole-5-carbonyl)-N—((S)-4,5,6,7-tetrahydro-2H-indazol-5-yl) methyl)-4-azaspiro[2.5]octane-7-carboxamide (55.0 mg) as a solid mixture of diastereomers (Example 341). $^1H$ NMR (400 MHz, DMSO-$d_6$) δ 13.89 (s, 1H), 12.20 (s, 1H), 8.25 (s, 1H), 7.94-7.88 (m, 1H), 7.30 (d, 1H), 7.23 (s, 1H), 7.02 (s, 1H), 4.47-4.42 (m, 1H), 3.85 (s, 3H), 3.18-2.98 (m, 3H), 2.82-2.58 (m, 3H), 2.35-1.99 (m, 2H), 1.86-1.66 (m, 4H), 1.52 (s, 1H), 1.39-1.27 (m, 1H), 1.23-1.19 (m, 1H), 1.06-0.79 (m, 2H), 0.64-0.59 (m, 2H). LCMS (ESI): 508.20 $[M+H]^+$.

This mixture of two diastereomers (50.0 mg) was separated using Chiral Prep-HPLC.

Column: CHIRALPAK IA column

Column dimension: 2×25 cm, 5 μm

Mobile Phase: 3/1 hexanes/DCM (0.5% 2 M $NH_3$·MeOH):EtOH=70:30 hold for 13 min

Flow rate: 20 mL/min

Detection: 220/254 nm

Example 341-A. The first eluting diastereomer (14.4 mg) was obtained as a solid.

The first eluting diastereomer had a retention time of 8.39 min.

$^1H$ NMR (400 MHz, $CD_3OD$) δ 8.11 (s, 1H), 7.45-7.16 (m, 2H), 7.10 (s, 1H), 4.75-4.48 (m, 1H), 3.92 (s, 3H), 3.28-3.17 (m, 2H), 2.85-2.51 (m, 4H), 2.41-2.37 (m, 1H), 2.22-2.11 (m, 1H), 2.01-1.63 (m, 4H), 1.52-1.40 (m, 1H), 1.31-1.26 (m, 2H), 1.06-1.02 (m, 1H), 0.80-0.58 (m, 3H), LCMS (ESI): 508.50 $[M+H]^+$.

Example 341-B. The second eluting diastereomer (13.9 mg) was obtained as a solid.

The second eluting diastereomer had a retention time of 10.95 min.

$^1H$ NMR (400 MHz, $CD_3OD$) δ 8.12 (s, 1H), 7.42-7.15 (m, 2H), 7.10 (s, 1H), 4.78-4.48 (m, 1H), 3.92 (s, 3H), 3.24-3.17 (m, 2H), 2.85-2.52 (m, 4H), 2.42-2.38 (m, 1H), 2.22-2.12 (m, 1H), 2.03-1.73 (m, 4H), 1.48 (s, 1H), 1.31-1.25 (m, 2H), 1.06-1.01 (m, 1H), 0.75-0.71 (m, 3H). LCMS (ESI): 508.50 $[M+H]^+$.

Example 342. A Diastereomeric Mixture of (8)-4-(3-(5-fluoro-2-methoxypyridin-4-yl)-1H-pyrazole-5-carbonyl)-N—(((R)-5,6,7,8-tetrahydroimidazo[1,5-a]pyridin-7-yl)methyl)-4-azaspiro[2.5]octane-7-carboxamide and (S)-4-(3-(5-fluoro-2-methoxypyridin-4-yl)-1H-pyrazole-5-carbonyl)-N—(((S)-5,6,7,8-tetrahydroimidazo[1,5-a]pyridin-7-yl)methyl)-4-azaspiro[2.5]octane-7-carboxamide

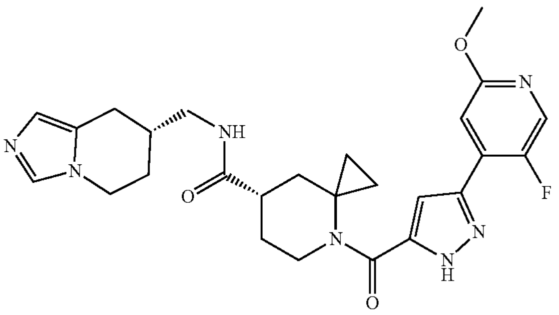

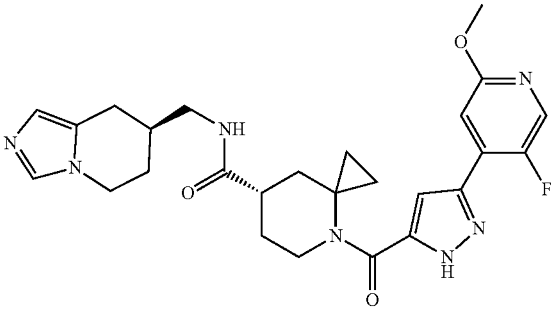

Step-1. Imidazo[1,5-a]pyridine-7-carbonitrile

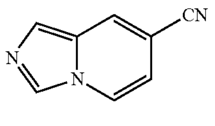 [SMILES: N#Cc1ccn2cncc2c1]

Zinc cyanide (595.9 mg, 5.08 mmol) and $Pd(PPh_3)_4$ (586.5 mg, 0.51 mmol) were added to a stirred mixture of 7-bromoimidazo[1,5-a]pyridine (1.00 g, 5.08 mmol) in DMF (5.00 mL). The resulting mixture was stirred at 100° C. for 14 h under nitrogen atmosphere. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (24/1 v/v) to obtain the title compound (500.0 mg) as a solid. LCMS (ESI): 144.0 $[M+H]^+$.

Step-2. 1-[5H,6H,7H,8H-imidazo[1,5-a]pyridin-7-yl]methanamine

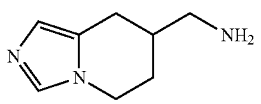 [SMILES: NCC1CCn2cncc2C1]

Pd/C (100.0 mg) was added to a stirred mixture of imidazo[1,5-a]pyridine-7-carbonitrile (Step-1, 250.0 mg, 1.75 mmol) in MeOH (6.00 mL) and AcOH (3.00 mL). The resulting mixture was stirred at 60° C. for 14 h under a $H_2$ atmosphere (30 atm). The resulting mixture was filtered, the filter cake was washed with MeOH. The filtrate was concentrated under reduced pressure to obtain the title compound (200.0 mg) as an oil. LCMS (ESI): 152.1 $[M+H]^+$ Step-3. (S)-4-(3-(5-fluoro-2-methoxypyridin-4-yl)-1H-pyrazole-5-carbonyl)-$N_4$ (R)-5,6,7,8-tetrahydroimidazo[1,5-a]pyridin-7-yl)methyl)-4-azaspiro[2.5]octane-7-carboxamide and (S)-4-(3-(5-fluoro-2-methoxypyridin-4-yl)-1H-pyrazole-5-carbonyl)-N—(((S)-5,6,7,8-tetrahydroimidazo[1,5-a]pyridin-7-yl)methyl)-4-azaspiro[2.5]octane-7-carboxamide

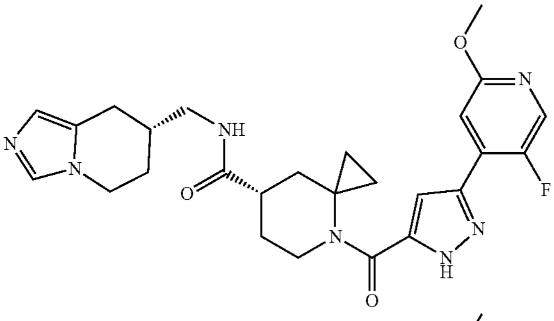

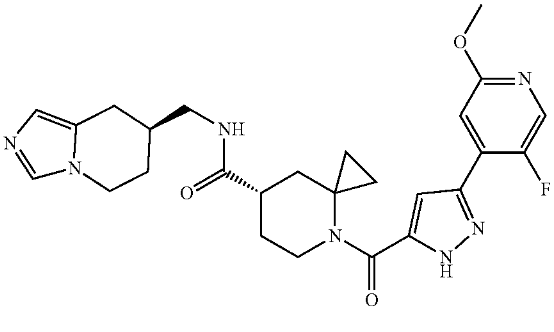

HOBt (144.4 mg, 1.07 mmol), EDCI (204.8 mg, 1.07 mmol), and 1-[5H,6H,7H,8H-imidazo[1,5-a]pyridin-7-yl]methanamine (Step-2, 181.0 mg, 1.20 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 200.0 mg, 0.53 mmol) and DIPEA (345.2 mg, 2.67 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-HPLC (using the following conditions: Column: XBridge Prep OBD C18

Column, 30×150 mm, 5 μm; Mobile Phase A: Water (10 mM $NH_4HCO_3$), Mobile Phase B: MeCN; Flow rate: 60 mL/min; Gradient: 13% B to 43% B in 10 min; Wave Length: 254 nm) to obtain (S)-4-(3-(5-fluoro-2-methoxypyridin-4-yl)-1H-pyrazole-5-carbonyl)-N—(((R)-5,6,7,8-tetrahydroimidazo[1,5-a]pyridin-7-yl)methyl)-4-azaspiro[2.5]octane-7-carboxamide and (5)-4-(3-(5-fluoro-2-methoxypyridin-4-yl)-1H-pyrazole-5-carbonyl)-N—(((S)-5,6,7,8-tetrahydroimidazo[1,5-a]pyridin-7-yl)methyl)-4-azaspiro[2.5]octane-7-carboxamide (88.0 mg) as a solid mixture of diastereomers (Example 342). $^1$H NMR (300 MHz, $CD_3OD$) δ 8.10 (d, 1H), 7.48 (s, 1H), 7.27 (d, 1H), 7.09 (d, 1H), 6.65 (s, 1H), 4.60-4.54 (m, 1H), 4.30-4.17 (m, 1H) 3.92 (s, 3H), 3.90-3.81 (m, 1H), 3.37-3.31 (m, 2H), 3.29-3.15 (m, 2H), 3.00-2.87 (m, 1H), 2.86-2.80 (m, 1H), 2.48-2.21 (m, 2H) 2.06-2.00 (m, 2H), 1.95-1.52 (m, 3H), 1.35-1.25 (m, 2H), 1.15-0.97 (m, 2H), 0.78-0.69 (m, 2H). LCMS (ESI): 508 $[M+H]^+$.

This mixture of two diastereomers (88.0 mg) was separated using Chiral Prep-HPLC.

Column: CHIRALPAK ART Cellulose-SB column

Column dimension: 2×25 cm, 5 μm

Mobile Phase: MTBE (0.5% 2M $NH_3$·MeOH): 1/1 MeOH/DCM=60:40 hold for 18 min

Flow rate: 16 mL/min

Detection: 220/254 nm

Example 342-A. The first eluting diastereomer (25.1 mg) was obtained as a solid.

The first eluting diastereomer had a retention time of 10.57 min.

$^1$H NMR (300 MHz, DMSO-$d_6$) δ 14.04 (s, 1H), 8.28 (s, 1H), 7.99 (s, 1H), 7.55 (s, 1H), 7.33 (d, 1H), 7.04 (s, 1H), 6.64 (s, 1H), 4.53-4.47 (m, 1H), 4.23-4.10 (m, 1H), 3.88 (s, 3H), 3.88-3.73 (m, 1H), 3.18-3.02 (m, 2H), 2.91-2.77 (m, 1H), 2.76-2.62 (m, 1H), 2.34-2.19 (m, 1H), 2.03-1.68 (m, 4H), 1.61-1.49 (m, 2H), 1.27-1.12 (m, 2H), 1.01-0.95 (m, 4H), 0.67-0.61 (m, 2H). LCMS (ESI): 508 $[M+H]^+$.

Example 342-B. The second eluting diastereomer (27.5 mg) was obtained as a solid.

The second eluting diastereomer had a retention time of 13.95 min, $^1$H NMR (300 MHz, DMSO-$d_6$) δ 14.04 (s, 1H), 8.28 (s, 1H), 7.98 (s, 1H), 7.61 (s, 1H), 7.33 (d, 1H), 7.05 (s, 1H), 6.68 (s, 1H), 4.55-4.49 (m, 1H), 4.22-4.11 (m, 1H), 3.88 (s, 3H), 3.88-3.74 (m, 1H), 3.17-3.05 (m, 2H) 2.90-2.77 (m, 1H), 2.56-2.50 (m, 1H), 2.35-2.14 (m, 1H), 2.00-1.68 (m, 4H), 1.59-1.53 (m, 2H), 1.38-1.10 (m, 2H), 1.07-0.79 (m, 2H), 0.77-0.46 (m, 2H). LCMS (ESI): 508 $[M+H]^+$.

Example 343. (S)-4-(5-(5-fluoro-2-methoxypyridin-4-yl)-1H-pyrazole-3-carbonyl)-N-((1-methyl-2-oxabicyclo[2.1.1]hexan-4-yl)methyl)-4-azaspiro[2.5]octane-7-carboxamide

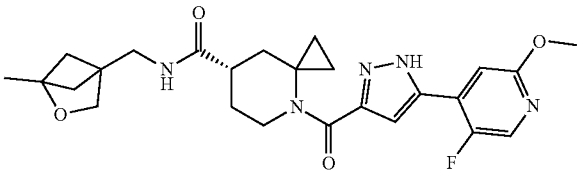

The title compound was prepared using a procedure similar to the one described for the synthesis of Example 325, except (1-methyl-2-oxabicyclo[2.1.1]hexan-4-yl)methanamine was used as a starting material. The residue was purified by reverse phase column chromatography (using the following conditions: column, C18 column; Mobile Phase A: Water (0.5% $NH_4HCO_3$), Mobile Phase B: MeCN; Gradient: 10% B to 30% B in 20 min; Detection: 254/220 nm) to obtain the title compound (74.7 mg) as a solid. $^1$H NMR (400 MHz, DMSO-$d_6$) δ 13.95 (s, 1H), 8.25 (d, 1H), 7.91 (s, 1H), 7.30 (d, 1H), 7.01 (s, 1H), 4.47-4.43 (m, 1H), 3.85 (s, 3H), 3.44-3.40 (m, 2H), 3.36-3.32 (m, 2H), 2.70-2.66 (m, 1H), 2.19-2.15 (m, 1H), 1.75-1.70 (m, 1H), 1.58-1.40 (m, 3H), 1.38-1.23 (m, 6H), 1.23-0.89 (m, 3H), 0.63-0.59 (m, 2H). LCMS (ESI): 484.0 $[M+H]^+$.

Example 344. A Diastereomeric Mixture of (R)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide and (S)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide

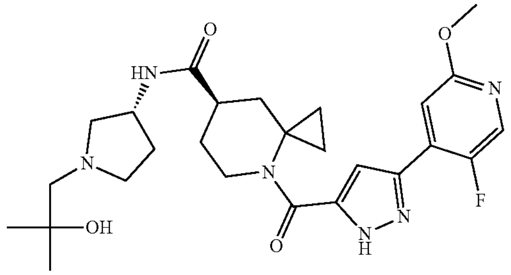

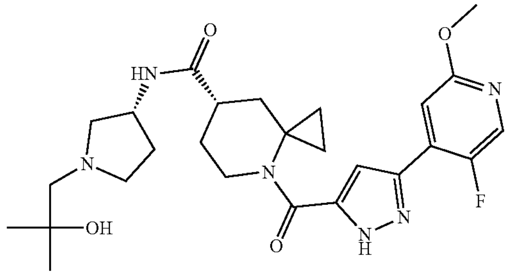

Step-1. 1-[(3R)-3-(dibenzylamino)pyrrolidin-1-yl]-2-methylpropan-2-ol

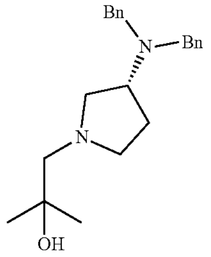 [SMILES: CC(C)(O)CN1CC[C@@H](N(Cc2ccccc2)Cc2ccccc2)C1]

2,2-Dimethyloxirane (324.8 mg, 4.51 mmol) and $K_2CO_3$ (622.6 mg, 4.51 mmol) were added to a stirred mixture of (3R)—N,N-dibenzylpyrrolidin-3-amine (400.0 mg, 1.50 mmol) in EtOH (4.00 mL) and water (0.40 mL). The resulting mixture was stirred at 110° C. for 14 h. The resulting mixture was concentrated under reduced pressure. The residue was purified by silica gel column chromatography eluting with DCM/MeOH (19/1 v/v) to obtain the title compound (410.0 mg) as a solid. LCMS (ESI): 339.2 $[M+H]^+$.

Step-2. 1-[(3R)-3-aminopyrrolidin-1-yl]-2-methylpropan-2-ol

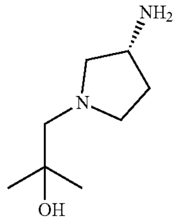

Pd/C (123.0 mg) was added to a stirred solution of 1-[(3R)-3-(dibenzylamino)pyrrolidin-1-yl]-2-methylpropan-2-ol (Step-1, 410.0 mg) in MeOH (4.00 mL) at 0° C. The resulting mixture was stirred at 25° C. for 14 h under a $H_2$ atmosphere. The resulting mixture was filtered, the filter cake was washed with MeOH. The filtrate was concentrated under reduced pressure to obtain the title compound (177.0 mg) as a solid. LCMS (ESI): 159.1 $[M+H]^+$.

Step-3a. (R)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide

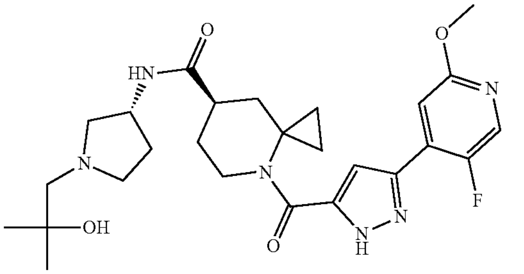 [SMILES: COc1cc(-c2cc(C(=O)N3CC[C@@H](C(=O)N[C@@H]4CCN(CC(C)(C)O)C4)CC34CC4)[nH]n2)c(F)cn1]

HOBt (72.6 mg, 0.54 mmol), EDCI (103.0 mg, 0.54 mmol), and 1-[(3R)-3-aminopyrrolidin-1-yl]-2-methylpropan-2-ol (Step-2, 85.0 mg, 0.54 mmol) were added to a stirred solution of (R)-4-(3-(5-fluoro-2-methoxypyridin-4-yl)-1H-pyrazole-5-carbonyl)-4-azaspiro[2.5]octane-7-carboxylic acid (INTERMEDIATE 527-B, 100.6 mg, 0.27 mmol) and DIPEA (173.6 mg, 1.34 mmol) in DMF (4.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 10 B to 30 B in 20 min; 220/254 nm) to obtain the title compound (47.2 mg) as a solid (Example 344-A). $^1H$ NMR (400 MHz, $CD_3OD$) δ 8.11 (d, 1H), 7.26 (d, 1H), 7.09 (d, 1H), 4.74-4.36 (m, 1H) 4.32-4.21 (m, 1H), 3.92 (s, 3H), 2.99-2.70 (m, 3H), 2.67-2.55 (m, 2H), 2.52-2.33 (m, 2H) 2.25-2.10 (m, 1H), 2.00-1.44 (m, 3H), 1.39-1.12 (m, 8H), 1.11-0.58 (m, 2H), 0.79-0.51 (m, 2H). LCMS (ESI): 515 $[M+H]^+$.

Step-3b. (S)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide

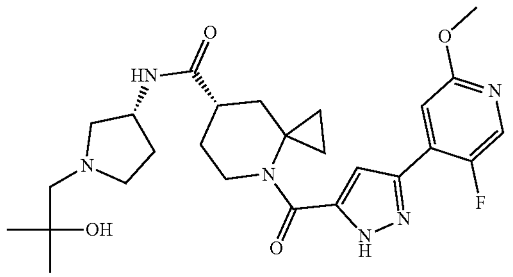 [SMILES: COc1cc(-c2cc(C(=O)N3CC[C@H](C(=O)N[C@@H]4CCN(CC(C)(C)O)C4)CC34CC4)[nH]n2)c(F)cn1]

HOBt (72.6 mg, 0.54 mmol), EDCI (103.0 mg, 0.54 mmol), and 1-[(3R)-3-aminopyrrolidin-1-yl]-2-methylpropan-2-ol (Step-2, 85.0 mg, 0.54 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 100.6 mg, 0.27 mmol) and DIPEA (173.6 mg, 1.34 mmol) in DMF (4.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 10 B to 30 B in 20 min; 220/254 nm) to obtain the tile compound (26.8 mg) as a solid (Example 344-B). $^1H$ NMR (400 MHz, $CD_3OD$) δ 8.11 (d, 1H), 7.26 (s, 1H), 7.09 (d, 1H), 4.67-4.46 (m, 1H), 4.37-4.20 (m, 1H), 3.92 (s, 3H), 3.70-3.35 (m, 2H), 3.27-2.66 (m, 5H), 2.56-2.20 (m, 2H), 2.05-1.54 (m, 3H), 1.38-1.15 (m, 8H), 1.15-0.82 (m, 2H), 0.81-0.52 (m, 2H). LCMS (ESI): 515 $[M+H]^+$.

Example 345. A Diastereomeric Mixture of (S)-4-(3-(5-fluoro-2-methoxypyridin-4-yl)-1H-pyrazole-5-carbonyl)-N—((S)-1-(2-hydroxy-2-methylpropyl) pyrrolidin-3-yl)-4-azaspiro[2.5]octane-7-carboxamide and (R)-4-(3-(5-fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide

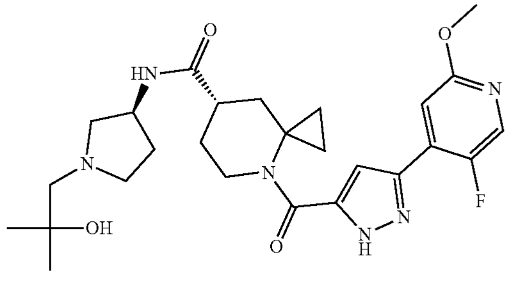

-continued

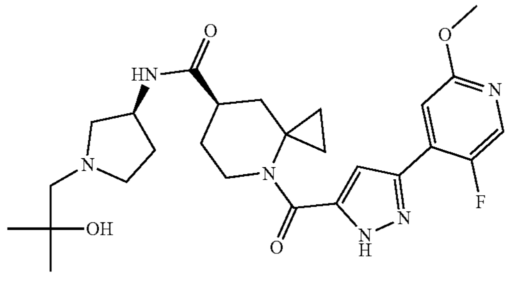

The title compound was prepared using a procedure similar to the one described for the synthesis of Example 345, (3S)—N,N-dibenzylpyrrolidin-3-amine was used as a starting material in Step-1. (S)-4-(3-(5-Fluoro-2-methoxypyridin-4-yl)-1H-pyrazole-5-carbonyl)-N-(1-(2-hydroxy-2-methylpropyl)pyrrolidin-3-yl)-4-azaspiro[2,5]octane-7-carboxamide (27.0 mg) was obtained as a solid (Example 345-A). $^1H$ NMR (400 MHz, $CD_3OD$) δ 8.11 (d, 1H), 7.27 (d, 1H), 7.09 (d, 1H), 4.60-4.56 (m, 1H), 4.31-4.22 (m, 1H), 3.92 (s, 3H), 2.95-2.73 (m, 3H), 2.64-2.53 (m, 2H), 2.52-2.32 (m, 3H), 2.29-2.12 (m, 1H), 1.99-1.49 (m, 3H), 1.35-1.11 (m, 8H), 0.95-0.91 (m, 2H), 0.75-0.69 (m, 2H). LCMS (ESI): 515.6 $[M+H]^+$.

(R)-4-(3-(5-Fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide (10.2 mg) was obtained as a solid (Example 345-B), $^1H$ NMR (400 MHz, $CD_3OD$) δ 8.11 (d, 1H), 7.26 (s, 1H), 7.09 (s, 1H), 4.69-4.41 (m, 1H), 4.28-4.24 (m, 1H), 3.92 (s, 3H), 2.95-2.69 (m, 3H), 2.68-2.52 (m, 2H), 2.52-2.29 (m, 3H), 2.26-2.12 (m, 1H), 1.99-1.53 (m, 3H), 1.42-1.08 (m, 8H), 1.09-0.80 (m, 2H), 0.73-0.69 (m, 2H). LCMS (ESI): 515.6 $[M+H]^+$.

Example 346. A Diastereomeric Mixture of (S)-4-(3-(5-fluoro-2-methoxypyridin-4-yl)-1H-pyrazole-5-carbonyl)-NVR)-3-methyl-5,6,7,8-tetrahydro-[1,2,4]triazolo[4,3-a]pyridin-7-yl)methyl)-4-azaspiro[2.5]octane-7-carboxamide and (8)-4-(3-(5-fluoro-2-methoxypyridin-4-yl)-1H-pyrazole-5-carbonyl)-N—(((S)-3-methyl-5,6,7,8-tetrahydro-[1,2,4]triazolo[4,3-a]pyridin-7-yl)methyl)-4-azaspiro[2.5]octane-7-carboxamide

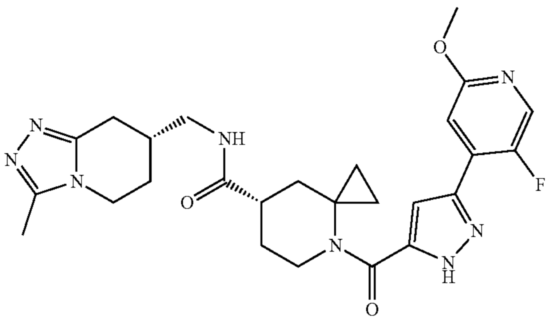

-continued

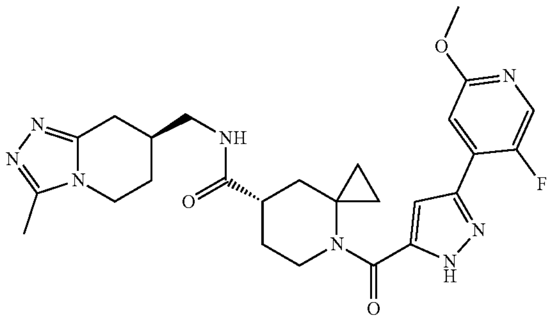

Step-1. 3-methyl-[1,2,4]triazolo[4,3-a]pyridine-7-carbonitrile

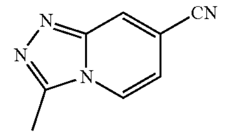

$Zn(CN)_2$ (789.2 mg, 6.72 mmol) and $Pd(PPh_3)_4$ (517.7 mg, 0.45 mmol) were added to a stirred solution of 7-promo-3-methyl-[1,2,4]triazolo[4,3-a]pyridine (950.0 mg, 4.48 mmol) in DMF (8.00 mL). The resulting mixture was stirred at 100° C. for 14 h under nitrogen atmosphere. The solution was diluted with EtOAc and washed with water. The aqueous layers were combined and concentrated under reduced pressure. The residue was purified by reverse phase column chromatography (using the following conditions: C18 column, mobile phase A: Water (0.5% $NH_4HCO_3$), mobile phase B: MeCN, gradient: 0 B to 20 B in 30 min; 220/254 nm) to obtain the title compound (212.0 mg) as a solid. LCMS (ESI): 159.1 $[M+H]^+$.

Step-2. 1-[3-methyl-5H,6H,7H,8H-[1,2,4]triazolo[4,3-a]pyridin-7-yl]methanamine

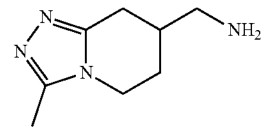

$PtO_2$ (180.0 mg) was added to a stirred solution of 3-methyl-[1,2,4]triazolo[4,3-a]pyridine-7-carbonitrile (Step-1, 180.0 mg, 1.14 mmol) in AcOH (5.00 mL). The resulting mixture was stirred at 25° C. for 3 h under a $H_2$ atmosphere. The solids were filtered out. The filtrate was concentrated under reduced pressure to obtain the title compound (180.0 mg) as a solid. LCMS (ESI): 167.1 $[M+H]^+$.

Step-3. (S)-4-(3-(5-fluoro-2-methoxypyridin-4-yl)-1H-pyrazole-5-carbonyl)-N—(((R)-3-methyl-5,6,7,8-tetrahydro-[1,2,4]triazolo[4,3-a]pyridin-7-yl)methyl)-4-azaspiro[2.5]octane-7-carboxamide and (S)-4-(3-(5-fluoro-2-methoxypyridin-4-yl)-1H-pyrazole-5-carbonyl)-N—(((S)-3-methyl-5,6,7,8-tetrahydro-[1,2,4]triazolo[4,3-a]pyridin-7-yl)methyl)-4-azaspiro[2.5]octane-7-carboxamide

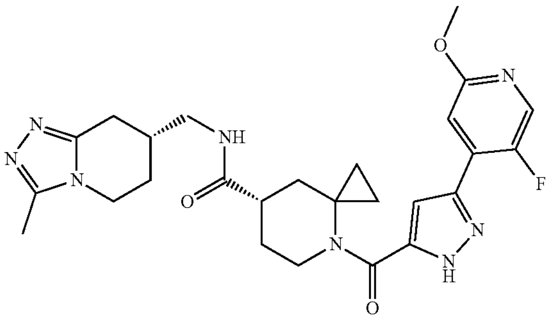

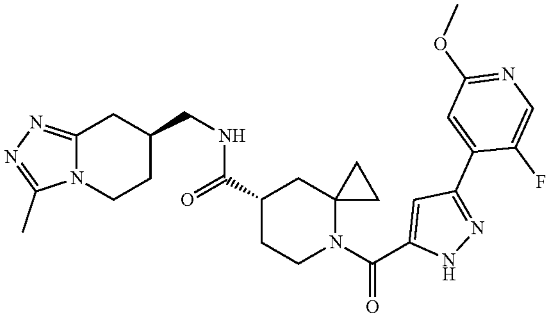

HOBt (54.1 mg, 0.40 mmol), EDCI (76.8 mg, 0.40 mmol) and 1-[3-methyl-5H,6H-7H,8H-[1,2,4]triazolo[4,3-a]pyridin-7-yl]methanamine (Step-2, 168.7 mg, 1.01 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 100.0 mg, 0.27 mmol) and DIPEA (207.1 mg, 1.60 mmol) in DMF (3.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by reverse phase column chromatography (using the following conditions: C18 column, mobile phase A: Water (0.5% $NH_4HCO_3$), mobile phase B: MeCN; gradient: 0 B to 20 B in 30 min; 220/254 nm) to obtain (S)-4-(3-(5-fluoro-2-methoxypyridin-4-yl)-1H-pyrazole-5-carbonyl)-N—(((R)-3-methyl-5,6,7,8-tetrahydro-[1,2,4]triazolo[4,3-a]pyridin-7-yl)methyl)-4-azaspiro[2.5]octane-7-carboxamide and (S)-4-(3-(5-fluoro-2-methoxypyridin-4-yl)-1H-pyrazole-5-carbonyl)-N—(((S)-3-methyl-5,6,7,8-tetrahydro-[1,2,4]triazolo[4,3-a]pyridin-7-yl)methyl)-4-azaspiro[2.5]octane-7-carboxamide (2.1 mg) as a solid mixture of diastereomers (Example 346). NMR (300 MHz, $CD_3OD$) δ 8.22-8.06 (m, 1H), 7.47-7.22 (m, 1H), 7.12 (s, 1H), 4.61 (s, 1H), 4.21-4.05 (m, 1H), 3.95 (s, 3H), 3.88-3.71 (m, 1H), 3.31-3.22 (m, 3H), 3.17-2.98 (m, 1H), 2.85 (s, 1H), 2.55-2.30 (m, 5H), 2.26-2.03 (m, 2H), 1.99-1.54 (m, 3H), 1.50-0.41 (m, 5H). LCMS (ESI): 523.2 $[M+H]^+$ This mixture of two diastereomers (28.0 mg) was separated using Chiral Prep-HPLC.

Column: CHIRALPAK IA column

Column dimension: 2×25 cm, 5 μm

Mobile Phase: MTBE (0.5% 2M $NH_3$·MeOH):1/1 MeOH/DCM=50:50 hold for 20 min

Flow rate: 16 mL/min

Detection: 220/254 nm

Example 346-A. The first eluting diastereomer (1.7 mg) was obtained as a solid.

The first eluting diastereomer had a retention time of 13.35 min.

$^1H$ NMR (300 MHz, $CD_3OD$) δ 8.14 (s, 1H), 7.49-7.16 (m, 1H), 7.12 (s, 1H), 4.62 (s, 1H), 4.31-4.06 (m, 1H), 3.95 (s, 3H), 3.91-3.73 (m, 1H), 3.23-2.97 (m, 2H), 2.86 (s, 1H), 2.67-2.32 (m, 5H), 2.20-2.06 (m, 2H), 2.03-1.58 (m, 3H), 1.31 (s, 2H), 1.19-0.86 (m, 2H), 0.76 (s, 3H). LCMS (ESI): 523.5 $[M+H]^+$.

Example 346-B. The second eluting diastereomer (3.7 mg) was obtained as a solid.

The first eluting diastereomer had a retention time of 17.07 min.

$^1H$ NMR (300 MHz, $CD_3OD$) δ 8.29-8.08 (m, 1H), 7.47-7.17 (m, 1H), 7.12 (s, 1H), 4.64 (s, 1.14), 4.26-4.06 (m, 1H), 3.95-3.75 (m, 4H), 3.19-3.00 (m, 2H), 2.97-2.73 (m, 1H), 2.67-2.32 (s, 5H), 2.30-2.06 (m, 2H), 2.04-1.53 (m, 3H), 1.31 (s, 2H), 1.19-0.87 (m, 2H), 0.76 (s, 3H). LCMS (ESI): 523.5 $[M+H]^+$.

Example 347. A Diastereomeric Mixture of (1r,4R)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1s,4S)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1r,4S)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1s,4R)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide

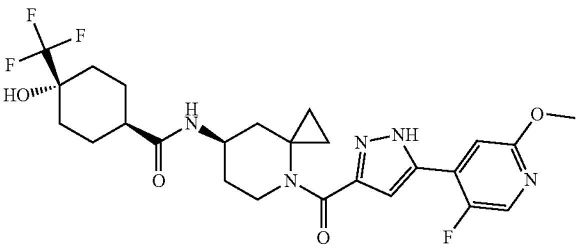

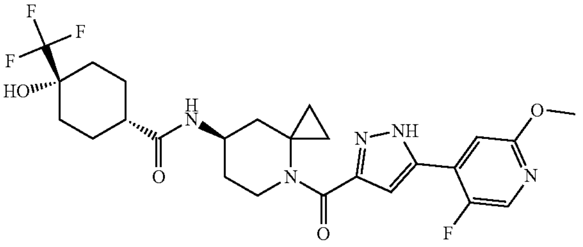

-continued

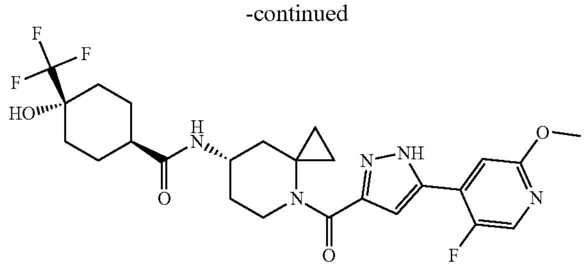

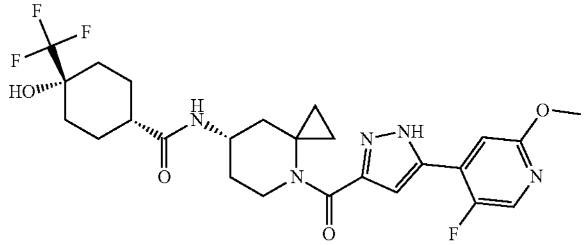

Step-1. Tert-butyl 7-[4-hydroxy-4-(trifluoromethyl) cyclohexaneamido]-4-azaspiro[2.5]octane-4-carboxylate

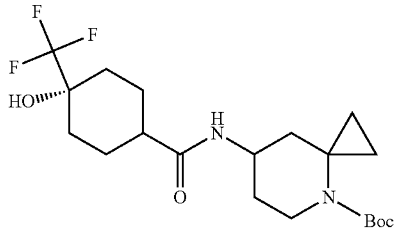

HOBt (254.8 mg, 1.89 mmol), EDCI (361.4 mg, 1.89 mmol), and tert-butyl 7-amino-4-azaspiro[2,5]octane-4-carboxylate (213.3 mg, 0.94 mmol) were added to a stirred mixture of 4-hydroxy-4-(trifluoromethyl)cyclohexane-1-carboxylic acid (200.0 mg, 0.94 mmol) and DIPEA (609.2 mg, 4.71 mmol) in DMF (4.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 3/20 v/v) to obtain the title compound (280.0 mg) as a solid. LCMS (ESI): 421.2 $[M+H]^+$.

Step-2. N-[4-azaspiro[2.5]octan-7-yl]-4-hydroxy-4-(trifluoromethyl)cyclohexane-1-carboxamide

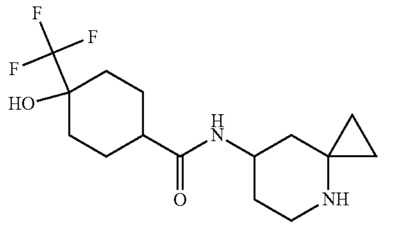 [SMILES: O=C(NC1CCNC2(CC2)C1)C1CCC(O)(C(F)(F)F)CC1]

TFA (4.00 mL) was added to a stirred mixture of tert-butyl 7-[4-hydroxy-4-(trifluoromethyl)cyclohexaneamido]-4-azaspiro[2.5]octane-4-carboxylate (Step-1, 280.0 mg, 0.67 mmol) in DCM (4.00 mL) at 0° C. The resulting mixture was stirred at 25° C. for 2 h. The resulting mixture was concentrated under reduced pressure to obtain the title compound (300.0 mg) as a solid. LCMS (ESI): 321.2 $[M+H]^+$.

Step-3. N-[4-[5-(5-fluoro-2-methoxypyridin-4-yl)-1-[[2-(trimethylsilyl)ethoxy]methyl]pyrazole-3-carbonyl]-4-azaspiro[2.5]octan-7-yl]-4-hydroxy-4-(trifluoromethyl)cyclohexane-1-carboxamide

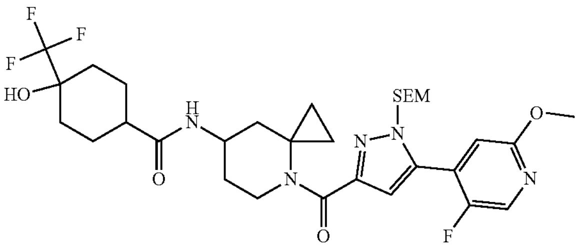 [SMILES: COc1cc(-c2cc(C(=O)N3CCC(NC(=O)C4CCC(O)(C(F)(F)F)CC4)CC34CC4)nn2COCC[Si](C)(C)C)c(F)cn1]

HATU (476.0 mg, 1.25 mmol) and N-[4-azaspiro[2.5]octan-7-yl]-4-hydroxy-4-(trifluoromethyl)cyclohexane-1-carboxamide (Step-2, 300.8 mg, 0.94 mmol) were added to a stirred mixture of 5-(5-fluoro-2-methoxypyridin-4-yl)-1-[[2-(trimethylsilyl)ethoxy]methyl]pyrazole-3-carboxylic acid (INTERMEDIATE 506, 230.0 mg, 0.63 mmol) and DIPEA (809.0 mg, 6.26 mmol) in DMF (3.00 mL). The resulting mixture was stirred at 25° C. for 5 h. The resulting mixture was diluted with EtOAc and washed with water. The organic layers were combined, dried over anhydrous $Na_2SO_4$, filtered; and concentrated under reduced pressure. The residue was purified by silica gel column chromatography eluting with petroleum ether/EtOAc (2/3 v/v) to obtain the title compound (400.0 mg) as a solid. LCMS (ESI): 670.3 $[M+H]^+$.

Step-4. (1r,4R)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1s,4S)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1r,4S)—N—VS)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1s,4R)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide

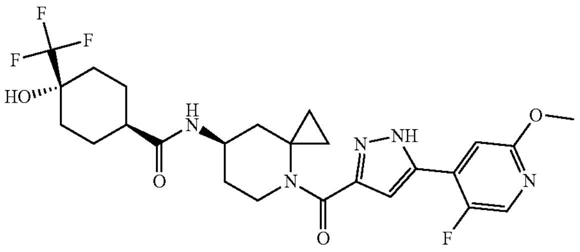

-continued

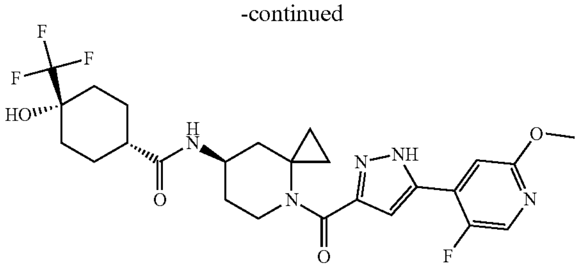

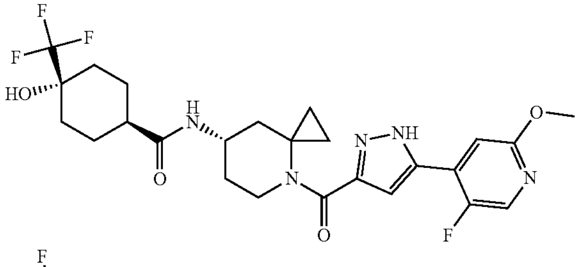

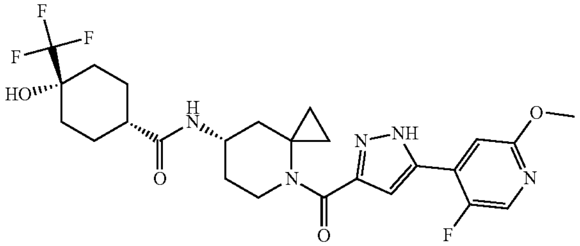

TFA (4.00 mL) was added to a stirred mixture of N-[4-[5-(5-fluoro-2-methoxypyridin-4-yl)-1-[[2-(trimethylsilyl)ethoxy]methyl]pyrazole-3-carbonyl]-4-azaspiro[2.5]octan-7-yl]-4-hydroxy-4-(trifluoromethyl)cyclohexane-1-carboxamide (Step-3, 400.0 mg, 0.60 mmol) in DCM (4.00 mL) at 0° C. The resulting mixture was stirred at 25° C. for 5 h. The resulting mixture was concentrated under reduced pressure. The residue was purified by Prep-TLC (Petroleum ether/EtOAc, 1/2 v/v) to obtain (1r,4R)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1s,4S)—N—VR)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide and (1r,4S)—N—((S)-4-(5-(5-fluoro-2-methoxypyridin-4-yl)-1H-pyrazole-3-carbonyl)-4-azaspiro[2,5]octan-7-yl)-4-hydroxy-4-(trifluoromethyl)cyclohexane-1-carboxamide and (1s,4R)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide (160.0 mg) as a solid mixture of diastereomers (Example 347). $^1$H NMR (400 MHz, DMSO-$d_6$) δ 8.24 (d, 1H), 7.90-7.73 (m, 1H), 7.30 (d, 1H), 7.01 (d, 1H), 5.66 (d, 1H), 4.6-4.25 (m, 1H), 4.2-4.01 (m, 1H), 3.85 (s, 3H), 2.42-2.32 (m, 1H), 2.19-1.61 (m, 7H), 1.62-1.04 (m, 5H), 1.13-0.43 (m, 4H). LCMS (ESI): 540 [M+H]$^+$.

This mixture of four diastereomers was (160.0 mg) was separated using Chiral Prep-HPLC.

Column: CHIRALPAK IE column

Column dimension: 2×25 cm, 5 μm

Mobile Phase: hexanes (0.5% 2 M $NH_3$·MeOH: EtOH=75:25 hold for 30 min

Flow rate: 20 mL/min

Detection: 220/254 nm

Example 347-A. The first eluting diastereomer (19.7 mg) was obtained as a solid.

The first eluting diastereomer had a retention time of 14.86 min.

$^1$H NMR (300 MHz, DMSO-$d_6$) δ 14.02 (s, 1H), 8.27 (d, 1H), 7.71 (d, 1. 4), 7.33 (d, 1H), 7.02 (d, 1H), 5.63 (s, 1H), 4.47-4.41 (m, 1H), 4.07-4.01 (m, 1H), 3.88 (s, 3H), 3.35-3.03 (m, 1H), 2.40-2.31 (m, 1H), 2.07-2.01 (m, 1H), 1.94-1.68 (m, 7H), 1.56-1.44 (m, 2H), 1.41-1.13 (m, 2H), 0.91-0.85 (m, 2H), 0.68-0.60 (m, 2H). LCMS (ESI): 540 [M+H]$^+$.

Example 347-B. The second eluting diastereomer (25.2 mg) was obtained as a solid.

The second eluting diastereomer had a retention time of 16.29 min.

$^1$H NMR (300 MHz, DMSO-$d_6$) δ 14.00 (s, 1H), 8.27 (d, 1H), 7.71 (d, 1H), 7.33 (d, 1H), 7.03 (d, 1H), 5.63 (s, 1H), 4.45-4.39 (m, 1H), 4.08-4.02 (m, 1H), 3.88 (s, 3H), 3.35-3.02 (m, 1H), 2.40-2.31 (m, 1H), 2.07-2.01 (m, 1H), 1.91-1.63 (m, 7H), 1.56-1.44 (m, 2H), 1.27-1.21 (m, 2H), 0.92-0.86 (m, 2H), 0.69-0.60 (m, 2H). LCMS (ESI): 540 [M+H]$^+$.

Example 347-C. The third eluting diastereomer (20.3 mg) was obtained as a solid.

The third eluting diastereomer had a retention time of 18.86 min.

$^1$H NMR (300 MHz, DMSO-$d_6$) δ 8.26 (d, 1H), 7.75 (d, 1H), 7.33 (d, 1H), 7.02 (d, 1H), 5.70 (s, 1H), 4.46-4.40 (m, 1H), 4.05-3.99 (m, 1H), 3.88 (s, 3H), 3.35-3.13 (m, 1H), 2.07-2.01 (m, 2H), 1.93-1.62 (m, 5H), 1.61-1.50 (m, 2H), 1.50-1.36 (m, 2H), 1.35-1.15 (m, 2H), 1.02-0.73 (m, 2H), 0.69-0.57 (m, 2H), LCMS (ESI): 540 [M+H]$^+$.

Example 347-D. The fourth eluting diastereomer (24.1 mg) was obtained as a solid.

The fourth eluting diastereomer had a retention time of 23.10 min.

$^1$H NMR (300 MHz, DMSO-$d_6$) δ 8.27 (d, 1H), 7.75 (d, 1H), 7.33 (d, 1H), 7.03 (d, 1H), 5.70 (s, 1H), 4.45-4.39 (m, 1H), 4.05-3.99 (m, 1H), 3.88 (s, 3H), 3.37-2.87 (m, 1H), 2.07-2.01 (m, 2H), 1.92-1.80 (m, 1H), 1.80-1.62 (m, 4H), 1.61-1.51 (m, 2H), 1.51-1.37 (m, 2H), 1.37-1.14 (m, 2H), 0.91-0.78 (m, 2H), 0.66-0.60 (m, 2H). LCMS (ESI): 540 [M+H]$^+$.

Example 348. (S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide

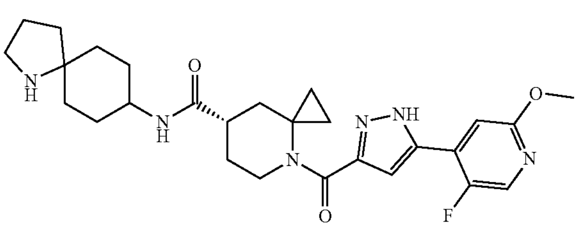 [SMILES: COc1cc(-c2cc(C(=O)N3CC[C@H](C(=O)NC4CCC5(CCCN5)CC4)CC34CC4)n[nH]2)c(F)cn1]

Step-1. (S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide

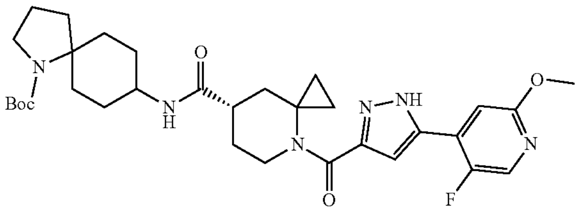 [SMILES: COc1cc(-c2cc(C(=O)N3CC[C@H](C(=O)NC4CCC5(CCCN5C(=O)OC(C)(C)C)CC4)CC34CC4)n[nH]2)c(F)cn1]

EDCI (56.5 mg, 0.30 mmol), HOBt (39.8 mg, 0.30 mmol), and tert-butyl 8-amino-1-azaspiro[4.5]decane-1-carboxylate (50.0 mg, 0.20 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 81.0 mg, 0.22 mmol) and DIPEA (127.0 mg, 0.98 mmol) in DMF (2.00 mL). The resulting solution was stirred at 25 for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DMC/MeOH (10/1 v/v) to obtain the title compound (100.0 mg) as a solid. LCMS (ESI): 611.3 $[M+H]^+$.

Step-2. (S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide

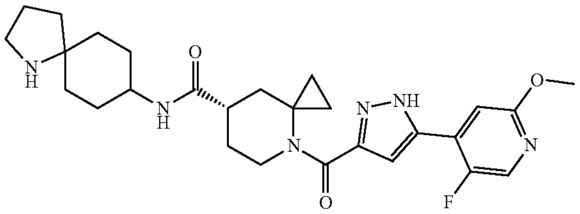 [SMILES: COc1cc(-c2cc(C(=O)N3CC[C@H](C(=O)NC4CCC5(CCCN5)CC4)CC34CC4)n[nH]2)c(F)cn1]

TFA (3.00 mL) was added to a stirred mixture of (S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide (Step-1. 100.0 mg, 0.16 mmol) in DCM (3.00 mL) at 0° C. The resulting mixture was stirred at 25° C. for 2 h. The resulting mixture was concentrated under reduced pressure. The residue was purified by silica gel column chromatography eluting with DCM/MeOH (10/1 v/v) to obtain the title compound (50.0 mg) as a solid. $^1H$ NMR (400 MHz, $CD_3OD$) δ 8.11 (d, 1H), 7.27 (d, 1H), 7.09 (s, 1H), 4.57-4.53 (m, 1H), 3.92 (s, 3H), 3.67-3.61 (m, 1H), 2.96-2.87 (m, 2H), 2.78-2.73 (m, 1H), 2.44-2.39 (m, 1H), 1.91-1.61 (m, 10H), 1.56-1.44 (m, 2H), 1.40-1.17 (m, 3H), 0.96-0.91 (m, 2H), 0.73-0.69 (m, 2H). LCMS (ESI): 511.5 $[M+H]^+$.

Example 349. (S)-4-(5-(5-fluoro-2-methoxypyridin-4-yl)-1H-pyrazole-3-carbonyl)-N-(1-(oxetan-3-yl)-1-azaspiro[4.5]decan-8-yl)-4-azaspiro[2.5]octane-7-carboxamide

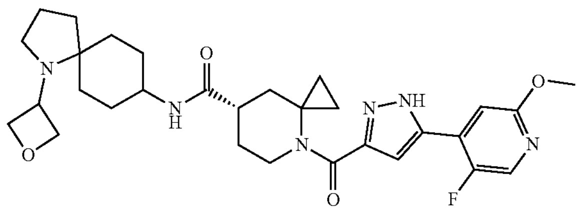 [SMILES: COc1cc(-c2cc(C(=O)N3CC[C@H](C(=O)NC4CCC5(CCCN5C5COC5)CC4)CC34CC4)n[nH]2)c(F)cn1]

3-oxetanone (35.3 mg, 0.49 mmol) and molecular sieves (4 Å) (50.0 mg) were added to a stirred mixture of (S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide (Example 348, 50.0 mg, 0.10 mmol) in MeOH (4.00 mL) and AcOH (0.10 mL). The resulting mixture was stirred at 80° C. for 1 h. $NaBH_3CN$ (18.5 mg, 0.29 mmol) was added to the reaction mixture at 25° C. The resulting mixture was stirred at 80° C. for 14 h. The resulting mixture was concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 50 B in 20 min; 220/254 nm) to obtain the title compound (2.2 mg) as a solid. $^1H$ NMR (300 MHz, $CD_3OD$) δ 8.13 (d, 1H), 7.29 (s, 1H), 7.11 (d, 1H), 4.88-4.78 (m, 2H), 4.73-4.63 (m, 2H), 4.61-4.55 (m, 1H), 4.45-4.30 (m, 1H), 3.95 (s, 3H), 3.61-3.55 (m, 1H), 3.11-3.01 (m, 2H), 2.79-2.73 (m, 1H), 2.43-2.37 (m, 1H), 2.01-1.93 (m, 1H), 1.90-1.79 (m, 7H), 1.54-1.18 (m, 9H), 1.10-0.84 (m, 1H), 0.76-0.70 (m, 2H). LCMS (ESI): 567.25 $[M+H]^+$.

Example 350. (S)—N-((1r,4S)-4-(2-aminoethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

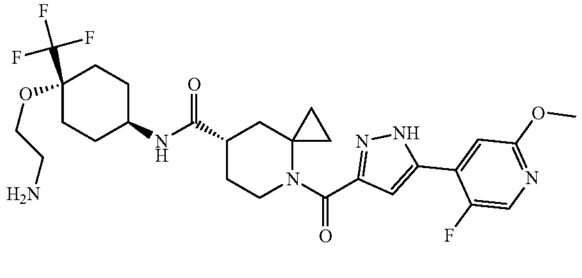 [SMILES: COc1cc(-c2cc(C(=O)N3CC[C@H](C(=O)N[C@H]4CC[C@@](OCCN)(C(F)(F)F)CC4)CC34CC4)n[nH]2)c(F)cn1]

Step-1. (tert-butoxycarbamoyl)(2-(1r,4r)-41-(dibenzylamino)-1-(trifluoromethyl)cyclohexyl)oxy)ethyl) sulfamic acid

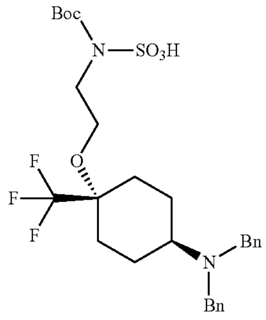 [SMILES: CC(C)(C)OC(=O)N(CCO[C@]1(C(F)(F)F)CC[C@@H](N(Cc2ccccc2)Cc2ccccc2)CC1)S(=O)(=O)O]

NaH (20.0 mg, 0.82 mmol) was added to a stirred mixture of (1r,4r)-4-(dibenzylamino)-1-(trifluoromethyl)cyclohexan-1-ol (200.0 mg, 0.55 mmol) in DMF (3.00 mL) at 0° C. The resulting mixture was stirred at 25° C. for 30 min. Then tert-butyl 1,2,3-oxathiazolidine-3-carboxylate 2,2-dioxide (184.0 mg, 0.82 mmol) was added to the reaction mixture. The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 13/1 v/v) to obtain the title compound (250.0 mg) as a solid. LCMS (ESI): $[M+H]^+$: 587.2.

Step-2. tert-butyl (2-0(1r,4r)-4-(dibenzylamino)-1-(trifluoromethyl)cyclohexyl)oxy)ethyl)carbamate

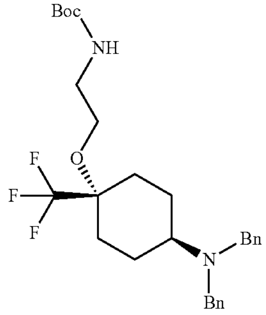 [SMILES: CC(C)(C)OC(=O)NCCO[C@]1(C(F)(F)F)CC[C@@H](N(Cc2ccccc2)Cc2ccccc2)CC1]

Sulfuric acid (0.40 mL) was added to a solution of (tert-butoxycarbonyl)(2-4(1r,4r)-4-(dibenzylamino)-1-(trifluoromethyl)cyclohexyl)oxy)ethyl)sulfamic acid (Step-1, 250.0 mg, 0.42 mmol) in $H_2O$ (2.00 mL) and DCM (2.00 mL) at 0° C. The resulting mixture was stirred at 25° C. for 14 h. The mixture was neutralized to pH 7 with saturated aqueous $NaHCO_3$. The aqueous layer was extracted with DCM. The organic layers were combined, dried over anhydrous $Na_2SO_4$, filtered, and concentrated under reduced pressure. The residue was purified by silica gel column chromatography eluting with petroleum ether/EtOAc (5/1 v/v) to obtain the title compound (200.0 mg) as a solid. LCMS (ESI): $[M+H]^+$: 507.3.

Step-3. tert-butyl (2-4(1r,4r)-4-amino-1-(trifluoromethyl)cyclohexyl)oxy)ethyl)carbamate

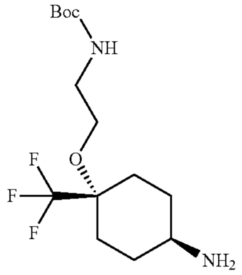 [SMILES: CC(C)(C)OC(=O)NCCO[C@]1(C(F)(F)F)CC[C@@H](N)CC1]

A solution of tert-butyl (2-(((1r,4r)-4-(dibenzylamino)-1-(trifluoromethyl)cyclohexyl)oxy)ethyl)carbamate (Step-2, 180.0 mg, 0.35 mmol) and Pd/C (60.0 mg) in MeOH (3.00 mL) was stirred at 25° C. for 14 h under a $H_2$ atmosphere. The solids were filtered out. The resulting filtrate was concentrated under vacuum to obtain the title compound (127.0 mg) as a solid. LCMS (ESI): $[M+H]^+$: 327.2.

Step-4. tert-butyl (2-(((1S,4r)-4-((S)-4-(5-(5-fluoro-2-methoxypyridin-4-yl)-1H-pyrazole-3-carbonyl)-4-azaspiro[2.5]octane-7-carboxamido)-1-(trifluoromethyl)cyclohexyl)oxy)ethyl)carbamate

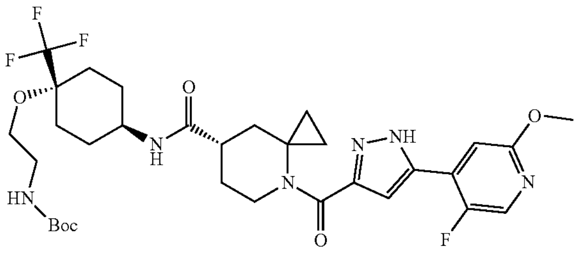 [SMILES: COc1cc(-c2cc(C(=O)N3CC[C@H](C(=O)N[C@H]4CC[C@@](OCCNC(=O)OC(C)(C)C)(C(F)(F)F)CC4)CC34CC4)n[nH]2)c(F)cn1]

EDCI (62.0 mg, 0.32 mmol) and HOBt (43.0 mg, 0.32 mmol), and tert-butyl (2-4(1r,4r)-4-amino-1-(trifluoromethyl)cyclohexyl)oxy)ethyl)carbamate (Step-3, 70.0 mg, 0.21 mmol) were added to a solution of (S)-4-[5-(5-fluoro-2-methoxypyridin-4-yl)-1H-pyrazole-3-carbonyl]-4-azaspiro[2,5]octane-7-carboxylic acid (INTERMEDIATE 527-A, 80.0 mg, 0.21 mmol) and DIPEA (83.0 mg, 0.64 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 2/1 v/v) to obtain the title compound (100.0 mg) as a solid. LCMS (ESI): 683.3 $[M+H]^+$.

Step-5. (S)—N-((1r,4S)-4-(2-aminoethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

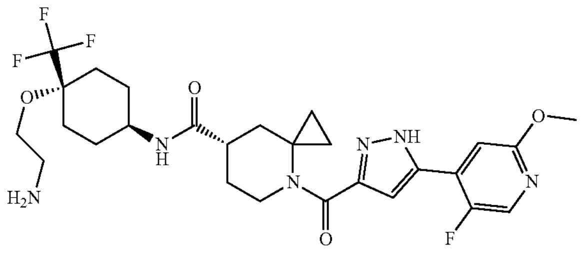 [SMILES: COc1cc(-c2cc(C(=O)N3CC[C@H](C(=O)N[C@H]4CC[C@@](OCCN)(C(F)(F)F)CC4)CC34CC4)n[nH]2)c(F)cn1]

HCl (1.00 mL, 4 M in 1,4-dioxane) was added to a solution of tert-butyl (2-(((1S,4r)-4-((S)-4-(5-(5-fluoro-2-methoxypyridin-4-yl)-1H-pyrazole-3-carbonyl)-4-azaspiro[2.5]octane-7-carboxamido)-1-(trifluoromethyl)cyclohexyl)oxy)ethyl)carbamate (Step-4, 100.0 mg, 0.14 mmol) in 1,4-dioxane (1.00 mL). The resulting mixture was stirred at 25° C. for 1 h. The resulting mixture was concentrated under vacuum. The residue was purified by reverse phase column chromatography (using the following conditions: Column: C18; mobile phase A: Water (0.5% $NH_4HCO_3$), mobile phase B: MeCN; gradient: 10 B to 40 B in 30 min; 220/254 nm) to obtain the title compound (29.3 mg) as a solid. $^1H$ NMR (400 MHz, DMSO-$d_6$) δ 8.25 (d, 1H), 7.85 (d, 1H), 7.30 (d, 1H), 7.01 (d, 1H), 4.44-4.39 (m, 1H), 3.88-3.83 (m, 4H), 3.48-3.43 (m, 2H), 2.85-2.65 (m, 2H), 2.38-2.19 (m, 2H), 1.88-1.63 (m, 8H), 1.56-1.49 (m, 3H), 1.24-0.86 (m, 3H), 0.67-0.60 (m, 2H). LCMS (ESI): 583 $[M+H]^+$.

Example 351. (S)—N-(1-(2,2-difluoropropyl)-1-azaspiro[4.5]decan-8-yl)-4-(5-(5-fluoro-2-methoxypyridin-4-yl)-1H-pyrazole-3-carbonyl)-41-azaspiro[2.5]octane-7-carboxamide

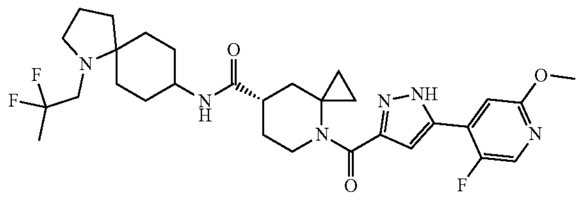 [SMILES: COc1cc(-c2cc(C(=O)N3CC[C@H](C(=O)NC4CCC5(CCCN5CC(C)(F)F)CC4)CC34CC4)n[nH]2)c(F)cn1]

Step-1. tert-butyl 8-(dibenzylamino)-1-azaspiro[4.5]decane-1-carboxylate

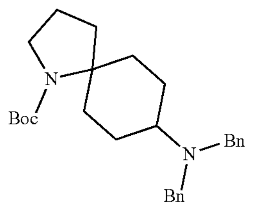 [SMILES: CC(C)(C)OC(=O)N1CCCC12CCC(N(Cc1ccccc1)Cc1ccccc1)CC2]

$K_2CO_3$ (543.3 mg, 3.93 mmol) was added to a stirred mixture of tert-butyl 8-amino-1-azaspiro[4.5]decane-1-carboxylate (500.0 mg, 1.97 mmol) and benzyl bromide (1.01 g, 5.90 mmol) in MeCN (6.00 mL). The resulting mixture was stirred at 25° C. for 14 h. The resulting mixture was concentrated under reduced pressure. The residue was purified by silica gel column chromatography eluting with petroleum ether/EtOAc (15/1 v/v) to obtain the title compound (650.0 mg) as a solid. LCMS (ESI): 435.3 $[M+H]^+$.

Step-2. N,N-dibenzyl-1-azaspiro[4.5]decan-8-amine

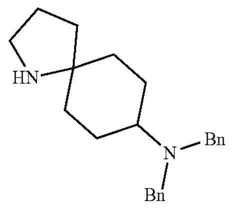 [SMILES: c1ccc(CN(Cc2ccccc2)C2CCC3(CCCN3)CC2)cc1]

TFA (2.00 mL) was added to a stirred mixture of tert-butyl 8-(dibenzylamino)-1-azaspiro[4.5]decane-1-carboxylate (Step-1, 650.0 mg, 1.50 mmol) in DCM (2.00 mL). The resulting mixture was stirred at 25° C. for 2 h. The resulting mixture was concentrated under reduced pressure. The residue was purified by silica gel column chromatography eluting with DCM/MeOH (6/1 v/v) to obtain the title compound (420.0 mg) as an oil. LCMS (ESI): 335.2 $[M+H]^+$.

Step-3. 1-[8-(dibenzylamino)-1-azaspiro[4.5]decan-1-yl]propan-2-one

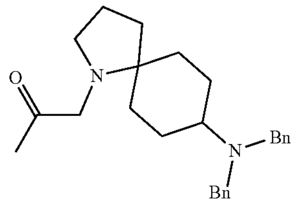 [SMILES: CC(=O)CN1CCCC12CCC(N(Cc1ccccc1)Cc1ccccc1)CC2]

$Cs_2CO_3$ (584.4 mg, 1.79 mmol) was added to a stirred mixture of N,N-dibenzyl-1-azaspiro[4.5]decan-8-amine (Step-2, 400.0 mg, 1.20 mmol) and bromoacetone (327.6 mg, 2.39 mmol) in MeCN (5.00 mL) at 0° C. The resulting mixture was stirred at 25° C., for 1 h. The resulting mixture was concentrated under reduced pressure. The residue was purified by silica gel column chromatography eluting with DCM/MeOH (13/1 v/v) to obtain the title compound (350.0 mg) as a solid. LCMS (ESI): 391.2 $[M+H]^+$.

Step-4. N,N-dibenzyl-1-(2,2-difluoropropyl)-1-azaspiro[4.5]decan-8-amine

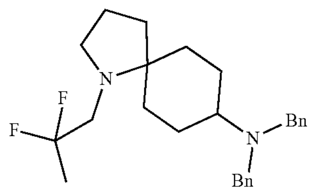 [SMILES: CC(F)(F)CN1CCCC12CCC(N(Cc1ccccc1)Cc1ccccc1)CC2]

DAST (350.8 mg, 2.18 mmol) was added to a stirred solution of 1-[8-(dibenzylamino)-1-azaspiro[4.5]decan-1-yl]propan-2-one (Step-3, 170.0 mg, 0.44 mmol) in DCM (2.00 mL) at 0° C. The resulting mixture was stirred at 25° C. for 14 h. The reaction mixture was quenched with saturated aqueous $NaHCO_3$. The aqueous layer was extracted with EtOAc. The organic layers were combined, dried over anhydrous $Na_7SO_4$, filtered, and concentrated under reduced pressure. The residue was purified by Prep-TLC (petroleum ether/EtOAc, 5/1 v/v) to obtain the title compound (28.0 mg) as a solid. LCMS (ESI): 413.2 $[M+H]^+$.

Step-5. 1-(2,2-difluoropropyl)-1-azaspiro[4.5]decan-8-amine

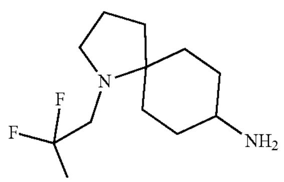 [SMILES: CC(F)(F)CN1CCCC12CCC(N)CC2]

Pd/C (9.0 mg) was added to a stirred mixture of N,N-dibenzyl-1-(2-difluoropropyl)-1-azaspiro[4.5]decan-8-amine (Step-4, 30.0 mg, 0.07 mmol) in MeOH (2.00 mL) at 0° C. The resulting mixture was stirred at 25° C. for 14 h under a $H_2$ atmosphere. The resulting mixture was filtered, the filter cake was washed with MeOH. The filtrate was concentrated under reduced pressure to obtain the title compound (15.0 mg) as a solid. LCMS (ESI): 233.1 $[M+H]^+$.

Step-6. (S)—N-(1-(2,2-difluoropropyl)-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide

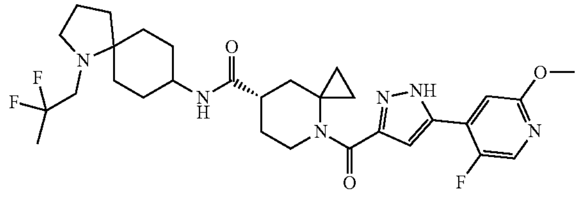 [SMILES: COc1cc(-c2cc(C(=O)N3CC[C@H](C(=O)NC4CCC5(CCCN5CC(C)(F)F)CC4)CC34CC4)n[nH]2)c(F)cn1]

EDCI (24.8 mg, 0.13 mmol), HOBt (17.5 mg, 0.13 mmol), and 1-(2,2-difluoropropyl)-1-azaspiro[4.5]decan-8-amine (15.0 mg, 0.07 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 29.0 mg, 0.08 mmol) and DIPEA (41.7 mg, 0.34 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-SFC (using the following conditions: Column: YMC-Actus Triart Diol-HILIC, 3×25 cm, 5 μm; Mobile Phase A: $CO_2$, Mobile Phase B: IPA (0.5% 2M $NH_3$·MeOH); Flow rate: 60 mL/min; Gradient: isocratic 30% B; Wavelength: 254 nm; RT1 (min): 9.12; Sample Solvent: MeOH, Injection Volume: 2 mL; Number Of Runs: 4) to obtain the title compound (0.9 mg) as a solid. LCMS (ESI): 589.6 [M+H]'.

Example 352. (S)—N-((1548)-4-((S)-2-amino-propoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

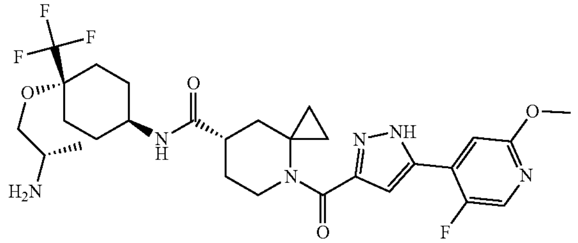 [SMILES: COc1cc(-c2cc(C(=O)N3CC[C@H](C(=O)N[C@H]4CC[C@@](OC[C@H](C)N)(C(F)(F)F)CC4)CC34CC4)n[nH]2)c(F)cn1]

The title compound was prepared using a procedure similar to the one described for the synthesis of Example 350, except tert-butyl (S)-4-methyl-1,2,3-oxathiazolidine-3-carboxylate 2,2-dioxide was used as starting material in Step-1. The resulting residue was purified by reverse phase column chromatography (using the following conditions: Column: C18; mobile phase A: Water (0.5% $NH_4HCO_3$), mobile phase B: MeCN; gradient: 20 B to 40 B in 20 min; 220/254 nm) to obtain the title compound (61.9 mg) as a solid. $^1H$ NMR (400 MHz, DMSO-$d_6$) δ 8.25 (d, 1H), 7.87 (d, 1H), 7.30 (d, 1H), 7.01 (d, 1H), 4.47-4.42 (m, 1H), 3.85 (s, 3H), 3.86-3.80 (m, 1H), 3.26-3.20 (m, 2H), 2.95-2.68 (m, 2H), 2.53-2.49 (m, 1H), 2.23-2.19 (m, 1H), 1.86-1.61 (m, 7H), 1.57-1.41 (m, 3H), 1.28-0.74 (m, 7H), 0.66-0.58 (m, 2H). LCMS (ESE): 597.25 $[M+H]^+$.

Example 353. (S)-4-(5-(5-fluoro-2-methoxypyridin-4-yl)-1H-pyrazole-3-carbonyl)-N-((1S,4S)-4-((S)-2-hydroxypropoxy)-4-(trifluoromethyl)cyclohexyl)-4-azaspiro[2.5]octane-7-carboxamide

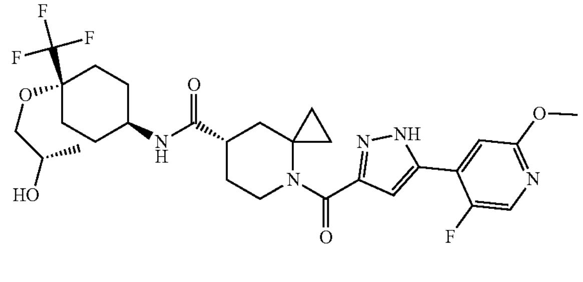 [SMILES: COc1cc(-c2cc(C(=O)N3CC[C@H](C(=O)N[C@H]4CC[C@@](OC[C@H](C)O)(C(F)(F)F)CC4)CC34CC4)n[nH]2)c(F)cn1]

Step-1. [(2S)-1-[[(1r,4r)-4-(dibenzylamino)-1-(trifluoromethyl)cyclohexyl]oxy]propan-2-yl]oxysulfonic acid

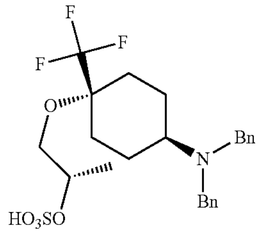

NaH (49.5 mg, 1.24 mmol, 60% dispersion in mineral oil) was added to a stirred mixture of (1r,4r)-4-(dibenzylamino)-1-(trifluoromethyl)cyclohexan-1-ol (300.0 mg, 0.83 mmol) in DMF (4.00 mL) at 0° C. The resulting mixture was stirred at 25° C. for 30 min. Then (S)-4-methyl-1,3,2-dioxathiolane 2,2-dioxide (171.1 mg, 1.24 mmol) was added to the reaction mixture. The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure to obtain the title compound (500.0 mg) as an oil. LCMS (EST): 502.2 $[M+H]^+$.

Step-2. [(2S)-1-[[(1r,4r)-4-(dibenzylamino)-1-(trifluoromethyl)cyclohexyl]oxy]propan-2-yl]oxysulfonic acid

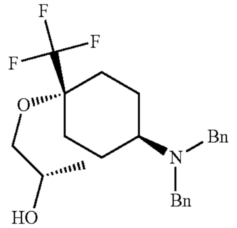 [SMILES: C[C@H](O)CO[C@]1(C(F)(F)F)CC[C@@H](N(Cc2ccccc2)Cc2ccccc2)CC1]

HCl (4.00 mL, 4 M in 1,4-dioxane) was added to a stirred mixture of [(2S)-1-[[(1r,4r)-4-(dibenzylamino)-1-(trifluoromethyl)cyclohexyl]oxy]propan-2-yl]oxysulfonic acid (Step-1, 475.0 mg, 0.95 mmol) in THF (4.00 mL) at 0° C. The resulting mixture was stirred at 25° C. for 14 h. The reaction mixture was neutralized to pH 7 with saturated aqueous $NaHCO_3$. The aqueous layer was extracted with EtOAc. The organic layers were combined, dried over anhydrous $Na_2SO_4$, filtered, and concentrated under reduced pressure. The residue was purified by silica gel column chromatography eluting with petroleum ether/EtOAc (4/1 v/v) to obtain the title compound (280.0 mg) as a solid. LCMS (ESI): 422.2 $[M+H]^+$.

Step-3. (2S)-1-[[(1r,4r)-4-amino-1-(trifluoromethyl)cyclohexyl]oxy]propan-2-ol

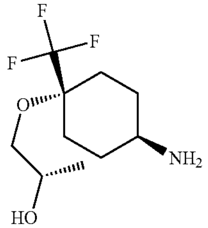 [SMILES: C[C@H](O)CO[C@]1(C(F)(F)F)CC[C@@H](N)CC1]

Pd/C (81.1 mg) was added to a stirred mixture of (28)-1-[[(1r,4r)-4-(dibenzylamino)-1-(trifluoromethyl)cyclohexyl]oxy]propan-2-ol (Step-2, 270.0 mg, 0.64 mmol) in MeOH (6.00 mL) at 0° C. The resulting mixture was stirred at 25° C. for 14 h under a $H_2$ atmosphere. The resulting mixture was filtered, the filter cake was washed with MeOH. The filtrate was concentrated under reduced pressure to obtain the title compound (180.0 mg) as an oil. LCMS (ESI): 242.1 $[M+H]^+$.

Step-4. (S)-4-(5-(5-fluoro-2-methoxypyridin-4-yl)-1H-pyrazole-3-carbonyl)-N-((1S,4S)-4-((S)-2-hydroxypropoxy)-4-(trifluoromethyl)cyclohexyl)-4-azaspiro[2.5]octane-7-carboxamide

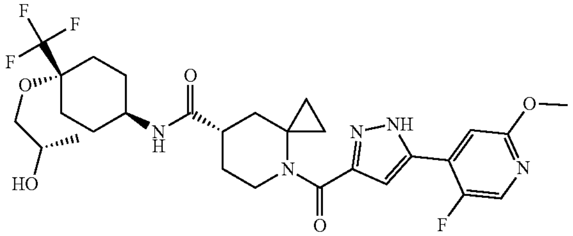 [SMILES: COc1cc(-c2cc(C(=O)N3CC[C@H](C(=O)N[C@H]4CC[C@@](OC[C@H](C)O)(C(F)(F)F)CC4)CC34CC4)n[nH]2)c(F)cn1]

HOBt (93.8 mg, 0.69 mmol), EDCI (133.1 mg, 0.69 mmol), and (2S)-1-[[(1r,4r)-4-amino-1-(trifluoromethyl)cyclohexyl]oxy]propan-2-ol (108.9 mg, 0.45 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 130.0 mg, 0.35 mmol) and DIPEA (224.4 mg, 1.74 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 40 B in 20 min; 220/254 nm) to obtain the title compound (83.7 mg) as a solid. $^1$H NMR (400 MHz, DMSO-$d_6$) δ 14.02 (s, 1H), 8.24 (s, 1H), 7.86 (s, 1H), 7.30 (d, 1H), 7.01 (s, 1H), 4.68-4.37 (m, 2H), 3.85 (s, 3H), 3.84-3.80 (m, 1H), 3.73-3.63 (m, 1H), 3.41-3.33 (m, 1H), 3.26-3.18 (m, 2H), 2.79-2.75 (m, 1H), 2.19-2.14 (m, 1H), 1.91-1.37 (m, 10H), 1.29-0.80 (m, 6H), 0.74-0.45 (m, 2H). LCMS (ESI): 598 $[M+H]^+$.

Example 354. (7S)—N-(8-oxabicyclo[3.2.1]octan-3-yl)-4-(5-(5-fluoro-2-methoxypyridin-4-yl)-1H-pyrazole-3-carbonyl)-4-azaspiro[2.5]octane-7-carboxamide

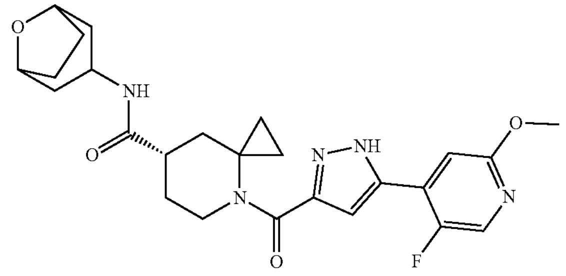 [SMILES: COc1cc(-c2cc(C(=O)N3CC[C@H](C(=O)NC4CC5CCC(C4)O5)CC34CC4)n[nH]2)c(F)cn1]

The title compound was prepared using a procedure similar to the one described for the synthesis of Example 325, except 8-oxabicyclo[3.2.1]octan-3-amine hydrochloride was used as a starting material. The resulting residue was purified by reverse phase column chromatography (using the following conditions: Column: C18; mobile phase A: Water (0.5% $NH_4HCO_3$), mobile phase B: MeCN; gradient: 20 B to 40 B in 20 min; 220/254 nm) to obtain the title compound (23.6 mg) as a solid. $^1$H NMR (400 MHz, DMSO-$d_6$) δ 8.31-8.21 (m, 1H), 7.59 (s, 1H), 7.30 (d, 1H), 7.04-6.98 (m, 1H), 4.49-4.44 (m, 1H), 4.19 (s, 2H), 3.85 (s, 3H), 3.74-3.68 (m, 1H), 2.78-2.74 (m, 1H), 2.19-2.15 (m, 1H), 2.03-1.85 (m, 4H), 1.82-1.66 (m, 3H), 1.62-1.37 (m, 3H), 1.25-1.03 (m, 2H), 0.96-0.92 (m, 2H), 0.64-0.60 (m, 2H). LCMS (ESI): 484 $[M+H]^+$.

Example 355. A Diastereomeric Mixture of (S)—N-((1S,3R)-3-(3,3-difluoropyrrolidin-1-yl)-2,2-dimethylcyclobutyl)-4-(5-(5-fluoro-2-methoxypyridin-, 1-yl)-1H-pyrazole-3-carbonyl)-4-azaspiro[2.5]octane-7-carboxamide and (S)—N-((1S,3S)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide

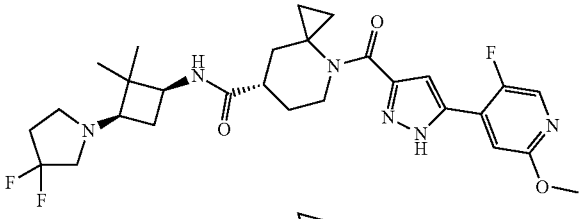

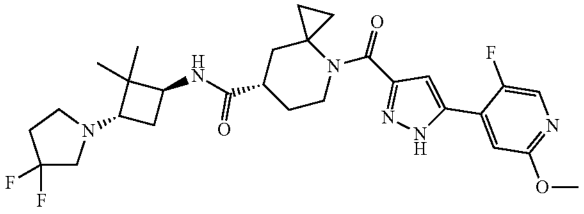

Step-1. tert-butyl N-[3-(3,3-difluoropyrrolidin-1-yl)-2,2-dimethylcyclobutyl]carbamat

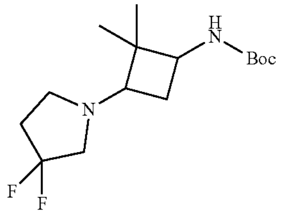 [SMILES: CC(C)(C)OC(=O)NC1CC(N2CCC(F)(F)C2)C1(C)C]

AcOH (0.06 mL) and tert-butyl N-(2,2-dimethyl-3-oxocyclobutyl)carbamate (497.7 mg, 2.33 mmol) was added to a stirred mixture of 3,3-difluoropyrrolidine hydrochloride (335.0 mg, 2.33 mmol) in DCE (6.00 mL). The resulting solution was stirred at 25° C. for 1 h, then sodium triacetoxyborohydride (989.1 mg, 4.67 mmol) was added to the reaction mixture. The resulting mixture was stirred at 25° C. for 14 h. The resulting mixture was concentrated under reduced pressure. The residue was purified by silica gel column chromatography eluting with petroleum ether/EtOAc (5/1 v/v) to obtain the title compound (700.0 mg) as an oil. LCMS (ESI): 305.2

Step-2. 3-(3,3-difluoropyrrolidin-1-yl)-2,2-dimethylcyclobutan-1-amine

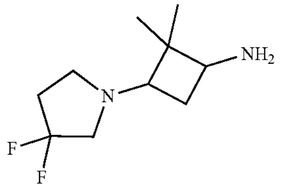

TFA (2.00 mL) was added to a stirred mixture of tert-butyl N-[3-(3,3-difluoropyrrolidin-1-yl)-2,2-dimethylcyclobutyl] carbamate (Step-1, 650.0 mg, 2.14 mmol) in DCM (2.00 mL). The resulting mixture was stirred at 25° C. for 2 h. The resulting mixture was concentrated under reduced pressure to obtain the title compound (350.0 mg) as an oil. LCMS (ESI): 205.1 $[M+H]^+$.

Step-3. (S)—N-((1S,3R)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide and (S)—N-((1S,3S)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide

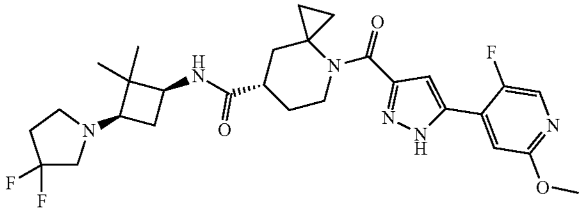

-continued

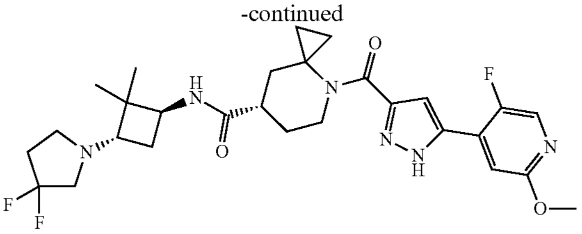

EDCI (153.5 mg, 0.80 mmol), HOBt (108.2 mg, 0.80 mmol), and 3-(3,3-difluoropyrrolidin-1-yl)-2,2-dimethylcyclobutan-1-amine (163.6 mg, 0.80 mmol) were added to a stirred mixture of (S)-4-[5-(5-fluoro-2-methoxypyridin-4-yl)-1H-pyrazole-3-carbonyl]-4-azaspiro[2,5]octane-7-carboxylic acid (INTERMEDIATE 527-A, 149.9 mg, 0.40 mmol) and DIPEA (517.6 mg, 4.01 mmol) in DMF (4.00 mL). The resulting solution was stirred at 25° C. for 14 h. The organic layers were combined, dried over anhydrous $Na_2SO_4$, filtered, and concentrated under reduced pressure. The residue was purified by silica gel column chromatography eluting with DCM/MeOH (9/1 v/v) to obtain (S)—N-((1S,3R)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide and (S)—N-((1S,3S)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide (100 mg) as a solid mixture of diastereomers. LCMS (ESI): 561.3 $[M+H]^+$.

This mixture of two diastereomers (100.0 mg) was separated using Chiral Prep-HPLC.

Column: XSelect CSH Prep C18 OBD column

Column dimension: 19×250 mm, 5 μm

Mobile Phase: water (10 mM $NH_4HCO_3$+0.1% $NH_3 \cdot H_2O$):MeCN=56:44 to 40:60 for 10 min Flow rate: 25 mL/min Detection: 220/254 nm Example 355-A. The first eluting diastereomer (5.1 mg) was obtained as a solid.

The first eluting diastereomer had a retention time of 6.90 min.

$^1$H NMR (400 MHz, DMSO-$d_6$) δ 13.97 (d, 1H), 8.37-8.14 (m, 1H), 8.04-7.58 (m, 1H), 7.34-7.26 (m, 1H), 7.02 (s, 1H), 4.53-4.48 (m, 1H), 3.85 (s, 3H), 3.75-3.53 (m, 1H), 2.82-2.71 (m, 2H), 2.71-2.56 (m, 2H), 2.24-2.02 (m, 5H), 1.86-1.38 (m, 3H), 1.31-0.91 (m, 6H), 0.88-0.77 (m, 4H), 0.68-0.44 (m, 3H). LCMS (ESI): 561.55 $[M+H]^+$.

Example 355-B. The second eluting diastereomer (20.8 mg) was obtained as a solid.

The second eluting diastereomer had a retention time of 7.42 min.

$^1$H NMR (400 MHz, DMSO-$d_6$) δ 13.98 (d, H), 8.25 (d, 1H), 8.05-7.58 (m, 1H), 7.29 (s, 1H), 7.02 (s, 1H), 4.69-4.31 (m, 1H), 3.85 (s, 3H), 3.76-3.53 (m, 1H), 2.88-2.52 (m, 5H), 2.27-1.94 (m, 4H), 1.93-1.34 (m, 4H), 1.34-0.74 (m, 9H), 0.74-0.38 (m, 3H). LCMS (ESI): 561.55 $[M+H]^+$.

Example 356. A Diastereomeric Mixture of (S)-4-(5-(5-fluoro-2-methoxypyridin-4-yl)-1H-pyrazole-3-carbonyl)-N—(((S)-5,6,7,8-tetrahydroimidazo[1,2-a]pyridin-6-yl)methyl)-4-azaspiro[2.5]octane-7-carboxamide and (S)-4-(5-(5-fluoro-2-methoxypyridin-4-yl)-1H-pyrazole-3-carbonyl)-N—(((R)-5,6,7,8-tetrahydroimidazo[1,2-a]pyridin-6-yl)methyl)-4-azaspiro[2.5]octane-7-carboxamide

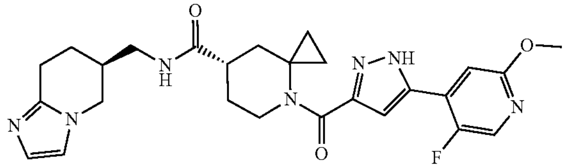

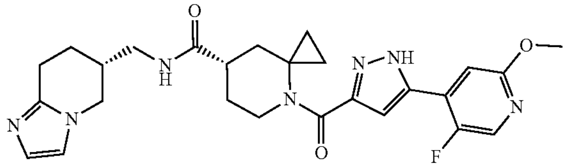

Step-1. N,N-diphenyl-5H,6H,7H,8H-imidazo[1,2-a]pyridine-6-carboxamide

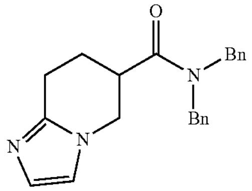 [SMILES: O=C(C1CCc2nccn2C1)N(Cc1ccccc1)Cc1ccccc1]

HATU (1.88 g, 4.94 mmol) and dibenzyl amine (584.1 mg, 2.96 mmol) were added to a stirred mixture of 5H,6H,7H,8H-imidazo[1,2-a]pyridine-6-carboxylic acid hydrochloride (500.0 mg, 2.47 mmol) and DIPEA (1.28 g, 9.87 mmol) in DMF (8.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (1.00 g) as an oil. LCMS (ESI): 346.2 $[M+H]^+$.

Step-2. dibenzyl([5H,6H,7H,8H-imidazo[1,2-a]pyridin-6-ylmethy])amine

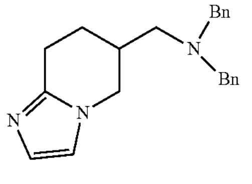 [SMILES: c1ccc(CN(Cc2ccccc2)CC2CCc3nccn3C2)cc1]

$LiAlH_4$ (318.6 mg, 8.40 mmol) was added to a stirred mixture of N,N-dibenzyl-5H,6H,7H,8H-imidazo[1,2-a]pyridine-6-carboxamide (Step-1, 580.0 mg, 1.68 mmol) in THF (10.00 mL) at 0° C. The resulting mixture was stirred at 80° C. for 30 min. The reaction was quenched with MeOH at 0° C. The resulting mixture was concentrated under reduced pressure. The residue was purified by silica gel column chromatography eluting with DCM/MeOH (24/1 v/v) to obtain the title compound (400.0 mg) as an oil. LCMS (ESI): 332.2 [M+H]$^+$.

Step-3. 1-[5H,6H,7H,8H-imidazo[1,2-a]pyridin-6-yl]methanamine

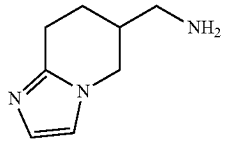 [SMILES: NCC1CCc2nccn2C1]

Pd/C (65.0 mg) was added to a stirred solution of dibenzyl ([5H,6H,7H,8H-imidazo[1,2-a]pyridin-6-ylmethyl])amine (Step-2, 250.0 mg, 0.75 mmol) in MeOH (4.00 mL) at 0° C. The resulting mixture was stirred at 25° C. for 14 h under a $H_7$ atmosphere. The resulting mixture was filtered, the filter cake was washed with MeOH. The filtrate was concentrated under reduced pressure to obtain the title compound (120.0 mg) as an oil. LCMS (ESI): 152.1 [M+H]$^+$.

Step-4. (S)-4-(5-(5-fluoro-2-methoxypyridin-4-yl)-1H-pyrazole-3-carbonyl)-N—(((S)-5,6,7,8-tetrahydroimidazo[1,2-a]pyridin-6-yl)methyl)-4-azaspiro[2.5]octane-7-carboxamide and (S)-4-(5-(5-fluoro-2-methoxypyridin-4-yl)-1H-pyrazole-3-carbonyl)-N—(((R)-5,6,7,8-tetrahydroimidazo[1,2-a]pyridin-6-yl)methyl)-4-azaspiro[2.5]octane-7-carboxamide

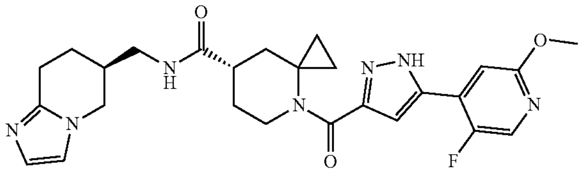

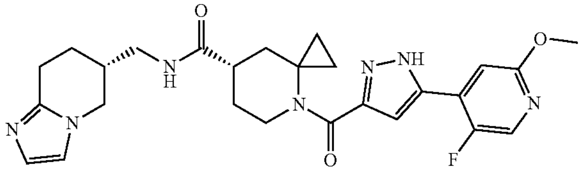

HOBt (108.3 mg, 0.80 mmol), EDCI (153.6 mg, 0.80 mmol), and 1-[5H,6H,7H,8H-imidazo[1,2-a]pyridin-6-yl] methanamine (Step-3, 90.9 mg, 0.60 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 150.0 mg, 0.40 mmol) and DIPEA (258.9 mg, 2.00 mmol) in DMF (5.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 40 B in 20 min; 220/254 nm) to obtain (S)-4-(5-(5-fluoro-2-methoxypyridin-4-yl)-1H-pyrazole-3-carbonyl)-N—(((S)-5,6,7,8-tetrahydroimidazo[1,2-a]pyridin-6-yl)methyl)-4-azaspiro[2,5]octane-7-carboxamide and (S)-4-(5-(5-fluoro-2-methoxypyridin-4-yl)-1H-pyrazole-3-carbonyl)-N—(((R)-5,6,7,8-tetrahydroimidazo[1,2-a]pyridin-6-yl)methyl)-4-azaspiro[2.5]octane-7-carboxamide (70 mg) as a solid mixture of diastereomers (Example 356). $^1$H NMR (400 MHz, $CD_3OD$) δ 8.09 (s, 1H), 7.28 (s, 1H), 7.09 (s, 1H), 6.90 (d, 2H), 4.58 (s, 1H), 4.13-4.04 (m, 1H), 3.91 (s, 3H), 3.67-3.57 (m, 1H), 3.40-3.25 (m, 2H), 3.00-2.63 (m, 3H), 2.46-2.42 (m, 1H), 2.24-2.15 (m, 1H), 2.09-2.00 (m, 1H), 1.97-1.53 (m, 3H), 1.46-1.15 (m, 2H), 1.15-0.78 (m, 2H), 0.78-0.42 (m, 2H). LCMS (ESI): 508 [M+H]$^+$.

This mixture of two diastereomers (70.0 mg) was separated using Chiral Prep-HPLC.

Column: CHIRALPAK IE column

Column dimension: 2×25 cm, 5 μm

Mobile Phase: 3/1 hexanes/DCM (0.5% 2 M $NH_3$·MeOH):EtOH=50:50 hold for 39 min

Flow rate: 17 mL/min

Detection: 220/254 nm

Example 356-A. The first eluting diastereomer (16.3 Tug) was obtained as a solid.

The first eluting diastereomer had a retention time of 23.19 min.

$^1$H NMR (400 MHz, DMSO-$d_6$) δ 8.25 (s, 1H), 8.01 (d, 1H), 7.30 (d, 1H), 7.02 (d, 1H), 6.95 (d, 1H), 6.77 (d, 1H), 4.46-4.42 (m, 1H), 4.03-3.94 (m, 1H), 3.85 (s, 3H), 3.57-3.46 (m, 1H), 3.22-2.99 (m, 2H), 2.86-2.54 (m, 3H), 2.38-1.97 (m, 2H) 1.95-1.84 (m, 1H), 1.78 (m, 1H), 1.58-1.44 (m, 2H), 1.24-1.18 (m, 2H), 1.06-0.69 (m, 2H), 0.65-0.57 (m, 2H). LCMS (ESI): 508.25 [M+H]$^+$.

Example 356-B. The second eluting diastereomer (12.6 mg) was obtained as a solid.

The second eluting diastereomer had a retention time of 32.53 min.

$^1$H NMR (400 MHz, DMSO-$d_6$) δ 8.24 (d, 1H), 7.99 (s, 1H), 7.30 (d, 1H), 7.01 (d, 1H), 6.94 (s, 1H), 6.76 (s, 1H), 4.7-4.43 (m, 1H), 4.03-3.94 (m, 1H), 3.85 (s, 3H), 3.57-3.47 (m, 1H), 3.17-3.05 (m, 2H), 2.87-2.54 (m, 3H), 2.25-2.20 (m, 2H), 1.95-1.85 (m, 1H), 1.78-1.74 (m, 1H), 1.58-1.44 (m, 2H), 1.24-1.18 (m, 2H), 0.93-0.87 (m, 2H), 0.66-0.57 (m, 2H). LCMS (ESI): 508.25 [M+H]$^+$.

Example 357. A Diastereomeric Mixture of (S)-4-(5-(5-fluoro-2-methoxypyridin-4-yl)-1H-pyrazole-3-carbonyl)-N—(((S)-3-(trifluoromethyl)-5,6-dihydro-8H-[1,2,4]triazolo[3,4-c][1,4]oxazin-6-yl)methyl)-4-azaspiro[2.5]octane-7-carboxamide and (S)-4-(5-(5-fluoro-2-methoxypyridin-4-yl)-1H-pyrazole-3-carbonyl)-N—(((R)-3-(trifluoromethyl)-5,6-dihydro-8H-[1,2,4]triazolo[3,4-c][1,4]oxazin-6-yl)methyl)-4-azaspiro[2.5]octane-7-carboxamide

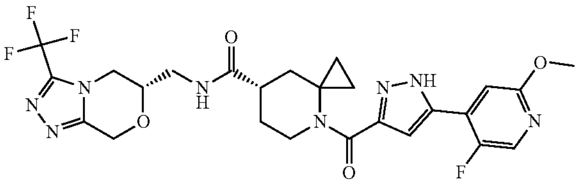

-continued

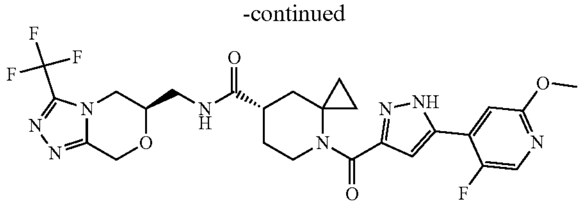

Step-1. 6-((dibenzylamino)methyl)morpholin-3-one

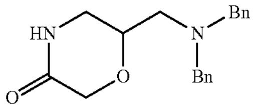 [SMILES: O=C1COC(CN(Cc2ccccc2)Cc2ccccc2)CN1]

A solution of 6-(aminomethyl)morpholin-3-one (1.00 g, 7.68 mmol) and benzyl bromide (2.63 g, 15.36 mmol), $Cs_2CO_3$ (6.26 g, 19.20 mmol) in MeCN (15.00 mL) was stirred at 25° C. for 14 h. The resulting mixture was concentrated under vacuum. The residue was purified by silica gel column chromatography eluting with DCM/MeOH (15/1 v/v) to obtain the title compound (470.0 mg) as a solid. LCMS (ESI): 311.2 $[M+H]^+$.

Step-2. 6-((dibenzylamino)methyl)morpholine-3-thione

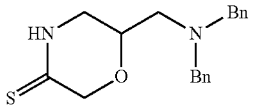 [SMILES: S=C1COC(CN(Cc2ccccc2)Cc2ccccc2)CN1]

A solution of 6-[(dibenzylamino)methyl]morpholin-3-one (Step-1, 450.0 mg, 1.45 mmol) and Lawesson reagent (586.4 mg, 1.45 mmol) in toluene (4.00 mL) was stirred at 110° C. for 5 h. The resulting mixture was concentrated under vacuum. The residue was purified by silica gel column chromatography eluting with DCM/MeOH (20/1 v/v) to obtain the title compound (175.0 mg) as a solid. LCMS (ESI): $[M+H]^+$: 327.1.

Step-3. N,N-dibenzyl-1-(3-(trifluoromethyl)-5,6-dihydro-8H-[1,2,4]triazolo[3,4-c][1,4]oxazin-6-yl) methanamine

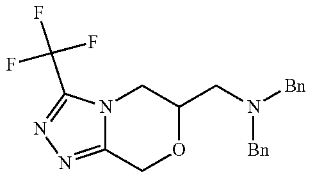 [SMILES: FC(F)(F)c1nnc2n1CC(CN(Cc1ccccc1)Cc1ccccc1)OC2]

A solution of 6-((dibenzylamino)methyl)morpholine-3-thione (Step-2, 75.0 mg, 0.23 mmol) and 2,2,2-trifluoroacetohydrazide (147.1 mg, 1.14 mmol) in xylene (1.00 mL) was stirred at 150° C. for 3 h. The resulting mixture was concentrated under vacuum. The residue was purified by Prep-TLC (DCM/MeOH, 30/1 v/v) to obtain the title compound (50.0 mg) as a solid. LCMS (ESI): $[M+H]^+$: 403.2.

Step-4. (3-(trifluoromethyl)-5,6-dihydro-8H-[1,2,4] triazolo[3,4-c][1,4]oxazin-6-yl)methanamine

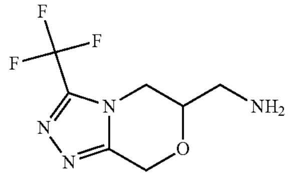 [SMILES: NCC1Cn2c(nnc2C(F)(F)F)CO1]

A solution of N,N-dibenzyl-1-(3-(trifluoromethyl)-5,6-dihydro-8H-[1,2,4]triazolo[3,4-c][1,4]oxazin-6-yl)methanamine (Step-3, 100.0 mg, 0.24 mmol) and Pd/C (100.0 mg) in MeOH (3.00 mL) was stirred at 25° C. for 14 h under a $H_2$ atmosphere. The solids were filtered out. The filtrate was concentrated under reduced pressure to obtain the title compound (55.0 mg) as an oil. LCMS (ESI): 223.1 $[M+H]^+$.

Step-5. (S)-4-(5-(5-fluoro-2-methoxypyridin-4-yl)-1H-pyrazole-3-carbonyl)-N—(((S)-3-(trifluoromethyl)-5,6-dihydro-8H-[1,2,4]triazolo[3,4-c][1,4] oxazin-6-yl)methyl)-4-azaspiro[2.5]octane-7-carboxamide and (S)-4-(5-(5-fluoro-2-methoxypyridin-4-yl)-1H-pyrazole-3-carbonyl)-N—(((R)-3-(trifluoromethyl)-5,6-dihydro-8H-[1,2,4] triazolo[3,4-c][1,4]oxazin-6-yl)methyl)-4-azaspiro [2.5]octane-7-carboxamide

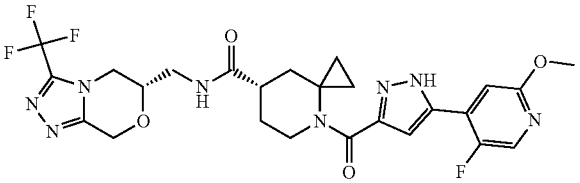

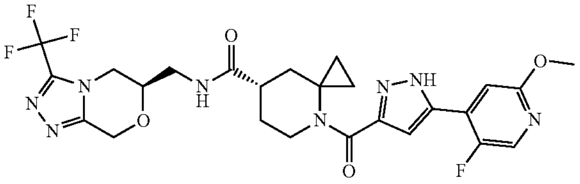

EDCI (64.5 mg, 0.33 mmol), HOBt (45.5 mg, 0.33 mmol), and (3-(trifluoromethyl)-5,6-dihydro-8H-[1,2,4]triazolo[3,4-c][1,4]oxazin-6-yl)methanamine (Step-4, 49.9 mg, 0.22 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 84.0 mg, 0.22 mmol) and DIPEA (145.0 mg, 1.12 mmol) in DMF (1.00 mL). The resulting mixture was stirred at 25° C. for 14 h. The resulting mixture was diluted with water and extracted with EtOAc. The organic layers were combined, dried over anhydrous $Na_2SO_4$, filtered, and concentrated under reduced pressure.

The residue was purified by reverse phase column chromatography (using the following conditions: Column: C18; mobile phase A: Water (0.5% $NH_4HCO_3$), mobile phase B: MeCN; gradient: 20 B to 40 B in 20 min; 220/254 nm) to obtain (S)-4-(5-(5-fluoro-2-methoxypyridin-4-yl)-1H-pyrazole-3-carbonyl)-N—(((S)-3-(trifluoromethyl)-5,6-dihydro-8H-[1,2,4]triazolo[3,4-c][1,4]oxazin-6-yl)methyl)-4-azaspiro[2.5]octane-7-carboxamide and (S)-4-(5-(5-fluoro-2-methoxypyridin-4-yl)-1H-pyrazole-3-carbonyl)-N—(((R)-3-(trifluoromethyl)-5,6-dihydro-8H-[1,2,4]triazolo[3,4-c][1,4]oxazin-6-yl)methyl)-4-azaspiro[2.5]octane-7-carboxamide (6.2 mg) as a solid mixture of diastereomers (Example 357). $^1$H NMR (300 MHz, DMSO-$d_6$) δ 14.23-13.48 (m, 1H), 8.34-8.21 (m, 1H), 8.17 (s, 1H), 7.35-7.27 (m, 1H), 7.04 (s, 1H), 5.25-5.13 (m, 1H), 4.94-4.83 (m, 1H), 4.55-4.49 (m, 1H), 4.30-4.20 (m, 1H), 4.04-3.90 (m, 2H), 3.88 (s, 3H), 3.48-3.34 (m, 3H), 2.21-2.15 (m, 1H) 1.80-1.74 (m, 1H), 1.58-1.52 (m, 1H), 1.36-1.10 (m, 1H), 1.00-0.94 (m, 2H), 0.79-0.55 (m, 3H). LCMS (ESI): 579.0 [M+H]$^+$.

This mixture of two diastereomers (240.0 mg) was separated using Chiral Prep-HPLC.

Column: CHIRALPAK ID column

Column dimension: 2×25 cm, 5 μm

Mobile Phase: MTBE (0.5% 2M $NH_3$·MeOH):1/1 MeOH/DCM=50:50 hold for 22 min

Flow rate: 20 mL/min

Detection: 220/254 nm

Example 357-A. The first eluting diastereomer (84.9 mg) was obtained as a solid.

The first eluting diastereomer had a retention time of 5.78 min.

$^1$H NMR (300 MHz, DMSO-$d_6$) δ 14.21-13.85 (m, 1H), 8.21 (d, 2H), 7.33 (s, 1H), 7.04 (s, 1H), 5.25-5.14 (m, 1H), 4.94-4.83 (m, 1H), 4.55-4.49 (m, 1H), 4.30-4.20 (m, 1H), 4.11-3.82 (m, 5H), 3.49-3.35 (m, 2H), 3.13 (s, 1H), 2.75 (s, 1H), 2.22-2.16 (m, 1H), 1.81-1.75 (m, 1H), 1.58-1.52 (m, 1H), 1.40-1.11 (m, 1H), 1.09-0.81 (m, 2H), 0.70-0.64 (m, 2H). LCMS (ESI): 579.1 [M+H]$^+$.

Example 357-B. The second eluting diastereomer (83.8 mg) was obtained as a solid.

The second eluting diastereomer had a retention time of 14.26 min.

$^1$H NMR (300 MHz, DMSO-$d_6$) δ 13.99 (s, 1H), 8.43-7.89 (m, 2H), 7.32 (d, 1H), 7.03 (s, 1H), 5.25-5.14 (m, 1H), 4.95-4.84 (m, 1H), 4.49-4.43 (m, 1H), 4.30-4.20 (m, 1H), 4.06-3.98 (m, 1H), 3.98-3.90 (m, 1H), 3.88 (s, 3H), 3.48-3.34 (m, 2H), 3.15-3.09 (m, 1H), 2.78-2.72 (m, 1H), 2.22-2.16 (m, 1H), 1.80-1.74 (m, 1H), 1.58-1.52 (m, 1H), 1.27-1.21 (m, 1H), 1.10-0.76 (m, 2H), 0.68-0.62 (m, 2H). LCMS (ESI): 579.1 [M+H]$^+$.

Example 358. (S)—N-((3-chloropyridin-2-yl)methyl)-4-(5-(5-fluoro-2-methoxypyridin-4-yl)-1H-pyrazole-3-carbonyl)-4-azaspiro[2.5]octane-7-carboxamide

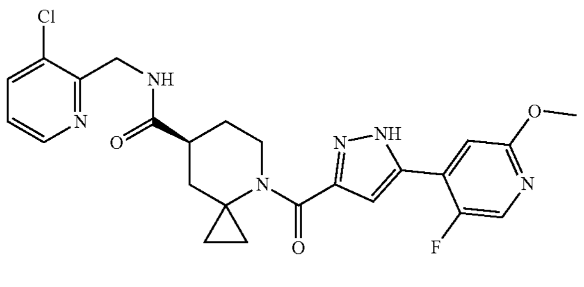 [SMILES: COc1cc(-c2cc(C(=O)N3CC[C@H](C(=O)NCc4ncccc4Cl)CC34CC4)n[nH]2)c(F)cn1]

The title compound was prepared using a procedure similar to the one described for the synthesis of Example 325, except 1-(3-chloropyridin-2-yl)methanamine was used as a starting material. The residue was purified by reverse phase column chromatography (using the following conditions: Column: C18; mobile phase A: Water (0.5% $NH_4HCO_3$), mobile phase B: MeCN; gradient: 20 B to 50 B in 30 min; 220/254 nm) to obtain the title compound (69.7 mg) as a solid. $^1$H NMR (400 MHz, $CD_3OD$) δ 8.54-8.40 (m, 1H), 8.11 (s, 1H), 7.89-7.80 (m, 1H), 7.42-7.01 (m, 3H), 4.60 (s, 3H), 3.92 (s, 3H), 3.36-3.31 (m, 1H), 3.17-2.79 (m, 1H), 2.77-2.25 (m, 1H), 2.21-1.56 (m, 2H), 1.51-1.23 (m, 1H), 1.19-0.93 (m, 1H), 0.88-0.55 (m, 3H). LCMS (ESI): 499 [M+H]$^+$.

Example 359. (S)-4-(5-(5-fluoro-2-methoxypyridin-4-yl)-1H-pyrazole-3-carbonyl)-N-((3-methylpyridin-2-yl)methyl)-4-azaspiro[2.5]octane-7-carboxamide

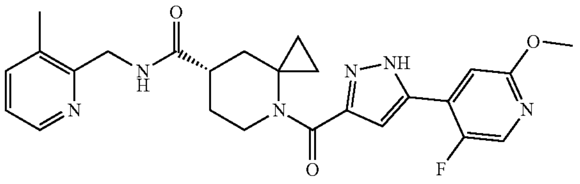 [SMILES: COc1cc(-c2cc(C(=O)N3CC[C@H](C(=O)NCc4ncccc4C)CC34CC4)n[nH]2)c(F)cn1]

The title compound was prepared using a procedure similar to the one described for the synthesis of Example 325, except 1-(3-methylpyridin-2-yl)methanamine was used as a starting material. The residue was purified by reverse phase column chromatography (using the following conditions: Column: C18; mobile phase A: Water (0.5% $NH_4HCO_3$), mobile phase B: MeCN; gradient: 10 B to 30 B in 20 min; 220/254 nm) to obtain the title compound (78.6 mg) as a solid. $^1$H NMR (400 MHz, DMSO-$d_6$) δ 8.36-8.29 (m, 1H), 8.26-8.17 (m, 2H), 7.58-7.51 (m, 1H), 7.30 (d, 1H), 7.23-7.15 (m, 1H), 7.01 (d, 1H), 4.53-4.21 (m, 3H), 3.85 (s, 3H), 3.00-2.96 (m, 1H), 2.82-2.77 (m, 1H), 2.24 (s, 3H), 2.23-2.20 (m, 1H), 1.77-1.73 (m, 1H), 1.57-1.52 (m, 1H), 1.34-1.12 (m, 1H), 1.05-0.47 (m, 4H). LCMS (ESI): 479.4 [M+H]$^+$.

Example 360. A Diastereomeric Mixture of (S)—N—((R)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide and (S)—N—((S)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide

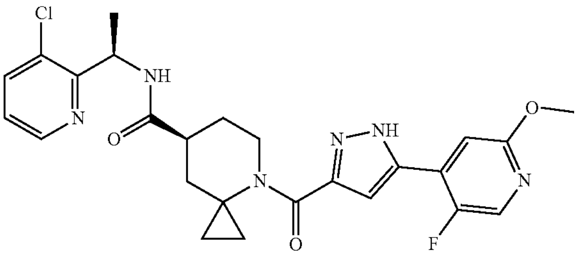

-continued

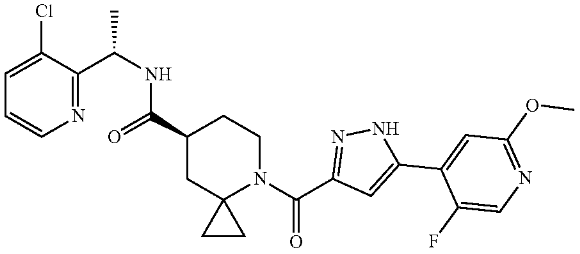

The title compound was prepared using a procedure similar to the one described for the synthesis of Example 325, except 1-(3-chloropyridin-2-yl)ethanamine was used as a starting material. The residue was purified by reverse phase column chromatography (using the following conditions: Column: C18; Mobile Phase A: Water (10 mM $NH_4HCO_3$), Mobile Phase B: MeCN; Flow rate: 40 mL/min; Gradient: 20 B to 40 B in 20 min; Detector, UV 254/220 nm) to obtain (S)—N—((R)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide and (S)—N—((S)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide (157 mg) as a solid mixture of diastereomers (Example 360) $^1$H NMR (300 MHz, DMSO-$d_6$) δ 13.98 (s, 1H), 8.55-8.47 (m, 1H), 8.32-8.22 (m, 2H), 7.93-7.84 (m, 1H), 7.39-7.27 (m, 2H), 7.01 (s, 1H), 5.40-5.29 (m, 1H), 4.49-4.43 (m, 1H), 3.87 (s, 3H), 2.82-2.76 (m, 2H), 2.15-2.09 (m, 1H), 1.77-1.71 (m, 1H), 1.54-1.48 (m, 1H), 1.36-1.27 (m, 3H), 1.26-1.20 (m, 1H), 0.97-0.91 (m, 2H), 0.66-0.60 (m, 2H). LCMS (ESI): 513.3; [M+H]$^+$.

This mixture of two diastereomers (157.0 mg) was separated using Chiral Prep-HPLC.

Column: CHIRALPAK IG column

Column dimension: 2×25 cm, 5 μm

Mobile Phase: 3/1 hexanes/DCM (0.5% 2 M $NH_3$·MeOH):EtOH=50:50 hold for 30 min

Flow rate: 17 mL/min

Detection: 220/254 nm

Example 360-A. The first eluting diastereomer (41.7 mg) was obtained as a solid.

The first eluting diastereomer had a retention time of 13.32 min.

$^1$H NMR (400 MHz, DMSO-$d_6$) δ 13.98 (s, 1H), 8.55-8.49 (m, 1H), 8.35-8.29 (m, 1H), 8.27 (s, 1H), 7.93-7.87 (m, 1H), 7.39-7.29 (m, 2H), 7.01 (s, 1H), 5.35 (q, 1H), 4.48 (s, 1H), 3.87 (s, 3H), 3.28-2.78 (m, 2H), 2.27-1.94 (m, 1H), 1.93-1.66 (m, 1H), 1.56-1.52 (m, 1H), 1.36-1.30 (m, 3H), 1.20-1.15 (m, 1H), 0.97-0.92 (m, 2H), 0.66-0.62 (m, 2H). LCMS (ESI): 513.40 [M+H]$^+$.

Example 360-B. The second eluting diastereomer (54.7 mg) was obtained as a solid.

The second eluting diastereomer had a retention time of 21.18 min.

$^1$H NMR (400 MHz, DMSO-$d_6$) δ 13.98 (s, 1H), 8.55-8.49 (m, 1H), 8.35-8.29 (m, 1H), 8.27 (s, 1H), 7.93-7.87 (m, 1H), 7.39-7.29 (m, 2H), 7.01 (s, 1H), 5.35 (q, 1H), 4.48 (s, 1H), 3.87 (s, 3H), 3.28-2.78 (m, 2H), 2.27-1.94 (m, 1H), 1.93-1.68 (m, 1H), 1.56-1.55 (m, 1H), 1.36-1.31 (m, 3H), 1.20-1.15 (m, 1H), 0.97-0.92 (m, 2H), 0.66-0.62 (m, 2H). LCMS (ESI): 513.35 [M+H]$^+$.

Example 361. (S)-4-(5-(5-fluoro-2-methoxypyridin-4-yl)-1H-pyrazole-3-carbonyl)-N-((5-fluoro-3-methylpyridin-2-yl)methyl)-4-azaspiro[2,5]octane-7-carboxamide

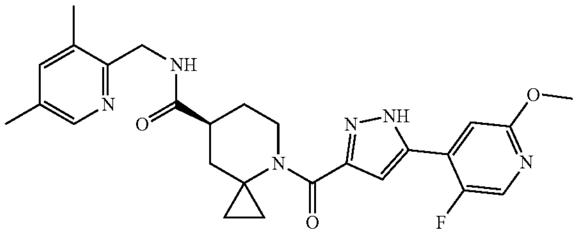

The title compound was prepared using a procedure similar to the one described for the synthesis of Example 325, except 1-(5-fluoro-3-methylpyridin-2-yl)methanamine was used as a starting material. The residue was purified by reverse phase column chromatography (using the following conditions: Column: C18; mobile phase A: Water (0.5% $NH_4HCO_3$), mobile phase B: MeCN; gradient: 30 to 50 B in 20 min; 220/254 nm) to obtain the title compound (66.5 mg) as a solid. $^1$H NMR (300 MHz, DMSO-$d_6$) δ 13.99 (d, 1H), 8.45-8.05 (m, 3H), 7.57 (dd, 1H), 7.32 (d, 1H), 7.04 (s, 1H), 4.65-4.24 (m, 3H), 3.88 (s, 3H), 2.89-2.68 (m, 1H), 2.30 (s, 3H), 2.26-2.11 (m, 1H), 1.90-1.68 (m, 1H), 1.68-1.37 (m, 1H), 1.37-1.09 (m, 2H), 1.08-0.78 (m, 2H), 0.78-0.38 (m, 2H). LCMS (ESI): 497.45 [M+H]$^+$.

Example 362. (S)—N-((3-chloro-5-fluoropyridin-2-yl)methyl)-4-(5-(5-fluoro-2-methoxypyridin-4-yl)-1H-pyrazole-3-carbonyl)-4-azaspiro[2.5]octane-7-carboxamide

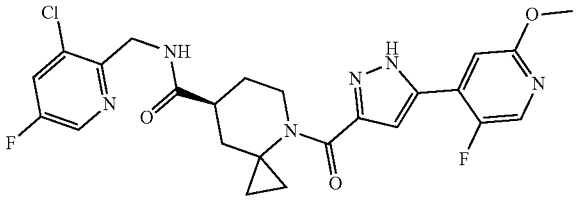 [SMILES: COc1cc(-c2cc(C(=O)N3CC[C@H](C(=O)NCc4ncc(F)cc4Cl)CC34CC4)n[nH]2)c(F)cn1]

The title compound was prepared using a procedure similar to the one described for the synthesis of Example 325, except 1-(3-chloro-5-fluoropyridin-2-yl)methanamine hydrochloride was used as a starting material. The residue was purified by Prep-HPLC (using the following conditions: Column: C18; Mobile Phase A: Water (10 mM $NH_4HCO_3$), Mobile Phase B: MeCN; Flow rate: 40 mL/min; Gradient: 20 B to 50 B in 20 min; Detector, UV 254/220 nm) to obtain the title compound (44.1 mg) as a solid. $^1$H NMR (400 MHz, DMSO-$d_6$) δ 8.57-8.51 (m, 1H), 8.40-8.20 (m, 2H), 8.12-8.04 (m, 1H), 7.30 (s, 1H), 7.02 (s, 1H), 4.60-4.40 (m, 3H), 3.85 (s, 3H), 3.25-2.76 (m, 2H), 2.17 (s, 1H), 1.80-1.76 (m, 1H), 1.54-1.50 (m, 1H), 1.34-1.07 (m, 1H), 0.98-0.93 (m, 1H), 0.73-0.43 (m, 3H). LCMS (ESI): 517.35 [M+H]$^+$.

Example 363. (S)-4-(5-(5-fluoro-2-methoxypyridin-4-yl)-1H-pyrazole-3-carbonyl)-N-((5-fluoro-3-(trifluoromethyl)pyridin-2-yl)methyl)-4-azaspiro[2.5]octane-7-carboxamide

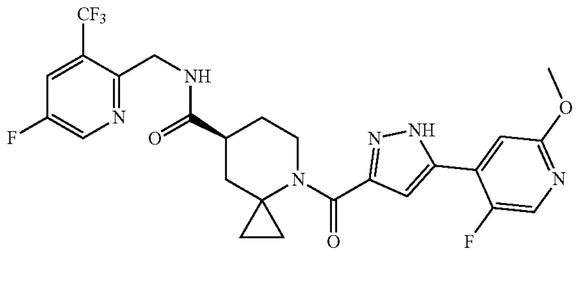 [SMILES: COc1cc(-c2cc(C(=O)N3CC[C@H](C(=O)NCc4ncc(F)cc4C(F)(F)F)CC34CC4)n[nH]2)c(F)cn1]

Step-1. 5-fluoro-N-methoxy-N-methyl-3-(trifluoromethyl)pyridine-2-carboxamide

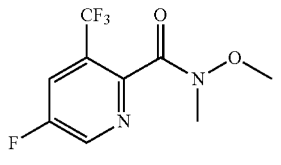 [SMILES: CON(C)C(=O)c1ncc(F)cc1C(F)(F)F]

HATU (109.1 mg, 0.29 mmol) and methoxy(methyl)amine hydrochloride (27.8 mg, 0.29 mmol) were added to a stirred mixture of 5-fluoro-3-(trifluoromethyl)pyridine-2-carboxylic acid (50.0 mg, 0.24 mmol) and DIPEA (154.5 mg, 1.20 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (3/1 v/v) to obtain the title compound (60.0 mg) as a an oil. LCMS (ESI): 253.06 $[M+H]^+$.

Step-2. 5-fluoro-3-(trifluoromethyl)pyridine-2-carbaldehyde

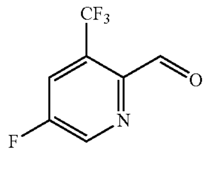

DIBAL-H (0.36 mL, 0.36 mmol, 1M) was added to a stirred mixture of 5-fluoro-N-methoxy-N-methyl-3-(trifluoromethyl)pyridine-2-carboxamide (Step-1, 45.0 mg, 0.18 mmol) in dry DCM (2.00 mL) at −78° C. under nitrogen atmosphere. The resulting mixture was stirred at −78° C. for 1.5 h under nitrogen atmosphere. The reaction mixture was quenched with MeOH at −78° C. The resulting solution was concentrated to about 2.00 mL under reduced pressure. The residue was used in the next step directly without further purification. LCMS (ESI): 194.02 $[M+H]^+$.

Step-3. (E)-N-[[5-fluoro-3-(trifluoromethyl)pyridin-2-yl]methylidene]hydroxylamine

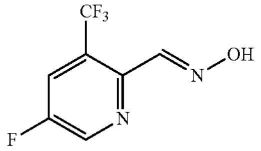 [SMILES: O/N=C/c1ncc(F)cc1C(F)(F)F]

Hydroxylamine hydrochloride (15.0 mg, 0.22 mmol) were added to a stirred mixture of 5-fluoro-3-(trifluoromethyl)pyridine-2-carbaldehyde (Step-2, 35.0 mg, 0.18 mmol) in MeOH (2.00 mL). The resulting mixture was stirred at 25° C. for 1 h. The resulting mixture was concentrated under reduced pressure. The residue was purified by Prep-TLC (petroleum ether/EtOAc, 1/1 v/v). The title compound was collected with MeOH and concentrated to about 2 mL. The solution was used in the next step directly without further purification. LCMS (ESI): 209.03 $[M+H]^+$.

Step-4. 1-[5-fluoro-3-(trifluoromethyl)pyridin-2-yl]methanamine

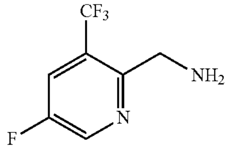 [SMILES: NCc1ncc(F)cc1C(F)(F)F]

Zn (141.4 mg, 2.16 mmol) was added to a stirred mixture of (E)-N-[[5-fluoro-3-(trifluoromethyl)pyridin-2-yl]methylidene]hydroxylamine in MeOH (Step-3, 2.00 mL) and AcOH (0.20 mL). The resulting mixture was stirred at 25° C. for 14 h. The resulting mixture was concentrated under reduced pressure. The residue was purified by Prep-TLC (DCM/MeOH, 5/1 v/v) to obtain the title compound (14.0 mg) as an oil. LCMS (ESI): 195.05 $[M+H]^+$.

Step-5. (S)-4-(5-(5-fluoro-2-methoxypyridin-4-yl)-1H-pyrazole-3-carbonyl)-N-((5-fluoro-3-(trifluoromethyl)pyridin-2-yl)methyl)-4-azaspiro[2.5]octane-7-carboxamide

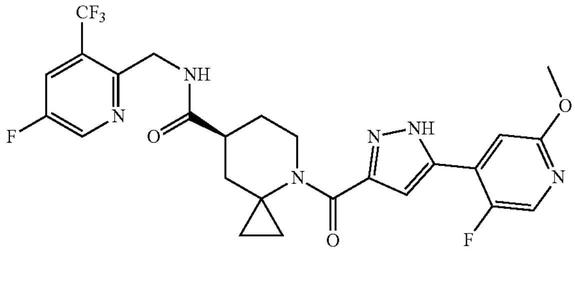 [SMILES: COc1cc(-c2cc(C(=O)N3CC[C@H](C(=O)NCc4ncc(F)cc4C(F)(F)F)CC34CC4)n[nH]2)c(F)cn1]

HOBt (9.8 mg, 0.07 mmol), EDCI (13.9 mg, 0.07 mmol), and 1-[5-fluoro-3-(trifluoromethyl)pyridin-2-yl]methanamine (Step-4, 7.0 mg, 0.04 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 15.0 mg, 0.04 mmol) and DIPEA (47.0 mg, 0.36 mmol) in DMF (1.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-HPLC (using the following conditions: Column: YMC-Actus Triart C18 ExRS, 30×150 mm, 5 μm; Mobile Phase A: Water (10 mM $NH_4HCO_3$), Mobile Phase B: MeCN; Flow rate: 60 mL/min; Gradient: 35% B to 59% B in 8 min, 59% B; Wave Length: 254/220 nm; RT1 (min): 7.08) to obtain the title compound (3.4 mg) as a solid.

$^1$H NMR (300 MHz, $CD_3OD$) δ 8.74-8.67 (m, 1H), 8.14 (d, 1H) 8.06-7.96 (m, 1H), 7.32-7.26 (m, 1H), 7.15-7.09 (m, 1H), 4.70-4.59 (m, 2H), 3.95 (s, 3H), 2.99-2.93 (m, 1H), 2.63-2.23 (m, 1H), 1.96 (s, 1H), 1.85-1.70 (m, 1H), 1.65-1.18 (m, 3H), 1.11-0.97 (m, 1H), 0.99-0.88 (m, 1H), 0.81-0.67 (m, 2H). LCMS (ESI): 551.25 $[M+H]^+$.

Example 364. (S)—N-((3-chloro-5-(2-hydroxypropan-2-yl)pyridin-2-yl)methyl)-4-(5-(5-fluoro-2-methoxypyridin-4-yl)-1H-pyrazole-3-carbonyl)-4-azaspiro[2.5]octane-7-carboxamide

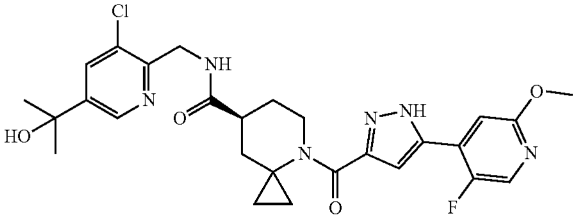 [SMILES: COc1cc(-c2cc(C(=O)N3CC[C@H](C(=O)NCc4ncc(C(C)(C)O)cc4Cl)CC34CC4)n[nH]2)c(F)cn1]

Step-1. 5-acetyl-3-chloropyridine-2-carbonitrile

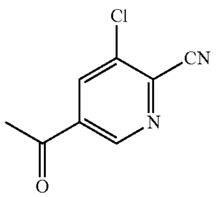

$Zn(CN)_2$ (370.8 mg, 3.16 mmol) and $Pd(PPh_3)_4$ (611.1 mg, 0.53 mmol) were added to a stirred mixture of 1-(5,6-dichloropyridin-3-yl)ethanone (1.00 g, 5.29 mmol) in DMF (5.00 mL). The resulting mixture was stirred at 120° C. for 3 h under nitrogen atmosphere. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (4/1 v/v) to obtain the title compound (610.0 mg) as a solid. LCMS (ESI): 181.6 $[M+H]^+$.

Step-2. 3-chloro-5-(2-hydroxypropan-2-yl)pyridine-2-carbonitrile

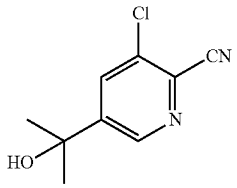

MeMgBr (2.50 mL, 7.50 mmol, 3 M) was added to a stirred mixture of 5-acetyl-3-chloropyridine-2-carbonitrile (Step-1, 300.0 mg, 1.66 mmol) in THF (3.00 mL) at −78° C. under nitrogen atmosphere. The resulting mixture was stirred at 25° C. for 14 h under nitrogen atmosphere. The reaction mixture was quenched with MeOH. The resulting mixture was concentrated under reduced pressure. The residue was purified by Prep-TLC (petroleum ether/EtOAc, 2/1 v/v) to obtain the title compound (200.0 mg) as a solid. LCMS (ESI): 197.6 $[M+H]^+$.

Step-3. 2-[6-(aminomethyl)-5-chloropyridin-3-yl]propan-2-ol

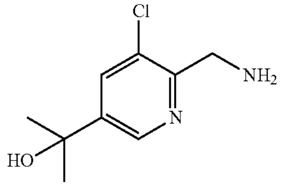

DIBAL-H (1.90 mL, 1.90 mmol) was added to a stirred mixture of 3-chloro-5-(2-hydroxypropan-2-yl)pyridine-2-carbonitrile (Step-2, 110.0 mg, 0.56 mmol) in DCM (3.50 mL) at −78° C. under nitrogen atmosphere. The resulting mixture was stirred at −78° C. for 1 h under nitrogen atmosphere. The reaction mixture was quenched by the addition of MeOH at −78° C. The resulting mixture was concentrated under reduced pressure. The residue was purified by silica gel column chromatography eluting with DCM/MeOH (5/1 v/v) to obtain the title compound (25.0 mg) as a solid. LCMS (ESI): 201.7 $[M+H]^+$.

Step-4. (S)—N—((3-chloro-5-(2-hydroxypropan-2-yl)pyridin-2-yl)methyl)-4-(5-(5-fluoro-2-methoxypyridin-4-yl)-1H-pyrazole-3-carbonyl)-4-azaspiro[2.5]octane-7-carboxamide

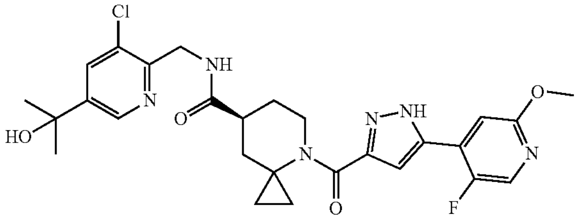 [SMILES: COc1cc(-c2cc(C(=O)N3CC[C@H](C(=O)NCc4ncc(C(C)(C)O)cc4Cl)CC34CC4)n[nH]2)c(F)cn1]

EDCI (28.7 mg, 0.15 mmol), HOBt (20.2 mg, 0.15 mmol), and 2-[6-(aminomethyl)-5-chloropyridin-3-yl]propan-2-ol (Step-3, 15.0 mg, 0.08 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 30.8 mg, 0.08 mmol) and DIPEA (48.3 mg, 0.37 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 40 B in 20 min, detector, UV 254/220 nm) to obtain the title compound (11.9 mg) as a solid.

$^1$H NMR (400 MHz, DMSO-$d_6$) δ 13.97 (s, 1H), 8.55 (d, 1H), 8.31-8.21 (m, 2H), 7.87 (d, 1H), 7.30 (d, 1H), 7.01 (s, 1H), 5.38-5.34 (m, 1H), 4.45-4.39 (m, 3H), 3.85 (s, 3H), 3.15-2.64 (m, 2H), 2.20-2.16 (m, 1H), 1.77 (s, 1H), 1.66-1.35 (m, 7H), 1.23-1.18 (m, 1H), 0.98-0.93 (m, 2H), 0.64-0.60 (m, 2H). LCMS (ESI): 557.15 $[M+H]^+$.

Example 365. (S)-4-(5-(5-fluoro-2-methoxypyridin-4-yl)-1H-pyrazole-3-carbonyl)-N-((4-(trifluoromethyl)-2-oxabicyclo[2.1.1]hexan-1-yl)methyl)-4-azaspiro[2.5]octane-7-carboxamide

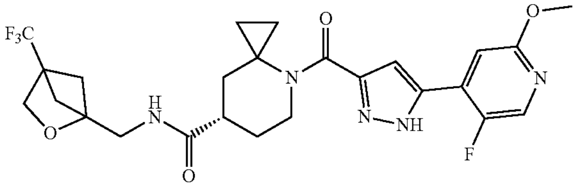 [SMILES: COc1cc(-c2cc(C(=O)N3CC[C@H](C(=O)NCC45CC(C(F)(F)F)(CO4)C5)CC34CC4)n[nH]2)c(F)cn1]

The title compound was prepared using a procedure similar to the one described for the synthesis of Example 325, except 1-[4-(trifluoromethyl)-2-oxabicyclo[2.1.1]hexan-1-yl]methanamine was used as a starting material. The residue was purified by silica gel column chromatography eluting with petroleum ether/EtOAc (1/5 v/v) to obtain the title compound (90.2 mg) as a solid. $^1$H NMR. (400 MHz, DMSO-$d_6$) δ 13.97 (s, 1H), 8.24 (d, 1H), 8.05 (d, 1H), 7.30 (d, 1H), 7.01 (d, 1H), 4.62-4.24 (m, 1H), 3.85 (s, 3H), 3.81-3.77 (m, 2H), 3.45-3.35 (m, 2H), 2.83-2.60 (m, 1H), 2.33-2.06 (m, 1H), 2.00-1.90 (m, 2H), 1.84-1.60 (m, 3H), 1.53-1.48 (m, 1H), 1.31-0.39 (m, 6H). LCMS (ESI): 538.30 $[M+H]^+$.

Example 366. A Diastereomeric Mixture of (S)—N—((S)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide and (S)—N—((R)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide

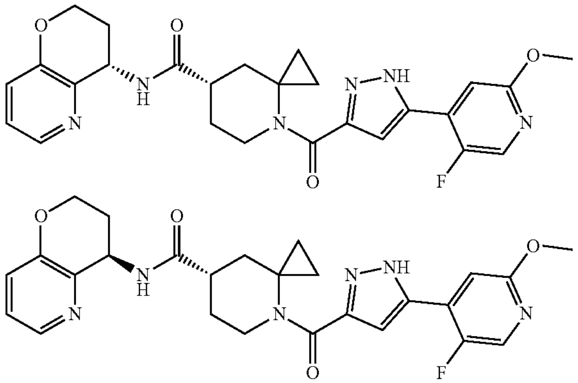

The title compound was prepared using a procedure similar to the one described for the synthesis of Example 325, except 2H,3H,4H-pyrano[3,2-b]pyridin-4-amine was used as a starting material. The residue was purified by silica gel column chromatography eluting with DCM/MeOH (10/1 v/v) to obtain (S)—N—((S)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide and (S)—N—((R)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide (100.0 mg) as a solid mixture of diastereomers (Example 366). $^1$H NMR (400 MHz, DMSO-$d_6$) δ 8.36-8.21 (m, 2H), 8.16-8.09 (m, 1H), 7.33-7.28 (m, 1H), 7.24-7.18 (m, 2H), 7.03 (s, 1H), 4.93-4.86 (m, 1H) 4.53-4.49 (m, 1H), 4.29-4.22 (m, 1H), 4.14-4.09 (m, 1H), 3.85 (s, 3H), 2.27-2.05 (m, 2H), 1.94-1.89 (m, 2H), 1.79-1.74 (m, 1H), 1.58-1.54 (m, 1H), 1.36-1.08 (m, 1H), 1.00-0.95 (m, 2H), 0.65-0.45 (m, 3H). LCMS (ESI): 507.45 $[M+H]^+$.

This mixture of two diastereomers (100.0 mg) was separated using Chiral Prep-SFC.

Column: CHIRALPAK IH column

Column dimension: 3×25 cm, 5 μm

Mobile Phase A: $CO_2$; Mobile Phase B: MeOH (0.1% 2 M $NH_3$·MeOH)

Flow rate: 80 mL/min

Gradient: isocratic 40% B

Detection: 254 nm

Example 366-A. The first eluting diastereomer (43.1 mg) was obtained as a solid.

The first eluting diastereomer had a retention time of 2.87 min.

$^1$H NMR (300 MHz, DMSO-$d_6$) δ 8.35-8.24 (m, 2H), 8.19-8.11 (m, 1H), 7.37-7.19 (m, 3H), 7.04 (s, 1H), 4.96-4.89 (m, 1H), 4.62-4.40 (m, 1H), 4.33-4.23 (m, 1H), 4.20-4.07 (m, 1H), 3.88 (s, 3H), 2.15-2.05 (m, 2H), 1.98-1.87 (m, 1H), 1.83-1.60 (m, 2H), 1.38-1.11 (m, 2H), 0.99-0.93 (m, 2H), 0.65-0.59 (m, 3H). LCMS (ESI): 507.45 $[M+H]^+$.

Example 366-B. The second eluting diastereomer (42.2 mg) was obtained as a solid.

The second eluting diastereomer had a retention time of 4.32 min.

$^1$H NMR (300 MHz, DMSO-$d_6$) δ 14.13-13.84 (m, 1H), 8.40-8.22 (m, 2H), 8.19-8.11 (m, 1H), 7.36-7.28 (m, 1H), 7.26-7.19 (m, 2H), 7.09-7.03 (m, 1H), 4.97-4.89 (m, 1H), 4.54-4.48 (m, 1H), 4.33-4.23 (m, 1H), 4.21-4.08 (m, 1H), 3.88 (s, 3H), 2.30-2.06 (m, 2H), 2.03-1.89 (m, 1H), 1.82-1.76 (m, 1H), 1.60-1.54 (m, 1H), 1.40-1.12 (m, 2H), 1.04-0.81-0.69-0.46 (m, 3H). LCMS (ESI): 507.45 [M+H]$^+$.

Example 367. A Diastereomeric Mixture of (2S, 4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide and (2S,4S)-1-(5-(5-fluoro-2-methoxypyridin-, 1-yl)-1H-pyrazole-3-carbonyl)-N-((1r,4S)-4-hydroxy-4-(trifluoromethyl)cyclohexyl)-2-(trifluoromethyl)piperidine-4-carboxamide

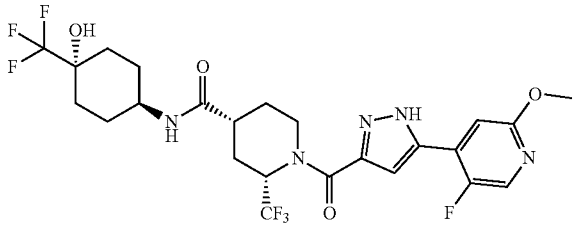

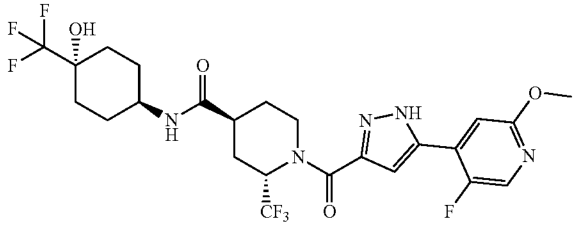

Step-1. Benzyl (4S)-5,5,5-trifluoro-2-methylidene-4-[[(S)-2-methylpropane-2-sulfinyl]amino]pentanoate

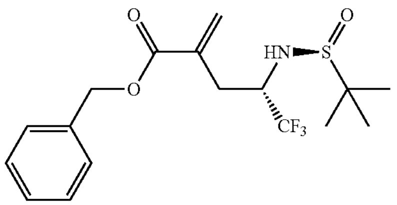 [SMILES: C=C(C[C@H](N[S@@](=O)C(C)(C)C)C(F)(F)F)C(=O)OCc1ccccc1]

Zn (0.61 g, 9.39 mmol) was added to a mixture of (S)-2-methyl-N-[(1E)-2,2,2-trifluoroethylidene]propane-2-sulfinamide (1.30 g, 6.26 mmol) and benzyl 2-(bromomethyl)prop-2-enoate (Step-2 from synthesis of Intermediate 532, 1.60 g, 6.26 mmol) in DMF (5.00 mL). The resulting mixture was stirred at 0° C. for 4 h under nitrogen atmosphere. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (7/1 v/v) to obtain the title compound (2.00 g) as a solid. LCMS (ESI): 378 [M+H]$^+$.

Step-2. (4S)-5,5,5-trifluoro-4-(2-methylpropane-2-sulfonamido)pentanoate

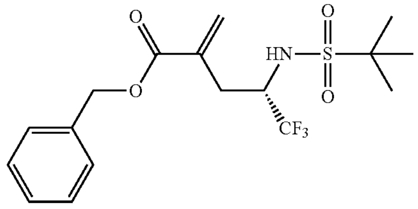 [SMILES: C=C(C[C@H](NS(=O)(=O)C(C)(C)C)C(F)(F)F)C(=O)OCc1ccccc1]

mCPBA (1.01 g, 5.83 mmol) was added to a mixture of benzyl (4S)-5,5,5-trifluoro-2-methylidene-4[[(S)-2-methylpropane-2-sulfinyl]amino]pentanoate (Step-1, 2.00 g, 5.30 mmol) in DCM (5.00 mL) at 0° C. The resulting mixture was stirred at 25° C. for 14 h. The resulting mixture was concentrated under reduced pressure. The residue was purified by silica gel column chromatography eluting with petroleum ether/EtOAc (7/1 v/v) to obtain the title compound (1.60 g) as a solid. LCMS (ESI): 394 [M+H]$^+$.

Step-3. (4S)-5,5,5-trifluoro-2-methylidene-4-[N-(prop-2-en-1-yl)2-methylpropane-2-sulfonamido] pentanoate

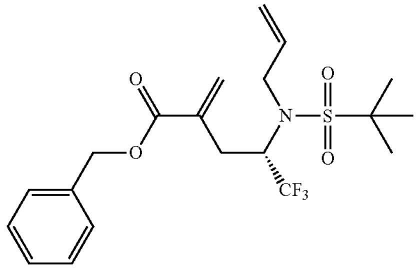 [SMILES: C=CCN([C@@H](CC(=C)C(=O)OCc1ccccc1)C(F)(F)F)S(=O)(=O)C(C)(C)C]

$Cs_2CO_3$ (4.10 g, 12.71 mmol) was added to a mixture of benzyl (4S)-5,5,5-trifluoro-2-methylidene-4-(2-methylpropane-2-sulfonamido)pentanoate (Step-2, 1.00 g, 2.54 mmol) and allyl bromide (615.0 mg, 5.08 mmol) in DMF (5.00 mL) at 0° C. The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (8/1 v/v) to obtain the title compound (950.0 mg) as a solid. LCMS (ESI): 434 [M+H]$^+$.

Step-4. benzyl (2S)-1-(2-methylpropane-2-sulfonyl)-2-(trifluoromethyl)-3,6-dihydro-2H-pyridine-4-carboxylate

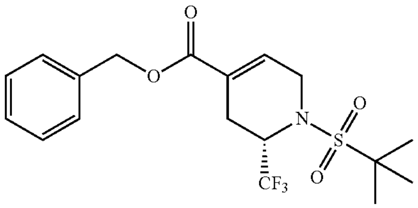 [SMILES: CC(C)(C)S(=O)(=O)N1CC=C(C(=O)OCc2ccccc2)C[C@H]1C(F)(F)F]

Grubbs Catalyst (2nd gen, 98.0 mg, 0.12 mmol) was added to a mixture of benzyl (4S)-5,5,5-trifluoro-2-methylidene-4-[N-(prop-2-en-1-yl)2-methylpropane-2-sulfonamido]pentanoate (Step-3, 500.0 mg, 1.15 mmol) in DCM (180.00 mL). The resulting mixture was stirred at 25° C. for 14 h under nitrogen atmosphere. The resulting mixture was concentrated under reduced pressure. The residue was purified by silica gel column chromatography eluting with petroleum ether/EtOAc (7/1 v/v) to obtain the title compound (400.0 mg) as a solid. LCMS (ESI): 406 $[M+H]^+$.

Step-5. (2S)-1-(2-methylpropane-2-sulfonyl)-2-(trifluoromethyl)piperidine-4-carboxylic acid

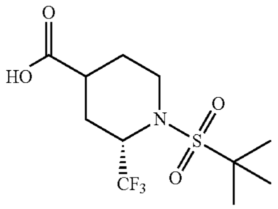 [SMILES: CC(C)(C)S(=O)(=O)N1CCC(C(=O)O)C[C@H]1C(F)(F)F]

$Pd(OH)_2$ (200.0 mg, 1.42 mmol) was added to a mixture of benzyl (2S)-1-(2-methylpropane-2-sulfonyl)-2-(trifluoromethyl)-3,6-dihydro-2H-pyridine-4-carboxylate (Step-4, 400.0 mg, 0.99 mmol) in MeOH (5.00 mL). The resulting mixture was stirred at 25° C. for 2 h under a $H_2$ atmosphere. The solids were filtered out and washed with MeOH. The resulting filtrate was concentrated under reduced pressure to obtain the title compound (300.0 mg) as a solid. LCMS (ESI): 318 $[M+H]^+$.

Step-6. (2S)-1-(2-methylpropane-2-sulfonyl)-N-[(1r,4r)-4-hydroxy-4-(trifluoromethyl)cyclohexyl]-2-(trifluoromethyl)piperidine-4-carboxamide

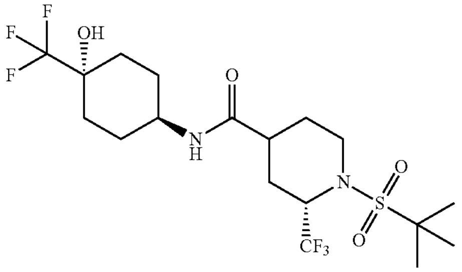 [SMILES: CC(C)(C)S(=O)(=O)N1CCC(C(=O)N[C@H]2CC[C@@](O)(C(F)(F)F)CC2)C[C@H]1C(F)(F)F]

HOBt (109.0 mg, 0.80 mmol), EDCI (154.0 mg, 0.80 mmol), and (1r,4r)-4-amino-1-(trifluoromethyl)cyclohexan-1-ol (98.0 mg, 0.54 mmol) were added to a mixture of (2S)-1-(2-methylpropane-2-sulfonyl)-2-(trifluoromethyl)piperidine-4-carboxylic acid (Step-5, 170.0 mg, 0.54 mmol) and DIPEA (346.0 mg, 2.68 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (20/1 v/v) to obtain the title compound (200.0 mg) as a solid. LCMS (ESI): 483 $[M+H]^+$.

Step-7. (2S)—N-[(1r,4r)-4-hydroxy-4-(trifluoromethyl)cyclohexyl]-2-(trifluoromethyl)piperidine-4-carboxamide

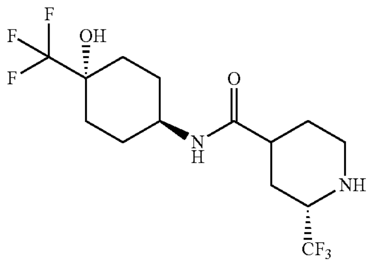 [SMILES: O=C(N[C@H]1CC[C@@](O)(C(F)(F)F)CC1)C1CCN[C@H](C(F)(F)F)C1]

TFA (187.0 mg, 1.24 mmol) was added to a mixture of (2S)-1-(2-methylpropane-2-sulfonyl)-N-[(1r,4r)-4-hydroxy-4-(trifluoromethyl)cyclohexyl]-2-(trifluoromethyl)piperidine-4-carboxamide (Step-6, 200.0 mg, 0.42 mmol) in DCM (3.00 mL). The resulting mixture was stirred at 25° C. for 1 h. The resulting mixture was concentrated under reduced pressure. The residue was purified by silica gel column chromatography eluting with DCM/MeOH (10/1 v/v) to obtain the title compound (120.0 mg) as a solid. LCMS (ESI): 363 $[M+H]^+$.

Step-8. (2S)-1-[5-(5-fluoro-2-methoxypyridin-4-yl)-1-[[2-(trimethylsilyl)ethoxy]methyl]pyrazole-3-carbonyl]-N-[(1r,4r)-4-hydroxy-4-(trifluoromethyl)cyclohexyl]-2-(trifluoromethyl)piperidine-4-carboxamide

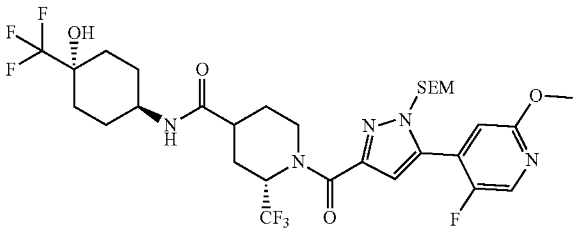 [SMILES: COc1cc(-c2cc(C(=O)N3CCC(C(=O)N[C@H]4CC[C@@](O)(C(F)(F)F)CC4)C[C@H]3C(F)(F)F)nn2COCC[Si](C)(C)C)c(F)cn1]

2-chloro-1-methylpyridin-1-ium iodide (888.0 mg, 3.48 mmol), TEA (88.0 mg, 0.87 mmol), and (2S)—N-[(1r,4r)-4-hydroxy-4-(trifluoromethyl)cyclohexyl]-2-(trifluoromethyl)piperidine-4-carboxamide (Step-7, 90.0 mg, 0.25 mmol) were added to a mixture of 5-(5-fluoro-2-methoxypyridin-4-yl)-1-[[2-(trimethylsilyl)ethoxy]methyl]pyrazole-3-carboxylic acid (INTERMEDIATE 506, 91.0 mg, 0.25 mmol) in DCM (3.00 mL). The resulting mixture was stirred at 25° C. for 14 h. The resulting mixture was concentrated under reduced pressure. The residue was purified by silica gel column chromatography eluting with DCM/MeOH (10/1 v/v) to obtain the title compound (120.0 mg) as a solid. LCMS (ESI): 712 $[M+H]^+$.

Step-9. (2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl) piperidine-4-carboxamide and (2S,4S)-1-(5-(5-fluoro-2-methoxypyridin-4-yl)-1H-pyrazole-3-carbonyl)-N-((1r,4S)-4-hydroxy-4-(trifluoromethyl) cyclohexyl)-2-(trifluoromethyl)piperidine-4-carboxamide

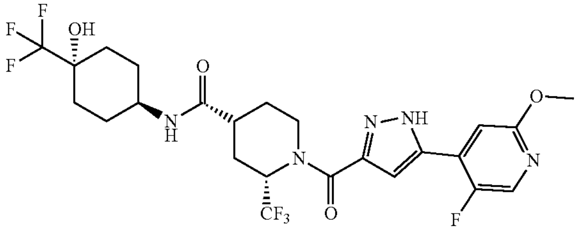

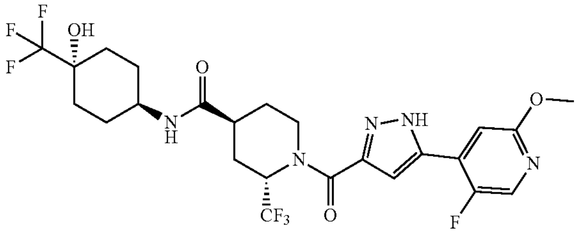

TFA (2 mL) was added to a mixture of (2S)-1-[5-(5-fluoro-2-methoxypyridin-4-yl)-1-[[2-(trimethylsilyl) ethoxy]methyl]pyrazole-3-carbonyl]-N-[(1r,4r)-4-hydroxy-4-(trifluoromethyl)cyclohexyl]-2-(trifluoromethyl) piperidine-4-carboxamide (Step-8, 120.0 mg, 0.17 mmol) in DCM (2.00 mL). The resulting mixture was stirred at 25° C. for 1 h. The resulting mixture was concentrated under reduced pressure. The residue was purified by silica gel column chromatography eluting with DCM/MeOH (10/1 v/v) to obtain (2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide and (2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide (50.0 mg) as a solid mixture of diastereomers (Example 367). $^1$H NMR (300 MHz, DMSO-$d_6$) δ 8.29 (d, 1H), 8.00 (d, 1H), 7.35 (d, 1H), 7.16 (d, 1H), 6.28-5.45 (m, 2H), 4.58 (d, 1H), 3.91-3.85 (m, 4H), 2.84-2.78 (m, 2H), 2.01-1.95 (m, 2H), 1.85-1.71 (m, 5H), 1.60-1.50 (m, 5H). LCMS (ESI): 582.4 $[M+H]^+$.

This mixture of two diastereomers (110.0 mg) was separated using Chiral Prep-HPLC.

Column: CHIRALPAK ART Cellulose-SB column

Column dimension: 2×25 cm, 5 μm

Mobile Phase: hexanes (0.5% 2 M $NH_3$·MeOH): EtOH=80:20 hold for 12 min

Flow rate: 20 mL/min

Detection: 220/254 nm

Example 367-A. The first eluting diastereomer (8.0 mg) was obtained as a solid.

The first eluting diastereomer had a retention time of 6.70 min.

$^1$H NMR (300 MHz, $CD_3OD$) δ 8.20-8.14 (m, 1H), 7.25-7.19 (m, 2H), 5.34-5.28 (m, 1H), 5.00-4.86 (m, 1H), 4.02-3.94 (m, 1H), 3.95 (s, 3H), 3.70-3.30 (m, 1H), 2.62-2.56 (m, 1H), 233-2.05 (m, 3H), 2.00-180 (m, 5H), 1.77-1.60 (m, 4H). LCMS (ESI): 582.05 $[M+H]^+$.

Example 367-B. The second eluting diastereomer (33.7 mg) was obtained as a solid.

The second eluting diastereomer had a retention time of 9.23 min.

$^1$H NMR (300 MHz, $CD_3OD$) δ 8.16 (s, 1H), 7.27-7.14 (m, 2H), 5.63-5.51 (m, 1H), 4.79-4.68 (m, 1H), 4.01-3.92 (m, 4H), 3.51-3.45 (m, 1H), 311-2.89 (m, 1H), 2.30-2.03 (m, 3H), 2.02-1.80 (m, 5H), 1.79-1.57 (m, 4H). LCMS (ESI): 582.00 $[M+H]^+$.

Example 368. A Diastereomeric Mixture of (2R, 4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide and (2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide

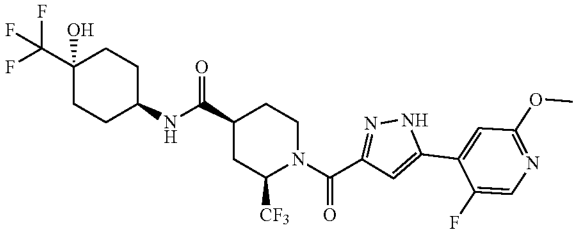

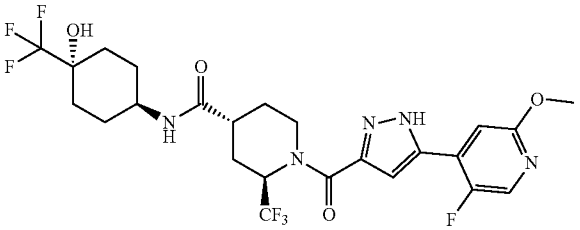

The title compound was prepared using a procedure similar to the one described for the synthesis of Example 367, except (R)-2-methyl-N-[(1E)-2,2,2-trifluoroethylidene]propane-2-sulfinamide was used as a starting material in Step-1. The resulting residue was purified by silica gel column chromatography eluting with DCM/MeOH (10/1 v/v) to obtain (2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide and (2R,4S)-1-(5-(5-fluoro-2-methoxypyridin-4-yl)-1H-pyrazole-3-carbonyl)-N-((1r,48S)-4-hydroxy-4-(trifluoromethyl)cyclohexyl)-2-(trifluoromethyl)piperidine-4-carboxamide (45.0 mg) as a solid mixture of diastereomers (Example 368). $^1$H NMR (400 MHz, DMSO-$d_6$) δ 14.56-13.92 (m, 1H), 8.42-8.14 (m, 1H), 8.09-7.79 (m, 1H), 7.53-6.95 (m, 2H), 5.69 (s, 1H), 5.52-5.28 (m, 1H), 4.81-4.37 (m, 1H), 3.95-3.65 (m, 4H), 2.97-2.70 (m, 2H), 104-1.63 (m, 7H), 1.59-1.39 (m, 5H). LCMS (ESI): 582.4 $[M+H]^+$.

Step-1. (2R)-1-benzyl-N-[(1r,4r)-4-hydroxy-4-(trifluoromethyl)cyclohexyl]-2-(trifluoromethyl)piperidine-4-carboxamide

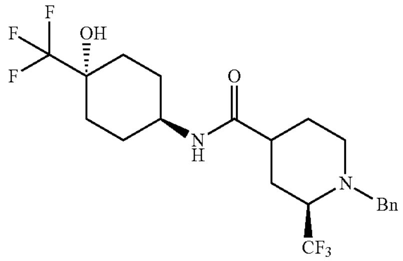 [SMILES: O=C(N[C@H]1CC[C@@](O)(C(F)(F)F)CC1)C1CCN(Cc2ccccc2)[C@@H](C(F)(F)F)C1]

Benzyl bromide (123.0 mg, 0.72 mmol) was added to a mixture of (2R)—N-[(1r,4r)-4-hydroxy-4-(trifluoromethyl)cyclohexyl]-2-(trifluoromethyl)piperidine-4-carboxamide (Step-7 from synthesis of Example 367 except using (R)-2-methyl-N-[(1E)-2,2,2-trifluoroethylidene]propane-2-sulfinamide as a starting material in Step-1, 200.0 mg, 0.55 mmol) and $K_2CO_3$ (153.0 mg, 1.10 mmol) in MeCN (5.00 mL). The resulting mixture was stirred at 60° C. for 14 h. The resulting mixture was concentrated under reduced pressure. The residue was purified by silica gel column chromatography eluting with petroleum ether/EtOAc (3/1 v/v) to obtain the title compound (200.0 mg) as a solid. LCMS (ESI): 453 $[M+H]^+$.

Step-2. (2R,4R)-1-benzyl-N-[(1r,4r)-4-hydroxy-4-(trifluoromethyl)cyclohexyl]-2-(trifluoromethyl)piperidine-4-carboxamide and (2R,4S)-1-benzyl-N-[(1r,4r)-4-hydroxy-4-(trifluoromethyl)cyclohexyl]-2-(trifluoromethyl)piperidine-4-carboxamide

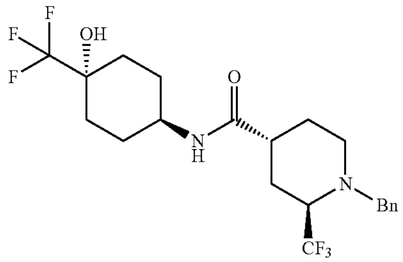

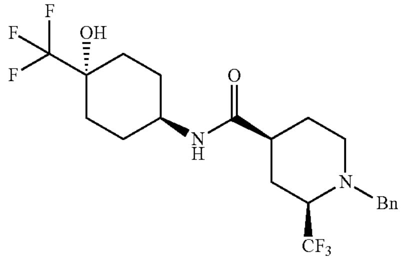

The diastereomeric mixture of (2R,4R)-1-benzyl-N-[(1r,4r)-4-hydroxy-4-(trifluoromethyl)cyclohexyl]-2-(trifluoromethyl)piperidine-4-carboxamide and (2R,4S)-1-benzyl-N-[(1r,4r)-4-hydroxy-4-(trifluoromethyl)cyclohexyl]-2-(trifluoromethyl)piperidine-4-carboxamide was separated by Prep-TLC (petroleum ether/EtOAc, 3/1 v/v).

The first eluting diastereomer (50.0 mg) was obtained as a solid.

The first eluting diastereomer had a Rf value of 0.5.

LCMS (ESI): 453 $[M+H]^+$.

The second eluting diastereomer (95.0 mg) was obtained as a solid.

The second eluting diastereomer had a Rf value of 0.4.

LCMS (ESI): 453 $[M+H]^+$.

Step-3. (2R,4R)—N-[(1r,4r)-4-hydroxy-4-(trifluoromethyl)cyclohexyl]-2-(trifluoromethyl)piperidine-4-carboxamide and (2R,4S)—N-[(1r,4r)-4-hydroxy-4-(trifluoromethyl)cyclohexyl]-2-(trifluoromethyl)piperidine-4-carboxamide

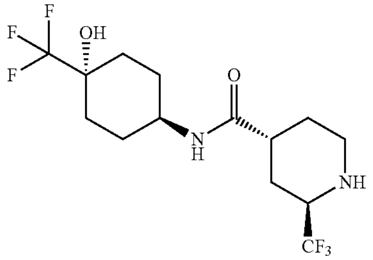

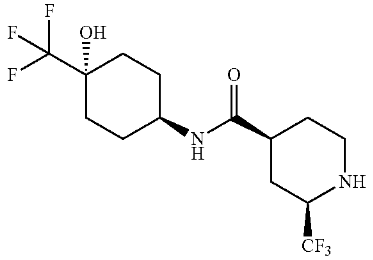

Step-3a. Pd/C (25.0 mg, 10% Pd) was added to a mixture of a single diastereomer from Step-2 (first eluting diastereomer, 50.0 mg, 0.11 mmol) in MeOH (2.00 mL). The resulting mixture was stirred at 25° C. for 2 h under a $H_2$ atmosphere. The resulting mixture was filtered, the filter cake was washed with MeOH. The filtrate was concentrated under reduced pressure to obtain the title compound (35.0 mg) as a solid single diastereomer. LCMS (ESI): 363 $[M+H]^+$.

Step-3b. Pd/C (46.0 mg, 10% Pd) was added to a mixture of a single diastereomer from Step-2 (second eluting diastereomer, 95.0 mg, 0.21 mmol) in MeOH (5.00 mL). The resulting mixture was stirred at 25° C. for 2 h under a $H_2$ atmosphere. The resulting mixture was filtered, the filter cake was washed with MeOH. The filtrate was concentrated under reduced pressure to obtain the title compound (65.0 mg) as a solid single diastereomer. LCMS (ESI): 363 $[M+H]^+$.

Step-4. (2R,4R)-1-[5-(5-fluoro-2-methoxypyridin-4-yl)-1-[[2-(trimethylsilyl)ethoxy]methyl]pyrazole-3-carbonyl]-N-[(1r,4r)-4-hydroxy-4-(trifluoromethyl)cyclohexyl]-2-(trifluoromethyl)piperidine-4-carboxamide and (2R,4S)-1-[5-(5-fluoro-2-methoxypyridin-4-yl)-1-[[2-(trimethylsilyl)ethoxy]methyl]pyrazole-3-carbonyl]-N-[(1r,4r)-4-hydroxy-4-(trifluoromethyl)cyclohexyl]-2-(trifluoromethyl)piperidine-4-carboxamide

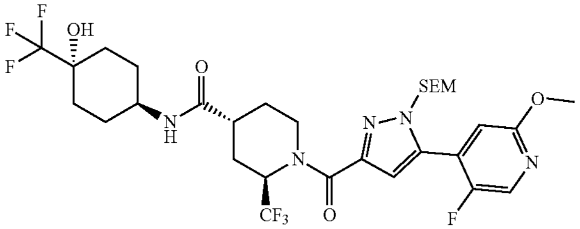

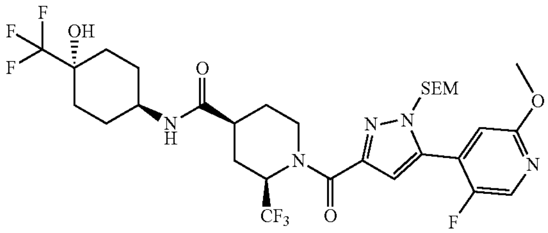

Step-4a. 2-chloro-1-methylpyridin-1-ium iodide (123.0 mg, 0.48 mmol), TEA (34.0 mg, 0.34 mmol), and a single diastereomer amine (Step-3a, 35.0 mg, 0.10 mmol) were added to a mixture of 5-(5-fluoro-2-methoxypyridin-4-yl)-1-[[2-(trimethylsilyl)ethoxy]methyl]pyrazole-3-carboxylic acid (INTERMEDIATE 506, 36.0 mg, 0.10 mmol) in DCM (3.00 mL). The resulting mixture was stirred at 25° C. for 14 h. The resulting mixture was concentrated under reduced pressure. The residue was purified by silica gel column chromatography eluting with DCM/MeOH (15/1 v/v) to obtain the title compound (50.0 mg) as a solid single diastereomer. LCMS (ESI): 712 $[M+H]^+$.

Step-4b. 2-chloro-1-methylpyridin-1-ium iodide (229.0 mg, 0.90 mmol), TEA (64.0 mg, 0.63 mmol), and a single diastereomer amine (Step-3b, 65.0 mg, 0.18 mmol) were added to a mixture of 5-(5-fluoro-2-methoxypyridin-4-yl)-1-[[2-(trimethylsilyl)ethoxy]methyl]pyrazole-3-carboxylic acid (INTERMEDIATE 506, 66.0 mg, 0.18 mmol) in DCM (5.00 mL). The resulting mixture was stirred at 25° C. for 14 h. The resulting mixture was concentrated under reduced pressure. The residue was purified by silica gel column chromatography eluting with DCM/MeOH (15/1 v/v) to obtain the title compound (90.0 mg) as a solid single diastereomer. LCMS (ESI): 712 $[M+H]^+$.

Step-5. (2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide and (2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide

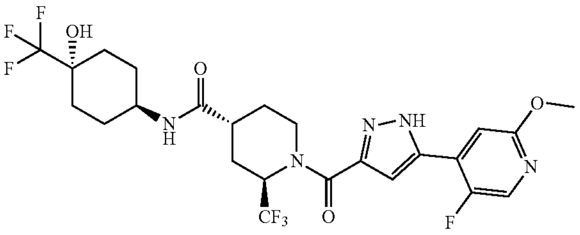

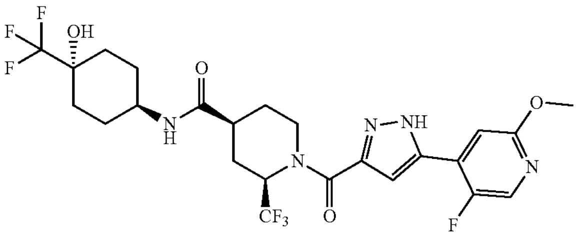

TFA (2.00 mL) was added to a mixture of a single diastereomer (Step-4a, 50.0 mg, 0.07 mmol) in DCM (2.00 mL). The resulting mixture was stirred at 25° C. for 1 h. The resulting mixture was concentrated under reduced pressure. The residue was purified by silica gel column chromatography eluting with DCM/MeOH (10/1 v/v) to obtain the title compound (27.4 mg) as a solid single diastereomer (Example 368-A). $^1$H NMR (300 MHz, CD-OD) δ 8.17 (s, 1H), 7.25-7.19 (m, 2H), 5.34-5.28 (m, 1H), 5.07-4.87 (m, 1H), 4.01-3.92 (m, 4H), 3.71-3.46 (m, 1H), 2.61-2.55 (m, 1H), 219-2.13 (m, 3H), 1.99-1.83 (n 5H), 1.76-1.60 (m, 4H). LCMS (ESI): 582.10 $[M+H]^+$.

TFA (3.00 mL) was added to a mixture of a single diastereomer (Step-4b, 90.0 mg, 0.13 mmol) in DCM (3.00 mL). The resulting mixture was stirred at 25° C. for 1 h. The resulting mixture was concentrated under reduced pressure. The residue was purified by silica gel column chromatography eluting with DCM/MeOH (10/1 v/v) to obtain the title compound (39.3 mg) as a solid single diastereomer (Example 368-B). $^1$H NMR (300 MHz, $CD_3OD$) δ 8.16 (s, 1H), 7.34-7.12 (m, 2H), 5.60-5.54 (m, 1H), 4.78-4.68 (m, 1H), 4.01-3.92 (m, 4H), 3.56-3.41 (m, 1H), 3.01-2.91 (m, 1H), 2.28-2.02 (m, 2H), 2.01-1.83 (m, 5H), 1.80-1.54 (m, 5H). LCMS (ESI): 582.10 $[M+H]^+$.

Example 369. A Diastereomeric Mixture of (R)—N-((1r,4R)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (R)—N-((1s,4S)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide

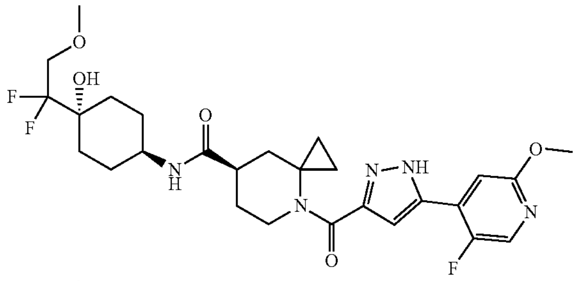

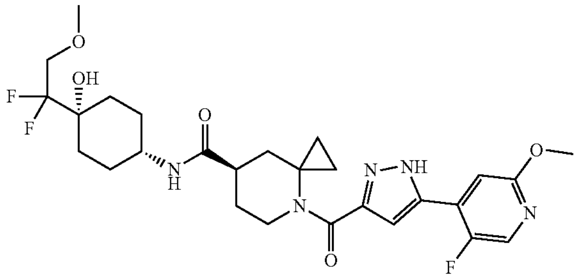

Step-1. Ethyl 2,2-difluoro-2-(8-((4-methoxybenzyl)oxy)-1,4-dioxaspiro[4.5]decan-8-yl)acetate

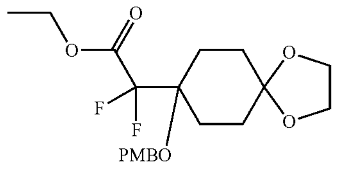

NaH (522.4 mg, 13.06 mmol, 60% dispersion in mineral oil) was added portionwise to a solution of ethyl 2,2-difluoro-2-(8-hydroxy-1,4-dioxaspiro[4.5]decan-8-yl)acetate (Step-1 from synthesis of Intermediate 537, 2.44 g, 8.71 mmol) in DMF (21.70 mL) at 0° C. After 5 min stirring at 0° C., 1-(chloromethyl)-4-methoxybenzene (1.64 g, 10.45 mmol) was slowly added to the reaction mixture and allowed to reach 22° C. The reaction mixture was stirred at 22° C. for 16 h. The reaction mixture was diluted with water and extracted three times with $Et_2O$. The combined organic layers were washed twice with water, dried over $Na_2SO_4$, filtered and concentrated under reduced pressure. The residue was purified by silica gel column chromatography eluting with 0% to 35% cyclohexane/EtOAc to obtain the title compound (2.95 g) as a solid. $^1H$ NMR (400 MHz, $CDCl_3$) δ 7.30-7.20 (m, 2H), 6.91-6.81 (m, 2H), 4.55 (s, 2H), 4.28 (q, 2H), 3.96-3.92 (m, 4H), 3.79 (s, 3H), 2.21-2.10 (m, 2H), 1.89 (dtd, 4H), 1.73-1.62 (m, 2H). $^1H$ NMR (376 MHz, $CDCl_3$) δ −111.01.

Step-2. 2,2-difluoro-2-(8-((4-methoxybenzyl)oxy)-1,4-dioxaspiro[4.5]decan-8-yl)ethan-1-ol

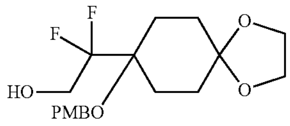

$LiAlH_4$ (3.35 mL, 8.03 mmol, 2.4 M in THF) was slowly added to a solution of ethyl 2,2-difluoro-2-(8-((4-methoxybenzyl)oxy)-1,4-dioxaspiro[4.5]decan-8-yl)acetate (Step-1, 2.68 g, 6.69 mmol) in anhydrous THF (33.40 mL) at 0° C. The reaction was stirred at 22° C. for 2 h. The resulting mixture was diluted with $Et_2O$ and cooled to 0° C., and then water was slowly added, followed by 15% aqueous NaOH solution and water. The resulting mixture was warmed to 22° C. and stirred for 15 min. The organic layers were combined, dried over anhydrous $Na_2SO_4$, filtered, and concentrated under reduced pressure. The residue was purified by silica gel column chromatography eluting with 0% to 60% cyclohexane/EtOAc to obtain the title compound (2.35 g) as a solid. $^1H$ NMR (400 MHz, $CDCl_3$) δ 7.29-7.21 (m, 2H), 6.88 (d, 2H), 4.53 (s, 2H), 4.02-3.89 (m, 6H), 3.80 (s, 3H), 2.27 (s, 1H), 2.12-2.02 (m, 2H), 2.00-1.80 (m, 4H), 1.73-1.62 (m, 2H).

Step-3. 8-(1,1-difluoro-2-methoxyethyl)-8-((4-methoxybenzyl)oxy)-1,4-dioxaspiro[4.5]decane

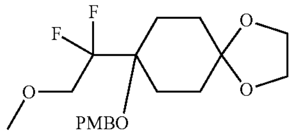

NaH (50.2 mg, 1.26 mmol, 60% in mineral oil) was added to a solution of 2,2-difluoro-2-(8-((4-methoxybenzyl)oxy)-1,4-dioxaspiro[4.5]decan-8-yl)ethan-1-ol (Step-2, 300.0 mg, 0.84 mmol) in DMF (2.80 mL) at 0° C. After 15 min, MeI (237.6 mg, 1.67 mmol) was added and the resulting mixture was stirred at 22° C. for 16 h. The reaction mixture was diluted with water and extracted with $Et_2O$. The combined organics were washed with water, dried over anhydrous sodium sulfate and concentrated under reduced pressure. The residue was purified by silica gel column chromatography eluting with 0% to 30% cyclohexane/EtOA to obtain the title compound (281.3 mg, 0.76 mmol) as a solid. $^1H$ NMR (400 MHz, $CDCl_3$) δ 7.32-7.26 (m, 2H), 6.90 (d, 2H), 4.53 (s, 2H), 3.99-3.96 (m, 4H), 3.87-3.75 (m, 5H), 3.49 (s, 3H), 2.09 (d, 2H), 1.91 (dtd, 4H), 1.69 (d, 2H).

Step-4. 4-(1,1-difluoro-2-methoxyethyl)-4-hydroxycyclohexan-1-one

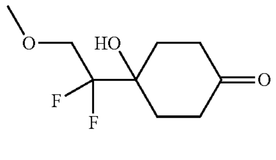

TFA (1.08 mL, 14.02 mmol) was added to a solution of 8-(1,1-difluoro-2-methoxyethyl)-8-((4-methoxybenzyl)oxy)-1,4-dioxaspiro[4.5]decane (Step-3, 261.0 mg, 0.70 mmol) and 1,2-dimethoxybenzene (96.8 mg, 0.70 mmol) in DCM (2.33 mL). The reaction mixture was stirred at 22° C. for 16 h. The reaction mixture was diluted with DCM and poured into sat. aqueous sodium bicarbonate. Layers were separated and the aqueous layer was further extracted with DCM. The combined organics were dried over sodium sulfate and concentrated under reduced pressure. The residue was purified by silica gel column chromatography eluting with 0% to 35% cyclohexane/EtOAc to obtain the title compound (134.4 mg, 0.65 mmol) as a solid. $^1H$ NMR (400 MHz, $CDCl_3$) δ 3.84 (t, 2H), 3.49 (s, 3H), 3.02 (s, 1H), 2.75 (td, 2H), 2.32 (ddt, 2H), 2.20-1.96 (m, 4H).

Step-5. 4-(1,1-difluoro-2-methoxyethyl)-4-hydroxy-cyclohexan-1-one oxime

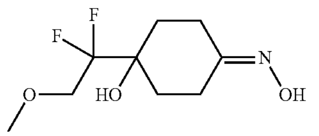

A solution of hydroxylamine hydrochloride (45.9 mg, 0.66 mmol), sodium acetate (59.1 mg, 0.72 mmol) in MeOH (3.00 mL) was stirred at 22° C. for 30 min. Then a solution of 4-(1,1-difluoro-2-methoxyethyl)-4-hydroxycyclohexan-1-one (Step-4, 125.0 mg, 0.60 mmol) in MeOH (1.00 mL) was added to the reaction mixture. The reaction mixture was stirred at 60° C. for 16 h. The reaction mixture was then cooled to 22° C. and MeOH was removed under reduced pressure. The residue was diluted with water and EtOAc. The aqueous was further extracted with EtOAc. The combined organics were dried over anhydrous sodium sulfate and concentrated under reduced pressure. The residue was purified by silica gel column chromatography eluting with 0% to 100% EtOAc/cyclohexane to obtain the title compound (129.1 mg, 0.58 mmol) as a solid. $^1H$ NMR (400 MHz, $CDCl_3$) δ 3.81 (t, 2H), 3.48 (s, 3H), 3.31-3.21 (m, 1H), 2.56 (td, 1H), 2.42-2.32 (m, 1H), 2.20 (td, 1H), 1.97 (dtt, 2H), 1.80 (dtd, 2H).

Step-6. tert-butyl (4-(1,1-difluoro-2-methoxyethyl)-4-hydroxycyclohexyl)carbamate

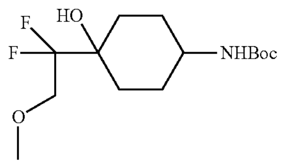

$NaBH_4$ (168.1 mg, 4.44 mmol) was added to a solution of 4-(1,1-difluoro-2-methoxyethyl)-4-hydroxycyclohexan-1-one oxime (Step-5, 124.0 mg, 0.56 mmol) and nickel(II) chloride hexahydrate (171.6 mg, 0.72 mmol) in MeOH (11.10 mL) at −78° C. The resulting mixture was allowed to warm up to 0° C. and stirred for 4 h. $Boc_2O$ (181.9 mg, 0.83 mmol) was then added and the reaction mixture was warmed to 22° C. and stirred for 16 h. The reaction mixture was quenched with brine at 0° C. Volatiles were removed under reduced pressure. The residue was purified by silica gel column chromatography eluting with 0% to 60% EtOAc/cyclohexane to obtain the title compound (154.5 mg, 0.50 mmol) as a solid. $^1H$ NMR (400 MHz, $CDCl_3$) δ 4.71-4.28 (m, 1H), 3.87-3.72 (m, 2H), 3.51-3.33 (m, 4H), 1.99-1.49 (m, 9H), 1.48-1.39 (m, 9H). $^{19}F$ NMR (376 MHz, DMSO) δ −119.65, −119.76.

Step-7. 4-amino-1-(1,1-difluoro-2-methoxyethyl)cyclohexan-1-ol

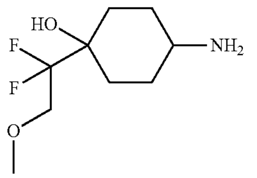

TFA (2.00 mL) was added to a stirred solution of tert-butyl N-[4-(1,1-difluoro-2-methoxyethyl)-4-hydroxycyclohexyl]carbamate (Step-6, 90.0 mg, 0.29 mmol) in DCM (2.00 mL). The resulting mixture was stirred at 22° C. for 30 min. The solution was concentrated under reduced pressure to obtain the title compound (60.0 mg) as an oil. LCMS (ESI): 210.1 [M+H]$^+$.

Step-8. (R)—N-((1r,4R)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (R)—N-(1s,4S)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide

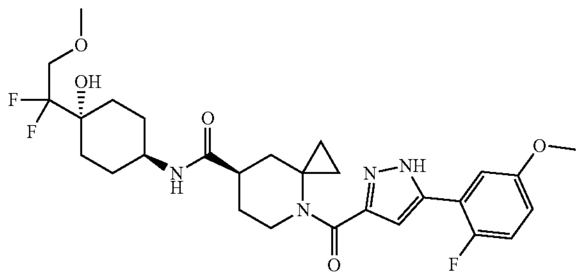

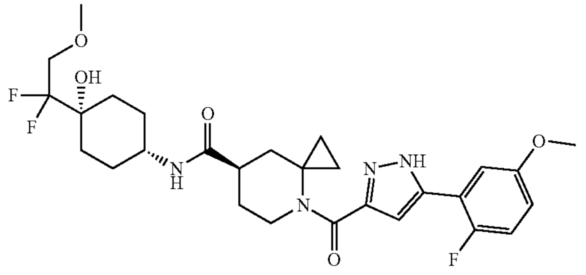

HOBt (58.5 mg, 0.43 mmol), EDCI (83.0 mg, 0.43 mmol), and 4-amino-1-(1,1-difluoro-2-methoxyethyl)cyclohexan-1-ol (60.4 mg, 0.29 mmol) were added to a stirred solution of (S)-4-[5-(5-fluoro-2-methoxypyridin-4-yl)-1H- pyrazole-3-carbonyl]-4-azaspiro[2.5]octane-7-carboxylic acid (INTERMEDIATE 527-A, 108.0 mg, 0.29 mmol) and DIPEA (223.7 mg, 1.73 mmol) in DMF (3.00 mL). The resulting mixture was stirred at 25° C. for 2 h. The solution was diluted with EtOAc and washed with water. The residue was purified by silica gel column chromatography eluting with DCM/MeOH (10/1 v/v) to obtain (R)—N-((1r,4R)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (R)—N-((1s,4S)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide (108 mg) as a solid mixture of diastereomers. LCMS (ESI): 566.3 $[M+H]^+$.

This mixture of two diastereomers (108.0 mg) was separated using Chiral Prep-HPLC.

Column: CHIRALPAK IE column

Column dimension: 2×25 cm, 5 μm

Mobile Phase: MTBE (0.5% 2M $NH_3$·MeOH):EtOH=50:50 hold for 13 min

Flow rate: 16 mL/min

Detection: 220/254 nm

Example 369-A. The first eluting diastereomer (16.2 mg) was obtained as a solid.

The first eluting diastereomer had a retention time of 5.86 min.

$^1$H NMR (400 MHz, DMSO-$d_6$) δ 14.19-13.80 (m, 1H), 8.33-8.21 (m, 1H), 7.82-7.66 (m, 1), 7.35-7.26 (m, 1H), 7.02 (s, 1H), 5.09 (s, 1H), 4.91-4.29 (m, 1H), 3.99-3.81 (m, 3H), 3.80-3.68 (m, 3H), 3.33 (s, 3H), 2.93-2.62 (m, 1H), 2.38-2.10 (m, 1H), 1.99-1.60 (m, 5H), 1.60-1.31 (m, 5H), 1.32-1.04 (m, 2H), 1.01-0.91 (m, 1H), 0.90-0.42 (m, 3H). LCMS (ESI): 566 $[M+H]^+$.

Example 369-B. The second eluting diastereomer (38.6 mg) was obtained as a solid.

The second eluting diastereomer had a retention time of 10.12 min.

$^1$H NMR (400 MHz, DMSO-$d_6$) δ 13.98 (s, 1H), 8.25 (d, 1H), 7.72 (d, 1H), 7.30 (d, 1H), 7.01 (s, 1H), 5.13 (s, 1H), 4.67-4.08 (m, 1H), 3.85 (s, 3H), 3.79-3.64 (m, 2H), 3.60-3.37 (m, 1H), 3.29 (s, 3H), 2.67-2.62 (m, 1H), 2.36-2.04 (m, 1H), 1.81-1.52 (m, 5H), 1.51-1.32 (m, 5H), 1.32-0.69 (m, 4H), 0.69-0.50 (m, 2H). LCMS (ESI): 566 $[M+H]^+$.

Example 370. A Diastereomeric Mixture of (R)—N-((5S,8s)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide and (R)—N-((5R,8r)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide

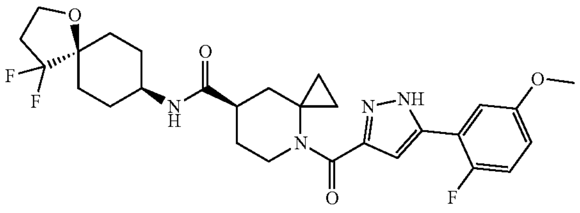

-continued

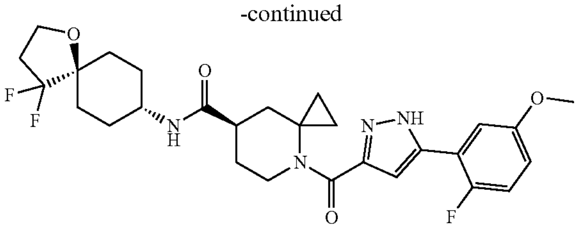

Step-1. 4,4-difluoro-1-oxaspiro[4.5]decan-8-amine

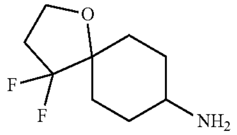 [SMILES: NC1CCC2(CC1)OCCC2(F)F]

TFA (3.00 mL) was added to a stirred solution of tert-butyl N-[4,4-difluoro-1-oxaspiro[4.5]decan-8-yl]carbamate (INTERMEDIATE 540, 180.0 mg, 0.62 mmol) in DCM (3.00 mL). The resulting mixture was stirred at 25° C. for 30 min. The solution was concentrated under reduced pressure to obtain the title compound (118.0 mg) as an oil. LCMS (ESI): 192.1 $[M+H]_+$.

Step-2. (R)—N-((5S,8s)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide and (R)—N-((5R,8r)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide

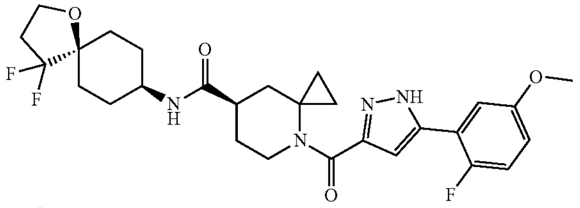

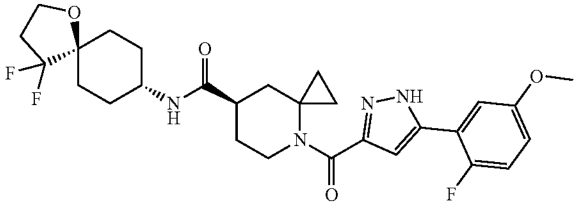

HOBt (108.3 mg, 0.80 mmol), EDCI (153.6 mg, 0.80 mmol), and 4,4-difluoro-1-oxaspiro[4.5]decan-8-amine (112.4 mg, 0.59 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 200.0 mg, 0.53 mmol) and DIPEA (414.3 mg, 3.20 mmol) in DMF (5.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (R)—N-((5S,8s)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide and (R)—N-((5R,8r)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide (190.0 mg) as an oil mixture of diastereomers. LCMS (ESI): 548.2 $[M+H]^+$.

This mixture of two diastereomers (190.0 mg) was separated using Chiral Prep-SFC.

Column: CHIRAL ART Cellulose-SB column

Column dimension: 3×25 cm, 5 μm

Mobile Phase A: $CO_2$; Mobile Phase B: MeOH (0.1% 2M $NH_3$·MeOH)

Flow rate: 80 mL/min

Gradient: isocratic 50% B

Detection: 220 nm

Example 370-A. The first eluting diastereomer (44.5 mg) was obtained as a solid.

The first eluting diastereomer had a retention time of 2.61 min.

$^1$H NMR (400 MHz, DMSO-$d_6$) δ 14.12-13.71 (m, 1H), 8.32-8.21 (m, 1H), 7.80 (d, 1H), 7.34-7.27 (m, 1H), 7.02 (s, 1H), 4.61-4.44 (m, 1H), 4.04-3.64 (m, 6H), 3.30 (s, 1H), 2.85-2.61 (m, 1H), 2.46-2.29 (m, 2H), 2.26-2.03 (m, 1H), 1.85-1.57 (m, 5H), 1.56-1.33 (m, 5H), 1.33-0.74 (m, 3H), 0.73-0.45 (m, 2H). LCMS (ESI): 548.55 $[M+H]^+$.

Example 370-B. The second eluting diastereomer (37.7 mg) was obtained as a solid.

The second eluting diastereomer had a retention time of 3.17 min.

$^1$H NMR (400 MHz, DMSO-$d_6$) δ 14.19-13.76 (m, 1H), 8.35-8.18 (m, 1H), 7.73 (d, 1H), 7.34-7.26 (m, 1H), 7.02 (s, 1H), 4.50 (s, 1H), 3.99-3.71 (m, 5H), 3.50 (s, 1H), 3.29 (s, 1H), 2.70-2.63 (m, 1H), 2.46-2.28 (m, 2H), 2.24-2.03 (m, 1H), 1.85-1.60 (m, 5H), 1.59-1.30 (m, 5H), 1.29-0.75 (m, 3H), 0.72-0.46 (m, 2H). LCMS (ESI): 548.55 $[M+H]^+$.

Example 371. (S)—N-((5,6-dihydro-8H-imidazo[2,1-c][1,4]oxazin-2-yl)methyl)-4-(5-(5-fluoro-2-methoxypyridin-4-yl)-1H-pyrazole-3-carbonyl)-4-azaspiro[2.5]octane-7-carboxamide

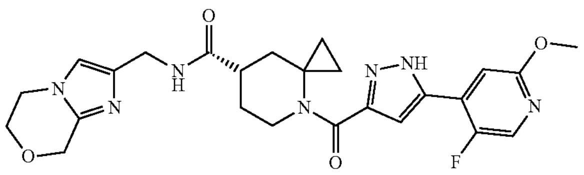

The title compound was prepared using a procedure similar to the one described for the synthesis of Example 325, except 1-[5H,6H,8H-imidazo[2,1-c][1,4]oxazin-2-yl]methanamine was used as a starting material. The residue was purified by reverse phase column chromatography (using the following conditions: Column: C18; mobile phase A: Water (0.5% $NH_4HCO_3$), mobile phase B: MeCN; gradient: 15 B to 40 B in 30 min; 220/254 min) to obtain the title compound (10.7 mg) as a solid.

$^1$H NMR (300 MHz, DMSO-$d_6$) δ 14.00 (s, 1H), 8.27 (s, 1H), 8.12 (s, 1H), 7.32 (d, 1H), 7.04 (s, 1H), 6.90 (s, 1H), 4.70-4.64 (m, 2H), 4.49-4.43 (m, 1H), 4.13-4.05 (m, 2H), 3.99-3.92 (m, 4H), 3.88 (s, 3H), 3.27-2.90 (m, 1H), 2.77-2.70 (m, 1H), 2.22-2.16 (m, 1H), 1.78-1.47 (m, 2H), 1.26-1.20 (m, 1H), 0.99-0.93 (m, 2H), 0.66-0.60 (m, 2H). LCMS (ESI): 510.5 $[M+H]^+$.

Example 372. A Diastereomeric Mixture of (S)-4-(5-(5-fluoro-2-methoxypyridin-4-yl)-1H-pyrazole-3-carbonyl)-N-(((1R,3S)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1S,3S)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1S,3R)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1R,3R)-1-imino-2,2-dimethyl-1-oxidotetrahydro-1H-1λ$^6$-thiophen-3-yl)methyl)-4-azaspiro[2.5]octane-7-carboxamide

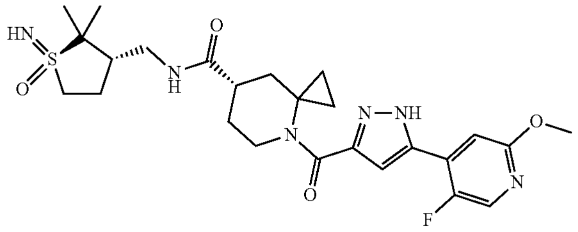

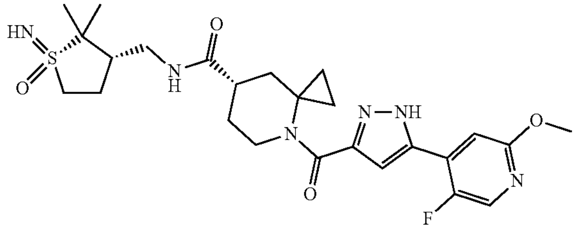

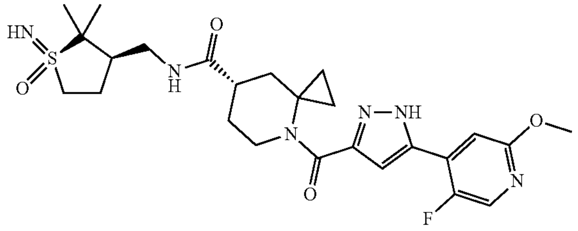

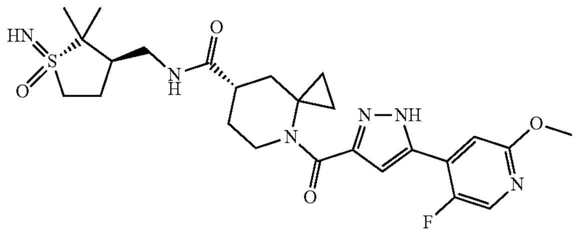

Step-1. 3-(aminomethyl)-1-imino-2,2-dimethyltetrahydro-1H-1λ$^6$-thiophene 1-oxide

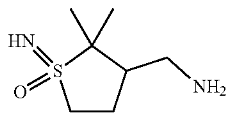

TFA (1.50 mL) was added to a stirred mixture of tert-butyl ((1-imino-2,2-dimethyl-1-oxidotetrahydro-1H-1λ$^6$-thiophen-3-yl)methyl)carbamate (150.0 mg, 0.54 mmol, CAS #: 2243512-1H-1λ$^6$, Enamine Ltd) in DCM (1.50 mL) at 0° C. The resulting mixture was stirred at 25° C. for 2 h. The resulting mixture was concentrated under reduced pressure to obtain the title compound (80.0 mg) as a solid. LCMS (ESI): 177.10 $[M+H]^+$.

Step-2. (S)-4-(5-(5-fluoro-2-methoxypyridin-4-yl)-1H-pyrazole-3-carbonyl)-N-(((1R,3S)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1S,3S)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1S,3R)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N—(((R,3R)-1-imino-2,2-dimethyl-1-oxidotetrahydro-1H-1λ$^6$-thiophen-3-yl)methyl)-4-azaspiro[2.5]octane-7-carboxamide

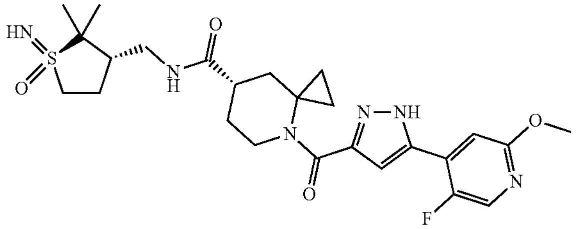

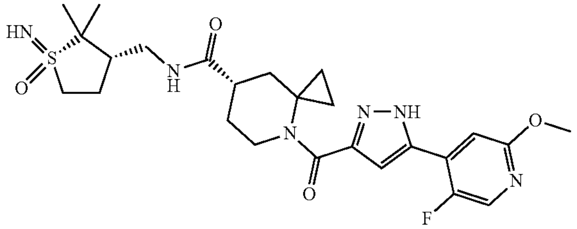

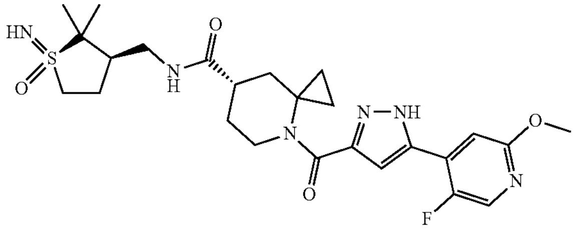

-continued

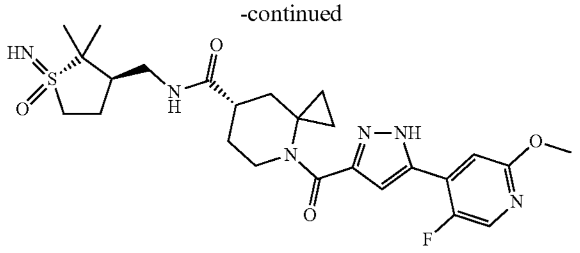

HATU (412.7 mg, 1.09 mmol) and 3-(aminomethyl)-1-imino-2,2-dimethyltetrahydro-1H-1λ$^6$-thiophene 1-oxide (Step-1, 95.7 mg, 0.54 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 203.6 mg, 0.54 mmol) and DIPEA (0.70 mL, 5.43 mmol) in DMF (6.00 mL). The solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC eluting with DCM/MeOH (18/1 v/v) to obtain (S)-4-(5-(5-fluoro-2-methoxypyridin-4-yl)-1H-pyrazole-3-carbonyl)-N-(((1R,3S)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1S,3S)-1-imino-2,2-dimethyl-1-oxidotetrahydro-1H-1λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1S,3R)-1-imino-2,2-dimethyl-1-oxidotetrahydro-1H-λ$^6$-thiophen-3-yl)methyl)-4-azaspiro[2.5]octane-7-carboxamide and (S)-4-(5-(5-fluoro-2-methoxypyridin-4-yl)-1H-pyrazole-3-carbonyl)-N-(((1R,3R)-1-imino-2,2-dimethyl-1-oxidotetrahydro-1H-1λ$^6$-thiophen-3-yl)methyl)-4-azaspiro[2.5]octane-7-carboxamide in two fractions, each containing two diastereomers.

Example 372-A. The first eluting peak (120.0 mg) was obtained as a solid Mixture of Diastereomers.

The first eluting peak had Rf value of 0.5.

The first eluting peak was further purified by Prep-HPLC (using the following conditions: Column: XBridge Prep OBD C18 Column, 30×150 mm, 5 μm; Mobile Phase A: Water (10 mM $NH_4HCO_3$), Mobile Phase B: MeCN; Flow rate: 60 mL/min; Gradient: 19% B to 49% B in 7 min; Wave Length: 254 nm; RT1 (min): 6.5) to obtain the title compound (100.0 mg) as a solid mixture of diastereomers.

$^1$H NMR (300 MHz, DMSO-$d_6$) δ 13.98 (s, 1H), 8.27 (s, 1H), 7.96 (d, 1H), 7.32 (d, 1H), 7.03 (d, 1H), 4.47-4.41 (m, 1H), 3.88 (s, 3H), 3.49-3.43 (m, 1H), 3.24-2.90 (m, 5H), 2.69-2.63 (m, 1H), 2.23-1.97 (m, 2H), 1.83-1.42 (m, 3H), 1.32-1.03 (m, 7H), 0.77-0.94 (m, 2H), 0.66-0.50 (m, 2H). LCMS (ESI): 533.4 $[M+H]^+$.

Example 372-B. The second eluting peak (90.0 mg) was obtained as a solid Mixture of Diastereomers.

The second eluting peak had Rf value of 0.3.

The second eluting peak was further purified by Prep-HPLC (using the following conditions: Column: YMC-Actus Triart C18 ExRS column, 30×150 mm, 5 μm; Mobile Phase A: Water (10 mM $NH_4HCO_3$), Mobile Phase B: MeCN; Flow rate: 60 mL/min; Gradient: 16% B to 35% B in 8 min, 35% B; Wave Length: 254/220 nm; RT1 (min): 7.8) to obtain the title compound (70.0 mg) as a solid mixture of diastereomers.

H[1]H NMR (300 MHz, DMSO-$d_6$) δ 13.97 (s, 1H), 8.27 (d, 1H), 7.96 (s, 1H), 7.32 (d, 1H), 7.03 (d, 1H), 4.47-4.41 (m, 1H), 3.88 (s, 3H), 3.67-3.61 (m, 1H), 3.30-2.82 (m, 5H), 2.70-2.64 (m, 1H), 2.34-1.94 (m, 3H), 1.84-1.48 (m, 3H), 1.22-1.06 (m, 7H), 0.97-0.91 (m, 1H), 0.66-0.60 (m, 2H). LCMS (ESI): 533.4 $[M+H]^+$.

The first eluting peak (Example 372-A, 100.0 mg) was further purified using Chiral Prep-HPLC to separate the two diastereomers.

Column: CHIRALPAK IE column

Column dimension: 2×25 cm, 5 μm

Mobile Phase: MTBE (0.5% 2M $NH_3$·MeOH): 1/1 MeOH/DCM=30:70 hold for 18 min

Flow rate: 20 mL/min

Detection: 220/254 nm

Example 372-C. The first eluting diastereomer (31.9 mg) was obtained as a solid.

The first eluting diastereomer had a retention time of 11.53 min.

$^1$H NMR (400 MHz, DMSO-$d_6$) δ 13.97 (d, 1H), 8.26 (d, 1H), 7.96 (s, 1H), 7.30 (s, 1H), 7.01 (s, 1H), 4.65-4.34 (m, 1H), 3.85 (s, 3H), 3.24-2.83 (m, 5H), 2.76-2.55 (m, 2H), 2.29-1.89 (m, 3H), 1.85-1.37 (m, 3H), 1.33-1.02 (m, 8H), 0.76-0.39 (m, 2H). LCMS (ESI): 533.5 $[M+H]^+$.

Example 372-D. The second eluting diastereomer (32.0 mg) was obtained as a solid.

The second eluting diastereomer had a retention time of 15.64 min.

$^1$H NMR (400 MHz, DMSO-$d_6$) δ 14.06-14.01 (m, 1H), 8.25 (s, 1H), 7.99 (s, 1H), 7.30 (d, 1H), 7.01 (s, 1H), 4.53-4.48 (m, 1H), 3.85 (s, 3H), 3.30-2.88 (m, 6H), 2.75-2.55 (m, 1H), 2.25-1.92 (m, 3H), 1.84-1.49 (m, 3H), 1.30-1.07 (m, 8H), 0.73-0.44 (m, 2H). LCMS (ESI): 533.5 $[M+H]^+$.

The second eluting peak (Example 372-B, 70.0 mg) was further purified using Chiral Prep-HPLC to separate the two diastereomers.

Column: CHIRALPAK IE column

Column dimension: 2×25 cm, 5 μm

Mobile Phase: MTBE (0.5% 2 M $NH_3$·MeOH): 1/1 MeOH/DCM=30:70 hold for 23 min

Flow rate: 20 mL/min

Detection: 220/254 nm

Example 372-E. The first eluting diastereomer (22.5 mg) was obtained as a solid.

The first eluting diastereomer had a retention time of 10.15 min.

$^1$H NMR (400 MHz, DMSO-$d_6$) δ 14.24-13.51 (m, 1H), 8.45-8.11 (m, 1H), 7.95 (s, 1H), 7.29 (d, 1H), 7.02 (s, 1H), 4.66-4.35 (m, 1H), 3.85 (s, 3H), 3.69-3.57 (m, 1H), 3.27-2.78 (m, 5H), 2.55-2.70 (m, 1H), 2.28-1.89 (m, 2H), 1.83-1.38 (m, 3H), 1.33-0.78 (m, 9H), 0.73-0.44 (m, 2H). LCMS (ESI): 533.5 $[M+H]^+$.

Example 372-F. The second eluting diastereomer (23.5 mg) was obtained as a solid.

The second eluting diastereomer had a retention time of 12.54 min.

$^1$H NMR (400 MHz, DMSO-$d_6$) δ 13.99 (s, 1H), 8.45-8.09 (m, 1H), 7.96 (s, 1H), 7.39-7.15 (m, 1H), 7.01 (s, 1H), 4.64-4.24 (m, 1H), 3.85 (s, 3H), 3.73-3.57 (m, 1H), 3.28-2.79 (m, 5H), 2.75-2.54 (m, 1H), 2.39-1.92 (m, 3H), 1.88-1.36 (m, 2H), 1.34-0.78 (m, 9H), 0.76-0.24 (m, 2H). LCMS (ESI): 533.5 $[M+H]^+$.

Example 373. A Diastereomeric Mixture of (S)-4-(5-(5-fluoro-2-methoxypyridin-4-yl)-1H-pyrazole-3-carbonyl)-N-((1r,4S)-4-hydroxy-4-(perfluoroethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1s,4R)-4-hydroxy-4-(perfluoroethyl)cyclohexyl)-4-azaspiro[2.5]octane-7-carboxamide

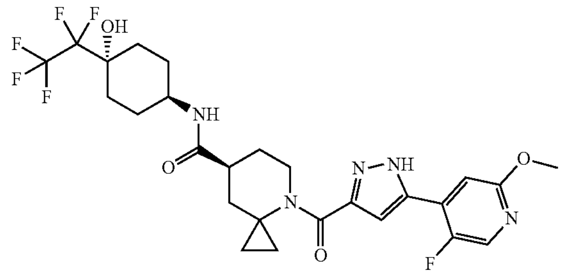

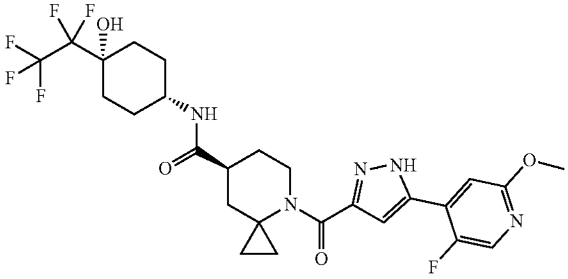

Step-1. 8-(perfluoroethyl)-1,4-dioxaspiro[4.5]decan-8-ol

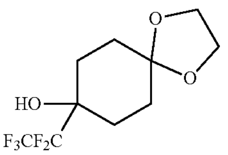

1,4-dioxaspiro[4.5]decan-8-one (1.00 g, 6.40 mmol) was dissolved in THF (23.70 mL) followed by sequential addition of trimethyl(perfluoroethyl)silane (2.51 g, 13.07 mmol) and tetrabutylammonium fluoride (13.32 mL, 1 M, 13.32 mmol) at 0° C., and then the resulting mixture was stirred at 22° C. The reaction mixture was quenched by stirring with $NH_4Cl$ (sat. aqueous) for 10 min at 22° C. The reaction mixture was then concentrated under vacuum, redissolved in DCM, and washed with water. The layers were separated and the aqueous was further extracted with DCM. The combined organic layers were dried over $Na_2SO_4$, filtered, and concentrated under vacuum. The resulting residue was purified by silica gel column chromatography eluting with 25% to 45% EtOAc/cyclohexane to obtain the title compound (1.26 g). $^1$H NMR (400 MHz, $CDCl_3$) δ 4.02-3.91 (m, 4H), 2.06-1.83 (m, 6H), 1.75 (s, 1H), 1.72-1.64 (m, 2H).

Step-2. 4-hydroxy-4-(perfluoroethyl)cyclohexan-1-one

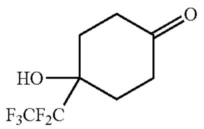

TFA (4.60 mL, 59.74 mmol) was added to a solution of 8-(perfluoroethyl)-1,4-dioxaspiro[4.5]decan-8-ol (Step-1, 1.10 g, 3.98 mmol) in DCM (19.91 mL). The resulting mixture was stirred at 22° C. for 16 h. The reaction mixture was concentrated under vacuum, re-dissolved in DCM, washed with $NaHCO_3$ (sat. aqueous), brine, dried over $Na_2SO_4$, filtered, and concentrated under vacuum. The resulting residue was purified by silica gel column eluting with 0% to 100% EtOA/DCM to obtain the title compound (240.0 mg) as an oil. $^1$H NMR (400 MHz, $CDCl_3$) δ 2.74 (td, 2H), 2.44-2.35 (m, 2H), 2.29-2.19 (m, 2H), 2.13 (td, 2H).

Step-3. 4-hydroxy-4-(perfluoroethyl)cyclohexan-1-one oxime

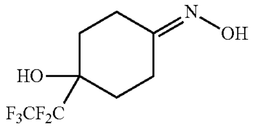

A solution of hydroxylamine hydrochloride (79.0 mg, 1.14 mmol), sodium acetate (102.0 mg, 1.24 mmol), and MeOH (1.30 mL) was stirred for 30 min. Then 4-hydroxy-4-(perfluoroethyl)cyclohexan-1-one (Step-2, 240.0 mg, 1.03 mmol) was added as a solution in MeOH (1.3 mL). The reaction mixture was then refluxed at 60° C. for 24 h. The reaction mixture was then cooled and diluted with EtOAc and water. The organic layer was washed with water and brine. The organic layer was dried over $Na_2SO_4$, filtered, and concentrated under vacuum. The residue was purified by silica gel column chromatography eluting with 25% to 45% EtOAc/cyclohexane to obtain the title compound (170.0 mg) as a solid. $^1$H NMR (400 MHz, $CDCl_3$) δ 3.37-3.27 (m, 1H), 2.53 (td, 1H), 2.44-2.34 (m, 1H), 2.16 (td, 1H), 2.11-2.01 (m, 2H), 1.96-1.79 (m, 3H).

Step-4. tert-butyl (4-hydroxy-4-(perfluoroethyl)cyclohexyl)carbamate

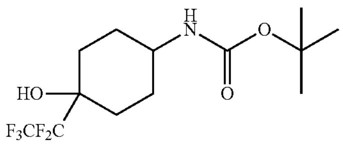

$NaBH_4$ (208.2 mg, 5.50 mmol) was added to a solution of 4-hydroxy-4-(perfluoroethyl)cyclohexan-1-one oxime (Step-3, 170.0 mg, 0.69 mmol) and nickel(II) chloride hexahydrate (212.51 mug, 0.89 mmol) in MeOH (49.00 mL) at −78° C. over 10 min. After complete addition the resulting slurry was allowed to warm up to 0° C. and stirred at this temperature for 6.5 h. $Boc_2O$ (225.0 mg, 1.03 mmol) was then added and the reaction mixture was warmed to 22° C. for 16 h. The reaction mixture was quenched with brine at 0° C. MeOH was removed under vacuum and the resulting slurry was redissolved in $Et_2O$. The organic layer was separated and the aqueous phase was extracted with $Et_2O$. The organic layers were combined, washed with brine, dried over $Na_2SO_4$, filtered, and concentrated under vacuum to obtain the title compound (209.0 mg) as a solid. $^1$H NMR (400 MHz, $CDCl_3$, mixture of diastereomers) δ 4.64-4.34 (m, 1H), 3.87-3.38 (m, 1H), 1.94 (d, 3H), 1.83-1.68 (m, 3H), 1.65-1.33 (m, 1H); 19FNMR (400 MHz, $CDCl_3$) δ −78.38, −78.50, −126.63, −126.82; TLC-MS (APCI): $[M+H]^-$: 332.1.

Step-5. 4-amino-1-(1,1,2,2,2-pentafluoroethyl)cyclohexan-1-ol

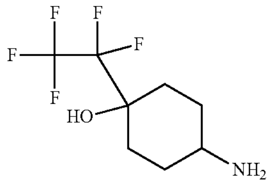 [SMILES: NC1CCC(O)(C(F)(F)C(F)(F)F)CC1]

TFA (2.00 mL) was added to a stirred solution of tert-butyl N-[4-hydroxy-4-(1,1,2,2,2-pentafluoroethyl)cyclohexyl]carbamate (Step-4, 160.0 mg, 0.48 mmol) in DCM (2.00 mL) at 0° C. The resulting mixture was stirred at 22° C. for 1 h. The resulting mixture was concentrated under reduced pressure to obtain the title compound (105.0 mg) as an oil. LCMS (ESI): 234.1 $[M+H]^+$.

Step-6. (S)-4-(5-(5-fluoro-2-methoxypyridin-4-yl)-1H-pyrazole-3-carbonyl)-N-((1r,4S)-4-hydroxy-4-(perfluoroethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1s,4R)-4-hydroxy-4-(perfluoroethyl)cyclohexyl)-4-azaspiro[2.5]octane-7-carboxamide

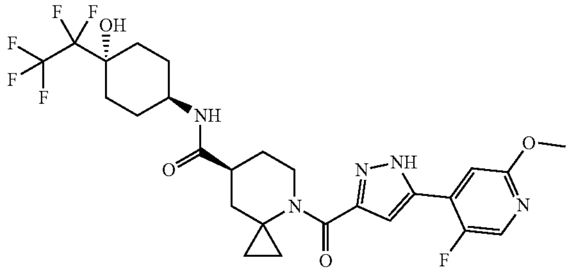

-continued

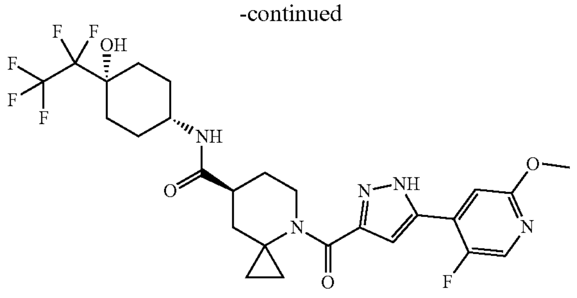

HOBt (129.8 mg, 0.96 mmol), EDCI (184.2 mg, 0.96 mmol), and 4-amino-1-(1,1,2,2,2-pentafluoroethyl)cyclohexan-1-ol (112.00 mg, 0.480 mmol, 1.00 equiv) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 197.8 mg, 0.53 mmol) and DIPEA (310.4 mg, 2.40 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column, C18; mobile phase A: Water (0.5% $NH_4HCO_3$), mobile phase B: MeCN; gradient: 35 B to 55 B in 20 min; 220/254 am) to obtain (S)-4-(5-(5-fluoro-2-methoxypyridin-4-yl)-1H-pyrazole-3-carbonyl)-N-((1r,4S)-4-hydroxy-4-(perfluoroethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1s,4R)-4-hydroxy-4-(perfluoroethyl)cyclohexyl)-4-azaspiro[2.5]octane-7-carboxamide (130.0 mg) as a solid mixture of diastereomers (Example 373). $^1H$ NMR (400 MHz, $CD_3OD$) δ 8.11 (d, 1H), 7.51-6.94 (m, 2H), 4.80-4.19 (m, 1H), 3.92 (s, 3H), 3.64-3.60 (m, 1H), 3.16-2.53 (m, 2H), 2.51-2.19 (m, 1H), 2.06-1.50 (m, 10H), 1.43-0.88 (m, 2H), 0.86-0.46 (m, 3H). LCMS (ESI): 590.4 $[M+H]^+$.

This mixture of two diastereomers (130.0 mg) was separated using Chiral Prep-HPLC.

Column: CHIRALPAK IG column

Column dimension: 2×25 cm, 5 min

Mobile Phase: 3/1 hexanes/DCM (0.5% 2 M $NH_3$·MeOH):9/1 DCM/EtOH:=70:30 hold for 11 min Flow rate: 20 mL/min Detection: 220/254 nm Example 373-A. The first eluting diastereomer (28.7 mg) was obtained as a solid.

The first eluting diastereomer had a retention time of 4.79 min.

$^1H$ NMR (400 MHz, DMSO-$d_6$) δ 14.19-13.49 (m, 1H), 8.29-8.20 (m, 1H), 7.80 (s, 1H), 7.30 (s, 1H), 7.01 (s, 1H), 5.78 (s, 1H), 4.52-4.48 (m, 1H), 3.85 (s, 3H), 3.82-3.77 (m, 1H), 2.80-2.76 (m, 1H), 2.19-2.14 (m, 1H), 1.80-1.75 (m, 5H), 1.58-1.52 (m, 6H), 1.34-0.77 (m, 3H), 0.77-0.33 (m, 2H). LCMS (ESI): 590.50 $[M+H]^+$.

Example 373-B. The second eluting diastereomer (53.7 mg) was obtained as a solid.

The second eluting diastereomer had a retention time of 7.36 min.

$^1H$ NMR (400 MHz, DMSO-$d_6$) δ 13.99 (s, 1H), 8.24 (s, 1H), 7.79-7.73 (m, 1H), 7.30 (d, 1H), 7.01 (s, 1H), 5.82 (s, 1H), 4.50-4.45 (m, 1H), 3.85 (s, 3H), 3.51-3.46 (m, 1H), 2.63-2.59 (m, 1H), 2.16-2.12 (m, 1H), 1.89-1.32 (m, 10H), 1.32-0.74 (m, 3H), 0.74-0.29 (m, 3H). LCMS (ESI): 590.45 $[M+H]^+$.

Example 374. A Diastereomeric Mixture of (S)—N-((4S,7r)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide and (S)—N-((4R,7s)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide

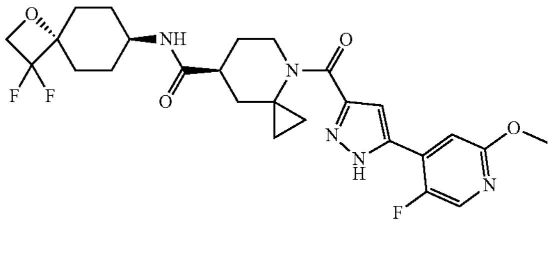

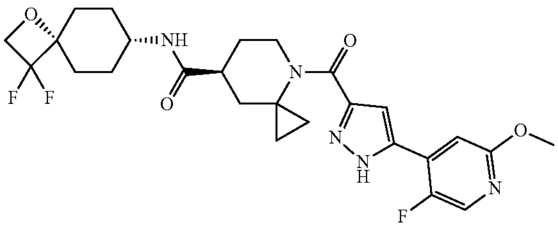

Step-1. 3,3-difluoro-1-oxaspiro[3.5]nonan-7-amine

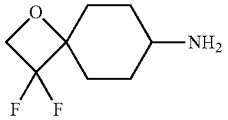 [SMILES: NC1CCC2(CC1)OCC2(F)F]

HCl (4.00 mL, 4 M in 1,4-dioxane) was added to tert-butyl N-[3,3-difluoro-1-oxaspiro[3.5]nonan-7-yl]carbamate (Step-7 from synthesis of INTERMEDIATE 537, 86.0 mg, 0.31 mmol). The resulting mixture was stirred at 25° C. for 30 min. The resulting mixture was concentrated under reduced pressure. The resulting residue was used in the next step directly without further purification. LCMS (ESI): 178.1 $[M+H]^+$.

Step-2. (S)—N-((4S,7r)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide and (S)—N-((4R,7s)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide

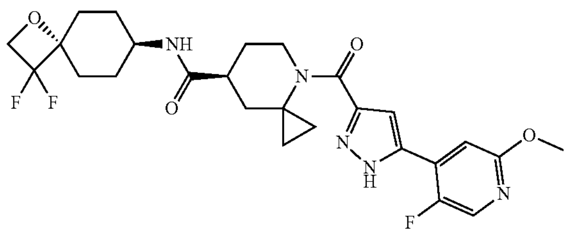

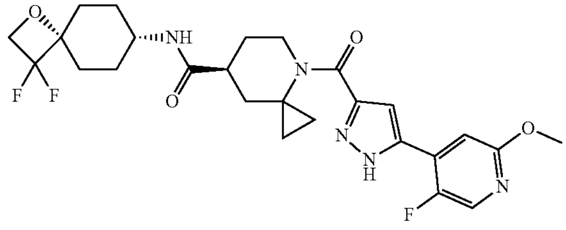

HOBt (83.7 mg, 0.62 mmol), EDCI (118.8 mg, 0.62 mmol), and 3,3-difluoro-1-oxaspiro[3.5]nonan-7-amine (Step-1, 54.9 mg, 0.31 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 116.0 mg, 0.31 mmol) and DIPEA (200.2 mg, 1.55 mmol) in DMF (4.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC eluting with DCM/MeOH (20/1 v/v) to obtain (S)—N-((4S,7r)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide and (S)—N-((4R,7s)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide (130.0 mg) as a solid mixture of diastereomers (Example 374). $^1$H NMR (400 MHz, $CD_3OD$) δ 8.13-8.08 (m, 1H), 7.26 (s, 1H), 7.09 (s, 1H), 4.70-4.57 (m, 2H), 3.92 (s, 3H), 3.70-3.66 (m, 1H), 2.79-2.74 (m, 1H), 2.44-2.21 (m, 2H), 2.13-2.05 (m, 1H), 1.97-1.62 (m, 7H), 1.59-1.39 (m, 2H), 1.27-1.22 (m, 2H), 1.11-0.81 (m, 2H), 0.73-0.68 (m, 2H). LCMS (ESI): 534.20 $[M+H]^+$.

This mixture of two diastereomers (130.0 mg) was separated using Chiral Prep-HPLC.

Column: CHIRAL ART Cellulose-SB column

Column dimension: 2×25 cm, 5 μm

Mobile Phase: MTBE (0.5% 2M $NH_3$·MeOH):EtOH=80:20 hold for 7 min

Flow rate: 20 mL/min

Detection: 220/254 nm

Example 374-A. The first eluting diastereomer (42.4 mg) was obtained as a solid.

The first eluting diastereomer had a retention time of 5.25 min.

$^1$H NMR (400 MHz, DMSO-$d_6$) δ 8.25 (s, 1H), 7.71 (d, 1H), 7.30 (d, 1H), 7.01 (s, 1H), 4.69-4.58 (m, 2H), 4.47-4.42 (m, 1H), 3.85 (s, 3H), 3.65-3.58 (m, 1H), 2.64-2.60 (m, 1H), 2.14-2.04 (m, 3H), 1.85-1.41 (m, 6H), 1.34-1.07 (m, 4H), 1.06-0.73 (m, 2H), 0.62-0.58 (m, 2H). LCMS (ESI): 533.20 $[M+H]^+$.

Example 374-B. The second eluting diastereomer (55.0 mg) was obtained as a solid.

The second eluting diastereomer had a retention time of 6.41 min.

$^1$H NMR (400 MHz, DMSO-$d_6$) δ 8.25 (d, 1H), 7.74 (d, 1H), 7.30 (d, 1H), 7.01 (s, 1H), 4.70-4.59 (m, 2H), 4.53-4.24 (m, 1H), 3.85 (s, 3H), 3.59-3.54 (m, 11H), 2.64-2.60 (m, 1H), 2.18-2.14 (m, 1H), 1.98-1.90 (m, 2H), 1.71-1.59 (m, 5H), 1.56-1.31 (m, 3H), 1.25-0.73 (m, 4H), 0.62-0.58 (m, 2H). LCMS (ESI): 533.20 $[M+H]^+$.

Example 375. A Diastereomeric Mixture of (S)—N-((1s,4R)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (S)—N-((1r,4S)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide

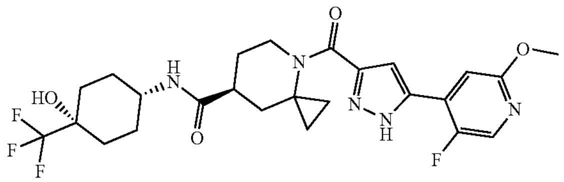

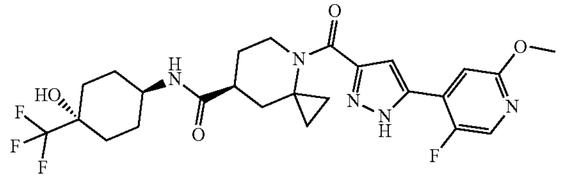

Step-1. 4-amino-1-(1,1-difluoroethyl)cyclohexan-1-ol

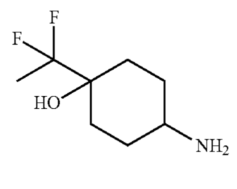

3,3-difluoro-1-oxaspiro[3.5]nonan-7-one oxime (Step-6 from synthesis of INTERMEDIATE 537, 33.0 mg, 0.17 mmol) was refluxed for 5 h in lithium triethylborohydride (2.07 mL, 1 M, 2.07 mmol) in a sealed tube under nitrogen. The reaction mixture was cooled down to 0° C. and quenched by addition of water. Volatiles were removed under reduced pressure. The residue was dissolved in DCM and filtered over a silica pad. The pad was flushed with DCM to remove impurities. The compound was finally collected by flushing with 2.5 M ammonia in MeOH. The filtrate was concentrated to dryness to obtain the title compound. The resulting residue was directly used in the next step.

Step-2. tert-butyl (4-(1,1-difluoroethyl)-4-hydroxycyclohexyl)carbamate

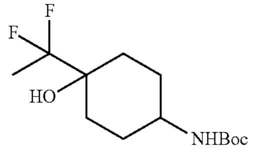 [SMILES: CC(C)(C)OC(=O)NC1CCC(O)(C(C)(F)F)CC1]

$Boc_2O$ (37.8 mg, 0.17 mmol) was added to a solution of 4-amino-1-(1,1-difluoroethyl)cyclohexan-1-ol (Step-1, 31.0 mg, 0.17 mmol) and $Et_3N$ (48.2 μL, 0.35 mmol) in DCM (0.35 mL). The reaction mixture was stirred at 22° C. for 16 h. Water was added to the reaction mixture. The layers were separated and the aqueous was further extracted with DCM. The organic layers were combined, dried over anhydrous $Na_2SO_4$, filtered, and concentrated under reduced pressure. The residue wad purified by silica gel column eluting with 0% to 50% cyclohexane/EtOAc to obtain the title compound (8.0 mg) as a solid. $^1H$ NMR (400 MHz, $CDCl_3$) δ 4.74-4.33 (m, 1H), 3.88-3.32 (m, 1H), 1.96-1.83 (m, 2H), 1.80-1.50 (m, 10H), 1.50-1.33 (m, 9H). $^{19}F$ NMR (376 MHz, $CDCl_3$) δ −106.55, −106.87.

Step-3. 4-amino-1-(1,1-difluoroethyl)cyclohexan-1-ol

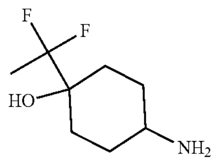

TFA (0.50 mL) was added to a stirred solution of tert-butyl (4-(1,1-difluoroethyl)-4-hydroxycyclohexyl)carbamate (Step-2, 7.0 mg, 0.025 mmol) in DCM (0.50 mL). The resulting mixture was stirred at 25° C. for 1 h. The resulting mixture was concentrated under vacuum to obtain the title compound (4.0 mg) as an oil. The resulting residue was used in the next step directly without further purification. LCMS (ESI): 180.1 $[M+H]^+$.

Step-4. (S)—N-((1s,4R)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (S)—N-((1r,4S)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide

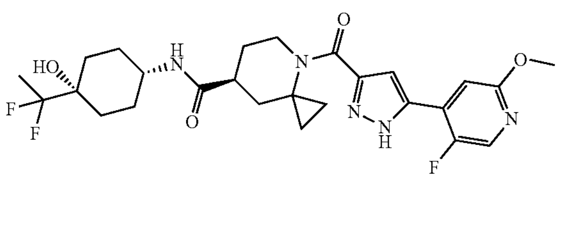

-continued

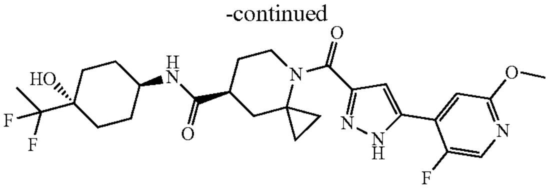

HOBt (10.8 mg, 0.08 mmol), EDCI (15.4 mg, 0.08 mmol), and 4-amino-1-(1,1-difluoroethyl)cyclohexan-1-ol (Step-3, 4.3 mg, 0.02 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 15.0 mg, 0.04 mmol) and DIPEA (25.9 mg, 0.20 mmol) in DMF (1.50 mL). The resulting mixture was stirred at 25° C. for 14 h. The resulting mixture was diluted with EtOAc and washed with water. The residue was purified by Prep-HPLC (using the following conditions: Column: YMC-Actus Triart C18 column, 30×250, 5 μm; Mobile Phase A: Water (10 mM $NH_4HCO_3$), Mobile Phase B: MeCN; Flow rate: 60 mL/min; Gradient: 27% B to 49% B in 8 min; Detector: 254/220 nm; RT: 7.23 min) to obtain (S)—N-((1s,4R)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (S)—N-((1r,4S)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide (5.8 mg) as a solid mixture of diastereomers (Example 375). $^1H$ NMR (400 MHz, $CD_3OD$) δ 8.11 (d, 1H), 7.26 (s, 1H), 7.12-7.07 (m, 1H), 4.73-4.26 (m, 2H), 3.92 (s, 3H), 3.03-2.66 (m, 1H), 2.62-2.17 (m, 1H), 2.08-1.47 (m, 13H), 1.42-0.57 (m, 6H). LCMS (ESI): 536.5 $[M+H]^+$.

This mixture of two diastereomers (30.0 mg) was separated using Chiral Prep-HPLC.

Column: CHIRALPAK IE column

Column dimension: 2×25 cm, 5 μm

Mobile Phase: MTBE (0.5% 2M $NH_3$·MeOH):EtOH=75:25 hold for 13 min

Flow rate: 20 mL/min

Detection: 220/254 nm

Example 375-A. The first eluting diastereomer (14.0 mg) was obtained as a solid.

The first eluting diastereomer had a retention time of 6.04 min.

$^1H$ NMR (300 MHz, $CD_3OD$) δ 8.20-8.10 (m, 1H), 7.52-6.94 (m, 2H), 4.77-4.26 (m, 1H), 3.95 (s, 3H), 3.64-3.58 (m, 1H), 2.83-2.77 (m, 1H), 2.43-2.37 (m, 1H), 1.96-1.68 (m, 6H), 1.67-1.49 (m, 7H), 1.45-0.90 (m, 3H), 0.85-0.51 (m, 3H). LCMS (ESI): 536.30 $[M+H]^+$.

Example 375-B. The second eluting diastereomer (7.7 mg) was obtained as a solid.

The second eluting diastereomer had a retention time of 9.73 min.

$^1H$ NMR (300 MHz, $CD_3OD$) δ 8.20-8.10 (m, 1H), 7.45-7.01 (m, 2H), 4.65-4.59 (m, 1H), 3.95 (s, 3H), 3.64-3.58 (m, 1H), 2.82-2.76 (m, 1H), 2.43-2.37 (m, 1H), 1.97-1.68 (m, 6H), 1.68-1.55 (m, 6H), 1.55-1.48 (m, 1H), 1.42-1.17 (m, 2H), 1.17-0.93 (m, 1H), 0.86-0.52 (m, 3H). LCMS (ESI): 536.30 $[M+H]^+$.

Example 376. A Diastereomeric Mixture of (S)-4-(5-(5-fluoro-2-methoxypyridin-4-yl)-1H-pyrazole-3-carbonyl)-N-((6R,8aR)-octahydroindolizin-6-yl)-4-azaspiro[2.5]octane-7-carboxamide and (S)-4-(5-(5-fluoro-2-methoxypyridin-4-yl)-1H-pyrazole-3-carbonyl)-N-((6R,8aS)-octahydroindolizin-6-yl)-4-azaspiro[2.5]octane-7-carboxamide and (S)-4-(5-(5-fluoro-2-methoxypyridin-4-yl)-1H-pyrazole-3-carbonyl)-N-((6S,8aR)-octahydroindolizin-6-yl)-4-azaspiro[2.5]octane-7-carboxamide and (S)-4-(5-(5-fluoro-2-methoxypyridin-4-yl)-1H-pyrazole-3-carbonyl)-N-((6S,8aS)-octahydroindolizin-6-yl)-4-azaspiro[2.5]octane-7-carboxamide

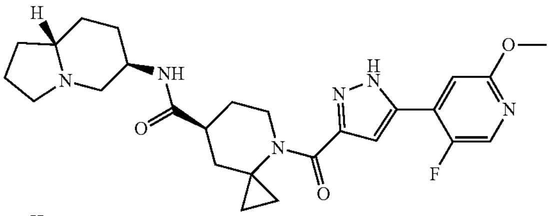

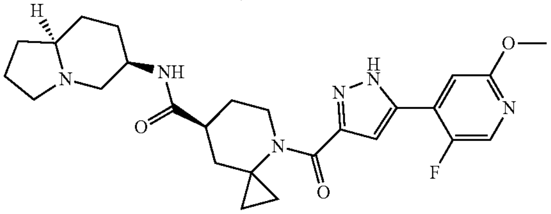

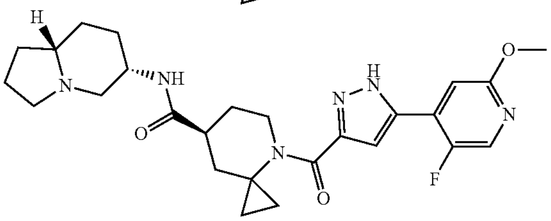

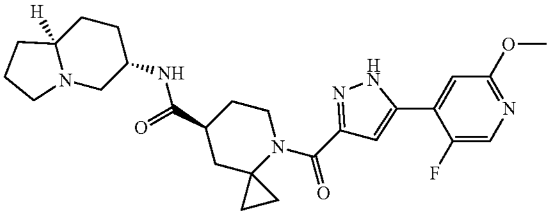

The title compound was prepared using a procedure similar to the one described for the synthesis of Example 325, except octahydroindolizin-6-amine hydrochloride was used as a starting material. The residue was purified by silica gel column chromatography eluting with DCM/MeOH (5/1 v/v) to obtain (S)-4-(5-(5-fluoro-2-methoxypyridin-4-yl)-1H-pyrazole-3-carbonyl)-N-((6R,8aR)-octahydroindolizin-6-yl)-4-azaspiro[2.5]octane-7-carboxamide and (S)-4-(5-(5-fluoro-2-methoxypyridin-4-yl)-1H-pyrazole-3-carbonyl)-N-((6R,8aS)-octahydroindolizin-6-yl)-4-azaspiro[2.5]octane-7-carboxamide and (S)-4-(5-(5-fluoro-2-methoxypyridin-4-yl)-1H-pyrazole-3-carbonyl)-N-((6S,8aR)-octahydroindolizin-6-yl)-4-azaspiro[2.5]octane-7-carboxamide and (S)-4-(5-(5-fluoro-2-methoxypyridin-4-yl)-1H-pyrazole-3-carbonyl)-N-((6S,8aS)-octahydroindolizin-6-yl)-4-azaspiro[2.5]octane-7-carboxamide in two fractions, each containing two diastereomers. The first fraction (90.0 mg with Rf value of 0.5) was obtained a solid and the second fraction (106.0 mg with Rf value of 0.3) was obtained as a solid. LCMS (ESI): 497.3 $[M+H]^+$.

The first fraction (90.0 mg) from Prep-TLC containing two diastereomers of the title compounds was separated using Chiral Prep-HPLC.

Column: CHIRALPAK IE column

Column dimension: 2×25 cm, 5 μm

Mobile Phase: 3/1 hexanes/DCM (0.5% 2 M $NH_3$·MeOH):EtOH=70:30 hold for 20 min

Flow rate: 20 mL/min

Detection: 220/254 nm

Example 376-A. The first eluting diastereomer (24.8 mg) was obtained as a solid.

The first eluting diastereomer had a retention time of 13.46 min.

$^1H$ NMR (400 MHz, $CD_3OD$) δ 8.13 (d, 1H), 7.28 (s, 1H), 7.10 (m, 1H), 4.58 (s, 1H), 4.30-3.99 (m, 1H), 3.94 (s, 3H), 3.64-3.41 (m, 1H), 2.80 (s, 1H), 2.70-2.46 (m, 3H), 2.41-2.26 (m, 1H), 2.24-2.11 (m, 1H), 2.10-2.01 (m, 1H), 2.00-1.91 (m, 2H), 1.80 (d, 2H), 1.65-1.58 (m, 1H), 1.58-1.50 (m, 2H), 1.49-1.38 (m, 4H), 1.10-0.82 (m, 2H), 0.68-0.79 (m, 2H). LCMS (ESI): 497.30 $[M+H]^+$.

Example 376-B. The second eluting diastereomer (21.8 mg) was obtained as a solid.

The second eluting diastereomer had a retention time of 16.13 min.

$^1H$ NMR (300 MHz, $CD_3OD$) δ 8.13 (d, 1H), 7.28 (s, 1H), 7.10 (d, 1H), 4.57 (s, 1H), 4.28-3.98 (m, 1H), 3.94 (s, 3H), 3.64-3.39 (m, 1H), 3.27-3.02 (m, 1H), 2.79 (s, 1H), 2.61-2.41 (m, 2H), 2.34 (s, 1H), 2.24-2.10 (m, 1H), 2.08-1.95 (m, 3H), 1.95-1.65 (m, 4H), 1.61-1.36 (m, 3H), 1.36-1.18 (m, 2H), 1.16-0.82 (m, 2H), 0.81-0.60 (m, 2H). LCMS (ESI): 497.30 $[M+H]^+$.

The second fraction (106.0 mg) from Prep-TLC containing two diastereomers of the title compounds was separated using Chiral Prep-HPLC.

Column: CHIRALPAK IG column

Column dimension: 2×25 cm, 5 μm

Mobile Phase: 3/1 hexanes/DCM (0.5% 2 M $NH_3$·MeOH):IPA=65:35 hold for 22 min

Flow rate: 20 mL/min

Detection: 220/254 nm

Example 376-C. The first eluting diastereomer (34.1 mg) was obtained as a solid.

The first eluting diastereomer had a retention time of 14.13 min.

$^1H$ NMR (400 MHz, $CD_3OD$) δ 8.14 (d, 1H), 7.29 (s, 1H), 7.12 (d, 1H), 4.78-4.25 (m, 1H), 4.07 (s, 1H), 3.95 (s, 3H), 3.79-3.37 (m, 1H), 3.18-2.58 (m, 4H), 2.56-2.34 (m, 1H), 2.34-2.25 (m, 1H), 2.25-2.10 (m, 3H), 1.99-1.66 (m, 6H), 1.50-1.38 (m, 3H), 1.19-0.84 (m, 2H), 0.72-0.82 (m, 2H). LCMS (ESI): 497.30 $[M+H]^+$.

Example 376-D. The second eluting diastereomer (27.3 mg) was obtained as a solid.

The second eluting diastereomer had a retention time of 19.00 min.

$^1H$ NMR (300 MHz, $CD_3OD$) δ 8.14 (d, 1H), 7.29 (d, 1H), 7.12 (d, 1H), 4.60 (s, 1H), 4.07 (s, 1H), 3.95 (s, 3H), 3.61-3.36 (m, 1H), 3.12-2.66 (m, 4H), 2.46 (s, 1H), 2.33-

1.54 (m, 11H), 1.49-1.27 (m, 2H), 1.19-0.85 (m, 2H), 0.82-0.65 (m, 2H). LCMS (ESI): 497.30 [M+H]$^+$.

Example 377. A Diastereomeric Mixture of (S)—N—((R)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide and (S)—N—((S)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide

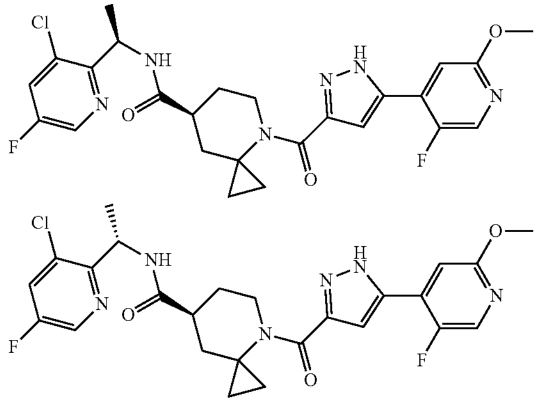

Step-1. N-[(1E)-(3-chloro-5-fluoropyridin-2-yl)methylidene]-2-methylpropane-2-sulfinamide

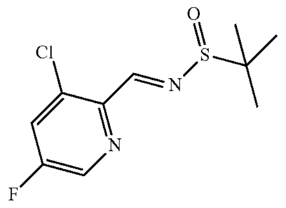 [SMILES: CC(C)(C)S(=O)/N=C/c1ncc(F)cc1Cl]

PTSA (31.0 mg, 0.18 mmol) and $MgSO_4$ (1.31 g, 10.91 mmol) were added to a mixture of 3-chloro-5-fluoropyridine-2-carbaldehyde (580.0 mg, 3.64 mmol) and tert-butanesulfinamide (441.0 mg, 3.64 mmol) in DCM (5.00 mL). The resulting mixture was stirred at 25° C. for 14 h. The resulting mixture was filtered, the filter cake was washed with DCM. The filtrate was concentrated under reduced pressure to obtain the title compound (850.0 mg) as a solid. LCMS (ESI): 263[M+H]$^+$.

Step-2. N-[1-(3-chloro-5-fluoropyridin-2-yl)ethyl]-2-methylpropane-2-sulfinamide

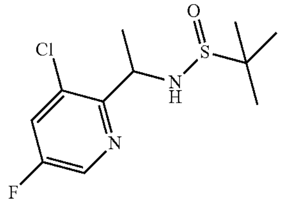 [SMILES: CC(NS(=O)C(C)(C)C)c1ncc(F)cc1Cl]

Bromo(methyl)magnesium (1.13 g, 9.48 mmol) was added to a stirred solution of N-[(1E)-(3-chloro-5-fluoropyridin-2-yl)methylidene]-2-methylpropane-2-sulfinamide (Step-1, 830.0 mg, 3.16 mmol) in THF (5.00 mL) at 0° C. The resulting mixture was stirred at 25° C. for 2 h under nitrogen atmosphere. The resulting mixture was concentrated under reduced pressure. The residue was purified by silica gel column chromatography eluting with DCM/MeOH (10/1 v/v) to obtain the title compound (800.0 mg) as a solid. LCMS (ESI): 279 [M+H]$^+$.

Step-3. 1-(3-chloro-5-fluoropyridin-2-yl)ethanamine

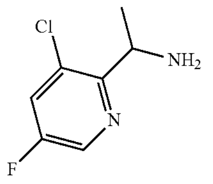

HCl (3.00 mL, 4 M in 1,4-dioxane) was added to a solution of N-[1-(3-chloro-5-fluoropyridin-2-yl)ethyl]-2-methylpropane-2-sulfinamide (Step-2, 150.0 mg, 0.54 mmol) in 1,4-dioxane (3.00 mL). The resulting mixture was stirred at 25° C. for 3 h. The resulting mixture was concentrated under reduced pressure to obtain the title compound (75.0 mg) as a solid. LCMS (ESI): 175 [M+H]$^+$.

Step-4. (S)—N—((R)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide and (S)—N—((S)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide

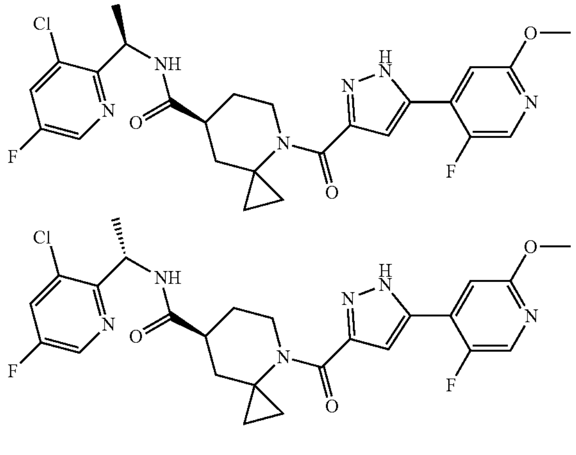

HOBt (75.0 mg, 0.56 mmol), EDCI (107.0 mg, 0.56 mmol), and 1-(3-chloro-5-fluoropyridin-2-yl)ethanamine (Step-3, 65.0 mg, 0.37 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 140.0 mg, 0.37 mmol) and DIPEA (241.0 mg, 1.86 mmol) in DMF (5.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)—N—((R)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide and (S)—N—((S)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide (160.0 mg) as a solid mixture of diastereomers (Example 377). $^1H$ NMR (300 MHz, DMSO-$d_6$) δ 14.06-13.85 (m, 1H), 8.58 (d, 1H), 8.38-8.22 (m, 2H), 8.12-8.02 (m, 1H), 7.35-7.29 (m, 1H), 7.02 (s, 1H), 5.38-5.27 (m, 1H), 4.50 (s, 1H), 3.91-3.85 (m, 3H), 2.92-2.66 (m, 1H), 2.21-2.15 (m, 1H), 1.77-1.71 (m, 1H), 1.51-1.45 (m, 1H), 1.37-1.28 (m, 4H), 1.17 (s, 1H), 0.99-0.93 (m, 2H), 0.69-0.63 (m, 2H). LCMS (ESI): 531.4 $[M+H]^+$.

This mixture of two diastereomers (160.0 mg) was separated using Chiral Prep-HPLC.

Column: CHIRALPAK IA column

Column dimension: 2×25 cm, 5 μm

Mobile Phase: 3/1 hexanes/DCM (0.5% 2 M $NH_3$·MeOH):EtOH=80:20 hold for 9 min

Flow rate: 20 mL/min

Detection: 220/254 nm

Example 377-A. The first eluting diastereomer (62.7 mg) was obtained as a solid.

The first eluting diastereomer had a retention time of 5.94 min.

$^1H$ NMR (300 MHz, DMSO-$d_6$) δ 13.95 (s, 1H), 8.58 (d, 1H), 8.34 (d, 1H), 8.26 (d, 1H), 8.12-8.02 (m, 1H), 7.32 (d, 1H), 7.00 (d, 1H), 5.39-5.24 (m, 1H), 4.44 (s, 1H), 3.87 (s, 3H), 3.13-2.70 (m, 2H), 2.15-2.09 (m, 1H), 1.79-1.70 (m, 1H), 1.57-1.51 (m, 1H), 1.33 (d, 3H), 1.26-1.11 (m, 1H), 0.91-0.85 (m, 2H), 0.66-0.60 (m, 2H). LCMS (ESI): 531.10 $[M+H]^+$.

Example 377-B. The second eluting diastereomer (59.4 mg) was obtained as a solid.

The second eluting diastereomer had a retention time of 7.05 min.

$^1H$ NMR (400 MHz, DMSO-$d_6$) δ 14.04-13.83 (m, 1H), 8.56 (d, 1H), 8.37-8.20 (m, 2H), 8.08-8.01 (m, 1H), 7.32-7.26 (m, 1H), 7.01 (s, 1H), 5.34-5.26 (m, 1H), 4.52-4.45 (m, 1H), 3.85 (s, 3H), 3.07-2.73 (m, 2H), 2.17-2.12 (m, 1H), 1.70-1.66 (m, 1H), 1.46-1.03 (m, 5H), 0.99-0.79 (m, 2H), 0.61-0.57 (m, 2H). LCMS (ESI): 531.10 $[M+H]_+$.

Example 378. A Diastereomeric Mixture of (S)—N-((1s,3R)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide and (S)—N-((1r,3S)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide

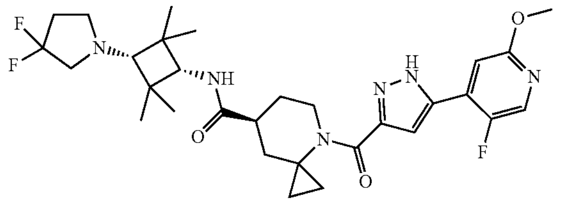

-continued

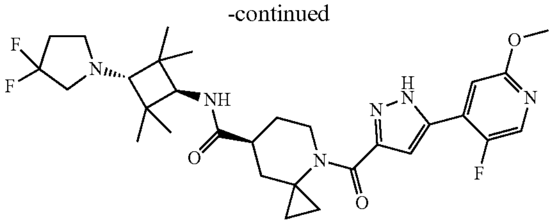

Step-1. tert-butyl N-[3-(3,3-difluoropyrrolidin-1-yl)-2,2,4,4-tetramethylcyclobutyl]carbamate

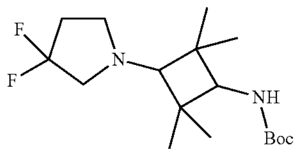 [SMILES: CC(C)(C)OC(=O)NC1C(C)(C)C(N2CCC(F)(F)C2)C1(C)C]

3,3-difluoropyrrolidine (146.5 mg, 1.37 mmol) and Ti(Oi-Pr)$_4$ (706.6 mg, 2.49 mmol) were added to a stirred mixture of tert-butyl N-(2,2,4,4-tetramethyl-3-oxocyclobutyl)carbamate (300.0 mg, 1.24 mmol) in EtOH (5.00 mL). The resulting mixture was stirred at 25° C. for 14 h. Then $NaBH_3CN$ (156.2 mg, 2.49 mmol) was added to the reaction mixture. The resulting mixture was stirred at 25° C. for 5 h. The resulting mixture was concentrated under reduced pressure. The residue was purified by Prep-TLC eluting with petroleum ether/EtOAc (8/1 v/v) to obtain the title compound (80.0 mg) as a solid. LCMS (ESI): 333.2 $[M+H]^+$.

Step-2. 3-(3,3-difluoropyrrolidin-1-yl)-2,2,4,4-tetramethylcyclobutan-1-amine

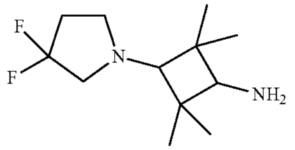 [SMILES: CC1(C)C(N)C(C)(C)C1N1CCC(F)(F)C1]

TFA (1.00 mL) was added to a stirred mixture of tert-butyl N-[3-(3,3-difluoropyrrolidin-1-yl)-2,2,4,4-tetramethylcyclobutyl]carbamate (Step-2, 50.0 mg, 0.11 mmol) in DCM (1.00 mL) at 0° C. The resulting mixture was stirred at 25° C. for 30 min. The resulting mixture was concentrated under reduced pressure to obtain the title compound and used in the next step directly without further purification. LCMS (ESI): 233.2 $[M+H]^+$.

Step-3. (S)—N-((1s,3R)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide and (S)—N-((1r,3S)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide

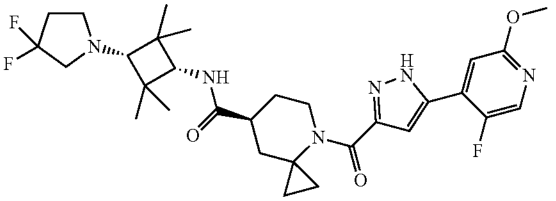

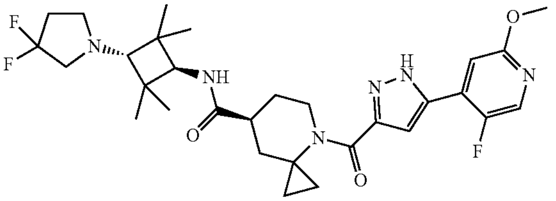

HOBt (39.6 mg, 0.29 mmol), EDCI (56.0 mg, 0.29 mmol), and 3-(3,3-difluoropyrrolidin-1-yl)-2,2,4,4-tetramethylcyclobutan-1-amine (34.0 mg, 0.15 mmol) were added to a stirred mixture of ($)-4-[5-(5-fluoro-2-methoxypyridin-4-yl)-1H-pyrazole-3-carbonyl]-4-azaspiro[2.5]octane-7-carboxylic acid (INTERMEDIATE 527-A, 60.3 mg, 0.16 mmol) and DIPEA (189.1 mg, 1.47 mmol) in DMF (1.50 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 40 B to 60 B in 20 min; 220/254 nm) to obtain (S)—N-((1s,3R)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide and (S)—N-((1r,3S)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide (40.0 mg) as a solid mixture of diastereomers (Example 378). $^1$H NMR (400 MHz, $CD_3OD$) δ 8.11 (d, 1H), 7.27 (s, 1H), 7.09 (s, 1H), 4.80-4.25 (m, 1H), 3.92 (s, 3H), 3.75-3.71 (m, 1H), 3.04-3.00 (m, 1H), 2.84-2.71 (m, 2H), 2.69-2.61 (m, 2H), 2.28-2.13 (m, 2H), 2.08-2.03 (m, 1H), 1.85-1.80 (m, 2H), 1.31-1.26 (m, 4H), 1.15-1.08 (m, 11H), 1.01-0.95 (m, 1H), 0.95-0.82 (m, 1H), 0.78-0.74 (m, 2H). LCMS (ESI): 589.25 $[M+H]^+$.

This mixture of two diastereomers (23.0 mg) was separated using Achiral Prep-HPLC.

Column: GreenSep Basic column
Column dimension: 3×15 cm, 5 μm
Mobile Phase A: $CO_2$; Mobile Phase B: IPA (0.5% 2M $NH_3$-MeOH)
Flow rate: 70 mL/min
Gradient: isocratic 30% B
Detection: 254 nm
Injection Volume: 1.5 mL Example 378-A. The first eluting diastereomer (7.1 mg) was obtained as a solid.

The first eluting diastereomer had a retention time of 6.38 min.

$^1$H NMR (400 MHz, $CD_3OD$) δ 8.11 (d, 1H), 7.27 (d, 1H), 7.09 (d, 1H), 4.64-4.60 (m, 4H), 3.92 (s, 3H), 2.84-2.73 (m, 2H), 2.80-2.70 (m, 1H), 2.28-2.10 (m, 1H), 2.09-2.02 (m, 1H), 1.84-1.80 (m, 2H), 1.31-1.27 (m, 5H), 1.18-1.08 (m, 11H), 0.93-0.85 (m, 2H), 0.74-0.70 (m, 2H). LCMS (ESI): 589.20 $[M+H]^+$.

Example 378-B. The second eluting diastereomer (1.0 mg) was obtained as a solid.

The second eluting diastereomer had a retention time of 8.70 min.

LCMS (ESI): 589.20 $[M+H]^+$.

Example 379. A Diastereomeric Mixture of (S)—N—((S)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide

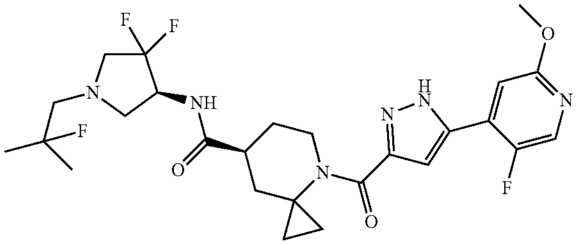

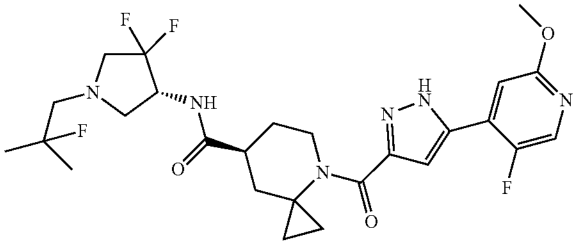

Step-1. tert-butyl 4-(dibenzylamino)-3,3-difluoropyrrolidine-1-carboxylate

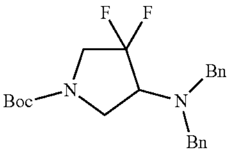 [SMILES: CC(C)(C)OC(=O)N1CC(N(Cc2ccccc2)Cc2ccccc2)C(F)(F)C1]

$K_2CO_3$ (932.8 mg, 6.75 mmol) and BnBr (1.15 g, 6.75 mmol) were added to a stirred solution of tert-butyl 4-amino-3,3-difluoropyrrolidine-1-carboxylate (500.0 mg, 2.25 mmol) in MeCN (10.00 mL). The resulting mixture was stirred at 60° C. for 14 h. The resulting solution was concentrated under reduced pressure. The residue was purified by silica gel column chromatography eluting with EtOAc/petroleum ether (1/10 v/v) to obtain the title compound (572.0 mg) as an oil. LCMS (ESI): 403.2 $[M+H]^+$.

Step-2. N,N-dibenzyl-4,4-difluoropyrrolidin-3-amine

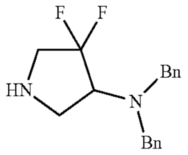 [SMILES: FC1(F)CNCC1N(Cc1ccccc1)Cc1ccccc1]

TFA (5.00 mL) was added to a stirred solution of tert-butyl 4-(dibenzylamino)-3,3-difluoropyrrolidine-1-carboxylate (Step-1, 572.0 mg, 1.42 mmol) in DCM (5.00 mL). The resulting mixture was stirred at 25° C. for 1 h. The resulting solution was concentrated under reduced pressure. The residue was purified by silica gel column chromatography eluting with DCM/MeOH (101 v/v) to obtain the title compound (420.0 mg) as an oil. LCMS (ESI): 303.2 $[M+H]^+$.

Step-3. 1-[4-(dibenzylamino)-3,3-difluoropyrrolidin-1-yl]-2-methylpropan-2-ol

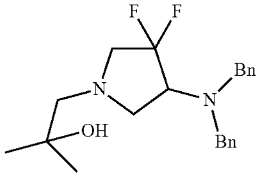 [SMILES: CC(C)(O)CN1CC(N(Cc2ccccc2)Cc2ccccc2)C(F)(F)C1]

2,2-dimethyloxirane (581.9 mg, 8.07 mmol) and $K_2CO_3$ (1.12 g, 8.07 mmol) were added to a stirred solution of N,N-dibenzyl-4,4-difluoropyrrolidin-3-amine (Step-2, 488.0 mg, 1.61 mmol) in EtOH (5.00 mL)/$H_2O$ (0.50 mL). The resulting mixture was stirred at 110° C. for 14 h. The resulting solution was concentrated under reduced pressure. The residue was purified by silica gel column chromatography eluting with EtOAc/petroleum ether (1/5 v/v) to obtain the title compound (384.0 mg) as an oil. LCMS (ESI): 375.2 $[M+H]^+$.

Step-4. N,N-dibenzyl-4,4-difluoro-1-(2-fluoro-2-methylpropyl)pyrrolidin-3-amine

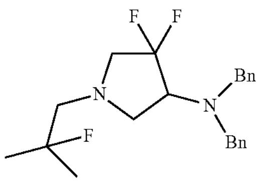 [SMILES: CC(C)(F)CN1CC(N(Cc2ccccc2)Cc2ccccc2)C(F)(F)C1]

DAST (322.0 mg, 2.00 mmol) was added to a stirred solution of i-[4-(dibenzylamino)-3,3-difluoropyrrolidin-1-yl]-2-methylpropan-2-ol (Step-3, 374.0 mg, 1.00 mmol) in DCM (5.00 mL) at 0° C. The resulting mixture was stirred at 25° C. for 2 h. The reaction mixture was quenched by the addition of MeOH. The solution was concentrated under reduced pressure. The residue was purified by silica gel column chromatography eluting with EtOAc/petroleum ether (1/10 v/v) to obtain the title compound (270.0 mg) as an oil. LCMS (ESI): 377.2 $[M+H]^+$.

Step-5. 4,4-difluoro-1-(2-fluoro-2-methylpropyl) pyrrolidin-3-amine

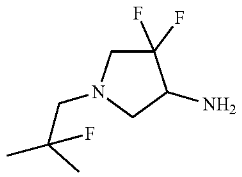

Pd/C (150.0 mg) was added to a stirred solution of N,N-dibenzyl-4,4-difluoro-1-(2-fluoro-2-methylpropyl)pyrrolidin-3-amine (Step-4, 270.0 mg, 0.72 mmol) in MeOH (5.00 mL). The resulting mixture was stirred at 25° C. for 14 h. Then the solids were filtered out and the filtrate was concentrated under reduced pressure to obtain the title compound (80.0 mg) as an oil. LCMS (ESI): 197.1 $[M+H]^+$.

Step-6. (S)—N—((S)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-(2-fluoro-2-methylpropyl) pyrolidin-3-yl)-4-(5-(5-fluoro-2-methoxypyridin-4-yl)-1H-pyrazole-3-carbonyl)-4-azaspiro[2.5]octane-7-carboxamide

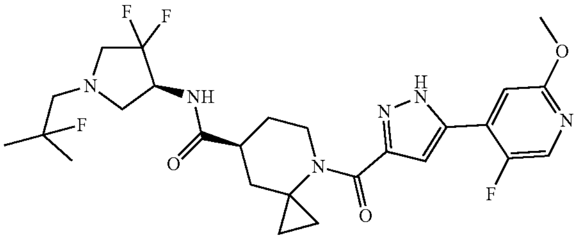

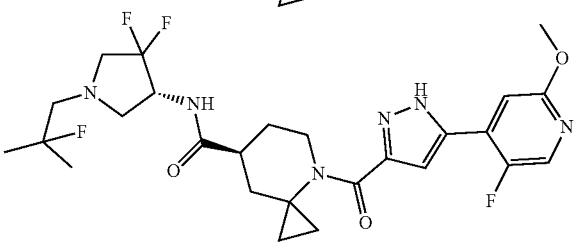

HOBt (72.3 mg, 0.54 mmol), EDCI (102.6 mg, 0.54 mmol), and 4-difluoro-1-(2-fluoro-2-methylpropyl)pyrrolidin-3-amine (70.0 mg, 0.36 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 133.6 mg, 0.36 mmol) and DIPEA (138.3 mg, 1.07 mmol) in DMF (5.00 mL). The resulting mixture was stirred at 25° C. for 1 h. The resulting solution was diluted with EtOAc and washed with water.

The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 40 B to 60 B in 20 min; 220/254 nm) to obtain (S)—N—((S)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide (105.0 mg) as a solid mixture of diastereomers (Example 379). $^1$H NMR (400 MHz, DMSO-$d_6$) δ 14.03 (s, 1H), 8.27 (d, 1H), 8.13 (s, 1H), 7.43-7.20 (m, 1H), 7.03 (s, 1H), 4.67-4.32 (m, 2H), 3.87 (s, 3H), 3.31-3.13 (m, 3H), 2.91-2.69 (m, 2H), 2.70-2.52 (m, 2H), 2.49-2.37 (m, 1H), 2.29-2.00 (m, 1H), 1.77 (s, 1H), 1.65-1.40 (m, 1H), 1.39-1.34 (m, 3H), 1.33-1.28 (m, 3H), 1.27-1.23 (m, 1H), 1.08-0.83 (m, 2H), 0.80-0.46 (m, 2H). LCMS (ESI): 553.30 $[M+H]^+$.

This mixture of two diastereomers (105.0 mg) was separated using Chiral Prep-HPLC.

Column: CHIRAL ART Cellulose-SB column

Column dimension: 2×25 cm, 5 μm

Mobile Phase: MTBE (0.5% 2M $NH_3$·MeOH):1/1 MeOH/DCM=80:20 hold for 8 min

Flow rate: 20 mL/min

Detection: 220/254 nm

Example 379-A. The first eluting diastereomer (34.8 mg) was obtained as a solid.

The first eluting diastereomer had a retention time of 4.66 min.

$^1$H NMR (400 MHz, DMSO-$d_6$) δ 14.03 (s, 1H), 8.39-8.00 (m, 2H), 7.38-7.20 (m, 1H), 7.01 (s, 1H), 4.65-4.26 (m, 2H), 3.85 (s, 3H), 3.28-3.09 (m, 3H), 2.93-2.67 (m, 2H), 2.68-2.51 (m, 2H), 2.46-2.33 (m, 1H), 2.22-1.97 (m, 1H), 1.88-1.37 (m, 2H), 1.35-1.05 (m, 8H), 1.05-0.79 (m, 1H), 0.73-0.44 (m, 2H). LCMS (ESI): 553.30 $[M+H]^+$.

Example 379-B. The second eluting diastereomer (30.5 mg) was obtained as a solid.

The second eluting diastereomer had a retention time of 6.99 min.

$^1$H NMR (400 MHz, DMSO-$d_6$) δ 14.15-13.83 (m, 1H), 8.45-8.01 (m, 2H), 7.47-7.22 (m, 1H), 7.12-6.90 (m, 1H), 4.63-4.29 (m, 2H), 3.85 (s, 3H), 3.30-3.11 (m, 3H), 2.73 (m, 2H), 2.65-2.51 (m, 11H), 2.47-2.38 (m, 2H), 2.16 (s, 1H), 1.86-1.40 (m, 2H), 1.36-1.17 (m, 8H), 1.10-0.82 (m, 1H), 0.75-0.51 (m, 2H). LCMS (ESI): 553.20 $[M+H]^+$.

Example 380. A Diastereomeric Mixture of (S)-4-(5-(5-fluoro-2-methoxypyridin-4-yl)-1H-pyrazole-3-carbonyl)-N—((R)-6-methyl-3,4-dihydro-2H-pyrano[3,2-b]pyridin-4-yl)-4-azaspiro[2.5]octane-7-carboxamide and (S)-4-(5-(5-fluoro-2-methoxypyridin-4-yl)-1H-pyrazole-3-carbonyl)-N—((S)-6-methyl-3,4-dihydro-2H-pyrano[3,2-b]pyridin-4-yl)-4-azaspiro[2.5]octane-7-carboxamide

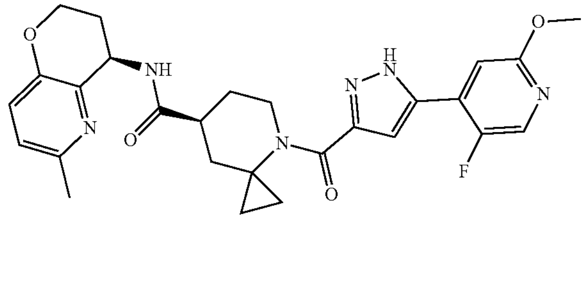

-continued

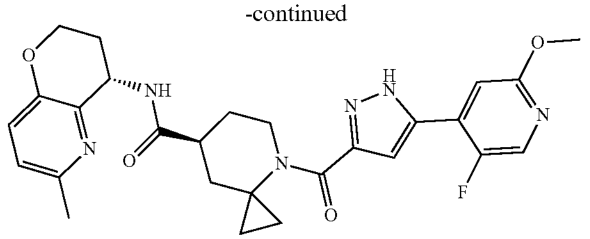

Step-1. 2-bromo-3-(but-3-en-1-yloxy)-6-methylpyridine

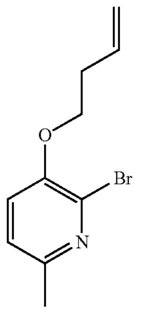

3-buten-1-ol (1.15 g, 15.96 mmol) and $PPh_3$ (4.18 g, 15.96 mmol) were added to a stirred solution of 2-bromo-6-methylpyridin-3-ol (2.00 g, 10.64 mmol) in THF (15.00 mL). Then DEAD (2.78 g, 15.96 mmol) was added dropwise to the resulting mixture under the atmosphere of nitrogen. The resulting mixture was stirred at 25° C. for 14 h. The solution was concentrated under reduced pressure. The residue was purified by silica gel column chromatography eluting with DCM/MeOH (15/1 v/v) to obtain the title compound (2.50 g) as a solid. LCMS (ESI): 242.0 $[M+H]^+$.

Step-2. 6-methyl-4-methylidene-2H,3H-pyrano[3,2-b]pyridine

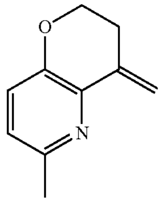

$PPh_3$ (487.5 mg, 1.86 mmol), $Pd(OAc)_2$ (139.1 mg, 0.62 mmol), AcOK (3.04 g, 30.98 mmol) and TEA·HCl (1.71 g, 12.39 mmol) were added to a stirred solution of 2-bromo-3-(but-3-en-1-yloxy)-6-methylpyridine (Step-1, 1.50 g, 6.20 mmol) in DMF (15.00 mL). The resulting mixture was stirred at 105° C. for 14 h under the atmosphere of nitrogen. The solution was diluted with EtOAc and washed with water. The organic layers were combined, dried over anhydrous $Na_2SO_4$, filtered, and concentrated under reduced pressure. The residue was purified by silica gel column chromatography eluting with EtOAc/petroleum ether (1/10 v/v) to obtain the title compound (530.0 mg) as an oil. LCMS (ESI): 162.1 $[M+H]^+$.

Step-3. 4-(hydroxymethyl)-6-methyl-2H,3H-pyrano[3,2-b]pyridin-4-ol

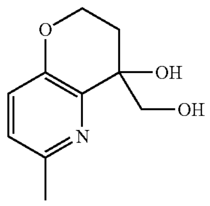

NMO (1.85 g, 15.82 mmol) and $OSO_4$ (26.8 mg, 0.11 mmol) in t-BuOH (1.07 g) were added to a stirred solution of 6-methyl-4-methylidene-2H,3H-pyrano[3,2-b]pyridine (Step-2, 850.0 mg, 5.27 mmol) in DCM (10.00 mL). The resulting mixture was stirred at 25° C. for 14 h. The resulting solution was concentrated under reduced pressure. The solution was diluted with EtOAc and washed with water. The organic layers were combined, dried over anhydrous $Na_2SO_4$, filtered, and concentrated under reduced pressure to obtain the title compound (967.0 mg) as an oil. LCMS (ESI): 196.1 $[M+H]^+$.

Step-4. 6-methyl-2H,3H-pyrano[3,2-b]pyridin-4-one

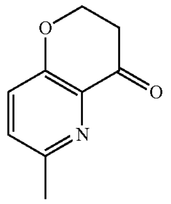

Sodium periodate (3.18 g, 14.86 mmol) was added to a stirred solution of 4-(hydroxymethyl)-6-methyl-2H,3H-pyrano[3,2-b]pyridin-4-ol (Step-3, 967.0 mg, 4.95 mmol) in THF (5.00 mL)/water (5.00 mL). The resulting mixture was stirred at 25° C. for 3 h. The solution was concentrated under reduced pressure. The solution was extracted with EtOAc. The organic layers were combined, dried over anhydrous $Na_2SO_4$, filtered, and concentrated under reduced pressure. The residue was purified by silica gel column chromatography eluting with EtOAc/petroleum ether (1/1 v/v) to obtain the title compound (329.0 mg) as a solid. LCMS (ESI): 164.1 $[M+H]^+$.

Step-5. N-[(4Z)-6-methyl-2H,3H-pyrano[3,2-b]pyridin-4-ylidene]hydroxylamine

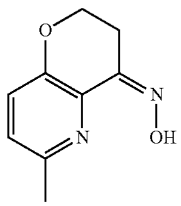

Hydroxylamine hydrochloride (157.9 mg, 2.27 mmol) was added to a stirred solution of 6-methyl-2H,3H-pyrano[3,2-b]pyridin-4-one (Step-4, 309.0 mg, 1.89 mmol) in MeOH (5.00 mL). The resulting mixture was stirred at 25° C. for 1 h. The solution was concentrated under reduced pressure, then basified to pH 7 with aqueous $NaHCO_3$. The solution was extracted with EtOAc. The organic layers were combined, dried over anhydrous $Na_2SO_4$, filtered, and concentrated under reduced pressure to obtain the title compound (337.0 mg) as a solid. LCMS (ESI): 179.1 $[M+H]^+$.

Step-6. 6-methyl-2H,3H,4H-pyrano[3,2-b]pyridin-4-amine

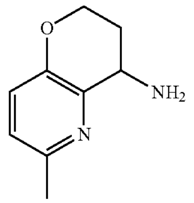

$NH_4OAc$ (160.4 mg, 2.08 mmol) was added to a stirred solution of N-[(4Z)-6-methyl-2H,3H-pyrano[3,2-b]pyridin-4-ylidene]hydroxylamine (Step-5, 337.0 mg, 1.89 mmol) in EtOH (1.00 mL)/$NH_4OH$ (5.00 mL). Then Zn (1.24 g, 18.91 mmol) was added to the resulting mixture at 0° C. The resulting mixture was stirred at 25° C. for 14 h. The solids were filtered out and washed with MeOH. The organic layers were concentrated under reduced pressure. The residue was purified by silica gel column chromatography eluting with DCM/MeOH (10/1 v/v) to obtain the title compound (174.0 mg) as a solid. LCMS (ESI): 165.1 $[M+H]^+$.

Step-7. (S)-4-(5-(5-fluoro-2-methoxypyridin-4-yl)-1H-pyrazole-3-carbonyl)-N—((R)-6-methyl-3,4-dihydro-2H-pyrano[3,2-b]pyridin-4-yl)-4-azaspiro[2.5]octane-7-carboxamide and (S)-4-(5-(5-fluoro-2-methoxypyridin-4-yl)-1H-pyrazole-3-carbonyl)-N—((S)-6-methyl-3,4-dihydro-2H-pyrano[3,2-b]pyridin-4-yl)-4-azaspiro[2.5]octane-7-carboxamide

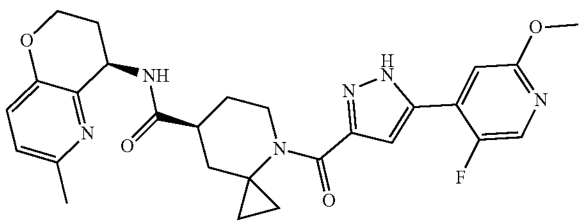

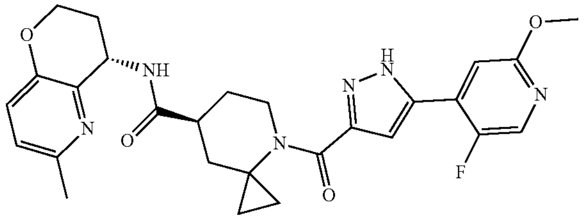

HOBt (123.4 mg, 0.91 mmol), EDCI (175.1 mg, 0.91 mmol), and 6-methyl-2H,3H,4H-pyrano[3,2-b]pyridin-4- amine (Step-6, 100.0 mg, 0.61 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 228.0 mg, 0.61 mmol) and DIPEA (236.1 mg, 1.83 mmol) in DMF (3.00 mL). The resulting mixture was stirred at 25° C. for 1 h. The solution was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18 column: mobile phase A: Water (0.5% $NH_4HCO_3$), mobile phase B: MeCN; gradient: 20 B to 50 B in 30 min; 220/254 nm) to obtain (S)-4-(5-(5-fluoro-2-methoxypyridin-4-yl)-1H-pyrazole-3-carbonyl)-N—((R)-6-methyl-3,4-dihydro-2H-pyrano[3,2-b]pyridin-4-yl)-4-azaspiro[2.5]octane-7-carboxamide and (S)-4-(5-(5-fluoro-2-methoxypyridin-4-yl)-1H-pyrazole-3-carbonyl)-N—((S)-6-methyl-3,4-dihydro-2H-pyrano[3,2-b]pyridin-4-yl)-4-azaspiro[2.5]octane-7-carboxamide (103.0 mg) as a solid mixture of diastereomers (Example 380). $^1$H NMR (300 MHz, DMSO-$d_6$) δ 14.38-13.52 (m, 1H), 8.40-8.20 (m, 2H), 7.37-7.29 (m, 1H), 7.21-6.95 (m, 3H), 4.93-4.78 (m, 1H), 4.53 (s, 1H), 4.33-4.01 (m, 2H), 3.88 (s, 3H), 3.32 (s, 1H), 2.66 (s, 1H), 2.37 (s, 3H), 2.27-2.00 (m, 2H), 2.00-1.43 (m, 3H), 1.40-1.10 (m, 1H), 0.98 (s, 2H), 0.77-0.45 (m, 2H). LCMS (ESI): 521.05 $[M+H]^+$.

This mixture of two diastereomers (103.0 mg) was separated using Chiral Prep-HPLC.

Column: CHIRALPAK ID column

Column dimension: 2×25 cm, 5 μm

Mobile Phase: MTBE (0.5% 2M $NH_3$·MeOH): MeOH=50:50 hold for 10 min

Flow rate: 19 mL/min

Detection: 220/254 nm

Example 380-A. The first eluting diastereomer (31.3 mg) was obtained as a solid.

The first eluting diastereomer had a retention time of 6.34 min.

$^1$H NMR (400 MHz, DMSO-$d_6$) δ 14.17-13.78 (m, 1H), 8.47-8.12 (m, 2H), 7.42-7.20 (m, 1H), 7.16-6.95 (m, 3H), 4.93-4.74 (m, 1H), 4.52 (s, 1H), 4.31-4.16 (m, 1H), 4.10-4.05 (m, 1H), 3.86 (s, 3H), 2.90-2.60 (m, 1H), 2.35 (s, 3H), 2.26-1.97 (m, 2H), 1.96-1.83 (m, 1H), 1.82-1.48 (m, 2H), 1.43-1.06 (m, 2H), 1.05-0.76 (m, 2H), 0.68-0.43 (m, 2H). LCMS (ESI): 521.30 $[M+H]^+$.

Example 380-B. The second eluting diastereomer (32.8 mg) was obtained as a solid.

The second eluting diastereomer had a retention time of 7.68 min.

$^1$H NM (400 MHz, DMSO-$d_6$) δ 14.03 (s, 1H), 8.46-8.14 (m, 2H), 7.30 (s, 1H), 7.15-6.98 (m, 3H), 4.83 (s, 1H), 4.49 (s, 1H), 4.31-4.15 (m, 1H), 4.14-3.97 (m, 1H), 3.86 (s, 3H), 2.86-2.59 (m, 2H), 2.34 (s, 3H), 2.14-1.95 (m, 1H), 1.95-1.83 (m, 1H), 1.82-1.66 (m, 1H), 1.64-1.39 (m, 1H), 1.21 (s, 2H), 1.05-0.72 (m, 2H), 0.69-0.43 (m, 21). LCMS (ESI): 521.30 $[M+H]^+$.

Example 381. (S)-4-(5-(5-fluoro-2-methoxypyridin-4-yl)-1H-pyrazole-3-carbonyl)-N-(5-methylpyrazolo[1,5-a]pyrimidin-3-yl)-4-azaspiro[2.5]octane-7-carboxamide

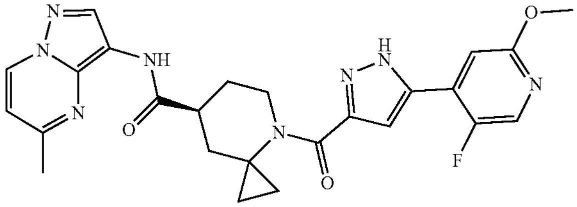 [SMILES: COc1cc(-c2cc(C(=O)N3CC[C@H](C(=O)Nc4cnn5ccc(C)nc45)CC34CC4)n[nH]2)c(F)cn1]

The title compound was prepared using a procedure similar to the one described for the synthesis of Example 325, except 5-methylpyrazolo[1,5-a]pyrimidin-3-amine hydrochloride was used as a starting material. The resulting residue was purified by reverse phase column chromatography (using the following conditions: Column: C18; mobile phase A: Water (0.5% $NH_4HCO_3$), mobile phase B: MeCN; gradient: 50 B to 80 B in 30 min; 220/254 nm) to obtain the title compound (54.2 mg) as a solid. $^1$H NMR (300 MHz, DMSO-$d_6$) δ 14.29-13.71 (m, 1H), 10.08 (s, 1H), 8.87 (d, 1H), 8.48 (s, 1H), 8.27 (s, 1H), 7.33 (d, 1H), 7.06 (s, 1H), 6.89 (d, 1H), 4.82-4.29 (m, 1H), 3.88 (s, 3H), 3.22-2.99 (m, 2H), 2.55 (s, 3H), 2.03-1.78 (m, 1H), 1.77-1.51 (m, 1H), 1.48-0.90 (m, 3H), 0.84-0.56 (m, 3H). LCMS (ESI): 505.05 $[M+H]^+$.

Example 382. A Diastereomeric Mixture of (S)-4-(5-(5-fluoro-2-methoxypyridin-4-yl)-1H-pyrazole-3-carbonyl)-N—(((S)-3-methyl-4,5,6,7-tetrahydro-1H-indazol-5-yl)methyl)-4-azaspiro[2.5]octane-7-carboxamide and (S)-4-(5-(5-fluoro-2-methoxypyridin-4-yl)-1H-pyrazole-3-carbonyl)-N—(((R)-3-methyl-4,5,6,7-tetrahydro-1H-indazol-5-yl)methyl)-4-azaspiro[2.5]octane-7-carboxamide

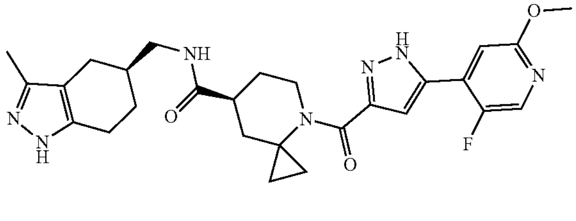

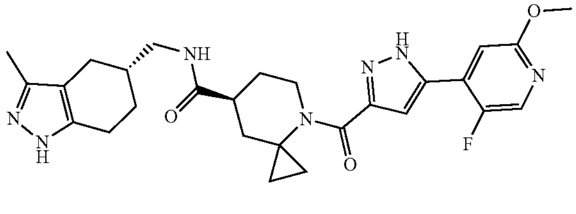

Step-1. 3-methyl-4,5,6,7-tetrahydro-1H-indazole-5-carbonyl chloride

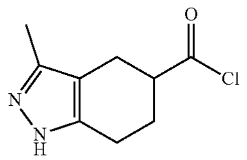

$(COCl)_2$ (422.6 mg, 3.33 mmol) was added to a stirred solution of 3-methyl-4,5,6,7-tetrahydro-1H-indazole-5-carboxylic acid (200.0 mg, 1.11 mmol) in DMF (0.05 mL) and DCM (5.00 mL). The resulting mixture was stirred at 25° C. for 30 min. The resulting solution was used in the next step directly without further purification.

Step-2. N,N-dibenzyl-3-methyl-4,5,6,7-tetrahydro-1H-indazole-5-carboxamide

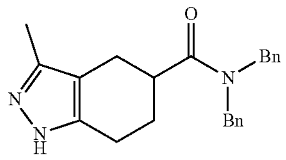 [SMILES: Cc1n[nH]c2c1CC(C(=O)N(Cc1ccccc1)Cc1ccccc1)CC2]

The solution of 3-methyl-4,5,6,7-tetrahydro-1H-indazole-5-carbonyl chloride (Step-1, 1.11 mmol) was added to a solution of dibenzyl amine (327.7 mg, 1.66 mmol) and DIPEA (429.4 mg, 3.31 mmol) in DCM (5.00 mL) at 0° C. The resulting solution was stirred at 25° C. for 2 h. The solution was concentrated under reduced pressure. The residue was purified by silica gel column chromatography eluting with DCM/MeOH (10/1 v/v) to obtain the title compound (245.0 mg) as an oil. LCMS (ESI): 360.2 $[M+H]^+$.

Step-3. dibenzyl[(3-methyl-4,5,6,7-tetrahydro-1H-indazol-5-yl)methyl]amine

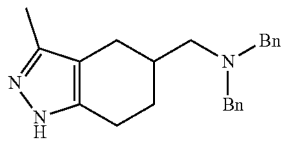 [SMILES: Cc1n[nH]c2c1CC(CN(Cc1ccccc1)Cc1ccccc1)CC2]

$LiAlH_4$ in THF (1.03 mL, 1.03 mmol, 1M) was added to a stirred solution of N,N-dibenzyl-3-methyl-4,5,6,7-tetrahydro-1H-indazole-5-carboxamide (Step-2, 185.0 mg, 0.52 mmol) in THF (2.00 mL) under the atmosphere of nitrogen. The resulting mixture was stirred at 0° C. for 1 h. Then the resulting mixture was stirred at 60° C. for 14 h. The solution was concentrated under reduced pressure. The residue was purified by reverse phase column chromatography (using the following conditions: Column: C18 column; mobile phase A: Water (0.5% $NH_4HCO_3$), mobile phase B: MeCN; gradient: 5 B to 30 B in 30 min; 220/254 nm) to obtain the title compound (85.0 mg) as an oil. LCMS (ESI): 346.2 $[M+H]^+$.

Step-4. dibenzyl[(3-methyl-4,5,6,7-tetrahydro-1H-indazol-5-yl)methyl]amine

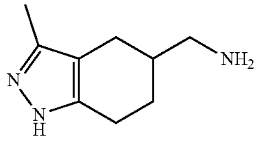

Pd/C (45.0 mg) was added to a stirred solution of dibenzyl [(3-methyl-4,5,6,7-tetrahydro-1H-indazol-5-yl)methyl] amine (Step-3, 85.0 mg, 0.25 mmol) in MeOH (2.00 mL). The resulting mixture was stirred at 25° C. for 3 h under a $H_2$ atmosphere. The solids were filtered out. The solution was concentrated under reduced pressure to obtain the title compound (38.0 mg) as an oil. LCMS (ESI): 166.1 $[M+H]^+$.

Step-5. (S)-4-(5-(5-fluoro-2-methoxypyridin-4-yl)-1H-pyrazole-3-carbonyl)-N—(((S)-3-methyl-4,5,6,7-tetrahydro-1H-indazol-5-yl)methyl)-4-azaspiro[2.5] octane-7-carboxamide and (S)-4-(5-(5-fluoro-2-methoxypyridin-4-yl)-1R-pyrazole-3-carbonyl)-N—(((R)-3-methyl-4,5,6,7-tetrahydro-1H-indazol-5-yl) methyl)-4-azaspiro[2.5]octane-7-carboxamide

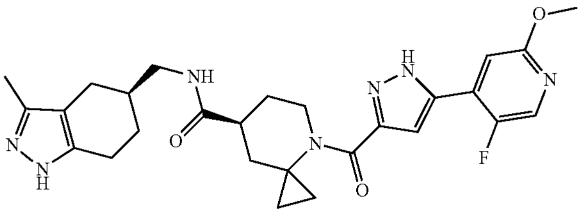

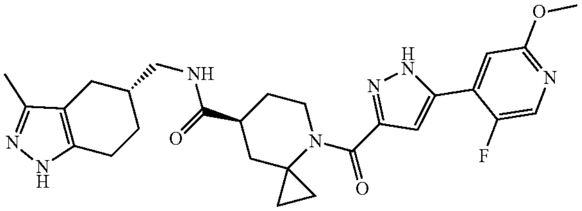

HOBt (40.5 mg, 0.30 mmol), EDCI (57.4 mg, 0.30 mmol), and 1-(3-methyl-4,5,6,7-tetrahydro-1H-indazol-5-yl)methanamine (Step-4, 33.0 mg, 0.20 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 74.8 mg, 0.20 mmol) and DIPEA (77.4 mg, 0.60 mmol) in DMF (2.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18 column; mobile phase A: Water (0.5% $NH_4HCO_3$), mobile phase B: MeCN; gradient: 20 B to 60 B in 30 min; 220/254 nm) to obtain (S)-4-(5-(5-fluoro-2-methoxypyridin-4-yl)-1H-pyrazole-3-carbonyl)-N—(((S)-3-methyl-4,5,6,7-tetrahydro-1H-indazol-5-yl)methyl)-4-azaspiro[2.5]octane-7-carboxamide and (S)-4-(5-(5-fluoro-2-methoxypyridin-4-yl)-1H-pyrazole-3-carbonyl)-N—(((R)-

3-methyl-4,5,6,7-tetrahydro-1H-indazol-5-yl)methyl)-4-azaspiro[2.5]octane-7-carboxamide (26.0 mg) as a solid mixture of diastereomers (Example 382). $^1$H NMR (300 MHz, DMSO-$d_6$) δ 14.29-13.75 (m, 1H), 11.94 (s, 1H), 8.50-8.19 (m, 1H), 7.92 (s, 1H), 7.47-7.25 (m, 1), 7.05 (s, 1H), 4.75-4.21 (m, 1H), 3.88 (s, 3H), 3.25-2.90 (m, 3H), 2.80-2.54 (m, 2H), 2.47-2.34 (m, 2H), 2.31-2.11 (m, 1H), 2.07-1.89 (m, 4H), 1.89-1.66 (m, 3H), 1.66-1.43 (m, 1H), 1.44-1.09 (m, 2H), 1.06-0.43 (m, 4H). LCMS (ESI): 522.15 $[M+H]^+$.

This mixture of two diastereomers (26.0 mg) was separated using Chiral Prep-HPLC.

Column: CHIRALPAK IA column

Column dimension: 2×25 cm, 5 μm

Mobile Phase: 3/1 hexanes/DCM (0.5% 2 M $NH_3$·MeOH):EtOH=70:30 hold for 15 min

Flow rate: 17 mL/min

Detection: 220/254 nm

Example 382-A. The first eluting diastereomer (4.0 mg) was obtained as a solid.

The first eluting diastereomer had a retention time of 9.21 min.

$^1$H NMR (400 MHz, DMSO-$d_6$) δ 14.30-13.75 (m, 1H), 11.78 (s, 1H), 8.45-8.09 (m, 1H), 7.90 (s, 1H), 7.30 (s, 1H), 7.02 (s, 1H), 4.51 (s, 1H), 3.85 (s, 3H), 3.20-3.00 (m, 2H), 2.76-2.62 (m, 1H), 2.48-2.29 (m, 3H), 2.02 (s, 3H), 1.98-1.86 (m, 1H), 1.85-1.62 (m, 3H), 1.52 (s, 1H), 1.34-1.00 (m, 4H), 1.02-0.78 (m, 2H), 0.77-0.46 (m, 2H). LCMS (ESI): 522.10 $[M+H]^+$.

Example 382-B. The second eluting diastereomer (4.2 mg) was obtained as a solid.

The second eluting diastereomer had a retention time of 11.60 min.

$^1$H NMR (400 MHz, DMSO-$d_6$) δ 14.12-13.81 (m, 1H), 11.82 (s, 1H), 8.24 (s, 1H), 7.90 (s, 1H), 7.30 (d, 1H), 7.02 (s, 1H), 4.50 (s, 1H), 3.85 (s, 3H), 3.22-2.91 (m, 2H), 2.82-2.61 (m, 1H), 2.46-2.30 (m, 3H), 2.02 (s, 3H), 1.95-1.86 (m, 1H), 1.86-1.67 (m, 3H), 1.64-1.41 (m, 1H), 1.41-1.07 (m, 4H), 1.04-0.75 (m, 2H), 0.77-0.44 (m, 2H). LCMS (ESI): 522.10 $[M+H]^+$.

Example 383. A Diastereomeric Mixture of (S)-4-(5-(5-fluoro-2-methoxypyridin-4-yl)-1H-pyrazole-3-carbonyl)-N—((R)-7-fluoro-3,4-dihydro-2H-pyrano[3,2-b]pyridin-4-yl)-4-azaspiro[2.5]octane-7-carboxamide and (S)-4-(5-(5-fluoro-2-methoxypyridin-4-yl)-1H-pyrazole-3-carbonyl)-N—((S)-7-fluoro-3,4-dihydro-2H-pyrano[3,2-b]pyridin-4-yl)-4-azaspiro[2.5]octane-7-carboxamide

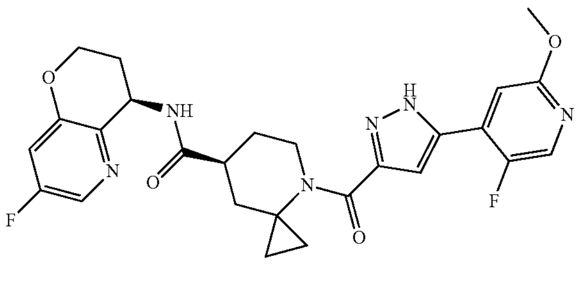

-continued

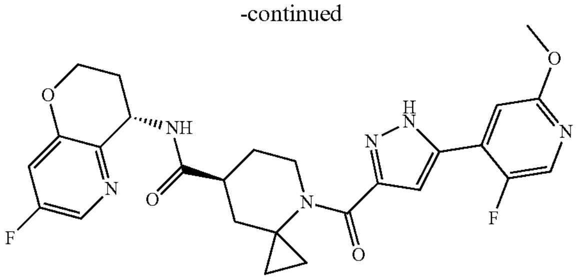

The title compound was prepared using a procedure similar to the one described for the synthesis of Example 380, except 2-bromo-5-fluoropyridin-3-ol was used as a starting material in Step-1. The resulting residue was purified by reverse phase column chromatography (using the following conditions: Column: C18 column; mobile phase A: Water (0.5% $NH_4HCO_3$), mobile phase B: MeCN; gradient: 30 B to 60 B in 30 min; 220/254 nm) to obtain (S)-4-(5-(5-fluoro-2-methoxypyridin-4-yl)-1H-pyrazole-3-carbonyl)-N—((R)-7-fluoro-3,4-dihydro-2H-pyrano[3,2-b]pyridin-4-yl)-4-azaspiro[2.5]octane-7-carboxamide and (S)-4-(5-(5-fluoro-2-methoxypyridin-4-yl)-1H-pyrazole-3-carbonyl)-N—((S)-7-fluoro-3,4-dihydro-2H-pyrano[3,2-b]pyridin-4-yl)-4-azaspiro[2.5]octane-7-carboxamide (22.8 mg) as a solid mixture of diastereomers (Example 383).

$^1$H NMR (300 MHz, $CD_3OD$) δ 8.28-8.04 (m, 2H), 7.41-7.17 (m, 1H), 7.16-7.05 (m, 2H), 5.10-5.00 (m, 1H), 4.75-4.48 (m, 1H), 4.42-4.14 (m, 2H), 3.95 (s, 3H), 2.88-2.82 (m, 1H), 2.47-2.41 (m, 1H), 2.33-2.20 (m, 1H), 2.16-2.10 (m, 1H), 192-1.68 (m, 2H), 1.34-1.28 (m, 2H), 1.17-0.87 (m, 2H), 0.77-0.71 (m, 2H). LCMS (ESI): 525.10 $[M+H]^+$.

This mixture of two diastereomers (22.8 mg) was separated using Chiral Prep-HPLC.

Column: CHIRALPAK IH column

Column dimension: 2×25 cm, 5 μm

Mobile Phase: MTBE (0.1% diethanolamine): EtOH=70:30 hold for 10 min

Flow rate: 20 mL/min

Detection: 220/254 min

Example 383-A. The first eluting diastereomer (4.0 mg) was obtained as a solid.

The first eluting diastereomer had a retention time of 6.22 min.

$^1$H NMR (400 MHz, $CD_3OD$) δ 8.12 (d, 1H), 8.05 (d, 1H), 7.30-7.24 (m, 1H), 7.14-7.07 (m, 2H), 5.06-5.01 (m, 1H), 4.75-4.48 (m, 1H), 4.38-4.26 (m, 1H), 4.26-4.16 (m, 1H), 3.92 (s, 3H), 2.85-2.80 (m, 1H), 2.46-2.4 (m, 1H), 2.29-2.01 (m, 2H), 1.99-1.78 (m, 2H), 1.32-1.26 (m, 2H), 1.08-0.80 (m, 2H), 0.72-0.68 (m, 2H). LCMS (ESI): 525.00 $[M+H]^+$.

Example 383-B. The second eluting diastereomer (3.5 mg) was obtained as a solid.

The second eluting diastereomer had a retention time of 8.81 inn.

$^1$H NMR (400 MHz, $CD_3OD$) δ 8.12 (d, 1H), 8.05 (d, 1H), 7.30-7.24 (m, 1H), 7.14-7.07 (m, 2H), 5.14-5.01 (m, 1H), 4.71-4.45 (m, 1H), 4.36-4.31 (m, 1H), 4.26-4.16 (m, 1H), 3.93 (s, 3H), 2.85-2.80 (m, 1H), 2.51-2.46 (m, 1H), 2.29-2.15 (m, 1H), 2.13-2.05 (m, 1H), 1.89-1.69 (m, 2H), 1.32-1.26 (m, 2H), 0.99-0.95 (m, 2H), 0.73-0.67 (m, 2H). LCMS (ESI): 525.00 $[M+H]^+$.

Example 384. (1R,3s,5S)—N-((3-chloro-5-fluoropyridin-2-yl)methyl)-8-(5-(5-fluoro-2-methoxypyridin-4-yl)-1H-pyrazole-3-carbonyl)-8-azabicyclo[3.2.1]octane-3-carboxamide

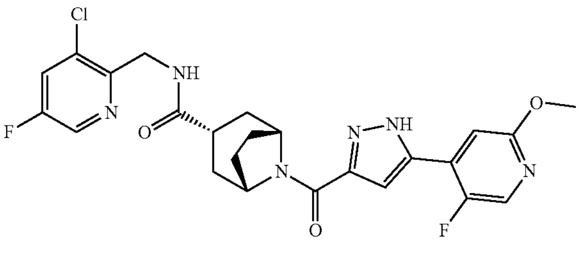 [SMILES: COc1cc(-c2cc(C(=O)N3[C@@H]4CC[C@H]3C[C@H](C(=O)NCc3ncc(F)cc3Cl)C4)n[nH]2)c(F)cn1]

The title compound was prepared using a procedure similar to the one described for the synthesis of Example 170-A, except 1-(3-chloro-5-fluoropyridin-2-yl)methanamine hydrochloride was used as starting material. The resulting residue was purified silica gel column chromatography eluting with DCM/MeOH (10/1 v/v) to obtain the title compound (94.6 mg) as a solid. $^1$H NMR (300 MHz, DMSO-$d_6$) δ 14.16-13.96 (m, 1H), 8.57 (d, 1H), 8.35-8.22 (m, 2H), 8.15-8.05 (m, 1H), 7.33 (d, 1H), 7.20-7.08 (m, 1H), 5.33-4.55 (m, 2H), 4.48-4.40 (m, 2H), 3.88 (s, 3H), 3.04-2.92 (m, 1H), 2.16-1.68 (m, 8H). LCMS (ESI): 517.4 [M+H]$^+$.

Example 385. A Enantiomeric Mixture of (R)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide and (S))—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide

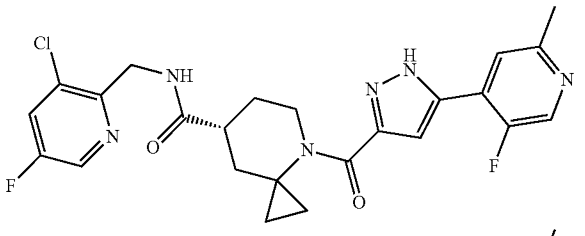

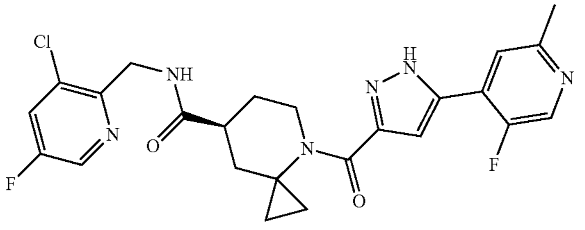

HATU (154.1 mg, 0.41 mmol) and 1-(3-chloro-5-fluoropyridin-2-yl)methanamine hydrochloride (73.2 mg, 0.37 mmol) were added to a stirred solution of 4-[5-(5-fluoro-2-methylpyridin-4-yl)-1H-pyrazole-3-carbonyl]-4-azaspiro[2.5]octane-7-carboxylic acid (INTERMEDIATE 526, 121.0 mg, 0.34 mmol) and DIPEA (174.6 mg, 1.35 mmol) in DMF (5.00 mL). The resulting mixture was stirred at 25° C. for 1 h. The solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (R)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide and (S)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide (120.0 mg) as an oil mixture of enantiomers. LCMS (ESI): 501.2 [M+H]$^+$.

This mixture of two diastereomers (120.0 mg) was separated using Chiral Prep-HPLC.

Column: CHIRALPAK IA column

Column dimension: 2×25 cm, 5 μm

Mobile Phase: MTBE (0.5% 2M $NH_3$·MeOH): 1/1 MeOH/DCM=50:50 hold for 12 min

Flow rate: 16 mL/min

Detection: 220/254 nm

Example 385-A. The first eluting diastereomer (19.2 mg) was obtained as a solid.

The first eluting diastereomer had a retention time of 5.34 min.

$^1$H NMR (400 MHz, DMSO-$d_6$) δ 14.22-13.68 (m, 1H), 8.64-8.46 (m, 2H), 8.34 (s, 1H), 8.17-8.03 (m, 1H), 7.94-7.72 (m, 1H), 7.03 (s, 1H), 5.04-4.08 (m, 3H), 3.55-3.04 (m, 3H), 2.96-2.71 (m, 1H), 2.25-1.99 (m, 1H), 1.80 (s, 1H), 1.56 (s, 1H), 1.40-1.11 (m, 1H), 1.07-0.82 (m, 2H), 0.79-0.41 (m, 3H). LCMS (ESI): 501.10 [M+H]$^+$.

Example 385-B. The second eluting diastereomer (15.5 mg) was obtained as a solid.

The second eluting diastereomer had a retention time of 9.07 min.

$^1$H NMR (300 MHz, DMSO-$d_6$) δ 14.17-13.73 (m, 1H), 8.67-8.44 (m, 2H), 8.35 (s, 1H), 8.20-8.03 (m, 1H), 7.81 (s, 1H), 7.03 (s, 1H), 4.80-4.15 (m, 3H), 3.48-2.96 (m, 3H), 2.90-2.69 (m, 1H), 2.30-1.96 (m, 1H), 1.94-1.68 (m, 1H), 1.66-1.47 (m, 1H), 1.37-1.11 (m, 1H), 1.08-0.83 (m, 2H), 0.82-0.42 (m, 3H). LCMS (ESI): 501.10 [M+H]$^+$.

Example 386. (S)-4-(5-(5-fluoro-2-methoxypyridin-4-yl)-1H-pyrazole-3-carbonyl)-N-((4-methylpyridazin-3-yl)methyl)-4-azaspiro[2.5]octane-7-carboxamide

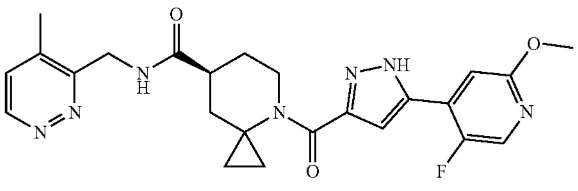 [SMILES: COc1cc(-c2cc(C(=O)N3CC[C@H](C(=O)NCc4nnccc4C)CC34CC4)n[nH]2)c(F)cn1]

The title compound was prepared using a procedure similar to the one described for the synthesis of Example 325, except 1-(4-methylpyridazin-3-yl)methanamine hydrochloride was used as a starting material. The residue was purified by reverse phase column chromatography (using the following conditions: Column: YMC-Actus Triart C18 ExRS column, 30×150 mm, 5 μm; Mobile Phase A: Water (10 mM $NH_4HCO_3$), Mobile Phase B: MeCN; Flow rate: 60 mL/min; Gradient: 17% B to 41% B in 8 min, 41% B; Wave Length: 254/220 nm; RT1 (min): 7.43) to obtain the title compound (20.8 mg) as a solid. $^1$H NMR (400 MHz, DMSO-$d_6$) δ 13.94 (s, 1H), 8.97 (d, 1H), 8.42 (s, 1H), 8.24

(s, 1H), 7.46 (d, 1H), 7.29 (d, 1H), 7.01 (d, 1H), 4.68-4.27 (m, 3H), 3.85 (s, 3H), 3.06-2.73 (m, 2H), 2.27 (s, 3H), 2.17-2.13 (m, 1H), 1.86-1.39 (m, 2H), 1.22 (s, 1H), 0.93-0.89 (m, 2H), 0.71-0.44 (m, 2H). LCMS(ESI): 480.4 $[M+H]^+$.

Example 387. (S)—N-((5-chloro-2-methylpyrimidin-4-yl)methyl)-4-(5-(5-fluoro-2-methoxypyridin-4-yl)-1H-pyrazole-3-carbonyl)-4-azaspiro[2,5]octane-7-carboxamide

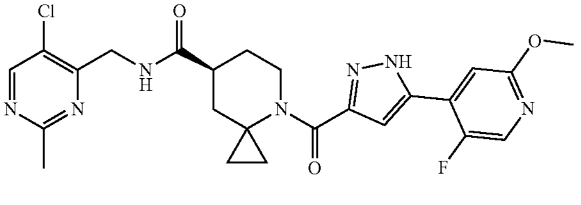 [SMILES: COc1cc(-c2cc(C(=O)N3CC[C@H](C(=O)NCc4nc(C)ncc4Cl)CC34CC4)n[nH]2)c(F)cn1]

Step-1. tert-butyl N-[(5-chloro-2-methylpyrimidin-4-yl)methyl]carbamate

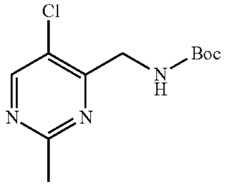 [SMILES: Cc1ncc(Cl)c(CNC(=O)OC(C)(C)C)n1]

$Pd(AMPhos)_2Cl_2$ (86.9 mg, 0.12 mmol) and $K_3PO_4$ (520.9 mg, 2.45 mmol) were added to a stirred mixture of 4,5-dichloro-2-methylpyrimidine (200.0 mg, 1.23 mmol) and potassium (((tert-butoxycarbonyl)amino)methyl)trifluoroborate (349.1 mg, 1.47 mmol) in 1,4-dioxane (3.00 mL) and water (0.60 mL) at 25° C. The resulting mixture was stirred at 90° C. for 14 h under nitrogen atmosphere. The resulting mixture was concentrated under reduced pressure. The residue was purified by Prep-TLC (petroleum ether/EtOAc, 4/1 v/v) to obtain the title compound (80.0 mg) as a solid. LCMS (ESI): 258.1 $[M+H]^+$.

Step-2. 1-(5-chloro-2-methylpyrimidin-4-yl)methanamine

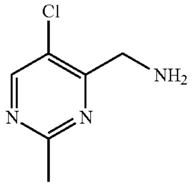

TEA (3.00 mL) was added to a stirred solution of tert-butyl N-[(5-chloro-2-methylpyrimidin-4-yl)methyl]carbamate (Step-1, 70.0 mg, 0.27 mmol) in DCM (3.00 mL) at 25° C. The resulting mixture was stirred at 25° C. for 30 min. The resulting mixture was concentrated under reduced pressure to obtain the title compound (30.0 mg) as an oil. LCMS (ESI): 158.0 $[M+H]_+$.

Step-3. (S)—N-((5-chloro-2-methylpyrimidin-4-yl)methyl)-4-(5-(5-fluoro-2-methoxypyridin-4-yl)-1H-pyrazole-3-carbonyl)-4-azaspiro[2.5]octane-7-carboxamide

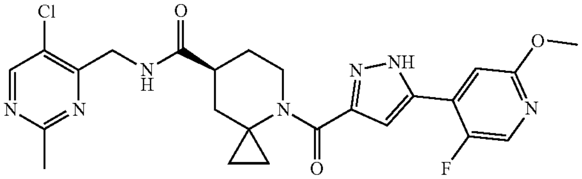 [SMILES: COc1cc(-c2cc(C(=O)N3CC[C@H](C(=O)NCc4nc(C)ncc4Cl)CC34CC4)n[nH]2)c(F)cn1]

HOBt (68.6 mg, 0.51 mmol), EDCI (97.3 mg, 0.51 mmol), and 1-(5-chloro-2-methylpyrimidin-4-yl)methanamine (Step-2, 40.0 mg, 0.25 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 95.0 mg, 0.25 mmol) and DIPEA (164.0 mg, 1.27 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 15 B to 35 B in 30 min; 220/254 nm) to obtain the title compound (6.7 mg) as a solid.

$^1H$ NMR (300 MHz, $CD_3OD$) δ 8.61 (s, 1H), 8.14 (s, 1H), 7.29 (s, 1H), 7.12 (s, 1H), 4.65-4.55 (m, 2H), 3.95 (s, 3H), 3.02-2.92 (m, 1H), 2.70-2.64 (m, 2-1), 2.48-2.42 (m, 1H), 2.16-1.65 (m, 3H), 1.52-1.23 (m, 4H), 1.08-0.58 (m, 3H). LCMS (ESI): 514.15 $[M+H]^+$.

Example 388. (S)—N-((3-chloropyrazin-2-yl)methyl)-4-(5-(5-fluoro-2-methoxypyridin-4-yl)-1H-pyrazole-3-carbonyl)-4-azaspiro[2.5]octane-7-carboxamide

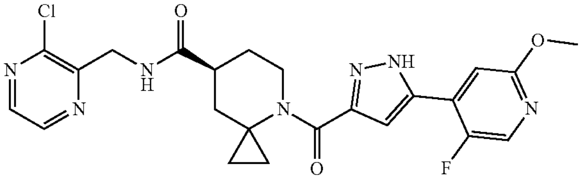

The title compound was prepared using a procedure similar to the one described for the synthesis of Example 325, except 1-(3-chloropyrazin-2-yl)methanamine was used as a starting material. The residue was purified by Prep-TLC eluting with EtOAc to obtain the title compound (91.2 mg) as a solid. $^1H$ NMR (300 MHz, DMSO-$d_6$) δ 14.22-13.76 (m, 1H), 8.63 (d, 1H), 8.44 (d, 2H), 8.48-8.20 (m, 1H), 7.32 (d, 1H), 7.04 (s, 1H), 4.55-4.47 (m, 3H), 4.07-4.01 (m, 1H), 3.88 (s, 3H), 2.92-2.75 (m, 1H), 2.22-2.05 (m, 1H), 1.85-1.79 (m, 1H), 1.59-1.53 (m, 1H), 1.43-1.13 (m, 1H), 1.11-0.85 (m, 2H), 0.79-0.43 (m, 2H). LCMS (ESI): 500.35 $[M+H]^+$.

Example 389. (S)-4-(5-(5-fluoro-2-methoxypyridin-4-yl)-1H-pyrazole-3-carbonyl)-N-((5-fluoro-3-methoxypyridin-2-yl)methyl)-4-azaspiro[2.5]octane-7-carboxamide

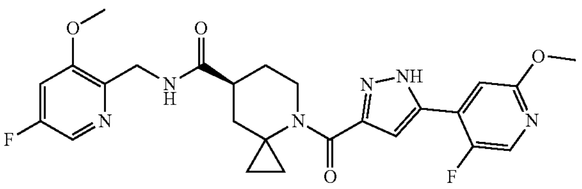 [SMILES: COc1cc(-c2cc(C(=O)N3CC[C@H](C(=O)NCc4ncc(F)cc4OC)CC34CC4)n[nH]2)c(F)cn1]

Step-1. 5-fluoro-3-methoxypyridine-2-carbonitrile

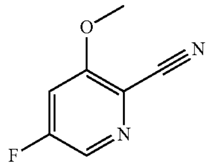

Zn (16.0 mg, 0.25 mmol) and Pd(dppf)$Cl_2$ (362.0 mg, 0.37 mmol) were added to a mixture of 2-chloro-5-fluoro-3-methoxypyridine (400.0 mg, 2.48 mmol) and zinc cyamide (291.0 mg, 2.48 mmol) in DMF (5.00 mL). The resulting mixture was stirred at 90° C. for 4 h under nitrogen atmosphere. The resulting mixture was diluted with EtOAc and washed with water. The organic layers were combined, dried over anhydrous $Na_2SO_4$, filtered, and concentrated under reduced pressure. The resulting mixture was concentrated under reduced pressure. The residue was purified by silica gel column chromatography eluting with petroleum ether/EtOAc (5/1 v/v) to obtain the title compound (310.0 mg) as a solid. LCMS (ESI): 153 $[M+H]^+$.

Step-2. 5-fluoro-3-methoxypyridine-2-carbonitrile

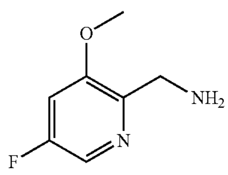

DIBAL-H (7. 62 mL, 7.62 mmol, 1M) was added to a mixture of 5-fluoro-3-methoxypyridine-2-carbonitrile (Step-1, 290.0 mg, 1.91 mmol) in DCM (5.00 mL). The resulting mixture was stirred at −78° C. for 4 h under nitrogen atmosphere. The resulting mixture was concentrated under reduced pressure. The residue was purified by silica gel column chromatography eluting with DCM/MeOH (15/1 v/v) to obtain the title compound (130.0 mg) as a solid. LCMS (ESI): 157 $[M+H]^+$.

Step-3. (S)-4-(5-(5-fluoro-2-methoxypyridin-4-yl)-1H-pyrazole-3-carbonyl)-N-((5-fluoro-3-methoxypyridin-2-yl)methyl)-4-azaspiro[2.5]octane-7-carboxamide

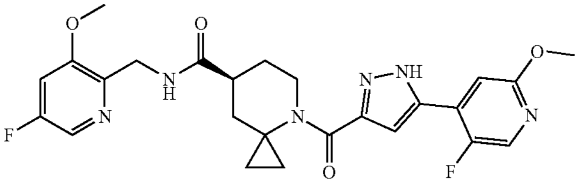 [SMILES: COc1cc(-c2cc(C(=O)N3CC[C@H](C(=O)NCc4ncc(F)cc4OC)CC34CC4)n[nH]2)c(F)cn1]

EDCI (221.0 mg, 1.15 mmol), HOBt (156.0 mg, 1.15 mmol), and 1-(5-fluoro-3-methoxypyridin-2-yl)methanamine (Step-2, 120.0 mg, 0.77 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 288.0 mg, 0.77 mmol) and DIPEA (497.0 mg, 3.84 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (31.0 mg) as a solid. $^1H$ NMR (300 MHz, DMSO-$d_6$) δ 10.90 (s, 1H), 8.27 (d, 1H), 8.17-8.06 (m, 2H), 7.53-7.42 (m, 1H), 7.33 (d, 1H), 7.03 (d, 1H), 4.63-4.29 (m, 3H), 3.91-3.77 (m, 6H), 3.19-2.77 (m, 2H), 2.25-2.19 (m, 1H), 1.79-1.73 (m, 1H), 1.58-1.52 (m, 1H), 1.27-1.21 (m, 1H), 0.93-0.87 (m, 2H), 0.68-0.59 (m, 2H). LCMS (ESI): 513.15 $[M+H]^+$.

Example 390. A Diastereomeric Mixture of (S)-4-(5-(5-fluoro-2-methoxypyridin-4-yl)-1H-pyrazole-3-carbonyl)-N—((R)-1-(pyridin-3-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-(pyridin-3-yl)pyrrolidin-3-yl)-4-azaspiro[2.5]octane-7-carboxamide

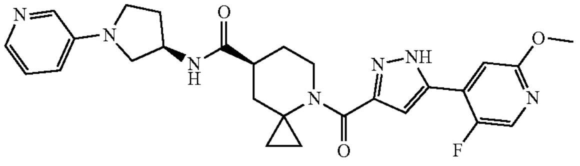

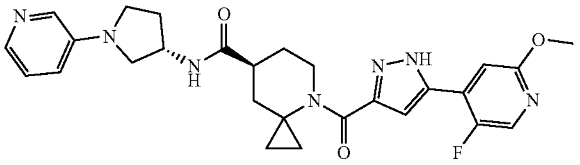

Step-1. N,N-dibenzyl-1-(pyridin-3-yl)pyrrolidin-3-amine

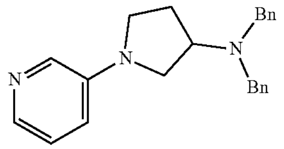 [SMILES: c1ccc(CN(Cc2ccccc2)C2CCN(c3cccnc3)C2)cc1]

3-Bromopyridine (474.5 mg, 3.00 mmol), BrettPhos (161.2 mg, 0.30 mmol), BrettPhos Pd G3 (272.2 mg, 0.30 mmol) and $Cs_2CO_3$ (2.45 g, 7.51 mmol) were added to a stirred mixture of N,N-dibenzylpyrrolidin-3-amine (800.0 mg, 3.00 mmol) in 1,4-dioxane (10.00 mL). The resulting solution was stirred at 110° C. for 14 h under nitrogen atmosphere. The mixture was allowed to cool down to 25° C. The resulting mixture was concentrated under reduced pressure. The residue was purified by silica gel column chromatography eluting with petroleum ether/EtOAc (3/2 v/v) to obtain the title compound (422.4 mg) as an oil. LCMS (ESI): 344.2 $[M+H]^+$.

Step-2. 1-(pyridin-3-yl)pyrrolidin-3-amine

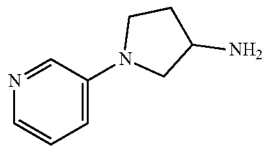 [SMILES: NC1CCN(c2cccnc2)C1]

Pd/C (126.0 mg) was added to a stirred mixture of N,N-dibenzyl-1-pyridin-3-yl)pyrrolidin-3-amine (Step-1, 210.0 mg, 0.61 mmol) in MeOH (3.00 mL) and THF (1.00 mL) at 0° C. The resulting mixture was stirred at 25° C. for 14 h under hydrogen atmosphere. The resulting mixture was filtered, the filter cake was washed with MeOH. The filtrate was concentrated under reduced pressure to obtain the title compound (90.0 mg) as an oil. LCMS (ESI): 164.1 $[M+H]^+$.

Step-3. (V)-4-(5-(5-fluoro-2-methoxypyridin-4-yl)-1H-pyrazole-3-carbonyl)-N—((R)-1-(pyridin-3-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-(pyridin-3-yl)pyrrolidin-3-yl)-4-azaspiro[2.5]octane-7-carboxamide

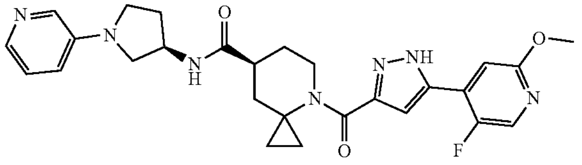

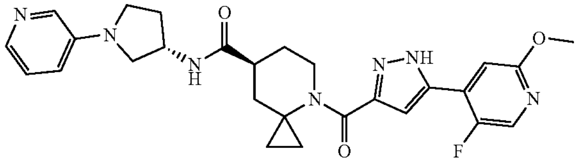

HOBt (132.5 mg, 0.98 mmol), EDCI (187.9 mg, 0.98 mmol) and 1-(pyridin-3-yl)pyrrolidin-3-amine (80.0 mg, 0.49 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 183.5 mg, 0.49 mmol) and DIPEA (316.7 mg, 2.45 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC eluting with DCM/MeOH (18/1 v/v) to obtain (S)-4-(5-(5-fluoro-2-methoxypyridin-4-yl)-1H-pyrazole-3-carbonyl)-N—((R)-1-(pyridin-3-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-(pyridin-3-yl)pyrrolidin-3-yl)-4-azaspiro[2.5]octane-7-carboxamide (110 mg) as a solid mixture of diastereomers (Example 390). $^1H$ NMR (400 MHz, DMSO-$d_6$) δ 14.28-13.68 (m, 1H), 8.39-8.04 (m, 2H), 7.90 (d, 1H), 7.82 (d, 1H), 7.30 (d, 1H), 7.19-7.09 (m, 1H), 7.02 (s, 1H), 6.91-6.81 (m, 1H), 4.66-4.22 (m, 2H), 3.85 (s, 3H), 3.58-3.42 (m, 1H), 3.31-3.22 (m, 1H), 3.12-2.78 (m, 2H), 2.76-2.54 (m, 1H), 2.26-2.00 (m, 3H), 1.96-1.37 (m, 2H), 1.36-0.75 (m, 3H), 0.75-0.34 (m, 3H). LCMS(ESI): 520.4 $[M+H]^+$.

This mixture of two diastereomers (110.0 mg) was separated using Chiral Prep-HPLC.

Column: CHIRAL ART Cellulose-SB column

Column dimension: 2×25 cm, 5 μm

Mobile Phase: MTBE (0.5% 2M $NH_3$·MeOH): MeOH=50:50 hold for 10.5 min

Flow rate: 20 mL/min

Detection: 220/254 nm

Example 390-A. The first eluting diastereomer (29.0 mg) was obtained as a solid.

The first eluting diastereomer had a retention time of 7.81 min.

$^1H$ NMR (300 MHz, DMSO-$d_6$) δ 14.27-13.68 (m, 1H), 8.26 (s, 1H), 8.15 (s, 1H), 7.93 (d, 1H), 7.88-7.80 (m, 1H), 7.32 (d, 1H), 7.21-7.10 (m, 1H), 7.04 (s, 1H), 6.95-6.84 (m, 1H), 4.72-4.19 (m, 2H), 3.88 (s, 3H), 3.56-3.45 (m, 1H), 3.45-3.33 (m, 1H), 3.13-2.90 (m, 2H), 2.72-2.66 (m, 1H), 2.26-2.09 (m, 2H), 1.95-1.78 (m, 1H), 1.77-1.71 (m, 1H), 1.58-152 (m, 1H), 1.33-1.15 (m, 1H), 1.07-0.83 (m, 2H), 0.77-0.35 (m, 3H). LCMS (ESI): 520.4 $[M+H]^+$.

Example 390-B. The second eluting diastereomer (22.5 mg) was obtained as a solid.

The second eluting diastereomer had a retention time of 8.25 min.

$^1H$ NMR (300 MHz, DMSO-$d_6$) δ 14.16-13.78 (m, 1H), 8.21 (d, 2H), 8.00-7.76 (m, 2H), 7.32 (d, 1H), 7.21-7.11 (m, 1H), 7.07-7.01 (m, 1H), 6.94-6.84 (m, 1H), 4.62-4.34 (m, 2H), 3.88 (s, 3H), 3.56-3.44 (m, 1H), 3.43-3.34 (m, 1H), 3.12-2.84 (m, 2H), 2.72-2.66 (m, 1H), 2.26-2.09 (m, 2H), 1.95-1.68 (m, 2H), 1.58-1.52 (m, 1H), 1.32-1.08 (m, 1H), 1.03-0.82 (m, 2H), 0.77-0.44 (m, 3H). LCMS (ESI): 520.4 $[M+H]^+$.

Example 391. (S)—N-((3-chloro-5-cyanopyridin-2-yl)methyl)-4-(5-(5-fluoro-2-methoxypyridin-4-yl)-1H-pyrazole-3-carbonyl)-4-azaspiro[2.5]octane-7-carboxamide

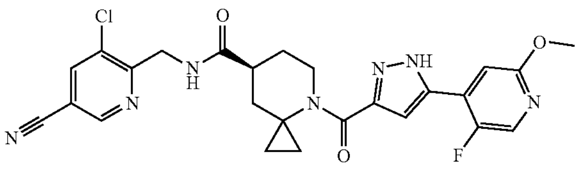 [SMILES: COc1cc(-c2cc(C(=O)N3CC[C@H](C(=O)NCc4ncc(C#N)cc4Cl)CC34CC4)n[nH]2)c(F)cn1]

Step-1. 6-(bromomethyl)-5-chloropyridine-3-carbonitrile

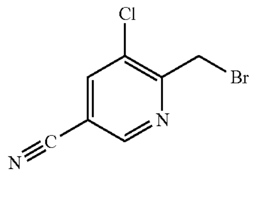 [SMILES: N#Cc1cnc(CBr)c(Cl)c1]

NBS (355.0 mg, 1.97 mmol) and AIBN (322.9 mg, 1.97 mmol) were added to a stirred mixture of 5-chloro-6-methylpyridine-3-carbonitrile (300.0 mg, 1.97 mmol) in $CCl_4$ (5.00 mL). The resulting mixture was stirred at 80° C. for 14 h under nitrogen atmosphere. The resulting mixture was concentrated under reduced pressure. The residue was purified by silica gel column chromatography eluting with petroleum ether/EtOAc (10/1 v/v) to obtain the title compound (120.0 mg) as a solid.

Step-2. 6-(azidomethyl)-5-chloropyridine-3-carbonitrile

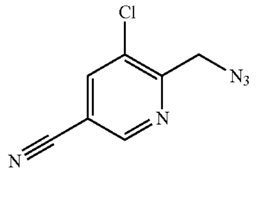 [SMILES: N#Cc1cnc(CN=[N+]=[N-])c(Cl)c1]

Azidosodium (50.6 mg, 0.78 mmol) was added to a stirred solution of 6-(bromomethyl)-5-chloropyridine-3-carbonitrile (step-1, 90.0 mg, 0.39 mmol) in DMF (4.00 mL) at 0° C. The resulting mixture was stirred at 0° C. for 1 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (12/1 v/v) to obtain the title compound (60.0 mg) as a solid. LCMS (ESI): 194.0 $[M+H]^+$.

Step-3. 6-(azidomethyl)-5-chloropyridine-3-carbonitrile

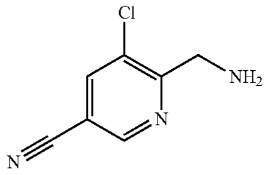 [SMILES: N#Cc1cnc(CN)c(Cl)c1]

Pd/C (5.5 mg) was added to a stirred mixture of 6-(azidomethyl)-5-chloropyridine-3-carbonitrile (Step-2, 50.0 mg, 0.26 mmol) in MeOH (4.00 mL) at 0° C. The resulting mixture was stirred at 0° C. for 30 min under hydrogen atmosphere. The resulting mixture was filtered, the filter cake was washed with MeOH. The filtrate was concentrated under reduced pressure to obtain the title compound (40.0 mg) as a solid. LCMS (ESI): 168.0 $[M+H]^+$.

Step-4. (S)—N-((3-chloro-5-cyanopyridin-2-yl)methyl)-4-(5-(5-fluoro-2-methoxypyridin-4-yl)-1H-pyrazole-3-carbonyl)-4-azaspiro[2.5]octane-7-carboxamide

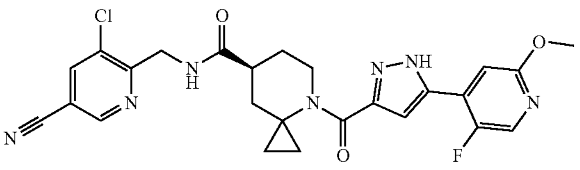 [SMILES: COc1cc(-c2cc(C(=O)N3CC[C@H](C(=O)NCc4ncc(C#N)cc4Cl)CC34CC4)n[nH]2)c(F)cn1]

HOBt (57.8 mg, 0.43 mmol) and EDCI (81.9 rug, 0.43 mmol), and 6-(aminomethyl)-5-chloropyridine-3-carbonitrile (Step-3, 35.8 mg, 0.21 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 80.0 mg, 0.21 mmol) and DIPEA (138.1 mg, 1.07 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 30 B to 60 B in 30 min; 220/254 nm) to obtain the title compound (17.8 mg) as a solid. $^1H$ NMR (400 MHz, DMSO-$d_6$) δ 13.98 (s, 1H), 8.93 (s, 1H), 8.54 (s, 1H), 8.43 (s, 1H), 8.24 (s, 1H), 7.29 (d, 1H), 7.01 (s, 1H), 4.80-4.35 (m, 3H), 3.85 (s, 3H), 2.83-2.78 (m, 1H), 2.33-2.03 (m, 1H), 1.81-1.76 (m, 1H), 1.54-1.49 (m, 1H), 1.23-1.19 (m, 2H), 0.98-0.94 (m, 2H), 0.65-0.60 (m, 2H). LCMS (ESI): 524.20 $[M+H]^+$.

Example 392. (S)—N-((3-chloro-5-(oxetan-3-yl)pyridin-2-yl)methyl)-4-(5-(5-fluoro-2-methoxypyridin-4-yl)-1H-pyrazole-3-carbonyl)-4-azaspiro[2.5]octane-7-carboxamide

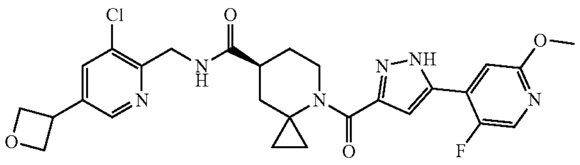 [SMILES: COc1cc(-c2cc(C(=O)N3CC[C@H](C(=O)NCc4ncc(C5COC5)cc4Cl)CC34CC4)n[nH]2)c(F)cn1]

Step-1. 1-(5-bromo-3-chloropyridin-2-yl)methanamine

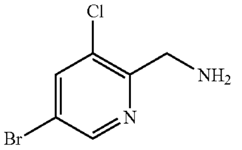

DIBAL-H (13.00 mL, 13.00 mmol, 1 M) was added to a stirred mixture of 5-bromo-3-chloropyridine-2-carbonitrile (1.00 g, 4.60 mmol) in dry DCM (6.00 mL) at −78° C. under nitrogen atmosphere. The resulting mixture was stirred at −78° C. for 1 h under nitrogen atmosphere. The resulting mixture was concentrated under reduced pressure. The residue was purified by silica gel column chromatography eluting with DCM/MeOH (10/1 v/v) to obtain the title compound (680.0 mg) as an oil. LCMS (ESI): 220.9 $[M+H]^+$.

Step-2. tert-butyl N-[(5-bromo-3-chloropyridin-2-yl)methyl]carbamate

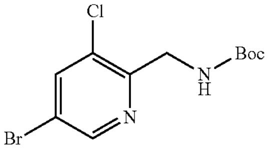 [SMILES: CC(C)(C)OC(=O)NCc1ncc(Br)cc1Cl]

TEA (685.3 mg, 6.77 mmol) and $Boc_2O$ (710.0 mg, 3.25 mmol) were added to a stirred mixture of 1-(5-bromo-3-chloropyridin-2-yl)methanamine (Step-1, 600.0 mg, 2.71 mmol) in DCM (6.00 mL). The resulting mixture was stirred at 25° C. for 14 h. The resulting mixture was concentrated under reduced pressure. The residue was purified by silica gel column chromatography eluting with petroleum ether/EtOAc (5/1 v/v) to obtain the title compound (430.0 mg) as an oil. LCMS (ESI): 320.9 $[M+H]^+$.

Step-3. tert-butyl N-[[3-chloro-5-(3-cyanoazetidin-1-yl)pyridin-2-yl]methyl]carbamate

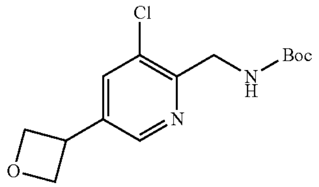 [SMILES: CC(C)(C)OC(=O)NCc1ncc(C2COC2)cc1Cl]

3-Iodooxetane (94.4 mg, 0.51 mmol), $NiCl_2$ (7.5 mg, 0.03 mmol), $(Ir[dF(CF_3)ppy]_2(dtbpy))PF_6$ (3.8 mg, 0.003 mmol), tris(trimethylsilyl)silane (84.8 mg, 0.34 mmol), 2,6-lutidine (73.3 mg, 0.68 mmol) and dtbpy (9.2 mg, 0.03 mmol) were added to a stirred mixture of tert-butyl N-[(5-bromo-3-chloropyridin-2-yl)methyl]carbamate (step-2, 110.0 mg, 0.34 mmol) in DME (10.00 mL). The resulting reaction mixture was irradiated for 1 h with Integrated Photoreactor Royal Blue (450 nm) LED light at 25° C. under nitrogen atmosphere. The resulting mixture was concentrated under reduced pressure. The residue was purified by silica gel column chromatography eluting with petroleum ether/EtOAc (2/1 v/v) to obtain the title compound (18.0 mg) as an oil. LCMS (ESI): 299.1 $[M+H]^+$.

Step-4. 1-[3-chloro-5-(oxetan-3-yl)pyridin-2-yl]methanamine

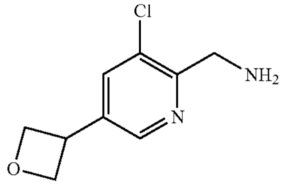 [SMILES: NCc1ncc(C2COC2)cc1Cl]

TFA (100 mL) was added to a stirred mixture of tert-butyl N-[[3-chloro-5-(3-cyanoazetidin-1-yl)pyridin-2-yl]methyl]carbamate (step-3, 10.0 mg, 0.03 mmol) in DCM (1.00 mL) at 0° C. The resulting mixture was stirred at 25° C. for 1 h. The resulting mixture was concentrated under reduced pressure to obtain the title compound and used directly in the next step without further purification. LCMS (ESI): 199.0 $[M+H]^+$.

Step-5. (S)—N-((3-chloro-5-(oxetan-3-yl)pyridin-2-yl)methyl)-4-(5-(5-fluoro-2-methoxypyridin-4-yl)-1H-pyrazole-3-carbonyl)-4-azaspiro[2.5]octane-7-carboxamide

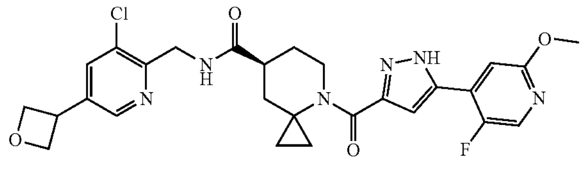 [SMILES: COc1cc(-c2cc(C(=O)N3CC[C@H](C(=O)NCc4ncc(C5COC5)cc4Cl)CC34CC4)n[nH]2)c(F)cn1]

HOBt (6.8 mg, 0.05 mmol) and EDCI (9.7 mg, 0.05 mmol), and 1-[3-chloro-5-(oxetan-3-yl)pyridin-2-yl]methanamine (Step-4, 5.0 mg, 0.025 mmol) was added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 9.4 mg, 0.025 mmol) and DIPEA (16.3 mg, 0.13 mmol) in DMF (1.00 mL). The resulting mixture was stirred at 25° C. for 2 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (2/1 v/v) to obtain the title compound (2.3 mg) as a solid.

$^1$H NMR (300 MHz, $CD_3OD$) δ 8.48 (d, 1H), 8.13 (d, 1H), 8.02 (d, 1H), 7.29 (d, 1H), 7.12 (d, 1H), 5.17-5.06 (m, 2H), 4.78-4.68 (m, 2H), 4.65-4.59 (m, 3H), 4.42-4.26 (m, 1H), 3.94 (s, 3H), 2.99-2.93 (m, 1H), 2.50-2.44 (m, 1H), 1.99-1.93 (m, 1H), 1.83-1.77 (m, 1H), 1.45-1.27 (m, 2H), 1.13-0.84 (m, 2H), 0.81-0.73 (m, 2H). LCMS (ESI): 555.15 $[M+H]^+$.

Example 393. (S)—N-((3-chloro-5-(3-cyanoazetidin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide

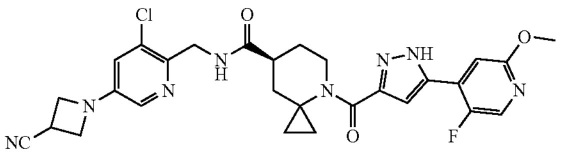 [SMILES: COc1cc(-c2cc(C(=O)N3CC[C@H](C(=O)NCc4ncc(N5CC(C#N)C5)cc4Cl)CC34CC4)n[nH]2)c(F)cn1]

Step-1. tert-butyl N-[[3-chloro-5-(3-cyanoazetidin-1-yl)pyridin-2-yl]methyl]carbamate

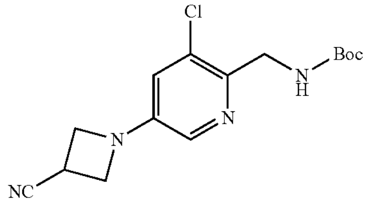 [SMILES: CC(C)(C)OC(=O)NCc1ncc(N2CC(C#N)C2)cc1Cl]

Azetidine-3-carbonitrile hydrochloride (173.9 mg, 1.47 mmol), $Cs_2CO_3$ (955.8 mg, 2.93 mmol), BrettPhos Pd G3 (133.0 mg, 0.15 mmol) and BrettPhos (78.7 mg, 0.15 mmol) were added to a stirred solution of tert-butyl A-[(5-bromo-3-chloropyridin-2-yl)methyl]carbamate (Step-2 from synthesis of Example 392, 471.7 mg, 1.47 mmol) in 1,4-dioxane (3.00 mL). The resulting mixture was stirred at 110° C. for 14 h under $N_2$ atmosphere. The resulting solution was concentrated under reduced pressure. The residue was purified by silica gel column chromatography eluting with EtOAc/petroleum ether (1/2 v/v) to obtain the title compound (42.0 mg) as an oil. LCMS (ESI): 323.1 $[M+H]^+$.

Step-2. 1-[6-(aminomethyl)-5-chloropyridin-3-yl]azetidine-3-carbonitrile

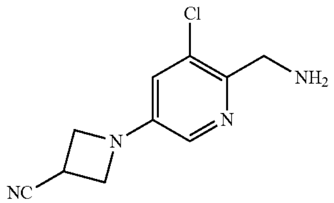 [SMILES: N#CC1CN(c2cnc(CN)c(Cl)c2)C1]

TFA (5.00 mL) was added to a stirred solution of tert-butyl N-[[3-chloro-5-(3-cyanoazetidin-1-yl)pyridin-2-yl]methyl]carbamate (Step-1, 40.0 mg, 0.12 mmol) in DCM (5.00 mL). The resulting mixture was stirred at 25° C. for 30 min. The resulting solution was concentrated under reduced pressure to obtain the title compound (25.0 mg) as a solid. LCMS (ESI): 223.1 $[M+H]^+$.

Step-3. (S)—N-((3-chloro-5-(3-cyanoazetidin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide

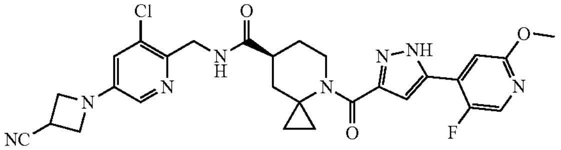 [SMILES: COc1cc(-c2cc(C(=O)N3CC[C@H](C(=O)NCc4ncc(N5CC(C#N)C5)cc4Cl)CC34CC4)n[nH]2)c(F)cn1]

HOBt (22.8 mg, 0.17 mmol), EDCI (32.3 mg, 0.17 mmol), and 1-[6-(aminomethyl)-5-chloropyridin-3-yl]azetidine-3-carbonitrile (Step-2, 25.0 mg, 0.11 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 42.0 mg, 0.11 mmol) and DIPEA (87.1 mg, 0.67 mmol) in DMF (3.00 mL). The resulting mixture was stirred at 25° C. for 2 h. The resulting solution was diluted with EtOAc and washed with water. The organic layers were combined, dried over anhydrous $Na_2SO_4$, filtered, and concentrated under reduced pressure. The residue was purified by Prep-HPLC (using the following conditions: Column: C18; mobile phase A: Water (0.5% $NH_4HCO_3$), mobile phase B: MeCN; gradient: 30 B to 50 B in 20 min; 220/254 nm) to obtain the title compound (12.0 mg) as a solid. $^1$H NMR (300 MHz, DMSO-$d_6$) δ 14.18-13.78 (m, 1H), 8.48-8.07 (m, 2H), 7.79 (s, 1H), 7.42-7.22 (m, 1H), 7.17-6.94 (m, 2H), 4.60-4.44 (m, 1H), 4.43-4.29 (m, 2H), 4.25-4.14 (m, 2H), 4.13-4.00 (m, 2H), 3.97-3.89 (m, 1H), 3.88 (s, 3H), 2.79-2.69 (m, 1H), 2.25-2.02 (m, 1H), 1.92-1.68 (m, 1H), 1.66-1.38 (m, 1H), 1.36-1.11 (m, 2H), 1.10-0.75 (m, 2H), 0.75-0.39 (m, 2H). LCMS (ESI): 579.30 $[M+H]^+$.

Example 394. (S)-4-(5-(5-fluoro-2-methoxypyridin-4-yl)-1H-pyrazole-3-carbonyl)-N-((2-methyl-5-(trifluoromethyl)oxazol-4-yl)methyl)-4-azaspiro[2.5]octane-7-carboxamide

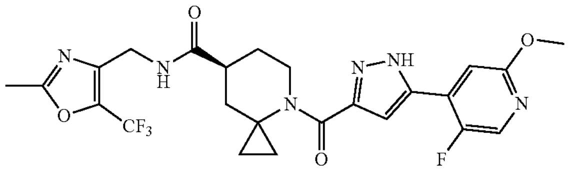

Step-1. N-methoxy-N,2-dimethyl-5-(trifluoromethyl)-1,3-oxazole-4-carboxamide

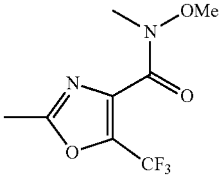 [SMILES: CON(C)C(=O)c1nc(C)oc1C(F)(F)F]

HATU (292.0 mg, 0.77 mmol) and N,O-dimethythydroxylamine (31.0 mg, 0.51 mmol) were added to a stirred mixture of 2-methyl-5-(trifluoromethyl)-1,3-oxazole-4-carboxylic acid (100.0 mg, 0.51 mmol) and DIPEA (199.0 mg, 1.54 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (1/1 v/v) to obtain the title compound (105.0 mg) as a solid. LCMS (ESI): 239 $[M+H]^+$.

Step-2. 2-methyl-5-(trifluoromethyl)-1,3-oxazole-4-carbaldehyde

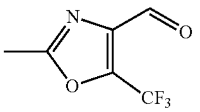

DIBAl-H (0.88 mL, 0.88 mmol, 1M) was added to a stirred mixture of N-methoxy-N,2-dimethyl-5-(trifluoromethyl)-1,3-oxazole-4-carboxamide (Step-1, 105.0 mg, 0.44 mmol) in dry DCM (5.00 mL) at −78° C. under nitrogen atmosphere. The resulting mixture was stirred at −78° C. for 2 h under nitrogen atmosphere. The resulting mixture was quenched with MeOH. The resulting mixture was concentrated under reduced pressure. The residue was purified by silica gel column chromatography eluting with petroleum ether/EtOAc (5/1 v/v) to obtain the title compound (75.0 mg) as an oil. LCMS (ESI): 180 $[M+H]^+$.

Step-3. 2-methyl-N-[(1E)-[2-methyl-5-(trifluoromethyl)-1,3-oxazol-4-yl]methylidene]propane-2-sulfinamide

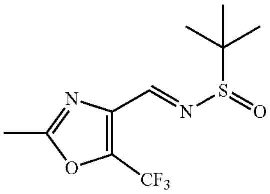 [SMILES: Cc1nc(/C=N/S(=O)C(C)(C)C)c(C(F)(F)F)o1]

PTSA (3.0 mg, 0.02 mmol) and $MgSO_4$ (121.0 mg, 1.00 mmol) were added to a stirred mixture of 2-methyl-5-(trifluoromethyl)-1,3-oxazole-4-carbaldehyde (Step-2, 60.0 mg, 0.34 mmol) and tert-butanesulfinamide (41.0 mg, 0.34 mmol) in DCM (3.00 mL). The resulting mixture was stirred at 25° C. for 14 h. The resulting mixture was concentrated under reduced pressure. The residue was purified by silica gel column chromatography eluting with petroleum ether/EtOAc (2/1 v/v) to obtain the title compound (60.0 mg) as a solid. LCMS (ESI): 283 $[M+H]^+$.

Step-4. 2-methyl-N-[[2-methyl-5-(trifluoromethyl)-1,3-oxazol-4-yl]methyl]propane-2-sulfinamide

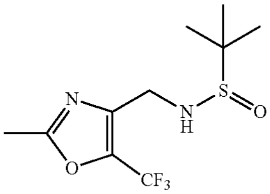 [SMILES: Cc1nc(CNS(=O)C(C)(C)C)c(C(F)(F)F)o1]

$NaBH_4$ (160 mg, 0.43 mmol) was added to a stirred mixture of 2-methyl-N-[(1E)-[2-methyl-5-(trifluoromethyl)-1,3-oxazol-4-yl]methylidene]propane-2-sulfinamide (Step-3, 60.0 mg, 0.21 mmol) in MeOH (3.00 mL) at 0° C. The resulting mixture was stirred at 25° C. for 2 h. The resulting mixture was concentrated under reduced pressure. The residue was purified by silica gel column chromatography eluting with DCM/MeOH (10/1 v/v) to obtain the title compound (50.0 mg) as a solid. LCMS (ESI): 285 $[M+H]^+$.

Step-5. 1-[2-methyl-5-(trifluoromethyl)-1,3-oxazol-4-yl]methanamine

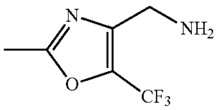

HCl (gas) in 1,4-dioxane (1.00 mL) was added to a stirred mixture of 2-methyl-N-[[2-methyl-5-(trifluoromethyl)-1,3-oxazol-4-yl]methyl]propane-2-sulfinamide (Step-4, 50.0 mg, 0.18 mmol) in 1,4-dioxane (1.00 mL). The resulting mixture was stirred at 25° C. for 1 h. The resulting mixture was concentrated under reduced pressure to obtain the title compound (40.0 mg) as a solid. LCMS (ESI): 181 $[M+H]^+$.

Step-6. (S)-4-(5-(5-fluoro-2-methoxypyridin-4-yl)-1H-pyrazole-3-carbonyl)-N-((2-methyl-5-(trifluoromethyl)oxazol-4-yl)methyl)-4-azaspiro[2.5]octane-7-carboxamide

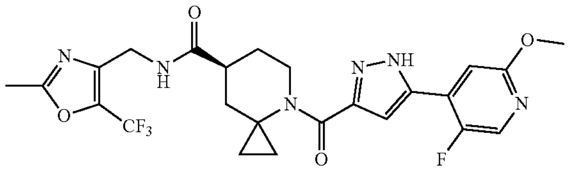

EDCI (56.0 mg, 0.29 mmol), HOBt (39.0 mg, 0.29 mmol), and 1-[2-methyl-5-(trifluoromethyl)-1,3-oxazol-4-yl]methanamine (Step-5, 35.0 mg, 0.19 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 73.0 mg, 0.19 mmol) and DIPEA (126.0 mg, 0.97 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (20.7 mg) as a solid. $^1H$ NMR (400 MHz, DMSO-$d_6$) δ 13.91 (s, 1H), 8.40 (s, 1H), 8.27 (d, 1H), 7.32 (d, 1H), 7.02 (s, 1H), 4.58-4.34 (m, 1H), 4.29-4.13 (m, 2H), 3.87 (s, 3H), 3.34-3.31 (m, 1H), 2.81-2.68 (m, 1H), 2.58-2.49 (m, 3H), 2.27-1.96 (m, 1H), 1.86-1.64 (m, 1H), 1.63-1.36 (m, 1H), 1.35-1.11 (m, 1H), 1.05-0.77 (m, 2H), 0.76-0.42 (m, 2H). LCMS (ESI): 537.15 $[M+H]^+$.

Example 395. A Diastereomeric Mixture of (S)—N—((S)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide and (S)—N—((R)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide

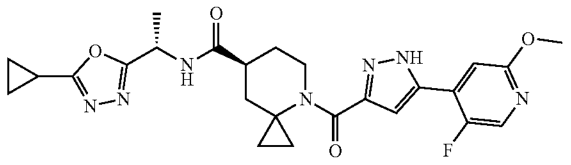

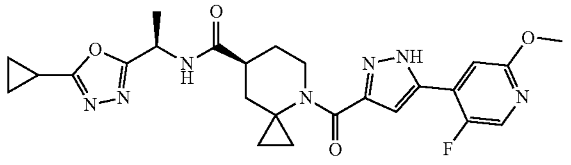

Step-1. ethyl 2-(cyclopropylformohydrazido)-2-oxoacetate

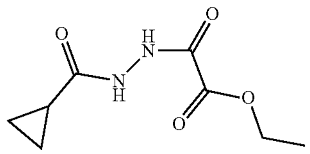

TEA (2.02 g, 19.98 mmol) and ethyl chloroglyoxylate (1.50 g, 10.99 mmol) were added to a stirred mixture of cyclopropanecarbohydrazide (1.00 g, 9.99 mmol) in DCM (15.00 mL) at 0° C. under nitrogen atmosphere. The resulting mixture was stirred at 25° C. under nitrogen atmosphere for 14 h. The resulting mixture was concentrated under reduced pressure. The residue was purified by silica gel column chromatography eluting with DCM/MeOH (12/1 v/v) to obtain the title compound (1.70 g) as an oil. LCMS (ESI): 201.1 $[M+H]^+$.

Step-2. ethyl 5-cyclopropyl-1,3,4-oxadiazole-2-carboxylate

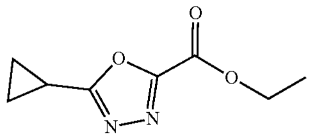

TsCl (1.73 g, 9.07 mmol) and TEA (1.08 g, 10.72 mmol) were added to a stirred mixture of ethyl 2-(cyclopropylformohydrazido)-2-oxoacetate (Step-1, 1.65 g, 8.24 mmol) in DCM (10.00 mL). The resulting mixture was stirred at 25° C. for 14 h. The resulting mixture was concentrated under reduced pressure. The residue was purified by silica gel column chromatography eluting with petroleum ether/EtOAc (4/1 v/v) to obtain the title compound (900.0 mg) as an oil. LCMS (ESI): 183.1 $[M+H]^+$.

Step-3. (5-cyclopropyl-1,3,4-oxadiazol-2-yl)methanol

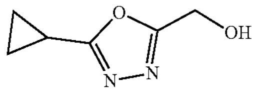

$NaBH_4$ (186.9 mg, 4.94 mmol) was added to a stirred mixture of ethyl 5-cyclopropyl-1,3,4-oxadiazole-2-carboxylate (Step-2, 900.0 mg, 4.94 mmol) in EtOH (8.00 mL) at 0° C. The resulting mixture was stirred at 25° C. for 1.5 h. The resulting mixture was concentrated under reduced pressure. The residue was purified by silica gel column chromatography eluting with DCM/MeOH (11/1 v/v) to obtain the title compound (550.0 mg) as an oil. LCMS (ESI): 141.1 $[M+H]^+$.

Step-4. 5-cyclopropyl-1,3,4-oxadiazole-2-carbaldehyde

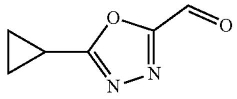

Phenyliodine(III) diacetate (1.43 g, 4.44 mmol) and TEMPO (69.6 mg, 0.45 mmol) were added to a stirred mixture of (5-cyclopropyl-1,3,4-oxadiazol-2-yl)methanol (Step-3, 520.0 mg, 3.71 mmol) in DCM (8.00 mL). The resulting mixture was stirred at 25° C. for 2 h. The resulting mixture was concentrated under reduced pressure. The residue was purified by Prep-TLC (petroleum ether/EtOAc, 1/2 v/v) to obtain the title compound (400.0 mg) as an oil. LCMS (ESI): 139.0 [M+H]+.

Step-5. N-[(1E)(5-cyclopropyl-1,3,4-oxadiazol-2-yl) methylidene]-2-methylpropane-2-sulfinamide

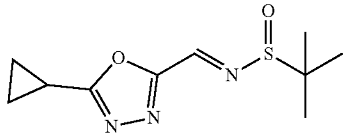 [SMILES: CC(C)(C)S(=O)/N=C/c1nnc(C2CC2)o1]

PTSA (24.9 mg, 0.15 mmol) and $MgSO_4$ (1.05 g, 8.69 mmol) were added to a stirred mixture of 5-cyclopropyl-1,3,4-oxadiazole-2-carbaldehyde (Step-4, 400.0 mg, 2.90 mmol) and tert-butanesulfinamide (351.0 mg, 2.90 mmol) in DCM (8.00 mL). The resulting mixture was stirred at 25° C. for 2 h. The resulting mixture was concentrated under reduced pressure. The residue was purified by Prep-TLC (petroleum ether/EtOAc, 2/1 v/v) to obtain the title compound (350.0 mg) as a solid. LCMS (ESI): 242.1 [M+H]+.

Step-6. N-[1-(5-cyclopropyl-1,3,4-oxadiazol-2-yl) ethyl]-2-methylpropane-2-sulfinamide

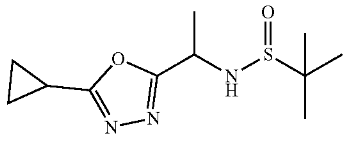 [SMILES: CC(NS(=O)C(C)(C)C)c1nnc(C2CC2)o1]

Bromo(methyl)magnesium (0.62 mL, 0.62 mmol, 1M) was added to a stirred mixture of N-[(1E)-(5-cyclopropyl-1,3,4-oxadiazol-2-yl)methylidene]-2-methylpropane-2-sulfinamide (Step-5, 100.0 mg, 0.41 mmol) in THF (3.00 mL) at −40° C. under nitrogen atmosphere. The resulting mixture was stirred at 25° C. for 1 h. The reaction mixture was quenched with MeOH at −30° C. The resulting mixture was concentrated under reduced pressure. The residue was purified by Prep-TLC eluting with EtOAc to obtain the title compound (50.0 mg) as a solid. LCMS (ESI): 258.1 [M+H]+.

Step-7. 1-(5-cyclopropyl-1,3,4-oxadiazol-2-yl)ethanamine

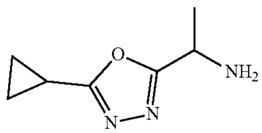

N-[1-(5-cyclopropyl-1,3,4-oxadiazol-2-yl)ethyl]-2-methylpropane-2-sulfinamide (Step-6, 50.0 mg, 0.19 mmol) was added to HCl (gas) in 1,4-dioxane (2.00 mL). The resulting mixture was stirred at 25° C. for 1 h. The resulting mixture was concentrated under reduced pressure to obtain the title compound (25.0 mg) as a solid and used directly in the next step without further purification. LCMS (ESI): 154.1 [M+H]+.

Step-8. (S)—N—((S)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide and (S)—N—((R)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide

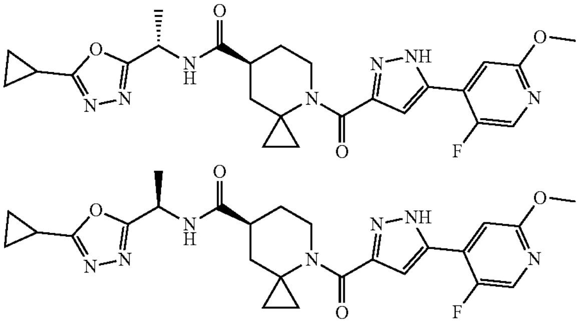

HOBt (52.9 mg, 0.39 mmol), EDCI (75.1 mg, 0.39 mmol), and 1-(5-cyclopropyl-1,3,4-oxadiazol-2-yl) ethanamine (Step-7, 30.0 mg, 0.20 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 73.3 mg, 0.20 mmol, 1.00 equiv) and DIPEA (253.1 mg, 1.96 mmol) in DMF (3.00 mL). The resulting mixture was stirred at 25° C. for 2 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 20/1 v/v) to obtain (S)—N—((S)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide and (S)—N—((R)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide (40.0 mg) as a solid mixture of diastereomers (Example 395). $^1H$ NMR (300 MHz, $CD_3OD$) δ 8.20-8.08 (m, 1H), 7.38 (d, 1H), 7.22-7.09 (m, 1H), 5.26-5.13 (m, 1H), 4.88-4.12 (m, 1H), 3.95 (s, 3H), 3.03-2.74 (m, 1H), 2.41-2.35 (m, 1H), 2.28-2.13 (m, 1H), 2.10-

1.67 (m, 2H), 1.63-152 (m, 3H), 1.44-1.26 (m, 2H), 125-1.13 (m, 2H), 1.13-1.00 (m, 3H), 1.00-0.64 (m, 3H). LCMS (ESI): 510.40 $[M+H]^+$.

This mixture of two diastereomers (43.0 mg) was separated using Chiral Prep-HPLC.

Column: CHIRALPAK IH column

Column dimension: 2×25 cm, 5 μm

Mobile Phase: MTBE (0.5% 2M $NH_3$·MeOH):EtOH=70:30 hold for 8.5 min

Flow rate: 20 mL/min

Detection: 220/254 nm

Example 395-A. The first eluting diastereomer (17.5 mg) was obtained as a solid.

The first eluting diastereomer had a retention time of 4.21 min.

$^1H$ NMR (400 MHz, $CD_3OD$) δ 8.21-8.09 (m, 1H), 7.41-7.09 (m, 2H), 5.25-5.15 (m, 1H), 4.82-4.36 (m, 1H), 3.94 (s, 3H), 2.90-2.86 (m, 1H), 2.80-2.26 (m, 1H), 2.26-2.15 (m, 1H), 2.10-1.72 (m, 2H), 1.60-1.54 (m, 3H), 1.34-129 (m, 2H), 1.26-1.14 (m, 2H), 1.17-1.03 (m, 3H), 0.79-0.75 (m, 3H). LCMS (ESI): 510.20 $[M+H]^+$.

Example 395-B. The second eluting diastereomer (19.2 mg) was obtained as a solid.

The second eluting diastereomer had a retention time of 6.55 min.

$^1H$ NMR (400 MHz, $CD_3OD$) δ 8.18-8.07 (m, 1H), 7.42-7.09 (m, 2H), 5.25-5.15 (m, 1H), 4.80-4.36 (m, 1H), 3.94 (s, 3H), 3.13-2.80 (m, 1H), 2.66-2.37 (m, 1H), 2.25-2.14 (m, 1H), 2.05-1.60 (m, 2H), 1.60-1.54 (m, 3H), 1.51-1.23 (m, 2H), 1.23-1.16 (m, 2H), 1.16-1.02 (m, 3H), 1.02-0.70 (m, 3H). LCMS (ESI): 510.15 $[M+H]^+$.

Example 396. A Diastereomeric Mixture of (S)-4-(5-(5-fluoro-2-methoxypyridin-4-yl)-1H-pyrazole-3-carbonyl)-N—((R)-1-(oxetan-3-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-(oxetan-3-yl)pyrrolidin-3-yl)-4-azaspiro[2.5]octane-7-carboxamide

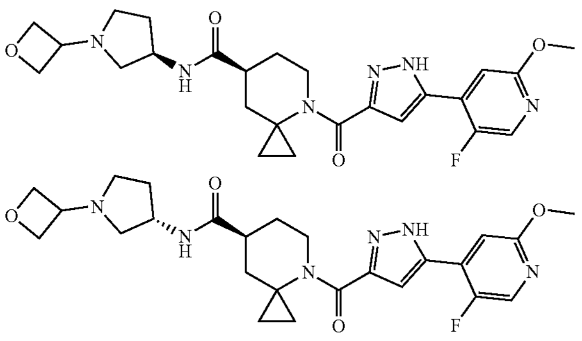

Step-1. N,N-dibenzyl-1-(oxetan-3-yl)pyrrolidin-3-amine

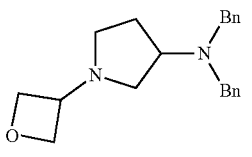 [SMILES: c1ccc(CN(Cc2ccccc2)C2CCN(C3COC3)C2)cc1]

3-Oxetanone (350.4 mg, 4.87 mmol) and 4 Å molecular sieves (720.0 mg) were added to a stirred mixture of tert-butyl 3-(dibenzylamino)pyrrolidine-1-carboxylate (500.0 mg, 1.87 mmol) in AcOH (0.80 mL) and MeOH (8.00 mL). The resulting mixture was stirred at 80° C. for 1 h, then $NaBH_3CN$ (185.2 mg, 2.94 mmol) was added. The resulting mixture was stirred at 80° C. for 14 h. The residue was purified by silica gel column chromatography eluting with petroleum ether/EtOAc (2/3 v/v) to obtain the title compound (400.0 mg) as an oil. LCMS (ESI): 323.21 $[M+H]^+$.

Step-2. 1-(oxetan-3-yl)pyrrolidin-3-amine

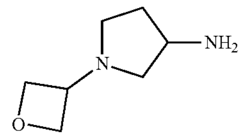

Pd/C (47.4 mg) was added to a stirred solution of N,N-dibenzyl-1-(oxetan-3-yl)pyrrolidin-3-amine (Step-1, 158.0 mg, 0.49 mmol) in MeOH (5.00 mL) at 0° C. The resulting mixture was stirred at 25° C. for 2 h under hydrogen atmosphere. The resulting mixture was filtered, the filter cake was washed with MeOH. The filtrate was concentrated under reduced pressure to obtain the title compound (61.0 mg) as a solid. LCMS (ESI): 143.11 $[M+H]^+$.

Step-3. (S)-4-(5-(5-fluoro-2-methoxypyridin-4-yl)-1H-pyrazole-3-carbonyl)-N—((R)-1-(oxetan-3-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-(oxetan-3-yl)pyrrolidin-3-yl)-4-azaspiro[2.5]octane-7-carboxamide

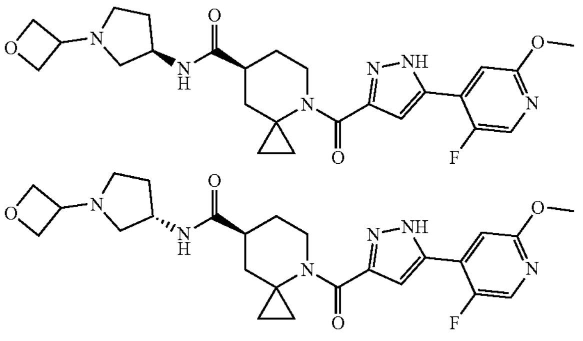

HOBt (76.0 mg, 0.56 mmol), EDCI (108.0 mg, 0.56 mmol) and 1-(oxetan-3-yl)pyrrolidin-3-amine (Step-2, 40.0 mg, 0.28 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 105.6 mg, 0.28 mmol) and DIPEA (360.0 mg, 2.79 mmol) in DMF (5.00 mL). The resulting solution was stirred at 25° C. for 1 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A:

Water (0.5% $NH_4HCO_3$), mobile phase B: MeCN; gradient: 20 B to 40 B in 25 min; 220/254 nm) to obtain (S)-4-(5-(5-fluoro-2-methoxypyridin-4-yl)-1H-pyrazole-3-carbonyl)-N—((R)-1-(oxetan-3-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-(oxetan-3-yl)pyrrolidin-3-yl)-4-azaspiro[2.5]octane-7-carboxamide (60.0 mg) as a solid mixture of diastereomers (Example 396). $^1H$ NMR (400 MHz, $CD_3OD$) δ 8.14-8.08 (m, 1H), 7.26 (d, 1H), 7.09 (d, 1H), 4.76-4.67 (m, 2H), 4.62-4.54 (m, 3H), 4.36-4.25 (m, 1H), 3.92 (s, 3H), 3.70-3.59 (m, 1H), 2.80-2.67 (m, 3H), 2.55-2.37 (m, 3H), 2.31-2.17 (m, 1H), 1.98-1.60 (m, 3H), 1.30-1.25 (m, 2H), 1.13-0.81 (m, 2H), 0.78-0.61 (m, 2H). LCMS (ESI): 499.30 $[M+H]^+$.

This mixture of two diastereomers (44.0 mg) was separated using Chiral Prep-HPLC.

Column: CHIRALPAK ID column
Column dimension: 2×25 cm, 5 μm
Mobile Phase: MTBE (0.5% 2M $NH_3$·MeOH):1/1 MeOH/DCM=40:60 hold for 12 min
Flow rate: 20 mL/imin
Detection: 220/254 nm Example 396-A. The first eluting diastereomer (11.0 mg) was obtained as a solid.

The first eluting diastereomer had a retention time of 6.83 min.

$^1H$ NMR (300 MHz, $CD_3OD$) δ 8.14 (s, 1H), 7.51-7.19 (m, 1H), 7.12 (s, 1H), 4.80-4.69 (m, 2H), 4.67-4.53 (m, 3H), 4.42-4.24 (m, 1H), 3.95 (s, 3H), 3.79-3.59 (m, 1H), 3.00-2.67 (m, 3H), 2.65-2.12 (m, 4H), 2.05-1.51 (m, 3H), 1.44-0.91 (m, 3H), 0.88-0.53 (m, 3H). LCMS (ESI): 499.4 $[M+H]^+$.

Example 396-B. The second eluting diastereomer (11.7 mg) was obtained as a solid.

The second eluting diastereomer had a retention time of 9.65 min.

$^1H$ NMR (300 MHz, $CD_3OD$) δ 8.14 (s, 1H), 7.54-6.91 (m, 2H), 4.82-4.69 (m, 2H), 4.67-4.53 (m, 3H), 4.42-4.25 (m, 1H), 3.95 (s, 3H), 3.77-3.59 (m, 1H), 2.93-2.67 (m, 3H), 2.62-2.40 (m, 3H), 2.39-2.10 (m, 1H), 2.02-1.56 (m, 3H), 1.47-0.90 (m, 3H), 0.88-0.53 (m, 3H). LCMS (ESI): 499.4 $[M+H]^+$.

Example 397. (S)-4-(5-(5-fluoro-2-methoxypyridin-4-yl)-1H-pyrazole-3-carbonyl)-N-((3-methylpyrazin-2-yl)methyl)-4-azaspiro[2.5]octane-7-carboxamide

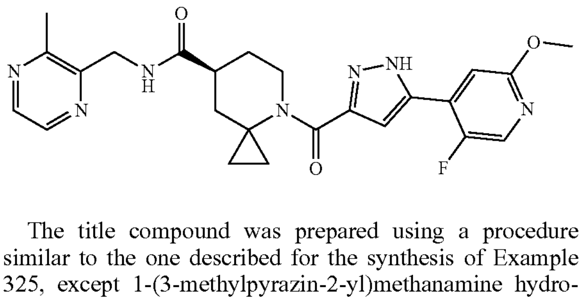

The title compound was prepared using a procedure similar to the one described for the synthesis of Example 325, except 1-(3-methylpyrazin-2-yl)methanamine hydrochloride was used as a starting material. The resulting residue was purified by reverse phase column chromatography (using the following conditions: Column: C18; mobile phase A: Water (0.5% $NH_4HCO_3$), mobile phase B: MeCN; gradient: 20 B to 50 B in 30 min; 220/254 nm) to obtain the title compound (61.0 mg) as a solid. $^1H$ NMR (400 MHz, DMSO-$d_6$) δ 14.12-13.75 (m, 1H), 8.69-7.89 (m, 4H), 7.29 (s, 1H), 7.02 (s, 1H), 4.75-4.09 (m, 3H), 3.85 (s, 3H), 3.30-3.28 (m, 2H), 2.97-2.66 (m, 1H), 2.29-2.00 (m, 1H), 1.93-1.37 (m, 3H), 1.32-0.82 (m, 3H), 0.73-0.43 (m, 3H). LCMS (ESI): 480.20$[M+H]^+$.

Example 398. A Diastereomeric Mixture of (S)—N((1r,4S)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (S)—N-((1s,4R)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide

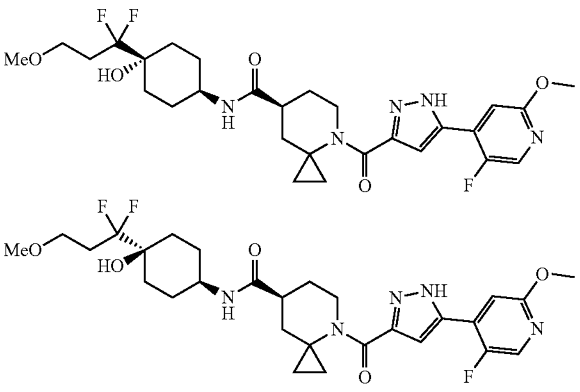

Step-1. 2,2-difluoro-2-(8-((4-methoxybenzyl)oxy)-1,4-dioxaspiro[4.5]decan-8-yl)acetaldehyde

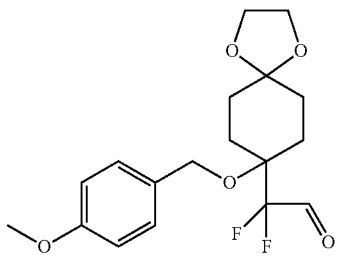 [SMILES: COc1ccc(COC2(C(F)(F)C=O)CCC3(CC2)OCCO3)cc1]

Dess-Martin periodinane (426.0 mg, 1.00 mmol) was slowly added to a solution of 2,2-difluoro-2-(8-((4-methoxybenzyl)oxy)-1,4-dioxaspiro[4.5]decan-8-yl)ethan-1-ol (Step-2 from synthesis of Example 369, 300.0 mg, 0.84 mmol) in anhydrous DCM (6.98 mL) at 0° C. under $N_2$ atmosphere. The reaction mixture was stirred at 0° C. for 10 min, then at 22° C. for 2.5 h. The reaction mixture was diluted with DCM then cooled to 0° C. The suspension was carefully quenched by the addition of a saturated aqueous $Na_2S_2O_3$ solution (7.00 mL) followed by a saturated aqueous $NaHCO_3$ solution (7.00 mL). The ice-bath was removed and the biphasic mixture was vigorously stirred at 22° C. for 1 h. The layers were separated and the organic layer was washed with a saturated aqueous $NaHCO_3$ solution, brine, dried over anhydrous $Na_2SO_4$, filtered and concentrated under reduced pressure to obtain the title compound (287.0 mg) as an oil which was used in the next step without further purification. TLC-MS (APCI): 357.4 $[M+H]^+$.

Step-2. Mixture of (Z)-8-(1,1-difluoro-3-methoxyallyl)-8-((4-methoxybenzyl)oxy)-1,4-dioxaspiro[4.5]decane and (Z)-3-fluoro-3-(8-((4-methoxybenzyl)oxy)-1,4-dioxaspiro[4.5]decan-8-yl)acrylaldehyde

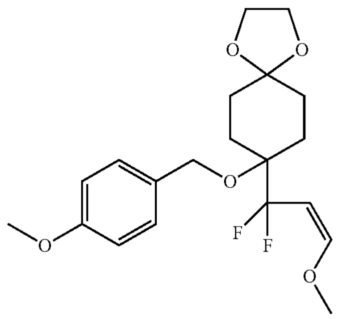

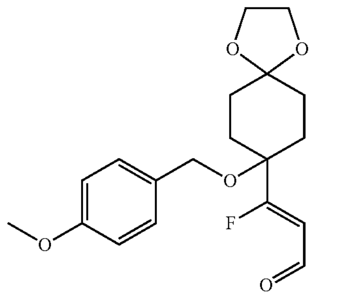

(methoxymethyl)triphenylphosphonium chloride (243.4 mg, 0.71 mmol) was dissolved in THF (2.85 mL) and cooled to 0° C. before potassium tert-butoxide (144.0 mg, 1.28 mmol) was added dropwise and the mixture was allowed to stir for 45 min. After this time, 2,2-difluoro-2-(8-((4-methoxybenzyl)oxy)-1,4-dioxaspiro[4.5]decan-8-yl)acetaldehyde (Step-1, 254.0 mg, 0.71 mmol) was added as a solution in THF (2.00 mL), and the reaction was allowed to warm slowly to 22° C. for 16 h. The reaction mixture was then concentrated to dryness and partitioned between EtOAc and $H_2O$. The organic layer was further washed with water, brine, dried ($Na_2SO_4$), filtered, and concentrated under reduced pressure. The residue was purified by silica gel column chromatography (0 to 100% EtOAc in DCM, product stains with $KMnO_4$) to obtain 8-(1,1-difluoro-3-methoxyallyl)-8-((4-methoxybenzyl)oxy)-1,4-dioxaspiro[4.5]decane (108.0 mg) and 3,3-difluoro-3-(8-((4-methoxybenzyl)oxy)-1,4-dioxaspiro[4.5]decan-8-yl)propanal as an inseparable impurity estimated to be 50 wt % by $^1H$ NMR. The material was taken into the next step without further purification. $^1H$ NMR (400 MHz, $CDCl_3$, with overlapping signals from inseparable impurity) δ 7.22-7.16 (m, 2H), 6.84-6.77 (m, 2H), 6.12 (dt, 1H), 4.94 (dt, 1H), 4.26 (s, 2H), 3.93-3.85 (m, 4H), 3.73 (s, 3H), 3.65 (s, 3H), 2.11-1.71 (m, 6H), 1.64-1.54 (m, 1H). TLC-MS (APCI): 385.3 $[M+H]^+$.

Step-3. 8-(1,1-difluoro-3-methoxypropyl)-1,4-dioxaspiro[4.5]decan-8-ol

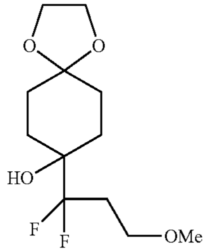 [SMILES: COCCC(F)(F)C1(O)CCC2(CC1)OCCO2]

(Z)-8-(1,1-difluoro-3-methoxyallyl)-8-((4-methoxybenzyl)oxy)-1,4-dioxaspiro[4.5]decane (Step-2, 110.0 mg, 50% Wt, 0.14 mmol) was dissolved in EtOAc under $N_2$. Pd/C (30.5 mg, 10% Wt, 0.03 mmol) was then added and the atmosphere was replaced with $H_2$ via a balloon. The reaction mixture was stirred at 22° C. for 18 h before being filtered over a pad of celite. The resulting residue was purified by silica gel column chromatography (30% to 50% EtOAc in Cyclohexane) to obtain the title compound (37.0 mg) as an oil. $^1H$ NMR (400 MHz, $CDCl_3$) δ 3.99-3.92 (m, 4H), 3.63 (t, 2H), 3.38 (s, 3H), 2.24 (tt, 6.1 Hz, 2H), 2.01-1.83 (m, 4H), 1.77-1.69 (m, 2H), 1.69-1.61 (m, 2H). TLC-MS (APCI): 267.1 $[M+H]^+$.

Step-4. 4-(1,1-difluoro-3-methoxypropyl)-4-hydroxycyclohexan-1-one

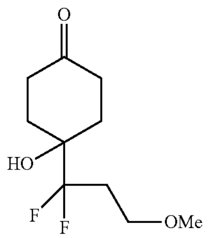 [SMILES: COCCC(F)(F)C1(O)CCC(=O)CC1]

TFA (0.12 mL, 1.46 mmol) was added to a solution of 8-(1,1-difluoro-3-methoxypropyl)-1,4-dioxaspiro[4.5]decan-8-ol (Step-3, 39.0 mg, 0.15 mmol) in DCM (1.47 mL) at 0° C. The resulting mixture was warmed to 22° C. for 18 h. The reaction mixture was concentrated and the residue was used directly in the next step without further purification. $^1H$ NMR (400 MHz, CDCl3) δ 3.68 (t, 2H), 3.45 (s, 3H), 2.76 (td, 2H), 2.39-2.24 (m, 4H), 2.16-2.00 (m, 4H).

Step-5. 4-(1,1-difluoro-3-methoxypropyl)-4-hydroxycyclohexan-1-one oxime

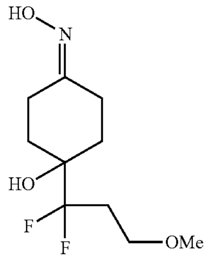 [SMILES: COCCC(F)(F)C1(O)CCC(=NO)CC1]

Hydroxylamine hydrochloride (11.0 mg, 0.16 mmol) was added to a solution of sodium acetate (15.0 mg, 0.18 mmol) in MeOH (0.40 mL). The resulting mixture was stirred for 30 min. Then 4-(1,1-difluoro-3-methoxypropyl)-4-hydroxycyclohexan-1-one (Step-4, 33.0 mg, 0.15 mmol) was added as a solution in MeOH (0.40 mL). The reaction mixture was stirred at 60° C. for 5 h with a reflux condenser. The reaction mixture was then cooled to 22° C. and diluted with EtOAc and water. The organic layer was washed with $H_2O$ and brine, and dried over $Na_2SO_4$, filtered, and concentrated under reduced pressure. The residue was purified by silica gel column chromatography (50 to 60% EtOAc in Cyclohexane) to obtain the title compound (19.0 mg) as a solid. $^1H$ NMR (400 MHz, $CDCl_3$) δ 3.87 (bs, 1H), 3.64 (t, 2H), 3.41 (s, 3H), 3.30-3.21 (m, 1H), 2.67-2.52 (m, 2H), 2.35-2.18 (m, 3H), 2.02-1.92 (m, 2H), 1.90-1.71 (m, 2H). TLC-MS (APCI): 238.1 $[M+H]^+$.

Step-6. tert-butyl (4-(1,1-difluoro-3-methoxypropyl)-4-hydroxycyclohexyl)carbamate

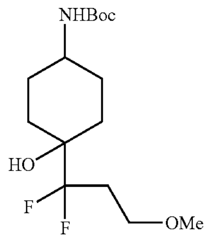 [SMILES: COCCC(F)(F)C1(O)CCC(NC(=O)OC(C)(C)C)CC1]

$NaBH_4$ (24.2 mg, 0.64 mmol) was added to a solution of 4-(1,1-difluoro-3-methoxypropyl)-4-hydroxycyclohexan-1-one oxime (Step-5, 19.0 mg, 0.08 mmol) and nickel (II) chloride hexahydrate (24.7 mg, 0.10 mmol) in MeOH (1.60 mL) at −78° C. The resulting mixture was allowed to warm up to 0° C. and stirred at this temperature for 7 h. $Boc_2O$ (26.2 mg, 0.12 mmol) was then added and the reaction mixture was warmed to 22° C. for 18 h. The reaction mixture was quenched with brine at 0° C. MeOH was removed under reduced pressure and the resulting residue was extracted with $Et_2O$. The organic layers were washed with brine, dried over $Na_2SO_4$, filtered, and concentrated under reduced pressure to obtain the title compound (18.4 mg) as a solid. $^1H$ NMR (400 MHz, $CDCl_3$, mixture of diastereomers) δ 4.67 (s, 1H, minor isomer), 4.40 (s, 1H, major isomer), 3.83 (s, 1H, minor isomer), 3.67-3.56 (m, 2H, overlapping signals), 3.50-3.26 (m, 4H, overlapping signals), 3.10 (s, 1H), 2.30-2.16 (m, 2H), 1.96-1.81 (m, 2H), 1.79-1.59 (m, 4H), 1.55-1.37 (m, 1H, overlapping signals). $^{19}F$ NMR (376 MHz, $CDCl_3$) δ −111.27, −111.62. TLC-MS (APCI): 324.1 $[M+H]^+$.

Step-7. 4-amino-1-(1,1-difluoro-3-methoxypropyl)cyclohexan-1-ol

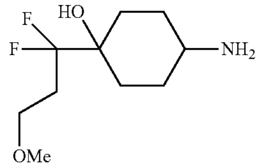 [SMILES: COCCC(F)(F)C1(O)CCC(N)CC1]

TFA (1.00 mL) was added to a stirred mixture of tert-butyl N-[4-(1,1-difluoro-3-methoxypropyl)-4-hydroxycyclohexyl]carbamate (Step-6, 16.8 mg, 0.05 mmol) in DCM (1.00 mL). The resulting mixture was stirred at 25° C. for 30 min. The resulting mixture was concentrated under reduced pressure to obtain the title compound (11.0 mg) as a solid. LCMS (ESI): 224.1 $[M+H]^+$.

Step-8. (S)—N-((1r,4S)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (S)—N-((1s,4R)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide

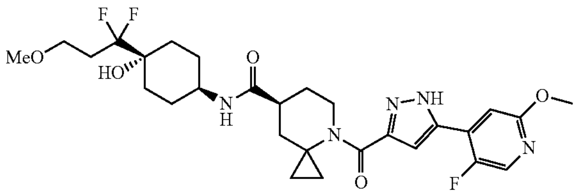

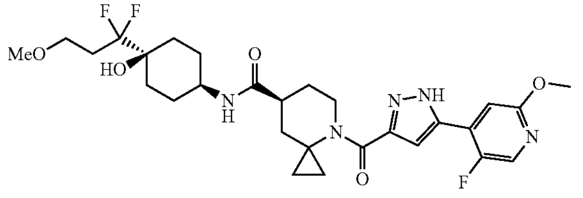

HOBt (13.3 mg, 0.10 mmol), EDCI (18.9 mg, 0.10 mmol), and 4-amino-1-(1,1-difluoro-3-methoxypropyl)cyclohexan-1-ol (11.0 mg, 0.05 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 20.3 mg, 0.05 mmol) and DIPEA (63.7 mg, 0.50 mmol) in DMF (2.00 mL). The resulting mixture was stirred at 25° C. for 30 min. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 10/1 v/v) to obtain (S)—N-((1r,4S)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide and (S)—N-((1s,4R)-4-(1,1- difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide (15.0 mg) as a solid mixture of diastereomers. LCMS (ESI): 580.3 [M+H]$^+$.

This mixture of two diastereomers (15.0 mg) was separated using Chiral Prep-HPLC.

Column: CHIRAL ART Cellulose-SB column

Column dimension: 3×25 cm, 5 μm

Mobile Phase: MTBE (0.5% 2M $NH_3$·MeOH):1/1 MeOH/DCM=40:60 hold for 25 min

Flow rate: 18 mL/min

Detection: 220/254 nm

Example 398-A. The first eluting diastereomer (1.1 mg) was obtained as a solid.

The first eluting diastereomer had a retention time of 6.49 min.

LCMS (ESI): 580.20 [M+H]$^+$.

Example 398-B. The second eluting diastereomer (3.5 mg) was obtained as a solid.

The second eluting diastereomer had a retention time of 21.41 min.

$^1$H NMR (400 MHz, $CD_3OD$) δ 8.11 (d, 1H), 7.27 (s, 1H), 7.09 (s, 1H), 3.92 (s, 3H), 3.69-3.55 (m, 5H), 2.32-2.21 (m, 3H), 2.12-1.95 (m, 1H), 1.81-1.71 (m, 3H), 1.68-1.58 (m, 3H), 1.41-1.20 (m, 8H), 1.00-0.86 (m, 2H), 0.80-0.58 (m, 2H). LCMS (ESI): 580.25 [M+H]$^+$.

Example 399. A Diastereomeric Mixture of (S)—N-((1s,4R)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1r,4S)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

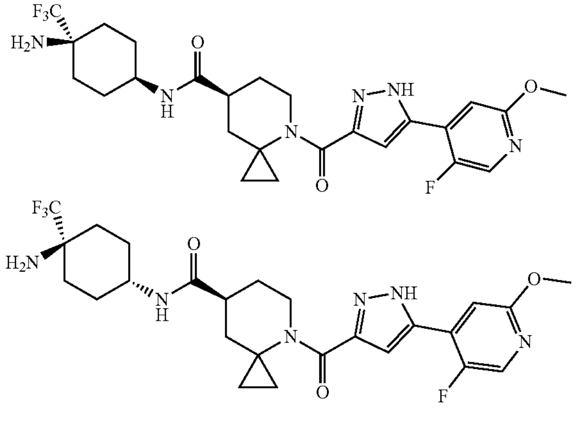

Step-1. 2-methyl-N-(1,4-dioxaspiro[4.5]decan-8-ylidene)propane-2-sulfinamide

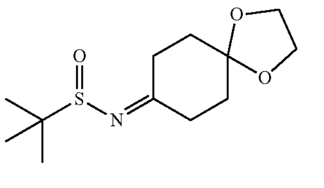 [SMILES: CC(C)(C)S(=O)N=C1CCC2(CC1)OCCO2]

1,4-dioxaspiro[4.5]decan-8-one (1.50 g, 9.60 mmol) and 2-methylpropane-2-sulfinamide (1.40 g, 11.53 mmol) were dissolved in THF (19.20 mL). Tetraethoxytitanium (2.82 mL, 13.45 mmol) was added and the resulting solution was stirred at 22° C. for 16 h. The mixture was quenched with 50 mL of 1/1 aqueous saturated solution of $NaHCO_3$/brine. The resulting mixture was stirred for 30 min then filtered through celite and the solid was washed with EtOAc. The mixture was extracted with EtOAc and the combined organic layers were dried over anhydrous $Na_2SO_4$, filtered and concentrated. The residue was purified by silica gel column chromatography eluting with DCM/EtOAc (0% to 40%) to obtain the title compound (1.10 g) as a solid. $^1$H NMR (400 MHz, $CDCl_3$) δ 4.00-3.87 (m, 4H), 3.10 (ddd, 1H), 2.88 (ddd, 1H), 2.62 (dd, 2H), 2.54-2.47 (m, 1H), 2.06-1.98 (m, 1H), 1.91 (dt, 2H), 1.23 (s, 9H).

Step-2. 2-methyl-N-(8-(trifluoromethyl)-1,4-dioxaspiro[4.5]decan-8-yl)propane-2-sulfinamide

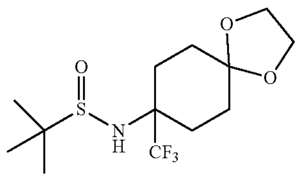 [SMILES: CC(C)(C)S(=O)NC1(C(F)(F)F)CCC2(CC1)OCCO2]

TBAF (5.78 mL, 5.78 mmol, 1 M in THF) was added to a solution of 2-methyl-N-(1,4-dioxaspiro[4.5]decan-8-ylidene)propane-2-sulfinamide (Step-1, 1.00 g, 3.86 mmol) in THF (38.50 mL) at −20° C., followed by a slow addition of trimethyl(trifluoromethyl)silane (1.65 g, 11.57 mmol) under vigorous stirring. The reaction mixture was allowed to reach 22° C. and stirred for 16 h. The mixture was quenched by addition of aqueous saturated solution of $NaHCO_3$. THF was removed under reduced pressure and the residue was diluted with water and EtOAc. The organic layers were combined, dried over anhydrous $Na_2SO_4$, filtered, and concentrated under reduced pressure. The residue was purified by silica gel column chromatography (Cyclohexane/EtOAc, 0% to 100%) to obtain the title compound (163.0 mg) as a solid. $^1$H NMR (400 MHz, $CDCl_3$) δ 3.98-3.91 (m, 4H), 3.30 (s, 1H), 2.14-1.96 (m, 5H), 1.81-1.63 (m, 3H), 1.25 (s, 9H). $^{19}$F NMR (376 MHz, $CDCl_3$) δ -80.42.

Step-3. 2-methyl-N-(4-oxo-1-(trifluoromethyl)cyclohexyl)propane-2-sulfinamide

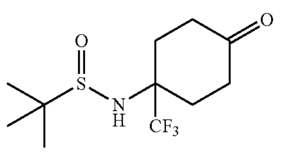 [SMILES: CC(C)(C)S(=O)NC1(C(F)(F)F)CCC(=O)CC1]

TFA (0.38 mL, 4.95 mmol) was added to a solution of 2-methyl-N-(8-(trifluoromethyl)-1,4-dioxaspiro[4.5]decan-8-yl)propane-2-sulfinamide (Step-2, 163.0 mg, 0.49 mmol) in DCM (2.50 mL). The reaction mixture was stirred at 22° C. for 16 h. The reaction mixture was diluted with DCM and washed with $NaHCO_3$ (sat. aq.). The organic layer was dried over anhydrous sodium sulfate, filtered and concentrated under reduced pressure. The residue was purified by silica gel column chromatography (Cyclohexane/Ethyl Acetate, 0% to 100%) to obtain the title compound (123.3 mg) as a solid. $^{1}$H NMR (400 MHz, $CDCl_3$) δ 3.57 (s, 1H), 2.92 (td, 1H), 2.64-2.37 (m, 4H), 2.30-2.16 (m, 3H), 1.29 (s, 9H).

Step-4. N-(4-(hydroxyimino)-1-(trifluoromethyl) cyclohexyl)-2-methylpropane-2-sulfinamide

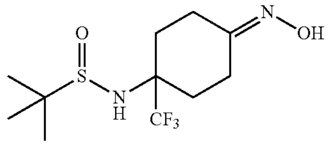 [SMILES: CC(C)(C)S(=O)NC1(C(F)(F)F)CCC(=NO)CC1]

Hydroxylamine hydrochloride (33.0 mg, 0.48 mmol) was added to a solution of sodium acetate (42.5 mg, 0.52 mmol) in MeOH (2.10 mL). The resulting mixture was allowed to stir for 30 min. Then a solution of 2-methyl-N-(4-oxo-1-(trifluoromethyl)cyclohexyl)propane-2-sulfinamide (Step-3, 123.3 mg, 0.43 mmol) in MeOH (1.00 mL) was added to the reaction mixture. The reaction mixture was stirred at 60° C. for 16 h. The reaction mixture was then cooled to 22° C. and MeOH was removed under reduced pressure. The residue was diluted with water and EtOAc. The aqueous was further extracted twice with EtOAc. The organic layer was dried over anhydrous sodium sulfate, filtered and concentrated under reduced pressure. The residue was purified by silica gel column chromatography (EtOAc/Cyclohexane, 0% to 100%) to obtain the title compound (93.6 mg) as a solid. $^{1}$H NMR (400 MHz, $CDCl_3$) δ 3.42 (s, 1H), 325-3.14 (m, 1H), 2.63-1.72 (m, 7H), 1.19 (d, 9H). $^{19}$F NMR (376 MHz, $CDCl_3$) δ −80.78, −80.87.

Step-5. tert-butyl (4-((tert-butylsulfinyl)amino)-4-(trifluoromethyl)cyclohexyl)carbamate

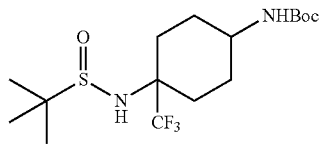 [SMILES: CC(C)(C)OC(=O)NC1CCC(NS(=O)C(C)(C)C)(C(F)(F)F)CC1]

$NaBH_4$ (9.3 mg, 0.25 mmol) was added to a solution of N-(4-(hydroxyimino)-1-(trifluoromethyl)cyclohexyl)-2-methylpropane-2-sulfinamide (Step-4, 74.0 mg, 0.25 mmol) and nickel(II) chloride hexahydrate (76.1 mg, 0.32 mmol) in MeOH (4.90 mL) at −78° C. The resulting mixture was allowed to warm up to 0° C. and stirred at this temperature for 4 h. $Boc_2O$ (80.7 mg, 0.37 mmol) was then added and the reaction mixture was warmed to 22° C. for 18 h. The reaction mixture was quenched with brine at 0° C. Volatiles were removed under reduced pressure. The residue was diluted with water and EtOAc. The organic layers were combined, dried over anhydrous $Na_2SO_4$, filtered, and concentrated under reduced pressure. The residue was purified by silica gel column chromatography (EtOAc/Cyclohexane, 0% to 90%) to obtain the title compound (96.0 mg) as a solid. $^{1}$H NMR (400 MHz, $CD_3OD$) δ 3.44-3.33 (m, 1H), 2.28-1.65 (m, 8H), 1.47-1.42 (m, 9H), 1.32-126 (m, 9H). $^{19}$F NMR (376 MHz, $CD_3OD$) δ −81.53, −81.94.

Step-6. N-[4-amino-1-(trifluoromethyl)cyclohexyl]-2-methylpropane-2-sulfinamide

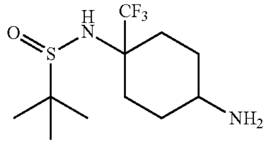 [SMILES: CC(C)(C)S(=O)NC1(C(F)(F)F)CCC(N)CC1]

TFA (2.00 mL) was added to a mixture of tert-butyl N-[4-[(2-methylpropane-2-sulfinyl)amino]-4-(trifluoromethyl)cyclohexyl]carbamate (Step-5, 34.0 mg, 0.09 mmol) in DCM (2.00 mL). The resulting mixture was stirred at 25° C. for 1 h. The resulting mixture was concentrated under reduced pressure to obtain the title compound (40.0 mg) as an oil. LCMS (ESI): 287 [M+H]$^+$.

Step-7. (7S)—N-(4-((tert-butylsulfinyl)amino)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

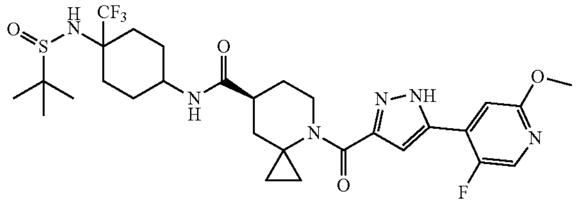 [SMILES: COc1cc(-c2cc(C(=O)N3CC[C@H](C(=O)NC4CCC(NS(=O)C(C)(C)C)(C(F)(F)F)CC4)CC34CC4)n[nH]2)c(F)cn1]

HOBt (25.0 mg, 0.18 mmol), EDCI (35.0 mg, 0.18 mmol), and N-[4-amino-1-(trifluoromethyl)cyclohexyl]-2-methylpropane-2-sulfinamide (Step-6, 35.0 mg, 0.12 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 46.0 mg, 0.12 mmol) and DIPEA (79.0 mg, 0.61 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (55.0 mg). LCMS (ESI): 643 [M+H]$^+$.

Step-8. (S)—N-((1s,4R)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1r,4S)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

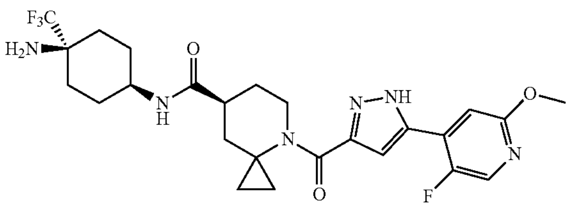

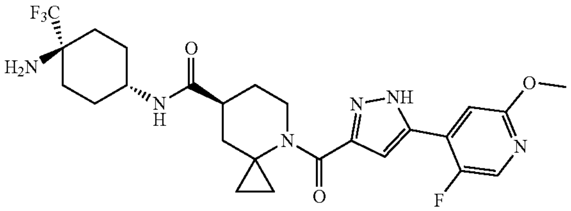

HCl (gas) in 1,4-dioxane (3.00 mL, 4 M) was added to a mixture of (7S)—N-(4-((tert-butylsulfinyl)amino)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide (Step-7, 50.0 mg, 0.08 mmol) in 1,4-dioxane (3.00 mL). The resulting mixture was stirred at 25° C. for 2 h. The resulting mixture was concentrated under reduced pressure. The residue was purified by Prep-TLC (DCM/MeOH, 2/1 v/v) to obtain (S)—N-((1s,4R)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1r,4S)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide in two fractions. LCMS (ESI): 539 $[M+H]^+$.

Example 399-A. The first eluting peak (12.3 mg) was obtained as a solid.

The first eluting peak had Rf value of 0.4.

$^1$H NMR (300 MHz, $CD_3OD$) δ 8.14 (d, 1H), 7.45-7.17 (m, 1H), 7.12 (s, 1H), 4.79-4.52 (m, 1H), 3.95 (s, 3H), 3.65-3.59 (m, 1H), 2.82-2.76 (m, 1H), 2.43-2.37 (m, 1H), 1.95-1.68 (m, 11H), 1.39-0.97 (m, 3H), 0.79-0.73 (m, 2H). LCMS (ESI): 539.10 $[M+H]^+$.

Example 399-B. The second eluting peak (1.1 mg) was obtained as a solid.

The second eluting peak had Rf value of 0.3.

$^1$H NMR (300 MHz, $CD_3OD$) δ 8.14 (s, 1H), 7.45-7.09 (m, 2H), 4.83-4.41 (m, 1H), 3.95 (s, 3H), 3.92-3.87 (m, 1H), 2.94-2.88 (m, 1H), 2.44-2.38 (m, 1H), 2.06-1.64 (m, 9H), 1.58-1.46 (m, 2H), 1.39-1.20 (m, 2H), 1.08-1.02 (m, 1H), 0.78-0.72 (m, 2H). LCMS (ESI): 539.20 $[M+H]^+$.

Example 400. (S)—N-((3,5-difluoropyridin-2-yl)methyl)-4-(5-(5-fluoro-2-methoxypyridin-4-yl)-1H-pyrazole-3-carbonyl)-4-azaspiro[2.5]octane-7-carboxamide

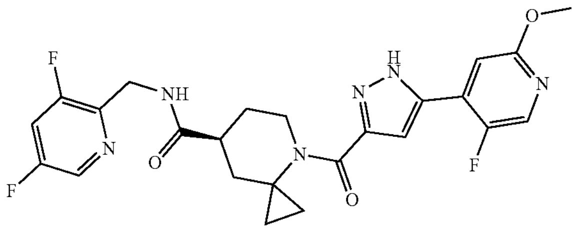 [SMILES: COc1cc(-c2cc(C(=O)N3CC[C@H](C(=O)NCc4ncc(F)cc4F)CC34CC4)n[nH]2)c(F)cn1]

The title compound was prepared using a procedure similar to the one described for the synthesis of Example 325, except 1-(3,5-difluoropyridin-2-yl)methanamine dihydrochloride was used as a starting material. The resulting residue was purified by reverse phase column chromatography (using the following conditions: Column: C18 column; mobile phase A: Water (0.5% $NH_4HCO_3$), mobile phase B: MeCN; gradient: 20 B to 50 B in 30 min; 220/254 nm) to obtain the title compound (72.0 mg) as a solid. $^1$H NMR (400 MHz, DMSO-$d_6$) δ 14.16-13.83 (m, 1H), 8.47 (d, 1H), 8.43-821 (m, 2H), 7.98-7.87 (m, 1H), 7.32 (s, 1H), 7.04 (s, 1H), 4.68-4.38 (m, 3H), 3.88 (s, 3H), 3.33-3.29 (m, 1H), 2.78-2.74 (m, 1H), 2.20-2.16 (m, 1H), 1.80-1.75 (m, 1H), 1.55-1.51 (m, 1H), 1.20-1.15 (m, 1H), 1.06-0.39 (m, 4H). LCMS (ESI): 501.25 $[M+H]^+$.

Example 401. A Diastereomeric Mixture of (2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide and (2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide and (2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide and (2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide

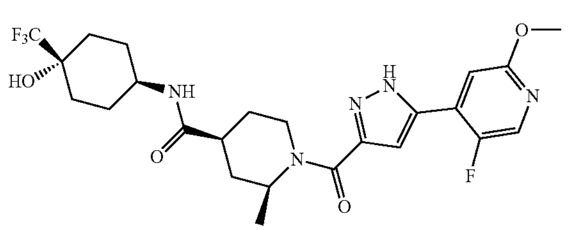

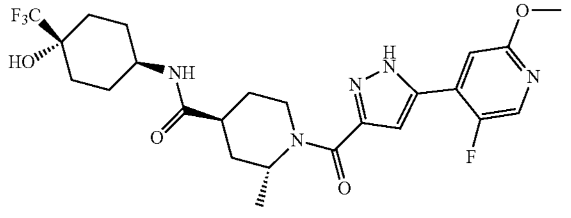

-continued

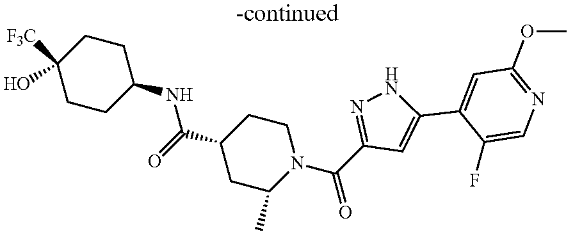

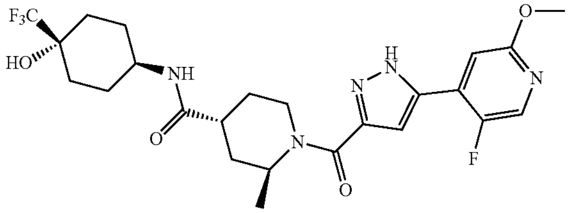

Step-1. methyl 1-[5-(5-fluoro-2-methoxypyridin-4-yl)-1-[[2-(trimethylsilyl)ethoxy]methyl]pyrazole-3-carbonyl]-2-methylpiperidine-4-carboxylate

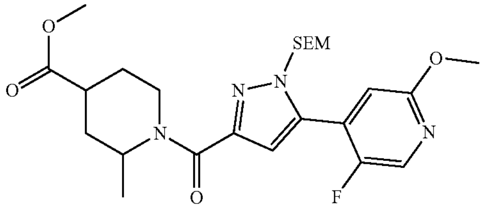 [SMILES: COC(=O)C1CCN(C(=O)c2cc(-c3cc(OC)ncc3F)n(COCC[Si](C)(C)C)n2)C(C)C1]

HATU (706.8 mg, 1.86 mmol) and methyl 2-methylpiperidine-4-carboxylate hydrochloride (300.0 mg, 1.55 mmol) were added to a stirred solution of 5-(5-fluoro-2-methoxypyridin-4-yl)-1-[[2-(trimethylsilyl)ethoxy]methyl]pyrazole-3-carboxylic acid (INTERMEDIATE 506, 569.2 mg, 1.55 mmol) and DIPEA (600.6 mg, 4.65 mmol) in DMF (10.00 mL). The resulting mixture was stirred at 25° C. for 14 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (3/1 v/v) to obtain the title compound (700.0 mg) as an oil. LCMS (ESI): 507.2 $[M+H]^+$.

Step-2. 1-[5-(5-fluoro-2-methoxypyridin-4-yl)-1-[[2-(trimethylsilyl)ethoxy]methyl]pyrazole-3-carbonyl]-2-methylpiperidine-4-carboxylic acid

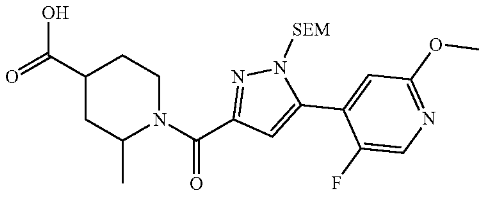 [SMILES: COc1cc(-c2cc(C(=O)N3CCC(C(=O)O)CC3C)nn2COCC[Si](C)(C)C)c(F)cn1]

Lithium hydroxide (116.0 mg, 2.76 mmol) was added to a stirred solution of methyl 1-[5-(5-fluoro-2-methoxypyridin-4-yl)-1-[[2-(trimethylsilyl)ethoxy]methyl]pyrazole-3-carbonyl]-2-methylpiperidine-4-carboxylate (Step-1, 700.0 mg, 1.38 mmol) in THF (2.00 mL), MeOH (2.00 mL) and $H_2O$ (2.00 mL). The resulting mixture was stirred at 25° C. for 14 h. The mixture was acidified to pH 3 with aqueous HCl (1M). The resulting mixture was diluted with EtOAc, washed with water. The organic layers were combined, dried over anhydrous $Na_2SO_4$, filtered, and concentrated under reduced pressure to obtain the title compound (600.0 mg) as a solid. LCMS (ESI): 493.2 $[M+H]^+$.

Step-3. 1-[5-(5-fluoro-2-methoxypyridin-4-yl)-1-[[2-(trimethylsilyl)ethoxy]methyl]pyrazole-3-carbonyl]-2-methyl-N-[(1r,4r)-4-hydroxy-4-(trifluoromethyl)cyclohexyl]piperidine-4-carboxamide

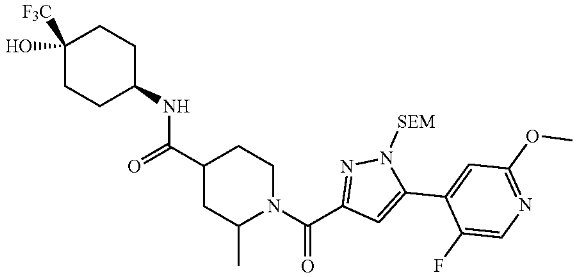 [SMILES: COc1cc(-c2cc(C(=O)N3CCC(C(=O)N[C@H]4CC[C@@](O)(C(F)(F)F)CC4)CC3C)nn2COCC[Si](C)(C)C)c(F)cn1]

HOBt (259.2 mg, 1.92 mmol), EDCI (367.7 mg, 1.92 mmol) and (1r,4r)-4-amino-1-(trifluoromethyl)cyclohexan-1-ol hydrochloride (280.9 mg, 1.28 mmol) were added to a stirred solution of 1-[5-(5-fluoro-2-methoxypyridin-4-yl)-1-[[2-(trimethylsilyl)ethoxy]methyl]pyrazole-3-carbonyl]-2-methylpiperidine-4-carboxylic acid (Step-2, 630.0 mg, 1.28 mmol) and DIPEA (826.4 mg, 6.39 mmol) in DMF (5.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 10/1 v/v) to obtain the title compound (800.0 mg) as a solid. LCMS (ESI): 658.3 $[M+H]^+$.

Step-4. (2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide and (2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide and (2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide and (2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide

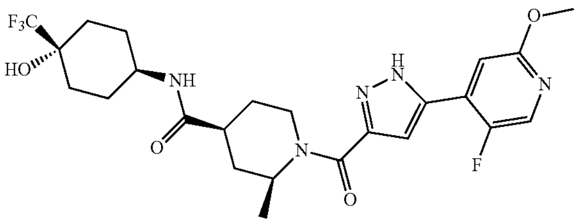

-continued

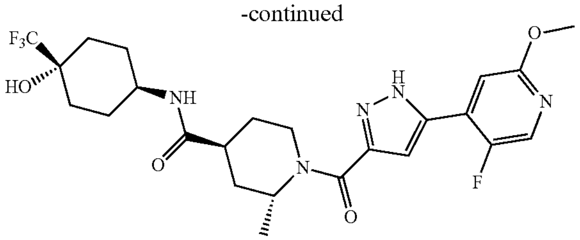

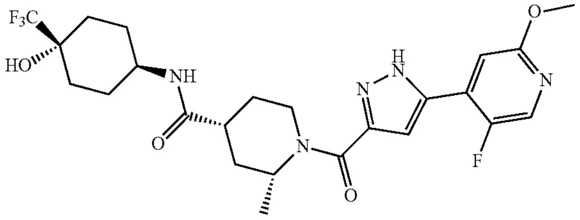

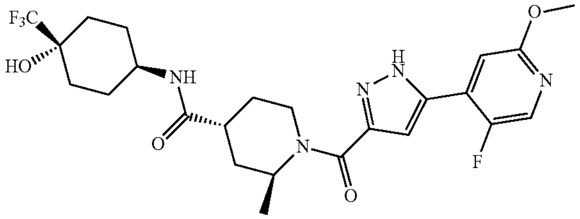

TFA (5.00 mL) was added to a stirred solution of tert-butyl 1-[5-(5-fluoro-2-methoxypyridin-4-yl)-1-[[2-(trimethylsilyl)ethoxy]methyl]pyrazole-3-carbonyl]-2-methyl-N-[(1r,4r)-4-hydroxy-4-(trifluoromethyl)cyclohexyl]piperidine-4-carboxamide (Step-3, 780.0 mg, 1.19 mmol) in DCM (5.00 mL). The resulting mixture was stirred at 25° C. for 1 h. The residue was purified by silica gel column chromatography eluting with DCM/MeOH (10/1 v/v) to obtain (2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide and (2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide and (2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide and (2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide (332.0 mg) as a solid mixture of diastereomers. $^1H$ NMR (300 MHz, DMSO-$d_6$) δ 8.28 (d, 1H), 7.83 (d, 1H), 7.32 (d, 1H), 7.04 (d, 1H), 5.72-5.66 (m, 1H), 4.42-4.36 (m, 1H), 4.20-3.84 (m, 6H), 1.88-1.60 (m, 8H), 1.55-1.45 (m, 4H), 1.25-1.17 (m, 3H). LCMS (ESI): 528.15. $[M+H]^+$.

This mixture of four diastereomers (330.0 mg) was separated using Chiral Prep-HPLC.

Column: CHIRAL ART Cellulose-SB column

Column dimension: 2×25 cm, 5 μm

Mobile Phase: hexanes (0.5% 2 M $NH_3$·MeOH): EtOH=70:30 hold for 11 min

Flow rate: 20 mL/min

Detection: 220/254 nm

Example 401-A and Example 401-B. The first eluting peak (160.0 mg) was Obtained as a Solid Mixture of Two Diastereomers.

The first eluting peak had a retention time of 3.11 min.

Example 401-C. The second eluting diastereomer (7.0 mg) was obtained as a solid.

The second eluting diastereomer had a retention time of 5.61 min.

$^1H$ NMR (300 MHz, DMSO-$d_6$) δ 14.17-13.70 (m, 1H), 8.35-8.13 (m, 1H), 7.83 (d, 1H), 7.32 (d, 1H), 7.14-6.81 (m, 1H), 5.78-5.51 (m, 1H), 5.02-4.28 (m, 1H), 3.97-3.64 (m, 4H), 3.31-3.26 (m, 3H), 1.89-1.66 (m, 6H), 1.62-1.38 (m, 5H), 1.35-1.08 (m, 4H). LCMS (ESI): 528.05 $[M+H]^+$.

Example 401-D. The third eluting diastereomer (7.1 mg) was obtained as a solid.

The third eluting diastereomer had a retention time of 7.95 min.

$^1H$ NMR (300 MHz, DMSO-$d_6$) δ 14.17-13.77 (m, 1H), 8.46-8.11 (m, 1H), 7.87-7.79 (m, 1H), 7.31 (d, 1H), 7.14-6.86 (m, 1H), 5.72-5.66 (m, 1H), 5.07-4.25 (m, 1H), 3.87 (s, 3H), 3.85-3.80 (m, 1H), 3.31-3.28 (m, 3H), 1.82-1.67 (m, 6H), 1.56-1.50 (m, 5H), 1.31-1.12 (i, 4H). LCMS (ESI): 528.05 $[M+H]^+$.

The first eluting peak (160.0 mg) containing two diastereomers of the title compounds was separated using Chiral Prep-HPLC.

Column: CHIRALPAK IE column

Column dimension: 2×25 cm, 5 μm

Mobile Phase: hexanes (0.5% 2 M $NH_3$·MeOH): EtOH=80:20 hold for 22 min

Flow rate: 20 mL/min

Detection: 220/254 nm

Example 401-A. The first eluting diastereomer (68.6 mg) was obtained as a solid.

The first eluting diastereomer had a retention time of 14.40 min.

$^1H$ NMR (300 MHz, DMSO-$d_6$) δ 8.28 (d, 1H), 7.83 (d, 1H), 7.32 (d, 1H), 7.04 (d, 1H), 5.71-5.65 (m, 1H), 4.42-4.36 (m, 1H), 4.13-3.84 (m, 4H), 3.71-3.35 (m, 3H), 1.99-1.62 (m, 8H), 1.55-1.45 (m, 4H), 1.26-1.17 (m, 3H). LCMS (ESI): 528.05 $[M+H]^+$.

Example 401-B. The second eluting diastereomer (58.2 mg) was obtained as a solid.

The second eluting diastereomer had a retention time of 16.94 min.

$^1H$ NMR (300 MHz, DMSO-$d_6$) δ 14.18-13.66 (m, 1H), 8.41-8.10 (m, 1H), 7.82 (d, 1H), 7.30 (d, 1H), 7.17-6.87 (m, 1H), 5.82-5.55 (m, 1H), 4.59-4.17 (m, 1H), 4.07-3.72 (m, 4H), 3.57-3.30 (m, 3H), 2.00-1.35 (m, 12H), 1.28-1.05 (m, 3H). LCMS (ESI): 528.05 $[M+H]^+$.

Example 402. (S)—N((3-chloro-5-methoxypyridin-2-yl)methyl)-4-(5-(5-fluoro-2-methoxypyridin-4-yl)-1H-pyrazole-3-carbonyl)-4-azaspiro[2.5]octane-7-carboxamide

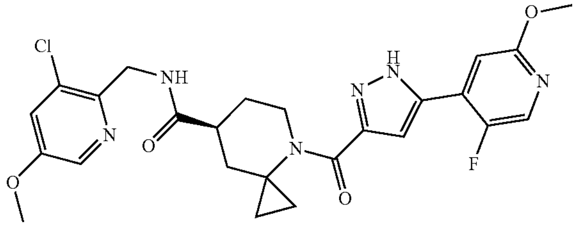 [SMILES: COc1cnc(CNC(=O)[C@H]2CCN(C(=O)c3cc(-c4cc(OC)ncc4F)[nH]n3)C3(CC3)C2)c(Cl)c1]

The title compound was prepared using a procedure similar to the one described for the synthesis of Example 389, except 2-bromo-3-chloro-5-methoxypyridine was used as a starting material. The resulting residue was purified by silica gel column chromatography eluting with petroleum ether/EtOAc (1/2 v/V) to obtain the title compound (43.4 mg) as a solid. $^{1}$H NMR (300 MHz, DMSO-$d_6$) δ 14.27-13.76 (m, 1H), 8.38-8.09 (m, 3H), 7.59 (d, 1H), 7.31 (d, 1H), 7.04 (s, 1H), 4.74-4.22 (m, 2H), 4.03-3.70 (m, 6H), 1.91-1.40 (m, 3H), 1.38-1.07 (m, 3H), 1.07-0.34 (m, 5H). LCMS (ESI): 529.10 $[M+H]^+$.

Example 403. A Diastereomeric Mixture of (2R,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide and (2S,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide and (2S,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide and (2R,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide

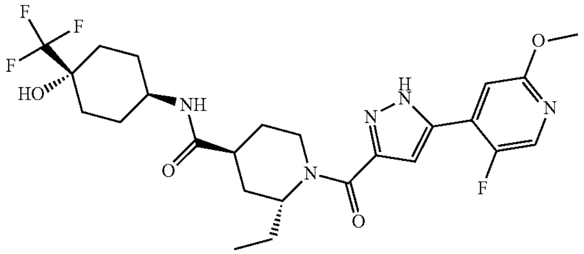

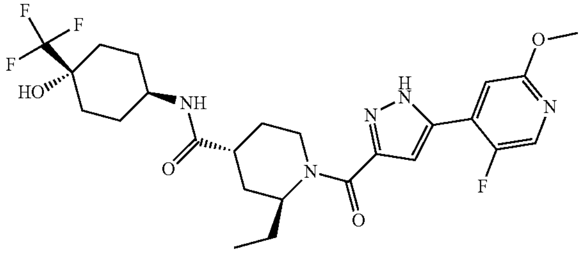

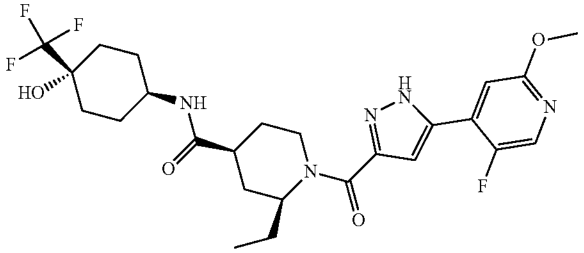

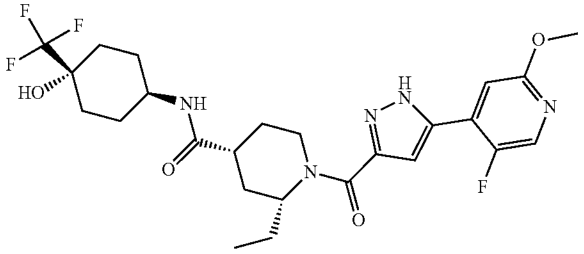

Step-1. methyl 2-ethenylpyridine-4-carboxylate

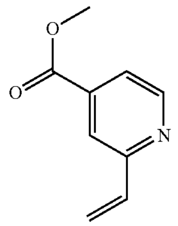

2-Ehenyl-4,4,5,5-tetramethyl-1,3,2-dioxaborolane (1.57 g, 10.18 mmol), $K_3PO_4$ (3.93 g, 18.52 mmol) and Pd(dppf)$Cl_2$ (1.35 g, 1.85 mmol) were added to a stirred solution of methyl 2-bromopyridine-4-carboxylate (2.00 g, 9.26 mmol) in 1,4-dioxane (15.00 mL)/$H_2O$ (1.50 mL). The resulting mixture was stirred at 70° C. for 14 h under nitrogen atmosphere. The resulting solution was concentrated under reduced pressure. The residue was purified by silica gel column chromatography eluting with EtOAc/petroleum ether (1/3 v/v) to obtain the title compound (1.30 g) as an oil. LCMS (ESI): 164.1 $[M+H]^+$.

Step-2. methyl 2-ethylpiperidine-4-carboxylate

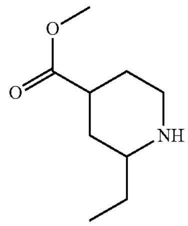

$PtO_2$ (1.30 g) was added to a stirred solution of methyl 2-ethenylpyridine-4-carboxylate (Step-1, 1.30 g, 7.97 mmol) in AcOH (3.00 mL). The resulting mixture was stirred at 25° C. for 14 h under hydrogen atmosphere. The resulting solution was concentrated under reduced pressure. The residue was purified via silica gel column with DCM/MeOH (5/1 v/v) to obtain the title compound (112.0 mg) as an oil. LCMS (ESI): 172.1 $[M+H]^+$.

Step-3. methyl 2-ethyl-1-[5-(5-fluoro-2-methoxy-pyridin-4-yl)-1-[[2-(trimethylsilyl)ethoxy]methyl]pyrazole-3-carbonyl]piperidine-4-carboxylate

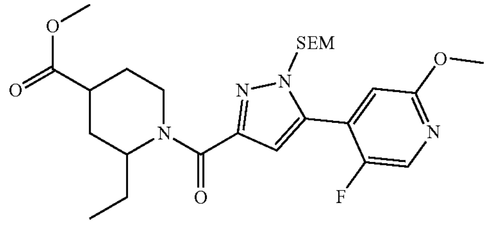 [SMILES: CCC1CC(C(=O)OC)CCN1C(=O)c1cc(-c2cc(OC)ncc2F)n(COCC[Si](C)(C)C)n1]

HATU (266.5 mg, 0.70 mmol) and methyl 2-ethylpiperidine-4-carboxylate (Step-2, 100.0 mg, 0.58 mmol) were added to a stirred solution of 5-(5-fluoro-2-methoxypyridin-4-yl)-1-[[2-(trimethylsilyl)ethoxy]methyl]pyrazole-3-carboxylic acid (INTERMEDIATE 506, 214.6 mg, 0.58 mmol) and DIPEA (377.4 mg, 2.92 mmol) in DMF (3.00 mL). The resulting mixture was stirred at 25° C. for 14 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with EtOAc/petroleum ether (1/5 v/v) to obtain the title compound (220.0 mg) as a solid. LCMS (ESI): 521.3 $[M+H]^+$.

Step-4. 2-ethyl-1-[5-(5-fluoro-2-methoxypyridin-4-yl)-1-[[2-(trimethylsilyl)ethoxy]methyl]pyrazole-3-carbonyl]piperidine-4-carboxylic acid

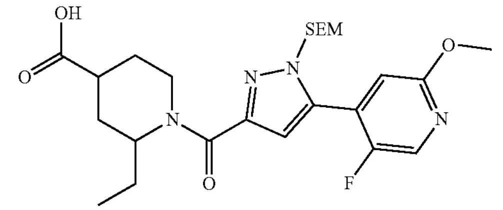 [SMILES: CCC1CC(C(=O)O)CCN1C(=O)c1cc(-c2cc(OC)ncc2F)n(COCC[Si](C)(C)C)n1]

Lithium hydroxide (51.6 mg, 1.23 mmol) was added to a stirred solution of methyl 2-ethyl-1-[5-(5-fluoro-2-methoxypyridin-4-yl)-1-[[2-(trimethylsilyl)ethoxy]methyl]pyrazole-3-carbonyl]piperidine-4-carboxylate (Step-3, 320.0 mg, 0.62 mmol) in MeOH (3.00 mL)/THF (3.00 mL)/$H_2O$ (3.00 mL). The resulting mixture was stirred at 25° C. for 1 h. The solution was concentrated under reduced pressure, then acidified to pH 3 with HCl (1M). The residue was extracted with EtOAc. The organic layers were combined, dried over anhydrous $Na_2SO_4$, filtered, and concentrated under reduced pressure to obtain the title compound (295.0 mg) as a solid. LCMS (ESI): 507.4 $[M+H]^+$.

Step-5. 2-ethyl-1-[5-(5-fluoro-2-methoxypyridin-4-yl)-1-[[2-(trimethylsilyl)ethoxy]methyl]pyrazole-3-carbonyl]-N-[(1r,4r)-4-hydroxy-4-(trifluoromethyl)cyclohexyl]piperidine-4-carboxamide

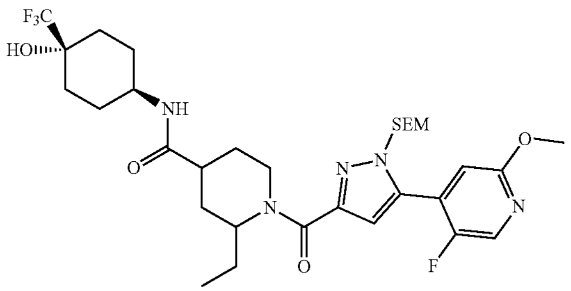 [SMILES: CCC1CC(C(=O)N[C@H]2CC[C@@](O)(C(F)(F)F)CC2)CCN1C(=O)c1cc(-c2cc(OC)ncc2F)n(COCC[Si](C)(C)C)n1]

HOBt (104.0 mg, 0.77 mmol), EDCI (147.6 mg, 0.77 mmol), and (1r,4r)-4-amino-1-(trifluoromethyl)cyclohexan-1-ol hydrochloride (112.7 mg, 0.51 mmol) were added to a stirred solution of 2-ethyl-1-[5-(5-fluoro-2-methoxypyridin-4-yl)-1-[[2-(trimethylsilyl)ethoxy]methyl]pyrazole-3-carbonyl]piperidine-4-carboxylic acid (Step-4, 260.0 mg, 0.51 mmol) and DIPEA (199.0 mg, 1.54 mmol) in DMF (3.00 mL). The resulting mixture was stirred at 25° C. for 2 h. The solution was diluted with EtOAc and washed with water. The organic layers were combined, dried over anhydrous $Na_2SO_4$, filtered, and concentrated under reduced pressure. The residue was purified by silica gel column chromatography eluting with EtOAc/petroleum ether (1/1 v/v) to obtain the title compound (297.0 mg) as a solid. LCMS (ESI): 672.3 $[M+H]^+$.

Step-6. (2R,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide and (2S,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide and (2S,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide and (2R,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide

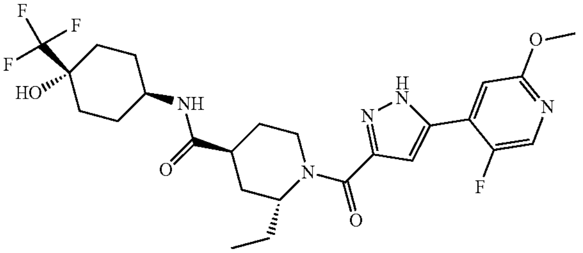

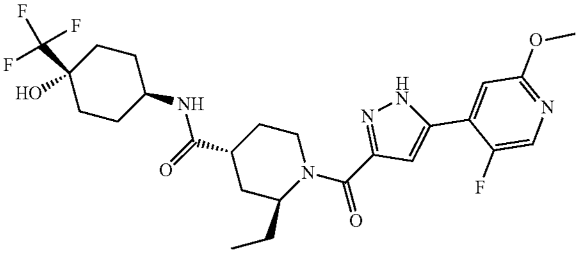

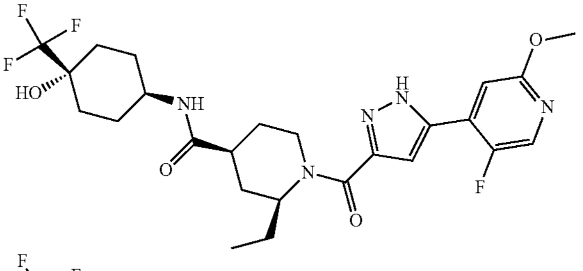

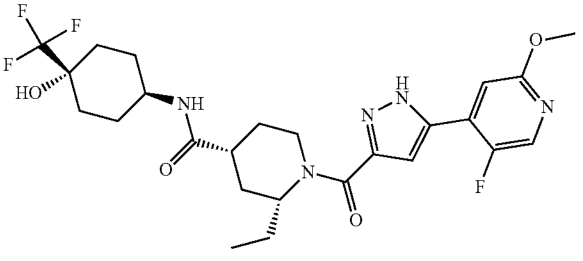

TFA (3.00 mL) was added to a stirred solution of 2-ethyl-1-[5-(5-fluoro-2-methoxypyridin-4-yl)-1-[[2-(trimethylsilyl)ethoxy]methyl]pyrazole-3-carbonyl]-N-[(1r,4r)-4-hydroxy-4-(trifluoromethyl)cyclohexyl]piperidine-4-carboxamide (Step-5, 297.0 mg, 0.44 mmol) in DCM (3.00 mL). The resulting mixture was stirred at 25° C. for 2 h. The solution was concentrated under reduced pressure. The residue was purified by silica gel column chromatography eluting with DCM/MeOH (10/1 v/v) to obtain (2R,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide and (2S,4R)-2-ethyl-1-(5-(5-fluoro-2-methoxypyridin-4-yl)-1H-pyrazole-3-carbonyl)-N-((1r,4R)-4-hydroxy-4-(trifluoromethyl) cyclohexyl)piperidine-4-carboxamide and (2S,4S)-2-ethyl-1-(5-(5-fluoro-2-methoxypyridin-4-yl)-1H-pyrazole-3-carbonyl)-N-((1r,4S)-4-hydroxy-4-(trifluoromethyl) cyclohexyl)piperidine-4-carboxamide and (2R,4R)-2-ethyl-1-(5-(5-fluoro-2-methoxypyridin-4-yl)-1H-pyrazole-3-carbonyl)-N-((1r,4R)-4-hydroxy-4-(trifluoromethyl) cyclohexyl)piperidine-4-carboxamide (160.0 mg) as a solid mixture of diastereomers (Example 403). $^1$H NMR (400 MHz, DMSO-$d_6$) δ 13.95 (s, 1H), 8.42-8.18 (M, 1H), 7.94-7.70 (m, 1H), 7.30 (d, 1H), 7.01 (d, 1H), 5.77-5.56 (m, 1H), 4.41-4.13 (m, 2H), 3.90-3.80 (m, 4H), 2.98-2.59 (m, 1H), 2.17-1.89 (m, 1H), 1.85-1.62 (m, 8H), 1.61-1.33 (m, 5H), 1.15-1.25 (m, 1H), 0.97-0.67 (m, 3H). LCMS (ESI): 542 [M+H]$^+$.

This mixture of four diastereomers (160.0 mg) was separated using Chiral Prep-HPLC.

Column: CHIRALPAK ID column

Column dimension: 2×25 cm, 5 μm

Mobile Phase: MTBE (0.5% 2M $NH_3$·MeOH):EtOH=90:10 hold for 14 min

Flow rate: 20 mL/min

Detection: 220/254 nm

Example 403-A. The first eluting diastereomer (40.7 mg) was obtained as a solid.

The first eluting diastereomer had a retention time of 5.41 min.

$^1$H NMR (400 MHz, DMSO-$d_6$) δ 13.96 (s, 1H), 8.26 (s, 1H), 7.94-7.73 (m, 1H), 7.30 (d, 1H), 7.01 (s, 1H), 5.72-5.65 (m, 1H), 4.31-4.21 (m, 2H), 3.90-3.80 (m, 4H), 2.95-2.56 (m, 1H), 2.03-1.85 (m, 1H), 1.81-1.61 (m, 8H), 1.59-1.35 (m, 5H), 1.31-1.11 (m, 1H), 0.92-0.66 (m, 3H). LCMS (ESI): 542.30 [M+H]$^+$.

Example 403-B. The second eluting diastereomer (36.4 mg) was obtained as a solid.

The second eluting diastereomer had a retention time of 6.72 min.

$^1$H NMR (400 MHz, DMSO-$d_6$) δ 13.96 (s, 1H), 8.26 (s, 1H), 7.94-7.62 (m, 1H), 7.30 (d, 1H), 7.02 (s, 1H), 5.72-5.66 (m, 1H), 4.34-4.24 (m, 2H), 3.90-3.79 (m, 4H), 3.02-2.62 (m, 1H), 2.10-1.83 (m, 1H), 1.85-1.62 (m, 8H), 1.59-1.36 (m, 5H), 1.33-1.04 (m, 1H), 0.97-0.63 (m, 3H). LCMS (ESI): 542.30 [M+H]$^+$.

Example 403-C. The third eluting diastereomer (7.3 mg) was obtained as a solid.

The third eluting diastereomer had a retention time of 9.69 min.

$^1$H NMR (400 MHz, DMSO-$d_6$) δ 13.95 (s, 1H), 8.26 (s, 1H), 7.80 (d, 1H), 7.30 (d, 1H), 7.00 (s, 1H), 5.68 (s, 1H), 4.69-4.65 (m, 1H), 4.45-4.37 (m, 1H), 3.85 (s, 3H), 3.83-3.77 (m, 1H), 3.18-3.13 (m, 1H), 20.75-2.71 (m, 1H), 1.84-1.41 (m, 13H), 1.30-1.11 (m, 1H), 0.89-0.65 (m, 3H). LCMS (ESI): 542.30 [M+H]$^+$.

Example 403-D. The fourth eluting diastereomer (7.7 mg) was obtained as a solid.

The fourth eluting diastereomer had a retention time of 12.92 min.

$^1$H NMR (400 MHz, DMSO-$d_6$) δ 13.95 (s, 1H), 8.26 (s, 1H), 7.80 (d, 1H), 7.30 (d, 1H), 7.00 (s, 1H), 5.68 (s, 1H), 4.69-4.65 (m, 1H), 4.45-4.37 (m, 1H), 3.85 (s, 3H), 3.83-3.77 (m, 1H), 3.18-3.13 (m, 1H), 2.75-2.71 (m, 1H), 1.84-1.41 (m, 13H), 1.30-1.11 (m, 1H), 0.89-0.65 (m, 3H). LCMS (ESI): 542.30 [M+H]$^+$.

Example 404. (S)-4-(5-(5-fluoro-2-methoxypyridin-4-yl)-1H-pyrazole-3-carbonyl)-N-((5-fluoro-3-(4-methylpiperazin-1-yl)pyridin-2-yl)methyl)-4-azaspiro[2.5]octane-7-carboxamide

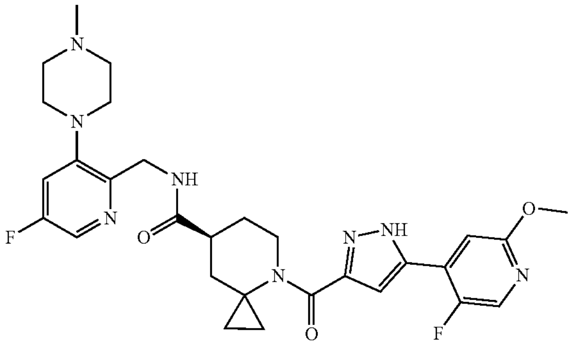 [SMILES: COc1cc(-c2cc(C(=O)N3CC[C@H](C(=O)NCc4ncc(F)cc4N4CCN(C)CC4)CC34CC4)n[nH]2)c(F)cn1]

Step-1. 1-(3-bromo-5-fluoropyridin-2-yl)methanamine

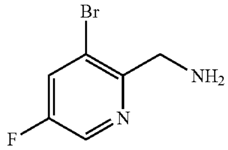

DIBAL-H (15.00 mL, 14.93 mmol) was added to a stirred mixture of 3-bromo-5-fluoropyridine-2-carbonitrile (1.00 g, 4.98 mmol) in DCM (5.00 mL) at −78° C. under $N_2$ atmosphere. The resulting solution was stirred at −78° C. for 1 h under $N_2$ atmosphere. The resulting solution was quenched with MeOH at −78° C. and concentrated under reduced pressure. The residue was purified by silica gel column chromatography eluting with DCM/MeOH (10/1 v/v) to obtain the title compound (333.6 mg) as an oil. LCMS (ESI): 205.0 [M+H]$^+$.

Step-2. tert-butyl N-[(3-bromo-5-fluoropyridin-2-yl) methyl]carbamate

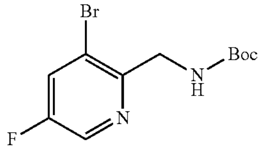 [SMILES: CC(C)(C)OC(=O)NCc1ncc(F)cc1Br]

$(Boc)_2O$ (400.6 mg, 1.84 mmol) and $NEt_3$ (386.9 mg, 3.83 mmol) were added to a stirred solution of 1-(3-bromo-5-fluoropyridin-2-yl)methanamine (Step-1, 313.6 mg, 1.53 mmol) in DCM (4.00 mL). The solution was stirred at 25° C. for 14 h. The solution was concentrated under reduced pressure. The residue was purified by silica gel column chromatography eluting with DCM/MeOH (30/1 v/v) to obtain the title compound (305.0 mg) as an oil. LCMS (ESI): 305.0

Step-3. tert-butyl N-[[5-fluoro-3-(4-methylpiperazin-1-yl)pyridin-2-yl]methyl]carbamate

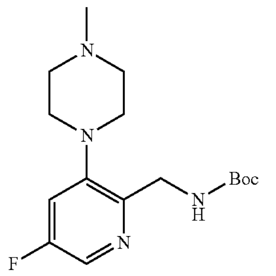 [SMILES: CN1CCN(c2cc(F)cnc2CNC(=O)OC(C)(C)C)CC1]

Pd-PEPPSI-IPentCl 2-methylpyridine (o-picoline) (110.2 mg, 0.13 mmol, CAS #: 1612981-29-8), $Cs_2CO_3$ (427.1 mg, 1.31 mmol), and 1-methyl-piperazine (98.5 mg, 0.98 mmol) were added to a stirred solution of tert-butyl N-[(3-bromo-5-fluoropyridin-2-yl)methyl]carbamate (Step-2, 200.0 mg, 0.66 mmol) in toluene (10.00 mL). The solution was stirred at 130° C. for 14 h under $N_2$ atmosphere. The resulting solution was concentrated under reduced pressure. The residue was purified by silica gel column chromatography eluting with DCM/MeOH (12/1 v/v) to obtain the title compound (35.7 mg) as an oil. LCMS (ESI): 325.2 $[M+H]^+$.

Step-4. 1-[5-fluoro-3-(4-methylpiperazin-1-yl)pyridin-2-yl]methanamine

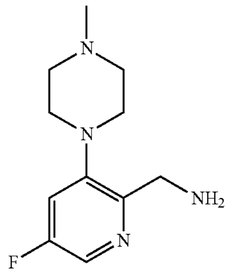 [SMILES: CN1CCN(c2cc(F)cnc2CN)CC1]

TFA (100 mL) was added to a stirred solution of tert-butyl N-[[5-fluoro-3-(4-methylpiperazin-1-yl)pyridin-2-yl]methyl]carbamate (Step-3, 30.0 mg, 0.09 mmol) in DCM (1.00 mL). The resulted mixture was stirred at 25° C. for 30 min. The resulting mixture was concentrated under reduced pressure to obtain the title compound as an oil. LCMS (ESI): 225.1 $[M+H]^+$.

Step-5. (S)-4-(5-(5-fluoro-2-methoxypyridin-4-yl)-1H-pyrazole-3-carbonyl)-N-((5-fluoro-3-(4-methylpiperazin-1-yl)pyridin-2-yl)methyl)-4-azaspiro[2.5]octane-7-carboxamide

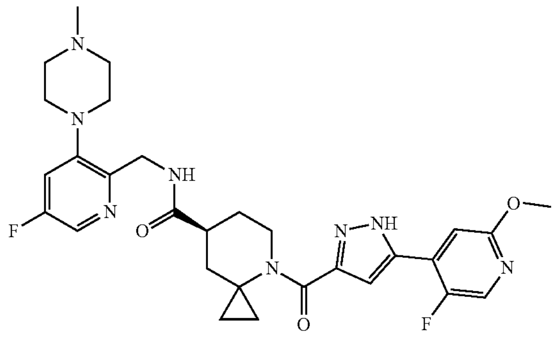 [SMILES: COc1cc(-c2cc(C(=O)N3CC[C@H](C(=O)NCc4ncc(F)cc4N4CCN(C)CC4)CC34CC4)n[nH]2)c(F)cn1]

HOBt (18.7 mg, 0.14 mmol), EDCI (26.5 mg, 0.14 mmol) and 1-[5-fluoro-3-(4-methylpiperazin-1-yl)pyridin-2-yl]methanamine (20.7 mg, 0.09 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 34.6 mg, 0.09 mmol) and DIEA (35.8 mg, 0.28 mmol) in DMF (1.00 mL). The resulting solution was stirred at 25° C. for 14 h. The solution was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 30 B to 50 B in 20 min; 220/254 nm) to obtain the title compound (3.2 mg) as a solid. $^1H$ NMR (400 MHz, $CD_3OD$) δ 8.21 (d, 1H), 8.14 (d, 1H), 7.54-7.39 (m, 1H), 7.35-7.21 (m, 1H), 7.12 (s, 1H), 4.62-4.45 (m, 2H), 3.95 (s, 3H), 3.74-3.59 (m, 1H), 3.12-3.01 (m, 4H), 3.00-2.87 (m, 4H), 2.58 (s, 3H), 2.51-2.19 (m, 1H), 2.01-1.71 (m, 2H), 1.67-1.49 (m, 1H), 1.29-1.09 (m, 2H), 1.02-0.83 (m, 2H), 0.81-0.58 (m, 2H). LCMS (ESI): 581.10 $[M+H]^+$.

Example 405. A Diastereomeric Mixture of (R)—N-((5R,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide and (R)—N-((5S,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide and (S)—N-((5S,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide and (S)—N-((5R,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide

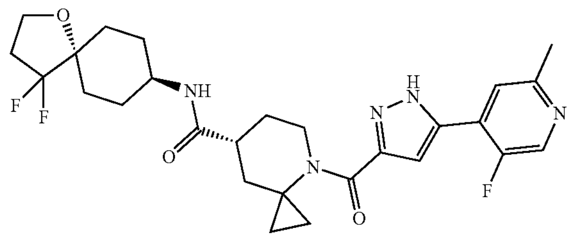

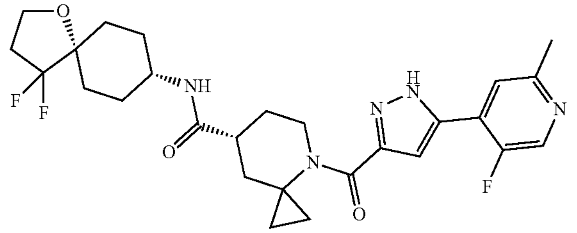

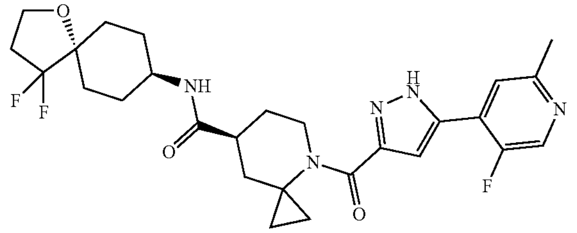

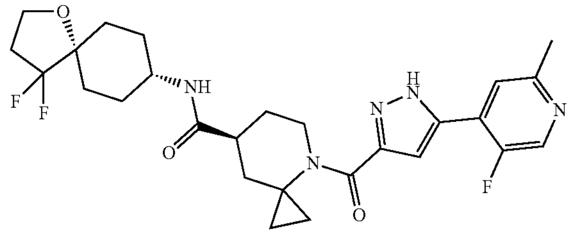

HOBt (94.2 mg, 0.70 mmol), EDCI (133.3 mg, 0.70 mmol), and 4,4-difluoro-1-oxaspiro[4.5]decan-8-amine (Step-1 from synthesis of Example 370, 79.0 mg, 0.31 mmol) were added to a stirred solution of 4-[5-(5-fluoro-2-methylpyridin-4-yl)-1H-pyrazole-3-carbonyl]-4-azaspiro[2.5]octane-7-carboxylic acid (INTERMEDIATE 526, 120.0 mg, 0.28 mmol) and DIPEA (258.9 mg, 1.40 mmol) in DMF (3.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 15 B to 50 B in 20 min; 220/254 nm) to obtain (R)—N-((5R,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide and (R)—N-((5S,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide and (S)—N-((5S,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide and (S)—N-((5R,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide (100.0 mg) as a solid mixture of diastereomers (Example 405). $^1H$ NMR (400 MHz, $CD_3OD$) δ 8.49-8.29 (m, 1H), 7.92 (d, 1H), 7.13 (s, 1H), 4.60 (s, 1H), 3.97-3.77 (m, 3H), 3.64-3.60 (m, 1H), 2.92-2.67 (m, 1H), 2.55-2.35 (m, 3H), 2.02-1.41 (m, 12H), 1.38-0.88 (m, 3H), 0.76-0.71 (m, 3H). LCMS (ESI): 532.15 $[M+H]^+$.

This mixture of four diastereomers (100.0 mg) was separated using Chiral Prep-HPLC.

Column: CHIRALPAK IA column

Column dimension: 2×25 cm, 5 μm

Mobile Phase: MTBE (0.5% 2M $NH_3$·MeOH):1/1 MeOH/DCM=50:50 hold for 12 min

Flow rate: 20 mL/min

Detection: 220/254 nm

Example 405-A and Example 405-B. The first eluting peak (40.0 mg) was Obtained as a Solid Mixture of Two Diastereomers.

The first eluting peak had a retention time of 4.22 min.

Example 405-C. The second eluting diastereomer (8.6 mg) was obtained as a solid.

The second eluting diastereomer had a retention time of 5.68 min.

$^1H$ NMR (300 MHz, $CD_3OD$) δ 8.49-8.38 (m, 1H), 8.03-7.90 (m, 1H), 7.75-7.69 (m, 1H), 7.15 (s, 1H), 4.81-4.50 (m, 1H), 4.06-3.91 (m, 2H), 3.90-3.77 (m, 1H), 2.99-2.74 (m, 1H), 2.59 (s, 3H), 2.56-2.40 (m, 2H), 2.03-1.48 (m, 1H), 1.42-1.20 (m, 2H), 1.17-0.98 (m, 1H), 0.86-0.63 (m, 3H). LCMS (ESI): 532.35 $[M+H]^+$.

Example 405-D. The third eluting diastereomer (7.1 mg) was obtained as a solid.

The third eluting diastereomer had a retention time of 12.84 min.

$^1H$ NMR (300 MHz, $CD_3OD$) δ 8.42 (s, 1H), 7.98-7.92 (m, 1H), 7.81-7.63 (m, 1H), 7.15 (s, 1H), 4.78-4.55 (m, 1H), 4.06-3.89 (m, 2H), 3.77-3.54 (m, 1H), 2.91-2.68 (m, 1H), 2.62-2.36 (m, 4H), 1.99-1.69 (m, 6H), 1.69-1.43 (m, 5H), 1.39-1.20 (m, 2H), 1.16-0.90 (m, 2H), 0.86-0.64 (m, 3H). LCMS (ESI): 532.35 $[M+H]^+$.

The first eluting peak (40.0 mg) containing two diastereomers of the title compounds was separated using Chiral Prep-HPLC.

Column: CHIRALPAK AD-H column

Column dimension: 2×25 cm, 5 μm

Mobile Phase: hexanes (0.5% 2 M $NH_3$·MeOH): EtOH=70:30 hold for 36 min

Flow rate: 20 mL/min

Detection: 220/254 nm

Example 405-A. The first eluting diastereomer (4.1 mg) was obtained as a solid.

The first eluting diastereomer had a retention time of 21.97 min.

$^1H$ NMR (400 MHz, $CD_3OD$) δ 8.40 (s, 1H), 7.89-7.84 (m, 1H), 7.13 (s, 1H), 4.67-4.15 (m, 1H), 4.01-3.75 (m, 3H), 3.16-2.78 (m, 1H), 2.61-2.52 (m, 2H), 2.54-2.38 (m, 2H), 2.25-2.01 (m, 1H), 1.99-1.71 (m, 5H), 1.69-1.47 (m, 4H), 1.39-1.14 (m, 4H), 1.10-0.95 (m, 1H), 0.94-0.83 (m, 1H), 0.80-0.62 (m, 2H). LCMS (ESI): 532.20 $[M+H]^+$.

Example 405-B. The second eluting diastereomer (10.8 mg) was obtained as a solid.

The second eluting diastereomer had a retention time of 28.6 min.

$^1$H NMR (400 MHz, $CD_3OD$) δ 8.41 (s, 1H), 7.86-7.82 (m, 1H), 7.13 (s, 1H), 4.71-4.18 (m, 1H), 3.98-3.88 (m, 2H), 3.74-3.40 (m, 1H), 3.10-2.65 (m, 1H), 2.56 (s, 3H), 2.50-2.34 (m, 3H), 2.16-1.62 (m, 6H), 1.60-1.43 (m, 4H), 1.37-1.17 (m, 2H), 1.10-0.87 (m, 2H), 0.80-0.58 (m, 2H). LCMS (ESI): 532.20 $[M+H]^+$.

Example 406. (S)-4-(5-(5-fluoro-2-methoxypyridin-4-yl)-1H-pyrazole-3-carbonyl)-N-(1-((1-fluorocyclopropyl)methyl)azetidin-3-yl)-4-azaspiro[2.5]octane-7-carboxamide

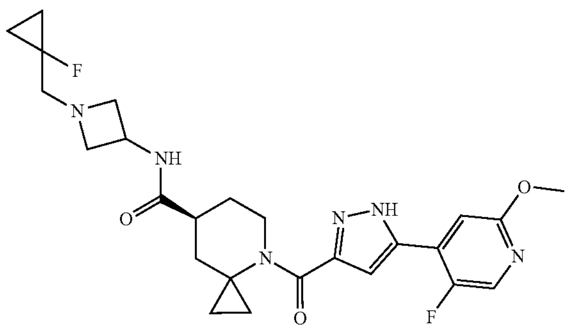 [SMILES: COc1cc(-c2cc(C(=O)N3CC[C@H](C(=O)NC4CN(CC5(F)CC5)C4)CC34CC4)n[nH]2)c(F)cn1]

Step-1. tert-butyl 3-[bis[(4-methoxyphenyl)methyl]amino]azetidine-1-carboxylate

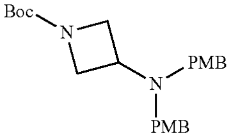

$K_2CO_3$ (2.40 g, 17.42 mmol) and 1-(bromomethyl)-4-methoxybenzene (2.90 g, 14.52 mmol) were added to a stirred mixture of tert-butyl 3-aminoazetidine-1-carboxylate (1.00 g, 5.81 mmol) in MeCN (10.00 mL). The resulting mixture was stirred at 25° C. for 3 h under nitrogen atmosphere. The resulting mixture was concentrated under reduced pressure. The residue was purified by silica gel column chromatography eluting with petroleum ether/EtOAc (5/1 v/v) to obtain the title compound (2.10 g) as a solid. LCMS (ESI): 413 $[M+H]^+$.

Step-2. N,N-bis[(4-methoxyphenyl)methyl]azetidin-3-amine

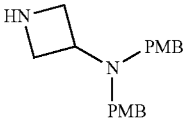

HCl (gas) in 1,4-dioxane (5.00 ml, 4M) were added to a stirred mixture of tert-butyl 3-[bis[(4-methoxyphenyl)methyl]amino]azetidine-1-carboxylate (Step-1, 2.10 g, 5.09 mmol) in 1,4-dioxane (5.00 mL). The resulting mixture was stirred at 25° C. for 1 h. The resulting mixture was concentrated under vacuum. The residue was purified by silica gel column chromatography eluting with DCM/MeOH (5/1 v/v) to obtain the title compound (1.50 g) as a solid. LCMS (ESI): 313 $[M+H]^+$.

Step-3. 1-(1-fluorocyclopropanecarbonyl)-N,N-bis[(4-methoxyphenyl)methyl]azetidin-3-amine

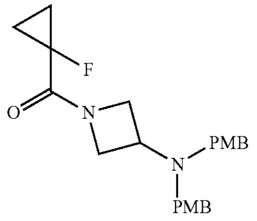

HATU (913.0 mg, 2.40 mmol) and N,N-bis[(4-methoxyphenyl)methyl]azetidin-3-amine (Step-2, 500.0 mg, 1.60 mmol) were added to a stirred mixture of 1-fluorocyclopropane-1-carboxylic acid (167.0 mg, 1.60 mmol) and DIPEA (621.0 mg, 4.80 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (3/1 v/v) to obtain the title compound (400.0 mg) as a solid. LCMS (ESI): 399 $[M+H]^+$.

Step-4. 1-[(1-fluorocyclopropyl)methyl]-N,N-bis[(4-methoxyphenyl)methyl]azetidin-3-amine

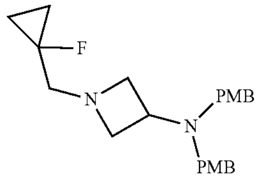

$BH_3$-$Me_2S$ (4.50 mL, 9.03 mmol) was added to a stirred mixture of 1-(1-fluorocyclopropanecarbonyl)-N,N-bis[(4-methoxyphenyl)methyl]azetidin-3-amine (Step-3, 360.0 mg, 0.90 mmol) in THF (5.00 mL). The resulting mixture was stirred at 80° C. for 14 h under nitrogen atmosphere. The resulting mixture was quenched with MeOH. The resulting mixture was concentrated under reduced pressure. The residue was purified by silica gel column chromatography eluting with petroleum ether/EtOAc (5/1 v/v) to obtain the title compound (220.0 mg) as a solid. LCMS (ESI): 385 $[M+H]^+$.

Step-5. 1-[(1-fluorocyclopropyl)methyl]azetidin-3-amine

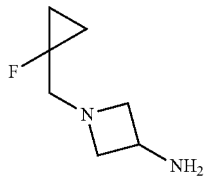

Ceric ammonium nitrate (301.0 mg, 0.55 mmol) was added to a stirred mixture of 1-[(1-fluorocyclopropyl)methyl]-N,N-bis[(4-methoxyphenyl)methyl]azetidin-3-amine (Step-4, 100.0 mg, 0.26 mmol) in $H_2O$ (0.50 mL) and MeCN (5.00 mL). The resulting mixture was stirred 25° C. for 14 h. The resulting mixture was concentrated under reduced pressure. The residue was purified by silica gel column chromatography eluting with DCM/MeOH (10/1 v/V) to obtain the title compound (35.0 mg) as a solid. LCMS (ESI): 145 $[M+H]^+$.

Step-6. (S)-4-(5-(5-fluoro-2-methoxypyridin-4-yl)-1H-pyrazole-3-carbonyl)-N-(1-((1-fluorocyclopropyl)methyl)azetidin-3-yl)-4-azaspiro[2.5]octane-7-carboxamide

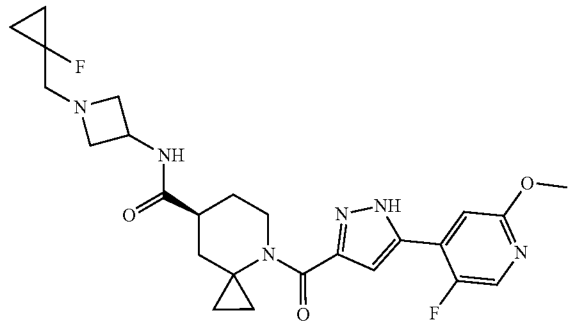 [SMILES: COc1cc(-c2cc(C(=O)N3CC[C@H](C(=O)NC4CN(CC5(F)CC5)C4)CC34CC4)n[nH]2)c(F)cn1]

EDCI (60.0 mg, 0.31 mmol), HOBt (43.0 mg, 0.31 mmol), and 1-[(1-fluorocyclopropyl)methyl]azetidin-3-amine (Step-5, 30.0 mg, 0.21 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 78.0 mg, 0.21 mmol) and DIPEA (134.0 mg, 1.04 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (15.5 mg) as a solid. $^1H$ NMR (300 MHz, $CD_3OD$) δ 8.14 (d, 1H), 7.35-7.23 (m, 1H), 7.11 (d, 1H), 4.65-4.41 (m, 2H), 3.94 (s, 3H), 3.84-3.72 (m, 2H), 3.21-3.08 (m, 2H), 2.96-2.70 (m, 3H), 2.62-2.09 (m, 1H), 2.03-1.65 (m, 2H), 1.49-1.08 (m, 2H), 1.07-0.92 (m, 4H), 0.79-0.61 (m, 4H). LCMS (ESI): 501.20$[M+H]^+$.

Example 407. A Diastereomeric Mixture of (S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,2-dimethylpiperidine-4-carboxamide and (R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,2-dimethylpiperidine-4-carboxamide

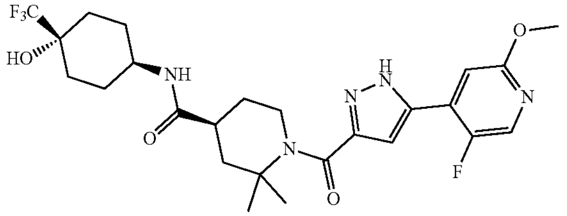

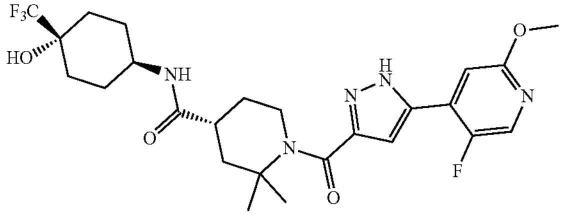

Step-1. methyl 1-[5-(5-fluoro-2-methoxypyridin-4-yl)-1-[[2-(trimethylsilyl)ethoxy]methyl]pyrazole-3-carbonyl]-2,2-dimethylpiperidine-4-carboxylate

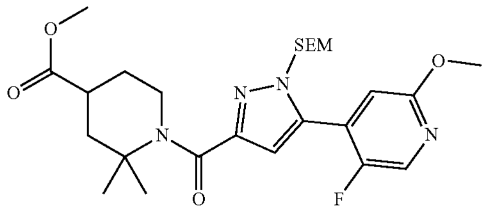 [SMILES: COC(=O)C1CCN(C(=O)c2cc(-c3cc(OC)ncc3F)n(COCC[Si](C)(C)C)n2)C(C)(C)C1]

HATU (367.0 mg, 0.97 mmol) and methyl 2,2-dimethylpiperidine-4-carboxylate hydrochloride (100.0 mg, 0.48 mmol) were added to a stirred mixture of 5-(5-fluoro-2-methoxypyridin-4-yl)-1-[[2-(trimethylsilyl)ethoxy]methyl]pyrazole-3-carboxylic acid (INTERMEDIATE 506, 195.0 mg, 0.53 mmol) and DIPEA (623.0 mg, 4.83 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 3/1 v/v) to obtain the title compound (250.0 mg) as an oil. LCMS (ESI): 521.26 $[M+H]^+$.

Step-2. 1-[5-(5-fluoro-2-methoxypyridin-4-yl)-1-[[2-(trimethylsilyl)ethoxy]methyl]pyrazole-3-carbonyl]-2,2-dimethylpiperidine-4-carboxylic acid

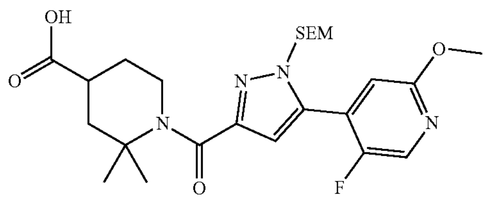 [SMILES: COc1cc(-c2cc(C(=O)N3CCC(C(=O)O)CC3(C)C)nn2COCC[Si](C)(C)C)c(F)cn1]

$LiOH \cdot H_2O$ (57.7 mg, 1.44 mmol) was added to a stirred mixture of methyl 1-[5-(5-fluoro-2-methoxypyridin-4-yl)-1-[[2-(trimethylsilyl)ethoxy]methyl]pyrazole-3-carbonyl]-2,2-dimethylpiperidine-4-carboxylate (Step-1, 250.0 mg, 0.48 mmol) in THF (1.50 mL), $H_2O$ (1.50 mL) and MeOH (1.50 mL). The resulting mixture was stirred at 25° C. for 2 h. The mixture was acidified to pH 3 with HC (aq.). The resulting mixture was extracted with EtOAc. The organic layers were combined, dried over anhydrous $Na_2SO_4$, filtered, and concentrated under reduced pressure. The residue was purified by silica gel column chromatography eluting with petroleum ether/EtOAc (2/1 v/v) to obtain the title compound (220.0 mg) as an oil. LCMS (ESI): 507.24 $[M+H]^+$.

Step-3. 1-[5-(5-fluoro-2-methoxypyridin-4-yl)-1-[[2-(trimethylsilyl)ethoxy]methyl]pyrazole-3-carbonyl]-2,2-dimethyl-N-[(1r,4r)-4-hydroxy-4-(trifluoromethyl)cyclohexyl]piperidine-4-carboxamide

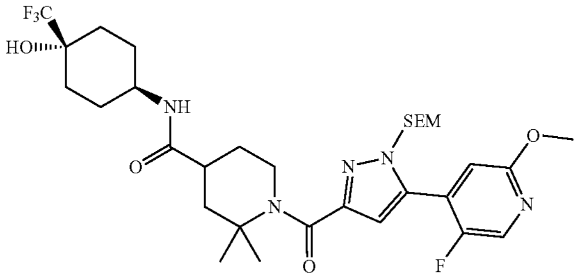 [SMILES: COc1cc(-c2cc(C(=O)N3CCC(C(=O)N[C@H]4CC[C@@](O)(C(F)(F)F)CC4)CC3(C)C)nn2COCC[Si](C)(C)C)c(F)cn1]

EDCI (169.8 mg, 0.89 mmol), HOBt (120.0 mg, 0.89 mmol), and (1r,4r)-4-(chloroamino)-1-(trifluoromethyl)cyclohexan-1-ol (107.1 mg, 0.49 mmol) were added to a stirred solution of 1-[5-(5-fluoro-2-methoxypyridin-4-yl)-1-[[2-(trimethylsilyl)ethoxy]methyl]pyrazole-3-carbonyl]-2,2-dimethylpiperidine-4-carboxylic acid (Step-2, 225.0 mg, 0.45 mmol) and DIPEA (573.6 mg, 4.46 mmol) in DMF (2.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 2/1 v/v) to obtain the title compound (264.0 mg) as an oil. LCMS (ESI): 672.32 $[M+H]^+$.

Step-4. (S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,2-dimethylpiperidine-4-carboxamide and (R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,2-dimethylpiperidine-4-carboxamide

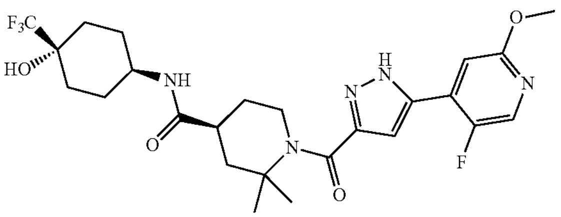

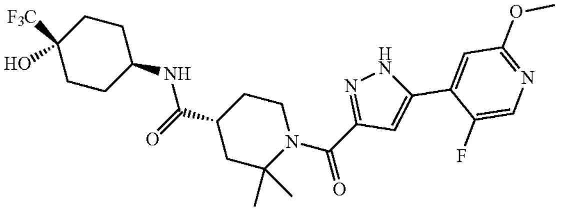

TFA (3.00 mL) was added to a stirred mixture of 1-[5-(5-fluoro-2-methoxypyridin-4-yl)-1-[[2-(trimethylsilyl)ethoxy]methyl]pyrazole-3-carbonyl]-2,2-dimethyl-N-[(1r,4r)-4-hydroxy-4-(trifluoromethyl)cyclohexyl]piperidine-4-carboxamide (Step-3, 234.0 mg, 0.35 mmol) in DCM (3.00 mL) at 0° C. The resulting mixture was stirred at 25° C. for 1 h. The resulting mixture was concentrated under reduced pressure. The residue was purified by Prep-TLC (petroleum ether/EtOAc, 1/1 v/v) to obtain (s)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,2-dimethylpiperidine-4-carboxamide and (R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,2-dimethylpiperidine-4-carboxamide (160.0 mg) as a solid mixture of diastereomers (Example 407). $^1H$ NMR (300 MHz, $CD_3OD$) δ 8.19-8.07 (m, 1H), 7.45-7.13 (m, 1H), 7.08-6.87 (m, 1H), 4.02-3.94 (m, 1H), 3.94 (s, 3H), 3.82-3.76 (m, 1H), 3.69-3.44 (m, 1H), 2.94-2.78 (m, 1H), 2.11-2.00 (m, 1H), 1.99-1.82 (m, 5H), 1.80-1.57 (m, 10H), 1.34-1.28 (m, 1H), 0.97-0.87 (m, 1H). LCMS (ESI): 542.30 $[M+H]^+$.

This mixture of two diastereomers (150.0 mg) was separated using Chiral Prep-HPLC.

Column: CHIRALPAK ID column

Column dimension: 2×25 cm, 5 μm

Mobile Phase: MTBE (0.5% 2M $NH_3 \cdot MeOH$): EtOH=95:5 hold for 18 min

Flow rate: 20 mL/min

Detection: 220/254 nm

Example 407-A. The first eluting diastereomer (43.2 mg) was obtained as a solid.

The first eluting diastereomer had a retention time of 8.62 min.

$^1H$ NMR (400 MHz, DMSO-$d_6$) δ 13.92 (s, 1H), 8.24 (s, 1H), 7.85 (d, 1H), 7.29 (d, 1H), 6.94 (s, 1H), 5.69 (s, 1H), 3.85 (s, 3H), 3.86-3.79 (m, 1H), 3.73-3.62 (m, 1H), 3.53-3.35 (m, 1H), 2.75-2.64 (m, 1H), 1.97-1.36 (m, 17H), 1.19-1.13 (m, 1H). LCMS (ESI): 542.25 $[M+H]^+$.

Example 407-B. The second eluting diastereomer (37.9 mg) was obtained as a solid.

The second eluting diastereomer had a retention time of 14.69 min.

$^1H$ NMR (400 MHz, DMSO-$d_6$) δ 13.94-13.90 (m, 1H), 8.26-8.21 (m, 1H), 7.85 (d, 1H), 7.29 (d, 1H), 6.96-6.91 (m, 1H), 5.71-5.67 (m, 1H), 3.89-3.79 (m, 4H), 3.86-3.79 (m, 1H), 3.73-3.62 (m, 1H), 2.75-2.64 (m, 1H), 1.96-1.49 (m, 17H), 1.26-1.08 (m, 1H). LCMS (ESI): 542.25 $[M+H]^+$.

Example 408. A Diastereomeric Mixture of (S)-4-(5-(5-fluoro-2-methoxypyridin-4-yl)-1H-pyrazole-3-carbonyl)-N-((1s,4R)-4-(hydroxymethyl)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-(hydroxymethyl)-4-(trifluoromethyl)cyclohexyl)-4-azaspiro[2.5]octane-7-carboxamide

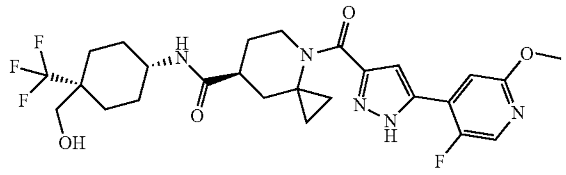

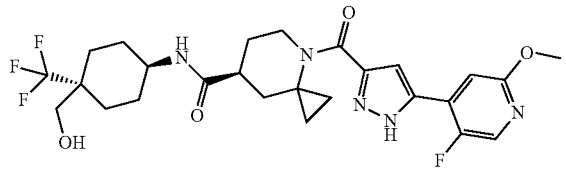

Step-1. 4-(hydroxymethyl)-4-(trifluoromethyl)cyclohexan-1-one

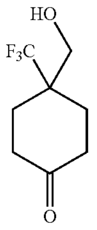

A solution of (8-(trifluoromethyl)-1,4-dioxaspiro[4.5]decan-8-yl)methanol (50.0 mg, 0.21 mmol) in AcOH (80% aqueous solution, 0.27 M) was stirred at 65° C. for 18 h. The reaction mixture was concentrated under reduced pressure. The residue was purified by silica gel column chromatography (EtOAc in Cyclohexane, 0% to 100%) to obtain the title compound (7.0 mg) as an oil. TLC-MS (APCI): 229.1 $[M+MeOH+H]^+$.

Step-2. 4-(hydroxymethyl)-4-(trifluoromethyl)cyclohexan-1-one oxime

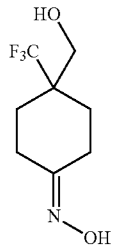 [SMILES: OCC1(C(F)(F)F)CCC(=NO)CC1]

Hydroxylamine hydrochloride (2.7 mg, 0.04 mmol) was added to a solution of sodium acetate (3.5 mg, 0.04 mmol) in MeOH (0.10 mL). The resulting mixture was stirred for 30 min. Then a solution of 4-(hydroxymethyl)-4-(trifluoromethyl)cyclohexan-1-one (Step-1, 7.0 mg, 0.04 mmol) in MeOH (0.10 mL) was added to the reaction mixture. The reaction mixture was stirred at 60° C. for 48 h. The reaction mixture was then cooled to 22° C. and diluted with EtOAc and water. The organic layers were combined, dried over anhydrous $Na_2SO_4$, filtered, and concentrated under reduced pressure to obtain the title compound (7.4 mg) as an oil. TLC-MS (APCI): 212.1 $[M+H]^+$.

Step-3. tert-butyl (4-(hydroxymethyl)-4-(trifluoromethyl)cyclohexyl)carbamate

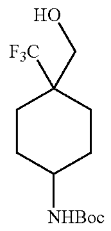

$NaBH_4$ (10.0 mg, 0.27 mmol) was added to a solution of 4-(hydroxymethyl)-4-(trifluoromethyl)cyclohexan-1-one oxime (Step-2, 7.0 mg, 0.03 mmol) and nickel(II) chloride hexahydrate (10.2 mg, 0.04 mmol) in MeOH (49.00 mL) at −78° C. The resulting mixture was allowed to warm up to 0° C. and stirred at this temperature for 6.5 h. $Boc_2O$ (10.8 mg, 0.05 mmol) was added to the reaction mixture and the reaction mixture was warmed to 22° C. for 18 h. The reaction mixture was quenched with brine at 0° C. MeOH was removed under reduced pressure and the resulting mixture was diluted with $Et_2O$. The organic layers were combined, dried over anhydrous $Na_2SO_4$, filtered, and concentrated under reduced pressure. The residue was purified by silica gel column chromatography (EtOAc in Cyclohexane, 20% to 50%) to obtain the title compound (8.1 mg) as a solid (~90% purity). $^1H$ NMR (400 MHz, $CDCl_3$), mixture of diastereomers) δ 4.60-4.35 (m, 1H), 3.84-3.63 (m, 2H), 3.61-3.36 (m, 1H), 1.99-1.50 (m, 9H), 1.44 (s, 9H). $^{19}F$ NMR (376 MHz, $CDCl_3$, mixture of diastereomers) δ −71.95, −76.51.

Step-4. [4-amino-1-(trifluoromethyl)cyclohexyl] methanol

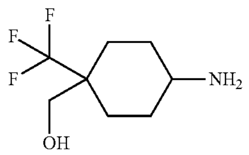 [SMILES: NC1CCC(CO)(C(F)(F)F)CC1]

TFA (0.50 mL) was added to a stirred solution of tert-butyl N-[4-(hydroxymethyl)-4-(trifluoromethyl)cyclohexyl] carbamate (Step-3, 8.1 mg, 0.03 mmol) in DCM (0.50 mL). The resulting mixture was stirred at 25° C. for 1 h. The solution was concentrated under reduced pressure to obtain the title compound (5.3 mg) as an oil. LCMS (ESI): 198.1 $[M+H]^+$.

Step-5. (S)-4-(5-(5-fluoro-2-methoxypyridin-4-yl)-1H-pyrazole-3-carbonyl)-N-((1s,4R)-4-(hydroxymethyl)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-(hydroxymethyl)-4-(trifluoromethyl) cyclohexyl)-4-azaspiro[2.5]octane-7-carboxamide

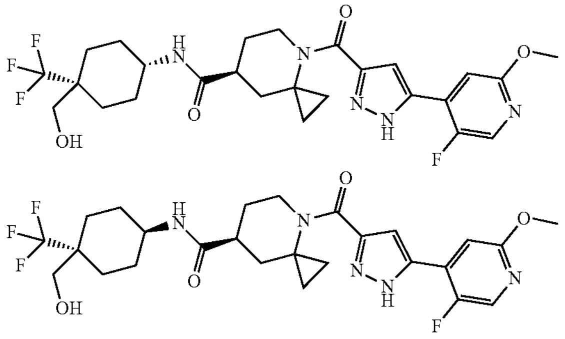

HOBt (5.5 mg, 0.04 mmol), EDCI (7.7 mg, 0.04 mmol), and [4-amino-1-(trifluoromethyl)cyclohexyl]methanol (5.3 mg, 0.03 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 10.1 mg, 0.03 mmol) and DIPEA (17.4 mg, 0.14 mmol) in DMF (1.00 mL). The resulting mixture was stirred at 25° C. for 14 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)-4-(5-(5-fluoro-2-methoxypyridin-4-yl)-1H-pyrazole-3-carbonyl)-N-((1s,4R)-4-(hydroxymethyl)-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1r,4S)-4-(hydroxymethyl)-4-(trifluoromethyl)cyclohexyl)-4-azaspiro[2.5]octane-7-carboxamide (8.0 mg) as a solid mixture of diastereomers (Example 408). $^1$H NMR (400 MHz, $CD_3OD$) δ 8.12 (s, 1H), 7.48-6.84 (m, 2H), 4.61 (s, 1H), 3.92 (s, 3H), 3.81-3.41 (m, 3H), 3.03-2.21 (m, 2H), 2.02-1.48 (m, 9H), 1.38-1.17 (m, 3H), 0.81-0.49 (m, 4H). LCMS (ESI): 554.20 $[M+H]^+$.

This mixture of two diastereomers (8.0 mg) was separated using Chiral Prep-HPLC.

Column: CHIRALPAK IE column

Column dimension: 2×25 cm, 5 μm

Mobile Phase: MTBE (0.5% 2M $NH_3$·MeOH):EtOH=50:50 hold for 13 min

Flow rate: 18 mL/min

Detection: 220/254 nm

Example 408-A. The first eluting diastereomer (1.8 mg) was obtained as a solid.

The first eluting diastereomer had a retention time of 4.93 min.

LCMS (ESI): 554.30 $[M+H]^+$.

Example 408-B. The second eluting diastereomer (0.3 mg) was obtained as a solid.

The second eluting diastereomer had a retention time of 10.35 min.

LCMS (ESI): 554.35 $[M+H]^+$.

Example 409. (7S)—N-(1-(tert-butylsulfinyl)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide

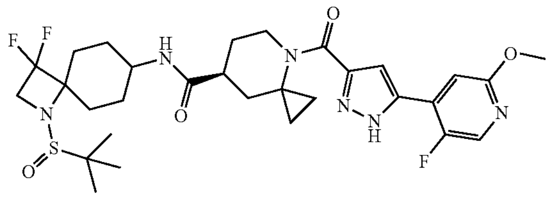 [SMILES: COc1cc(-c2cc(C(=O)N3CC[C@H](C(=O)NC4CCC5(CC4)N(S(=O)C(C)(C)C)CC5(F)F)CC34CC4)n[nH]2)c(F)cn1]

Step-1. ethyl 2-(8-((tert-butylsulfinyl)amino)-1,4-dioxaspiro[4.5]decan-8-yl)-2,2-difluoroacetate

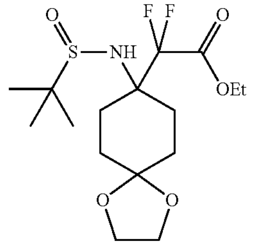 [SMILES: CCOC(=O)C(F)(F)C1(NS(=O)C(C)(C)C)CCC2(CC1)OCCO2]

A mixture of zinc (2.51 g, 38.4 mmol) and copper(I) chloride (1.27 g, 12.8 mmol) were stirred and heated for 1 min with a heat gun under nitrogen atmosphere. After cooling to 22° C., dry THF (30.00 mL) was added and the reaction mixture was stirred at 70° C. for 30 min. The mixture was cooled to 22° C. and ethyl 2-bromo-2,2-difluoroacetate (6.50 g, 32.0 mmol) was added dropwise at 22° C. After stirring 10 min at 22° C., a solution of 2-methyl-N-(1,4-dioxaspiro[4.5]decan-8-ylidene)propane-2-sulfinamide (Step-1 from synthesis of Example 399, 3.32 g, 12.8 mmol) in dry THF (13.00 mL) was added dropwise, and the reaction mixture was then stirred at 60° C. for 18 h. The mixture was quenched with saturated aqueous $NH_4Cl$/ brine (1/1 v/v) and extracted with EtOAc. The combined organic layers were washed with brine, dried, over $Na_2SO_4$, filtered and concentrated under reduced pressure. The residue was purified by silica gel column chromatography (EtOAc in DCM, 0 to 100%) to obtain the title compound (1.44 g, 3.76 mmol) as an oil. $^1$H NMR (400 MHz, $CDCl_3$) δ 4.34 (q, 2H), 3.98-3.89 (m, 4H), 3.68 (s, 1H), 2.25-2.04 (m, 3H), 2.04-1.92 (m, 3H), 1.83-1.74 (m, 1H), 1.71-1.62 (m, 3H), 1.36 (t, 3H), 1.25 (s, 9H).

Step-2. N-(8-(1,1-difluoro-2-hydroxyethyl)-1,4-dioxaspiro[4.5]decan-8-yl)-2-methylpropane-2-sulfinamide

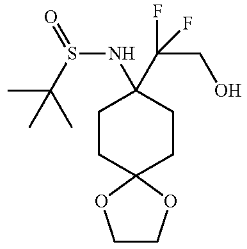 [SMILES: CC(C)(C)S(=O)NC1(C(F)(F)CO)CCC2(CC1)OCCO2]

$LiAlH_4$ (6.26 mL, 15.0 mmol, 2.4 M) was added dropwise to a solution of ethyl 2-(8-((tert-butylsulfinyl)amino)-1,4-dioxaspiro[4.5]decan-8-yl)-2,2-difluoroacetate (Step-1, 1.44 g, 3.76 mmol) in THF (47.00 ml) at 0° C. The reaction mixture was stirred for 1 h at 0° C. The resulting mixture was diluted with $Et_2O$, cooled to 0° C., and quenched by sequential addition of water (0.57 mL), NaOH (0.86 mL, 15% aqueous), and water (1.71 mL). The mixture was warmed to 22° C. for 15 min, stirred with $MgSO_4$ for 15 min, and the precipitate was filtered, and the filter cake was washed with EtOAc and $Et_2O$. The filtrate was concentrated under reduced pressure to obtain the title compound (1.00 g) as an oil. $^1$H NMR (400 MHz, $CDCl_3$) δ 4.02 (ddd, 1H), 3.95-3.93 (m, 4H), 3.92-3.77 (m, 2H), 2.35-2.26 (m, 1H), 2.18-2.02 (m, 2H), 1.81-1.60 (m, 5H), 1.28 (s, 9H).

Step-3. 1-(tert-butylsulfinyl)-3,3-difluoro-8,11-dioxa-1-azadispiro[3.2.47.24]tridecane

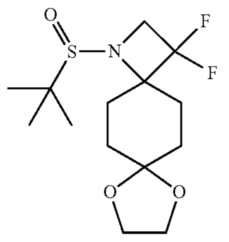 [SMILES: CC(C)(C)S(=O)N1CC(F)(F)C12CCC1(CC2)OCCO1]

Triphenylphosphine (1.15 g, 4.39 mmol) and DIAD (1.18 g, 5.86 mmol) were added to a solution of the N-(8-(1,1-difluoro-2-hydroxyethyl)-1,4-dioxaspiro[4.5]decan-8-yl)-2-methylpropane-2-sulfinamide (Step-2, 1.00 g, 2.93 mmol) in dry THF (84.00 mL). The reaction mixture was stirred at 22° C. for 18 h. The resulting mixture was concentrated under reduced pressure. The residue was purified by silica gel column chromatography (EtOAc in DCM, 0% to 50%) to obtain the title compound (708.0 mg). $^1$H NMR (400 MHz, $CDCl_3$) δ 4.53 (td, 1H), 3.88-3.84 (m, 4H), 3.49 (dt, 1H), 2.24-2.17 (m, 2H), 2.17-2.10 (m, 1H), 1.85-1.78 (m, 1H), 1.75-1.63 (m, 4H), 1.07 (s, 9H).

Step-4. 1-(tert-butylsulfinyl)-3,3-difluoro-1-azaspiro[3.5]nonan-7-one

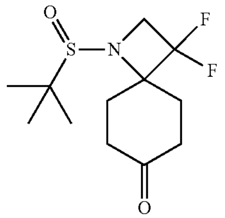 [SMILES: CC(C)(C)S(=O)N1CC(F)(F)C12CCC(=O)CC2]

A solution of 1-(tert-butylsulfinyl)-3,3-difluoro-8,11-dioxa-1-azadispiro[3.2.47.24]tridecane (Step-3, 413.0 mg, 75.2% Wt, 0.96 mmol) in AcOH (80% aqueous solution, 0.27 M) was stirred at 65° C. for 18 h. The reaction was concentrated under reduced pressure and the residue was purified by silica gel collum chromatography (EtOAc in Cyclohexane, 20 to 100%) to obtain the title compound (180.0 mg) as a solid. $^1$H NMR (400 MHz, $CDCl_3$) δ 4.71 (td, 1H), 3.66 (dt, 1H), 2.65-2.37 (m, 8H), 1.17 (s, 9H).

Step-5. 1-(tert-butylsulfinyl)-3,3-difluoro-1-azaspiro[3.5]nonan-7-one oxime

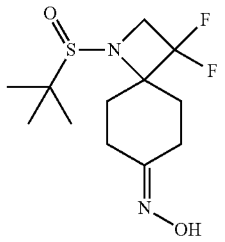 [SMILES: CC(C)(C)S(=O)N1CC(F)(F)C12CCC(=NO)CC2]

Hydroxylamine hydrochloride (95.8 mg, 1.38 mmol) was added to a solution of sodium acetate (205.0 mg, 1.50 mmol) in MeOH (3.13 mL). The resulting mixture was stirred for 30 min at 22° C. A solution of 1-(tert-butylsulfinyl)-3,3-difluoro-1-azaspiro[3.5]nonan-7-one (Step-4, 350.0 mg 1.25 mmol) in MeOH (3.13 mL) was added to the reaction mixture. The reaction mixture was stirred at 60° C. for 48 h. The reaction mixture was then cooled to 22° C. and diluted with EtOAc and water. The organic layers were combined, dried over anhydrous $Na_2SO_4$, filtered, and concentrated under reduced pressure to obtain the title compound (252.0 mg) as a solid. $^1$H NMR (400 MHz $CDCl_3$) δ 4.73-4.60 (m, 1H), 3.61 (qd, 1H), 3.33-3.14 (m, 1H), 2.80-2.09 (m, 7H), 1.14 (s, 9H).

Step-6. tert-butyl (1-(tert-butylsulfinyl)-3,3-difluoro-1-azaspiro[3.5]nonan-7-yl)carbamate

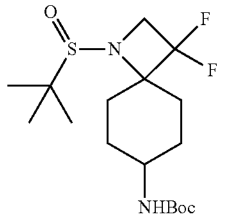 [SMILES: CC(C)(C)OC(=O)NC1CCC2(CC1)N(S(=O)C(C)(C)C)CC2(F)F]

$NaBH_4$ (257.0 mg, 6.79 mmol) was added to a solution of 1-(tert-butylsulfinyl)-3,3-difluoro-1-azaspiro[3.5]nonan-7-one oxime (Step-5, 250.0 mg, 0.85 mmol) and nickel(II) chloride hexahydrate (262.0 mg, 1.10 mmol) in MeOH (49.00 mL) at −78° C. The resulting mixture was allowed to warm up to 0° C. and stirred at this temperature for 6.5 h. $Boc_2O$ (278 mg, 1.27 mmol) was added and the reaction was warmed to 22° C. for 18 h. The reaction was quenched with brine at 0° C. MeOH was removed under reduced pressure and the resulting residue was diluted with $Et_2O$. The organic layers were combined, dried over anhydrous $Na_2SO_4$, filtered, and concentrated under reduced pressure. The residue was purified by silica gel column chromatography (EtOAc in Cyclohexane, 20% to 40%) to obtain (111.7 mg) as a solid. $^1H$ NMR (400 MHz, CDCl3, mixture of diastereomers) δ 4.64-4.52 (m, 1H), 4.36 (s, 1H), 3.70-3.36 (m, 2H), 2.55-2.30 (m, 1H), 2.30-1.96 (m, 4H), 1.96-1.73 (m, 3H), 1.46-1.43 (m, 9H), 1.18-1.11 (m, 9H). $^{19}$FNMR (400 MHz, $CDCl_3$, mixture of diastereomers) δ −105.18, −105.70, −107.56, −108.37, −111.24, −111.45, −111.76, −111.97. TLC-MS (APCI): 381.4 $[M+H]^+$.

Step-7. 3,3-difluoro-1-(2-methylpropane-2-sulfinyl)-1-azaspiro[3.5]nonan-7-amine

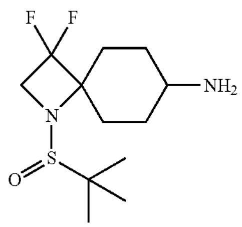 [SMILES: CC(C)(C)S(=O)N1CC(F)(F)C12CCC(N)CC2]

TFA (3.00 mL) was added to a stirred solution of tert-butyl N-[3,3-difluoro-1-(2-methylpropane-2-sulfinyl)-1-azaspiro[3.5]nonan-7-yl]carbamate (Step-6, 80.0 mg, 0.21 mmol) in DCM (3.00 mL). The resulting mixture was stirred at 25° C. for 30 min. The resulting mixture was concentrated under reduced pressure to obtain the title compound (58.0 mg) as an oil. LCMS (ESI): 281.1 $[M+H]^+$.

Step-8. (7S)—N-(1-(tert-butylsulfinyl)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide

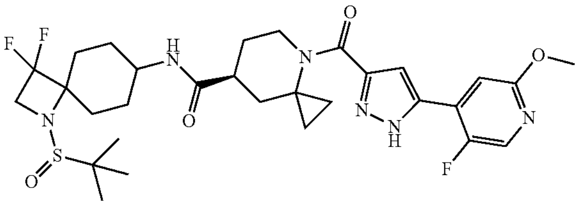 [SMILES: COc1cc(-c2cc(C(=O)N3CC[C@H](C(=O)NC4CCC5(CC4)N(S(=O)C(C)(C)C)CC5(F)F)CC34CC4)n[nH]2)c(F)cn1]

HOBt (42.7 mg, 0.32 mmol), EDCI (60.5 mg, 0.32 mmol), and 3,3-difluoro-1-(2-methylpropane-2-sulfinyl)-1-azaspiro[3.5]nonan-7-amine (Step-7, 59.0 mg, 0.21 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 78.8 mg, 0.21 mmol) and DIPEA (163.2 mg, 1.26 mmol) in DMF (2.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 3/1 v/v) to obtain the title compound (35.0 mg) as a solid. $^1H$ NMR (300 MHz, $CD_3OD$) δ 8.14 (s, 1H), 7.33-7.24 (m, 1H), 7.11 (s, 1H), 4.67-4.44 (m, 2H), 3.95 (s, 3H), 3.90-3.81 (m, 1H), 3.81-3.69 (m, 1H), 2.51-2.19 (m, 1H), 2.16-1.85 (m, 3H), 1.83-1.35 (m, 7H), 1.34-1.13 (m, 13H), 1.08-0.84 (m, 1H), 0.78-0.70 (m, 2H). LCMS (ESI): 637.05 $[M+H]^+$.

Example 410. A Diastereomeric Mixture of (S)—N ((4S,7r)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide and (S)—N-((4R,7s)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide

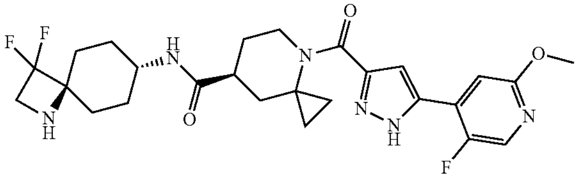

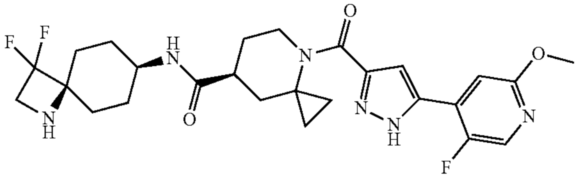

HCl (gas) in EtOAc (2.00 mL) was added to (7S)—N-(1-(tert-butylsulfinyl)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide (Example 409, 35.0 mg, 0.06 mmol). The resulting solution was stirred at 25° C. for 1 h. The resulting solution was concentrated under reduced pressure. The residue was purified by silica gel column chromatography eluting with DCM/MeOH (10/1 v/v) to obtain (S)—N-((4S,7r)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide and (S)—N-((4R,7s)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide (25.0 mg) as a solid mixture of diastereomers. LCMS (ESI): 533.2 $[M+H]^+$.

This mixture of two diastereomers (25.0 mg) was separated using Chiral Prep-HPLC.

Column: CHIRALPAK ID column

Column dimension: 2×25 cm, 5 μm

Mobile Phase: MTBE (0.5% 2M $NH_3$·MeOH): MeOH=50:50 hold for 17 min

Flow rate: 20 mL/min

Detection: 220/254 nm

Example 410-A. The first eluting diastereomer (10.1 mg) was obtained as a solid.

The first eluting diastereomer had a retention time of 8.43 min.

$^1$H NMR (300 MHz, DMSO-$d_6$) δ 13.98 (s, 1H), 8.25 (s, 1H), 7.83-7.48 (m, 1H), 7.39-7.21 (m, 1H), 7.01 (s, 1H), 5.04-4.14 (m, 1H), 3.89-3.80 (m, 4H), 3.74-3.61 (m, 2H), 3.59-3.43 (m, 1H), 2.81-2.65 (m, 1H), 2.12-1.92 (m, 2H), 1.84-1.59 (m, 4H), 1.56-1.37 (m, 3H), 1.36-1.12 (m, 3H), 1.11-0.82 (m, 2H), 0.81-0.44 (m, 3H). LCMS (ESI): 533.10 $[M+H]^+$.

Example 410-B. The second eluting diastereomer (8.0 mg) was obtained as a solid.

The second eluting diastereomer had a retention time of 14.94 min.

$^1$H NMR (300 MHz, DMSO-$d_6$) δ 13.99 (s, 1H), 8.25 (s, 1H), 7.80-7.65 (m, 1H), 7.37-7.23 (m, 1H), 7.01 (s, 1H), 4.80-4.22 (m, 1H), 3.86-3.78 (m, 3H), 3.78-3.64 (m, 2H), 3.55-3.45 (m, 2H), 2.81-2.58 (m, 1H), 1.93-1.76 (m, 2H), 1.75-1.48 (m, 61H), 1.47-1.27 (m, 2H), 1.25-1.02 (m, 2H), 1.00-0.77 (m, 2H), 0.76-0.38 (m, 3H). LCMS (ESI): 533.05 $[M+H]^+$.

Example 411. A Diastereomeric Mixture of (S)-4-(5-(5-fluoro-2-methoxypyridin-4-yl)-1H-pyrazole-3-carbonyl)-N—((R)-1-(4-hydroxybicyclo[2.2.2]octan-1-yl)ethyl)-4-azaspiro[2.5]octane-7-carboxamide and (S)-4-(5-(5-fluoro-2-methoxypyridin-4-yl)-1H-pyrazole-3-carbonyl)-N—((S)-1-(4-hydroxybicyclo[2.2.2]octan-1-yl)ethyl)-4-azaspiro[2.5]octane-7-carboxamide

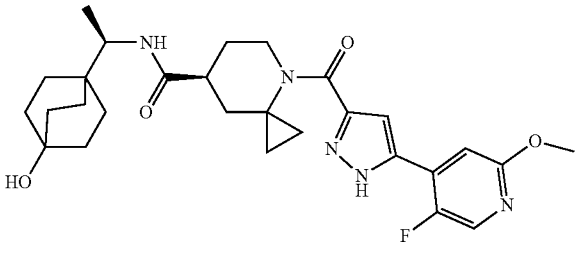

-continued

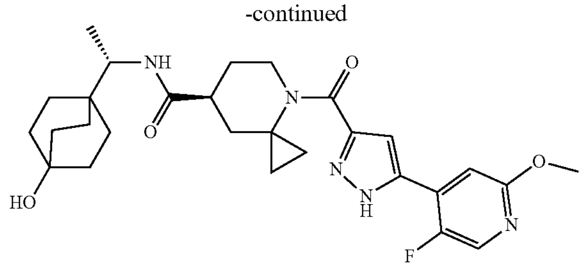

The title compound was prepared using a procedure similar to the one described for the synthesis of Example 325, except 4-(1-aminoethyl)bicyclo[2.2.2]octan-1-ol hydrochloride was used as a starting material. The residue was purified by reverse phase column chromatography (using the following conditions: Column: C18; mobile phase A: Water (0.5% $NH_4HCO_3$), mobile phase B: MeCN; gradient: 20 B to 40 B in 30 min; 220/254 nm) to obtain (100.0 mg) as a solid mixture of diastereomers (Example 411). $^1$H NMR (400 MHz, DMSO-d6) δ 8.25 (s, 1H), 7.46-7.25 (m, 2H), 7.00 (s, 1H), 4.80-4.07 (m, 1H), 3.85 (s, 3H), 3.70-3.47 (m, 2H), 2.75-2.60 (m, 1H), 2.24-2.05 (m, 1H), 1.75-1.61 (m, 1H), 1.55-1.32 (m, 14H), 1.28-1.11 (m, 1H), 1.02-0.80 (m, 4H), 0.69-0.55 (m, 2H). LCMS (ESI): 526.10 $[M+H]^+$.

This mixture of two diastereomers (100.0 mg) was separated using Chiral Prep-HPLC.

Column: CHIRAL ART Cellulose-SB column

Column dimension: 2×25 cm, 5 μm

Mobile Phase: MTBE (0.1% diethanolamine):EtOH:=90:10 hold for 12 min

Flow rate: 20 mL/min

Detection: 220/254 nm

Example 411-A. The first eluting diastereomer (14.4 mg) was obtained as a solid.

The first eluting diastereomer had a retention time of 7.32 min.

$^1$H NMR (400 MHz, DMSO-$d_6$) δ 14.25-13.65 (m, 1H), 8.36-8.14 (m, 1H), 7.44-7.18 (m, 2H), 7.00 (s, 1H), 4.63-4.14 (m, 1H), 3.85 (s, 3H), 3.61-3.47 (m, 2H), 2.77-2.67 (m, 1H), 2.66-2.52 (m, 1H), 2.38-2.07 (m, 1H), 1.88-1.62 (m, 1H), 1.52-1.33 (m, 12H), 1.27-1.04 (m, 1H), 1.02-0.70 (m, 5H), 0.70-0.45 (m, 2H). LCMS (ESI): 526.10 $[M+H]^+$.

Example 411-B. The second eluting diastereomer (12.1 mg) was obtained as a solid.

The second eluting diastereomer had a retention time of 10.60 min.

$^1$H NMR (400 MHz, DMSO-$d_6$) δ 14.20-13.58 (m, 1H), 8.32-8.14 (m, 1H), 7.39 (d, 1H), 7.34-7.25 (m, 1H), 7.09-6.89 (m, 1H), 4.62-4.29 (m, 1H), 3.87 (s, 3H), 3.63-3.49 (m, 2H), 2.82-2.59 (m, 1H), 2.58-2.53 (m, 1H), 2.27-1.94 (m, 1H), 1.78-1.58 (m, 1H), 1.50-1.35 (m, 12H), 1.33-1.08 (m, 2H), 1.06-0.91 (m, 1H), 0.90-0.80 (m, 3H), 0.72-0.56 (m, 2H). LCMS (ESI): 526.10 $[M+H]^+$.

Example 412. (S)—N-((4,6-dimethylpyridazin-3-yl)methyl)-4-(5-(5-fluoro-2-methoxypyridin-4-yl)-1H-pyrazole-3-carbonyl)-4-azaspiro[2.5]octane-7-carboxamide

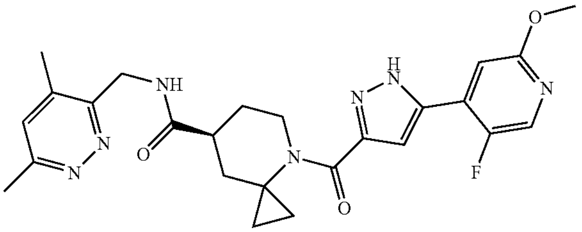

The title compound was prepared using a procedure similar to the one described for the synthesis of Example 389, except 3-chloro-4,6-dimethylpyridazine was used as a starting material. The resulting residue was purified by Prep-TLC (DCM/MeOH, 20/1 v/v) to obtain the title compound (79.0 mg) as a solid. $^{1}$H NMR (400 MHz, DMSO-$d_6$) δ 13.98 (s, 1H), 8.55-8.06 (m, 2H), 7.42-7.22 (m, 2H), 7.01 (s, 1H), 4.70-4.30 (m, 3H), 3.85 (s, 3H), 2.96-2.64 (m, 1H), 2.56-2.51 (m, 3H), 2.32-2.12 (m, 4H), 1.86-1.66 (m, 1H), 1.65-1.39 (m, 1H), 1.29-1.11 (m, 2H), 0.97-0.80 (m, 2H), 0.70-0.30 (m, 2H). LCMS (ESI): 494.30 $[M+H]^+$.

Example 413. (R)—N-((5-chloropyrimidin-2-yl)methyl)-4-(5-(5-fluoro-2-methoxypyridin-4-yl)-1H-pyrazole-3-carbonyl)-4-azaspiro[2.5]octane-7-carboxamide

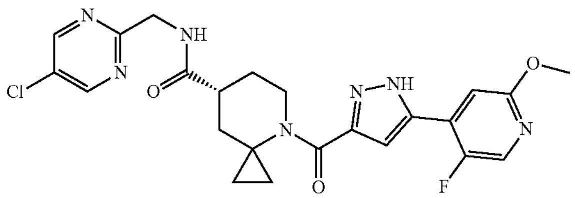 [SMILES: COc1cc(-c2cc(C(=O)N3CC[C@@H](C(=O)NCc4ncc(Cl)cn4)CC34CC4)n[nH]2)c(F)cn1]

The title compound was prepared using a procedure similar to the one described for the synthesis of Example 325, except 1-(5-chloropyrimidin-2-yl)methanamine hydrochloride was used as a starting material. The resulting residue was purified by reverse phase column chromatography (using the following conditions: Column: C18; mobile phase A: Water (0.5% $NH_4HCO_3$), mobile phase B: MeCN; gradient: 10 B to 40 B in 30 min; 220/254 nm) to obtain the title compound (86.4 mg) as a solid. $^{1}$H NMR (400 MHz, DMSO-$d_6$) δ 14.14-13.80 (m, 1H), 8.87 (s, 2H), 8.47 (s, 1H), 8.24 (s, 1H), 7.35-7.17 (m, 1H), 7.01 (s, 1H), 4.51-4.34 (m, 2H), 3.85 (s, 3H), 3.59-3.31 (m, 3H), 2.91-2.66 (m, 1H), 2.34-2.01 (m, 1H), 1.90-1.63 (m, 1H), 1.61-1.41 (m, 1H), 1.38-1.10 (m, 1H), 1.07-0.76 (m, 1H), 0.70-0.56 (m, 2H). LCMS (ESI): 500.00 $[M+H]^+$.

Example 414. A Diastereomeric Mixture of (S)-4-(5-(5-fluoro-2-methoxypyridin-4-yl)-1H-pyrazole-3-carbonyl)-N-((3S,4R)-4-morpholinotetrahydrofuran-3-yl)-4-azaspiro[2.5]octane-7-carboxamide and (S)-4-(5-(5-fluoro-2-methoxypyridin-4-yl)-1H-pyrazole-3-carbonyl)-N-((3R,4S)-4-morpholinotetrahydrofuran-3-yl)-4-azaspiro[2.5]octane-7-carboxamide

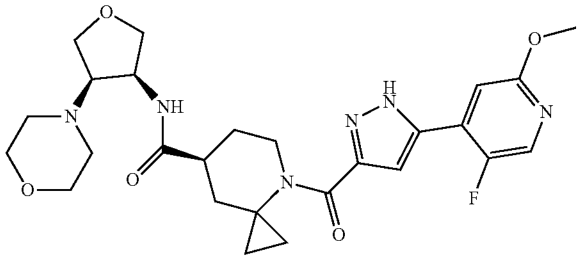

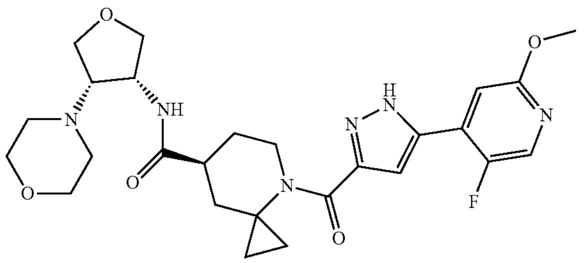

Step-1. tert-butyl N-[4-(morpholin-4-yl)oxolan-3-yl]carbamate

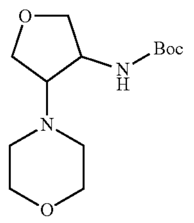 [SMILES: CC(C)(C)OC(=O)NC1COCC1N1CCOCC1]

Morpholine (216.5 mg, 2.49 mmol) was added to a stirred mixture of tert-butyl N-(4-oxooxolan-3-yl)carbamate (100.0 mg, 0.50 mmol) in MeOH (2.50 mL) and AcOH (0.10 mL). The resulting solution was stirred at 25° C. for 1 h. Then $NaBH_3CN$ (93.7 mg, 1.49 mmol) was added to the solution and stirred at 25° C. for 2 h. The resulting mixture was concentrated under vacuum. The resulting residue was purified by silica gel column chromatography eluting with petroleum ether/EtOAc (1/1 v/v) to obtain the title compound (103.9 mg) as an oil. LCMS (ESI): 273.2 $[M+H]^+$.

Step-2. 4-(morpholin-4-yl)oxolan-3-amine

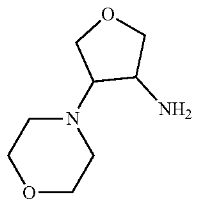 [SMILES: NC1COCC1N1CCOCC1]

HCl (gas) in 1,4-dioxane (1.50 mL) was added to tert-butyl N-[4-(morpholin-4-yl)oxolan-3-yl]carbamate (Step-1, 90.0 mg, 0.33 mmol). The resulting solution was stirred at 25° C. for 2 h. The resulting mixture was concentrated under reduced pressure to obtain the title compound as a solid and used directly in the next step without further purification. LCMS (ESI): 173.2 [M+H]$^+$.

Step-3. (S)-4-(5-(5-fluoro-2-methoxypyridin-4-yl)-1H-pyrazole-3-carbonyl)-N-((3S,4R)-4-morpholinotetrahydrofuran-3-yl)-4-azaspiro[2.5]octane-7-carboxamide and (S)-4-(5-(5-fluoro-2-methoxypyridin-4-yl)-1H-pyrazole-3-carbonyl)-N-((3R,4S)-4-morpholinotetrahydrofuran-3-yl)-4-azaspiro[2.5]octane-7-carboxamide

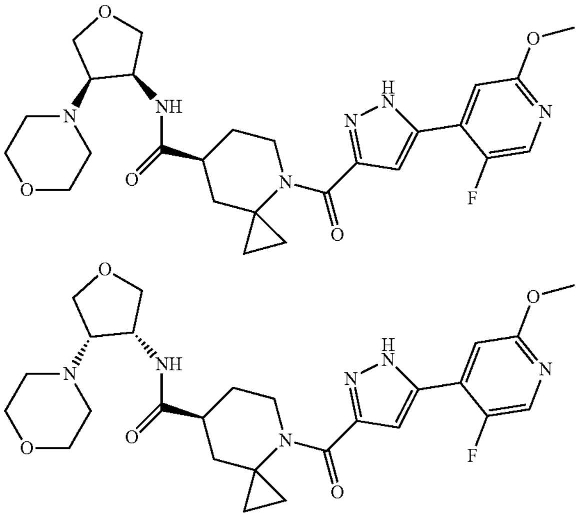

HOBt (44.7 mg, 0.33 mmol), EDCI (63.5 mg, 0.33 mmol), and 4-(morpholin-4-yl)oxolan-3-amine (Step-2, 56.9 mg, 0.33 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 82.5 mg, 0.22 mmol) and DIPEA (142.2 mg, 1.10 mmol) in DMF (3.00 mL). The resulting solution was stirred at 25° C. for 14 h. The solution was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 40 B in 20 min; 220/254 nm) to obtain (S)-4-(5-(5-fluoro-2-methoxypyridin-4-yl)-1H-pyrazole-3-carbonyl)-N-((3S,4R)-4-morpholinotetrahydrofuran-3-yl)-4-azaspiro[2.5]octane-7-carboxamide and (S)-4-(5-(5-fluoro-2-methoxypyridin-4-yl)-1H-pyrazole-3-carbonyl)-N-((3R,4S)-4-morpholinotetrahydrofuran-3-yl)-4-azaspiro[2.5]octane-7-carboxamide (71.0 mg) as a solid mixture of diastereomers. LCMS (ESI): 529.3 [M+H]$^+$.

This mixture of two diastereomers (71.0 mg) was separated using Chiral Prep-HPLC.

Column: CHIRALPAK IE column
Column dimension: 2×25 cm, 5 μm
Mobile Phase: 3/1 hexanes/DCM (0.5% 2 M $NH_3$·MeOH):EtOH=60:40 hold for 35 min
Flow rate: 18 mL/min
Detection: 220/254 nm Example 414-A. The first eluting diastereomer (19.7 mg) was obtained as a solid.

The first eluting diastereomer had a retention time of 22.26 min.

$^1$H NMR (400 MHz, $CD_3OD$) δ 8.14 (s, 1H), 7.44-6.98 (m, 2H), 4.49-4.27 (m, 1H), 4.12-3.98 (m, 2H), 3.99-3.90 (m, 4H), 3.78-3.64 (m, 6H), 3.04-2.89 (m, 2H), 2.56-2.52 (m, 2H), 2.40-2.34 (m, 3H), 1.98-1.79 (m, 1H), 1.78-1.61 (m, 1H), 1.32-1.30 (m, 1H), 1.15-1.00 (m, 1H), 0.95-0.73 (m, 4H). LCMS (ESI): 529.25 [M+H]$^+$.

Example 414-B. The second eluting diastereomer (14.0 mg) was obtained as a solid.

The second eluting diastereomer had a retention time of 27.21 min.

$^1$H NMR (400 MHz, $CD_3OD$) δ 8.14 (s, 1H), 7.54-6.92 (m, 2H), 4.76-4.51 (m, 1H), 4.47-4.28 (m, 1H), 4.17-3.91 (m, 4H), 3.88-3.60 (m, 6H), 3.07-2.86 (m, 2H), 2.56-2.49 (m, 2H), 2.46-2.29 (m, 2H), 2.01-1.53 (m, 2H), 1.51-1.12 (m, 4H), 1.11-0.96 (m, 2H), 0.95-0.57 (m, 2H). LCMS (ESI): 529.15 [M+H]$^+$.

Example 415. A Diastereomeric Mixture of (S)—N—((S)-1-(5,6-dihydro-8-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide and (S)—N—((R)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide

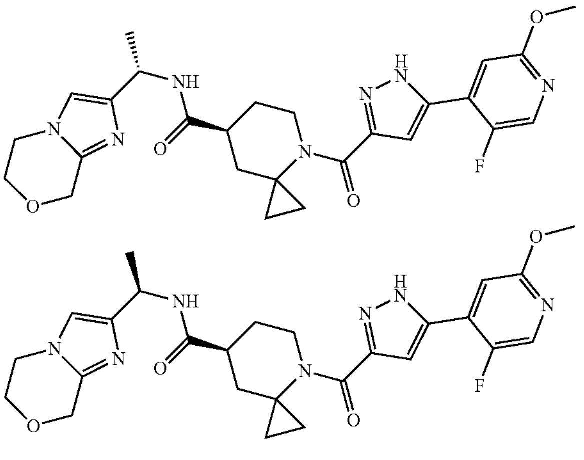

The title compound was prepared using a procedure similar to the one described for the synthesis of Example 377, except 5H,6H,8H-imidazo[2,1-c][1,4]oxazine-2-carbaldehyde was used as a starting material. The resulting residue was purified by Prep-TLC (DCM/MeOH, 15/1 v/v) to obtain (S)—N—((S)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide and (S)—N—((R)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide (88.0 mg) as a solid mixture of diastereomers (Example 415). $^1$H NMR (300 MHz, $CD_3OD$) δ 8.19-8.08 (m, 1H), 7.46-6.98 (m, 2H), 6.92 (s, 1H), 5.01-4.92 (m, 1H), 4.78-4.72 (m, 2H), 4.09-3.99 (m, 4H), 3.95 (s, 3H), 2.87-2.81 (m, 1H), 2.44-2.38 (m, 1H), 2.06-1.59 (m, 2H), 1.48-1.40 (m, 3H), 1.34-1.28 (m, 2H), 1.21-0.85 (m, 2H), 0.78-0.72 (m, 3H). LCMS (ESI): 524.20 $[M+H]^+$.

This mixture of two diastereomers (80.0 mg) was separated using Chiral Prep-HPLC.

Column: CHIRALPAK IH column
Column dimension: 2×25 cm, 5 μm
Mobile Phase: MTBE (0.5% 2M $NH_3$·MeOH):EtOH=85:15 hold for 15 min
Flow rate: 20 mL/min
Detection: 220/254 nm Example 415-A. The first eluting diastereomer (38.5 mg) was obtained as a solid.

The first eluting diastereomer had a retention time of 9.26 min.

$^1$H NMR (400 MHz, $CD_3OD$) δ 8.13 (s, 1H), 7.44-7.05 (m, 2H), 6.92 (s, 1H), 5.02-4.92 (m, 1H), 4.78-4.72 (m, 2H), 4.63-4.55 (m, 1H), 4.09-3.98 (m, 4H), 3.94 (s, 3H), 3.11-2.74 (m, 1H), 2.73-2.19 (m, 1H), 1.96-1.54 (m, 2H), 1.52-1.39 (m, 3H), 1.39-1.19 (m, 2H), 1.22-0.95 (m, 1H), 0.81-0.67 (m, 3H). LCMS (ESI): 524.20 $[M+H]^+$.

Example 415-B. The second eluting diastereomer (30.1 mg) was obtained as a solid.

The second eluting diastereomer had a retention time of 11.17 min.

$^1$H NMR (400 MHz, $CD_3OD$) δ 8.13 (s, 1H), 7.28 (s, 1H), 7.11 (s, 1H), 6.92 (s, 1H), 5.02-4.92 (m, 1H), 4.77-4.73 (m, 2H), 4.70-4.46 (m, 1H), 4.09-3.99 (m, 4H), 3.94 (s, 3H), 3.25-2.86 (m, 1H), 2.83-2.34 (m, 1H), 2.09-1.63 (m, 2H), 1.47-1.41 (m, 3H), 1.33-1.29 (m, 2H), 1.28-1.23 (m, 1H), 0.75-0.71 (m, 3H). LCMS (ESI): 524.20 $[M+H]^+$.

Example 416. (S)-4-(5-(5-fluoro-2-methoxypyridin-4-yl)-1H-pyrazole-3-carbonyl)-N-(pyrazolo[1,5-a]pyridin-7-ylmethyl)-4-azaspiro[2.5]octane-7-carboxamide

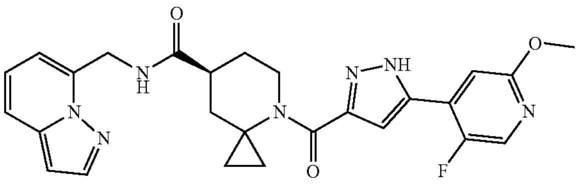 [SMILES: COc1cc(-c2cc(C(=O)N3CC[C@H](C(=O)NCc4cccc5ccnn45)CC34CC4)n[nH]2)c(F)cn1]

The title compound was prepared using a procedure similar to the one described for the synthesis of Example 325, except pyrazolo[1,5-a]pyridin-7-ylmethanamine was used as a starting material. The residue was purified by Prep-TLC (DCM/MeOH, 20/1 v/v) to obtain the title compound (34.8 mg) as a solid. $^1$H NMR (400 MHz, DMSO-$d_6$) δ 14.11-13.84 (m, 1H), 8.60 (s, 1H), 8.34-8.17 (m, 1H), 8.07-8.02 (m, 1H), 7.68-7.61 (m, 1H), 7.35-7.27 (m, 1H), 7.25-7.17 (m, 1H), 7.04 (s, 1H), 6.73-6.65 (m, 2H), 4.81-4.44 (m, 2H), 3.85 (s, 3H), 3.06-2.58 (m, 1H), 2.39-2.03 (m, 1H), 2.06-0.37 (m, 9H). LCMS (ESI): 504.15 $[M+H]^+$.

Example 417. (S)-4-(5-(5-fluoro-2-methoxypyridin-4-yl)-1H-pyrazole-3-carbonyl)-N-(1-(oxetan-3-yl)piperidin-4-yl)-4-azaspiro[2.5]octane-7-carboxamide

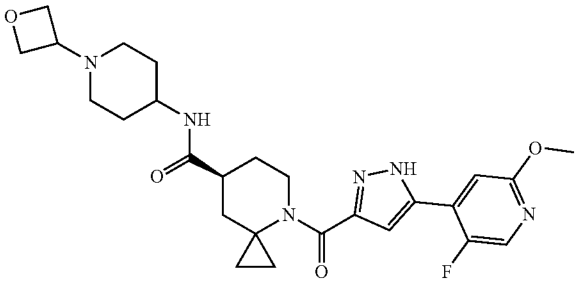 [SMILES: COc1cc(-c2cc(C(=O)N3CC[C@H](C(=O)NC4CCN(C5COC5)CC4)CC34CC4)n[nH]2)c(F)cn1]

The title compound was prepared using a procedure similar to the one described for the synthesis of Example 325, except 1-(oxetan-3-yl)piperidin-4-amine was used as a starting material. The residue was purified by reverse phase column chromatography (using the following conditions: Column: C18; mobile phase A: Water (0.5% $NH_4HCO_3$), mobile phase B: MeCN; gradient: 30 B to 50 B in 20 min; 220/254 nm) to obtain the title compound (39.8 mg) as a solid.

$^1$H NMR (300 MHz, $CD_3OD$) δ 8.14 (d, 1H), 7.29 (d, 1H), 7.18-6.99 (m, 1H), 4.82-4.63 (m, 3H), 4.63-4.41 (m, 3H), 3.94 (s, 3H), 3.77-3.57 (m, 1H), 3.56-3.40 (m, 1H), 3.32-2.97 (m, 1H), 2.89-2.62 (m, 3H), 2.60-2.27 (m, 1H), 2.19-1.67 (m, 5H), 1.64-1.40 (m, 2H), 1.39-1.13 (m, 1H), 1.08-0.81 (m, 2H), 0.79-0.59 (m, 2H). LCMS (ESI): 513.15 $[M+H]^+$.

Example 418. A Diastereomeric Mixture of (S)-4-(5(5-fluoro-2-methoxypyridin-4-yl)-1H-pyrazole-3-carbonyl)-N-((1r,4S)-4-morpholinocyclohexyl)-4-azaspiro[2.5]octane-7-carboxamide and (S)-4-(5-(5-fluoro-2-methoxypyridin-4-yl)-1H-pyrazole-3-carbonyl)-N-((1s,4R)-4-morpholinocyclohexyl)-4-azaspiro[2.5]octane-7-carboxamide

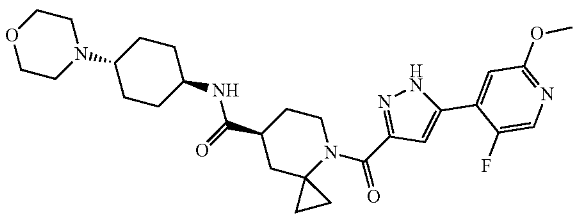

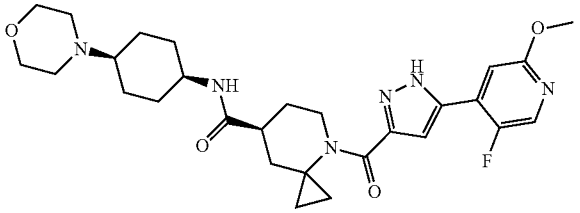

The title compound was prepared using a procedure similar to the one described for the synthesis of Example 325, except 4-(morpholin-4-yl)cyclohexan-1-amine was used as a starting material. The residue was purified by silica gel column chromatography eluting with petroleum ether/EtOAc (1/3 v/v) to obtain (S)-4-(5-(5-fluoro-2-methoxypyridin-4-yl)-1H-pyrazole-3-carbonyl)-N-((1r,4S)-4-morpholinocyclohexyl)-4-azaspiro[2.5]octane-7-carboxamide and (S)-4-(5-(5-fluoro-2-methoxypyridin-4-yl)-1H-pyrazole-3-carbonyl)-N-((1s,4R)-4-morpholinocyclohexyl)-4-azaspiro[2.5]octane-7-carboxamide in two fractions.

Example 418-A. The first eluting peak (25.5 mg) was obtained as a solid.

The first eluting peak had Rf value of 0.33.

$^1$H NMR (300 MHz, DMSO-$d_6$) δ 14.22-13.75 (m, 1H), 8.27 (s, 1H), 7.70 (s, 1H), 7.32 (d, 1H), 7.03 (s, 1H), 4.54-4.48 (m, 1H), 3.88 (s, 3H), 3.75-3.69 (m, 1H), 3.61-3.55 (m, 4H), 2.84-2.60 (m, 1H), 2.46-2.39 (m, 4H), 2.23-2.05 (m, 2H), 1.89-1.32 (m, 10H), 1.18-1.12 (m, 2H), 1.02-0.96 (m, 2H), 0.69-0.63 (m, 2H). LCMS (ESI): 541.2 $[M+H]^+$.

Example 418-B. The first eluting peak (24.9 mg) was obtained as a solid.

The first eluting peak had Rf value of 0.15.

$^1$H NMR (300 MHz, DMSO-$d_6$) δ 13.99 (s, 1H), 8.27 (d, 1H), 7.69 (d, 1H), 7.32 (d, 1H), 7.03 (s, 1H), 4.47-4.41 (m, 1H), 3.87 (s, 3H), 3.59-3.50 (m, 5H), 2.65-2.59 (m, 1H), 2.49-2.40 (m, 4H), 2.19-2.10 (m, 2H), 1.84-1.64 (m, 5H), 1.55-1.49 (m, 1H), 1.31-1.03 (m, 6H), 0.97-0.79 (m, 2H), 0.65-0.59 (m, 2H). LCMS (ESI): 541.30 $[M+H]^+$.

Example 419. A Diastereomeric Mixture of (S)-4-(5-(5-fluoro-2-methoxypyridin-4-yl)-1H-pyrazole-3-carbonyl)-N-((1R,5S,7r)-9-methyl-3-oxa-9-azabicyclo[3.3.1]nonan-7-yl)-4-azaspiro[2.5]octane-7-carboxamide and (S)-4-(5-(5-fluoro-2-methoxypyridin-4-yl)-1H-pyrazole-3-carbonyl)-N-((1R,5S,7s)-9-methyl-3-oxa-9-azabicyclo[3.3.1]nonan-7-yl)-4-azaspiro[2.5]octane-7-carboxamide

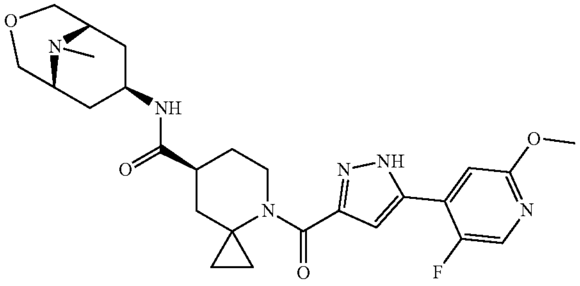

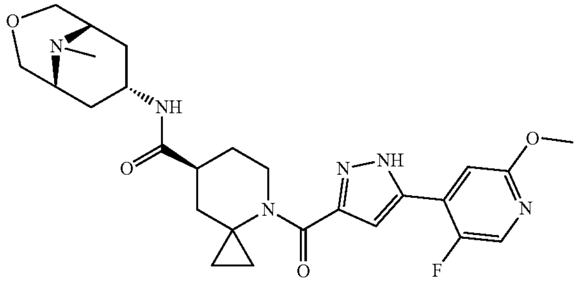

The title compound was prepared using a procedure similar to the one described for the synthesis of Example 325, except 9-methyl-3-oxa-9-azabicyclo[3.3.1]nonan-7-amine dihydrochloride was used as a starting material. The residue was purified by Prep-TLC (DCM/MeOH, 7/1 v/v) to obtain (S)-4-(5-(5-fluoro-2-methoxypyridin-4-yl)-1H-pyrazole-3-carbonyl)-N-((1R,5S,7r)-9-methyl-3-oxa-9-azabicyclo[3.3.1]nonan-7-yl)-4-azaspiro[2.5]octane-7-carboxamide and (S)-4-(5-(5-fluoro-2-methoxypyridin-4-yl)-1H-pyrazole-3-carbonyl)-N-((1R,5S,7s)-9-methyl-3-oxa-9-azabicyclo[3.3.1]nonan-7-yl)-4-azaspiro[2.5]octane-7-carboxamide in two fractions.

Example 419-A. The first eluting peak (22.6 mg) was obtained as a solid.

The first eluting peak had Rf value of 0.6.

$^1$H NMR (400 MHz, $CD_3OD$) δ 8.14 (d, 1H), 7.28 (s, 1H), 7.11 (s, 1H), 4.62-4.58 (m, 1H), 4.37-4.29 (m, 1H), 4.03-3.92 (m, 5H), 3.82-3.75 (m, 2H), 2.84-2.66 (m, 3H), 2.57-2.35 (m, 5H), 2.04-1.57 (m, 3H), 1.47-1.23 (m, 4H), 1.12-0.86 (m, 2H), 0.76-0.72 (m, 2H). LCMS (ESI): 513.25 $[M+H^+]$.

Example 419-B. The second eluting peak (23.8 mg) was obtained as a solid.

The second eluting peak had Rf value of 0.3.

$^1$H NMR (400 MHz, $CD_3OD$) δ 8.14 (d, 1H), 7.29 (s, 1H), 7.12 (s, 1H), 4.62-4.58 (m, 1H), 3.97-3.89 (m, 5H), 3.83-3.73 (m, 2H), 3.33-3.20 (m, 1H), 2.78-2.73 (m, 3H), 2.59-2.32 (m, 4H), 2.03-1.67 (m, 6H), 1.33-1.29 (m, 2H), 1.10-0.84 (m, 2H), 0.76-0.72 (m, 2H). LCMS (ESI): 513.30 $[M+H]^+$.

Example 420. (S)-4-(5-(5-fluoro-2-methoxypyridin-4-yl)-1H-pyrazole-3-carbonyl)-N-(1-(methylsulfonyl)piperidin-4-yl)-4-azaspiro[2.5]octane-7-carboxamide

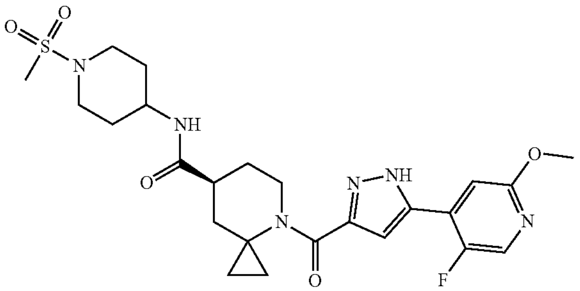 [SMILES: COc1cc(-c2cc(C(=O)N3CC[C@H](C(=O)NC4CCN(S(C)(=O)=O)CC4)CC34CC4)n[nH]2)c(F)cn1]

The title compound was prepared using a procedure similar to the one described for the synthesis of Example 325, except 1-(methylsulfonyl)piperidin-4-amine was used as a starting material. The residue was purified by reverse phase column chromatography (using the following conditions: Column: C18; mobile phase A: Water (0.5% $NH_4HCO_3$), mobile phase B: MeCN; gradient: 20 B to 40 B in 20 min; 220/254 nm) to obtain the title compound (106.2 mug) as a solid.

$^1$H NMR (300 MHz, DMSO-$d_6$) δ 14.21-13.68 (m, 1H), 8.28 (s, 1H), 7.87 (d, 1H), 7.33 (d, 1H), 7.04 (s, 1H), 4.73-4.29 (m, 1H), 3.88 (s, 3H), 3.72-3.66 (m, 1H), 3.65-3.42 (m, 2H), 2.89-2.76 (m, 6H), 2.73-2.61 (m, 1H), 2.24-2.07 (m, 1H), 1.94-1.67 (m, 3H), 1.61-1.30 (m, 3H), 1.31-1.08 (m, 1H), 1.08-0.77 (m, 2H), 0.72-0.55 (m, 2H). LCMS (ESI): 535.05 $[M+H]^+$.

Example 421. A Diastereomeric Mixture of (S)-4-(5-(5-fluoro-2-methoxypyridin-4-yl)-1H-pyrazole-3-carbonyl)-N—((S)-1-(oxetan-3-yl)piperidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(oxetan-3-yl)piperidin-3-yl)-4-azaspiro[2.5]octane-7-carboxamide

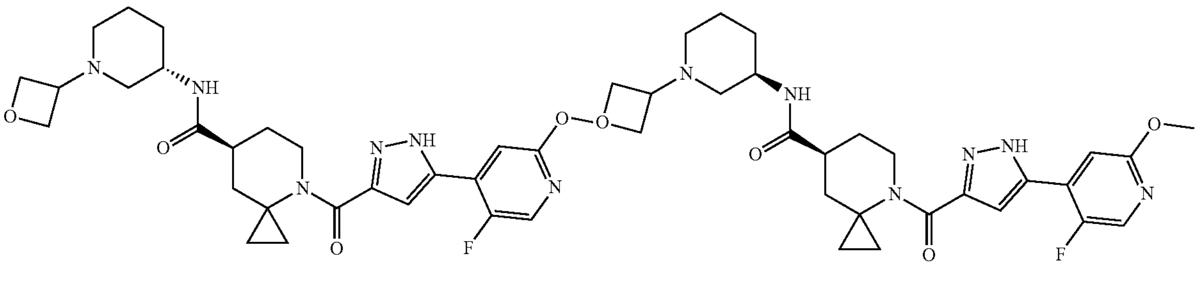

Step-1. tert-butyl 3-(dibenzylamino)piperidine-1-carboxylate

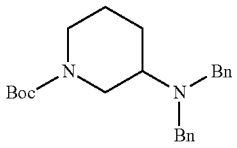 [SMILES: CC(C)(C)OC(=O)N1CCCC(N(Cc2ccccc2)Cc2ccccc2)C1]

$Cs_2CO_3$ (4.07 g, 12.48 mmol) and BnBr (2.13 g, 12.48 mmol) were added to a stirred solution of tert-butyl 3-aminopiperidine-1-carboxylate (1.00 g, 4.99 mmol) in MeCN (10.00 mL). The resulting mixture was stirred at 25° C. for 14 h. The solution was concentrated under reduced pressure. The residue was purified by silica gel column chromatography eluting with EtOAc/petroleum ether (1/10 v/v) to obtain the title compound (1.15 g) as an oil. LCMS (ESI): 381.3 $[M+H]^+$.

Step-2. N,N-dibenzylpiperidin-3-amine

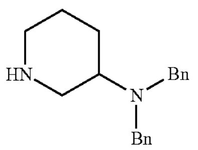 [SMILES: c1ccc(CN(Cc2ccccc2)C2CCCNC2)cc1]

TFA (5.00 mL) was added to a stirred solution of tert-butyl 3-(dibenzylamino)piperidine-1-carboxylate (Step-1, 1.15 g, 3.02 mmol) in DCM (5.00 mL) at 0° C. The resulting mixture was stirred at 25° C. for 14 h. The solution was concentrated under reduced pressure. The residue was purified by silica gel column chromatography eluting with DCM/MeOH (10/1 v/v) to obtain the title compound (840.0 mg) as a solid. LCMS (ESI): 281.2 $[M+H]^+$.

Step-3. N,N-dibenzyl-1-(oxetan-3-yl)piperidin-3-amine

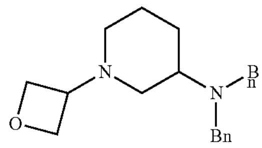 [SMILES: c1ccc(CN(Cc2ccccc2)C2CCCN(C3COC3)C2)cc1]

3-Oxetanone (1.05 g, 14.62 mmol) and AcOH (40.00 μL) was added to a stirred solution of N,N-dibenzylpiperidin-3-amine (Step-2, 820.0 mg, 2.92 mmol) in MeOH (5.00 mL). The resulting mixture was stirred at 80° C. for 1 h. Then $NaBH_3CN$ (551.3 mg, 8.77 mmol) was added to the resulting mixture. The resulting mixture was stirred at 80° C. for 5 h. The solution was concentrated under reduced pressure. The residue was purified by silica gel column chromatography eluting with EtOAc/petroleum ether (1/3 v/v) to obtain the title compound (663.0 mg) as an oil. LCMS (ESI): 337.2 $[M+H]^+$.

Step-4. 1-(oxetan-3-yl)piperidin-3-amine

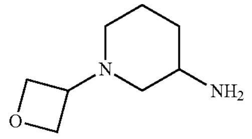 [SMILES: NC1CCCN(C2COC2)C1]

Pd/C (100.0 mg) was added to a stirred solution of N,N-dibenzyl-1-(oxetan-3-yl)piperidin-3-amine (Step-3, 300.0 mg, 0.89 mmol) in MeOH (3.00 mL). The resulting mixture was stirred at 25° C. for 14 h under the hydrogen atmosphere. The solids were filtered out. The organic layers were combined, dried over anhydrous $Na_2SO_4$, filtered, and concentrated under reduced pressure to obtain the title compound (139.0 mg) as an oil. LCMS (ESI): 157.1 $[M+H]^+$.

Step-5. (S)-4-(5-(5-fluoro-2-methoxypyridin-4-yl)-1H-pyrazole-3-carbonyl)-N—((S)-1-(oxetan-3-yl)piperidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(oxetan-3-yl)piperidin-3-yl)-4-azaspiro[2.5]octane-7-carboxamide

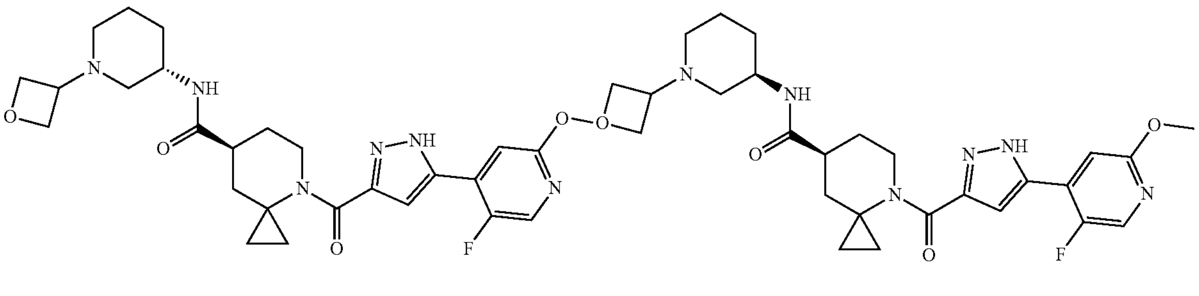

HOBt (167.4 mg, 1.24 mmol), EDCI (237.4 mg, 1.24 mmol), and 1-(oxetan-3-yl)piperidin-3-amine (Step-4, 129.0 mg, 0.83 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 309.1 mg, 0.83 mmol) and DIPEA (320.2 mg, 2.48 mmol) in DMF (3.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by reverse phase column chromatography (using the following conditions: C18; mobile phase A: Water (0.5% $NH_4HCO_3$), mobile phase B: MeCN; gradient: 20 B to 40 B in 20 min; 220/254 nm) to obtain (S)-4-(5-(5-fluoro-2-methoxypyridin-4-yl)-H-pyrazole-3-carbonyl)-N—(S)-1-(oxetan-3-yl)piperidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(oxetan-3-yl)piperidin-3-yl)-4-azaspiro[2.5]octane-7-carboxamide (160.0 mg) as a solid mixture of diastereomers (Example 421). $^1$H NMR (400 MHz, DMSO-$d_6$) δ 13.98 (s, 1H), 8.25 (s, 1H), 7.70 (d, 1H), 7.30 (d, 1H), 7.01 (s, 1H), 4.62-4.21 (m, 5H), 3.85 (s, 3H), 3.74-3.54 (m, 1H), 3.41-3.34 (m, 1H), 3.19-2.82 (m, 1H), 2.76-2.59 (m, 1H), 2.46-2.27 (m, 2H), 2.19-2.10 (m, 1H), 1.90-1.54 (m, 5H), 1.54-1.34 (m, 2H), 1.29-1.04 (m, 2H), 1.03-0.76 (m, 2H), 0.72-0.44 (m, 2H). LCMS (ESI): 513.30 $[M+H]^+$.

This mixture of two diastereomers (165.0 mg) was separated using Chiral Prep-HPLC.

Column: CHIRALPAK ID column

Column dimension: 2×25 cm, 5 μm

Mobile Phase: 1/1 hexanes/DCM (0.5% 2 M $NH_3$·MeOH):EtOH=70:30 hold for 8 min

Flow rate: 20 mL/min

Detection: 220/254 nm

Example 421-A. The first eluting diastereomer (66.5 mg) was obtained as a solid.

The first eluting diastereomer had a retention time of 5.54 min.

$^1$H NMR (400 MHz, DMSO-$d_6$) δ 13.96 (s, 1H), 8.25 (d, 1H), 7.70 (d, 1H), 7.30 (d, 1H), 7.01 (s, 1H), 4.65-4.16 (m, 6H), 3.85 (s, 3H), 3.74-3.54 (m, 1H), 3.49-3.32 (m, 1H), 3.13-2.80 (m, 1H), 2.74-2.51 (m, 3H), 2.27-1.99 (m, 1H), 1.89-1.55 (m, 5H), 1.53-1.34 (m, 2H), 1.28-1.06 (m, 2H), 1.05-0.76 (m, 1H), 0.72-0.39 (m, 2H). LCMS (ESI): 535.30 $[M+H]^+$.

Example 421-B. The second eluting diastereomer (54.2 mg) was obtained as a solid.

The second eluting diastereomer had a retention time of 6.78 min.

$^1$H NMR (400 MHz, DMSO-$d_6$) δ 13.95 (s, 1H), 8.25 (d, 1H), 7.70 (d, 1H), 7.30 (d, 1H), 7.01 (s, 1H), 4.96-4.16 (m, 6H), 3.85 (s, 3H), 3.73-3.56 (m, 1H), 3.42-3.32 (m, 1H), 3.14-2.71 (m, 1H), 2.45-2.37 (m, 3H), 2.27-2.05 (m, 1H), 1.90-1.58 (m, 5H), 1.58-1.35 (m, 2H), 1.29-1.05 (m, 2H), 1.00-0.80 (m, 1H), 0.67-0.50 (m, 2H). LCMS (ESI): 535.30 $[M+H]^+$.

Example 422. A Diastereomeric Mixture of (S)—N-((3R,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3S,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3R,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3S,4R)-4-fluoro-1-methylpiperidin-3-yl)-4-(5-(5-fluoro-2-methoxypyridin-4-yl)-1-pyrazole-3-carbonyl)-4-azaspiro[2.5]octane-7-carboxamide

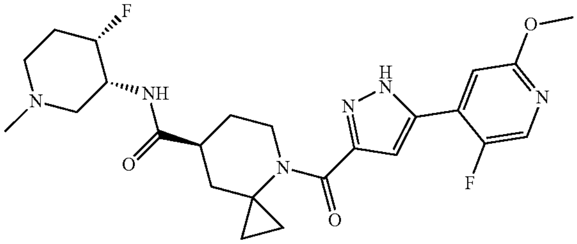

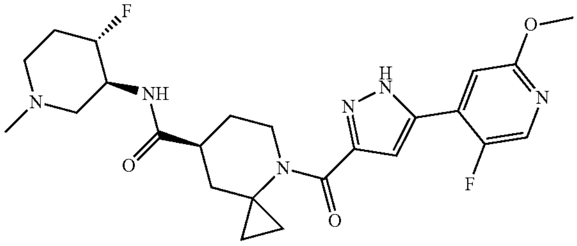

-continued

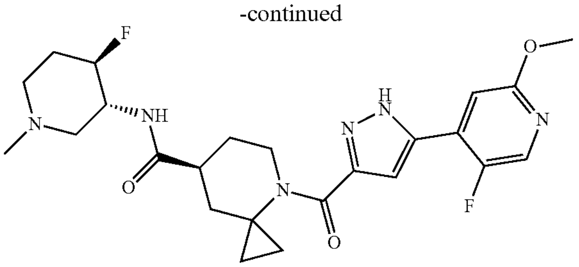

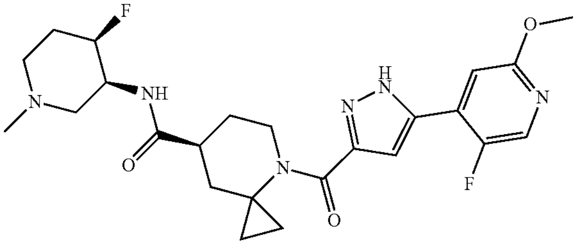

The title compound was prepared using a procedure similar to the one described for the synthesis of Example 325, except 4-fluoro-1-methylpiperidin-3-amine was used as a starting material. The residue was purified by silica gel column chromatography eluting with DCM/MeOH (10/1 v/V) to obtain (S)—N-((3R,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3S,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide and (_S)—N-((3R,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3S,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide (300.0 mg) as a solid mixture of diastereomers (Example 422). $^1$H NMR (400 MHz, DMSO-$d_6$) δ 14.00 (s, 1H), 8.27 (d, 1H), 7.97 (d, 1H), 7.33 (d, 1H), 7.03 (s, 1H), 4.81-4.19 (m, 2H), 3.88 (m, 4H), 2.92-2.54 (m, 3H), 2.25-1.93 (m, 6H), 1.93-1.62 (m, 4H), 1.58-1.10 (m, 2H), 1.05-0.78 (m, 2H), 0.64 (m, 2H). LCMS (ESI): 489.20 [M+H]$^+$.

This mixture of four diastereomers (300.0 mg) was separated using Chiral Prep-HPLC.

Column: CHIRALPAK ART Amylose-SA column

Column dimension: 2×25 cm, 5 μm

Mobile Phase: 1/1 hexanes/DCM (0.5% 2 M $NH_3$·MeOH):EtOH=95:5 hold for 17 min

Flow rate: 20 mL/min

Detection: 220/254 nm

Example 422-A and Example 422-B. The first eluting peak (145.0 mg) was Obtained as a Solid Mixture of Two Diastereomers.

The first eluting peak had a retention time of 7.91 min.

Example 422-C. The second eluting diastereomer (61.8 mg) was obtained as a solid.

The second eluting diastereomer had a retention time of 11.66 min.

$^1$H NMR (400 MHz, DMSO-$d_6$) δ 14.01 (s, 1H), 8.27 (d, 1H), 7.97 (d, 1H), 7.32 (d, 1H), 7.03 (s, 1H), 4.84-4.03 (m, 2H), 4.00-3.96 (m, 1H), 3.88 (s, 3H), 2.83-2.79 (m, 1H), 2.59-2.50 (m, 1H), 2.49-2.42 (m, 2H), 2.18 (s, 3H), 2.14-2.04 (m, 3H), 1.97-1.67 (m, 3H), 1.56-1.52 (m, 1H), 1.22-1.17 (m, 1H), 0.99-0.95 (m, 2H), 0.66-0.61 (m, 2H). LCMS (ESI): 489.20 [M+H]$^+$.

Example 422-D. The third eluting diastereomer (52.5 mg) was obtained as a solid.

The third eluting diastereomer had a retention time of 13.99 min.

$^1$H NMR (400 MHz, DMSO-$d_6$) δ 14.01 (s, 1H), 8.27 (s, 1H), 7.98 (d, 1H), 7.33 (d, 1H), 7.03 (s, 1H), 4.81-4.58 (m, 1H), 4.50-4.45 (m, 1H), 4.06-3.93 (m, 1H), 3.88 (s, 3H), 2.83-2.79 (m, 1H), 2.56-2.52 (m, 1H), 2.49-2.43 (m, 2H), 2.18 (s, 3H), 2.11-2.01 (m, 3H), 1.96-1.65 (m, 3H), 1.59-1.30 (m, 1H), 1.29-0.91 (m, 2H), 0.90-0.80 (m, 1H), 0.66-0.62 (m, 2H). LCMS (ESI): 489.15 [M+H]$^+$.

The first eluting peak (145.0 mg) containing two diastereomers of the title compounds was separated using Chiral Prep-HPLC.

Column: CHIRALPAK IE column

Column dimension: 2×25 cm, 5 μm

Mobile Phase: 3/1 hexanes/DCM (0.5% 2 M $NH_3$·MeOH):EtOH=50:50 hold for 28 min

Flow rate: 15 mL/min

Detection: 220/254 nm

Example 422-A. The first eluting diastereomer (48.5 mg) was obtained as a solid.

The first eluting diastereomer had a retention time of 18.31 min.

$^1$H NMR (400 MHz, DMSO-$d_6$) δ 13.98 (s, 1H), 8.27 (d, 1H), 7.94 (d, 1H), 7.32 (d, 1H), 7.05-7.00 (m, 1H), 4.57-4.23 (m, 2H), 3.95-3.80 (m, 4H), 3.20-2.82 (m, 1H), 2.78-2.54 (m, 4H), 2.16 (s, 3H), 2.11-1.95 (m, 2H), 1.91-1.82 (m, 1H), 1.80-1.62 (m, 2H), 1.56-1.51 (m, 1H), 1.23-1.18 (m, 1H), 0.96-0.91 (m, 2H), 0.66-0.61 (m, 2H). LCMS (ESI): 489.20 [M+H]$^+$.

Example 422-B. The second eluting diastereomer (46.3 mg) was obtained as a solid.

The second eluting diastereomer had a retention time of 23.35 min.

$^1$H NMR (400 MHz, DMSO-$d_6$) δ 13.98 (s, 1H), 8.31-8.21 (s, 1H), 7.94 (d, 1H), 7.32 (d, 1H), 7.03 (d, 1H), 4.54-4.24 (m, 2H), 3.95-3.78 (m, 4H), 2.90-3.22 (n 1H), 2.79-2.54 (m, 4H), 2.16 (s, 3H), 2.11-1.94 (m, 2H), 1.93-1.84 (m, 1H), 1.79-1.62 (m, 2H), 1.56-1.52 (m, 1H), 1.38-1.08 (m, 1H), 1.06-0.53 (m, 4H). LCMS (ESI): 489.15 [M+H]$^+$.

Example 423. A Diastereomeric Mixture of (S)—N-((3S,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3R,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3S,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3R,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide

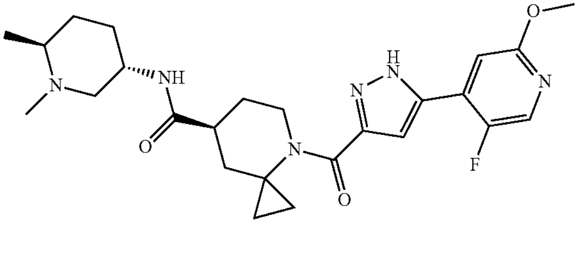

-continued

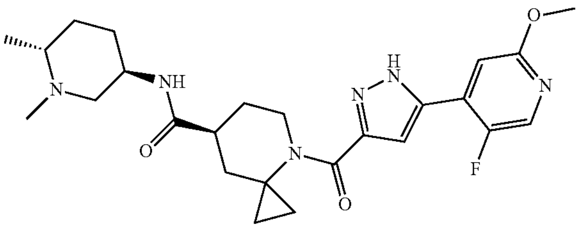

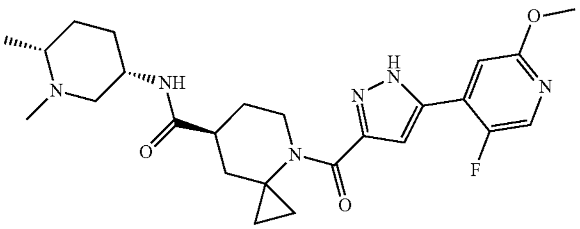

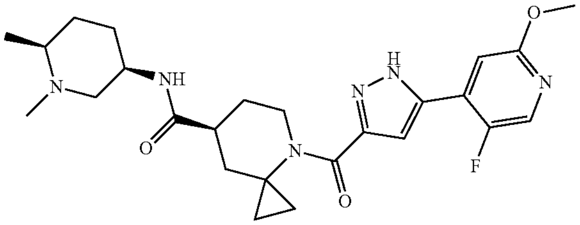

Step-1. tert-butyl N-(tert-butoxycarbonyl)-N-(6-methylpyridin-3-yl)carbamate

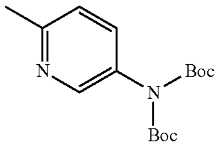 [SMILES: Cc1ccc(N(C(=O)OC(C)(C)C)C(=O)OC(C)(C)C)cn1]

$(Boc)_2O$ (16.14 g, 73.98 mmol), DMAP (225.9 mg, 1.85 mmol) and $NEt_3$ (5.61 g, 55.48 mmol) were added to a stirred solution of 6-methylpyridin-3-amine (2.00 g, 18.49 mmol) in THF (5.00 mL). The resulting mixture was stirred at 60° C. for 4 h. The resulting mixture was concentrated under reduced pressure. The residue was purified by silica gel column chromatography eluting with petroleum ether/EtOAc (1/1 v/v) to obtain the title compound (1.61 g) as a solid. LCMS (ESI): 309.2 $[M+H]^+$.

Step-2. tert-butyl N-(tert-butoxycarbonyl)-N-(6-methylpiperidin-3-yl)carbamate

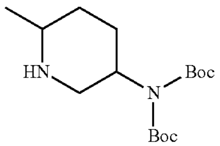 [SMILES: CC1CCC(N(C(=O)OC(C)(C)C)C(=O)OC(C)(C)C)CN1]

$PtO_2$ (1.00 g, 4.40 mmol) was added to a stirred solution of tert-butyl N-(tert-butoxycarbonyl)-N-(6-methylpyridin-3-yl)carbamate (Step-1, 1.00 g, 3.24 mmol) in AcOH (3.00 mL). The resulting mixture was stirred at 25° C. for 14 h under hydrogen atmosphere. The resulting mixture was concentrated under reduced pressure. The residue was purified by silica gel column chromatography eluting with DCM/MeOH (10/1 v/v) to obtain the title compound (500.0 mg) as an oil. LCMS (ESI): 315.2 $[M+H]^+$.

Step-3. tert-butyl N-(tert-butoxycarbonyl)-N-(1,6-dimethylpiperidin-3-yl)carbamate

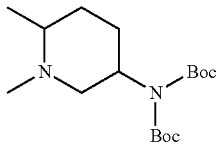 [SMILES: CC1CCC(N(C(=O)OC(C)(C)C)C(=O)OC(C)(C)C)CN1C]

Formaldehyde (387.3 mg, 4.78 mmol, 37% aqueous solution) was added to a stirred solution of tert-butyl N-(tert-butoxycarbonyl)-N-(6-methylpiperidin-3-yl)carbamate (Step-2, 500.0 mg, 1.59 mmol) in MeOH (5.00 mL) and AcOH (1.00 mL), then $NaBH_3CN$ (296.2 mg, 4.78 mmol) was added. The resulting solution was stirred at 25° C. for 14 h. The resulting mixture was concentrated under reduced pressure. The residue was purified by Prep-TLC (petroleum ether/EtOAc, 10/1 v/v) to obtain the title compound (500.0 mg) as a solid. LCMS (ESI): 329.2 $[M+H]^+$.

Step-4. 1,6-dimethylpiperidin-3-amine

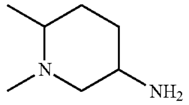

TFA (2.00 mL) was added to a stirred solution of tert-butyl N-(tert-butoxycarbonyl)-N-(1,6-dimethylpiperidin-3-yl)carbamate (Step-3, 500.0 mg, 1.52 mmol) in DCM (2.00 mL). The resulting mixture was stirred at 25° C. for 1 h. The resulting mixture was concentrated under reduced pressure. The resulting in 1,6-dimethylpiperidin-3-amine (180.0 mg) as a solid. LCMS (ESI): 129.1 $[M+H]^+$.

Step-5. (S)—N-((3S,6S)-1,6-dimethylpiperidine-3-yl)-4-(5-(5-fluoro-2-methoxypyridin-4-yl)-1H-pyrazole-3-carbonyl)-4-azaspiro[2.5]octane-7-carboxamide and (S)—N-((3R,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3S,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3R,6S)-1,6-dimethylpiperidin-3-yl)-4-(5-(5-fluoro-2-methoxypyridin-4-yl)-H-pyrazole-3-carbonyl)-4-azaspiro[2.5]octane-7-carboxamide

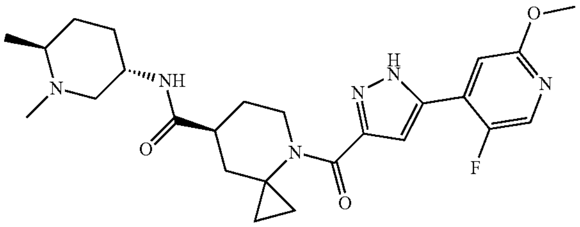

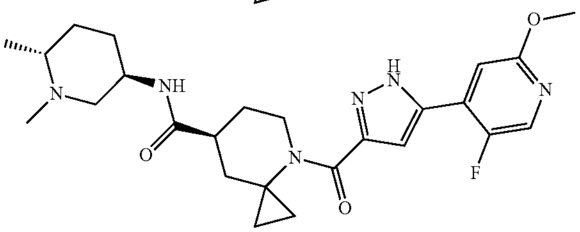

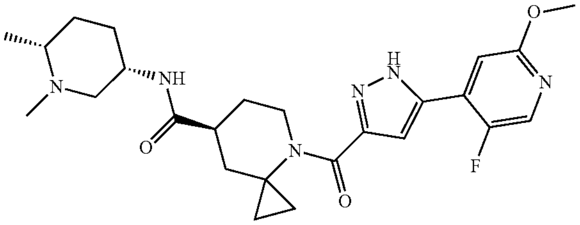

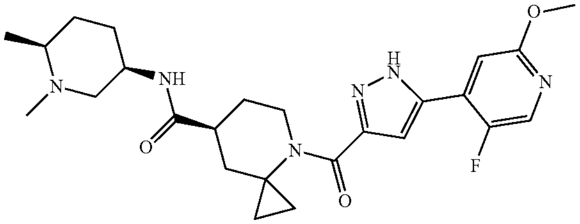

HOBt (94.9 mg, 0.70 mmol), EDCI (134.6 mg, 0.70 mmol) and 1,6-dimethylpiperidin-3-amine (Step-4, 60.0 mg, 0.47 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 175.2 mg, 0.47 mmol) and DIPEA (362.9 mg, 2.81 mmol) in DMF (3.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (8/1 v/v) to obtain (S)—N-((3S,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3R,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3S,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide and (S)—N-((3R,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide (132.0 mg) as a solid mixture of diastereomers. $^1$H NMR (400 MHz, DMSO-$d_6$) δ 13.98 (s, 1H), 8.27 (s, 1H), 7.77-7.55 (m, 1H), 7.41-7.21 (m, 1H), 7.03 (s, 1H), 4.72-4.13 (m, 1H), 3.88 (s, 3H), 3.74-3.53 (m, 1H), 2.96-2.71 (m, 3H), 2.71-2.57 (m, 2H), 2.25-2.05 (m, 3H), 1.87-1.66 (m, 3H), 1.64-1.43 (m, 2H), 1.35-1.07 (m, 4H), 1.06-0.90 (m, 4H), 0.89-0.43 (m, 2H). LCMS (ESI): 485.30 $[M+H]^+$.

This mixture of four diastereomers (130.0 mg) was separated using Chiral Prep-HPLC.

Column: CHIRALPAK IE column

Column dimension: 2×25 cm, 5 μm

Mobile Phase: 1/1 hexanes/DCM (0.5% 2 M $NH_3$·MeOH):IPA=70:30 hold for 18 min

Flow rate: 20 mL/min

Detection: 220/254 nm

Example 423-A. The first eluting diastereomer (50.0 mg) was obtained as a solid.

The first eluting diastereomer had a retention time of 11.21 min.

$^1$H NMR (400 MHz, DMSO-$d_6$) δ 13.98 (s, 1H), 8.27 (s, 1H), 7.78-7.58 (m, 1H), 7.40-7.27 (m, 1), 7.03 (s, 1H), 4.83-4.01 (m, 1H), 3.88 (s, 3H), 3.72-3.56 (m, 1H), 3.48-3.20 (m, 3H), 2.87-2.58 (m, 3H), 2.10 (s, 3H), 1.85-1.42 (m, 6H), 1.30-1.07 (m, 3H), 1.01 (s, 3H), 0.70-0.53 (m, 2H). LCMS (ESI): 485.25 $[M+H]^+$.

Example 423-B. The second eluting diastereomer (1.0 mg) was obtained as a solid.

The second eluting diastereomer had a retention time of 12.99 min.

LCMS (ESI): 485.20 $[M+H]^+$.

Example 423-C. The third eluting diastereomer (50.0 mg) was obtained as a solid.

The third eluting diastereomer had a retention time of 14.86 min.

$^1$H NMR (400 MHz, DMSO-$d_6$) δ 13.97 (s, 1H), 8.41-8.09 (m, 1H), 7.89-7.52 (m, 1H), 7.48-7.21 (m, 1), 7.14-6.84 (m, 1H), 4.72-4.18 (m, 1H), 3.88 (s, 3H), 3.73-3.54 (m, 1H), 3.53-3.19 (m, 3H), 2.85-2.64 (m, 3H), 2.10 (s, 3H), 1.88-1.41 (m, 6H), 129-1.08 (m, 3H), 1.01-0.91 (s, 3H), 0.73-0.53 (m, 2H). LCMS (ESI): 485.20 $[M+H]^+$.

Example 424. A Diastereomeric Mixture of (S)-4-(5-(5-fluoro-2-methoxypyridin-4-yl)-1H-pyrazole-3-carbonyl)-N—((R)-1,6,6-trimethylpiperidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide

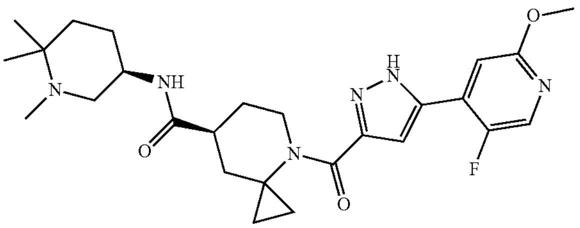

-continued

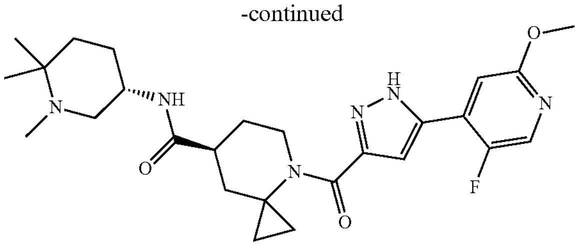

Step-1. tert-butyl 5-(dibenzylamino)-2,2-dimethylpiperidine-1-carboxylate

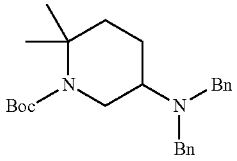 [SMILES: CC(C)(C)OC(=O)N1CC(N(Cc2ccccc2)Cc2ccccc2)CCC1(C)C]

$K_2CO_3$ (453.9 mg, 3.28 mmol) and benzyl bromide (562.5 mg, 3.29 mmol) were added to a stirred mixture of tert-butyl 5-amino-2,2-dimethylpiperidine-1-carboxylate (250.0 mg, 1.10 mmol) in MeCN (4.00 mL). The resulting mixture was stirred at 80° C. for 3 h. The resulting mixture was concentrated under reduced pressure. The residue was purified by Prep-TLC (petroleum ether/EtOAc, 8/1 v/v) to obtain the title compound (130.0 mg) as an oil. LCMS (ESI): 409.28 $[M+H]^+$.

Step-2. N,N-dibenzyl-6,6-dimethylpiperidin-3-amine

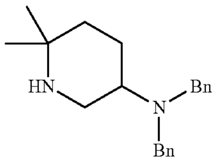 [SMILES: CC1(C)CCC(N(Cc2ccccc2)Cc2ccccc2)CN1]

TFA (1.50 mL) was added to a stirred mixture of tert-butyl 5-(dibenzylamino)-2,2-dimethylpiperidine-1-carboxylate (Step-1, 130.0 mg, 0.32 mmol) in DCM (1.50 mL) at 0° C. The resulting mixture was stirred at 25° C. for 1 h. The resulting mixture was concentrated under reduced pressure to obtain the title compound (98.0 mg) as a solid. This was used in the next step directly without further purification. LCMS (ESI): 309.23 $[M+H]^+$.

Step-3. N,N-dibenzyl-1,6,6-trimethylpiperidin-3-amine

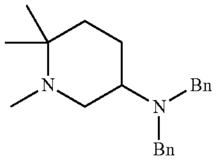 [SMILES: CN1CC(N(Cc2ccccc2)Cc2ccccc2)CCC1(C)C]

$NaBH_3CN$ (60.0 mg, 0.96 mmol) and formaldehyde (77.4 mg, 0.95 mmol, 37% aqueous solution) were added to a stirred mixture of N,N-dibenzyl-6,6-dimethylpiperidin-3-amine (Step-2, 98.2 mg, 0.32 mmol) in MeOH (2.00 mL) and AcOH (0.20 mL). The resulting mixture was stirred at 25° C. for 14 h. The resulting mixture was concentrated under reduced pressure. The residue was purified by Prep-TLC (DCM/MeOH, 18/1 v/v) to obtain the title compound (50.0 mg) as a solid. LCMS (ESI): 323.24 $[M+H]^+$.

Step-4. 1,6,6-trimethylpiperidin-3-amine

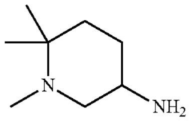

Pd/C (25.0 mg) was added to a stirred solution of N,N-dibenzyl-1,6,6-trimethylpiperidin-3-amine (Step-3, 50.0 mg, 0.16 mmol) in MeOH (3.00 mL) at 0° C. The resulting mixture was stirred at 25° C. for 14 h under hydrogen atmosphere. The resulting mixture was filtered, the filter cake was washed with MeOH. The filtrate was concentrated under reduced pressure to obtain the title compound (15.4 mg) as a solid. This was used in the next step directly without further purification. LCMS (ESI): 143.15 $[M+H]^+$.

Step-5. (S)-4-(5-(5-fluoro-2-methoxypyridin-4-yl)-1H-pyrazole-3-carbonyl)-N—((R)-1,6,6-trimethylpiperidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide

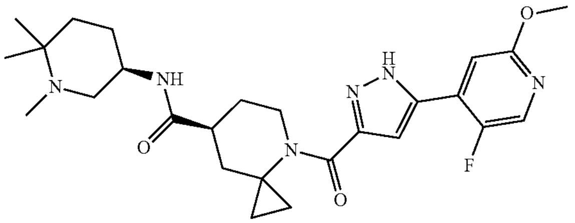

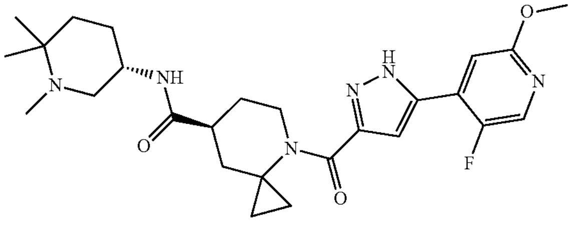

HOBt (29.3 mg, 0.22 mmol), EDCI (41.4 mg, 0.22 mmol) 1,6,6-trimethylpiperidin-3-amine (Step-4, 15.4 mg, 0.11 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 28.4 mg, 0.08 mmol) and DIPEA (70.0 mg, 0.54 mmol) in DMF (1.00 mL). The resulting solution was stirred at 25° C. for 4 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 18/1 v/v) to obtain (S)-4-(5-(5-fluoro-2-methoxypyridin-4-yl)-1H-pyrazole-3-carbonyl)-N—((R)-1,6,6-trimethylpiperidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide (30.0 mg) as a solid mixture of diastereomers (Example 424). $^1H$ NMR (400 MHz, $CD_3OD$) δ 8.13 (d, 1H), 7.31-7.25 (m, 1H), 7.14-7.08 (m, 1H), 4.59-4.55 (m, 1H), 3.95 (s, 3H), 3.93-3.89 (m, 1H), 2.92-2.71 (m, 2H), 2.48-2.35 (m, 2H), 2.30 (s, 3H), 1.93-1.71 (m, 3H), 1.68-1.48 (m, 3H), 1.36-1.26 (m, 2H), 1.17 (s, 3H), 1.12-1.05 (m, 4H), 1.00-0.85 (m, 1H), 0.80-0.59 (m, 2H). LCMS (ESI): 499.40 $[M+H]^+$.

This mixture of two diastereomers (30.0 mg) was separated using Chiral Prep-HPLC.

Column: CHIRALPAK IG column

Column dimension: 2×25 cm, 5 μm

Mobile Phase: 1/1 hexanes/DCM (0.5% 2 M $NH_3$·MeOH):EtOH=93:7 hold for 29 min

Flow rate: 20 mL/min

Detection: 220/254 nm

Example 424-A. The first eluting diastereomer (6.0 mg) was obtained as a solid.

The first eluting diastereomer had a retention time of 20.02 min.

$^1H$ NMR (400 MHz, $CD_3OD$) δ 8.14 (d, 1H), 7.29 (d, 1H), 7.11 (d, 1H), 4.69-4.39 (m, 1H), 3.99-3.90 (m, 4H), 2.99-2.73 (m, 2H), 2.56-2.45 (m, 1H), 2.38 (s, 3H), 1.94-1.72 (m, 2H), 1.73-1.52 (m, 3H), 1.36-1.27 (m, 4H), 1.20 (s, 3H), 1.14 (s, 3H), 1.03-0.83 (m, 2H), 0.81-0.65 (m, 2H). LCMS (ESI): 499.40 $[M+H]^+$.

Example 424-B. The second eluting diastereomer (4.0 mg) was obtained as a solid.

The second eluting diastereomer had a retention time of 24.77 min.

$^1H$ NMR (400 MHz, $CD_3OD$) δ 8.14 (d, 1H), 7.29 (d, 1H), 7.11 (d, 1H), 4.60-4.55 (m, 1H), 3.95 (s, 3H), 3.95-3.89 (m, 1H), 2.95-2.69 (m, 2H), 2.53-2.43 (m, 1H), 2.35 (s, 3H), 1.87-1.73 (m, 2H), 1.71-1.53 (m, 3H), 1.38-1.26 (m, 4H), 1.20 (s, 3H), 1.11 (s, 3H), 1.05-0.84 (m, 2H), 0.81-0.64 (m, 21). LCMS (ESI): 499.40 $[M+H]^+$.

Example 425. A Diastereomeric Mixture of (S)-4-(5-(5-fluoro-2-methoxypyridin-4-yl)-1H-pyrazole-3-carbonyl)-N—((S)-1-(2-fluoroethyl)-2,2-dimethylpiperidin-4-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-fluoroethyl)-2,2-dimethylpiperidin-4-yl)-4-azaspiro[2.5]octane-7-carboxamide

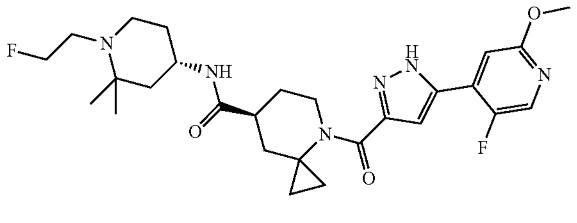

-continued

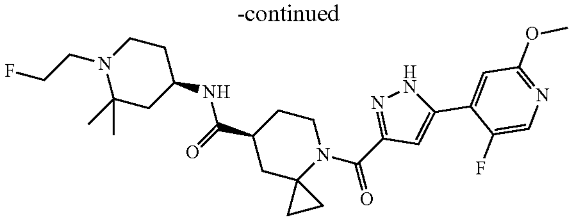

Step-1. tert-butyl 4-(dibenzylamino)-2,2-dimethylpiperidine-1-carboxylate

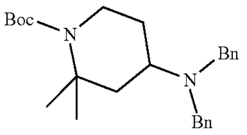 [SMILES: CC(C)(C)OC(=O)N1CCC(N(Cc2ccccc2)Cc2ccccc2)CC1(C)C]

BnBr (936.3 mg, 5.47 mmol) and $K_2CO_3$ (605.3 mg, 4.38 mmol) were added to a stirred mixture of tert-butyl 4-amino-2,2-dimethylpiperidine-1-carboxylate (500.0 mg, 2.19 mmol) in MeCN (6.00 mL). The resulting mixture was stirred at 25° C. for 14 h. The resulting mixture was concentrated under reduced pressure. The residue was purified by silica gel column chromatography eluting with petroleum ether/EtOAc (3/1 v/v) to obtain the title compound (790.0 mg) as an oil. LCMS (ESI): 409.3 $[M+H]^+$.

Step-2. N,N-dibenzyl-2,2-dimethylpiperidin-4-amine

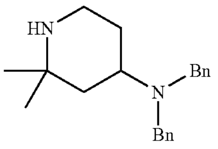 [SMILES: CC1(C)CC(N(Cc2ccccc2)Cc2ccccc2)CCN1]

TFA (5.00 mL) was added to a stirred mixture of tert-butyl 4-(dibenzylamino)-2,2-dimethylpiperidine-1-carboxylate (Step-1, 730.0 mg, 1.79 mmol) in DCM (5.00 mL). The resulting mixture was stirred at 25° C. for 1 h. The resulting mixture was concentrated under reduced pressure. The residue was purified by Prep-TLC (EtOAc) to obtain the title compound (500.0 mg) as a solid. LCMS (ESI): 309.2 $[M+H]^+$.

Step-3. N,N-dibenzyl-1-(2-fluoroethyl)-2,2-dimethylpiperidin-4-amine

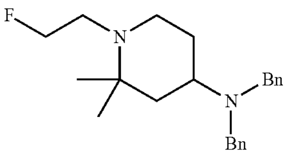 [SMILES: CC1(C)CC(N(Cc2ccccc2)Cc2ccccc2)CCN1CCF]

$Cs_2CO_3$ (316.9 mg, 0.97 mmol) and 1-bromo-2-fluoroethane (246.9 mg, 1.95 mmol) were added to a stirred mixture N,N-dibenzyl-2,2-dimethylpiperidin-4-amine (200.0 mg, 0.65 mmol) in MeCN (4.00 mL). The resulting mixture was stirred at 80° C. for 14 h. The resulting mixture was concentrated under reduced pressure. The residue was purified by silica gel column chromatography eluting with DCM/MeOH (10/1 v/v) to obtain the title compound (100.0 mg) as a solid. LCMS (ESI): 355.3 $[M+H]^+$.

Step-4. 1-(2-fluoroethyl)-2,2-dimethylpiperidin-4-amine

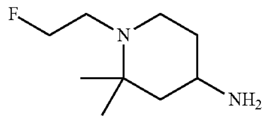

Pd/C (22.0 mg) was added to a stirred solution of N,N-dibenzyl-1-(2-fluoroethyl)-2,2-dimethylpiperidin-4-amine (110.0 mg, 0.31 mmol) in MeOH (3.00 mL) at 0° C. The resulting mixture was stirred at 25° C. for 14 h under hydrogen atmosphere. The solids were filtered out by filtration and washed with MeOH. The resulting filtrate was concentrated under reduced pressure to obtain the title compound (50.0 mg) as a solid. LCMS(ESI): 175.1 $[M+H]^+$.

Step-5. (S)-4-(5-(5-fluoro-2-methoxypyridin-4-yl)-1H-pyrazole-3-carbonyl)-N—((S)-1-(2-fluoroethyl)-2,2-dimethylpiperidin-4-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-fluoroethyl)-2,2-dimethylpiperidin-4-yl)-4-azaspiro[2.5]octane-7-carboxamide

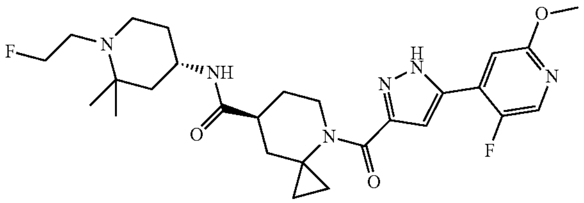

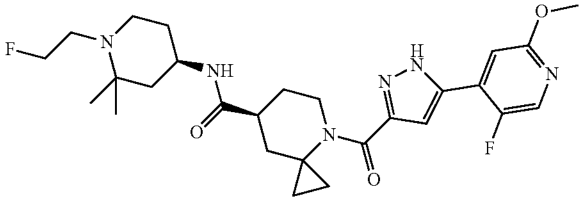

EDCI (109.3 mg, 0.57 mmol), HOBt (77.2 mg, 0.57 mmol) and 1-(2-fluoroethyl)-2,2-dimethylpiperidin-4-amine (Step-4, 50.0 mg, 0.29 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 107.0 mg, 0.29 mmol) and DIPEA (368.9 mg, 2.86 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-HPLC (using the following conditions: Column: XBridge Prep OBD C18 Column, 30×150 mm, 5 μm; Mobile Phase A: MeCN, Mobile Phase B: Water (10 mM $NH_4HCO_3$); Flow rate: 60 mL/min; Gradient: 30% B to 60% B in 15 min, 60% B; Wave Length: 254/220 nm; RT1 (min): 14.00) to obtain (S)-4-(5-(5-fluoro-2-methoxypyridin-4-yl)-1H-pyrazole-3-carbonyl)-N—(S)-1-(2-fluoroethyl)-2,2-dimethylpiperidin-4-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-fluoroethyl)-2,2-dimethylpiperidin-4-yl)-4-azaspiro[2.5]octane-7-carboxamide (80.0 mg) as a solid mixture of diastereomers (Example 425). H NMR (400 MHz, $CD_3OD$) δ 8.14 (d, 1H), 7.44-7.09 (m, 2H), 4.58-4.29 (m, 3H), 3.97-3.86 (m, 4H), 3.24-3.02 (m, 1H), 2.94-2.71 (m, 2H), 2.62-2.20 (m, 3H), 1.89-1.59 (m, 5H), 1.52-1.36 (m, 2H), 1.31-1.23 (m, 2H), 1.18-1.00 (m, 7H), 0.76-0.71 (m, 2H). LCMS (ESI): 531.40 $[M+H]^+$.

This mixture of two diastereomers (80.0 mg) was separated using Chiral Prep-HPLC.

Column: CHIRAL ART Cellulose-SC column

Column dimension: 2×25 cm, 5 μm

Mobile Phase: 3/1 hexanes/DCM (0.5% 2 M $NH_3$·MeOH):EtOH=70:30 hold for 16 min

Flow rate: 20 mL/min

Detection: 220/254 nm

Example 425-A. The first eluting diastereomer (34.0 mg) was obtained as a solid.

The first eluting diastereomer had a retention time of 11.48 min.

$^1$H NMR (400 MHz, $CD_3OD$) δ 8.13 (d, 1H), 7.29 (s, 1H), 7.11 (d, 1H), 4.67-4.31 (m, 3H), 4.03-3.82 (m, 4H), 3.24-3.00 (m, 1H), 2.97-2.85 (m, 1H), 2.84-2.69 (m, 1H), 2.67-2.48 (m, 1H), 2.43-2.20 (m, 2H), 1.94-1.75 (m, 3H), 1.74-1.58 (m, 1H), 1.57-1.36 (m, 2H), 1.35-1.21 (m, 2H), 1.19-1.02 (m, 7H), 1.01-0.84 (m, 1H), 0.80-0.63 (m, 2H). LCMS (ESI): 531.20 $[M+H]^+$.

Example 425-B. The second eluting diastereomer (36.0 mg) was obtained as a solid.

The second eluting diastereomer had a retention time of 11.48 min.

$^1$H NMR (400 MHz, $CD_3OD$) δ 8.13 (d, 1H), 7.38-7.19 (m, 1H), 7.11 (d, 1H), 4.72-4.24 (m, 3H), 4.01-3.81 (m, 4H), 3.25-2.97 (m, 1H), 2.96-2.84 (m, 1H), 2.84-2.70 (m, 1H), 2.63-2.48 (m, 1H), 2.47-2.20 (m, 2H), 1.97-1.71 (m, 3H), 1.71-1.58 (m, 1H), 1.56-1.35 (m, 2H), 1.34-1.20 (m, 2H), 1.19-1.02 (m, 7H), 1.01-0.82 (m, 1H), 0.79-0.61 (m, 2H). LCMS (ESI): 531.25 $[M+H]^+$.

Example 426. (S)—N-((3R,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

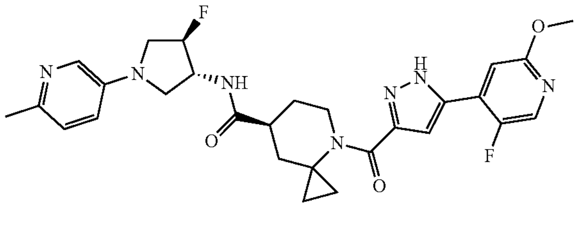

Step-1. tert-butyl (3R,4R)-3-(dibenzylamino)-4-fluoropyrrolidine-1-carboxylate

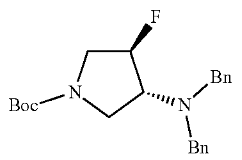 [SMILES: CC(C)(C)OC(=O)N1C[C@@H](F)[C@H](N(Cc2ccccc2)Cc2ccccc2)C1]

BnBr (419.0 mg, 2.45 mmol) and $K_2CO_3$ (406.0 mg, 2.94 mmol) were added to a stirred mixture of tert-butyl (3R,4R)-3-amino-4-fluoropyrrolidine-1-carboxylate (200.0 mg, 0.98 mmol) in MeCN (5.00 mL). The resulting mixture was stirred at 60° C. for 14 h. The resulting mixture was concentrated under reduced pressure. The residue was purified by silica gel column chromatography eluting with petroleum ether/EtOAc (7/1 v/v) to obtain the title compound (310.0 mg) as a solid. LCMS (ESI): 385 $[M+H]^+$.

Step-2. (3R,4R)—N,N-dibenzyl-4-fluoropyrrolidin-3-amine

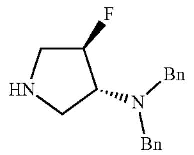 [SMILES: F[C@@H]1CNC[C@H]1N(Cc1ccccc1)Cc1ccccc1]

TFA (3.00 mL) were added to a stirred mixture of tert-butyl (3R,4R)-3-(dibenzylamino)-4-fluoropyrrolidine-1-carboxylate (Step-1, 310.0 mg, 0.81 mmol) in DCM (3.00 mL) at 0° C. The resulting mixture was stirred at 25° C. for 2 h. The resulting mixture was concentrated under reduced pressure. The residue was purified by silica gel column chromatography eluting with petroleum ether/EtOAc (1/1 v/v) to obtain the title compound (220.0 mg) as a solid. LCMS (ESI): 285 $[M+H]^+$.

Step-3. (3R,4R)—N,N-dibenzyl-4-fluoro-1-(6-methylpyridin-3-yl)pyrrolidin-3-amine

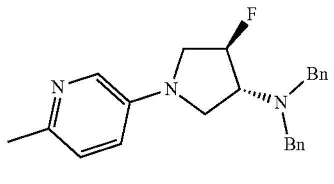 [SMILES: Cc1ccc(N2C[C@@H](F)[C@H](N(Cc3ccccc3)Cc3ccccc3)C2)cn1]

[1,3-Bis[2,6-bis(propan-2-yl)phenyl]-2,3-dihydro-1H-imidazol-2-yl]dichloro(3-chloropyridin-1-ium-1-yl)palladium (48.0 mg, 0.07 mmol) and $Cs_2CO_3$ (458.0 mg, 1.41 mmol) were added to a stirred mixture of (3R,4R)—N,N-dibenzyl-4-fluoropyrrolidin-3-amine (Step-2, 200.0 mg, 0.70 mmol) and 5-bromo-2-methylpyridine (121.0 mg, 0.70 mmol) in 1,4-dioxane (5.00 mL). The resulting mixture was stirred at 90° C. for 14 h under nitrogen atmosphere. The resulting mixture was concentrated under reduced pressure. The residue was purified by silica gel column chromatography eluting with petroleum ether/EtOAc (5/1 v/v) to obtain the title compound (230.0 mg) as a solid. LCMS (ESI): 376 $[M+H]^+$.

Step-4. (3R,4R)-4-fluoro-1-(6-methylpyridin-3-yl)pyrrolidin-3-amine

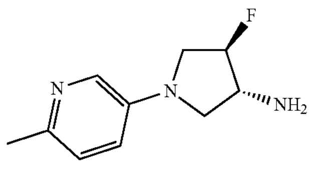

Pd/C (20.0 mg) was added to a stirred mixture of (3R,4R)—N,N-dibenzyl-4-fluoro-1-(6-methylpyridin-3-yl)pyrrolidin-3-amine (Step-3, 100.0 mg, 0.27 mmol) in MeOH (2.00 mL). The resulting mixture was stirred at 25° C. for 14 h under hydrogen atmosphere. The solids were filtered out by filtration and washed with MeOH. The filtrate was concentrated under reduced pressure to obtain the title compound (45.0 mg) as a solid. LCMS (ESI): 196 $[M+H]^+$.

Step-5. (S)—N-((3R,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

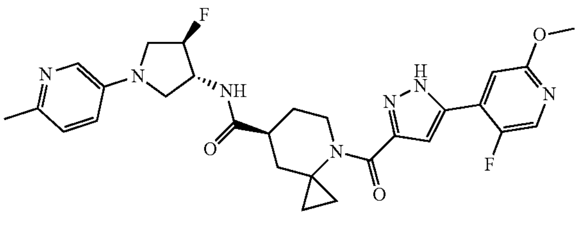

EDCI (59.0 mg, 0.31 mmol), HOBt (42.0 mg, 0.31 mmol) and (3R,4R)-4-fluoro-1-(6-methylpyridin-3-yl)pyrrolidin-3-amine (Step-4, 40.0 mg, 0.21 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 77.0 mg, 0.21 mmol) and DIPEA (132.0 mg, 1.02 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (46.9 mg) as a solid. $^1H$ NMR (300 MHz, DMSO-$d_6$) δ 14.12-13.86 (m, 1H), 8.31-8.19 (m, 2H), 7.86 (d, 1H), 7.33 (d, 1H), 7.11-6.98 (m, 2H), 6.97-6.87 (m, 1H), 5.26-4.97 (m, 1H), 4.62-4.35 (m, 2H), 3.88 (s, 3H), 3.70-3.58 (m, 2H), 3.58-3.40 (m, 2H), 3.26-3.16 (m, 1H), 2.71-2.65 (m, 1H), 2.35 (s, 3H), 2.20-2.14 (m, 1H), 1.79-1.73 (m, 1H), 1.58-1.52 (m, 1H), 1.23-1.17 (m, 1H), 1.05-0.45 (m, 4H). LCMS (ESI): 552.25 $[M+H]^+$.

Example 427. (S)—N-((3S,4S)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

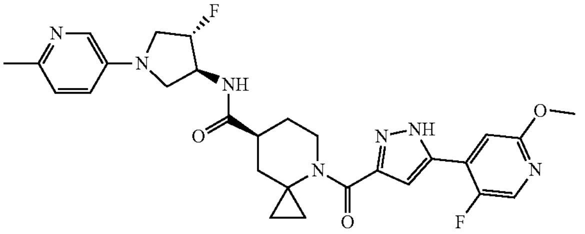

The title compound was prepared using a procedure similar to the one described for the synthesis of Example 426, except tert-butyl (3S,4S)-3-amino-4-fluoropyrrolidine-1-carboxylate was used as a starting material in Step-1. The resulting residue was purified by reverse phase column chromatography (using the following conditions: Column: C18; mobile phase A: Water (0.5% $NH_4HCO_3$), mobile phase B: MeCN; gradient: 20 B to 50 B in 30 min; 220/254 nm) to obtain the title compound (52.0 mg) as a solid. $^1H$ NMR (400 MHz, DMSO-$d_6$) δ 14.11-13.55 (m, 1H), 8.36-8.10 (m, 2H), 7.94-7.78 (m, 1H), 7.44-7.25 (m, 1H), 7.13-6.99 (m, 2H), 6.96-6.83 (m, 1H), 5.22-4.94 (m, 1H), 4.60-4.23 (m, 2H), 3.88 (s, 3H), 3.86-3.59 (m, 2H), 3.59-3.40 (m, 2H), 3.26-3.15 (m, 1H), 2.35 (s, 3H), 2.26-1.96 (m, 1H), 1.90-1.64 (m, 1H), 1.64-1.38 (m, 1H), 1.36-1.09 (m, 1H), 1.07-0.74 (m, 2H), 0.71-0.47 (m, 3H). LCMS (ESI): 552.25 $[M+H]^+$.

Example 428. (S)—N-((3S,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

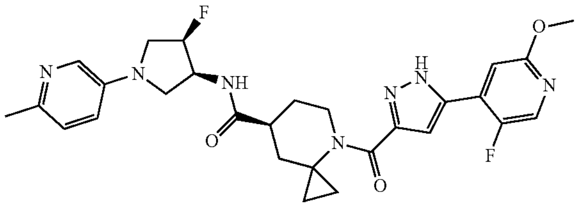

The title compound was prepared using a procedure similar to the one described for the synthesis of Example 426, except tert-butyl (3S,4R)-3-amino-4-fluoropyrrolidine-1-carboxylate was used as a starting material in Step-1. The resulting residue was purified by reverse phase column chromatography (using the following conditions: Column: C18; mobile phase A: Water (0.5% $NH_4HCO_3$), mobile phase B: MeCN; gradient: 20 B to 50 B in 30 min; 220/254 nm) to obtain the title compound (52.2 mg) as a solid. $^1H$ NMR (400 MHz, DMSO-$d_6$) δ 13.93 (s, 1H), 8.36-8.24 (m, 2H), 7.81 (d, 1H), 7.33 (d, 1H), 7.11-7.01 (m, 2H), 6.89-6.81 (m, 1H), 5.41-5.07 (m, 1H), 4.74-4.30 (m, 2H), 3.88 (s, 3H), 3.75-3.44 (m, 3H), 3.24-3.04 (m, 2H), 2.98-2.74 (m, 1H), 2.40-1.99 (m, 4H), 1.90-1.70 (m, 1H), 1.66-1.44 (m, 1H), 1.37-1.14 (m, 1H), 1.09-0.78 (m, 2H), 0.75-0.54 (m, 2H). LCMS (ESI): 552.25 $[M+H]^+$.

Example 429. (7S)-4-(5-(5-fluoro-2-methoxypyridin-4-yl)-1H-pyrazole-3-carbonyl)-N-(3-(oxetan-3-yl)-3-azabicyclo[3.1.0]hexan-6-yl)-4-azaspiro[2.5]octane-7-carboxamide

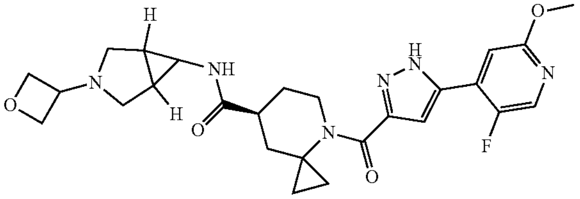 [SMILES: COc1cc(-c2cc(C(=O)N3CC[C@H](C(=O)NC4C5CN(C6COC6)CC54)CC34CC4)n[nH]2)c(F)cn1]

Step-1. tert-butyl 6-[(7S)-4-[5-(5-fluoro-2-methoxypyridin-4-yl)-1H-pyrazole-3-carbonyl]-4-azaspiro[2.5]octane-7-amido]-3-azabicyclo[3.1.0]hexane-3-carboxylate

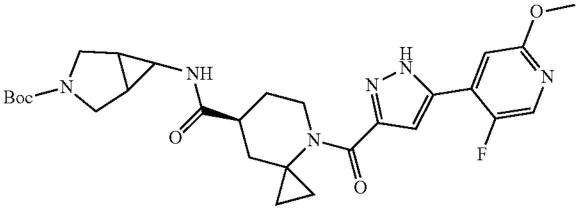 [SMILES: COc1cc(-c2cc(C(=O)N3CC[C@H](C(=O)NC4C5CN(C(=O)OC(C)(C)C)CC54)CC34CC4)n[nH]2)c(F)cn1]

HOBt (144.0 mg, 1.07 mmol), EDCI (204.0 mg, 1.07 mmol), and tert-butyl 6-amino-3-azabicyclo[3.1.0]hexane-3-carboxylate (116.0 mg, 0.54 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 200.0 mg, 0.54 mmol) and DIPEA (344.0 mg, 2.68 mmol) in DMF (5.00 mL). The resulting mixture was stirred at 25° C. for 2 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with EtOAc to obtain the title compound (200.7 mg) as an oil. LCMS (ESI): 555.2 $[M+H]^+$.

Step-2. (7S)—N-(3-azabicyclo[3.10]hexan-6-yl)-4-(5-(5-fluoro-2-methoxypyridin-4-yl)-1H-pyrazole-3-carbonyl)-4-azaspiro[2.5]octane-7-carboxamide

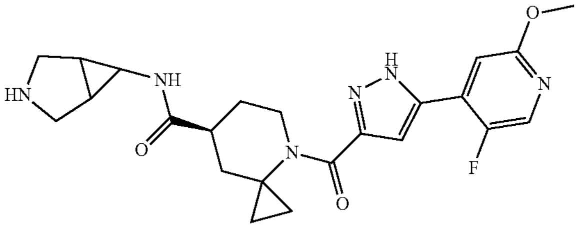 [SMILES: COc1cc(-c2cc(C(=O)N3CC[C@H](C(=O)NC4C5CNCC54)CC34CC4)n[nH]2)c(F)cn1]

TFA (1.50 mL) was added to a stirred mixture of tert-butyl 6-[(7S)-4-[5-(5-fluoro-2-methoxypyridin-4-yl)-1H-pyrazole-3-carbonyl]-4-azaspiro[2.5]octane-7-amido]-3-azabicyclo[3.1.0]hexane-3-carboxylate (Step-1, 170.0 mg, 0.31 mmol) in DCM (1.50 mL) at 0° C. The resulting mixture was stirred at 25° C. for 1 h. The resulting mixture was concentrated under reduced pressure to obtain the title compound (130.0 mg) as an oil. This was used in the next step directly without further purification. LCMS (ESI): 455.2 [M+H]$^+$.

Step-3. (7S)-4-(5-(5-fluoro-2-methoxypyridin-4-yl)-1H-pyrazole-3-carbonyl)-N-(3-(oxetan-3-yl)-3-azabicyclo[3.1.0]hexan-6-yl)-4-azaspiro[2.5]octane-7-carboxamide

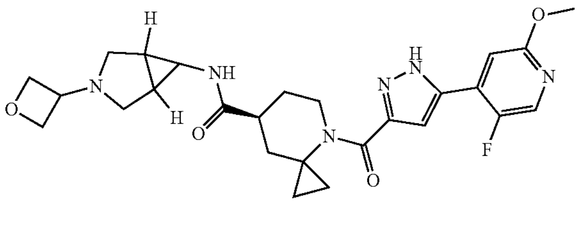 [SMILES: COc1cc(-c2cc(C(=O)N3CC[C@H](C(=O)NC4C5CN(C6COC6)CC54)CC34CC4)n[nH]2)c(F)cn1]

$NaBH_3CN$ (54.9 mg, 0.86 mmol) and 3-oxetanone (103.0 mg, 1.43 mmol) were added to a stirred mixture of (7S)—N-[3-azabicyclo[3.1.0]hexan-6-yl]-4-[5-(5-fluoro-2-methoxypyridin-4-yl)-1H-pyrazole-3-carbonyl]-4-azaspiro[2.5]octane-7-carboxamide (Step-2, 130.0 mg, 0.29 mmol) in AcOH (0.30 mL) and MeOH (3.00 mL) at 25° C. The resulting mixture was stirred at 80° C. for 3 h. The resulting mixture was concentrated under reduced pressure. The residue was purified by silica gel column chromatography eluting with DCM/MeOH (10/1 v/v) to obtain the title compound (60.4 mg) as a solid. $^1H$ NMR (400 MHz, DMSO-$d_6$) δ 13.97 (s, 1H), 8.27 (d, 1H), 7.83 (d, 1H), 7.32 (d, 1H), 7.02 (d, 1H), 4.72-4.57 (m, 1H), 4.54-4.46 (m, 2H), 4.43-4.31 (m, 3H), 3.87 (s, 3H), 3.67-3.56 (m, 1H), 3.01-2.80 (m, 3H), 2.65-2.52 (m, 1H), 2.33-2.09 (m, 2H), 1.81-1.69 (m, 1H), 1.58-1.41 (m, 3H), 1.31-1.09 (m, 2H), 1.08-0.72 (m, 2H), 0.63-0.59 (m, 2H). LCMS (ESI): 511.30 [M+H]$^+$.

Example 430. (S)—N-(5-chloropyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide

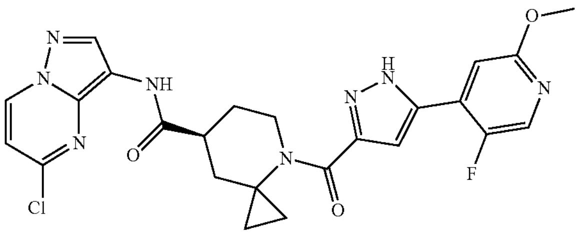 [SMILES: COc1cc(-c2cc(C(=O)N3CC[C@H](C(=O)Nc4cnn5ccc(Cl)nc45)CC34CC4)n[nH]2)c(F)cn1]

HATU (60.9 mg, 0.16 mmol, 1.20 equiv) and 5-Chloropyrazolo[1,5-a]pyrimidin-3-amine (22.5 mg, 0.13 mmol) were added to a stirred solution of (S)-4-[5-(5-fluoro-2-methoxypyridin-4-yl)-1-pyrazole-3-carbonyl]-4-azaspiro[2.5]octane-7-carboxylic acid (INTERMEDIATE 527-A, 50.0 mg, 0.13 mmol) and DIPEA (51.8 mg, 0.40 mmol) in DMF (2.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (15/1 v/v). Then the residue was further purified by Prep-HPLC (using the following conditions: Column: XBridge Prep OBD C18 Column, 30×150 mm, 5 μm; Mobile Phase A: Water (10 mM $NH_4HCO_3$), Mobile Phase B: MeCN; Flow rate: 60 mL/min; Gradient: 30% B to 40% B in 9 min, 40% B; Wave Length: 254/220 nm; RT1 (min): 8.9) to obtain the title compound (30.0 mg) as a solid. $^1H$ NMR (400 MHz, DMSO-$d_6$) δ 13.96 (s, 1H), 10.29 (s, 1H), 9.09 (d, 1H), 8.63 (s, 1H), 8.27 (d, 1H), 7.33 (d, 1H), 7.16-6.95 (m, 2H), 4.75-4.25 (m, 1H), 3.88 (s, 3H), 3.23-3.00 (m, 2H), 2.35-2.12 (m, 1H), 2.04-1.78 (m, 1H), 1.77-1.52 (m, 1H), 1.48-1.26 (m, 1H), 1.17-0.88 (m, 2H), 0.84-0.56 (m, 2H). LCMS (ESI): 525.10 [M+H]$^+$.

Example 431. A Diastereomeric Mixture of (S)-4-(5-(5-fluoro-2-methoxypyridin-4-yl)-1H-pyrazole-3-carbonyl)-N—((S)-1-(2-methylpyrimidin-4-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-methylpyrimidin-4-yl)pyrrolidin-3-yl)-4-azaspiro[2.5]octane-7-carboxamide

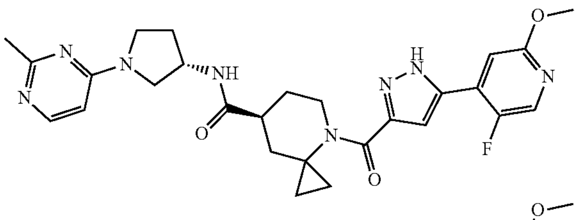

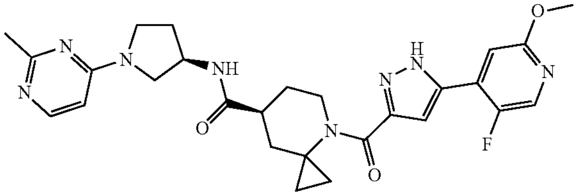

Step-1. tert-butyl 3-[(7S)-4-[5-(5-fluoro-2-methoxypyridin-4-yl)-1H-pyrazole-3-carbonyl]-4-azaspiro[2.5]octane-7-amido]pyrrolidine-1-carboxylate

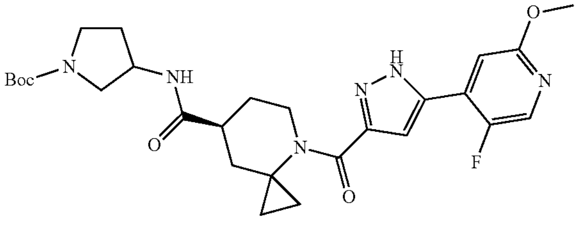 [SMILES: COc1cc(-c2cc(C(=O)N3CC[C@H](C(=O)NC4CCN(C(=O)OC(C)(C)C)C4)CC34CC4)n[nH]2)c(F)cn1]

HATU (487.5 mg, 1.28 mmol) and tert-butyl 3-aminopyrrolidine-1-carboxylate (199.0 mg, 1.07 mmol, 1.00 equiv) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 400.0 mg, 1.07 mmol) and DIPEA (414.3 mg, 3.20 mmol) in DMF (4.00 mL). The resulting solution was stirred at 25° C. for 14 h. The resulting solution was diluted with of EtOAc and washed with water. The organic layers were combined, dried over anhydrous $Na_2SO_4$, filtered, and concentrated under reduced pressure. The residue was purified by silica gel column chromatography eluting with DCM/MeOH (12/1 v/v) to obtain the title compound (550.0 mg) as a solid. LCMS (ESI): 543.3 $[M+H]^+$.

Step-2. (7S)-4-[5-(5-fluoro-2-methoxypyridin-4-yl)-1H-pyrazole-3-carbonyl]-N-(pyrrolidin-3-yl)-4-azaspiro[2.5]octane-7-carboxamide

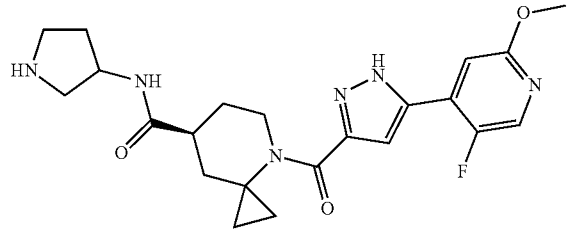 [SMILES: COc1cc(-c2cc(C(=O)N3CC[C@H](C(=O)NC4CCNC4)CC34CC4)n[nH]2)c(F)cn1]

TFA (10.00 mL) was added to a stirred solution of tert-butyl 3-[(7S)-4-[5-(5-fluoro-2-methoxypyridin-4-yl)-1H-pyrazole-3-carbonyl]-4-azaspiro[2.5]octane-7-amido]pyrrolidine-1-carboxylate (Step-1, 450.0 mg, 0.83 mmol) in DCM (10.00 mL). The resulting solution was stirred at 25° C. for 1 h. The resulting mixture was concentrated under reduced pressure and the residue was purified by silica gel column chromatography eluting with DCM/MeOH (5/1 v/v) to obtain the title compound (330.0 mg) as a solid. LCMS (EST): 443.2 $[M+H]^+$.

Step-3. (S)-4-(5-(5-fluoro-2-methoxypyridin-4-yl)-1H-pyrazole-3-carbonyl)-N—((S)-1-(2-methylpyrimidin-4-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-1-((R)-1-(2-methylpyrimidin-4-yl)pyrrolidin-3-yl)-4-azaspiro[2.5]octane-7-carboxamide

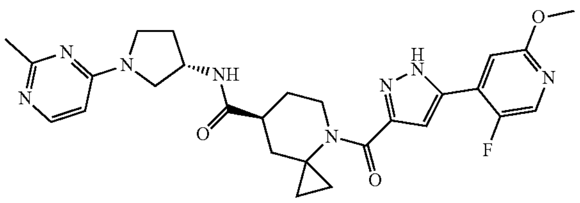

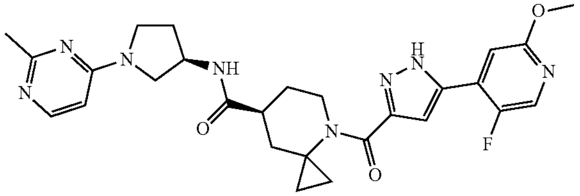

4-Chloro-2-methylpyrimidine (52.3 mg, 0.41 mmol) and DIPEA (87.6 mg, 0.68 mmol) were added to a stirred solution of (7S)-4-[5-(5-fluoro-2-methoxypyridin-4-yl)-1H-pyrazole-3-carbonyl]-N-(pyrrolidin-3-yl)-4-azaspiro[2.5]octane-7-carboxamide (Step-2, 150.0 mg, 0.34 mmol) in EtOH (2.00 mL). The resulting solution was stirred at 80° C. for 2 h. The resulting mixture was concentrated under reduced pressure and the residue was purified by silica gel column chromatography eluting with DCM/MeOH (15/1 v/v) to obtain (S)-4-(5-(5-fluoro-2-methoxypyridin-4-yl)-1H-pyrazole-3-carbonyl)-N—((S)-1-(2-methylpyrimidin-4-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-methylpyrimidin-4-yl)pyrrolidin-3-yl)-4-azaspiro[2.5]octane-7-carboxamide (110.0 mg) as an oil mixture of diastereomers. LCMS (ESI): 535.2 $[M+H]^+$.

This mixture of two diastereomers (100.0 mg) was separated using Chiral Prep-HPLC.

Column: CHIRALPAK ID column

Column dimension: 2×25 cm, 5 μm

Mobile Phase: 1/1 hexanes/DCM (0.5% 2 M $NH_3$·MeOH):EtOH=50:50 hold for 10 min

Flow rate: 20 mL/min

Detection: 220/254 nm

Example 431-A. The first eluting diastereomer (22.1 mg) was obtained as a solid.

The first eluting diastereomer had a retention time of 5.51 min.

$^1$H NMR (400 MHz, $CD_3OD$) δ 8.19-8.09 (m, 1H), 8.06-7.95 (m, 1H), 7.38-7.23 (m, 1H), 7.16-7.01 (m, 1H), 6.43-6.27 (m, 1H), 4.78-4.40 (m, 2H), 3.94 (s, 3H), 3.87-3.42 (m, 5H), 2.92-2.69 (m, 1H), 2.45 (s, 3H), 2.37-2.22 (m, 2H), 2.15-1.96 (m, 1H), 1.95-1.46 (m, 2H), 1.40-1.17 (m, 1H), 1.13-0.86 (m, 2H), 0.83-0.64 (m, 2H). LCMS (ESI): 535.25 $[M+H]^+$.

Example 431-B. The second eluting diastereomer (18.1 mg) was obtained as a solid.

The second eluting diastereomer had a retention time of 7.19 min.

$^1$H NMR (400 MHz, $CD_3OD$) δ 8.22-8.07 (m, 1H), 8.06-7.90 (m, 1H), 7.46-7.20 (m, 1H), 7.11 (s, 1H), 6.44-6.20 (m, 1H), 4.78-4.33 (m, 2H), 3.95 (s, 3H), 3.83-3.60 (m, 4H), 3.32-3.27 (m, 1H), 2.90-2.72 (m, 1H), 2.68-2.22 (m, 5H), 2.15-1.94 (m, 1H), 1.94-1.43 (m, 2H), 1.35-1.24 (m, 2H), 1.17-0.88 (m, 1H), 0.86-0.65 (m, 2H). LCMS (ESI): 535.25 $[M+H]^+$.

Example 432. (S)-4-(5-(5-fluoro-2-methoxypyridin-4-yl)-1H-pyrazole-3-carbonyl)-N-((3-(trifluoromethyl)pyrazin-2-yl)methyl)-4-azaspiro[2.5]octane-7-carboxamide

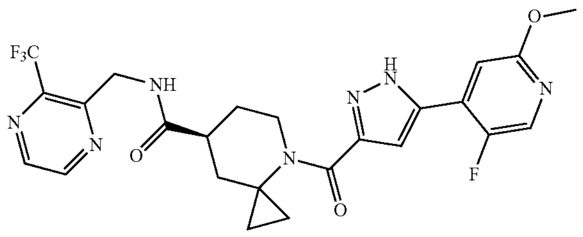 [SMILES: COc1cc(-c2cc(C(=O)N3CC[C@H](C(=O)NCc4nccnc4C(F)(F)F)CC34CC4)n[nH]2)c(F)cn1]

Step-1. tert-butyl N-[[3-(trifluoromethyl)pyrazin-2-yl]methyl]carbamate

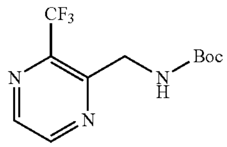

$Pd(AMPhos)_2Cl_2$ (135.8 mg, 0.19 mmol) and $K_3PO_4$ (814.0 mg, 3.83 mmol) were added to a stirred mixture of 2-chloro-3-(trifluoromethyl)pyrazine (350.0 mg, 1.92 mmol) and (((tert-butoxycarbonyl)amino)methyl)trifluoroborate potassium(I) (545.5 mg, 2.30 mmol) in 1,4-dioxane (5.00 mL) and water (1.00 mL). The resulting mixture was stirred at 90° C. for 14 h under nitrogen atmosphere. The resulting mixture was concentrated under reduced pressure. The residue was purified by Prep-TLC (petroleum ether/EtOAc, 3/1 v/v) to obtain the title compound (90.0 mg) as a solid. LCMS (ESI): 278.1 $[M+H]^+$.

Step-2. 1-[3-(trifluoromethyl)pyrazin-2-yl]methanamine

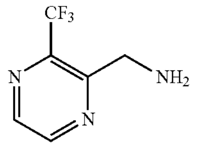 [SMILES: NCc1nccnc1C(F)(F)F]

TFA (2.00 mL) was added to a stirred mixture of tert-butyl N-[[3-(trifluoromethyl)pyrazin-2-yl]methyl]carbamate (Step-1, 80.0 mg, 0.29 mmol) in DCM (2.00 mL). The resulting mixture was stirred at 25° C. for 1 h. The resulting mixture was concentrated under reduced pressure to obtain the title compound (40.0 mg) as a solid. LCMS (ESI): 178.1 $[M+H]^+$.

Step-3. (S)-4-(5-(5-fluoro-2-methoxypyridin-4-yl)-1H-pyrazole-3-carbonyl)-N-((3-(trifluoromethyl)pyrazin-2-yl)methyl)-4-azaspiro[2.5]octane-7-carboxamide

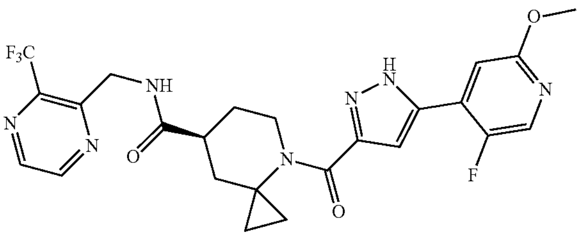 [SMILES: COc1cc(-c2cc(C(=O)N3CC[C@H](C(=O)NCc4nccnc4C(F)(F)F)CC34CC4)n[nH]2)c(F)cn1]

HOBt (61.0 mg, 0.45 mmol), EDCI (86.6 mg, 0.45 mmol), and 1-[3-(trifluoromethyl)pyrazin-2-yl]methanamine (Step-2, 40.0 mg, 0.23 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 84.5 mg, 0.23 mmol) and DIPEA (145.9 mg, 1.13 mmol) in DMF (6.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by prep-HPLC (using the following conditions: Column: YMC-Actus Triart C18 ExRS, 30×150 mm, 5 μm; Mobile Phase A: Water (10 mM $NH_4HCO_3$), Mobile Phase B: MeCN; Flow rate: 60 mL/min; Gradient: 35% B to 45% B in 8 min, 45% B; Wave Length: 254 nm; RT1 (min): 6.93) to obtain the title compound (40.0 mg) as a solid. $^1H$ NMR (400 MHz, $CD_3OD$) δ 8.83 (d, 1H), 8.65 (d, 1H), 8.13 (d, 1H), 7.28 (d, 1H), 7.11 (d, 1H), 4.80-4.68 (m, 2H), 4.66-4.39 (m, 1H), 3.94 (s, 3H), 3.05-2.86 (m, 1H), 2.69-2.29 (m, 1H), 2.09-1.90 (m, 1H), 1.87-1.63 (m, 1H), 1.57-1.25 (m, 2H), 1.22-0.49 (m, 4H). LCMS (ESI): 534.20 $[M+H]^+$.

Example 433. A Diastereomeric Mixture of (S)-4-(5-(5-fluoro-2-methoxypyridin-4-yl)-1H-pyrazole-3-carbonyl)-N-(1-((S)-tetrahydrofuran-3-yl)azetidin-3-yl)-4-azaspiro[2.5]octane-7-carboxamide and (S)-4-(5-(5-fluoro-2-methoxypyridin-4-yl)-1H-pyrazole-3-carbonyl)-N-(1-((R)-tetrahydrofuran-3-yl)azetidin-3-yl)-4-azaspiro[2.5]octane-7-carboxamide

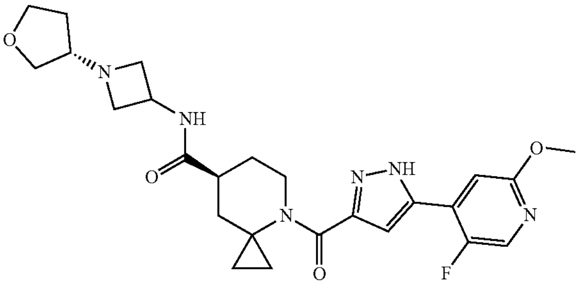

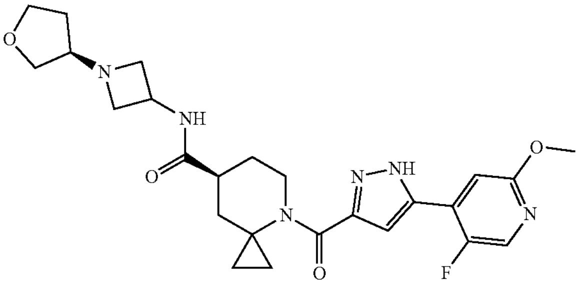

Step-1. tert-butyl 3-[(7S)-4-[5-(5-fluoro-2-methoxypyridin-4-yl)-1H-pyrazole-3-carbonyl]-4-azaspiro[2.5]octane-7-amido]azetidine-1-carboxylate

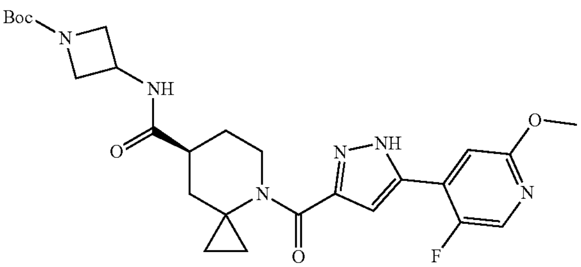 [SMILES: COc1cc(-c2cc(C(=O)N3CC[C@H](C(=O)NC4CN(C(=O)OC(C)(C)C)C4)CC34CC4)n[nH]2)c(F)cn1]

HATU (121.9 mg, 0.32 mmol) and tert-butyl 3-amino-azetidine-1-carboxylate (46.0 mg, 0.27 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 100.0 mg, 0.27 mmol) and DIPEA (103.6 mg, 0.80 mmol) in DMF (4.00 mL). The resulting mixture was stirred at 25° C. for 1 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (130.0 mg) as an oil. LCMS (EST): 529.3 $[M+H]^+$.

Step-2. (7S)—N-(azetidin-3-yl)-4-[5-(5-fluoro-2-methoxypyridin-4-yl)-1H-pyrazole-3-carbonyl]-4-azaspiro[2.5]octane-7-carboxamide

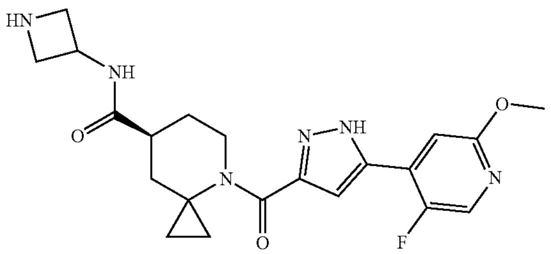 [SMILES: COc1cc(-c2cc(C(=O)N3CC[C@H](C(=O)NC4CNC4)CC34CC4)n[nH]2)c(F)cn1]

TFA (2.00 mL) was added to a stirred solution of tert-butyl 3-[(7S)-4-[5-(5-fluoro-2-methoxypyridin-4-yl)-1H-pyrazole-3-carbonyl]-4-azaspiro[2.5]octane-7-amido]azetidine-1-carboxylate (Step-1, 130.0 mg, 0.25 mmol) in DMF (2.00 mL). The resulting mixture was stirred at 25° C. for 1 h. The resulting solution was concentrated under reduced pressure to obtain the title compound (100.0 mg) as a solid. LCMS (ESI): 429.2 $[M+H]^+$.

Step-3. (S)-4-(5-(5-fluoro-2-methoxypyridin-4-yl)-1H-pyrazole-3-carbonyl)-N-(1-((S)-tetrahydrofuran-3-yl)azetidin-3-yl)-4-azaspiro[2.5]octane-7-carboxamide and (S)-4-(5-(5-fluoro-2-methoxypyridin-4-yl)-1H-pyrazole-3-carbonyl)-N-(1-((R)-tetrahydrofuran-3-yl)azetidin-3-yl)-4-azaspiro[2.5]octane-7-carboxamide

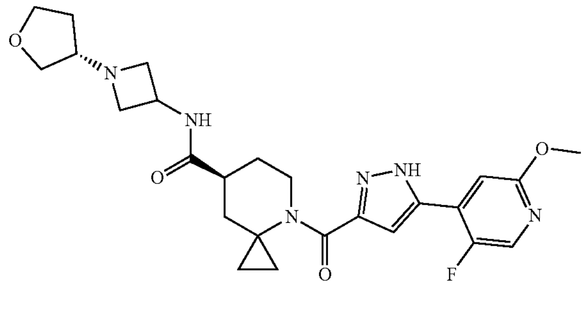

-continued

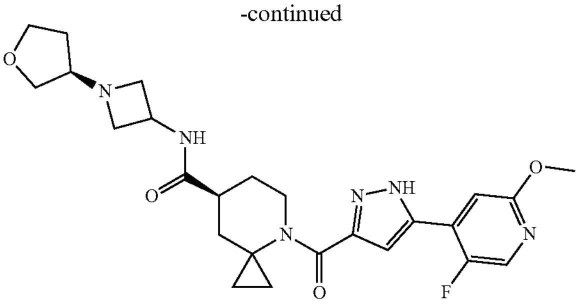

Dihydrofuran-3-one (100.5 mg, 1.17 mmol) was added to a stirred solution of (7S)—N-(azetidin-3-yl)-4-[5-(5-fluoro-2-methoxypyridin-4-yl)-1H-pyrazole-3-carbonyl]-4-azaspiro[2.5]octane-7-carboxamide (Step-2, 100.0 mg, 0.23 mmol) in MeOH (3.00 mL) and AcOH (0.50 mL). The resulting mixture was stirred at 25° C. for 1 h. Then $NaBH_3CN$ (44.0 mg, 0.70 mmol) was added to the reaction mixture. The resulting mixture was stirred at 25° C. for 4 h. The solution was diluted with water and extracted with EtOAc. The organic layers were combined, dried over anhydrous $Na_2SO_4$, filtered, and concentrated under reduced pressure. The residue was purified by silica gel column chromatography eluting with DCM/MeOH (20/1 v/v) to obtain (S)-4-(5-(5-fluoro-2-methoxypyridin-4-yl)-1H-pyrazole-3-carbonyl)-N-(1-((S)-tetrahydrofuran-3-yl)azetidin-3-yl)-4-azaspiro[2.5]octane-7-carboxamide and (S)-4-(5-(5-fluoro-2-methoxypyridin-4-yl)-1H-pyrazole-3-carbonyl)-N-(1-((R)-tetrahydrofuran-3-yl)azetidin-3-yl)-4-azaspiro[2.5]octane-7-carboxamide (73.2 mg) as a solid mixture of diastereomers (Example 433). $^1$H NMR (400 MHz, DMSO-$d_6$) δ 8.27 (s, 2H), 7.61-7.16 (m, 1H), 7.12-6.82 (m, 1H), 4.56-4.30 (m, 1H), 4.28-4.00 (m, 1H), 3.88 (s, 3H), 3.73-3.59 (m, 2H), 3.56-3.49 (m, 1H), 3.47-3.28 (m, 3H), 2.98-2.87 (m, 1H), 2.86-2.72 (m, 2H), 2.71-2.60 (m, 2H), 2.37-1.93 (m, 1H), 1.91-1.80 (m, 3H), 1.78-1.67 (m, 2H), 1.64-1.38 (m, 2H), 1.35-1.07 (m, 1H), 1.01-0.71 (m, 1H), 0.69-0.36 (m, 1H). LCMS (ESI): 499.25 $[M+H]^+$.

This mixture of two diastereomers (71.0 mg) was separated using Chiral Prep-HPLC.

Column: CHIRAL ART Amylose-SA column
Column dimension: 2×25 cm, 5 μm
Mobile Phase: 3/1 hexanes/DCM (0.5% 2 M $NH_3$·MeOH):EtOH=50:50 hold for 13 min
Flow rate: 20 mL/min
Detection: 220/254 nm Example 433-A. The first eluting diastereomer (24.5 mg) was obtained as a solid.

The first eluting diastereomer had a retention time of 5.53 min.

$^1$H NMR (300 MHz, $CD_3OD$) δ 8.07-7.96 (m, 1H), 7.24-7.10 (m, 1H), 7.04-6.94 (m, 1H), 4.67-4.37 (m, 1H), 4.35-4.18 (m, 1H), 3.76 (m, 4H), 3.69-3.59 (m, 1H), 3.57-3.41 (m, 4H), 3.07-2.95 (m, 2H), 2.94-2.80 (m, 2H), 2.78-2.57 (m, 1H), 2.50-2.07 (m, 1H), 1.93-1.68 (m, 2H), 1.66-1.43 (m, 2H), 1.38-1.05 (m, 1H), 1.01-0.72 (m, 2H), 0.69-0.49 (m, 2H). LCMS (ESI): 499.20 $[M+H]^+$.

Example 433-B. The second eluting diastereomer (22.0 mg) was obtained as a solid.

The second eluting diastereomer had a retention time of 10.07 min.

$^1$H NMR (300 MHz, $CD_3OD$) δ 8.01 (s, 1H), 7.16 (s, 1H), 6.99 (s, 1H), 4.70-4.36 (m, 1H), 4.35-4.14 (m, 1H), 3.87-3.71 (m, 4H), 3.69-3.58 (m, 1H), 3.57-3.39 (m, 4H), 3.07-

2.95 (m, 2H), 2.94-2.82 (m, 2H), 2.79-2.57 (m, 1H), 2.55-2.04 (m, 1H), 1.97-1.68 (m, 2H), 1.66-1.49 (m, 2H), 1.41-1.08 (m, 1H), 1.06-0.70 (m, 2H), 0.69-0.42 (m, 2H). LCMS (ESI): 499.20 $[M+H]^+$.

Example 434. (7S)—N-((3-chloro-5-(3,5-dimethylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide

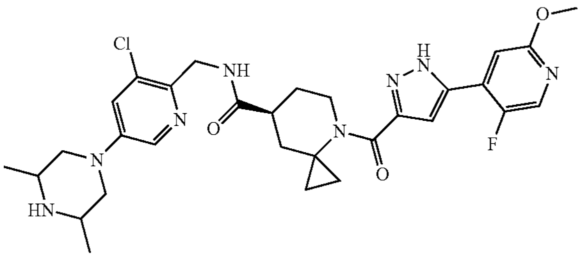

Step-1. tert-butyl 4-(5-chloro-6-cyanopyridin-3-yl)-2,6-dimethylpiperazine-1-carboxylate

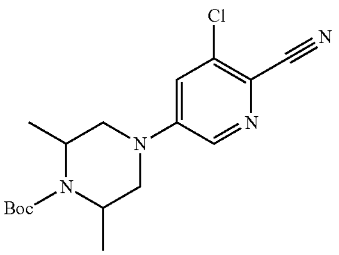 [SMILES: CC1CN(c2cnc(C#N)c(Cl)c2)CC(C)N1C(=O)OC(C)(C)C]

Tert-butyl 2,6-dimethylpiperazine-1-carboxylate (1.40 g, 6.52 mmol) and DIPEA (1.05 g, 8.15 mmol) were added to a stirred solution of 3-chloro-5-fluoropyridine-2-carbonitrile (850.0 mg, 5.43 mmol) in DMSO (5.00 mL). The resulting mixture was stirred at 100° C. for 1 h. The solution was diluted with EtOAc and washed with water. The organic layers were combined, dried over anhydrous $Na_2SO_4$, filtered, and concentrated under reduced pressure. The residue was purified by silica gel column chromatography eluting with EtOAc/petroleum ether (1/2 v/v) to obtain the title compound (1.83 g) as a solid. LCMS (ESI): 351.2 $[M+H]^+$.

Step-2. tert-butyl 4-[6-(aminomethyl)-5-chloropyridin-3-yl]-2,6-dimethylpiperazine-1-carboxylate

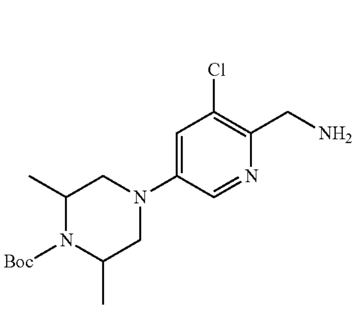 [SMILES: CC1CN(c2cnc(CN)c(Cl)c2)CC(C)N1C(=O)OC(C)(C)C]

DIBAL-H (15.39 mL, 15.39 mmol) was added to a stirred solution of tert-butyl 4-(5-chloro-6-cyanopyridin-3-yl)-2,6-dimethylpiperazine-1-carboxylate (Step-1, 1.80 g, 5.13 mmol) in DCM (10.00 mL) at −78° C. under nitrogen atmosphere. The resulting mixture was stirred at −78° C. for 1 h under nitrogen atmosphere. The resulting mixture was quenched with MeOH at −78° C. The solution was concentrated under reduced pressure. The residue was purified by silica gel column chromatography eluting with DCM/MeOH (5/1 v/v) to obtain the title compound (918.0 mg) as an oil. LCMS (ESI): 355.2 $[M+H]^+$.

Step-3. tert-butyl 4-[5-chloro-6-([[(7S)-4-[5-(5-fluoro-2-methoxypyridin-4-yl)-1H-pyrazole-3-carbonyl]-4-azaspiro[2.5]octan-7-yl]formamido]methyl)pyridin-3-yl]-2,6-dimethylpiperazine-1-carboxylate

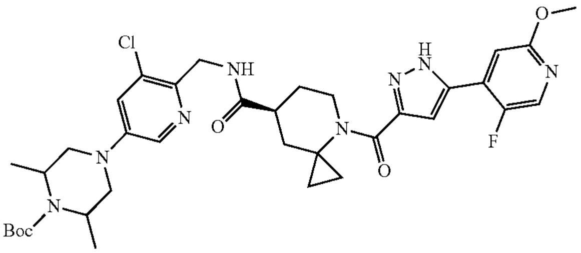

HOBt (81.2 mg, 0.60 mmol), EDCI (115.2 mg, 0.60 mmol), and tert-butyl 4-[6-(aminomethyl)-5-chloropyridin-3-yl]-2,6-dimethylpiperazine-1-carboxylate (Step-2, 170.6 mg, 0.48 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 150.0 mg, 0.40 mmol) and DIPEA (155.4 mg, 1.20 mmol) in DMF (3.00 mL). The resulting mixture was stirred at 25° C. for 14 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (280.0 mg) as a solid. LCMS (ESI): 711.3 $[M+H]^+$.

Step-4. (7S)—N-((3-chloro-5-(3,5-dimethylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide

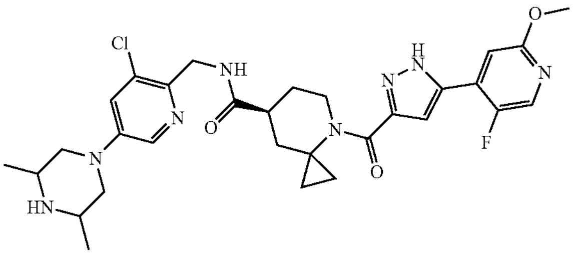

TFA (3.00 mL) was added to a stirred solution of tert-butyl 4-[5-chloro-6-([[(7S)-4-[5-(5-fluoro-2-methoxypyridin-4-yl)-1H-pyrazole-3-carbonyl]-4-azaspiro[2.5]octan-7- yl]formamido]methyl)pyridin-3-yl]-2,6-dimethylpiperazine-1-carboxylate (Step-3, 280.0 mg, 0.39 mmol) in DCM (3.00 mL) at 0° C. The resulting mixture was stirred at 25° C. for 1 h. The solution was concentrated under reduced pressure, then basified to pH 8 with TEA. The solution was concentrated under reduced pressure. The residue was purified by reverse phase column chromatography (using the following conditions: Column: C18 column; mobile phase A: Water (0.5% $NH_4HCO_3$), mobile phase B: MeCN; gradient: 30 B to 50 B in 20 min; 220/254 nm) to obtain the title compound (97.0 mg) as a solid. $^1H$ NMR (400 MHz, DMSO-$d_6$) δ 13.97 (s, 1H), 8.26 (d, 1H), 8.18 (d, 1H), 8.14 (d, 1H), 7.38 (d, 1H), 7.32 (d, 1H), 7.03 (d, 1H), 4.70-4.11 (m, 3H), 3.87 (s, 3H), 3.72-3.54 (m, 2H), 2.93-2.70 (m, 3H), 2.26-2.00 (m, 3H), 1.90-1.68 (m, 1H), 1.65-1.43 (m, 1H), 1.23 (s, 2H), 1.08-0.72 (m, 9H), 0.71-0.48 (m, 2H). LCMS (ESI): 611.40 $[M+H]^+$.

Example 435. A Diastereomeric Mixture of (S)—N—((S)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide

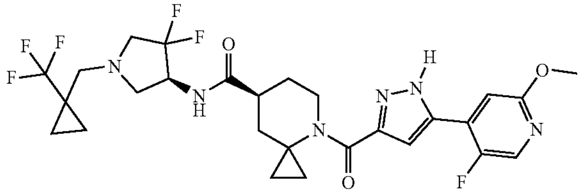

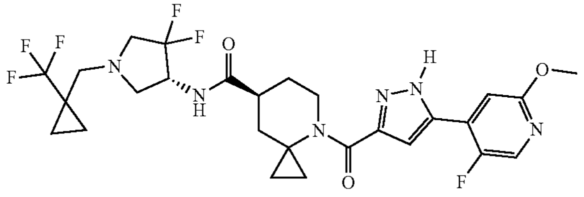

Step-1. 4-azido-3,3-difluoropyrrolidine 2,2,2-trifluoroacetate

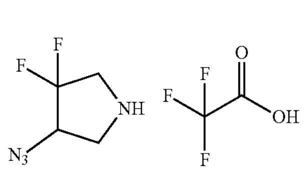

TFA (1.70 g, 14.95 mmol) was added to a solution of tert-butyl 4-azido-3,3-difluoropyrrolidine-1-carboxylate[1] (371.0 mg, 1.49 mmol) in DCM (2.99 mL) at 0° C. The reaction mixture was warmed to 22° C. for 3 h and concentrated under reduced pressure to obtain the title compound as an oil which was used without further purification. $^1H$ NMR (400 MHz, DMSO) δ 3.37 (ddd, 1H), 3.64-3.82 (m, 3H), 4.84-4.95 (m, 1H), 9.79 (s, 2H).

[1] Prepared according to US2015141402A1 without any deviation from the procedure.

Step-2. (4-azido-3,3-difluoropyrrolidin-1-yl)(1-(trifluoromethyl)cyclopropyl)methanone

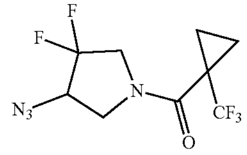 [SMILES: [N-]=[N+]=NC1CN(C(=O)C2(C(F)(F)F)CC2)CC1(F)F]

2-(3H-[1,2,3]triazolo[4,5-b]pyridin-3-yl)-1,1,3,3-tetramethylisouronium hexafluorophosphate(V) (516.0 mg, 1.36 mmol) and DIPEA (797.0 mg, 6.17 mmol) were added to a solution of 1-(trifluoromethyl)cyclopropane-1-carboxylic acid (190.0 mg, 1.23 mmol) in DMF (3.00 mL). The mixture was stirred for 20 min at 22° C. A solution of 4-azido-3,3-difluoropyrrolidine 2,2,2-trifluoroacetate (Step-1, 388.0 mg, 1.48 mmol) in DMF (1.93 mL) was added to the reaction mixture and stirred at 22° C. for 4 h. The reaction mixture was diluted with EtOAc and washed with water, brine. The organic layers were combined, dried over anhydrous $Na_2SO_4$, filtered, and concentrated under reduced pressure. The residue was purified by silica gel column chromatography eluting with 10% to 30% EtOAc in cyclohexane to obtain the title compound (221.0 mg) as an oil. TLC-MS (APCI): 285.1 $[M+H]^+$.

Step-3. Tert-butyl (4,4-difluoro-1-((1-(trifluoromethyl)cyclopropyl)methyl)pyrrolidin-3-yl)carbamate

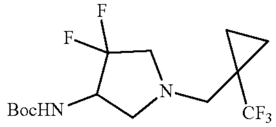 [SMILES: CC(C)(C)OC(=O)NC1CN(CC2(C(F)(F)F)CC2)CC1(F)F]

Aluminum(III) lithium hydride (1.27 mL, 1.27 mmol, 1 M) was added dropwise to a solution of (4-azido-3,3-difluoropyrrolidin-1-yl)(1-(trifluoromethyl)cyclopropyl) methanone (Step-2, 72.0 mg, 0.25 mmol) in $Et_2O$ (1.27 mL) in a sealed tube at 0° C. The reaction mixture was heated to 50° C. for 6 h. the resulting mixture was diluted with $Et_2O$ and quenched by sequential addition of water (0.05 mL), NaOH (15% aqueous, 0.05 mL), and water (0.15 mL) at 0° C. The resulting mixture was warmed to 22° C. for 15 min, dried over $MgSO_4$ and filtered over celite. $Boc_2O$ (82.9 mg, 0.38 mmol) was added to the filtrate and stirred at 22° C. for 18 h. The reaction mixture was concentrated under reduced pressure and the residue was purified by silica gel column chromatography eluting with 5% to 30% EtOAc in cyclohexane to obtain the title compound (53.0 mg) as a solid. TLC-MS (APCI): 345.3 $[M+H]^+$. $^1H$ NMR (400 MHz, $CD_3OD$) δ 4.33-4.17 (m, 1H), 330-3.19 (m, 2H), 2.78-2.64 (m, 21), 2.58 (d, 1H), 2.35 (t, 1H), 1.45 (s, 9H), 1.03-0.98 (m, 2H), 0.75-0.68 (m, 2H). $^{19}F$ NMR (376 MHz, DMSO) δ −68.02, −95.50 (d), −108.07 (d).

Step-4. 4,4-difluoro-1-[[1-(trifluoromethyl)cyclopropyl]methyl]pyrrolidin-3-amine

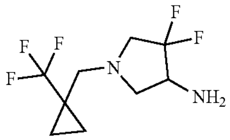 [SMILES: NC1CN(CC2(C(F)(F)F)CC2)CC1(F)F]

TFA (1.00 mL) was added to a stirred solution of tert-butyl N-(4,4-difluoro-1-[[1-(trifluoromethyl)cyclopropyl]methyl]pyrrolidin-3-yl)carbamate (Step-4, 38.0 mg, 0.11 mmol) in DCM (1.00 mL). The resulting solution was stirred at 25° C. for 1 h. The resulting solution was concentrated under reduced pressure to obtain the title compound (25.0 mg) as an oil. LCMS (ESI): 245.1 $[M+H]^+$.

Step-5. (S)—N((S)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide

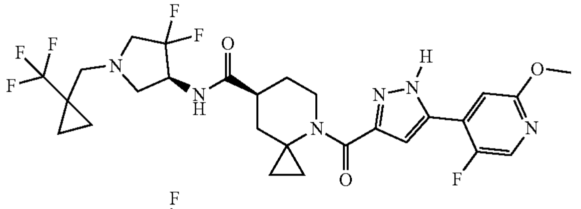

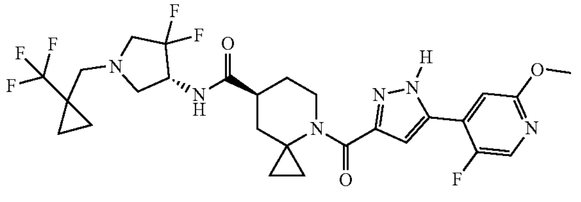

HOBt (17.4 mg, 0.13 mmol), EDCI (24.7 mg, 0.13 mmol), and 4,4-difluoro-1-[[1-(trifluoromethyl)cyclopropyl]methyl]pyrrolidin-3-amine (21.0 mg, 0.09 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 32.2 mg, 0.09 mmol) and DIPEA (66.7 mg, 0.52 mmol) in DMF (3.00 mL). The resulting solution was stirred at 25° C. for 14 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)—N—((S)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide (50.0 mg) as a solid mixture of diastereomers. LCMS (ESI): 601.2 $[M+H]^+$.

This mixture of two diastereomers (50.0 mg) was separated using Chiral Prep-HPLC.

Column: CHIRALPAK IF column

Column dimension: 2×25 cm, 5 μm

Mobile Phase: 1/1 hexanes/DCM (0.5% 2 M $NH_3$·MeOH):EtOH=70:30 hold for 10 min

Flow rate: 20 mL/min

Detection: 220/254 nm

Example 435-A. The first eluting diastereomer (10.7 mg) was obtained as a solid.

The first eluting diastereomer had a retention time of 5.92 min.

$^1$H NMR (400 MHz, $CD_3OD$) δ 8.41-7.82 (m, 1H), 7.70-6.84 (m, 2H), 4.75-4.37 (m, 1H), 3.95 (s, 3H), 3.28-3.17 (m, 2H), 3.00-2.77 (m, 2H), 2.76-2.57 (m, 2H), 2.55-2.42 (m, 1H), 2.39-2.13 (m, 1H), 1.99-1.54 (m, 2H), 1.49-1.18 (m, 3H), 1.17-0.96 (m, 3H), 0.96-0.82 (m, 1H), 0.83-0.59 (m, 4H). LCMS (ESI): 601.20 $[M+H]^+$.

Example 435-B. The second eluting diastereomer (10.2 mg) was obtained as a solid.

The second eluting diastereomer had a retention time of 9.08 min.

$^1$H NMR (400 MHz, $CD_3OD$) δ 8.32-7.70 (m, 1H), 7.61-6.88 (m, 2H), 4.71-4.32 (m, 1H), 3.95 (s, 3H), 3.28-3.18 (m, 2H), 3.00-2.77 (m, 2H), 2.76-2.57 (m, 2H), 2.54-2.37 (m, 2H), 2.00-1.70 (m, 2H), 1.56-1.17 (m, 3H), 1.15-0.96 (m, 3H), 0.96-0.51 (m, 5H). LCMS (ESI): 601.20 $[M+H]^+$.

Example 436. (1R,3s,5S)—N-(4-(1,1-difluoro-2-hydroxyethyl)-4-hydroxycyclohexyl)-8-(5-(5-fluoro-2-methoxypyridin-4-yl)-1H-pyrazole-3-carbonyl)-8-azabicyclo[3.2.1]octane-3-carboxamide

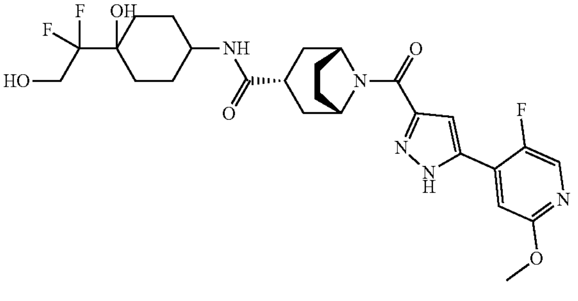

Step-1. 8-(1,1-difluoro-2-hydroxyethyl)-1,4-dioxaspiro[4.5]decan-8-ol

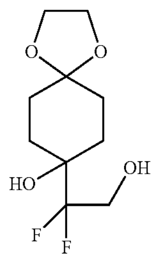

$LiAlH_4$ (1.08 mL, 2.60 mmol, 2.4 M in THF) was added to a stirred solution of 2,2-difluoro-2-(8-hydroxy-1,4-dioxaspiro[4.5]decan-8-yl)ethyl 4-methylbenzenesulfonate (Step-3 from synthesis of INTERMEDIATE 537, 509.5 mg, 1.30 mmol) in THF (6.49 mL) at 0° C. The reaction mixture was warmed up to 22° C. and stirred for 2 h. The resulting mixture was diluted with $Et_2O$ and cooled to 0° C., and then water was slowly added, followed by 15% aqueous NaOH solution and water. The resulting mixture was warmed to 22° C. and stirred for 15 min. The organic layers were combined, dried over anhydrous $Na_2SO_4$, filtered, and concentrated under reduced pressure. The residue was purified by silica gel column chromatography eluting with 0% to 100% EtOAc/cyclohexane to obtain the title compound (150.0 mg) as a solid. $^1H$ NMR (400 MHz, $CD_3OD$) δ 3.93-3.90 (m, 4H), 3.88 (t, 2H), 1.89-1.73 (m, 6H), 1.61 (dd, 2H). $^{19}F$ NMR (376 MHz, $CD_3OD$) δ −124.39.

Step-2. 4-(1,1-difluoro-2-hydroxyethyl)-4-hydroxy-cyclohexan-1-one

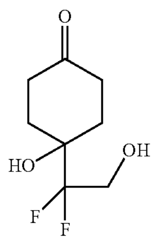

TFA (723.9 mg, 6.35 mmol) was added to a solution of 8-(1,1-difluoro-2-hydroxyethyl)-1,4-dioxaspiro[4.5]decan-8-ol (Step-1, 150.0 mg, 0.63 mmol) in DCM (6.70 mL). The mixture was stirred for 48 h at 22° C. Volatiles were removed under reduced pressure. Remaining TFA was co-evaporated twice with toluene. The residue was purified by silica gel column chromatography eluting with 0% to 100% EtOAc/cyclohexane to obtain the title compound (122.0 mg). $^1H$ NMR (400 MHz, $CD_3OD$) δ 4.00-3.80 (m, 3H), 2.69 (td, 1H), 2.29-2.20 (m, 1H), 2.19-2.09 (m, 1H), 2.07-1.97 (m, 1H), 1.93-1.59 (m, 4H). $^{19}F$ NMR (376 MHz, $CDCl_3$) δ −121.54, −122.53.

Step-3. 4-(1,1-difluoro-2-hydroxyethyl)-4-hydroxy-cyclohexan-1-one oxime

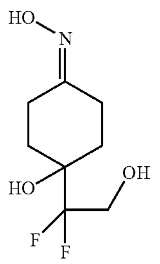

Hydroxylamine hydrochloride (33.6 mg, 0.48 mmol) was added to a solution of sodium acetate (43.3 mg, 0.53 mmol) in MeOH (2.40 mL). The resulting mixture was stirred for 30 min at 22° C. Then a solution of 4-(1,1-difluoro-2-hydroxyethyl)-4-hydroxycyclohexan-1-one (Step-2, 122.0 mg, 70.0% Wt, 0.44 mmol) in MeOH (1 mL) was added to the reaction mixture. The resulting mixture was stirred at 60° C. for 16 h. The reaction mixture was cooled to 22° C. and MeOH was removed under reduced pressure. The residue was dissolved in EtOAc and washed with water. The organic layers were combined, dried over anhydrous $Na_2SO_4$, filtered, and concentrated under reduced pressure. The residue was purified by silica gel column chromatography (0% to 100% EtOAc/Cyclohexane) to obtain the title compound (68.0 mg) as a solid. $^1H$ NMR (400 MHz, $CD_3OD$) δ 3.90 (t, 2H), 3.26-3.16 (m, 1H), 2.45 (td, 1H), 2.24 (ddt, 1H), 2.07 (td, 1H), 1.96 (dddd, 2H), 1.78-1.61 (m, 2H). $^{19}F$ NMR (376 MHz, $CD_3OD$) δ −124.10 (d).

Step-4. tert-butyl (4-(1,1-difluoro-2-hydroxyethyl)-4-hydroxycyclohexyl)carbamate

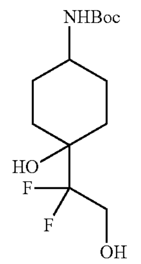

$NaBH_4$ (98.4 mg, 2.60 mmol) was added to a solution of 4-(1,1-difluoro-2-hydroxyethyl)-4-hydroxycyclohexan-1-one oxime (Step-3, 68.0 mg, 0.33 mmol) and nickel(II) chloride hexahydrate (100.4 mg, 0.42 mmol) in MeOH (6.50 mL) at −78° C. The resulting mixture was warmed to 0° C. and stirred at this temperature for 4 h. $Boc_2O$ (106.4 mg, 0.49 mmol) was then added and the reaction mixture was stirred at 22° C. for 18 h. The reaction mixture was quenched with brine at 0° C. Volatiles were removed under reduce pressure. The residue was purified by silica gel column chromatography (0% to 80% EtOAc/Cyclohexane) to obtain the title compound (88.0 mg) as a solid. $^1H$ NMR (400 MHz, Chloroform-d) δ 4.74 (d, 0.3H), 4.53 (d, 0.7H), 4.02-3.87 (m, 2H), 3.78 (s, 0.3H), 3.39 (s, 0.7H), 1.99-1.46 (m, 8H), 1.43 (s, 3H), 1.42-1.40 (m, 6H). $^{19}F$ NMR (376 MHz, Chloroform-d) δ −121.67, −122.09.

Step-5. 4-amino-1-(1,1-difluoro-2-hydroxyethyl) cyclohexan-1-ol hydrochloride

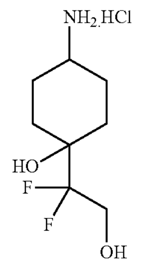

HCl (612.0 μL, 2.45 mmol, 4.0 M in 1,4-dioxane) was added to tert-butyl (4-(1,1-difluoro-2-hydroxyethyl)-4-hydroxycyclohexyl)carbamate (Step-4, 72.3 mg, 0.24 mmol). The solution was stirred for 1.5 h at 22° C. The resulting mixture was concentrated under reduced pressure to obtain the title compound (52.9 mg) as a solid. $^1H$ NMR (400 MHz, $CD_3OD$) δ 3.98-3.81 (m, 2H), 3.16-3.03 (m, 1H), 1.99-1.63 (m, 8H). $^{19}$F NMR (376 MHz, $CD_3OD$) δ −122.67, −124.22.

Step-6. (1R,3s,5S)—N-(4-(1,1-difluoro-2-hydroxyethyl)-4-hydroxycyclohexyl)-8-(5-(5-fluoro-2-methoxypyridin-4-yl)-1H-pyrazole-3-carbonyl)-8-azabicyclo[3.2.1]octane-3-carboxamide

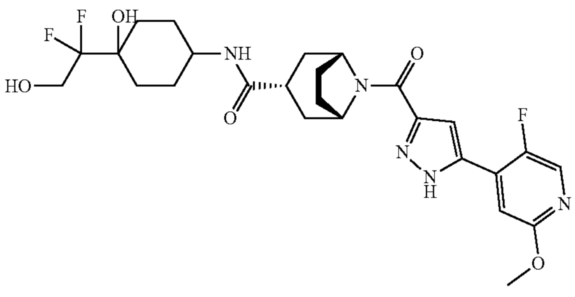

HATU (33.5 mg, 0.09 mmol) and 4-amino-1-(1,1-difluoro-2-hydroxyethyl)cyclohexan-1-ol hydrochloride (20.6 mg, 90% Wt, 0.08 mmol) were added to a solution of the (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 30.0 mg, 0.08 mmol) and DIPEA (20.7 mg, 0.16 mmol) in DMF (0.27 mL). The resulting mixture was stirred at 22° C. for 18 h. The residue was directly purified by reverse phase column chromatography (using the following conditions: C18 column, 10% to 95% MeOH/Water (0.1% HCOOH)) to obtain the title compound (35.7 mg) as a solid. $^{1}$H $N_1$R (400 MHz, $CDCl_3$) δ 8.28 (s, 1H), 7.71 (d, 1H), 7.33 (d, 1H), 7.13 (s, 1H), 5.29-5.07 (m, 1.7H), 5.01 (s, 0.7H), 4.98 (s, 0.3H), 4.72-4.59 (m, 1.3H), 3.87 (s, 3H), 3.82-3.65 (m, 2H), 3.41 (s, 1H), 3.01-2.87 (m, 0.3H), 2.84-2.71 (m, 0.7H), 2.10-1.38 (m, 16H).

Example 437. (1R,3s,5S)-8-(5-(5-fluoro-2-methoxypyridin-4-yl)-1H-pyrazole-3-carbonyl)-N—((R)-1-((1-(trifluoromethyl)cyclopropyl)methyl)pyrrolidin-3-yl)-8-azabicyclo[3.2.1]octane-3-carboxamide

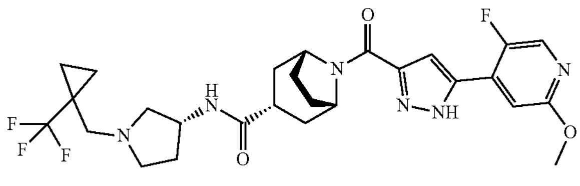

Step-1. (1-(trifluoromethyl)cyclopropyl)methanol

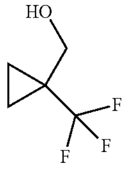

Borane-methyl sulfide complex (5.11 mL, 10.22 mmol, 2 M) was added dropwise to a solution of 1-(trifluoromethyl)cyclopropane-1-carboxylic acid (1.05 g, 6.81 mmol) in THF (13.63 mL). The resulting solution was stirred at 40° C. for 24 h and cooled to 0° C. and quenched by slow addition of aqueous saturated $NH_4CL$. The resulting mixture was filtered through celite. The residue was extracted with EtOAc. The combined organic layers were dried over anhydrous sodium sulfate, filtered, and concentrated to obtain the title compound (615.0 mg) as an oil and used in the next step without purification. $^{1}$H NMR (400 MHz, CDCl3) δ 3.83 (d, 2H), 0.95-0.88 (m, 2H), 0.74-0.67 (m, 2H). $^{19}$F NMR (376 MHz, CDCl3) δ −69.83.

Step-2. (1-(trifluoromethyl)cyclopropyl)methyl 4-methylbenzenesulfonate

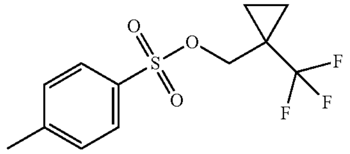 [SMILES: Cc1ccc(S(=O)(=O)OCC2(C(F)(F)F)CC2)cc1]

$Et_3N$ (1.84 mL, 13.17 mmol), DMAP (10.7 mg, 0.09 mmol) and tosyl chloride (1.26 g, 6.58 mmol) were added to a stirred solution of (1-(trifluoromethyl)cyclopropyl)methanol (Step-1, 615.0 mg, 4.39 mmol) in DCM (7.30 mL) at 0° C. The reaction mixture was stirred at 22° C. for 16 h. The reaction mixture was diluted with DCM and washed with saturated aq. $NH_4Cl$ solution, brine and dried over anhydrous sodium sulfate, filtered and concentrated under reduced pressure. The residue was purified by silica gel column chromatography (Cyclohexane/EtOAc, 0% to 80%) to obtain the title compound (73.0 mg) as a solid. $^{1}$H NMR (400 MHz, $CDCl_3$) δ 7.84-7.73 (m, 2H), 7.39-7.31 (m, 2H), 4.10 (s, 2H), 2.46 (s, 3H), 1.14-1.09 (m, 2H), 0.87-0.81 (m, 2H). $^{19}$F NMR (376 MHz, $CDCl_3$) δ −70.12.

Step-3. tert-butyl (R)-(1-((1-(trifluoromethyl)cyclopropyl)methyl)pyrrolidin-3-yl)carbamate

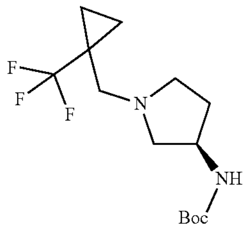 [SMILES: CC(C)(C)OC(=O)N[C@@H]1CCN(CC2(C(F)(F)F)CC2)C1]

A solution of (1-(trifluoromethyl)cyclopropyl)methyl 4-methylbenzenesulfonate (Step-2, 73.0 mg, 0.25 mmol) and tert-butyl (R)-pyrrolidin-3-ylcarbamate (60.1 mg, 0.32 mmol) in DMF (1.24 mL) was stirred at 60° C. for 16 h. Water was added to the reaction mixture and extracted with $Et_2O$. The combined organics were washed with water, dried over anhydrous sodium sulfate, filtered and concentrated under reduced pressure. The residue was purified by silica gel column chromatography (Cyclohexane/EtOAc, 0% to 40%) to obtain the title compound (39.3 mg) as a solid. $^{1}$H NMR (400 MHz, CDCl3) δ 4.84 (s, 1H), 4.15 (s, 1H), 2.98-2.85 (m, 1H), 2.76-2.63 (m, 2H), 2.53-2.40 (m, 2H), 2.32-2.16 (m, 2H), 1.63-1.52 (m, 1H), 1.44 (s, 9H), 1.06-0.95 (m, 2H), 0.68-0.52 (m, 2H). $^{19}$F NMR (376 MHz, CDCl3) δ −69.42, −76.49.

Step-4. (R)-2,2,2-trifluoro-N-(1-((1-(trifluoromethyl)cyclopropyl)methyl)pyrrolidin-3-yl)acetamide

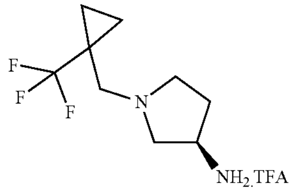

TFA (145.3 mg, 1.28 mmol) was added to a solution of tert-butyl (R)-(1-((1-(trifluoromethyl)cyclopropyl)methyl) pyrrolidin-3-yl)carbamate (Step-3, 39.3 mg, 0.13 mmol) in DCM (637.0 μL). The reaction mixture was stirred at 22° C. for 2 h. Volatiles were removed under reduced pressure. The residue was co-evaporated twice with cyclohexane to obtain the title compound as a solid and used in the next step without further purification. TLC-MS (APCI): 305.1 $[M+H]^+$.

Step-5. (1R,3s,5S)-8-(5-(5-fluoro-2-methoxypyridin-4-yl)-1H-pyrazole-3-carbonyl)-N—((R)-1-((1-(trifluoromethyl)cyclopropyl)methyl)pyrrolidin-3-yl)-8-azabicyclo[3.2.1]octane-3-carboxamide

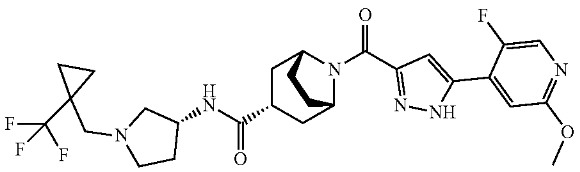

HATU (33.5 mg, 0.09 mmol) and (R)-2,2,2-trifluoro-N-(1-((1-(trifluoromethyl)cyclopropyl)methyl)pyrrolidin-3-yl) acetamide (Step-4, 24.4 mg, 0.08 mmol) were added to a solution of (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 30.0 mg, 0.08 mmol) and DIPEA (0.11 mL, 0.64 mmol) in DMF (367.0 μL). The resulting mixture was stirred at 22° C. for 18 h. The residue was purified by reverse phase column chromatography (using the following conditions: C18 column, 10% to 95% MeOH/Water (0.1% HCOOH)) to obtain the title compound containing $PF_6$ salts. The solid was dissolved in water and sat. aq. $NaHCO_3$ was added. The resulting mixture was vigorously stirred for 2 h. The solid was filtered off and washed with water, dried over anhydrous $Na_2SO_4$, filtered and concentrated to obtain the title compound (19.5 mg) as a solid. $^1$H NMR (400 MHz, DMSO) δ 14.09 (s, 0.4H), 13.97 (s, 0.6H), 8.31 (d, 0.6H), 8.24 (d, 0.4H), 7.92 (t, 1H), 7.33 (d, 1H), 7.15 (s, 0.6H), 7.09 (s, 0.4H), 5.21 (s, 0.6H), 4.68 (d, 1H), 4.60 (s, 0.4H), 4.11-4.01 (m, 1H), 3.87 (d, 3H), 2.88-2.74 (m, 1H), 2.70-2.57 (m, 3H), 2.44-2.25 (m, 2H), 2.14-1.42 (m, 10H), 0.98-0.88 (m, 2H), 0.76-0.67 (m, 2H). $^{19}$F NMR (376 MHz, DMSO) δ −67.90, −141.89, −142.82. TLC-MS (APCI): $[M+H]^+$=565.3.

Example 438. (1R,3s,5S)—N-(4-cyano-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide

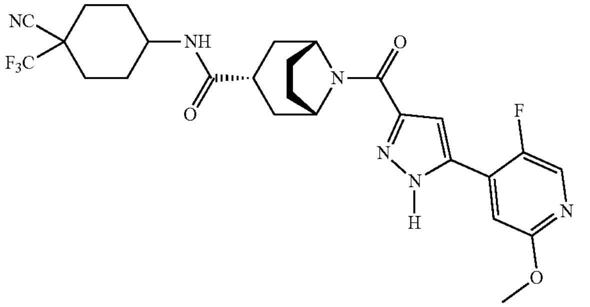

Step-1. 1,4-dioxaspiro[4.5]decane-8-carbonitrile

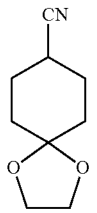

Potassium tert-butoxide (18.06 g, 160.92 mmol) was portion wise added over a period of 2 h to a mixture of 1,4-dioxaspiro[4.5]decan-8-one (10.56 g, 67.61 mmol) and TosMIC (17.16 g, 87.90 mmol) in DMF (189 mL) and ethanol (7 mL) at −10° C. The temperature was maintained below −5° C. After complete addition, the mixture was warmed to 0° C. and stirred another 1 h at 0° C. followed by 22° C. for another 2.5 h. The reaction mixture was diluted with diethyl ether and water. The mixture was stirred for 1 h. The organic layer was separated and washed with water followed by brine, dried over anhydrous sodium sulfate, filtered and concentrated under reduced pressure. The residue was distilled (110° C., 3 mbar) to obtain the title compound (5.43 g) as an oil. $^1$H NMR (400 MHz, $CDCl_3$) δ 4.00-3.84 (m, 4H), 2.64 (tt, 1H), 1.95 (dqt, 4H), 1.83 (ddd, 2H), 1.61 (ddd, 2H).

Step-2. A-(tert-butyldimethylsilyl)-1-(1,4-dioxaspiro[4.5]decan-8-ylidene)methanimine

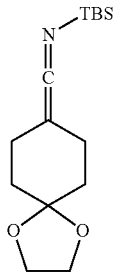

In a flame-dried Schlenk tube diisopropylamine (2.11 mL, 14.95 mmol) was dissolved in dry THF (6.64 mL) and BuLi (9.34 mL, 14.95 mmol, 1.6M in hexane) was added dropwise at −78° C. After stirring for 10 min at −78° C., a solution of 1,4-dioxaspiro[4.5]decane-8-carbonitrile (Step-1, 2.50 g, 14.95 mmol) in dry THF (6.64 mL) was added via Teflon cannula and the solution was stirred at −78° C. for 5 min. A solution of tert-butyldimethylchlorosilane (2.45 g, 16.45 mmol) in dry THF (5.98 mL) was added via Teflon cannula and the reaction mixture was warmed to 22° C. and stirred for 1.5 h. All volatiles were removed under high vacuum (1·10−2 mbar). The residue was dissolved in pentane (10.00 mL) and filtered on a Teflon pad. The solvent was removed under reduced pressure and the residue was purified by bulb-to-bulb distillation (130° C., 1·10−2 mbar) to obtain the title compound (3.02 g) as an oil. As these products are sensitive towards moisture the compound was stored under nitrogen atmosphere. $^{1}$H NMR (400 MHz, $CDCl_3$) δ 3.93-3.89 (m, 4H), 2.28-2.20 (m, 4H), 1.70-1.63 (m, 4H), 0.92 (s, 9H), 0.15-0.10 (m, 6H).

Step-3. 8-(trifluoromethyl)-1,4-dioxaspiro[4.5]decane-8-carbonitrile

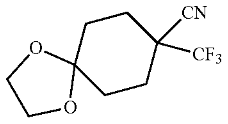 [SMILES: N#CC1(C(F)(F)F)CCC2(CC1)OCCO2]

N-(tert-butyldimethylsilyl)-1-(1,4-dioxaspiro[4.5]decan-8-ylidene)methanimine (2.50 g, 7.99 mmol, 90% Wt) was added to a mixture of V(O)salen (222.9 mg, 0.40 mmol)[2] and 1-(trifluoromethyl)-113-benzo[d][1,2]iodaoxol-3(1H)-one (Step-2, 4.21 g, 7.99 mmol, 60% Wt) in a flame-dried screw-cap vial at 0° C. The reaction mixture was diluted with DCM (2.00 mL) and stirred from 0° C. to 22° C. for 24 h. Volatiles were removed under reduced pressure and the reaction mixture was directly purified by silica gel column chromatography (Cyclohexane/EtOAc, 0% to 25%). The residue was further purified by silica gel column chromatography eluting with DCM to obtain the title compound (1.02 g) as a solid. $^{1}$H NMR (400 MHz, $CDCl_3$) δ 4.05-3.90 (m, 4H), 2.20-2.11 (m, 2H), 2.09-1.81 (m, 6H). $^{19}$F NMR (376 MHz, $CDCl_3$) 5-75.67.

[2] Prepared according to Früh, N. and Togni, A. (2014), Vanadium-Catalyzed Solvent-Free Synthesis of Quaternary α-Trifluoromethyl Nitriles by Electrophilic Trifluoromethylation. Angew. Chem. Int. Ed., 53: 10813-10816.

Step-4. 4-oxo-1-(trifluoromethyl)cyclohexane-1-carbonitrile

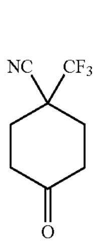

TFA (412.7 μL, 5.36 mmol) was added to a stirred solution of 8-(trifluoromethyl)-1,4-dioxaspiro[4.5]decane-8-carbonitrile (Step-3, 84.0 mg, 0.36 mmol) in DCM (0.70 mL) at 22° C. The resulting mixture was stirred at 22° C. for 48 h. The reaction mixture was diluted with DCM and washed with $NaHCO_3$ (sat. aqueous). The layers were separated and the aqueous was further extracted with DCM. The combined organics were dried over anhydrous sodium sulfate, filtered and concentrated under reduced pressure. The residue was purified by silica gel column chromatography eluting with DCM to obtain the title compound (50.5 mg) as an oil. $^{1}$H NMR (400 MHz, $CDCl_3$) δ 2.74 (td, 2H), 2.64-2.56 (m, 2H), 2.51 (ddt, 2H), 2.21-210 (m, 2H). $^{19}$F NMR (376 MHz, $CDCl_3$) δ −75.29.

Step-5. N-(4-cyano-4-(trifluoromethyl)cyclohexylidene)-2-methylpropane-2-sulfinamide

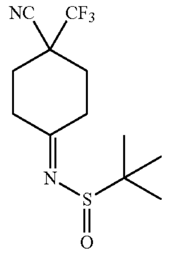 [SMILES: CC(C)(C)S(=O)N=C1CCC(C#N)(C(F)(F)F)CC1]

Titanium(IV) isopropoxide (107.0 μl, 0.35 mmol) was added to a solution of 4-oxo-1-(trifluoromethyl)cyclohexane-1-carbonitrile (Step-4, 48.0 mg, 0.25 mmol) and 2-methylpropane-2-sulfinamide (36.5 mg, 0.30 mmol) in THF (0.50 mL). The resulting solution was stirred at 22° C. for 4 h. The mixture was quenched with 20 mL of $NaHCO_3$ (sat., aq.)/NaCl (sat., aq.) (1/1 v/v). The resulting mixture was stirred for 30 min then filtered through celite and the solid was diluted with EtOAc. The mixture was extracted with EtOAc and the combined organic layers were dried over sodium sulfate, filtered and concentrated under reduced pressure. The residue was purified by silica gel column chromatography (DCM/EtOAc, 0% to 30%) to obtain the title compound (29.4 mg) as a solid. $^{1}$H NMR (400 MHz, $CDCl_3$) δ 3.92 (d, 1H), 2.81-2.55 (m, 3H), 2.47-2.36 (m, 2H), 2.10-1.96 (m, 2H), 1.25 (s, 9H). $^{19}$F NMR (376 MHz, $CDCl_3$) δ −75.47, −75.60.

Step-6. N-(4-cyano-4-(trifluoromethyl)cyclohexyl)-2-methylpropane-2-sulfinamide

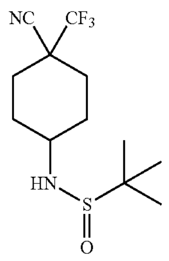 [SMILES: CC(C)(C)S(=O)NC1CCC(C#N)(C(F)(F)F)CC1]

$LiAlH_4$ (42.2 μL, 0.08 mmol, 2.0 M in $Et_2O$) was added dropwise to a solution of N-(4-cyano-4-(trifluoromethyl)cyclohexylidene)-2-methylpropane-2-sulfinamide (Step-5, 24.9 mg, 0.08 mmol) in THF (563.0 μL) at −78° C. The resulting solution was stirred at −78° C. for 30 min. The reaction mixture was diluted with $Et_2O$ (10.00 mL) and quenched with water at 0° C. Anhydrous sodium sulfate was added and the resulting mixture was stirred at 22° C. for 15 min. The solids were filtered over a Teflon pad and the filtrate was concentrated under reduced pressure to obtain the title compound (24.9 mg) as a solid and was directly used in the next step without further purification. $^{19}F$ NMR (376 MHz, $CDCl_3$) δ −75.89, −75.97.

Step-7. 4-amino-1-(trifluoromethyl)cyclohexane-1-carbonitrile hydrochloride

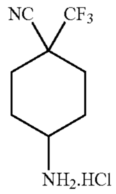

HCl (336.1 μL, 0.42 mmol, 1.25 M in MeOH) was added to a solution of N-(4-cyano-4-(trifluoromethyl)cyclohexyl)-2-methylpropane-2-sulfinamide (Step-6, 24.9 mg, 0.08 mmol) in solution in MeOH (168.0 μL). The reaction mixture was stirred at 22° C. for 10 min. The volatiles were removed under reduced pressure and the residue was triturated in $Et_2O$. The solid was filtered off and washed with $Et_2O$ to obtain the title compound (16.5 mg) as a solid. TLC-MS (APCI): $[M+H]^+$=229.1.

Step-8. (1R,3s,5S)—N-(4-cyano-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide

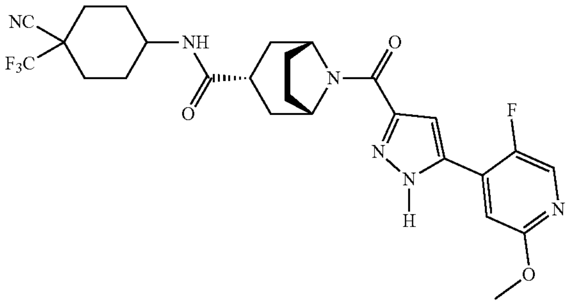

HATU (31.2 mg, 0.08 mmol) and 4-amino-1-(trifluoromethyl)cyclohexane-1-carbonitrile hydrochloride (Step-7, 16.5 mg, 0.07 mmol) were added to a solution of (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 27.1 mg, 0.07 mmol) and DIPEA (25.0 μL, 0.14 mmol) in DMF (240.0 μL). The reaction mixture was stirred at 22° C. for 18 h. The reaction mixture was directly purified by reverse phase column chromatography (using the following conditions: C18 column, 5% to 95% MeOH/Water (0.1% HCOOH)) to obtain the title compound (16.5 mg) as a solid. $^1H$ NMR (400 MHz, $CDCl_3$) δ 8.28 (s, 1H), 7.89 (d, 1H), 7.33 (d, 1H), 7.13 (s, 1H), 5.38-4.55 (m, 2H), 3.88 (s, 3H), 3.70-3.55 (m, 1H), 2.85-2.71 (m, 1H), 2.21-1.58 (m, 14H), 1.49-1.32 (m, 2H). $^{19}F$ NMR (376 MHz, $CDCl_3$) δ −70.10, −137.16, −137.99

Example 439. A Diastereomeric Mixture of (S)—N ((1s,4R)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1r,4S)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

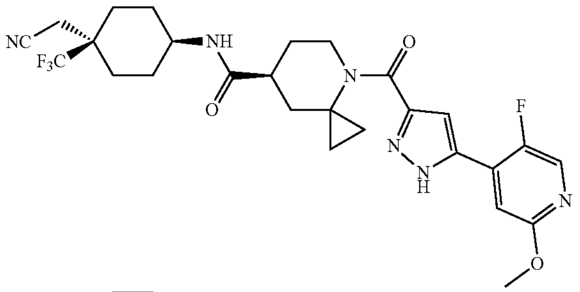

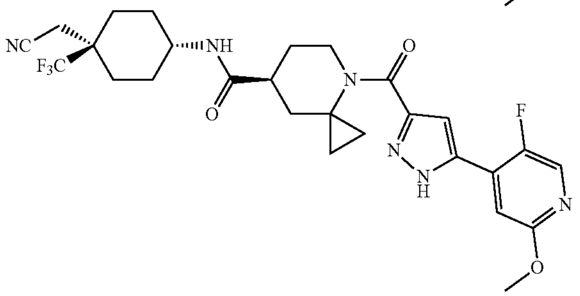

Step-1. 8-(trifluoromethyl)-1,4-dioxaspiro[4.5]decane-8-carbaldehyde

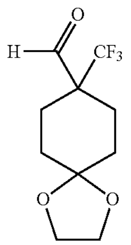 [SMILES: O=CC1(C(F)(F)F)CCC2(CC1)OCCO2]

DIBAL-H (1.22 mL, 1.22 mmol, 1M in DCM) was added dropwise to a solution of 8-(trifluoromethyl)-1,4-dioxaspiro[4.5]decane-8-carbonitrile (Step-4 f-om synthesis of Example 438, 261.0 mg, 1.11 mmol) in solution in DCM (5.50 mL) at −40° C. under vigorous stirring. The reaction mixture was stirred at −40° C. for 1 h. The reaction mixture was quenched by addition of sat. aq. $NH_4Cl$ at −40° C. and then warmed up to 22° C. The reaction mixture was diluted with $Et_2O$. The organic layers were combined, dried over anhydrous $Na_2SO_4$, filtered, and concentrated under reduced pressure to obtain the title compound (234.0 mg) as a solid. $^1H$ NMR (400 MHz, $CDCl_3$) δ 9.65 (s, 1H), 3.96-3.92 (m, 4H), 2.29-2.13 (m, 2H), 2.05-1.93 (m, 2H), 1.78-1.69 (m, 2H), 1.54 (td, 2H). $^{19}F$ NMR (376 MHz, $CDCl_3$) δ −72.59.

Step-2. (8-(trifluoromethyl)-1,4-dioxaspiro[4.5]decan-8-yl)methanol

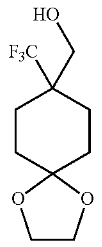

$NaBH_4$ (56.9 mg, 1.50 mmol) was added to a solution of 8-(trifluoromethyl)-1,4-dioxaspiro[4.5]decane-8-carbaldehyde (Step-1, 358.0 mg, 1.50 mmol) in MeOH (7.50 mL) at 0° C. The reaction mixture was stirred at 0° C. for 2 h. The reaction mixture was quenched by addition of sat. aq. $NH_4Cl$. MeOH was removed under reduced pressure. The residue was diluted with water and extracted with $Et_2O$. The combined organics were dried over anhydrous sodium sulfate, filtered and concentrated under reduced pressure. The residue was purified by silica gel column chromatography (EtOAc/Cyclohexane, 0% to 50%) to obtain the title compound (255.0 mg) an oil. $^1H$ NMR (400 MHz, $CDCl_3$) δ 3.97-3.94 (m, 4H), 3.79 (s, 2H), 1.95-1.59 (m, 9H). $^{19}F$ NMR (376 MHz, $CDCl_3$) δ −74.81.

Step-3. (8-(trifluoromethyl)-1,4-dioxaspiro[4.5]decan-8-yl)methyl 4-methylbenzenesulfonate

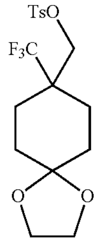

nBuLi (308.31 μL, 0.49 mmol, 1.60 molar) was added dropwise to a solution of (8-(trifluoromethyl)-1,4-dioxaspiro[4.5]decan-8-yl)methanol (Step-2, 79.0 mg, 0.33 mmol) in THF (0.66 mL) at 0° C. The mixture was stirred at 0° C. for 10 min. A solution of tosyl chloride (75.2 mg, 0.39 mmol) in THF (0.50 mL) was added to the reaction mixture. After 15 min stirring at 0° C., the reaction mixture was warmed up to 22° C. and stirred for 16 h. The reaction mixture was quenched by addition of water and extracted with $Et_2O$. The combined organics were dried over anhydrous sodium sulfate, filtered and concentrated under reduced pressure. The residue was purified by silica gel column chromatography (EtOAc/Cyclohexane, 0% to 50%) to obtain the title compound (87.0 mg) as a solid. $^1H$ NMR (400 MHz, $CDCl_3$) δ 7.82-7.75 (m, 2H), 7.38-7.33 (m, 2H), 4.10 (s, 2H), 3.96-3.91 (m, 4H), 1.96-1.85 (m, 2H), 1.79-1.63 (m, 4H), 1.60-1.48 (m, 2H). $^{19}F$ NMR (376 MHz, CDCl3) δ −75.69.

Step-4. 2-(8-(trifluoromethyl)-1,4-dioxaspiro[4.5]decan-8-yl)acetonitrile

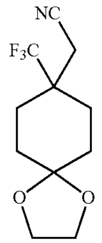

A solution of (8-(trifluoromethyl)-1,4-dioxaspiro[4.5]decan-8-yl)methyl 4-methylbenzenesulfonate (Step-3, 120.0 mg, 0.30 mmol), sodium iodide (13.7 mg, 0.09 mmol) and NaCN (44.7 mg, 0.91 mmol) was heated at 120° C. for 24 h in a sealed tube. The reaction mixture was diluted with water and the aqueous was extracted with $Et_2O$. The combined organics was washed with water, dried over anhydrous sodium sulfate, filtered and concentrated under reduced pressure. The residue was purified by silica gel column chromatography (EtOAc/Cyclohexane, 0% to 50%) to obtain the title compound (62.7 mg) as a solid. $^1H$ NMR (400 MHz, CDCl3) δ 4.00-3.90 (m, 4H), 2.67 (s, 2H), 2.10-2.01 (m, 2H), 1.90-1.74 (m, 4H), 1.67-1.57 (m, 2H). $^{19}F$ NMR (376 MHz, $CDCl_3$) δ −77.06.

Step-5. 2-(4-oxo-1-(trifluoromethyl)cyclohexyl)acetonitrile

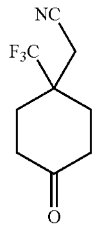 [SMILES: N#CCC1(C(F)(F)F)CCC(=O)CC1]

TFA (290.7 μL, 3.77 mmol) was added to a stirred solution of 2-(8-(trifluoromethyl)-1,4-dioxaspiro[4.5]decan-8-yl)acetonitrile (Step-4, 62.7 mg, 0.25 mmol) in DCM (0.50 mL). The resulting mixture was stirred at 22° C. for 48 h. The reaction mixture was diluted with DCM and washed with sat. aq. $NaHCO_3$. The combined organics were dried over anhydrous sodium sulfate, filtered and concentrated under reduced pressure. The residue was purified by silica gel column chromatography (EtOAc/Cyclohexane, 0% to 60%) to obtain the title compound (51.0 mg) as an oil. $^1H$ NMR (400 MHz, $CDCl_3$) δ 2.78 (s, 2H), 2.61-2.39 (m, 4H), 2.32-2.23 (m, 2H), 2.16-2.06 (m, 2H). $^{19}F$ NMR (376 MHz, $CDCl_3$) δ −76.32.

Step-6. N-(4-(cyanomethyl)-4-(trifluoromethyl)cyclohexylidene)-2-methylpropane-2-sulfinamide

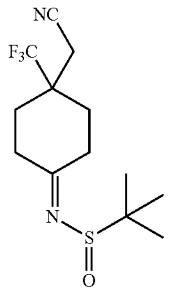 [SMILES: CC(C)(C)S(=O)N=C1CCC(CC#N)(C(F)(F)F)CC1]

Titanium ethoxide (103.5 μL, 0.50 mmol) was added to a solution of 2-(4-oxo-1-(trifluoromethyl)cyclohexyl)acetonitrile (Step-5, 51.0 mg, 0.25 mmol) and 2-methylpropane-2-sulfinamide (36.2 mg, 0.30 mmol) in THF (0.50 mL). The resulting solution was stirred at 22° C. for 16 h. The mixture was quenched with 20 mL of $NaHCO_3$ (sat., aq.)/NaCl (sat., aq.) (1/1 v/v). The mixture was stirred for 30 min then filtered through celite and the solid was washed with EtOAc. The mixture was extracted with EtOAce and the combined organic layers were dried over sodium sulfate, filtered and concentrated. The residue was purified by silica gel column chromatography (EtOAc/Cyclohexane, 0% to 100%) to obtain the title compound (35.9 mg) as a solid and used in the next step without further purification. $^1$H NMR (400 MHz, $CDCl_3$) δ 5.14-5.03 (m, 1H), 4.75 (d, 1H), 2.74 (d, 2H), 2.70-2.61 (m, 2H), 2.56-2.42 (m, 2H), 2.31-1.94 (m, 3H), 1.25 (s, 9H). TLC-MS, (APCI): 309.1 $[M+H]^+$.

Step-7. N-((1s,4s)-4-(cyanomethyl)-4-(trifluoromethyl)cyclohexyl)-2-methylpropane-2-sulfinamide and N-((1r,4r)-4-(cyanomethyl)-4-(trifluoromethyl) cyclohexyl)-2-methylpropane-2-sulfinamide

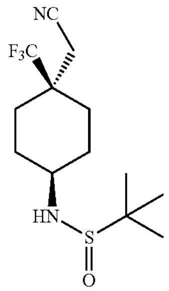
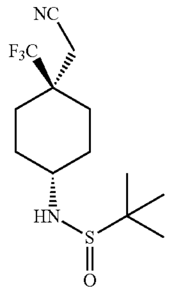

$LiAlH_4$ (52.4 μL, 0.10 mmol, 2.0M in $Et_2O$) was added dropwise to a solution of N-(4-(cyanomethyl)-4-(trifluoromethyl)cyclohexylidene)-2-methylpropane-2-sulfinamide (Step-6, 35.9 mg, 0.10 mmol, 90% Wt) in THF (698.0 μL) at −78° C. The resulting solution was stirred at −78° C. for 2 h. The reaction mixture was diluted with $Et_2O$ and quenched with water at −78° C. Anhydrous sodium sulfate was added and the mixture was stirred at 22° C. for 15 min. The solids were filtered over a Teflon pad and concentrated under reduced pressure. The residue was purified by silica gel column chromatography (EtOAc/Cyclohexane, 30% to 100%) to obtain N-((1s,4s)-4-(cyanomethyl)-4-(trifluoromethyl)cyclohexyl)-2-methylpropane-2-sulfinamide and N-((1r,4r)-4-(cyanomethyl)-4-(trifluoromethyl)cyclohexyl)-2-methylpropane-2-sulfinamide in two fractions.

The first eluting fraction (16.2 mg) was obtained as a solid.

$^1$H NMR (400 MHz, $CDCl_3$) δ 3.25 (tt, 1H), 3.13 (d, 1H), 2.16-2.05 (m, 2H), 1.96-1.87 (m, 2H), 1.87-1.73 (m, 2H), 1.49-1.29 (m, 2H), 1.26-117 (m, 9H). $^{19}$F NMR (376 MHz, $CDCl_3$) δ −78.21.

The second eluting fraction (8.9 mg) was obtained as a solid.

$^1$H NMR (400 MHz, $CDCl_3$) δ 3.52-3.42 (m, 1H), 3.04 (d, 1H), 2.61 (s, 2H), 2.13-2.01 (m, 2H), 1.97-1.77 (m, 2H), 1.76-1.56 (m, 2H), 1.34-1.24 (m, 2H), 1.24-1.19 (m, 9H). $^{19}$F NMR (376 MHz, CDCl3) δ −75.27.

Step-8. 2-((1s,4s)-4-amino-1-(trifluoromethyl)cyclohexyl)acetonitrile hydrochloride and 2-((1r,4r)-4-amino-1-(trifluoromethyl)cyclohexyl)acetonitrile hydrochloride

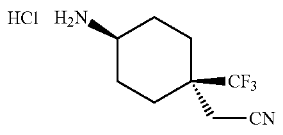

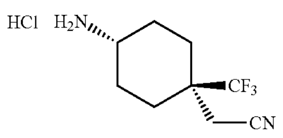

HCl (212.6 μL, 0.27 mmol, 1.25 M in MeOH) was added to a solution of N-(4-(cyanomethyl)-4-(trifluoromethyl)cyclohexyl)-2-methylpropane-2-sulfinamide (the first eluting isomer from Step-7, 16.5 mg, 0.05 mmol) in MeOH (265.0 μL). The reaction mixture was stirred at 22° C. for 15 min. The volatiles were removed under reduced pressure and the residue was triturated in EtOAc and $Et_2O$. The solid was filtered off and washed with $Et_2O$ to obtain isomer 1 (9.0 mg) as solids.

Isomer 1:

$^1$H NMR (400 MHz, $CD_3OD$) δ 3.18 (tt, 1H), 2.93 (s, 2H), 2.10-2.02 (m, 2H), 2.01-1.93 (m, 2H), 1.92-1.80 (m, 2H), 1.63-1.47 (m, 2H). $^{19}$F NMR (376 MHz, $CD_3OD$) δ −79.85.

HCl (80.29 μL, 100.4 μmol, 1.25 M in MeOH) was added to a solution of N-(4-(cyanomethyl)-4-(trifluoromethyl)cyclohexyl)-2-methylpropane-2-sulfinamide (the second eluting isomer from Step-7, 8.9 mg, 20.07 μmol) in MeOH (100.0 μL). The reaction mixture was stirred at 22° C. for 10 min. The volatiles were removed under reduced pressure and the residue was triturated in EtOAc and $Et_2O$. The solid was filtered off and washed with $Et_2O$ to obtain isomer 2 (3.8 mg) as a solid.

Isomer 2:

$^1$H NMR (400 MHz, $CD_3OD$) δ 3.28-3.19 (m, 1H), 2.82 (s, 2H), 2.28-2.17 (m, 2H), 2.05-1.94 (m, 2H), 1.81-1.64 (m, 4H). $^{19}$F NMR (376 MHz, $CD_3OD$) δ −72.88.

Step-9. (S)—N-((1s,4R)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and ('S)—N-((1r,4S)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

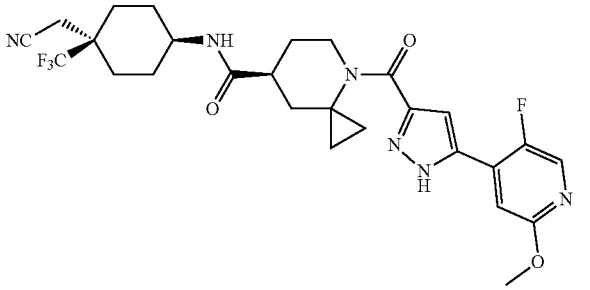

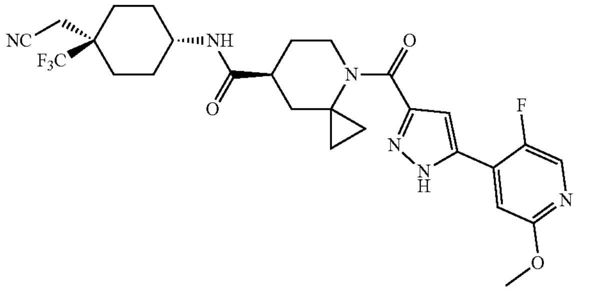

HATU (14.6 mg, 0.04 mmol) and Isomer 1 from Step-8 (8.2 mg, 0.03 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 12.7 mg, 0.03 mmol) and DIPEA (13.2 mg, 0.10 mmol) in DMF (0.20 mL). The resulting solution was stirred at 22° C. for 18 h. The reaction mixture was directly purified by reverse phase column chromatography (using the following conditions: C18 column, 10% to 95% MeOH/Water (0.1% HCOOH)) to obtain a single isomer of the title compound (10.5 mg) as a solid (Example 439-A). $^1H$ NMR (400 MHz, $CD_3OD$) δ 8.12 (s, 1H), 7.37-7.17 (m, 1H), 7.10 (s, 1H), 4.58 (s, 1H), 3.93 (s, 3H), 3.81 (s, 1H), 2.83 (s, 2H), 2.47-2.29 (m, 1H), 2.13-2.00 (m, 2H), 2.00-1.52 (m, 8H), 1.40-0.61 (m, 8H). TLC-MS, (APCI): 563.4 $[M+H]^+$.

HATU (6.1 mg, 0.02 mmol) and Isomer 2 from Step-8 (3.6 mg, 0.01 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 5.5 mg, 0.01 mmol) and DIPEA (5.7 mg, 0.04 mmol) in DMF (0.2 mL). The resulting solution was stirred at 22° C. for 18 h. The reaction mixture was directly purified by reverse phase column chromatography (using the following conditions: C18 column, 10% to 95% MeOH/Water (0.1% HCOOH)) to obtain a single isomer of the title compound different from Example 439-A (2.0 mg) as a solid (Example 439-B). $^1H$ NMR (400 MHz, $CD_3OD$) δ 8.20-8.06 (m, 1H), 7.40-7.16 (m, 2H), 7.10 (s, 1H), 4.58 (s, 1H), 4.02-3.81 (m, 3H), 3.64 (s, 1H), 2.91 (s, 2H), 2.80 (d, 1H), 2.38 (s, 1H), 1.97-1.64 (m, 7H), 1.45-0.64 (m, 10H). TLC-MS, (APCI): 563.4 $[M+H]^+$.

Example 440. (S)-4-(5-(5-fluoro-2-methoxypyridin-4-yl)-1H-pyrazole-3-carbonyl)-N-((2-(2-fluoro-2-methylpropyl)-2-azabicyclo[2.1.1]hexan-4-yl)methyl)-4-azaspiro[2.5]octane-7-carboxamide

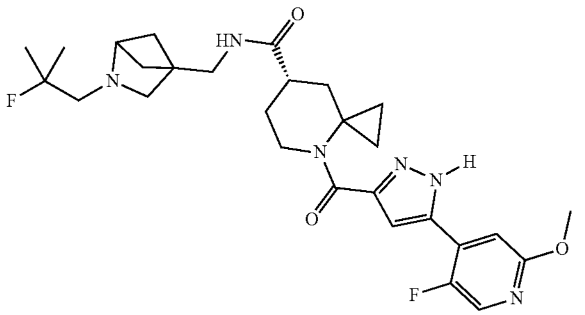 [SMILES: COc1cc(-c2cc(C(=O)N3CC[C@H](C(=O)NCC45CC(C4)N(CC(C)(C)F)C5)CC34CC4)n[nH]2)c(F)cn1]

Step-1. tert-butyl 4-((tosyloxy)methyl)-2-azabicyclo[2.1.1]hexane-2-carboxylate

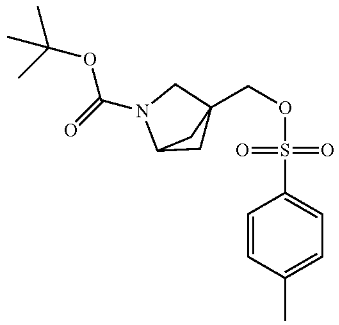 [SMILES: Cc1ccc(S(=O)(=O)OCC23CC(C2)N(C(=O)OC(C)(C)C)C3)cc1]

Tosyl chloride (412.0 mg, 2.16 mmol) and triethylamine (548.0 μL, 3.93 mmol) were added to a solution of tert-butyl 4-(hydroxymethyl)-2-azabicyclo[2.1.1]hexane-2-carboxylate (419.0 mg, 1.96 mmol) in anhydrous DCM (3.45 mL) at 0° C. under nitrogen atmosphere. The reaction mixture was stirred at 22° C. for 16 h. The reaction mixture was quenched with water and The organic layers were dried over anhydrous sodium sulfate, filtered and concentrated under reduced pressure. The residue was purified by silica gel column chromatography (EtOAc/Cyclohexane, 0% to 40%) to obtain the title compound (626.0 mg) as a solid. $^1H$ NMR (400 M Hz, $CDCl_3$) δ 7.81-7.74 (m, 2H), 7.38-7.32 (m, 2H), 4.32 (t, 1H), 4.19 (s, 2H), 3.18 (s, 2H), 2.45 (s, 3H), 1.81-1.74 (m, 2H), 1.45 (s, 9H), 1.45-1.41 (m, 2H).

Step-2. tert-butyl 4-(azidomethyl)-2-azabicyclo[2.1.1.]hexane-2-carboxylate

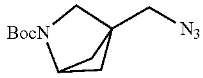 [SMILES: CC(C)(C)OC(=O)N1CC2(CN=[N+]=[N-])CC1C2]

Sodium azide (84.9 mg, 1.31 mmol) was added to a solution of tert-butyl 4-((tosyloxy)methyl)-2-azabicyclo[2.1.1]hexane-2-carboxylate (Step-1, 300.0 mg, 0.82 mmol)

in anhydrous DMF (0.81 mL) in a sealed tube under nitrogen. The reaction mixture was stirred at 50° C. for 18 h. The mixture was diluted with water. The aqueous was extracted with $Et_2O$. The combined organic layers were washed with water, dried over anhydrous sodium sulfate, filtered and concentrated under reduced pressure. The residue was purified by silica gel column chromatography (EtOAc/Cyclohexane, 0% to 40%) to obtain the title compound (195.5 mg) as a solid. $^1$H NMR (400 MHz, $CDCl_3$) δ 4.36 (t, 1H), 3.53 (s, 2H), 3.25 (s, 2H), 1.86-1.79 (m, 2H), 1.51 (dd, 2H), 1.47 (s, 9H).

Step-3. 4-(azidomethyl)-2-azabicyclo[2.1.1]hexane hydrochloride

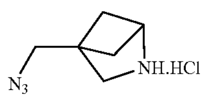

HCl (1.45 mL, 5.79 mmol, 4.0 M in 1,4-dioxane) was added to a solution of tert-butyl 4-(azidomethyl)-2-azabicyclo[2.1.1]hexane-2-carboxylate (Step-2, 137.9 mg, 0.58 mmol) in 1,4-dioxane (1.15 mL) under nitrogen. The reaction mixture was stirred at 22° C. for 16 h. Volatiles were removed under reduced pressure to obtain the title compound (101.0 mg) as a solid. $^1$H NMR (400 MHz, $CD_3OD$) δ 4.20 (t, 1H), 3.73 (s, 2H), 3.26 (s, 2H), 2.14-2.04 (m, 2H), 1.68-1.58 (m, 2H).

Step-4. 4-(azidomethyl)-2-(2-fluoro-2-methylpropyl)-2-azabicyclo[2.1.1]hexane

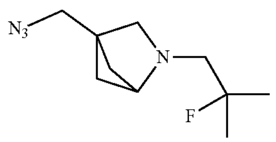

DIPEA (202.0 µL, 1.16 mmol) and 2-fluoro-2-methylpropyl trifluoromethanesulfonate (194.7 mg, 0.87 mmol) were added to a solution of 4-(azidomethyl)-2-azabicyclo[2.1.1]hexane hydrochloride (Step-3, 101.1 mg, 0.58 mmol) in 1,4-Dioxane/DMF (98/3 v/v, 1.40 mL) in a sealed tube under nitrogen. The reaction mixture was heated at 80° C. for 16 h. The resulting mixture was concentrated under reduced pressure. The residue was diluted with water and EtOAc. The organic layer was further extracted with EtOAc. The combined organic layers were dried over anhydrous sodium sulfate, filtered and concentrated under reduced pressure. The residue was purified by silica gel column chromatography (EtOAc/MeOH, 0% to 10%) to obtain the title compound (50.6 mg) as an oil. $^1$H NMR (400 MHz, $CD_3OD$) δ 3.51 (s, 2H), 3.47-3.43 (m, 1H), 2.76 (d, 2H), 2.72 (s, 2H), 1.68-1.57 (m, 4H), 1.40 (s, 3H), 1.35 (s, 3H). $^{19}$F NMR (376 MHz, $CD_3OD$) δ −142.39.

Step-5. (2-(2-fluoro-2-methylpropyl)-2-azabicyclo[2.1.1]hexan-4-yl)methanamine

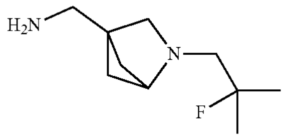

A solution of 4-(azidomethyl)-2-(2-fluoro-2-methylpropyl)-2-azabicyclo[2.1.1]hexane (Step-4, 17.4 mg, 0.08 mmol) and palladium hydroxide on carbon (5.0 mg, 0.04 mmol) in MeOH (0.20 mL) under hydrogen atmosphere (1 atm) was stirred at 22° C. for 18 h. The reaction mixture was filtered on a Teflon pad and concentrated under reduced pressure to obtain the title compound (13.7 mg). $^1$H NMR (400 MHz, $CD_3OD$) δ 3.43-3.40 (m, 1H), 2.82 (s, 2H), 2.75 (d, 2H), 2.67 (s, 2H), 1.62-1.51 (m, 4H), 1.40 (s, 3H), 1.35 (s, 3H). $^{19}$F NMR (376 MHz, $CD_3OD$) δ −142.14.

Step-6. (S)-4-(5-(5-fluoro-2-methoxypyridin-4-yl)-1H-pyrazole-3-carbonyl)-N-((2-(2-fluoro-2-methylpropyl)-2-azabicyclo[2.1.1]hexan-4-yl)methyl)-4-azaspiro[2.5]octane-7-carboxamide

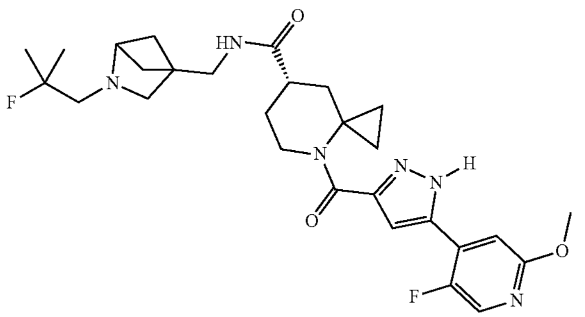 [SMILES: COc1cc(-c2cc(C(=O)N3CC[C@H](C(=O)NCC45CC(C4)N(CC(C)(C)F)C5)CC34CC4)n[nH]2)c(F)cn1]

HATU (18.4 mg, 0.05 mmol) and (2-(2-fluoro-2-methylpropyl)-2-azabicyclo[2.1.1]hexan-4-yl)methanamine (12.9 mg, 0.06 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 16.0 mg, 0.04 mmol) and DIPEA (0.02 mL, 0.10 mmol) in DMF (0.2 mL). The resulting solution was stirred at 22° C. for 18 h. The reaction mixture was directly purified by reverse phase column chromatography (using the following conditions: C18 column, 5% to 95% MeOH/Water (0.1% HCOOH)) to obtain the title compound (10.0 mg) as a solid. $^1$H NMR (400 MHz, DMSO-d6) δ 13.99 (s, 1H), 8.27 (s, 1H), 7.88 (s, 1H), 7.32 (d, 1H), 7.03 (s, 1H), 4.47 (s, 0.77H), 3.87 (s, 3H), 3.54-3.06 (m, 6.23H), 2.85-2.62 (m, 5H), 1.74 (s, 1H), 1.55-1.38 (m, 5H), 1.36 (s, 3H), 1.30 (s, 3H), 1.07-0.47 (m, 4H). $^{19}$F NMR (376 MHz, DMSO) δ −69.48, −71.37, −138.48.

Example 441. (1R,3s,5S)—N-(4-amino-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide

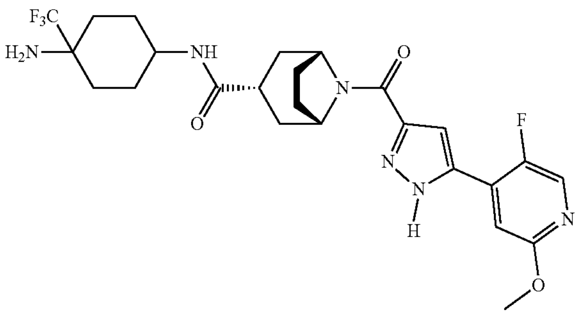

Step-1. 2-methyl-N-(1,4-dioxaspiro[4.5]decan-8-ylidene)propane-2-sulfinamide

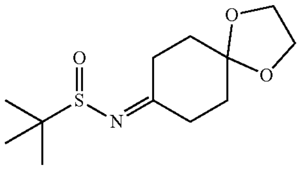 [SMILES: CC(C)(C)S(=O)N=C1CCC2(CC1)OCCO2]

Tetraethoxytitanium (2.82 mL, 13.45 mmol) was added to a mixture of 1,4-dioxaspiro[4.5]decan-8-one (1.50 g, 9.6 mmol) and 2-methylpropane-2-sulfinamide (1.40 g, 11.53 mmol) in THF (19.20 mL). The resulting solution was stirred at 22° C. for 16 h. The mixture was quenched with 50 mL of $NaHCO_3$ (sat., aq.)/NaCl (sat., aq.) (1/1 v/v). The mixture was stirred for 30 min and filtered through celite and the solid was washed with EtOAc. The mixture was extracted with EtOAc and the combined organic layers were dried over sodium sulfate, filtered and concentrated. The residue was purified by silica gel column chromatography (DCV/EtOAc, 0% to 40%) to obtain the title compound (1.10 g) as a solid. $^1H$ NMR (400 MHz, $CDCl_3$) δ 4.00-3.97 (m, 4H), 3.10 (ddd, 1H), 2.88 (ddd, 1H), 2.62 (dd, 2H), 2.54-2.47 (m, 1H), 2.06-1.98 (m, 1H), 1.91 (dt, 2H), 1.23 (s, 9H-1).

Step-2. 2-methyl-N-(8-(trifluoromethyl)-1,4-dioxaspiro[4.5]decan-8-yl)propane-2-sulfinamide

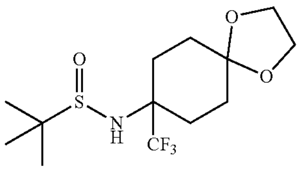 [SMILES: CC(C)(C)S(=O)NC1(C(F)(F)F)CCC2(CC1)OCCO2]

TBAF (5.78 mL, 5.78 mmol, 1 M in THF) was added to a solution of 2-methyl-N-(1,4-dioxaspiro[4.5]decan-8-ylidene)propane-2-sulfinamide (Step-1, 1.00 g, 3.86 mmol) in THE (38.50 mL) at −20° C. Trimethyl(trifluoromethyl)silane (1.65 g, 11.57 mmol) was slowly added to the reaction mixture with vigorous stirring. The reaction mixture was stirred at 22° C. over 16 h. The mixture was quenched by addition of $NaHCO_3$ (sat. aq.). THE was removed under reduced pressure and the residue was diluted with water and EtOAc. The aqueous was further extracted with EtOAc. The combined organic layers were dried over anhydrous sodium sulfate, filtered and concentrated under reduced pressure. The residue was purified by silica gel column chromatography (Cyclohexane/EtOAc, 0% to 100%) to obtain the title compound (163.0 mg) as a solid. $^1H$ NMR (400 MHz, $CDCl_3$) δ 3.98-3.91 (m, 4H), 3.30 (s, 1H), 2.14-1.96 (m, 5H), 1.81-1.63 (m, 3H), 1.25 (s, 9H). $^{19}F$ NMR (376 MHz, $CDCl_3$) δ −80.42.

Step-3. 2-methyl-N-(4-oxo-1-(trifluoromethyl)cyclohexyl)propane-2-sulfinamide

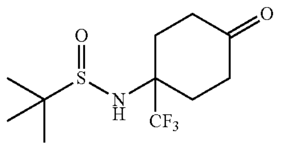 [SMILES: CC(C)(C)S(=O)NC1(C(F)(F)F)CCC(=O)CC1]

TFA (381.2 μL, 4.95 mmol) was added to a solution 2-methyl-N-(8-(trifluoromethyl)-1,4-dioxaspiro[4.5]decan-8-yl)propane-2-sulfinamide (Step-2, 163.0 mg, 0.50 mmol) in DCM (2.50 mL). The reaction mixture was stirred at 22° C. for 16 h. The reaction mixture was diluted with DCM and washed with $NaHCO_3$ (sat. aq.). The organic layer was dried over anhydrous sodium sulfate, filtered and concentrated under reduced pressure. The residue was purified by silica gel column chromatography (Cyclohexane/EtOAc, 0% to 100%) to obtain the title compound (123.3 mg) as an oil. $^1H$ NMR (400 MHz, $CDCl_3$) δ 3.57 (s, 1H), 2.92 (td, 1H), 2.64-2.37 (m, 4H), 2.30-2.16 (m, 3H), 1.29 (s, 9H).

Step-4. N-(4-(hydroxyimino)-1-(trifluoromethyl)cyclohexyl)-2-methylpropane-2-sulfinamide

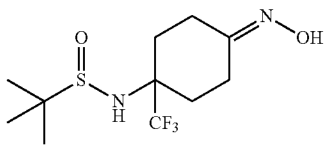 [SMILES: CC(C)(C)S(=O)NC1(C(F)(F)F)CCC(=NO)CC1]

Hydroxylamine hydrochloride (33.0 mg, 0.48 mmol) was added to a mixture of sodium acetate (42.5 mg, 0.52 mmol), and MeOH (2.10 mL). The resulting mixture was stirred at 22° C. for 30 min. Then a solution of 2-methyl-N-(4-oxo-1-(trifluoromethyl)cyclohexyl)propane-2-sulfinamide (Step-3, 1233 mg, 0.43 mmol) in MeOH (1.00 mL) was added to the reaction mixture. The reaction mixture was stirred at 60° C. for 16 h. The reaction mixture was then cooled to 22° C. and MeOH was removed under reduced pressure. The residue was diluted with water and EtOAc. The aqueous was further extracted with EtOAc. The combined organic layers were dried over anhydrous sodium sulfate, filtered and concentrated under reduced pressure. The residue was purified by silica gel column chromatography (EtOAc/Cyclohexane, 0% to 100%) to obtain the title compound (93.6 mg) as a solid. $^1$H NMR (400 MHz, $CDCl_3$) δ 3.42 (s, 1H), 3.25-3.14 (m, 1H), 2.63-1.72 (m, 7H), 1.19 (d, 9H). $^{19}$F NMR (376 MHz, $CDCl_3$) δ −80.78, −80.87.

Step-5. tert-butyl (4-((tert-butylsulfinyl)amino)-4-(trifluoromethyl)cyclohexyl)carbamate

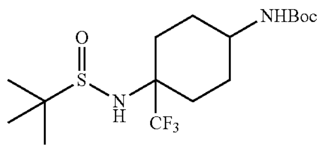 [SMILES: CC(C)(C)OC(=O)NC1CCC(NS(=O)C(C)(C)C)(C(F)(F)F)CC1]

$NaBH_4$ (9.32 mg, 0.25 mmol) was added to a solution of A-(4-(hydroxyimino)-1-(trifluoromethyl)cyclohexyl)-2-methylpropane-2-sulfinamide (Step-4, 74.0 mg, 0.25 mmol) and nickel(II) chloride hexahydrate (76.1 mg, 0.32 mmol) in MeOH (4.90 mL) at −78° C. The resulting mixture was warmed up to 0° C. and stirred at this temperature for 4 h. $Boc_2o$ (80.7 mg, 0.37 mmol) was then added and the reaction mixture was stirred at 22° C. for 18 h. The reaction mixture was quenched with brine at 0° C. Volatiles were removed under reduced pressure. The residue was diluted with water and EtOAc. The aqueous was further extracted with EtOAc. The organic layers were combined and dried over anhydrous sodium sulfate, filtered and concentrated. The residue was purified by silica gel column chromatography (EtOAc/Cyclohexane, 0% to 90%) to obtain the title compound (96.0 mg) as a solid. $^1$H NMR (400 MHz, $CD_3OD$) δ 3.44-3.33 (m, 1H), 2.28-1.65 (m, 8H), 1.47-1.42 (m, 9H), 1.32-1.26 (m, 9H). $^{19}$F NMR (376 MHz, $CD_3OD$) δ −81.53, −81.94.

Step-6. N-(4-amino-1-(trifluoromethyl)cyclohexyl)-2-methylpropane-2-sulfinamide

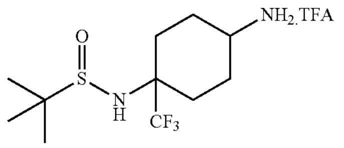

TFA (41.86 μL, 0.54 mmol) was added to a solution of tert-butyl (4-((tert-butylsulfinyl)amino)-4-(trifluoromethyl) cyclohexyl)carbamate (Step-5, 30.0 mg, 0.08 mmol) in DCM (388.0 L) at 0° C. The reaction mixture was warmed up to 22° C. and stirred for 1.5 h. Volatiles were removed under reduced pressure. The residue was co-evaporated twice with cyclohexane to obtain the title compound (22.2 mg) as an oil. $^1$H NMR (400 MHz, $CD_3OD$) δ 3.17-3.06 (m, 1H), 2.36-1.58 (m, 8H), 1.23-1.16 (m, 9H). $^{19}$F NMR (376 MHz, $CD_3OD$) δ −77.36, −82.14.

Step-7. (1R,3s,5S)—N-(4-((tert-butylsulfinyl) amino)-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide

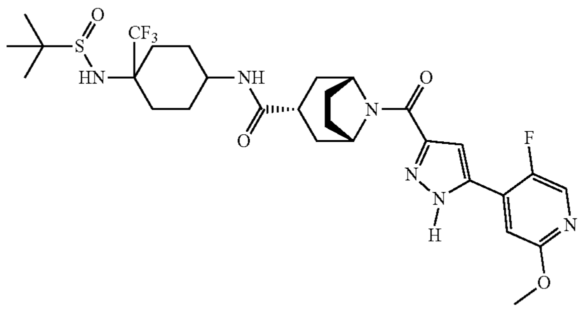

HATU (28.2 mg, 0.07 mmol) and 2-methyl-N-(4-((2,2,2-trifluoroacetyl)-14-azanyl)-1-(trifluoromethyl)cyclohexyl) propane-2-sulfinamide (25.1 mg, 0.07 mmol) were added to a solution of (1R,3s,5S)-8-(5-(5-fluoro-2-methoxypyridin-4-yl)-1H-pyrazole-3-carbonyl)-8-azabicyclo[3.2.1]octane-3-carboxylic acid (INTERMEDIATE 508, 24.5 mg, 0.07 mmol) and DIPEA (57.0 μL, 0.33 mmol) in DMF (218.0 μL). The reaction mixture was stirred at 22° C. for 18 h. The mixture was directly purified by reverse phase column chromatography (using the following conditions: C18 column, 5% to 95% MeOH/Water (0.1% HCOOH)) to obtain the title compound (30.6 mg) as a solid. $^1$H NMR (400 MHz, DMSO) δ 8.28 (d, 1H), 7.82 (d, 1H), 7.33 (d, 1H), 7.13 (d, 1H), 5.40 (s, 1H), 5.07-4.55 (m, 2H), 3.88 (s, 3H), 3.81-3.72 (m, 0.4H), 3.59-3.44 (m, 0.6H), 2.97-2.89 (m, 0.4H), 2.87-2.76 (m, 0.6H), 2.23-1.48 (m, 16H), 1.25-1.14 (m, 9H).

Step-8. (1R,3s,5S)—N-(4-amino-4-(trifluoromethyl) cyclohexyl)-8-(5-(5-fluoro-2-methoxypyridin-4-yl)-1H-pyrazole-3-carbonyl)-8-azabicyclo[3.2.1]octane-3-carboxamide

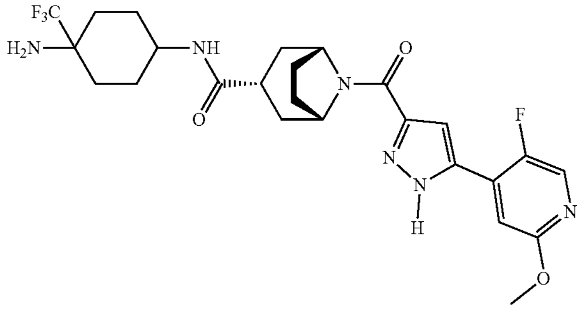

HCl (209.5 μL, 0.25 mmol, 1.2 M in MeOH) was added to a solution of (1R,3s,5S)—N-(4-((tert-butylsulfinyl) amino)-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide (Step-1, 20.2 mg, 0.03 mmol) in MeOH (314.0 μL) at −78° C. The resulting mixture was stirred at −78° C. for 2.5 h. Volatiles were removed under reduced pressure and the residue was purified by reverse phase column chromatography (using the following conditions: C18 column, 5% to 95% Water (0.1% HCOOH)/

MeOH)) to obtain the title compound (9.7 mg) as a solid. $^1$H NMR (400 MHz, DMSO) δ 13.98 (s, 1H), 8.28 (d, 1H), 7.73 (t, 1H), 7.33 (d, 1H), 7.13 (d, 1H), 4.95 (s, 1H), 4.68 (d, 1H), 3.87 (s, 3H), 3.81-3.71 (m, 0.3H), 3.48-3.38 (m, 0.7H), 2.98-2.87 (m, 0.3H), 2.84-2.72 (M, 0.7H), 2.18-1.16 (m, 18H). $^{19}$F NMR (376 MHz, DMSO) δ −81.98, −82.66. TLC-MS (APCI): 539.3 $[M+H]^+$.

Example 442. (S)-4-(5-(5-fluoro-2-methoxypyridin-4-yl)-1H-pyrazole-3-carbonyl)-N-(2-(2-fluoro-2-methylpropyl)-2-azabicyclo[2.1.1]hexan-4-yl)-4-azaspiro[2.5]octane-7-carboxamide

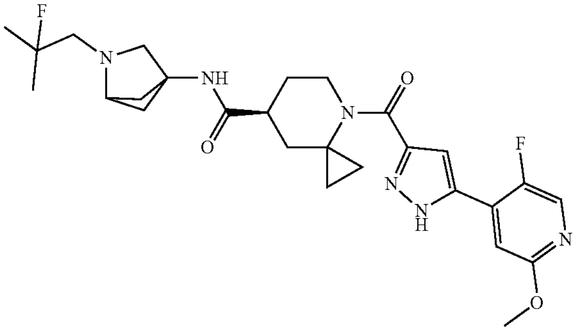 [SMILES: COc1cc(-c2cc(C(=O)N3CC[C@H](C(=O)NC45CC(C4)N(CC(C)(C)F)C5)CC34CC4)n[nH]2)c(F)cn1]

Step-1. 2-(tert-butoxycarbonyl)-2-azabicyclo[2.1.1]hexane-4-carboxylic acid

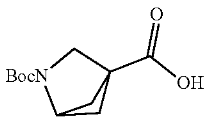

Pyridinium dichromate (3.53 g, 9.38 mmol) was added to a solution of tert-butyl 4-(hydroxymethyl)-2-azabicyclo[2.1.1]hexane-2-carboxylate (400.0 mg, 1.88 mmol) in DMF (10.00 mL). The mixture was stirred at 22° C. for 18 h. The reaction was diluted with water (20.0 mL) and EtOAc (20.0 mL). The aqueous layer was saturated with solid NaCl and extracted with EtOAc, washed with brine, dried over $MgSO_4$, filtered and concentrated under reduced pressure to obtain the title compound (510.0 mg) as an oil. $^1$H NMR (400 MHz, DMSO) δ 12.71 (s, 1H), 4.16 (t, 1H), 3.34 (s, 2H), 2.13-2.05 (m, 2H), 1.61-1.55 (m, 2H), 1.40 (s, 9H).

Step-2. tert-butyl 4-(((benzyloxy)carbonyl)amino)-2-azabicyclo[2.1.1]hexane-2-carboxylate

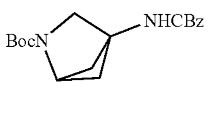

DPPA (702.6 mg, 2.553 mmol) was added to a mixture of 2-(tert-butoxycarbonyl)-2-azabicyclo[2.1.1]hexane-4-carboxylic acid (Step-1, 510.0 mg, 1.62 mol) in toluene (7.69 mL). The reaction mixture was refluxed for 1 h. The reaction mixture was cooled to 22° C. and benzyl alcohol (0.35 mL, 3.39 mmol) was added dropwise and the resulting mixture was refluxed for 18 h. The reaction mixture was cooled to 22° C. and concentrated under reduced pressure. The residue was purified by silica gel column chromatography (EtOAc in Cyclohexane, 0% to 50%) to obtain the title compound (476.0 mg) as an oil. $^1$H NMR (400 MHz, $CDCl_3$) δ 7.39-7.33 (m, 10H), 5.24 (s, 1H), 5.10 (s, 2H), 4.27 (t, 1H), 3.38 (s, 2H), 1.86-1.74 (m, 2H), 1.63-1.59 (m, 2H), 1.46 (s, 9H).

Step-3. benzyl (2-azabicyclo[2.1.1]hexan-4-yl)carbamate 2,2,2-trifluoroacetate

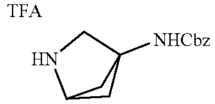 [SMILES: O=C(NC12CNC(C1)C2)OCc1ccccc1]

TFA (1.10 g, 9.62 mmol) was added to a solution of tert-butyl 4-(((benzyloxy)carbonyl)amino)-2-azabicyclo[2.1.1]hexane-2-carboxylate (Step-2, 476.0 mg, 0.96 mmol) in DCM (4.81 mL). The reaction mixture was stirred at 22° C. for 18 h. The resulting mixture was concentrated under reduced pressure to obtain the title compound and was used directly in the next step without further purification. TLC-MS (APCI): 233.2 $[M+H]^+$.

Step-4. benzyl (2-(2-fluoro-2-methylpropyl)-2-azabicyclo[2.1.1]hexan-4-yl)carbamate

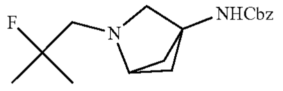 [SMILES: CC(C)(F)CN1CC2(NC(=O)OCc3ccccc3)CC1C2]

DIPEA (621.0 mg, 4.81 mmol) and 2-fluoro-2-methylpropyl trifluoromethanesulfonate (258.7 mg, 1.15 mmol) were added to a solution of benzyl (2-azabicyclo[2.1.1]hexan-4-yl)carbamate 2,2,2-trifluoroacetate (Step-3, 333.0 mg, 0.96 mmol) in 1,4-dioxane (4.80 mL). The reaction mixture was stirred at 80° C. for 18 h. The reaction mixture was diluted with water and extracted with DCM. The combined organic layers were washed with brine, dried over $Na_2SO_4$, filtered and concentrated under reduced pressure. The residue was purified by silica gel column chromatography (EtOAc in Cyclohexane, 35% to 55%) to obtain the title compound (155.0 mg) as an oil. $^1$H NMR (400 MHz, $CDCl_3$) δ 7.40-7.30 (m, 5H), 5.20 (s, 1H), 5.09 (s, 2H), 3.04-2.61 (m, 4H), 2.04-1.80 (m, 4H), 1.47-1.33 (m, 6H). $^{19}$F NMR (376 MHz, $CDCl_3$) δ −140.98. TLC-MS (APCI): 307.2 $[M+H]^+$.

Step-5. 2-(2-fluoro-2-methylpropyl)-2-azabicyclo[2.1.1]hexan-4-amine

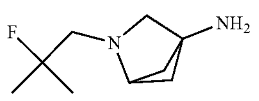

Pd/C (26.9 mg, 25.3 μmol, 10% Wt) was added to a mixture of benzyl (2-(2-fluoro-2-methylpropyl)-2-azabicyclo[2.1.1]hexan-4-yl)carbamate (Step-5, 155.0 mg, 0.51 mmol) in MeOH (3.37 mL). The resulting mixture was stirred at 22° C. for 18 h under a H2 atmosphere. The resulting reaction mixture was filtered through celite and rinsed with MeOH, and the filtrate was concentrated to obtain the title compound (74.0 mg) as an oil. TLC-MS (APCI): 173.1 $[M+H]^+$.

Step-6. (S)-4-(5-(5-fluoro-2-methoxypyridin-4-yl)-1H-pyrazole-3-carbonyl)-N-(2-(2-fluoro-2-methylpropyl)-2-azabicyclo[2.1.1]hexan-4-yl)-4-azaspiro[2.5]octane-7-carboxamide

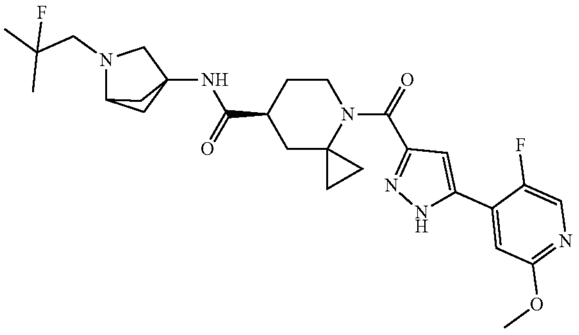 [SMILES: COc1cc(-c2cc(C(=O)N3CC[C@H](C(=O)NC45CC(C4)N(CC(C)(C)F)C5)CC34CC4)n[nH]2)c(F)cn1]

HATU (55.9 mg, 0.15 mmol) and 2-(2-fluoro-2-methylpropyl)-2-azabicyclo[2.1.1]hexan-4-amine (Step-5, 29.9 mg, 0.17 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 50.0 mg, 0.13 mmol) and DIPEA (81.13 mg, 0.63 mmol) in DMF (0.40 mL). The resulting solution was stirred at 22° C. for 18 h. The reaction mixture was concentrated under reduced pressure and diluted with EtOAc/water (1/1 v/v). The organic layer was washed with water, brine, dried over $Na_2SO_4$, filtered and concentrated under reduced pressure. The residue was purified by reverse phase column chromatography (using the following conditions: C18 column, 10% to 95% MeOH/Water (0.1% HCOOH)) to obtain the title compound (30.0 mg) as a solid. $^1H$ NMR (500 MHz, DMSO) δ 13.97 (s, 1H), 8.32 (s, 1H), 8.27 (s, 1H), 7.32 (d, 1H), 7.02 (s, 1H), 4.45 (s, 1H), 3.87 (s, 3H), 3.23 (s, 2H), 2.71 (s, 2H), 2.68-2.59 (m, 3H), 2.30-2.10 (m, 1H), 1.87-1.78 (m, 2H), 1.80-1.66 (m, 3H), 1.60-1.41 (m, 1H), 1.32 (s, 3H), 1.28 (s, 3H), 1.26-1.05 (m, 2H), 0.96 (s, 1H), 0.62 (s, 2H). TLC-MS (APCI): 529.3 $[M+H]^+$.

Example 443. (S)-4-(5-(5-fluoro-2-methoxypyridin-4-yl)-1H-pyrazole-3-carbonyl)-N-((1-(trifluoromethyl)-2-oxabicyclo[2.1.1]hexan-4-yl)methyl)-4-azaspiro[2.5]octane-7-carboxamide

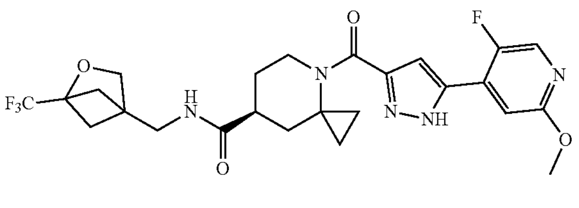

Step-1. diisopropyl 3-hydroxy-3-(trifluoromethyl)cyclobutane-1,1-dicarboxylate

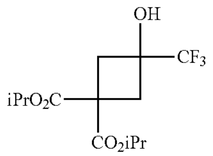

Trimethyl(trifluoromethyl)silane (593.0 mg, 4.17 mmol) was added to a solution of diisopropyl 3-oxocyclobutane-1,1-dicarboxylate (1.00 g, 4.13 mmol) and CsF (freshly dried at 150° C. for 2 h, 251.0 mg, 1.65 mmol) in dry THF (24.30 mL) at 0° C. The reaction mixture was stirred at 22° C. for 18 h. Sat. aq. $NH_4Cl$ (12.00 mL) was added and the resulting mixture was stirred for 15 min and TBAF (12.00 mL, 1 M in THF) was added. The resulting mixture was stirred for 1 h, then was extracted with EtOAc. The combined organic layers were washed with water, brine, dried over $MgSO_4$, filtered and concentrated to obtain the title compound (1.26 g) and was used in the next step without further purification. $^1H$ NMR (400 MHz, CDCl3) δ 5.16-5.04 (m, 2H), 3.09-3.01 (m, 2H), 2.68-2.54 (m, 2H), 1.29-1.21 (m, 12H). $^{19}F$ NMR (376 MHz, CDCl3) δ −84.68.

Step-2. (3-hydroxy-3-(trifluoromethyl)cyclobutane-1,1-diyl)dimethanol

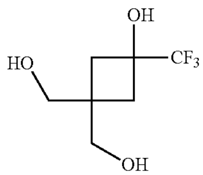 [SMILES: OCC1(CO)CC(O)(C(F)(F)F)C1]

$LiAlH_4$ (1.45 mL, 2.89 mmol, 2 M) was added dropwise to a solution of diisopropyl 3-hydroxy-3-(trifluoromethyl)cyclobutane-1,1-dicarboxylate (Step-1, 527.0 mg, 1.31 mmol) in THF (13.1 mL) at 0° C. The resulting mixture was stirred at 22° C. for 18 h. The reaction mixture was diluted with $Et_2O$ and quenched by sequential addition of water (0.14 mL), NaOH (15% aqueous, 0.14 mL), and water (0.42 mL). The organic layers were dried over $MgSO_4$, filtered, and concentrated. The residue was dissolved in DCM and the resulting solids were filtered to obtain the title compound (79.0 mg) as a solid. $^1H$ NMR (400 MHz, DMSO) δ 6.22 (s, 1H), 4.69-4.59 (m, 1H), 4.59-4.49 (m, 1H), 3.51 (s, 2H), 3.30 (s, 2H), 2.09 (d, 2H), 1.72 (d, 2H).

Step-3. (3-hydroxy-3-(trifluoromethyl)cyclobutane-1,1-diyl)bis(methylene)bis(4-methylbenzene-sulfonate)

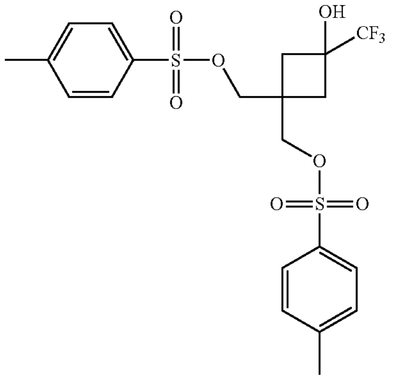 [SMILES: Cc1ccc(S(=O)(=O)OCC2(COS(=O)(=O)c3ccc(C)cc3)CC(O)(C(F)(F)F)C2)cc1]

Tosyl chloride (0.12 g, 0.65 mmol) was added to a solution of (3-hydroxy-3-(trifluoromethyl)cyclobutane-1,1-diyl)dimethanol (Step-2, 59.0 mg, 0.29 mmol) in pyridine (0.16 mL) and DCM (0.43 mL) at 0° C. The reaction mixture was stirred at 22° C. for 18 h. The reaction mixture was concentrated under reduced pressure, diluted with DCM, and cooled to 0° C. HCl (aq. 2 M) was added and the aqueous layer was extracted with DCM, dried over $Na_2SO_4$, filtered and concentrated under reduced pressure. The residue was purified by silica gel column chromatography (EtOAc in Cyclohexane, 10% to 40%) to obtain the title compound (98.0 mg) as a solid. $^1$H NMR (400 MHz, $CDCl_3$) δ 7.79-7.71 (m, 4H), 7.40-7.33 (m, 4H), 4.15 (s, 2H), 3.93 (s, 2H), 2.47 (s, 3H), 2.47 (s, 3H), 2.28 (d, 2H), 1.92 (d, 2H).

Step-4. (1-(trifluoromethyl)-2-oxabicyclo[2.1.1]hexan-4-yl)methyl 4-methylbenzenesulfonate

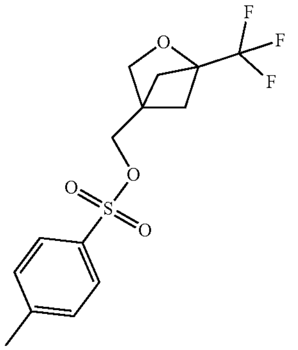 [SMILES: Cc1ccc(S(=O)(=O)OCC23COC(C(F)(F)F)(C2)C3)cc1]

NaH (6.0 mg, 0.15 mmol, 60% Wt) was added portion-wise to a solution of (3-hydroxy-3-(trifluoromethyl)cyclobutane-1,1-diyl)bis(methylene)bis(4-methylbenzene-sulfonate) (Step-3, 51.0 mg, 0.10 mmol) in THF (10.00 mL) at 0° C. The reaction mixture was stirred at 0° C. for 1 h and then refluxed for 5 h. The reaction mixture was cooled to 22° C. and quenched by sequential addition of water and brine. The aqueous layer was extracted with EtOAc, dried over $Na_2SO_4$, and concentrated under reduced pressure. The residue was purified by silica gel column chromatography (EtOAc in Cyclohexane, 0% to 20%) to obtain the title compound (24.0 mg) as a solid. $^1$H NMR (400 MHz, $CDCl_3$) δ 7.81-7.76 (m, 2H), 7.40-7.34 (m, 2H), 4.30 (s, 2H), 3.78 (s, 2H), 2.47 (s, 3H), 2.00 (dd, 2H), 1.80 (dd, 2H). $^{19}$F NMR (376 MHz, $CDCl_3$) δ −77.51.

Step-5. 4-(azidomethyl)-1-(trifluoromethyl)-2-oxabicyclo[2.1.1]hexane

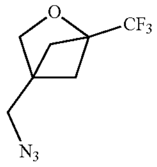 [SMILES: [N-]=[N+]=NCC12COC(C(F)(F)F)(C1)C2]

$NaN_3$ (6.8 mg, 0.10 mmol) was added to a solution of (1-(trifluoromethyl)-2-oxabicyclo[2.1.1]hexan-4-yl)methyl 4-methylbenzenesulfonate (Step-4, 22.0 mg, 0.07 mmol) in DMF (0.07 mL). The resulting mixture was heated to 40° C. and stirred for 18 h. The reaction mixture was cooled to 22° C. and diluted with EtOAc, washed with water, brine. The organic layers were dried over $Na_2SO_4$, filtered and concentrated under reduced pressure to obtain the title compound (7.0 mg) as a solid. $^1$H NMR (400 MHz, $CDCl_3$) δ 3.83 (s, 2H), 3.66 (s, 2H), 2.04 (dd, 2H), 1.86 (dd, 2H). $^{19}$F NMR (376 MHz, $CDCl_3$) δ −77.53.

Step-6. chloro((1-(trifluoromethyl)-2-oxabicyclo[2.1.1]hexan-4-yl)methyl)-15-azane

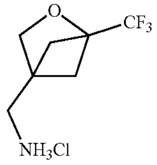

Triphenylphosphine (10.6 mg, 0.04 mmol) was added to a solution of 4-(azidomethyl)-1-(trifluoromethyl)-2-oxabicyclo[2.1.1]hexane (Step-5, 7.0 mg, 0.03 mmol) in EtOAc (0.23 mL). The resulting mixture was stirred at 22° C. for 18 h. HCl (0.04 mL, 0.17 mmol, 4.0 M) and one drop of water was added to the reaction mixture. The reaction mixture was stirred for 7 h and concentrated under reduced pressure and triturated in $Et_2O$ to obtain the title compound (10.0 mg) and used in the next step without further purification. TLC-MS (APCI): 182.1 $[M+H]^+$.

Step-7. (S)-4-(5-(5-fluoro-2-methoxypyridin-4-yl)-1H-pyrazole-3-carbonyl)-N-((1-(trifluoromethyl)-2-oxabicyclo[2.1.1]hexan-4-yl)methyl)-4-azaspiro[2.5]octane-7-carboxamide

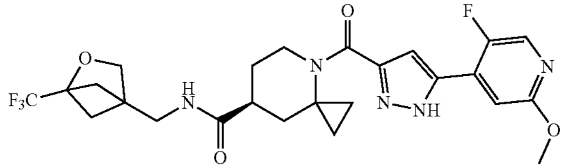 [SMILES: COc1cc(-c2cc(C(=O)N3CC[C@H](C(=O)NCC45COC(C(F)(F)F)(C4)C5)CC34CC4)n[nH]2)c(F)cn1]

HATU (11.5 mg, 0.03 mmol) and chloro((1-(trifluoromethyl)-2-oxabicyclo[2.1.1]hexan-4-yl)methyl)-15-azane (Step-6, 7.6 mg, 0.03 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 10.0 mg, 0.03 mmol) and DIPEA (16.0 mg, 0.13 mmol) in DMF (0.2 mL). The resulting solution was stirred at 22° C. for 18 h. The reaction mixture was directly purified by reverse phase column chromatography (using the following conditions: C18 column, 10% to 95% MeOH/Water (0.1% HCOOH)) and then repurified a second time by reverse phase column chromatography (using the following conditions: C18 column, 10% to 95% MeOH/Water (0.1% HCOOH)) to obtain the title compound (3.0 mg) as a solid. $^1$H NMR (400 MHz, $CD_3OD$) δ 0.66-0.81 (m, 2H), 1.23-1.34 (m, 4H), 1.61 (t, 1H), 1.73 (dd, 2H), 1.86 (s, 1H), 1.90-1.98 (m, 2H), 2.02 (s, 1H), 2.31-2.60 (m, 1H), 2.77-2.90 (m, 1H), 3.55 (s, 2H), 3.73 (s, 2H), 3.94 (s, 3H), 7.11 (s, 1H), 7.29 (d, 1H), 7.53-7.68 (m, 1H), 8.13 (d, 1H). $^{19}$F NMR (376 MHz, $CD_3OD$) δ −144.71, −79.14. TLC-MS (APCI): 538.2 $[M+H]^+$.

Example 444. 5-(5-(5-fluoro-2-methoxypyridin-4-yl)-1H-pyrazole-3-carbonyl)-N-((1r,4r)-4-hydroxy-4-(trifluoromethyl)cyclohexyl)-2-oxa-5-azaspiro[3.5]nonane-8-carboxamide

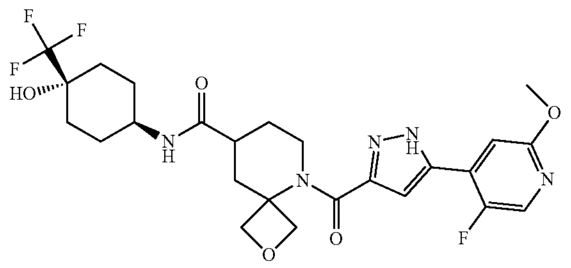 [SMILES: COc1cc(-c2cc(C(=O)N3CCC(C(=O)N[C@H]4CC[C@@](O)(C(F)(F)F)CC4)CC34COC4)n[nH]2)c(F)cn1]

Step-1. 5-benzyl-2-oxa-5-azaspiro[3.5]nonane-8-carbonitrile

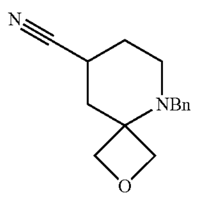 [SMILES: N#CC1CCN(Cc2ccccc2)C2(COC2)C1]

Potassium tert-butoxide (34.6 mg, 0.31 mmol) was added to a mixture of 5-benzyl-2-oxa-5-azaspiro[3.5]nonan-8-one (30.0 mg, 0.13 mmol) and toluenesulfonylmethyl isocyanide (32.9 mg, 0.17 mmol) in DMF (0.36 mL) and EtOH (0.01 mL) at −10° C. The resulting mixture was warmed to 0° C. and stirred for 1 h at 0° C., followed by at 22° C. for 2.5 h. The reaction mixture was diluted with $Et_2O$ and water. The resulting mixture was stirred vigorously for 1 h. The organic layer was washed with water, brine, dried over $MgSO_4$, filtered and concentrated under reduced pressure. The residue was purified by silica gel column chromatography (EtOAc in Cyclohexane, 0 to 50%) to obtain the title compound (14.0 mg) as an oil. $^1$H NMR (400 MHz, CDCl3) δ 7.41-7.26 (m, 5H), 4.83 (d, 1H), 4.77 (d, 1H), 4.54 (d, 1H), 4.43 (d, 1H), 4.04 (d, 1H), 3.75 (d, 1H), 2.78-2.63 (m, 2H), 2.42-2.31 (m, 2H), 2.25-2.14 (m, 1H), 1.85-1.72 (m, 2H).

Step-2. 5-benzyl-2-oxa-5-azaspiro[3.5]nonane-8-carboxylic acid

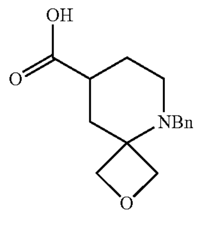 [SMILES: O=C(O)C1CCN(Cc2ccccc2)C2(COC2)C1]

NaOH (0.62 mL, 1.20 mmol, 2.0 M) was added to a solution of 5-benzyl-2-oxa-5-azaspiro[3.5]nonane-8-carbonitrile (Step-1, 30.0 mg, 0.12 mmol) in EtOH (0.62 mL) in a sealed vial. The reaction mixture was heated at 78° C. for 18 h. The reaction mixture was cooled and concentrated under reduced pressure. The residue was dissolved in water and washed with DCM. The aqueous layer was acidified to pH~6 with $KHSO_4$ (2.0 M aqueous), extracted with EtOAc, dried over $Na_2SO_4$, filtered and concentrated under reduced pressure. The residue was purified by silica gel column chromatography (MeOH/DCM, 0 to 10%) to obtain the title compound (16.0 mg) as a solid. TLC-MS (APCI): 262.0 $[M+H]^+$.

Step-3. 5-benzyl-N-((1r,4r)-4-hydroxy-4-(trifluoromethyl)cyclohexyl)-2-oxa-5-azaspiro[3.5]nonane-8-carboxamide

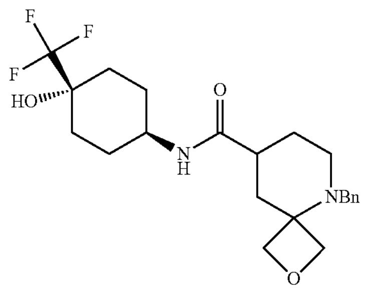 [SMILES: O=C(N[C@H]1CC[C@@](O)(C(F)(F)F)CC1)C1CCN(Cc2ccccc2)C2(COC2)C1]

HATU (75.0 mg, 0.20 mmol) and (1r,4r)-4-amino-1-(trifluoromethyl)cyclohexan-1-ol (43.0 mg, 0.23 mmol) were added to a solution of 5-benzyl-2-oxa-5-azaspiro[3.5]nonane-8-carboxylic acid (Step-2, 47.0 mg, 0.18 mmol) and DIPEA (58.0 mg, 0.45 mmol) in DMF (1.80 mL). The resulting mixture was stirred at 22° C. for 18 h. The reaction mixture was diluted with EtOAc and washed with water and brine. The organic layers were dried over $Na_2SO_4$, filtered, and concentrated under reduced pressure. The residue was purified by silica gel column chromatography (DCM/MeOH, 0 to 20%) to obtain the title compound (66.0 mg) as a solid. TLC-MS (APCI): 426.9 $[M+H]^+$.

Step-4. N-((1r,4r)-4-hydroxy-4-(trifluoromethyl)cyclohexyl)-2-oxa-5-azaspiro[3.5]nonane-8-carboxamide

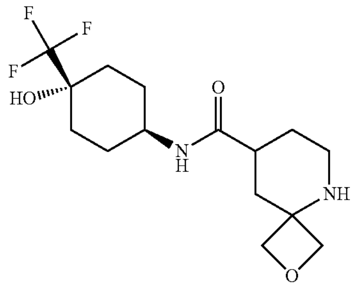 [SMILES: O=C(N[C@H]1CC[C@@](O)(C(F)(F)F)CC1)C1CCNC2(COC2)C1]

Pd/C (9.8 mg, 9.19 μmol, 10% Wt) was added to a solution of 5-benzyl-N-((1r,4r)-4-hydroxy-4-(trifluoromethyl)cyclohexyl)-2-oxa-5-azaspiro[3.5]nonane-8-carboxamide (Step-3, 56.0 mg, 0.13 mmol) in MeOH (1.31 mL) under a $H_2$ atmosphere. The resulting mixture was stirred at 22° C. for 18 h. The resulting mixture was filtered over celite and the filtrate was concentrated under reduced pressure. The residue was purified by silica gel column chromatography (MeOH/DCM, 0% to 20%) to obtain the title compound (34.0 mg) as a solid. $^1$H NMR (400 MHz, $CDCl_3$) δ 4.66-4.56 (m, 2H), 4.53-4.37 (m, 2H), 4.00-3.88 (m, 1H), 3.06 (dt, 1H), 2.70 (td, 1H), 2.47 (tt, 1H), 2.31-2.20 (m, 1H), 1.98-1.81 (m, 4H), 1.81-1.57 (m, 7H). $^{19}$F NMR (376 MHz, $CD_3OD$) δ −85.21.

Step-5. 5-(5-(5-fluoro-2-methoxypyridin-4-yl)-1H-pyrazole-3-carbonyl)-N-((1r,4r)-4-hydroxy-4-(trifluoromethyl)cyclohexyl)-2-oxa-5-azaspiro[3.5]nonane-8-carboxamide

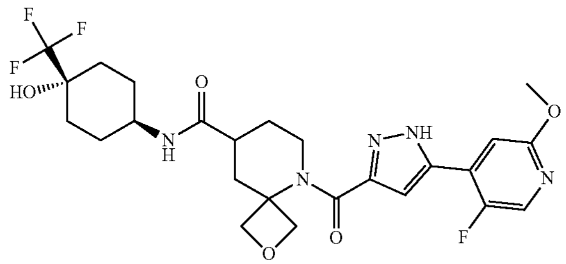 [SMILES: COc1cc(-c2cc(C(=O)N3CCC(C(=O)N[C@H]4CC[C@@](O)(C(F)(F)F)CC4)CC34COC4)n[nH]2)c(F)cn1]

HOBt (18.4 mg, 0.12 mmol), EDCI (23.1 mg, 0.12 mmol), and N-((1r,4r)-4-hydroxy-4-(trifluoromethyl)cyclohexyl)-2-oxa-5-azaspiro[3.5]nonane-8-carboxamide (27.0 mg, 0.08 mmol) were added to a solution of 5-(5-fluoro-2-methoxypyridin-4-yl)-1H-pyrazole-3-carboxylic acid (Step-4, 20.9 mg, 0.09 mmol) and DIPEA (51.9 mg, 0.40 mmol) in DMF (0.24 mL). The resulting mixture was stirred at 22° C. for 18 h. The resulting reaction mixture was directly purified by reverse phase column chromatography (using the following conditions: C18 column, 10% to 95% MeOH/Water (0.1% HCOOH)) and purified further by a second reverse phase column chromatography (using the following conditions: C18 column, 10% to 95% MeOH/Water (0.1% HCOOH)). The resulting residue was then purified by silica gel column chromatography (MeOH/DCM, 0 to 20%) and prep-TLC (MeOH/DCM, 10%) to obtain the title compound (2.5 mg) as a solid. $^1$H NMR (500 MHz, $CD_3OD$) δ 8.13 (d, 1H), 7.25 (s, 1H), 7.15 (d, 1H), 5.39-5.30 (m, 1H), 4.98 (s, 1H), 4.74 (d, 1H), 4.56 (d, 1H), 4.46 (s, 1H), 3.93 (s, 3H), 3.13-2.98 (m, 1H), 2.82 (s, 1H), 2.41-2.13 (m, 3H), 2.07-2.01 (m, 1H), 1.95-1.81 (m, 3H), 1.76-1.49 (m, 7H). $^{19}$F NMR (471 MHz, $CD_3OD$) δ −85.24, −144.28. TLC-MS (APCI): 556.3 $[M+H]^+$.

Example 445. A Diastereomeric Mixture of (S)-4-(5-(5-fluoro-2-methoxypyridin-4-yl)-1H-pyrazole-3-carbonyl)-N-(5-((R)-1-hydroxyethyl)pyrazolo[1,5-a]pyrimidin-3-yl)-4-azaspiro[2.5]octane-7-carboxamide and (S)-4-(5-(5-fluoro-2-methoxypyridin-4-yl)-1H-pyrazole-3-carbonyl)-N-(5-((S)-1-hydroxyethyl)pyrazolo[1,5-a]pyrimidin-3-yl)-4-azaspiro[2.5]octane-7-carboxamide

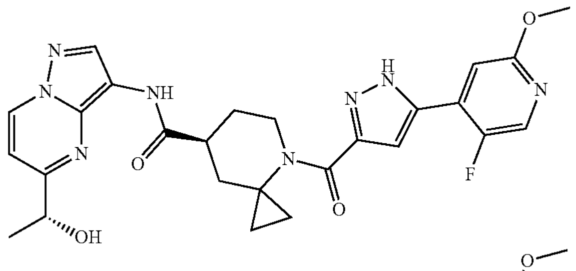

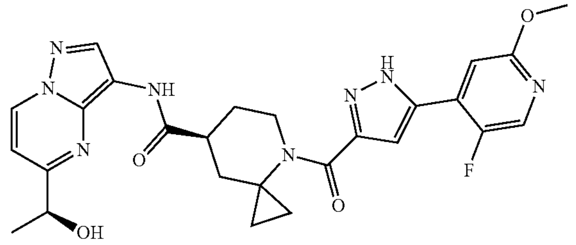

Step-1. (7S)—N-[5-chloropyrazolo[1,5-a]pyrimidin-3-yl]-4-[5-(5-fluoro-2-methoxypyridin-4-yl)-1H-pyrazole-3-carbonyl]-4-azaspiro[2.5]octane-7-carboxamide

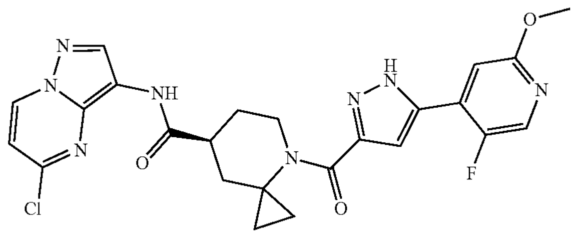 [SMILES: COc1cc(-c2cc(C(=O)N3CC[C@H](C(=O)Nc4cnn5ccc(Cl)nc45)CC34CC4)n[nH]2)c(F)cn1]

HATU (406.0 mg, 1.07 mmol) and 5-chloropyrazolo[1,5-a]pyrimidin-3-amine (150.0 mg, 0.89 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 333.1 mg, 0.89 mmol) and DIPEA (345.0 mg, 2.67 mmol) in DMF (5.00 mL). The resulting solution was stirred at 25° C. for 1 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (15/1 v/v) to obtain the title compound (460.0 mg) as a solid. LCMS (ESI): 525.2 [M+H]+.

Step-2. (7S)—N-[5-(1-ethoxyethenyl)pyrazolo[1,5-a]pyrimidin-3-yl]-4-[5-(5-fluoro-2-methoxypyridin-4-yl)-1H-pyrazole-3-carbonyl]-4-azaspiro[2.5]octane-7-carboxamide

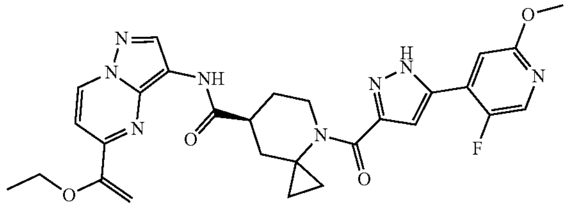 [SMILES: C=C(OCC)c1ccn2ncc(NC(=O)[C@H]3CCN(C(=O)c4cc(-c5cc(OC)ncc5F)[nH]n4)C4(CC4)C3)c2n1]

Tributyl(1-ethoxyethenyl)stannane (402.5 mg, 1.11 mmol) and $Pd(PPh_3)_4$ (99.1 mg, 0.09 mmol) were added to a stirred solution of (7S)—N-[5-chloropyrazolo[1,5-a]pyrimidin-3-yl]-4-[5-(5-fluoro-2-methoxypyridin-4-yl)-1H-pyrazole-3-carbonyl]-4-azaspiro[2.5]octane-7-carboxamide (Step-1, 450.0 mg, 0.86 mmol) in DMF (3.00 mL). The resulting mixture was stirred at 100° C. for 3 h under nitrogen atmosphere. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (480.0 mg) as an oil. LCMS (ESI): 561.2 [M+H]+.

Step-3. (7S)—N-[5-acetylpyrazolo[1,5-a]pyrimidin-3-yl]-4-[5-(5-fluoro-2-methoxypyridin-4-yl)-1H-pyrazole-3-carbonyl]-4-azaspiro[2.5]octane-7-carboxamide

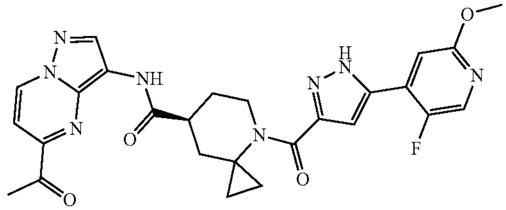 [SMILES: COc1cc(-c2cc(C(=O)N3CC[C@H](C(=O)Nc4cnn5ccc(C(C)=O)nc45)CC34CC4)n[nH]2)c(F)cn1]

HCl (2.00 mL) was added to a stirred solution of (7S)—N-[5-(1-ethoxyethenyl)pyrazolo[1,5-a]pyrimidin-3-yl]-4-[5-(5-fluoro-2-methoxypyridin-4-yl)-1H-pyrazole-3-carbonyl]-4-azaspiro[2.5]octane-7-carboxamide (Step-2, 480.0 mg, 0.86 mmol) in MeOH (2.00 mL) at 0° C. The resulting mixture was stirred at 25° C. for 2 h. The solution was concentrated under reduced pressure. The residue was purified by silica gel column chromatography eluting with DCM/MeOH (15/1 v/v) to obtain the title compound (170.0 mg) as an oil. LCMS (ESI): 533.2 [M+H]+.

Step-4. (S)-4-(5-(5-fluoro-2-methoxypyridin-4-yl)-1H-pyrazole-3-carbonyl)-N-(5-((R)-1-hydroxyethyl)pyrazolo[1,5-a]pyrimidin-3-yl)-4-azaspiro[2.5]octane-7-carboxamide and (S)-4-(5-(5-fluoro-2-methoxypyridin-4-yl)-1H-pyrazole-3-carbonyl)-N-(5-((S)-1-hydroxyethyl)pyrazolo[1,5-a]pyrimidin-3-yl)-4-azaspiro[2.5]octane-7-carboxamide

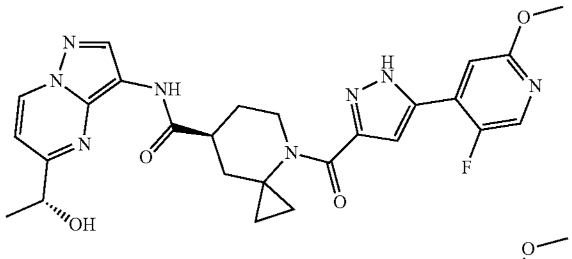

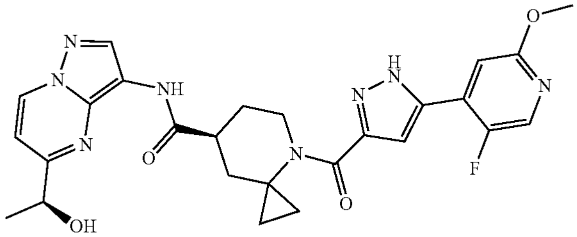

$NaBH_4$ (10.7 mg, 0.28 mmol) was added to a stirred solution of (7S)—N-[5-acetylpyrazolo[1,5-a]pyrimidin-3-yl]-4-[5-(5-fluoro-2-methoxypyridin-4-yl)-1H-pyrazole-3-carbonyl]-4-azaspiro[2.5]octane-7-carboxamide (Step-3, 150.0 mg, 0.28 mmol) in MeOH (2.00 mL) at 0° C. The resulting mixture was stirred at 25° C. for 14 h. The solution was concentrated under reduced pressure. The residue was purified by silica gel column chromatography eluting with DCM/MeOH (15/1 v/v) to obtain the title compound (42.0 mg) as a solid (Example 445). $^1$H NMR (400 MHz, $CD_3OD$) δ 8.78 (d, 1H), 8.54 (s, 1H), 8.13 (d, 1H), 7.43-7.06 (m, 3H), 4.99-4.87 (m, 1H), 4.79-4.60 (m, 1H), 3.95 (s, 3H), 3.26-3.06 (m, 1H), 2.61-2.39 (m, 1H), 2.26-1.76 (m, 2H), 1.66-1.40 (m, 4H), 1.36-1.23 (m, 2H), 1.20-1.01 (m, 1H), 0.94-0.60 (m, 3H). LCMS (ESI): 535.15 [M+H]+.

This mixture of two diastereomers (40.0 mg) was separated using Chiral Prep-SFC.

Column: CHIRALPAK IH column

Column dimension: 2×25 cm, 5 μm

Mobile Phase A: $CO_2$; Mobile Phase B: IPA (0.5% 2M $NH_3$-MeOH)

Flow rate: 50 mL/min

Gradient: isocratic 35% B

Detection: 220 nm

Injection Volume: 2 mL

Example 445-A. The first eluting diastereomer (10.6 mg) was obtained as a solid.

The first eluting diastereomer had a retention time of 7.42 min.

$^1$H NMR (400 MHz, $CD_3OD$) δ 8.78 (d, 1H), 8.54 (s, 1H), 8.14 (d, 1H), 7.29 (s, 1H), 7.13 (d, 2H), 5.05-4.89 (m, 1H), 4.78-4.13 (m, 1H), 3.95 (s, 3H), 3.26-3.05 (m, 1H), 2.75-2.36 (m, 1H), 2.25-1.72 (m, 2H), 1.63-1.42 (m, 3H), 1.40-1.23 (m, 2H), 1.22-0.96 (m, 1H), 0.95-0.71 (m, 3H). LCMS (ESI): 535.20 [M+H]+.

Example 445-B. The second eluting diastereomer (10.0 mg) was obtained as a solid.

The second eluting diastereomer had a retention time of 9.70 min.

$^1$H NMR (400 MHz, $CD_3OD$) δ 8.78 (d, 1H), 8.54 (s, 1H), 8.23-8.08 (m, 1H), 7.34-7.20 (m, 1H), 7.19-7.05 (m, 2H), 5.05-4.90 (m, 1H), 4.80-4.10 (m, 1H), 3.95 (s, 3H), 3.24-3.08 (m, 1H), 2.82-2.40 (m, 1H), 2.26-1.76 (m, 2H), 1.65-1.43 (m, 3H), 1.38-1.23 (m, 2H), 1.18-1.01 (m, 1H), 0.98-0.64 (m, 3H). LCMS (ESI): 535.15 $[M+H]^+$.

Example 446. (S)—N-((3-chloro-5-(oxetan-3-yloxy)pyridin-2-yl)methyl)-4-(5-(5-fluoro-2-methoxypyridin-4-yl)-1H-pyrazole-3-carbonyl)-4-azaspiro[2.5]octane-7-carboxamide

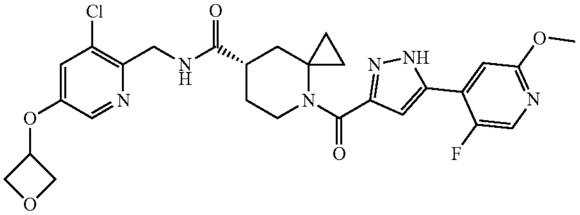 [SMILES: COc1cc(-c2cc(C(=O)N3CC[C@H](C(=O)NCc4ncc(OC5COC5)cc4Cl)CC34CC4)n[nH]2)c(F)cn1]

Step-1. 3-chloro-5-(oxetan-3-yloxy)picolinonitrile

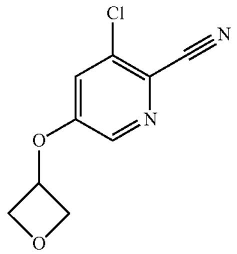 [SMILES: N#Cc1ncc(OC2COC2)cc1Cl]

NaH (153.6 mg, 3.84 mmol, 60% dispersion in mineral oil) was added to a stirred solution of oxetan-3-ol (500.0 mg, 3.21 mmol) in DMF (50.00 mL) at 0° C. The resulting mixture was stirred at 0° C. for 30 min. 3-chloro-5-fluoropyridine-2-carbonitrile (500.0 mg, 3.21 mmol) was added to the resulting mixture at 0° C. The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (2/1 v/v) to obtain the title compound (600.0 mg) as a solid. LCMS (ESI): 211.0 [M+H].

Step-2. 3-chloro-5-(oxetan-3-yloxy)pyridine-2-carbonitrile

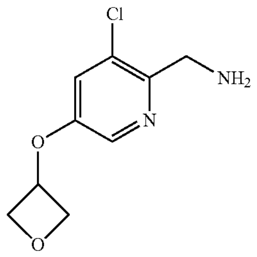 [SMILES: NCc1ncc(OC2COC2)cc1Cl]

DIBAL-H (3.56 mL, 3.56 mmol) was added to a stirred mixture of 3-chloro-5-(oxetan-3-yloxy)pyridine-2-carbonitrile (Step-1, 250.0 mg, 1.19 mmol) in DCM (5.00 mL) at −78 degrees C. under nitrogen atmosphere. The resulting mixture was stirred at −78° C. for 10 min under nitrogen atmosphere. The reaction mixture was quenched with MeOH at −78° C. under nitrogen atmosphere. The resulting mixture was concentrated under reduced pressure. The residue was purified by silica gel column chromatography eluting with DCM/MeOH (10/1 v/v) to obtain the title compound (60.0 mg) as a solid. LCMS (ESI): 215.0 $[M+H]^+$.

Step-3. (S)—N-((3-chloro-5-(oxetan-3-yloxy)pyridin-2-yl)methyl)-4-(5-(5-fluoro-2-methoxypyridin-4-yl)-1H-pyrazole-3-carbonyl)-4-azaspiro[2.5]octane-7-carboxamide

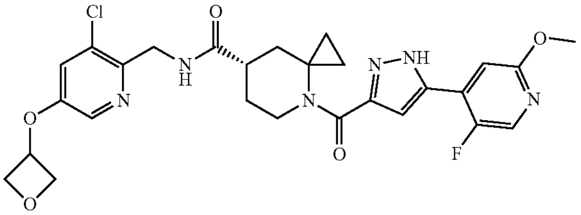 [SMILES: COc1cc(-c2cc(C(=O)N3CC[C@H](C(=O)NCc4ncc(OC5COC5)cc4Cl)CC34CC4)n[nH]2)c(F)cn1]

HOBt (72.0 mg, 0.53 mmol), EDCI (102.0 mg, 0.53 mmol), and 3-chloro-5-(oxetan-3-yloxy)pyridine-2-carbonitrile (Step-2, 57.0 mg, 0.27 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 100.0 mg, 0.27 mmol) and DIPEA (172.0 mg, 1.34 mmol) in DMF (5.00 mL). The resulting mixture was stirred for at 25° C. for 2 h. The resulting mixture was diluted with EtOAc and washed with water. The organic layers were combined, dried over anhydrous $Na_2SO_4$, filtered, and concentrated under reduced pressure. The residue was purified by Prep-HPLC (using the following conditions: Column: Xselect CSH C18 OBD Column, 30+150 mm 5 μm, Mobile Phase A: Water (0.1% FA), Mobile Phase B: MeCN; Flow rate: 60 mL/min; Gradient: 35% B to 45% B in 8 min, 45% B; Wave Length: 220 nm; RT1 (min): 4.58) to obtain the title compound (12.0 mg) as a solid. $^1$H NMR (400 MHz, $CD_3OD$) δ 8.16-8.03 (m, 2H), 7.40-7.21 (m, 2H), 7.10 (d, 1H), 5.50-5.29 (m, 1H), 5.12-4.96 (m, 2H), 4.75-4.63 (m, 2H), 4.62-4.43 (m, 3H), 3.94 (s, 3H), 3.06-2.81 (m, 1H), 2.65-2.25 (m, 1H), 2.13-1.63 (m, 2H), 1.48-1.17 (m, 2H), 1.13-0.60 (m, 4H). LCMS (ESI): 571.10 $[M+H]^+$.

Example 447. (7S)—N-((5-(3,5-dimethylpiperazin-1-yl)pyrimidin-2-yl)methyl)-4-(5-(5-fluoro-2-methoxypyridin-4-yl)-1H-pyrazole-3-carbonyl)-4-azaspiro[2.5]octane-7-carboxamide

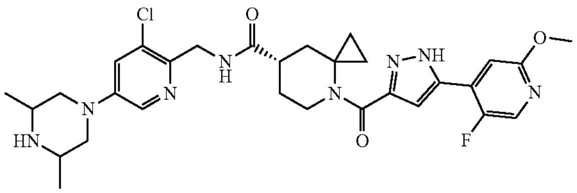

Step-1. tert-butyl 4-(2-cyanopyrimidin-5-yl)-2,6-dimethylpiperazine-1-carboxylate

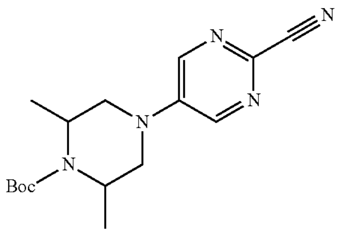 [SMILES: CC1CN(c2cnc(C#N)nc2)CC(C)N1C(=O)OC(C)(C)C]

DIPEA (756.0 mg, 5.85 mmol) and tert-butyl 2,6-dimethylpiperazine-1-carboxylate (501.0 mg, 2.34 mmol) were added to a mixture of 5-fluoropyrimidine-2-carbonitrile (240.0 mg, 1.95 mmol) in MeCN (5.00 mL). The resulting mixture was stirred at 100° C. for 4 h under nitrogen atmosphere. The resulting mixture was concentrated under reduced pressure. The residue was purified by silica gel column chromatography eluting with DCM/MeOH (10/1 v/v) to obtain the title compound (500.0 mg) as a solid. LCMS (ESI): 318 $[M+H]^+$.

Step-2. tert-butyl 4-[2-(aminomethyl)pyrimidin-5-yl]-2,6-dimethylpiperazine-1-carboxylate

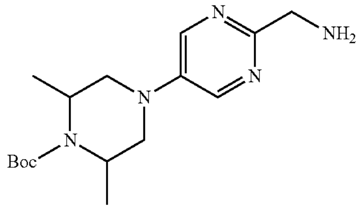 [SMILES: CC1CN(c2cnc(CN)nc2)CC(C)N1C(=O)OC(C)(C)C]

$LiAlH_4$ (4.30 mL, 4.35 mmol) was added to a mixture of tert-butyl 4-(2-cyanopyrimidin-5-yl)-2,6-dimethylpiperazine-1-carboxylate (Step-1, 460.0 mg, 1.45 mmol) in THF (5.00 mL) at 0° C. The resulting mixture was stirred at 0° C. for 1 h under nitrogen atmosphere. The resulting mixture was quenched with MeOH. The resulting mixture was concentrated under reduced pressure. The residue was purified by silica gel column chromatography eluting with DCM/MeOH (5/1 v/v) to obtain the title compound (150.0 mg) as a solid. LCMS (ESI): 322 $[M+H]^+$.

Step-3. tert-butyl 4-(2-(((S)-4-(5-(5-fluoro-2-methoxypyridin-4-yl)-1H-pyrazole-3-carbonyl)-4-azaspiro[2.5]octane-7-carboxamido)methyl)pyrimidin-5-yl)-2,6-dimethylpiperazine-1-carboxylate

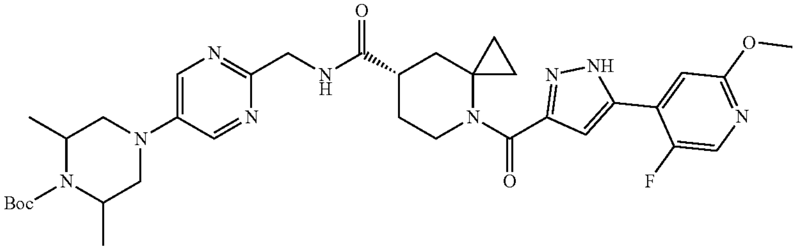

EDCI (116.0 mg, 0.61 mmol) and HOBt (82.0 mg, 0.61 mmol), and tert-butyl 4-[2-(aminomethyl)pyrimidin-5-yl]-2,6-dimethylpiperazine-1-carboxylate (Step-2, 130.0 mg, 0.40 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 151.0 mg, 0.40 mmol) and DIPEA (261.0 mg, 2.02 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (120.0 mg) as a solid. LCMS (ESI): 678 $[M+H]^+$.

Step-4. (7S)—N((5-(3,5-dimethylpiperazin-1-yl)pyrimidin-2-yl)methyl)-4-(5-(5-fluoro-2-methoxy-pyridin-4-yl)-1H-pyrazole-3-carbonyl)-4-azaspiro[2.5]octane-7-carboxamide

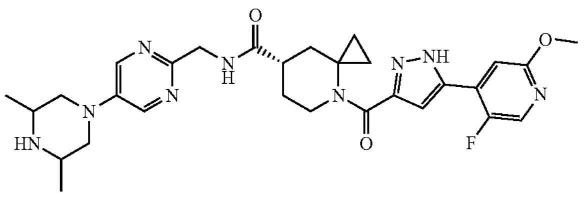

TFA (3.00 mL) were added to a mixture of tert-butyl 4-[2-([[(7S)-4-[5-(5-fluoro-2-methoxypyridin-4-yl)-1H-pyrazole-3-carbonyl]-4-azaspiro[2.5]octan-7-yl]formamido]methyl)pyrimidin-5-yl]-2,6-dimethylpiperazine-1-carboxylate (Step-3, 120.0 mg, 0.177 mmol) in DCM (3.00 mL). The resulting mixture was stirred at 25° C. for 1 h. The resulting mixture was concentrated under vacuum. The residue was purified by silica gel column chromatography eluting with DCM/MeOH (10/1 v/v) to obtain the title compound (70.0 mg) as a solid. $^1H$ NMR (400 MHz, DMSO-$d_6$) δ 13.98 (s, 1H), 8.43 (s, 2H), 8.28 (d, 2H), 7.32 (d, 1H), 7.03 (d, 1H), 4.37-4.31 (m, 3H), 3.88 (s, 3H), 3.74-3.67 (m, 2H), 2.96-2.91 (m, 2H), 2.84-2.73 (m, 2H), 2.71-2.66 (m, 1H), 2.36-2.18 (m, 3H), 1.81-1.77 (m, 1H), 1.58-1.53 (m, 1H), 1.27-1.22 (m, 1H), 1.10-1.04 (m, 6H), 0.94-0.89 (m, 2H), 0.69-0.60 (m, 2H). LCMS (ESI): 578.30 $[M+H]^+$.

Example 448. (S)—N-(1-cyanocyclopropyl)-4-(5-(5-fluoro-2-methoxypyridin-4-yl)-1H-pyrazole-3-carbonyl)-4-azaspiro[2.5]octane-7-carboxamide

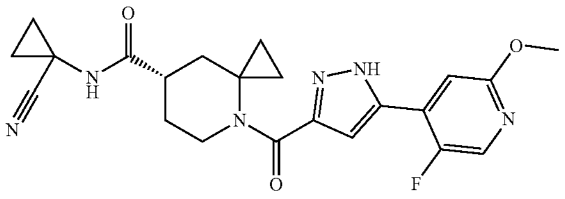 [SMILES: COc1cc(-c2cc(C(=O)N3CC[C@H](C(=O)NC4(C#N)CC4)CC34CC4)n[nH]2)c(F)cn1]

The title compound was prepared using a procedure similar to the one described for the synthesis of Example 325, except 1-aminocyclopropane-1-carbonitrile hydrochloride was used as a starting material. The residue was purified by silica gel column chromatography eluting with DCM/MeOH (10/1 v/v) to obtain the title compound (60.0 mg) as a solid. $^1H$ NMR (400 MHz, DMSO-$d_6$) δ 14.26-13.59 (m, 1H), 8.92-8.54 (m, 1H), 8.27 (s, 1H), 7.33 (s, 1H), 7.14-6.58 (m, 1H), 4.72-4.04 (m, 1H), 3.88 (s, 3H), 2.94-2.57 (m, 1H), 2.36-1.99 (m, 2H), 1.93-1.55 (m, 1H), 1.54-1.38 (m, 3H), 1.38-1.18 (m, 1H), 1.17-1.03 (m, 2H), 1.03-0.80 (m, 2H), 0.79-0.44 (m, 2H). LCMS (ESI): 439.20 $[M+H]^+$.

Example 450. A Diastereomeric Mixture of (S)—N—((S)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide

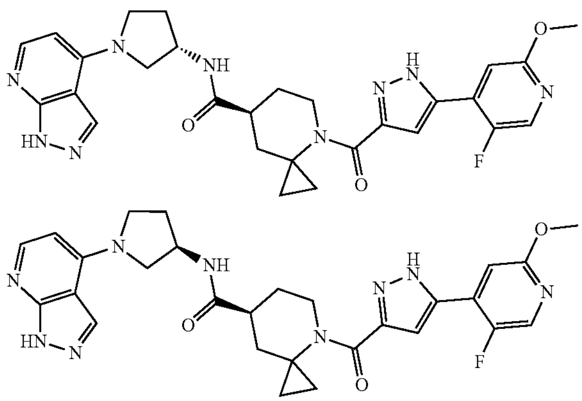

Step-1. N,N-dibenzyl-1-[1H-pyrazolo[3,4-b]pyridin-4-yl]pyrrolidin-3-amine

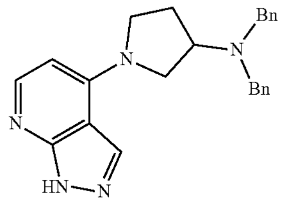 [SMILES: c1ccc(CN(Cc2ccccc2)C2CCN(c3ccnc4[nH]ncc34)C2)cc1]

Pd-PEPPSI-IPentCl 2-methylpyridine (o-picoline) (157.0 mg, 0.19 mmol, CAS #: 1612891-29-8), 4-bromo-1H-pyrazolo[3,4-b]pyridine (260.2 mg, 1.31 mmol) and $Cs_2CO_3$ (61.2 mg, 3.75 mmol) were added to a stirred solution of N,N-dibenzylpyrrolidin-3-amine (500.0 mg, 1.88 mmol) in 1,4-dioxane (5.00 mL) at 25° C. The resulting mixture was stirred at 90° C. for 14 h under nitrogen atmosphere. The residue was purified by silica gel column chromatography eluting with DCM/MeOH (10/1 v/v) to obtain the title compound (227.0 mg) as a solid. LCMS (ESI): 384.2 $[M+H]^+$.

Step-2. 1-[1H-pyrazolo[3,4-b]pyridin-4-yl]pyrrolidin-3-amine

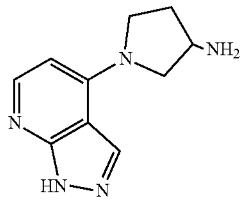 [SMILES: NC1CCN(c2ccnc3[nH]ncc23)C1]

$BF_3HF$-$Et_2O$ (943.0 mg, 5.86 mmol) and Pd/C (134.6 mg) were added to a stirred solution of N,N-dibenzyl-1-[1H-pyrazolo[3,4-b]pyridin-4-yl]pyrrolidin-3-amine (Step-1, 449.0 mg, 1.17 mmol) in THF (6.00 mL) and MeOH (6.00 mL). The resulting mixture was stirred at 25° C. for 7 days under hydrogen atmosphere. The resulting mixture was filtered, the filter cake was washed with MeOH. The filtrate was concentrated under reduced pressure to obtain the title compound (180.0 mg) as a solid. LCMS (ESI): 204.1 $[M+H]^+$.

Step-3. (S)—N—((S)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide

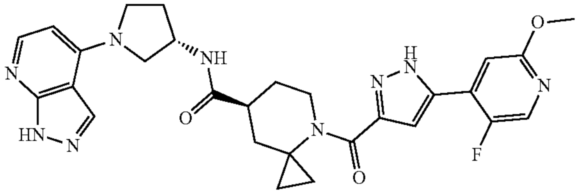

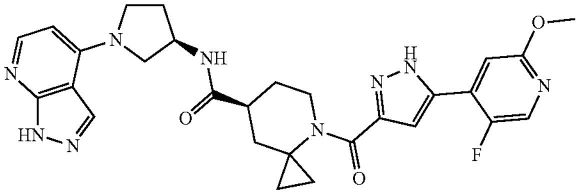

HOBt (148.0 mg, 1.10 mmol), EDCI (210.0 mg, 1.10 mmol), and 1-[1H-pyrazolo[3,4-b]pyridin-4-yl]pyrrolidin-3-amine (Step-2, 90.0 mg, 0.44 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 206.0 mg, 0.55 mmol) and DIPEA (285.0 mg, 2.22 mmol) in DMF (6.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: phase A: Water (0.5% $NH_4HCO_3$), mobile phase B: MeCN; gradient: 20 B to 40 B in 20 min; detector, UV 254/220 nm) to obtain (S)—N—((S)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide (150.0 mg) as a solid mixture of diastereomers (Example 450). $^1$H NMR (400 MHz, $CD_3OD$) δ 8.28 (s, 1H), 8.13 (d, 1H), 8.02 (d, 1H), 7.28 (d, 1H), 7.10 (d, 1H), 6.17 (d, 1H), 4.63-4.56 (m, 2H), 4.17-3.75 (m, 6H), 3.64-3.60 (m, 1H), 2.86-2.82 (m, 1H), 2.47-2.34 (m, 2H), 2.21-2.12 (m, 1H), 1.89-1.85 (m, 2H), 1.33-1.26 (m, 2H), 1.00-0.95 (m, 2H), 0.76-0.65 (m, 2H). LCMS (ESI): 560.40 $[M+H]^+$.

This mixture of two diastereomers (100.0 mg) was separated using Chiral Prep-HPLC.

Column: CHIRALPAK ART Cellulose-SB column

Column dimension: 2×25 cm, 5 μm

Mobile Phase: 3/1 hexanes/DCM (0.5% 2 M $NH_3$·MeOH):EtOH=70:30 hold for 9.5 min Flow rate: 20 mL/min Detection: 220/254 nm Example 450-A. The first eluting diastereomer (20.6 mg) was obtained as a solid.

The first eluting diastereomer had a retention time of 5.25 min.

$^1$H NMR (400 MHz, $CD_3OD$) δ 8.19-8.09 (m, 2H), 7.99 (d, 1H), 7.26 (d, 1H), 7.09 (d, 1H), 6.10 (d, 1H), 4.59-4.55 (m, 2H), 3.96-3.91 (m, 4H), 3.83-3.79 (m, 2H), 3.60-3.55 (m, 1H), 2.86-2.81 (m, 1H), 2.61-2.28 (m, 2H), 2.19-2.09 (m, 1H), 1.87-1.82 (m, 2H), 1.33-1.29 (m, 2H), 1.00-0.95 (m, 2H), 0.75-0.66 (m, 2H). LCMS (ESI): 560.45 $[M+H]^+$.

Example 450-B

The second eluting diastereomer (24.6 mg) was obtained as a solid.

The second eluting diastereomer had a retention time of 6.97 min.

$^1$H NMR (400 MHz, $CD_3OD$) δ 8.18-8.09 (m, 2H), 7.99 (d, 1H), 7.26 (d, 1H), 7.09 (d, 1H), 6.10 (d, 1H), 4.62-4.53 (m, 2H), 4.08-3.67 (m, 6H), 3.59-3.55 (m, 1H), 2.86-2.82 (m, 1H), 2.54-2.31 (m, 2H), 2.18-2.09 (m, 1H), 2.00-1.63 (m, 2H), 1.34-1.25 (m, 2H), 1.16-0.80 (m, 2H), 0.73-0.64 (m, 2H). LCMS (ESI): 560.40 $[M+H]^+$.

Example 451. (S)—N-((3-chloro-6-methylpyrazin-2-yl)methyl)-4-(5-(5-fluoro-2-methoxypyridin-4-yl)-1H-pyrazole-3-carbonyl)-4-azaspiro[2.5]octane-7-carboxamide

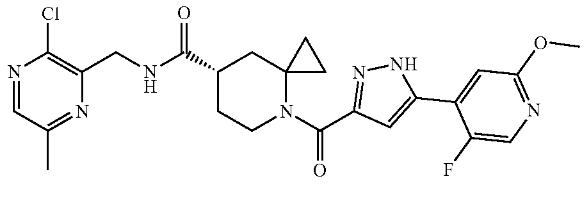 [SMILES: COc1cc(-c2cc(C(=O)N3CC[C@H](C(=O)NCc4nc(C)cnc4Cl)CC34CC4)n[nH]2)c(F)cn1]

Step-1. 1-(3-chloro-6-methylpyrazin-2-yl)methanamine

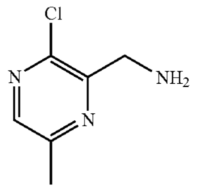

DIBAL-H (11.72 mL, 11.72 mmol) was added to a stirred solution of 3-chloro-6-methylpyrazine-2-carbonitrile (300.0 mg, 1.95 mmol) in DCM (3.00 mL) at −78 degree C. under nitrogen atmosphere. The resulting mixture was stirred at −78° C. for 15 min under nitrogen atmosphere. The reaction mixture was quenched by the addition of MeOH at −78° C. under nitrogen atmosphere. The resulting mixture was concentrated under reduced pressure. The residue was purified by silica gel column chromatography eluting with DCM/MeOH (15/1 v/v) to obtain the title compound (70.0 mg) as an oil. LCMS (ESI): 158.04 $[M+H]^+$.

Step-2. (S)—N-((3-chloro-6-methylpyrazin-2-yl)methyl)-4-(5-(5-fluoro-2-methoxypyridin-4-yl)-1H-pyrazole-3-carbonyl)-4-azaspiro[2.5]octane-7-carboxamide

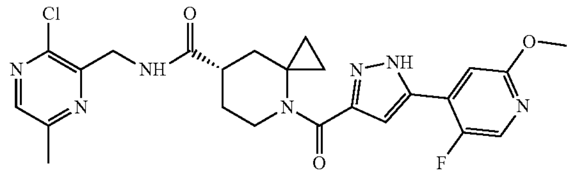 [SMILES: COc1cc(-c2cc(C(=O)N3CC[C@H](C(=O)NCc4nc(C)cnc4Cl)CC34CC4)n[nH]2)c(F)cn1]

HOBt (68.6 mg, 0.36 mmol), EDCI (48.3 mg, 0.36 mmol), and 1-(3-chloro-6-methylpyrazin-2-yl)methanamine (Step-1, 40.0 mg, 0.25 mmol) were added to a stirred solution (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 66.5 mg, 0.18 mmol) and DIPEA (46.3 mg, 0.36 mmol) in DMF (2.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 10 B to 30 B in 30 min; 220/254 nm) to obtain the title compound (22.0 mg) as a solid. $^1H$ NMR (400 MHz, $CD_3OD$) δ 8.24-8.20 (m, 1H), 8.16-8.11 (m, 1H), 7.31-7.26 (m, 1H), 7.14-7.09 (m, 1H), 4.62-4.57 (m, 3H), 3.95 (s, 3H), 3.08-2.88 (m, 1H), 2.54 (s, 3H), 2.49-2.39 (m, 1H), 2.08-1.67 (m, 2H), 1.60-0.95 (m, 3H), 0.94-0.55 (m, 3H). LCMS (ESI): 514.25 $[M+H]^+$.

Example 452. A Diastereomeric Mixture of (S)-4-(5-(5-fluoro-2-methoxypyridin-4-yl)-1H-pyrazole-3-carbonyl)-N—((S)-1-(6-methylpyridazin-4-yl)pyrrolidin-3-yl)-4-azaspiro[2.5]octane-7-carboxamide and ('S)-4-(5-(5-fluoro-2-methoxypyridin-4-yl)-1H-pyrazole-3-carbonyl)-N—((R)-1-(6-methylpyridazin-4-yl)pyrrolidin-3-yl)-4-azaspiro[2.5]octane-7-carboxamide

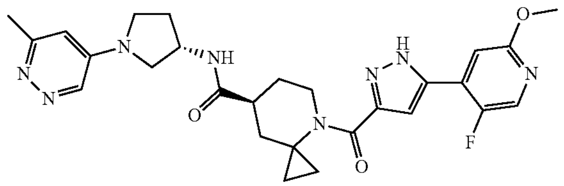

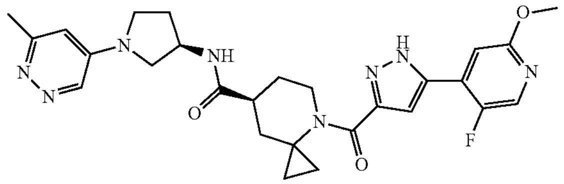

Step-1. N,N-dibenzyl-1-(6-methylpyridazin-4-yl)pyrrolidin-3-amine

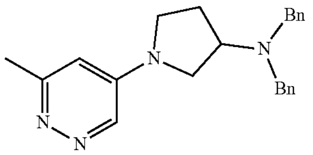 [SMILES: Cc1cc(N2CCC(N(Cc3ccccc3)Cc3ccccc3)C2)cnn1]

DIPEA (582.2 mg, 4.51 mmol) was added to a stirred mixture of N,N-dibenzylpyrrolidin-3-amine (400.0 mg, 1.50 mmol) and 5-chloro-3-methylpyridazine (193.0 mg, 1.50 mmol) in DMSO (5.00 mL). The resulting mixture was stirred at 100° C. for 5 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (13/1 v/v) to obtain the title compound (280.0 mg) as an oil. LCMS (ESI): 359.2 $[M+H]^+$.

Step-2. 1-(6-methylpyridazin-4-yl)pyrrolidin-3-amine

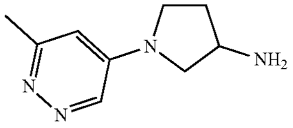

Pd/C (240.0 mg) and HCl (6 M) (137.6 mg, 2.01 mmol) were added to a stirred mixture of N,N-dibenzyl-1-(6-methylpyridazin-4-yl)pyrrolidin-3-amine (Step-1, 240.0 mg, 0.67 mmol) in MeOH (6.00 mL). The resulting mixture was stirred at 25° C. for 2 days under hydrogen atmosphere.

The resulting mixture was filtered, the filter cake was washed with MeOH. The filtrate was concentrated under reduced pressure to obtain the title compound (110.0 mg) as a solid. LCMS (ESI): 179.1 $[M+H]^+$.

Step-3. (S)-4-(5-(5-fluoro-2-methoxypyridin-4-yl)-1H-pyrazole-3-carbonyl)-N—((S)-1-(6-methylpyridazin-4-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(6-methylpyridazin-4-yl)pyrrolidin-3-yl)-4-azaspiro[2.5]octane-7-carboxamide

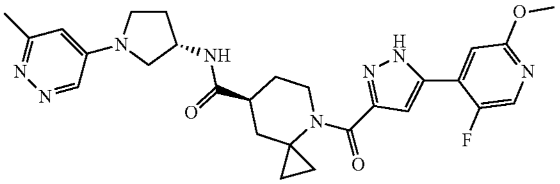

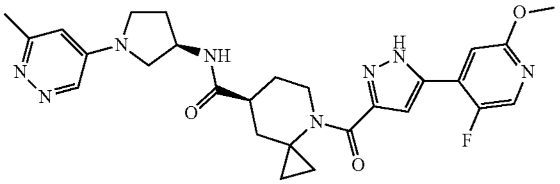

HOBt (166.8 mg, 1.23 mmol), EDCI (236.6 mg, 1.23 mmol), and 1-(6-methylpyridazin-4-yl)pyrrolidin-3-amine (Step-2, 110.0 mg, 0.62 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 231.0 mg, 0.62 mmol) and DIPEA (797.6 mg, 6.17 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (5/1 v/v) and further purified by reverse phase column chromatography (using the following conditions: column, C18; mobile phase, A: Water (0.5% $NH_4HCO_3$), mobile phase B: MeCN; gradient: 20 B to 30 B in 20 min; detector, UV 254/220 nm) to obtain (S)-4-(5-(5-fluoro-2-methoxypyridin-4-yl)-1H-pyrazole-3-carbonyl)-N—((S)-1-(6-methylpyridazin-4-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(6-methylpyridazin-4-yl)pyrrolidin-3-yl)-4-azaspiro[2.5]octane-7-carboxamide (140.0 mg) as a solid mixture of diastereomers (Example 452). $^1$H NMR (400 MHz, $CD_3OD$) δ 8.44 (s, 1H), 8.13 (s, 1H), 7.28 (s, 1H), 7.10 (s, 1H), 6.58 (s, 1H), 4.66-4.49 (m, 2H), 3.95 (s, 3H), 3.75-3.66 (m, 1H), 3.60-3.51 (m, 2H), 3.31-3.26 (m, 1H), 2.82 (s, 1H), 2.50 (s, 3H), 2.46-2.27 (m, 2H), 2.13-2.02 (m, 1H), 1.87-1.83 (m, 2H), 1.42-0.83 (m, 3H), 0.79-0.56 (m, 3H). LCMS (ESI): 535.40 $[M+H]^+$.

This mixture of two diastereomers (130.0 mg) was separated using Chiral Prep-HPLC.

Column: CHIRALPAK IE column

Column dimension: 2×25 cm, 5 μm

Mobile Phase: MTBE (0.5% 2M $NH_3$·MeOH):EtOH=50:50 hold for 45 min

Flow rate: 14 mL/min

Detection: 220/254 nm

Example 452-A. The first eluting diastereomer (35.0 mg) was obtained as a solid.

The first eluting diastereomer had a retention time of 34.30 min.

$^1$H NMR (400 MHz, $CD_3OD$) δ 8.44 (d, 1H), 8.13 (d, 1H), 7.28 (s, 1H), 7.11 (s, 1H), 6.59 (t, 1H), 4.58-4.50 (m, 2H), 3.95 (s, 3H), 3.76-3.67 (m, 1H), 3.60-3.49 (m, 2H), 3.32-3.25 (m, 1H), 2.82 (s, 1H), 2.53-2.48 (m, 3H), 2.45-2.27 (nm, 2H), 2.14-2.03 (m, 1H), 1.87-1.82 (m, 2H), 1.33-1.29 (m, 2H), 1.06-1.01 (m, 2H), 0.75-0.70 (m, 2H). LCMS (ESI): 535.45 $[M+H]^+$.

Example 452-B. The second eluting diastereomer (35.0 mg) was obtained as a solid.

The second eluting diastereomer had a retention time of 43.64 min.

$^1$H NMR (400 MHz, $CD_3OD$) δ 8.43 (q, 1H), 8.13 (d, 1H), 7.28 (s, 1H), 7.10 (s, 1H), 6.61-6.54 (m, 1H), 4.57-4.49 (m, 2H), 3.94 (s, 3H), 3.73-3.68 (m, 1H), 3.58-3.51 (m, 2H), 3.31-3.23 (m, 1H), 2.85-2.80 (m, 1H), 2.51 (s, 3H), 2.44-2.27 (m, 2H), 2.13-2.04 (m, 1H), 1.89-1.67 (m, 2H), 1.44-1.17 (m, 2H), 1.03-0.99 (m, 2H), 0.73-0.69 (m, 2H). LCMS (ESI): 535.45 $[M+H]^+$.

Example 453. A Diastereomeric Mixture of (S)-4-(5-(5-fluoro-2-methoxypyridin-4-yl)-1H-pyrazole-3-carbonyl)-N—((S)-1-(2-methylpyrimidin-5-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-methylpyrimidin-5-yl)pyrrolidin-3-yl)-4-azaspiro[2.5]octane-7-carboxamide

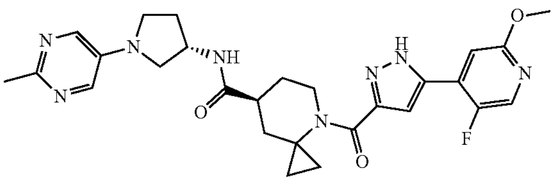

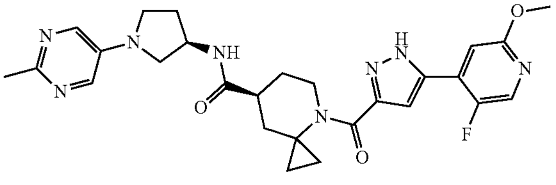

Step-1. tert-butyl 3-(1,3-dioxoisoindol-2-yl)pyrrolidine-1-carboxylate

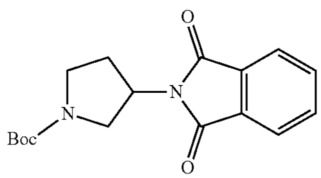 [SMILES: CC(C)(C)OC(=O)N1CCC(N2C(=O)c3ccccc3C2=O)C1]

N-carbethoxyphthalimide (1.18 g, 5.37 mmol) and TEA (0.71 g, 6.98 mmol) were added to a stirred solution of tert-butyl 3-aminopyrrolidine-1-carboxylate (1.00 g, 5.37 mmol) in THE (15.00 mL). The resulting solution was stirred at 80° C. for 3 h. The resulting mixture was concentrated under reduced pressure. The residue was purified by silica gel column chromatography eluting with petroleum ether/EtOAc (1/1 v/v) to obtain the title compound (780.0 mg) as a solid. LCMS (ESI): 317.1 $[M+H]^+$.

Step-2. 2-(pyrrolidin-3-yl)isoindole-1,3-dione

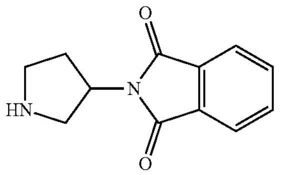 [SMILES: O=C1c2ccccc2C(=O)N1C1CCNC1]

TFA (6.00 mL) was added to a stirred solution of tert-butyl 3-(1,3-dioxoisoindol-2-yl)pyrrolidine-1-carboxylate (Step-1, 700.0 mg, 2.21 mmol) in DCM (6.00 mL). The resulting solution was stirred at 25° C. for 2 h. The resulting mixture was concentrated under reduced pressure. The residue was purified by silica gel column chromatography eluting with DCM/MeOH (9/1 v/V) to obtain the title compound (450.0 mg) as ae solid. LCMS (ESI): $[M+H]^+$: 217.1.

Step-3. 2-[1-(2-methylpyrimidin-5-yl)pyrrolidin-3-yl]isoindole-1,3-dione

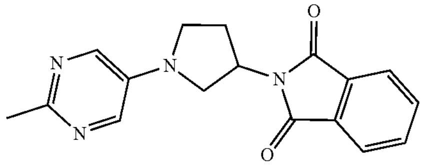 [SMILES: Cc1ncc(N2CCC(N3C(=O)c4ccccc4C3=O)C2)cn1]

$Cs_2CO_3$ (1.78 g, 5.46 mmol), Pd-PEPPSI-IPentCl 2-methylpyridine (o-picoline) (297.0 mg, 0.27 mmol, CAS #: 1612891-29-8), and 5-bromo-2-methylpyrimidine (472.1 mg, 2.73 mmol) were added to a stirred solution of 2-(pyrrolidin-3-yl)isoindole-1,3-dione (Step-2, 590.0 mg, 2.73 mmol) in 1,4-dioxane (15.00 mL). The resulting solution was stirred at 90° C. for 14 h under nitrogen atmosphere. The resulting mixture was concentrated under reduced pressure. The residue was purified by silica gel column chromatography eluting with DCM/MeOH (20/1 v/V) to obtain the title compound (260.0 mg) as a solid. LCMS (ESI): $[M+H]^+$: 309.1.

Step-4. 1-(2-methylpyrimidin-5-yl)pyrrolidin-3-amine

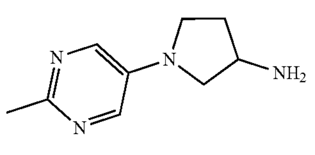

Hydrazine (249.4 mg, 7.78 mmol) was added to a stirred solution of 2-[1-(2-methylpyrimidin-5-yl)pyrrolidin-3-yl]isoindole-1,3-dione (Step-3, 240.0 mg, 0.78 mmol) in ethyl alcohol (6.00 mL). The resulting solution was stirred at 60° C. for 30 min. The resulting mixture was concentrated under reduced pressure. The residue was purified by silica gel column chromatography eluting with DCM/MeOH (12/1 v/v) to obtain the title compound (123.0 mg) as a solid. LCMS (ESI): 179.1 $[M+H]^+$.

Step-5. (S)-4-(5-(5-fluoro-2-methoxypyridin-4-yl)-1H-pyrazole-3-carbonyl)-N—((S)-1-(2-methylpyrimidin-5-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-methylpyrimidin-5-yl)pyrrolidin-3-yl)-4-azaspiro[2.5]octane-7-carboxamide

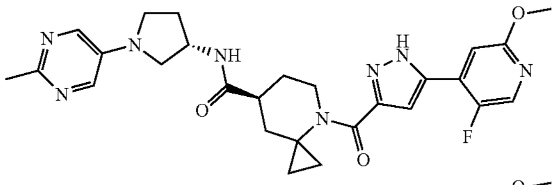

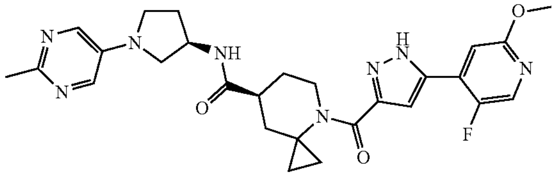

HOBt (127.0 mg, 0.94 mmol), EDCI (179.0 mg, 0.94 mmol), and 1-(2-methylpyrimidin-5-yl)pyrrolidin-3-amine (Step-4, 110.0 mg, 0.61 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 176.0 mg, 0.47 mmol) and DIPEA (303.0 mg, 2.34 mmol) in DMF (5.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: column, C18; mobile phase, $NH_4HCO_3$ in water and MeCN, 30% to 50% gradient in 20 min; detector, UV 254/220 nm) to obtain (S)-4-(5-(5-fluoro-2-methoxypyridin-4-yl)-1H-pyrazole-3-carbonyl)-N—((S)-1-(2-methylpyrimidin-5-yl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((R)-1-(2-methylpyrimidin-5-yl)pyrrolidin-3-yl)-4-azaspiro[2.5]octane-7-carboxamide (180.0 mg) as a solid mixture of diastereomers (Example 453). $^1H$ NMR (400 MHz, $CD_3OD$) δ 8.21-7.97 (m, 3H), 7.38-6.99 (m, 2H), 4.71-4.40 (m, 2H), 3.94 (s, 3H), 3.69-3.57 (m, 1H), 3.56-3.44 (m, 1H), 3.44-3.35 (m, 1H), 3.26-3.11 (m, 2H), 2.92-2.73 (m, 1H), 2.64-2.52 (m, 3H), 2.52-2.40 (m, 1H), 2.39-2.22 (m, 1H), 2.14-1.97 (m, 1H), 1.96-1.59 (m, 2H), 1.45-1.16 (m, 1H), 1.16-0.81 (m, 2H), 0.82-0.58 (m, 2H). LCMS (ESI): 535.40 $[M+H]^+$.

This mixture of two diastereomers (150.0 mg) was separated using Chiral Prep-HPLC.

Column: CHIRALPAK ID column
Column dimension: 2×25 cm, 5 μm
Mobile Phase: 1/1 hexanes/DCM (0.5% 2 M $NH_3$·MeOH):EtOH=80:20 hold for 23 min
Flow rate: 20 mL/min
Detection: 220/254 nm Example 453-A. The first eluting diastereomer (55.0 mg) was obtained as a solid.

The first eluting diastereomer had a retention time of 14.48 min.

$^1$H NMR (400 MHz, $CD_3OD$) δ 8.25-7.93 (m, 3H), 7.41-7.28 (m, 1H), 7.27-6.97 (m, 1H), 4.75-4.31 (m, 2H), 3.95 (s, 3H), 3.67-3.56 (m, 1H), 3.54-3.45 (m, 1H), 3.44-3.36 (m, 1H), 3.28-3.12 (m, 1H), 2.96-2.72 (m, 1H), 2.55 (s, 3H), 2.47-2.22 (m, 2H), 2.13-1.95 (m, 1H), 1.93-1.59 (m, 2H), 1.52-1.18 (m, 2H), 1.18-0.83 (m, 2H), 0.82-0.49 (m, 2H). LCMS (ESI): 535.40 $[M+H]^+$.

Example 453-B. The second eluting diastereomer (60.0 mg) was obtained as a solid.

The second eluting diastereomer had a retention time of 20.18 min.

$^1$H NMR (400 MHz, $CD_3OD$) δ 8.52-7.84 (m, 3H), 7.48-6.92 (m, 2H), 4.76-4.42 (m, 2H), 3.95 (s, 3H), 3.68-3.57 (m, 1H), 3.56-3.45 (m, 1H), 3.45-3.36 (m, 1H), 3.26-3.17 (m, 1H), 2.94-2.70 (m, 1H), 2.56 (s, 3H), 2.49-2.24 (m, 2H), 2.15-1.98 (m, 1H), 1.97-1.59 (m, 2H), 1.47-1.17 (m, 2H), 1.15-0.81 (m, 2H), 0.81-0.54 (m, 2H). LCMS (ESI): 535.40 $[M+H]^+$.

Example 454. A Diastereomeric Mixture of (S)-4-(5-(5-fluoro-2-methoxypyridin-4-yl)-1H-pyrazole-3-carbonyl)-N—((R)-1-((3-hydroxyoxetan-3-yl)methyl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-((3-hydroxyoxetan-3-yl)methyl)pyrrolidin-3-yl)-4-azaspiro[2.5]octane-7-carboxamide

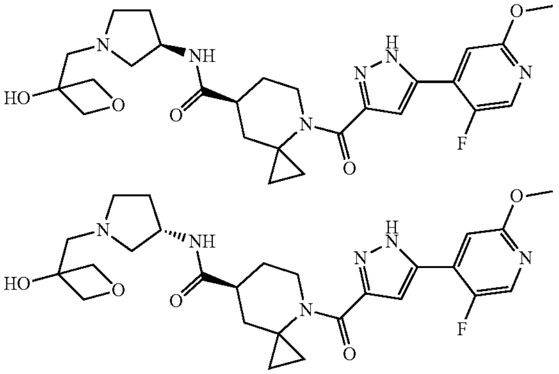

Step-1. 3-{[3-(dibenzylamino)pyrrolidin-1-yl]methyl}oxetan-3-ol

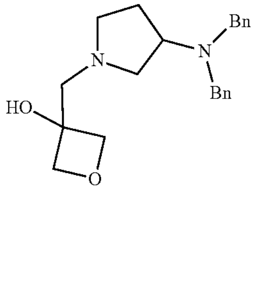 [SMILES: OC1(CN2CCC(N(Cc3ccccc3)Cc3ccccc3)C2)COC1]

TEA (177.0 mg, 1.75 mmol) and 1,5-dioxaspiro[2.3]hexane (150.0 mg, 1.75 mmol) were added to a mixture of N,N-dibenzylpyrrolidin-3-amine (310.0 mg, 1.16 mmol) in MeOH (5.00 mL). The resulting mixture was stirred at 80° C. for 14 h. The resulting mixture was concentrated under reduced pressure. The residue was purified by silica gel column chromatography eluting with petroleum ether/EtOAc (1/1 v/v) to obtain the title compound (340.0 mg) as a solid. LCMS (ESI): 353.0 $[M+H]^+$.

Step-2. 3-[(3-aminopyrrolidin-1-yl)methyl]oxetan-3-ol

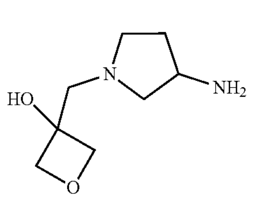 [SMILES: NC1CCN(CC2(O)COC2)C1]

Pd/C (120.0 mg) was added to a mixture of 3-{[3-(dibenzylamino)pyrrolidin-1-yl]methyl}oxetan-3-ol (Step-1, 320.0 mg, 0.91 mmol) in MeOH (5.00 mL). The resulting mixture was stirred at 25° C. for 14 h under hydrogen atmosphere. The resulting mixture was filtered, the filter cake was washed with MeOH. The filtrate was concentrated under reduced pressure to obtain the title compound (120.0 mg) as a solid. LCMS (ESI): 173 $[M+H]^+$.

Step-3. (S)-4-(5-(5-fluoro-2-methoxypyridin-4-yl)-1H-pyrazole-3-carbonyl)-N—((R)-1-((3-hydroxyoxetan-3-yl)methyl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-((3-hydroxyoxetan-3-yl)methyl)pyrrolidin-3-yl)-4-azaspiro[2.5]octane-7-carboxamide

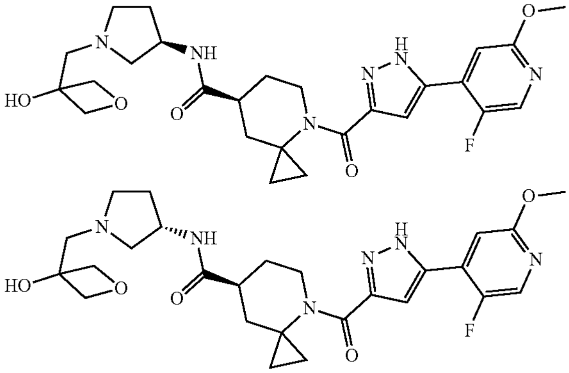

HOBt (129.0 mg, 0.96 mmol), EDCI (184.0 mg, 0.96 mmol), and 3-[(3-aminopyrrolidin-1-yl)methyl]oxetan-3-ol (Step-2, 110.0 mg, 0.64 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 239.0 mg, 0.64 mmol) and DIPEA (413.0 mg, 3.20 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)-4-(5-(5-fluoro-2-methoxypyridin-4-yl)-1H-pyrazole-3-carbonyl)-N—((R)-1-((3-hydroxyoxetan-3-yl)methyl)pyrrolidin-3-yl)-4-azaspiro[2.5]octane-7-carboxamide and (S)-4-(5-(5-fluoro-2-methoxypyridin-4-yl)-1H-pyrazole-3-carbonyl)-N—((S)-1-((3-hydroxyoxetan-3-yl)methyl)pyrrolidin-3-yl)-4-azaspiro[2.5]octane-7-carboxamide (110.0 mg) as a solid mixture of diastereomers (Example 454). $^1$H NMR (400 MHz, DMSO-$d_6$) δ 12.81 (s, 1H), 8.27 (d, 1H), 7.95 (d, 1H), 7.32 (d, 1H), 7.03 (d, 1H), 5.40 (s, 1H), 4.42-4.32 (m, 4H), 4.16-4.07 (m, 1H), 3.88 (s, 3H), 3.39-3.27 (m, 4H), 2.79-2.61 (m, 4H), 2.40-2.33 (m, 1H), 2.23-2.16 (m, 1H), 2.10-1.97 (m, 1H), 1.74-1.69 (m, 1H), 1.54-1.42 (m, 2H), 1.20-1.16 (m, 1H), 0.93-0.88 (m, 2H), 0.67-0.58 (m, 2H). LCMS (ESI): 529.45 $[M+H]^+$.

This mixture of two diastereomers (100.0 mg) was separated using Chiral Prep-HPLC.

Column: CHIRALPAK IE column

Column dimension: 2×25 cm, 5 μm

Mobile Phase: 1/1 hexanes/DCM (0.5% 2 M $NH_3$·MeOH):EtOH=80:20 hold for 25 min

Flow rate: 20 mL/min

Detection: 220/254 nm

Example 454-A. The first eluting diastereomer (38.2 mg) was obtained as a solid.

The first eluting diastereomer had a retention time of 18.42 min.

$^1$H NMR (400 MHz, DMSO-$d_6$) δ 13.99 (s, 1H), 8.27 (s, 1H), 7.95 (d, 1H), 7.33 (d, 1H), 7.03 (s, 1H), 5.40 (s, 1H), 4.68-4.30 (m, 5H), 4.15-4.08 (m, 1H), 3.88 (s, 3H), 2.82-2.63 (m, 6H), 2.41-2.31 (m, 1H), 2.27-2.11 (m, 1H), 2.10-1.97 (m, 1H), 1.75-1.71 (m, 1H), 1.57-1.45 (m, 2H), 1.30-1.09 (m, 2H), 0.99-0.94 (m, 2H), 0.65-0.61 (m, 2H). LCMS (ESI): 529.45 $[M+H]^+$.

Example 454-B. The second eluting diastereomer (39.2 mg) was obtained as a solid.

The second eluting diastereomer had a retention time of 21.78 min.

$^1$H NMR (400 MHz, DMSO-$d_6$) δ 13.99 (s, 1H), 8.27 (d, 1H), 7.96 (d, 1H), 7.32 (d, 1H), 7.03 (s, 1H), 5.41 (s, 1H), 4.42-4.33 (m, 5H), 4.17-4.07 (m, 1H), 3.88 (s, 3H), 2.80-2.60 (m, 6H), 2.41-2.33 (m, 1H), 2.20-2.16 (m, 1H), 2.10-1.97 (m, 2H), 1.76-1.69 (m, 1H), 1.58-1.42 (m, 2H), 1.21-1.16 (m, 1H), 0.95-0.91 (m, 2H), 0.67-0.58 (m, 2H). LCMS (ESI): 529.45 $[M+H]^+$.

Example 455. (S)-4-(5-(5-fluoro-2-methoxypyridin-4-yl)-1H-pyrazole-3-carbonyl)-N-((5-methoxypyrimidin-2-yl)methyl)-4-azaspiro[2.5]octane-7-carboxamide

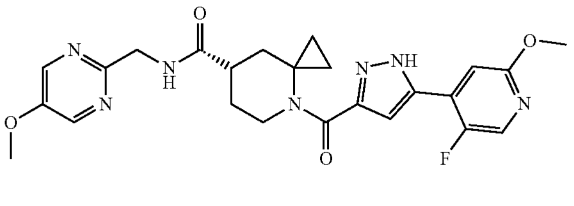

Step-1. 5-methoxypyrimidine-2-carbonitrile

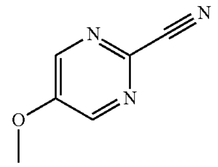

Sodium methoxide (2.19 g, 40.62 mmol) was added to stirred a mixture of 5-fluoropyrimidine-2-carbonitrile (1.00 g, 8.12 mmol) in DMF (10.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (3/1 v/v) to obtain the title compound (570.0 mg) as a solid. LCMS (ESI): 136.0 $[M+H]^+$.

Step-2. 1-(5-methoxypyrimidin-2-yl)methanamine

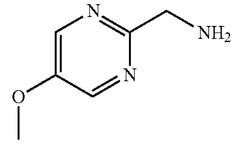

$LiAlH_4$ (2.96 mL, 1.04 mmol) was added to a stirred mixture of 5-methoxypyrimidine-2-carbonitrile (Step-1, 200.0 mg, 1.48 mmol) in THF (10.00 mL) at 0° C. under nitrogen atmosphere. The resulting mixture was stirred at 0° C. for 30 mins under nitrogen atmosphere. The reaction mixture was quenched with MeOH at 0° C. The resulting mixture was concentrated under reduced pressure. The residue was purified by silica gel column chromatography eluting with DCM/MeOH (10/1 v/v) to obtain the title compound (60.0 mg) as a solid. LCMS (ESI): 140.1 $[M+H]^+$.

Step-3. (S)-4-(5-(5-fluoro-2-methoxypyridin-4-yl)-1H-pyrazole-3-carbonyl)-N-((5-methoxypyrimidin-2-yl)methyl)-4-azaspiro[2.5]octane-7-carboxamide

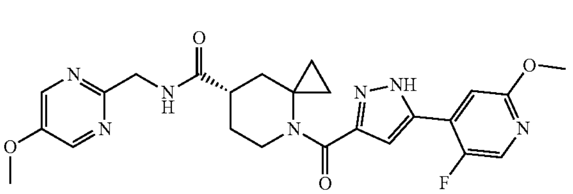 [SMILES: COc1cnc(CNC(=O)[C@H]2CCN(C(=O)c3cc(-c4cc(OC)ncc4F)[nH]n3)C3(CC3)C2)nc1]

EDCI (110.2 mg, 0.57 mmol), HOBt (77.7 mg, 0.57 mmol), and 1-(5-methoxypyrimidin-2-yl)methanamine (Step-2, 40.0 mg, 0.29 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 107.6 mg, 0.29 mmol) and DIPEA (185.8 mg, 1.44 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) and further purified by Prep-HPLC (using the following conditions: Column: YMC-Actus Triart C18 ExRS, 30 mm×150 mm, 5 μm; Mobile Phase A: Water (10 mM $NH_4H$ $CO_3$), Mobile Phase B: MeCN; Flow rate: 60 mL/min; Gradient: 25% B to 35% B in 8 min, 35% B; Wavelength: 254 nm; RT1 (min): 7.9) to obtain the title compound (2.0 mg). $^1H$ NMR (400 MHz, $CD_3OD$) δ 8.46 (s, 2H), 8.13 (d, 1H), 7.29 (d, 1H), 7.11 (d, 1H), 4.57-4.52 (m, 3H), 3.98-3.92 (m, 6H), 2.97-2.92 (m, 1H), 2.49-2.44 (m, 1H), 1.99-1.95 (m, 1H), 1.81-1.77 (m, 1H), 1.54-1.27 (m, 1H), 1.26-0.85 (m, 2H), 0.84-0.58 (m, 3H). LCMS (ESI): 496.40 $[M+H]^+$.

Example 456. (S)—N-((5-cyanopyrimidin-2-yl) methyl)-4-(5-(5-fluoro-2-methoxypyridin-4-yl)-1H-pyrazole-3-carbonyl)-4-azaspiro[2.5]octane-7-carboxamide

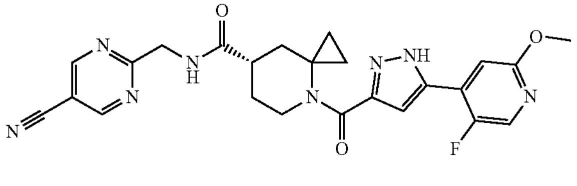 [SMILES: COc1cc(-c2cc(C(=O)N3CC[C@H](C(=O)NCc4ncc(C#N)cn4)CC34CC4)n[nH]2)c(F)cn1]

Step-1. tert-butyl N-[(5-bromopyrimidin-2-yl) methyl]carbamate

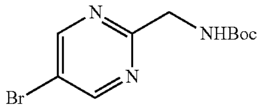 [SMILES: CC(C)(C)OC(=O)NCc1ncc(Br)cn1]

Di-tert-butyl dicarbonate (145.8 mg, 0.67 mmol) and DIPEA (115.1 mg, 0.89 mmol) were added to a solution of 1-(5-bromopyrimidin-2-yl)methanamine hydrochloride (100.0 mg, 0.45 mmol) in DCM (3.00 mL). The resulting solution was stirred at 25° C. for 14 h. The resulting solution was concentrated under reduced pressure. The residue was purified by Prep-TLC (DCM/MeOH, 10/1 v/v) to obtain the title compound (120.0 mg) as a solid. LCMS (ESI): 288.0 $[M+H]^+$.

Step-2. tert-butyl N-[(5-cyanopyrimidin-2-yl) methyl]carbamate

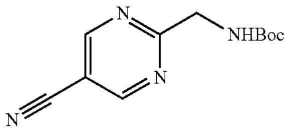 [SMILES: CC(C)(C)OC(=O)NCc1ncc(C#N)cn1]

$Zn(CN)_2$ (81.5 mg, 0.69 mmol), dppf (38.3 mg, 0.07 mmol) and $Pd(dba)_2$ (39.9 mg, 0.07 mmol) were added to a solution of tert-butyl N-[(5-bromopyrimidin-2-yl)methyl] carbamate (Step-1, 200.0 mg, 0.69 mmol) in 1,4-dioxane (5.00 mL). The resulting solution was stirred at 120° C. for 14 h. The resulting mixture was concentrated under reduced pressure. The residue was purified by silica gel column chromatography eluting with DCM/MeOH (10/1 v/v) to obtain the title compound (100.0 mg) as a solid. LCMS (ESI): 235.1 $[M+H]^+$.

Step-3. 2-(aminomethyl)pyrimidine-5-carbonitrile

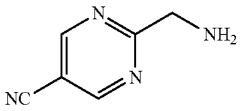

TFA (1.00 mL) was added to a solution of tert-butyl N-[(5-cyanopyrimidin-2-yl)methyl]carbamate (Step-2, 100.0 mg, 0.43 mmol) in DMF (1.00 mL). The resulting solution was stirred at 25° C. for 1 h. The solution was concentrated under reduced pressure to obtain the title compound (55.0 mg) as a solid and directly used in the next step without further purification. LCMS (ESI): 135.0 $[M+H]^+$.

Step-4. (S)—N-((5-cyanopyrimidin-2-yl)methyl)-4-(5-(5-fluoro-2-methoxypyridin-4-yl)-1H-pyrazole-3-carbonyl)-4-azaspiro[2.5]octane-7-carboxamide

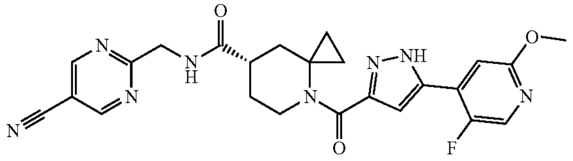 [SMILES: COc1cc(-c2cc(C(=O)N3CC[C@H](C(=O)NCc4ncc(C#N)cn4)CC34CC4)n[nH]2)c(F)cn1]

HOBt (75.6 mg, 0.56 mmol), EDCI (107.2 mg, 0.56 mmol), and 2-(aminomethyl)pyrimidine-5-carbonitrile (Step-3, 50.0 mg, 0.37 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 139.5 mg, 0.37 mmol) and DIPEA (240.9 mg, 1.87 mmol) in DMF (3.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 10/1 v/v) to obtain the title compound (55.0 mg) as a solid. $^1H$ NMR (400 MHz, DMSO-$d_6$) δ 13.98 (s, 1H), 9.25 (s, 2H), 8.54 (s, 1H), 8.27 (s, 1H), 7.32 (d, 1H), 7.03 (s, 1H), 4.79-4.17 (m, 3H), 3.88 (s, 3H), 3.29-3.10 (m, 1H), 2.90-2.73 (m, 1H), 2.37-2.02 (m, 1H), 1.97-1.69 (m, 1H), 1.66-1.43 (m, 1H), 1.42-1.20 (m, 1H), 1.20-0.79 (m, 2H), 0.77-0.46 (m, 2H). LCMS (ESI): 491.35 $[M+H]^+$.

Example 457. (S)-4-(5-(5-fluoro-2-methoxypyridin-4-yl)-1H-pyrazole-3-carbonyl)-N-((5-(trifluoromethyl)pyrimidin-2-yl)methyl)-4-azaspiro[2.5]octane-7-carboxamide

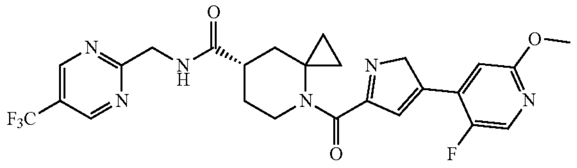 [SMILES: COc1cc(C2=CC(C(=O)N3CC[C@H](C(=O)NCc4ncc(C(F)(F)F)cn4)CC34CC4)=NC2)c(F)cn1]

The title compound was prepared using a procedure similar to the one described for the synthesis of Example 325, except 1-[5-(trifluoromethyl)pyrimidin-2-yl]methanamine hydrochloride was used as a starting material. The residue was purified by reverse flash chromatography (using the following conditions: phase A: Water (0.5% $NH_4HCO_3$), mobile phase B: MeCN; gradient: 30 B to 40 B in 20 min; detector, UV 254/220 nm) to obtain the title compound (75.0 mg) as a solid. $^1$H NMR (400 MHz, DMSO-$d_6$) δ 13.95 (s, 1H), 9.22 (d, 2H), 8.60-8.52 (m, 1H), 8.27 (d, 1H), 7.32 (d, 1H), 7.03 (s, 1H), 4.59-4.53 (m, 2H), 4.47 (s, 1H), 3.88 (s, 3H), 3.20-3.15 (m, 1H), 2.85-2.80 (m, 1H), 2.24-2.20 (m, 1H), 1.85-1.81 (m, 1H), 1.58-1.53 (m, 1H), 1.32-1.27 (m, 1H), 1.14-0.75 (m, 2H), 0.68-0.64 (m, 2H). LCMS (ESI): 534.15 $[M+H]_+$.

Example 458. (S)—N-(1-(3,5-dichloropyridin-2-yl)cyclopropyl)-4-(5-(5-fluoro-2-methoxypyridin-4-yl)-1H-pyrazole-3-carbonyl)-4-azaspiro[2.5]octane-7-carboxamide

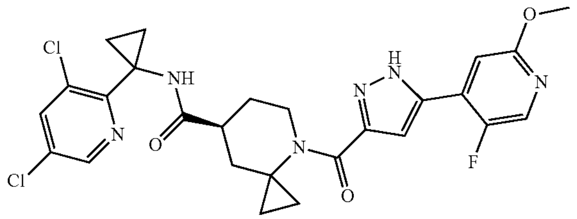 [SMILES: COc1cc(-c2cc(C(=O)N3CC[C@H](C(=O)NC4(c5ncc(Cl)cc5Cl)CC4)CC34CC4)n[nH]2)c(F)cn1]

Step-1. 1,3-diethyl 2-(3,5-dichloropyridin-2-yl)propanedioate

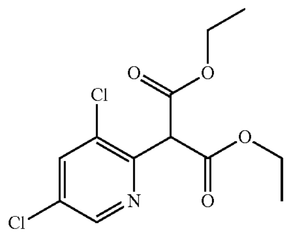 [SMILES: CCOC(=O)C(C(=O)OCC)c1ncc(Cl)cc1Cl]

Diethyl malonate (1.85 g, 11.57 mmol) and $Cs_2CO_3$ (3.77 g, 11.57 mmol) were added to a stirred solution of 3,5-dichloro-2-fluoropyridine (960.0 mg, 5.78 mmol) in DMSO (10.00 mL). The resulting mixture was stirred at 110° C. for 3 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (5/1 v/v) to obtain the title compound (1.50 g) as an oil. LCMS (ESI): 306.0 $[M+H]^+$.

Step-2. ethyl 2-(3,5-dichloropyridin-2-yl)acetate

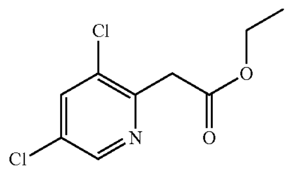

Lithium chloride (519.3 mg, 12.25 mmol) and $H_2O$ (88.3 mg, 4.90 mmol) were added to a stirred solution of 1,3-diethyl 2-(3,5-dichloropyridin-2-yl)propanedioate (Step-1, 1.50 g, 4.90 mmol) in DMSO (6.00 mL). The resulting solution was stirred at 120° C. for 14 h. The resulting solution was diluted with EtOAc and washed with water. The organic layer was concentrated under reduced pressure. The residue was purified by silica gel column chromatography eluting with petroleum ether/EtOAc (5/1 v/v) to obtain the title compound (887.0 mg) as an oil. LCMS (ESI): 234.0 $[M+H]^+$.

Step-3. ethyl 1-(3-chloro-5-fluoropyridin-2-yl)cyclopropane-1-carboxylate

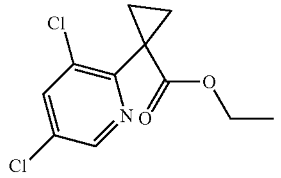 [SMILES: CCOC(=O)C1(c2ncc(Cl)cc2Cl)CC1]

Diphenyl(vinyl)sulfonium trifluoromethanesulfonate (1.31 g, 2.18 mmol) was added to a solution of ethyl 2-(3,5-dichloropyridin-2-yl)acetate (Step-2, 425.0 mg, 1.82 mmol) in DMSO (5.00 mL). The resulting solution was stirred at 25° C. for 2 min. Then DBU (829.2 mg, 5.45 mmol) was added to the resulting mixture at 0° C. under nitrogen atmosphere. The resulting mixture was stirred at 25° C. for 14 h. The residue was purified by silica gel column chromatography eluting with petroleum ether/EtOAc (5/1 v/v) to obtain the title (380.0 mg) as an oil. LCMS (ESI): 260.0 $[M+H]^+$.

Step-4. 1-(3,5-dichloropyridin-2-yl)cyclopropane-1-carboxamide

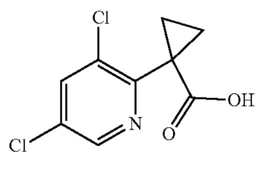 [SMILES: O=C(O)C1(c2ncc(Cl)cc2Cl)CC1]

Lithium hydroxide (123.2 mg, 2.93 mmol) was added to a stirred solution of ethyl 1-(3,5-dichloropyridin-2-yl)cyclopropane-1-carboxylate (Step-3, 380.0 mg, 1.47 mmol) in $H_2O$ (150 mL)/MeOH (1.50 mL)/THF (1.50 mL). The resulting mixture was stirred at 70° C. for 3 h. The resulting solution was concentrated under reduced pressure, then acidified to pH 3 with HCl (1 M). The solution was extracted with EtOAc. The organic layers were combined, dried over anhydrous $Na_2SO_4$, filtered, and concentrated under reduced pressure to obtain the title compound (300.0 mg) as a solid. LCMS (ESI): 232.0 $[M+H]^+$.

Step-5. 1-(3,5-dichloropyridin-2-yl)cyclopropane-1-carboxamide

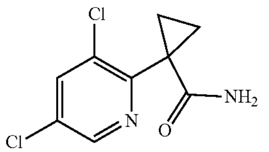 [SMILES: NC(=O)C1(c2ncc(Cl)cc2Cl)CC1]

HATU (589.9 mg, 1.55 mmol) and $NH_4Cl$ (76.1 mg, 1.42 mmol) were added to a stirred solution of 1-(3,5-dichloropyridin-2-yl)cyclopropane-1-carboxylic acid (Step-4, 300.0 mg, 1.29 mmol) and DIPEA (501.2 mg, 3.88 mmol) in DMF (5.00 mL). The resulting mixture was stirred at 25° C. for 1 h. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (290.0 mg) as a solid. LCMS (ESI): 231.0 $[M+H]^+$.

Step-6. methyl (1-(3,5-dichloropyridin-2-yl)cyclopropyl)carbamate

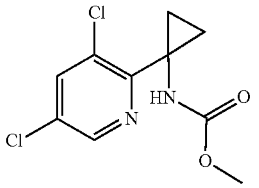 [SMILES: COC(=O)NC1(c2ncc(Cl)cc2Cl)CC1]

KOH (92.3 mg, 1.64 mmol) and $PhI(OAc)_2$ (492.1 mg, 1.23 mmol) were added to a stirred solution of 1-(3,5-dichloropyridin-2-yl)cyclopropane-1-carboxamide (Step-5, 190.0 mg, 0.82 mmol) in MeOH (5.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 20/1 v/v) to obtain the title compound (150.0 mg) as a solid. LCMS (ESI): 261.0 $[M+H]^+$.

Step-7. 1-(3,5-dichloropyridin-2-yl)cyclopropan-1-amine

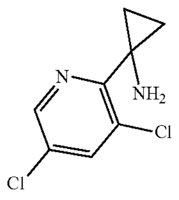 [SMILES: NC1(c2ncc(Cl)cc2Cl)CC1]

NaOH (180.0 mg, 4.50 mmol) was added to a stirred solution of methyl (1-(3,5-dichloropyridin-2-yl)cyclopropyl)carbamate (Step-6, 150.0 mg, 0.57 mmol) in EtOH (3.00 mL) and $H_2O$ (1.50 mL). The reaction mixture was heated to 120° C. for 30 min using microwave. The resulting solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (80.0 mg) as a solid. LCMS (ESI): 203.0 $[M+H]^+$.

Step-8. (S)—N-(1-(3,5-dichloropyridin-2-yl)cyclopropyl)-4-(5-(5-fluoro-2-methoxypyridin-4-yl)-1H-pyrazole-3-carbonyl)-4-azaspiro[2.5]octane-7-carboxamide

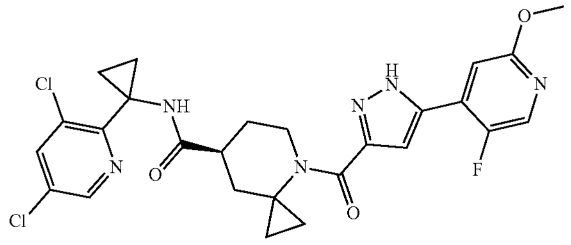 [SMILES: COc1cc(-c2cc(C(=O)N3CC[C@H](C(=O)NC4(c5ncc(Cl)cc5Cl)CC4)CC34CC4)n[nH]2)c(F)cn1]

1-(3,5-dichloropyridin-2-yl)cyclopropan-1-amine (Step-7, 70.0 mg, 0.35 mmol) and HATU (157.3 mg, 0.41 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 129.1 mg, 0.35 mmol) and DIPEA (133.7 mg, 1.04 mmol) in DMF (3.00 mL). The resulting solution was stirred at 25° C. for 1 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 10/1 v/v) to obtain the title compound (100.0 mg) as a solid. $^1H$ NMR (400 MHz, DMSO-$d_6$) 13.78 (s, 1H), 8.62 (s, 1H), 8.54-8.40 (m, 1H), 8.34-8.19 (m, 1H), 8.15-8.02 (m, 1H), 7.36-7.27 (m, 1H), 7.04-6.93 (m, 1H), 4.72-4.08 (m, 1H), 3.88 (s, 3H), 2.95-2.60 (m, 2H), 2.37-1.99 (m, 1H), 1.81-1.59 (m, 1H), 1.57-1.28 (m, 3H), 1.27-1.12 (m, 1H), 1.11-0.96 (m, 2H), 0.96-0.74 (m, 2H), 0.73-0.34 (m, 2H). LCMS (ESI): 559.05 $[M+H]^+$.

Example 459. A Diastereomeric Mixture of (S)—N—((S)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide

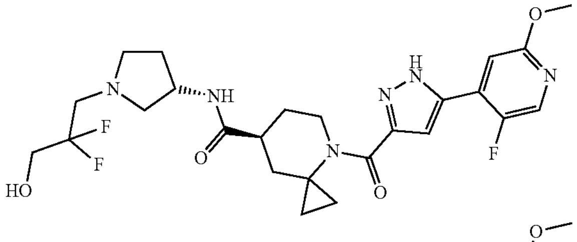

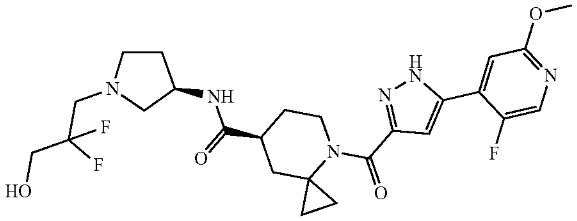

Step-1. ethyl 3-[3-(dibenzylamino)pyrrolidin-1-yl]-2,2-difluoro-3-oxopropanoate

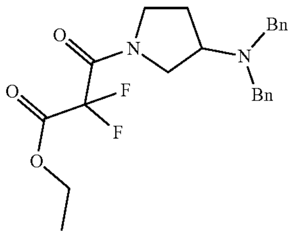 [SMILES: CCOC(=O)C(F)(F)C(=O)N1CCC(N(Cc2ccccc2)Cc2ccccc2)C1]

1,3-Diethyl 2,2-difluoropropanedioate (883.6 mg, 4.50 mmol) and $AlMe_3$ (6.77 mL, 6.77 mmol) were added to a stirred solution of AN-dibenzylpyrrolidin-3-amine (600.0 mg, 2.25 mmol) in toluene (5.00 mL) at 25° C. The resulting solution was stirred at 80° C. for 14 h under nitrogen atmosphere. The resulting mixture was concentrated under reduced pressure. The residue was purified by Prep-TLC (DCM/MeOH, 30/1 v/v) to obtain the title compound (600.9 mg) as a solid LCMS (ESI): 4170.2 $[M+H]^+$.

Step-2. 3-[3-(dibenzylamino)pyrrolidin-1-yl]-2,2-difluoropropan-1-ol

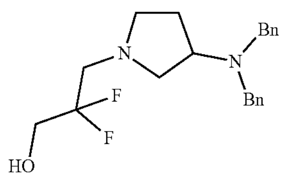 [SMILES: OCC(F)(F)CN1CCC(N(Cc2ccccc2)Cc2ccccc2)C1]

$Zn(OAc)_2$ (44.1 mg, 0.24 mmol) and methyldimethoxysilane (763.6 mg, 7.21 mmol) were added to a stirred solution of ethyl 3-[3-(dibenzylamino)pyrrolidin-1-yl]-2,2-difluoro-3-oxopropanoate (Step-1, 500.0 mg, 1.20 mmol) in THF (6.00 mL). The resulting mixture was stirred at 65° C. for 14 h under nitrogen atmosphere. The resulting mixture was concentrated under reduced pressure. The residue was purified by Prep-TLC (DCM/MeOH, 30/1 v/v) to obtain the title compound (250.0 mg) as an oil. LCMS (ESI): 361.2 $[M+H]^+$.

Step-3. 3-(3-aminopyrrolidin-1-yl)-2,2-difluoropropan-1-ol

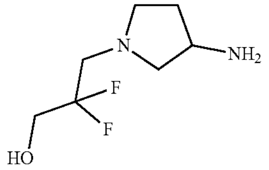 [SMILES: NC1CCN(CC(F)(F)CO)C1]

Pd/C (125.0 mg) was added to a stirred solution of 3-[3-(dibenzylamino)pyrrolidin-1-yl]-2,2-difluoropropan-1-ol (Step-2, 250.0 mg, 0.69 mmol) in MeOH (5.00 mL). The resulting solution was stirred at 25° C. for 4 h under hydrogen atmosphere. The resulting mixture was filtered, the filter cake was washed with MeOH. The filtrate was concentrated under reduced pressure to obtain the title compound (100.0 mg) as an oil. LCMS (ESI): 181.1 $[M+H]^+$.

Step-4. (S)—N—(S)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide

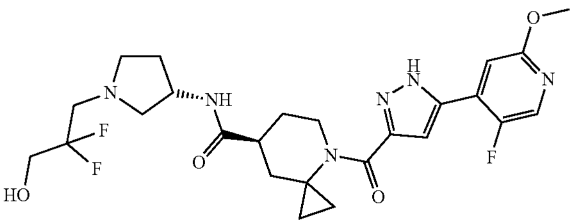

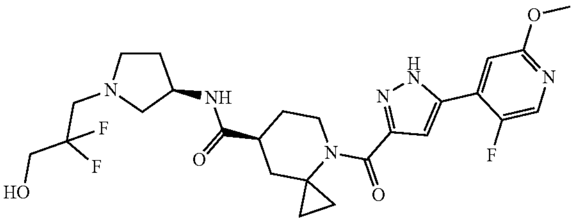

HOBt (74.2 mg, 0.55 mmol), EDCI (105.2 mg, 0.55 mmol), and 3-(3-aminopyrrolidin-1-yl)-2,2-difluoropropan-1-ol (Step-3, 98.9 mg, 0.55 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 137.0 mg, 0.37 mmol) and DIPEA (236.5 mg, 1.83 mmol) in DMF (4.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 10/1 v/v) to obtain (S)—N—((S)-1-(2,2-difluoro-3-hydroxypropyl)pyrrolidin-3-yl)-4-(5-(5-fluoro-2-methoxy-pyridin-4-yl)-1H-pyrazole-3-carbonyl)-4-azaspiro[2.5]octane-7-carboxamide and (S)—N—((R)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide (150.0 mg) as a solid mixture of diastereomers (Example 459). $^1H$ NMR (400 MHz, $CD_3OD$) δ 8.30-8.01 (m, 1H), 7.53-7.23 (m, 1H), 7.23-7.03 (m, 1H), 4.75-4.42 (m, 1H), 4.41-4.20 (m, 1H), 3.95 (s, 3H), 3.84-3.61 (m, 2H), 3.02-2.85 (m, 3H), 2.85-2.71 (m, 1H), 2.69-2.56 (m, 2H), 2.51-2.31 (m, 1H), 2.30-2.14 (m, 1H), 2.00-1.49 (m, 3H), 1.43-1.16 (m, 3H), 1.16-0.96 (m, 2H), 0.95-0.84 (m, 1H), 0.83-0.59 (m, 2H). LCMS (ESI): 537.30 $[M+H]^+$.

This mixture of two diastereomers (150.0 mg) was separated using Chiral Prep-HPLC.

Column: CHIRALPAK 1E column

Column dimension: 2×25 cm, 5 μm

Mobile Phase: 3/1 hexanes/DCM (0.5% 2 M $NH_3$·MeOH):IPA=70:30 hold for 17 min

Flow rate: 20 mL/min

Detection: 220/254 nm

Example 459-A. The first eluting diastereomer (40.0 mg) was obtained as a solid.

The first eluting diastereomer had a retention time of 12.11 min.

$^1H$ NMR (400 MHz, DMSO-$d_6$) δ 13.96 (d, 1H), 8.39-8.14 (m, 1H), 8.05-7.85 (m, 1H), 7.46-7.23 (m, 1H), 7.04 (s, 1H), 5.52-5.22 (m, 1H), 4.70-4.22 (m, 1H), 4.20-4.04 (m, 1H), 3.88 (s, 3H), 3.75-3.53 (m, 2H), 3.24-2.94 (m, 1H), 2.92-2.60 (m, 6H), 2.45-2.26 (m, 1H), 2.25-1.93 (m, 2H), 1.89-1.64 (m, 1H), 1.62-1.38 (m, 2H), 1.38-1.14 (m, 1H), 1.12-0.73 (m, 2H), 0.72-0.42 (m, 2H). LCMS (ESI): 537.20 $[M+H]^+$.

Example 459-B. The second eluting diastereomer (50.0 mg) was obtained as a solid.

The second eluting diastereomer had a retention time of 14.81 min.

$^1H$ NMR (400 MHz, DMSO-$d_6$) δ 13.96 (d, 1H), 8.41-8.14 (m, 1H), 8.07-7.77 (m, 1H), 7.43-7.23 (m, 1H), 7.03 (s, 1H), 5.59-5.15 (m, 1H), 4.65-4.22 (m, 1H), 4.20-4.02 (m, 1H), 3.88 (s, 3H), 3.77-3.51 (m, 2H), 3.25-2.95 (m, 1H), 2.92-2.61 (m, 6H), 2.47-2.31 (m, 1H), 2.29-1.98 (m, 2H), 1.85-1.64 (m, 1H), 1.63-1.38 (m, 2H), 1.37-0.79 (m, 3H), 0.77-0.49 (m, 2H). LCMS (ESI): 537.20 $[M+H]^+$.

Example 460. A Diastereomeric Mixture of (S)—N-((1R,4S)-4-((3,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,4R)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide

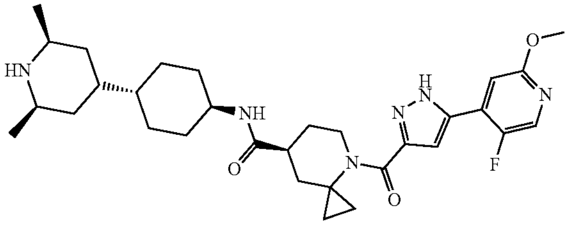

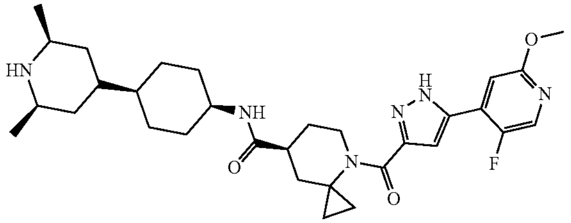

Step-1. tert-butyl (2R,6S)-4-[4-(dibenzylamino)cyclohexyl]-2,6-dimethylpiperazine-1-carboxylate

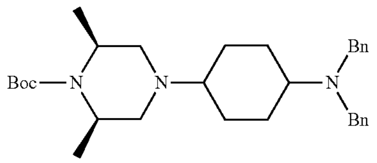 [SMILES: C[C@@H]1CN(C2CCC(N(Cc3ccccc3)Cc3ccccc3)CC2)C[C@H](C)N1C(=O)OC(C)(C)C]

4-(Dibenzylamino)cyclohexan-1-one (1.00 g, 3.41 mmol) and $NaBH_3CN$ (642.5 mg, 10.23 mmol) were added to a stirred mixture of tert-butyl (2R,6S)-2,6-dimethylpiperazine-1-carboxylate (730.4 mg, 3.41 mmol) in AcOH (0.06 mL) and MeOH (6.00 mL). The resulting mixture was stirred at 25° C. for 2 h. The resulting mixture was concentrated under reduced pressure. The residue was purified by silica gel column chromatography eluting with petroleum ether/EtOAc (7/1 v/v) to obtain the title compound (800.0 mg) as a solid. LCMS (ESI): 492.3 $[M+H]^+$.

Step-2. tert-butyl (2S,6R)-4-(4-aminocyclohexyl)-2,6-dimethylpiperazine-1-carboxylate

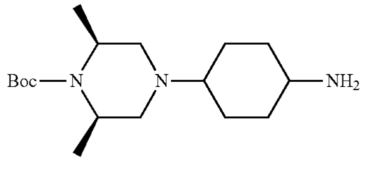 [SMILES: C[C@@H]1CN(C2CCC(N)CC2)C[C@H](C)N1C(=O)OC(C)(C)C]

Pd/C (80.0 mg) was added to a stirred solution of tert-butyl (2R,6S)-4-[4-(dibenzylamino)cyclohexyl]-2,6-dimethylpiperazine-1-carboxylate (Step-1, 400.0 mg, 0.81 mmol) in MeOH (6.00 mL) at 0° C. The resulting mixture was stirred at 25° C. for 14 h under hydrogen atmosphere. The resulting mixture was filtered, the filter cake was washed with MeOH. The filtrate was concentrated under reduced pressure to obtain the title compound and was used in the next step directly without further purification. LCMS (ESI): 312.3 $[M+H]^+$.

Step-3. tert-butyl (2S,6R)-4-(4-((S)-4-(5-(5-fluoro-2-methoxypyridin-4-yl)-1H-pyrazole-3-carbonyl)-4-azaspiro[2.5]octane-7-carboxamido)cyclohexyl)-2,6-dimethylpiperazine-1-carboxylate

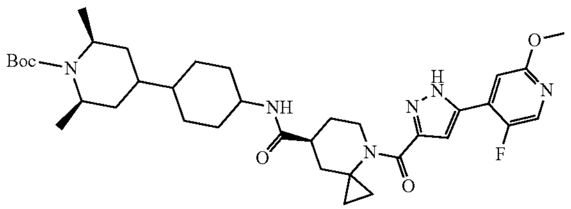 [SMILES: COc1cc(-c2cc(C(=O)N3CC[C@H](C(=O)NC4CCC(C5C[C@@H](C)N(C(=O)OC(C)(C)C)[C@@H](C)C5)CC4)CC34CC4)n[nH]2)c(F)cn1]

HOBt (130.2 mg, 0.96 mmol), EDCI (184.6 mg, 0.96 mmol), and tert-butyl (2R,6S)-4-(4-aminocyclohexyl)-2,6-dimethylpiperazine-1-carboxylate (Step-2, 150.0 mg, 0.48 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 180.3 mg, 0.48 mmol) and DIPEA (311.2 mg, 2.41 mmol) in DMF (6.00 mL). The resulting mixture was stirred at 25° C. for 2 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (250.0 mg) as a solid. LCMS (ESI): 668.3 $[M+H]^+$.

Step-4. (S)—N-((1R,4S)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,4R)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide

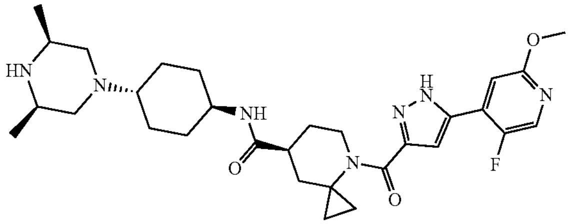

-continued

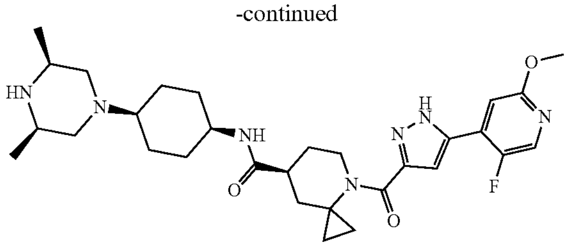

Trifluoroacetaldehyde (2.00 mL) was added to a stirred solution of tert-butyl (2S,6R)-4-(4-((S)-4-(5-(5-fluoro-2-methoxypyridin-4-yl)-1H-pyrazole-3-carbonyl)-4-azaspiro[2.5]octane-7-carboxamido)cyclohexyl)-2,6-dimethylpiperazine-1-carboxylate (step-3, 250.0 mg, 0.37 mmol) in DCM (2.00 mL) at 0° C. The resulting mixture was stirred at 25° C. for 1 h. The resulting mixture was concentrated under reduced pressure. The residue was purified by silica gel column chromatography eluting with DCM/MeOH (4/1 v/V) to obtain (S)—N-((1R,4S)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,4R)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide (160.0 mg) as a solid mixture of diastereomers. LCMS (ESI): 568.3 $[M+H]^+$.

This mixture of two diastereomers (160.0 mg) was separated using Chiral Prep-HPLC.

Column: CHIRAL ART Amylose-SA column

Column dimension: 2×25 cm, 5 μm

Mobile Phase: 3/1 hexanes/DCM (0.5% 2 M $NH_3$·MeOH):EtOH=50:50 hold for 6.5 min Flow rate: 20 mL/min Detection: 220/254 nm Example 460-A. The first eluting diastereomer (2.0 mg) was obtained as a solid.

The first eluting diastereomer had a retention time of 3.67 min.

$^1H$ NMR (400 MHz, $CD_3OD$) δ 8.13 (d, 1H), 7.29 (d, 1H), 7.11 (d, 1H), 4.61-4.56 (m, 1H), 3.95 (s, 3H), 3.93-3.88 (m, 1H), 2.96-2.83 (m, 6H), 2.66-2.25 (m, 3H), 2.12-1.46 (m, 12H), 1.48-1.21 (m, 1H), 1.20-1.04 (m, 6H), 0.94-0.89 (m, 1H), 0.84-0.61 (m, 2H). LCMS (ESI): 568.35 $[M+H]^+$.

Example 460-B. The second eluting diastereomer (2.0 mg) was obtained as a solid.

The second eluting diastereomer had a retention time of 5.40 min.

$^1H$ NMR (400 MHz, $CD_3OD$) δ 8.13 (d, 1H), 7.29 (d, 1H), 7.11 (d, 1H), 4.59-4.54 (m, 1H), 3.95 (s, 3H), 3.61-3.56 (m, 1H), 2.99-2.79 (m, 5H), 2.78-2.65 (m, 1H), 2.46-2.41 (m, 1H), 2.36-2.26 (m, 2H), 2.00-1.85 (m, 7H), 1.47-1.34 (m, 2H), 1.33-1.20 (m, 4H), 1.12-1.06 (m, 6H), 0.99-0.94 (m, 1H), 0.77-0.70 (m, 2H). LCMS (ESI): 568.30 $[M+H]^+$.

Example 461. A Diastereomeric Mixture of (S)—N—((R)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

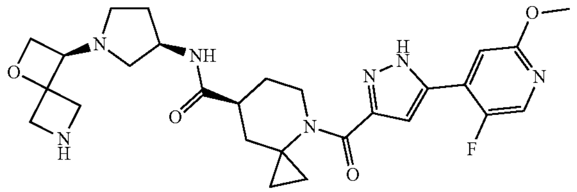

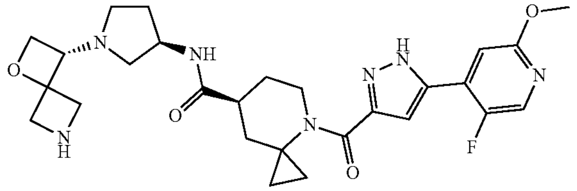

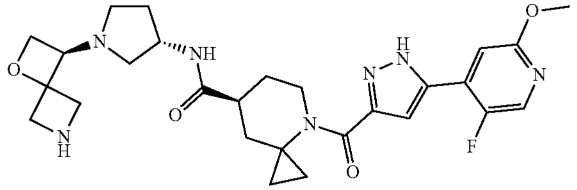

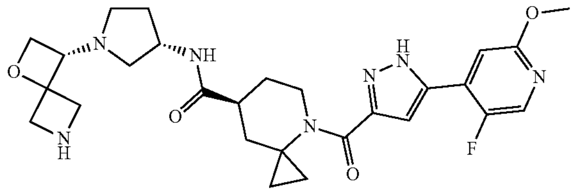

Step-1. tert-butyl 3-[(7S)-4-[5-(5-fluoro-2-methoxypyridin-4-yl)-1H-pyrazole-3-carbonyl]-4-azaspiro[2.5]octane-7-amido]pyrrolidine-1-carboxylate

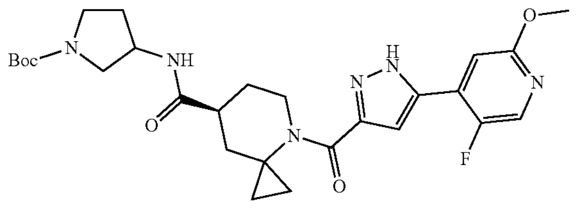 [SMILES: COc1cc(-c2cc(C(=O)N3CC[C@H](C(=O)NC4CCN(C(=O)OC(C)(C)C)C4)CC34CC4)n[nH]2)c(F)cn1]

HATU (243.8 mg, 0.64 mmol) and tert-butyl 3-aminopyrrolidine-1-carboxylate (99.5 mg, 0.53 mmol) were added to a stirred mixture of (S)-4-[5-(5-fluoro-2-methoxypyridin-4-yl)-1-pyrazole-3-carbonyl]-4-azaspiro[2.5]octane-7-carboxylic acid (INTERMEDIATE E 527-A, 200.0 mg, 0.53 mmol) and DIPEA (207.1 mg, 1.60 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/EtOAc (13/1 v/v) to obtain the title compound (270.0 mg) as a solid. LCMS (ESI): 543.3 $[M+H]^+$.

Step-2. (7S)-4-[5-(5-fluoro-2-methoxypyridin-4-yl)-1H-pyrazole-3-carbonyl]-N-(pyrrolidin-3-yl)-4-azaspiro[2.5]octane-7-carboxamide

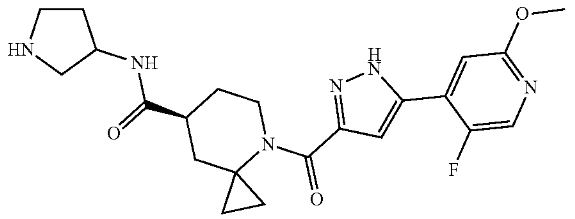 [SMILES: COc1cc(-c2cc(C(=O)N3CC[C@H](C(=O)NC4CCNC4)CC34CC4)n[nH]2)c(F)cn1]

TFA (3.00 mL) was added to a stirred mixture of tert-butyl 3-[(7S)-4-[5-(5-fluoro-2-methoxypyridin-4-yl)-1H-pyrazole-3-carbonyl]-4-azaspiro[2.5]octane-7-amido]pyrrolidine-1-carboxylate (Step-1, 270.0 mg, 0.50 mmol) in DCM (3.00 mL). The resulting mixture was stirred at 25° C. for 1 h. The resulting mixture was concentrated under reduced pressure to obtain the title compound (210.0 mg) as an oil and it was used in the next step directly without further purification. LCMS (ESI): 443.2 $[M+H]^+$.

Step-3. tert-butyl 3-[3-[(7S)-4-[5-(5-fluoro-2-methoxypyridin-4-yl)-1H-pyrazole-3-carbonyl]-4-azaspiro[2.5]octane-7-amino]pyrrolidin-1-yl]-1-oxa-6-azaspiro[3.3]heptane-6-carboxylate

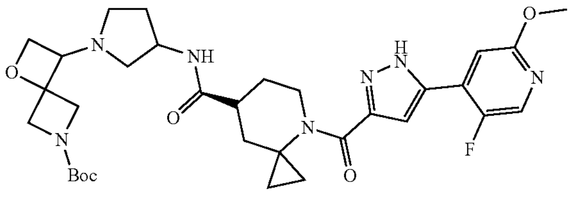

Tert-butyl 3-oxo-1-oxa-6-azaspiro[3.3]heptane-6-carboxylate (433.7 mg, 2.04 mmol), 4A MS (720.0 mg) and AcOH (0.20 mL) were added to a stirred mixture of (7S)-4-[5-(5-fluoro-2-methoxypyridin-4-yl)-1H-pyrazole-3-carbonyl]-N-(pyrrolidin-3-yl)-4-azaspiro[2.5]octane-7-carboxamide (Step-2, 180.0 mg, 0.41 mmol) in MeOH (8.00 mL). The resulting mixture was stirred at 80° C. for 1 h. $NaBH_3CN$ (76.7 mg, 1.22 mmol) was added to the reaction mixture dropwise at 25° C. The resulting mixture was stirred at 80° C. for 14 h. The resulting mixture was concentrated under reduced pressure. The residue was purified by silica gel column chromatography eluting with DCM/MeOH (13/1 v/v) to obtain the title compound (240.0 mg) as an oil. LCMS (ESI): 640.3 $[M+H]^+$.

Step-4. (S)—N—((R)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N((S)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

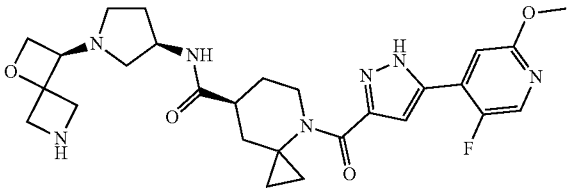

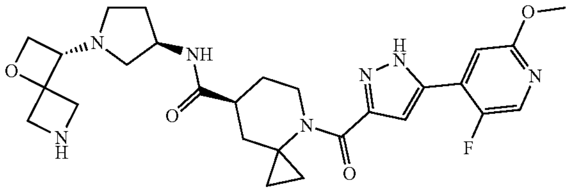

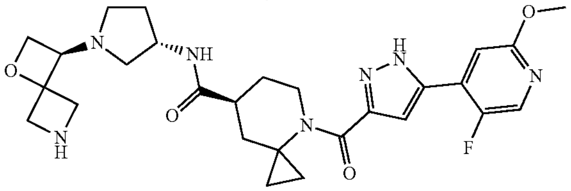

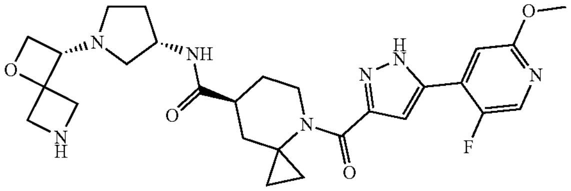

TFA (3.00 mL) was added to a stirred mixture of tert-butyl 3-{3-[(7S)-4-[5-(5-fluoro-2-methoxypyridin-4-yl)-1H-pyrazole-3-carbonyl]-4-azaspiro[2.5]octane-7-amido]pyrrolidin-1-yl}-1-oxa-6-azaspiro[3.3]heptane-6-carboxylate (Step-3, 240.0 mg, 0.38 mmol) in DCM (3.00 mL) at 0° C. The resulting mixture was stirred at 25° C. for 1 h. The resulting mixture was concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 25 B in 10 min; detector, UV 254/220 nm) to obtain (S)—N—((R)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide (120.0 mg) as a solid mixture of diastereomers (Example 461). $^1$H NMR (400 MHz, $CD_3OD$) δ 8.16 (d, 1H), 7.28 (d, 1H), 7.11 (d, 1H), 4.64-4.49 (m, 1H), 4.46-4.29 (m, 3H), 4.17-4.09 (m, 1H), 3.94 (s, 3H), 3.84-3.77 (m, 1H), 3.75-3.66 (m, 2H), 3.51-3.43 (m, 1H), 2.96-2.7 (m, 3H), 2.66-2.56 (m, 1H), 2.55-2.41 (m, 2H), 2.34-2.2 (m, 1H), 1.93-1.64 (m, 3H), 1.33-1.25 (m, 2H), 1.01-0.95 (m, 2H), 0.78-0.69 (m, 2H). LCMS (ESI): 540.40 $[M+H]^+$.

This mixture of four diastereomers (100.0 mg) was separated using Chiral Prep-HPLC.

Column: CHIRAL ART Amylose-SA column

Column dimension: 2×25 cm, 5 μm

Mobile Phase: 3/1 hexanes/DCM (0.3% IPA):MeOH=90:10 hold for 22 min

Flow rate: 20 mL/min

Detection: 220/254 nm

Example 461-A and Example 461-B. The first eluting peak (55.0 mg) was obtained as a solid mixture of two diasteromers.

The first eluting peak had a retention time of 12.70 min.

Example 461-C. The second eluting diastereomer (23.0 mg) was obtained as a solid.

The second eluting diastereomer had a retention time of 15.32 min.

$^1$H NMR (400 MHz, $CD_3OD$) δ 8.13 (d, 1H), 728 (d, 1H), 7.11 (d, 1H), 4.69-4.49 (m, 1H), 4.47-4.39 (m, 1H), 4.39-4.27 (m, 2H), 4.18-4.07 (m, 1H), 3.94 (s, 3H), 3.84-3.77 (m, 1H), 3.74-3.66 (m, 2H), 3.51-3.43 (m, 1H), 2.95-2.75 (m, 3H), 2.61-2.41 (m, 3H), 2.33-2.21 (m, 1H), 1.94-1.65 (m, 3H), 1.4-1.19 (m, 2H), 0.94-0.89 (m, 2H), 0.78-0.69 (m, 2H). LCMS (ESI): 540.45 $[M+H]^+$.

Example 461-D. The third eluting diastereomer (22.0 mg) was obtained as a solid.

The third eluting diastereomer had a retention time of 19.79 min.

$^1$H NMR (400 MHz, $CD_3OD$) δ 8.13 (d, 1H), 7.29 (d, 1H), 7.11 (d, 1H), 4.6-4.55 (m, 1H), 4.46-4.29 (m, 3H), 4.15-4.06 (m, 1H), 3.95 (s, 3H), 3.82-3.74 (m, 1H), 3.72-3.63 (m, 2H), 3.5-3.4 (m, 1H), 3-2.69 (m, 3H), 2.69-2.54 (m, 2H), 2.53-2.34 (m, 1H), 2.34-2.21 (m, 1H), 1.92-1.65 (m, 3H), 1.38-1.21 (m, 2H), 0.98-0.94 (m, 2H), 0.78-0.69 (m, 2H). LCMS (ESI): 540.45 $[M+H]^+$.

The first eluting peak (55.0 mg) containing two diastereomers of the title compounds was separated using Chiral Prep-HPLC.

Column: CHIRALPAK ID column

Column dimension: 2×25 cm, 5 μm

Mobile Phase: MTBE (0.5% 2M $NH_3$·MeOH):3/1 MeOH/DCM=40:60 hold for 19 min

Flow rate: 20 mL/min

Detection: 220/254 nm

Example 461-A. The first eluting diastereomer (20.0 mg) was obtained as a solid.

The first eluting diastereomer had a retention time of 8.23 min.

$^1$H NMR (400 MHz, $CD_3OD$) δ 8.13 (d, 1H), 7.28 (d, 1H), 7.11 (d, 1H), 4.49-4.69 (m, 1H), 4.39-4.47 (m, 1H), 4.27-4.39 (m, 2H), 4.07-4.18 (m, 1H), 3.94 (s, 3H), 3.77-3.84 (m, 1H), 3.66-3.74 (m, 2H), 3.43-3.51 (m, 1H), 2.75-2.95 (m, 3H), 2.41-2.61 (m, 3H), 2.21-2.33 (m, 1H), 1.65-1.94 (m, 3H), 1.19-1.4 (m, 2H), 0.89-0.94 (m, 2H), 0.69-0.78 (m, 2H). LCMS (ESI): 540.45 $[M+H]^+$.

Example 461-B. The second eluting diastereomer (21.0 mg) was obtained as a solid.

The second eluting diastereomer had a retention time of 13.50 min.

$^1$H NMR (400 MHz, $CD_3OD$) δ 8.13 (d, 1H), 7.28 (d, 1H), 7.11 (d, 1H), 4.49-4.69 (m, 1H), 4.39-4.47 (m, 1H), 4.27-4.39 (m, 2H), 4.07-4.18 (m, 1H), 3.94 (s, 3H), 3.77-3.84 (m, 1H), 3.66-3.74 (m, 2H), 3.43-3.51 (m, 1H), 2.75-2.95 (m, 3H), 2.41-2.61 (m, 3H), 2.21-2.33 (m, 1H), 1.65-1.94 (m, 3H), 1.19-1.4 (m, 2H), 0.89-0.94 (m, 2H), 0.69-0.78 (m, 2H). LCMS (ESI): 540.40 $[M+H]^+$.

Example 462. A Diastereomeric Mixture of (S)—N-((5-((1R,4R)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide and (S)—N-((5-((1S,4S)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide

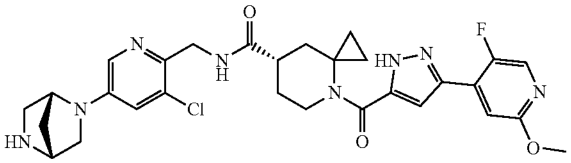

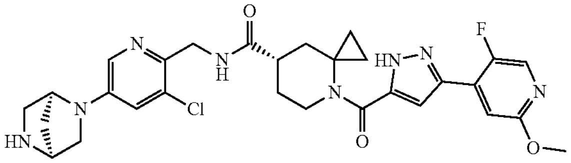

Step-1. tert-butyl 5-(5-chloro-6-cyanopyridin-3-yl)-2,5-diazabicyclo[2.2.1]heptane-2-carboxylate

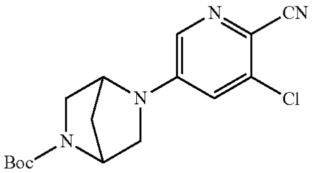 [SMILES: CC(C)(C)OC(=O)N1CC2CC1CN2c1cnc(C#N)c(Cl)c1]

DIPEA (619.2 mg, 4.79 mmol) and tert-butyl 2,5-diazabicyclo[2.2.1]heptane-2-carboxylate (759.9 mg, 3.83 mmol) were added to a stirred mixture of 3-chloro-5-fluoropyridine-2-carbonitrile (500.0 mg, 3.19 mmol) in MeCN (6.00 mL). The resulting mixture was stirred at 100° C. for 1 h under nitrogen atmosphere. The resulting mixture was concentrated under reduced pressure. The residue was purified by silica gel column chromatography eluting with petroleum ether/EtOAc (5/1 v/v) to obtain the title compound (954.0 mg) as a solid. LCMS (ESI): 335.12 $[M+H]^+$.

Step-2. tert-butyl 5-[6-(aminomethyl)-5-chloropyridin-3-yl]-2,5-diazabicyclo[2.2.1]heptane-2-carboxylate

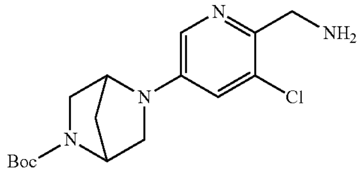 [SMILES: CC(C)(C)OC(=O)N1CC2CC1CN2c1cnc(CN)c(Cl)c1]

DIBAL-H (3.58 mL, 3.59 mmol) was added to a stirred mixture of tert-butyl 5-(5-chloro-6-cyanopyridin-3-yl)-2,5-diazabicyclo[2.2.1]heptane-2-carboxylate (Step-1, 400.0 mg, 1.20 mmol) in DCM (8.00 mL) at −78° C. under nitrogen atmosphere. The resulting mixture was stirred at −78° C. for 10 min under nitrogen atmosphere. The resulting mixture was concentrated under reduced pressure. The residue was purified by silica gel column chromatography eluting with DCM/MeOH (9/1 v/v) to obtain the title compound (225.0 mg) as a solid. LCMS (ESI): 339.15 $[M+H]^+$.

Step-3. tert-butyl 5-[5-chloro-6-({[(7S)-4-[5-(5-fluoro-2-methoxypyridin-4-yl)-2H-pyrazole-3-carbonyl]-4-azaspiro[2.5]octan-7-yl]formamido}methyl)pyridin-3-yl]-2,5-diazabicyclo[2.2.1]heptane-2-carboxylate

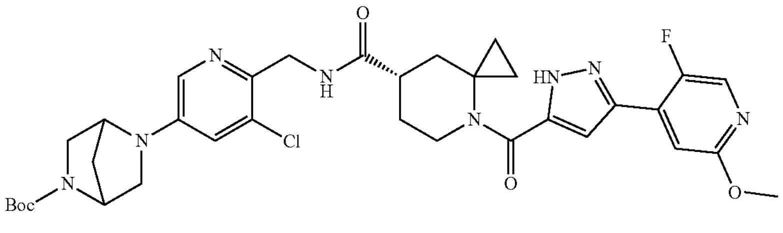 [SMILES: COc1cc(-c2cc(C(=O)N3CC[C@H](C(=O)NCc4ncc(N5CC6CC5CN6C(=O)OC(C)(C)C)cc4Cl)CC34CC4)[nH]n2)c(F)cn1]

HOBt (95.7 mg, 0.71 mmol), EDCI (135.8 mg, 0.71 mmol), and tert-butyl 5-[6-(aminomethyl)-5-chloropyridin-3-yl]-2,5-diazabicyclo[2.2.1]heptane-2-carboxylate (Step-2, 120.0 mg, 0.35 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 132.6 mg, 0.35 mmol) and DIPEA (228.9 mg, 1.77 mmol) in DMF (24.00 mL). The resulting solution was stirred at 25° C. for 2 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (140.0 mg) as a solid. LCMS (ESI): 695.28 $[M+H]^+$.

Step-4. (S)—N-((5-((1R,4R)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide and (S)—N-((5-((1S,4S)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide

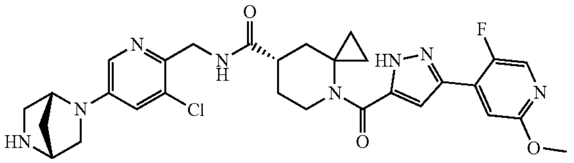

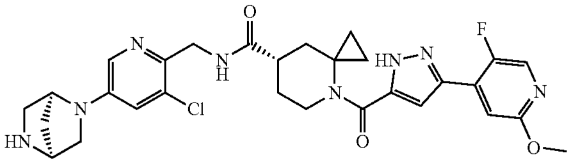

TFA (2.00 mL) was added to a stirred solution of tert-butyl 5-[5-chloro-6-({[(7S)-4-[5-(5-fluoro-2-methoxypyridin-4-yl)-2H-pyrazole-3-carbonyl]-4-azaspiro[2.5]octan-7-yl]formamido}methyl)pyridin-3-yl]-2,5-diazabicyclo[2.2.1]heptane-2-carboxylate (Step-3, 120.0 mg, 0.17 mmol) in DCM (2.00 mL) at 0° C. The resulting mixture was stirred at 25° C. for 1 h. The residue was purified by reverse phase column chromatography (using the following conditions: Column: C18; mobile phase A: Water (0.5% $NH_4HCO_3$), mobile phase B: MeCN; gradient: 20 B to 50 B in 30 min; 220/254 nm) to obtain (S)—N-((5-((1R,4R)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide and (S)—N-((5-((1S,4S)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide (100.0 mg) as a solid mixture of diastereomers (Example 462). $^1$H NMR (400 MHz, $CD_3OD$) δ 8.14 (d, 1H), 7.86 (d, 1H), 7.29 (d, 1H), 7.13-7.08 (m, 2H), 4.60-4.43 (m, 4H), 3.95 (s, 3H), 3.91-3.80 (m, 1H), 3.66-3.55 (m, 1H), 3.14-3.07 (m, 1H), 3.04-2.96 (m, 2H), 2.95-2.84 (m, 1H), 2.66-2.17 (m, 1H), 2.04-1.79 (m, 4H), 1.42-1.26 (m, 2H), 1.05-0.84 (m, 2H), 0.78-0.70 (m, 2H). LCMS (ESI): 595.40 $[M+H]^+$.

This mixture of two diastereomers (100.0 mg) was separated using Chiral Prep-HPLC.

Column: CHIRAL ART Amylose-SA column

Column dimension: 2×25 cm, 5 μm

Mobile Phase: 3/1 hexanes/DCM (0.5% 2 M $NH_3$·MeOH):MeOH=50:50 hold for 16 min

Flow rate: 20 mL/min

Detection: 220/254 nm

Example 462-A. The first eluting diastereomer (8.1 mg) was obtained as a solid.

The first eluting diastereomer had a retention time of 6.79 min.

$^1$H NMR (400 MHz, $CD_3OD$) δ 8.13 (d, 1H), 7.85 (d, 1H), 7.29 (d, 1H), 7.14-7.07 (m, 2H), 4.56-4.43 (m, 4H), 3.95 (s, 3H), 3.88-3.83 (m, 1H), 3.64-3.57 (m, 1H), 3.16-2.80 (m, 4H), 2.64-2.34 (m, 1H), 2.04-1.95 (m, 2H), 1.93-1.82 (m, 2H), 1.45-1.21 (m, 2H), 1.03-0.88 (m, 2H), 0.81-0.68 (m, 2H). LCMS (ESI): 595.45 $[M+H]^+$.

Example 462-B. The second eluting diastereomer (22.1 mg) was obtained as a solid.

The second eluting diastereomer had a retention time of 12.12 min.

$^1$H NMR (400 MHz, $CD_3OD$) δ 8.13 (d, 1H), 7.85 (d, 1H), 7.29 (d, 1H), 7.14-7.07 (m, 2H), 4.55-4.43 (m, 4H), 3.95 (s, 3H), 3.89-3.82 (m, 1H), 3.64-3.57 (m, 1H), 3.12-3.07 (m, 1H), 3.07-2.92 (m, 3H), 2.62-2.40 (m, 1H), 2.05-1.72 (m, 4H), 1.42-1.21 (m, 2H), 1.18-0.93 (m, 2H), 0.81-0.68 (m, 2H). LCMS (ESI): 595.15 $[M+H]^+$.

Example 463. (S)-4-(3-(5-fluoro-2-methoxypyridin-4-yl)-1H-pyrazole-5-carbonyl)-N-((3-hydroxyoxetan-3-yl)methyl)-4-azaspiro[2.5]octane-7-carboxamide

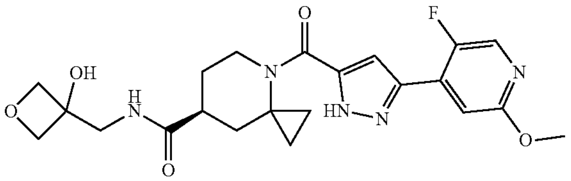 [SMILES: COc1cc(-c2cc(C(=O)N3CC[C@H](C(=O)NCC4(O)COC4)CC34CC4)[nH]n2)c(F)cn1]

Step-1. 3-[(dibenzylamino)methyl]oxetan-3-ol

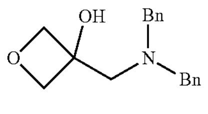 [SMILES: OC1(CN(Cc2ccccc2)Cc2ccccc2)COC1]

TEA (220.0 mg, 2.18 mmol) and 1,5-dioxaspiro[2.3]hexane (149.8 mg, 1.74 mmol) were added to a stirred solution of dibenzyl amine (286.0 mg, 1.45 mmol) in MeOH (5.00 mL) under nitrogen atmosphere. The resulting solution was stirred at 80° C. for 14 h under nitrogen atmosphere. The resulting solution was concentrated under reduced pressure. The residue was purified by silica gel column chromatography eluting with petroleum ether/EtOAc (5/1 v/v) to obtain the title compound (374.0 mg) as a solid. LCMS (ESI): 284.2 $[M+H]^+$.

Step-2. 3-(aminomethyl)oxetan-3-ol

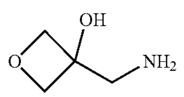

Pd/C (170.0 mg, 10%) was added to a stirred solution of 3-[(dibenzylamino)methyl]oxetan-3-ol (Step-1, 340.0 mg) in MeOH (5.00 mL). The resulting solution was stirred at 25° C. for 14 h under the atmosphere of $H_2$. The solids were filtered out and washed with MeOH. The resulting solution was concentrated under reduced pressure to obtain the title compound (118.0 mg) as a solid. LCMS (ESI): 104.1 $[M+H]^+$.

Step-3. (S)-4-(3-(5-fluoro-2-methoxypyridin-4-yl)-1H-pyrazole-5-carbonyl)-N-((3-hydroxyoxetan-3-yl)methyl)-4-azaspiro[2.5]octane-7-carboxamide

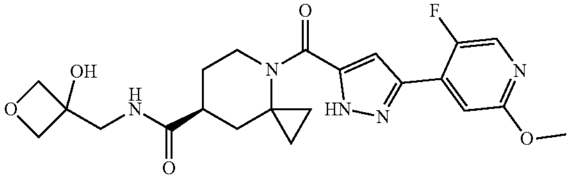 [SMILES: COc1cc(-c2cc(C(=O)N3CC[C@H](C(=O)NCC4(O)COC4)CC34CC4)[nH]n2)c(F)cn1]

HOBt (54.1 mg, 0.40 mmol), EDCI (76.8 mg, 0.40 mmol), and 3-(aminomethyl)oxetan-3-ol (Step-2, 30.3 mg, 0.29 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 100.0 mg, 0.27 mmol) and DIPEA (172.6 mg, 1.34 mmol) in DMF (3.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 10/1 v/v) to obtain the title compound (60.0 mg) as a solid. $^1H$ NMR (400 MHz, DMSO-$d_6$) δ 13.97 (s, 1H), 8.27 (s, 1H), 8.08-7.93 (m, 1H), 7.40-7.23 (m, 1H), 7.03 (s, 1H), 5.88-5.74 (m, 1H), 4.62-4.23 (m, 5H), 3.88 (s, 3H), 3.43-3.33 (m, 2H), 2.87-2.65 (m, 1H), 2.38-2.00 (m, 1H), 1.87-1.68 (m, 1H), 1.67-1.42 (m, 1H), 1.34-1.11 (m, 1H), 1.08-0.77 (m, 2H), 0.78-0.32 (m, 3H). LCMS (ESI): 460.10 $[M+H]^+$.

Example 464. A Diastereomeric Mixture of (S)—N—((R)-1-((R)-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((R)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

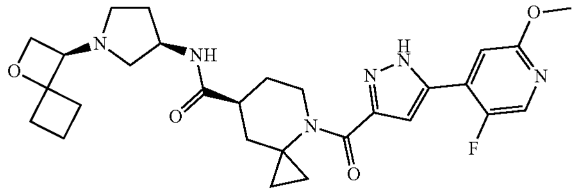

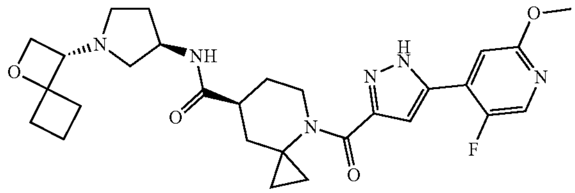

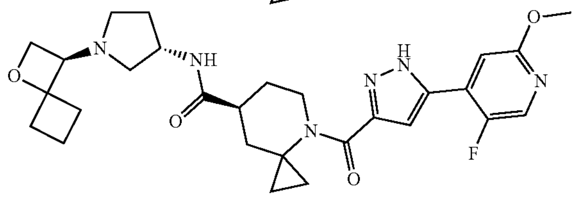

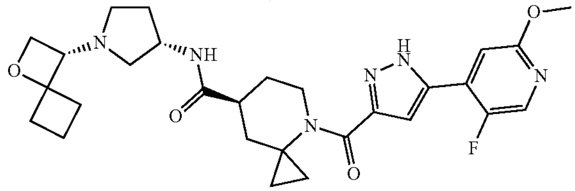

The title compound was prepared using a procedure similar to the one described for the synthesis of Example 433, except tert-butyl 3-aminopyrrolidine-1-carboxylate was used as a starting material in Step-1 and 1-Oxaspiro[3.3]heptan-3-one was used as a starting material in Step-3. The residue was purified by Prep-TLC (DCM/MeOH, 10/1 v/v) to obtain (S)—N—((R)-1-((R)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-((R)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—(((S)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide (270.0 mg) as a solid mixture of diastereomers (Example 464). $^1$H NMR (400 MHz, DMSO-$d_6$) δ 13.92 (s, 1H), 8.34-8.19 (m, 1H), 8.06-7.92 (m, 1H), 7.38-7.25 (m, 1H), 7.09-6.96 (m, 1H), 4.70-4.32 (m, 1H), 4.31-4.23 (m, 1H), 4.22-4.01 (m, 2H), 3.88 (s, 3H), 3.23-3.09 (m, 1H), 2.85-2.65 (m, 2H), 2.65-2.53 (m, 2H), 2.46-2.30 (m, 2H), 2.29-2.01 (m, 4H), 2.01-1.85 (m, 2H), 1.84-1.34 (m, 5H), 1.31-1.09 (m, 1H), 1.06-0.75 (m, 2H), 0.73-0.58 (m, 2H). LCMS (ESI): 539.20 $[M+H]^+$.

This mixture of four diastereomers (270.0 mg) was separated using Chiral Prep-HPLC.

Column: CHIRALPAK IG column

Column dimension: 2×25 cm, 5 μm

Mobile Phase: 1/1 hexanes/DCM (0.5% 2 M $NH_3$·MeOH):EtOH=85:15 hold for 17 min

Flow rate: 20 mL/min

Detection: 220/254 nm

Example 464-A and Example 464-B. The first eluting peak (100.0 mg) was obtained as an Oil.

The first eluting peak had a retention time of 9.73 min.

Example 464-C and Example 464-D. The second eluting peak (100.0 mg) was obtained as an Oil.

The second eluting peak had a retention time of 12.90 min.

The first eluting peak (100.0 mg) containing two diastereomers of the title compounds was separated using Chiral Prep-HPLC.

Column: CHIRALPAK IE column

Column dimension: 2×25 cm, 5 μm

Mobile Phase: MTBE (0.5% 2M $NH_3$·MeOH):IPA=50:50 hold for 36 min

Flow rate: 11 mL/min

Detection: 220/254 nm

Example 464-A. The first eluting diastereomer (42.0 mg) was obtained as a solid.

The first eluting diastereomer had a retention time of 22.77 min.

$^1$H NMR (400 MHz, DMSO-$d_6$) δ 13.98 (s, 1H), 8.27 (s, 1H), 8.07-7.91 (m, 1H), 7.38-7.26 (m, 1H), 7.02 (s, 1H), 4.61-4.32 (m, 1H), 4.31-4.23 (m, 1H), 4.22-4.09 (m, 2H), 3.88 (s, 3H), 3.22-3.12 (m, 1H), 2.78-2.54 (m, 5H), 2.43-2.25 (m, 2H), 2.22-2.03 (m, 4H), 2.01-1.88 (m, 1H), 1.80-1.31 (m, 5H), 1.30-0.73 (m, 3H), 0.72-0.55 (m, 2H). LCMS (ESI): 539.20 $[M+H]^+$.

Example 464-B. The second eluting diastereomer (39.0 mg) was obtained as a solid.

The first second diastereomer had a retention time of 30.82 min.

$^1$H NMR (400 MHz, DMSO-$d_6$) δ 14.38-13.63 (m, 1H), 8.40-8.15 (m, 1H), 7.99 (s, 1H), 7.32 (s, 1H), 7.04 (s, 1H), 4.63-4.38 (m, 1H), 4.37-4.23 (m, 1H), 4.23-4.04 (m, 2H), 3.88 (s, 3H), 3.24-3.13 (m, 1H), 2.77-2.65 (m, 2H), 2.64-2.54 (m, 3H), 2.44-2.29 (m, 2H), 2.28-2.19 (m, 1H), 2.19-2.02 (m, 3H), 2.01-1.86 (m, 1H), 1.81-1.34 (m, 5H), 1.33-0.83 (m, 3H), 0.78-0.42 (m, 2H). LCMS (ESI): 539.20 $[M+H]^+$.

The second eluting peak (100.0 mg) containing two diastereomers of the title compounds was separated using Chiral Prep-H PLC.

Column: CHIRALPAK ID column

Column dimension: 2×25 cm, 5 μm

Mobile Phase: 1/1 hexanes/DCM (0.5% 2 M $NH_3$·MeOH):IPA=80:20 hold for 19 min

Flow rate: 20 mL/min

Detection: 220/254 nm

Example 464-C. The first eluting diastereomer (37.0 mg) was obtained as a solid.

The first eluting diastereomer had a retention time of 12.46 min.

$^1$H NMR (400 MHz, DMSO-$d_6$) δ 13.98 (s, 1H), 8.35-8.21 (m, 1H), 8.07-7.91 (m, 1H), 7.38-7.27 (m, 1H), 7.11-6.96 (m, 1H), 4.63-433 (m, 1H), 4.32-4.23 (m, 1H), 4.23-4.04 (m, 2H), 3.88 (s, 3H), 3.24-3.10 (m, 1H), 2.92-2.54 (m, 5H), 2.42-2.26 (m, 2H), 2.24-2.02 (m, 4H), 2.01-1.86 (m, 1H), 1.81-1.31 (m, 5H), 1.31-0.75 (m, 3H), 0.74-0.45 (m, 2H). LCMS (ESI): 539.25 [M+H].

Example 464-D. The second eluting diastereomer (36.0 mg) was obtained as a solid.

The first second diastereomer had a retention time of 15.30 min.

$^1$H NMR (400 MHz, DMSO-$d_6$) δ 13.98 (s, 1H), 8.37-8.14 (m, 1H), 8.14-7.85 (m, 1H), 7.52-7.23 (m, 1H), 7.03 (s, 1H), 4.68-4.33 (m, 1H), 4.30-4.24 (m, 1H), 4.22-4.04 (m, 2H), 3.88 (s, 3H), 3.25-3.12 (m, 1H), 2.82-2.54 (m, 4H), 2.43-2.30 (m, 2H), 2.29-2.02 (m, 5H), 2.01-1.87 (m, 1H), 1.83-1.35 (m, 5H), 1.32-0.74 (m, 3H), 0.71-0.49 (m, 2H). LCMS (ESI): 539.25 $[M+H]^+$.

Example 465. (S)-4-(5-(5-fluoro-2-methoxypyridin-4-yl)-1H-pyrazole-3-carbonyl)-N-((1,4,5-trimethyl-1H-imidazol-2-yl)methyl)-4-azaspiro[2.5]octane-7-carboxamide

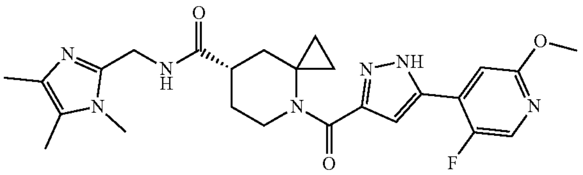

Step-1. 1,4,5-trimethylimidazole

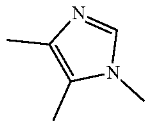

$CH_3I$ (3.25 g, 22.89 mmol) was added to a stirred solution of 4,5-dimethyl-1H-imidazole (2.00 g, 20.81 mmol) in DMSO (10.00 mL). The resulting solution was stirred at 25° C. for 1 h under nitrogen atmosphere. Then KOH (2.57 g, 45.77 mmol) was added to the reaction mixture and the resulting mixture was stirred at 65° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 5/1 v/v) to obtain the title compound (400.0 mg) as an oil. LCMS (ESI): 111.2 $[M+H]^+$.

Step-2. 1,4,5-trimethylimidazole-2-carbaldehyde

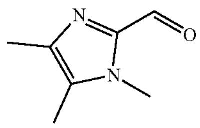

n-BuLi (279.1 mg, 4.36 mmol) was added to a stirred solution of 1,4,5-trimethylimidazole (Step-1, 400.0 mg, 3.63 mmol) in THF (2.00 mL) at −78° C. under nitrogen atmosphere. The mixture was stirred at −78° C. for 30 min under nitrogen atmosphere, then DMF (4.00 mL) was added at −78° C. and the resulting mixture was stirred at 25° C. for 2 h. The residue was diluted with EtOAc and washed with water. The organic layers were combined, dried over anhydrous $Na_2SO_4$, filtered, and concentrated under reduced pressure. The residue was purified by Prep-TLC (DCM/MeOH, 15/1 v/v) to obtain the title compound (300.0 mg) as a solid. LCMS (ESI): 139.2 $[M+H]^+$.

Step-3. 2-methyl-N-[(1E)-(1,4,5-trimethylimidazol-2-yl)methylidene]propane-2-sulfinamide

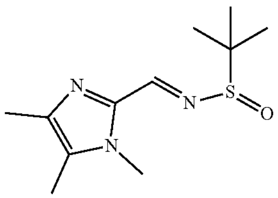 [SMILES: Cc1nc(/C=N/S(=O)C(C)(C)C)n(C)c1C]

PTSA (112.2 mg, 0.65 mmol) and $MgSO_4$ (784.0 mg, 6.51 mmol) were added to a stirred solution of 1,4,5-trimethylimidazole-2-carbaldehyde (Step-2, 300.0 mg, 2.17 mmol) and tert-butanesulfinamide (657.9 mg, 5.43 mmol) in DCM (5.00 mL). The resulting mixture was stirred at 45° C. for 14 h under nitrogen atmosphere. Then, the mixture was concentrated under reduced pressure. The residue was purified by Prep-TLC (DCM/MeOH, 10/1 v/v) to obtain the title compound (150.0 mg) as a solid. LCMS (ESI): 242.4 $[M+H]^+$.

Step-4. N-[(1,4-dimethylimidazol-2-yl)methyl]-2-methylpropane-2-sulfinamide

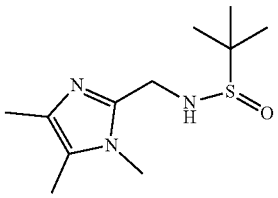 [SMILES: Cc1nc(CNS(=O)C(C)(C)C)n(C)c1C]

$NaBH_4$ (62.7 mg, 1.66 mmol) was added to a stirred solution of 2-Methyl-N-[(1E)-(1,4,5-trimethylimidazol-2-yl)methylidene]propane-2-sulfinamide (Step-3, 200.0 mg, 0.83 mmol) in MeOH (4.00 mL). The resulting mixture was stirred at 25° C. for 2 h under nitrogen atmosphere. The resulting mixture was concentrated under reduced pressure. The residue was purified by Prep-TLC (DCM/MeOH, 10/1 v/v) to obtain the title compound (180.0 mg) as a solid. LCMS (ESI): 244.4 $[M+H]^+$.

Step-5. 1-(1,4,5-trimethylimidazol-2-yl)methanamine

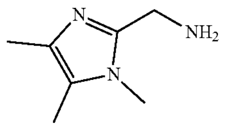

HCl (gas) in 1,4-dioxane (4.00 mL) was added to a stirred solution of 2-methyl-N-[(1,4,5-trimethylimidazol-2-yl)methyl]propane-2-sulfinamide (Step-4, 200.0 mg, 0.82 mmol) in 1,4-dioxane (4.00 mL). The resulting solution was stirred at 25° C. for 1 h. The resulting mixture was concentrated under reduced pressure to obtain the title compound. The residue was used in the next step directly without further purification. LCMS (ESI): 140.1 $[M+H]^+$.

Step-5. (S)-4-(5-(5-fluoro-2-methoxypyridin-4-yl)-1H-pyrazole-3-carbonyl)-N-((1,4,5-trimethyl-1H-1-imidazol-2-yl)methyl)-4-azaspiro[2.5]octane-7-carboxamide

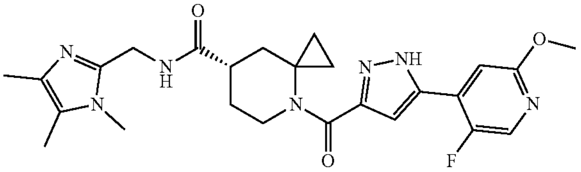

HOBt (230.6 mg, 1.71 mmol), EDCI (327.2 mg, 1.71 mmol), and 1-(1,4,5-trimethylimidazol-2-yl)methanamine (Step-4, 190.1 mg, 1.37 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 426.0 mg, 1.14 mmol) and DIPEA (735.3 mg, 5.69 mmol) in DMF (2.00 mL). The resulting solution was stirred at 25° C. for 14 h. The solution was then diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 30 B in 20 min; 220/254 nm) to obtain the title compound (86.4 mg) as a solid. $^1H$ NMR (400 MHz, DMSO-$d_6$) δ 13.98 (s, 1H), 8.33-8.26 (m, 1H), 8.25-8.17 (m, 1H), 7.32 (d, 1H), 7.10-6.95 (m, 1H), 4.62-4.35 (m, 1H), 4.32-4.15 (m, 2H), 3.88 (s, 3H), 3.31 (s, 3H), 3.24-2.84 (m, 1H), 2.83-2.60 (m, 1H), 2.30-2.10 (m, 1H), 2.09-2.00 (m, 6H), 1.90-1.68 (m, 1H), 1.65-1.41 (m, 1H), 1.34-1.06 (m, 1H), 1.01-0.72 (m, 2H), 0.71-0.49 (m, 2H). LCMS (ESI): 496.25 $[M+H]^+$.

Example 466. A Diastereomeric Mixture of (S)—N-(5-((1S,2S)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide and (S)—N-(5-((1R,2R)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide

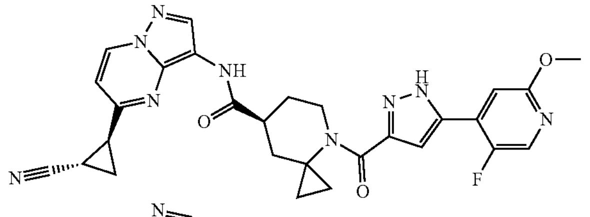

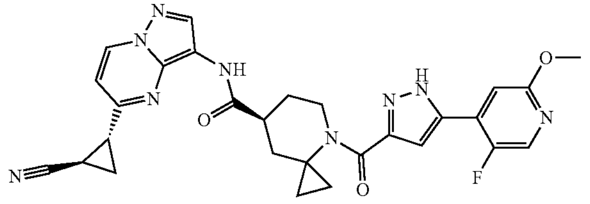

Step-1. tert-butyl N-[5-chloropyrazolo[1,5-a]pyrimidin-3-yl]carbamate

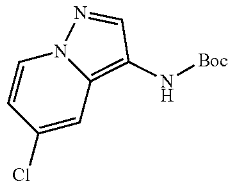 [SMILES: CC(C)(C)OC(=O)Nc1cnn2ccc(Cl)cc12]

DIPEA (767.0 mg, 5.93 mmol) was added to a mixture of 5-chloropyrazolo[1,5-a]pyrimidin-3-amine (500.0 mg, 2.97 mmol) and $Boc_2O$ (971.0 mg, 4.45 mmol) in DCM (5.00 mL). The resulting mixture was stirred at 25° C. for 14 h. The resulting mixture was concentrated under reduced pressure. The residue was purified by silica gel column chromatography eluting with DCM/MeOH (10/1 v/v) to obtain the title compound (620.0 mg) as a solid. LCMS (ESI): 269 $[M+H]^+$.

Step-2. 2-(4,4,5,5-tetramethyl-1,3,2-dioxaborolan-2-yl)cyclopropane-1-carbonitrile

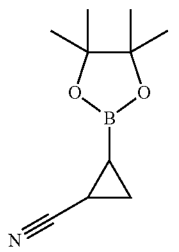

2,9-Dimethyl-1,10-phenanthroline (621.0 mg, 2.98 mmol) and $[Ir(OOD)OMe]_2$ (1.98 g, 2.98 mmol) were added to a mixture of cyclopropyl cyamide (2.00 g, 29.81 mmol) and 4,4,5,5-tetramethyl-2-(tetramethyl-1,3,2-dioxaborolan-2-yl)-1,3,2-dioxaborolane (6.06 g, 23.85 mmol) in THF (10.00 mL). The resulting mixture was stirred at 90° C. for 14 h under nitrogen atmosphere. The resulting mixture was concentrated under reduced pressure. The residue was purified by silica gel column chromatography eluting with petroleum ether/EtOAc (7/1 v/v) to obtain the title compound (1.80 g) as a solid.

Step-3. tert-butyl N-[5-(2-cyanocyclopropyl)pyrazolo[1,5-a]pyrimidin-3-yl]carbamate

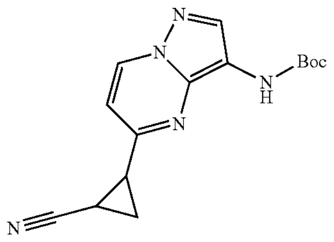 [SMILES: CC(C)(C)OC(=O)Nc1cnn2ccc(C3CC3C#N)nc12]

$Pd(PCy_3)_2Cl_2$ (82.0 mg, 0.11 mmol) and $K_3PO_4$ (474.0 mg, 2.23 mmol) were added to a mixture of tert-butyl N-{5-chloropyrazolo[1,5-a]pyrimidin-3-yl}carbamate (Step-1, 300.0 mg, 1.12 mmol) and 2-(4,4,5,5-tetramethyl-1,3,2-dioxaborolan-2-yl)cyclopropane-1-carbonitrile (Step-2, 1.10 g, 5.58 mmol) in 1,4-dioxane (5.00 mL) and $H_2O$ (0.50 mL). The resulting mixture was stirred at 90° C. for 14 h under nitrogen atmosphere. The resulting mixture was concentrated under reduced pressure. The residue was purified by silica gel column chromatography eluting with DCM/MeOH (15/1 v/v) to obtain the title compound (170.0 mg) as a solid. LCMS (ESI): 300 $[M+H]^+$.

Step-4. 2-{3-aminopyrazolo[1,5-a]pyrimidin-5-yl}cyclopropane-1-carbonitrile

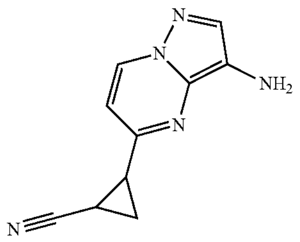 [SMILES: N#CC1CC1c1ccn2ncc(N)c2n1]

TFA (3.00 mL) was added to a mixture of tert-butyl N-[5-(2-cyanocyclopropyl)pyrazolo[1,5-a]pyrimidin-3-yl]carbamate (Step-3, 170.0 mg, 0.57 mmol) in DCM (3.00 mL). The resulting mixture was stirred at 25° C. for 1 h. The resulting mixture was concentrated under reduced pressure to obtain the title compound (140.0 mg) as a solid. LCMS (ESI): 200 $[M+H]^+$.

Step-5. (S)—N-(5-((1S,2S)-2-cyanocyclopropyl) pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide and (S)—N-(5-((1R,2R)-2-cyanocyclopropyl)pyrazolo[1,5-a] pyrimidin-3-yl)-4-(5-(5-fluoro-2-methoxypyridin-4-yl)-1H-pyrazole-3-carbonyl)-4-azaspiro[2.5]octane-7-carboxamide

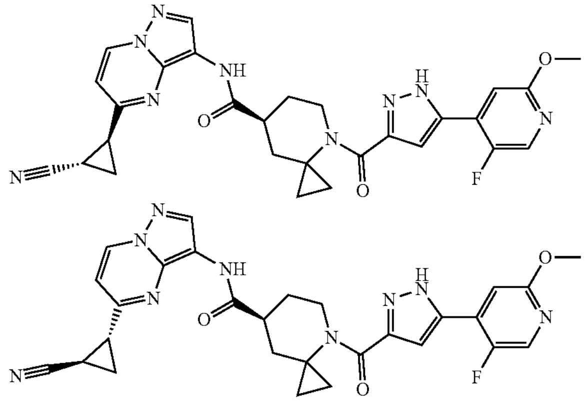

HATU (344.0 mg, 0.90 mmol) and 2-{3-aminopyrazolo[1,5-a]pyrimidin-5-yl}cyclopropane-1-carbonitrile (Step-4, 120.0 mg, 0.60 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 226.0 mg, 0.60 mmol) and DIPEA (234.0 mg, 1.81 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)—N-(5-((1S,2)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide and (S)—N-(5-((1R,2R)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide (100.0 mg) as a solid mixture of diastereomers (Example 466). $^1$H NMR (400 MHz, DMSO-$d_6$) δ 13.94 (s, 1H), 9.86 (s, 1H), 8.95 (d, 1H), 8.51 (s, 1H), 8.26 (d, 1H), 7.34 (d, 1H), 7.12-7.03 (m, 2H), 4.84-4.25 (m, 1H), 3.88 (s, 3H), 3.20-3.00 (m, 3H), 2.41-2.25 (m, 2H), 2.00-1.49 (m, 4H), 1.44-1.22 (m, 1H), 1.12-0.88 (m, 2H), 0.81-0.60 (m, 2H). LCMS (ESI): 556.45 $[M+H]^+$.

This mixture of two diastereomers (100.0 mg) was separated using Chiral Prep-HPLC.

Column: CHIRALPAK IG column

Column dimension: 2×25 cm, 5 μm

Mobile Phase: 1/1 hexanes/DCM (0.5% 2 M $NH_3$·MeOH):EtOH=50:50 hold for 24 min

Flow rate: 18 mL/min

Detection: 220/254 nm

Example 466-A. The first eluting diastereomer (32.0 mg) was obtained as a solid.

The first eluting diastereomer had a retention time of 16.72 min.

$^1$H NMR (400 MHz, $CD_3OD$) δ 8.72 (d, 1H), 8.49 (s, 1H), 8.14 (s, 1H), 7.38 (s, 1H), 7.18 (d, 1H), 7.06 (d, 1H), 4.71-4.24 (m, 1H), 3.95 (s, 3H), 3.24-3.15 (m, 1H), 2.97-2.88 (m, 1H), 2.66-2.47 (m, 1H), 2.41-2.34 (m, 1H), 2.28-1.94 (m, 2H), 1.91-1.80 (m, 2H), 1.79-1.71 (m, 1H), 1.52-1.46 (m, 1H), 1.18-1.03 (m, 1H), 0.98-0.69 (m, 3H). LCMS (ESI): 556.40 $[M+H]^+$.

Example 466-B. The second eluting diastereomer (24.4 mg) was obtained as a solid.

The second eluting diastereomer had a retention time of 21.46 min.

$^1$H NMR (400 MHz, $CD_3OD$) δ 8.72 (d, 1H), 8.49 (s, 1H), 8.14 (d, 1H), 7.29 (s, 1H), 7.14 (s, 1H), 7.06 (d, 1H), 4.73-4.44 (m, 1H), 3.95 (s, 3H), 3.24-3.09 (m, 1H), 2.98-2.88 (m, 1H), 2.81-2.44 (m, 1H), 2.41-2.31 (m, 1H), 2.25-1.94 (m, 2H), 1.91-1.80 (m, 2H), 1.78-1.71 (m, 1H), 1.53-1.40 (m, 1H), 1.37-1.26 (m, 1H), 0.89-0.74 (m, 3H). LCMS (ESI): 556.25 $[M+H]^+$.

Example 467. A Diastereomeric Mixture of (S)—N-((5-((1R,4R)-2,5-diazabicyclo[2.2.1]heptan-2-yl) pyrimidin-2-yl)methyl)-4-(3-(5-fluoro-2-methoxy-pyridin-4-yl)-1H-pyrazole-5-carbonyl)-4-azaspiro [2.5]octane-7-carboxamide and (S)—N-((5-((1S, 4S)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide

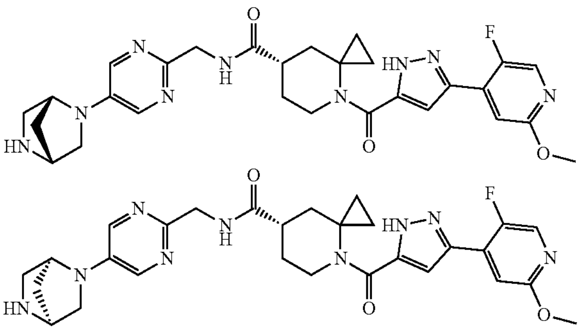

The title compound was prepared using a procedure similar to the one described for the synthesis of Example 447, except tert-butyl 2,5-diazabicyclo[2.2.1]heptane-2-carboxylate was used as a starting material in Step-1. The residue was purified by reverse phase column chromatography (using the following conditions: C18 column; mobile phase A: Water (0.5% $NH_4HCO_3$), mobile phase B: MeCN; gradient: 20 B to 30 B in 20 min; detector, UV 254 nm) to obtain (S)—N-((5-((1R,4R)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide and (S)—N-((5-((1S,4S)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide (100.0 mg) as a solid mixture of diastereomers (Example 467). $^1$H NMR (400 MHz, $CD_3OD$) δ 8.16-8.10 (m, 3H), 7.28 (d, 1H), 7.11 (d, 1H), 4.87-4.82 (m, 2H), 4.50-4.45 (m, 2H), 3.94 (s, 3H), 3.91-3.85 (m, 1H), 3.66-3.59 (m, 1H), 3.15-3.08 (m, 1H), 3.05-2.88 (m, 3H), 2.49-2.44 (m, 1H), 2.04-1.92 (m, 2H), 1.92-1.84 (m, 1H), 1.81-1.77 (m, 1H), 1.72-1.15 (m, 2H), 1.00-0.96 (m, 2H), 0.79-0.71 (m, 2H). LCMS (ESI): 562.45 $[M+H]^+$.

This mixture of two diastereomers (100.0 mg) was separated using Chiral Prep-HPLC.

Column: CHIRALPAK IE column

Column dimension: 2×25 cm, 5 μm

Mobile Phase: DCM (0.5% 2 M $NH_3$·MeOH):MeOH=30:70 hold for 25 min

Flow rate: 18 mL/min

Detection: 220/254 nm

Example 467-A. The first eluting diastereomer (40.0 mg) was obtained as a solid.

The first eluting diastereomer had a retention time of 16.98 min.

$^1$H NMR (400 MHz, $CD_3OD$) δ 8.13 (d, 3H), 7.29 (d, 1H), 7.11 (d, 1H), 4.70-4.49 (m, 2H), 4.48-4.42 (m, 2H), 3.95 (s, 3H), 3.90-3.85 (m, 1H), 3.67-3.59 (m, 1H), 3.15-3.08 (m, 1H), 3.06-2.78 (m, 3H), 2.49-2.44 (m, 1H), 2.13-1.89 (n 2H), 1.88-1.82 (m, 1H), 1.81-1.70 (m, 1H), 1.51-1.19 (m, 2H), 1.08-0.86 (m, 2H), 0.79-0.71 (m, 2H). LCMS (ESI): 562.45 $[M+H]^+$.

Example 467-B. The second eluting diastereomer (20.0 mg) was obtained as a solid.

The second eluting diastereomer had a retention time of 22.34 min.

$^1$H NMR (400 MHz, $CD_3OD$) δ 8.13 (d, 3H), 7.29 (d, 1H), 7.14-7.09 (m, 1H), 4.59-4.54 (m, 1H), 4.53-4.45 (m, 3H), 3.95 (s, 3H), 3.85-3.80 (m, 1H), 3.66-3.58 (m, 1H), 3.13-3.06 (m, 1H), 3.04-2.91 (m, 3H), 2.49-2.44 (m, 1H), 2.01-1.94 (m, 2H), 1.90-1.83 (m, 1H), 1.81-1.77 (m, 1H), 1.44-1.36 (m, 2H), 1.00-0.96 (m, 2H), 0.79-0.71 (m, 2H). LCMS (ESI): 562.45 $[M+H]^+$.

Example 468. A Diastereomeric Mixture of (R)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide and (S)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide

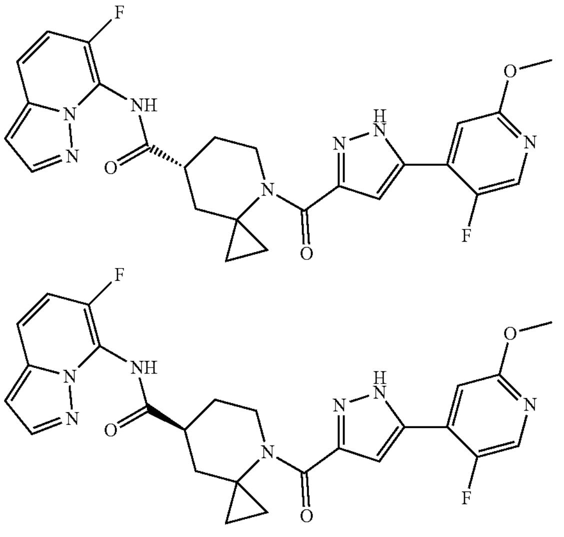

Step-1. methyl 7-bromo-6-fluoropyrazolo[1,5-a]pyridine-3-carboxylate

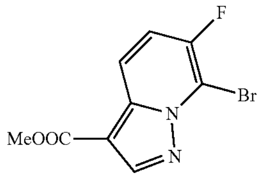 [SMILES: COC(=O)c1cnn2c(Br)c(F)ccc12]

TMPMgClLiCl (2.39 mL, 2.80 mmol, 1 M) was added to a stirred solution of methyl 6-fluoropyrazolo[1,5-a]pyridine-3-carboxylate (500.0 mg, 2.58 mmol) in THF (10.00 mL) at −78° C. under nitrogen atmosphere. The resulting mixture was stirred at −78° C. for 30 min under nitrogen atmosphere. Then $CF_2Br$—$CF_2Br$ (995.8 mg, 3.86 mmol) was added to the reaction mixture at −78° C. under nitrogen atmosphere. The resulting mixture was stirred at −78° C. for 2 h under nitrogen atmosphere. The resulting mixture was quenched with MeOH at −78° C. under nitrogen atmosphere. The resulting mixture was concentrated under reduced pressure. The residue was purified by Prep-TLC (DCM/MeOH, 60/1 v/v) to obtain the title compound (450.0 mg) as a solid. LCMS (ESI): 273.0 $[M+H]^+$.

Step-2. 7-bromo-6-fluoropyrazolo[1,5-a]pyridine

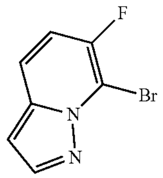 [SMILES: Fc1ccc2ccnn2c1Br]

$H_2SO_4$ (4.00 mL) was added to a stirred mixture of methyl 7-bromo-6-fluoropyrazolo[1,5-a]pyridine-3-carboxylate (Step-1, 150.0 mg, 0.55 mmol) in $H_2O$ (4.00 mL) at 0° C. The resulting mixture was stirred at 0° C. for 30 min and then heated to 100° C. for 1 h. The resulting mixture was diluted with EtOAc and washed with $Na_2CO_3$ (aq.). The organic layers were combined, dried over anhydrous $Na_2SO_4$, filtered, and concentrated under reduced pressure. The residue was purified by Prep-TLC (petroleum ether/EtOAc, 3/1 v/v) to obtain the title compound (90.0 mg) as a solid. LCMS (ESI): 215.0 $[M+H]^+$.

Step-3. 4-[5-(5-fluoro-2-methoxypyridin-4-yl)-1-{[2-(trimethylsilyl) ethoxyl] methyl}pyrazole-3-carbonyl]-4-azaspiro[2.5]octane-7-carboxamide

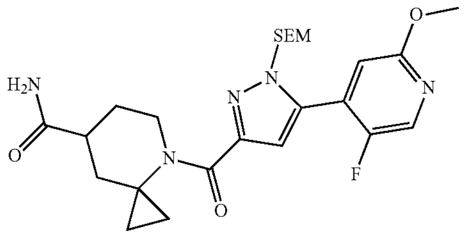 [SMILES: COc1cc(-c2cc(C(=O)N3CCC(C(N)=O)CC34CC4)nn2COCC[Si](C)(C)C)c(F)cn1]

HATU (339.1 mg, 0.89 mmol) and $NH_4Cl$ (63.6 mg, 1.19 mmol) were added to a stirred solution of 4-[5-(5-fluoro-2-methoxypyridin-4-yl)-1-{[2-(trimethylsilyl) ethoxy] methyl} pyrazole-3-carbonyl]-4-azaspiro[2.5]octane-7-carboxylic acid (INTERMEDIATE 541, 300.0 ng, 0.59 mmol) and DIPEA (230.5 mg, 1.78 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 12/1 v/v) to obtain the title compound (250.0 mg) as an oil. LCMS (ESI): 504.2 [M+H]$^+$.

Step-4. 4-[5-(5-fluoro-2-methoxypyridin-4-yl)-1-{[2-(trimethylsilyl) ethoxy] methyl}pyrazole-3-carbonyl]-4-azaspiro[2.5] octane-7-carboxamide

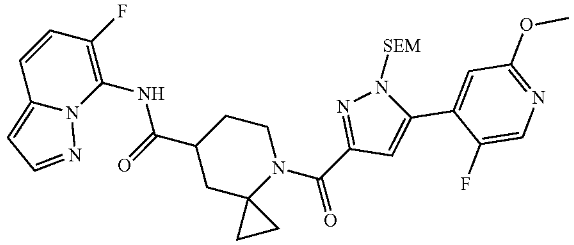 [SMILES: COc1cc(-c2cc(C(=O)N3CCC(C(=O)Nc4c(F)ccc5ccnn45)CC34CC4)nn2COCC[Si](C)(C)C)c(F)cn1]

XantPhos Pd $G_2$ (225.7 mg, 0.25 mmol), XantPhos (147.1 mg, 0.25 mmol), and $Cs_2CO_3$ (414.0 mg, 1.27 mmol) were added to a stirred solution of 4-[5-(5-fluoro-2-methoxypyridin-4-yl)-1-{[2-(trimethylsilyl) ethoxy] methyl} pyrazole-3-carbonyl]-4-azaspiro[2.5] octane-7-carboxamide (Step-3, 320.0 mg, 0.64 mmol) and 7-bromo-6-fluoropyrazolo[1,5-a] pyridine (Step-2, 273.2 mg, 1.27 mmol) in 1,4-dioxane (8.00 mL). The resulting mixture was stirred at 110° C. for 48 h under nitrogen atmosphere. The resulting mixture was concentrated under vacuum. The residue was purified by Prep-TLC (petroleum ether/EtOAc, 3/1 v/v) to obtain the title compound (340.0 mg) as an oil. LCMS (ESI): 638.3 [M+H]$^+$.

Step-5. (R)-4-(5-(5-fluoro-2-methoxypyridin-4-yl)-1H-pyrazole-3-carbonyl)-N-(6-fluoropyrazolo[1,5-a] pyridin-7-yl)-4-azaspiro[2.5]octane-7-carboxamide and (S)-4-(5-(5-fluoro-2-methoxypyridin-4-yl)-1H-pyrazole-3-carbonyl)-N-(6-fluoropyrazolo[1,5-a] pyridin-7-yl)-4-azaspiro[2.5]octane-7-carboxamide

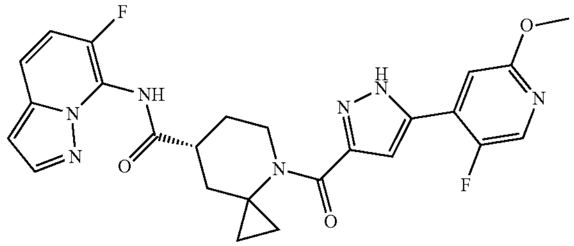

-continued

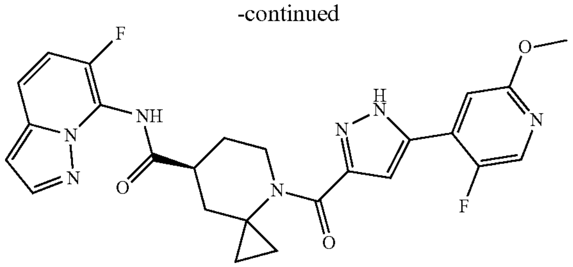

TFA (5.00 mL) was added to a stirred solution of 4-[5-(5-fluoro-2-methoxypyridin-4-yl)-1-{[2-(trimethylsilyl) ethoxy]methyl}pyrazole-3-carbonyl]-N-{6-fluoropyrazolo [1,5-a]pyridin-7-yl}-4-azaspiro[2.5]octane-7-carboxamide (340.0 mg, 0.53 mmol) in DCM (5.00 mL). The resulting mixture was stirred at 25° C. for 2 h. The resulting mixture was concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 30 B in 20 min; 220/254 nm) to obtain (R)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide and (S)-4-(5-(5-fluoro-2-methoxypyridin-4-yl)-1H-pyrazole-3-carbonyl)-N-(6-fluoropyrazolo[1,5-a] pyridin-7-yl)-4-azaspiro[2.5]octane-7-carboxamide (260.0 mg) as a solid mixture of diastereomers (Example 468). $^1$H NMR (400 MHz, $CD_3OD$) δ 8.13 (d, 1H), 8.00 (d, 1H), 7.71-7.59 (m, 1H), 7.37-7.24 (m, 2H), 7.13 (d, 1H), 6.75 (d, 1H), 4.73-4.49 (m, 2H), 3.95 (s, 3H), 3.27-3.20 (m, 1H), 2.72-2.30 (m, 1H), 2.24-2.04 (m, 1H), 1.99-1.74 (m, 1H), 1.72-1.52 (m, 1H), 1.27-0.96 (m, 2H), 0.90-0.80 (m, 2H). LCMS (ESI): 508.15 [M+H]$^+$.

This mixture of two diastereomers (260.0 mg) was separated using Chiral Prep-HPLC.

Column: CHIRALPAK ID column

Column dimension: 2×25 cm, 5 μm

Mobile Phase: 3/1 hexanes/DCM (0.1% FA):EtOH=70:30 hold for 17 min

Flow rate: 20 mL/min

Detection: 220/254 nm

Example 468-A. The first eluting diastereomer (42.0 mg) was obtained as a solid.

The first eluting diastereomer had a retention time of 12.42 min.

$^1$H NMR (400 MHz, DMSO-$d_6$) δ 13.99 (s, 1H), 10.44 (s, 1H), 8.27 (d, 1H), 8.05 (d, 1H), 7.81-7.66 (m, 1H), 7.48-7.26 (m, 2H), 7.16-6.97 (m, 1H), 6.77 (d, 1H), 4.64-4.36 (m, 1H), 3.88 (s, 3H), 3.20-3.06 (m, 2H), 2.05-1.91 (m, 1H), 1.77-1.61 (m, 1H), 1.57-1.42 (m, 1H), 1.11-0.86 (m, 2H), 0.81-0.66 (m, 3H). LCMS (ESI): 508.25 [M+H]$^+$.

Example 468-B. The second eluting diastereomer (52.2 mg) was obtained as a solid.

The second eluting diastereomer had a retention time of 15.46 min.

$^1$H NMR (400 MHz, DMSO-$d_6$) δ 13.93 (s, 1H), 10.43 (s, 1H), 8.34-8.19 (m, 1H), 8.12-8.01 (m, 1H), 7.78-7.65 (m, 1H), 7.48-7.26 (m, 2H), 7.13-7.01 (m, 1H), 6.87-6.67 (m, 1H), 4.50 (s, 1H), 3.88 (s, 3H), 3.27-3.01 (m, 2H), 2.09-1.87

(m, 1H), 1.80-1.57 (m, 1H), 1.57-1.39 (m, 1H), 1.14-0.83 (m, 2H), 0.81-0.45 (m, 3H). LCMS (ESI): 508.15 $[M+H]^+$.

Example 469. A Diastereomeric Mixture of (S)—N-((5-((1S,6R)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide and (S)—N-((5-((1R,6S)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide

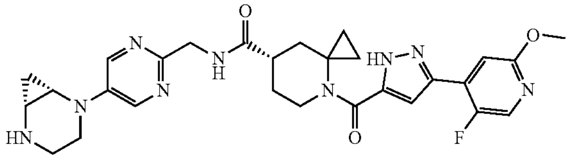

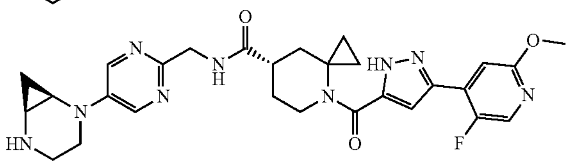

The title compound was prepared using a procedure similar to the one described for the synthesis of Example 447, except tert-butyl 2,5-diazabicyclo[4.1.0]heptane-2-carboxylate was used as a starting material in Step-1. The residue was purified by reverse phase column chromatography (using the following conditions: Column: C18; mobile phase A: Water (0.5% $NH_4HCO_3$), mobile phase B: MeCN; gradient: 20 B to 50 B in 20 min; 220/254 nm) to obtain (S)—N-((5-((1S,6R)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide and (S)—N-((5-((1R,6S)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide (60.0 mg) as a solid mixture of diastereomers (Example 469). $^1H$ NMR (400 MHz, $CD_3OD$) δ 8.43 (s, 2H), 8.27 (s, 1H), 8.17-8.07 (m, 1H), 7.33-7.24 (m, 1H), 7.15-7.08 (m, 1H), 4.68-4.39 (m, 3H), 3.94 (s, 3H), 3.40 (s, 2H), 3.28-3.03 (m, 3H), 2.94 (s, 1H), 2.83-2.70 (m, 1H), 2.47 (s, 1H), 2.14-1.58 (m, 2H), 1.51-1.28 (m, 2H), 1.22-1.10 (m, 1H), 1.00 (s, 2H), 0.84-0.59 (m, 3H). LCMS (ESI): 562.50 $[M+H]^+$.

This mixture of two diastereomers (60.0 mg) was separated using Chiral Prep-HPLC.

Column: CHIRALPAK IF column
Column dimension: 2×25 cm, 5 μm
Mobile Phase: 1/1 hexanes/DCM (0.5% 2 M $NH_3$·MeOH):EtOH:=60:40 hold for 45 min
Flow rate: 15 mL/min
Detection: 220/254 nm Example 469-A. The first eluting diastereomer (20.0 mg) was obtained as a solid.

The first eluting diastereomer had a retention time of 22.95 min.

$^1H$ NMR (400 MHz, $CD_3OD$) δ 8.46-8.33 (m, 2H), 8.16-8.09 (m, 1H), 7.29 (s, 1H), 7.16-7.07 (m, 1H), 4.64-4.42 (m, 2H), 3.99-3.88 (m, 2H), 3.69-3.36 (m, 1H), 3.26-3.12 (m, 2H), 3.06-299 (m, 2H), 2.98-2.79 (m, 3H), 2.63-2.31 (m, 2H), 2.11-1.90 (m, 1H), 1.87-1.67 (m, 1H), 1.53-1.18 (m, 2-1), 1.17-0.85 (m, 3H), 0.82-0.59 (m, 2H), 0.46-0.29 (m, 1H). LCMS (ESI): 562.20 $[M+H]^+$.

Example 469-B. The second eluting diastereomer (20.0 mg) was obtained as a solid.

The second eluting diastereomer had a retention time of 34.46 min.

$^1H$ NMR (400 MHz, $CD_3OD$) δ 8.48-8.33 (m, 2H), 8.18-8.04 (m, 1H), 7.29 (s, 1H), 7.12 (s, 1H), 4.67-4.43 (m, 2H), 3.95 (s, 3H), 3.61-3.37 (m, 1H), 3.26-3.11 (m, 2H), 3.07-2.97 (m, 2H), 2.97-2.83 (m, 2H), 2.66-2.22 (m, 2H), 2.08-1.88 (m, 1H), 1.88-1.68 (m, 1H), 1.58-1.22 (m, 2H), 1.19-0.89 (m, 3H), 0.85-0.57 (m, 2H), 0.48-0.32 (m, 1H). LCMS (ESI): 562.15 $[M+H]^+$.

Example 470. A Diastereomeric Mixture of (S)—N—((R)-4,4-difluoro-1-((1-hydroxycyclopropyl)methyl)pyrrolidin-3-yl)-4-(3-(5-fluoro-2-methoxypyridin-4-yl)-1-pyrazole-5-carbonyl)-4-azaspiro[2.5]octane-7-carboxamide and (S)—N—((S)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide

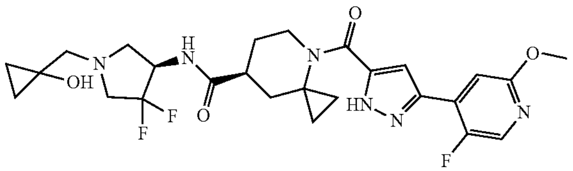

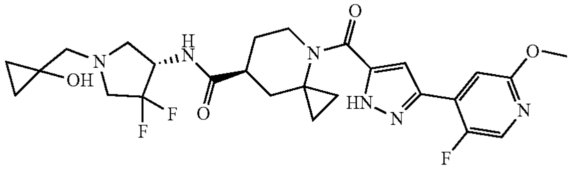

Step-1. tert-butyl 4-(dibenzylamino)-3,3-difluoropyrrolidine-1-carboxylate

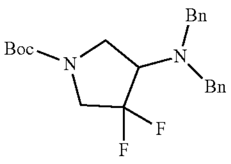 [SMILES: CC(C)(C)OC(=O)N1CC(N(Cc2ccccc2)Cc2ccccc2)C(F)(F)C1]

$K_2CO_3$ (1.55 g, 11.25 mmol) and BnBr (1.92 g, 0.01 mmol) were added to a stirred solution of tert-butyl 4-amino-3,3-difluoropyrrolidine-1-carboxylate (1.00 g, 4.50 mmol) in MeCN (10.00 mL). The resulting solution was stirred at 60° C. for 14 h. The resulting mixture was concentrated under reduced pressure. The residue was purified by silica gel column chromatography eluting with petroleum ether/EtOAc (10/1 v/v) to obtain the title compound (1.23 g) as a solid. LCMS (ESI): 403.2 $[M+H]^+$.

Step-2. N,N-dibenzyl-4,4-difluoropyrrolidin-3-amine

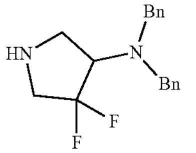 [SMILES: FC1(F)CNCC1N(Cc1ccccc1)Cc1ccccc1]

TFA (6.00 mL) was added to a stirred solution of tert-butyl 4-(dibenzylamino)-3,3-difluoropyrrolidine-1-carboxylate (Step-1, 1.20 g, 2.98 mmol) in DCM (6.00 mL). The resulting solution was stirred at 25° C. for 1 h. The resulting mixture was concentrated under reduced pressure. The residue was purified by silica gel column chromatography eluting with DCM/MeOH (10/1 v/v) to obtain the title compound (850.0 mg) as an oil. LCMS (ESI): 303.2 $[M+H]^+$.

Step-3. 1-[4-(dibenzylamino)-3,3-difluoropyrrolidine-1-carbonyl]cyclopropan-1-ol

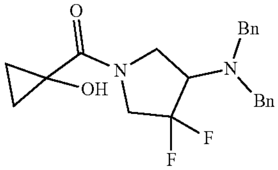 [SMILES: O=C(N1CC(N(Cc2ccccc2)Cc2ccccc2)C(F)(F)C1)C1(O)CC1]

HOBt (635.3 mg, 4.70 mmol), EDCI (901.3 mg, 4.70 mmol), and N,N-dibenzyl-4,4-difluoropyrrolidin-3-amine (Step-2, 568.7 mg, 1.88 mmol) were added to a stirred solution of 1-hydroxycyclopropane-1-carboxylic acid (240.0 mg, 2.35 mmol) and DIPEA (1.52 g, 11.76 mmol) in DMF (10.00 mL). The resulting mixture was stirred at 25° C. for 1 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (6/1 v/v) to obtain the title compound (400.0 mg) as a solid. LCMS (ESI): 387.2 $[M+H]^+$.

Step-4. 1-{[4-(dibenzylamino)-3,3-difluoropyrrolidin-1-yl]methyl}cyclopropan-1-ol

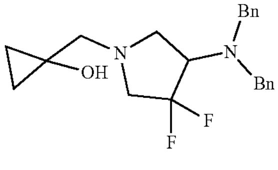 [SMILES: OC1(CN2CC(N(Cc3ccccc3)Cc3ccccc3)C(F)(F)C2)CC1]

$LiAlH_4$-THF (0.28 mL, 0.29 mmol) was added to a stirred solution of 1-[4-(dibenzylamino)-3,3-difluoropyrrolidine-1-carbonyl]cyclopropan-1-ol (Step-3, 110.0 mg, 0.29 mmol) in THF (5.00 mL) at 0° C. under nitrogen atmosphere. The resulting mixture was stirred at 60° C. for 14 h under nitrogen atmosphere. The resulting mixture was quenched with MeOH at 0° C. The resulting mixture was concentrated under reduced pressure. The residue was purified by silica gel column chromatography eluting with petroleum ether/EtOAc (3/1 v/v) to obtain the title compound (65.0 mg) as a solid. LCMS (ESI): 373.2 $[M+H]^+$.

Step-5. 1-[(4-amino-3,3-difluoropyrrolidin-1-yl)methyl]cyclopropan-1-ol

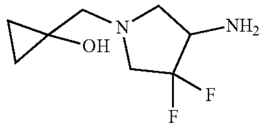 [SMILES: NC1CN(CC2(O)CC2)CC1(F)F]

Pd/C (22.0 mg) was added to a stirred solution of 1-{[4-(dibenzylamino)-3,3-difluoropyrrolidin-1-yl]methyl}cyclopropan-1-ol (Step-4, 110.0 mg, 0.30 mmol) in MeOH (2.00 mL) at 0° C. The resulting mixture was stirred at 25° C. for 14 h under hydrogen atmosphere. The resulting mixture was filtered, the filter cake was washed with MeOH. The filtrate was concentrated under reduced pressure to obtain the title compound (50.0 mg) as a solid. LCMS (ESI): 193.1 $[M+H]^+$.

Step-6. (S)—N—((R)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide and (S)—N—((S)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide

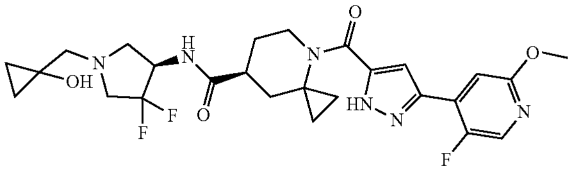

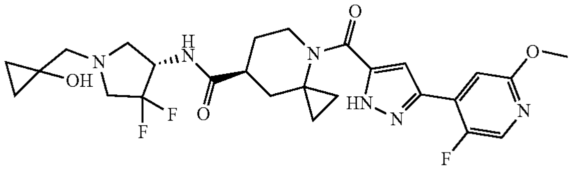

HOBt (70.3 mg, 0.52 mmol), EDCI (99.7 mg, 0.52 mmol), and 1-[(4-amino-3,3-difluoropyrrolidin-1-yl)methyl]cyclopropan-1-ol (Step-5, 50.0 mg, 0.26 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 97.4 mg, 0.26 mmol) and DIPEA (168.1 mg, 1.30 mmol) in DMF (2.00 mL). The resulting mixture was stirred at 25° C. for 1 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 50 B in 30 min;

220/254 urn) to obtain (S)—N—((R)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide and (S)—N—((S)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide (80.0 mg) as a solid mixture of diastereomers (Example 470). $^1$H NMR (400 MHz, $CD_3OD$) δ 8.13 (s, 1H), 7.51-7.16 (m, 1H), 7.11 (s, 1H), 4.75-4.42 (m, 2H), 3.95 (s, 3H), 3.60-3.37 (m, 1H), 3.27-3.12 (m, 2H), 3.11-2.96 (m, 1H), 2.95-2.79 (m, 1H), 2.74-2.63 (m, 1H), 2.62-2.53 (m, 1H), 2.52-2.27 (m, 1H), 2.05-1.58 (m, 2H), 1.50-1.19 (m, 2H), 1.17-0.89 (m, 2H), 0.88-0.61 (m, 4H), 0.59-0.43 (m, 2H). LCMS (ESI): 549.40 $[M+H]^+$.

This mixture of two diastereomers (80.0 mg) was separated using Chiral Prep-HPLC.

Column: CHIRAL ART Amylose-SA column

Column dimension: 2×25 cm, 5 μm

Mobile Phase: MTBE (0.5% 2M $NH_3$. MeOH):EtOH=50:50 hold for 16 min

Flow rate: 20 mL/min

Detection: 220/254 nm

Example 470-A. The first eluting diastereomer (25.0 mg) was obtained as a solid.

The first eluting diastereomer had a retention time of 7.37 min.

$^1$H NMR (400 MHz, $CD_3OD$) δ 8.13 (s, 1H), 7.52-6.77 (m, 2H), 4.74-4.40 (m, 2H), 3.95 (s, 3H), 3.26-3.13 (m, 2H), 3.10-2.96 (m, 1H), 2.96-2.76 (m, 1H), 2.75-2.51 (m, 3H), 2.51-2.25 (m, 1H), 2.08-1.55 (m, 2H), 1.44-1.19 (m, 2H), 1.16-0.88 (m, 2H), 0.86-0.61 (m, 4H), 0.57-0.42 (m, 2H). LCMS (ESI): 549.45 $[M+H]^+$.

Example 470-B. The second eluting diastereomer (30.0 mg) was obtained as a solid.

The second eluting diastereomer had a retention time of 12.26 min.

$^1$H NMR (400 MHz, $CD_3OD$) δ 8.13 (s, 1H), 7.54-6.94 (m, 2H), 4.74-4.42 (m, 2H), 3.95 (s, 3H), 3.29-3.12 (m, 2H), 3.11-2.96 (m, 1H), 2.95-2.79 (m, 1H), 2.74-2.52 (m, 3H), 2.51-2.20 (m, 1H), 2.04-1.61 (m, 2H), 1.48-1.23 (m, 2H), 1.21-0.89 (m, 1H), 0.88-0.63 (m, 5H), 0.60-0.41 (m, 2H). LCMS (ESI): 549.25 $[M+H]^+$.

Example 471. (7S)-4-(5-(5-fluoro-2-methoxypyridin-4-yl)-1H-pyrazole-3-carbonyl)-N-(pyrrolidin-3-yl)-4-azaspiro[2.5]octane-7-carboxamide

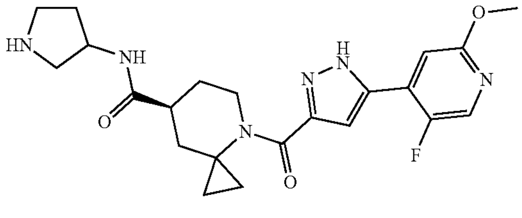 [SMILES: COc1cc(-c2cc(C(=O)N3CC[C@H](C(=O)NC4CCNC4)CC34CC4)n[nH]2)c(F)cn1]

Step-1. tert-butyl 3-[(7S)-4-[5-(5-fluoro-2-methoxypyridin-4-yl)-1H-pyrazole-3-carbonyl]-4-azaspiro[2.5]octane-7-amido]pyrrolidine-1-carboxylate

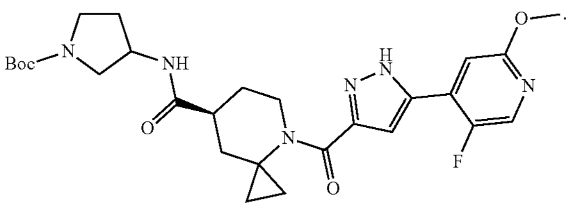 [SMILES: COc1cc(-c2cc(C(=O)N3CC[C@H](C(=O)NC4CCN(C(=O)OC(C)(C)C)C4)CC34CC4)n[nH]2)c(F)cn1]

tert-butyl 3-aminopyrrolidine-1-carboxylate (249.0 mg, 1.34 mmol) and HATU (609.0 mg, 1.60 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 500.0 mg, 1.34 mmol) and DIPEA (518.0 mg, 4.01 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (700.0 mg) as a solid. LCMS (ESI): 543 $[M+H]^+$.

Step-2. (7S)-4-(5-(5-fluoro-2-methoxypyridin-4-yl)-1H-pyrazole-3-carbonyl)-N-(pyrrolidin-3-yl)-4-azaspiro[2.5]octane-7-carboxamide

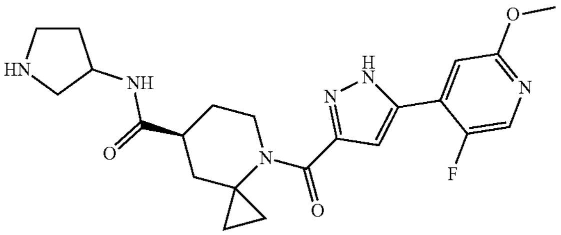 [SMILES: COc1cc(-c2cc(C(=O)N3CC[C@H](C(=O)NC4CCNC4)CC34CC4)n[nH]2)c(F)cn1]

TFA (3.00 mL) were added to a mixture of tert-butyl 3-[(7S)-4-[5-(5-fluoro-2-methoxypyridin-4-yl)-1H-pyrazole-3-carbonyl]-4-azaspiro[2.5]octane-7-amido]pyrrolidine-1-carboxylate (Step-1, 700.0 mg, 1.29 mmol) in DCM (3.00 mL). The resulting mixture was stirred at 25° C. for 1 h. The resulting mixture was concentrated under reduced pressure. The residue was purified by silica gel column chromatography eluting with DCM/MeOH (10/1 v/v) to obtain the title compound (520.0 mg) as a solid. $^1$H NMR (400 MHz, DMSO-$d_6$) δ 8.26 (d, 1H), 7.96 (m, 1H), 7.33 (d, 1H), 7.02 (d, 1H), 4.64-4.29 (m, 1H), 4.21-4.01 (m, 1H), 3.88 (s, 3H), 2.98-2.58 (m, 7H), 2.29-2.08 (m, 1H), 2.06-1.82 (m, 1H), 1.81-1.65 (m, 1H), 1.60-1.39 (m, 2H), 1.31-1.10 (m, 1H), 1.02-0.79 (m, 2H), 0.70-0.57 (m, 2H). LCMS (ESI): 443.35 $[M+H]^+$.

Example 472. A Diastereomeric Mixture of (S)—N—((R)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide

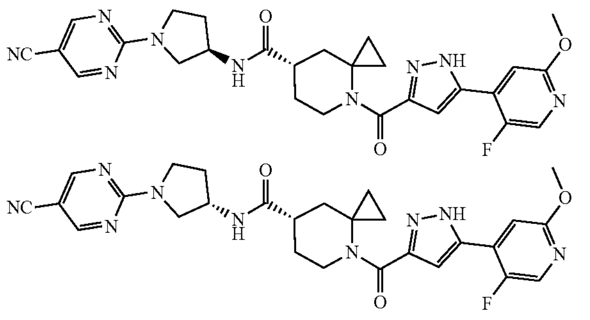

DIPEA (219.0 mg, 1.70 mmol) were added to a mixture of (7S)-4-[5-(5-fluoro-2-methoxypyridin-4-yl)-1H-pyrazole-3-carbonyl]-N-(pyrrolidin-3-yl)-4-azaspiro[2.5]octane-7-carboxamide (Example 471, 150.0 mg, 0.34 mmol) and 2-chloropyrimidine-5-carbonitrile (33.0 mg, 0.24 mmol) in EtOH (5.00 mL). The resulting mixture was stirred at 25° C. for 14 h. The resulting mixture was concentrated under reduced pressure. The residue was purified by silica gel column chromatography eluting with DCM/MeOH (10/1 v/v) to obtain (S)—N—((R)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide (120.0 mg) as a solid mixture of diastereomers (Example 472). $^1$H NMR (400 MHz, DMSO-$d_6$) δ 13.94 (s, 1H), 8.79-8.72 (m, 2H), 8.27 (d, 1H), 8.16 (d, 1H), 7.32 (d, 1H), 7.03 (s, 1H), 4.61-4.27 (m, 2H), 3.88 (s, 3H), 3.78-3.68 (m, 1H), 3.68-3.60 (m, 2H), 3.48-3.39 (m, 1H), 3.30-2.81 (m, 1H), 2.74-2.52 (m, 1H), 2.23-2.10 (m, 2H), 1.95-1.83 (m, 1H), 1.78-1.73 (m, 1H), 1.66-1.41 (m, 1H), 1.33-1.11 (m, 1H), 0.97-0.93 (m, 2H), 0.64-0.60 (m, 2H). LCMS (ESI): 546.25 $[M+H]^+$.

This mixture of two diastereomers (120.0 mg) was separated using Chiral Prep-HPLC.

Column: CHIRAL ART Amylose-SA column

Column dimension: 2×25 cm, 5 μm

Mobile Phase: 1/1 hexanes/DCM (0.5% 2 M $NH_3$·MeOH):MeOH=50:50 hold for 12.5 min Flow rate: 20 mL/min Detection: 220/254 nm Example 472-A. The first eluting diastereomer (40.2 mg) was obtained as a solid.

The first eluting diastereomer had a retention time of 7.86 min.

$^1$H NMR (400 MHz, DMSO-$d_6$) δ 13.97 (s, 1H), 8.91-8.69 (m, 2H), 8.27 (d, 1H), 8.15 (d, 1H), 7.32 (d, 1H), 7.16-6.91 (m, 1H), 4.72-4.24 (m, 2H), 3.88 (s, 3H), 3.78-3.69 (m, 1H), 3.67-3.61 (m, 2H), 3.52-3.41 (m, 1H), 3.26-2.86 (m, 1H), 2.79-2.57 (m, 1H), 2.25-2.06 (m, 2H), 2.00-1.82 (m, 1H), 1.79-1.70 (m, 1H), 1.64-1.44 (m, 1H), 1.31-1.10 (m, 1H), 1.03-0.79 (m, 2H), 0.76-0.52 (m, 2H). LCMS (ESI): 546.45 $[M+H]^+$.

Example 472-B. The second eluting diastereomer (38.2 mg) was obtained as a solid.

The second eluting diastereomer had a retention time of 10.56 min.

$^1$H NMR (400 MHz, DMSO-$d_6$) δ 13.97 (s, 1H), 8.81-8.69 (m, 2H), 8.27 (d, 1H), 8.16 (d, 1H), 7.32 (d, 1H), 7.03 (d, 1H), 4.65-4.26 (m, 2H), 3.88 (s, 3H), 3.80-3.71 (m, 1H), 3.69-3.60 (m, 2H), 3.52-3.38 (m, 1H), 3.28-2.83 (m, 1H), 2.82-2.61 (m, 1H), 2.30-2.06 (m, 2H), 1.98-1.86 (m, 1H), 1.83-1.69 (m, 1H), 1.63-1.45 (m, 1H), 1.30-1.12 (m, 1H), 1.04-0.79 (m, 2H), 0.74-0.53 (m, 2H). LCMS (ESI): 546.45 $[M+H]^+$.

Example 473. (S)-4-(5-(5-fluoro-2-methoxypyridin-4-yl)-1H-pyrazole-3-carbonyl)-N-((1-isopropyl-3-methyl-1H-1,2,4-triazol-5-yl)methyl)-4-azaspiro[2.5]octane-7-carboxamide

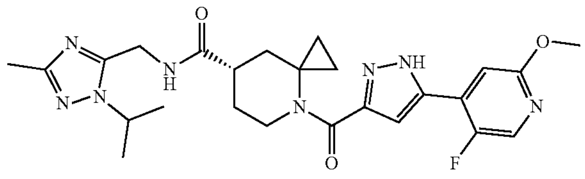

Step-1. ethyl 2-isopropyl-5-methyl-1,2,4-triazole-3-carboxylate

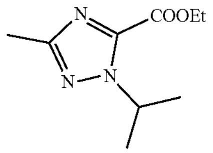

NaH (309.4 mg, 7.73 mmol, 60% dispersion in mineral oil) was added to a stirred solution of ethyl 5-methyl-2H-1,2,4-triazole-3-carboxylate (1.00 g, 6.45 mmol) in DMF (10.00 mL). The resulting mixture was stirred at 0° C. for 30 min, then 2-iodopropane (1.64 g, 9.67 mmol) was added to the reaction mixture. The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (20/1 v/v) to obtain the title compound (665.0 mg) as an oil. LCMS (ESI): 198.1 $[M+H]^+$.

Step-2. (2-isopropyl-5-methyl-1,2,4-triazol-3-yl)methanol

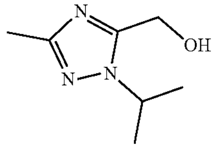

$LiBH_4$ (530.1 mg, 24.34 mmol) was added to a stirred solution of ethyl 2-isopropyl-5-methyl-1,2,4-triazole-3-carboxylate (Step-1, 600.0 mg, 3.04 mmol) in THY (5.00 mL)/EtOH (5.00 mL) at 0° C. The resulting mixture was stirred at 25° C. for 14 h. The resulting solution was concentrated under reduced pressure. The residue was purified by silica gel column chromatography eluting with DCM/MeOH (12/1 v/v) to obtain the title compound (250.0 mg) as a solid. LCMS (ESI): 156.1 $[M+H]^+$.

Step-3. 2-isopropyl-5-methyl-1,2,4-triazole-3-carbaldehyde

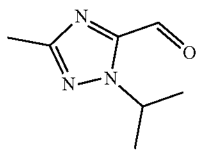

$MnO_2$ (756.2 mg, 8.70 mmol) was added to a stirred solution of (2-isopropyl-5-methyl-1,2,4-triazol-3-yl)methanol (Step-2, 270.0 mg, 1.74 mmol) in DCM (10.00 mL). The resulting mixture was stirred at 25° C. for 14 h. The resulting mixture was filtered, the filter cake was washed with DCM. The solution was concentrated under reduced pressure to obtain the title compound and the residue was used in the next step directly without further purification. LCMS (ESI): 154.1 $[M+H]^+$.

Step-4. N-[(1E)-(2-isopropyl-5-methyl-1,2,4-triazol-3-yl)methylidene]-2-methylpropane-2-sulfinamide

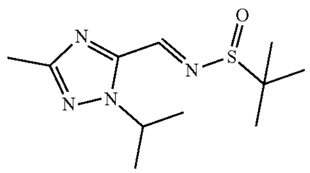 [SMILES: Cc1nc(/C=N/S(=O)C(C)(C)C)n(C(C)C)n1]

Tert-butanesulfinamide (213.6 mg, 1.76 mmol), PTSA (15.2 mg, 0.09 mmol) and $MgSO_4$ (636.5 mg, 5.29 mmol) were added to a stirred solution of crude of 2-isopropyl-5-methyl-1,2,4-triazole-3-carbaldehyde (Step-3, 266.0 mg, 1.76 mmol 1.00 equiv) in DCM (10.00 mL). The resulting mixture was stirred at 25° C. for 14 h. The resulting solution was concentrated under reduced pressure. The residue was purified by silica gel column chromatography eluting with DCM/MeOH (10/1 v/v) to obtain the title compound (180.0 mg) as a solid. LCMS (ESI): 257.1 $[M+H]^+$.

Step-5. N-[(2-isopropyl-5-methyl-1,2,4-triazol-3-yl)methyl]-2-methylpropane-2-sulfinamide

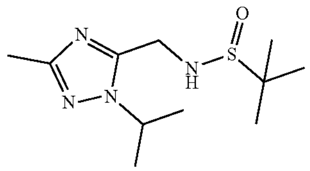 [SMILES: Cc1nc(CNS(=O)C(C)(C)C)n(C(C)C)n1]

$NaBH_4$ (47.2 mg, 1.25 mmol) was added to a stirred solution of N-[(1E)-(2-isopropyl-5-methyl-1,2,4-triazol-3-yl)methylidene]-2-methylpropane-2-sulfinamide (Step-4, 160.0 mg, 0.62 mmol) in MeOH (4.00 mL). The resulting mixture was stirred at 25° C. for 14 h. The resulting solution was concentrated under reduced pressure. The residue was purified by silica gel column chromatography eluting with DCM/MeOH (10/1 v/v) to obtain the title compound (160.0 mg) as an oil. LCMS (ESI): 259.2 $[M+H]^+$.

Step-6. 1-(2-isopropyl-5-methyl-1,2,4-triazol-3-yl) methanamine

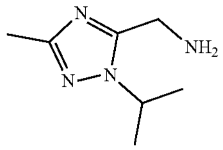

HCl (gas) in 1,4-dioxane (4.00 mL) was added to a stirred solution of N-[(2-isopropyl-5-methyl-1,2,4-triazol-3-yl)methyl]-2-methylpropane-2-sulfinamide (Step-5, 150.0 mg, 0.58 mmol) in 1,4-dioxane (4.00 mL). The resulting mixture was stirred at 25° C. for 14 h. The resulting mixture was filtered, the filter cake was washed with MeOH. The filtrate was concentrated under reduced pressure to obtain the title compound as an oil. LCMS (ESI): 155.1 $[M+H]^+$.

Step-7. (S)-4-(5-(5-fluoro-2-methoxypyridin-4-yl)-1H-pyrazole-3-carbonyl)-N-((1-isopropyl-3-methyl-1H-1,2,4-triazol-5-yl)methyl)-4-azaspiro[2.5]octane-7-carboxamide

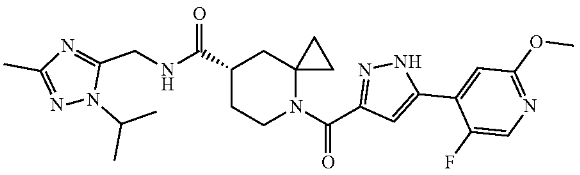

HOBt (98.0 mg, 0.73 mmol), EDCI (139.1 mg, 0.73 mmol) and 1-(2-isopropyl-5-methyl-1,2,4-triazol-3-yl) methanamine (Step-6, 89.5 mg, 0.58 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 181.1 mg, 0.48 mmol) and DIPEA (186.9 mg, 1.45 mmol) in DMF (5.00 mL). The resulting mixture was stirred a 25° C. for 14 h. The resulting mixture was diluted with EtOAC and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (85.0 mg) as a solid. $^1H$ NMR (400 MHz, DMSO-$d_6$) δ 14.01 (s, 1H), 8.48 (s, 1H), 8.27 (s, 1H), 7.32 (d, 1H), 7.03 (s, 1H), 4.78-4.50 (m, 1H), 4.49-4.27 (m, 2H), 3.88 (s, 3H), 3.27-2.87 (m, 1H), 2.84-2.69 (m, 1H), 2.28-2.10 (m, 4H), 1.90-1.69 (m, 1H), 1.60-1.42 (m, 1H), 1.37-1.27 (m, 6H), 1.27-1.12 (m, 1H), 1.08-0.81 (m, 2H), 0.76-0.40 (m, 3H). LCMS (ESI): 511.20 $[M+H]^+$.

Example 474. A Diastereomeric Mixture of (S)—N-((1S,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

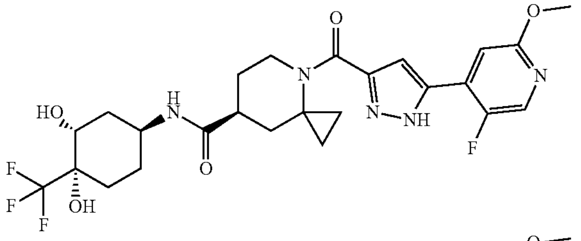

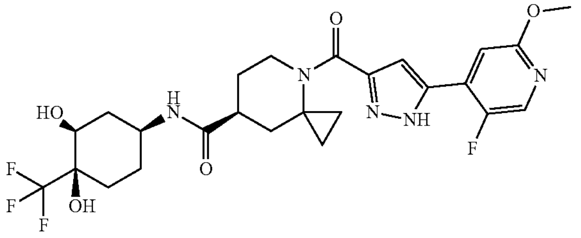

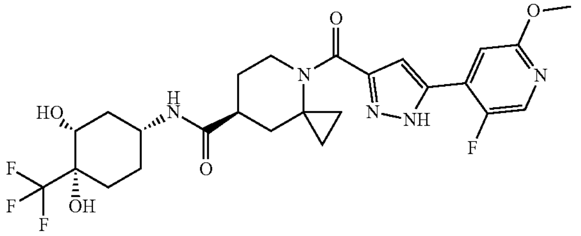

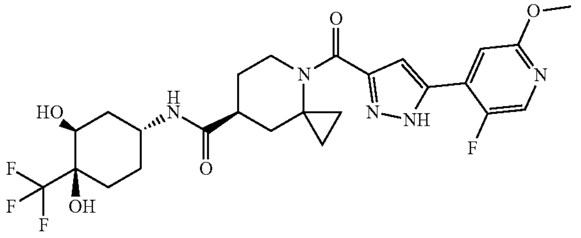

Step-1. N,N-dibenzyl-4-(trifluoromethyl)cyclohex-3-ep-1-amine

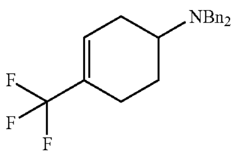

$SOCl_2$ (785.7 mg, 6.60 mmol) and pyridine (522.4 mg, 6.60 mmol) were added to a stirred mixture of (1r,4r)-4-(dibenzylamino)-1-(trifluoromethyl)cyclohexan-1-ol (800.0 mg, 2.20 mmol) in THF (10.00 mL). The resulting mixture was stirred at 50° C. for 14 h. The resulting mixture was concentrated under reduced pressure. The residue was purified by silica gel column chromatography eluting with DCM/MeOH (16/1 v/v) to obtain the title compound (620.0 mg) as a yellow solid. LCMS (ESI): 346.2 $[M+H]^+$.

Step-2. (1S,2R)-4-(dibenzylamino)-1-(trifluoromethyl)cyclohexane-1,2-diol and (1R,2S)-4-(dibenzylamino)-1-(trifluoromethyl)cyclohexane-1,2-diol

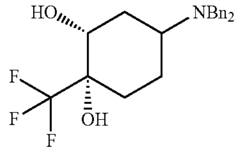

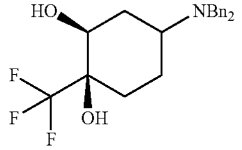

$OsO_4$ (8.5 mg, 0.03 mmol) and t-BuOH (348.5 mg, 4.70 mmol) were added to a stirred mixture of N,N-dibenzyl-4-(trifluoromethyl)cyclohex-3-en-1-amine (Step-1, 580.0 mg, 1.68 mmol) and NMO (590.1 mg, 5.04 mmol) in DCM (10 mL). The resulting mixture was stirred at 25° C. for 14 h. The resulting mixture was concentrated under reduced pressure. The residue was purified by Prep-TLC (DCM/MeOH 20:1) to obtain the title compound (160.0 mg) as a solid mixture of diastereomers. LCMS (ESI): 380.2 $[M+H]^+$.

Step-3. (1S,2R)-4-amino-1-(trifluoromethyl)cyclohexane-1,2-diol and (1R,2S)-4-amino-1-(trifluoromethyl)cyclohexane-1,2-diol

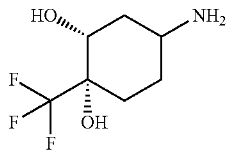

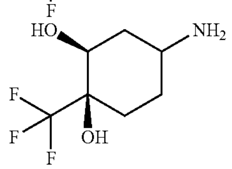

Pd/C (48.0 mg) was added to a stirred mixture of (1S,2R)-4-(dibenzylamino)-1-(trifluoromethyl)cyclohexane-1,2-diol and (1R,2S)-4-(dibenzylamino)-1-(trifluoromethyl)cyclohexane-1,2-diol (Step-2, 160.0 mg, 0.42 mmol) in MeOH (5.00 mL) at 0° C. The resulting mixture was stirred at 25° C. for 8 h under hydrogen atmosphere. The resulting mixture was filtered, the filter cake was washed with MeOH. The filtrate was concentrated under reduced pressure to obtain the title compound (70.0 mg) as a solid mixture of diastereomers and the residue was used in the next step directly without further purification. LCMS (ESI): 199.2 [M+H]+.

Step-4. A Diastereomeric Mixture of (S)—N-((1S,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide; and a second diastereomeric mixture of (S)—N-((1R,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

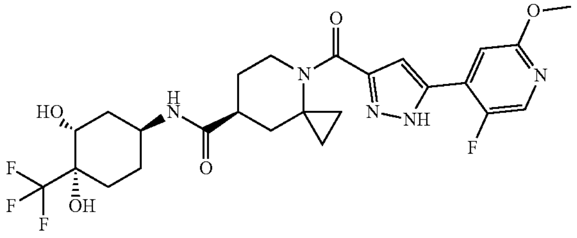

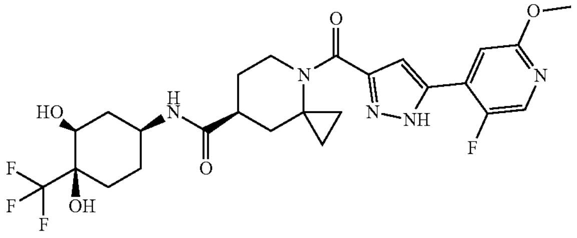

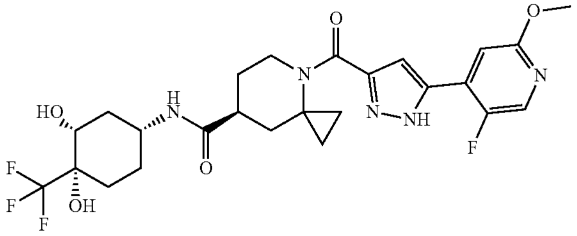

-continued

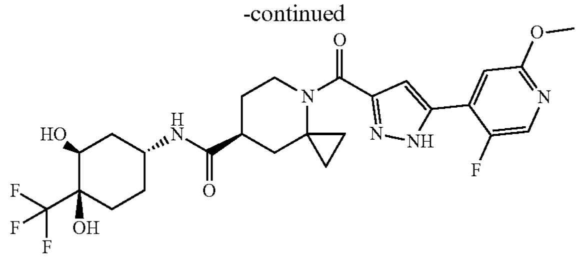

HOBt (20.4 mg, 0.15 mmol), EDCI (28.9 mg, 0.15 mmol), and (1S,2R)-4-amino-1-(trifluoromethyl)cyclohexane-1,2-diol and (1R,2S)-4-amino-1-(trifluoromethyl)cyclohexane-1,2-diol (Step-3, 15.0 mg, 0.08 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 28.2 mg, 0.08 mmol) and DIPEA (48.7 mg, 0.38 mmol) in DMF (2.00 mL). The resulting mixture was stirred at 25° C. for 4 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 9/1 v/v) to obtain (S)—N-((1S,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,3R,45)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide (20.0 mg) as a solid mixture of diastereomers.

This mixture of four diastereomers (20.0 mg) was separated using Chiral Prep-HPLC.

Column: Xselect CSH C18 OBD column

Column dimension: 3×15 cm, 5 μm

Mobile Phase: Water (10 mM $NH_4HCO_3$):MeCN=80:20 hold for 12 min

Flow rate: 60 mL/min

Detection: 220/254 nm

Example 474-A. The first eluting peak (11.9 mg) was obtained as a solid mixture of two diasteromers.

The first eluting peak had a retention time of 10.20 min.

$^1H$ NMR (400 MHz, $CD_3OD$) δ 8.13 (d, 1H), 7.29 (d, 1H), 7.11 (d, 1H), 4.59-4.55 (m, 1H), 3.95 (s, 3H), 3.93-3.85 (m, 1H), 3.80-3.62 (m, 1H), 2.81-2.76 (m, 1H), 2.46-2.42 (m, 1H), 1.99-1.89 (m, 2H), 1.80-1.60 (m, 3H), 1.58-1.50 (m, 2H), 1.46-1.15 (m, 3H), 1.11-0.79 (m, 2H), 0.77-0.69 (m, 2H). LCMS (ESI): 556.30 [M+H]+.

Example 474-B. The second eluting peak (3.7 mg) was obtained as a solid mixture of two diasteromers.

The second eluting peak had a retention time of 11.28 min.

$^1H$ NMR (400 MHz, $CD_3OD$) δ 8.13 (d, 1H), 7.29 (d, 1H), 7.14-7.09 (m, 1H), 4.61-4.56 (m, 1H), 4.14-4.00 (m, 2H), 3.95 (s, 3H), 2.92-2.88 (m, 1H), 2.48-2.43 (m, 1H), 1.90-1.78 (m, 6H), 1.65-1.59 (m, 1H), 1.50-1.01 (m, 3H), 0.96-0.88 (m, 2H), 0.77-0.72 (m, 2H). LCMS (ESI): 556.30 [M+H]+.

Step-5. (S)—N-((1S,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,3S,4R)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

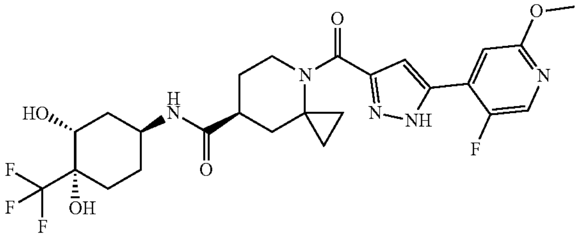

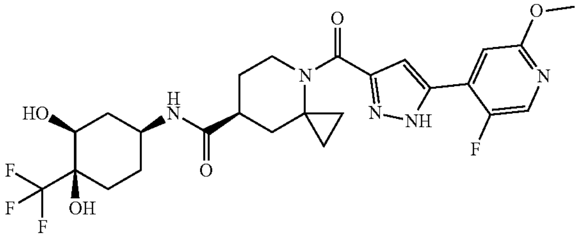

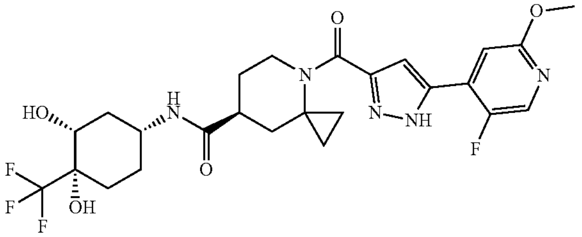

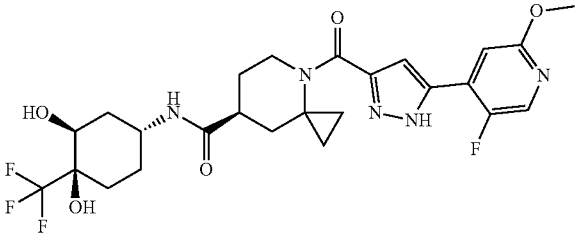

The mixture of four diastereomers (100.0 mg) was separated using Chiral Prep-HPLC.

Column: CHIRAL ART Amylose-SA column

Column dimension: 2×25 cm, 5 μm

Mobile Phase: 3/1 hexanes/DCM (0.5% 2 M $NH_3$·MeOH):EtOH=50:50 hold for 26 min

Flow rate: 20 mL/min

Detection: 220/254 nm

Example 474-C. The first eluting diastereomer (3.8 mg) was obtained as a solid.

The first eluting diastereomer had a retention time of 5.80 min.

LCMS (ESI): 556.25 $[M+H]^+$.

Example 474-D. The second eluting diastereomer (23.9 mg) was obtained as a solid.

The second eluting diastereomer had a retention time of 11.24 min.

$^1$H NMR (400 MHz, $CD_3OD$) δ 8.14 (s, 1H), 7.23-7.19 (m, 1H), 7.11 (s, 1H), 4.82 (s, 0H), 4.79-4.20 (m, 1H), 4.13 (s, 0H), 3.97-3.93 (m, 4H), 3.93-3.85 (m, 1H), 2.89-2.15 (m, 2H), 1.91-1.56 (m, 8H), 1.40-1.19 (m, 2H), 1.04-0.53 (m, 4H). LCMS (ESI): 556.15 $[M+H]^+$.

Example 474-E. The third eluting diastereomer (24.9 mg) was obtained as a solid.

The third eluting diastereomer had a retention time of 16.06 min.

$^1$H NMR (400 MHz, $CD_3OD$) δ 8.14 (s, 1H), 7.57-6.84 (m, 2H), 4.80-4.21 (m, 1H), 3.97-3.85 (m, 4H), 3.74-3.69 (m, 1H), 2.81-2.76 (m, 1H), 2.65-2.30 (m, 1H), 2.10-1.50 (m, 8H), 1.43-0.56 (m, 6H). LCMS (ESI): 556.25 $[M+H]^+$.

Example 474-F. The fourth eluting diastereomer (2.4 mg) was obtained as a solid.

The fourth eluting diastereomer had a retention time of 22.31 min.

$^1$H NMR (400 MHz, $CD_3OD$) δ 8.14 (d, 1H), 7.29 (s, 1H), 4.11 (s, 1H), 4.61-4.57 (m, 1H), 4.11-4.01 (m, 2H), 3.95 (s, 3H), 2.92-2.88 (m, 1H), 2.45-2.41 (m, 1H), 1.90-1.78 (m, 6H), 1.78-1.74 (m, 1H), 1.41-1.21 (m, 4H), 1.09-0.93 (m, 1H), 0.77-0.73 (m, 2H). LCMS (ESI): 556.10 $[M+H]^+$.

Example 475. A Diastereomeric Mixture of (S)-4-(5-(5-fluoro-2-methoxypyridin-4-yl)-1H-pyrazole-3-carbonyl)-N—((S)-1-(5-methyl-4,5,6,7-tetrahydropyrazolo[1,5-a]pyrazin-2-yl)ethyl)-4-azaspiro[2.5]octane-7-carboxamide and (S)-4-(5-(5-fluoro-2-methoxypyridin-4-yl)-1H-pyrazole-3-carbonyl)-N—((R)-1-(5-methyl-4,5,6,7-tetrahydropyrazolo[1,5-a]pyrazin-2-yl)ethyl)-4-azaspiro[2.5]octane-7-carboxamide

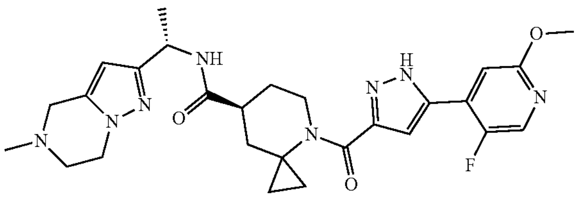

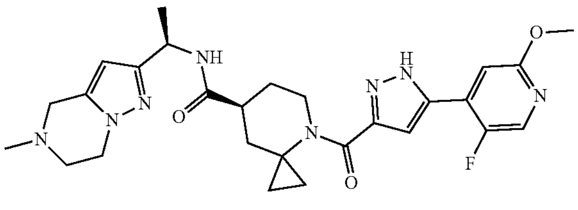

Step-1. ethyl 5-methyl-4H,6H,7H-pyrazolo[1,5-a]pyrazine-2-carboxylate

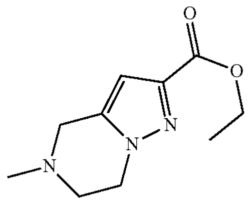

AcOH (0.50 mL) and HCHO (283.0 mg, 9.43 mmol) were added to a stirred mixture of ethyl 4H,5H,6H,7H-pyrazolo[1,5-a]pyrazine-2-carboxylate (920.0 mg, 4.71 mmol) in MeOH (5.00 mL). The resulting mixture was stirred at 25° C. for 30 min. Then $NaBH_3CN$ (888.4 mg, 14.14 mmol) was added to the reaction mixture. The resulting mixture was stirred at 25° C. for 14 h. The resulting mixture was concentrated under reduced pressure. The residue was purified by silica gel column chromatography eluting with petroleum ether/EtOAc (5/1 v/v) to obtain the title compound (950.0 mg) as an oil. LCMS (ESI): 210.1 $[M+H]^+$.

Step-2. {5-methyl-4H,6H,7H-pyrazolo[1,5-a]pyrazin-2-yl}methanol

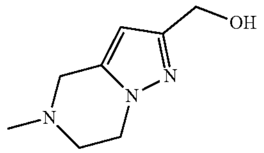

Ethyl 5-methyl-4H,6H,7H-pyrazolo[1,5-a]pyrazine-2-carboxylate (Step-1, 890.0 mg, 4.25 mmol) in THF (5.00 mL) was added to a stirred solution of $LiAlH_4$ (8.51 mL, 8.51 mmol) at 0° C. under nitrogen atmosphere. The resulting mixture was stirred at 0° C. for 30 min under nitrogen atmosphere. The reaction was quenched with MeOH at 0° C. The resulting mixture was concentrated under reduced pressure. The residue was purified by silica gel column chromatography eluting with DCM/MeOH (10/1 v/v) to obtain the title compound (530.0 mg) as a solid. LCMS (ESI): 168.1 $[M+H]^+$.

Step-3. 5-methyl-4H,6H,7H-pyrazolo[1,5-a]pyrazine-2-carbaldehyde

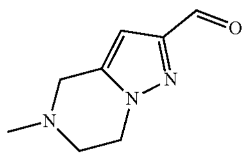

Dess-Martin periodinane (2.69 g, 6.34 mmol) was added to a stirred solution of {5-methyl-4H,6H,7H-pyrazolo[1,5-a]pyrazin-2-yl}methanol (Step-2, 530.0 mg, 3.17 mmol) in DCM (10.00 mL) in portions at 0° C. The resulting mixture was stirred at 25° C. for 14 h. The resulting mixture was concentrated under reduced pressure. The residue was purified by silica gel column chromatography eluting with DCM/MeOH (15/1 v/v) to obtain the title compound (250.0 mg) as an oil. LCMS (ESI): 166.1 $[M+H]^+$.

Step-4. (R)-2-methyl-N-[(1E)-{5-methyl-4H,6H,7H-pyrazolo[1,5-a]pyrazin-2-yl}methylidene]propane-2-sulfinamide

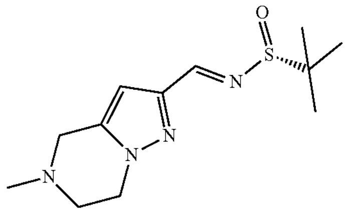 [SMILES: CN1CCn2nc(/C=N/[S@](=O)C(C)(C)C)cc2C1]

PTSA (13.0 mg, 0.08 mmol) and $MgSO_4$ (546.5 mg, 4.54 mmol) were added to a stirred mixture of 5-methyl-4H,6H,7H-pyrazolo[1,5-a]pyrazine-2-carbaldehyde (Step-3, 250.0 mg, 1.51 mmol) and (R)-2-methylpropane-2-sulfinamide (183.4 mg, 1.51 mmol) in DCM (10.00 mL). The resulting mixture was stirred at 25° C. for 14 h. The resulting mixture was concentrated under reduced pressure. The residue was purified by silica gel column chromatography eluting with DCM/MeOH (18/1 v/v) to obtain the title compound (230.0 mg) as a solid. LCMS (ESI): 269.1 $[M+H]^+$.

Step-5. (R)-2-methyl-N-[(1S)-1-{5-methyl-4H,6H,7H-pyrazolo[1,5-a]pyrazin-2-yl}ethyl]propane-2-sulfinamide

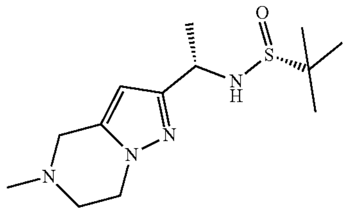 [SMILES: C[C@H](N[S@](=O)C(C)(C)C)c1cc2n(n1)CCN(C)C2]

Bromo(methyl)magnesium (0.28 mL, 0.84 mmol, 3.0 M solution) was added to a stirred mixture of (R)-2-methyl-N-[(1E)-{5-methyl-4H,6H,7H-pyrazolo[1,5-a]pyrazin-2-yl}methylidene]propane-2-sulfinamide (Step-4, 45.0 mg, 0.17 mmol) in THF (2.00 mL) at 0° C. under nitrogen atmosphere. The resulting mixture was stirred for 3.5 h at 50° C. under nitrogen atmosphere. The reaction was quenched with MeOH at 0° C. The resulting mixture was concentrated under reduced pressure. The residue was purified by silica gel column chromatography eluting with DCM/MeOH (6/1 v/v) to obtain the title compound (15.0 mg) as a solid. LCMS (ESI): 285.2 $[M+H]^+$.

Step-6. (1S)-1-{5-methyl-4H,6H,7H-pyrazolo[1,5-a]pyrazin-2-yl}ethanamine

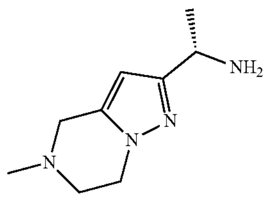

HCl (gas) in 1,4-dioxane (1.50 mL) was added to (R)-2-methyl-N-[(1S)-1-{5-methyl-4H,6H,7H-pyrazolo[1,5-a]pyrazin-2-yl}ethyl]propane-2-sulfinamide (Step-5, 15.0 mg, 0.05 mmol) at 25° C. The resulting mixture was stirred at 25° C. for 30 min. The resulting mixture was concentrated under reduced pressure to obtain the title compound (9.0 mg) as a solid. LCMS (ESI): 181.1 $[M+H]^+$.

Step-7. (S)-4-(5-(5-fluoro-2-methoxypyridin-4-yl)-1H-pyrazole-3-carbonyl)-N—((S)-1-(5-methyl-4,5,6,7-tetrahydropyrazolo[1,5-a]pyrazin-2-yl)ethyl)-4-azaspiro[2.5]octane-7-carboxamide and (S)-4-(5-(5-fluoro-2-methoxypyridin-4-yl)-1H-pyrazole-3-carbonyl)-N—((R)-1-(5-methyl-4,5,6,7-tetrahydropyrazolo[1,5-a]pyrazin-2-yl)ethyl)-4-azaspiro[2.5]octane-7-carboxamide

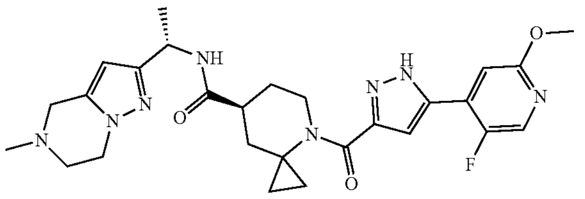

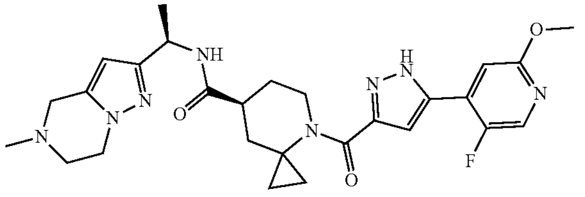

HOBt (13.5 mg, 0.10 mmol), EDCI (19.1 mg, 0.10 mmol), and (1S)-1-{5-methyl-4H,6H,7H-pyrazolo[1,5-a]pyrazin-2-yl}ethanamine (Step-6, 9.0 mg, 0.05 mmol) were added to a stirred mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 18.7 mg, 0.05 mmol) and DIPEA (64.5 mg, 0.50 mmol) in DMF (1.50 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH (9/1 v/v) to obtain (S)-4-(5-(5-fluoro-2-methoxypyridin-4-yl)-1H-pyrazole-3-carbonyl)-N—((S)-1-(5-methyl-4,5,6,7-tetrahydropyrazolo[1,5-a]pyrazin-2-yl)ethyl)-4-azaspiro[2.5]octane-7-carboxamide and (S)-4-(5-(5-fluoro-2-methoxypyridin-4-yl)-1H-pyrazole-3-carbonyl)-N—((R)-1-(5-methyl-4,5,6,7-tetrahydropyrazolo[1,5-a]pyrazin-2-yl)ethyl)-4-azaspiro[2.5]octane-7-carboxamide (170.0 mg) as a solid mixture of diastereomers. LCMS (ESI): 537.3 $[M+H]^+$.

This mixture of two diastereomers (17.0 mg) was separated using Chiral Prep-HPLC.

Column: CHIRAL ART Amylose-SA column

Column dimension: 2×25 cm, 5 μm

Mobile Phase: MTBE (0.5% 2M $NH_3$·MeOH):EtOH=50:50 hold for 10 min

Flow rate: 20 mL/min

Detection: 220/254 nm

Example 475-A. The first eluting diastereomer (2.6 mg) was obtained as a solid.

The first eluting diastereomer had a retention time of 5.23 min.

$^1$H NMR (400 MHz, $CD_3OD$) δ 8.14 (d, 1H), 7.44-6.99 (m, 2) 6.01-5.96 (m, 1H), 5.05 (d, 1H), 4.70-4.39 (m, 1H), 4.17-4.10 (m, 2H), 3.95 (s, 3H), 3.68-3.64 (m, 2H), 2.99-2.92 (m, 2H), 2.87-2.82 (m, 1H), 2.60-2.09 (m, 4H), 1.91-1.68 (m, 2H), 1.48-1.42 (m, 3H), 1.33-1.29 (m, 2H), 1.10-0.90 (m, 2H), 0.89-0.40 (m, 2H). LCMS (ESI): 537.25 $[M+H]^+$.

Example 475-B. The second eluting diastereomer (4.5 mg) was obtained as a solid.

The second eluting diastereomer had a retention time of 8.32 min.

$^1$H NMR (400 MHz, $CD_3OD$) δ 8.12 (s, 1H), 7.46-6.99 (m, 2H), 6.01-5.97 (m, 1H), 5.08-5.02 (m, 1H), 4.80-4.28 (m, 1H), 4.17-4.10 (m, 2H), 3.95 (s, 3H), 3.68-3.63 (m, 2H), 3.07-2.74 (n 3H), 2.71-2.40 (m, 4H), 2.05-1.56 (m, 2H), 1.48-1.42 (m, 3H), 1.39-1.30 (m, 2H), 1.30-0.82 (m, 2H), 0.81-0.63 (m, 2H). LCMS (ESI): 537.25 $[M+H]^+$.

Example 476. (S)-4-(3-(5-fluoro-2-methoxypyridin-4-yl)-1H-pyrazole-5-carbonyl)-N-((5-(trifluoromethyl)-1H-imidazol-2-yl)methyl)-4-azaspiro[2.5]octane-7-carboxamide

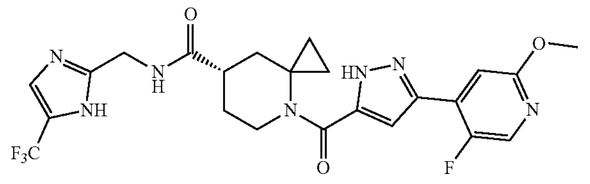 [SMILES: COc1cc(-c2cc(C(=O)N3CC[C@H](C(=O)NCc4ncc(C(F)(F)F)[nH]4)CC34CC4)[nH]n2)c(F)cn1]

Step-1. 2-(1H-imidazol-2-ylmethyl)isoindole-1,3-dione

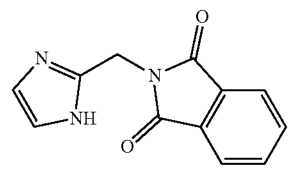 [SMILES: O=C1c2ccccc2C(=O)N1Cc1ncc[nH]1]

$Et_3N$ (677.2 mg, 6.69 mmol) and N-carbethoxyphthalimide (1.13 g, 5.15 mmol) were added to a stirred solution of 1-(1H-imidazol-2-yl)methanamine (500.0 mg, 5.15 mmol) in THF (5.00 mL). The resulting mixture was stirred at 80° C. for 14 h under nitrogen atmosphere. The resulting mixture was concentrated under reduced pressure. The residue was purified by silica gel column chromatography eluting with DCM/MeOH (19/1 v/v) to obtain the title compound (630.0 mg) as a solid. LCMS (ESI): 228.07 $[M+H]^+$.

Step-2. 2-{[4-(trifluoromethyl)-3H-imidazol-2-yl]methyl}isoindole-1,3-dione

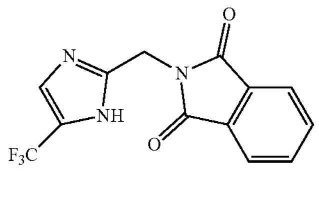 [SMILES: O=C1c2ccccc2C(=O)N1Cc1ncc(C(F)(F)F)[nH]1]

NaH (63.4 mg, 2.64 mmol, 60% dispersion in mineral oil) and trifluoroiodomethane (1.03 g, 5.28 mmol) were added to a stirred mixture of 2-(1H-imidazol-2-ylmethyl)isoindole-1,3-dione (Step-1, 400.0 mg, 1.76 mmol) in DMF (3.00 mL) at 0° C. The resulting mixture was stirred at 60° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (1/1 v/v) to obtain the title compound (100.0 mg) as a solid. LCMS (ESI): 296.06 $[M+H]^+$.

Step-3. 1-[4-(trifluoromethyl)-3H-imidazol-2-yl]methanamine

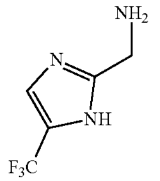 [SMILES: NCc1ncc(C(F)(F)F)[nH]1]

Hydrazine (32.6 mg, 1.02 mmol) was added to a stirred mixture of 2-{[4-(trifluoromethyl)-3H-imidazol-2-yl]methyl}isoindole-1,3-dione (Step-2, 100.0 mg, 0.34 mmol) in EtOH (1.00 mL). The resulting mixture was stirred at 60° C. for 30 min. The resulting mixture was concentrated under reduced pressure. The residue was purified by SiliaBond® Propylsulfonic Acid (SCX-2) eluting with $NH_3$ in MeOH (7 M) to obtain the title compound (50.0 mg) as a solid. LCMS (ESI): 166.05 $[M+H]^+$.

Step-4. (S)-4-(3-(5-fluoro-2-methoxypyridin-4-yl)-1H-pyrazole-5-carbonyl)-N-((5-(trifluoromethyl)-1H-imidazol-2-yl)methyl)-4-azaspiro[2.5]octane-7-carboxamide

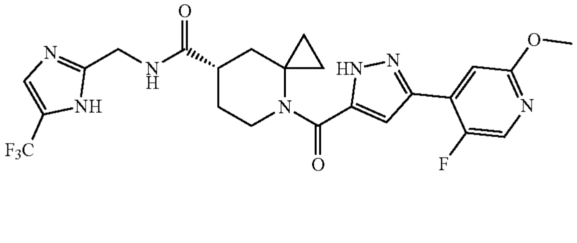 [SMILES: COc1cc(-c2cc(C(=O)N3CC[C@H](C(=O)NCc4ncc(C(F)(F)F)[nH]4)CC34CC4)[nH]n2)c(F)cn1]

HOBt (65.5 mg, 0.48 mmol), EDCI (92.9 mg, 0.48 mmol), and 1-[4-(trifluoromethyl)-3H-imidazol-2-yl]methanamine (Step-3, 40.0 mg, 0.24 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 90.7 mg, 0.24 mmol) and DIPEA (156.6 mg, 1.21 mmol) in DMF (2.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 30 B to 60 B in 30 min; 220/254 nm) to obtain the title compound (12.0 mg) as a solid. $^1H$ NMR (400 MHz, DMSO-$d_6$) δ 14.16-12.25 (m, 1H), 8.59-8.34 (m, 1H), 8.27 (d, 1H), 7.65 (d, 1H), 7.32 (d, 1H), 7.03 (d, 1H), 4.44 (s, 1H), 4.30 (d, 2H), 3.88 (s, 3H), 3.22-2.96 (m, 1H), 2.84-2.62 (m, 1H), 2.33-2.00 (m, 1H), 1.89-1.69 (m, 1H), 1.66-1.42 (m, 1H), 1.37-1.15 (m, 1H), 1.09-0.77 (m, 21H), 0.71-0.53 (m, 2H). LCMS (ESI): 522.10 $[M+H]^+$.

Example 477. 4-(5-(2-acetyl-5-fluoropyridin-4-yl)-1H-pyrazole-3-carbonyl)-N-((3-chloro-5-fluoropyridin-2-yl)methyl)-4-azaspiro[2.5]octane-7-carboxamide

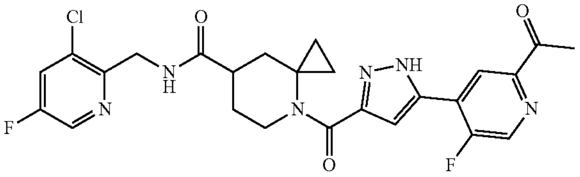 [SMILES: CC(=O)c1cc(-c2cc(C(=O)N3CCC(C(=O)NCc4ncc(F)cc4Cl)CC34CC4)n[nH]2)c(F)cn1]

Step-1. methyl 5-(2-chloro-5-fluoropyridin-4-yl)-1-{[2-(trimethylsilyl)ethoxy]methyl}pyrazole-3-carboxylate

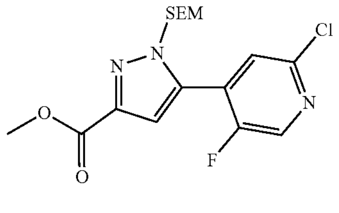 [SMILES: COC(=O)c1cc(-c2cc(Cl)ncc2F)n(COCC[Si](C)(C)C)n1]

$PdCl_2(AMPHOS)_2$ (1.27 g, 1.79 mmol) and CsF (2.72 g, 17.90 mmol) were added to the solution of methyl 5-bromo-1-{[2-(trimethylsilyl)ethoxy]methyl}pyrazole-3-carboxylate (3.00 g, 8.95 mmol) and 2-chloro-5-fluoropyridin-4-ylboronic acid (3.14 g, 17.90 mmol) in 1,4-dioxane (10.00 mL) and $H_2O$ (1.00 mL). The resulting mixture was stirred at 95° C. for 2 h under nitrogen atmosphere. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 5/1 v/v) to obtain the title compound (1.20 g) as a solid. LCMS (ESI): 386.1 $[M+H]^+$.

Step-2. 5-(2-chloro-5-fluoropyridin-4-yl)-1-{[2-(trimethylsilyl)ethoxy]methyl}pyrazole-3-carboxylic acid

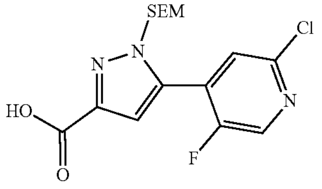 [SMILES: C[Si](C)(C)CCOCn1nc(C(=O)O)cc1-c1cc(Cl)ncc1F]

Lithium hydroxide (108.7 mg, 2.59 mmol) was added to the solution of methyl 5-(2-chloro-5-fluoropyridin-4-yl)-1-{[2-(trimethylsilyl)ethoxy]methyl}pyrazole-3-carboxylate (Step-1, 500.0 mg, 1.30 mmol) in $H_2O$ (8.00 mL), THF (8.00 mL) and MeOH (8.00 mL). The resulting mixture was stirred at 25° C. for 14 h. The resulting mixture was diluted with EtOAc, washed with HCl (1 M). The organic layers were combined, dried over anhydrous $Na_2SO_4$, filtered, and concentrated under reduced pressure. The residue was purified by Prep-TLC (DCM/MeOH, 12/1 v/v) to obtain the title compound (480.0 mg) as a solid. LCMS (ESI): 372.2 $[M+H]^+$.

Step-3. methyl 4-[5-(2-chloro-5-fluoropyridin-4-yl)-1-{[2-(trimethylsilyl)ethoxy]methyl}pyrazole-3-carbonyl]-4-azaspiro[2.5]octane-7-carboxylate

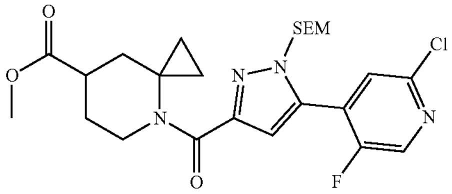 [SMILES: COC(=O)C1CCN(C(=O)c2cc(-c3cc(Cl)ncc3F)n(COCC[Si](C)(C)C)n2)C2(CC2)C1]

HATU (539.9 mg, 1.42 mmol) and methyl 4-azaspiro[2.5]octane-7-carboxylate (220.3 mg, 1.30 mmol) were added to a solution of 5-(2-chloro-5-fluoropyridin-4-yl)-1-{[2-(trimethylsilyl)ethoxy]methyl}pyrazole-3-carboxylic acid (Step-2, 440.0 mg, 1.18 mmol) and DIPEA (458.8 mg, 3.55 mmol) in DMF (8.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (17/1 v/v) to obtain the title compound (600.0 mg) as an oil. LCMS (ESI): 523.3 $[M+H]^+$.

Step-4. methyl 4-{5-[2-(1-ethoxyethenyl)-5-fluoropyridin-4-yl]-1-{[2-(trimethylsilyl)ethoxy]methyl}pyrazole-3-carbonyl}-4-azaspiro[2.5]octane-7-carboxylate

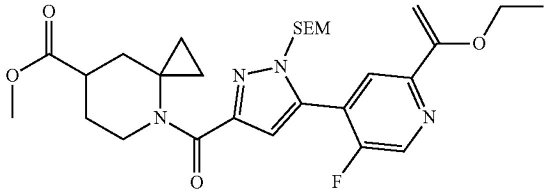 [SMILES: C=C(OCC)c1cc(-c2cc(C(=O)N3CCC(C(=O)OC)CC34CC4)nn2COCC[Si](C)(C)C)c(F)cn1]

$Pd(PPh_3)_4$ (132.6 mg, 0.12 mmol) was added to a stirred mixture of methyl 4-[5-(2-chloro-5-fluoropyridin-4-yl)-1-{[2-(trimethylsilyl)ethoxy]methyl}pyrazole-3-carbonyl]-4-azaspiro[2.5]octane-7-carboxylate (Step-3, 600.0 mg, 1.15 mmol) and tributyl(1-ethoxyethenyl)stannane (538.6 mg, 1.49 mmol) in DMF (8.00 mL). The resulting mixture was stirred at 100° C. for 14 h under nitrogen atmosphere. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 2/1 v/v) to obtain the title compound (600.0 mg) as a solid. LCMS (ESI): 559.3 $[M+H]^+$.

Step-5. methyl 4-[5-(2-acetyl-5-fluoropyridin-4-yl)-1H-pyrazole-3-carbonyl]-4-azaspiro[2.5]octane-7-carboxylate

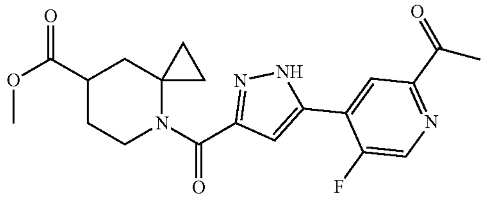 [SMILES: COC(=O)C1CCN(C(=O)c2cc(-c3cc(C(C)=O)ncc3F)[nH]n2)C2(CC2)C1]

HCl (10.00 mL) was added in a solution of methyl 4-{5-[2-(1-ethoxyethenyl)-5-fluoropyridin-4-yl]-1-{[2-(trimethylsilyl)ethoxy]methyl}pyrazole-3-carbonyl}-4-azaspiro[2.5]octane-7-carboxylate (Step-4, 600.0 mg, 1.07 mmol) in MeOH (10.00 mL). The solution was stirred at 25° C. for 14 h. The mixture was washed with $NaHCO_3$ (aq.) and concentrated under reduced pressure. The residue was purified by silica gel column chromatography eluting with DCM/MeOH (10/1 v/v) to obtain the title compound (360.0 mg) as a solid. LCMS (ESI): 401.2 $[M+H]^+$.

Step-6. 4-[5-(2-acetyl-5-fluoropyridin-4-yl)-1H-pyrazole-3-carbonyl]-4-azaspiro[2.5]octane-7-carboxylic acid

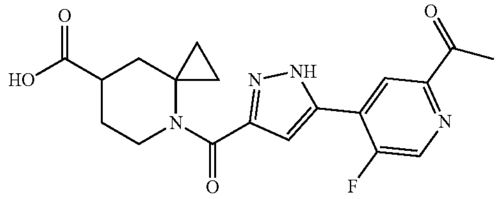 [SMILES: CC(=O)c1cc(-c2cc(C(=O)N3CCC(C(=O)O)CC34CC4)n[nH]2)c(F)cn1]

Lithium hydroxide (75.5 mg, 1.80 mmol) was added to a stirred mixture of methyl 4-[5-(2-acetyl-5-fluoropyridin-4-yl)-1H-pyrazole-3-carbonyl]-4-azaspiro[2.5]octane-7-carboxylate (Step-5, 360.0 mg, 0.90 mmol) in THF (4.00 mL), $H_2O$ (2.00 mL) and MeOH (2.00 mL). The resulting mixture was stirred at 25° C. for 2 h. The mixture was diluted with EtOAc and washed with HCl (1 M, aq.). The organic layers were combined, dried over anhydrous $Na_2SO_4$, filtered, and concentrated under reduced pressure. The residue was purified by Prep-TLC (DCM/MeOH 10/1 v/v) to obtain the title compound (290.0 mg) as an oil. LCMS (ESI): 387.1 $[M+H]^+$.

Step-7. 4-(5-(2-acetyl-5-fluoropyridin-4-yl)-1H-pyrazole-3-carbonyl)-N-((3-chloro-5-fluoropyridin-2-yl)methyl)-4-azaspiro[2.5]octane-7-carboxamide

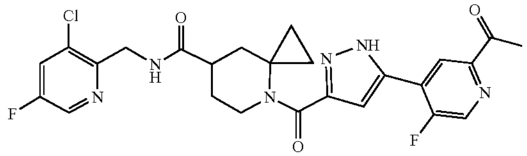 [SMILES: CC(=O)c1cc(-c2cc(C(=O)N3CCCC(C(=O)NCC4=C(\Cl)C/C=C(/F)C/C=N\4)CC34CC4)n[nH]2)c(F)cn1]

HATU (318.8 mg, 0.84 mmol) and 1-(3-chloro-5-fluoropyridin-2-yl)methanamine (112.2 mg, 0.70 mmol) were added to a stirred solution of 4-[5-(2-acetyl-5-fluoropyridin-4-yl)-1f-pyrazole-3-carbonyl]-4-azaspiro[2.5]octane-7-carboxylic acid (Step-6, 270.0 mg, 0.70 mmol) and DIPEA (270.9 mg, 2.10 mmol) in DMF (5.00 mL). The resulting mixture was stirred at 25° C. for 14 h. The resulting mixture was diluted with EtOAc, washed with water and concentrated. The residue was purified by Prep-TLC (DCM/MeOH, 15/1 v/v) to obtain the title compound (92.0 mg) as a solid. $^1H$ NMR (400 MHz, DMSO-$d_6$) δ 14.18 (s, 1H), 8.82 (s, 1H), 8.65-8.50 (m, 2H), 8.35 (s, 1H), 8.17-8.02 (m, 1H), 7.10 (s, 1H), 4.58-4.41 (m, 2H), 2.90-2.73 (m, 1H), 2.72-2.62 (m, 3H), 2.50-2.50 (m, 3H), 2.31-2.09 (m, 1H), 1.92-1.70 (m, 1H), 1.36-1.13 (m, 1H), 1.07-0.86 (m, 1H), 0.77-0.53 (m, 3H). LCMS (ESI): 529.20 $[M+H]^+$.

Example 478. A Diastereomeric Mixture of (R)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide and (S)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide and (S)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide

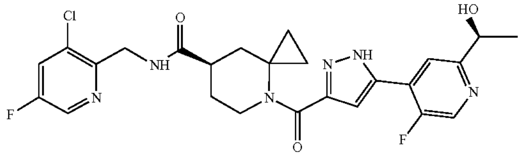

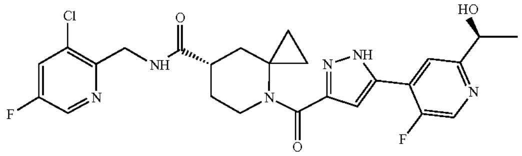

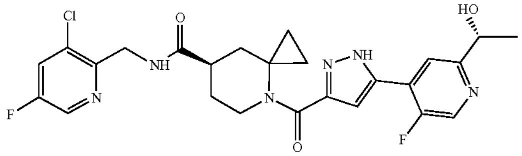

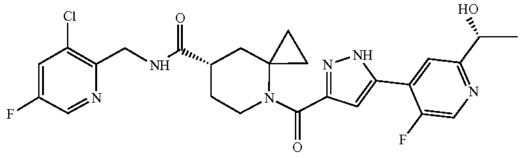

$NaBH_4$ (3.2 mg, 0.09 mmol) was added to a solution of 4-(5-(2-acetyl-5-fluoropyridin-4-yl)-1H-pyrazole-3-carbonyl)-N-((3-chloro-5-fluoropyridin-2-yl)methyl)-4-azaspiro[2.5]octane-7-carboxamide (Example 477, 90.0 mg, 0.17 mmol) in MeOH (2.00 mL) at 0° C. The solution was stirred at 25° C. for 14 h. The resulting mixture was concentrated under reduced pressure. The residue was purified by reverse phase column chromatography (using the following conditions: Column: C18 column; mobile phase A: Water (0.5% $NH_4HCO_3$), mobile phase B: MeCN; gradient: 30 B to 50 B in 30 min; 220/254 nm) to obtain (R)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide and (S)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide and (S)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide (70.0 mg) as a solid mixture of diastereomers (Example 478). $^1H$ NMR (400

MHz, $CD_3OD$) δ 8.54-8.45 (m, 1H), 8.45-8.36 (m, 1H), 8.34-7.84 (m, 1H), 7.84-7.75 (m, 1H), 7.16 (s, 1H), 4.95-4.89 (m, 1H), 4.65-4.55 (m, 3H), 3.04-2.77 (m, 1H), 2.54-2.30 (m, 1H), 2.10-1.86 (m, 1H), 1.74 (d, 1H), 1.57-1.47 (m, 3H), 1.43-1.32 (m, 1H), 1.22-0.95 (m, 2H), 0.89-0.63 (m, 3H). LCMS (ESI): 531.20 $[M+H]^+$.

This mixture of four diastereomers was separated using Chiral Prep-HPLC.

Column: CHIRAL ART Cellulose-SC column

Column dimension: 2×2$^5$ cm, 5 μm

Mobile Phase: DCM (0.5% 2 M $NH_3$·MeOH):MeOH=50:50 hold for 12 min

Flow rate: 20 mL/min

Detection: 220/254 nm

Example 478-A and Example 478-B. The first eluting peak (70.0 mg) was obtained as a solid mixture of two diasteromers.

The first eluting peak had a retention time of 6.13 min.

LCMS (ESI): 531.25 $[M+H]^+$.

Example 478-C. The second eluting diastereomer (11.5 mg) was obtained as a solid.

The second eluting diastereomer had a retention time of 9.22 min.

$^1$H NMR (400 MHz, $CD_3OD$) δ 8.48 (s, 1H), 8.45-8.40 (m, 1H), 8.14-8.09 (m, 1H), 7.85-7.78 (m, 1H), 7.16 (s, 1H), 4.96-4.88 (m, 1H), 4.67-4.53 (m, 3H), 2.98-2.93 (m, 1H), 2.47-2.43 (m, 1H), 1.98-1.94 (m, 1H), 1.82-1.77 (m, 1H), 1.55-1.49 (m, 3H), 1.45-1.27 (m, 2H), 1.07-1.03 (m, 2H), 0.79-0.74 (m, 2H). LCMS (ESI): 531.25 $[M+H]^+$.

Example 478-D. The third eluting diastereomer (12.2 mg) was obtained as a solid.

The third eluting diastereomer had a retention time of 11.21 min.

$^1$H NMR (400 MHz, DMSO-$d_6$) δ 8.45 (s, 2H), 8.32-7.94 (m, 1H), 7.88-7.74 (m, 1H), 7.16 (s, 1H), 4.96-4.91 (m, 1H), 4.69-4.5 (m, 3H), 3.06-2.85 (m, 1H), 2.79-2.21 (m, 1H), 2.11-1.72 (m, 2H), 1.59-1.47 (m, 3H), 1.46-1.34 (m, 1H), 1.34-1.24 (m, 11H), 1.22-0.99 (m, 1H), 0.98-0.85 (m, 1H), 0.83-0.7 (m, 2H). LCMS (ESI): 531.20 $[M+H]^+$.

The first eluting peak (70.0 mg) containing two diastereomers of the title compounds was separated using Chiral Prep-HPLC.

Column: CHIRALPAK ID column

Column dimension: 2×25 cm, 5 μm

Mobile Phase: MTBE (0.5% 2M $NH_3$. MeOH):3/2 MeOH/DCM=50:50 hold for 33 min

Flow rate: 14 mL/min

Detection: 220/254 in

Example 478-A. The first eluting diastereomer (8.1 mg) was obtained as a solid.

The first eluting diastereomer had a retention time of 19.27 min.

$^1$H NMR (400 MHz, $CD_3OD$) δ 8.63-8.36 (m, 2H), 8.22-7.95 (m, 1H), 7.86-7.69 (m, 1H), 7.16 (s, 1H), 4.95-4.87 (m, 1H), 4.62-4.57 (m, 3H), 3.06-2.87 (m, 1H), 2.68-2.25 (m, 1H), 2.07-1.89 (m, 1H), 1.86-1.67 (m, 1H), 1.55-1.46 (m, 3H), 1.43-1.35 (m, 2H), 1.23-0.63 (m, 4H). LCMS (ESI): 531.25 $[M+H]^+$.

Example 478-B. The second eluting diastereomer (10.3 mg) was obtained as a solid.

The second eluting diastereomer had a retention time of 26.26 min.

$^1$H NMR (400 MHz, $CD_3OD$) δ 8.48 (s, 1H), 8.45-8.39 (m, 1H), 8.36-7.88 (m, 1H), 7.84-7.74 (m, 1H), 7.16 (s, 1H), 4.97-4.88 (m, 1H), 4.64-4.57 (m, 2H), 2.99-2.85 (m, 1H), 2.80-2.11 (m, 2H), 2.07-1.88 (m, 1H), 1.87-1.67 (m, 1H), 1.53 (s, 1H), 1.52-1.50 (m, 2H), 1.47-1.33 (m, 1H), 1.24-0.82 (m, 2H), 0.82-0.68 (m, 3H). LCMS (ESI): 531.25 $[M+H]^+$.

Example 479. A Diastereomeric Mixture of (S)-4-(5-(5-fluoro-2-methoxypyridin-4-yl)-1H-pyrazole-3-carbonyl)-N—((R)-5,6,7,8-tetrahydroimidazo[1,2-a]pyridin-8-yl)-4-azaspiro[2.5]octane-7-carboxamide and (S)-4-(5-(5-fluoro-2-methoxypyridin-4-yl)-1H-pyrazole-3-carbonyl)-N—((S)-5,6,7,8-tetrahydroimidazo[1,2-a]pyridin-8-yl)-4-azaspiro[2.5]octane-7-carboxamide

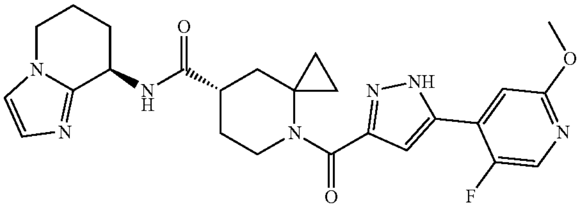

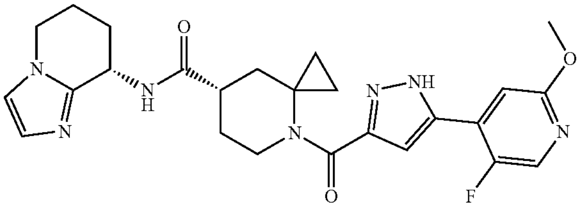

The title compound was prepared using a procedure similar to the one described for the synthesis of Example 325, except 5,6,7,8-tetrahydroimidazo[1,2-a]pyridin-8-amine dihydrochloride was used as a starting material. The residue was purified by reverse phase column chromatography (using the following conditions: Column: C18; mobile phase A: Water (0.5% $NH_4HCO_3$), mobile phase B: MeCN; gradient: 20 B to 50 B in 20 mm; 220/254 nm) to obtain (S)-4-(5-(5-fluoro-2-methoxypyridin-4-yl)-1H-pyrazole-3-carbonyl)-N—((R)-5,6,7,8-tetrahydroimidazo[1,2-a]pyridin-8-yl)-4-azaspiro[2.5]octane-7-carboxamide and (S)-4-(5-(5-fluoro-2-methoxypyridin-4-yl)-1H-pyrazole-3-carbonyl)-N—((S)-5,6,7,8-tetrahydroimidazo[1,2-a]pyridin-8-yl)-4-azaspiro[2.5]octane-7-carboxamide (154.0 mg) as a solid mixture of diasteromers (Example 479). $^1$H NMR (400 MHz, $CD_3OD$) δ 8.13 (s, 1H), 7.54-6.78 (m, 414), 5.23-5.00 (m, 1H), 4.59 (s, 1H), 4.15-3.98 (m, 2H), 3.95 (s, 3H), 2.83 (s, 1H), 2.43 (s, 1H), 2.30-1.57 (m, 6H), 1.52-1.21 (m, 2H), 1.04 (s, 1H), 0.73 (s, 3H). LCMS (ESI): 494.25 $[M+H]^+$.

This mixture of two diastereomers (154.0 mg) was separated using Chiral Prep-HPLC.

Column: ART Cellulose-SC column

Column dimension: 2×25 cm, 5 μm

Mobile Phase: 1/1 hexanes/DCM (0.5% 2 M $NH_3$·MeOH):EtOH=70:30 hold for 14 min

Flow rate: 20 mL/min

Detection: 220/254 urn

Example 479-A. The first eluting diastereomer (52.2 mg) was obtained as a solid.

The first eluting diastereomer had a retention time of 8.22 min.

$^1$H NMR (400 MHz, $CD_3OD$) δ 8.13 (s, 1H), 7.29 (s, 1H), 7.11 (s, 1H), 7.03 (d, 1H), 6.97 (d, 1H), 5.18-5.06 (m, 1H), 4.58 (s, 1H), 4.17-4.00 (m, 2H), 3.95 (s, 3H), 3.25-3.04 (m,

1H), 2.84 (s, 1H), 2.41 (s, 1H), 2.27-2.07 (m, 2H), 2.06-1.93 (m, 2H), 1.93-1.64 (m, 2H), 1.54-1.23 (m, 1H), 1.03 (s, 2H), 0.73 (s, 2H). LCMS (ESI): 494.30 $[M+H]^+$.

Example 479-B. The second eluting diastereomer (52.2 mg) was obtained as a solid.

The second eluting diastereomer had a retention time of 11.10 min.

$^1H$ NMR (400 MHz, $CD_3OD$) δ 8.14 (s, 1H), 7.29 (s, 1H), 7.12 (s, 1H), 7.03 (d, 1H), 6.97 (d, 1H), 5.18-5.03 (m, 1H), 4.63 (s, 1H), 4.16-4.01 (m, 2H), 3.95 (s, 3H), 3.24-2.99 (m, 1H), 2.84 (s, 1H), 2.47 (s, 1H), 2.26-2.09 (m, 2H), 2.08-1.98 (m, 1H), 1.96-1.63 (m, 3H), 1.54-1.36 (m, 1H), 1.06 (s, 2H), 0.73 (s, 2H). LCMS (ESI): 494.30 $[M+H]^+$.

Example 480. An Enantiomeric Mixture of (S)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide

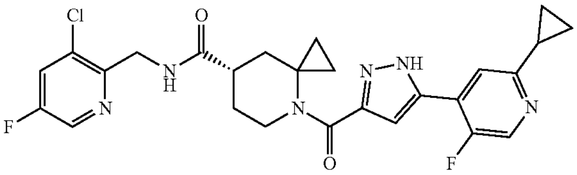

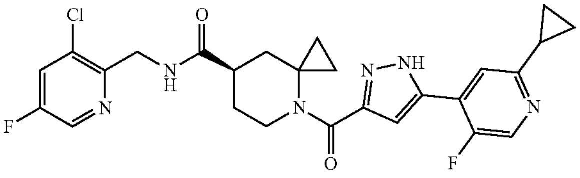

Step-1. methyl 5-(2-cyclopropyl-5-fluoropyridin-4-yl)-1-{[2-(trimethylsilyl)ethoxy]methyl}pyrazole-3-carboxylate

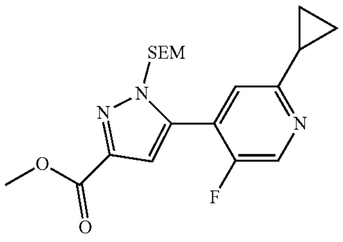 [SMILES: COC(=O)c1cc(-c2cc(C3CC3)ncc2F)n(COCC[Si](C)(C)C)n1]

Cyclopropyltrifluoro-$\lambda^4$-borane potassium (383.5 mg, 2.59 mmol), $Cs_2CO_3$ (844.3 mg, 2.59 mmol) and Pd(dppf)$Cl_2$ (189.6 mg, 0.26 mmol) were added to a stirred solution of methyl 5-(2-chloro-5-fluoropyridin-4-yl)-1-{[2-(trimethylsilyl)ethoxy]methyl}pyrazole-3-carboxylate (Step-1 from synthesis of Example 477, 500.0 mg, 1.30 mmol) in toluene (5.00 mL)/$H_2O$ (0.50 mL). The resulting mixture was stirred at 110° C. for 14 h under nitrogen atmosphere. The resulting mixture was concentrated under reduced pressure. The residue was purified by silica gel column chromatography eluting with petroleum ether/EtOAc (5/1 v/v) to obtain the title compound (236.0 mg) as an oil. LCMS (ESI): 392.2 $[M+H]^+$.

Step-2. 5-(2-cyclopropyl-5-fluoropyridin-4-yl)-1-{[2-(trimethylsilyl)ethoxy]methyl}pyrazole-3-carboxylic acid

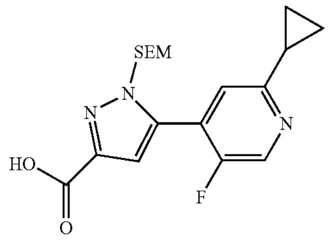 [SMILES: C[Si](C)(C)CCOCn1nc(C(=O)O)cc1-c1cc(C2CC2)ncc1F]

Lithiumol hydrate (50.6 mg, 1.21 mmol) was added to a stirred solution of methyl 5-(2-cyclopropyl-5-fluoropyridin-4-yl)-1-{[2-(trimethylsilyl)ethoxy]methyl}pyrazole-3-carboxylate (Step-1, 236.0 mg, 0.60 mmol) in THF (2.00 mL)/MeOH (2.00 mL)/$H_2O$ (2.00 mL). The resulting mixture was stirred at 25° C. for 14 h. The resulting mixture was concentrated under reduced pressure. Then the mixture was acidified to pH 3 with HCl (1 M). The aqueous layer was extracted with EtOAc. The organic layers were combined, dried over anhydrous $Na_2SO_4$, filtered, and concentrated under reduced pressure to obtain the title compound (203.0 mg) as a solid. LCMS (ESI): 378.2 $[M+H]^+$.

Step-3. methyl 4-[5-(2-cyclopropyl-5-fluoropyridin-4-yl)-1-{[2-(trimethylsilyl)ethoxy]methyl}pyrazole-3-carbonyl]-4-azaspiro[2.5]octane-7-carboxylate

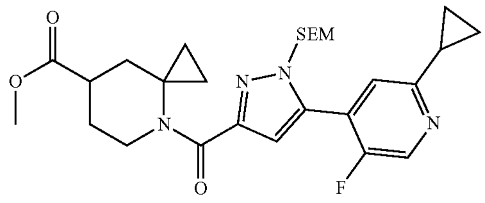 [SMILES: COC(=O)C1CCN(C(=O)c2cc(-c3cc(C4CC4)ncc3F)n(COCC[Si](C)(C)C)n2)C2(CC2)C1]

Methyl 4-azaspiro[2.5]octane-7-carboxylate (90.2 mg, 0.53 mol) HATU (193.5 mg, 0.51 mmol) were added to a stirred solution of 5-(2-cyclopropyl-5-fluoropyridin-4-yl)-1-{[2-(trimethylsilyl)ethoxy]methyl}pyrazole-3-carboxylic acid (Step-2, 183.0 mg, 0.49 mmol) and DIPEA (188.0 mg, 1.46 mmol) in DMF (3.00 mL). The resulting mixture was stirred at 25° C. for 1 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (3/1 v/v) to obtain the title compound (213.0 mg) as an oil. LCMS (ESI): 529.3 $[M+H]^+$.

Step-4. 4-[5-(2-cyclopropyl-5-fluoropyridin-4-yl)-1-{[2-(trimethylsilyl)ethoxy]methyl}pyrazole-3-carbonyl]-4-azaspiro[2.5]octane-7-carboxylic acid

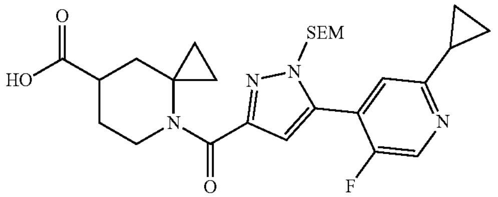 [SMILES: C[Si](C)(C)CCOCn1nc(C(=O)N2CCC(C(=O)O)CC23CC3)cc1-c1cc(C2CC2)ncc1F]

Lithiumol hydrate (33.8 mg, 0.81 mmol) was added to a stirred solution of methyl 4-[5-(2-cyclopropyl-5-fluoropyridin-4-yl)-1-{[2-(trimethylsilyl)ethoxy]methyl}pyrazole-3-carbonyl]-4-azaspiro[2.5]octane-7-carboxylate (Step-3, 213.0 mg, 0.40 mmol) in THF (2.00 mL)/MeOH (2.00 mL)/$H_2O$ (2.00 mL). The resulting mixture was stirred at 25° C. for 14 h. The resulting mixture was concentrated under reduced pressure. Then the mixture was acidified to pH 3 with HCl (1 M). The aqueous layer was extracted with EtOAc. The organic layers were combined, dried over anhydrous $Na_2SO_4$, filtered, and concentrated under reduced pressure to obtain the title compound (210.0 mg) as a solid. LCMS (ESI): 515.2 $[M+H]^+$.

Step-5. 1-(3-chloro-5-fluoropyridin-2-yl)methanamine

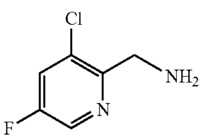

DIBAL-H (19.16 mL, 19.16 mmol) was added to a stirred solution of 3-chloro-5-fluoropyridine-2-carbonitrile (1.00 g, 6.39 mmol) in DCM (6.00 mL) at −78° C. under nitrogen atmosphere. The resulting mixture was stirred at −78° C. for 10 min under nitrogen atmosphere. The resulting mixture was concentrated under reduced pressure. The residue was purified by silica gel column chromatography eluting with DCM/MeOH (12/1 v/v) to obtain the title compound (395.0 mg) as a solid. LCMS (ESI): 161.0 $[M+H]^+$.

Step-6. N-[(3-chloro-5-fluoropyridin-2-yl)methyl]-4-[5-(2-cyclopropyl-5-fluoropyridin-4-yl)-1-{[2-(trimethylsilyl)ethoxy]methyl}pyrazole-3-carbonyl]-4-azaspiro[2.5]octane-7-carboxamide

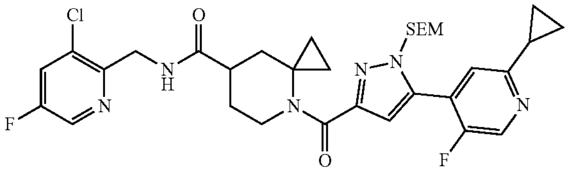 [SMILES: C[Si](C)(C)CCOCn1nc(C(=O)N2CCC(C(=O)NCc3ncc(F)cc3Cl)CC23CC3)cc1-c1cc(C2CC2)ncc1F]

HATU (168.4 mg, 0.44 mmol) and 1-(3-chloro-5-fluoropyridin-2-yl)methanamine (Step-5, 94.9 mg, 0.59 mmol) were added to a stirred solution of 4-[5-(2-cyclopropyl-5-fluoropyridin-4-yl)-1-{[2-(trimethylsilyl)ethoxy]methyl}pyrazole-3-carbonyl]-4-azaspiro[2.5]octane-7-carboxylic acid (Step-4, 190.0 mg, 0.37 mmol) and DIPEA (143.1 mg, 1.11 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (15/1 v/v) to obtain the title compound (210.0 mg) as an oil. LCMS (ESI): 657.3 [M+H]

Step-7. (S)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2,5]octane-7-carboxamide

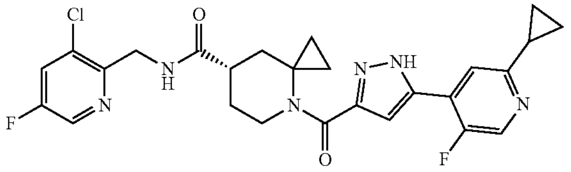

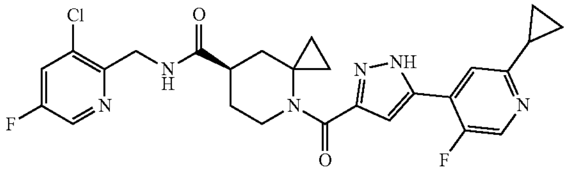

TFA (2.00 mL) was added to a stirred solution of N-[(3-chloro-5-fluoropyridin-2-yl)methyl]-4-[5-(2-cyclopropyl-5-fluoropyridin-4-yl)-1-{[2-(trimethylsilyl)ethoxy]methyl}pyrazole-3-carbonyl]-4-azaspiro[2.5]octane-7-carboxamide (210.0 mg, 0.32 mmol) in DCM (2.00 mL). The resulting mixture was stirred at 25° C. for 14 h. The resulting mixture was concentrated under reduced pressure. The residue was purified by reverse phase column chromatography (using the following conditions: Column: C18; mobile phase A: Water (0.5% $NH_4HCO_3$), mobile phase B: MeCN; gradient: 40 B to 70 B in 20 min; 220/254 nm) to obtain (S)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide (80.0 mg) as a solid mixture of enantiomers (Example 480). $^1H$ NMR (400 MHz, CD OD) δ 8.52-8.27 (m, 2H), 7.90-7.54 (m, 2H), 7.13 (s, 1H), 4.60 (s, 3H), 2.95 (s, 1H), 2.43 (s, 1H), 2.28-2.07 (m, 1H), 2.05-1.55 (m, 2H), 1.47-1.16 (m, 3H), 1.11-0.92 (m, 5H), 0.85-0.60 (m, 2H). LCMS (ESI): 527.15 $[M+H]^+$.

This mixture of two enantiomers (80.0 mg) was separated using Chiral Prep-HPLC.

Column: CHIRALPAK ID column

Column dimension: 2×25 cm, 5 μm

Mobile Phase: 3/1 hexanes/DCM (0.5% 2 M $NH_3$·MeOH):IPA=50:50 hold for 29 min

Flow rate: 14 mL/min

Detection: 220/254 nm

Example 480-A. The first eluting enantiomer (21.0 mg) was obtained as a solid.

The first eluting enantiomer had a retention time of 19.29 min.

$^1$H NMR (400 MHz, $CD_3OD$) δ 8.51-8.28 (m, 2H), 7.94-7.52 (m, 2H), 7.14 (s, 1H), 4.60 (s, 3H), 3.07-2.84 (m, 1H), 2.43 (s, 1H), 2.28-2.10 (m, 1H), 2.04-1.89 (m, 1H), 1.86-1.67 (m, 1H), 1.57-1.21 (m, 2H), 1.18-0.92 (m, 6H), 0.77 (s, 2H). LCMS (ESI): 527.20 $[M+H]^+$.

Example 480-B. The second eluting enantiomer (23.0 mg) was obtained as a solid.

The second eluting enantiomer had a retention time of 24.97 min.

$^1$H NMR (400 MHz, $CD_3OD$) δ 8.51-8.28 (m, 2H), 7.94-7.59 (m, 2H), 7.13 (s, 1H), 4.60 (s, 3H), 2.95 (s, 1H), 2.43 (s, 1H), 2.27-2.11 (m, 1H), 2.04-1.86 (m, 1H), 1.85-1.67 (m, 1H), 1.52-1.18 (m, 2H), 1.17-0.93 (m, 6H), 0.92-0.59 (m, 2H). LCMS (PSI): 527.20 $[M+H]^+$.

Example 481. A Diastereomeric Mixture of (S)-4-(5-(5-fluoro-2-methoxypyridin-4-yl)-1H-pyrazole-3-carbonyl)-N-((3-((1S,2S)-2-(hydroxymethyl)cyclopropyl)pyrazin-2-yl)methyl)-4-azaspiro[2.5]octane-7-carboxamide and (S)-4-(5-(5-fluoro-2-methoxypyridin-4-yl)-1H-pyrazole-3-carbonyl)-N-((3-((1R,2R)-2-(hydroxymethyl)cyclopropyl)pyrazin-2-yl)methyl)-4-azaspiro[2.5]octane-7-carboxamide

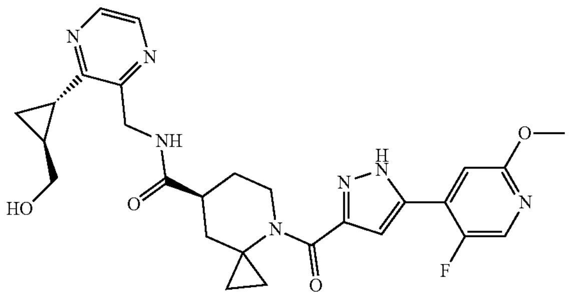

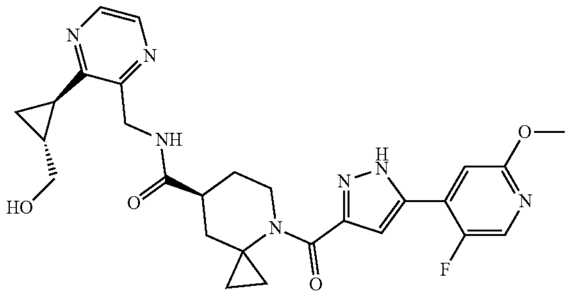

Step-1. ethyl (1S,2S)-2-(3-cyanopyrazin-2-yl)cyclopropane-1-carboxylate and ethyl (1R,2R)-2-(3-cyanopyrazin-2-yl)cyclopropane-1-carboxylate

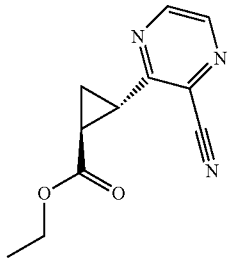

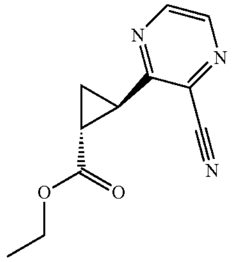

Pd(dppf)$Cl_2$ (366.0 mg, 0.50 mmol) and $Cs_2CO_3$ (1.63 g, 5.00 mmol) were added to a mixture of 3-bromopyrazine-2-carbonitrile (460.0 mg, 2.50 mmol) and (1S,2S)-2-(trifluoro-$\lambda^4$-boranyl)cyclopropane-1-carboxylate potassium (825.0 mg, 3.75 mmol) in toluene (10.00 mL) and $H_2O$ (1.00 mL). The resulting mixture was stirred at 25° C. for 30 min and heated to 110° C. for 14 h. The resulting mixture was concentrated under reduced pressure. The residue was purified by silica gel column chromatography eluting with petroleum ether/EtOAc (1/1 v/v) to obtain the title compound (410.0 mg) as a solid. LCMS (ESI): 218 $[M+H]^+$.

Step-2. ethyl (1S,2S)-2-(3-(aminomethyl)pyrazin-2-yl)cyclopropane-1-carboxylate and ethyl (1R,2R)-2-(3-(aminomethyl)pyrazin-2-yl)cyclopropane-1-carboxylate

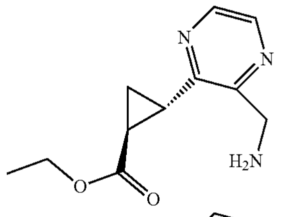

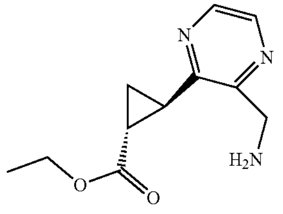

Pd/C (54.0 mg) was added to a mixture of ethyl (1S,2S)-2-(3-cyanopyrazin-2-yl)cyclopropane-1-carboxylate and ethyl (1R,2R)-2-(3-cyanopyrazin-2-yl)cyclopropane-1-carboxylate (Step-1, 270.0 mg, 1.24 mmol) and AcOH (0.50 mL) in EtOH (5.00 mL). The resulting mixture was stirred at 25° C. for 14 h under hydrogen pressure. The resulting mixture was filtered, the filter cake was washed with EtOH. The filtrate was concentrated under reduced pressure to obtain the title compound (70.0 mg) as a solid. LCMS (ESI): 222 $[M+H]^+$.

Step-3. ethyl (1S,2S)-2-(3-(((S)-4-(5-(5-fluoro-2-methoxypyridin-4-yl)-1H-pyrazole-3-carbonyl)-4-azaspiro[2.5]octane-7-carboxamido)methyl)pyrazin-2-yl)cyclopropane-1-carboxylate and ethyl (1R,2R)-2-(3-(((S)-4-(5-(5-fluoro-2-methoxypyridin-4-yl)-1H-pyrazole-3-carbonyl)-4-azaspiro[2.5]octane-7-carboxamido)methyl)pyrazin-2-yl)cyclopropane-1-carboxylate

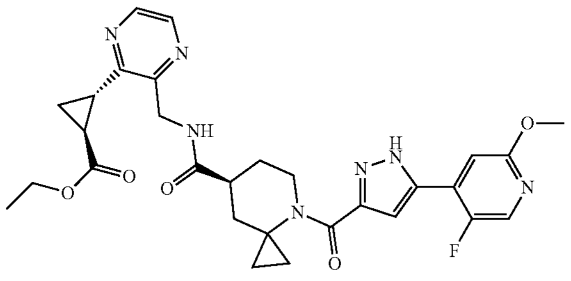

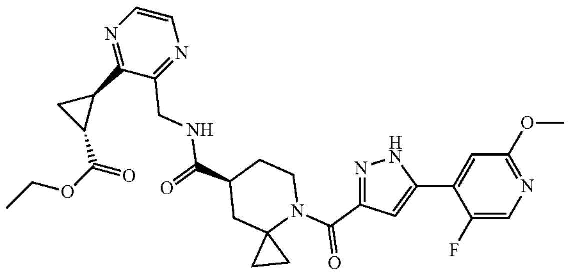

EDCI (131.0 mg, 0.68 mmol), HOBt (92.0 mg, 0.68 mmol), and ethyl (1S,2S)-2-(3-(aminomethyl)pyrazin-2-yl) cyclopropane-1-carboxylate and ethyl (1R,2R)-2-(3-(aminomethyl)pyrazin-2-yl)cyclopropane-1-carboxylate (Step-2, 151.0 mg, 0.68 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 170.0 mg, 0.45 mmol) and DIPEA (293.4 mg, 2.27 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (210.0 mg) as a solid. LCMS (ESI): 578 $[M+H]^+$.

Step-4. (S)-4-(5-(5-fluoro-2-methoxypyridin-4-yl)-1H-pyrazole-3-carbonyl)-N-((3-((1S,2S)-2-(hydroxymethyl)cyclopropyl)pyrazin-2-yl)methyl)-4-azaspiro[2.5]octane-7-carboxamide and (S)-4-(5-(5-fluoro-2-methoxypyridin-4-yl)-1H-pyrazole-3-carbonyl)-N-((3-((1R,2R)-2-(hydroxymethyl) cyclopropyl)pyrazin-2-yl)methyl)-4-azaspiro[2.5] octane-7-carboxamide

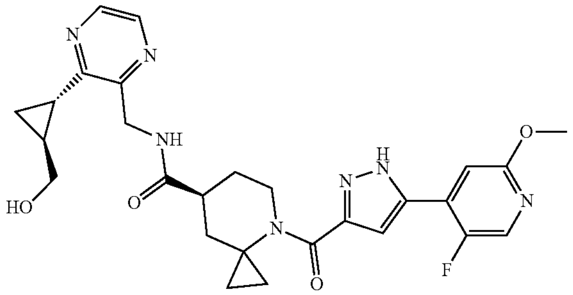

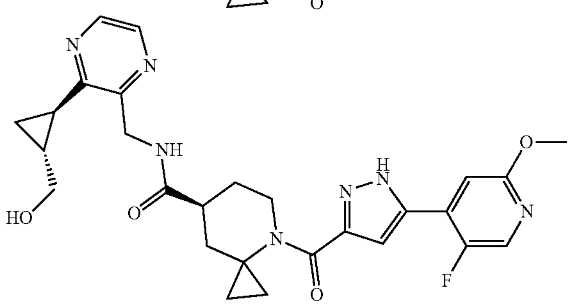

$LiAlH_4$ (0.33 mL, 0.33 mmol) was added to a mixture of ethyl (1S,2S)-2-(3-(((S)-4-(5-(5-fluoro-2-methoxypyridin-4-yl)-1H-pyrazole-3-carbonyl)-4-azaspiro[2.5]octane-7-carboxamido)methyl)pyrazin-2-yl)cyclopropane-1-carboxylate and ethyl (1R,2R)-2-(3-(((S)-4-(5-(5-fluoro-2-methoxypyridin-4-yl)-1H-pyrazole-3-carbonyl)-4-azaspiro[2.5]octane-7-carboxamido)methyl)pyrazin-2-yl)cyclopropane-1-carboxylate (Step-3, 190.0 mg, 0.33 mmol) in THF (5.00 mL) at 0° C. under nitrogen atmosphere. The resulting mixture was stirred at 0° C. for 2 h under nitrogen atmosphere. The reaction was quenched with MeOH at 0° C. The resulting mixture was concentrated under reduced pressure. The residue was purified by silica gel column chromatography eluting with DCM/MeOH (10/1 v/v) to obtain (S)-4-(5-(5-fluoro-2-methoxypyridin-4-yl)-1H-pyrazole-3-carbonyl)-N-((3-((1S,2)-2-(hydroxymethyl)cyclopropyl)pyrazin-2-yl) methyl)-4-azaspiro[2.5]octane-7-carboxamide and (S)-4-(5-(5-fluoro-2-methoxypyridin-4-yl)-1H-pyrazole-3-carbonyl)-N-((3-((1R,2R)-2-(hydroxymethyl)cyclopropyl) pyrazin-2-yl)methyl)-4-azaspiro[2.5]octane-7-carboxamide (100.0 mg) as a solid mixture of diastereomers (Example 481). $^1H$ NMR (400 MHz, DMSO-$d_6$) δ 13.99 (s, 1H), 8.52-8.16 (m, 4H), 7.33 (d, 1H), 7.03 (s, 1H), 4.76-4.35 (m, 4H), 3.88 (s, 3H), 3.57-3.50 (m, 1H), 3.42-3.33 (m, 1H), 3.29-3.05 (m, 1H), 2.83-2.78 (m, 2H), 2.18-2.08 (m, 3H), 1.83-1.78 (m, 1H), 1.60-1.52 (m, 2H), 1.26-1.15 (m, 1H), 1.01-0.93 (m, 2H), 0.66-0.62 (m, 2H). LCMS (ESI): 536.45 $[M+H]^+$.

This mixture of two diastereomers (100.0 mg) was separated using Chiral Prep-HPLC.

Column: CHIRALPAK IG column

Column dimension: 2×25 cm, 5 μm

Mobile Phase: 1/1 hexanes/DCM (0.5% 2 M $NH_3$·MeOH):EtOH=50:50 hold for 21 min

Flow rate: 17 mL/min

Detection: 220/254 nm

Example 481-A. The first eluting diastereomer (14.2 mg) was obtained as a solid.

The first eluting diastereomer had a retention time of 10.63 min.

$^1$H NMR (400 MHz, DMSO-$d_6$) δ 13.98 (s, 1H), 8.50-8.14 (m, 4H), 7.32 (d, 1H), 7.03 (s, 1H), 4.66-4.51 (m, 3H), 4.50-4.45 (m, 1H), 3.88 (s, 3H), 3.59-3.51 (m, 1H), 3.32-3.27 (m, 1H), 2.83-2.78 (m, 2H), 2.16-2.11 (m, 1H), 1.82-1.77 (m, 1H), 1.59-1.54 (m, 2H), 1.32-1.22 (m, 2H), 1.22-1.12 (m, 1H), 1.08-0.79 (m, 3H), 0.66-0.62 (m, 2H). LCMS (ESI): 536.20 $[M+H]^+$.

Example 481-B. The second eluting diastereomer (12.9 mg) was obtained as a solid.

The second eluting diastereomer had a retention time of 16.73 min.

$^1$H NMR (400 MHz, DMSO-$d_6$) δ 13.99 (s, 1H), 8.50-8.16 (m, 4H), 7.33 (d, 1H), 7.03 (s, 1H), 4.67-4.52 (m, 3H), 4.48-4.43 (m, 1H), 3.88 (s, 3H), 3.57-3.50 (m, 1H), 3.40-3.33 (m, 1H), 2.83-2.78 (m, 1H), 2.35-2.06 (m, 2H), 1.83-1.78 (m, 1H), 1.60-1.52 (m, 2H), 1.26-1.15 (m, 3H), 1.01-0.93 (m, 3H), 0.66-0.62 (m, 2H). LCMS (ESI): 536.20 $[M+H]^+$.

Example 482. (S)—N-((2-((3S,5R)-3,5-dimethylpiperazin-1-yl)-5-(trifluoromethyl)oxazol-4-yl)methyl)-4-(5-(5-fluoro-2-methoxypyridin-4-yl)-1H-pyrazole-3-carbonyl)-4-azaspiro[2.5]octane-7-carboxamide

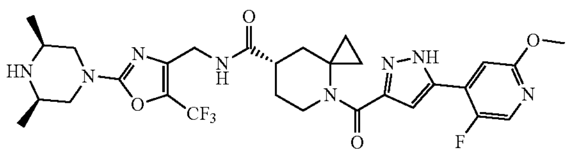

Step-1. ethyl 5-(trifluoromethyl)-1,3-oxazole-4-carboxylate

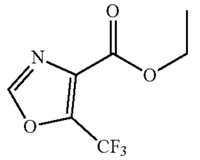

Trifluoroacetic anhydride (11.14 g, 53.04 mmol) was added to a stirred solution of ethyl 2-isocyanoacetate (5.00 g, 44.20 mmol) and DBU (8.08 g, 53.04 mmol) in THF (10.00 mL) at 0° C. The resulting mixture was stirred at 25° C. for 14 h. The resulting mixture was diluted with DCM and washed with of HCl (1 M). The organic layers were combined, dried over anhydrous $Na_2SO_4$, filtered, and concentrated under reduced pressure. The residue was purified by silica gel column chromatography eluting with DCM/EtOAc (10/1 v/v) to obtain the title compound (2.44 g) as an oil. LCMS (ESI): 210.0 $[M+H]^+$.

Step-2. ethyl 2-iodo-5-(trifluoromethyl)-1,3-oxazole-4-carboxylate

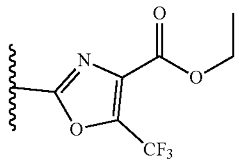 [SMILES: *c1nc(C(=O)OCC)c(C(F)(F)F)o1]

LiHMDS (7.89 mL, 7.89 mmol) was added to a stirred solution of ethyl 5-(trifluoromethyl)-1,3-oxazole-4-carboxylate (Step-1, 1.10 g, 5.26 mmol) in THF (10.00 mL) at −78° C. under the atmosphere of nitrogen. The resulting mixture was stirred at −78° C. for 30 min under the atmosphere of nitrogen. Then 12 (1.60 g, 6.31 mmol) was added to the resulting mixture at −78° C. The resulting mixture was stirred at −78° C. for 1 h under the atmosphere of nitrogen. The resulting mixture was concentrated under reduced pressure. The residue was purified by silica gel column chromatography eluting with petroleum ether/EtOAc (4/1 v/v) to obtain the title compound (850.0 mg) as a solid. LCMS (ESI): 335.9 $[M+H]^+$.

Step-3. methyl tert-butyl (2R,6S)-4-[4-(ethoxycarbonyl)-5-(trifluoromethyl)-1,3-oxazol-2-yl]-2,6-dimethylpiperazine-1-carboxylate

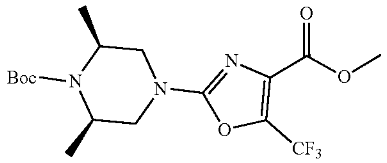 [SMILES: COC(=O)c1nc(N2C[C@@H](C)N(C(=O)OC(C)(C)C)[C@@H](C)C2)oc1C(F)(F)F]

Tert-butyl (2R,6S)-2,6-dimethylpiperazine-1-carboxylate (543.7 mg, 2.54 mmol) and $Cs_2CO_3$ (1.65 g, 5.07 mmol) were added to a stirred solution of ethyl 2-iodo-5-(trifluoromethyl)-1,3-oxazole-4-carboxylate (Step-2, 850.0 mg, 2.54 mmol) in 1,4-dioxane (5.00 mL). The resulting mixture was stirred at 90° C. for 3 h under the atmosphere of nitrogen. The resulting mixture was concentrated under reduced pressure. The residue was purified by silica gel column chromatography eluting with petroleum ether/EtOAc (2/1 v/v) to obtain the title compound (648.0 mg) as an oil. LCMS (ESI): 408.2 $[M+H]^+$.

Step-4. 2-[(3R,5S)-4-(tert-butoxycarbonyl)-3,5-dimethylpiperazin-1-yl]-5-(trifluoromethyl)-1,3-oxazole-4-carboxylic acid

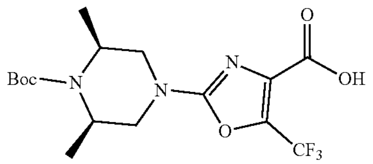 [SMILES: C[C@@H]1CN(c2nc(C(=O)O)c(C(F)(F)F)o2)C[C@H](C)N1C(=O)OC(C)(C)C]

Lithium hydroxide (135.4 mg, 3.23 mmol) was added to a stirred solution of tert-butyl (2R,6S)-4-[4-(ethoxycarbonyl)-5-(trifluoromethyl)-1,3-oxazol-2-yl]-2,6-dimethylpiperazine-1-carboxylate (Step-3, 680.0 mg, 1.61 mmol) in THF (2.00 mL)/MeOH (2.00 mL)/$H_2O$ (2.00 mL). The resulting mixture was stirred at 25° C. for 1 h. The resulting mixture was concentrated under reduced pressure. Then the mixture was acidified to pH 3 with HCl (1.2 M). The aqueous layer was extracted with EtOAc. The organic layers were combined, dried over anhydrous $Na_2SO_4$, filtered, and concentrated under reduced pressure to obtain the title compound (622.0 mg) as a solid. LCMS (ESI): 394.2 $[M+H]^+$.

Step-5. tert-butyl (2R,6S)-4-[4-(hydroxymethyl)-5-(trifluoromethyl)-1,3-oxazol-2-yl]-2,6-dimethylpiperazine-1-carboxylate

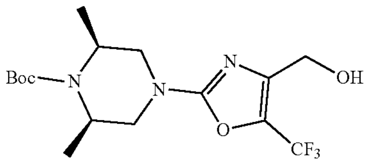 [SMILES: C[C@@H]1CN(c2nc(CO)c(C(F)(F)F)o2)C[C@H](C)N1C(=O)OC(C)(C)C]

2-Methylpropyl carbonochloridate (78.1 mg, 0.57 mmol) and N-methylmorpholine (57.9 mg, 0.57 mmol) were added to a stirred solution of 2-[(3R,5S)-4-(tert-butoxycarbonyl)-3,5-dimethylpiperazin-1-yl]-5-(trifluoromethyl)-1,3-oxazole-4-carboxylic acid (Step-4, 150.0 mg, 0.38 mmol) in DME (3.00 mL) at 0° C. The resulting mixture was stirred at 0° C. for 30 min. The resulting mixture was filtered, the filter cake was washed with DME. Then a solution of $NaBH_4$ (28.9 mg, 0.76 mmol) in $H_2O$ (1.00 mL) was added to the above resulting solution at 0° C. The resulting mixture was stirred at 0° C. for 30 min. The resulting mixture was concentrated under reduced pressure. The residue was purified by silica gel column chromatography eluting with DCM/MeOH (15/1 v/v) to obtain the title compound (139.0 mg) of tert-butyl (2R,6S)-4-[4-(hydroxymethyl)-5-(trifluoromethyl)-1,3-oxazol-2-yl]-2,6-dimethylpiperazine-1-carboxylate as a light yellow oil. LCMS (ESI): 380.2 $[M+H]^+$.

Step-6. tert-butyl (2R,6S)-4-[4-(azidomethyl)-5-(trifluoromethyl)-1,3-oxazol-2-yl]-2,6-dimethylpiperazine-1-carboxylate

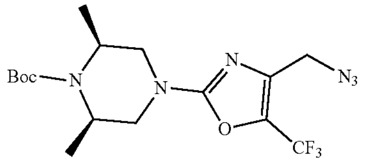 [SMILES: C[C@@H]1CN(c2nc(CN=[N+]=[N-])c(C(F)(F)F)o2)C[C@H](C)N1C(=O)OC(C)(C)C]

DBU (103.5 mg, 0.68 mmol) and DPPA (187.2 mg, 0.68 mmol) were added dropwise to a stirred solution of tert-butyl (2R,6S)-4-[4-(hydroxymethyl)-5-(trifluoromethyl)-1,3-oxazol-2-yl]-2,6-dimethylpiperazine-1-carboxylate (Step-5, 129.0 mg, 0.34 mmol) in THF (5.00 mL) at 0° C. The resulting mixture was stirred at 0° C. for 5 min and stirred at 25° C. for 14 h. The resulting mixture was concentrated under reduced pressure. The residue was purified by silica gel column chromatography eluting with petroleum ether/EtOAc (3/1 v/v) to obtain the title compound (135.0 mg) as an oil. LCMS (ESI): 405.2 $[M+H]^+$.

Step-7. tert-butyl (2R,6S)-4-[4-(aminomethyl)-5-(trifluoromethyl)-1,3-oxazol-2-yl]-2,6-dimethylpiperazine-1-carboxylate

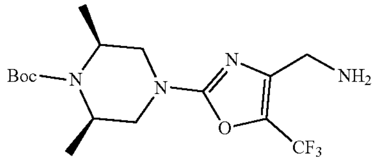 [SMILES: C[C@@H]1CN(c2nc(CN)c(C(F)(F)F)o2)C[C@H](C)N1C(=O)OC(C)(C)C]

Pd/C (25.0 mg) was added to a stirred solution of tert-butyl (2R,6S)-4-[4-(azidomethyl)-5-(trifluoromethyl)-1,3-oxazol-2-yl]-2,6-dimethylpiperazine-1-carboxylate (Step-6, 121.0 mg, 0.30 mmol) in MeOH (3.00 mL). The resulting mixture was stirred at 25° C. for 3 h under the atmosphere of hydrogen. The resulting mixture was filtered, the filter cake was washed with MeOH. The filtrate was concentrated under reduced pressure to obtain the title compound (83.0 mg) as an oil. LCMS (ESI): 379.2 $[M+H]^+$.

Step-8. tert-butyl (2R,6S)-4-[4-({[(7S)-4-[5-(5-fluoro-2-methoxypyridin-4-yl)-1H-pyrazole-3-carbonyl]-4-azaspiro[2.5]octan-7-yl]formamido}methyl)-5-(trifluoromethyl)-1,3-oxazol-2-yl]-2,6-dimethylpiperazine-1-carboxylate

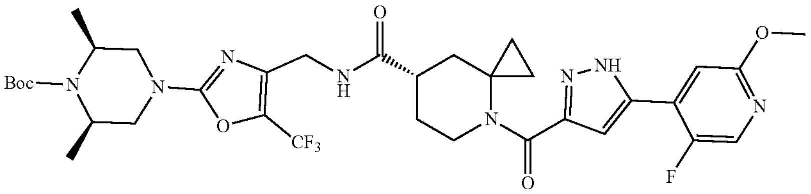 [SMILES: COc1cc(-c2cc(C(=O)N3CC[C@H](C(=O)NCc4nc(N5C[C@@H](C)N(C(=O)OC(C)(C)C)[C@@H](C)C5)oc4C(F)(F)F)CC34CC4)n[nH]2)c(F)cn1]

Tert-butyl (2R,6S)-4-[4-(aminomethyl)-5-(trifluoromethyl)-1,3-oxazol-2-yl]-2,6-dimethylpiperazine-1-carboxylate (Step-7, 63.2 mg, 0.17 mmol) and $T_3P$ (132.8 mg, 0.21 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 52.1 mg, 0.14 mmol) and TEA (84.5 mg, 0.83 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (68.0 mg) as an oil. LCMS (ESI): 735.3 $[M+H]^+$.

Step-9. (7S)—N-({2-[(3R,5S)-3,5-dimethylpiperazin-1-yl]-5-(trifluoromethyl)-1,3-oxazol-4-yl}methyl)-4-[5-(5-fluoro-2-methoxypyridin-4-yl)-1H-pyrazole-3-carbonyl]-4-azaspiro[2.5]octane-7-carboxamide

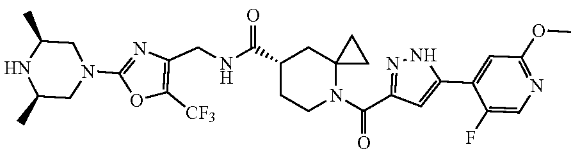

TFA (1.00 mL) was added to a stirred solution of tert-butyl (2R,6S)-4-[4-({[(7S)-4-[5-(5-fluoro-2-methoxypyridin-4-yl)-1H-pyrazole-3-carbonyl]-4-azaspiro[2.5]octan-7-yl]formamido}methyl)-5-(trifluoromethyl)-1,3-oxazol-2-yl]-2,6-dimethylpiperazine-1-carboxylate (Step-8, 60.0 mg, 0.08 mmol) in DCM (1.00 mL). The resulting mixture was stirred at 25° C. for 1 h. The resulting mixture was concentrated under reduced pressure. The residue was purified by reverse phase column chromatography (using the following conditions: Column: C18; mobile phase A: Water (0.5% $NH_4HCO_3$), mobile phase 3: MeCN; gradient: 30 B to 50 B in 20 min; 220/254 nm) to obtain the title compound (28.0 mg) as a solid. $^1H$ NMR (400 MHz, $CD_3OD$) δ 8.17-8.09 (m, 1H), 7.29 (d, 1H), 7.16-7.05 (m, 1H), 4.72-4.40 (m, 1H), 4.41-4.20 (m, 1H), 4.01-3.87 (m, 5H), 3.10-2.78 (m, 4H), 2.74-2.58 (m, 2H), 2.57-2.31 (m, 1H), 1.98-1.62 (m, 2H), 1.46-1.26 (m, 2H), 1.20-1.07 (m, 6H), 1.05-0.83 (m, 2H), 0.83-0.63 (m, 2H). LCMS (ESI): 635.25 $[M+H]^+$.

Example 483. An enantiomeric mixture of (S)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(2-ethyl-5-fluoropyridin-4-yl)-H-pyrazole-3-carbonyl)-4-azaspiro[2.5]octane-7-carboxamide

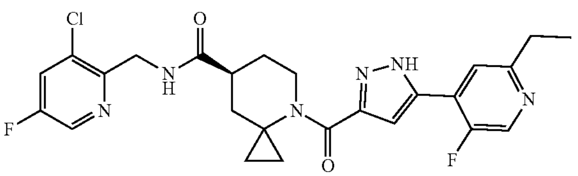

-continued

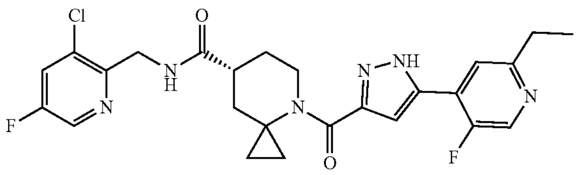

Step-1. methyl 5-(2-ethenyl-5-fluoropyridin-4-yl)-1-{[2-(trimethylsilyl)ethoxy]methyl}pyrazole-3-carboxylate

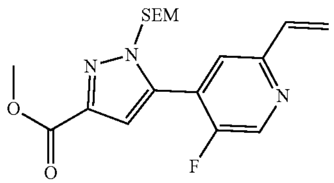 [SMILES: C=Cc1cc(-c2cc(C(=O)OC)nn2COCC[Si](C)(C)C)c(F)cn1]

2-ethenyl-4,4,5,5-tetramethyl-1,3,2-dioxaborolane (135.7 mg, 0.88 mmol), $K_3PO_4$ (187.0 mg, 0.88 mmol) and $Pd(dppf)Cl_2$ (64.5 mg, 0.09 mmol) were added to a stirred solution of methyl 5-(2-chloro-5-fluoropyridin-4-yl)-1-{[2-(trimethylsilyl)ethoxy]methyl}pyrazole-3-carboxylate (Step-1 from synthesis of Example 477, 170.0 mg, 0.44 mmol) in 1,4-dioxane (3.00 mL)/$H_2O$ (0.30 mL). The resulting mixture was stirred at 90° C. for 14 h under the atmosphere of nitrogen. The resulting mixture was filtered, the filter cake was washed with DCM. The filtrate was concentrated under reduced pressure. The residue was purified by silica gel column chromatography eluting with petroleum ether/EtOAc (5/1 v/v) to obtain the title compound (158.0 mg) as an oil. LCMS (ESI): 378.2 $[M+H]^+$.

Step-2. methyl 5-(2-ethyl-5-fluoropyridin-4-yl)-1-{[2-(trimethylsilyl)ethoxy]methyl}pyrazole-3-carboxylate

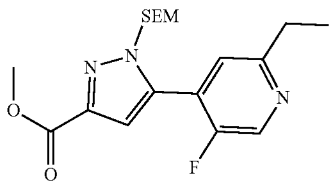 [SMILES: CCc1cc(-c2cc(C(=O)OC)nn2COCC[Si](C)(C)C)c(F)cn1]

Pd/C (55.0 mg, 0.52 mmol) was added to a stirred solution of methyl 5-(2-ethenyl-5-fluoropyridin-4-yl)-1-{[2-(trimethylsilyl)ethoxy]methyl}pyrazole-3-carboxylate (158.0 mg, 0.42 mmol) in MeOH (2.00 mL). The resulting mixture was stirred at 25° C. for 3 h under the atmosphere of hydrogen. The resulting mixture was filtered, the filter cake was washed with MeOH. The filtrate was concentrated under reduced pressure to obtain the title compound as an oil. The residue was used directly without further purification. LCMS (ESI): 380.2 $[M+H]^+$.

Step-3. 5-(2-ethyl-5-fluoropyridin-4-yl)-1-{[2-(trimethylsilyl)ethoxy]methyl}pyrazole-3-carboxylic acid

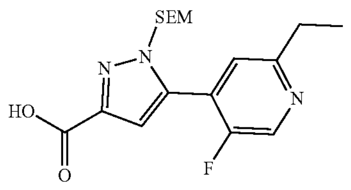 [SMILES: CCc1cc(-c2cc(C(=O)O)nn2COCC[Si](C)(C)C)c(F)cn1]

Lithium hydroxide (30.1 mg, 0.72 mmol) was added to a stirred solution of methyl 5-(2-ethyl-5-fluoropyridin-4-yl)-1-{[2-(trimethylsilyl)ethoxy]methyl}pyrazole-3-carboxylate (Step-2, 136.0 mg, 0.36 mmol) in MeOH (1.00 mL)/THF (1.00 mL)/$H_2O$ (1.00 mL). The resulting mixture was stirred at 25° C. for 14 h. The resulting mixture was concentrated under reduced pressure. The residue was acidified to pH 3 with HG (1 M). The aqueous layer was extracted with EtOAc. The organic layers were combined, dried over anhydrous $Na_2SO_4$, filtered, and concentrated under reduced pressure to obtain the title compound (130.0 mg) as a solid. LCMS (ESI): 366.2 $[M+H]^+$.

Step-4. methyl 4-[5-(2-ethyl-5-fluoropyridin-4-yl)-1-{[2-(trimethylsilyl)ethoxy]methyl}pyrazole-3-carbonyl]-4-azaspiro[2.5]octane-7-carboxylate

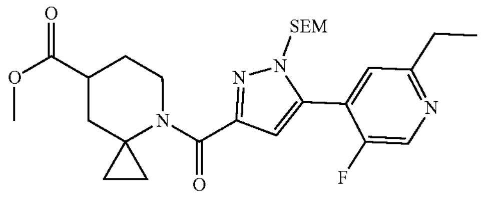 [SMILES: CCc1cc(-c2cc(C(=O)N3CCC(C(=O)OC)CC34CC4)nn2COCC[Si](C)(C)C)c(F)cn1]

Methyl 4-azaspiro[2.5]octane-7-carboxylate (77.8 mg, 0.46 mmol) and HATU (174.8 mg, 0.46 mmol, 1.20 equiv) were added to a stirred solution of 5-(2-ethyl-5-fluoropyridin-4-yl)-1-{[2-(trimethylsilyl)ethoxy]methyl}pyrazole-3-carboxylic acid (Step-3, 140.0 mg, 0.38 mmol) and DIPEA (148.5 mg, 1.15 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (1/1 v/v) to obtain the title compound (137.0 mg) as an oil. LCMS (ESI): 517.3 $[M+H]^+$.

Step-5. 4-[5-(2-ethyl-5-fluoropyridin-4-yl)-1-{[2-(trimethylsilyl)ethoxy]methyl}pyrazole-3-carbonyl]-4-azaspiro[2.5]octane-7-carboxylic acid

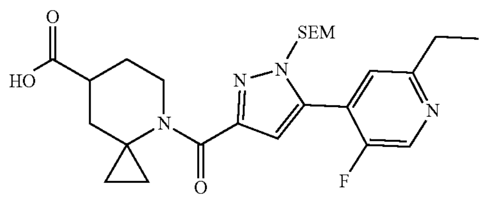 [SMILES: CCc1cc(-c2cc(C(=O)N3CCC(C(=O)O)CC34CC4)nn2COCC[Si](C)(C)C)c(F)cn1]

LiOH·$H_2O$ (22.3 mg, 0.53 mmol) was added to a stirred solution of methyl 4-[5-(2-ethyl-5-fluoropyridin-4-yl)-1-{[2-(trimethylsilyl)ethoxy]methyl}pyrazole-3-carbonyl]-4-azaspiro[2.5]octane-7-carboxylate (Step-4, 137.0 mg, 0.27 mmol) in MeOH (1.00 mL)/THF (1.00 mL)/$H_2O$ (1.00 mL). The resulting mixture was stirred at 25° C. for 1 h. The resulting mixture was concentrated under reduced pressure, then acidified to pH 3 with HCl (1 M). The aqueous layer was extracted with EtOAc. The organic layers were combined, dried over anhydrous $Na_2SO_4$, filtered, and concentrated under reduced pressure to obtain the title compound (130.0 mg) as an oil. LCMS (ESI): 503.2 $[M+H]^+$.

Step-6. N-[(3-chloro-5-fluoropyridin-2-yl)methyl]-4-[5-(2-ethyl-5-fluoropyridin-4-yl)-1-{[2-(trimethylsilyl)ethoxy]methyl}pyrazole-3-carbonyl]-4-azaspiro[2.5]octane-7-carboxamide

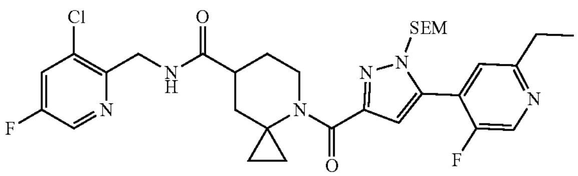 [SMILES: CCc1cc(-c2cc(C(=O)N3CCC(C(=O)NCc4ncc(F)cc4Cl)CC34CC4)nn2COCC[Si](C)(C)C)c(F)cn1]

1-(3-chloro-5-fluoropyridin-2-yl)methanamine (57.5 mg, 0.36 mmol) and HATU (95.3 mg, 0.25 mmol) were added to a stirred solution of 4-[5-(2-ethyl-5-fluoropyridin-4-yl)-1-{[2-(trimethylsilyl)ethoxy]methyl}pyrazole-3-carbonyl]-4-azaspiro[2.5]octane-7-carboxylic acid (Step-5, 120.0 mg, 0.24 mmol) and DIPEA (92.6 mg, 0.72 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (15/1 v/v) to obtain the title compound (122.0 mg) as a solid. LCMS (ESI): 645.3 $[M+H]^+$.

Step-7. (S)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide

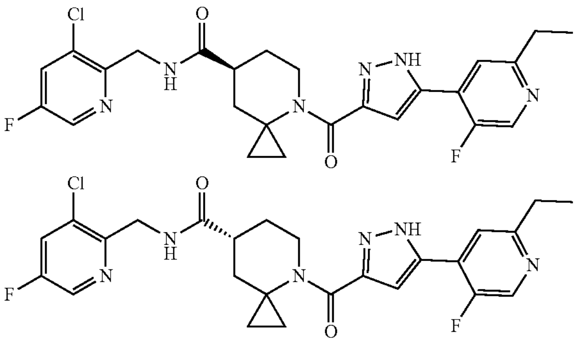

TFA (2.00 mL) was added to a stirred solution of N-[(3-chloro-5-fluoropyridin-2-yl)methyl]-4-[5-(2-ethyl-5-fluoro-pyridin-4-yl)-1-{[2-(trimethylsilyl)ethoxy]methyl}pyrazole-3-carbonyl]-4-azaspiro[2.5]octane-7-carboxamide (Step-6, 112.0 mg, 0.17 mmol) in DCM (2.00 mL). The resulting mixture was stirred at 25° C. for 2 h. The resulting mixture was concentrated under reduced pressure. The residue was purified by reverse phase column chromatography (using the following conditions: Column: C18; mobile phase A: Water (0.5% $NH_4CO_3$), mobile phase B: MeCN; gradient: 20 B to 50 B in 30 min; 220/254 nm) to obtain (S)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide and (R)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide (44.1 mg) as a solid mixture of enantiomers (Example 483). $^1H$ NMR (400 MHz, $CD_3OD$) δ 8.50-8.39 (m, 2H), 7.97-7.70 (m, 2H), 7.16 (s, 1H), 4.60 (s, 3H), 3.08-2.73 (m, 3H), 2.43 (s, 1H), 2.16-1.63 (m, 2H), 1.58-1.26 (m, 4H), 1.20-0.95 (m, 2H), 0.76 (m, 3H). LCMS (ESI): 515.15 $[M+H]^+$.

This mixture of two diastereomers (42.0 mg) was separated using Chiral Prep-HPLC.

Column: CHIRALPAK ART Amylose-SA column

Column dimension: 2×25 cm, 5 μm

Mobile Phase: 3/1 hexanes/DCM (0.5% 2 M $NH_3$·MeOH):EtOH=50:50 hold for 13 min

Flow rate: 20 mL/min

Detection: 220/254 nm

Example 483-A. The first eluting diastereomer (11.4 mg) was obtained as a solid.

The first eluting diastereomer had a retention time of 6.64 min.

$^1H$ NMR (400 MHz, $CD_3OD$) δ 8.53-8.29 (m, 2H), 8.10-7.52 (m, 21), 7.16 (s, 1H), 4.60 (s, 3H), 3.04-2.77 (m, 3H), 2.43 (s, 1H), 2.23-1.65 (m, 2H), 1.52-1.27 (m, 4H), 1.06 (s, 2H), 0.77 (s, 3H). LCMS (ESI): 515.20 $[M+H]^+$.

Example 483-B. The second eluting diastereomer (11.2 mg) was obtained as a solid.

The second eluting diastereomer had a retention time of 10.61 min.

$^1H$ NMR (400 MHz, $CD_3OD$) δ 8.56-8.35 (m, 2H), 8.04-7.62 (m, 2H), 7.16 (s, 1H), 4.60 (s, 3H), 3.02-2.76 (m, 3H), 2.43 (s, 1H), 2.05-1.64 (m, 2H), 1.48-1.23 (m, 4H), 1.22-0.95 (m, 2H), 0.76 (s, 3H). LCMS (ESI): 515.10 $[M+H]^+$.

Example 484. An enantiomeric mixture of (S)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide and (R)—N((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide

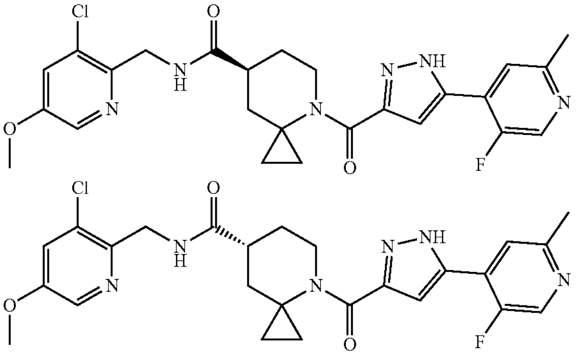

Step-1. 3-chloro-5-methoxypyridine-2-carbonitrile

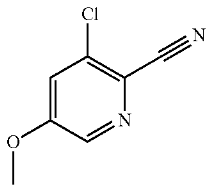

Sodium methoxide (259.0 mg, 4.79 mmol) was added to a mixture of 3-chloro-5-fluoropyridine-2-carbonitrile (500.0 mg, 3.19 mmol) in MeOH (5.00 mL). The resulting mixture was stirred at 25° C. for 4 h. The resulting mixture was concentrated under reduced pressure. The residue was purified by silica gel column chromatography eluting with petroleum ether/EtOAc (3/1 v/v) to obtain (420.0 mg) as a solid. LCMS (ESI): 169 $[M+H]^+$.

Step-2. 1-(3-chloro-5-methoxypyridin-2-yl)methanamine

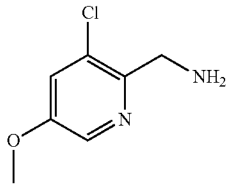

DIBAL-H (8.30 mL, 8.30 mmol) was added to a mixture of 3-chloro-5-methoxypyridine-2-carbonitrile (Step-1, 200.0 mg, 1.19 mmol) in DCM (5.00 mL) at −78° C. The resulting mixture was stirred at −78° C. for 1 h under nitrogen atmosphere. The reaction was quenched with MeOH at −78° C. The resulting mixture was concentrated under reduced pressure. The residue was purified by silica gel column chromatography eluting with DCM/MeOH (7/1 v/v) to obtain the title compound (170.0 mg) as a solid. LCMS (ESI): 173 [M+H]+.

Step-3. (S)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide and (R)—N-((3-chloro-5-methoxypyridin-2-yl)methyl)-4-(5-(5-fluoro-2-methylpyridin-4-yl)-1H-pyrazole-3-carbonyl)-4-azaspiro[2,5]octane-7-carboxamide

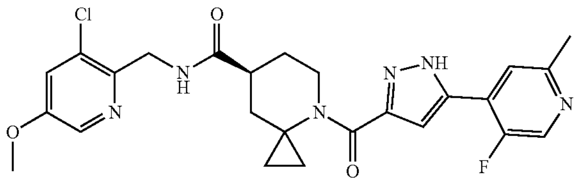

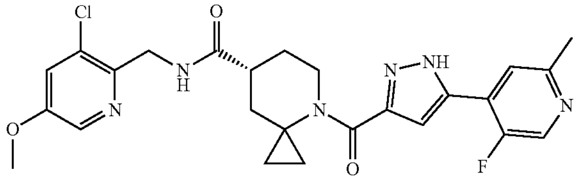

EDCI (120.0 mg, 0.63 mmol), HOBt (85.0 mg, 0.63 mmol), and 1-(3-chloro-5-methoxypyridin-2-yl)methanamine (Step-2, 108.0 mg, 0.63 mmol) were added to a mixture of 4-[5-(5-fluoro-2-methylpyridin-4-yl)-1H-pyrazole-3-carbonyl]-4-azaspiro[2.5]octane-7-carboxylic acid (INTERMEDIATE 526, 150.0 mg, 0.42 mmol) and DIPEA (270.5 mg, 2.10 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide and (R)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide (150.0 mg) as a solid mixture of enantiomers (Example 484). $^1$H NMR (400 MHz, $CD_3OD$) δ 8.43 (d, 1H), 8.19 (d, 1H), 7.83 (m, 1H), 7.50 (d, 1H), 7.15 (s, 1H), 4.77-4.58 (m, 3H), 3.89 (s, 3H), 3.04-2.84 (m, 1H), 2.71-2.51 (m, 3H), 2.51-2.27 (m, 1H), 2.11-1.60 (m, 2H), 1.55-1.23 (m, 11H), 1.20-0.94 (m, 2H), 0.91-0.57 (m, 3H). LCMS (ESI): 513.10[M+H]+.

This mixture of two diastereomers (150.0 mg) was separated using Chiral Prep-HPLC.

Column: CHIRAL ART Cellulose-SC column

Column dimension: 2×25 cm, 5 μm

Mobile Phase: DCM (0.5% 2 M $NH_3$·MeOH):EtOH=70:30 hold for 12 min

Flow rate: 20 mL/min

Detection: 220/254 nm

Example 484-A. The first eluting diastereomer (50.6 mg) was obtained as a solid.

The first eluting diastereomer had a retention time of 4.01 min.

$^1$H NMR (400 MHz, $CD_3OD$) δ 8.42 (s, 1H), 8.19 (d, 1H), 7.83 (m, 1H), 7.50 (d, 1H), 7.15 (s, 1H), 4.55 (s, 3H), 3.89 (s, 3H), 3.02-2.86 (m, 1H), 2.58 (s, 3H), 2.50-2.30 (m, 1H), 2.07-1.68 (m, 2H), 1.50-1.33 (m, 1H), 1.23-0.89 (m, 2H), 0.84-0.63 (m, 3H). LCMS (ESI): 513.15[M+H]+.

Example 484-B. The second eluting diastereomer (52.3 mg) was obtained as a solid.

The second eluting diastereomer had a retention time of 8.31 min.

$^1$H NMR (400 MHz, $CD_3OD$) δ 8.42 (s, 1H), 8.19 (d, 1H), 7.88 (m, 1H), 7.50 (d, 1H), 7.15 (s, 1H), 4.55 (s, 3H), 3.90 (s, 3H), 3.06-2.83 (m, 1H), 2.58 (s, 3H), 2.49-2.33 (m, 1H), 2.07-1.68 (m, 2H), 1.51-1.33 (m, 1H), 1.21-0.89 (m, 2H), 0.88-0.62 (m, 3H). LCMS (ESI): 513.10 [M+H]+.

Example 485. (S)-4-(5-(5-fluoro-2-methoxypyridin-4-yl)-N-pyrazole-3-carbonyl)-N-((5-(trifluoromethyl)-2-((3S,5R)-3,4,5-trimethylpiperazin-1-yl)oxazol-4-yl)methyl)-4-azaspiro[2.5]octane-7-carboxamide

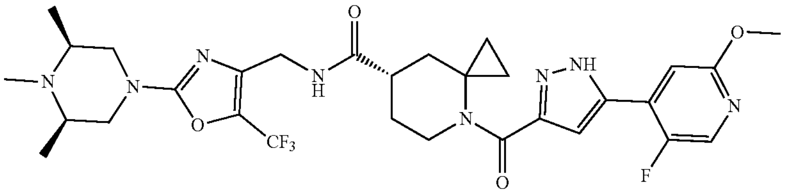

HCHO (2.1 mg, 0.07 mmol), $ZnCl_2$ (9.7 mg, 0.07 mmol) and $NaBH_3CN$ (4.5 mg, 0.07 mmol) were added to a stirred solution of (S)—N-((2-((3S,5R)-3,5-dimethylpiperazin-1-yl)-5-(trifluoromethyl)oxazol-4-yl)methyl)-4-(5-(5-fluoro-2-methoxypyridin-4-yl)-1H-pyrazole-3-carbonyl)-4-azaspiro[2.5]octane-7-carboxamide (Example 482, 15.0 mg, 0.02 mmol) in MeOH (1.00 mL). The resulting mixture was stirred at 60° C. for 2 h under the atmosphere of nitrogen. The resulting mixture was concentrated under reduced pressure. The residue was purified by Prep-HPLC (using the following conditions: Column: XBridge Prep Phenyl OBD Column, 19×250 mm, 5 μm; Mobile Phase A: Water (10 mM $NH_4HCO_3$), Mobile Phase B: MeCN; Flow rate: 25 mL/min; Gradient: 40% B to 50% 13 in 8 min, 50% B; Wave Length: 220254 n/m; RT1 (min): 7) to obtain the title compound (8.0 mg) as a solid. $^1$H NMR (400 MHz, $CD_3OD$) δ 8.14 (s, 1H), 7.29 (s, 1H), 7.12 (s, 1H), 6.27 (s, 1H), 5.72-5.57 (m, 1H), 4.73-4.41 (m, 1H), 4.06-3.81 (m, 5H), 3.14-2.96 (m, 1H), 2.93-2.82 (m, 2H), 2.62-2.10 (m, 6H), 2.05-1.57 (m, 2H), 1.47-1.25 (m, 2H), 1.27-1.12 (m, 7H), 1.07-0.86 (m, 1H), 0.86-0.60 (m, 2H). LCMS (ESI): 649.40 $[M+H]^+$.

Example 486. A Diastereomeric Mixture of (S)-5-(5-(5-fluoro-2-methoxypyridin-4-yl)-1H-pyrazole-3-carbonyl)-N-((1r,4S)-4-hydroxy-4-(trifluoromethyl) cyclohexyl)-5-azaspiro[3.5]nonane-8-carboxamide and (R)-5-(5-(5-fluoro-2-methoxypyridin-4-yl)-1H-pyrazole-3-carbonyl)-N-((1r,4R)-4-hydroxy-4-(trifluoromethyl)cyclohexyl)-5-azaspiro[3. 5]nonane-8-carboxamide

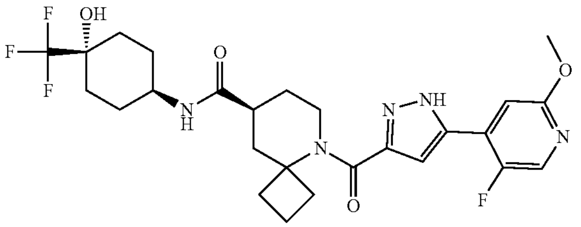

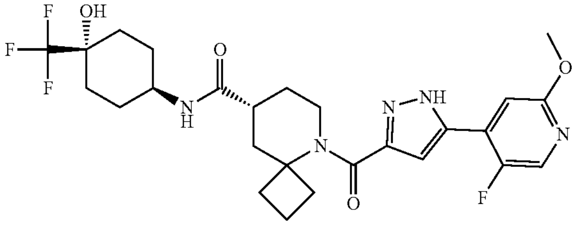

Step-1. methyl 5-[5-(5-fluoro-2-methoxypyridin-4-yl)-1-{[2-(trimethylsilyl)ethoxy]methyl}pyrazole-3-carbonyl]-5-azaspiro[3.5]nonane-8-carboxylate

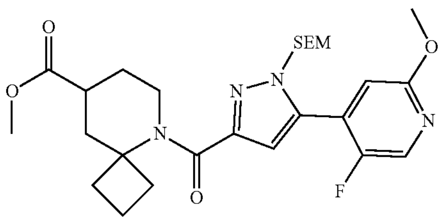 [SMILES: COC(=O)C1CCN(C(=O)c2cc(-c3cc(OC)ncc3F)n(COCC[Si](C)(C)C)n2)C2(CCC2)C1]

HATU (497.0 mg, 1.31 mmol) and methyl 5-azaspiro[3.5] nonane-8-carboxylate (199.0 mg, 1.09 mmol) were added to a mixture of 5-(5-fluoro-2-methoxypyridin-4-yl)-1-{[2-(trimethylsilyl)ethoxy]methyl}pyrazole-3-carboxylic acid (INTERMEDIATE 506, 400.0 mg, 1.09 mmol) and DIPEA (422.0 mg, 3.27 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (540.0 mg) as a solid. LCMS (ESI): 533 $[M+H]^+$.

Step-2. 5-[5-(5-fluoro-2-methoxypyridin-4-yl)-1-{[2-(trimethylsilyl)ethoxy]methyl}pyrazole-3-carbonyl]-5-azaspiro[3.5]nonane-8-carboxylic acid

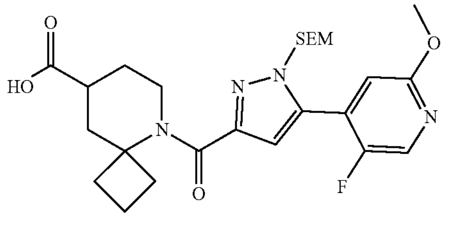 [SMILES: COc1cc(-c2cc(C(=O)N3CCC(C(=O)O)CC34CCC4)nn2COCC[Si](C)(C)C)c(F)cn1]

LiOH·$H_2O$ (49.0 mg, 2.03 mmol) was added to a mixture of methyl 5-[5-(5-fluoro-2-methoxypyridin-4-yl)-1-{[2-(trimethylsilyl)ethoxy]methyl}pyrazole-3-carbonyl]-5-azaspiro[3.5]nonane-8-carboxylate (Step-1, 540.0 mg, 101 mmol) in THF (3.00 mL), MeOH (3.00 mL) and H2O (3.00 mL). The resulting mixture was stirred at 25° C. for 14 h. The mixture was acidified to pH 3 with HCl (aq.). The aqueous layer was extracted with EtOAc. The organic layers were combined, dried over anhydrous $Na_2SO_4$, filtered, and concentrated under reduced pressure to obtain the title compound (500.0 mg) as a solid. LCMS (ESI): 519 $[M+H]^+$.

Step-3. 5-[5-(5-fluoro-2-methoxypyridin-4-yl)-1-{[2-(trimethylsilyl)ethoxy]methyl}pyrazole-3-carbonyl]-N-[(1r,4r)-4-hydroxy-4-(trifluoromethyl)cyclohexyl]-5-azaspiro[3.5]nonane-8-carboxamide

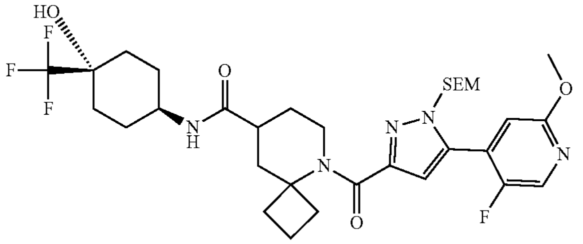 [SMILES: COc1cc(-c2cc(C(=O)N3CCC(C(=O)N[C@H]4CC[C@@](O)(C(F)(F)F)CC4)CC34CCC4)nn2COCC[Si](C)(C)C)c(F)cn1]

EDCI (288.0 mg, 1.50 mmol), HOBt (203.0 mg, 1.50 mmol), and (1r,4r)-4-amino-1-(trifluoromethyl)cyclohexan-1-ol (184.0 mg, 1.00 mmol) were added to a mixture of 5-[5-(5-fluoro-2-methoxypyridin-4-yl)-1-{[2-(trimethylsilyl)ethoxy]methyl}pyrazole-3-carbonyl]-5-azaspiro[3.5] nonane-8-carboxylic acid (Step-2, 520.0 mg, 1.00 mmol) and DIPEA (648.0 mg, 5.02 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (600.0 mg) as a solid. LCMS (ESI): 684 $[M+H]^+$.

Step-4. (S)-5-(5-(5-fluoro-2-methoxypyridin-4-yl)-1H-pyrazole-3-carbonyl)-N-((1r,4S)-4-hydroxy-4-(trifluoromethyl)cyclohexyl)-5-azaspiro[3.5]nonane-8-carboxamide and (R)-5-(5-(5-fluoro-2-methoxypyridin-4-yl)-1H-pyrazole-3-carbonyl)-N-((1r,4R)-4-hydroxy-4-(trifluoromethyl)cyclohexyl)-5-azaspiro[3.5]nonane-8-carboxamide

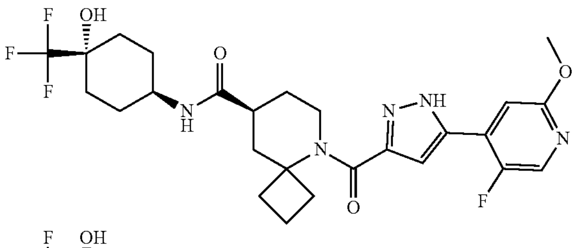

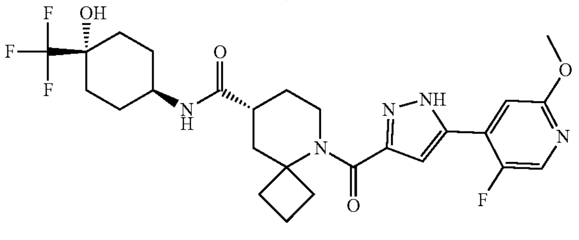

TFA (5.00 mL) was added to a mixture of 5-[5-(5-fluoro-2-methoxypyridin-4-yl)-1-{[2-(trimethylsilyl)ethoxy]methyl}pyrazole-3-carbonyl]-N-[(1r,4r)-4-hydroxy-4-(trifluoromethyl)cyclohexyl]-5-azaspiro[3.5]nonane-8-carboxamide (Step-3, 600.0 mg, 0.88 mmol) in DCM (5.00 mL). The resulting mixture was stirred at 25° C. for 2 h. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)-5-(5-(5-fluoro-2-methoxypyridin-4-yl)-1H-pyrazole-3-carbonyl)-N-((1r,4S)-4-hydroxy-4-(trifluoromethyl)cyclohexyl)-5-azaspiro[3.5]nonane-8-carboxamide and (R)-5-(5-(5-fluoro-2-methoxypyridin-4-yl)-1H-pyrazole-3-carbonyl)-N-((1r,4R)-4-hydroxy-4-(trifluoromethyl)cyclohexyl)-5-azaspiro[3.5]nonane-8-carboxamide (400.0 mg) as a solid mixture of diastereomers (Example 486). $^1$H NMR (400 MHz, DMSO-$d_6$) δ 13.91 (s, 1H), 8.27 (d, 1H), 7.79 (d, 1H), 7.32 (d, 1H), 7.01 (d, 1H), 5.69 (s, 1H), 4.03 (m, 1H), 3.90-3.86 (m, 3H), 3.85-3.79 (m, 1H), 3.07-3.03 (m, 1H), 2.80-2.69 (m, 1H), 2.44-2.40 (m, 2H), 2.25-2.18 (m, 1H), 2.10-2.00 (m, 1H), 1.98-1.82 (m, 2H), 1.82-1.68 (m, 5H), 1.58-1.47 (m, 6H), 1.36-1.23 (m, 1H). LCMS (ESI): 554.20 [M+H]$^+$.

This mixture of two diastereomers (400.0 mg) was separated using Chiral Prep-HPLC.

Column: CHIRAL ART Amylose-SA column

Column dimension: 2×25 cm, 5 μm

Mobile Phase: 3/1 hexanes/DCM (0.5% 2 M $NH_3$·MeOH):EtOH=80:20 hold for 10 min

Flow rate: 20 mL/min

Detection: 220/254 nm

Example 486-A. The first eluting diastereomer (165.0 mg) was obtained as a solid.

The first eluting diastereomer had a retention time of 4.77 min.

Example 486-B. The second eluting diastereomer (170.0 mg) was obtained as a solid.

The second eluting diastereomer had a retention time of 7.47 min.

$^1$H NMR (400 MHz, DMSO-$d_6$) δ 13.97 (s, 1H), 8.27 (s, 1H), 7.79 (d, 1H), 7.32 (d, 1H), 7.08-6.91 (m, 1H), 5.69 (s, 1H), 4.49-3.62 (m, 5H), 3.18-2.88 (m, 1H), 2.83-2.62 (m, 1H), 2.44-2.31 (m, 1H), 2.28-2.18 (m, 1H), 2.15-1.98 (m, 1H), 1.95-1.83 (m, 2H), 1.82-1.64 (m, 5H), 1.62-1.42 (m, 6H), 1.40-0.67 (m, 2H). LCMS (ESI): 554.25 [M+H]$^+$.

$^1$H NMR (400 MHz, DMSO-$d_6$) δ 13.97 (s, 1H), 8.27 (s, 1H), 7.79 (d, 1H), 7.32 (d, 1H), 7.08-6.91 (m, 1H), 5.69 (s, 1H), 4.49-3.62 (m, 5H), 3.18-2.88 (m, 1), 2.83-2.62 (m, 1H), 2.44-2.31 (m, 1H), 2.28-2.18 (m, 1H), 2.15-1.98 (m, 1H), 1.95-1.83 (m, 2H), 1.82-1.64 (m, 5H), 1.62-1.42 (m, 6H), 1.40-0.67 (m, 2H). LCMS (ESI): 554.25 [M+±H].

Example 487. (S)—N-(5-cyanopyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide

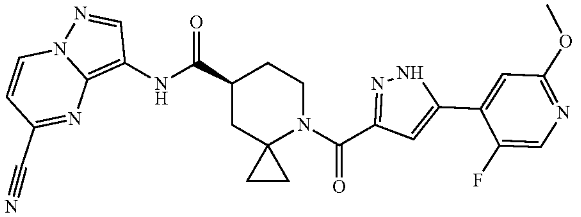 [SMILES: COc1cc(-c2cc(C(=O)N3CC[C@H](C(=O)Nc4cnn5ccc(C#N)nc45)CC34CC4)n[nH]2)c(F)cn1]

$Zn(CN)_2$ (29.1 mg, 0.25 mmol) and $Pd(PPh_3)_4$ (22.0 mg, 0.02 mmol) were added to a stirred solution of (7S)—N-{5-chloropyrazolo[1,5-a]pyrimidin-3-yl}-4-[5-(5-fluoro-2-methoxypyridin-4-yl)-1H-pyrazole-3-carbonyl]-4-azaspiro[2.5]octane-7-carboxamide (Step-1 from synthesis of Example 445, 100.0 mg, 0.19 mmol) in DMF (2.00 mL). The resulting mixture was stirred at 120° C. for 14 h under the atmosphere of nitrogen. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 55 B in 30 min; 254/220 nm) to obtain the title compound (54.1 mg) as a solid. $^1$H NMR (400 MHz, DMSO-$d_6$) δ 14.20-13.67 (m, 1H), 10.66-10.40 (m, 1H), 9.32 (d, 1H), 8.84 (s, 1H), 8.38-8.18 (m, 1H), 7.49 (d, 1H), 7.32 (d, 1H), 7.07 (s, 1H), 4.76-4.12 (m, 1H), 4.04-3.79 (m, 3H), 3.25-3.05 (m, 2H), 2.38-2.12 (m, 1H), 1.97-1.80 (m, 1H), 1.68 (s, 1H), 1.54-1.26 (m, 1H), 1.20-0.89 (m, 1H), 0.87-0.77 (m, 1H), 0.76-0.66 (m, 1H), 0.66-0.53 (m, 1H). LCMS (ESI): 516.20 [M+H]$^+$.

Example 488. (7S)—N-(1-(6-cyanopyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide

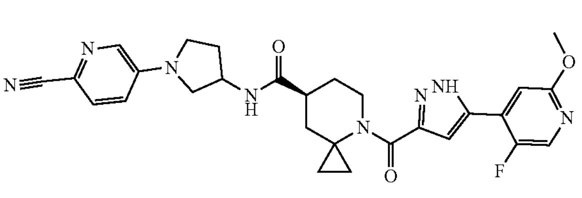 [SMILES: COc1cc(-c2cc(C(=O)N3CC[C@H](C(=O)NC4CCN(c5ccc(C#N)nc5)C4)CC34CC4)n[nH]2)c(F)cn1]

DIPEA (58.4 mg, 0.45 mmol) was added to a stirred mixture of (7S)-4-[5-(5-fluoro-2-methoxypyridin-4-yl)-1H-pyrazole-3-carbonyl]-N-(pyrrolidin-3-yl)-4-azaspiro[2.5]octane-7-carboxamide (Example 471, 100.0 mg, 0.23 mmol) and 5-fluoropyridine-2-carbonitrile (27.6 mg, 0.23 mmol) in MeCN (1.00 mL). The resulting mixture was stirred at 80° C. for 2 h tinder nitrogen atmosphere. The resulting mixture was concentrated under reduced pressure. The residue was purified by reverse phase column chromatography (using the following conditions: Column: C18; mobile phase A: Water (0.5% $NH_4HCO_3$), mobile phase B: MeCN; gradient: 15 B to 50 B in 30 min; 220/254 nm) to obtain the title compound (30.0 mg) as a solid. $^1$H NMR (400 MHz, DMSO-$d_6$) δ 14.11-13.87 (m, 1H), 8.33-8.23 (m, 1H), 8.20-8.16 (m, 1H), 8.07-8.03 (m, 1H), 7.73-7.67 (m, 1H), 7.40-7.28 (m, 1H), 7.07-7.00 (m, 1H), 6.99-6.93 (m, 1H), 4.65-4.28 (m, 21H), 3.88 (s, 3H), 3.68-3.54 (m, 1H), 3.51-3.38 (m, 2H), 3.24-3.09 (m, 1H), 2.28-2.08 (m, 2H), 1.99-1.85 (m, 1H), 1.83-1.66 (m, 1H), 1.63-1.42 (m, 1H), 1.31-1.20 (m, 2H), 1.18-1.04 (m, 1H), 1.03-0.86 (m, 1H), 0.82-0.41 (m, 3H). LCMS (ESI): 545.20 [M+H]$^+$.

Example 489. A Diastereomeric Mixture of (S)—N—((R)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((S)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide

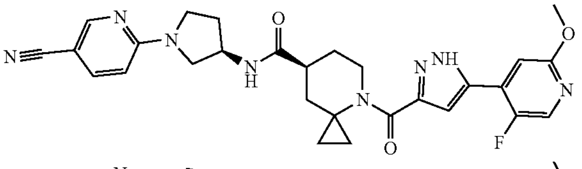

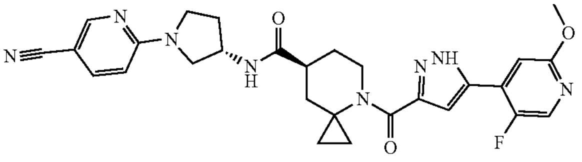

The title compound was prepared using a procedure similar to the one described for the synthesis of Example 488, except 6-fluoropyridine-3-carbonitrile was used as a starting material. The residue was purified by silica gel column chromatography eluting with DCM/MeOH (15/1 v/v) to obtain the title compound (95.0 mg) as a solid (Example 489). $^1$H NMR (400 MHz, DMSO-$d_6$) δ 13.99 (s, 1H), 8.48 (d, 1H), 8.27 (s, 1H), 8.15 (s, 1H), 7.88-7.73 (m, 1H), 7.32 (d, 1H), 7.03 (s, 1H), 6.57 (d, 1H), 4.69-4.13 (m, 2H), 3.88 (s, 3H), 3.73-3.33 (m, 4H), 2.76-2.60 (m, 2H), 2.28-2.06 (m, 2H), 2.02-1.43 (m, 3H), 1.03-0.75 (m, 2H), 0.73-0.49 (m, 3H). LCMS (ESI): 545.25 [M+H]$^+$.

This mixture of two diastereomers (95.0 mg) was separated using Chiral Prep-HPLC.

Column: CHIRALPAK IE column
Column dimension: 2×25 cm, 5 μm
Mobile Phase: MTBE (0.5% 2M NH MeOH):MeOH=70:30 hold for 16 min
Flow rate: 20 mL/min
Detection: 220/254 nm Example 489-A. The first eluting diastereomer (32.6 mg) was obtained as a solid.

The first eluting diastereomer had a retention time of 10.94 min.

$^1$H NMR (400 MHz, DMSO-$d_6$) δ 13.97 (s, 1H), 8.48 (d, 1H), 8.31-8.19 (m, 1H), 8.15 (d, 1H), 7.89-7.72 (m, 1H), 7.32 (d, 1H), 7.03 (s, 1H), 6.57 (d, 1H), 4.70-4.07 (m, 2H), 3.88 (s, 3H), 3.75-3.45 (m, 4H), 2.80-2.60 (m, 2H), 2.30-2.01 (m, 2H), 1.97-1.83 (m, 1H), 1.80-1.66 (m, 1H), 1.64-1.39 (m, 1H), 0.99-0.92 (m, 2H), 0.89-0.70 (m, 1H), 0.68-0.53 (m, 2H). LCMS (ESI): 545.25 [M+H]$^+$.

Example 489-B. The second eluting diastereomer (37.2 mg) was obtained as a solid.

The second eluting diastereomer had a retention time of 13.84 min.

$^1$H NMR (400 MHz, DMSO-$d_6$) δ 13.98 (s, 1H), 8.48 (d, 14H), 8.35-8.23 (m, 1H), 8.15 (s, 1H), 7.89-7.72 (m 1H), 7.32 (d, 1H), 7.03 (s, 1H), 6.57 (d, 1H), 4.74-4.08 (m, 1H), 3.98-3.79 (m, 4H), 3.73-3.34 (m, 4H), 2.79-2.59 (m, 2H), 2.31-2.03 (m, 2H), 1.97-1.85 (m, 1H), 1.82-1.68 (m, 1H), 164-1.46 (m, 1H), 1.02-0.77 (m, 3H), 0.71-0.49 (m, 2H). LCMS (ESI): 545.15 [M+H]$^+$.

Example 490. A Diastereomeric Mixture of (S)—N—((S)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide

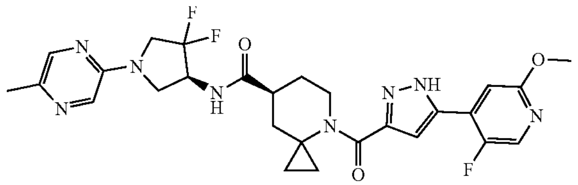

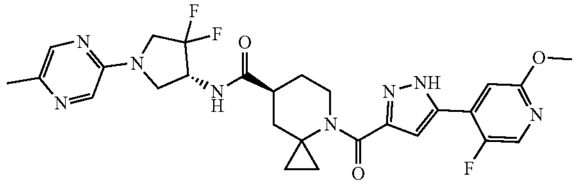

Step-1. tert-butyl 3,3-difluoro-4-[(7S)-4-[5-(5-fluoro-2-methoxypyridin-4-yl)-1H-pyrazole-3-carbonyl]-4-azaspiro[2.5]octane-7-amido]pyrrolidine-1-carboxylate

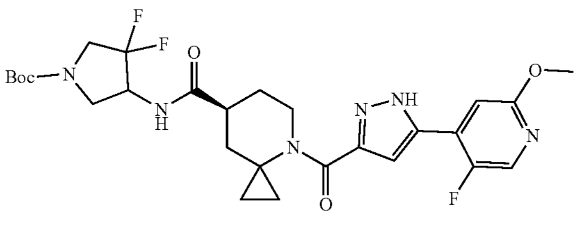 [SMILES: COc1cc(-c2cc(C(=O)N3CC[C@H](C(=O)NC4CN(C(=O)OC(C)(C)C)CC4(F)F)CC34CC4)n[nH]2)c(F)cn1]

HOBt (108.3 mg, 0.80 mmol), EDCI (153.6 mg, 0.80 mmol), tert-butyl 4-amino-3,3-difluoropyrrolidine-1-carboxylate (118.7 mg, 0.53 mmol) were added to a stirred mixture of (7S)-4-[5-(5-fluoro-2-methoxypyridin-4-yl)-1H-pyrazole-3-carbonyl]-4-azaspiro[2.5]octane-7-carboxylic acid (200.0 mg, 0.53 mmol) and DIPEA (207.1 mg, 1.60 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 12/1 v/v) to obtain the title compound (300.0 mg) as a solid. LCMS (ESI): 579.2 $[M+H]^+$.

Step-2. (7S)—N-(4,4-difluoropyrrolidin-3-yl)-4-[5-(5-fluoro-2-methoxypyridin-4-yl)-1H-pyrazole-3-carbonyl]-4-azaspiro[2.5]octane-7-carboxamide

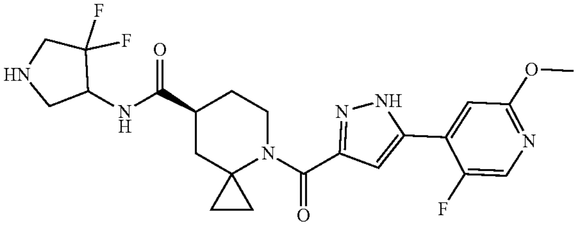 [SMILES: COc1cc(-c2cc(C(=O)N3CC[C@H](C(=O)NC4CNCC4(F)F)CC34CC4)n[nH]2)c(F)cn1]

TFA (3.00 mL) was added to a solution of tert-butyl 3,3-difluoro-4-[(7S)-4-[5-(5-fluoro-2-methoxypyridin-4-yl)-1H-pyrazole-3-carbonyl]-4-azaspiro[2.5]octane-7-amido]pyrrolidine-1-carboxylate (Step-1, 300.0 rug, 0.52 mmol) in DCM (3.00 mL) at 0° C. The resulting mixture was stirred at 25° C. for 1 h. The resulting mixture was concentrated under reduced pressure. The residue was purified by Prep-TLC (DCM/MeOH, 5/1 v/v) to obtain the title compound (220.0 mg) as a solid. LCMS (ESI): 479.2 $[M+H]^+$.

Step-3. (S)—N—((S)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-(5-methylpyrazin-2-yl) pyrrolidin-3-yl)-4-(5-(5-fluoro-2-methoxypyridin-4-yl)-1H-pyrazole-3-carbonyl)-4-azaspiro[2.5]octane-7-carboxamide

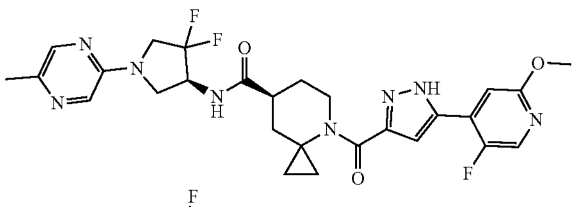

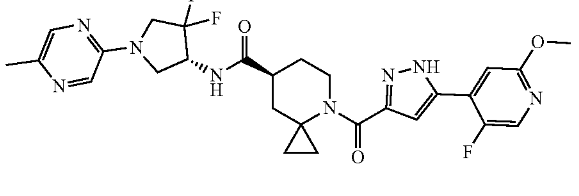

Pd-PEPPSI-iHeptCl (24.9 mg, 0.03 mmol, CAS #: 905459-27-0) and $Cs_2CO_3$ (204.3 mg, 0.63 mmol) were added to a stirred solution of (7S)—N-(4,4-difluoropyrrolidin-3-yl)-4-[5-(5-fluoro-2-methoxypyridin-4-yl)-1H-pyrazole-3-carbonyl]-4-azaspiro[2.5]octane-7-carboxamide (150.0 mg, 0.31 mmol) and 2-chloro-5-methyl-pyrazine (80.6 mg, 0.63 mmol) in 1,4-dioxane (4.00 mL). The resulting mixture was stirred at 80° C. for 14 h under nitrogen atmosphere. The resulting mixture was concentrated under reduced pressure. The residue was purified by Prep-TLC (DCM/MeOH, 10/1 v/v) to obtain (S)—N—((S)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide and (S)—N—((R)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide (45.0 mg) as a solid mixture of diastereomers (Example 490). $^1H$ NMR (400 MHz, $CD_3OD$) δ 8.14 (s, 1H), 8.04 (s, 1H), 7.94-7.86 (m, 1H), 7.31-7.27 (m, 1H), 7.12 (s, 1H), 5.01-4.90 (m, 2H), 4.09-3.97 (m, 1H), 3.97-3.87 (m, 5H), 3.54-3.39 (m, 2H), 2.96-2.92 (m, 1H), 2.41 (s, 3H), 1.92-1.88 (m, 2H), 1.39-1.22 (m, 2H), 1.09-1.04 (m, 1H), 0.78-0.73 (m, 3H). LCMS (ESI): 571.60 $[M+H]^+$.

This mixture of two diastereomers (43.0 mg) was separated using Chiral Prep-HPLC.

Column: CHIRAL ART Cellulose-SC column
Column dimension: 2×25 cm, 5 μm
Mobile Phase: 1/1 hexanes/DCM (0.5% 2 M $NH_3$·MeOH):EtOH=80:20 hold for 22 min
Flow rate: 20 mL/in
Detection: 220/254 nm Example 490-A. The first eluting diastereomer (4.4 mg) was obtained as a solid.

The first eluting diastereomer had a retention time of 10.83 min.

$^1H$ NMR (400 MHz, $CD_3OD$) δ 8.20-8.11 (m, 1H), 8.09-8.00 (m, 1H), 7.95-7.83 (m, 1H), 7.37-7.25 (m, 1H), 7.19-7.03 (m, 1H), 5.11-4.90 (m, 1H), 4.67-4.51 (m, 2H), 4.11-4.00 (m, 1H), 4.00-3.94 (m, 5H), 3.52-3.41 (m, 1H), 3.02-2.89 (m, 1H), 2.41 (s, 3H), 1.99-1.87 (m, 1H), 1.85-1.73 (m, 1H), 1.40-1.26 (m, 2H), 1.09-0.87 (m, 2H), 0.81-0.69 (m, 2H). LCMS (ESI): 571.15 $[M+H]^+$.

Example 490-B. The second eluting diastereomer (5.8 mg) was obtained as a solid.

The second eluting diastereomer had a retention time of 17.48 min.

$^1H$ NMR (400 MHz, $CD_3OD$) δ 8.20-8.10 (m, 1H), 8.08-7.98 (m, 1H), 7.92-7.84 (m, 1H), 7.29 (s, 1H), 7.16-7.00 (m, 1H), 5.04-4.90 (m, 3H), 4.67-4.31 (m, 1H), 4.09-3.95 (m, 5H), 3.50-3.40 (m, 1H), 2.94 (s, 1H), 2.41 (s, 3H), 1.96-1.68 (m, 2H), 1.45-1.32 (m, 1H), 1.16-0.90 (m, 2H), 0.88-0.66 (m, 3H). LCMS (FSI): 571.25 $[M+H]^+$.

Example 491. (S)—N-((3-chloro-5-isopropoxypyridin-2-yl)methyl)-4-(5-(5-fluoro-2-methoxypyridin-4-yl)-1H-pyrazole-3-carbonyl)-4-azaspiro[2.5]octane-7-carboxamide

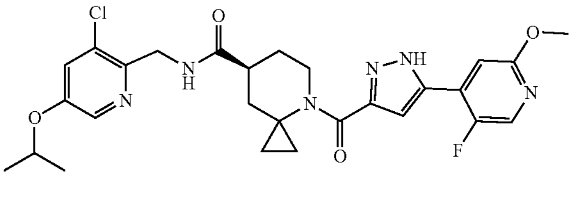 [SMILES: COc1cc(-c2cc(C(=O)N3CC[C@H](C(=O)NCc4ncc(OC(C)C)cc4Cl)CC34CC4)n[nH]2)c(F)cn1]

The title compound was prepared using a procedure similar to the one described for the synthesis of Example 484, except NaH and isopropyl alcohol were used as starting materials in Step-1. The residue was purified by silica gel column chromatography eluting with DCM/MeOH (10/1 v/v) to obtain the title compound (310.0 mg) as a solid. $^1H$ NMR (400 MHz, DMSO-$d_6$) δ 13.86 (s, 1H), 8.27 (d, 1H), 8.19 (d, 2H), 7.58 (d, 1H), 7.32 (d, 1H), 7.03 (s, 1H), 4.81-4.69 (m, 1H), 4.52-4.27 (m, 2H), 3.88 (s, 3H), 3.30-3.28 (m, 1H), 3.23-2.90 (m, 1H), 2.85-2.65 (m, 1H), 2.31-2.05 (m, 1H), 1.87-1.70 (m, 1H), 1.65-1.48 (m, 1H), 1.36-1.16 (m, 6H), 1.09-0.79 (m, 2H), 0.77-0.52 (m, 3H). LCMS (ESI): 557.25 $[M+H]^+$.

Example 492. A Diastereomeric Mixture of (S)-4-(5-(5-fluoro-2-methoxypyridin-4-yl)-1H-pyrazole-3-carbonyl)-N—((S)-3-methyl-5,6,7,8-tetrahydro-[1,2,4]triazolo[4,3-a]pyridin-8-yl)-4-azaspiro[2.5]octane-7-carboxamide and (S)-4-(5-(5-fluoro-2-methoxypyridin-4-yl)-1H-pyrazole-3-carbonyl)-N—((R)-3-methyl-5,6,7,8-tetrahydro-[1,2,4]triazolo[4,3-a]pyridin-8-yl)-4-azaspiro[2.5]octane-7-carboxamide

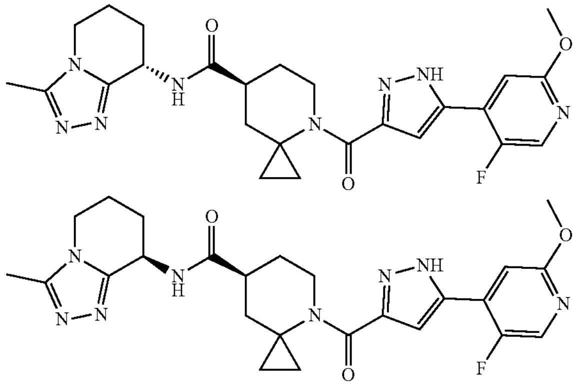

The title compound was prepared using a procedure similar to the one described for the synthesis of Example 325, except 3-methyl-5H,6H,7H,8H-[1,2,4]triazolo[4,3-a]pyridin-8-amine was used as a starting material. The residue was purified reverse phase column chromatography (using the following conditions: Column: C18; mobile phase A: Water (0.5% $NH_4HCO_3$), mobile phase B: MeCN; gradient: 15 B to 50 B in 30 min; 220/254 nm) to obtain (S)-4-(5-(5-fluoro-2-methoxypyridin-4-yl)-1H-pyrazole-3-carbonyl)-N—((S)-3-methyl-5,6,7,8-tetrahydro-[1,2,4]triazolo[4,3-a]pyridin-8-yl)-4-azaspiro[2.5]octane-7-carboxamide and (S)-4-(5-(5-fluoro-2-methoxypyridin-4-yl)-1H-pyrazole-3-carbonyl)-N—((R)-3-methyl-5,6,7,8-tetrahydro-[1,2,4]triazolo[4,3-a]pyridin-8-yl)-4-azaspiro[2.5]octane-7-carboxamide (159.2 mg) as a solid mixture of diastereomers (Example 492). $^1H$ NMR (400 MHz, $CD_3OD$) δ 8.14 (d, 1H), 7.45-7.27 (m, 1H), 7.16 (d, 1H), 5.31-5.06 (m, 1H), 4.78-4.46 (m, 1H), 4.05-3.97 (m, 1H), 3.97-3.85 (m, 4H), 2.86 (s, 1H), 2.56-2.29 (m, 4H), 2.26-2.12 (m, 2H), 2.12-1.97 (m, 2H), 1.97-1.58 (m, 3H), 1.49-1.22 (m, 1H), 1.16-0.97 (m, 1H), 0.84-0.61 (m, 3H). LCMS (ESI): 509.25 $[M+H]^+$.

This mixture of two diastereomers (157.0 mg) was separated using Chiral Prep-1-HPLC.

Column: CHIRAL ART Cellulose-SC column

Column dimension: 2×25 cm, 5 μm

Mobile Phase: DCM (0.5% 2 M $NH_3$·MeOH):EtOH=50:50 hold for 7 min

Flow rate: 20 mL/min

Detection: 220/254 nm

Example 492-A. The first eluting diastereomer (38.9 mg) was obtained as a solid.

The first eluting diastereomer had a retention time of 4.01 min.

$^1H$ NMR (400 MHz, $CD_3OD$) δ 8.12 (s, 1H), 7.37 (s, 1H), 7.27-7.04 (m, 1H), 5.24-5.13 (m, 1H), 4.76-4.33 (m, 1H), 4.05-3.97 (m, TH), 3.95 (s, 3H), 3.93-3.86 (m, 1H), 3.00-2.73 (m, 1H), 2.52-2.29 (m, 4H), 2.26-2.12 (m, 2H), 2.06 (s, 2H), 1.93-1.64 (m, 2H), 1.48-1.19 (m, 2H), 1.16-0.82 (m, 2H), 0.82-0.57 (m, 2H). LCMS (ESI): 509.25 $[M+H]^+$.

Example 492-B. The second eluting diastereomer (44.0 mg) was obtained as a solid.

The second eluting diastereomer had a retention time of 5.45 min.

$^1H$ NMR (400 MHz, $CD_3OD$) δ 8.13 (s, 1H), 7.37 (s, 1H), 7.27-7.04 (m, 1H), 5.25-5.13 (m, 1H), 4.78-4.38 (m, 1H), 4.06-3.84 (m, 5H), 3.15-3.00 (m, 1H), 2.94-2.77 (m, 1H), 2.55-2.29 (m, 3H), 2.26-2.13 (m, 2H), 2.13-2.00 (m, 1H), 1.97-1.64 (m, 3H), 1.59-1.36 (m, 1H), 1.40-1.21 (m, 2H), 1.20-0.87 (m, 1H), 0.85-0.54 (m, 2H). LCMS (ESI): 509.25 $[M+H]^+$.

Example 493. A Diastereomeric Mixture of (R)-4-(5-(5-fluoro-2-methoxy-3-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(5-fluoro-2-methoxy-3-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide

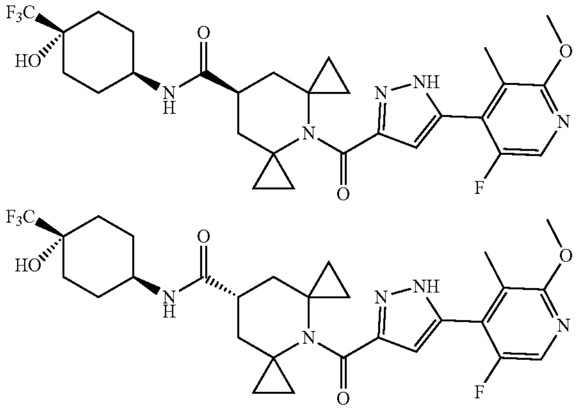

Step-1. (5-fluoro-2-methoxypyridin-3-yl)methanol

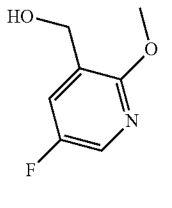

2-Methylpropyl carbonochloridate (1.20 g, 8.77 mmol) and N-methylmorpholine (0.89 g, 8.77 mmol) were added to a solution of 5-fluoro-2-methoxypyridine-3-carboxylic acid (1.00 g, 5.84 mmol) in DME (20.00 mL) at 0° C. The resulting mixture was stirred at 0° C. for 30 min. The resulting mixture was filtered, the filter cake was washed with DME (5.00 mL). Then $NaBH_4$ (0.44 g, 11.69 mmol) was added to the filtrate at 0° C. The resulting mixture was stirred at 0° C. for 1 h. The resulting mixture was concentrated under vacuum. The residue was purified by silica gel column chromatography eluting with petroleum ether/EtOAc (5/1 v/v) to obtain the title compound (914.0 mg) as a solid. LCMS (ESI): 158.00 $[M+H]^+$.

Step-2. 3-(chloromethyl)-5-fluoro-2-methoxypyridine

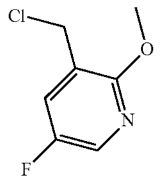

$SOCl_2$ (1.38 g, 11.63 mmol) was added to a stirred mixture of (5-fluoro-2-methoxypyridin-3-yl)methanol (Step-1, 914.0 mg, 5.82 mmol) in DCM (5.00 mL) at 0° C. The resulting mixture was stirred at 0° C. for 14 h. The resulting mixture was concentrated under vacuum to obtain the title compound (900.0 mg) as a solid. LCMS (ESI): 176.10 [M1-H].

Step-3. 5-fluoro-2-methoxy-3-methylpyridine

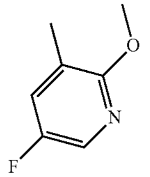

Zn (1.01 g, 15.38 mmol) was added to a stirred mixture of 3-(chloromethyl)-5-fluoro-2-methoxypyridine (Step-2, 900.0 mg, 5.13 mmol) in AcOH (5.00 mL). The resulting mixture was stirred at 120° C. for 3 h. The resulting mixture was filtered, the filtrate was diluted with EtOAc and washed with $NaHCO_3$. The residue was purified by silica gel column chromatography eluting with petroleum ether/EtOAc (3/1 v/v) to obtain the title compound (380.0 mg) as a solid. LCMS (ESI): 142.20 $[M+EH]^+$.

Step-4. 5-fluoro-4-iodo-2-methoxy-3-methylpyridine

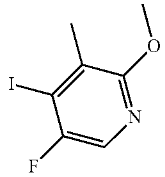

LDA (265.6 mg, 2.48 mmol) and $I_2$ (755.3 mg, 2.98 mmol) were added to a stirred solution of 5-fluoro-2-methoxy-3-methylpyridine (Step-3, 350.0 mg, 2.48 mmol) in THF (4.00 mL). The resulting mixture was stirred at −78° C. for 2 h under nitrogen atmosphere. The resulting mixture was concentrated under vacuum. The residue was purified by Prep-TLC (petroleum ether) to obtain the title compound (160.0 mg) as a solid. LCMS (ESI): 268.20 $[M+H]^+$.

Step-5. ethyl 5-(5-fluoro-2-methoxy-3-methylpyridin-4-yl)-1-(oxan-2-yl)pyrazole-3-carboxylate

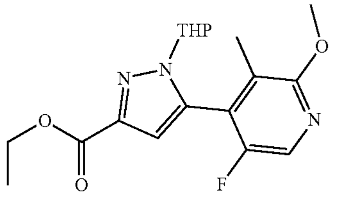

PEPPSI™-IPr catalyst (35.5 mg, 0.05 mmol, CAS #: 905459-27-0) and $K_3PO_4$ (333.9 mg, 1.57 mmol) were added to a stirred mixture of 5-fluoro-4-iodo-2-methoxy-3-methylpyridine (Step-4, 140.0 mg, 0.52 mmol) and 5-(ethoxycarbonyl)-2-(oxan-2-yl)pyrazol-3-ylboronic acid (Step-4, 140.5 mg, 0.52 mmol) in 1,4-dioxane (2.00 mL) and $H_2O$ (0.20 mL). The resulting mixture was stirred at 70° C. for 14 h under nitrogen atmosphere. The resulting mixture was concentrated under vacuum. The residue was purified by Prep-TLC (petroleum ether/EtOAc, 3/1 v/v) to obtain the title compound (140.0 mg) as a solid. LCMS (ESI): 364.30 $[M+H]^+$.

Step-6. 5-(5-fluoro-2-methyoxy-3-methylpyridin-4-yl)-11-(oxan-2-yl)pyrazole-3-carboxylic acid

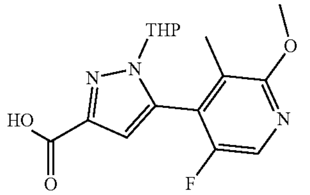

Lithium hydroxide (32.3 mg, 0.77 mmol) was added to a stirred solution of ethyl 5-(5-fluoro-2-methoxy-3-methylpyridin-4-yl)-1-(oxan-2-yl)pyrazole-3-carboxylate (Step-5, 140.0 mg, 0.39 mmol) in THF (2.00 mL), MeOH (1.00 mL) and $H_2O$ (1.00 mL). The resulting mixture was stirred at 25° C. for 2 h. The resulting mixture was diluted with EtOAc and washed with HCl (aq. 1M). The organic layers were combined, dried over anhydrous $Na_2SO_4$, filtered, and concentrated under reduced pressure. The residue was purified by Prep-TLC (DCM/MeOH, 12/1 v/v) to obtain the title compound (80.0 mg) as a solid. LCMS (ESI): 336.10 $[M+]^+$.

Step-7. 4-[5-(5-fluoro-2-methoxy-3-methylpyridin-4-yl)-1-(oxan-2-yl)pyrazole-3-carbonyl]-N-[(1r,4r)-4-hydroxy-4-(trifluoromethyl)cyclohexyl]-4-azaspiro[2,5]octane-7-carboxamide

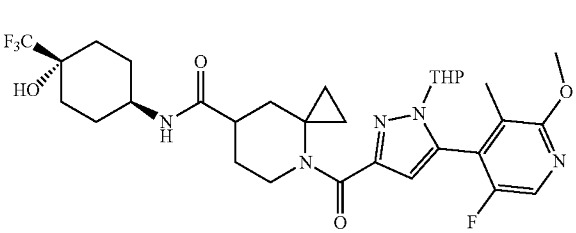

HOBt (42.3 mg, 0.31 mmol), EDCI (60.0 mg, 0.31 mmol), and A-[(1r,4r)-4-hydroxy-4-(trifluoromethyl)cyclohexyl]-4-azaspiro[2.5]octane-7-carboxamide (66.9 mg, 0.21 mmol) were added to a stirred mixture of 5-(5-fluoro-2-methoxy-3-methylpyridin-4-yl)-1-(oxan-2-yl)pyrazole-3-carboxylic acid (Step-6, 70.0 mg, 0.21 mmol) and DIPEA (134.9 mg, 1.05 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 15/1 v/v) to obtain the title compound (85.0 mg) as a solid. LCMS (ESI): 638.30 $[M+H]^+$.

Step-8. (R)-4-(5-(5-fluoro-2-methoxy-3-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(5-fluoro-2-methoxy-3-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide

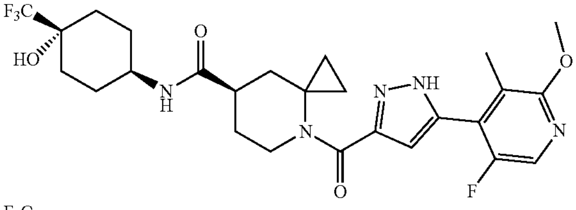

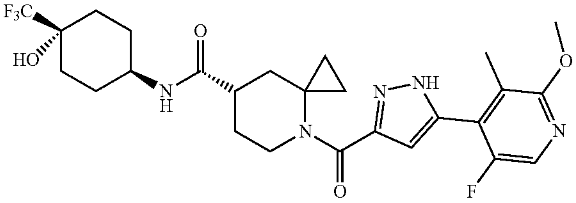

TFA (2.00 mL) was added in a solution of 4-[5-(5-fluoro-2-methoxy-3-methylpyridin-4-yl)-1-(oxan-2-yl)pyrazole-3-carbonyl]-N-[(1r,4r)-4-hydroxy-4-(trifluoromethyl)cyclohexyl]-4-azaspiro[2.5]octane-7-carboxamide (Step-7, 77.0 mg, 0.12 mmol) in DCM (2.00 mL). The solution was stirred at 25° C. for 1 h. The resulting mixture was concentrated under reduced pressure. The residue was purified by Prep-TLC (DCM/MeOH, 12/1 v/v) to obtain (R)-4-(5-(5-fluoro-2-methoxy-3-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(5-fluoro-2-methoxy-3-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide (37.0 mg) as a solid mixture of diastereomers (Example 493). $^1$H NMR (400 MHz, $CD_3OD$) δ 8.06-7.90 (m, 1H), 6.93-6.65 (m, 1H), 4.75-4.55 (m, 1H), 4.08-3.89 (m, 4H), 3.00-2.81 (m, 1H), 2.68-2.29 (m, 1H), 2.21 (s, 3H), 1.94-1.88 (nm, 4H), 1.82-1.59 (m, 4H), 1.44-1.21 (m, 3H), 1.16-0.99 (m, 1H), 0.96-0.85 (m, 1H), 0.82-0.69 (m, 3H). LCMS (ESI): 554.15 $[M+H]^+$.

This mixture of two diastereomers (35.0 mg) was separated using Chiral Prep-HPLC.

Column: CHIRAL ART Cellulose-SC column

Column dimension: 2×25 cm, 5 μm

Mobile Phase: 3/1 hexanes/DCM (0.5% 2 M $NH_3$·MeOH):EtOH=50:50 hold for 8.5 min Flow rate: 20 mL/min Detection: 220/254 nm Example 493-A. The first eluting diastereomer (11.6 mg) was obtained as a solid.

The first eluting diastereomer had a retention time of 4.15 min.

$^1$H NMR (400 MHz, $CD_3OD$) δ 7.97 (s, 1H), 6.80 (s, 1H), 4.77-4.49 (m, 1H), 3.98 (s, 2H), 3.96-3.94 (m, 2H), 3.01-2.84 (m, 1H), 2.68-2.25 (m, 1H), 2.21 (s, 3H), 1.98-1.77 (m, 7H), 1.76-1.58 (m, 5H), 1.35-1.12 (m, 1H), 1.09-0.98 (m, 1H), 0.80-0.66 (m, 2H). LCMS (ESI): 554.25 $[M+H]^+$.

Example 493-B. The second eluting diastereomer (12.1 mg) was obtained as a solid.

The second eluting diastereomer had a retention time of 6.32 min.

$^1$H NMR (400 MHz, $CD_3OD$) δ 7.89 (s, 1H), 6.70 (s, 1H), 4.50-4.40 (m, 1H), 3.90-3.84 (m, 4H), 2.70-2.90 (m, 1H), 2.55-2.18 (m, 1H), 2.10 (s, 3H), 1.87-1.69 (m, 7H), 1.65-1.52 (m, 5H), 1.08-1.17 (m, 1H), 0.98-0.75 (m, 1H), 0.69-0.58 (m, 2H). LCMS (ESI): 554.25 $[M+H]^+$.

Example 494. (S)—N-(6-acetylpyrazolo[1,5-a]pyridin-3-yl)-4-(5-(5-fluoro-2-methoxypyridin-4-yl)-1H-pyrazole-3-carbonyl)-4-azaspiro[2.5]octane-7-carboxamide

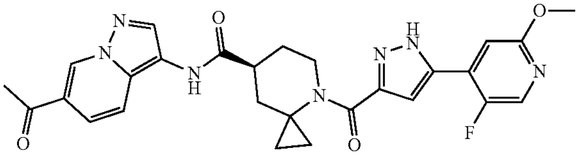 [SMILES: COc1cc(-c2cc(C(=O)N3CC[C@H](C(=O)Nc4cnn5cc(C(C)=O)ccc45)CC34CC4)n[nH]2)c(F)cn1]

Step-1. (7S)—N-{6-bromopyrazolo[1,5-a]pyridin-3-yl}-4-[5-(5-fluoro-2-methoxypyridin-4-yl)-1H-pyrazole-3-carbonyl]-4-azaspiro[2.5]octane-7-carboxamide

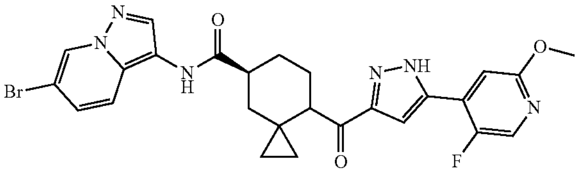 [SMILES: COc1cc(-c2cc(C(=O)C3CC[C@H](C(=O)Nc4cnn5cc(Br)ccc45)CC34CC4)n[nH]2)c(F)cn1]

6-bromopyrazolo[1,5-a]pyridin-3-amine (300.0 mg, 1.42 mmol) and HATU (591.7 mg, 1.56 mmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 529.7 mg, 1.42 mmol) and DIPEA (548.5 mg, 4.25 mmol) in DMF (8.00 nM). The solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 3/1 v/v) to obtain the title compound (650.0 mg) as an oil. LCMS (ESI): 568.1 $[M+H]^+$.

Step-2. (7S)—N-[6-(1-ethoxyethenyl)pyrazolo[1,5-a]pyridin-3-yl]-4-[5-(5-fluoro-2-methoxypyridin-4-yl)-1H-pyrazole-3-carbonyl]-4-azaspiro[2.5]octane-7-carboxamide

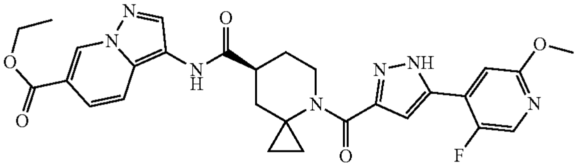 [SMILES: CCOC(=O)c1ccc2c(NC(=O)[C@H]3CCN(C(=O)c4cc(-c5cc(OC)ncc5F)[nH]n4)C4(CC4)C3)cnn2c1]

Tributyl (1-ethoxyethenyl)stannane (536.9 mg, 1.49 mmol), $Pd(PPh_3)_4$ (132.1 mg, 0.11 mmol) were added to a solution of (7S)—N-{6-bromopyrazolo[1,5-a]pyridin-3-yl}-4-[5-(5-fluoro-2-methoxypyridin-4-yl)-1H-pyrazole-3-carbonyl]-4-azaspiro[2.5]octane-7-carboxamide (Step-1, 650.0 mg, 1.14 mmol) in DMF (10.00 mL). The solution was stirred at 100° C. for 14 h under $N_2$. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 3/1 v/v) to obtain the title compound (380.0 mg) as a solid. LCMS (ESI): 560.2 $[M+H]^+$.

Step-3. (S)—N-(6-acetylpyrazolo[1,5-a]pyridin-3-yl)-4-(5-(5-fluoro-2-methoxypyridin-4-yl)-1H-pyrazole-3-carbonyl)-4-azaspiro[2.5]octane-7-carboxamide

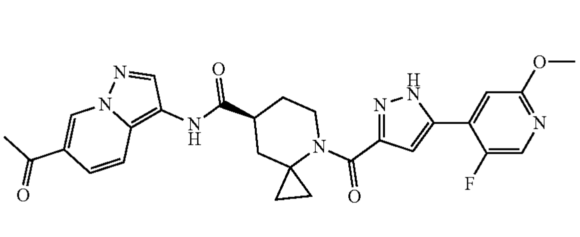 [SMILES: COc1cc(-c2cc(C(=O)N3CC[C@H](C(=O)Nc4cnn5cc(C(C)=O)ccc45)CC34CC4)n[nH]2)c(F)cn1]

PTSA (116.9 mg, 0.68 mmol) was added to a solution of (7S)—N-[6-(i-ethoxyethenyl)pyrazolo[1,5-a]pyridin-3-yl]-4-[5-(5-fluoro-2-methoxypyridin-4-yl)-1H-pyrazole-3-carbonyl]-4-azaspiro[2.5]octane-7-carboxamide (Step-2, 380.0 mg, 0.68 mmol) in $(CH_3)_2C0$ (5.00 mL) at 25° C. The resulting solution was stirred at 60° C. for 14 h. The resulting mixture was concentrated under reduced pressure. The residue was purified by reverse phase column chromatography (using the following conditions: Column: C18; mobile phase A: Water (0.5% $NH_4HCO_3$), mobile phase B: MeCN; gradient: 30 B to 50 B in 20 min; 220/254 nm) to obtain the title compound (300.0 mg) as a solid. $^1H$ NMR (400 MHz, CD-OD) δ 9.26-9.18 (m, 1H), 8.47-8.35 (m, 1H), 8.20-8.09 (m, 1H), 7.75-7.60 (m, 2H), 7.45-7.18 (m, 1H), 7.14 (s, 1H), 4.74-4.54 (m, 1H), 3.95 (s, 3H), 3.20-3.03 (m, 1H), 2.65 (s, 3H), 2.59-2.40 (m, 1H), 2.14-1.97 (m, 1), 1.96-1.77 (m, 1H), 1.61-1.39 (m, 1H), 1.39-1.23 (m, 1H), 1.22-1.00 (m, 1H), 0.96-0.64 (m, 3H). LCMS (ESI): 532.25 $[M+H]^+$.

Example 495. A Diastereomeric Mixture of (S)-4-(5-(5-fluoro-2-methoxypyridin-4-yl)-1H-pyrazole-3-carbonyl)-N-(6-((S)-1-hydroxyethyl)pyrazolo[1,5-a]pyridin-3-yl)-4-azaspiro[2.5]octane-7-carboxamide and (S)-4-(5-(5-fluoro-2-methoxypyridin-4-yl)-1H-pyrazole-3-carbonyl)-N-(6-((R)-1-hydroxyethyl)pyrazolo[1,5-a]pyridin-3-yl)-4-azaspiro[2.5]octane-7-carboxamide

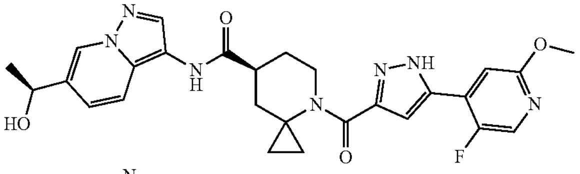

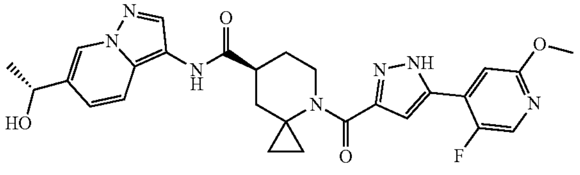

$NaBH_4$ (21.4 mg, 0.56 mmol) was added to a solution of (7S)—N-{6-acetylpyrazolo[1,5-a]pyridin-3-yl}-4-[5-(5-fluoro-2-methoxypyridin-4-yl)-1H-pyrazole-3-carbonyl]-4-azaspiro[2.5]octane-7-carboxamide (Example 494, 300.0 mg, 0.56 mmol) in MeOH (10.00 mL) at 0° C. Then solution was stirred at 25° C. for 14 h. The resulting mixture was concentrated under reduced pressure. The residue was purified by Prep-TLC (DCM/MeOH, 10/1 v/v) to obtain (S)-4-(5-(5-fluoro-2-methoxypyridin-4-yl)-1H-pyrazole-3-carbonyl)-N-(6-((S)-1-hydroxyethyl)pyrazolo[1,5-a]pyridin-3-yl)-4-azaspiro[2.5]octane-7-carboxamide and (S)-4-(5-(5-fluoro-2-methoxypyridin-4-yl)-1H-pyrazole-3-carbonyl)-N-(6-((R)-1-hydroxyethyl)pyrazolo[1,5-a]pyridin-3-yl)-4-azaspiro[2.5]octane-7-carboxamide (150.0 mg) as a solid mixture of diastereomers (Example 495). $^1H$ NMR (400 MHz, DMSO-$d_6$) δ 9.91 (s, 1H), 8.40 (s, 1H), 8.31-8.24 (m, 1H), 8.17 (s, 1H), 7.72-7.63 (m, 1H), 7.37-7.30 (m, 1H), 7.23-7.15 (m, 1H), 7.10-7.02 (m, 1H), 4.85-4.69 (m, 1H), 4.68-4.34 (m, 1H), 3.88 (s, 3H), 3.07-2.86 (m, 1H), 2.41-2.21 (m, 1H), 2.08-1.81 (m, 1H), 1.77-1.51 (m, 1H), 1.46-1.14 (m, 4H), 1.11-0.80 (m, 2H), 0.79-0.47 (m, 3H). LCMS (ESI): 534.20 $[M+H]^+$.

This mixture of two diastereomers (150.0 mg) was separated using Chiral Prep-HPLC.

Column: ART Amylose-SA column

Column dimension: 2×25 cm, 5 μm

Mobile Phase: 1/1 hexanes/DCM (0.5% 2 M $NH_3$·MeOH):EtOH=85:15 hold for 21 min

Flow rate: 20 mL/min

Detection: 220/254 nm

Example 495-A. The first eluting diastereomer (53.0 mg) was obtained as a solid.

The first eluting diastereomer had a retention time of 11.88 min.

$^1$H NMR (400 MHz, $CD_3OD$) δ 8.61-8.38 (m, 1H), 8.20-8.08 (m, 2H), 7.67-7.60 (m, 1H), 7.34-7.08 (m, 3H), 4.78-4.44 (m, 1H), 3.95 (s, 3H), 3.24-2.78 (m, 2H), 2.76-2.29 (m, 1H), 2.23-1.97 (m, 1H), 1.97-1.76 (m, 1H), 1.61-1.39 (m, 4H), 1.39-1.20 (m, 1H), 1.20-0.94 (m, 2H), 0.93-0.65 (m, 2H). LCMS (ESI): 534.25 $[M+H]^+$.

Example 495-B. The second eluting diastereomer (55.0 mg) was obtained as a solid.

The second eluting diastereomer had a retention time of 18.01 min.

$^1$H NMR (400 MHz, $CD_3OD$) δ 8.61-8.36 (m, 1H), 8.19-8.09 (m, 2H), 7.67-7.59 (m, 1H), 7.34-7.21 (m, 2H), 7.18-7.10 (m, 1H), 4.74-4.45 (m, 1H), 3.94 (s, 3H), 3.19-2.89 (m, 2H), 2.80-2.33 (m, 1H), 2.15-1.74 (m, 2H), 1.66-1.38 (m, 4H), 1.39-1.22 (m, 1H), 1.21-0.87 (m, 2H), 0.80 (m, 21-). LCMS (ESI): 534.30 $[M+H]^+$.

Example 496. (7S)—N-(7',8'-dihydro-6'H-spiro[oxetane-3,5'-quinolin]-8'-yl)-4-(5-(5-fluoro-2-methoxypyridin-4-yl)-1H-pyrazole-3-carbonyl)-4-azaspiro[2.5]octane-7-carboxamide

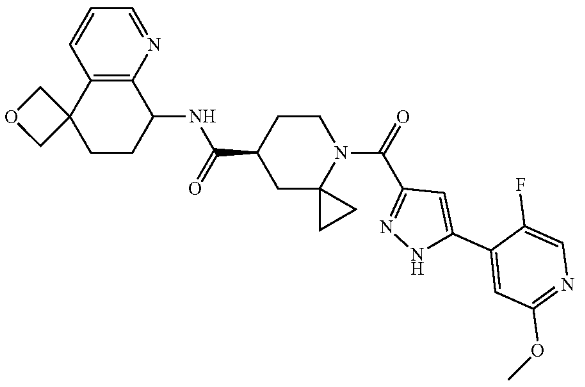 [SMILES: COc1cc(-c2cc(C(=O)N3CC[C@H](C(=O)NC4CCC5(COC5)c5cccnc54)CC34CC4)n[nH]2)c(F)cn1]

Step-1. Dimethyl 8-methylene-7,8-dihydroquinoline-5,5(6H)-dicarboxylate

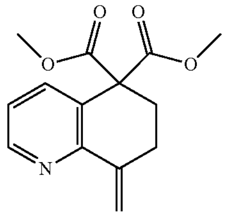 [SMILES: C=C1CCC(C(=O)OC)(C(=O)OC)c2cccnc21]

NaHMDS (72.7 mg, 0.40 mL, 1 M, 396.6 μmol) was added dropwise to a solution of methyl 8-methylene-5,6,7,8-tetrahydroquinoline-5-carboxylate[3] (62.0 mg, 305.1 μmol) in THF (1.52 mL) at −78° C. The resulting mixture was stirred at −78° C. for 30 min and then methyl carbonochloridate (37.5 mg, 0.03 mL, 396.6 μmol) was added. The resulting mixture was stirred at −78° C. for 2.5 h and then quenched at −78° C. with $NH_4Cl$ (sat. aqueous, 1.5 mL) and allowed to warm to 22° C. After vigorous stirring for 30 min, the layers were separated and aqueous layer was extracted with EtOAc. The organic layers were combined, washed with brine, dried ($Na_2SO_4$), filtered, and concentrated in vacuo. The residue was purified by silica gel column chromatography (10 to 40% EtOAc in cyclohexane) to obtain the title compound (63.0 mg) as an oil. $^1$H NMR (400 MHz, $CDCl_3$) δ 2.46-2.53 (m, 2H), 2.65-2.74 (m, 2H), 3.82-3.77 (m, 6H), 5.24 (s, 1H), 6.37 (s, 1H), 7.22 (dd, 1H), 7.73 (d, 1H), 8.54-8.59 (m, 1H).

3 Prepared according to WO2018168818A1 without any deviation from the reported procedure.

Step-2. (8-methylene-5,6,7,8-tetrahydroquinoline-5,5-diyl)dimethanol

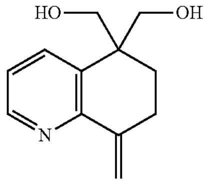

$LiAlH_4$ (256.0 mg, 3.37 mL, 6.74 mmol) was added to a solution of dimethyl 8-methylene-7,8-dihydroquinoline-5,5(6H)-dicarboxylate (Step-1, 734.0 mg, 2.81 mmol) in THE (28.1 mL) at −78° C. The resulting mixture was stirred at −78° C. for 30 min and warmed to −10° C. for 7 h. The reaction mixture was diluted with $Et_2O$ and warmed to 0° C. Water (0.26 mL), NaOH (15% aqueous, 0.26 mL), and water (0.78 mL) were added sequentially and the mixture was warmed to 22° C. for 15 min and $MgSO_4$ was added and the reaction mixture was stirred for an additional 15 min. The resulting mixture was filtered over Celite and concentrated in vacuo. The residue was purified by silica gel column chromatography (0 to 10% EtOAc in cyclohexane) to obtain the title compound (350.0 mg) as a solid. $^1$H NMR (400 MHz, DMSO) δ 1.77-1.86 (m, 2H), 2.59 (t, 2H), 3.49 (dd, 2H), 3.58-3.63 (m, 2H), 4.66 (t, 2H), 5.05 (dt, 1H), 6.09 (dt, 1H), 7.20 (dd, 1H), 7.83 (dd, 1H), 8.38 (dd, 1H).

Step-3. (5-(hydroxymethyl)-8-methylene-5,6,7,8-tetrahydroquinolin-5-yl)methyl 4-methylbenzenesulfonate

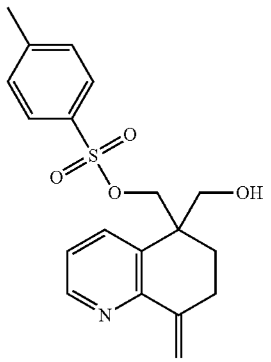 [SMILES: C=C1CCC(CO)(COS(=O)(=O)c2ccc(C)cc2)c2cccnc21]

A solution of (8-methylene-5,6,7,8-tetrahydroquinoline-5,5-diyl)dimethanol (Step-2, 100.0 mg, 0.49 mmol) and pyridine (119.0 mg, 0.12 mL, 1.51 mmol) in DCM (0.541 mL) was cooled to 0° C. A solution of Ts-Cl (97.5 mg, 0.51 mmol) in DCM (1.00 mL) was added to the reaction mixture over 1 h and the reaction mixture was stirred at 0° C. for 30 min and then at 22° C. for 18 h. The reaction mixture was concentrated in vacuo. The residue was purified by silica gel column chromatography (20 to 40% EtOAc in cyclohexane) to obtain the title compound (51.0 mg) as a solid. TLC-MS (APCI): $[M+H]^+$: 360.1.

Step-4. 8'-methylene-7',8'-dihydro-6'H-spiro[oxetane-3,5'-quinoline]

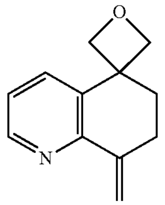

NaH (2.2 mg, 60% Wt, 56.0 μmol) was added to a solution of (5-(hydroxymethyl)-8-methylene-5,6,7,8-tetrahydroquinolin-5-yl)methyl 4-methylbenzenesulfonate (Step-3, 10.0 mg, 28 μmol) in THF (2.8 mL) at 0° C. After continuing to stir at this temperature for 5 min, the reaction mixture was warmed to reflux for 18 h. The reaction mixture was quenched with brine and extracted with EtOAc. The combined organic layers were washed with water, brine, dried ($Na_2SO_4$), filtered, and concentrated in vacuo. The residue was purified by silica gel column chromatography (20% to 40% EtOAc in cyclohexane) to obtain the title compound (4.0 mg) as a solid. $^1H$ NMR (400 MHz, $CDCl_3$) δ 8.53 (dd, 1H), 8.24 (dd, 1H), 7.32 (dd, 1H), 6.30-6.24 (m, 1H), 5.22-5.17 (m, 1H), 4.77 (d, 2H), 4.71 (d, 2H), 2.61-2.55 (m, 2H), 2.30-2.23 (m, 2H).

Step-5. 6',7'-dihydro-8'H-spiro[oxetane-3,5'-quinolin]-8'-one

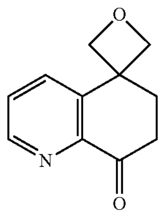 [SMILES: O=C1CCC2(COC2)c2cccnc21]

Potassium osmate dihydrate (1.53 mg, 4.17 μmmol) and sodium periodate (71.3 mg, 0.33 mmol) were added to a solution of 8'-methylene-7',8'-dihydro-6'H-spiro[oxetane-3,5'-quinoline](Step-4, 15.6 mg, 83.3 μmol) in 1,4-dioxane (0.41 mL) and water (0.41 mL) at 0° C. The reaction mixture was stirred at 0° C. for 5 h and then pyridine (13.2 mg, 0.17 mmol) was added and the reaction mixture was warmed to 22° C. for 18 h. The reaction mixture was diluted with DCM and washed with $Na_2S_2O_3$ (15% aqueous solution), dried ($Na_2SO_4$), filtered and concentrated in vacuo. The residue was purified by silica gel column chromatography (0 to 10% MeOH in DCM) to obtain the title compound (13.6 mg) as an oil. $^1H$ NMR (400 MHz, $CDCl_3$) δ 8.83 (d, 1H), 8.47 (d, 1H), 7.68 (dd, 1H), 4.82 (d, 2H), 4.77 (d, 2H), 2.82-2.74 (m, 2H), 2.59-2.52 (m, 2H).

Step-6. tert-butyl (7',8'-dihydro-6'H-spiro[oxetane-3,5'-quinolin]-8'-yl)carbamate

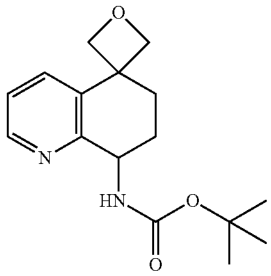 [SMILES: CC(C)(C)OC(=O)NC1CCC2(COC2)c2cccnc21]

Sodium cyanoborohydride (41.5 mg, 0.66 mmol) and ammonium acetate (203.7 mg, 2.64 mmol) were added to a solution of 6',7'-dihydro-8'H-spiro[oxetane-3,5'-quinolin]-8'-one (Step-5, 25.0 mg, 0.13 mmol) in EtOH (2.64 mL). The reaction mixture was heated to 80° C. in a sealed tube for 18 h. The reaction was cooled to 22° C. and $Boc_2O$ (0.1 g, 0.40 mmol) was added. The reaction mixture was stirred at 22° C. for 2 h and then concentrated in vacuo. The residue was dissolved in DCM and washed with $NaHCO_3$ (sat. aqueous). The aqueous layer was extracted with DCM, and the combined organic layers were washed with brine, dried ($Na_2SO_4$), filtered, and concentrated in vacuo. The residue was purified by silica gel column chromatography (0 to 10% MeOH in DCM) and further purified by silica gel column chromatography (20 to 100% EtOAc in cyclohexane, followed by 0 to 20% MeOH in DCM) to obtain the title compound (4.4 mg) as a solid. $^1H$ NMR (400 MHz, CDCl3) δ 8.52 (dd, 1H), 8.27 (dd, 1H), 7.35 (ddd, 1H), 5.58 (s, 1H), 4.82 (d, 1H), 4.73 (d, 1H), 4.70 (d, 1H), 4.62 (dd, 1H), 4.58 (dt, 1H), 2.47-2.37 (m, 1H), 2.37-2.18 (m, 1H), 2.17-2.07 (m, 1H), 2.01 (q, 1H), 1.47 (s, 9H).

Step-7. 7',8'-dihydro-6'H-spiro[oxetane-3,5'-quinolin]-8'-amine md 2,2,2-trifluoroacetate

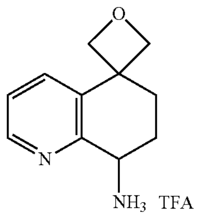 [SMILES: NC1CCC2(COC2)c2cccnc21]

TFA (18 mg, 0.16 mmol) was added to a solution of tert-butyl (7',8'-dihydro-6'H-spiro[oxetane-3,5'-quinolin]-8'-yl)carbamate (Step-6, 4.5 mg, 15.50 μmol) in DCM (0.16 mL). The resulting mixture was stirred at 22° C. for 18 h. The reaction mixture was concentrated under reduced pressure to obtain the title compound as an oil which was taken into the next step without further purification. TLC-MS (APCI): $[M+H]^+$: 191.1.

Step-8. (7S)—N-(7',8'-dihydro-6'H-spiro[oxetane-3,5'-quinolin]-8'-yl)-4-(5-(5-fluoro-2-methoxypyridin-4-yl)-1H-pyrazole-3-carbonyl)-4-azaspiro[2.5]octane-7-carboxamide

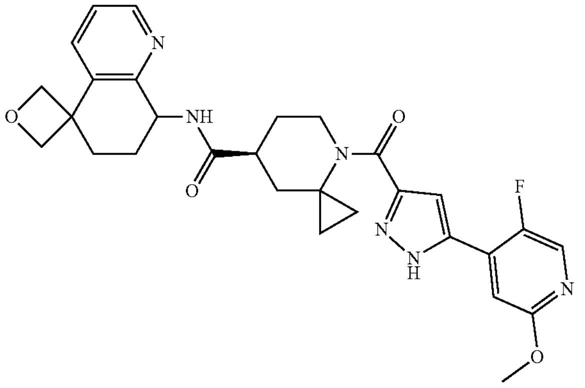 [SMILES: COc1cc(-c2cc(C(=O)N3CC[C@H](C(=O)NC4CCC5(COC5)c5cccnc54)CC34CC4)n[nH]2)c(F)cn1]

HATU (5.6 mg, 15.00 mmol) and 7',8'-dihydro-6'H-spiro[oxetane-3,5'-quinolin]-8'-amine 2,2,2-trifluoroacetate (4.9 mg, 16.00 μmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 5.0 mg, 13.00 μmol) and DIPEA (14.0 mg, 0.11 mmol) in DMF (0.2 mL). The resulting solution was stirred at 22° C. for 18 h. The residue was purified directly by reverse phase column chromatography (using the following conditions: C18 column, 10% to 95% MeOH/Water (0.1% HCOOH)) followed by a second purification by silica gel column chromatography (0 to 10% MeOH in DCM) to obtain the title compound (3.36 mg) as a solid. $^1$H NMR (400 MHz, $CD_3OD$) δ 8.50-8.36 (m, 2H), 8.12 (s, 1H), 7.48 (dd, 1H), 7.40-7.15 (m, 1H), 7.10 (s, 1H), 4.97 (t, 1H), 4.82-4.66 (m, 4H), 3.93 (s, 3H), 2.81 (s, 1H), 2.56-2.17 (m, 4H), 2.12-1.73 (m, 4H), 1.39-1.26 (m, 2H), 1.09-0.97 (m, 1H), 0.94-0.82 (m, 1H), 0.71 (s, 2H). TLC-MS (APCI): $[M+H]^+$: 547.2.

Example 497. (7S)—N-(5-ethyl-2-oxa-5-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide

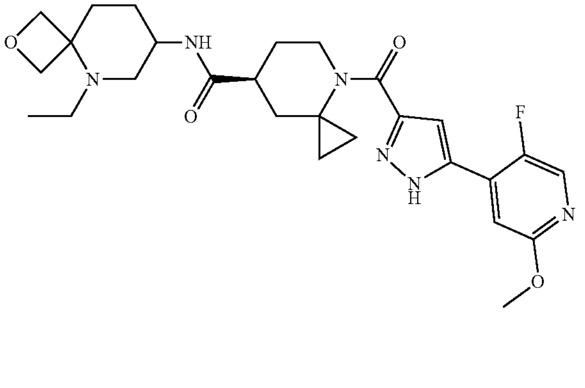 [SMILES: CCN1CC(NC(=O)[C@H]2CCN(C(=O)c3cc(-c4cc(OC)ncc4F)[nH]n3)C3(CC3)C2)CCC12COC2]

Step-1. N-(3-allyloxetan-3-yl)-N-ethyl-2-methylpropane-2-sulfinamide

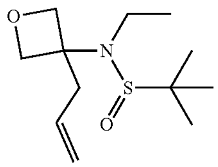 [SMILES: C=CCC1(N(CC)S(=O)C(C)(C)C)COC1]

NaH (662.6 mg, 16.56 mmol, 60% Wt) was added portion-wise to a solution of N-(3-allyloxetan-3-yl)-2-methylpropane-2-sulfinamide (1.50 g, 6.90 mmol) in anhydrous THF (17.25 mL) and DMF (34.51 mL). The resulting mixture was stirred at 0° C. under nitrogen for 1.5 h. Ethyl iodide (2.79 mL, 34.51 mmol) was added in one portion and the reaction mixture was stirred at 22° C. for 16 h. The reaction mixture was diluted with water and extracted with $Et_2O$. The combined organics were washed with water, dried over anhydrous sodium sulfate, filtered and concentrated under reduced pressure. The residue was purified by silica gel column chromatography (0% to 70% EtOAc in cyclohexane) to obtain the title compound (1.18 g) as an oil. $^1$H NMR (400 MHz, CDCl3) δ 6.00 (dddd, 1H), 5.42-5.19 (m, 2H), 4.89-4.75 (m, 2H), 4.40 (ddd, 1H), 4.29 (ddd, 1H), 3.31 (dq, 1H), 2.90-2.62 (m, 3H), 1.26 (s, 9H), 1.05 (t, 3H).

Step-2. 3-allyl-N-ethyloxetan-3-amine hydrochloride

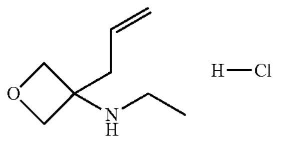

HCl (184.1 mg, 5.05 mmol, 4 M in 1,4-dioxane) was added to a solution of N-(3-allyloxetan-3-yl)-N-ethyl-2-methylpropane-2-sulfinamide (Step-1, 1.18 g, 4.81 mmol) in MeOH (24.04 mL) at −78° C. under vigorous stirring. After 5 min, volatiles were removed under reduced pressure at 0° C. The residue was triturated in $Et_2O$ and the solid was filtered off to obtain the title compound (810.0 mg) as a solid. $^1$H NMR (400 MHz, DMSO) δ 5.99 (ddt, 1H), 5.42-5.21 (m, 2H), 4.73 (d, 2H), 4.44 (d, 2H), 3.02-2.92 (m, 2H), 2.67 (dd, 2H), 1.24 (t, 3H).

Step-3. methyl 2-(((3-allyloxetan-3-yl)(ethyl)amino)methyl)acrylate

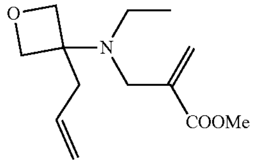 [SMILES: C=CCC1(N(CC)CC(=C)C(=O)OC)COC1]

Methyl2-(bromomethyl)acrylate (856.9 mg, 4.79 mmol) was added to a solution of 3-allyl-N-ethyloxetane-3-amine hydrochloride (Step-2, 810.0 mg, 4.56 mmol) and triethylamine (1.30 mL, 9.35 mmol) in DCM (22.8 mL) at 0° C. under nitrogen. The reaction mixture was allowed to reach 22° C. and stirred for 16 h. Water was added and the aqueous was extracted with DCM. The combined organics were dried over anhydrous sodium sulfate, filtered and concentrated under reduced pressure. The residue was purified by silica gel column chromatography (0% to 25% EtOAc in cyclohexane) to obtain the title compound (1.05 g) as an oil. $^1H$ NMR (400 MHz, $CDCl_3$) δ 6.27-6.22 (m, 1H), 6.10-6.08 (m, 1H), 6.07-5.95 (m, 1H), 5.26-5.15 (m, 2H), 4.56 (d, 2H), 4.41-4.25 (m, 2H), 3.76 (s, 3H), 3.26 (t, 2H), 2.61-2.44 (m, 4H), 0.92 (t, 3H).

Step-4. methyl 5-ethyl-2-oxa-5-azaspiro[3.5]non-7-ene-7-carboxylate

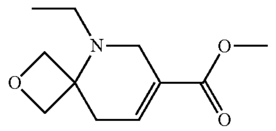

In a sealed tube, nitrogen was bubbled in a solution of methyl 2-(((3-allyloxetan-3-yl)(ethyl)amino)methyl)acrylate (Step-3, 1.05 g, 4.39 mmol) in DCM (169.00 mL) for 15 min. Grubbs II (372.0 mg, 0.44 mmol) was added and the reaction mixture was stirred at 45° C. for 18 h. DCM was removed under reduced pressure and the residue was purified by silica gel column chromatography (0% to 15% EtOAc in MeOH) to obtain the title compound (872.0 mg) as an oil. $^1H$ NMR (400 MHz, $CDCl_3$) δ 7.03-6.94 (m, 1H), 4.66 (d, 2H), 4.26 (d, 2H), 3.74 (s, 3H), 3.51-3.40 (m, 2H), 2.69-2.56 (m, 2H), 2.36 (q, 2H), 1.13 (t, 3H).

Step-5. methyl 5-ethyl-2-oxa-5-azaspiro[3.5]nonane-7-carboxylate

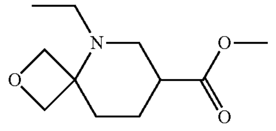

Pd/C (15.0 mg, 10 wt. %) was added to a solution of methyl 5-ethyl-2-oxa-5-azaspiro[3.5]non-7-ene-7-carboxylate (Step-4, 250.0 mg, 1.18 mmol) in MeOH (7.40 mL) and the resulting mixture was stirred at 22° C. for 16 h under hydrogen atmosphere (1 atm). The reaction mixture was stirred on a Teflon pad and the filtrate was concentrated under reduced pressure. The residue was purified by silica gel column chromatography (0% to 100% EtOAc in cyclohexane) to obtain the title compound (158.0 mg) as an oil. $^1H$ NMR (400 MHz, $CDCl_3$) δ 4.71-4.62 (m, 2H), 4.35 (d, 1H), 4.30-4.23 (m, 1H), 3.67 (s, 3H), 3.10-2.99 (m, 1H), 2.98-2.86 (m, 1H), 2.65-2.51 (m, 1H), 2.46-2.30 (m, 2H), 2.12 (dt, 1H), 1.99-1.88 (m, 1H), 1.74 (t, 1H), 1.66-1.51 (m, 1H), 1.13 (t, 3H).

Step-6. 5-ethyl-2-oxa-5-azaspiro[3.5]nonane-7-carboxylic acid

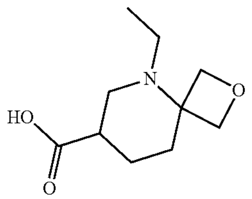

LiOH (29.2 mg, 1.22 mmol) was added to a solution of methyl 5-ethyl-2-oxa-5-azaspiro[3.5]nonane-7-carboxylate (Step-5, 153.0 mg, 0.72 mmol) in $H_2O$ (1.43 mL) and THF (1.43 mL). The reaction mixture was stirred at 22° C. for 2 h. The reaction mixture was concentrated to dryness to obtain the title compound and used in the next step without further purification. TLC-MS (APCI): $[M+H]^+$=200.1

Step-7. tert-butyl (5-ethyl-2-oxa-5-azaspiro[3.5]nonan-7-yl)carbamate

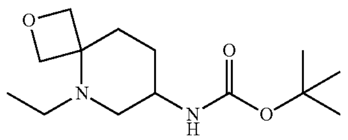 [SMILES: CCN1CC(NC(=O)OC(C)(C)C)CCC12COC2]

In a sealed tube, triethylamine (392 μL, 2.81 mmol) was added to a solution of 5-ethyl-2-oxa-5-azaspiro[3.5]nonane-7-carboxylic acid (Step-6, 140.0 mg, 0.70 mmol) in anhydrous tert-butanol (3.50 mL) followed by the addition of diphenylphosphoryl azide (181.8 μL, 0.84 mmol). The tube was sealed and the reaction mixture was stirred at 90° C. for 16 h. The solvent was removed under reduced pressure and the residue was diluted with water. The aqueous was extracted with EtOAc. The combined organics were dried over anhydrous sodium sulfate, filtered and concentrated under reduced pressure. The residue was purified by silica gel column chromatography (0% to 100% EtOAc in cyclohexane) to obtain the title compound (75.4 mg) as a solid. $^1H$ NMR (400 MHz, $CDCl_3$) δ 4.80-4.63 (m, 2H), 4.36-4.25 (m, 2H), 3.69 (s, 1H), 2.97-2.16 (m, 4H), 2.04 (s, 2H), 1.81-1.68 (m, 2H), 1.45 (s, 9H), 1.12 (t, 3H).

Step-8. 1-((5-ethyl-2-oxa-5-azaspiro[3.5]nonan-7-yl)-$\lambda^4$-azanyl)-2,2,2-trifluoroethan-1-one

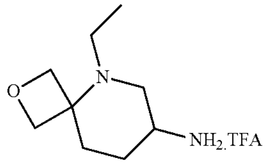

TFA (54.1 μL, 0. 70 mmol) was added to a solution of tert-butyl (5-ethyl-2-oxa-5-azaspiro[3.5]nonan-7-yl)carbamate (Step-7, 38.0 mg, 0.14 mmol) in in DCM (0.70 mL). The reaction mixture was stirred at 22° C. for 2 h under nitrogen. Volatiles were removed under reduced pressure and remaining TFA was removed by co-evaporation with toluene to obtain the title compound. The residue was used in the next step without further purification. TLC-MS (APCI). $[M+H]^+$=171.1.

Step-9. (7S)—N-(5-ethyl-2-oxa-5-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide

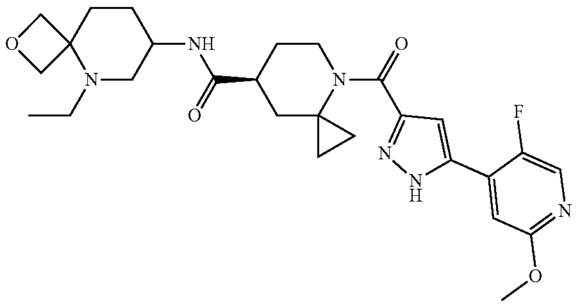 [SMILES: CCN1CC(NC(=O)[C@H]2CCN(C(=O)c3cc(-c4cc(OC)ncc4F)[nH]n3)C3(CC3)C2)CCC12COC2]

HATU (39.1 mg, 0.10 mmol) and 5-ethyl-2-oxa-5-azaspiro[3.5]nonan-7-amine (Step-8, 17.5 mg, 0.10 mmol) were added to a solution of(S)-4-[5-(5-fluoro-2-methoxy-pyridin-4-yl)-1H-pyrazole-3-carbonyl]-4-azaspiro[2.5]octane-7-carboxylic acid (INTERMEDIATE 527-A, 35.0 mg, 0.09 mmol) and DIPEA (82.0 μL, 0.47 mmol) in DMF (0.50 mL). The resulting solution was stirred for at 22° C. for 16 h. The reaction mixture was directly purified by reverse phase column chromatography (using the following conditions: C18 column, 5% to 95% MeOH/Water (0.1% HCOOH)) to obtain the title compound (17.5 mg) as a solid. $^1H$ NMR (400 MHz, DMSO) δ 13.97 (d, 1H), 8.27 (d, 1H), 7.59 (s, 1H), 7.31 (d, 1H), 7.03 (s, 1H), 4.94-4.38 (m, 3H), 4.26 (d, 1H), 4.14 (d, 1H), 3.87 (s, 3H), 3.75-3.60 (m, 1H), 3.26-3.01 (m, 1H), 2.92-2.80 (m, 1H), 2.79-2.70 (m, 1H), 2.70-2.57 (m, 1H), 2.41-2.24 (m, 1H), 2.21-2.09 (m, 1H), 2.05-1.87 (m, 2H), 1.79-1.39 (m, 4H), 1.34-1.17 (m, 1.63H), 1.15-0.96 (m, 3.35H), 0.96-0.73 (m, 1H), 0.71-0.44 (m, 2H).

Example 498. (S)—N-(5,5-dimethyl-6,7-dihydro-5H-pyrazolo[5,1-b][1,3]oxazin-3-yl)-4-(5-(5-fluoro-2-methoxypyridin-4-yl)-1H-pyrazole-3-carbonyl)-4-azaspiro[2.5]octane-7-carboxamide

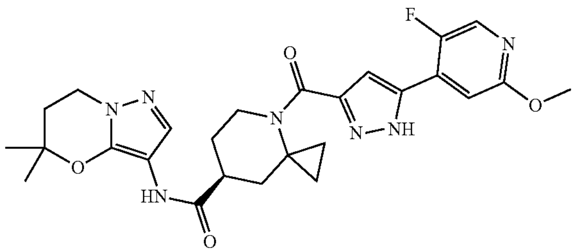

Step-1. 3-hydroxy-3-methylbutyl methanesulfonate

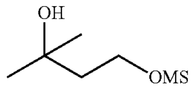

TEA (1.46 g, 14.4 mmol) was added to a solution of 3-methylbutane-1,3-diol (1.00 g, 9.60 mmol) in DCM (8.00 mL) at 0° C. A solution of Ms-Cl (121 g, 10.6 mmol) in DCM (4.53 mL) was added and the reaction mixture was stirred at 0° C. for 4 h. The reaction mixture was quenched with $NaHCO_3$ (sat. aqueous). The organic layer was dried ($Na_2SO_4$), filtered and concentrated in vacuo to obtain the title compound (1.52 g) as an oil. The residue was used in the next step directly without further purification. $^1H$ NMR (400 MHz, $CDCl_3$) δ 4.42 (t, 2H), 3.02 (s, 3H), 1.96 (t, 2H), 1.33-1.29 (m, 6H).

Step-2. 2-methyl-4-(4-nitro-1H-pyrazol-1-yl)butan-2-ol

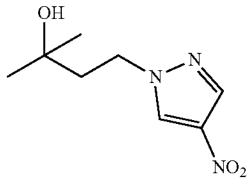

4-nitro-1H-pyrazole (0.39 g, 3.45 mmol) was added to a solution of 3-hydroxy-3-methylbutyl methanesulfonate (Step-1, 1.57 g, 8.62 mmol), $K_2CO_3$ (953.0 mg, 6.90 mmol), and KI (1.43 g, 8.62 mmol) in MeCN (33.00 mL) at 5° C. The reaction mixture was stirred at this temperature for 10 min and slowly heated to 80° C. for 18 h. The reaction mixture was diluted with water, extracted with EtOAc, dried ($Na_2SO_4$), filtered and concentrated in vacuo. The residue was purified by silica gel column chromatography (5 to 50% EtOAc in cyclohexane) to obtain the title compound (632.0 mg) as an oil. $^1H$ NMR (400 MHz, $CDCl_3$) δ 8.17 (d, 1H), 8.08-8.03 (m, 1H), 4.37-4.30 (m, 2H), 2.14-2.06 (m, 2H), 1.32-1.30 (m, 6H).

Step-3. 5,5-dimethyl-3-nitro-6,7-dihydro-5H-pyrazolo[5,1-b][1,3]oxazine

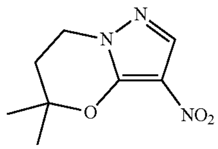

LiHMDS (7.61 mL, 7.61 mmol, 1M) was added dropwise to a solution of 2-methyl-4-(4-nitro-1H-pyrazol-1-yl)butan-2-ol (Step-2, 632.0 mg, 3.17 mmol) in THF (9.61 mL) at −78° C. The resulting mixture was stirred at this temperature for 2 h. A solution of perchloroethane (901.0 mg, 3.81 mmol) in THF (1.59 mL) was added and the mixture was warmed up to 22° C. for 18 h. The reaction mixture was quenched with $NH_4Cl$ (sat. aqueous), and extracted with DCM and EtOAc. The organic layers were combined, dried over anhydrous $Na_2SO_4$, filtered, and concentrated under reduced pressure to obtain the title compound (621.0 mg) as a solid. The residue was used in the next step without further purification. $^1H$ NMR (400 MHz, $CDCl_3$) δ 7.96 (s, 1H), 4.17 (t, 2H), 2.18 (t, 2H), 1.63-1.58 (m, 6H).

Step-4. 5,5-dimethyl-6,7-dihydro-5H-pyrazolo[5,1-b][1,3]oxazin-3-amine

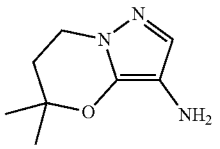

In a round bottom flask equipped with a condenser, zinc (119.4 mg, 1.83 mmol) was added to a mixture of ammonium chloride (97.7 mg, 1.83 mmol) and 5,5-dimethyl-3-nitro-6,7-dihydro-5H-pyrazolo[5,1-b][1,3]oxazine (Step-3, 36.0 mg, 0.18 mmol) in DCM (0.3 mL) and MeOH (0.3 mL) under vigorous stirring. The resulting mixture was vigorously stirred at 22° C. for 2 h. The solid was filtered off and the filtrate was concentrated under reduced pressure. The residue was purified by silica gel column chromatography (0% to 20% MeOH in DCM) to obtain the title compound (10.7 mg) as an oil. $^1H$ NMR (400 MHz, $CDCl_3$) δ 7.15 (s, 1H), 4.09 (t, 2H), 2.65 (s, 2H), 2.05 (t, 2H), 1.46-1.43 (m, 6H).

Step-5. (S)—N-(5,5-dimethyl-6,7-dihydro-5H-pyrazolo[5,1-b][1,3]oxazin-3-yl)-4-(5-(5-fluoro-2-methoxypyridin-4-yl)-1H-pyrazole-3-carbonyl)-4-azaspiro[2.5]octane-7-carboxamide

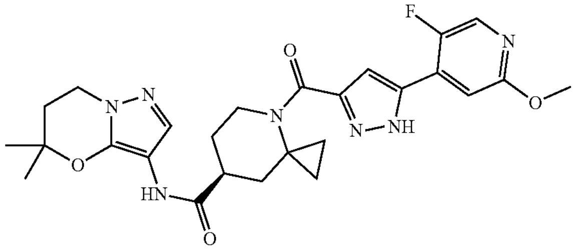

HATU (23.5 mg, 61.7 μmol) and 5,5-dimethyl-6,7-dihydro-5H-pyrazolo[5,1-b][1,3]oxazin-3-amine (Step-4, 10.3 mg, 61.7 μmol) were added to a solution of(S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 21.0 mg, 56.1 μmol) and DIPEA (18.1 mg, 0.14 mmol) in DMF (0.40 mL). The resulting solution was stirred at 22° C. for 16 h. The reaction mixture was directly purified by reverse phase column chromatography (using the following conditions: C18 column, 5% to 95% MeOH/Water (0.1% HCOOH)) to obtain the title compound (12.0 mg) as a solid. $^1H$ NMR (400 MHz, DMSO-$d_6$) δ 13.97 (s, 1H), 9.10 (s, 1H), 8.27 (d, 1H), 7.43 (s, 1H), 7.33 (d, 1H), 7.04 (s, 1H), 4.67-4.23 (m, 1H), 4.04 (t, 2H), 3.88 (s, 3H), 3.33 (s, 2H), 2.90 (s, 1H), 2.37-2.13 (m, 1H), 2.07 (t, 2H), 1.79 (s, 1H), 1.69-1.47 (m, 1H), 1.42-1.38 (m, 6H), 1.34-1.17 (m, 1H), 1.13-0.46 (m, 3H). $^{19}F$ NMR (471 MHz, $CD_3OD$) δ −143.34. TLC-MS (APCI): $[M+H]^+$: 524.2.

Example 499. (S)—N-((1-(aminomethyl)-2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide

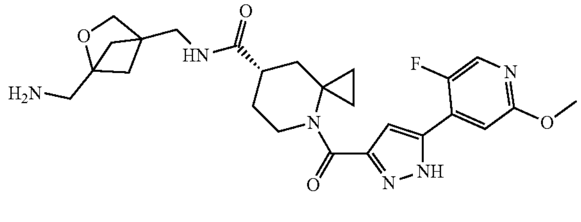 [SMILES: COc1cc(-c2cc(C(=O)N3CC[C@H](C(=O)NCC45COC(CN)(C4)C5)CC34CC4)n[nH]2)c(F)cn1]

Step-1. tert-butyl ((4-(aminomethyl)-2-oxabicyclo[2.1.1]hexan-1-yl)methyl)carbamate

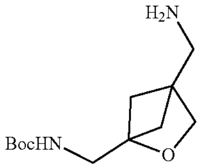 [SMILES: CC(C)(C)OC(=O)NCC12CC(CN)(CO1)C2]

$NaBH_4$ (31.8 mg, 0.84 mmol) was added portionwise to a solution of tert-butyl ((4-cyano-2-oxabicyclo[2.1.1]hexan-1-yl)methyl)carbamate (50.0 mg, 0.21 mmol)[4] and nickel(II) chloride hexahydrate (64.8 mg, 0.27 mmol) in MeOH (4.20 mL) at 0° C. under vigorous stirring. After complete addition the resulting mixture was allowed to warm up to 22° C. and stirred at this temperature for 5 h. The reaction mixture was concentrated under reduced pressure. The residue was purified by silica gel column (0% to 20% MeOH (2.5M ammonia) in DCM) to obtain the title compound (38.0 mg) as an oil. $^1H$ NMR (400 MHz, $CDCl_3$) δ 4.88 (s, 1H), 3.54 (s, 2H), 3.40 (d, 2H), 2.00 (br s, 2H), 1.77-1.67 (m, 21-), 1.65-1.51 (m, 2H), 1.41 (s, 9H).

[4] Prepared according to V. V. Levterov, Y. Panasyuk, V. O. Pivnytska, P. K. Mykhailiuk, Angew. Chem. Int. Ed. 2020, 59, 7161.

Step-2. tert-butyl (S)-((4-((4-(5-(5-fluoro-2-methoxypyridin-4-yl)-1H-pyrazole-3-carbonyl)-4-azaspiro[2.5]octane-7-carboxamido)methyl)-2-oxabicyclo[2.1.1]hexan-1-yl)methyl)carbamate

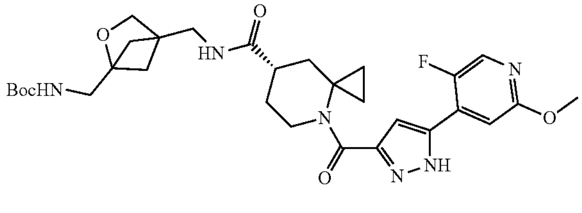 [SMILES: COc1cc(-c2cc(C(=O)N3CC[C@H](C(=O)NCC45COC(CNC(=O)OC(C)(C)C)(C4)C5)CC34CC4)n[nH]2)c(F)cn1]

HATU (39.1 mg, 102.8 μmol) and tert-butyl ((4-(aminomethyl)-2-oxabicyclo[2.1.1]hexan-1-yl)methyl)carbamate (Step-1, 38.5 mg, 158.9 μmol) were added to a solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 35.0 mg, 93.5 μmol) and DIPEA (49.0 μL, 280.5 μmol) in DMF (0.3 mL). The resulting solution was stirred for at 22° C. for 16 h. The reaction mixture was directly purified by reverse phase column chromatography (using the following conditions: C18 column, 5% to 95% MeOH/Water (0.1% HCOOH)) to obtain the title compound (35.2 mg) as a solid. $^1$H NMR (400 MHz, DMSO-$d_6$) δ 8.27 (d, 1H), 8.01-7.91 (m, 1H), 7.32 (d, 1H), 7.03 (d, 1H), 6.85 (t, 1H), 4.62-3.98 (m, 2H), 3.88 (s, 3H), 3.46 (s, 2H), 3.37-3.32 (m, 2H), 3.17 (s, 2H), 3.16 (s, 1H), 2.76-2.64 (m, 1H), 2.32-2.11 (m, 1H), 1.80-1.67 (m, 1H), 1.55-1.49 (m, 2H), 1.36 (s, 9H), 1.32-1.26 (m, 2H), 1.22-1.13 (m, 1H), 1.02-0.79 (m, 2H), 0.69-0.51 (m, 2H). $^{19}$F NMR (376 MHz, DMSO) δ −142.38.

Step-3. (S)—N-((1-(aminomethyl)-2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide

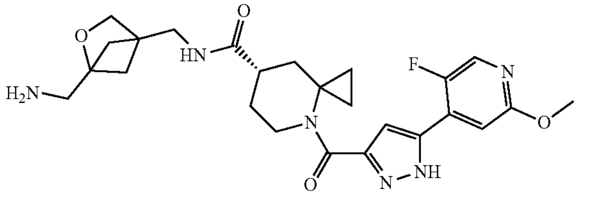 [SMILES: COc1cc(-c2cc(C(=O)N3CC[C@H](C(=O)NCC45COC(CN)(C4)C5)CC34CC4)n[nH]2)c(F)cn1]

HCl (250.6 μL, 1.0 mmol, 4 M in 1,4-dioxane) was added to a solution of tert-butyl (S)-((4-((4-(5-(5-fluoro-2-methoxypyridin-4-yl)-1H-pyrazole-3-carbonyl)-4-azaspiro[2.5]octane-7-carboxamido)methyl)-2-oxabicyclo[2.1.1]hexan-1-yl)methyl)carbamate (Step-2, 30.0 mg, 50.1 μmol) in MeOH (0.25 mL) at 0° C. The reaction mixture was allowed to reach 22° C. and stirred for 2.5 h. Volatiles were removed under reduced pressure. The residue was dissolved in DMF and triethylamine (48.9 μL, 350.8 μmol). The resulting solution was purified by reverse phase column chromatography (using the following conditions: C18 column, 5% to 95% MeOH/Water (0.1% HCOOH)) and further purified by silica gel column chromatography (0% to 20% MeOH (2.5 M ammonia) in DCM) to obtain the title compound (4.0 mg) as a solid. $^1$H NMR (400 MHz, $CD_3OD$) δ 8.02 (d, 1H), 7.17 (d, 1H), 7.00 (d, 1H), 4.62-4.21 (m, 1H), 3.83 (s, 3H), 3.51 (s, 2H), 3.41 (s, 2H), 2.80 (s, 2H), 2.78-2.67 (m, 1H), 2.43-2.25 (m, 1H), 1.84-1.58 (m, 2H), 1.52 (dd, 2H), 1.42 (dd, 2H), 1.29-1. 12 (m, 2H), 0.93-0.52 (m, 4H). $^{19}$F NMR (376 MHz, $CD_3OD$) δ −144.95.

Example 500. (S)-4-(3-(5-fluoro-2-methoxypyridin-4-yl)-1H-pyrazole-5-carbonyl)-N-((2-(trifluoromethyl)pyridin-3-yl)methyl)-4-azaspiro[2.5]octane-7-carboxamide

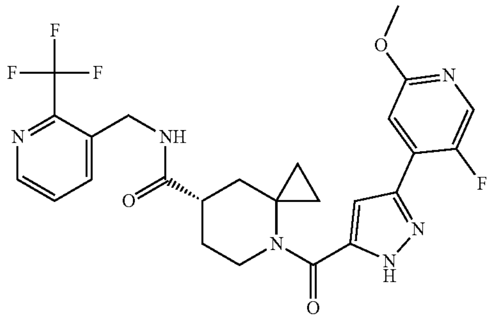 [SMILES: COc1cc(-c2cc(C(=O)N3CC[C@H](C(=O)NCc4cccnc4C(F)(F)F)CC34CC4)[nH]n2)c(F)cn1]

The title compound was prepared using a procedure similar to the one described for the synthesis of Example 325, except 1-[2-(trifluoromethyl)pyridin-3-yl]methanamine was used as a starting material. The residue was purified by silica gel column chromatography eluting with DCM/MeOH (8/1 v/v) to obtain the title compound (84.7 mg) as a solid. $^1$H NMR (400 MHz, $CD_3OD$) δ 8.58 (d, 1H), 8.14 (d, 1H), 7.97 (d, 1H), 7.73-7.59 (m, 1H), 7.43-6.98 (m, 2H) 4.73-4.52 (m, 3H), 3.95 (s, 3H), 3.05-2.81 (m, 1H), 2.72-2.29 (m, 1H), 2.05-1.70 (m, 2H), 1.58-1.19 (m, 2H), 1.06 (s, 2H), 0.87-0.59 (m, 2H). LCMS (ESI): 533.25 $[M+H]^+$.

Example 501. A Diastereomeric Mixture of (S)-4-(5-(5-fluoro-2-methoxypyridin-4-yl)-1H-pyrazole-3-carbonyl)-N-((1R,3R,4S)-3-hydroxy-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1S,3S,4R)-3-hydroxy-4-(trifluoromethyl) cyclohexyl)-4-azaspiro[2.5]octane-7-carboxamide

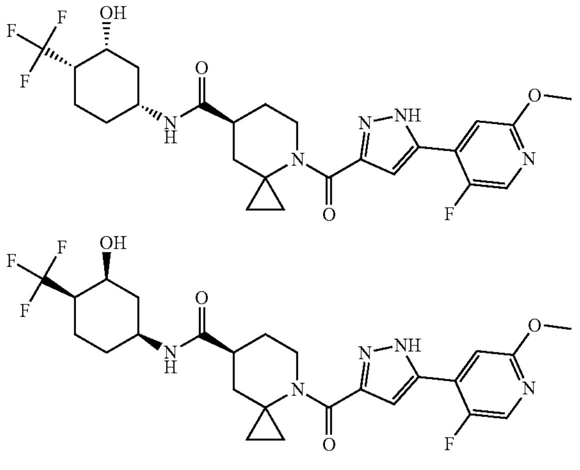

Step-1. 5-amino-2-(trifluoromethyl)phenol

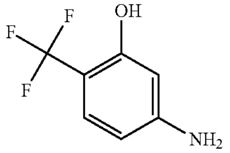

$BBr_3$ (28.3 mL, 28.24 mmol) was added to a solution of 3-methoxy-4-(trifluoromethyl)aniline (270.0 mg, 1.41 mmol) in DCE (5.00 mL) at 0° C. The resulting mixture was stirred at 25° C. for 14 h. The resulting mixture was concentrated under vacuum. The residue was purified by silica gel column chromatography eluting with DCM/MeOH (15/1 v/v) to obtain the title compound (260.0 mg) as a solid. LCMS (ESI): 178.00 [M+H]T Step-2. 5-amino-2-(trifluoromethyl)cyclohexan-1-ol

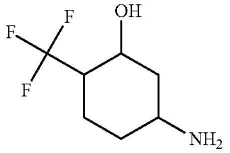

$PtO_2$ (260.0 mg, 1.15 mmol) was added to a stirred solution of 5-amino-2-(trifluoromethyl)phenol (Step-1, 260.0 mg, 1.47 mmol) in AcOH (3.00 mL). The resulting mixture was stirred at was stirred at 25° C. for 14 h under hydrogen atmosphere. The resulting mixture was concentrated under vacuum. The residue was purified by silica gel column chromatography eluting with DCM/MeOH (10/1 v/v) to obtain the title compound (50.0 mg) as a solid. LCMS (ESI): 184.00 [M+H]+

Step-3. (S)-4-(5-(5-fluoro-2-methoxypyridin-4-yl)-1H-pyrazole-3-carbonyl)-N-((1R,3R,4S)-3-hydroxy-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1S,3S,4R)-3-hydroxy-4-(trifluoromethyl) cyclohexyl)-4-azaspiro[2.5]octane-7-carboxamide

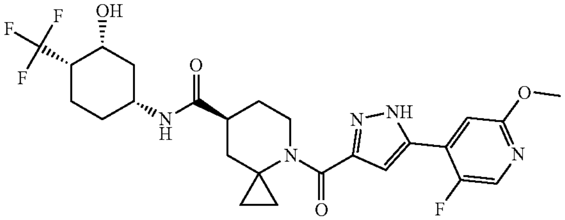

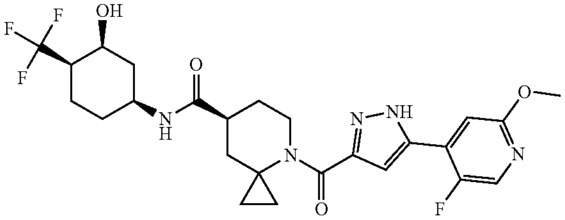

HOBt (49.8 mg, 0.37 mmol), EDCI (70.6 mg, 0.37 mmol), and 5-amino-2-(trifluoromethyl)cyclohexan-1-ol (Step-2, 45.0 mg, 0.25 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 92.0 mg, 0.25 mmol) and DIPEA (158.8 mg, 1.23 mmol) in DMF (1.00 mL). The resulting mixture was stirred 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 30 B to 50 B in 30 min; 220/254 nm) to obtain (S)-4-(5-(5-fluoro-2-methoxypyridin-4-yl)-1H-pyrazole-3-carbonyl)-N-((1R,3R,4S)-3-hydroxy-4-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1S,3S,4R)-3-hydroxy-4-(trifluoromethyl)cyclohexyl)-4-azaspiro[2.5]octane-7-carboxamide (40.0 mg) as a solid mixture of diastereomers (Example 501). $^1H$ NMR (400 MHz, $CD_3OD$) δ 8.22-8.00 (m, 1H), 7.46-7.16 (m, 1H), 7.14-7.04 (m, 1H), 4.74-4.37 (m, 1H), 4.36-4.27 (m, 1-H), 4.20-4.04 (m, 1H), 3.95 (s, 3H), 2.91-2.65 (m, 1H), 2.46-2.21 (m, 2H), 2.15-1.73 (m, 5H), 1.71-1.51 (m, 3H), 1.48-1.24 (m, 2H), 1.19-0.85 (m, 2H), 0.84-0.62 (m, 2H). LCMS (ESI): 540.20 $[M+H]^+$.

This mixture of two diastereomers (40.0 mg) was separated using Chiral Prep-HPLC.

Column: CHIRAL ART Amylose-SA column

Column dimension: 2×25 cm, 5 μm

Mobile Phase: hexanes (0.5% 2 M $NH_3$·MeOH):1/1 MeOH/DCM=70:30 hold for 17 min

Flow rate: 20 mL/min

Detection: 220/254 nm

Example 501-A. The first eluting diastereomer (10.0 mg) was obtained as a solid.

The first eluting diastereomer had a retention time of 8.72 min.

$^1H$ NMR (400 MHz, $CD_3OD$) δ 8.14 (s, 1H), 7.46-7.18 (m, 1H), 7.11 (m, 1H), 4.73-4.50 (m, 1H), 4.43-4.25 (m, 1H), 4.19-4.03 (m, 1H), 3.95 (s, 3H), 2.87-2.69 (m, 1H), 2.46-2.24 (m, 2H), 2.10-1.74 (m, 5H), 1.73-1.55 (m, 3H), 1.49-1.22 (m, 3H), 1.16-0.86 (m, 2H), 0.85-0.62 (m, 2H). LCMS (ESI): 540.30 $[M+H]^+$.

Example 501-B. The second eluting diastereomer (9.2 mg) was obtained as a solid.

The second eluting diastereomer had a retention time of 14.43 min.

$^1H$ NMR (400 MHz, $CD_3OD$) δ 8.22-8.01 (m, 1H), 7.45-7.17 (m, 1H), 7.15-6.96 (m, 1H), 4.71-4.44 (m, 1H), 4.39-4.26 (m, 1H), 4.18-4.03 (m, 1H), 3.95 (s, 3H), 2.88-2.67 (m, 1H), 2.47-2.23 (m, 2H), 2.13-1.85 (m, 5H), 1.83-1.75 (m, 1H), 1.71-1.53 (m, 2H), 1.48-1.24 (m, 3H), 1.19-0.91 (m, 1H), 0.86-0.61 (m, 3H). LCMS (ESI): 540.30 $[M+H]^+$.

Example 502. A Diastereomeric Mixture of (S)-4-(5-(5-fluoro-2-methoxypyridin-4-yl)-1H-pyrazole-3-carbonyl)-N—((S)-2-(trifluoromethyl)-5,6,7,8-tetrahydroimidazo[1,2-a]pyridin-8-yl)-4-azaspiro[2.5]octane-7-carboxamide and (S)-4-(5-(5-fluoro-2-methoxypyridin-4-yl)-1H-pyrazole-3-carbonyl)-N—((R)-2-(trifluoromethyl)-5,6,7,8-tetrahydroimidazo[1,2-a]pyridin-8-yl)-4-azaspiro[2.5]octane-7-carboxamide

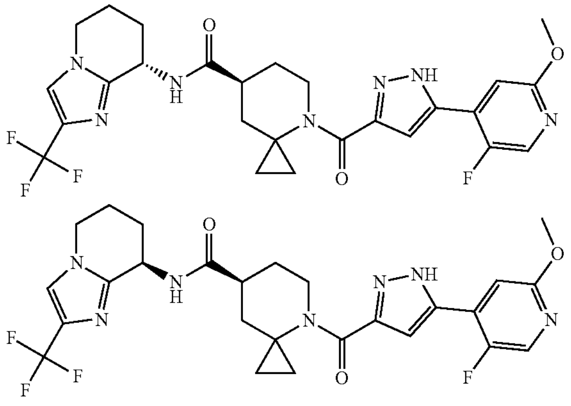

Step-1. 8-bromo-2-(trifluoromethyl)imidazo[1,2-a]pyridine

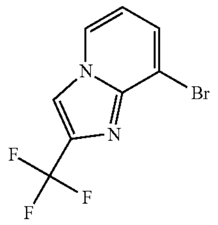 [SMILES: FC(F)(F)c1cn2cccc(Br)c2n1]

3-bromo-1,1,1-trifluoropropan-2-one (331.1 mg, 1.73 mmol) was added to a solution of 3-bromopyridin-2-amine (300.0 mg, 1.73 mmol) in EtOH (4.00 mL). The resulting mixture was refluxed at 160° C. for 1 h. The resulting mixture was concentrated under reduced pressure. The residue was purified by Prep-TLC (petroleum ether/EtOAc, 1/1 v/v) to obtain the title compound (350.0 mg) as a solid. LCMS (ESI): 265.00 $[M+H]^+$.

Step-2. N,N-dibenzyl-2-(trifluoromethyl)imidazo[1,2-a]pyridin-8-amine

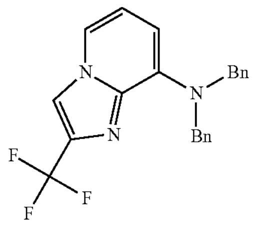 [SMILES: FC(F)(F)c1cn2cccc(N(Cc3ccccc3)Cc3ccccc3)c2n1]

Pd-PEPPSI-iHeptCl (73.5 mg, 0.08 mmol, CAS #: 905459-27-0), $Cs_2CO_3$ (491.7 mg, 1.51 mmol) and dibenzyl amine (148.9 mg, 0.76 mmol) were added to a stirred solution of 8-bromo-2-(trifluoromethyl)imidazo[1,2-a]pyridine (Step-1, 200.0 mg, 0.76 mmol) in 1,4-dioxane (4.00 mL). The resulting mixture was stirred at 80° C. for 14 h under nitrogen atmosphere. The resulting mixture was concentrated under reduced pressure. The residue was purified by Prep-TLC (petroleum ether/EtOAc, 1/1 v/v) to obtain the title compound (250.0 mg) as a solid. LCMS (ESI): 382.00 $[M+H]^+$.

Step-3. 2-(trifluoromethyl)-5H,6H,7H,8H-imidazo[1,2-a]pyridin-8-amine

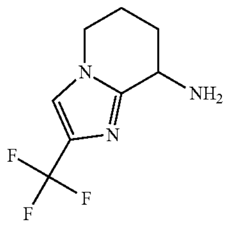 [SMILES: NC1CCCn2cc(C(F)(F)F)nc21]

Pd/C (114.9 mg, 10%) was added to a stirred solution of N,N-dibenzyl-2-(trifluoromethyl)imidazo[1,2-a]pyridin-8-amine (Step-2, 230.0 mg, 0.60 mmol) in MeOH (1.50 mL) and AcOH (0.50 mL) at 0° C. The resulting mixture was stirred at 25° C. for 14 h under hydrogen atmosphere. The resulting mixture was filtered, the filter cake was washed with MeOH. The filtrate was concentrated under reduced pressure. The residue was purified by SiliaBond® Propylsulfonic Acid (SCX-2) eluting with $NH_3$ in MeOH (7 M) to obtain the title compound (120.0 mg) as a solid. LCMS (ESI): 206.00 $[M+H]^+$.

Step-4. (S)-4-(5-(5-fluoro-2-methoxypyridin-4-yl)-1H-pyrazole-3-carbonyl)-N—((S)-2-(trifluoromethyl)-5,6,7,8-tetrahydroimidazo[1,2-a]pyridin-8-yl)-4-azaspiro[2.5]octane-7-carboxamide and (S)-4-(5-(5-fluoro-2-methoxypyridin-4-yl)-1H-pyrazole-3-carbonyl)-N—((R)-2-(trifluoromethyl)-5,6,7,8-tetrahydroimidazo[1,2-a]pyridin-8-yl)-4-azaspiro[2.5]octane-7-carboxamide

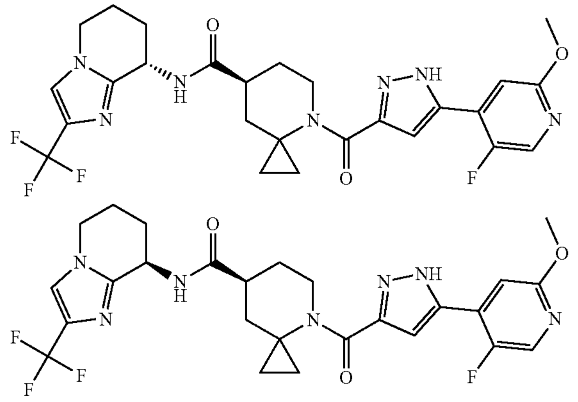

HOBt (59.3 mg, 0.44 mmol), EDCI (84.1 mg, 0.44 mmol), and 2-(trifluoromethyl)-5H,6H,7H,8H-imidazo[1,2-a]pyridin-8-amine (Step-3, 120.0 mg, 0.58 mmol) were added to a stirred solution of (5S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 109.5 mg, 0.29 mmol) and DIPEA (189.0 mg, 1.46 mmol) in DMF (2.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 40 B in 30 min; 220/254 nm) to obtain (S)-4-(5-(5-fluoro-2-methoxypyridin-4-yl)-1H-pyrazole-3-carbonyl)-N—((S)-2-(trifluoromethyl)-5,6,7,8-tetrahydroimidazo[1,2-a]pyridin-8-yl)-4-azaspiro[2.5]octane-7-carboxamide and (S)-4-(5-(5-fluoro-2-methoxypyridin-4-yl)-1H-pyrazole-3-carbonyl)-N—((R)-2-(trifluoromethyl)-5,6,7,8-tetrahydroimidazo[1,2-a]pyridin-8-yl)-4-azaspiro[2.5]octane-7-carboxamide (40.0 mg) as a solid (Example 502). $^1H$ NMR (400 MHz, $CD_3OD$) δ 8.21-8.04 (m, 1H), 7.59-7.46 (m, 1H), 7.37-7.21 (m, 11H), 7.12 (s, 1H), 5.18-5.04 (m, 1H), 4.68-4.47 (m, 1H), 4.18-4.02 (m, 2H), 3.95 (s, 3H), 2.92-2.76 (m, 1H), 2.71-2.29 (m, 1H), 2.28-2.09 (m, 3H), 2.09-1.94 (m, 1H), 1.93-1.83 (m, 1H), 1.83-1.67 (m, 1H), 1.59-1.15 (m, 2H), 1.14-0.85 (m, 2H), 0.84-0.64 (m, 2H). LCMS (ESI): 562.30 $[M+H]^+$.

This mixture of two diastereomers (40.0 mg) was separated using Chiral Prep-HPLC.

Column: CHIRAL ART Cellulose-SC column

Column dimension: 2×25 cm, 5 μm

Mobile Phase: hexanes (0.5% 2 M $NH_3$·MeOH):1/1 MeOH/DCM=50:50 hold for 10 min

Flow rate: 20 mL/min

Detection: 220/254 nm

Example 502-A. The first eluting diastereomer (10.3 mg) was obtained as a solid.

The first eluting diastereomer had a retention time of 7.66 min.

$^1H$ NMR (400 MHz, $CD_3OD$) δ 8.13 (s, 1H), 7.54 (s, 1H), 7.42-7.20 (m, 1H), 7.14-7.00 (m, 1H), 5.18-5.02 (m, 1H), 4.74-4.22 (m, 1H), 4.19-4.01 (m, 2H), 3.95 (s, 3H), 2.94-2.77 (m, 1H), 2.67-2.29 (m, 1H), 2.26-1.96 (m, 4H), 1.95-1.72 (m, 2H), 1.46-1.15 (m, 3H), 1.14-0.95 (m, 1H), 0.83-0.58 (m, 2H). LCMS (ESI): 562.30 $[M+H]^+$.

Example 502-B. The second eluting diastereomer (11.1 mg) was obtained as a solid.

The second eluting diastereomer had a retention time of 9.60 min.

$^1H$ NMR (400 MHz, $CD_3OD$) δ 8.14 (s, 1H), 7.63-7.48 (m, 1H), 7.43-7.21 (m, 1H), 7.18-7.04 (m, 1H), 5.18-5.06 (m, 1H), 4.76-4.41 (m, 1H), 4.17-4.06 (m, 2H), 3.95 (s, 3H), 2.96-2.79 (m, 1H), 2.60-2.32 (m, 1H), 2.28-2.10 (m, 2H), 2.09-1.97 (m, 1H), 1.95-1.82 (m, 2H), 1.83-1.64 (m, 1H), 1.63-1.38 (m, 1H), 1.36-1.24 (m, 2H), 1.22-0.97 (m, 1H), 0.84-0.60 (m, 2H). LCMS (ESI): 562.35 $[M+H]^+$.

Example 503. (S)-4-(3-(5-fluoro-2-methoxypyridin-4-yl)-1H-pyrazole-5-carbonyl)-N-((4-(trifluoromethyl)-1H-imidazol-5-yl)methyl)-4-azaspiro[2.5]octane-7-carboxamide

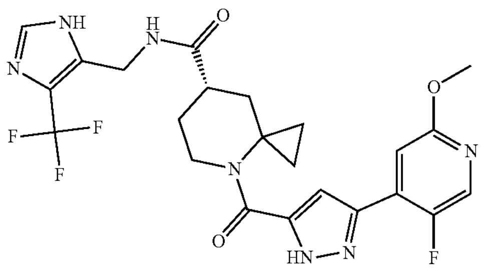 [SMILES: COc1cc(-c2cc(C(=O)N3CC[C@H](C(=O)NCc4[nH]cnc4C(F)(F)F)CC34CC4)[nH]n2)c(F)cn1]

Step-1. 5-(trifluoromethyl)-3H-imidazole-4-carbaldehyde

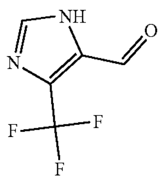 [SMILES: O=Cc1[nH]cnc1C(F)(F)F]

Dess-Martin (1.02 g, 2.41 mmol) was added to a stirred solution of [5-(trifluoromethyl)-3H-imidazol-4-yl]methanol (200.0 mg, 1.20 mmol) in DCM (5.00 mL). The resulting mixture was stirred at 25° C. for 2 h. The resulting mixture was concentrated under reduced pressure. The residue was purified by silica gel column chromatography eluting with DCM/MeOH (15/1 v/v) to obtain the title compound (197.0 mg) as a solid. LCMS (ESI): 165.0 $[M+H]^+$.

Step-2. 2-methyl-N-[(1E)-[5-(trifluoromethyl)-3H-imidazol-4-yl]methylidene]propane-2-sulfinamide

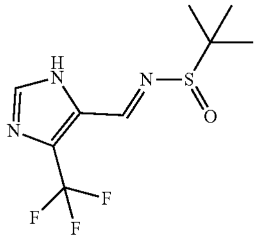 [SMILES: CC(C)(C)S(=O)/N=C/c1[nH]cnc1C(F)(F)F]

Tert-butanesulfinamide (218.3 mg, 1.80 mmol), PTSA (20.7 mg, 0.12 mmol) and $MgSO_4$ (433.5 mg, 3.60 mmol) were added to a stirred solution of 5-(trifluoromethyl)-3H-imidazole-4-carbaldehyde (Step-1, 197.0 mg, 1.20 mmol) in DCM (5.00 mL). The resulting mixture was stirred at 25° C. for 14 h. The resulting mixture was concentrated under reduced pressure. The residue was purified by silica gel column chromatography eluting with petroleum ether/EtOAc (1/1 v/v) to obtain the title compound (320.0 mg) as an oil. LCMS (ESI): 268.0 $[M+H]^+$.

Step-3. 2-methyl-N-{[5-(trifluoromethyl)-3H-imidazol-4-yl]methyl}propane-2-sulfinamide

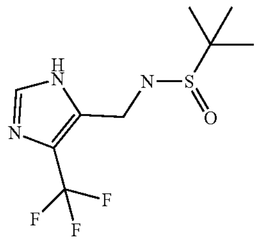 [SMILES: CC(C)(C)S(=O)NCc1[nH]cnc1C(F)(F)F]

$NaBH_4$ (90.6 mg, 2.39 mmol) was added to a stirred solution of 2-methyl-N-[(1E)-[5-(trifluoromethyl)-3H-imidazol-4-yl]methylidene]propane-2-sulfinamide (Step-2, 320.0 mg, 1.20 mmol) in MeOH (5.00 mL). The resulting mixture was stirred at 25° C. for 14 h. The resulting mixture was concentrated under reduced pressure. The residue was purified by silica gel column chromatography eluting with DCM/MeOH (15/1 v/v) to obtain the title compound (154.0 mg) as a solid. LCMS (ESI): 270.0 $[M+H]^+$.

Step-4. 1-[5-(trifluoromethyl)-3H-imidazol-4-yl]methanamine

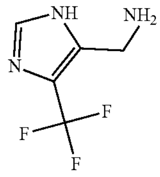 [SMILES: NCc1[nH]cnc1C(F)(F)F]

A solution of 2-methyl-N-{[5-(trifluoromethyl)-3H-imidazol-4-yl]methyl}propane-2-sulfinamide (Step-3, 154.0 mg, 0.57 mmol) in HCl (gas)/1,4-dioxane (5.00 mL) was stirred at 25° C. for 1 h. The resulting mixture was concentrated under reduced pressure to obtain the title compound as a solid and used directly in the next step without further purification. LCMS (ESI): 166.0 $[M+H]^+$.

Step-5. (S)-4-(3-(5-fluoro-2-methoxypyridin-4-yl)-1H-pyrazole-5-carbonyl)-N-((4-(trifluoromethyl)-1H-imidazol-5-yl)methyl)-4-azaspiro[2.5]octane-7-carboxamide

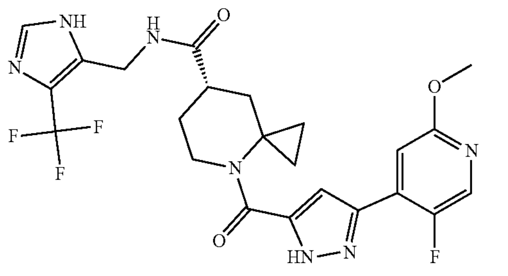 [SMILES: COc1cc(-c2cc(C(=O)N3CC[C@H](C(=O)NCc4[nH]cnc4C(F)(F)F)CC34CC4)[nH]n2)c(F)cn1]

HOBt (76.9 mg, 0.57 mmol), EDCI (109.1 mg, 0.57 mmol), 1-[5-(trifluoromethyl)-3H-imidazol-4-yl]methanamine (Step-4, 93.9 mg, 0.57 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 142.0 mg, 0.38 mmol) and DIPEA (294.1 mg, 2.27 mmol) in DMF (5.00 mL). The resulting mixture was stirred at 25° C. for 14 h. The resulting mixture was diluted with EtOAc and washed with water. The organic layer was concentrated under reduced pressure. The residue was purified by silica gel column chromatography eluting with DCM/MeOH (10/1 v/v) to obtain the title compound (117.2 mg) as a solid. $^1H$ NMR (400 MHz, $CD_3OD$) δ 8.14 (s, 1H), 7.72 (s, 1H), 7.51-7.17 (m, 1H), 7.11 (s, 1H), 4.71-4.53 (m, 1H), 4.51-4.42 (m, 2H), 3.95 (s, 3H), 2.97-2.75 (m, 1H), 2.56-2.20 (m, 1H), 1.99-1.58 (m, 2H), 1.39-1.18 (m, 2H), 1.13-0.87 (m, 2H), 0.81-0.61 (m, 2H). LCMS (ESI): 522.30 $[M+H]^+$.

Example 504. A Diastereomeric Mixture of (S)—N-((1S,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N((1R,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

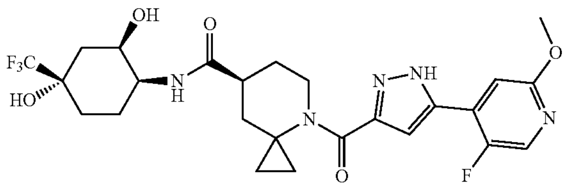

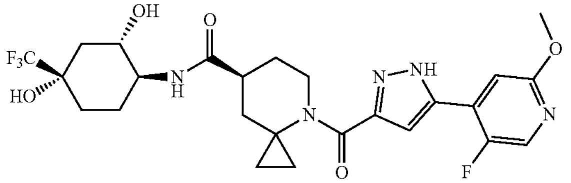

-continued

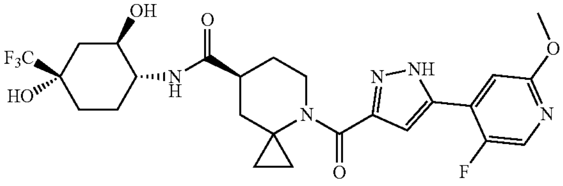

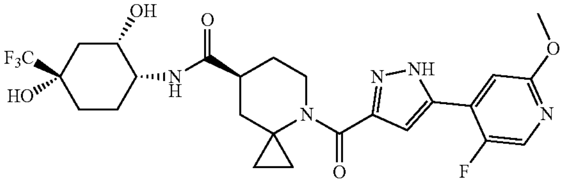

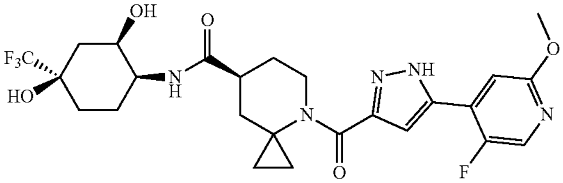

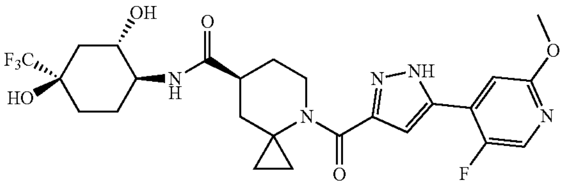

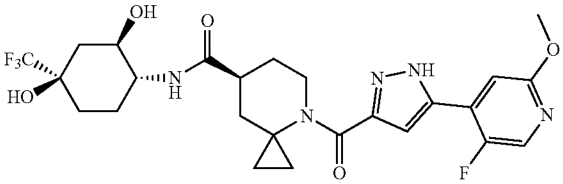

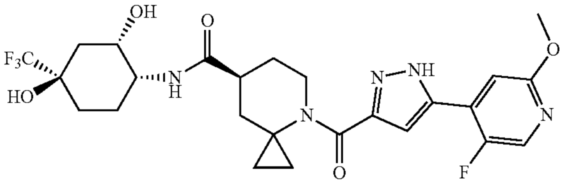

Step-1. 5-hydroxy-2-oxo-5-(trifluoromethyl)cyclohexyl benzoate

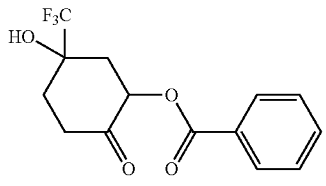 [SMILES: O=C(OC1CC(O)(C(F)(F)F)CCC1=O)c1ccccc1]

Methylamino benzoate (332.0 mg, 2.20 mmol) was added to a stirred solution of 4-hydroxy-4-(trifluoromethyl)cyclohexan-1-one (400.0 mg, 2.20 mmol) in DMSO (5.00 mL). The resulting mixture was stirred at 25° C. for 14 h. The resulting mixture was diluted with EtOAc and washed with water. The resulting mixture was concentrated under reduced pressure. The residue was purified by silica gel column chromatography eluting with petroleum ether/EtOAc (2/1 v/v) to obtain the title compound (637.0 mg) as a solid. LCMS (ESI): 303.0 [M+H]+.

Step-2. 2-amino-5-hydroxy-5-(trifluoromethyl)cyclohexyl benzoate

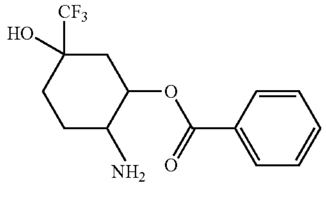 [SMILES: NC1CCC(O)(C(F)(F)F)CC1OC(=O)c1ccccc1]

$NaBH_3CN$ (675.7 mg, 10.76 mmol) and $NH_4OAc$ (3.32 g, 43.02 mmol) were added to a stirred solution of 5-hydroxy-2-oxo-5-(trifluoromethyl)cyclohexyl benzoate (Step-1, 630.0 mg, 2.15 mmol) in EtOH (5.00 mL). The resulting mixture was stirred at 80° C. for 14 h under the atmosphere of nitrogen. The resulting mixture was concentrated under reduced pressure. The residue was purified by silica gel column chromatography eluting with DCM/MeOH (10/1 v/v) to obtain the title compound (310.0 mg) as an oil. LCMS (ESI): 304.1 [M+H]V Step-3. 4-amino-1-(trifluoromethyl)cyclohexane-1,3-diol

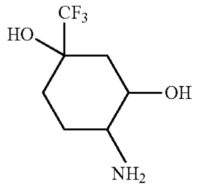

Lithium hydroxide (124.5 mg, 2.97 mmol) was added to a stirred solution of 2-amino-5-hydroxy-5-(trifluoromethyl)cyclohexyl benzoate (Step-2, 300.0 mg, 0.99 mmol) in THF (2.00 mL)/MeOH (2.00 mL)/$H_2O$ (2.00 mL). The resulting mixture was stirred at 100° C. for 14 h. The resulting mixture was concentrated under reduced pressure. This residue was purified by Propylsulfonic Acid (SCX-2) eluting with $NH_3$-MeOH (7 M) to obtain the title compound (190.0 mg) as an oil. LCMS (ESI): 200.0 [M+H]+.

Step-4. (S)—N-((1S,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide

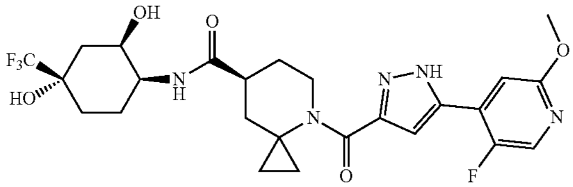

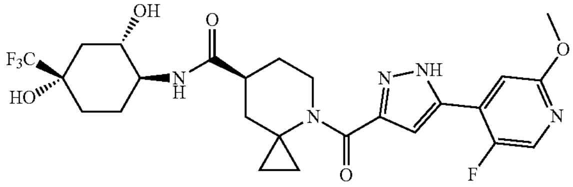

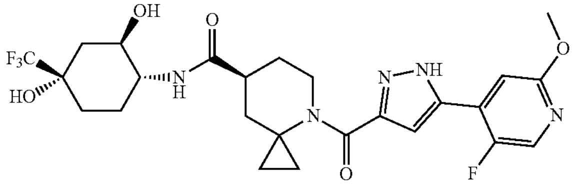

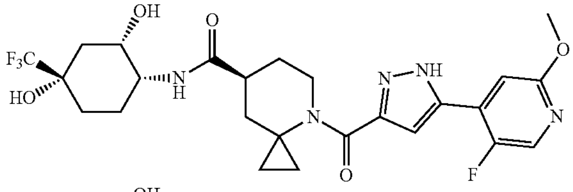

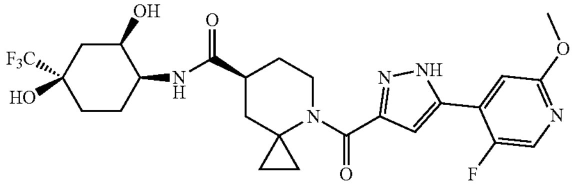

-continued

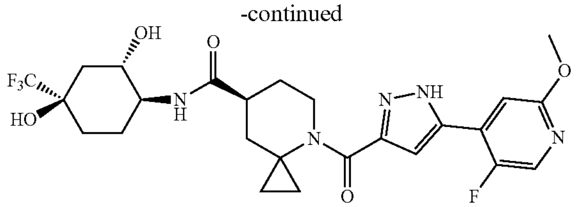

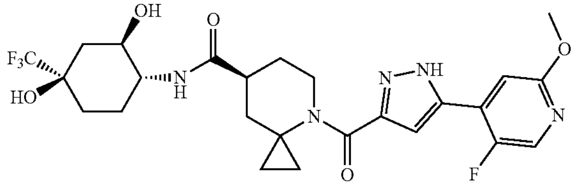

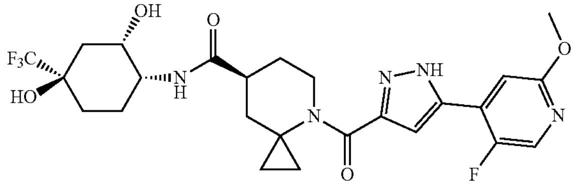

HOBt (57.0 mg, 0.42 mmol, 1.5 equiv), EDCI (80.8 mg, 0.42 mmol), and 4-amino-1-(trifluoromethyl)cyclohexane-1,3-diol (Step-3, 111.9 mg, 0.56 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 105.2 mg, 0.28 mmol) and DIPEA (109.0 mg, 0.84 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain (S)—N-((1S,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1S,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide and (S)—N-((1R,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide (150.0 mg) as an oil mixture of diastereomers of (7S)—N-[2,4-dihydroxy-4-(trifluoromethyl)cyclohexyl]-4-[5-(5-fluoro-2-methoxypyridin-4-yl)-1H-pyrazole-3-carbonyl]-4-azaspiro[2.5]octane-7-carboxamide as a light yellow oil. LCMS (ESI): 556.2 $[M+H]^+$.

This mixture of eight diastereomers (150.0 mg) was separated using Chiral Prep-HPLC.

Column: XBridge Prep OBD C18 column

Column dimension: 30×150 mm, 5 μm

Mobile Phase: Water (10 nM $NH_4HCO_3$):MeCN=79:21 to 69:31 for 8 min

Flow rate: 20 mL/min

Detection: 254 nm

Example 504-A. The first eluting peak (37.0 mg) was obtained as a solid Mixture of Four Diastereomers.

The first eluting peak had a retention time of 10.00 min. LCMS (ESI): 556.2 $[M+H]^+$.

Example 504-B. The second eluting peak (77.0 mg) was obtained as a solid Mixture of Four Diastereomers.

The second eluting peak had a retention time of 13.00 min.

LCMS (ESI): 556.2 $[M+H]^+$.

The first eluting peak (33.0 mg) containing four diastereomers of the title compounds from the first separation was separated using Chiral Prep-HPLC.

Column: CHIRAL ART Amylose-SA column

Column dimension: 2×25 cm, 5 μm

Mobile Phase: hexanes (0.5% 2 M $NH_3$·MeOH):1/1 MeOH/EtOH=60:40 hold for 22 min Flow rate: 20 mL/min Detection: 220/254 nm Example 504-C. The first eluting peak (7.9 mg) was obtained as a solid mixture of two diastereomers.

The first eluting peak had a retention time of 11.52 min. $^1$H NMR (400 MHz, $CD_3OD$) δ 8.13 (s, 1H), 7.42-7.19 (m, 1H), 7.11 (s, 1H), 4.70-4.42 (m, 1H), 4.26-4.15 (m, 1H), 4.14-4.04 (m, 1H), 3.95 (s, 3H), 3.15-2.93 (m, 1H), 2.55-2.24 (m, 1H), 1.99-1.77 (m, 5H), 1.78-1.65 (m, 2H), 1.64-1.54 (m, 1H), 1.42-1.24 (m, 2H), 1.14-0.97 (m, 1H), 0.83-0.68 (m, 3H). LCMS (ESI): 556.25 $[M+H]^+$.

Example 504-D. The second eluting peak (8.0 mg) was obtained as a solid mixture of two diastereomers The second eluting peak had a retention time of 16.53 min.

$^1$H NMR (400 MHz, $CD_3OD$) δ 8.14 (s, 1H), 7.44-7.19 (m, 1H), 7.12 (s, 1H), 4.74-4.42 (m, 1H), 4.24-4.16 (m, 1H), 4.14-4.05 (m, 1H), 3.95 (s, 3H), 3.22-2.95 (m, 1H), 2.62-2.28 (m, 1H), 2.01-1.77 (m, 5H), 1.76-1.66 (m, 2H), 1.65-1.56 (m, 1H), 1.43-1.20 (m, 2H), 1.12-0.96 (m, 1H), 0.86-0.64 (m, 3H). LCMS (ESI): 556.25 $[M+H]^+$.

The second eluting peak (77.0 mg) containing four diastereomers of the title compounds from the first separation was separated using Chiral Prep-HPLC.

Column: CHIRAL ART Cellulose-SB column

Column dimension: 2×25 cm, 5 μm

Mobile Phase: hexanes (0.5% 2 M $NH_3$·MeOH):1/i MeOH/EtOH=80:20 hold for 31 min Flow rate: 20 mL/min Detection: 220/254 nm Example 504-E. The first eluting peak (18.7 Mg) was obtained as a solid mixture of two diasteromers.

The first eluting peak had a retention time of 24.86 min. $^1$H NMR (400 MHz, $CD_3OD$) δ 8.13 (s, 1H), 7.28 (s, 1H), 7.11 (s, 1H), 4.71-4.43 (m, 1H), 3.95 (s, 3H), 3.83-3.70 (m, 1H), 3.69-3.54 (m, 1H), 2.94-2.74 (m, 1H), 2.59-2.30 (m, 1H), 2.28-2.09 (m, 1H), 2.02-1.74 (m, 3H), 1.74-1.62 (m, 3H), 1.62-1.52 (m, 1H), 1.42-1.22 (m, 2H), 1.13-0.86 (m, 2H), 0.83-0.65 (m, 2H). LCMS (ESI): 556.25 $[M+H]^+$.

Example 504-F. The second eluting peak (13.9 mg) was obtained as a solid Mixture of Two Diastereomers.

The second eluting peak had a retention time of 29.05 min.

$^1$H NMR (400 MHz, $CD_3OD$) δ 8.13 (s, 1H), 7.29 (s, 1H), 7.11 (s, 1H), 4.71-4.36 (m, 1H), 3.95 (s, 3H), 3.83-3.70 (m, 1H), 3.69-3.55 (m, 1H), 2.99-2.73 (m, 1H), 2.62-2.32 (m, 1H), 2.28-2.12 (m, 1H), 1.99-1.74 (m, 4H), 1.75-1.63 (m, 2H), 1.61-1.49 (m, 1H), 1.44-1.26 (m, 2H), 1.18-0.88 (m, 2H), 0.88-0.62 (m, 2H). LCMS (ESI): 556.25 $[M+H]^+$.

Example 505. (S)-4-(3-(5-fluoro-2-methoxypyridin-4-yl)-1H-pyrazole-5-carbonyl)-N-((3-(trifluoromethyl)isoxazol-4-yl)methyl)-4-azaspiro[2.5]octane-7-carboxamide

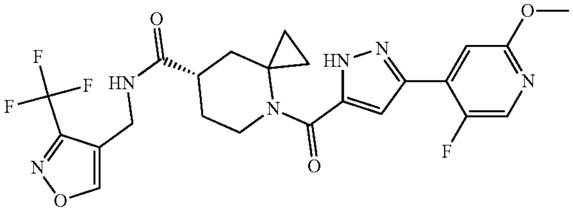 [SMILES: COc1cc(-c2cc(C(=O)N3CC[C@H](C(=O)NCc4conc4C(F)(F)F)CC34CC4)[nH]n2)c(F)cn1]

The title compound was prepared using a procedure similar to the one described for the synthesis of Example 325, except 1-[3-(trifluoromethyl)-1,2-oxazol-4-yl]methanamine was used as a starting material. The residue was purified by reverse phase column chromatography (using the following conditions: Column: C18; mobile phase A: Water (0.5% $NH_4HCO_3$), mobile phase B: MeCN; gradient: 30 B to 50 B in 20 min; 220/254 nm) to obtain the title compound (84.9 mg) as a solid. $^1$H NMR (400 MHz, $CD_3OD$) δ 8.88 (s, 1H), 8.13 (s, 1H), 7.39-7.15 (m, 1H), 7.11 (s, 1H), 4.70-4.42 (m, 1H), 4.41-4.23 (m, 2H), 3.95 (s, 3H), 2.95-2.72 (m, 1H), 2.60-2.18 (m, 1H), 2.07-1.46 (m, 2H), 1.47-1.17 (m, 2H), 1.18-0.97 (m, 1H), 0.83-0.52 (m, 3H). LCMS (ESI): 523.20 $[M+H]^+$.

Example 506. An Enantiomeric Mixture of (S)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide and (R)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide

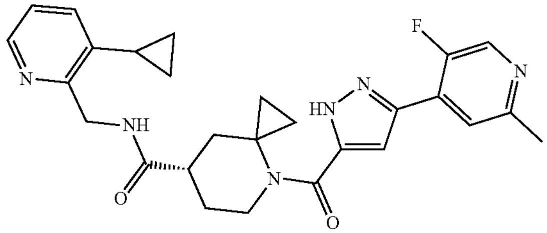

-continued

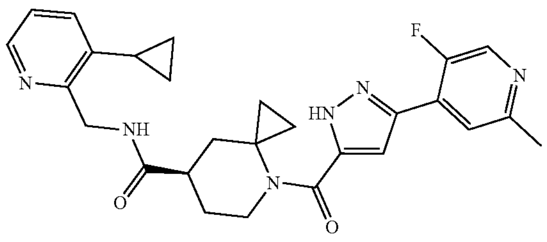

Step-1,3-cyclopropylpyridine-2-carbonitrile

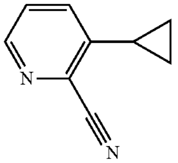 [SMILES: N#Cc1ncccc1C1CC1]

Cyclopropyltrifluoro-λ$^4$-borane potassium (646.9 mg, 4.37 mmol), Pd(dppf)$Cl_2$ (319.9 mg, 0.44 mmol) and $CS_2CO_3$ (1424.3 mug, 4.37 mmol) were added to a stirred solution of 3-bromopyridine-2-carbonitrile (400.0 mg, 2.19 mmol) in toluene (5.00 mL) and $H_2O$ (0.50 mL). The resulting mixture was stirred at 110° C. for 14 h under nitrogen atmosphere. The resulting mixture was concentrated under reduced pressure. The residue was purified by silica gel column chromatography eluting with DCM/MeOH (20/1 v/v) to obtain the title compound (320.0 mg) as a solid. LCMS (ESI): 145.00 $[M+H]^+$.

Step-2. 1-(3-cyclopropylpyridin-2-yl)methanamine

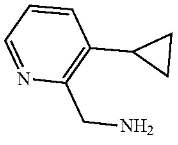

$LiAlH_4$ (168.5 mg, 4.44 mmol) was added in a stirred solution of 3-cyclopropylpyridine-2-carbonitrile (Step-1, 320.0 mg, 2.22 mmol) in THF (4.00 mL) at 0° C. The resulting mixture was stirred at 0° C. for 1 h under nitrogen atmosphere. The resulting mixture was concentrated under vacuum. The residue was purified by silica gel column chromatography eluting with DCM/MeOH (10/1 v/v) to obtain the title compound (300.0 mg) as a solid. LCMS (ESI): 149.00 $[M+H]^+$.

Step-3. (S)—N((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide and (R)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide

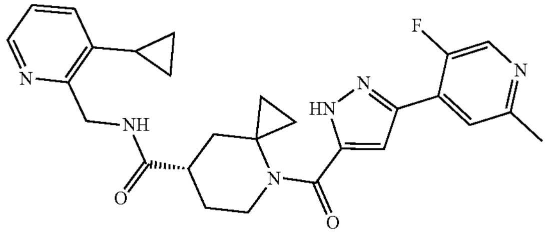

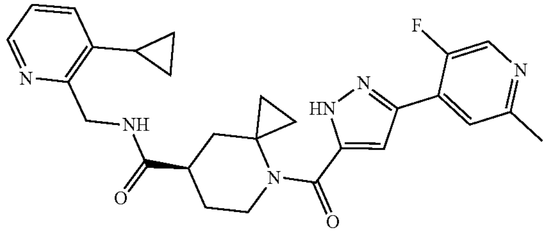

HOBt (157.3 mg, 1.164 mmol), EDCI (223.1 mg, 1.16 mmol), and 1-(3-cyclopropylpyridin-2-yl)methanamine (Step-2, 115.0 mg, 0.78 mmol) were added to a stirred solution of 4-[5-(5-fluoro-2-methylpyridin-4-yl)-1H-pyrazole-3-carbonyl]-4-azaspiro[2.5]octane-7-carboxylic acid (INTERMEDIATE 526, 278.1 mg, 0.78 mmol) and DIPEA (501.4 mg, 3.88 mmol) in DMF (2.00 mL). The resulting mixture was stirred for at 25° C. for 14 h. The resulting mixture was diluted with EtOAc and washed with water. The residue was purified by reverse phase column chromatography (using the following conditions: Column: C18; mobile phase A: Water (0.5% $NH_4HCO_3$), mobile phase B: MeCN; gradient: 20 B to 40 B in 30 min; 220/254 nm) to obtain (S)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide and (R)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide (92.0 mg) as a solid mixture of diastereomers (Example 506). $^1$H NMR (400 MHz, $CD_3OD$) δ 8.51-8.38 (m, 1H), 8.36-8.24 (m, 1H), 7.84 (s, 1H), 7.53-7.39 (m, 1H), 7.33-7.20 (m, 1H), 7.19-7.02 (m, 1H), 4.78-4.64 (m, 3H), 4.63-4.47 (m, 1H), 3.05-2.84 (m, 1H), 2.72-2.53 (m, 3H), 2.52-2.34 (m, 1H), 2.10-1.88 (m, 2H), 1.87-1.68 (m, 1H), 1.49-1.28 (m, 1), 1.19-0.89 (m, 4H), 0.84-0.65 (m, 4H). LCMS (ESI): 489.25 $[M+H]^+$.

This mixture of two diastereomers (92.0 mg) was separated using Chiral Prep-HPLC.

Column: CHIRALPAK ID column

Column dimension: 2×25 cm, 5 μm

Mobile Phase: hexanes (0.5% 2 M $NH_3$·MeOH): 1/1 MeOH/DCM=50:50 hold for 14 min Flow rate: 20 mL/min Detection: 220/254 nm Example 506-A. The first eluting diastereomer (27.0 mg) was obtained as a solid.

The first eluting diastereomer had a retention time of 8.66 min.

$^1$H NMR (400 MHz, $CD_3OD$) δ 8.42 (s, 1H), 8.36-8.21 (m, 1H), 7.98-7.61 (m, 1H), 7.53-7.41 (m, 1H), 7.32-7.22 (m, 1H), 7.20-7.09 (m, 1H), 4.79-4.66 (m, 2H), 4.62-4.49 (m, 1H), 3.21-2.71 (m, 2H), 2.58 (s, 3H), 2.53-2.29 (m, 1H), 2.10-1.89 (m, 2H), 1.87-1.69 (m, 1H), 1.49-1.25 (m, 2H), 1.15-0.94 (m, 3H), 0.85-0.66 (m, 4H). LCMS (ESI): 489.45 $[M+H]^+$.

Example 506-B. The second eluting diastereomer (22.0 mg) was obtained as a solid.

The second eluting diastereomer had a retention time of 11.58 min.

$^1$H NMR (400 MHz, $CD_3OD$) δ 8.51-8.37 (m, 1H), 8.37-8.26 (m, 1H), 8.01-7.64 (m, 1H), 7.53-7.42 (m, 1H), 7.32-722 (m, 1H), 7.15 (s, 1H), 4.78-4.67 (m, 2H), 4.62-4.47 (m, 1H), 3.19-2.72 (m, 2H), 2.67-2.53 (m, 3H), 2.52-2.33 (m, 1H), 2.10-1.65 (m, 3H), 1.51-1.22 (m, 2H), 1.17-0.90 (m, 3H), 0.84-0.60 (m, 4H). LCMS (ESI): 489.40 $[M+H]^+$.

Example 507. (S)-4-(3-(5-fluoro-2-methoxypyridin-4-yl)-1H-pyrazole-5-carbonyl)-N-((1-methyl-4-(trifluoromethyl)-1H-pyrazol-5-yl)methyl)-4-azaspiro [2.5]octane-7-carboxamide

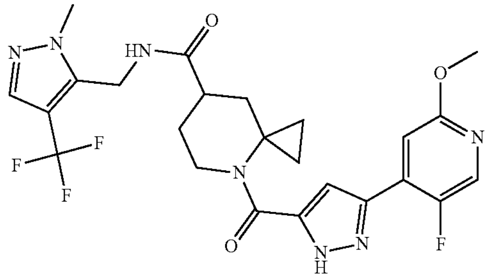 [SMILES: COc1cc(-c2cc(C(=O)N3CCC(C(=O)NCc4c(C(F)(F)F)cnn4C)CC34CC4)[nH]n2)c(F)cn1]

The title compound was prepared using a procedure similar to the one described for the synthesis of Example 325, except 1-[2-Methyl-4-(trifluoromethyl)pyrazol-3-yl] methanamine was used as a starting material. The residue was purified by silica gel column chromatography eluting with DCM/MeOH (15/1 v/v) to obtain the title compound (117.1 mg) as a solid. $^1$H NMR (400 MHz, DMSO-$d_6$) δ 13.97 (s, 1H), 8.42-8.21 (m, 2H), 7.78 (s, 1H), 7.32 (d, 1H), 7.03 (s, 1H), 4.49-4.31 (m, 3H), 3.95-3.76 (m, 6H), 3.25-2.95 (m, 1H), 2.84-2.65 (m, 1H), 2.27-2.02 (m, 1H), 1.93-1.65 (m, 1H), 1.54 (s, 1H), 1.33-1.11 (m, 1H), 1.08-0.81 (m, 2H), 0.73-0.39 (m, 2H). LCMS (ESI): 536.15 $[M+H]^+$.

Example 508. (S)-4-(3-(5-fluoro-2-methoxypyridin-4-yl)-1H-pyrazole-5-carbonyl)-N-((1-methyl-5-(trifluoromethyl)-1H-1,2,3-triazol-4-yl)methyl)-4-azaspiro[2.5]octane-7-carboxamide

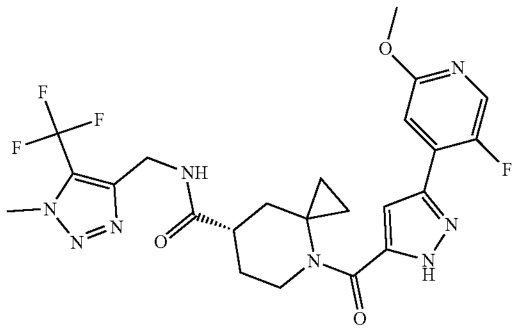 [SMILES: COc1cc(-c2cc(C(=O)N3CC[C@H](C(=O)NCc4nnn(C)c4C(F)(F)F)CC34CC4)[nH]n2)c(F)cn1]

The title compound was prepared using a procedure similar to the one described for the synthesis of Example 325, except 1-[1H-methyl-5-(trifluoromethyl)-1,2,3-triazol-4-yl]methanamine was used as a starting material. The residue was purified by reverse phase column chromatography (using the following conditions: Column: C18; mobile phase A: Water (0.5% $NH_4HCO_3$), mobile phase B: MeCN; gradient: 20 B to 50 B in 20 min; 220/254 nm) to obtain the title compound (85.3 mg) as a solid. $^1$H NMR (400 MHz, DMSO-$d_6$) δ 14.24-13.78 (m, 1H), 8.42 (s, 1H), 8.27 (s, 1H), 7.42-7.22 (m, 1H), 7.02 (s, 1H), 4.74-4.36 (m, 3H), 4.25-4.03 (m, 3H), 3.88 (s, 3H), 2.99-2.70 (m, 1H), 2.27-2.03 (m, 1H), 1.92-1.64 (m, 1H), 1.61-1.38 (m, 1H), 1.33-1.12 (m, 2H), 1.05-0.74 (m, 2H), 0.70-0.59 (m, 2H). LCMS (ESI): 537.50 $[M+H]^+$.

Example 509. (S)-4-(3-(5-fluoro-2-methoxypyridin-4-yl)-1H-pyrazole-5-carbonyl)-N-((1-methyl-3-(trifluoromethyl)-1H-pyrazol-4-yl)methyl)-4-azaspiro [2.5]octane-7-carboxamide

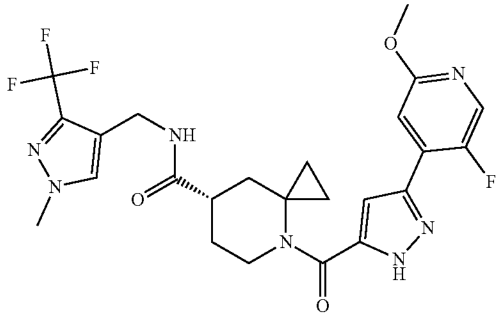 [SMILES: COc1cc(-c2cc(C(=O)N3CC[C@H](C(=O)NCc4cn(C)nc4C(F)(F)F)CC34CC4)[nH]n2)c(F)cn1]

The title compound was prepared using a procedure similar to the one described for the synthesis of Example 325, except 1-[1-methyl-3-(trifluoromethyl)pyrazol-4-yl] methanamine was used as a starting material. The residue was purified by Prep-TLC (DCM/MeOH, 10/1 v/v) to obtain the title compound (100.0 mg) as a solid. $^1$H NMR (400 MHz, $CD_3OD$) δ 8.13 (s, 1H), 7.66 (s, 1H), 7.28 (s, 1H), 7.15-6.98 (m, 1H), 4.58 (s, 1H), 4.30 (s, 2H), 3.93 (d, 6H), 2.82 (s, 1H), 2.40 (s, 1H), 2.08-1.55 (m, 2H), 1.16 (d, 3H), 0.72 (s, 3H). LCMS (ESI): 536.25 $[M+H]^+$.

Example 510. (S)-4-(3-(5-fluoro-2-methoxypyridin-4-yl)-1H-pyrazole-5-carbonyl)-N-((3-(trifluoromethyl)pyridin-2-yl)methyl)-4-azaspiro[2.5]octane-7-carboxamide

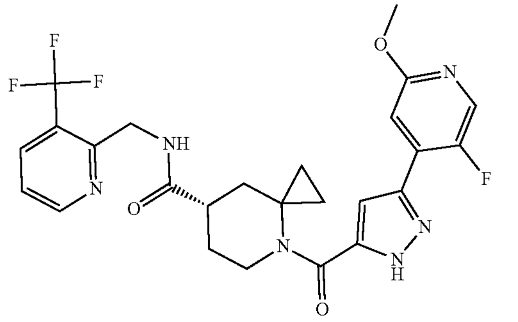 [SMILES: COc1cc(-c2cc(C(=O)N3CC[C@H](C(=O)NCc4ncccc4C(F)(F)F)CC34CC4)[nH]n2)c(F)cn1]

The title compound was prepared using a procedure similar to the one described for the synthesis of Example 325, except 1-[3-(trifluoromethyl)pyridin-2-yl]methanamine was used as a starting material. The residue was purified by Prep-TLC (DCM/MeOH, 10/1 v/v) to obtain the title compound (80.0 mg) as a solid. $^1$H NMR (400 MHz, $CD_3OD$) δ 8.84-8.72 (m, 1H), 8.22-8.04 (m, 2H), 7.56-7.45 (m, 1H), 7.43-7.16 (m, 1H), 7.11 (s, 1H), 4.78-4.60 (m, 2H), 3.94 (s, 3H), 3.11-2.77 (m, 2H), 2.78-2.18 (m, 1H), 2.12-1.67 (m, 2H), 1.53-1.21 (m, 2H), 1.18-0.95 (m, 1H), 0.94-0.54 (m, 3H). LCMS (ESI): 533.20 $[M+H]^+$.

Example 511. A Diastereomeric Mixture of (S)—N—(((S)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide and (S)—N—(((R)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide

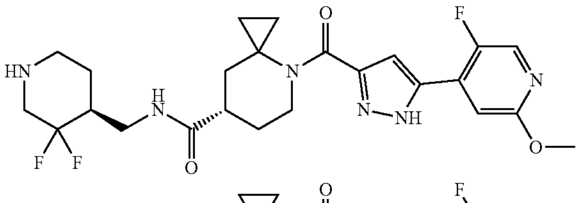

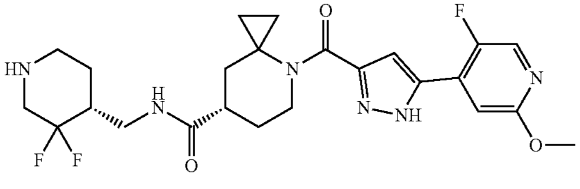

Step-1. tert-butyl 3,3-difluoro-4-({[(7S)-4-[5-(5-fluoro-?2-methoxypyridin-4-yl)-1H-pyrazole-3-carbonyl]-4-azaspiro[2.5]octan-7-yl]formamido}methyl)piperidine-1-carboxylate

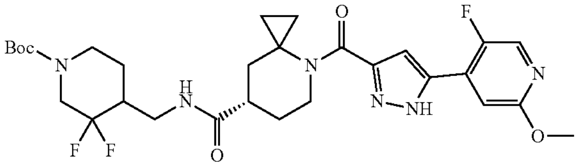 [SMILES: COc1cc(-c2cc(C(=O)N3CC[C@H](C(=O)NCC4CCN(C(=O)OC(C)(C)C)CC4(F)F)CC34CC4)n[nH]2)c(F)cn1]

EDCI (77.0 mg, 0.40 mmol), HOBt (55.0 mg, 0.40 mmol), and tert-butyl 4-(aminomethyl)-3,3-difluoropiperidine-1-carboxylate (67.0 mg, 0.27 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 100.0 mg, 0.27 mmol) and DIPEA (173.0 mg, 1.34 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (140 mg) as a solid. LCMS (ESI): 607 $[M+H]^+$.

Step-2. (S)—N—(((S)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide and (S)—N—(((R)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide

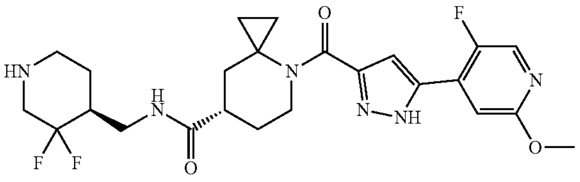

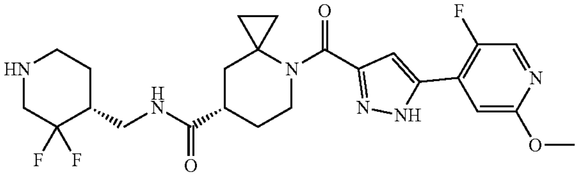

TFA (3.00 mL) was added to a mixture of tert-butyl 3,3-difluoro-4-({[(7S)-4-[5-(5-fluoro-2-methoxypyridin-4-yl)-1H-pyrazole-3-carbonyl]-4-azaspiro[2.5]octan-7-yl]formamido}methyl)piperidine-1-carboxylate (Step-1, 130.0 mg, 0.21 mmol) in DCM (3.00 mL) at 0° C. The resulting mixture was stirred at 25° C. for 2 h. The residue was purified by silica gel column chromatography eluting with DCM/MeOH (10/1 v/v) to obtain (S)—N—(((S)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide and (S)—N—(((R)-3,3-difluoropiperidin-4-yl)methyl)-4-(5-(5-fluoro-2-methoxypyridin-4-yl)-1H- pyrazole-3-carbonyl)-4-azaspiro[2.5]octane-7-carboxamide (95.0 mg) as a solid mixture of diastereomers (Example 511). $^1$H NMR (400 MHz, DMSO-$d_6$) δ 13.98 (s, 1H), 8.27 (d, 1H), 7.94-7.84 (m, 1H), 7.32 (d, 1H), 7.03 (d, 1H), 4.68-4.22 (m, 1H), 3.88 (s, 3H), 3.45-3.35 (m, 1H), 3.07-2.93 (m, 2H), 2.90-2.80 (m, 1H), 2.75-2.59 (m, 2H), 2.46-2.32 (m, 2H), 2.30-2.13 (m, 1H), 2.11-1.92 (m, 1H), 1.82-1.64 (m, 2H), 1.62-1.40 (m, 1H), 1.32-1.11 (m, 2H), 1.06-0.78 (m, 2H), 0.70-0.52 (m, 2H). LCMS (ESI): 507.25 $[M+H]^+$.

This mixture of two diastereomers (50.0 mg) was separated using Chiral Prep-HPLC.

Column: CHIRAL ART Amylose-SA column

Column dimension: 2×25 cm, 5 μm

Mobile Phase: hexanes (0.5% 2 M $NH_3$·MeOH):1/1 MeOH/DCM=40:60 hold for 22 min

Flow rate: 20 mL/min

Detection: 220/254 nm

Example 511-A. The first eluting diastereomer (22.7 mg) was obtained as a solid.

The first eluting diastereomer had a retention time of 14.49 min.

$^1$H NMR (400 MHz, $CD_3OD$) δ 8.13 (d, 1H), 7.35-7.20 (m, 1H), 7.11 (d, 1H), 4.75-4.36 (m, 1H), 3.95 (s, 3H), 3.59-3.49 (m, 1H), 3.28-3.19 (m, 1H), 3.16-3.06 (m, 2H), 3.05-2.98 (m, 1H), 2.88-2.51 (m, 3H), 2.51-2.28 (m, 1H), 2.25-2.07 (m, 1H), 2.06-1.54 (m, 3H), 1.53-1.38 (m, 1H), 1.37-0.83 (m, 3H), 0.81-0.61 (m, 2H). LCMS (ESI): 507.25 $[M+H]^+$.

Example 511-B. The second eluting diastereomer (17.5 mg) was obtained as a solid.

The second eluting diastereomer had a retention time of 18.59 min.

$^1$H NMR (400 MHz, $CD_3OD$) δ 8.14 (d, 1H), 7.34-7.23 (m, 1H), 7.11 (d, 1H), 4.74-4.32 (m, 1H), 3.95 (s, 3H), 3.60-3.47 (m, 1H), 3.29-3.19 (m, 1H), 3.17-3.06 (m, 2H), 3.06-2.97 (m, 1H), 2.89-2.68 (m, 2H), 2.63-2.52 (m, 1H), 2.51-2.31 (m, 1H), 2.26-2.07 (m, 1H), 1.98-1.57 (m, 3H), 1.52-1.39 (m, 1H), 1.36-0.86 (m, 3H), 0.82-0.65 (m, 2H). LCMS (ESI): 507.25 $[M+H]^+$.

Example 512. (S)-4-(3-(5-fluoro-2-methoxypyridin-4-yl)-1H-pyrazole-5-carbonyl)-N-((5-fluoropyrimidin-2-yl)methyl)-4-azaspiro[2.5]octane-7-carboxamide

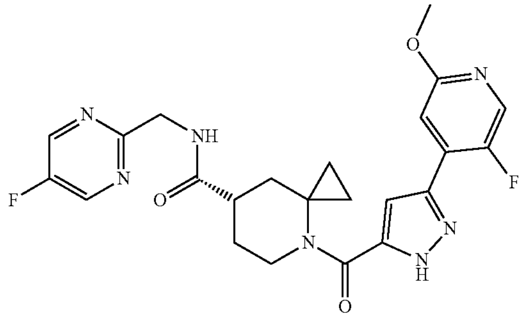

The title compound was prepared using a procedure similar to the one described for the synthesis of Example 325, except 1-(5-fluoropyrimidin-2-yl)methanamine was used as a starting material. The residue was purified by silica gel column chromatography eluting with DCM/MeOH (10/1 v/v) to obtain the title compound (122.2 mg) as a solid. $^1$H NMR (400 MHz, DMSO-$d_6$) δ 13.99 (s, 1H), 8.85 (s, 2H), 8.54-8.38 (m, 1H), 8.27 (s, 1H), 7.32 (d, 1H), 7.03 (s, 1H), 4.74-4.24 (m, 3H), 3.88 (s, 3H), 3.24-2.93 (m, 1H), 2.90-2.73 (m, 1H), 2.38-2.08 (m, 1H), 1.95-1.72 (m, 1H), 1.67-1.44 (m, 1H), 1.39-1.15 (m, 1H), 1.11-0.78 (m, 2H), 0.75-0.42 (m, 2H). LCMS (ESI): 484.20 $[M+H]^+$.

Example 513. (S)-4-(3-(5-fluoro-2-methoxypyridin-4-yl)-1H-pyrazole-5-carbonyl)-N-((2-(trifluoromethyl)pyridin-3-yl)methyl)-4-azaspiro[2.5]octane-7-carboxamide

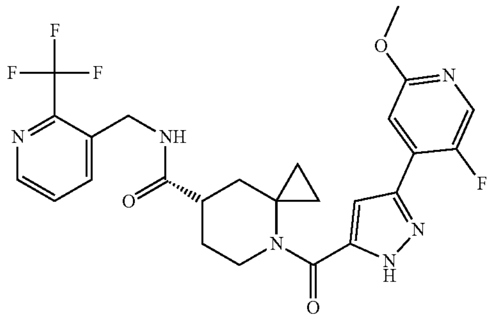

The title compound was prepared using a procedure similar to the one described for the synthesis of Example 325, except 1-[2-(trifluoromethyl)pyridin-3-yl]methanamine was used as a starting material. The residue was purified by silica gel column chromatography eluting with DCM/MeOH (8/1 v/v) to obtain the title compound (84.7 mg) as a solid. $^1$H NMR (400 MHz, $CD_3OD$) δ 8.58 (d, 1H), 8.14 (d, 1H), 7.97 (d, 1H), 7.73-7.59 (m, 1H), 7.43-6.98 (m, 2H), 4.73-4.52 (m, 3H), 3.95 (s, 3H), 3.05-2.81 (m, 1H), 2.72-2.29 (m, 1H), 2.05-1.70 (m, 2H), 1.58-1.19 (m, 2H), 1.06 (s, 2H), 0.87-0.59 (m, 2H). LCMS (ESI): 533.25 $[M+H]^+$.

Example 514. A Diastereomeric Mixture of (S)-4-(5-(5-fluoro-2-methoxypyridin-4-yl)-1H-pyrazole-3-carbonyl)-N—((S)-5-hydroxy-4,5,6,7-tetrahydropyrazolo[1,5-a]pyridin-3-yl)-4-azaspiro[2.5]octane-7-carboxamide and (S)-4-(5-(5-fluoro-2-methoxypyridin-4-yl)-1H-pyrazole-3-carbonyl)-N—((R)-5-hydroxy-4,5,6,7-tetrahydropyrazolo[1,5-a]pyridin-3-yl)-4-azaspiro[2.5]octane-7-carboxamide

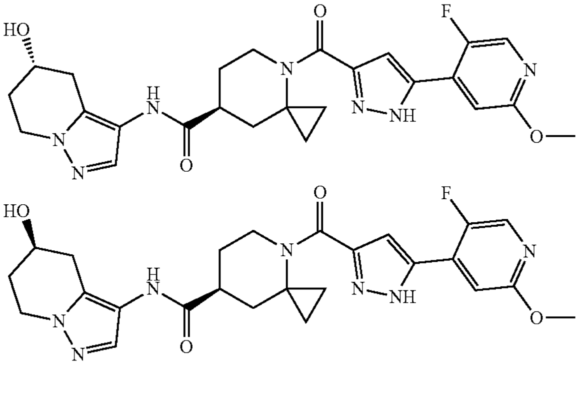

Step-1. 5-methoxypyrazolo[1,5-a]pyridine-3-carboxylic acid

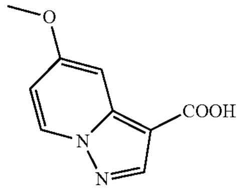

LiOH·$H_2O$ (267.0 mg, 6.36 mmol) were added to a mixture of ethyl 5-methoxypyrazolo[1,5-a]pyridine-3-carboxylate (700.0 mg, 3.18 mmol) in THF (3.00 mL), MeOH (3.00 mL), and $H_2O$ (3.00 mL). The resulting mixture was stirred at 25° C. for 14 h. The resulting mixture was concentrated under reduced pressure. The mixture was acidified to pH 3 with HCl (aq.). The aqueous layer was extracted with EtOAc. The organic layers were combined, dried over anhydrous $Na_2SO_4$, filtered, and concentrated under reduced pressure to obtain the title compound (550.0 mg) as a solid. LCMS (ESI): 193 $[M+H]^+$.

Step-2. tert-butyl N-{5-methoxypyrazolo[1,5-a]pyridin-3-yl}carbamate

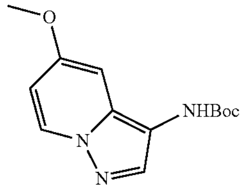 [SMILES: COc1ccn2ncc(NC(=O)OC(C)(C)C)c2c1]

DPPA (1.97 g, 7.16 mmol), t-BuOH (2.76 g, 37.21 mmol) and DIPEA (1.48 g, 11.45 mmol) were added to a mixture of 5-methoxypyrazolo[1,5-a]pyridine-3-carboxylic acid (Step-1, 550.0 mg, 2.86 mmol) in toluene (10.00 mL). The resulting mixture was stirred at 110° C. for 14 h. The resulting mixture was concentrated under reduced pressure. The residue was purified by silica gel column chromatography eluting with petroleum ether/EtOAc (1/1 v/v) to obtain the title compound (500.0 mg) as a solid. LCMS (ESI): 264 $[M+H]^+$.

Step-3. tert-butyl N-{5-methoxy-4H,5H,6H,7H-pyrazolo[1,5-a]pyridin-3-yl}carbamate

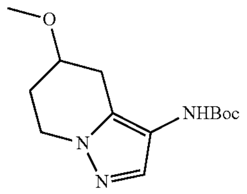 [SMILES: COC1CCn2ncc(NC(=O)OC(C)(C)C)c2C1]

Pd/C (30.0 mg, 10%) was added to a mixture of tert-butyl N-{5-methoxypyrazolo[1,5-a]pyridin-3-yl}carbamate (Step-2, 120.0 mg, 0.38 mmol) in MeOH (5.00 mL). The resulting mixture was stirred at 80° C. under 20 psi of hydrogen pressure for 14 h. The solids were filtered out by filtration and washed with MeOH. The resulting filtrate was concentrated under reduced pressure to obtain the title compound (95.0 mg) as a solid. LCMS (ESI): 268 $[M+H]^+$.

Step-4. 5-methoxy-4H,5H,6H,7H-pyrazolo[1,5-a]pyridin-3-amine

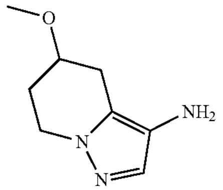

TFA (3.00 mL) was added to a mixture of tert-butyl N-{5-methoxy-4H,5H,6H,7H-pyrazolo[1,5-a]pyridin-3-yl}carbamate (Step-3, 90.0 mg, 0.34 mmol) in DCM (3.00 mL). The resulting mixture was stirred at 25° C. for 2 h. The resulting mixture was concentrated under reduced pressure to obtain the title compound (60.0 mg) as an oil. LCMS (ESI): 168 $[M+H]^+$.

Step-5. 5-[5-(5-fluoro-2-methoxypyridin-4-yl)-1-{[2-(trimethylsilyl)ethoxy]methyl}pyrazole-3-carbonyl]-N-[(1r,4r)-4-hydroxy-4-(trifluoromethyl)cyclohexyl]-5-azaspiro[3.5]nonane-8-carboxamide

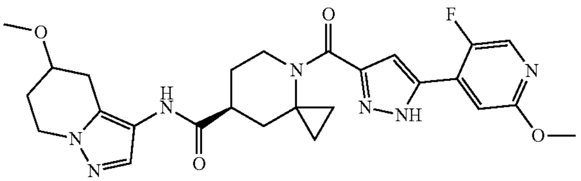

EDCI (103.0 mg, 0.54 mmol), HOBt (72.7 mg, 0.54 mmol), and 5-methoxy-4H,5H,6H,7H-pyrazolo[1,5-a]pyridin-3-amine (Step-4, 60.0 mg, 0.36 mmol) were added to a mixture of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 134.0 mg, 0.36 mmol) and DIPEA (232.0 mg, 1.80 mmol) in DMF (5.00 mL). The resulting mixture was stirred at 25° C. for 14 h. The resulting mixture was diluted with EtOAc and washed with water. The residue was purified by silica gel column chromatography eluting with DCM/MeOH (15/1 v/V) to obtain the title compound (110.0 mg) as a solid. LCMS (ESI): 524 $[M+H]^+$.

Step-6. (S)-4-(5-(5-fluoro-2-methoxypyridin-4-yl)-1H-pyrazole-3-carbonyl)-N—((S)-5-hydroxy-4,5,6,7-tetrahydropyrazolo[1,5-a]pyridin-3-yl)-4-azaspiro[2.5]octane-7-carboxamide and (S)-4-(5-(5-fluoro-2-methoxypyridin-4-yl)-1H-pyrazole-3-carbonyl)-N—((R)-5-hydroxy-4,5,6,7-tetrahydropyrazolo[1,5-a]pyridin-3-yl)-4-azaspiro[2.5]octane-7-carboxamide

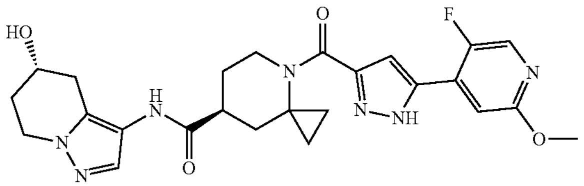

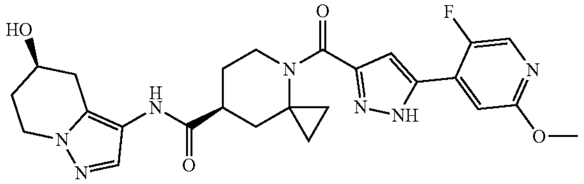

$BBr_3$ (526.0 mg, 2.10 mmol) was added to a mixture of (7S)-4-[5-(5-fluoro-2-methoxypyridin-4-yl)-1H-pyrazole-3-carbonyl]-N-{5-methoxy-4H,5H,6H,7H-pyrazolo[1,5-a]pyridin-3-yl}-4-azaspiro[2.5]octane-7-carboxamide (Step-5, 110.0 mg, 0.21 mmol) in DCE (5.00 mL). The resulting mixture was stirred at 25° C. for 14 h. The resulting mixture was concentrated under reduced pressure. The residue was purified by silica gel column chromatography eluting with DCM/MeOH (15/1 v/v) to obtain (S)-4-(5-(5-fluoro-2-methoxypyridin-4-yl)-1H-pyrazole-3-carbonyl)-N—((S)-5-hydroxy-4,5,6,7-tetrahydropyrazolo[1,5-a]pyridin-3-yl)-4-azaspiro[2.5]octane-7-carboxamide and (S)-4-(5-(5-fluoro-2-methoxypyridin-4-yl)-1H-pyrazole-3-carbonyl)-N—((R)-5-hydroxy-4,5,6,7-tetrahydropyrazolo[1,5-a]pyridin-3-yl)-4-azaspiro[2.5]octane-7-carboxamide (100.0 mg) as a solid mixture of diastereomers (Example 514). $^1$H NMR (400 MHz, DMSO-d6) δ 13.93 (s, 1H), 9.26 (s, 1H), 8.27 (d, 1H), 7.50 (s, 1H), 7.33 (d, 1H), 7.09-7.00 (m, 1H), 5.06 (d, 1H), 4.70-4.28 (m, 1H), 4.15-4.04 (m, 2H), 4.04-3.96 (m, 1H), 3.88 (s, 3H), 2.97-2.87 (m, 1H), 2.86-2.79 (m, 1H), 2.61-2.55 (m, 1H), 2.36-2.12 (m, 1H), 2.08-1.98 (m, 1H), 1.97-1.90 (m, 1H), 1.88-1.76 (m, 1H), 1.72-1.45 (m, 2H), 1.41-1.16 (m, 1H), 1.13-0.82 (m, 2H), 0.78-0.47 (m, 2H). LCMS (ESI): 510.25 $[M+H]^+$.

This mixture of two diastereomers (1100.0 mg) was separated using Chiral Prep-H PLC.

Column: CHIRALPAK IE column

Column dimension: 2×25 cm, 5 μm

Mobile Phase: MTBE (0.5% 2 M $NH_3$·MeOH):1/1 MeOH/DCM=50:50 hold for 27 min

Flow rate: 18 mL/min

Detection: 220/254 nm

Example 514-A. The first eluting diastereomer (27.3 mg) was obtained as a solid.

The first eluting diastereomer had a retention time of 16.48 min.

$^1$H NMR (400 MHz, DMSO-d6) δ 13.99 (s, 1H), 9.26 (s, 1H), 8.27 (s, 1H), 7.50 (s, 11H), 7.33 (d, 1H), 7.05 (s, 1H), 5.05 (d, 1H), 4.68-4.30 (m, 1H), 4.15-4.04 (m, 2H), 4.04-3.95 (m, 1H), 3.88 (s, 3H), 2.97-2.73 (m, 2H), 2.36-2.13 (m, 1H), 2.07-1.98 (m, 1H), 1.97-1.90 (m, 1H), 1.88-1.73 (m, 1H), 1.71-1.49 (m, 2H), 1.42-1.17 (m, 2H), 1.13-0.79 (m, 2H), 0.76-0.43 (m, 2H). LCMS (ESI): 510.25 $[M+H]^+$.

Example 514-B. The second eluting diastereomer (29.5 mg) was obtained as a solid.

The second eluting diastereomer had a retention time of 22.15 min.

$^1$H NMR (400 MHz, DMSO-$d_6$) δ 13.98 (s, 1H), 9.26 (s, 1H), 8.27 (d, 1H), 7.50 (s, 1H), 7.33 (d, 1H), 7.05 (s, 1H), 5.05 (d, 1H), 4.73-4.21 (m, 1H), 4.15-4.04 (m, 2H), 4.02-3.95 (m, 1H), 3.88 (s, 3H), 2.96-2.87 (m, 1H), 2.87-2.76 (m, 1H), 2.69-2.55 (m, 1H), 2.36-2.13 (m, 1H), 2.08-1.98 (m, 11H), 1.97-1.89 (m, 1H), 1.89-1.74 (m, 1H), 1.70-1.48 (m, 1H), 1.37-1.16 (m, 2H), 1.12-0.79 (m, 2H), 0.74-0.62 (m, 2H). LCMS (ESI): 510.25 $[M+H]^+$.

Example 515. (S)-4-(3-(5-fluoro-2-methoxypyridin-4-yl)-1H-pyrazole-5-carbonyl)-N-((3-(trifluoromethyl)bicyclo[1.1.1]pentan-1-yl)methyl)-4-azaspiro[2.5]octane-7-carboxamide

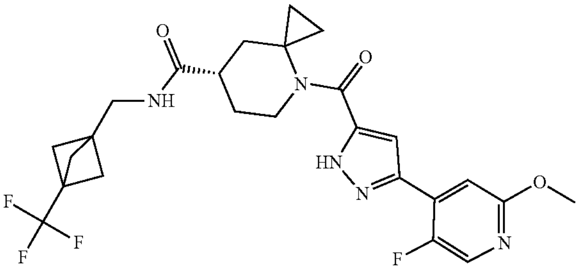 [SMILES: COc1cc(-c2cc(C(=O)N3CC[C@H](C(=O)NCC45CC(C(F)(F)F)(C4)C5)CC34CC4)[nH]n2)c(F)cn1]

The title compound was prepared using a procedure similar to the one described for the synthesis of Example 430, except 1-[3-(trifluoromethyl)bicyclo[1.1.1]pentan-1-yl]methanamine was used as a starting material. The residue was purified by Prep-TLC (DCM/MeOH, 10/1 v/v) to obtain the title compound (80.0 mg) as a solid. $^1$H NMR (400 MHz, DMSO-$d_6$) δ 14.20-13.67 (m, 1H), 8.36-8.18 (m, 1H), 7.92 (s, 1H), 7.32 (s, 1H), 7.04 (s, 1H), 4.53 (s, 1H), 3.88 (s, 3H), 3.26-3.14 (m, 2H), 2.84-2.61 (m, 1H), 2.36-2.07 (m, 1H), 1.95-1.68 (m, 7H), 1.66-1.42 (m, 1H), 1.38-1.07 (m, 2H), 1.06-0.77 (m, 2H), 0.75-0.48 (m, 2H). LCMS (ESI): 552.25 $[M+H]^+$.

Example 516. (S)-4-(5-(5-fluoro-2-methoxypyridin-4-yl)-1H-pyrazole-3-carbonyl)-N-((4-(trifluoromethyl)pyridin-3-yl)methyl)-4-azaspiro[2.5]octane-7-carboxamide

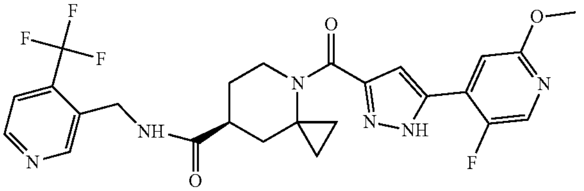 [SMILES: COc1cc(-c2cc(C(=O)N3CC[C@H](C(=O)NCc4cnccc4C(F)(F)F)CC34CC4)n[nH]2)c(F)cn1]

The title compound was prepared using a procedure similar to the one described for the synthesis of Example 325, except 1-[4-(trifluoromethyl)pyridin-3-yl]methanamine was used as a starting material. The residue was purified by silica gel column chromatography eluting with DCM/MeOH (10/1 v/v) to obtain the title compound (112.2 mg) as a solid. $^1$H NMR (400 MHz, DMSO-$d_6$) δ 13.98 (d, 1H), 8.82-8.68 (m, 2H), 8.51 (s, 1H), 8.26 (s, 1H), 7.72 (d, 1H), 7.32 (d, 1H), 7.04 (s, 1H), 4.68-4.24 (m, 3H), 3.88 (s, 3H), 2.92-2.73 (m, 1H), 2.36-2.11 (m, 1H), 2.00-1.75 (m, 1H), 1.68-1.46 (m, 1H), 1.41-1.19 (m, 2H), 1.09-0.82 (m, 2H), 0.76-0.49 (m, 2H). LCMS (ESI): 533.25 [M+H]$^+$.

Example 517. (S)-4-(3-(5-fluoro-2-methoxypyridin-4-yl)-1H-pyrazole-5-carbonyl)-N-((2-methyl-4-(trifluoromethyl)thiazol-5-yl)methyl)-4-azaspiro[2.5]octane-7-carboxamide

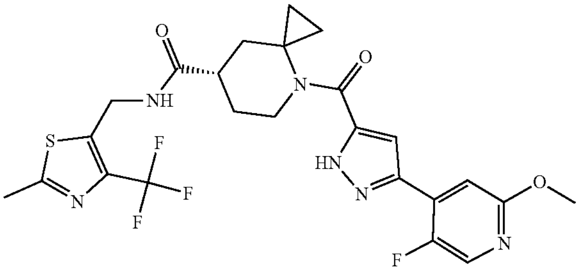

The title compound was prepared using a procedure similar to the one described for the synthesis of Example 325, except 1-[2-methyl-4-(trifluoromethyl)-1,3-thiazol-5-yl]methanamine was used as a starting material. The residue was purified by Prep-TLC (DCM/MeOH, 10/1 v/v) to obtain the title compound (77.0 mg) as a solid. $^1$H NMR (400 MHz, $CD_3OD$) δ 8.14 (s, 1H), 7.50-7.01 (m, 2H), 4.64 (s, 3H), 3.95 (s, 3H), 2.92-2.76 (m, 1H), 2.76-2.57 (m, 3H), 2.55-2.27 (m, 1H), 2.10-1.58 (m, 2H), 1.45-1.20 (m, 2H), 1.18-0.96 (m, 1H), 0.96-0.58 (m, 3H). LCMS (ESI): 553.15 [M+H]$_+$.

Example 518. A Diastereomeric Mixture of (S)-4-(5-(5-fluoro-2-methoxypyridin-4-yl)-1H-pyrazole-3-carbonyl)-N—((R)-1-(hydroxymethyl)-3-methyl-2-oxabicyclo[2.1.1]hexan-4-yl)-4-azaspiro[2.5]octane-7-carboxamide and (S)-4-(5-(5-fluoro-2-methoxypyridin-4-yl)-1H-pyrazole-3-carbonyl)-N—((S)-1-(hydroxymethyl)-3-methyl-2-oxabicyclo[2.1.1]hexan-4-yl)-4-azaspiro[2.5]octane-7-carboxamide

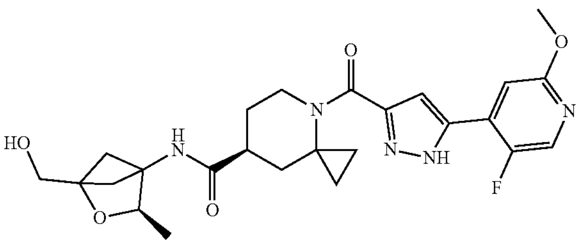

-continued

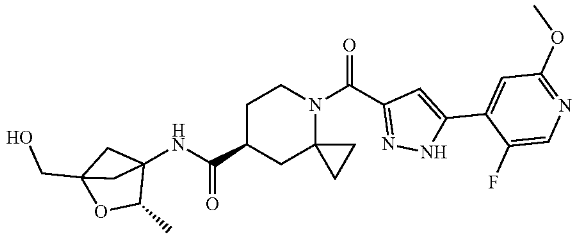

The title compound was prepared using a procedure similar to the one described for the synthesis of Example 430, except {4-amino-3-methyl-2-oxabicyclo[2.1.1]hexan-1-yl}methanol was used as a starting material. The residue was purified by silica gel column chromatography eluting with DCM/MeOH (10/1 v/v) to obtain (S)-4-(5-(5-fluoro-2-methoxypyridin-4-yl)-1H-pyrazole-3-carbonyl)-N—((R)-1-(hydroxymethyl)-3-methyl-2-oxabicyclo[2.1.1]hexan-4-yl)-4-azaspiro[2.5]octane-7-carboxamide and (S)-4-(5-(5-fluoro-2-methoxypyridin-4-yl)-1H-pyrazole-3-carbonyl)-N—((S)-1-(hydroxymethyl)-3-methyl-2-oxabicyclo[2.1.1]hexan-4-yl)-4-azaspiro[2.5]octane-7-carboxamide (50.0 mg) as a solid mixture of diastereomers (Example 518). $^1$H NMR (400 MHz, DMSO-$d_6$) δ 13.97 (d, 1H), 8.36-8.22 (m, 2H), 7.32 (d, 1H), 7.04 (s, 1H), 4.74-4.61 (m, 1H), 4.58-4.30 (m, 1H), 4.18 (d, 1H), 3.88 (s, 3H), 3.50 (d, 2H), 2.26-2.04 (m, 1H), 1.92-1.40 (m, 5H), 1.33-1.22 (m, 2H), 1.21-1.11 (m, 2H), 1.07-0.92 (m, 3H), 0.89-0.78 (m, 1H), 0.74-0.63 (m, 1H), 0.60-0.51 (m, 1H). LCMS (ESI): 500.25 [M+H]$^+$.

This mixture of two diastereomers (50.0 mg) was separated using Chiral Prep-HPLC.

Column: CHIRAL ART Cellulose-SC column

Column dimension: 2×25 cm, 5 μm

Mobile Phase: hexanes (0.5% 2 M $NH_3$·MeOH):1/1 EtOH/DCM=50:50 hold for 13.5 min Flow rate: 20 mL/min Detection: 220/254 nm Example 518-A. The first eluting diastereomer (18.4 mg) was obtained as a solid.

The first eluting diastereomer had a retention time of 9.55 min.

$^1$H NMR (400 MHz, DMSO-$d_6$) δ 13.97 (d, 1H), 8.36-8.21 (m, 2H), 7.32 (d, 1H), 7.03 (s, 1H), 4.71-4.60 (m, 1H), 4.59-4.34 (m, 1H), 4.24-4.14 (m, 1H), 3.88 (s, 3H), 3.53-3.47 (m, 2H), 2.23-2.04 (m, 11H), 1.91-1.77 (m, 3H), 1.77-1.67 (m, 2H), 1.61-1.44 (m, 1H), 1.31-1.13 (m, 3H), 1.07-0.93 (m, 3H), 0.90-0.78 (m, 11H), 0.73-0.62 (m, 1H), 0.60-0.51 (m, 1H). LCMS (ESI): 500.25 [M+H]$^+$.

Example 518-B. The second eluting diastereomer (16.5 mg) was obtained as a solid.

The second eluting diastereomer had a retention time of 12.08 min.

$^1$H NMR (400 MHz, DMSO-$d_6$) δ 8.36-8.22 (m, 2H), 7.33 (d, 1H), 7.03 (d, 1H), 4.74-4.60 (m, 1H), 4.57-4.27 (m, 1H), 4.26-4.11 (m, 1H), 3.88 (s, 3H), 3.50 (d, 2H), 2.29-2.03 (m, 1H), 1.89-1.79 (m, 3H), 1.77-1.68 (m, 2H), 1.61-1.42 (m, 1H), 1.30-1.10 (m, 2H), 1.08-0.92 (m, 4H), 0.88-0.78 (m, 1H), 0.71-0.52 (m, 2H). LCMS (ESI): 500.25 [M+H]$^+$.

Example 519. (S)-4-(3-(5-fluoro-2-methoxypyridin-4-yl)-1H-pyrazole-5-carbonyl)-N-((1-(trifluoromethyl)-H-imidazol-2-yl) methy)-4-azaspiro[2.5]octane-7-carboxamide

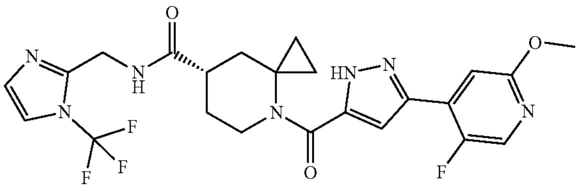 [SMILES: COc1cc(-c2cc(C(=O)N3CC[C@H](C(=O)NCc4nccn4C(F)(F)F)CC34CC4)[nH]n2)c(F)cn1]

The title compound was prepared using a procedure similar to the one described for the synthesis of Example 325, except 1-[1-(trifluoromethyl)imidazol-2-yl]methanamine was used as a starting material. The residue was purified by reverse phase column chromatography (using the following conditions: Column: C18; mobile phase A: Water (0.5% $NH_4HCO_3$), mobile phase B: MeCN; gradient: 10 B to 50 B in 30 min; 220/254 nm) to obtain the title compound (102.0 mg) as a solid. $^1H$ NMR (400 MHz, $CD_3OD$) δ 8.13 (s, 1H), 7.65-7.45 (m, 1H), 7.41-7.16 (m, 1H), 7.15-7.04 (m, 2H), 4.75-4.41 (m, 3H), 4.08-3.83 (m, 3H), 2.99-2.82 (m, 1H), 2.68-2.26 (m, 1H), 2.21-1.55 (m, 2H), 1.50-1.20 (m, 2H), 1.18-0.97 (m, 1H), 0.95-0.71 (m, 3H). LCMS (ESI): 522.20 $[M+H]^+$.

Example 520. (S)-4-(5-(5-fluoro-2-methoxypyridin-4-yl)-1H-pyrazole-3-carbonyl)-N-(1-(hydroxymethyl)-2-oxabicyclo[2.1.1]hexan-4-yl)-4-azaspiro[2,5]octane-7-carboxamide

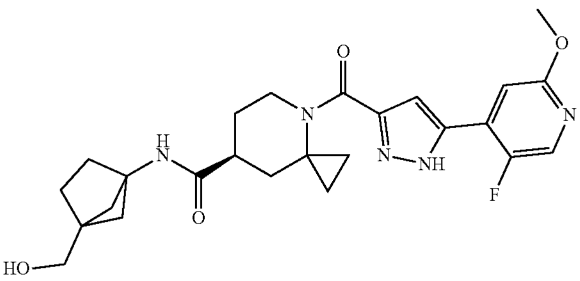 [SMILES: COc1cc(-c2cc(C(=O)N3CC[C@H](C(=O)NC45CCC(CO)(C4)C5)CC34CC4)n[nH]2)c(F)cn1]

The title compound was prepared using a procedure similar to the one described for the synthesis of Example 325, except {4-amino-2-oxabicyclo[2.1.1]hexan-1-yl}methanol was used as a starting material. The residue was purified by reverse phase column chromatography (using the following conditions: Column: C18; mobile phase A: Water (0.5% $NH_4HCO_3$), mobile phase B: MeCN; gradient: 20 B to 50 B in 30 min; 220/254 nm) to obtain the title compound (88.0 mg) as a solid. $^1H$ NMR (400 MHz, $CD_3OD$) δ 8.14 (s, 1H), 7.45-7.17 (m, 1H), 7.11 (s, 1H), 4.76-4.45 (m, 1H), 4.20-3.91 (m, 3H), 3.81 (s, 2H), 3.78-3.62 (m, 2H), 2.95-2.69 (m, 1H), 2.48-2.21 (m, 1H), 2.15-2.00 (m, 2H), 1.96-1.83 (m, 2H), 1.83-1.62 (m, 1H), 1.45-1.27 (m, 2H), 1.20-1.00 (m, 2H), 0.97-0.84 (m, 1H), 0.82-0.71 (m, 2H). LCMS (ESI): 486.15 $[M+H]^+$.

Example 521. (S)—N-((3-chloro-5-(4-methylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide

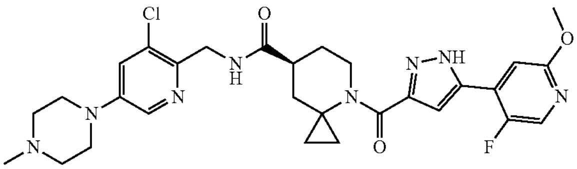 [SMILES: COc1cc(-c2cc(C(=O)N3CC[C@H](C(=O)NCc4ncc(N5CCN(C)CC5)cc4Cl)CC34CC4)n[nH]2)c(F)cn1]

Step-1. 3-chloro-5-(4-methylpiperazin-1-yl)pyridine-2-carbonitrile

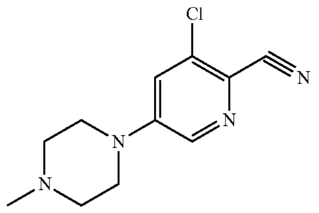 [SMILES: CN1CCN(c2cnc(C#N)c(Cl)c2)CC1]

1-methyl-piperazine (128.0 mg, 1.28 mmol) and DIPEA (330.3 mg, 2.56 mmol) were added to a solution of 3-chloro-5-fluoropyridine-2-carbonitrile (200.0 mg, 1.28 mmol) in DMSO (4.00 mL). The solution was stirred at 120° C. for 2 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH 101 v/v) to obtain the title compound (290.0 mg) as a solid. LCMS (ESI): 237.1 $[M+H]^+$.

Step-2. 1-[3-chloro-5-(4-methylpiperazin-1-yl)pyridin-2-yl]methanamine

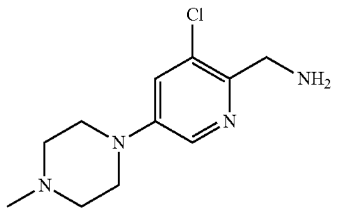 [SMILES: CN1CCN(c2cnc(CN)c(Cl)c2)CC1]

DIBAL-H (721.0 mg, 5.07 mmol) was added to a solution of 3-chloro-5-(4-methylpiperazin-1-yl)pyridine-2-carbonitrile (Step-1, 150.0 mg, 0.63 mmol) in THF (10.00 mL). The resulting solution was stirred at −78° C. for 1 h, then solution was stirred at 25° C. for 14 h. The resulting mixture was concentrated under reduced pressure. The residue was purified by Prep-TLC (DCM/MeOH, 5/1 v/v) to obtain the title compound (80.0 mg) as an oil. LCMS (ESI): 241.1 $[M+H]^+$.

Step-3. (S)—N-((3-chloro-5-(4-methylpiperazin-1-yl)pyridin-2-yl)methyl)-4-(5-(5-fluoro-2-methoxy-pyridin-4-yl)-1H-pyrazole-3-carbonyl)-4-azaspiro[2.5]octane-7-carboxamide

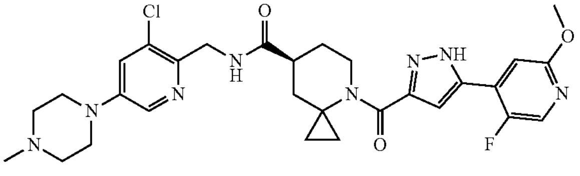 [SMILES: COc1cc(-c2cc(C(=O)N3CC[C@H](C(=O)NCc4ncc(N5CCN(C)CC5)cc4Cl)CC34CC4)n[nH]2)c(F)cn1]

HOBt (54.7 mg, 0.41 mmol), EDCI (77.6 mg, 0.41 mmol), and 1-[3-chloro-5-(4-methylpiperazin-1-yl)pyridin-2-yl]methanamine (Step-2, 65.0 mg, 0.27 mmol) were added to a solution of(S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 101.1 mg, 0.27 mmol) and DIPEA (174.5 mg, 1.35 mmol) in DMF (2.00 mL). The resulting solution was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (DCM/MeOH, 101 v/v) to obtain the title compound (100.0 mg) as a solid. $^1$H NMR (400 MHz, DMSO-$d_6$) δ 13.98 (s, 1H), 8.32-8.07 (m, 3H), 7.45-7.38 (m, 1H), 7.35-7.27 (m, 1H), 7.03 (s, 1H), 4.63-4.21 (m, 2H), 3.88 (s, 3H), 3.27-3.15 (m, 4H), 2.89-2.66 (m, 1H), 2.46-2.37 (m, 4H), 2.22 (s, 3H), 1.89-1.68 (m, 1H), 1.65-1.43 (m, 1H), 1.34-1.11 (m, 3H), 1.05-0.89 (m, 2H), 0.89-0.75 (m, 1H), 0.73-0.53 (m, 2H). LCMS (ESI): 597.25 [M+H]$^+$.

Example 522. (S)-4-(3-(5-fluoro-2-methoxypyridin-4-yl)-1H-pyrazole-5-carbonyl)-N-((1-hydroxy-3,3-dimethyl-1,3-dihydrobenzo[c][1,2]oxaborol-6-yl)methyl)-4-azaspiro[2.5]octane-7-carboxamide

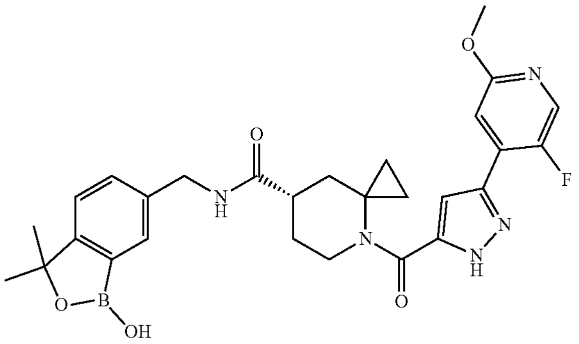 [SMILES: COc1cc(-c2cc(C(=O)N3CC[C@H](C(=O)NCc4ccc5c(c4)B(O)OC5(C)C)CC34CC4)[nH]n2)c(F)cn1]

The title compound was prepared using a procedure similar to the one described for the synthesis of Example 430, except 6-(aminomethyl)-3,3-dimethylbenzo[c][1,2]oxaborol-1(3H)-ol was used as a starting material. The residue was purified by Prep-HPLC (using the following conditions: Column: Atlantis T3 Prep OBD Column, 19×100 mm 5 μm, Mobile Phase A: Water (0.1% FA), Mobile Phase B: MeCN (0.1% FA); Flow rate: 30 mL/min; Gradient: 40% B to 50% B in 8 min; Wavelength: 254 nm) to obtain the title compound (4.4 mg) as solid. $^1$H NMR (400 MHz, $CD_3OD$) δ ppm 8.12 (br s, 1H) 7.49 (br s, 1H) 7.36 (br s, 1H) 7.28 (d, 2H) 7.10 (br s, 1H) 5.02-4.96 (m, 2H) 4.38 (s, 2H) 3.93 (s, 3H) 3.53-3.48 (m, 1H) 2.84 (br s, 1H) 1.92-1.88 (m, 2H) 1.49 (s, 6H) 1.33-1.29 (m, 2H) 0.71 (br s, 2H). LCMS (ESI): 548.12 [M+H]$^+$.

Example 523. (S)-4-(3-(5-fluoro-2-methoxypyridin-4-yl)-1H-pyrazole-5-carbonyl)-N-(1-hydroxy-1,3-dihydrobenzo[c][1,2]oxaborol-5-yl)-4-azaspiro[2.5]octane-7-carboxamide

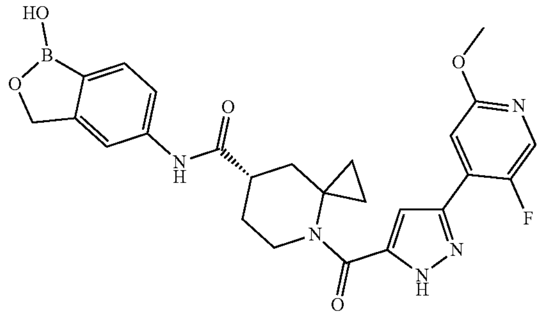 [SMILES: COc1cc(-c2cc(C(=O)N3CC[C@H](C(=O)Nc4ccc5c(c4)COB5O)CC34CC4)[nH]n2)c(F)cn1]

The title compound was prepared using a procedure similar to the one described for the synthesis of Example 430, except 5-aminobenzo[c][1,2]oxaborol-1(3H)-ol was used as a starting material. The residue was purified by Prep-HPLC (using the following conditions: Column: Atlantis T3 Prep OBD Column, 19×100 mm 5 μm, Mobile Phase A: Water (0.1% FA), Mobile Phase B: MeCN (0.1% FA) Flow rate: 30 mL/min; Gradient: 35% B to 50% B in 8 min; Wavelength: 254 nm) to obtain the title compound (12.1 mg) as solid. $^1$H NMR (400 MHz, $CD_3OD$) δ ppm 8.12 (br s, 1H) 7.66-7.79 (m, 1H) 7.58 (br d, 1H) 7.40 (br d, 1H) 7.21-7.35 (m, 1H) 7.11 (br s, 1H) 4.90-5.16 (m, 2H) 3.93 (s, 3H) 3.48 (s, 2H) 2.91-3.06 (m, 1H) 1.88-2.09 (m, 1H) 1.74-1.92 (m, 1H) 1.38 (d, 2H) 1.29 (br s, 1H) 0.89-0.78 (m, 3H). LCMS (ESI): 506.30 [M+H]$^+$.

Example 524. A Diastereomeric Mixture of (S)-4-(5-(5-fluoro-2-methoxypyridin-4-yl)-1H-pyrazole-3-carbonyl)-N-((1R,3S)-3-hydroxy-3-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1S,3S)-3-hydroxy-3-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1R,3R)-3-hydroxy-3-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1S,3R)-3-hydroxy-3-(trifluoromethyl)cyclohexyl)-4-azaspiro[2.5]octane-7-carboxamide

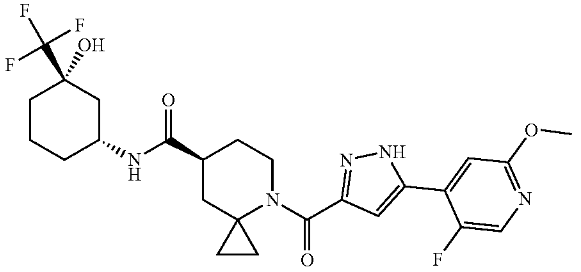

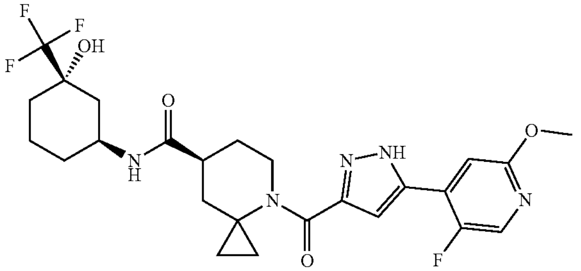

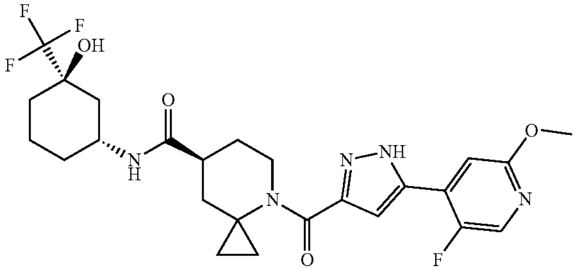

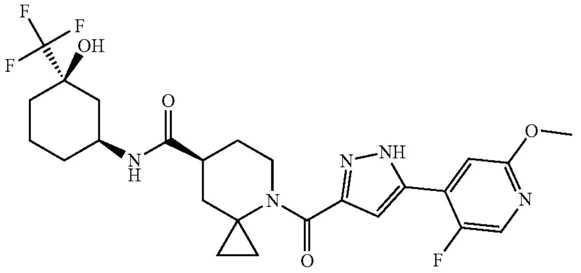

The title compound was prepared using a procedure similar to the one described for the synthesis of Example 325, except 3-amino-1-(trifluoromethyl)cyclohexan-1-ol was used as a starting material. The residue was purified by reverse phase column chromatography (using the following conditions: Column: C18; mobile phase A: Water (0.5% $NH_4HCO_3$), mobile phase B: MeCN; gradient: 20 B to 50 B in 30 min; 220/254 nm) to obtain (S)-4-(5-(5-fluoro-2-methoxypyridin-4-yl)-1H-pyrazole-3-carbonyl)-N-((1R,3S)-3-hydroxy-3-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1S,3S)-3-hydroxy-3-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1R,3R)-3-hydroxy-3-(trifluoromethyl)cyclohexyl)-4-azaspiro[2.5]octane-7-carboxamide and (S)-4-(5-(5-fluoro-2-methoxypyridin-4-yl)-1H-pyrazole-3-carbonyl)-N-((1S,3R)-3-hydroxy-3-(trifluoromethyl)cyclohexyl)-4-azaspiro[2.5]octane-7-carboxamide (160.0 mg) as a solid mixture of diastereomers (Example 524). $^1H$ NMR (400 MHz, $CD_3OD$) δ 8.14 (s, 1H), 7.45-7.16 (m, 1H), 7.11 (s, 1H), 4.69-4.43 (m, 1H), 4.25-3.97 (m, 1H), 3.95 (s, 3H), 2.91-2.67 (m, 1H), 2.52-2.22 (m, 1H), 2.10-1.85 (m, 3H), 1.85-1.65 (m, 5H), 1.65-1.54 (m, 1H), 1.54-1.38 (m, 1H), 1.37-1.13 (m, 2H), 1.13-0.93 (m, 1H), 0.88-0.55 (m, 3H). LCMS (ESI): 540.30 $[M+H]^+$.

This mixture of four diastereomers (50.0 mg) was separated using Chiral Prep-HPLC.

Column: CHIRALPAK ART Cellulose-SC column
Column dimension: 2×25 cm, 5 μm
Mobile Phase: MTBE (0.5% 2M $NH_3$·MeOH):1/1 MeOH/DCM=80:20 hold for 40 min
Flow rate: 20 mL/min
Detection: 220/254 nm Example 524-A. The first eluting diastereomer (30.0 mg) was obtained as a solid.

The first eluting diastereomer had a retention time of 9.75 min.

$^1H$ NMR (400 MHz, $CD_3OD$) δ 8.14 (s, 1H), 7.48-7.17 (m, 1H), 7.11 (s, 1H), 4.78-4.34 (m, 1H), 4.14-3.98 (m, 1H), 3.95 (s, 3H), 2.86-2.66 (m, 1H), 2.52-2.27 (m, 1H), 2.08-1.95 (m, 1H), 1.95-1.83 (m, 2H), 1.82-1.60 (m, 4H), 1.55-1.39 (m, 2H), 1.39-1.14 (m, 3H), 1.13-0.87 (m, 1H), 0.87-0.53 (m, 3H). LCMS (ESI): 540.30 $[M+H]^+$.

Example 524-B and 524-C. The second eluting peak (60.0 mg) was obtained as a solid mixture of two diastereomers.

The second eluting peak had a retention time of 25.08 min.

Example 524-D. The third eluting diastereomer (29.0 mg) was obtained as a solid.

The first eluting diastereomer had a retention time of 36.51 min.

$^1H$ NMR (400 MHz, $CD_3OD$) δ 8.14 (s, 1H), 7.42-7.16 (m, 1H), 7.11 (s, 1H), 4.76-4.41 (m, 1H), 4.26-4.11 (m, 1H), 3.95 (s, 3H), 2.92-2.66 (m, 1H), 2.52-2.19 (m, 1H), 2.13-1.65 (m, 9H), 1.66-1.49 (m, 2H), 1.47-1.23 (m, 1H), 1.15-0.86 (m, 1), 0.86-0.57 (m, 3H). LCMS (ESI): 540.30 $[M+H]^+$.

The second eluting peak (60.0 mg) containing two diastereomers of the title compounds was separated using Chiral Prep-HPLC.

Column: CHIRALPAK IH column
Column dimension: 2×25 cm, 5 μm
Mobile Phase: hexanes (0.5% 2 M $NH_3$·MeOH):1/1 MeOH/DCM=85:15 hold for 14.5 min
Flow rate: 20 mL/min
Detection: 220/254 nm Example 524-B. The first eluting diastereomer (23.0 mg) was obtained as a solid.

The first eluting diastereomer had a retention time of 8.87 min.

$^1H$ NMR (400 MHz, $CD_3OD$) δ 8.13 (s, 1H), 7.45-7.17 (m, 1H), 7.11 (s, 1H), 4.72-4.35 (m, 1H), 4.14-4.00 (m, 1H), 3.95 (s, 3H), 2.87-2.64 (m, 1H), 2.52-2.26 (m, 1H), 2.04-

1.96 (m, 1H), 1.96-1.84 (m, 2H), 1.83-1.62 (m, 4H), 1.55-1.38 (m, 2H), 1.39-1.13 (m, 3H), 1.13-0.87 (m, 1H), 0.86-0.58 (m, 3H). LCMS (ESI): 540.30 $[M+H]^+$.

Example 524-C. The second eluting diastereomer (15.5 mg) was obtained as a solid.

The second eluting diastereomer had a retention time of 12.75 min.

$^1$H NMR (400 MHz, $CD_3OD$) δ 8.14 (s, 1H), 7.45-7.16 (m, 1H), 7.11 (s, 1H), 4.75-4.42 (m, 1H), 4.26-4.15 (m, 1H), 3.95 (s, 3H), 2.92-2.66 (m, 1H), 2.47-1.95 (m, 1H), 1.95-1.86 (m, 3H), 1.86-1.68 (m, 5H), 1.67-1.51 (m, 2H), 1.43-1.26 (m, 1H), 1.19-0.93 (m, 2H), 0.75 (s, 3H). LCMS (ESI): 540.30 $[M+H]^+$.

Example 525. (S)-4-(3-(5-fluoro-2-methoxypyridin-4-yl)-1H-pyrazole-5-carbonyl)-N-((3-(trifluoromethyl)pyridin-4-yl)methyl)-4-azaspiro[2.5]octane-7-carboxamide

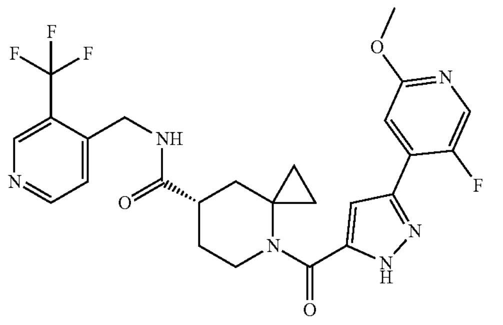 [SMILES: COc1cc(-c2cc(C(=O)N3CC[C@H](C(=O)NCc4ccncc4C(F)(F)F)CC34CC4)[nH]n2)c(F)cn1]

The title compound was prepared using a procedure similar to the one described for the synthesis of Example 325, except 1-[3-(trifluoromethyl)pyridin-4-yl]methanamine was used as a starting material. The residue was purified by reverse phase column chromatography (using the following conditions: column, C18; mobile phase A, Water (0.5% $NH_4HCO_3$), mobile phase B: MeCN; gradient 30 B to 50 B in 20 min; 220/254 nm) to obtain the title compound (75.1 mg) as a solid. $^1$H NMR (400 MHz, $CD_3OD$) δ 8.93-8.68 (m, 2H), 8.12 (s, 1H), 7.52 (d, 1H), 7.28 (d, 1H), 7.17-7.02 (m, 1H), 4.65-4.55 (m, 2H), 3.94 (s, 3H), 3.57-3.39 (m, 1H-1), 3.27-3.05 (m, 1H), 3.05-2.85 (m, 1H), 2.76-2.25 (m, 1H), 2.18-1.65 (m, 2H), 1.58-1.24 (m, 11H), 1.23-0.95 (m, 1H), 0.92-0.58 (m, 3H). LCMS (ESI): 533.30 $[M+H]^+$.

Example 526. (S)—N-((5-chloro-1-methyl-3-(trifluoromethyl)-1H-pyrazol-4-yl)methyl)-4-(3-(5-fluoro-2-methoxypyridin-4-yl)-1H-pyrazole-5-carbonyl)-4-azaspiro[2.5]octane-7-carboxamide

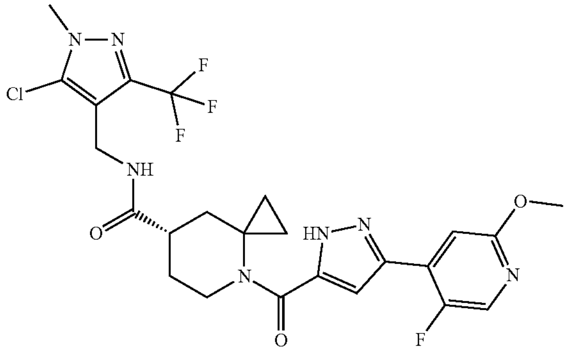 [SMILES: COc1cc(-c2cc(C(=O)N3CC[C@H](C(=O)NCc4c(C(F)(F)F)nn(C)c4Cl)CC34CC4)[nH]n2)c(F)cn1]

Step-1. 5-chloro-1-methyl-3-(trifluoromethyl)pyrazole-4-carbaldehyde

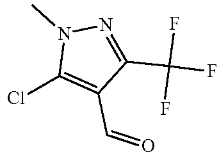

Dess-Martin periodinane (790.7 mg, 1.86 mmol) was added to a stirred solution of [5-chloro-1-methyl-3-(trifluoromethyl)pyrazol-4-yl]methanol (200.0 mg, 0.93 mmol) in DCM (4.00 mL). The resulting mixture was stirred at 0° C. for 2 h. The resulting mixture was concentrated under reduced pressure. The residue was purified by silica gel column chromatography eluting with petroleum ether/EtOAc (31 v/v) to obtain the title compound (190.0 mg) as a solid. LCMS (ESI): 213.00 $[M+H]^+$.

Step-2. N-[(1E)-[5-chloro-1-methyl-3-(trifluoromethyl)pyrazol-4-yl]methylidene]-2-methylpropane-2-sulfinamide

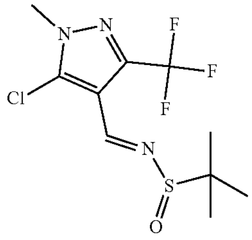 [SMILES: Cn1nc(C(F)(F)F)c(/C=N/S(=O)C(C)(C)C)c1Cl]

PTSA (30.7 mg, 0.18 mmol), tert-butanesulfinamide (216.7 mg, 1.79 mmol) and $MgSO_4$ (322.8 mg, 2.68 mmol) were added to a stirred solution of 5-chloro-1-methyl-3-(trifluoromethyl)pyrazole-4-carbaldehyde (Step-1, 190.0 mg, 0.89 mmol) in DCM (10.00 mL). The resulting mixture was stirred at 25° C. for 14 h. The resulting mixture was concentrated under reduced pressure. The residue was purified by silica gel column chromatography eluting with petroleum ether/EtOAc (3/1 v/V) to obtain the title compound (95.0 mg) as a solid. LCMS (ESI): 316.00 $[M+H]^+$.

Step-3. N-{[5-chloro-1-methyl-3-(trifluoromethyl) pyrazol-4-yl]methyl}-2-methylpropane-2-sulfinamide

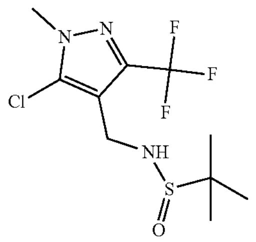 [SMILES: Cn1nc(C(F)(F)F)c(CNS(=O)C(C)(C)C)c1Cl]

$NaBH_4$ (23.3 mg, 0.62 mmol) was added to a stirred solution of N-[(1E)-[5-chloro-1-methyl-3-(trifluoromethyl) pyrazol-4-yl]methylidene]-2-methylpropane-2-sulfinamide (Step-2, 95.0 mg, 0.31 mmol) in MeOH (1.00 mL). The resulting mixture was stirred at 25° C. for 14 h. The residue was purified by silica gel column chromatography eluting with PE/EA (3/1 v/v) to obtain the title compound (65.0 mg) as a solid. LCMS (ESI): 318.00 $[M+H]^+$.

Step-4. 1-[5-chloro-1-methyl-3-(trifluoromethyl) pyrazol-4-yl]methanaminium

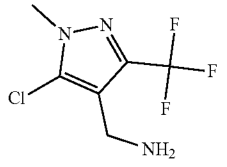

HCl (gas) in 1,4-dioxane (2.00 mL was added in a solution of N-{[5-chloro-1-methyl-3-(trifluoromethyl)pyrazol-4-yl]methyl}-2-methylpropane-2-sulfinamide (Step-3, 65.0 mg, 0.21 mmol) in 1,4-dioxane (2.00 mL). The resulting mixture was stirred at 25° C. for 1 h. The resulting mixture was concentrated under reduced pressure. The residue was purified by silica gel column chromatography eluting with petroleum ether/EtOAc (3/1 v/v) to obtain the title compound (43.0 mg) as a solid. LCMS (ESI): 214.00 $[M+H]^+$.

Step-5. (S)—N-((5-chloro-1-methyl-3-(trifluoromethyl)-1H-pyrazol-4-yl)methyl)-4-(3-(5-fluoro-2-methoxypyridin-4-yl)-1H-pyrazole-5-carbonyl)-4-azaspiro[2.5]octane-7-carboxamide

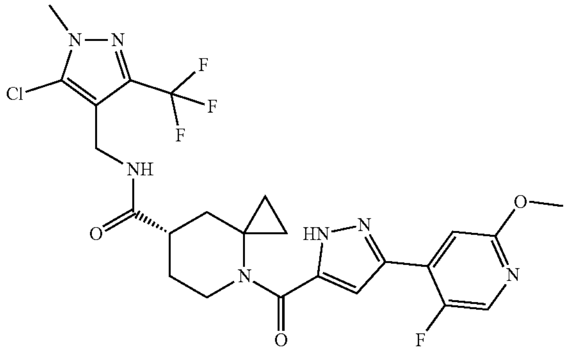 [SMILES: COc1cc(-c2cc(C(=O)N3CC[C@H](C(=O)NCc4c(C(F)(F)F)nn(C)c4Cl)CC34CC4)[nH]n2)c(F)cn1]

HOBt (47.5 mg, 0.35 mmol), EDCI (67.3 mg, 0.35 mmol), and 1-[5-chloro-1-methyl-3-(trifluoromethyl)pyrazol-4-yl]methanamine (Step-4, 50.0 mg, 0.23 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 61.4 mg, 0.16 mmol) and DIPEA (181.5 mg, 1.40 mmol) in DMF (1.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4CO_3$), mobile phase B: MeCN; gradient: 30 B to 50 B in 20 min; 220/254 nm) to obtain the title compound (37.0 mg) as a solid.

$^1H$ NMR (400 MHz, $CD_3OD$) δ 8.21-8.03 (m, 1H), 7.35-7.20 (m, 1H), 7.17-7.00 (m, 1H), 4.67-4.51 (m, 1H), 4.34-4.23 (m, 2H), 4.00-3.81 (m, 6H), 2.90-2.68 (m, 1H), 2.54-2.28 (m, 1H), 1.92-1.61 (m, 2H), 1.39-1.14 (m, 2H), 1.03-0.91 (m, 2-1), 0.77-0.69 (m, 2H). LCMS (ESI): 570.20 $[M+H]^+$.

Example 527. (S)-4-(5-(5-fluoro-2-methoxypyridin-4-yl)-1H-pyrazole-3-carbonyl)-N-((5-methoxy-3-(trifluoromethyl)pyridin-2-yl)methyl)-4-azaspiro [2.5]octane-7-carboxamide

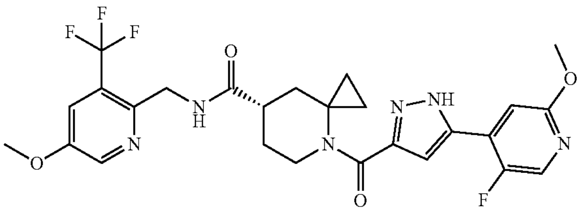 [SMILES: COc1cnc(CNC(=O)[C@H]2CCN(C(=O)c3cc(-c4cc(OC)ncc4F)[nH]n3)C3(CC3)C2)c(C(F)(F)F)c1]

Step-1. 5-methoxy-3-(trifluoromethyl)pyridine-2-carbonitrile

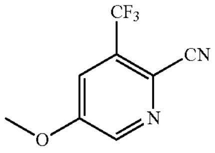

NaOMe (78.5 mg, 1.45 mmol) was added to a stirred solution of 5-chloro-3-(trifluoromethyl)pyridine-2-carbonitrile (300.0 mg, 1.45 mmol) in DMF (3.00 mL). The resulting mixture was stirred at −78° C. to 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (3/1 v/v) to obtain the title compound (65.0 mg) as an oil. LCMS (ESI): 203.0 $[M+H]^+$.

Step-2. 1-[5-methoxy-3-(trifluoromethyl)pyridin-2-yl]methanamine

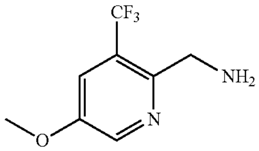

Pd/C (10.0 mg, 0.09 mmol) was added to a stirred solution of 5-methoxy-3-(trifluoromethyl)pyridine-2-carbonitrile (Step-1, 45.0 mg, 0.22 mmol) in AcOH (2.00 mL). The resulting mixture was stirred at 25° C. for 1 h under the atmosphere of hydrogen. The resulting mixture was filtered, the filter cake was washed with MeOH. The filtrate was concentrated under reduced pressure to obtain the title compound as an oil and used directly in the next step without further purification. LCMS (ESI): 207.0 $[M+H]^+$.

Step-3. (S)-4-(5-(5-fluoro-2-methoxypyridin-4-yl)-1H-pyrazole-3-carbonyl)-N-((5-methoxy-3-(trifluoromethyl)pyridin-2-yl)methyl)-4-azaspiro[2.5]octane-7-carboxamide

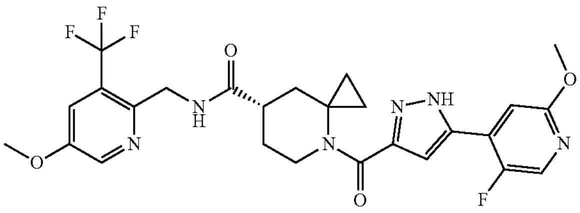 [SMILES: COc1cnc(CNC(=O)[C@H]2CCN(C(=O)c3cc(-c4cc(OC)ncc4F)[nH]n3)C3(CC3)C2)c(C(F)(F)F)c1]

HOBt (29.5 mg, 0.22 mmol), EDCI (41.9 mg, 0.22 mmol), and 1-[5-methoxy-3-(trifluoromethyl)pyridin-2-yl]methanamine (Step-2, 45.0 mg, 0.22 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 54.5 mg, 0.15 mmol) DIPEA (150.5 mg, 1.17 mmol) in DMF (3.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (10/1 v/v) to obtain the title compound (46.7 mg) as a solid. $^1H$ NMR (400 MHz, $CD_3OD$) δ 8.46 (d, 1H), 8.13 (s, 1H), 7.63 (d, 1H), 7.45-7.17 (m, 1H), 7.11 (s, 1H), 4.61 (s, 3H), 4.02-3.88 (m, 6H), 3.10-2.83 (m, 1H), 2.56-2.35 (m, 1H), 2.10-1.87 (m, 1H), 1.83-1.63 (m, 1H), 1.53-1.23 (m, 3H), 1.18-0.89 (m, 1H), 0.84-0.62 (m, 2H). LCMS (ESI): 563.35 $[M+H]^+$.

Example 528. A Diastereomeric Mixture of (R)-4-(5-(6-cyanopyrimidin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(6-cyanopyrimidin-4-yl)-1H-pyrazole-3-carbonyl)-N-((1r,4S)-4-hydroxy-4-(trifluoromethyl)cyclohexyl)-4-azaspiro[2.5]octane-7-carboxamide

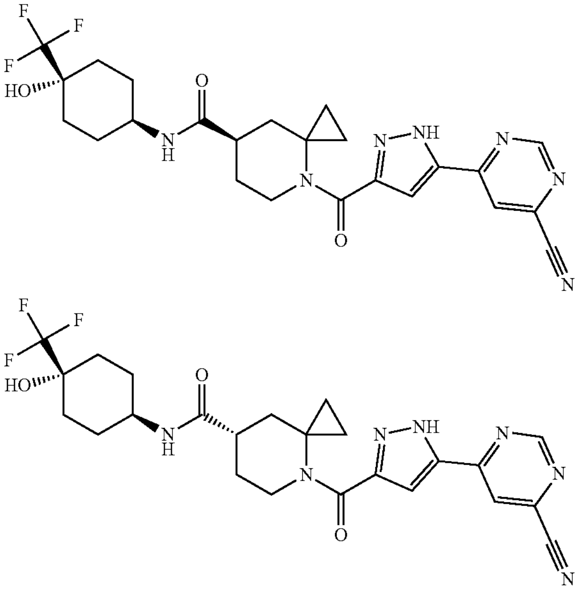

Step-1. ethyl 5-(6-cyanopyrimidin-4-yl)-1-(oxan-2-yl)pyrazole-3-carboxylate

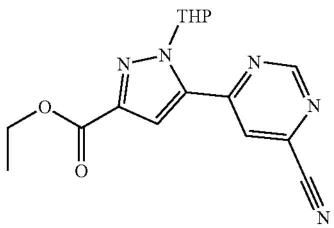

Pd(dppf)$Cl_2$ (524.0 mg, 0.72 mmol) and $K_3PO_4$ (1.52 g, 7.17 mmol) were added to a stirred solution of 6-chloropyrimidine-4-carbonitrile (500.0 mg, 3.58 mmol) and 5-(ethoxycarbonyl)-2-(oxan-2-yl)pyrazol-3-ylboronic acid (1.25 g, 4.66 mmol) in 1,4-dioxane (10.00 mL)/$H_2O$ (1.00 mL). The resulting mixture was stirred at 70° C. for 14 h under the atmosphere of nitrogen. The resulting mixture was concentrated under reduced pressure. The residue was purified by silica gel column chromatography eluting with DCM/MeOH (15/1 v/v) to obtain the title compound (720.0 mg) as a solid. LCMS (ESI): 328.1 $[M+H]^+$.

Step-2. 5-(6-cyanopyrimidin-4-yl)-1-(oxan-2-yl)pyrazole-3-carboxylic acid

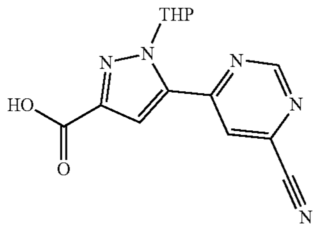

Trimethylstannanol (829.0 mg, 4.58 mmol) was added to a stirred solution of ethyl 5-(6-cyanopyrimidin-4-yl)-1-(oxan-2-yl)pyrazole-3-carboxylate (Step-1, 500.0 mg, 1.53 mmol) in DCE (5.00 mL) at 80° C. for 14 h under the atmosphere of nitrogen. The resulting mixture was concentrated under reduced pressure. The residue was purified by silica gel column chromatography eluting with DCM/MeOH (15/1 v/v) to obtain the title compound (300.0 mg) as a solid. LCMS (ESI): 300.1 $[M+H]^+$.

Step-3. tert-butyl 7-[[(1r,4r)-4-hydroxy-4-(trifluoromethyl)cyclohexyl]carbamoyl]-4-azaspiro[2.5]octane-4-carboxylate

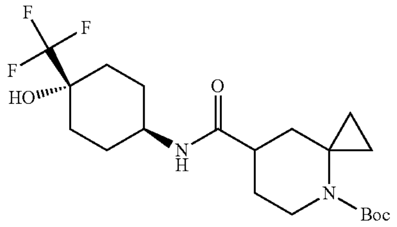 [SMILES: CC(C)(C)OC(=O)N1CCC(C(=O)N[C@H]2CC[C@@](O)(C(F)(F)F)CC2)CC12CC2]

EDCI (389.4 mg, 2.03 mmol), HOBt (275.2 mg, 2.04 mmol), and (1r,4r)-4-amino-1-(trifluoromethyl)cyclohexan-1-ol hydrochloride (222.9 mg, 1.02 mmol) were added to a stirred solution of 4-(tert-butoxycarbonyl)-4-azaspiro[2.5]octane-7-carboxylic acid (260.0 mg, 1.02 mmol) and DIPEA (1.32 g, 10.18 mmol) in DMF (10.00 mL). The resulting mixture was stirred at 25° C. for 14 h. The resulting mixture was diluted with EtOAc and washed with water. The organic layer was concentrated under reduced pressure. The residue was purified by silica gel column chromatography eluting with petroleum ether/EtOAc (4/1 v/v) to obtain the title compound (400.0 mg) as an oil. LCMS (ESI): 421.2 $[M+H]^+$.

Step-4. N-[(1r,4r)-4-hydroxy-4-(trifluoromethyl)cyclohexyl]-4-azaspiro[2.5]octane-7-carboxamide

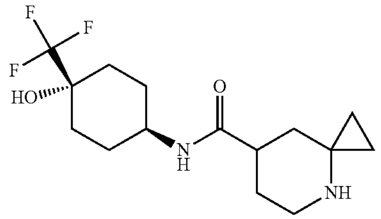 [SMILES: O=C(N[C@H]1CC[C@@](O)(C(F)(F)F)CC1)C1CCNC2(CC2)C1]

TFA (4.00 mL) was added to a stirred solution of tert-butyl 7-[[(1r,4r)-4-hydroxy-4-(trifluoromethyl)cyclohexyl]carbamoyl]-4-azaspiro[2.5]octane-4-carboxylate (Step-3, 370.0 mg, 0.88 mmol) in DCM (4.00 mL) at 0° C. The resulting mixture was stirred at 25° C. for 1 h. The resulting mixture was concentrated under reduced pressure. The residue was purified by Prep-TLC (petroleum ether/EtOAc, 2/1 v/v) to obtain the title compound (200.0 mg) as an oil. LCMS (ESI): 321.1 $[M+H]^+$.

Step-5. 4-[5-(6-cyanopyrimidin-4-yl)-1-(oxan-2-yl)pyrazole-3-carbonyl]-N-[(1r,4r)-4-hydroxy-4-(trifluoromethyl)cyclohexyl]-4-azaspiro[2.5]octane-7-carboxamide

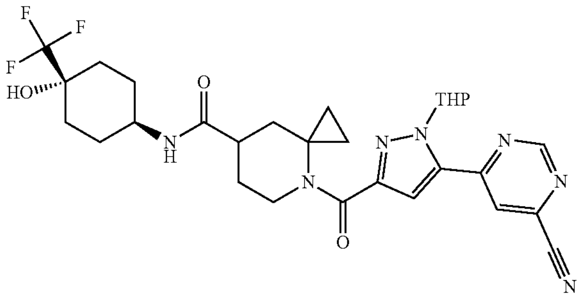

HATU (427.0 mg, 1.12 mmol) and N-[(1r,4r)-4-hydroxy-4-(trifluoromethyl)cyclohexyl]-4-azaspiro[2.5]octane-7-carboxamide (Step-4, 300.0 mg, 0.94 mmol) were added to a stirred solution of 5-(6-cyanopyrimidin-4-yl)-1-(oxan-2-yl)pyrazole-3-carboxylic acid (Step-2, 280.0 mg, 0.94 mmol) and DIPEA (363.0 mg, 2.81 mmol) in DMF (5.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by silica gel column chromatography eluting with petroleum ether/EtOAc (1/1 v/v) to obtain the title compound (350.0 mg) as a solid. LCMS (ESI): 602.2 $[M+H]^+$.

Step-6. (R)-4-(5-(6-cyanopyrimidin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(6-cyanopyrimidin-4-yl)-1H-pyrazole-3-carbonyl)-N-((1r,4S)-4-hydroxy-4-(trifluoromethyl)cyclohexyl)-4-azaspiro[2.5]octane-7-carboxamide

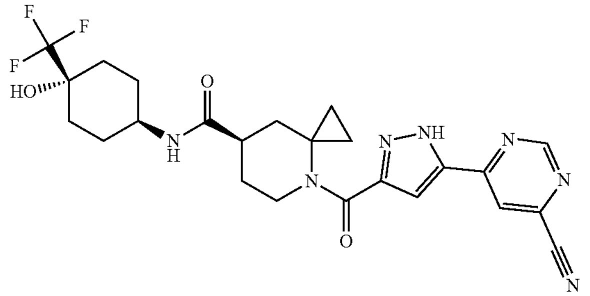

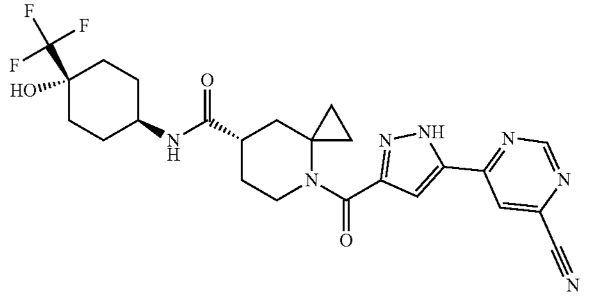

TFA (3.00 mL) was added to a stirred solution of 4-[5-(6-cyanopyrimidin-4-yl)-1-(oxan-2-yl)pyrazole-3-carbonyl]-N-[(1r,4r)-4-hydroxy-4-(trifluoromethyl)cyclohexyl]-4-azaspiro[2.5]octane-7-carboxamide (350.0 mg, 0.58 mmol) in DCM (3.00 mL). The resulting mixture was stirred at 25° C. for 14 h. The resulting mixture was concentrated under reduced pressure. The residue was purified by silica gel column chromatography eluting with DCM/MeOH (10/1) to obtain (R)-4-(5-(6-cyanopyrimidin-4-yl)-1H-pyrazole-3-carbonyl)-N-((1r,4R)-4-hydroxy-4-(trifluoromethyl)cyclohexyl)-4-azaspiro[2.5]octane-7-carboxamide and (S)-4-(5-(6-cyanopyrimidin-4-yl)-1H-pyrazole-3-carbonyl)-N-((1r,4S)-4-hydroxy-4-(trifluoromethyl)cyclohexyl)-4-azaspiro[2.5]octane-7-carboxamide (130.0 mg) as a solid mixture of diastereomers (Example 528). $^1$H NMR (400 MHz, DMSO-$d_6$) δ 14.28 (s, 1H), 9.38 (s, 1H), 8.74-8.50 (m, 1H), 7.81 (s, 1H), 7.61-7.19 (m, 1H), 5.69 (s, 1H), 4.86-4.11 (m, 1H), 3.90-3.74 (m, 1H), 2.91-2.71 (m, 1H), 2.31-2.02 (m, 1H), 1.88-1.66 (m, 5H), 1.64-1.40 (m, 5H), 1.34-0.82 (m, 3H), 0.76-0.43 (m, 3H). LCMS (ESI): 518.25 [M+H]$^+$.

This mixture of two diastereomers (128.0 mg) was separated using Chiral Prep-HPLC.

Column: CHIRALPAK ART Amylose-SA column, Column dimension: 2×25 cm, 5 μm, Mobile Phase: 1/1 hexanes/DCM (0.5% 2 M $NH_3$·MeOH):EtOH=85:15 hold for 12 min, Flow rate: 20 mL/min, Detection: 220/254 nm.

Example 528-A. The first eluting diastereomer (51.9 mg) was obtained as a solid.

The first eluting diastereomer had a retention time of 5.68 min.

$^1$H NMR (400 MHz, DMSO-$d_6$) δ 14.31 (s, 1H), 9.39 (d, 1H), 8.60 (s, 1H), 7.81 (d, 1H), 7.36 (s, 1H), 5.78-5.61 (m, 1H), 4.80-4.07 (m, 1H), 3.96-3.77 (m, 1H), 3.08-2.90 (m, 1H), 2.89-2.71 (m, 1H), 2.31-2.10 (m, 1H), 1.87-1.67 (m, 5H), 1.62-1.42 (m, 5H), 1.28-1.17 (m, 1H), 1.05-0.91 (m, 1H), 0.89-0.79 (m, 1H), 0.73-0.53 (m, 2H). LCMS (ESI): 518.20 [M+H]$^+$.

Example 528-B. The second eluting diastereomer (49.1 mg) was obtained as a solid.

The second eluting diastereomer had a retention time of 10.19 min.

$^1$H NMR (400 MHz, DMSO-$d_6$) δ 14.66-14.15 (m, 1H), 9.49-9.30 (m, 1H), 8.76-8.51 (m, 1H), 7.97-7.67 (m, 1H), 7.62-7.20 (m, 1H), 5.69 (s, 1H), 4.84-4.06 (m, 1H), 3.95-3.76 (m, 1H), 3.20-2.92 (m, 1H), 2.92-2.73 (m, 1H), 2.29-2.06 (m, 1H), 1.92-1.67 (m, 5H), 1.65-1.43 (m, 5H), 1.35-1.16 (m, 1H), 1.16-1.03 (m, 1H), 1.02-0.81 (m, 1H), 0.75-0.44 (m, 2H). LCMS (ESI): 518.20 [M+H]$^+$.

Example 529. A Diastereomeric Mixture of (S)-4-(5-(2-chloro-5-fluoropyridin-4-yl)-1H-pyrazole-3-carbonyl)-N-((1r,4S)-4-hydroxy-4-(trifluoromethyl)cyclohexyl)-4-azaspiro[2.5]octane-7-carboxamide and (R)-4-(5-(2-chloro-5-fluoropyridin-4-yl)-1H-pyrazole-3-carbonyl)-N-((1r,4R)-4-hydroxy-4-(trifluoromethyl)cyclohexyl)-4-azaspiro[2.5]octane-7-carboxamide

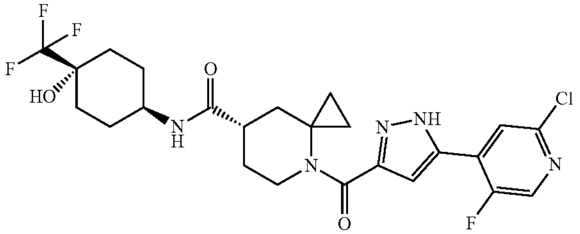

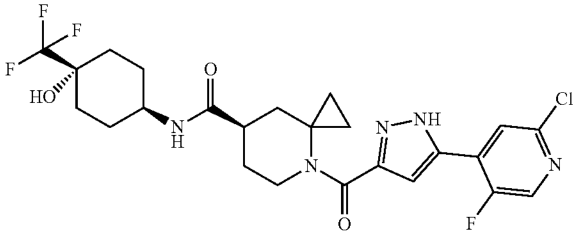

Step-1. methyl 5-bromo-1-[[2-(trimethylsilyl)ethoxy]methyl]pyrazole-3-carboxylate

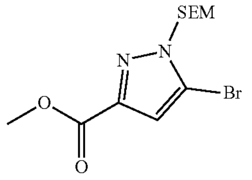 [SMILES: COC(=O)c1cc(Br)n(COCC[Si](C)(C)C)n1]

$K_2CO_3$ (26.97 g, 195.11 mmol) was added to a stirred solution of methyl 5-bromo-1H-pyrazole-3-carboxylate (20.00 g, 97.56 mmol) in DMF (50.00 mL). Then SEMCl (24.40 g, 146.33 mmol) was added to the resulting mixture at 0° C. The resulting solution was stirred at 25° C. for 14 h. The resulting solution was diluted with EtOAc and washed with water. The organic layer was concentrated under reduced pressure. The residue was purified by silica gel column chromatography eluting with EtOAc/petroleum ether (1/3 v/v) to obtain the title compound (29.00 g) as an oil. LCMS (ESI): 335.1 $[M+H]^+$.

Step-2. methyl 5-(2-chloro-5-fluoropyridin-4-yl)-1-[[2-(trimethylsilyl)ethoxy]methyl]pyrazole-3-carboxylate

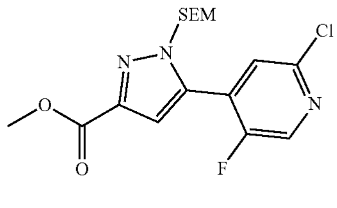 [SMILES: COC(=O)c1cc(-c2cc(Cl)ncc2F)n(COCC[Si](C)(C)C)n1]

2-Chloro-5-fluoropyridin-4-ylboronic acid (679.9 mg, 3.88 mmol), CsF (906.2 mg, 5.97 mmol) and Pd $(AmPhos)_2Cl_2$ (422.4 mg, 0.60 mmol) were added to a stirred solution of methyl 5-bromo-1-[[2-(trimethylsilyl)ethoxy]methyl]pyrazole-3-carboxylate (Step-1, 1.00 g, 2.98 mmol) in 1,4-dioxane (5.00 mL)/$H_2O$ (0.50 mL). The resulting mixture was stirred at 95° C. for 2 h under the atmosphere of nitrogen. The solution was concentrated under reduced pressure. The residue was purified by silica gel column chromatography eluting with EtOAc/petroleum ether (1/5 v/v) to obtain the title compound (350.0 mg) as an oil. LCMS (ESI): 386.1 $[M+H]^+$.

Step-3. 5-(2-chloro-5-fluoropyridin-4-yl)-1-[[2-(trimethylsilyl)ethoxy]methyl]pyrazole-3-carboxylic acid

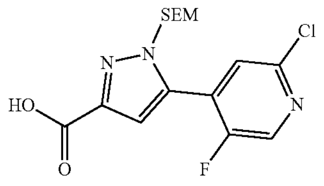 [SMILES: C[Si](C)(C)CCOCn1nc(C(=O)O)cc1-c1cc(Cl)ncc1F]

Lithium hydroxide (76.1 mg, 1.81 mmol) was added to a stirred solution of methyl 5-(2-chloro-5-fluoropyridin-4-yl)-1-[[2-(trimethylsilyl)ethoxy]methyl]pyrazole-3-carboxylate (Step-2, 350.0 mg, 0.91 mmol) in MeOH (2.00 mL)/THF (2.00 mL)/$H_2O$ (2.00 mL). The resulting mixture was stirred at 25° C. for 2 h. The solution was concentrated under reduced pressure, then was acidified to pH 3 with HCl (1 M). The solution was extracted with ethyl acetate. The organic layers were combined, dried over anhydrous $Na_2SO_4$, filtered, and concentrated under reduced pressure to obtain the title compound (301.0 mg) as a solid. LCMS (ESI): 372.1 $[M+H]^+$.

Step-4. methyl 4-[5-(2-chloro-5-fluoropyridin-4-yl)-1-[[2-(trimethylsilyl)ethoxy]methyl]pyrazole-3-carbonyl]-4-azaspiro[2.5]octane-7-carboxylate

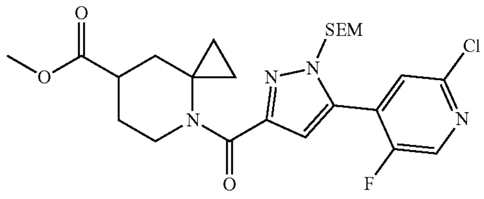 [SMILES: COC(=O)C1CCN(C(=O)c2cc(-c3cc(Cl)ncc3F)n(COCC[Si](C)(C)C)n2)C2(CC2)C1]

Methyl 4-azaspiro[2.5]octane-7-carboxylate hydrochloride (177.1 mg, 0.86 mmol) and HATU (357.1 mg, 0.94 mmol) were added to a stirred solution of 5-(2-chloro-5-fluoropyridin-4-yl)-1-[[2-(trimethylsilyl)ethoxy]methyl]pyrazole-3-carboxylic acid (Step-3, 291.0 mg, 0.78 mmol) and DIPEA (303.4 mg, 2.35 mmol) in DMF (5.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by silica gel column chromatography eluting with EtOAc/petroleum ether (1/3 v/v) to obtain the title compound (362.0 mg) as an oil. LCMS (ESI): 523.2 $[M+H]^+$.

Step-5. 4-[5-(2-chloro-5-fluoropyridin-4-yl)-1-[[2-(trimethylsilyl)ethoxy]methyl]pyrazole-3-carbonyl]-4-azaspiro[2.5]octane-7-carboxylic acid

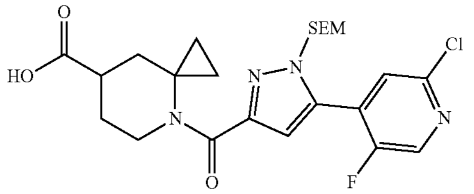 [SMILES: C[Si](C)(C)CCOCn1nc(C(=O)N2CCC(C(=O)O)CC23CC3)cc1-c1cc(Cl)ncc1F]

Lithium hydroxide (58.1 mg, 1.38 mmol) was added to a stirred solution of methyl 4-[5-(2-chloro-5-fluoropyridin-4-yl)-1-[[2-(trimethylsilyl)ethoxy]methyl]pyrazole-3-carbonyl]-4-azaspiro[2.5]octane-7-carboxylate (Step-4, 362.0 mg, 0.69 mmol) in THF (2.00 mL)/MeOH (2.00 mL)/$H_2O$ (2.00 mL). The resulting mixture was stirred at 25° C. for 1 h. The solution was concentrated under reduced pressure, then acidified to pH 3 with HCl (1 M). The solution was extracted with ethyl acetate. The organic layers were combined, dried over anhydrous $Na_2SO_4$, filtered, and concentrated under reduced pressure to obtain the title compound (339.0 mg) as an oil. LCMS (ESI): 509.2 $[M+H]^+$.

Step-6. methyl 4-[5-(2-chloro-5-fluoropyridin-4-yl)-1-[[2-(trimethylsilyl)ethoxy]methyl]pyrazole-3-carbonyl]-4-azaspiro[2.5]octane-7-carboxylate

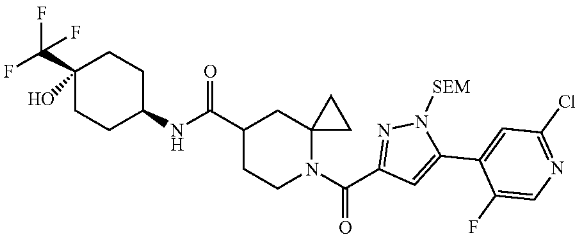 [SMILES: C[Si](C)(C)CCOCn1nc(C(=O)N2CCC(C(=O)N[C@H]3CC[C@@](O)(C(F)(F)F)CC3)CC23CC3)cc1-c1cc(Cl)ncc1F]

(1r,4r)-4-Amino-1-(trifluoromethyl)cyclohexan-1-ol hydrochloride (137.6 mg, 0.63 mmol) and HATU (285.9 mg, 0.75 mmol) were added to a stirred solution of 4-[5-(2-chloro-5-fluoropyridin-4-yl)-1-[[2-(trimethylsilyl)ethoxy]methyl]pyrazole-3-carbonyl]-4-azaspiro[2.5]octane-7-carboxylic acid (Step-5, 319.0 mg, 0.63 mmol) and DIPEA (243.0 mg, 1.88 mmol) in DMF (3.00 mL). The resulting mixture was stirred at 25° C. for 14 h. The solution was diluted with EtOAc and washed with water. The organic layers were combined, dried over anhydrous $Na_2SO_4$, filtered, and concentrated under reduced pressure. The residue was purified by silica gel column chromatography eluting with DCM/MeOH (15/1 v/v) to obtain the title compound (410.0 mg) as a solid. LCMS (ESI): 674.3 $[M+H]^+$.

Step-7. (S)-4-(5-(2-chloro-5-fluoropyridin-4-yl)-1H-pyrazole-3-carbonyl)-N-((1r,4S)-4-hydroxy-4-(trifluoromethyl)cyclohexyl)-4-azaspiro[2.5]octane-7-carboxamide and (R)-4-(5-(2-chloro-5-fluoropyridin-4-yl)-1H-pyrazole-3-carbonyl)-N-((1r,4R)-4-hydroxy-4-(trifluoromethyl)cyclohexyl)-4-azaspiro[2.5]octane-7-carboxamide

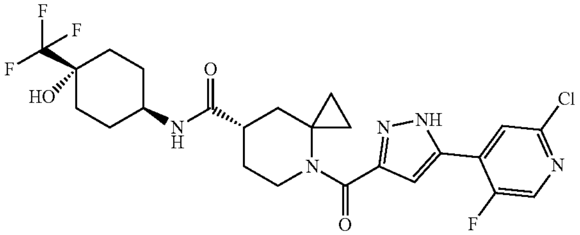

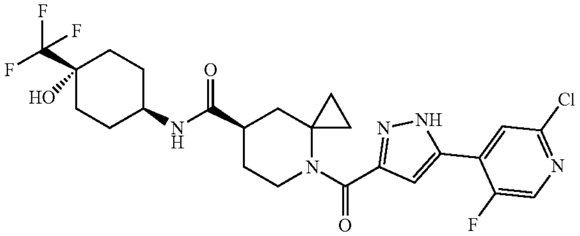

TFA (5.00 mL) was added to a stirred solution of 4-[5-(2-chloro-5-fluoropyridin-4-yl)-1-[[2-(trimethylsilyl)ethoxy]methyl]pyrazole-3-carbonyl]-N-[(1r,4r)-4-hydroxy-4-(trifluoromethyl)cyclohexyl]-4-azaspiro[2.5]octane-7-carboxamide (Step-6, 410.0 mg, 0.61 mmol) in DCM (5.00 mL). The resulting mixture was stirred at 25° C. for 14 h. The solution was concentrated under reduced pressure, then basified to pH 8 with TEA. Then solution was concentrated under reduced pressure. The residue was purified by reverse phase column chromatography (using the following conditions: Column: C18; mobile phase A: Water (0.5% $NH_4HCO_3$), mobile phase B: MeCN; gradient: 20 B to 50 Bin 30 min; 220/254 nm) to obtain the title compound (182.2 mg) as a solid. $^1H$ NMR (400 MHz, DMSO-$d_6$) δ 14.10 (s, 1H), 8.56 (d, J=2.4 Hz, 1H), 8.04 (d, J=5.2 Hz, 1H), 7.80 (d, J=6.8 Hz, 1H), 7.11 (d, J=2.8 Hz, 1H), 5.68 (s, 1H), 4.75-4.09 (m, 1H), 3.94-3.76 (m, 1H), 2.93-2.69 (m, 1H), 2.30-2.08 (m, 1H), 1.90-1.66 (m, 5H), 1.62-1.39 (m, 5H), 1.29-1.10 (m, 2H), 1.03-0.79 (m, 2H), 0.75-0.53 (m, 2H). LCMS (ESI): 544.10 $[M+H]^+$.

This mixture of two diastereomers (200.0 mg) was separated using Chiral Prep-HPLC.

Column: CHIRALPAK ART Amylose-SA column

Column dimension: 2×25 cm, 5 μm

Mobile Phase: hexanes (0.5% 2 M $NH_3$·MeOH): MeOH=20:80 hold for 13 min

Flow rate: 20 mL/min

Detection: 220/254 nm

Example 529-A. The first eluting diastereomer (82.2 mg) was obtained as a solid.

The first eluting diastereomer had a retention time of 4.91 min.

Example 529-B. The second eluting diastereomer (72.1 mg) was obtained as a solid.

The second eluting diastereomer had a retention time of 9.40 min.

$^1H$ NMR (400 MHz, DMSO-$d_6$) δ 14.13 (s, 1H), 8.57 (d, 1H), 8.04 (d, 1H), 7.82 (d, 1H), 7.12 (d, 1H), 5.70 (s, 1H), 4.68-4.04 (m, 1H), 3.91-3.73 (m, 1H), 3.30-3.11 (m, 1H), 2.90-2.71 (m, 1H), 2.38-2.04 (m, 1H), 1.90-1.65 (m, 5H), 1.64-1.41 (m, 5H), 1.33-0.78 (m, 3H), 0.78-0.53 (m, 2H). LCMS (ESI): 544.15 $[M+H]^+$.

$^1H$ NMR (400 MHz, DMSO-$d_6$) δ 14.12 (s, 1H), 8.57 (d, 1H), 8.04 (d, 1H), 7.82 (d, 1H), 7.12 (d, 1H), 5.70 (s, 1H), 4.72-4.07 (m, 1H), 3.91-3.74 (m, 1H), 3.30-2.88 (m, 1H), 2.88-2.71 (m, 1H), 2.37-2.10 (m, 1H), 1.89-1.65 (m, 5H), 1.63-1.40 (m, 5H), 1.32-1.10 (m, 1H), 1.04-0.77 (m, 2H), 0.74-0.52 (m, 2H). LCMS (ESI): 544.10 $[M+H]^+$.

Example 530. (S)-4-(5-(5-fluoro-2-methoxypyridin-4-yl)-1H-pyrazole-3-carbonyl)-N-((5-methoxy-3-(trifluoromethyl)pyrazin-2-yl)methyl)-4-azaspiro[2.5]octane-7-carboxamide

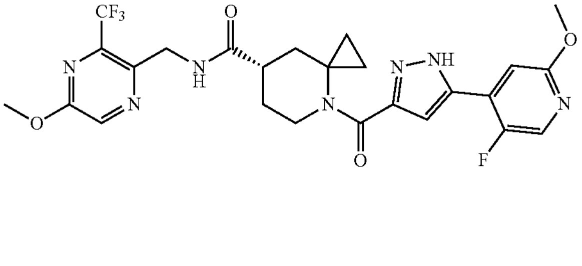 [SMILES: COc1cc(-c2cc(C(=O)N3CC[C@H](C(=O)NCc4ncc(OC)nc4C(F)(F)F)CC34CC4)n[nH]2)c(F)cn1]

Step-1. Methyl 3-chloro-5-methoxypyrazine-2-carboxylate

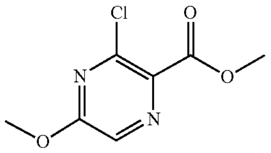

Sodium methoxide (0.52 g, 9.66 mmol) was added to a stirred solution of methyl 3,5-dichloropyrazine-2-carboxylate (1.00 g, 4.83 mmol) in MeOH (10.00 mL). The resulting mixture was stirred at 25° C. for 14 h. The resulting mixture was concentrated under vacuum. The residue was purified by silica gel column chromatography eluting with petroleum ether/EtOAc (51 v/v) to obtain the title compound (730.0 mg) as a solid. LCMS (ESI): 203.00 $[M+H]^+$.

Step-2. Methyl 5-methoxy-3-(trifluoromethyl)pyrazine-2-carboxylate

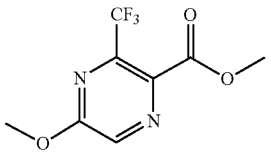

CuI (1.37 g, 7.21 mmol) and methyl 2,2-difluoro-2-sulfoacetate (2.77 g, 14.41 mmol) were added to a stirred solution of methyl 3-chloro-5-methoxypyrazine-2-carboxylate (Step-1, 730.0 mg, 3.60 mmol) in DMF (5.00 mL). The resulting mixture was stirred at 80° C. for 14 h under the atmosphere of nitrogen. The resulting mixture was diluted with EtOAc and washed with water. The residue was purified by silica gel column chromatography eluting with petroleum ether/EtOAc (4/1 v/v) to obtain the title compound (600.0 mg) as a solid. LCMS (ESI): 237.0 $[M+H]^+$.

Step-3. 5-methoxy-3-(trifluoromethyl)pyrazine-2-carboxylic acid

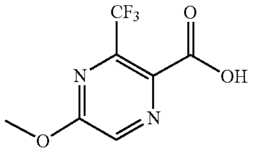

$LiOH \cdot H_2O$ (106.6 mg, 2.54 mmol) was added to a stirred solution of methyl 5-methoxy-3-(trifluoromethyl)pyrazine-2-carboxylate (Step-2, 300.0 mg, 1.27 mmol) in THF (4.00 mL)/MeOH (2.00 mL)/$H_2O$ (2.00 mL). The resulting mixture was stirred at 25° C. for 1 h. The resulting mixture was concentrated under vacuum. The mixture was acidified to pH 3 with HCl (1 M) and extracted with EtOAc. The organic layers were combined, dried over anhydrous $Na_2SO_4$, filtered, and concentrated under reduced pressure to obtain the title compound (280.0 mg) as a solid. LCMS (ESI): 223.0 $[M+H]^+$.

Step-4. [5-methoxy-3-(trifluoromethyl)pyrazin-2-yl]methanol

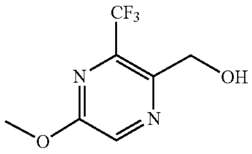

2-methylpropyl chloroformate (344.3 mg, 2.52 mmol) and N-methylmorpholine (191.3 rug, 1.89 mmol) were added to a stirred solution of 5-methoxy-3-(trifluoromethyl)pyrazine-2-carboxylic acid (Step-3, 280.0 mg, 1.26 mmol) in DME (7.00 mL) at 0° C. The resulting mixture was stirred at 0° C. for 1 h. The resulting mixture was filtered, the filter cake was washed with DME (3.00 mL). Then a solution of $NaBH_4$ (71.5 mg, 1.89 mmol) in $H_2O$ (1.00 mL) was added to the stirred mixture of the filtrate. The resulting mixture was stirred at 0° C. to 25° C. for 14 h. The resulting mixture was concentrated under vacuum. The residue was purified by Prep-TLC (petroleum ether/EtOAc, 4/1 v/v) to obtain the title compound (130.0 mg) as a solid. LCMS (ESI): 209.0 $[M+H]^+$.

Step-5. [5-methoxy-3-(trifluoromethyl)pyrazin-2-yl]methyl methanesulfonate

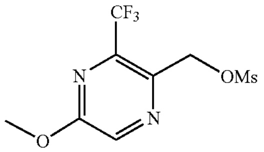 [SMILES: COc1cnc(COS(C)(=O)=O)c(C(F)(F)F)n1]

$NEt_3$ (126.4 mg, 1.25 mmol) and MsCl (143.1 mg, 1.25 mmol) were added to a stirred solution of [5-methoxy-3-(trifluoromethyl)pyrazin-2-yl]methanol (Step-4, 130.0 mg, 0.63 mmol) in DCM (4.00 mL) at 0° C. The resulting mixture was stirred at 0° C. to 25° C. for 14 h. The resulting mixture was concentrated under vacuum. The residue was purified by Prep-TLC (petroleum ether/EtOAc, 5/1 v/v) to obtain the title compound (120.0 mg) as an oil. LCMS (ESI): 287.0 $[M+H]^+$.

Step-6. 2-{[5-methoxy-3-(trifluoromethyl)pyrazin-2-yl]methyl}isoindole-1,3-dione

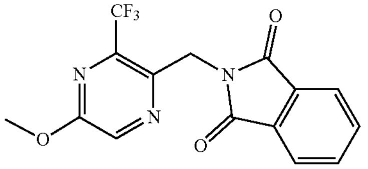 [SMILES: COc1cnc(CN2C(=O)c3ccccc3C2=O)c(C(F)(F)F)n1]

2-potassioisoindole-1,3-dione (129.4 mg, 0.70 mmol) was added to a stirred solution of [5-methoxy-3-(trifluoromethyl)pyrazin-2-yl]methyl methanesulfonate (Step-5, 100.0 mg, 0.35 mmol) in DMF (4.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by Prep-TLC (petroleum ether/EtOAc, 4/1 v/v) to obtain the title compound (85.0 mg) as a solid. LCMS (ESI): 338.0 $[M+H]^+$.

Step-7. 1-[5-methoxy-3-(trifluoromethyl)pyrazin-2-yl]methanamine

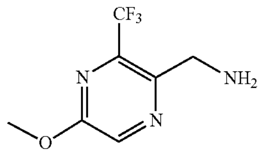

Hydrazine (16.2 mg, 0.50 mmol) was added to a stirred solution of 2-{[5-methoxy-3-(trifluoromethyl)pyrazin-2-yl]methyl}isoindole-1,3-dione (Step-6, 85.0 mg, 0.25 mmol) in EtOH (3.00 mL). The resulting mixture was stirred at 50° C. for 2 h. The resulting mixture was concentrated under vacuum. The residue was purified by SiliaBond® Propylsulfonic Acid (SCX-2) eluting with $NH_3$ in MeOH (7 M) to obtain the title compound (50.0 mg) as a solid. LCMS (ESI): 208.0 $[M+H]^+$.

Step-8. (S)-4-(5-(5-fluoro-2-methoxypyridin-4-yl)-1H-pyrazole-3-carbonyl)-N-((5-methoxy-3-(trifluoromethyl)pyrazin-2-yl)methyl)-4-azaspiro[2.5]octane-7-carboxamide

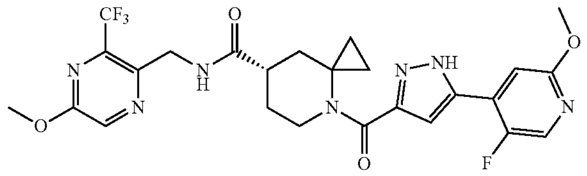 [SMILES: COc1cc(-c2cc(C(=O)N3CC[C@H](C(=O)NCc4ncc(OC)nc4C(F)(F)F)CC34CC4)n[nH]2)c(F)cn1]

1-[5-methoxy-3-(trifluoromethyl)pyrazin-2-yl]methanamine (Step-7, 60.0 mg, 0.29 mmol) and HATU (80.8 mg, 0.21 mmol) were added to a stirred solution of (S)-4-[5-(5-fluoro-2-methoxypyridin-4-yl)-1H-pyrazole-3-carbonyl]-4-azaspiro[2.5]octane-7-carboxylic acid (INTERMEDIATE 527-A, 72.3 mg, 0.19 mmol) and DIPEA (124.8 mg, 0.97 mmol) in DMF (1.00 mL). The resulting mixture was stirred at 25° C. for 14 h. The resulting mixture was diluted with EtOAc and washed with water. The organic layers were combined, dried over anhydrous $Na_2SO_4$, filtered, and concentrated under reduced pressure. The residue was purified by reverse phase column chromatography (using the following conditions: Column: C18; mobile phase A: Water (0.5% $NH_4HCO_3$), mobile phase B: MeCN; gradient: 30 B to 50 B in 20 min; 220/254 nm) to obtain the title compound (43.5 mg) as a solid. $^1$H NMR (400 MHz, $CD_3OD$) δ 8.44 (s, 1H), 8.13 (s, 1H), 7.43-7.18 (m, 1H), 7.11 (s, 1H), 4.72-4.55 (m, 2H), 4.04 (s, 3H), 3.94 (s, 3H), 3.53-3.36 (m, 1H), 3.00-2.80 (m, 1H), 2.56-2.27 (m, 1H), 2.10-1.85 (m, 1H), 1.79-167 (m, 1H), 1.51-1.21 (m, 2H), 1.17-0.94 (m, 1H), 0.81-0.59 (m, 3H). LCMS (ESI): 564.25 $[M+H]^+$.

TR-FRET Assay to Measure Co—R Peptide Recruitment to PPARγ

The $His_6$-TEV-PPARγ-(234-505) protein for assay was expressed and purified according to Korpal, M., et al., *Evasion of immnunosurveillance by genomic alterations of PPARgamna/RXRalpha in bladder cancer*. Nature communications, 2017. 8(1): p. 103.

The assay buffer was comprised of 50 mM Potassium Chloride (Sigma), 50 mM HEPES pH 7.4 (Teknova), 2 mM DTT (Boston Bioproducts), 0.1 mg/mL bovine gamma-globulin (Sigma), and 0.001% Pluronic F-127 (Thermo Fisher). A 2× working stock of $His_6$-PPARγ-(234-505) was diluted to a final concentration of 10 nM in assay buffer. The 2× detection solution contained anti-6×His-Terbium antibody (CisBio) and FITC labeled Co—R peptide (SMRT-ID2 from New England Peptide) at final concentrations of 5 and 200 nM respectively.

An acoustic dispenser delivered 4 nL of compound or DMSO from an 11-point master dose response (MDR) source plate into 384 well assay plates (Corning, 3820), with top final concentration of 20 μM. In these assay plates, the positive control in column 24 contained 500 nM (final) T0070907 and the negative control in column 23 contained an identical volume of DMSO. Then, 5 μL of 2+ protein working stock or controls were added to the plate and incubated for 20 minutes at room temperature. Reagents additions were performed with either a Combi (Thermo) or Mantis (Formulatory) pipetting device. The incubation was followed by addition of 5 μL of the 2× detection solution. Plates were covered, centrifuged, and incubated for an additional hour. The TR-FRET data was recorded with an Envision plate reader (Perkin Elmer), using settings recommended by Thermo Fisher. The TR-FRET signal of the positive and negative control's recruitment of FITC-Co—R peptide was used to normalize the TR-FRET signal to percent response and to determine the assay Z prime. Experiments were performed in triplicate and analyzed in GraphPad Prism 7.

Results of the assay are reported in Table 1.

TABLE 1

Biological Assay Results

| Example # | TR-FRET i-Ag; $AC_{50}$ (nM) | CTGlo 144 h UMUC9.5; G150 (nM) |
|---|---|---|
| 101 | 29.4 | 304.6 |
| 101a | 40000.0 | >10000 |
| 101b | 9.2 | 84.0 |
| 102 | 321.5 | 643.3 |
| 103 | 256.7 | 319.5 |
| 104a | 40000.0 | >10000 |
| 104b | 47.6 | 98.6 |
| 105 | 536.7 | 1023.8 |
| 106 | 465.3 | 2193.9 |
| 107 | 341.7 | n.d. |
| 108a | 160.1 | 674.1 |
| 108 | 177.9 | 830.2 |
| 109 | 372.9 | n.d. |
| 110 | 574.7 | 1208.6 |
| 110a | 2161.7 | 3185.8 |
| 110b | 217.4 | 697.2 |
| 111b | 519.3 | 639.7 |
| 111a | 40000.0 | n.d. |
| 112 | 30.3 | 111.1 |
| 113a | 14286.4 | >10000.000 |

TABLE 1-continued

Biological Assay Results

| Example # | TR-FRET i-Ag; $AC_{50}$ (nM) | CTGlo 144 h UMUC9.5; G150 (nM) |
|---|---|---|
| 113b | 672.1 | 2400.1 |
| 114 | 78.5 | 120.0 |
| 114b | 15.8 | 26.8 |
| 114a | 3469.9 | 4432.7 |
| 115 | n.d. | 427.8 |
| 115a | 716.6 | 1317.6 |
| 115b | 59.5 | 263.4 |
| 117 | 56.2 | 292.9 |
| 118 | n.d. | 121.2 |
| 118b | 963.5 | 2962.2 |
| 118a | 15.5 | 116.4 |
| 119 | 336.7 | >5000.000 |
| 120 | 226.8 | 765.5 |
| 121 | 807.1 | 2223.9 |
| 122 | 11.0 | 66.1 |
| 123 | 12.8 | 100.4 |
| 124 | 981.8 | 5020.0 |
| 125 | 24.6 | 301.0 |
| 126 | 706.8 | 2455.0 |
| 127 | 644.0 | 2925.5 |
| 128 | 863.6 | 2555.0 |
| 129 | 272.6 | 1021.3 |
| 130 | 75.9 | 685.2 |
| 131 | 493.7 | 2608.5 |
| 132 | 24.6 | 136.3 |
| 133 | 291.6 | 1744.8 |
| 134 | 238.3 | 1093.8 |
| 135 | 482.6 | 2652.0 |
| 136 | 887.4 | 6096.5 |
| 137 | 129.7 | 678.5 |
| 138 | 500.5 | 1469.5 |
| 139 | 336.4 | 1793.9 |
| 140 | 85.4 | 633.5 |
| 141 | 678.6 | 2602.3 |
| 142 | 903.5 | 3140.6 |
| 143 | 909.8 | 3309.5 |
| 144 | 44.7 | 333.6 |
| 145 | 688.4 | 4121.0 |
| 146 | 262.2 | 1411.5 |
| 147 | 267.9 | 954.6 |
| 148 | 712.2 | 3172.0 |
| 149 | 49.3 | 417.7 |
| 150 | 269.2 | 779.1 |
| 151 | 48.1 | 538.9 |
| 152 | 853.0 | 825.0 |
| 153 | 621.4 | 2090.9 |
| 154 | 77.4 | 166.1 |
| 155 | 103.4 | 121.5 |
| 156 | 32.1 | 105.5 |
| 157 | 129.9 | 212.5 |
| 158 | 296.1 | 544.5 |
| 159 | 27.1 | 62.4 |
| 160 | 11.6 | 20.6 |
| 160-A | 11.5 | 38.2 |
| 160-B | 14228.5 | >10000.000 |
| 161 | 940.9 | 1951.5 |
| 162 | 588.2 | 908.0 |
| 163 | 447.0 | 747.3 |
| 164 | 607.9 | 1005.7 |
| 165 | 178.6 | 435.4 |
| 166 | 299.7 | >10000.000 |
| 167 | 112.3 | 4035.0 |
| 168 | 45.7 | 486.8 |
| 169 | 4.5 | 2.1 |
| 169-A | 79.0 | 272.8 |
| 169-B | 2.3 | 1.4 |
| 170-A | 4.7 | 11.8 |
| 170-B | 1107.9 | 3556.2 |
| 171 | 209.8 | 1548.7 |
| 172 | 16.5 | 162.6 |
| 173 | 673.8 | 2099.1 |
| 174 | 124.9 | 407.0 |
| 175 | 349.2 | 1640.0 |
| 176 | 375.5 | 1843.5 |

TABLE 1-continued

Biological Assay Results

| Example # | TR-FRET i-Ag; $AC_{50}$ (nM) | CTGlo 144 h UMUC9.5; G150 (nM) |
|---|---|---|
| 177 | 29.8 | 68.9 |
| 178 | 343.7 | 1259.1 |
| 179 | 321.2 | 1534.0 |
| 180 | 143.5 | 707.0 |
| 181 | 56.2 | 85.6 |
| 182 | 422.4 | 1604.4 |
| 183 | 232.8 | 1646.1 |
| 184 | 215.3 | 383.8 |
| 185 | 734.7 | 1551.1 |
| 186 | 201.8 | 339.2 |
| 187 | 41.7 | 114.5 |
| 188 | 79.8 | 211.0 |
| 189 | 118.8 | 521.4 |
| 190 | 24.0 | 91.8 |
| 191 | 837.8 | 2013.0 |
| 192 | 83.3 | 374.6 |
| 193 | 393.9 | 1199.2 |
| 194 | 808.2 | 483.8 |
| 195 | 212.0 | 348.1 |
| 196 | 609.6 | 1031.9 |
| 197 | 197.3 | 3931.9 |
| 198 | 917.5 | 4158.1 |
| 199 | 32.0 | 139.7 |
| 200 | 112.2 | 71.5 |
| 201 | 77.5 | 171.3 |
| 202 | 136.4 | 1590.4 |
| 203 | 77.4 | 96.4 |
| 204 | 20.2 | 83.3 |
| 205 | 911.6 | 3114.8 |
| 206 | 13.8 | 86.6 |
| 207 | 888.9 | 5670.2 |
| 208 | 34.7 | 290.3 |
| 209 | 318.7 | 2369.4 |
| 210 | 259.3 | 1684.5 |
| 211 | 461.8 | 3258.6 |
| 212 | 79.2 | 782.5 |
| 213 | 570.7 | 1639.9 |
| 214 | 193.7 | 1586.4 |
| 215 | 264.9 | >5000.000 |
| 216 | 696.7 | 3103.1 |
| 217 | 309.4 | 3633.2 |
| 218 | 13.8 | 137.8 |
| 219 | 94.5 | 1611.7 |
| 220 | 286.2 | 2127.6 |
| 221 | 279.4 | 1729.0 |
| 222 | 18.5 | 208.1 |
| 223 | 627.8 | >10000.000 |
| 224 | 554.3 | 5177.2 |
| 225 | 327.0 | 1719.2 |
| 226 | 42.8 | 426.8 |
| 227 | 947.4 | 5963.6 |
| 228 | 489.7 | >10000.000 |
| 229 | 70.6 | 614.4 |
| 230 | 134.1 | 696.8 |
| 231 | 998.7 | 5444.2 |
| 232 | 515.7 | 2145.4 |
| 233 | 196.2 | 3426.8 |
| 234 | 927.0 | >10000.000 |
| 235 | 404.2 | 2359.4 |
| 236 | 466.0 | 5355.8 |
| 237 | 722.4 | >10000.000 |
| 238 | 838.8 | 5163.5 |
| 239 | 245.6 | 1397.1 |
| 240 | 707.8 | 6050.0 |
| 241 | 880.4 | 3483.2 |
| 242 | 74.2 | 1657.0 |
| 243 | 25.8 | 414.3 |
| 244 | 605.3 | 5563.2 |
| 245 | 9.8 | n.d. |
| 245-A | 8.3 | 4.1 |
| 245-B | 109.0 | 414.6 |
| 246 | 382.7 | 1230.0 |
| 247 | 565.1 | 2231.8 |
| 248 | 66.3 | 411.4 |

TABLE 1-continued

Biological Assay Results

| Example # | TR-FRET i-Ag; $AC_{50}$ (nM) | CTGlo 144 h UMUC9.5; G150 (nM) |
|---|---|---|
| 248-A | 340.8 | 2532.3 |
| 248-B | 32.2 | 207.3 |
| 249 | 26.4 | 244.3 |
| 249-A | 29.3 | 189.3 |
| 249-B | 55.5 | 384.0 |
| 250 | 24.7 | 430.3 |
| 251 | 253.6 | 1377.9 |
| 252 | 182.5 | 1146.6 |
| 253 | 51.0 | 387.1 |
| 254 | 58.8 | >2000.000 |
| 255 | 63.3 | 151.2 |
| 255-A | 49.6 | 140.7 |
| 255-B | 1758.7 | 4119.5 |
| 256 | 488.4 | 184.8 |
| 256-A | 92.4 | 72.6 |
| 256-B | 15908.7 | 3522.6 |
| 257-A | 215.0 | 263.8 |
| 257-B | 28.0 | 79.1 |
| 258 | 17.0 | 20.0 |
| 259-A | 417.6 | 1483.5 |
| 259-B | 6.5 | 31.3 |
| 260 | 969.6 | 4034.5 |
| 261 | 78.4 | 490.1 |
| 262 | 29.2 | 332.2 |
| 263-A | 90.0 | 381.6 |
| 263-B | 4238.6 | 6958.5 |
| 264-A | 657.8 | 4892.6 |
| 264-B | 11069.1 | >10000.000 |
| 265 | 87.7 | 458.3 |
| 266-A | 140.3 | 306.6 |
| 266-B | 144.4 | 483.3 |
| 267 | 14.2 | 103.9 |
| 268 | 7.0 | 36.5 |
| 269 | 12.0 | 160.3 |
| 270 | 23.4 | 306.0 |
| 271 | 6.1 | 30.3 |
| 272 | 9.0 | 110.8 |
| 273 | 26.7 | 212.7 |
| 274 | 20.0 | n.d. |
| 275-A | 5.5 | 11.4 |
| 275-B | 129.9 | 249.8 |
| 276 | 813.3 | >4000.000 |
| 277 | 3.3 | 29.0 |
| 278 | 75.1 | 477.9 |
| 279 | 24.6 | 289.7 |
| 280-A | 895.4 | 5801.6 |
| 280-B | 6.5 | 15.3 |
| 280-C | 101.3 | 282.6 |
| 280-D | 14.9 | 44.9 |
| 281 | 100.9 | 631.7 |
| 282 | 59.0 | 292.9 |
| 283 | 7.5 | 70.8 |
| 284 | 2.3 | 12.1 |
| 285 | 7.9 | 16.3 |
| 286-A | 304.0 | 459.9 |
| 286-B | 2.2 | 1.5 |
| 287-A | 2.3 | 2.4 |
| 287-B | 117.8 | 184.3 |
| 288-A | 4.4 | 0.9 |
| 288-B | 39.0 | 56.8 |
| 289-A | 3607.8 | 135.2 |
| 289-B | 2.8 | 18.6 |
| 289-C | 9.1 | 52.1 |
| 289-D | 157.6 | 153.5 |
| 290 | 400.2 | 832.9 |
| 290-A | 131.8 | 506.1 |
| 290-B | 5632.8 | 3362.0 |
| 291 | 69.6 | 150.3 |
| 292-A | 4.9 | 24.6 |
| 292-B | 248.7 | 909.4 |
| 293-A | 280.5 | 873.7 |
| 293-B | 1642.5 | 3241.1 |
| 293-C | 2.8 | 1.6 |
| 293-D | 17.0 | 86.0 |

TABLE 1-continued

Biological Assay Results

| Example # | TR-FRET i-Ag; $AC_{50}$ (nM) | CTGlo 144 h UMUC9.5; G150 (nM) |
|---|---|---|
| 294-A | 5.4 | 18.9 |
| 294-B | 106.5 | 235.5 |
| 295-A | 2094.9 | >4000.000 |
| 295-B | 432.6 | >4000.000 |
| 296 | 19.8 | 4.1 |
| 297 | 119.8 | 383.0 |
| 298-A | 6506.2 | >4000.000 |
| 298-B | 833.3 | >4000.000 |
| 298-C | 306.0 | 1148.6 |
| 298-D | 5506.8 | >4000.000 |
| 298-E | 33.8 | 131.6 |
| 298-F | 10438.9 | >4000.000 |
| 299-A | 23.5 | 95.5 |
| 299-B | 206.7 | 587.3 |
| 299-C | 8.3 | 50.7 |
| 299-D | 38.7 | 137.1 |
| 299-E | 221.3 | 884.1 |
| 299-F | 771.2 | 589.8 |
| 300-A | 17971.7 | >4000.000 |
| 300-B | 995.3 | 1506.2 |
| 301 | 15.9 | 74.8 |
| 302-A | 4.9 | 28.4 |
| 302-B | 80.9 | 270.3 |
| 303 | 7.3 | 41.5 |
| 303-A | 2.6 | 20.5 |
| 303-B | 29.8 | 82.0 |
| 304 | 44.4 | 201.3 |
| 304-A | 8.3 | 62.9 |
| 304-B | 105.8 | 514.1 |
| 305 | 217.0 | 2271.4 |
| 306-A | 13.9 | 78.8 |
| 306-B | 514.5 | 1035.5 |
| 306-C | 58.6 | 267.5 |
| 306-D | 13.9 | 37.4 |
| 306-E | 580.4 | 1053.3 |
| 306-F | 607.5 | 606.8 |
| 307 | 22.1 | 173.3 |
| 308-A | 2.8 | 5.6 |
| 308-B | 548.3 | 1006.2 |
| 308-C | 2.0 | 5.9 |
| 308-D | 25.6 | 192.4 |
| 308-E | 635.1 | 2557.2 |
| 308-F | 6359.6 | 192.4 |
| 309-A | 2.9 | 5.4 |
| 309-B | 49.5 | 301.7 |
| 309-C | 720.3 | 6197.7 |
| 309-D | 1324.8 | 3675.9 |
| 310 | 14.0 | 99.0 |
| 311-A | 106.3 | 413.5 |
| 311-B | 9.4 | 42.5 |
| 311-C | 996.6 | 2346.1 |
| 311-D | 32.6 | 241.7 |
| 312-A | 171.7 | 493.3 |
| 312-B | 2.5 | 1.8 |
| 313-A | 1289.9 | 3891.6 |
| 313-B | 3.5 | 13.9 |
| 314 | 347.0 | >10000.000 |
| 315 | 863.4 | >10000.000 |
| 316 | 67.9 | 3385.3 |
| 317 | 344.0 | >10000.000 |
| 318 | 339.9 | 371.7 |
| 319 | 124.2 | 231.5 |
| 320 | 10.4 | 29.5 |
| 321-A | 2.7 | 1.7 |
| 321-B | 12.3 | 28.9 |
| 321-C | 39.8 | 130.3 |
| 321-D | 42.6 | 62.2 |
| 322-A | 337.7 | 138.5 |
| 322-B | 436.4 | 669.8 |
| 322-C | 3196.4 | >4000.000 |
| 323-A | 243.7 | 541.9 |
| 323-B | 6.7 | 2.3 |
| 324-A | 70.2 | 54.7 |
| 324-B | 1.5 | 0.6 |

TABLE 1-continued

Biological Assay Results

| Example # | TR-FRET i-Ag; $AC_{50}$ (nM) | CTGlo 144 h UMUC9.5; G150 (nM) |
|---|---|---|
| 325-A | 187.3 | 2891.8 |
| 325-B | 149.5 | 112.8 |
| 326-A | 88.5 | 93.2 |
| 326-B | 485.1 | 1311.4 |
| 326-C | 155.9 | 287.0 |
| 326-D | 2566.6 | 2891.8 |
| 327-A | 100.8 | 1847.3 |
| 327-B | 15298.9 | >4000.000 |
| 327-C | 300.8 | 2106.0 |
| 327-D | 18801.0 | >4000.000 |
| 328-A | 53.4 | 685.1 |
| 328-B | 3647.4 | >10000.000 |
| 328-C | 1239.2 | 1822.9 |
| 328-D | 1633.8 | >10000.000 |
| 329-A | 7.5 | 24.3 |
| 329-B | 452.0 | 1654.5 |
| 330-A | 102.9 | 71.7 |
| 330-B | 6.4 | 1.1 |
| 331-A | 5.7 | 4.2 |
| 331-B | 410.2 | 946.0 |
| 332-A | 15.6 | 13.8 |
| 332-B | 679.5 | 1816.6 |
| 333-A | 1958.6 | 9443.9 |
| 333-B | 6.7 | 33.2 |
| 334 | 72.6 | 284.3 |
| 335 | 416.9 | 6153.8 |
| 336 | 109.4 | 1050.7 |
| 337-A | 262.6 | 447.3 |
| 337-B | 2077.4 | 8161.2 |
| 338-A | 9.3 | 16.2 |
| 338-B | 722.8 | 1323.8 |
| 339-A | 475.8 | 3796.3 |
| 339-B | 6.9 | 19.5 |
| 340-A | 6.5 | 4.4 |
| 340-B | 19.0 | 10.7 |
| 341 | 5.0 | 10.3 |
| 341-A | 6.1 | 6.6 |
| 341-B | 8.1 | 12.2 |
| 342 | 78.3 | 1127.9 |
| 342-A | 50.8 | 1210.5 |
| 342-B | 42.8 | 682.5 |
| 343 | 20.0 | 93.0 |
| 344-A | 14784.7 | >10000.000 |
| 344-B | 123.3 | 569.9 |
| 345-A | 161.2 | 444.9 |
| 345-B | 7248.6 | >10000.000 |
| 346 | 371.4 | >10000.000 |
| 346-A | 504.4 | 2789.9 |
| 346-B | 1116.9 | 2411.8 |
| 347 | 316.6 | 1859.7 |
| 347-A | 81.6 | 395.8 |
| 347-B | 198.3 | 599.5 |
| 347-C | 5075.8 | >10000.000 |
| 347-D | 20000.0 | >10000.000 |
| 348 | 304.9 | >10000.000 |
| 349 | 186.5 | 835.8 |
| 350 | 5.3 | 175.8 |
| 351 | 255.9 | 450.1 |
| 352 | 7.7 | 133.9 |
| 353 | 6.6 | 6.0 |
| 354 | 24.1 | 28.6 |
| 355-A | 10.4 | 3.5 |
| 355-B | 9.4 | 3.3 |
| 356 | 112.7 | 4787.8 |
| 356-A | 101.8 | 4641.2 |
| 356-B | 152.4 | 9555.9 |
| 357 | 45.1 | 2186.8 |
| 357-A | 316.8 | >10000.000 |
| 357-B | 62.5 | 1483.9 |
| 358 | 5.1 | 3.4 |
| 359 | 8.0 | 19.9 |
| 360 | 21.8 | 8.7 |
| 360-A | 9.2 | 22.6 |
| 360-B | 20.0 | 24.4 |

TABLE 1-continued

Biological Assay Results

| Example # | TR-FRET i-Ag; $AC_{50}$ (nM) | CTGlo 144 h UMUC9.5; G150 (nM) |
|---|---|---|
| 361 | 10.2 | 17.8 |
| 362 | 3.7 | 8.7 |
| 363 | 6.0 | 3.5 |
| 364 | 13.1 | 56.2 |
| 365 | 10.0 | 21.9 |
| 366 | 28.8 | 41.4 |
| 366-A | 45.3 | 62.8 |
| 366-B | 23.3 | 32.3 |
| 367 | 22.0 | 12.0 |
| 367-A | 56.7 | 160.8 |
| 367-B | 12.7 | 6.8 |
| 368 | 243.8 | 497.0 |
| 368-A | 1384.9 | 3540.9 |
| 368-B | 298.1 | 705.2 |
| 369-A | 5.4 | 5.4 |
| 369-B | 580.8 | 1243.9 |
| 370-A | 5.0 | 0.9 |
| 370-B | 34.7 | 49.3 |
| 371 | 36.4 | 338.5 |
| 372-A | 695.9 | >10000.000 |
| 372-B | 841.3 | >10000.000 |
| 372-C | 790.6 | >10000.000 |
| 372-D | 1413.1 | >10000.000 |
| 372-E | 576.9 | >10000.000 |
| 372-F | 845.6 | >10000.000 |
| 373 | 11.7 | 3.0 |
| 373-A | 3.2 | 0.9 |
| 373-B | 69.4 | 127.9 |
| 374 | 13.1 | 15.8 |
| 374-A | 8.1 | 6.6 |
| 374-B | 50.0 | 61.0 |
| 375 | 6.4 | 1.6 |
| 375-A | 3.4 | 1.3 |
| 375-B | 157.6 | 231.3 |
| 376-A | 897.0 | 1730.6 |
| 376-B | 1595.9 | 3875.0 |
| 376-C | 19.2 | 23.6 |
| 376-D | 129.4 | 71.4 |
| 377 | 20.2 | 25.9 |
| 377-A | 6.3 | 25.2 |
| 377-B | 41.1 | 43.6 |
| 378 | 130.4 | 224.2 |
| 378-A | 192.4 | 326.3 |
| 378-B | n.d. | 604.9 |
| 379 | 12.2 | 11.0 |
| 379-A | 32.1 | 57.6 |
| 379-B | 7.7 | 7.2 |
| 380 | 30.6 | 43.7 |
| 380-A | 19.3 | 22.6 |
| 380-B | 45.4 | 138.6 |
| 381 | 12.3 | 5.8 |
| 382 | 4.0 | 10.0 |
| 382-A | 5.2 | 18.3 |
| 382-B | 5.1 | 11.7 |
| 383 | 33.1 | 43.1 |
| 383-A | 27.4 | 70.4 |
| 383-B | 17.5 | 39.0 |
| 384 | 15.2 | 82.1 |
| 385-A | 466.1 | 929.0 |
| 385-B | 5.8 | 10.7 |
| 386 | 181.2 | 231.2 |
| 387 | 14.4 | 22.5 |
| 388 | 11.4 | 17.6 |
| 389 | 10.3 | 13.0 |
| 390 | 4.2 | 7.1 |
| 390-A | 6.8 | 5.6 |
| 390-B | 5.8 | 37.6 |
| 391 | 19.5 | 81.3 |
| 392 | 9.1 | 45.2 |
| 393 | 9.2 | 106.2 |
| 394 | 8.7 | 24.5 |
| 395 | 274.0 | 761.3 |
| 395-A | 270.4 | 499.9 |
| 395-B | 670.6 | 593.0 |

TABLE 1-continued

Biological Assay Results

| Example # | TR-FRET i-Ag; $AC_{50}$ (nM) | CTGlo 144 h UMUC9.5; G150 (nM) |
|---|---|---|
| 396 | 97.7 | 293.1 |
| 396-A | 66.2 | 253.6 |
| 396-B | 90.5 | 212.7 |
| 397 | 23.4 | 59.9 |
| 398-A | 7.0 | 6.5 |
| 398-B | 1462.9 | 1525.4 |
| 399-A | 298.5 | 176.3 |
| 399-B | 4.6 | 8.5 |
| 400 | 12.6 | 24.3 |
| 401 | 21.3 | 41.7 |
| 401-A | 25.7 | 90.9 |
| 401-B | 33.6 | 93.8 |
| 401-C | 36.4 | 137.9 |
| 401-D | 5.9 | 6.6 |
| 402 | 10.8 | 2.9 |
| 403 | 300.0 | 630.0 |
| 403-A | 954.6 | 1997.2 |
| 403-B | 776.7 | 1627.9 |
| 403-C | 245.4 | 1235.4 |
| 403-D | 27.3 | 66.7 |
| 404 | 164.1 | 887.4 |
| 405 | 27.9 | 8.3 |
| 405-A | 352.9 | 730.6 |
| 405-B | 503.1 | 441.7 |
| 405-C | 2.8 | 1.6 |
| 405-D | 48.0 | 99.5 |
| 406 | 34.1 | 73.3 |
| 407 | 30.3 | 23.0 |
| 407-A | 16.0 | 14.0 |
| 407-B | 1687.3 | 1336.7 |
| 408 | 6.3 | 7.2 |
| 408-A | 4.5 | 3.9 |
| 408-B | n.d. | 50.9 |
| 409 | 30.9 | 39.1 |
| 410-A | 25.1 | 133.8 |
| 410-B | 222.3 | 428.2 |
| 411 | 37.2 | 60.1 |
| 411-A | 159.8 | 526.8 |
| 411-B | 18.8 | 64.9 |
| 412 | 79.2 | 198.2 |
| 413 | 15.2 | 55.0 |
| 414-A | 44.1 | 114.7 |
| 414-B | 20000.0 | >10000.000 |
| 415 | 163.3 | 523.8 |
| 415-A | 88.1 | 303.6 |
| 415-B | 283.1 | 867.3 |
| 416 | 6.1 | 7.4 |
| 417 | 680.9 | 1156.4 |
| 418-A | 67.4 | 151.5 |
| 418-B | 1232.7 | 1969.8 |
| 419-A | 358.8 | 853.6 |
| 419-B | 620.8 | 3275.7 |
| 420 | 230.5 | 1374.0 |
| 421 | 181.5 | 365.0 |
| 421-A | 216.2 | 437.2 |
| 421-B | 389.5 | 359.2 |
| 422 | 173.7 | 284.8 |
| 422-A | 66.1 | 150.5 |
| 422-B | 38.0 | 165.2 |
| 422-C | 246.3 | 439.9 |
| 422-D | 128.2 | 414.6 |
| 423 | 1890.8 | 2467.1 |
| 423-A | 4998.3 | 5420.8 |
| 423-B | 124.3 | 173.7 |
| 423-C | 3040.9 | 4175.4 |
| 424 | 941.9 | 1946.3 |
| 424-A | 1033.3 | 2983.3 |
| 424-B | 208.6 | 929.0 |
| 425 | 900.8 | >10000.000 |
| 425-A | 2510.4 | >10000.000 |
| 425-B | 917.4 | >10000.000 |
| 426 | 24.0 | 50.9 |
| 427 | 10.5 | 4.2 |
| 428 | 54.7 | 141.4 |

TABLE 1-continued

Biological Assay Results

| Example # | TR-FRET i-Ag; $AC_{50}$ (nM) | CTGlo 144 h UMUC9.5; G150 (nM) |
|---|---|---|
| 429 | 346.9 | 1039.6 |
| 430 | 5.0 | 8.4 |
| 431-A | 111.2 | 594.7 |
| 431-B | 17.8 | 49.6 |
| 432 | 4.1 | 9.1 |
| 433 | 89.6 | 695.4 |
| 433-A | 126.4 | 346.9 |
| 433-B | 61.1 | 249.4 |
| 434 | 11.9 | 45.3 |
| 435-A | 9.2 | 59.5 |
| 435-B | 7.1 | 3.9 |
| 436 | 131.9 | >10000.000 |
| 437 | 14.8 | 67.6 |
| 438 | 309.3 | 1145.3 |
| 439-A | 46.6 | 61.8 |
| 439-B | 6.9 | 5.6 |
| 440 | 409.8 | 927.2 |
| 441 | 56.7 | 349.8 |
| 442 | 399.3 | 582.6 |
| 443 | 21.4 | 40.3 |
| 444 | 113.4 | >10000.000 |
| 445 | 1.2 | 22.4 |
| 445-A | 0.6 | 15.4 |
| 445-B | 11.0 | 115.5 |
| 446 | 1.3 | 27.4 |
| 447 | 508.4 | 3628.3 |
| 448 | 122.5 | 1643.5 |
| 450 | 1.5 | 113.8 |
| 450-A | 3.3 | 162.4 |
| 450-B | 6.8 | 834.4 |
| 451 | n.d. | 9.6 |
| 452 | 33.4 | 2386.9 |
| 452-A | 8.7 | 2008.6 |
| 452-B | 141.6 | >10000.000 |
| 453 | 25.6 | 44.2 |
| 453-A | 6.0 | 14.7 |
| 453-B | 8.2 | 398.0 |
| 454 | 195.5 | 999.2 |
| 454-A | 88.7 | 1786.2 |
| 454-B | 100.0 | 1878.1 |
| 455 | 67.9 | 213.1 |
| 456 | n.d. | 311.6 |
| 457 | 13.4 | 414.5 |
| 458 | 3.8 | 26.6 |
| 459 | 11.7 | 102.0 |
| 459-A | 8.0 | 274.9 |
| 459-B | 13.1 | 83.4 |
| 460-A | 800.0 | >10000.000 |
| 460-B | 1982.8 | >10000.000 |
| 461 | 439.7 | >10000.000 |
| 461-A | 271.7 | >10000.000 |
| 461-B | 323.9 | >10000.000 |
| 461-C | 375.3 | >10000.000 |
| 461-D | 387.9 | >10000.000 |
| 462 | 14.1 | 512.9 |
| 462-A | 22.5 | 551.0 |
| 462-B | 14.4 | 572.8 |
| 463 | 179.6 | 5203.8 |
| 464 | 9.3 | 36.4 |
| 464-A | 17.9 | 198.5 |
| 464-B | 11.8 | 124.3 |
| 464-C | 10.4 | 51.6 |
| 464-D | 7.6 | 25.2 |
| 465 | 88.6 | 842.4 |
| 466 | 5.1 | 51.2 |
| 466-A | 6.8 | 61.0 |
| 466-B | 4.0 | 52.9 |
| 467 | 950.7 | >10000.000 |
| 467-A | 326.6 | >10000.000 |
| 467-B | 644.1 | >10000.000 |
| 468 | 8.3 | 80.0 |
| 468-A | 495.6 | 5031.1 |
| 468-B | 11.1 | 60.8 |
| 469 | 78.5 | 9019.5 |

TABLE 1-continued

Biological Assay Results

| Example # | TR-FRET i-Ag; $AC_{50}$ (nM) | CTGlo 144 h UMUC9.5; G150 (nM) |
|---|---|---|
| 469-A | 92.6 | 7770.2 |
| 469-B | 115.4 | 9899.9 |
| 470 | 112.1 | 897.1 |
| 470-A | 87.4 | 813.0 |
| 470-B | 21.1 | 215.6 |
| 471 | 62.6 | >10000.000 |
| 472 | 2.9 | 24.2 |
| 472-A | 11.5 | 41.1 |
| 472-B | 21.9 | 1365.4 |
| 473 | 442.6 | 3385.4 |
| 474-A | 336.3 | 6205.7 |
| 474-B | 4.6 | 50.6 |
| 474-C | 5.4 | 23.6 |
| 474-D | 330.9 | 2021.8 |
| 474-E | 1504.9 | 1927.0 |
| 474-F | 71.6 | 2540.3 |
| 475-A | 432.8 | 2838.4 |
| 475-B | 102.2 | 583.0 |
| 476 | 17.4 | 406.2 |
| 477 | 42.8 | 307.2 |
| 478 | 38.8 | 415.0 |
| 478-A | 40.0 | 290.8 |
| 478-B | 56.0 | 675.4 |
| 478-C | 3060.3 | >10000.000 |
| 478-D | 15274.4 | >10000.000 |
| 479 | 131.7 | 1470.0 |
| 479-A | 884.8 | 3162.2 |
| 479-B | 95.3 | 1068.7 |
| 480 | 17.6 | 371.1 |
| 480-A | 2313.1 | 5078.1 |
| 480-B | 18.1 | 206.3 |
| 481 | 129.4 | 1221.0 |
| 481-A | 170.6 | 4414.6 |
| 481-B | 45.7 | 1166.3 |
| 482 | 29.5 | 270.5 |
| 483 | 6.2 | 44.5 |
| 483-A | 215.8 | 1520.6 |
| 483-B | 0.9 | 7.2 |
| 484 | 3.8 | 20.5 |
| 484-A | 1.5 | 5.7 |
| 484-B | 72.4 | 459.2 |
| 485 | 26.7 | 350.4 |
| 486 | 5.2 | 44.5 |
| 486-A | 1061.9 | 574.6 |
| 486-B | 2.9 | 22.8 |
| 487 | 0.7 | 2.4 |
| 488 | 0.9 | 6.6 |
| 489 | 0.7 | 5.5 |
| 489-A | 1.9 | 6.3 |
| 489-B | 6.0 | 465.1 |
| 490 | 1.9 | 17.3 |
| 490-A | 2.3 | 14.8 |
| 490-B | 9.7 | 77.8 |
| 491 | 0.3 | 11.0 |
| 492 | 453.5 | >10000.000 |
| 492-A | 1512.5 | >10000.000 |
| 492-B | 738.0 | >10000.000 |
| 493 | 12.6 | 88.6 |
| 493-A | 3.2 | 16.9 |
| 493-B | 101.4 | 484.2 |
| 494 | 6.7 | 80.8 |
| 495 | 15.7 | 185.6 |
| 495-A | 23.2 | 286.6 |
| 495-B | 13.3 | 143.6 |
| 496 | 9.6 | 68.2 |
| 497 | 87.7 | 644.7 |
| 498 | 2.9 | 21.9 |
| 499 | 294.5 | >10000.000 |
| 500 | 7.5 | 13.3 |
| 501 | 5.4 | 13.0 |
| 501-A | 7.8 | 21.4 |
| 501-B | 51.1 | 258.5 |
| 502 | 11.8 | 50.6 |
| 502-A | 109.7 | 750.3 |
| 502-B | 5.3 | 66.1 |
| 503 | 8.1 | 145.6 |
| 504-A | 2128.6 | >10000.000 |
| 504-B | 48.7 | 1837.0 |
| 504-E | 687.0 | 2262.9 |
| 504-F | 6887.2 | >10000.000 |
| 504-C | 15.7 | 258.4 |
| 504-D | 2.5 | 74.7 |
| 505 | 6.9 | 10.3 |
| 506 | 10.3 | 20.6 |
| 506-A | 4123.4 | 3277.7 |
| 506-B | 3.6 | 8.3 |
| 507 | 17.4 | 14.1 |
| 508 | 5.6 | 8.5 |
| 509 | 4.2 | 7.0 |
| 510 | 3.8 | 1.8 |
| 511 | 10.6 | 95.2 |
| 511-A | 17.2 | 63.5 |
| 511-B | 18.5 | 78.4 |
| 512 | 11.2 | 97.2 |
| 513 | 6.1 | 15.4 |
| 514 | 33.7 | >10000.000 |
| 514-A | 149.1 | 4198.9 |
| 514-B | 59.6 | 4309.9 |
| 515 | 5.0 | 6.0 |
| 516 | 3.3 | 10.0 |
| 517 | 7.9 | 20.3 |
| 518 | 148.9 | 4054.0 |
| 518-A | 130.5 | 3129.8 |
| 518-B | 995.6 | >10000.000 |
| 519 | 4.3 | 19.1 |
| 520 | 783.7 | >10000.000 |
| 521 | 1.8 | 19.8 |
| 522 | 1.4 | 14.3 |
| 523 | 5.3 | 54.3 |
| 524 | 128.4 | 341.0 |
| 524-A | n.d. | 110.0 |
| 524-B | n.d. | 430.1 |
| 524-C | n.d. | 367.3 |
| 524-D | n.d. | 890.2 |
| 525 | 7.0 | 19.0 |
| 526 | 3.7 | 7.1 |
| 527 | n.d. | 5.0 |
| 528 | 6.0 | 478.7 |
| 528-A | 2088.1 | >10000.000 |
| 528-B | 14.0 | 404.9 |
| 529 | 10.6 | 34.2 |
| 529-A | 756.1 | 5558.9 |
| 529-B | 1.4 | 9.2 |
| 530 | n.d. | n.d. |

$AC_{50}$ values for additional compounds disclosed herein may be obtained in the same manner using the assay above.

In Table 1, n.d. means not determined.

Cell Seeding for Proliferation Assay

UM-UC-9 engineered cells were cultured in Dulbecco's Modified Eagle Medium (DMEM) supplemented with 10% FBS, 25 mM glucose (high glucose), 4.0 mM L-glutamine, 2.0 mM GlutaMAX™, 1.0 mM pyruvate, 1.0% non-essential amino acids (NEAA) in a 95% humidified incubator at 37° C. with 5% $CO_2$. Cell banks of UM-UC-9 engineered assay-ready cells (ARCs) were prepared from a very active growth stage. Vials of ARCs containing approximately $5\times10^6$ cells per vial were stored in liquid nitrogen vapor phase cryostorage until use.

For making assay plates, ARCs were recovered from cryostorage, strained in a 70 μM cell strainer, verified for cell viability >90% and counted using a cell counter (Cellometer Auto 1000, Nexelom). Each cell line was seeded into 384-well plates (50 μl/well) using DMEM medium at a density previously determined to be in log growth phase 7 days post-seeding (500 cells/well) using a bulk reagent dispenser (Multidrop™ Combi, Thermo Scientific) with a large-bore plastic-tip cassette pre-sanitized with 70% ethanol. One plate of cells was designated as the pretreatment time-zero (T0) control. Freshly seeded plates were allowed to sit lidded for 30 minutes within a biosafety cabinet for cells to settle distributed within the plate wells uniformly and then placed into an automated incubator (STX110, Liconic) at 37° C., 5% $CO_2$, and 95% relative humidity.

Preparation of Test Compound in Assay-Ready Plate

Compounds were stored in a low-temperature sample archive as 10 mM dimethyl sulfoxide (DMSO) solutions at −20° C. under reduced humidity (−45° C. dew point) and protected from light. All samples in the automated archive are stored in 2D barcoded polypropylene tubes, tracked through a laboratory information management system (LIMS), and have been verified for identity and purity by NMR (Chemistry, H3 Biomedicine) and by LCMS (Analytical Chemistry, H3 Biomedicine) at the time of sample registration. Identity by mass matching and purity are again verified at the time of sample request fulfillment by redundant LCMS methods (acidic and basic separation protocols; Analytical Chemistry, H3 Biomedicine). Samples retrieved from low-temperature archive storage were solubilized by heated sonication (Bransonic® Ultrasonic Bath, Branson), transferred (Microlab Starlet, Hamilton) and serially-diluted (Viaflo Assist, Integra) by low-volume liquid handlers, and tracked in LIMS by automation log files to create a ID barcoded master dose-response plate (MDR) to serve as a standard source for all assay-ready plates (ARP) used within an experiment. ARPs prepared by acoustic transfer (ATS-100, EDC) of nL volumes from the MDR source were heat-sealed (PlateLoc, Agilent) and stored at −20° C. prior to use (<7 days from production). Tracking of liquid transfers via acoustic dispenser log files were used to update the LIMS system for all ARP plate maps.

Measurement of Pretreatment Control Cells and Sample Anti-Proliferative Effects on Treated Cells On day 0 (pretreatment cells) or day 7 (treated cells), a cell proliferation assay was performed using an automated robotic assay platform (ACell, High-Res Biosolutions). Cell ARP's were removed from incubation, their plate lid discarded, and using a bulk reagent dispenser (Multidrop™ Combi, Thermo Scientific with a small-bore metal-tip cassette) 25 μL (1/2 volume) of Cell Titer-Glo® 2.0 Cell Viability Assay reagent (Promega) was added to wells of columns 1-23 (column 24 will be used as plate background or positive control). Cell ARP's were incubated at room temperature in an automation hotel position for a total of 1.0 minute while the next plate was delivered to the bulk reagent dispenser and then lid-free cell ARP's were returned to incubate at 37° C. for 2.5 hours. Cell ARP's were processed again sequentially every ~two minutes, moving ARP's to incubate at room temperature in an automation hotel position for a total of 1.0 minute before delivery to the plate reader (EnVision® 2104 multimode plate reader with ultra-sensitive luminescence, PerkinElmer). Relative luminescence was measured at 0.1 sec per well. After use, all ARP's were discarded to a Biosafety Waste Receptacle to be processed as BL2 level waste, in accordance with current regulations.

Data Analysis

Data Normalization

Cell proliferation is evaluated using the compound treatment plate (TEST) vehicle/DMSO control wells as the negative control ($N_{TEST}$) and the pretreatment plate (T0) cell signal as the positive control ($N_{T0}$). Data are converted to percent inhibition and falls into the range from 0% to 100% of growth where 0% equals the pretreatment signal and 100% equals uninhibited or maximal growth.

Cell viability is evaluated using the pretreatment plate (T0) cell signal as the negative control ($N_{T0}$) and the compound treatment plate (TEST) background control wells as the positive control ($P_{TEST}$), which is similar to data generated using cell toxic compound controls such as Bortezomib or Staurosporine. Data are converted to percent inhibition and falls into the range from −100% to 0% where 0% equals the pretreatment signal and −100% equals maximal cell death.

Response % data for all TEST wells are then computed by one of two formulas depending on if the TEST well signal ($SIGNAL_{TEST}$) is above or below the value of '$N_{T0}$', as follows:

If '$SIGNAL_{TEST}$' is greater than '$N_{T0}$' then use Calculation #1, else use Calculation #2.

$$\text{Response }\%=100\times(SIGNAL_{TEST}-\text{Average}(P_{TEST})-N_{T0})/(\text{Average}(N_{TEST})-\text{Average}(P_{TEST})-N_{T0})$$ Calculation #1

$$\text{Response }\%=100\times(SIGNAL_{TEST}-\text{Average}(P_{TEST})-N_{T0})/N_{T0}$$ Calculation #2

Where:

The '$N_{T0}$' value is computed by background subtraction of the average of the active 'P' control wells from the average of the active 'N' control wells on the T0 plate.

"$N_{T0}$"=Average (N−Average (P))

The 4 Parametric Logistic Fit

The data was fitted by using Ecabia data analysis software developed at H3 Biomedicine, Inc.

The fit was performed through minimization of the root mean squared error between observed and calculated values of the four parameter logistic equation using the simplex optimizer of the Apache Commons Math library. Boundary conditions for the fit parameters were set as: Top fixed at 100% response, bottom between −100% and 100% response, hill slope between −3 and −0.3, inflection point unrestricted. (These default parameters could be changed for individual curves if appropriate).

$GI_{50}$ $GI_{50}$ (the concentration of test article at which cell growth is inhibited by 50% compared to vehicle treated cells) was computed as the concentration where the fitted curves crossed the 50% response level. If a calculated value was below the lowest tested concentration $C_{min}$ the value was set to '<$C_{min}$'. If a calculated value was above the highest tested concentration $C_{max}$ or no value existed because the bottom of the curve was above the given response level, the value was set to '>$C_{max}$'. Averages and standard deviations were computed from replicates of the experiment.

Cell culture. All human cell lines except UM-UC9 and UM-UC14 were purchased from ATCC. Parental 5637 and SW780 (both PPARγ amplified) lines were maintained in ATCC-formulated RPMI-1640 medium containing 10% fetal bovine serum (FBS). Parental Cal29 (PPARγ active) cell line was maintained in Dulbecco's Modified Eagle Medium (DMEM) containing 10% heat-inactivated FBS. Parental HT-1197 (RXRα-$S_{427}$F) and HT-1376 (PPARγ high) bladder cancer cell lines were maintained in Eagle's Minimum Essential medium (EMEM) containing 10% FBS. KMBC2 (PPARγ amplified) cell line was maintained in DMEM/Ham's F-12 1:1 containing 10% FBS. RT4 cell line (PPARγ mutant) was maintained in ATCC-formulated McCoy's 5a Medium Modified containing 10% FBS. RT112 cell line (PPARγ active) was maintained in ATCC-formulated RPMI-1640 medium containing 10% heat-inactivated FBS. SW1710 (PPARγ low human bladder cancer cell line) was maintained in DMEM containing 15% heat-inactivated FBS. UM-UC9 (PPARγ amplified), UM-UC14 (PPARγ amplified), and UM-UC3 (PPARγ low) human bladder cancer cell lines were purchased from Sigma-Aldrich/ECACC and maintained in EMEM containing 10% FBS, 1% NEAA and 2 mM L-Glutamine. Non-bladder cancer cell lines were also tested in parallel as controls. Colorectal cancer cell line HCT-116 (PPARγ low) was maintained in ATCC-formulated McCoy's 5a Medium Modified containing 10% FBS. Colorectal cancer cell line RKO (PPARγ low) was maintained in ATCC-formulated EMEM containing 10% FBS. Lung cancer cell line A549 (PPARγ low) was maintained in F-12K medium containing 10% FBS. Liver cancer cell line Hep3B (PPARγ low) was maintained in EMEM containing 10% heat-inactivated FBS and 2 mM L-Glutamine. Rat bladder cancer cell line AY-27 (PPARγ low), a gift from OncoDesign (France), was maintained in RPMI 1640 medium containing 10% FBS, 2 mM L-Glutamine, sodium bicarbonate and Penicillin/Streptomycin. All cell lines were tested for, and free of mycoplasma contamination.

Short-Term Viability Assays:

For viability assays, 500 cells were seeded in each well of a 384-well plate one day before compound addition. Dose response was measured in 11 point serial dilutions with a top dose of 10 μM. The percentage of DMSO was controlled throughout and a DMSO only control was included. Hundred forty four hours after dosing, CellTiter-Glo reagent was added, incubated, and assayed on an EnVision Multilabel Reader (PerkinElmer). Luminescence values from each treatment were normalized to the average value of the respective DMSO control. The dose response curve plots were generated in GraphPad Prism and $GI_{50}$'s calculated from nonlinear regression analysis. $GI_{50}$'s were plotted in Spotfire.

Results are reported in Table 1 in the CTGlo 144 h UMUC9.5; GI50 (nM) column.

Colony Formation Assays:

- Day 1: Cells are harvested using 0.25% Trypsin, made into single-cell suspension and counted. Each cell line and treatment condition is run in three replicates each in a 6-well plate. Seeding densities range from 125-2000 cells per well in 2 ml medium depending on the cell line.
- Day 2: Compounds are diluted in RPMI 1640 medium to make a 100× solution, of which 20 μl was added per well. DMSO is utilized as a vehicle control and its concentration is maintained at 0.1% across the panel.

Media is changed and fresh compound administered every 3-4 days for up to 2-3 weeks depending on the colony size in the DMSO controls. All plates for a given cell line are terminated at the same time. Viable colonies are stained at the end of study. Following media aspiration, 0.5% crystal violet is added to the wells for about 1 h. Crystal violet solution is removed and wells carefully washed with water to remove residual staining solution. The plates are air-dried overnight prior to imaging.

Compounds disclosed herein can be tested using the above method. Active compounds can demonstrate significant anti-proliferative activity across the panel of PPARγ active/high/mutant lines whereas inactive compounds can demonstrate no activity in PPARγ inactive/null cell lines. Such testing can be used for confirming potency and selectivity of compounds disclosed herein.

RT4 Xenograft Study

Animal experiments were conducted in accordance with internal animal care and use committee (IACUC) guidelines defined by the H3 Biomedicine IACUC. Cells were maintained in monolayer cultures in relevant media at 37° C. in a 5% $CO_2$ humidified incubator. On the day of inoculation, cells were harvested by trypsinization, washed, and re-suspended in ice-cold Phosphate-Buffered Saline (PBS). Male immunodeficient BALB/C nude mice (from Charles River laboratory) were inoculated subcutaneously with $5\times10^6$ cells near the right axillary area in a 1:1 ratio (50 μL each) with Matrigel™ in a volume of 0.1 mL in PBS, using a 26-gauge needle. When the mean tumor volume reached approximately 200 $mm^3$ animals were randomly and evenly divided into groups and treatments initiated. Treatments continued until tumors reached ~2000 $mm^3$ or until significant body weight loss was noted (>20% loss relative to starting body weight). Statistical analyses were performed using the GraphPad Prism version 5.04 (GraphPad Software, La Jolla, CA).

Anti-tumor activity in the RT4 xenograft model was examined using compound X. Compound X is a compound according to Formula (IIIB) prepared and tested according to the methods described herein. Compound X was dosed orally every day at doses ranging from 3 to 10 mg/kg. The administration volume was calculated from the individual mouse body weights prior to dose administration. The body weights were measured daily while the tumor volumes were measured twice a week. Tumor volumes (TV) were calculated based on the formula:

$$TV=\text{length}\times\text{width}^2\times0.5$$

length: largest diameter of tumor (mm)

width: diameter perpendicular to length (mm)

The Tumor Growth Inhibition % (TGI) was calculated according to the following formula:

$$\text{Tumor Growth Inhibition \% } (TGI) = \frac{\text{Average Control } TV \text{ Day } X - \text{Treatment } TV \text{ Day } X}{\text{Average Control } TV \text{ Day } X} \times 100$$

Where Day X is the endpoint measurement.

Compound X was given orally once daily for the duration of the study. Data represent the mean±SEM (Tumor Volume), or the mean±SEM (% body weight change) (N=8 for treatment groups, N=8 for Vehicle control). *p<0.0001 versus vehicle control on last day of study (Two-Way ANOVA followed by the Tukey's multiple comparison test).

The results show the anti-tumor and body weight effects of compound X in the RT4 xenograft model carrying the T475M PPARγ variant grown in immunocompromised mice. Compound X inhibited xenograft growth in a dose dependent manner with 3 mg/kg QD and 10 mg/kg QD significantly inhibiting growth compared to the control (TGI of 53% and 77% and p<0.0001 for both doses, respectively). All doses and regimens were well tolerated with no significant body weight loss.

The following compounds were tested in the TR-FRET assay to measure Co—R Peptide Recruitment to PPARγ and were found to have an $AC_{50}$ greater than 1000 nM:

(7R*)-4-(5-{5-[(1S)-1-hydroxyethyl]-2-methylpyridin-4-yl}-1H-pyrazole-3-carbonyl)-N-[(1r,4r)-4-hydroxy-4-(trifluoromethyl)cyclohexyl]-4-azaspiro[2.5]octane-7-carboxamide;

1-[5-(5-chloro-2-methoxypyridin-4-yl)-1H-pyrazole-3-carbonyl]-N-{4-hydroxybicyclo[2.2.2]octan-1-yl}piperidine-4-carboxamide;

2-[5-(5-chloro-2-methoxypyridin-4-yl)-1H-pyrazole-3-carbonyl]-N-[(3-chlorophenyl)methyl]-7,7-difluoro-2-azabicyclo[4.1.0]heptane-5-carboxamide;

1-[5-(5-chloro-2-methoxypyridin-4-yl)-1H-pyrazole-3-carbonyl]-N-{[6-(trifluoromethyl)-[1,2,4]triazolo[4,3-a]pyridin-3-yl]methyl}piperidine-4-carboxamide;

1-[5-(5-chloro-2-methoxypyridin-4-yl)-1H-pyrazole-3-carbonyl]-N-(1,4-dimethyl-1H-imidazol-2-yl)piperidine-4-carboxamide;

1-[5-(5-chloro-2-methoxypyridin-4-yl)-1H-pyrazole-3-carbonyl]-N-[(3-chlorophenyl)methyl]-4-(2,2,2-trifluoroethoxy)piperidine-4-carboxamide;

2-[5-(5-chloro-2-methoxypyridin-4-yl)-1H-pyrazole-3-carbonyl]-N-[(3-chlorophenyl)methyl]-2-azabicyclo[3.1.0]hexane-5-carboxamide;

rel-(1R,5R)-2-[5-(5-chloro-2-methoxypyridin-4-yl)-1H-pyrazole-3-carbonyl]-N-[(3-chlorophenyl)methyl]-2-azabicyclo[3.1.0]hexane-5-carboxamide;

1-[5-(5-chloro-2-methoxypyridin-4-yl)-1H-pyrazole-3-carbonyl]-N-[(3-chlorophenyl)methyl]-4-(hydroxymethyl)piperidine-4-carboxamide;

1-[5-(5-chloro-2-methoxypyridin-4-yl)-1H-pyrazole-3-carbonyl]-N-[(4-oxo-3,4-dihydrophthalazin-1-yl)methyl]piperidine-4-carboxamide;

1-[5-(5-chloro-2-methoxypyridin-4-yl)-1H-pyrazole-3-carbonyl]-N-[(2-methyl-2,3-dihydro-1H-isoindol-5-yl)methyl]piperidine-4-carboxamide;

1-[5-(5-chloro-2-methoxypyridin-4-yl)-1H-pyrazole-3-carbonyl]-N-{[2-(trifluoromethyl)phenyl]methyl}piperidine-4-carboxamide;

N-[(1H-1,3-benzodiazol-5-yl)methyl]-1-[5-(5-chloro-2-methoxypyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(2,6-difluoro-3-methylphenyl)methyl]piperidine-4-carboxamide;

1-[5-(5-chloro-2-methoxypyridin-4-yl)-1H-pyrazole-3-carbonyl]-N-(3-hydroxycyclopentyl)piperidine-4-carboxamide;

1-[5-(5-chloro-2-methoxypyridin-4-yl)-1H-pyrazole-3-carbonyl]-N-[(1H-indazol-5-yl)methyl]piperidine-4-carboxamide;

N-(1-benzylpyrrolidin-3-yl)-1-[5-(5-chloro-2-methoxypyridin-4-yl)-1H-pyrazole-3-carbonyl]piperidine-4-carboxamide;

1-[5-(5-chloro-2-methoxypyridin-4-yl)-1H-pyrazole-3-carbonyl]-N-({imidazo[1,2-a]pyrazin-6-yl}methyl)piperidine-4-carboxamide;

1-[5-(5-chloro-2-methoxypyridin-4-yl)-1H-pyrazole-3-carbonyl]-N-[(6-oxo-1,6-dihydropyridin-2-yl)methyl]piperidine-4-carboxamide;

1-[5-(5-chloro-2-methoxypyridin-4-yl)-1H-pyrazole-3-carbonyl]-N-[(3-chlorophenyl)methyl]-4-(methoxymethyl)piperidine-4-carboxamide;

(1S,4R,5R*)—N-[(3-chlorophenyl)methyl]-2-[5-(5-fluoro-2-methoxypyridin-4-yl)-1H-pyrazole-3-carbonyl]-2-azabicyclo[2.2.1]heptane-5-carboxamide;

1-[5-(5-chloro-2-methoxypyridin-4-yl)-1H-pyrazole-3-carbonyl]-N-({imidazo[1,2-a]pyrimidin-2-yl}methyl)piperidine-4-carboxamide;

(1R,5S,6r*)-N-(3-chlorobenzyl)-3-(5-(5-fluoro-2-methoxypyridin-4-yl)-1H-pyrazole-3-carbonyl)-3-azabicyclo[3.1.1]heptane-6-carboxamide;

(1R,5S,6s*)-N-(3-chlorobenzyl)-3-(5-(5-fluoro-2-methoxypyridin-4-yl)-1H-pyrazole-3-carbonyl)-3-azabicyclo[3.1.1]heptane-6-carboxamide;

(1R,5S,8R*)—N-[(3-chlorophenyl)methyl]-3-[5-(5-fluoro-2-methoxypyridin-4-yl)-1H-pyrazole-3-carbonyl]-3-azabicyclo[3.2.1]octane-8-carboxamide;

(3S)—N-[(3-chlorophenyl)methyl]-1-[5-(5-fluoro-2-methoxypyridin-4-yl)-1H-pyrazole-3-carbonyl]piperidine-3-carboxamide;

(3R)—N-[(3-chlorophenyl)methyl]-1-[5-(5-fluoro-2-methoxypyridin-4-yl)-1H-pyrazole-3-carbonyl]piperidine-3-carboxamide;

1-[5-(5-chloro-2-methoxypyridin-4-yl)-1H-pyrazole-3-carbonyl]-N-[3-(trifluoromethyl)-1,2-oxazol-5-yl]piperidine-4-carboxamide;

1-[5-(5-chloro-2-methoxypyridin-4-yl)-1H-pyrazole-3-carbonyl]-N-[(4-chloropyridin-2-yl)methyl]piperidine-4-carboxamide;

1-[5-(5-chloro-2-methoxypyridin-4-yl)-1H-pyrazole-3-carbonyl]-N-(5-chloropyridazin-4-yl)piperidine-4-carboxamide;

1-[5-(5-chloro-2-methoxypyridin-4-yl)-1H-pyrazole-3-carbonyl]-N-(2,3-difluorophenyl)piperidine-4-carboxamide;

1-[5-(5-chloro-2-methoxypyridin-4-yl)-1H-pyrazole-3-carbonyl]-N-(4-methoxy-4-methylcyclohexyl)piperidine-4-carboxamide;

1-[5-(5-chloro-2-methoxypyridin-4-yl)-1H-pyrazole-3-carbonyl]-N-[1-(oxetan-3-yl)ethyl]piperidine-4-carboxamide;

1-[5-(5-chloro-2-methoxypyridin-4-yl)-1H-pyrazole-3-carbonyl]-N-(2,6-difluoro-4-methoxyphenyl)piperidine-4-carboxamide;

1-[5-(5-chloro-2-methoxypyridin-4-yl)-1H-pyrazole-3-carbonyl]-N-[(1r,3r,5r,7r)-adamantan-2-yl]piperidine-4-carboxamide;

1-[5-(5-chloro-2-methoxypyridin-4-yl)-1H-pyrazole-3-carbonyl]-N-[(4,5-dimethyl-1,3-thiazol-2-yl)methyl]piperidine-4-carboxamide;

1-[5-(5-chloro-2-methoxypyridin-4-yl)-1H-pyrazole-3-carbonyl]-N-[4-(methanesulfonylmethyl)phenyl]piperidine-4-carboxamide;

1-[5-(5-chloro-2-methoxypyridin-4-yl)-1H-pyrazole-3-carbonyl]-N-[(5-methylpyrazin-2-yl)methyl]piperidine-4-carboxamide;

1-[5-(5-chloro-2-methoxypyridin-4-yl)-1H-pyrazole-3-carbonyl]-N-[(1-cyanocyclopropyl)methyl]piperidine-4-carboxamide;

1-[5-(5-chloro-2-methoxypyridin-4-yl)-1H-pyrazole-3-carbonyl]-N-[(5-methyl-1,2-oxazol-3-yl)methyl]piperidine-4-carboxamide;

1-[5-(5-chloro-2-methoxypyridin-4-yl)-1H-pyrazole-3-carbonyl]-N-[(3-ethyloxetane-3-yl)methyl]piperidine-4-carboxamide;

1-[5-(5-chloro-2-methoxypyridin-4-yl)-1H-pyrazole-3-carbonyl]-N-[(4-methylpyridine-2-yl)methyl]piperidine-4-carboxamide;

1-[5-(5-chloro-2-methoxypyridin-4-yl)-1H-pyrazole-3-carbonyl]-N-[(6-methylpyridin-2-yl)methyl]piperidine-4-carboxamide;

1-[5-(5-chloro-2-methoxypyridin-4-yl)-1H-pyrazole-3-carbonyl]-N-[(2-cyanophenyl)methyl]piperidine-4-carboxamide;

1-[5-(5-chloro-2-methoxypyridin-4-yl)-1H-pyrazole-3-carbonyl]-N-[(pyrazin-2-yl)methyl]piperidine-4-carboxamide;
1-[5-(5-chloro-2-methoxypyridin-4-yl)-1H-pyrazole-3-carbonyl]-N-{[3-fluoro-5-(trifluoromethyl)phenyl]methyl}piperidine-4-carboxamide;
N-(1-tert-butylpiperidin-4-yl)-1-[5-(5-chloro-2-methoxypyridin-4-yl)-1H-pyrazole-3-carbonyl]piperidine-4-carboxamide;
1-[5-(5-chloro-2-methoxypyridin-4-yl)-1H-pyrazole-3-carbonyl]-N-(1-cyclobutylpiperidin-4-yl)piperidine-4-carboxamide;
1-[5-(5-chloro-2-methoxypyridin-4-yl)-1H-pyrazole-3-carbonyl]-N-[(1-methylazetidin-3-yl)methyl]piperidine-4-carboxamide;
1-[5-(5-chloro-2-methoxypyridin-4-yl)-1H-pyrazole-3-carbonyl]-N-(5-phenyl-1H-pyrazol-3-yl)piperidine-4-carboxamide;
1-[5-(5-chloro-2-methoxypyridin-4-yl)-1H-pyrazole-3-carbonyl]-N-(1-methyl-1H-1,3-benzodiazol-2-yl)piperidine-4-carboxamide;
N-[(3-chlorophenyl)methyl]-1-[5-(2-methoxy-5-methylpyridin-4-yl)-1H-pyrazole-3-carbonyl]piperidine-4-carboxamide;
1-[5-(5-chloro-2-methoxypyridin-4-yl)-1H-pyrazole-3-carbonyl]piperidine-4-carboxylic acid;
1-[5-(5-chloro-2-methoxypyridin-4-yl)-1H-pyrazole-3-carbonyl]-N-[(1-methyl-1H-imidazol-2-yl)methyl]piperidine-4-carboxamide;
1-[5-(2-methoxypyridin-4-yl)-1H-pyrazole-3-carbonyl]-N-(2-phenylpropan-2-yl)piperidine-4-carboxamide;
N-(4,4-difluorocyclohexyl)-1-[5-(2-methoxypyridin-4-yl)-1H-pyrazole-3-carbonyl]piperidine-4-carboxamide;
1-[5-(2-methoxypyridin-4-yl)-1H-pyrazole-3-carbonyl]-N-(4-oxocyclohexyl)piperidine-4-carboxamide;
N-(4-methylcyclohexyl)-1-{5-[2-(pyrrolidin-1-yl)pyridin-4-yl]-1H-pyrazole-3-carbonyl}piperidine-4-carboxamide;
1-{5-[2-(dimethylamino)pyridin-4-yl]-1H-pyrazole-3-carbonyl}-N-(4-methylcyclohexyl)piperidine-4-carboxamide;
1-{5-[2-(methylamino)pyridin-4-yl]-1H-pyrazole-3-carbonyl}-N-(4-methylcyclohexyl)piperidine-4-carboxamide;
1-[5-(2-methoxypyridin-4-yl)-1H-pyrazole-3-carbonyl]-4-methyl-N-(4-methylcyclohexyl)piperidine-4-carboxamide;
1-{5-[2-(difluoromethoxy)pyridin-4-yl]-1H-pyrazole-3-carbonyl}-N-(4-methylcyclohexyl)piperidine-4-carboxamide;
1-[5-(2-methoxypyridin-4-yl)-1H-pyrazole-3-carbonyl]-N-[(1s,4r)-4-ethylcyclohexyl]piperidine-4-carboxamide;
4-(3-{4-[(4-methylcyclohexyl)carbamoyl]piperidine-1-carbonyl}-11-pyrazol-5-yl)pyridine-2-carboxylic acid;
2-(2-chloro-5-{1-[5-(pyridin-4-yl)-1H-pyrazole-3-carbonyl]piperidine-4-amido}phenoxy)acetic acid;
N-[(4-methyl-1,3-thiazol-2-yl)methyl]-1-[5-(pyridin-4-yl)-1H-pyrazole-3-carbonyl]piperidine-4-carboxamide;
rel-1-[5-(pyridin-4-yl)-1H-pyrazole-3-carbonyl]-N-[(1r,4r)-4-phenylcyclohexyl]piperidine-4-carboxamide;
N-[(4-ethyl-1,3-thiazol-2-yl)methyl]-1-[5-(pyridin-4-yl)-1H-pyrazole-3-carbonyl]piperidine-4-carboxamide;
N-[(6-tert-butylpyridine-3-yl)methyl]1-[5-(pyridin-4-yl)-1H-pyrazole-3-carbonyl]piperidine-4-carboxamide;
N-[1-(3-chlorophenyl)cyclopropyl]-1-[5-(pyridin-4-yl)-1H-pyrazole-3-carbonyl]piperidine-4-carboxamide;
1-[5-(pyridin-4-yl)-1H-pyrazole-3-carbonyl]-N-[(1s,4r)-4-ethylcyclohexyl]piperidine-4-carboxamide;
1-[5-(pyridin-4-yl)-1H-pyrazole-3-carbonyl]-N-[(1s,4s)-4-cyanocyclohexyl]piperidine-4-carboxamide;
N-[(2-methylpyridin-4-yl)methyl]-1-[5-(pyridin-4-yl)-1H-pyrazole-3-carbonyl]piperidine-4-carboxamide;
N-({5H,6H,7H-cyclopenta[b]pyridin-3-yl}methyl)-1-[5-(pyridin-4-yl)-1H-pyrazole-3-carbonyl]piperidine-4-carboxamide;
N-[(5,6-dimethylpyridin-3-yl)methyl]-1-[5-(pyridin-4-yl)-1H-pyrazole-3-carbonyl]piperidine-4-carboxamide;
N-[(2,6-dimethylpyridin-4-yl)methyl]-1-[5-(pyridin-4-yl)-1H-pyrazole-3-carbonyl]piperidine-4-carboxamide;
N-(4-phenylcyclohexyl)-1-[5-(pyridin-3-yl)-1H-pyrazole-3-carbonyl]piperidine-4-carboxamide;
N-[(3,4-dichlorophenyl)methyl]-1-[5-(pyridin-3-yl)-1H-pyrazole-3-carbonyl]piperidine-4-carboxamide;
N-[(2,5-dichlorophenyl)methyl]-1-[5-(pyridin-3-yl)-1H-pyrazole-3-carbonyl]piperidine-4-carboxamide;
N-[(3S)-1-benzylpyrrolidin-3-yl]-1-[5-(pyridin-3-yl)-1H-pyrazole-3-carbonyl]piperidine-4-carboxamide;
N-[(3R)-1-benzylpyrrolidin-3-yl]-1-[5-(pyridin-3-yl)-1H-pyrazole-3-carbonyl]piperidine-4-carboxamide;
N-[(4-chlorophenyl)methyl]-1-[5-(pyridin-3-yl)-1H-pyrazole-3-carbonyl]piperidine-4-carboxamide;
N-[(2-chlorophenyl)methyl]-1-[5-(pyridin-3-yl)-1H-pyrazole-3-carbonyl]piperidine-4-carboxamide:
1-[3-(pyridin-3-yl)-1H-pyrazole-5-carbonyl]-N-[(1r,4r)-4-methylcyclohexyl]piperidine-4-carboxamide;
2-{1-[5-(pyridin-4-yl)-1H-pyrazole-3-carbonyl]piperidine-4-carbonyl}-1,2,3,4-tetrahydroisoquinoline;
N-ethyl-1-[5-(pyridin-4-yl)-1H-pyrazole-3-carbonyl]piperidine-4-carboxamide;
N-(4-methoxypyridin-2-yl)-1-[5-(pyridin-4-yl)-1H-pyrazole-3-carbonyl]piperidine-4-carboxamide;
N-(2-cyanoethyl)-N-methyl-1-[5-(pyridin-4-yl)-1H-pyrazole-3-carbonyl]piperidine-4-carboxamide;
N-(2,6-dimethylphenyl)-1-[5-(pyridin-4-yl)-1H-pyrazole-3-carbonyl]piperidine-4-carboxamide;
N-(6-methylpyridazin-3-yl)-1-[5-(pyridin-4-yl)-1H-pyrazole-3-carbonyl]piperidine-4-carboxamide;
N-methyl-N-(2-methylpropyl)-1-[5-(pyridin-4-yl)-1H-pyrazole-3-carbonyl]piperidine-4-carboxamide;
N-[(5-methyl-1,2,4-oxadiazol-3-yl)methyl]-1-[5-(pyridin-4-yl)-1H-pyrazole-3-carbonyl]piperidine-4-carboxamide;
N-(4-methoxy-2-methylphenyl)-1-[5-(pyridin-4-yl)-1H-pyrazole-3-carbonyl]piperidine-4-carboxamide;
N-(5-fluoropyridin-2-yl)-1-[5-(pyridin-4-yl)-1H-pyrazole-3-carbonyl]piperidine-4-carboxamide;
N-(2,2-dimethylpropyl)-1-[5-(pyridin-4-yl)-1H-pyrazole-3-carbonyl]piperidine-4-carboxamide;
N-[3-(morpholin-4-yl)propyl]-1-[5-(pyridin-4-yl)-1H-pyrazole-3-carbonyl]piperidine-4-carboxamide;
N-benzyl-N-methyl-1-[5-(pyridin-4-yl)-1H-pyrazole-3-carbonyl]piperidine-4-carboxamide;
(3R)-1-{1-[5-(pyridin-4-yl)-1H-pyrazole-3-carbonyl]piperidine-4-carbonyl}pyrrolidin-3-ol;
(3S)—N,N-dimethyl-1-{1-[5-(pyridin-4-yl)-1H-pyrazole-3-carbonyl]piperidine-4-carbonyl}pyrrolidin-3-amine;
4-{1-[5-(pyridin-4-yl)-1H-pyrazole-3-carbonyl]piperidine-4-carbonyl}morpholine;
(3R)—N,N-dimethyl-1-{1-[5-(pyridin-4-yl)-1H-pyrazole-3-carbonyl]piperidine-4-carbonyl}pyrrolidin-3-amine;
N-(3-methylpyridin-4-yl)-1-[5-(pyridin-4-yl)-1H-pyrazole-3-carbonyl]piperidine-4-carboxamide;
N-(pyridazin-3-yl)-1-[5-(pyridin-4-yl)-1H-pyrazole-3-carbonyl]piperidine-4-carboxamide;
N-[(1-methyl-1H-pyrazol-4-yl)methyl]-1-[5-(pyridin-4-yl)-1H-pyrazole-3-carbonyl]piperidine-4-carboxamide;

N-(pentan-3-yl)-1-[5-(pyridin-4-yl)-1H-pyrazole-3-carbonyl]piperidine-4-carboxamide;
N-[2-(dimethylamino)ethyl]-1-[5-(pyridin-4-yl)-1H-pyrazole-3-carbonyl]piperidine-4-carboxamide;
N-(1,3-oxazol-2-yl)-1-[5-(pyridin-4-yl)-1H-pyrazole-3-carbonyl]piperidine-4-carboxamide;
N-(2-ethoxyethyl)-1-[5-(pyridin-4-yl)-1H-pyrazole-3-carbonyl]piperidine-4-carboxamide;
1-{1-[5-(pyridin-4-yl)-1H-pyrazole-3-carbonyl]piperidine-4-carbonyl}-6-oxa-1-azaspiro[3.3]heptane;
N-methyl-N-propyl-1-[5-(pyridin-4-yl)-1H-pyrazole-3-carbonyl]piperidine-4-carboxamide;
1-methyl-4-{l-[5-(pyridin-4-yl)-1H-pyrazole-3-carbonyl]piperidine-4-carbonyl}-1,4-diazepane;
1-phenyl-4-{1-[5-(pyridin-4-yl)-1H-pyrazole-3-carbonyl]piperidine-4-carbonyl}piperazine;
N-(cyclopropylmethyl)-1-[5-(pyridin-4-yl)-1H-pyrazole-3-carbonyl]piperidine-4-carboxamide;
1-[5-(pyridin-4-yl)-1H-pyrazole-3-carbonyl]-N-[2-(pyrrolidin-1-yl)ethyl]piperidine-4-carboxamide;
N-[(1R)-1-(4-methylphenyl)ethyl]-1-[5-(pyridin-4-yl)-1H-pyrazole-3-carbonyl]piperidine-4-carboxamide;
1-[5-(pyridin-4-yl)-1H-pyrazole-3-carbonyl]-N-[(pyridin-4-yl)methyl]piperidine-4-carboxamide;
1-{1-[5-(pyridin-4-yl)-1H-pyrazole-3-carbonyl]piperidine-4-carbonyl}-4-(2,2,2-trifluoroethyl)piperazine;
1-[5-(pyridin-4-yl)-1H-pyrazole-3-carbonyl]-N-[(1r,4r)-4-methylcyclohexyl]piperidine-4-carboxamide;
N-methyl-N-(1-methylpiperidin-4-yl)-1-[5-(pyridin-4-yl)-1H-pyrazole-3-carbonyl]piperidine-4-carboxamide;
N-(2-methylcyclohexyl)-1-[5-(pyridin-4-yl)-1H-pyrazole-3-carbonyl]piperidine-4-carboxamide;
N-[(4-tert-butylphenyl)methyl]-N-methyl-1-[5-(pyridin-4-yl)-1H-pyrazole-3-carbonyl]piperidine-4-carboxamide;
N-[(1R)-1-phenylethyl]-1-[5-(pyridin-4-yl)-1H-pyrazole-3-carbonyl]piperidine-4-carboxamide;
[(2S)-1-{1-[5-(pyridin-4-yl)-1H-pyrazole-3-carbonyl]piperidine-4-carbonyl}pyrrolidin-2-yl]methanol;
N-(1-methylpiperidin-4-yl)-1-[5-(pyridin-4-yl)-1H-pyrazole-3-carbonyl]piperidine-4-carboxamide;
N-(4,4-difluorocyclohexyl)-1-[5-(pyridin-4-yl)-1H-pyrazole-3-carbonyl]piperidine-4-carboxamide;
N-methyl-2-(4-{1-[5-(pyridin-4-yl)-1H-pyrazole-3-carbonyl]piperidine-4-carbonyl}piperazin-1-yl)acetamide;
1-[5-(pyridin-4-yl)-1H-pyrazole-3-carbonyl]-N-[(1s,4s)-4-hydroxycyclohexyl]piperidine-4-carboxamide;
N-(1-methanesulfonylpiperidin-4-yl)-1-[5-(pyridin-4-yl)-1H-pyrazole-3-carbonyl]piperidine-4-carboxamide;
1-methyl-4-{1-[5-pyridin-4-yl)-1H-pyrazole-3-carbonyl]piperidine-4-carbonyl}piperazine;
N-[3-(dimethylamino)propyl]-1-[5-(pyridin-4-yl)-1H-pyrazole-3-carbonyl]piperidine-4-carboxamide:
N-(4-methoxycyclohexyl)-1-[5-(pyridin-4-yl)-1H-pyrazole-3-carbonyl]piperidine-4-carboxamide;
1-[5-(pyridin-4-yl)-1H-pyrazole-3-carbonyl]-N-[(1r,4r)-4-hydroxycyclohexyl]piperidine-4-carboxamide;
1-(2-methanesulfonylethyl)-4-{1-[5-(pyridin-4-yl)-1H-pyrazole-3-carbonyl]piperidine-4-carbonyl}piperazine;
N-(oxan-4-yl)-1-[5-(pyridin-4-yl)-1H-pyrazole-3-carbonyl]piperidine-4-carboxamide;
N-(4-methyloxan-4-yl)-1-[5-(pyridin-4-yl)-1H-pyrazole-3-carbonyl]piperidine-4-carboxamide;
4-{3-[4-(4-methylpiperidine-1-carbonyl)piperidine-1-carbonyl]-1H-pyrazol-5-yl}pyridine;
N-(4-chlorophenyl)-1-[5-(pyridin-4-yl)-1H-pyrazole-3-carbonyl]piperidine-3-carboxamide;
N-cyclopropyl-1-[5-(pyridin-4-yl)-1H-pyrazole-3-carbonyl]piperidine-4-carboxamide;
N-(4-methylphenyl)-1-[5-(pyridin-4-yl)-1H-pyrazole-3-carbonyl]piperidine-4-carboxamide;
N-cyclopropyl-1-[5-(pyridin-4-yl)-1H-pyrazole-3-carbonyl]piperidine-3-carboxamide;
N-(2,3-dihydro-1,4-benzodioxin-6-yl)-1-[5-(pyridin-4-yl)-1H-pyrazole-3-carbonyl]piperidine-3-carboxamide;
N-[(3-methylphenyl)methyl]-1-[5-(pyridin-4-yl)-1H-pyrazole-3-carbonyl]piperidine-3-carboxamide;
N-(2-phenylpropyl)-1-[5-(pyridin-4-yl)-1H-pyrazole-3-carbonyl]piperidine-3-carboxamide;
N-(3-chloro-4-methylphenyl)-1-[5-(pyridin-4-yl)-1H-pyrazole-3-carbonyl]piperidine-4-carboxamide;
N-[(2H-1,3-benzodioxol-5-yl)methyl]-1-[5-(pyridin-4-yl)-1H-pyrazole-3-carbonyl]piperidine-3-carboxamide;
4-{3-[4-(4-phenylpiperidine-1-carbonyl)piperidine-1-carbonyl]-1H-pyrazol-5-yl}pyridine;
N-[(3R)-1-benzylpyrrolidin-3-yl]-1-[5-(pyridin-4-yl)-1H-pyrazole-3-carbonyl]piperidine-4-carboxamide;
N-(4-chlorophenyl)-1-[5-(pyridin-4-yl)-1H-pyrazole-3-carbonyl]piperidine-4-carboxamide;
4-{3-[4-(piperidine-1-carbonyl)piperidine-1-carbonyl]-1H-pyrazol-5-yl}pyridine;
N-(4-methoxyphenyl)-1-[5-(pyridin-4-yl)-1H-pyrazole-3-carbonyl]piperidine-4-carboxamide;
N-cyclohexyl-1-[5-(pyridin-4-yl)-1H-pyrazole-3-carbonyl]piperidine-4-carboxamide;
1-[5-(5-chloro-2-methoxypyridin-4-yl)-1H-pyrazole-3-carbonyl]-N-[(oxan-2-yl)methyl]piperidine-4-carboxamide;
N-phenyl-1-[5-(pyridin-4-yl)-1H-pyrazole-3-carbonyl]piperidine-4-carboxamide;
1-[5-(5-chloro-2-methoxypyridin-4-yl)-1H-pyrazole-3-carbonyl]-N-[(1-hydroxycyclopropyl)methyl]piperidine-4-carboxamide;
N-cyclopentyl-1-[5-(pyridin-4-yl)-1H-pyrazole-3-carbonyl]piperidine-4-carboxamide;
N-[(1R)-1-(4-tert-butylphenyl)ethyl]-1-[5-(pyridin-4-yl)-1H-pyrazole-3-carbonyl]piperidine-4-carboxamide;
(1R,4S,5R*)—N-[(3-chlorophenyl)methyl]-2-[5-(5-fluoro-2-methoxypyridin-4-yl)-1H-pyrazole-3-carbonyl]-2-azabicyclo[2.2.2]octane-5-carboxamide;
N-(3-methylbutyl)-1-[5-(pyridin-4-yl)-1H-pyrazole-3-carbonyl]piperidine-4-carboxamide;
N-[(4,5-dimethyl-1,3-thiazol-2-yl)methyl]-1-[5-(pyridin-4-yl)-1H-pyrazole-3-carbonyl]piperidine-4-carboxamide;
N-[(2,5-dimethoxyphenyl)methyl]-1-[5-(pyridin-4-yl)-1H-pyrazole-3-carbonyl]piperidine-4-carboxamide;
1-[5-(5-chloro-2-methoxypyridin-4-yl)-1H-pyrazole-3-carbonyl]-N-[(pyridazin-3-yl)methyl]piperidine-4-carboxamide;
1-[5-(5-chloro-2-methoxypyridin-4-yl)-1H-pyrazole-3-carbonyl]-N-(5-oxopyrrolidin-3-yl)piperidine-4-carboxamide;
1-[5-(5-chloro-2-methoxypyridin-4-yl)-1H-pyrazole-3-carbonyl]-N-[(6-oxo-1,6-dihydropyrimidin-2-yl)methyl]piperidine-4-carboxamide;
N-(3-chlorophenyl)-1-[5-(pyridin-4-yl)-1H-pyrazole-3-carbonyl]piperidine-4-carboxamide;
N-[(2,3-dimethoxyphenyl)methyl]-1-[5-(pyridin-4-yl)-1H-pyrazole-3-carbonyl]piperidine-4-carboxamide;
N-[(4-cyclopropyl-1,3-thiazol-2-yl)methyl]-1-[5-(pyridin-4-yl)-1H-pyrazole-3-carbonyl]piperidine-4-carboxamide;
1-[5-(5-chloro-2-methoxypyridin-4-yl)-1H-pyrazole-3-carbonyl]-N-[(6-methoxypyridin-3-yl)methyl]piperidine-4-carboxamide;

(1S,4R,5R*)-2-[5-(5-fluoro-2-methoxypyridin-4-yl)-1H-pyrazole-3-carbonyl]-N-[(1r,4r)-4-hydroxy-4-(trifluoromethyl)cyclohexyl]-2-azabicyclo[2.2.1]heptane-5-carboxamide;

(7R*)-4-[5-(2-ethoxy-5-fluoropyridin-4-yl)-1H-pyrazole-3-carbonyl]-N-[(1r,4r)-4-methoxy-4-(trifluoromethyl)cyclohexyl]-4-azaspiro[2.5]octane-7-carboxamide;

(7R*)-4-[5-(2-ethoxy-5-fluoropyridin-4-yl)-1H-pyrazole-3-carbonyl]-N-[(1r,4r)-4-methoxy-4-(trifluoromethyl)cyclohexyl]-4-azaspiro[2.5]octane-7-carboxamide;

(7R*)-4-{5-[5-fluoro-2-(propan-2-yloxy)pyridin-4-yl]-1H-pyrazole-3-carbonyl}-N-[(1r,4r)-4-hydroxy-4-(trifluoromethyl)cyclohexyl]-4-azaspiro[2.5]octane-7-carboxamide;

(1R,5S,6S)—N-[(3-chiorophenyl)methyl]-3-[5-(5-fluoro-2-methoxypyridin-4-yl)-1H-pyrazole-3-carbonyl]-3-azabicyclo[3.1.0]hexane-6-carboxamide;

1-[5-(2-methoxypyridin-4-yl)-1H-pyrazole-3-carbonyl]-N-[(1r,4r)-4-methylcyclohexyl]piperidine-4-carboxamide;

7R*)-4-[5-(2-ethoxy-5-fluoropyridin-4-yl)-H-pyrazole-3-carbonyl]-N-[(1r,4r)-4-hydroxy-4-(trifluoromethyl)cyclohexyl]-4-azaspiro[2.5]octane-7-carboxamide;

(7R*)-4-[5-(2-ethoxy-5-fluoropyridin-4-yl)-1H-pyrazole-3-carbonyl]-N-[(1r,4r)-4-hydroxy-4-(trifluoromethyl)cyclohexyl]-4-azaspiro[2.5]octane-7-carboxamide;

1-[5-(5-chloro-2-methoxypyridin-4-yl)-1H-pyrazole-3-carbonyl]-N-(3,3-difluorocyclobutyl)piperidine-4-carboxamide;

1-[5-(5-chloro-2-methoxypyridin-4-yl)-1H-pyrazole-3-carbonyl]-N-[(1-methyl-5-oxopyrrolidin-3-yl)methyl]piperidine-4-carboxamide;

(2R,4r,6S)—N-{[(7S)-4-[5-(5-fluoro-2-methoxypyridin-4-yl)-1H-pyrazole-3-carbonyl]-4-azaspiro[2.5]octan-7-yl]methyl}-2,6-dimethylpiperidine-4-carboxamide;

1-[5-(5-chloro-2-methoxypyridin-4-yl)-1H-pyrazole-3-carbonyl]-N-{imidazo[1,2-a]pyridin-3-yl}piperidine-4-carboxamide;

1-[5-(5-chloro-2-methoxypyridin-4-yl)-1H-pyrazole-3-carbonyl]-N-(3,6-dimethylpyrazin-2-yl)piperidine-4-carboxamide;

1-[5-(5-chloro-2-methoxypyridin-4-yl)-1H-pyrazole-3-carbonyl]-N-[(1s,4s)-4-hydroxy-4-methylcyclohexyl]piperidine-4-carboxamide;

1-[5-(2-cyclopropoxypyridin-4-yl)-1H-pyrazole-3-carbonyl]-N-(4-methylcyclohexyl)piperidine-4-carboxamide;

1-[5-(5-chloro-2-methoxypyridin-4-yl)-1H-pyrazole-3-carbonyl]-N-[(6-oxo-1,6-dihydropyridin-3-yl)methyl]piperidine-4-carboxamide;

1-[5-(pyridin-4-yl)-1H-pyrazole-3-carbonyl]-N-[3-(trifluoromethyl)phenyl]piperidine-4-carboxamide;

1-[5-(5-chloro-2-methoxypyridin-4-yl)-1H-pyrazole-3-carbonyl]-N-[2-(3-chlorophenyl)propan-2-yl]piperidine-4-carboxamide;

N-[(2,6-dimethoxyphenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(1-methyl-1H-imidazol-4-yl)methyl]piperidine-4-carboxamide;

(1R,4S,5R*)-2-[5-(5-fluoro-2-methoxypyridin-4-yl)-H-pyrazole-3-carbonyl]-N-[(1r,4r)-4-hydroxy-4-(trifluoromethyl)cyclohexyl]-2-azabicyclo[2.2.1]heptane-5-carboxamide;

N-(1-phenylpiperidin-3-yl)-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(1s,4s)-4-hydroxy-4-(trifluoromethyl)cyclohexyl]piperidine-4-carboxamide;

1-[5-(5-chloro-2-methoxypyridin-4-yl)-1H-pyrazole-3-carbonyl]-N-({1-methyl-4-oxo-1H,4H,5H-pyrazolo[3,4-d]pyrimidin-6-yl}methyl)piperidine-4-carboxamide;

1-[5-(5-chloro-2-methoxypyridin-4-yl)-1H-pyrazole-3-carbonyl]-N-{[1-(dimethylamino)cyclopentyl]methyl}piperidine-4-carboxamide;

N-{[4-(tert-butoxy)phenyl]methyl}-1-[5-(pyridin-4-yl)-1H-pyrazole-3-carbonyl]piperidine-4-carboxamide;

(1R,4S)-2-[5-(5-fluoro-2-methoxypyridin-4-yl)-1H-pyrazole-3-carbonyl]-N-[(1r,4r)-4-hydroxy-4-(trifluoromethyl)cyclohexyl]-2-azabicyclo[2.2.1]heptane-5-carboxamide;

1-[5-(5-chloro-2-methoxypyridin-4-yl)-1H-pyrazole-3-carbonyl]-N-[(1r*,4r**)-4-hydroxy-4-methylcyclohexyl]piperidine-4-carboxamide;

1-[5-(5-chloro-2-methoxypyridin-4-yl)-1H-pyrazole-3-carbonyl]-N-[(pyrimidin-4-yl)methyl]piperidine-4-carboxamide;

N-[(4-methylthiophen-2-yl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-{2-oxabicyclo[2.1.1]hexan-4-yl}piperidine-4-carboxamide;

N-[4-(2-hydroxyethyl)cyclohexyl]-1-[5-(pyridin-4-yl)-1H-pyrazole-3-carbonyl]piperidine-4-carboxamide;

N-[(2S)-2-phenylpropyl]-1-[5-(pyridin-4-yl)-1H-pyrazole-3-carbonyl]piperidine-4-carboxamide;

N-(4-methylcyclohexyl)-1-[5-(pyridin-4-yl)-1H-pyrazole-3-carbonyl]piperidine-4-carboxamide;

(7R*)-4-(5-{5-[(1R)-1-hydroxyethyl]-2-methylpyridin-4-yl}-1H-pyrazole-3-carbonyl)-N-[(1r,4r)-4-hydroxy-4-(trifluoromethyl)cyclohexyl]-4-azaspiro[2.5]octane-7-carboxamide;

N-[(3-methoxyphenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(4-methylmorpholin-2-yl)methyl]piperidine-4-carboxamide;

7-[5-(5-chloro-2-methoxypyridin-4-yl)-1H-pyrazole-3-carbonyl]-N-[(3-chlorophenyl)methyl]-3-oxa-7-azabicyclo[3.3.1]nonane-9-carboxamide;

1-[5-(5-chloro-2-methoxypyridin-4-yl)-1H-pyrazole-3-carbonyl]-N-[(3-fluorooxetan-3-yl)methyl]piperidine-4-carboxamide;

N-[(4-methoxyphenyl)methyl]-1-[5-(pyridin-4-yl)-1H-pyrazole-3-carbonyl]piperidine-4-carboxamide;

(7S)-4-[5-(5-fluoro-2-methoxypyridin-4-yl)-1H-pyrazole-3-carbonyl]-N-{8-methyl-8-azabicyclo[3.2. 1]octan-2-yl}-4-azaspiro[2.5]octane-7-carboxamide;

1-[5-(5-chloro-2-methoxypyridin-4-yl)-1H-pyrazole-3-carbonyl]-N-[(pyrimidin-2-yl)methyl]piperidine-4-carboxamide:

1-[5-(5-chloro-2-methoxypyridin-4-yl)-1H-pyrazole-3-carbonyl]-N-(2,2-dimethyl-1,3-dioxan-5-yl)piperidine-4-carboxamide;

(7R*)-4-[5-(5-fluoro-2-methoxypyridin-4-yl)-1H-pyrazole-3-carbonyl]-N-[(4r,7r)-1-oxaspiro[3.5]nonan-7-yl]-4-azaspiro[2.5]octane-7-carboxamide;

N-[(3-chlorophenyl)methyl]-2-[5-(5-fluoro-2-methoxypyridin-4-yl)-1H-pyrazole-3-carbonyl]-2-azabicyclo[2.2.1]heptane-5-carboxamide;

1-[5-(2-cyanopyridin-4-yl)-1H-pyrazole-3-carbonyl]-N-(4-methylcyclohexyl)piperidine-4-carboxamide;

1-[5-(5-chloro-2-methoxypyridin-4-yl)-1H-pyrazole-3-carbonyl]-N-{1-methyl-2-oxabicyclo[2.2.1]heptan-4-yl}piperidine-4-carboxamide;

N-[(2-methoxy-3-methylphenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[2-(2-oxo-1,2-dihydropyridin-1-yl)ethyl]piperidine-4-carboxamide;

(1R,3S,5S)—N-(1,1-dioxo-1$\lambda^6$-thian-4-yl)-8-[5-(5-fluoro-2-methoxypyridin-4-yl)-1H-pyrazole-3-carbonyl]-8-azabicyclo[3.2.1]octane-3-carboxamide;

N-[(2H-1,3-benzodioxol-5-yl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-(5-methylpyrazin-2-yl)piperidine-4-carboxamide;

1-[5-(5-chloro-2-methoxypyridin-4-yl)-1H-pyrazole-3-carbonyl]-N-{1-methyl-2-oxabicyclo[2.1.1]hexan-4-yl}piperidine-4-carboxamide;

1-[5-(5-chloro-2-methoxypyridin-4-yl)-1H-pyrazole-3-carbonyl]-N-({imidazo[1,2-a]pyrimidin-6-yl}methyl)piperidine-4-carboxamide;

4-{5-[5-fluoro-2-(oxetan-3-yloxy)pyridin-4-yl]-1H-pyrazole-3-carbonyl}-N-[(1r,4r)-4-hydroxy-4-(trifluoromethyl)cyclohexyl]-4-azaspiro[2.5]octane-7-carboxamide;

N-[(3-chlorophenyl)methyl]-3-[5-(5-fluoro-2-methoxypyridin-4-yl)-1H-pyrazole-3-carbonyl]-3-azabicyclo[3.2.1]octane-8-carboxamide;

1-[5-(5-chloro-2-methoxypyridin-4-yl)-1H-pyrazole-3-carbonyl]-N-methyl-N-(4-methylcyclohexyl)piperidine-4-carboxamide;

1-[5-(5-chloro-2-methoxypyridin-4-yl)-1H-pyrazole-3-carbonyl]-N-[1-(pyrazin-2-yl)ethyl]piperidine-4-carboxamide;

1-[5-(5-fluoro-2-methoxypyridin-4-yl)-1H-pyrazole-3-carbonyl]-N-[(5s,8r*)-1-azaspiro[4.5]decan-8-yl]piperidine-4-carboxamide;

(7S)-4-[5-(5-fluoro-2-methoxypyridin-4-yl)-1H-pyrazole-3-carbonyl]-N-(1-imino-1-oxo-12-thian-4-yl)-4-azaspiro[2.5]octane-7-carboxamide;

1-[5-(5-chloro-2-methoxypyridin-4-yl)-1H-pyrazole-3-carbonyl]-N-[(3-chlorophenyl)methyl]-4-cyanopiperidine-4-carboxamide;

N-[(2-chlorophenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(1,4-dioxan-2-yl)methyl]piperidine-4-carboxamide;

N-(4-methylcyclohexyl)-1-{5-[2-(trifluoromethyl)pyridin-4-yl]-1H-pyrazole-3-carbonyl}piperidine-4-carboxamide;

N-(1-acetylpyrrolidin-3-yl)-1-[5-(5-chloro-2-methoxypyridin-4-yl)-1H-pyrazole-3-carbonyl]piperidine-4-carboxamide;

1-[5-(5-chloro-2-methoxypyridin-4-yl)-1H-pyrazole-3-carbonyl]-N-(3-hydroxypyrazin-2-yl)piperidine-4-carboxamide;

N-[(1S)-1-phenylethyl]-1-[5-(pyridin-4-yl)-1H-pyrazole-3-carbonyl]piperidine-4-carboxamide;

8-[5-(5-chloro-2-methoxypyridin-4-yl)-1-H-pyrazole-3-carbonyl]-N-[(3-chlorophenyl)methyl]-3-cyano-8-azabicyclo[3.2.1]octane-3-carboxamide;

N-(4,4-dimethylcyclohexyl)-1-[5-(2-methoxypyridin-4-yl)-1H-pyrazole-3-carbonyl]piperidine-4-carboxamide;

N-benzyl-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(1,3-dioxolan-2-yl)methyl]piperidine-4-carboxamide;

1-[5-(5-chloro-2-methoxypyridin-4-yl)-1H-pyrazole-3-carbonyl]-N-[(1,3-oxazol-5-yl)methyl]piperidine-4-carboxamide;

(1S,4R,5R*)-2-[5-(5-fluoro-2-methoxypyridin-4-yl)-1H-pyrazole-3-carbonyl]-N-[(1r,4r)-4-hydroxy-4-(trifluoromethyl)cyclohexyl]-2-azabicyclo[2.2.1]heptane-5-carboxamide;

(7S)-4-[5-(5-fluoro-2-methoxypyridin-4-yl)-1H-pyrazole-3-carbonyl]-N-[(1R,2R*,5R)-8-methyl-8-azabicyclo[3.2.1]octan-2-yl]-4-azaspiro[2.5]octane-7-carboxamide;

1-[5-(5-chloro-2-methoxypyridin-4-yl)-1H-pyrazole-3-carbonyl]-N-[(3-chlorophenyl)methyl]-4-methoxypiperidine-4-carboxamide;

1-[5-(5-chloro-2-methoxypyridin-4-yl)-1H-pyrazole-3-carbonyl]-N-[(2-methyl-1,3-dioxolan-2-yl)methyl]piperidine-4-carboxamide;

N-[(4-tert-butyl-1,3-thiazol-2-yl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-({3H-imidazo[4,5-b]pyridin-2-yl}methyl)piperidine-4-carboxamide;

(1R,3S,5S)-8-[5-(5-fluoro-2-methoxypyridin-4-yl)-1H-pyrazole-3-carbonyl]-N-methyl-N-[(1r*,4s)-4-hydroxy-4-(trifluoromethyl)cyclohexyl]-8-azabicyclo[3.2.1]octane-3-carboxamide;

N-(3-methylcyclohexyl)-1-[5-(pyridin-4-yl)-1H-pyrazole-3-carbonyl]piperidine-4-carboxamide;

N-[(2-methoxy-4,6-dimethylpyridin-3-yl)methyl]-1-[5-(pyridin-4-yl)-1H-pyrazole-3-carbonyl]piperidine-4-carboxamide;

N-[(2R)-2-phenylpropyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(4-hydroxyoxan-4-yl)methyl]piperidine-4-carboxamide;

(1R,5S,6R)—N-[(3-chlorophenyl)methyl]-3-[5-(5-fluoro-2-methoxypyridin-4-yl)-1H-pyrazole-3-carbonyl]-3-azabicyclo[3.1.0]hexane-6-carboxamide;

N-[(3-chloro-2-methoxyphenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[1-(pyrimidin-2-yl)ethyl]piperidine-4-carboxamide;

1-[5-(5-fluoro-2-methoxypyridin-4-yl)-1H-pyrazole-3-carbonyl]-N-(1-phenylcyclopropyl)piperidine-4-carboxamide;

N-[(2-fluorophenyl)methyl]-1-[5-(pyridin-4-yl)-1H-pyrazole-3-carbonyl]piperidine-4-carboxamide;

(1R,4S,5R*)—N-[(3-chlorophenyl)methyl]-2-[5-(5-fluoro-2-methoxypyridin-4-yl)-1H-pyrazole-3-carbonyl]-2-azabicyclo[2.2.2]octane-5-carboxamide;

N-[(2-methoxyphenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(1,2,4-oxadiazol-3-yl)methyl]piperidine-4-carboxamide;

(1R,3S,5S)-8-[5-(5-fluoro-2-methoxypyridin-4-yl)-1H-pyrazole-3-carbonyl]-N-methyl-N-[(1r*,4r)-4-hydroxy-4-(trifluoromethyl)cyclohexyl]-8-azabicyclo[3.2.1]octane-3-carboxamide;

1-[5-(5-chloro-2-methoxypyridin-4-yl)-1H-pyrazole-3-carbonyl]-N-({[1,2,4]triazolo[4,3-a]pyridin-6-yl}methyl)piperidine-4-carboxamide;

1-[5-(5-chloro-2-methoxypyridin-4-yl)-1H-pyrazole-3-carbonyl]-N-{3-fluorobicyclo[1.1.1]pentan-1-yl}piperidine-4-carboxamide;

rel-1-[5-(5-chloro-2-methoxypyridin-4-yl)-1H-pyrazole-3-carbonyl]-N-[(4r)-4-methoxy-4-methylcyclohexyl]piperidine-4-carboxamide;

1-[5-(5-chloro-2-methoxypyridin-4-yl)-1H-pyrazole-3-carbonyl]-N-[(1,3-oxazol-2-yl)methyl]piperidine-4-carboxamide;

1-[5-(5-chloro-2-methoxypyridin-4-yl)-1H-pyrazole-3-carbonyl]-N-[(1-hydroxycyclobutyl)methyl]piperidine-4-carboxamide;

1-[5-(5-chloro-2-methoxypyridin-4-yl)-1H-pyrazole-3-carbonyl]-N-[(4-cyanopyridin-2-yl)methyl]piperidine-4-carboxamide;

N-[(1S)-1-(4-methylphenyl)ethyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-(6-methylpyrazin-2-yl)piperidine-4-carboxamide;

1-[5-(5-chloro-2-methoxypyridin-4-yl)-1H-pyrazole-3-carbonyl]-N-[(8R)-5,6,7,8-tetrahydroquinolin-8-yl]piperidine-4-carboxamide;

1-[5-(5-chloro-2-methoxypyridin-4-yl)-1H-pyrazole-3-carbonyl]-N-[2-(trifluoromethyl)cyclopropyl]piperidine-4-carboxamide;

1-[5-(5-chloro-2-methoxypyridin-4-yl)-1H-pyrazole-3-carbonyl]-N-(1,1-dioxo-3,4-dihydro-2H-1$\lambda^6$-benzothiopyran-4-yl)piperidine-4-carboxamide;

(7R*)-4-{5-[5-fluoro-2-(propan-2-yloxy)pyridin-4-yl]-1H-pyrazole-3-carbonyl}-N-[(1r,4r)-4-hydroxy-4-(trifluoromethyl)cyclohexyl]-4-azaspiro[2.5]octane-7-carboxamide;

1-[5-(5-chloro-2-methoxypyridin-4-yl)-1H-pyrazole-3-carbonyl]-N-({[1,2,4]triazolo[4,3-a]pyridin-3-yl}methyl)piperidine-4-carboxamide;

1-[5-(5-chloro-2-methoxypyridin-4-yl)-1H-pyrazole-3-carbonyl]-N-cyclopropylpiperidine-4-carboxamide;

1-[5-(5-chloro-2-methoxypyridin-4-yl)-1H-pyrazole-3-carbonyl]-N-[(1,3-dioxan-2-yl)methyl]piperidine-4-carboxamide;

1-[5-(2-cyclopropylpyridin-4-yl)-1H-pyrazole-3-carbonyl]-N-(4-methylcyclohexyl)piperidine-4-carboxamide;

1-[5-(5-chloro-2-methoxypyridin-4-yl)-1H-pyrazole-3-carbonyl]-N-[(5-methyl-1,2,4-oxadiazol-3-yl)methyl]piperidine-4-carboxamide;

1-[5-(5-fluoro-2-methoxypyridin-4-yl)-1H-pyrazole-3-carbonyl]-N-{4-hydroxybicyclo[2.2.1]heptan-1-yl} piperidine-4-carboxamide;

1-[5-(5-chloro-2-methoxypyridin-4-yl)-1H-pyrazole-3-carbonyl]-N-(cinnolin-4-yl)piperidine-4-carboxamide;

1-[5-(5-chloro-2-methoxypyridin-4-yl)-1H-pyrazole-3-carbonyl]-N-(4-methyloxan-4-yl)piperidine-4-carboxamide;

1-[5-(5-chloro-2-methoxypyridin-4-yl)-1H-pyrazole-3-carbonyl]-N-[(4,6-dimethyl-2-oxo-1,2-dihydropyridin-3-yl)methyl]piperidine-4-carboxamide;

N-[(1S)-1-phenylpropyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-(2,2-dioxo-3,4-dihydro-1H-2$\lambda^6$-benzothiopyran-4-yl)piperidine-4-carboxamide;

N-(2-phenylethyl)-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(1-methyl-1H-pyrazol-3-yl)methyl]piperidine-4-carboxamide;

1-[5-(5-chloro-2-methoxypyridin-4-yl)-1H-pyrazole-3-carbonyl]-N-[(3-methyloxetan-3-yl)methyl]piperidine-4-carboxamide;

(1R,5S,8R*)—N-[(3-chlorophenyl)methyl]-3-[5-(5-fluoro-2-methoxypyridin-4-yl)-1H-pyrazole-3-carbonyl]-3-azabicyclo[3.2.1]octane-8-carboxamide;

(7R)-4-[5-(5-fluoro-2-methoxypyridin-4-yl)-1H-pyrazole-3-carbonyl]-N-[(3RS,6R)-1-methyl-6-(trifluoromethyl)piperidin-3-yl]-4-azaspiro[2.5]octane-7-carboxamide;

1-[5-(5-chloro-2-methoxypyridin-4-yl)-1H-pyrazole-3-carbonyl]-N-[1-(3-chlorophenyl)cyclopropyl]piperidine-4-carboxamide;

N-(1-cyclobutylethyl)-1-[5-(5-fluoro-2-methoxypyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(4,4-difluoro-5-oxopyrrolidin-2-yl)methyl]piperidine-4-carboxamide;

1-[5-(pyridin-4-yl)-1H-pyrazole-3-carbonyl]-N-[(1r,4s)-4-ethylcyclohexyl]piperidine-4-carboxamide;

1-[5-(5-chloro-2-methoxypyridin-4-yl)-1H-pyrazole-3-carbonyl]-N-(2-phenylpropan-2-yl)piperidine-4-carboxamide;

N-[(2-methoxy-5-methylphenyl)methyl]-1-[5-(pyridin-4-yl)-1H-pyrazole-3-carbonyl]piperidine-4-carboxamide;

(7S)-4-[5-(5-fluoro-2-methoxypyridin-4-yl)-1H-pyrazole-3-carbonyl]-N-{[(1s,4s)-2-(2-fluoro-2-methylpropyl)-2-azabicyclo[2.1.1]hexan-1-yl]methyl}-4-azaspiro[2.5]octane-7-carboxamide;

1-[5-(5-chloro-2-methoxypyridin-4-yl)-1H-pyrazole-3-carbonyl]-N-[(4-fluoropyridin-2-yl)methyl]piperidine-4-carboxamide;

1-[5-(5-chloro-2-methoxypyridin-4-yl)-1H-pyrazole-3-carbonyl]-N-[4-(trifluoromethyl)pyridin-2-yl]piperidine-4-carboxamide;

1-[5-(5-fluoro-2-methoxypyridin-4-yl)-1H-pyrazole-3-carbonyl]-N-(oxan-2-yl)piperidine-4-carboxamide;

N-[(4-chlorophenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-({imidazo[1,2-a]pyridin-7-yl}methyl)piperidine-4-carboxamide;

7-[5-(5-fluoro-2-methoxypyridin-4-yl)-1H-pyrazole-3-carbonyl]-N-[(1r,4r)-4-hydroxy-4-(trifluoromethyl)cyclohexyl]-7-azaspiro[3.5]nonane-2-carboxamide;

1-[5-(5-chloro-2-methoxypyridin-4-yl)-1H-pyrazole-3-carbonyl]-N-[(2R,4R)-2-methyl-3,4-dihydro-2H-1-benzopyran-4-yl]piperidine-4-carboxamide;

1-[5-(5-chloro-2-methoxypyridin-4-yl)-1H-pyrazole-3-carbonyl]-N-(4-cyanocyclohexyl)piperidine-4-carboxamide;

1-[5-(5-chloro-2-methoxypyridin-4-yl)-1H-pyrazole-3-carbonyl]-N-({[1,2,4]triazolo[1,5-a]pyridin-6-yl}methyl)piperidine-4-carboxamide;

1-[5-(5-chloro-2-methoxypyridin-4-yl)-1H-pyrazole-3-carbonyl]-N-(6-fluoro-1,1-dioxo-3,4-dihydro-2H-1$\lambda^6$-benzothiopyran-4-yl)piperidine-4-carboxamide;

1-[5-(pyridin-4-yl)-1H-pyrazole-3-carbonyl]-N-[(1s,4s)-4-methylcyclohexyl]piperidine-4-carboxamide;

(7R*)—N-[(3aR,7aS)-1-methyl-octahydro-1H-indol-5-yl]-4-[5-(5-fluoro-2-methoxypyridin-4-yl)-1H-pyrazole-3-carbonyl]-4-azaspiro[2.5]octane-7-carboxamide;

1-[5-(5-chloro-2-methoxypyridin-4-yl)-1H-pyrazole-3-carbonyl]-N-(1,3-dioxan-5-yl)piperidine-4-carboxamide;

N-(4-phenylcyclohexyl)-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[5-(propan-2-yl)-1,3-thiazol-2-yl]piperidine-4-carboxamide;

(7S)-4-[5-(5-fluoro-2-methoxypyridin-4-yl)-1H-pyrazole-3-carbonyl]-N-[(1R,2R*,5R)-8-methyl-8-azabicyclo[3.2.1]octan-2-yl]-4-azaspiro[2.5]octane-7-carboxamide;

1-[5-(5-chloro-2-methoxypyridin-4-yl)-1H-pyrazole-3-carbonyl]-N-[(1,2-oxazol-3-yl)methyl]piperidine-4-carboxamide;

N-[(4,5-dimethylthiophen-2-yl)methyl]-1-[5-(pyridin-4-yl)-1H-pyrazole-3-carbonyl]piperidine-4-carboxamide;

(7R)-4-[5-(5-fluoro-2-methoxypyridin-4-yl)-1H-pyrazole-3-carbonyl]-N-(1-imino-1-oxo-1λ$^6$-thian-4-yl)-4-azaspiro[2.5]octane-7-carboxamide;

N-[(4-tert-butylphenyl)methyl]-1-[5-(pyridin-4-yl)-1H-pyrazole-3-carbonyl]piperidine-4-carboxamide;

(1R,3S,5S)-8-[5-(5-fluoro-2-methoxypyridin-4-yl)-1H-pyrazole-3-carbonyl]-N-[4-(trifluoromethyl)bicyclo[2.2.2]octan-1-yl]-8-azabicyclo[3.2.1]octane-3-carboxamide;

N-[(2,5-dichlorophenyl)methyl]-1-[5-(pyridin-4-yl)-1H-pyrazole-3-carbonyl]piperidine-4-carboxamide;

(1S,4R,5R*)—N-[(3-chlorophenyl)methyl]-2-[5-(5-fluoro-2-methoxypyridin-4-yl)-1H-pyrazole-3-carbonyl]-2-azabicyclo[2.2.1]heptane-5-carboxamide;

N-[(3-chlorophenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(6-methylpyridin-3-yl)methyl]piperidine-4-carboxamide;

(7S)—N-[(3R,4S)-4-fluoro-1-(6-methylpyridin-3-yl)pyrrolidin-3-yl]-4-[5-(5-fluoro-2-methoxypyridin-4-yl)-1H-pyrazole-3-carbonyl]-4-azaspiro[2.5]octane-7-carboxamide;

1-[5-(5-chloro-2-methoxypyridin-4-yl)-1H-pyrazole-3-carbonyl]-N-(4-ethyl-4-hydroxycyclohexyl)piperidine-4-carboxamide;

1-[5-(2-methoxy-3-methylpyridin-4-yl)-1H-pyrazole-3-carbonyl]-N-(4-methylcyclohexyl)piperidine-4-carboxamide;

1-[5-(5-chloro-2-methoxypyridin-4-yl)-1H-pyrazole-3-carbonyl]-N-[(6-cyanopyridin-3-yl)methyl]piperidine-4-carboxamide;

1-[5-(5-chloro-2-methoxypyridin-4-yl)-1H-pyrazole-3-carbonyl]-N-(3,3-difluoro-1-methylcyclobutyl)piperidine-4-carboxamide;

N-[(4-chloro-2-methoxyphenyl)methyl]-1-[5-(pyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(3-chiorophenyl)methyl]-3,3-difluoropiperidine-4-carboxamide;

rel-(1R,5R)-2-[5-(5-chloro-2-methoxypyridin-4-yl)-1H-pyrazole-3-carbonyl]-N-[(3-chlorophenyl)methyl]-2-azabicyclo[3.1.0]hexane-5-carboxamide;

1-[5-(5-chloro-2-methoxypyridin-4-yl)-1H-pyrazole-3-carbonyl]-N-[(2-methyloxolan-2-yl)methyl]piperidine-4-carboxamide;

1-[5-(5-chloro-2-methoxypyridin-4-yl)-1H-pyrazole-3-carbonyl]-N-[(1,3-dioxan-4-yl)methyl]piperidine-4-carboxamide;

1-[5-(5-chloro-2-methoxypyridin-4-yl)-1H-pyrazole-3-carbonyl]-N-[(8S)-5,6,7,8-tetrahydroquinolin-8-yl]piperidine-4-carboxamide;

1-[5-(5-chloro-2-methoxypyridin-4-yl)-1H-pyrazole-3-carbonyl]-N-[1-(i-methyl-1H-pyrazol-4-yl)ethyl]piperidine-4-carboxamide;

1-[5-(3-fluoropyridin-4-yl)-1H-pyrazole-3-carbonyl]-N-(4-methylcyclohexyl)piperidine-4-carboxamide;

1-[5-(5-chloro-2-methoxypyridin-4-yl)-1H-pyrazole-3-carbonyl]-N-({2,3-dimethylimidazo[1,2-a]pyridin-7-yl}methyl)piperidine-4-carboxamide;

1-[5-(5-chloro-2-methoxypyridin-4-yl)-1H-pyrazole-3-carbonyl]-N-[(3,3-dimethyloxetan-2-yl)methyl]piperidine-4-carboxamide;

1-[5-(3-cyanopyridin-4-yl)-1H-pyrazole-3-carbonyl]-N-(4-methylcyclohexyl)piperidine-4-carboxamide;

N-{bicyclo[1.1.1]pentan-1-yl}-1-[5-(5-chloro-2-methoxypyridin-4-yl)-1H-pyrazole-3-carbonyl]piperidine-4-carboxamide;

1-[5-(5-chloro-2-methoxypyridin-4-yl)-1H-pyrazole-3-carbonyl]-N-[(3-methyloxolan-3-yl)methyl]piperidine-4-carboxamide;

rel-1-[5-(5-chloro-2-methoxypyridin-4-yl)-1H-pyrazole-3-carbonyl]-N-[(4r)-4-methoxy-4-methylcyclohexyl]piperidine-4-carboxamide;

1-[5-(5-fluoro-2-methoxypyridin-4-yl)-1H-pyrazole-3-carbonyl]-N-[(5r,8r*)-1-azaspiro[4.5]decan-8-yl]piperidine-4-carboxamide;

1-[5-(5-chloro-2-methoxypyridin-4-yl)-1H-pyrazole-3-carbonyl]-N-({5,7-dimethyl-2-oxo-1H,2H-pyrazolo[1,5-a]pyrimidin-6-yl}methyl)piperidine-4-carboxamide;

1-[5-(5-fluoro-2-methoxypyridin-4-yl)-1H-pyrazole-3-carbonyl]-N-(2-methyl-1,3-dioxan-5-yl)piperidine-4-carboxamide;

1-[5-(5-chloro-2-methoxypyridin-4-yl)-1H-pyrazole-3-carbonyl]-N-(4-fluoro-1,2-benzoxazol-3-yl)piperidine-4-carboxamide;

1-[5-(5-chloro-2-methoxypyridin-4-yl)-1H-pyrazole-3-carbonyl]-N-[(oxolan-2-yl)methyl]piperidine-4-carboxamide;

N-(4-methylcyclohexyl)-1-[5-(pyrimidin-4-yl)-1H-pyrazole-3-carbonyl]piperidine-4-carboxamide;

1-[5-(5-chloro-2-methoxypyridin-4-yl)-1H-pyrazole-3-carbonyl]-N-(2-oxo-1,2,5,6,7,8-hexahydroquinolin-5-yl)piperidine-4-carboxamide;

1-[5-(5-chloro-2-methoxypyridin-4-yl)-1H-pyrazole-3-carbonyl]-N-(2-hydroxy-2,3-dihydro-1H-inden-1-yl)piperidine-4-carboxamide;

(1R,3R,5S)—N-[(1r,4r)-4-hydroxy-4-(trifluoromethyl)cyclohexyl]-8-{5-[3-(trifluoromethyl)pyridin-4-yl]-1H-pyrazole-3-carbonyl}-8-azabicyclo[3.2.1]octane-3-carboxamide;

N-[(5-chloro-2-methoxyphenyl)methyl]-1-[5-(pyridin-4-yl)-1H-pyrazole-3-carbonyl]piperidine-4-carboxamide;

3-[5-(5-chloro-2-methoxypyridin-4-yl)-1H-pyrazole-3-carbonyl]-N-[(3-chlorophenyl)methyl]-3-azabicyclo[4.1.0]heptane-6-carboxamide;

1-[5-(5-chloro-2-methoxypyridin-4-yl)-1H-pyrazole-3-carbonyl]-N-[(oxan-3-yl)methyl]piperidine-4-carboxamide;

1-[5-(5-chloro-2-methoxypyridin-4-yl)-1H-pyrazole-3-carbonyl]-N-{[5-(difluoromethyl)pyrimidin-2-yl]methyl}piperidine-4-carboxamide;

1-[5-(5-chloro-2-methoxypyridin-4-yl)-1H-pyrazole-3-carbonyl]-N-[(1,3,5-trimethyl-1H-pyrazol-4-yl)methyl]piperidine-4-carboxamide; and 1-[5-(5-chloro-2-methoxypyridin-4-yl)-1H-pyrazole-3-carbonyl]-N-[(4R)-5,8-difluoro-3,4-dihydro-2H-1-benzopyran-4-yl]piperidine-4-carboxamide.

In the compounds having a TR-FRET $AC_{50}$ greater than 1000 nM, the chirality of the stereocenters labeled with an asterisk ("*") was not determined.

What is claimed is:

1. A compound of Formula (I)

Formula (I)

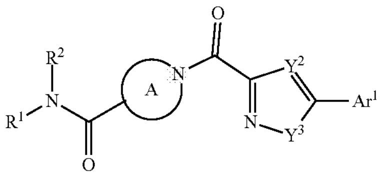

or a pharmaceutically acceptable salt thereof, wherein:

$Ar^1$ is chosen from

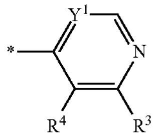 and 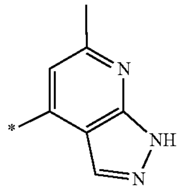

wherein $Y^1$ is chosen from N and C—$X^1$ wherein $X^1$ is chosen from hydrogen, hydroxyl, halogen, and $C_1$-$C_4$ alkyl;

$R^3$ is chosen from hydrogen, optionally substituted alkyl, optionally substituted amine, halogen, cyano, and optionally substituted alkoxy; and $R^4$ is chosen from hydrogen and optionally substituted alkyl;

either $Y^2$ is chosen from C—$X^2$ and N and $Y^3$ is NH, or $Y^2$ is N and $Y^3$ is $C(X^2)_2$, wherein each $X^2$ is independently chosen from hydrogen and halogen;

Ring A is chosen from

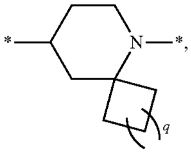, 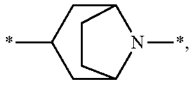, and

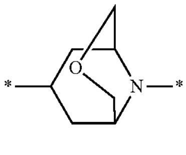

wherein q is 0 or 1;

$R^1$ is chosen from $-(CHR^5)_k-(CR^6R^7)_n-(O)_m$-Ring B, wherein k is 0 or 1, n is 0 or 1, m is 0 or 1, $R^5$ is chosen from hydrogen and optionally substituted alkyl, $R^6$ is chosen from hydrogen and halogen, $R^7$ chosen from hydrogen and halogen, and Ring B is chosen from optionally substituted aryl,
optionally substituted heteroaryl,
optionally substituted cycloalkyl,
optionally substituted heterocycloalkyl,
optionally substituted cycloalkenyl, and
optionally substituted heterocycloalkenyl; and $R^2$ is chosen from hydrogen and optionally substituted alkyl.

2. The compound or pharmaceutically acceptable salt according to claim 1, wherein Ring B is chosen from optionally substituted 5- to 10-membered aryl,
optionally substituted 5- to 10-membered heteroaryl,
optionally substituted 3- to 10-membered cycloalkyl,
optionally substituted 4- to 10-membered heterocycloalkyl,
optionally substituted 6- to 10-membered cycloalkenyl, and
optionally substituted 6- to 10-membered heterocycloalkenyl.

3. The compound or pharmaceutically acceptable salt according to claim 1, wherein Ring B is chosen from optionally substituted 5- to 6-membered monocyclic aryl, optionally substituted 10-membered bicyclic aryl, optionally substituted 5- to 6-membered monocyclic heteroaryl, optionally substituted 9- to 10-membered bicyclic heteroaryl, optionally substituted 3- to 10-membered monocyclic alkyl, optionally substituted 7- to 10-membered bridged bicyclic alkyl, optionally substituted 7- to 10-membered spirocyclic bicyclic alkyl, optionally substituted 4- to 10-membered monocyclic heterocycloalkyl, optionally substituted 7- to 10-membered bridged bicyclic heterocycloalkyl, optionally substituted 7- to 10-membered spirocyclic bicyclic heterocycloalkyl, optionally substituted 5- to 6-membered monocyclic cycloalkenyl, optionally substituted 8- to 10-membered bicyclic cycloalkenyl, optionally substituted 5- to 6-membered monocyclic heterocycloalkenyl, and optionally substituted 8- to 10-membered bicyclic heterocycloalkenyl.

4. The compound or pharmaceutically acceptable salt according to claim 1, wherein Ring B is chosen from optionally substituted 5- to 6-membered monocyclic aryl, optionally substituted 10-membered bicyclic aryl, optionally substituted 5- to 6-membered monocyclic heteroaryl having one to three ring heteroatoms chosen from oxygen and nitrogen, optionally substituted 9- to 10-membered bicyclic heteroaryl having one to three ring heteroatoms chosen from oxygen and nitrogen, optionally substituted 3- to 10-membered monocyclic alkyl, optionally substituted 7- to 10-membered bridged bicyclic alkyl, optionally substituted 7- to 10-membered spirocyclic bicyclic alkyl, optionally substituted 4- to 10-membered monocyclic heterocycloalkyl having one to three ring heteroatoms chosen from oxygen, silicon, and nitrogen, optionally substituted 7- to 10-membered bridged bicyclic heterocycloalkyl having one to three ring heteroatoms chosen from oxygen and nitrogen, optionally substituted 7- to 10-membered spirocyclic bicyclic heterocycloalkyl having one to three ring heteroatoms chosen from oxygen and nitrogen, optionally substituted 5- to 6-membered monocyclic cycloalkenyl, optionally substituted 8- to 10-membered bicyclic cycloalkenyl, optionally substituted 5- to 6-membered monocyclic heterocycloalkenyl having one to three ring heteroatoms chosen from oxygen and nitrogen, and optionally substituted 8- to 10-membered bicyclic heterocycloalkenyl having one to three ring heteroatoms chosen from oxygen and nitrogen.

5. The compound or pharmaceutically acceptable salt thereof according to claim 1, wherein the compound is chosen from compounds of Formulae (III)-(V):

Formula (III)

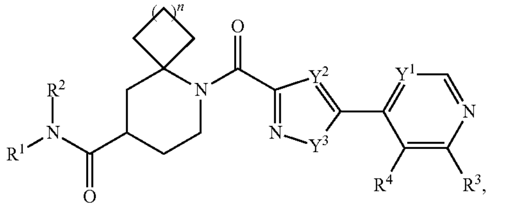

Formula (IV)

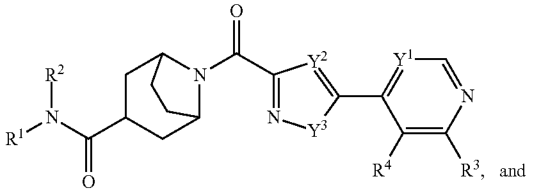

and

Formula (V)

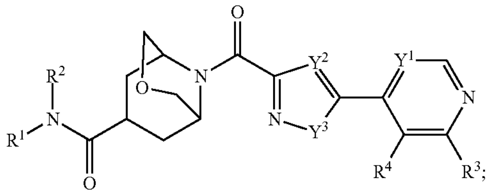

wherein:

$Y^1$ is chosen from N and C—$X^1$ wherein $X^1$ is chosen from hydrogen, hydroxyl, halogen, and $C_1$-$C_4$ alkyl;

$R^3$ is chosen from hydrogen, optionally substituted alkyl, optionally substituted amine, halogen, cyano, and optionally substituted alkoxy;

$R^4$ is chosen from hydrogen and alkyl; and either $Y^2$ is chosen from C—$X^2$ and N and $Y^3$ is NH, or $Y^2$ is N and $Y^3$ is $C(X^2)_2$, wherein each $X^2$ is independently chosen from hydrogen and halogen;

q is 0 or 1;

$R^1$ is chosen from —$(CHR^5)_k$—$(CR^6R^7)_n$—$(O)_m$-Ring B, wherein k is 0 or 1, n is 0 or 1, m is 0 or 1, $R^5$ is chosen from hydrogen and optionally substituted alkyl, $R^6$ is chosen from hydrogen and halogen, $R^7$ chosen from hydrogen and halogen, and Ring B is chosen from optionally substituted 5- to 6-membered monocyclic aryl, optionally substituted 10-membered bicyclic aryl, optionally substituted 5- to 6-membered monocyclic heteroaryl having one to three ring heteroatoms chosen from oxygen and nitrogen, optionally substituted 9- to 10-membered bicyclic heteroaryl having one to three ring heteroatoms chosen from oxygen and nitrogen, optionally substituted 3- to 10-membered monocyclic alkyl, optionally substituted 7- to 10-membered bridged bicyclic alkyl, optionally substituted 7- to 10-membered spirocyclic bicyclic alkyl, optionally substituted 4- to 10-membered monocyclic heterocycloalkyl having one to three ring heteroatoms chosen from oxygen, silicon, and nitrogen, optionally substituted 7- to 10-membered bridged bicyclic heterocycloalkyl having one to three ring heteroatoms chosen from oxygen and nitrogen, optionally substituted 7- to 10-membered spirocyclic bicyclic heterocycloalkyl having one to three ring heteroatoms chosen from oxygen and nitrogen, optionally substituted 5- to 6-membered monocyclic cycloalkenyl, optionally substituted 8- to 10-membered bicyclic cycloalkenyl, optionally substituted 5- to 6-membered monocyclic heterocycloalkenyl having one to three ring heteroatoms chosen from oxygen and nitrogen, and optionally substituted 8- to 10-membered bicyclic heterocycloalkenyl having one to three ring heteroatoms chosen from oxygen and nitrogen; and $R^2$ is chosen from hydrogen and optionally substituted alkyl.

6. The compound or pharmaceutically acceptable salt according to claim 1, wherein Ring B is chosen from

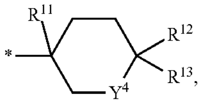

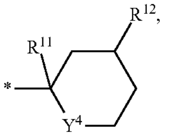

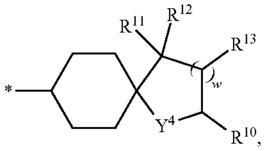

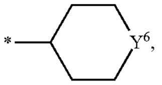

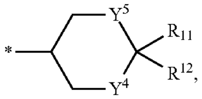

and

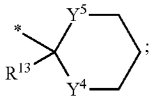

wherein:

w is 0 or 1;

$Y^4$ and $Y^5$ are each independently chosen from optionally substituted —$(CH_2)$—, optionally substituted —(NH)—, and —O—;

$Y^6$ is chosen from optionally substituted —$(CH_2)$—, optionally substituted —(NH)—, tetraalkylsilane, and —O—;

$R^{10}$ is chosen from hydrogen, halogen, optionally substituted alkyl, and carbonyl; and $R^{11}$, $R^{12}$, and $R^{13}$ are each independently chosen from hydrogen, halogen, optionally substituted alkyl, hydroxyl, optionally substituted amine, and optionally substituted alkoxy.

7. The compound or pharmaceutically acceptable salt according to claim 1, wherein Ring B is chosen from

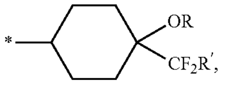

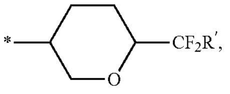

-continued

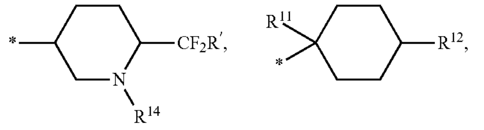

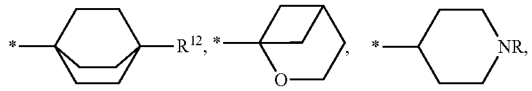

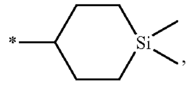

and

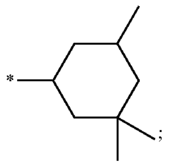

wherein

R11 and R12 are each independently chosen from hydrogen, halogen, optionally substituted alkyl, hydroxyl, optionally substituted amine, and optionally substituted alkoxy;

R14 is chosen from hydrogen and optionally substituted alkyl;

R is chosen from hydrogen, optionally substituted alkyl, and aryl; and

R' is chosen from hydrogen, optionally substituted alkyl, and halogen.

8. The compound or pharmaceutically acceptable salt according to claim 1, wherein Ring B is chosen from

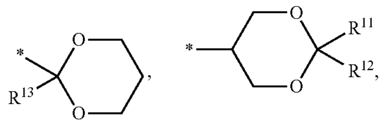

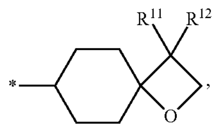

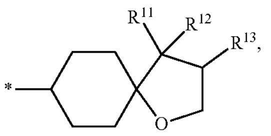

and

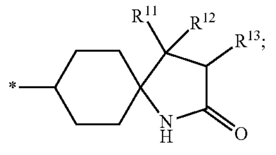

wherein $R^{11}$, $R^{12}$, and $R^{13}$ are each independently chosen from hydrogen, halogens, hydroxyl, optionally substituted alkyls, optionally substituted amines, and optionally substituted alkoxys.

9. The compound or pharmaceutically acceptable salt according to claim 1, wherein Ring B is chosen from

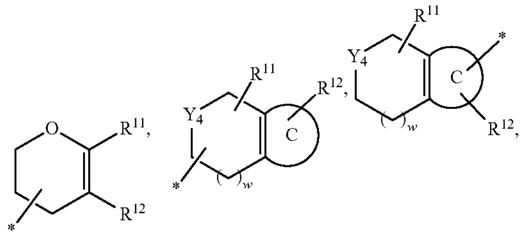

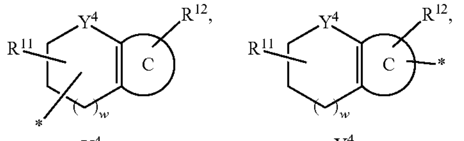

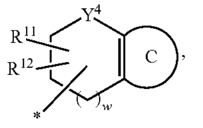

and

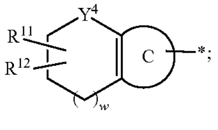

wherein w is 0 or 1, $Y^4$ is chosen from $SO_2$, optionally substituted sulfonamides, optionally substituted amides, optionally substituted $-(CH_2)-$, optionally substituted $-(NH)-$, and $-O-$;

$R^{11}$ and $R^{12}$ are each independently chosen from hydrogen, halogens, optionally substituted alkyls, hydroxyl, optionally substituted amines, and optionally substituted alkoxys; and Ring C is chosen from 5-membered aromatic rings, 5-membered heteroaromatic rings comprising 1 or 2 ring nitrogen atoms, 6-membered aromatic rings, and 6-membered heteroaromatic rings comprising 1 or 2 ring nitrogen atoms.

10. The compound or pharmaceutically acceptable salt according to claim 1, wherein Ring B is chosen from

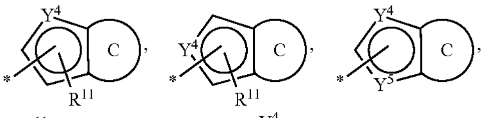

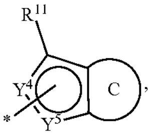

and

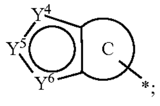

wherein $Y^4$, $Y^5$, and $Y^6$ are each independently chosen from optionally substituted $-(CH)-$, optionally substituted $-(NH)-$, and $-O-$;

$R^{11}$ is chosen from hydrogen, halogens, optionally substituted alkyls, hydroxyl, optionally substituted amines, and optionally substituted alkoxys; and Ring C is chosen from 5-membered aromatic rings, 5-membered heteroaromatic rings comprising 1 or 2 ring nitrogen atoms, 6-membered aromatic rings, and 6-membered heteroaromatic rings comprising 1 or 2 ring nitrogen atoms.

11. The compound or pharmaceutically acceptable salt according to claim 1, wherein Ring B is chosen from

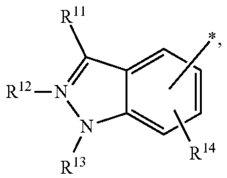
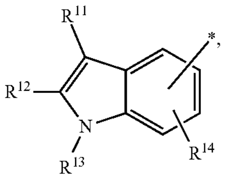
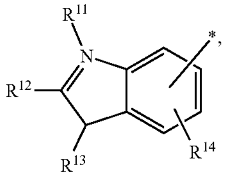
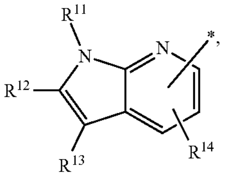
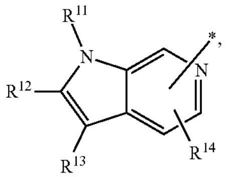
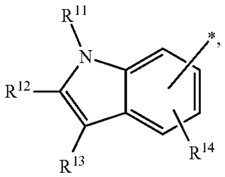
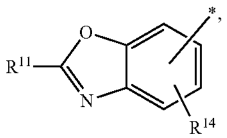
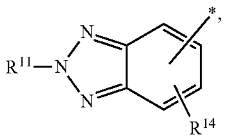
and
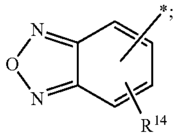

wherein when $R^{11}$ is not bonded to nitrogen, $R^{11}$ is chosen from hydrogen, halogens, optionally substituted alkyls, and hydroxyl, and $R^{11}$ is otherwise chosen from hydrogen and optionally substituted alkyls;

when $R^{12}$ is not bonded to nitrogen, $R^{12}$ is chosen from hydrogen, halogens, optionally substituted alkyls, and hydroxyl, and $R^{12}$ is otherwise chosen from hydrogen, and optionally substituted alkyls;

when $R^{13}$ is not bonded to nitrogen, $R^{13}$ is chosen from hydrogen, halogens, optionally substituted alkyls, and hydroxyl, and $R^{13}$ is otherwise chosen from hydrogen, and optionally substituted alkyls; and $R^{14}$ is chosen from hydrogen, halogens, optionally substituted alkyls, hydroxyl, optionally substituted amines, and optionally substituted alkoxys.

12. The compound or pharmaceutically acceptable salt according to claim 1, wherein Ring B is chosen from

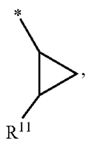
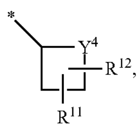
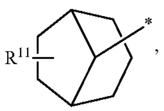

-continued

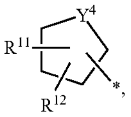
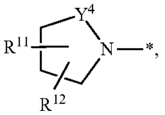
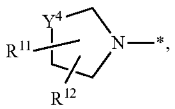
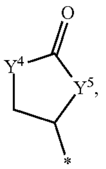
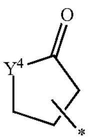
,
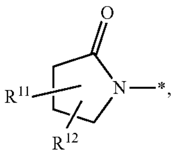
and
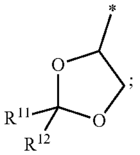

wherein $Y^4$, and $Y^5$ are each independently chosen from optionally substituted —$(CH_2)$—, optionally substituted —(NH)—, and —O—; and $R^{11}$ and $R^{12}$ are independently chosen from hydrogen, cyano, halogens, optionally substituted alkyls, hydroxyl, optionally substituted amines, aryl, heteroaryl, and optionally substituted alkoxys.

13. The compound or pharmaceutically acceptable salt according to claim 1, wherein Ring B is chosen from

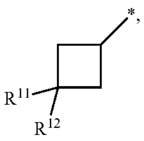
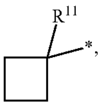
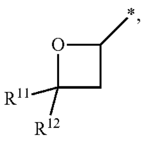
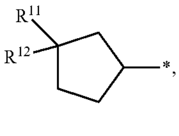
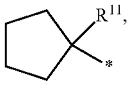
and
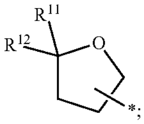

wherein $R^{11}$ and $R^{12}$ independently are chosen from hydrogen, halogens, optionally substituted alkyls, hydroxyl, optionally substituted amines, and optionally substituted alkoxys.

14. The compound or pharmaceutically acceptable salt according to claim 1, wherein Ring B is chosen

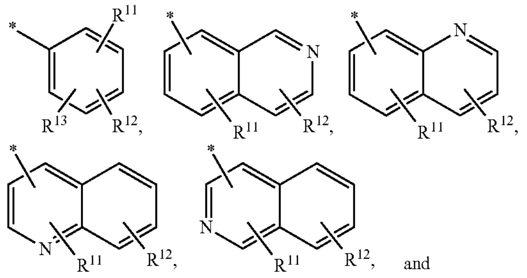

and

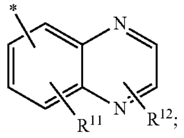

wherein $R^{11}$, $R^{12}$, and $R^{13}$ are independently chosen from hydrogen, halogens, optionally substituted alkyls, hydroxyl, optionally substituted amines, and optionally substituted alkoxys.

15. The compound or pharmaceutically acceptable salt according to claim 1, wherein Ring B is chosen from

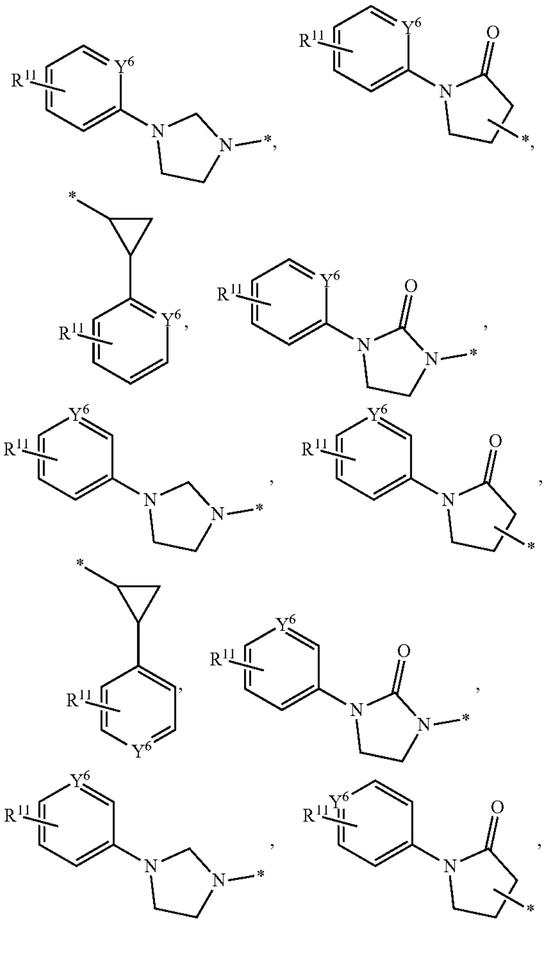

-continued

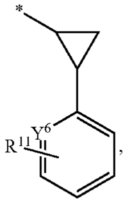

, and

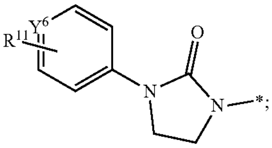

wherein $Y^6$ is chosen from optionally substituted —(CH)— and optionally substituted —(NH)—, and $R^{11}$ is chosen from hydrogen, halogens, optionally substituted alkyls, hydroxyl, optionally substituted amines, and optionally substituted alkoxys.

16. The compound or pharmaceutically acceptable salt according to claim 1, wherein Ring B is chosen from

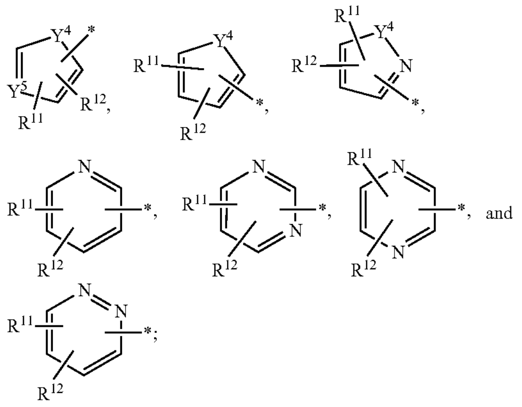

wherein $Y^4$ is chosen from optionally substituted —$(CH_2)$—, optionally substituted —(NH)—, and —O—;

$Y^5$ is chosen from optionally substituted —(CH)— and N; and $R^{11}$ and $R^{12}$ are chosen from hydrogen, halogens, optionally substituted alkyls, hydroxyl, optionally substituted amines, and optionally substituted alkoxys.

17. The compound or pharmaceutically acceptable salt according to claim 1, wherein Ring B is chosen from

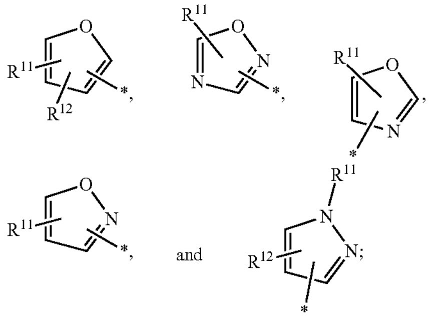

wherein $R^{11}$ and $R^{12}$ are chosen from hydrogen, halogens, optionally substituted alkyls, hydroxyl, optionally substituted amines, and optionally substituted alkoxys.

18. The compound or pharmaceutically acceptable salt according to claim 1, wherein Ring B is chosen from

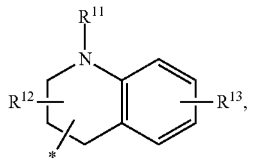
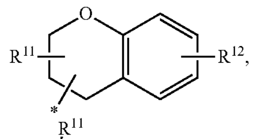
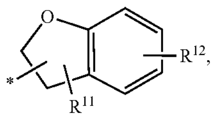
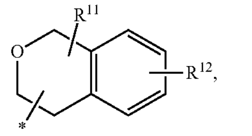
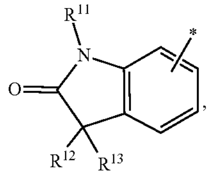
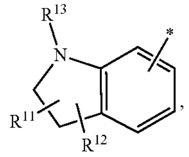
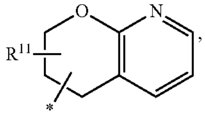
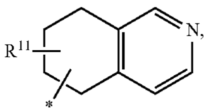
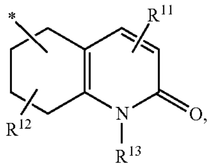
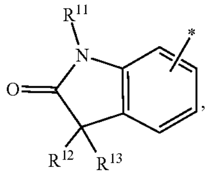
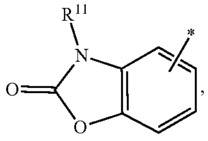
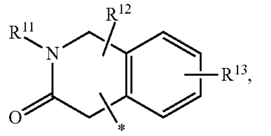
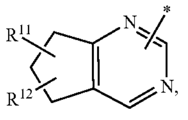
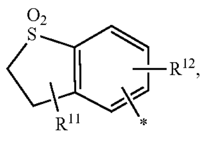
and
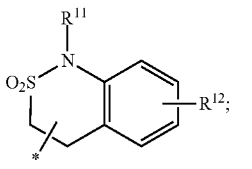

wherein $R^{11}$, $R^{12}$, and $R^{13}$ are independently chosen from hydrogen, halogens, optionally substituted alkyls, hydroxyl, optionally substituted amines, and optionally substituted alkoxys.

19. The compound or pharmaceutically acceptable salt according to claim 1, wherein $R^1$ is chosen from $—(CHR^5)_k—(CR^6R^7)_n—(O)_m$-Ring B, wherein k is 0 or 1, n is 0 or 1, m is 0 or 1, $R^5$ is chosen from hydrogen and methyl, $R^6$ is chosen from hydrogen and halogens, $R^7$ chosen from hydrogen and halogens; and $R^2$ is chosen from hydrogen and methyl.

20. A compound chosen from:

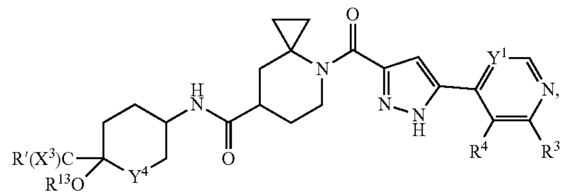
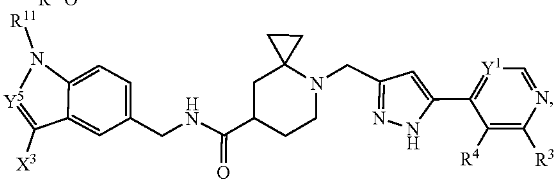
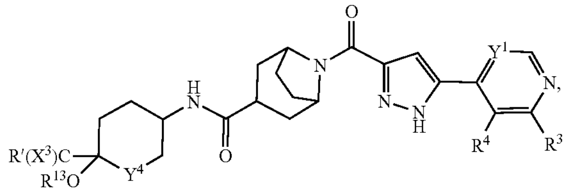
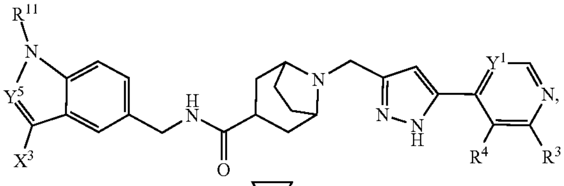
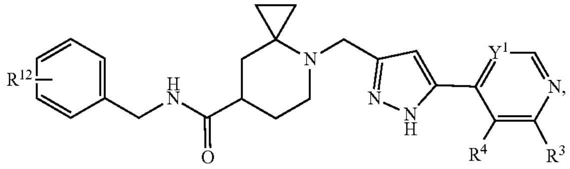
and
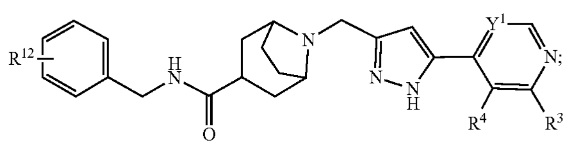

or a pharmaceutically acceptable salt thereof, wherein $Y^1$ is chosen from N and $C—X^1$ wherein $X^1$ is chosen from hydrogen, hydroxyl, halogen, and $C_1$-$C_4$ alkyl;

$R^3$ is chosen from hydrogen, optionally substituted $C_1$-$C_3$ alkyl, halogen, cyano, and optionally substituted $C_1$-$C_3$ alkoxy; and $R^4$ is chosen from hydrogen and alkyl;

$Y^4$ is chosen from $CH_2$, O, and $N—R^{11}$;

$X^3$ is chosen from hydrogen and halogen;

R' is chosen from hydrogen and $C_1$-$C_3$ alkyl optionally substituted with at least one halogen;

$R^{11}$ is chosen from hydrogen and $C_1$-$C_3$ alkyl;

$R^{12}$ is chosen from hydrogen, halogen, and $C_1$-$C_3$ alkyl; and $R^{13}$ is chosen from hydrogen, halogen, $C_2$-$C_4$ alkoxy, and $C_1$-$C_3$ alkyls.

21. A compound chosen from:

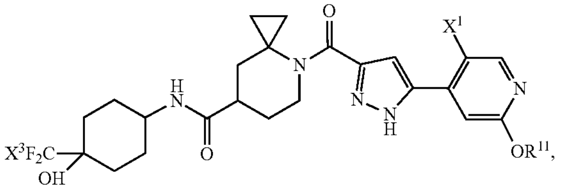,

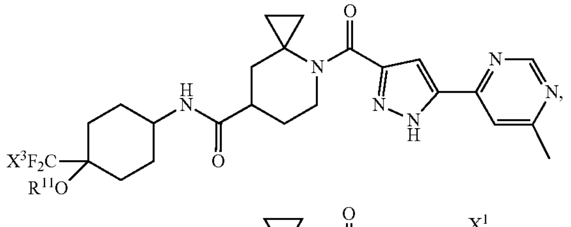,

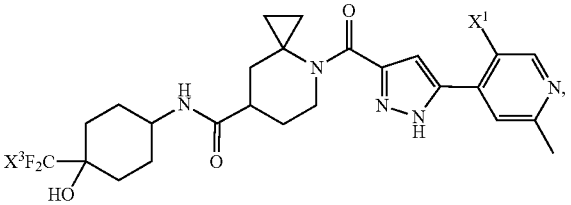,

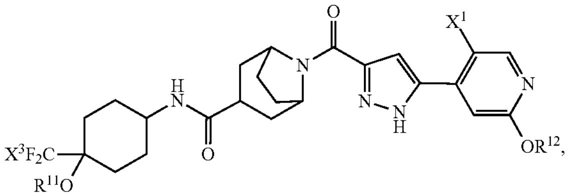,

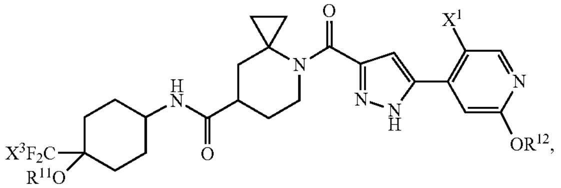,

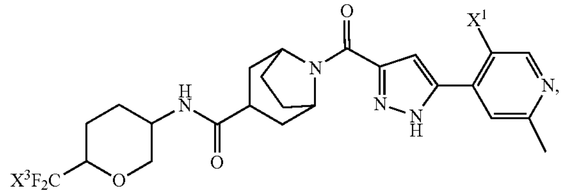,

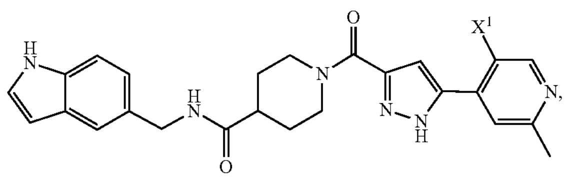,

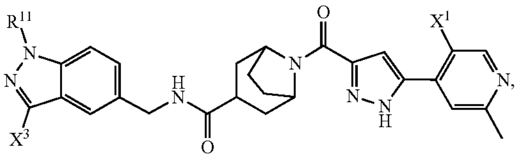 and

-continued

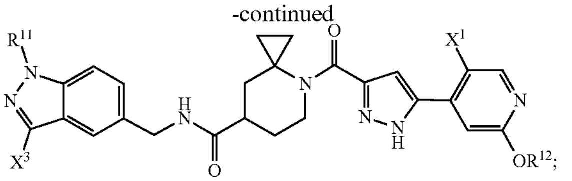;

or a pharmaceutically acceptable salt thereof, wherein $X^1$ is chosen from hydrogen, hydroxyl, halogen, and $C_1$-$C_4$ alkyl;

$X^3$ is chosen from hydrogen and halogen; and $R^{11}$ and $R^{12}$ are independently chosen from hydrogen and $C_1$-$C_3$ alkyl.

22. The compound or pharmaceutically acceptable salt according to claim 6, wherein $R^{10}$, $R^{11}$, $R^{12}$, or $R^{13}$ is chosen from optionally substituted alkyl and the optionally substituted alkyl is chosen from haloalkyl.

23. The compound or pharmaceutically acceptable salt according to claim 22, wherein the haloalkyl is trifluoromethyl.

24. At least one compound chosen from:

1-(5-(5-chloro-2-methoxypyridin-4-yl)-1H-pyrazole-3-carbonyl)-N-((1s,4s)-4-methylcyclohexyl)piperidine-4-carboxamide;

1-(5-(5-chloro-2-methoxypyridin-4-yl)-1H-pyrazole-3-carbonyl)-N-((1r,4r)-4-methylcyclohexyl)piperidine-4-carboxamide;

1-(4-fluoro-5-(2-methoxypyridin-4-yl)-1H-pyrazole-3-carbonyl)-N-(4-methylcyclohexyl)piperidine-4-carboxamide;

(S)-1-(5-(5-chloro-2-methoxypyridin-4-yl)-1H-pyrazole-3-carbonyl)-N-(1-(3-fluorophenyl)ethyl)piperidine-4-carboxamide;

N-((1s,4s)-4-(difluoromethyl)cyclohexyl)-1-(5-(5-fluoro-2-methoxypyridin-4-yl)-1H-pyrazole-3-carbonyl)piperidine-4-carboxamide;

N-((1r,4r)-4-(difluoromethyl)cyclohexyl)-1-(5-(5-fluoro-2-methoxypyridin-4-yl)-1H-pyrazole-3-carbonyl)piperidine-4-carboxamide;

1-(5-(2-methoxypyridin-4-yl)-1H-pyrazole-3-carbonyl)-N-(4-methylcyclohexyl)piperidine-4-carboxamide;

N-(4-methylcyclohexyl)-1-[5-(2-methylpyridin-4-yl)-1H-pyrazole-3-carbonyl]piperidine-4-carboxamide;

1-(5-(2-methoxypyridin-4-yl)-1H-pyrazole-3-carbonyl)-N-((1s,4s)-4-methylcyclohexyl)piperidine-4-carboxamide;

N-((1s,4s)-4-ethylcyclohexyl)-1-(5-(2-methoxypyridin-4-yl)-1H-pyrazole-3-carbonyl)piperidine-4-carboxamide;

N-((1r,4r)-4-ethylcyclohexyl)-1-(5-(2-methoxypyridin-4-yl)-1H-pyrazole-3-carbonyl)piperidine-4-carboxamide;

1-(5-(3-chloropyridin-4-yl)-1H-pyrazole-3-carbonyl)-N-(4-methylcyclohexyl)piperidine-4-carboxamide;

1-[4-chloro-5-(2-methoxypyridin-4-yl)-1H-pyrazole-3-carbonyl]-N-[(1s,4s)-4-methylcyclohexyl]piperidine-4-carboxamide;

1-[4-chloro-5-(2-methoxypyridin-4-yl)-1H-pyrazole-3-carbonyl]-N-[(1s,4s)-4-methylcyclohexyl]piperidine-4-carboxamide;

1-[5-(6-methoxypyrimidin-4-yl)-1H-pyrazole-3-carbonyl]-N-[(1r,4r)-4-methylcyclohexyl]piperidine-4-carboxamide;

1-[5-(6-methoxypyrimidin-4-yl)-1H-pyrazole-3-carbonyl]-N-[(1s,4s)-4-methylcyclohexyl]piperidine-4-carboxamide;

1-[5-(5-chloro-2-methoxypyridin-4-yl)-1H-pyrazole-3-carbonyl]-N-[(3-chlorophenyl)methyl]piperidine-4-carboxamide;

N-((1s,4s)-4-(difluoromethyl)cyclohexyl)-1-(5-(2-methoxypyridin-4-yl)-1H-pyrazole-3-carbonyl)piperidine-4-carboxamide;

N-((1r,4r)-4-(difluoromethyl)cyclohexyl)-1-(5-(2-methoxypyridin-4-yl)-1H-pyrazole-3-carbonyl)piperidine-4-carboxamide;

1-(5-(5-fluoro-2-methoxypyridin-4-yl)-1H-pyrazole-3-carbonyl)-N-((1s,4s)-4-methylcyclohexyl)piperidine-4-carboxamide;

1-(5-(5-fluoro-2-methoxypyridin-4-yl)-1H-pyrazole-3-carbonyl)-N-((1r,4r)-4-methylcyclohexyl)piperidine-4-carboxamide;

(R)-1-[5-(5-chloro-2-methoxypyridin-4-yl)-1H-pyrazole-3-carbonyl]-N-[1-(3-chlorophenyl)ethyl]piperidine-4-carboxamide;

(S)-1-[5-(5-chloro-2-methoxypyridin-4-yl)-1H-pyrazole-3-carbonyl]-N-[1-(3-chlorophenyl)ethyl]piperidine-4-carboxamide;

1-[5-(5-chloro-2-methoxypyridin-4-yl)-1H-pyrazole-3-carbonyl]-N-(1-phenylpyrrolidin-3-yl)piperidine-4-carboxamide;

1-[5-(5-chloro-2-methoxypyridin-4-yl)-1H-pyrazole-3-carbonyl]-N-[(1s,4s)-4-(trifluoromethyl)cyclohexyl] piperidine-4-carboxamide;

1-[5-(5-chloro-2-methoxypyridin-4-yl)-1H-pyrazole-3-carbonyl]-N-[(1r,4r)-4-(trifluoromethyl)cyclohexyl]piperidine-4-carboxamide;

1-(5-(5-chloro-2-methoxypyridin-4-yl)-1H-pyrazole-3-carbonyl)-N-(imidazo[1,2-a]pyridin-2-ylmethyl)piperidine-4-carboxamide;

1-(5-(5-chloro-2-methoxypyridin-4-yl)-1H-pyrazole-3-carbonyl)-N-((5-chloropyridin-2-yl)methyl)piperidine-4-carboxamide;

1-[5-(5-Chloro-2-methoxypyridin-4-yl)-1H-pyrazole-3-carbonyl]-N-(2-methyl-1,3-dioxan-5-yl) piperidine-4-carboxamide;

N-((1H-indol-5-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(2,3,6-trifluorobenzyl)piperidine-4-carboxamide;

1-(5-(5-chloro-2-methoxypyridin-4-yl)-1H-pyrazole-3-carbonyl)-N-((1,3-dimethyl-1H-pyrazol-4-yl)methyl) piperidine-4-carboxamide;

1-(5-(5-chloro-2-methoxypyridin-4-yl)-1H-pyrazole-3-carbonyl)-N-(2-chloro-5-fluorobenzyl)piperidine-4-carboxamide;

1-(5-(5-chloro-2-methoxypyridin-4-yl)-1H-pyrazole-3-carbonyl)-N-(1-(2,2,2-trifluoroethyl)-1H-pyrazol-4-yl) piperidine-4-carboxamide;

1-(5-(5-chloro-2-methoxypyridin-4-yl)-1H-pyrazole-3-carbonyl)-N-((5-fluoropyridin-2-yl)methyl)piperidine-4-carboxamide;

1-(5-(5-chloro-2-methoxypyridin-4-yl)-1H-pyrazole-3-carbonyl)-N-(1-cyanocyclobutyl)piperidine-4-carboxamide;

1-(5-(5-chloro-2-methoxypyridin-4-yl)-1H-pyrazole-3-carbonyl)-N-((6-(trifluoromethyl)pyridin-2-yl)methyl) piperidine-4-carboxamide;

1-(5-(5-chloro-2-methoxypyridin-4-yl)-1H-pyrazole-3-carbonyl)-N-((3-(trifluoromethyl)pyridin-2-yl)methyl) piperidine-4-carboxamide;

1-(5-(5-chloro-2-methoxypyridin-4-yl)-1H-pyrazole-3-carbonyl)-N-((4-methylpyridin-3-yl)methyl)piperidine-4-carboxamide;

1-(5-(5-chloro-2-methoxypyridin-4-yl)-1H-pyrazole-3-carbonyl)-N-(isochroman-4-yl)piperidine-4-carboxamide;

1-(5-(5-chloro-2-methoxypyridin-4-yl)-1H-pyrazole-3-carbonyl)-N-((1R,2S)-2-phenylcyclopropyl)piperidine-4-carboxamide;

1-(5-(5-chloro-2-methoxypyridin-4-yl)-1H-pyrazole-3-carbonyl)-N-((1-hydroxycyclohexyl)methyl)piperidine-4-carboxamide;

1-(5-(5-chloro-2-methoxypyridin-4-yl)-1H-pyrazole-3-carbonyl)-N-((4,4-dimethyloxetan-2-yl)methyl)piperidine-4-carboxamide;

1-(5-(5-chloro-2-methoxypyridin-4-yl)-1H-pyrazole-3-carbonyl)-N-((2-methyloxazol-5-yl)methyl)piperidine-4-carboxamide;

1-(5-(5-chloro-2-methoxypyridin-4-yl)-1H-pyrazole-3-carbonyl)-N-(pyrazolo[1,5-a]pyridin-7-ylmethyl)piperidine-4-carboxamide;

1-(5-(5-chloro-2-methoxypyridin-4-yl)-1H-pyrazole-3-carbonyl)-N-((5-chloropyrimidin-2-yl)methyl)piperidine-4-carboxamide;

1-(5-(5-chloro-2-methoxypyridin-4-yl)-1H-pyrazole-3-carbonyl)-N-((5-(trifluoromethyl)pyridin-2-yl)methyl) piperidine-4-carboxamide;

1-(5-(5-chloro-2-methoxypyridin-4-yl)-1H-pyrazole-3-carbonyl)-N-((3-chloropyridin-2-yl)methyl)piperidine-4-carboxamide;

1-(5-(5-chloro-2-methoxypyridin-4-yl)-1H-pyrazole-3-carbonyl)-N-((1,5-dimethyl-1H-pyrazol-3-yl)methyl) piperidine-4-carboxamide;

1-(5-(5-chloro-2-methoxypyridin-4-yl)-1H-pyrazole-3-carbonyl)-N-(1-(4-chlorophenoxy)propan-2-yl)piperidine-4-carboxamide;

1-(5-(5-chloro-2-methoxypyridin-4-yl)-1H-pyrazole-3-carbonyl)-N-(3,3-difluorocyclohexyl)piperidine-4-carboxamide;

1-(5-(5-chloro-2-methoxypyridin-4-yl)-1H-pyrazole-3-carbonyl)-N-(4-hydroxy-4-(trifluoromethyl)cyclohexyl)piperidine-4-carboxamide;

1-(5-(5-chloro-2-methoxypyridin-4-yl)-1H-pyrazole-3-carbonyl)-N-((3-methoxycyclobutyl)methyl)piperidine-4-carboxamide;

1-(5-(5-chloro-2-methoxypyridin-4-yl)-1H-pyrazole-3-carbonyl)-N-((3-fluoropyridin-2-yl)methyl)piperidine-4-carboxamide;

1-(5-(5-chloro-2-methoxypyridin-4-yl)-1H-pyrazole-3-carbonyl)-N-(3-(difluoromethyl)phenyl)piperidine-4-carboxamide;

1-(5-(5-chloro-2-methoxypyridin-4-yl)-1H-pyrazole-3-carbonyl)-N-((3,3-difluorocyclobutyl)methyl)piperidine-4-carboxamide;

1-(5-(5-chloro-2-methoxypyridin-4-yl)-1H-pyrazole-3-carbonyl)-N-(2,2-difluoro-2-phenylethyl)piperidine-4-carboxamide;

1-(5-(5-chloro-2-methoxypyridin-4-yl)-1H-pyrazole-3-carbonyl)-N-(3,3,5-trimethylcyclohexyl)piperidine-4-carboxamide;

1-(5-(5-chloro-2-methoxypyridin-4-yl)-1H-pyrazole-3-carbonyl)-N-(4-(difluoromethoxy)benzyl)piperidine-4-carboxamide;

N-(benzo[d]oxazol-6-ylmethyl)-1-(5-(5-chloro-2-methoxypyridin-4-yl)-1H-pyrazole-3-carbonyl)piperidine-4-carboxamide;

(R)-1-(5-(5-chloro-2-methoxypyridin-4-yl)-1H-pyrazole-3-carbonyl)-N-(1-(3-fluorophenyl)ethyl)piperidine-4-carboxamide;

N-(5-chloro-2-fluorobenzyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(2,3-difluorobenzyl)piperidine-4-carboxamide;

N-(3-chloro-2-fluorobenzyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(3-fluorobenzyl)piperidine-4-carboxamide;

1-(5-(5-chloro-2-methoxypyridin-4-yl)-1H-pyrazole-3-carbonyl)-N-((3,4-dihydro-2H-pyran-2-yl)methyl)piperidine-4-carboxamide;

N-(3-chlorobenzyl)-1-(5-(5-fluoro-2-methoxypyridin-4-yl)-1H-pyrazole-3-carbonyl)piperidine-4-carboxamide;

(1R,3s,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide;

(1R,3r,5S)—N-(3-chlorobenzyl)-8-(5-(5-fluoro-2-methoxypyridin-4-yl)-1H-pyrazole-3-carbonyl)-8-azabicyclo[3.2.1]octane-3-carboxamide;

N-(3-chlorobenzyl)-1-(5-(5-fluoro-2-methoxypyridin-4-yl)-1H-pyrazole-3-carbonyl)-N-methylpiperidine-4-carboxamide;

1-(5-(5-chloro-2-methoxypyridin-4-yl)-1H-pyrazole-3-carbonyl)-N-(1-(trifluoromethyl)cyclopentyl)piperidine-4-carboxamide;

1-(5-(5-chloro-2-methoxypyridin-4-yl)-1H-pyrazole-3-carbonyl)-N-(1,4-dimethylcyclohexyl)piperidine-4-carboxamide;

1-(5-(5-chloro-2-methoxypyridin-4-yl)-1H-pyrazole-3-carbonyl)-N-(4-(trifluoromethoxy)benzyl)piperidine-4-carboxamide;

N-(bicyclo[3.2.1]octan-8-yl)-1-(5-(5-fluoro-2-methoxypyridin-4-yl)-1H-pyrazole-3-carbonyl)piperidine-4-carboxamide;

N-[(3-chlorophenyl)methyl]-1-[5-(5-fluoro-2-methoxypyridin-4-yl)-1H-1,2,4-triazole-3-carbonyl]piperidine-4-carboxamide;

1-(5-(5-chloro-2-methoxypyridin-4-yl)-1H-pyrazole-3-carbonyl)-N-((2-oxoindolin-5-yl)methyl)piperidine-4-carboxamide;

N-((1H-pyrrolo[2,3-b]pyridin-5-yl)methyl)-1-(5-(5-chloro-2-methoxypyridin-4-yl)-1H-pyrazole-3-carbonyl)piperidine-4-carboxamide;

(R)-4-(5-(5-fluoro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(1R,3s,5S)-8-(5-(5-fluoro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide;

1-(5-(5-chloro-2-methoxypyridin-4-yl)-1H-pyrazole-3-carbonyl)-N-(3-chlorobenzyl)-4-hydroxypiperidine-4-carboxamide;

1-(5-(5-chloro-2-methoxypyridin-4-yl)-1H-pyrazole-3-carbonyl)-N-(3-chlorobenzyl)-2-methylpiperidine-4-carboxamide;

1-(5-(5-chloro-2-methoxypyridin-4-yl)-1H-pyrazole-3-carbonyl)-N-(3-chlorobenzyl)-3-methylpiperidine-4-carboxamide;

1-(5-(5-chloro-2-methoxypyridin-4-yl)-1H-pyrazole-3-carbonyl)-N-(3-chlorobenzyl)-4-fluoropiperidine-4-carboxamide;

1-(5-(5-chloro-2-methoxypyridin-4-yl)-1H-pyrazole-3-carbonyl)-N-(3,3-difluorocyclopentyl)piperidine-4-carboxamide;

1-(5-(5-chloro-2-methoxypyridin-4-yl)-1H-pyrazole-3-carbonyl)-N-((5-methylpyridin-2-yl)methyl)piperidine-4-carboxamide;

1-(5-(5-chloro-2-methoxypyridin-4-yl)-1H-pyrazole-3-carbonyl)-N-(3-chlorobenzyl)-3-fluoropiperidine-4-carboxamide;

1-(5-(5-chloro-2-methoxypyridin-4-yl)-1H-pyrazole-3-carbonyl)-N-((6-(trifluoro-15-methyl)pyridin-3-yl)methyl)piperidine-4-carboxamide;

1-(5-(5-chloro-2-methoxypyridin-4-yl)-1H-pyrazole-3-carbonyl)-N-((5-chloropyridin-3-yl)methyl)piperidine-4-carboxamide;

N-((1H-indazol-6-yl)methyl)-1-(5-(5-chloro-2-methoxypyridin-4-yl)-1H-pyrazole-3-carbonyl)piperidine-4-carboxamide;

N-((1H-indol-3-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(isoquinolin-6-ylmethyl)piperidine-4-carboxamide;

1-(5-(5-chloro-2-methoxypyridin-4-yl)-1H-pyrazole-3-carbonyl)-N-(5-oxo-1-phenylpyrrolidin-3-yl)piperidine-4-carboxamide;

1-(5-(5-chloro-2-methoxypyridin-4-yl)-1H-pyrazole-3-carbonyl)-N-(chroman-4-yl)piperidine-4-carboxamide;

1-(5-(5-chloro-2-methoxypyridin-4-yl)-1H-pyrazole-3-carbonyl)-N-((2,2-dimethyl-1,3-dioxolan-4-yl)methyl)piperidine-4-carboxamide;

1-(5-(5-chloro-2-methoxypyridin-4-yl)-1H-pyrazole-3-carbonyl)-N-(1-methyl-1,2,3,4-tetrahydroquinolin-4-yl)piperidine-4-carboxamide;

1-(5-(5-chloro-2-methoxypyridin-4-yl)-1H-pyrazole-3-carbonyl)-N-((1-methyl-1H-indol-3-yl)methyl)piperidine-4-carboxamide;

N-((1H-indol-6-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((5-methylfuran-2-yl)methyl)piperidine-4-carboxamide;

N-((1H-indol-4-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(5,6,7,8-tetrahydroisoquinolin-5-yl)piperidine-4-carboxamide;

N-((1H-indazol-4-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((3-chloro-5-(trifluoromethyl)pyridin-2-yl)methyl)piperidine-4-carboxamide;

N-((1H-indol-7-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(6-fluorochroman-4-yl)piperidine-4-carboxamide;

1-(5-(5-chloro-2-methoxypyridin-4-yl)-1H-pyrazole-3-carbonyl)-N-(1-phenylpiperidin-4-yl)piperidine-4-carboxamide;

N-((2H-benzo[d][1,2,3]triazol-5-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((1r,4r)-4-hydroxy-4-methylcyclohexyl)piperidine-4-carboxamide;

1-(5-(5-chloro-2-methoxypyridin-4-yl)-1H-pyrazole-3-carbonyl)-N-((1r,4r)-4-hydroxy-4-(trifluoromethyl)cyclohexyl)piperidine-4-carboxamide;

N-((3-fluoro-1H-indazol-5-yl)methyl)-1-(5-(5-fluoro-2-methoxypyridin-4-yl)-1H-pyrazole-3-carbonyl)piperidine-4-carboxamide;

N-((1H-indazol-3-yl)methyl)-1-(5-(5-chloro-2-methoxypyridin-4-yl)-1H-pyrazole-3-carbonyl)piperidine-4-carboxamide;

N-((1H-pyrrolo[2,3-b]pyridin-3-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((2-methyl-1H-indol-5-yl)methyl)piperidine-4-carboxamide;

1-[5-(5-fluoro-2-methoxypyridin-4-yl)-1H-pyrazole-3-carbonyl]-N-[(3-methyl-1H-indazol-5-yl)methyl]piperidine-4-carboxamide;

1-(5-(5-chloro-2-methoxypyridin-4-yl)-1H-pyrazole-3-carbonyl)-N-(1-isopropyl-1H-pyrazol-4-yl)piperidine-4-carboxamide;

1-(5-(5-chloro-2-methoxypyridin-4-yl)-1H-pyrazole-3-carbonyl)-N-((1-methyl-1H-indol-5-yl)methyl)piperidine-4-carboxamide;

1-(5-(5-chloro-2-methoxypyridin-4-yl)-1H-pyrazole-3-carbonyl)-N-(2-oxo-1-phenylpyrrolidin-3-yl)piperidine-4-carboxamide;

N-(5-chloro-2,3-dihydrobenzofuran-3-yl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-((4-(trifluoromethyl)pyrimidin-2-yl)methyl)piperidine-4-carboxamide;

1-(5-(5-chloro-2-methoxypyridin-4-yl)-1H-pyrazole-3-carbonyl)-N-((5-methylimidazo[1,2-a]pyridin-2-yl)methyl)piperidine-4-carboxamide;

1-(5-(5-chloro-2-methoxypyridin-4-yl)-1H-pyrazole-3-carbonyl)-N-((5-(trifluoromethyl)pyrimidin-2-yl)methyl)piperidine-4-carboxamide;

N-((1H-pyrrolo[2,3-c]pyridin-5-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(5,5-dimethyltetrahydrofuran-3-yl)piperidine-4-carboxamide;

1-(5-(5-chloro-2-methoxypyridin-4-yl)-1H-pyrazole-3-carbonyl)-N-((8-fluoroimidazo[1,2-a]pyridin-2-yl)methyl)piperidine-4-carboxamide;

1-(5-(5-chloro-2-methoxypyridin-4-yl)-1H-pyrazole-3-carbonyl)-N-((2-methyl-1H-benzo[d]imidazol-5-yl)methyl)piperidine-4-carboxamide;

1-(5-(5-chloro-2-methoxypyridin-4-yl)-1H-pyrazole-3-carbonyl)-N-((2-methyl-1,3-dioxan-2-yl)methyl)piperidine-4-carboxamide;

1-(5-(5-chloro-2-methoxypyridin-4-yl)-1H-pyrazole-3-carbonyl)-N-((6-methylimidazo[1,2-a]pyridin-2-yl)methyl)piperidine-4-carboxamide;

1-(5-(5-chloro-2-methoxypyridin-4-yl)-1H-pyrazole-3-carbonyl)-N-((1-methyl-1H-indazol-3-yl)methyl)piperidine-4-carboxamide;

1-(5-(5-chloro-2-methoxypyridin-4-yl)-1H-pyrazole-3-carbonyl)-N-((6-chloroimidazo[1,2-a]pyridin-2-yl)methyl)piperidine-4-carboxamide;

1-(5-(5-chloro-2-methoxypyridin-4-yl)-1H-pyrazole-3-carbonyl)-N-((4,4-difluorotetrahydrofuran-2-yl)methyl)piperidine-4-carboxamide;

1-(5-(5-chloro-2-methoxypyridin-4-yl)-1H-pyrazole-3-carbonyl)-N-((5-(trifluoromethyl)oxazol-4-yl)methyl)piperidine-4-carboxamide;

1-(5-(5-chloro-2-methoxypyridin-4-yl)-1H-pyrazole-3-carbonyl)-N-(1-(2-fluorophenyl)pyrrolidin-3-yl)piperidine-4-carboxamide;

1-(5-(5-chloro-2-methoxypyridin-4-yl)-1H-pyrazole-3-carbonyl)-N-((1-methyl-1H-benzo[d]imidazol-5-yl)methyl)piperidine-4-carboxamide;

1-(5-(5-chloro-2-methoxypyridin-4-yl)-1H-pyrazole-3-carbonyl)-N-(2-methyl-5,6,7,8-tetrahydroquinazolin-5-yl)piperidine-4-carboxamide;

1-(5-(5-chloro-2-methoxypyridin-4-yl)-1H-pyrazole-3-carbonyl)-N-((5-(difluoromethyl)isoxazol-3-yl)methyl)piperidine-4-carboxamide;

N-((1H-pyrrolo[2,3-b]pyridin-6-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(2-methyl-1,2,3,4-tetrahydroisoquinolin-4-yl)piperidine-4-carboxamide;

1-(5-(5-chloro-2-methoxypyridin-4-yl)-1H-pyrazole-3-carbonyl)-N-((3-methyl-2-oxo-2,3-dihydrobenzo[d]oxazol-5-yl)methyl)piperidine-4-carboxamide;

1-(5-(5-chloro-2-methoxypyridin-4-yl)-1H-pyrazole-3-carbonyl)-N-((1-methyl-1H-indazol-6-yl)methyl)piperidine-4-carboxamide;

N-((2-oxabicyclo[3.1.1]heptan-1-yl)methyl)-1-(5-(5-chloro-2-methoxypyridin-4-yl)-1H-pyrazole-3-carbonyl)piperidine-4-carboxamide;

1-(5-(5-chloro-2-methoxypyridin-4-yl)-1H-pyrazole-3-carbonyl)-N-(1-methyl-2,2-dioxido-3,4-dihydro-1H-benzo[c][1,2]thiazin-4-yl)piperidine-4-carboxamide;

1-(5-(5-chloro-2-methoxypyridin-4-yl)-1H-pyrazole-3-carbonyl)-N-((1-methyl-1H-pyrazolo[3,4-b]pyridin-5-yl)methyl)piperidine-4-carboxamide;

(S)-1-(5-(5-chloro-2-methoxypyridin-4-yl)-1H-pyrazole-3-carbonyl)-N-(6-cyanochroman-4-yl)piperidine-4-carboxamide;

1-(5-(5-chloro-2-methoxypyridin-4-yl)-1H-pyrazole-3-carbonyl)-N-(1-methyl-2-oxo-1,2,5,6,7,8-hexahydroquinolin-5-yl)piperidine-4-carboxamide;

1-(5-(5-chloro-2-methoxypyridin-4-yl)-1H-pyrazole-3-carbonyl)-N-((1-methyl-2-oxoindolin-5-yl)methyl)piperidine-4-carboxamide;

1-(5-(5-chloro-2-methoxypyridin-4-yl)-1H-pyrazole-3-carbonyl)-N-(3,4-dihydro-2H-pyrano[2,3-b]pyridin-4-yl)piperidine-4-carboxamide;
1-(5-(5-chloro-2-methoxypyridin-4-yl)-1H-pyrazole-3-carbonyl)-N-((1,1-dioxido-2,3-dihydrobenzo[b]thiophen-5-yl)methyl)piperidine-4-carboxamide;
1-(5-(5-chloro-2-methoxypyridin-4-yl)-1H-pyrazole-3-carbonyl)-N-((4-(difluoromethyl)pyrimidin-2-yl)methyl)piperidine-4-carboxamide;
1-(5-(5-chloro-2-methoxypyridin-4-yl)-1H-pyrazole-3-carbonyl)-N-((6-(difluoromethyl)pyridin-2-yl)methyl)piperidine-4-carboxamide;
1-(5-(5-chloro-2-methoxypyridin-4-yl)-1H-pyrazole-3-carbonyl)-N-(2-methyl-3-oxo-1,2,3,4-tetrahydroisoquinolin-4-yl)piperidine-4-carboxamide;
1-(5-(5-chloro-2-methoxypyridin-4-yl)-1H-pyrazole-3-carbonyl)-N-((6,7-dihydro-5H-cyclopenta[d]pyrimidin-2-yl)methyl)piperidine-4-carboxamide;
1-(5-(5-chloro-2-methoxypyridin-4-yl)-1H-pyrazole-3-carbonyl)-N-((3,3-dimethyl-2-oxoindolin-5-yl)methyl)piperidine-4-carboxamide;
1-(5-(5-chloro-2-methoxypyridin-4-yl)-1H-pyrazole-3-carbonyl)-N-((5-fluoro-1H-benzo[d]imidazol-4-yl)methyl)piperidine-4-carboxamide;
1-(5-(5-chloro-2-methoxypyridin-4-yl)-1H-pyrazole-3-carbonyl)-N-(3-oxo-1,2,3,4-tetrahydroisoquinolin-4-yl)piperidine-4-carboxamide;
(S)-4-(5-(5-chloro-2-methoxypyridin-4-yl)-1H-pyrazole-3-carbonyl)-N-(3-chlorobenzyl)-4-azaspiro[2.5]octane-7-carboxamide;
(R)-4-(5-(5-chloro-2-methoxypyridin-4-yl)-1H-pyrazole-3-carbonyl)-N-(3-chlorobenzyl)-4-azaspiro[2.5]octane-7-carboxamide;
1-(5-(5-chloro-2-methoxypyridin-4-yl)-1H-pyrazole-3-carbonyl)-N-(3-fluoro-3-methylcyclobutyl)piperidine-4-carboxamide;
1-(5-(5-chloro-2-methoxypyridin-4-yl)-1H-pyrazole-3-carbonyl)-N-(5-methyltetrahydrofuran-3-yl)piperidine-4-carboxamide;
1-(5-(5-chloro-2-methoxypyridin-4-yl)-1H-pyrazole-3-carbonyl)-N-((3R,6R)-1-methyl-6-(trifluoromethyl)piperidin-3-yl)piperidine-4-carboxamide;
1-(5-(5-chloro-2-methoxypyridin-4-yl)-1H-pyrazole-3-carbonyl)-N-((3S,6R)-1-methyl-6-(trifluoromethyl)piperidin-3-yl)piperidine-4-carboxamide;
1-(5-(5-chloro-2-methoxypyridin-4-yl)-1H-pyrazole-3-carbonyl)-N-((3S,6S)-1-methyl-6-(trifluoromethyl)piperidin-3-yl)piperidine-4-carboxamide;
1-(5-(5-chloro-2-methoxypyridin-4-yl)-1H-pyrazole-3-carbonyl)-N-((3R,6S)-1-methyl-6-(trifluoromethyl)piperidin-3-yl)piperidine-4-carboxamide;
1-(5-(5-chloro-2-methoxypyridin-4-yl)-1H-pyrazole-3-carbonyl)-N-((3S,6S)-6-(trifluoromethyl)tetrahydro-2H-pyran-3-yl)piperidine-4-carboxamide;
1-(5-(5-chloro-2-methoxypyridin-4-yl)-1H-pyrazole-3-carbonyl)-N-((3R,6R)-6-(trifluoromethyl)tetrahydro-2H-pyran-3-yl)piperidine-4-carboxamide;
1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide;
1-(5-(5-chloro-2-methoxypyridin-4-yl)-1H-pyrazole-3-carbonyl)-N-((3R,6S)-6-(trifluoromethyl)tetrahydro-2H-pyran-3-yl)piperidine-4-carboxamide;
N-((1H-indol-2-yl)methyl)-1-(5-(5-chloro-2-methoxypyridin-4-yl)-1H-pyrazole-3-carbonyl)piperidine-4-carboxamide;
1-(5-(5-chloro-2-methoxypyridin-4-yl)-1H-pyrazole-3-carbonyl)-N-(6-methylpyridin-2-yl)piperidine-4-carboxamide;
1-(5-(5-chloro-2-methoxypyridin-4-yl)-1H-pyrazole-3-carbonyl)-N-(3-methoxychroman-4-yl)piperidine-4-carboxamide;
1-(5-(5-chloro-2-methoxypyridin-4-yl)-1H-pyrazole-3-carbonyl)-N-(1-(4-fluorophenyl)pyrrolidin-3-yl)piperidine-4-carboxamide;
N-((1H-pyrrolo[3,2-c]pyridin-4-yl)methyl)-1-(5-(5-chloro-2-methoxypyridin-4-yl)-1H-pyrazole-3-carbonyl)piperidine-4-carboxamide;
(S)-1-(5-(5-chloro-2-methoxypyridin-4-yl)-1H-pyrazole-3-carbonyl)-N-(3-chlorobenzyl)-2,2-dimethylpiperidine-4-carboxamide;
(R)-1-(5-(5-chloro-2-methoxypyridin-4-yl)-1H-pyrazole-3-carbonyl)-N-(3-chlorobenzyl)-2,2-dimethylpiperidine-4-carboxamide;
(S)-5-(5-(5-chloro-2-methoxypyridin-4-yl)-1H-pyrazole-3-carbonyl)-N-(3-chlorobenzyl)-5-azaspiro[3.5]nonane-8-carboxamide;
(R)-5-(5-(5-chloro-2-methoxypyridin-4-yl)-1H-pyrazole-3-carbonyl)-N-(3-chlorobenzyl)-5-azaspiro[3.5]nonane-8-carboxamide;
(1R,3s,5S)-8-(5-(5-chloro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;
(1R,3s,5S)-8-(5-(5-chloro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;
(1R,3S,5S)—N-[(3-fluoro-1H-indazol-5-yl)methyl]-8-[5-(5-fluoro-2-methoxypyridin-4-yl)-1H-pyrazole-3-carbonyl]-8-azabicyclo[3.2.1]octane-3-carboxamide;
(1R,3s,5S)-8-(5-(5-chloro-2-methoxypyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;
(1R,3s,5S)-8-(5-(5-chloro-2-methoxypyridin-4-yl)-1H-pyrazole-3-carbonyl)-N-((1s,4S)-4-hydroxy-4-(trifluoromethyl)cyclohexyl)-8-azabicyclo[3.2.1]octane-3-carboxamide;
1-(5-(5-chloro-2-methoxypyridin-4-yl)-1H-pyrazole-3-carbonyl)-N-(5,6-dimethylpyrazin-2-yl)piperidine-4-carboxamide;
1-(5-(5-chloro-2-methoxypyridin-4-yl)-1H-pyrazole-3-carbonyl)-N-(1H-indol-4-yl)piperidine-4-carboxamide;
1-[5-(5-chloro-2-methylpyridin-4-yl)-1H-pyrazole-3-carbonyl]-N-[(3-chlorophenyl)methyl]piperidine-4-carboxamide;
1-[5-(5-fluoro-2-methylpyridin-4-yl)-1H-pyrazole-3-carbonyl]-N-[(1r,4r)-4-hydroxy-4-(trifluoromethyl)cyclohexyl]piperidine-4-carboxamide;
1-[5-(5-fluoro-2-methylpyridin-4-yl)-1H-pyrazole-3-carbonyl]-N-[(1s,4s)-4-hydroxy-4-(trifluoromethyl)cyclohexyl]piperidine-4-carboxamide;
1-(5-(5-chloro-2-methoxypyridin-4-yl)-1H-pyrazole-3-carbonyl)-N-((1r,4r)-4-hydroxy-4-methylcyclohexyl)piperidine-4-carboxamide;
1-(5-(5-chloro-2-methoxypyridin-4-yl)-1H-pyrazole-3-carbonyl)-N-((1s,4s)-4-hydroxy-4-methylcyclohexyl)piperidine-4-carboxamide;
1-(5-(5-chloro-2-methoxypyridin-4-yl)-1H-pyrazole-3-carbonyl)-N-(2-methyl-2,3-dihydrobenzofuran-3-yl)piperidine-4-carboxamide;

(2S,5R)-1-(5-(5-chloro-2-methoxypyridin-4-yl)-1H-pyrazole-3-carbonyl)-N-(3-chlorobenzyl)-2,5-dimethylpiperidine-4-carboxamide;

(2R,5S)-1-(5-(5-chloro-2-methoxypyridin-4-yl)-1H-pyrazole-3-carbonyl)-N-(3-chlorobenzyl)-2,5-dimethylpiperidine-4-carboxamide;

(2R,5R)-1-(5-(5-chloro-2-methoxypyridin-4-yl)-1H-pyrazole-3-carbonyl)-N-(3-chlorobenzyl)-2,5-dimethylpiperidine-4-carboxamide;

(2S,5S)-1-(5-(5-chloro-2-methoxypyridin-4-yl)-1H-pyrazole-3-carbonyl)-N-(3-chlorobenzyl)-2,5-dimethylpiperidine-4-carboxamide;

N-[(3-chlorophenyl)methyl]-1-[5-(5-fluoro-2-methylpyridin-4-yl)-1H-pyrazole-3-carbonyl]piperidine-4-carboxamide;

(1R,3S,5S)—N-[(3-chlorophenyl)methyl]-8-[5-(5-fluoro-2-methylpyridin-4-yl)-1H-pyrazole-3-carbonyl]-8-azabicyclo[3.2.1]octane-3-carboxamide;

N-[(3-fluoro-1H-indazol-5-yl)methyl]-1-[5-(5-fluoro-2-methylpyridin-4-yl)-1H-pyrazole-3-carbonyl]piperidine-4-carboxamide;

1-[5-(5-chloro-2-ethylpyridin-4-yl)-1H-pyrazole-3-carbonyl]-N-[(3-chlorophenyl)methyl]piperidine-4-carboxamide;

1-[5-(5-fluoro-2-methylpyridin-4-yl)-1H-pyrazole-3-carbonyl]-N-(1H-indol-5-ylmethyl)piperidine-4-carboxamide;

N-[(2,3-dimethyl-1H-indol-5-yl)methyl]-1-[5-(5-fluoro-2-methoxypyridin-4-yl)-1H-pyrazole-3-carbonyl]piperidine-4-carboxamide;

(2R,4R)-1-(5-(5-chloro-2-methoxypyridin-4-yl)-1H-pyrazole-3-carbonyl)-N-(3-chlorobenzyl)-2-methylpiperidine-4-carboxamide;

1-(5-(5-chloro-2-methoxypyridin-4-yl)-1H-pyrazole-3-carbonyl)-N-(3-chlorobenzyl)-2,6-dimethylpiperidine-4-carboxamide;

(1R,3s,5S)-8-(5-(5-fluoro-2-methoxypyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

1-(5-(5-fluoro-2-methoxypyridin-4-yl)-1H-pyrazole-3-carbonyl)-N-(1-oxaspiro[3.5]nonan-7-yl)piperidine-4-carboxamide;

(1R,3s,5S)—N-((3-fluoro-1-methyl-1H-indazol-5-yl)methyl)-8-(5-(5-fluoro-2-methoxypyridin-4-yl)-1H-pyrazole-3-carbonyl)-8-azabicyclo[3.2.1]octane-3-carboxamide;

N-((3,3-dimethylindolin-5-yl)methyl)-1-(5-(5-fluoro-2-methoxypyridin-4-yl)-1H-pyrazole-3-carbonyl)piperidine-4-carboxamide;

(1R,3s,5S)—N-((1r,4R)-4-hydroxy-4-(trifluoromethyl)cyclohexyl)-8-(5-(6-methylpyrimidin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide;

1-(5-(5-fluoro-2-methoxypyridin-4-yl)-1H-pyrazole-3-carbonyl)-N-(1-(3-methyl-1H-indazol-5-yl)ethyl)piperidine-4-carboxamide;

9-(5-(5-fluoro-2-methoxypyridin-4-yl)-1H-pyrazole-3-carbonyl)-N-((1r,4r)-4-hydroxy-4-(trifluoromethyl)cyclohexyl)-3-oxa-9-azabicyclo[3.3.1]nonane-7-carboxamide;

(1R,3R,5S)-8-[5-(5-fluoro-2-methylpyridin-4-yl)-1H-pyrazole-3-carbonyl]-N-[(1r,4r)-4-hydroxy-4-(trifluoromethyl)cyclohexyl]-8-azabicyclo[3.2.1]octane-3-carboxamide;

(1R,3s,5S)—N-((3-fluoro-1H-indazol-5-yl)methyl)-8-(5-(5-fluoro-2-methylpyridin-4-yl)-1H-pyrazole-3-carbonyl)-8-azabicyclo[3.2.1]octane-3-carboxamide;

(1R,3R,5S)—N-[(2,3-dimethyl-1H-indol-5-yl)methyl]-8-[5-(5-fluoro-2-methoxypyridin-4-yl)-1H-pyrazole-3-carbonyl]-8-azabicyclo[3.2.1]octane-3-carboxamide;

(R)-4-(5-(5-chloro-2-methoxypyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-chloro-2-methoxypyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(R)-4-(5-(5-fluoro-2-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide;

(R)—N-((3-fluoro-1H-indazol-5-yl)methyl)-4-(5-(5-fluoro-2-methoxypyridin-4-yl)-1H-pyrazole-3-carbonyl)-4-azaspiro[2.5]octane-7-carboxamide;

(1R,3s,5S)-8-(5-(5-fluoro-2-methylpyridin-4-yl)-1H-pyrazole-3-carbonyl)-N-((3R,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6R)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6S)-6-(trifluoromethyl)tetrahydro-2H-pyran-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((R)-1-(3-(trifluoromethyl)-1,2,4-oxadiazol-5-yl)ethyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((S)-1-(3-(trifluoromethyl)-1,2,4-oxadiazol-5-yl)ethyl)-8-azabicyclo[3.2.1]octane-3-carboxamide;

(1R,3s,5S)—N-(1,1-dimethylsilinan-4-yl)-8-(5-(5-fluoro-2-methoxypyridin-4-yl)-1H-pyrazole-3-carbonyl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((1r,4R)-4-methoxy-4-(trifluoromethyl)cyclohexyl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((1s,4S)-4-methoxy-4-(trifluoromethyl)cyclohexyl)-8-azabicyclo[3.2.1]octane-3-carboxamide;

(R)-4-(5-(5-fluoro-2-methylpyridin-4-yl)-1H-pyrazole-3-carbonyl)-N-((1r,4R)-4-methoxy-4-(trifluoromethyl)cyclohexyl)-4-azaspiro[2.5]octane-7-carboxamide;

(R)-4-(5-(5-fluoro-2-methylpyridin-4-yl)-1H-pyrazole-3-carbonyl)-N-((1s,4S)-4-methoxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1r,4S)-4-methoxy-4-(trifluoromethyl)cyclohexyl)-4-azaspiro[2.5]octane-7-carboxamide;

(S)-4-(5-(5-fluoro-2-methylpyridin-4-yl)-1H-pyrazole-3-carbonyl)-N-((1s,4R)-4-methoxy-4-(trifluoromethyl)cyclohexyl)-4-azaspiro[2.5]octane-7-carboxamide;

(1R,3R,5S)-8-[5-(5-fluoro-2-methoxypyridin-4-yl)-1H-pyrazole-3-carbonyl]-N-[(1r,4r)-4-methoxy-4-(trifluoromethyl)cyclohexyl]-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1s,4s)-4-methoxy-4-(trifluoromethyl)cyclohexyl]-8-azabicyclo[3.2.1]octane-3-carboxamide;

(1R,3s,5S)-8-(5-(5-fluoro-2-methoxypyridin-4-yl)-1H-pyrazole-3-carbonyl)-N-((5R,8r)-2-oxo-1-azaspiro[4.5]decan-8-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((5S,8s)-2-oxo-1-azaspiro[4.5]decan-8-yl)-8-azabicyclo[3.2.1]octane-3-carboxamide;

4-[5-(5-fluoro-2-methoxypyridin-4-yl)-1H-pyrazole-3-carbonyl]-N—[(R)-1-(2-fluorophenyl)pyrrolidin-3-yl]-4-azaspiro[2.5]octane-7-carboxamide;

(1R,3S,5S)-8-[5-(5-fluoro-2-methoxypyridin-4-yl)-1H-pyrazole-3-carbonyl]-N-[1-oxaspiro[3.5]nonan-7-yl]-8-azabicyclo[3.2.1]octane-3-carboxamide;

(2R,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4S,5S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2R,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2R,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4S,5R)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,5-dimethylpiperidine-4-carboxamide;

(2S,4R,5S)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2R,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(2S,4R,5R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,5-dimethylpiperidine-4-carboxamide;

(1R,3S,5S)—N-[(3S,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3R,6S)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(1R,3S,5S)—N-[(3S,6R)-1-ethyl-6-(trifluoromethyl)piperidin-3-yl]-8-[5-(5-fluoro-2-methoxypyridin-4-yl)-1H-pyrazole-3-carbonyl]-8-azabicyclo[3.2.1]octane-3-carboxamide;

(R)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide;

(S)-4-(5-(6-methylpyrimidin-4-yl)-1H-pyrazole-3-carbonyl)-N-(1-oxaspiro[3.5]nonan-7-yl)-4-azaspiro[2.5]octane-7-carboxamide;

(1R,3s,5S)-8-(5-(5-fluoro-2-methoxypyridin-4-yl)-1H-pyrazole-3-carbonyl)-N-(4-hydroxy-4-(perfluoroethyl)cyclohexyl)-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1r,4r)-4-(difluoromethyl)-4-methoxycyclohexyl]-8-azabicyclo[3.2.1]octane-3-carboxamide;

(1R,3R,5S)-8-[5-(5-fluoro-2-methoxypyridin-4-yl)-1H-pyrazole-3-carbonyl]-N-[(1s,4s)-4-(difluoromethyl)-4-methoxycyclohexyl]-8-azabicyclo[3.2.1]octane-3-carboxamide;

(1R,3s,5S)—N-((1r,4R)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(1R,3s,5S)—N-((1s,4S)-4-ethoxy-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(1R,3S,5S)-8-[5-(5-fluoro-2-methoxypyridin-4-yl)-1H-pyrazole-3-carbonyl]-N-[(1r,4r)-4-(2-methoxyethoxy)-4-(trifluoromethyl)cyclohexyl]-8-azabicyclo[3.2.1]octane-3-carboxamide;

(1R,3S,5S)-8-[5-(5-fluoro-2-methoxypyridin-4-yl)-1H-pyrazole-3-carbonyl]-N-[(1s,4s)-4-(2-methoxyethoxy)-4-(trifluoromethyl)cyclohexyl]-8-azabicyclo[3.2.1]octane-3-carboxamide;

(1R,3S,5S)-8-[5-(5-fluoro-2-methoxypyridin-4-yl)-1H-1,2,4-triazole-3-carbonyl]-N-[(1r,4r)-4-hydroxy-4-(trifluoromethyl)cyclohexyl]-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide;

(1R,3s,5S)—N-(3,3-difluoro-1-oxaspiro[3.5]nonan-7-yl)-8-(5-(5-fluoro-2-methoxypyridin-4-yl)-1H-pyrazole-3-carbonyl)-8-azabicyclo[3.2.1]octane-3-carboxamide;

(S)—N-((1r,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1s,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1r,4R)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1s,4S)-4-ethoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1r,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1s,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1r,4R)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(R)—N-((1s,4S)-4-methoxy-4-(trifluoromethyl)cyclohexyl)-4-(5-(6-methylpyrimidin-4-yl)-1H-pyrazole-3-carbonyl)-4-azaspiro[2.5]octane-7-carboxamide;

4-(4-(5-hydroxy-2-methylpyridin-4-yl)-1H-imidazole-2-carbonyl)-N-((1r,4r)-4-hydroxy-4-(trifluoromethyl)cyclohexyl)-4-azaspiro[2.5]octane-7-carboxamide;

(1R,3s,5S)-8-(5-(5-fluoro-2-methylpyridin-4-yl)-1H-pyrazole-3-carbonyl)-N-((3S,6S)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6S)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3R,6R)-1-methyl-6-(trifluoromethyl)piperidin-3-yl)-8-azabicyclo[3.2.1]octane-3-carboxamide;

(1R,3s,5S)-8-(5-(5-fluoro-2-methylpyridin-4-yl)-1H-pyrazole-3-carbonyl)-N-((3S,6R)-1-methyl-6-(trifluoromethyl)piperidin-3-yl)-8-azabicyclo[3.2.1]octane-3-carboxamide;

(R)—N-((1r,4S)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4R)-4-ethoxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.2.2]octan-1-yl)methyl)-4-azaspiro[2.5]octane-7-carboxamide;

(1R,3s,5S)-8-(5-(2,3-dimethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)—N-((1r,4R)-4-hydroxy-4-(trifluoromethyl)cyclohexyl)-8-(5-(6-methyl-1H-pyrazolo[3,4-b]pyridin-4-yl)-1H-pyrazole-3-carbonyl)-8-azabicyclo[3.2.1]octane-3-carboxamide;

(1R,3s,5S)-8-(5-(2-ethylpyridin-4-yl)-1H-pyrazole-3-carbonyl)-N-((1r,4R)-4-hydroxy-4-(trifluoromethyl)cyclohexyl)-8-azabicyclo[3.2.1]octane-3-carboxamide;

(1R,3s,5S)—N-((1r,4R)-4-hydroxy-4-(trifluoromethyl)cyclohexyl)-8-(5-(2-(hydroxymethyl)pyridin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-(3-(trifluoromethyl)-1-oxaspiro[3.5]nonan-7-yl)-8-azabicyclo[3.2.1]octane-3-carboxamide;

(1R,3s,5S)—N-(3,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide;

(1R,3s,5S)—N-(4,4-difluoro-1-oxaspiro[4.5]decan-8-yl)-8-(5-(5-fluoro-2-methoxypyridin-4-yl)-1H-pyrazole-3-carbonyl)-8-azabicyclo[3.2.1]octane-3-carboxamide;

(S)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide;

(S)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3S,6S)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3R,6R)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3S,6R)-1-methyl-6-(trifluoromethyl)piperidin-3-yl)-4-azaspiro[2.5]octane-7-carboxamide;

(R)-4-(5-(5-fluoro-2-methoxypyridin-4-yl)-1H-pyrazole-3-carbonyl)-N-((3R,6S)-1-methyl-6-(trifluoromethyl)piperidin-3-yl)-4-azaspiro[2.5]octane-7-carboxamide;

(R)—N-((1r,4R)-4-ethoxy-4-(trifluoromethyl)cyclohexyl)-4-(5-(5-fluoro-2-methylpyridin-4-yl)-1H-pyrazole-3-carbonyl)-4-azaspiro[2.5]octane-7-carboxamide;

(S)—N-((1r,4S)-4-ethoxy-4-(trifluoromethyl)cyclohexyl)-4-(5-(5-fluoro-2-methylpyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((1r,4R)-4-methoxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-methoxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((4S,7r)-1-oxaspiro[3.5]nonan-7-yl)-4-azaspiro[2.5]octane-7-carboxamide;

(S)-4-(5-(5-fluoro-2-methoxypyridin-4-yl)-1H-pyrazole-3-carbonyl)-N-((4R,7s)-1-oxaspiro[3.5]nonan-7-yl)-4-azaspiro[2.5]octane-7-carboxamide;

(1R,3s,5S)-8-(5-(5-fluoro-2-methoxypyridin-4-yl)-1H-pyrazole-3-carbonyl)-N-((3S,6S)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6S)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3R,6R)-1-(2-fluoro-2-methylpropyl)-6-(trifluoromethyl)piperidin-3-yl)-8-azabicyclo[3.2.1]octane-3-carboxamide;

(1R,3s,5S)-8-(5-(5-fluoro-2-methoxypyridin-4-yl)-1H-pyrazole-3-carbonyl)-N-((3S,6R)-1-(2-fluoro-2-methylpropyl)-6-(trifluoromethyl)piperidin-3-yl)-8-azabicyclo[3.2.1]octane-3-carboxamide;

(R)-4-(5-(5-fluoro-2-methoxypyridin-4-yl)-1H-pyrazole-3-carbonyl)-N-((5R,8r)-1-methyl-2-oxo-1-azaspiro[4.5]decan-8-yl)-4-azaspiro[2.5]octane-7-carboxamide;

(R)-4-(5-(5-fluoro-2-methoxypyridin-4-yl)-1H-pyrazole-3-carbonyl)-N-((5S,8s)-1-methyl-2-oxo-1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-((5S,8r)-1-methyl-2-oxo-1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-((5R,8s)-1-methyl-2-oxo-1-azaspiro[4.5]decan-8-yl)-4-azaspiro[2.5]octane-7-carboxamide;

(R)—N-((5R,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(R)—N-((5S,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((5S,8r)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((5R,8s)-1-ethyl-2-oxo-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(2-(dimethylamino)ethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(R)-4-(5-(5-fluoro-2-methoxypyridin-4-yl)-1H-pyrazole-3-carbonyl)-N-((1r,4R)-4-(2-hydroxyethoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-(2-hydroxyethoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N—((R)-1-(2,2,2-trifluoroethyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N—((S)-1-(2,2,2-trifluoroethyl)pyrrolidin-3-yl)-4-azaspiro[2.5]octane-7-carboxamide;

(R)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.2.1]heptan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide;

4-(5-(5-fluoro-2-methoxypyridin-4-yl)-1H-pyrazole-3-carbonyl)-N-((4-hydroxybicyclo[2.1.1]hexan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((3-hydroxybicyclo[1.1.1]pentan-1-yl)methyl)-4-azaspiro[2.5]octane-7-carboxamide;

(S)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(R)—N-((2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide;

(R)—N-((1r,4R)-4-hydroxy-4-(trifluoromethyl)cyclohexyl)-4-(5-(6-methoxypyrimidin-4-yl)-1H-pyrazole-3-carbonyl)-4-azaspiro[2.5]octane-7-carboxamide;

(R)—N-((1r,4R)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)—N-((1r,4S)-4-hydroxy-4-(trifluoromethyl)cyclohexyl)-4-(5-(6-methylpyrimidin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1 S,4S)-4-((S)-2-methoxypropoxy)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1R,4S)-4-((R)-2-methoxypropoxy)-4-(trifluoromethyl)cyclohexyl)-4-azaspiro[2.5]octane-7-carboxamide;

(S)-4-(3-(5-fluoro-2-methoxypyridin-4-yl)-1H-pyrazole-5-carbonyl)-N—(((R)-4,5,6,7-tetrahydro-2H-indazol-5-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-4,5,6,7-tetrahydro-2H-indazol-5-yl)methyl)-4-azaspiro[2.5]octane-7-carboxamide;

(S)-4-(3-(5-fluoro-2-methoxypyridin-4-yl)-1H-pyrazole-5-carbonyl)-N—(((R)-5,6,7,8-tetrahydroimidazo[1,5-a]pyridin-7-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-5,6,7,8-tetrahydroimidazo[1,5-a]pyridin-7-yl)methyl)-4-azaspiro[2.5]octane-7-carboxamide;

(S)-4-(5-(5-fluoro-2-methoxypyridin-4-yl)-1H-pyrazole-3-carbonyl)-N-((1-methyl-2-oxabicyclo[2.1.1]hexan-4-yl)methyl)-4-azaspiro[2.5]octane-7-carboxamide;

(R)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—((R)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide;

(R)-4-(3-(5-fluoro-2-methoxypyridin-4-yl)-1H-pyrazole-5-carbonyl)-N—((S)-1-(2-hydroxy-2-methylpropyl)pyrrolidin-3-yl)-4-azaspiro[2.5]octane-7-carboxamide;

(S)-4-(3-(5-fluoro-2-methoxypyridin-4-yl)-1H-pyrazole-5-carbonyl)-N—(((R)-3-methyl-5,6,7,8-tetrahydro-[1,2,4]triazolo[4,3-a]pyridin-7-yl)methyl)-4-azaspiro[2.5]octane-7-carboxamide;

(S)-4-(3-(5-fluoro-2-methoxypyridin-4-yl)-1H-pyrazole-5-carbonyl)-N—(((S)-3-methyl-5,6,7,8-tetrahydro-[1,2,4]triazolo[4,3-a]pyridin-7-yl)methyl)-4-azaspiro[2.5]octane-7-carboxamide;

(1r,4R)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1s,4S)—N—((R)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1r,4S)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(1s,4R)—N—((S)-4-(5-(5-fluoro-2-methoxypyridin-4-yl)-1H-pyrazole-3-carbonyl)-4-azaspiro[2.5]octan-7-yl)-4-hydroxy-4-(trifluoromethyl)cyclohexane-1-carboxamide;

(S)-4-(5-(5-fluoro-2-methoxypyridin-4-yl)-1H-pyrazole-3-carbonyl)-N-(1-azaspiro[4.5]decan-8-yl)-4-azaspiro[2.5]octane-7-carboxamide;

(S)-4-(5-(5-fluoro-2-methoxypyridin-4-yl)-1H-pyrazole-3-carbonyl)-N-(1-(oxetan-3-yl)-1-azaspiro[4.5]decan-8-yl)-4-azaspiro[2.5]octane-7-carboxamide;

(S)—N-((1r,4S)-4-(2-aminoethoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-(1-(2,2-difluoropropyl)-1-azaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((1 S,4S)-4-((S)-2-aminopropoxy)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1 S,4S)-4-((S)-2-hydroxypropoxy)-4-(trifluoromethyl)cyclohexyl)-4-azaspiro[2.5]octane-7-carboxamide;

(7S)—N-(8-oxabicyclo[3.2.1]octan-3-yl)-4-(5-(5-fluoro-2-methoxypyridin-4-yl)-1H-pyrazole-3-carbonyl)-4-azaspiro[2.5]octane-7-carboxamide;

(S)—N-((1 S,3R)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide;

(S)—N-((1 S,3S)-3-(3,3-difluoropyrrolidin-1-yl)-2,2-dimethylcyclobutyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—(((S)-5,6,7,8-tetrahydroimidazo[1,2-a]pyridin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-5,6,7,8-tetrahydroimidazo[1,2-a]pyridin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((S)-3-(trifluoromethyl)-5,6-dihydro-8H-[1,2,4]triazolo[3,4-c][1,4]oxazin-6-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-3-(trifluoromethyl)-5,6-dihydro-8H-[1,2,4]triazolo[3,4-c][1,4]oxazin-6-yl)methyl)-4-azaspiro[2.5]octane-7-carboxamide;

(S)—N-((3-chloropyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3-methylpyridin-2-yl)methyl)-4-azaspiro[2.5]octane-7-carboxamide;

(S)—N—((R)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((S)-1-(3-chloropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-methylpyridin-2-yl)methyl)-4-azaspiro[2.5]octane-7-carboxamide;

(S)—N-((3-chloro-5-fluoropyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-(trifluoromethyl)pyridin-2-yl)methyl)-4-azaspiro[2.5]octane-7-carboxamide;

(S)—N-((3-chloro-5-(2-hydroxypropan-2-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((4-(trifluoromethyl)-2-oxabicyclo[2.1.1]hexan-1-yl)methyl)-4-azaspiro[2.5]octane-7-carboxamide;

(S)—N—((S)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide;

(S)—N—((R)-3,4-dihydro-2H-pyrano[3,2-b]pyridin-4-yl)-4-(5-(5-fluoro-2-methoxypyridin-4-yl)-1H-pyrazole-3-carbonyl)-4-azaspiro[2.5]octane-7-carboxamide;

(2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide;

(2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide;

(2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-(trifluoromethyl)piperidine-4-carboxamide;

(2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-(trifluoromethyl)piperidine-4-carboxamide;

(R)—N-((1r,4R)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(R)—N-((1s,4S)-4-(1,1-difluoro-2-methoxyethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(R)—N-((5S,8s)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(R)—N-((5R,8r)-4,4-difluoro-1-oxaspiro[4.5]decan-8-yl)-4-(5-(5-fluoro-2-methoxypyridin-4-yl)-1H-pyrazole-3-carbonyl)-4-azaspiro[2.5]octane-7-carboxamide;

(S)—N-((5,6-dihydro-8H-imidazo[2,1-c][1,4]oxazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(((1R,3S)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1 S,3S)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1 S,3R)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-(((1R,3R)-1-imino-2,2-dimethyl-1-oxidotetrahydro-1H-116-thiophen-3-yl)methyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-hydroxy-4-(perfluoroethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1s,4R)-4-hydroxy-4-(perfluoroethyl)cyclohexyl)-4-azaspiro[2.5]octane-7-carboxamide;

(S)—N-((4S,7r)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4R,7s)-3,3-difluoro-1-oxaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(1,1-difluoroethyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((6R,8aR)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6R,8aS)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6S,8aR)-octahydroindolizin-6-yl)-4-azaspiro[2.5]octane-7-carboxamide;

(S)-4-(5-(5-fluoro-2-methoxypyridin-4-yl)-1H-pyrazole-3-carbonyl)-N-((6S,8aS)-octahydroindolizin-6-yl)-4-azaspiro[2.5]octane-7-carboxamide;

(S)—N—((R)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((S)-1-(3-chloro-5-fluoropyridin-2-yl)ethyl)-4-(5-(5-fluoro-2-methoxypyridin-4-yl)-1H-pyrazole-3-carbonyl)-4-azaspiro[2.5]octane-7-carboxamide;

(S)—N-((1s,3R)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide;

(S)—N-((1r,3S)-3-(3,3-difluoropyrrolidin-1-yl)-2,2,4,4-tetramethylcyclobutyl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-(2-fluoro-2-methylpropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-6-methyl-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N—((S)-6-methyl-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N-(5-methylpyrazolo[1,5-a]pyrimidin-3-yl)-4-azaspiro[2.5]octane-7-carboxamide;

(S)-4-(5-(5-fluoro-2-methoxypyridin-4-yl)-1H-pyrazole-3-carbonyl)-N—(((S)-3-methyl-4,5,6,7-tetrahydro-1H-indazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—(((R)-3-methyl-4,5,6,7-tetrahydro-1H-indazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-7-fluoro-3,4-dihydro-2H-pyrano[3,2-b]pyridin-4-yl)-4-azaspiro[2.5]octane-7-carboxamide;

(S)-4-(5-(5-fluoro-2-methoxypyridin-4-yl)-1H-pyrazole-3-carbonyl)-N—((S)-7-fluoro-3,4-dihydro-2H-pyrano[3,2-b]pyridin-4-yl)-4-azaspiro[2.5]octane-7-carboxamide;

(1R,3s,5S)—N-((3-chloro-5-fluoropyridin-2-yl)methyl)-8-(5-(5-fluoro-2-methoxypyridin-4-yl)-1H-pyrazole-3-carbonyl)-8-azabicyclo[3.2.1]octane-3-carboxamide;

(R)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-methylpyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((4-methylpyridazin-3-yl)methyl)-4-azaspiro[2.5]octane-7-carboxamide;

(S)—N-((5-chloro-2-methylpyrimidin-4-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloropyrazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-fluoro-3-methoxypyridin-2-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-1-(pyridin-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(pyridin-3-yl)pyrrolidin-3-yl)-4-azaspiro[2.5]octane-7-carboxamide;

(S)—N-((3-chloro-5-cyanopyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-(oxetan-3-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-(3-cyanoazetidin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((2-methyl-5-(trifluoromethyl)oxazol-4-yl)methyl)-4-azaspiro[2.5]octane-7-carboxamide;

(S)—N—((S)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((R)-1-(5-cyclopropyl-1,3,4-oxadiazol-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1-(oxetan-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(oxetan-3-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((3-methylpyrazin-2-yl)methyl)-4-azaspiro[2.5]octane-7-carboxamide;

(S)—N-((1r,4S)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-(1,1-difluoro-3-methoxypropyl)-4-hydroxycyclohexyl)-4-(5-(5-fluoro-2-methoxypyridin-4-yl)-1H-pyrazole-3-carbonyl)-4-azaspiro[2.5]octane-7-carboxamide;

(S)—N-((1s,4R)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-amino-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((3,5-difluoropyridin-2-yl)methyl)-4-(5-(5-fluoro-2-methoxypyridin-4-yl)-1H-pyrazole-3-carbonyl)-4-azaspiro[2.5]octane-7-carboxamide;

(2S,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide;

(2R,4S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2-methylpiperidine-4-carboxamide;

(2R,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide;

(2S,4R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2-methylpiperidine-4-carboxamide;

(S)—N-((3-chloro-5-methoxypyridin-2-yl)methyl)-4-(5-(5-fluoro-2-methoxypyridin-4-yl)-1H-pyrazole-3-carbonyl)-4-azaspiro[2.5]octane-7-carboxamide;

(2R,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide;

(2S,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide;

(2S,4S)-2-ethyl-1-(5-(5-fluoro-2-methoxypyridin-4-yl)-1H-pyrazole-3-carbonyl)-N-((1r,4S)-4-hydroxy-4-(trifluoromethyl)cyclohexyl)piperidine-4-carboxamide;

(2R,4R)-2-ethyl-1-(5-(5-fluoro-2-methoxypyridin-4-yl)-1H-pyrazole-3-carbonyl)-N-((1r,4R)-4-hydroxy-4-(trifluoromethyl)cyclohexyl)piperidine-4-carboxamide;

(S)-4-(5-(5-fluoro-2-methoxypyridin-4-yl)-1H-pyrazole-3-carbonyl)-N-((5-fluoro-3-(4-methylpiperazin-1-yl)pyridin-2-yl)methyl)-4-azaspiro[2.5]octane-7-carboxamide;

(R)—N-((5R,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(R)—N-((5S,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(S)—N-((5S,8r)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(S)—N-((5R,8s)-4,4-difluoro-1-oxaspiro[4.5]decan-8-yl)-4-(5-(5-fluoro-2-methylpyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(1-((1-fluorocyclopropyl)methyl)azetidin-3-yl)-4-azaspiro[2.5]octane-7-carboxamide;

(S)-1-(5-(5-fluoro-2-methoxypyridin-4-yl)-1H-pyrazole-3-carbonyl)-N-((1r,4S)-4-hydroxy-4-(trifluoromethyl)cyclohexyl)-2,2-dimethylpiperidine-4-carboxamide;

(R)-1-(5-(5-fluoro-2-methoxypyridin-4-yl)-1H-pyrazole-3-carbonyl)-N-((1r,4R)-4-hydroxy-4-(trifluoromethyl)cyclohexyl)-2,2-dimethylpiperidine-4-carboxamide;

(S)-4-(5-(5-fluoro-2-methoxypyridin-4-yl)-1H-pyrazole-3-carbonyl)-N-((1s,4R)-4-(hydroxymethyl)-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-(hydroxymethyl)-4-(trifluoromethyl)cyclohexyl)-4-azaspiro[2.5]octane-7-carboxamide;

(7S)—N-(1-(tert-butylsulfinyl)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4S,7r)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-((4R,7s)-3,3-difluoro-1-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1-(4-hydroxybicyclo[2.2.2]octan-1-yl)ethyl)-4-azaspiro[2.5]octane-7-carboxamide;

(S)-4-(5-(5-fluoro-2-methoxypyridin-4-yl)-1H-pyrazole-3-carbonyl)-N—((S)-1-(4-hydroxybicyclo[2.2.2]octan-1-yl)ethyl)-4-azaspiro[2.5]octane-7-carboxamide;

(S)—N-((4,6-dimethylpyridazin-3-yl)methyl)-4-(5-(5-fluoro-2-methoxypyridin-4-yl)-1H-pyrazole-3-carbonyl)-4-azaspiro[2.5]octane-7-carboxamide;

(R)—N-((5-chloropyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3S,4R)-4-morpholinotetrahydrofuran-3-yl)-4-azaspiro[2.5]octane-7-carboxamide;

(S)-4-(5-(5-fluoro-2-methoxypyridin-4-yl)-1H-pyrazole-3-carbonyl)-N-((3R,4S)-4-morpholinotetrahydrofuran-3-yl)-4-azaspiro[2.5]octane-7-carboxamide;

(S)—N—((S)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide;

(S)—N—((R)-1-(5,6-dihydro-8H-imidazo[2,1-c][1,4]oxazin-2-yl)ethyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(pyrazolo[1,5-a]pyridin-7-ylmethyl)-4-azaspiro[2.5]octane-7-carboxamide;

(S)-4-(5-(5-fluoro-2-methoxypyridin-4-yl)-1H-pyrazole-3-carbonyl)-N-(1-(oxetan-3-yl)piperidin-4-yl)-4-azaspiro[2.5]octane-7-carboxamide;

(S)-4-(5-(5-fluoro-2-methoxypyridin-4-yl)-1H-pyrazole-3-carbonyl)-N-((1r,4S)-4-morpholinocyclohexyl)-4-azaspiro[2.5]octane-7-carboxamide;

(S)-4-(5-(5-fluoro-2-methoxypyridin-4-yl)-1H-pyrazole-3-carbonyl)-N-((1s,4R)-4-morpholinocyclohexyl)-4-azaspiro[2.5]octane-7-carboxamide;

(S)-4-(5-(5-fluoro-2-methoxypyridin-4-yl)-1H-pyrazole-3-carbonyl)-N-((1R,5S,7r)-9-methyl-3-oxa-9-azabicyclo[3.3.1]nonan-7-yl)-4-azaspiro[2.5]octane-7-carboxamide;

(S)-4-(5-(5-fluoro-2-methoxypyridin-4-yl)-1H-pyrazole-3-carbonyl)-N-((1R,5S,7s)-9-methyl-3-oxa-9-azabicyclo[3.3.1]nonan-7-yl)-4-azaspiro[2.5]octane-7-carboxamide;

(S)-4-(5-(5-fluoro-2-methoxypyridin-4-yl)-1H-pyrazole-3-carbonyl)-N-(1-(methylsulfonyl)piperidin-4-yl)-4-azaspiro[2.5]octane-7-carboxamide;

(S)-4-(5-(5-fluoro-2-methoxypyridin-4-yl)-1H-pyrazole-3-carbonyl)-N—((S)-1-(oxetan-3-yl)piperidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(oxetan-3-yl)piperidin-3-yl)-4-azaspiro[2.5]octane-7-carboxamide;

(S)—N-((3R,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4S)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4R)-4-fluoro-1-methylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,6R)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)—N-((3R,6S)-1,6-dimethylpiperidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2-fluoroethyl)-2,2-dimethylpiperidin-4-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-fluoroethyl)-2,2-dimethylpiperidin-4-yl)-4-azaspiro[2.5]octane-7-carboxamide;

(S)—N-((3R,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4S)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3S,4R)-4-fluoro-1-(6-methylpyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(7S)-4-(5-(5-fluoro-2-methoxypyridin-4-yl)-1H-pyrazole-3-carbonyl)-N-(3-(oxetan-3-yl)-3-azabicyclo[3.1.0]hexan-6-yl)-4-azaspiro[2.5]octane-7-carboxamide;

(S)—N-(5-chloropyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(2-methylpyrimidin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-methylpyrimidin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((3-(trifluoromethyl)pyrazin-2-yl)methyl)-4-azaspiro[2.5]octane-7-carboxamide;

(S)-4-(5-(5-fluoro-2-methoxypyridin-4-yl)-1H-pyrazole-3-carbonyl)-N-(1-((S)-tetrahydrofuran-3-yl)azetidin-3-yl)-4-azaspiro[2.5]octane-7-carboxamide;

(S)-4-(5-(5-fluoro-2-methoxypyridin-4-yl)-1H-pyrazole-3-carbonyl)-N-(1-((R)-tetrahydrofuran-3-yl)azetidin-3-yl)-4-azaspiro[2.5]octane-7-carboxamide;

(7S)—N-((3-chloro-5-(3,5-dimethylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-((1-(trifluoromethyl)cyclopropyl)methyl)pyrrolidin-3-yl)-4-(5-(5-fluoro-2-methoxypyridin-4-yl)-1H-pyrazole-3-carbonyl)-4-azaspiro[2.5]octane-7-carboxamide;

(1R,3s,5S)—N-(4-(1,1-difluoro-2-hydroxyethyl)-4-hydroxycyclohexyl)-8-(5-(5-fluoro-2-methoxypyridin-4-yl)-1H-pyrazole-3-carbonyl)-8-azabicyclo[3.2.1]octane-3-carboxamide;

(1R,3s,5S)-8-(5-(5-fluoro-2-methoxypyridin-4-yl)-1H-pyrazole-3-carbonyl)-N—((R)-1-((1-(trifluoromethyl)cyclopropyl)methyl)pyrrolidin-3-yl)-8-azabicyclo[3.2.1]octane-3-carboxamide;

(1R,3s,5S)—N-(4-cyano-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(S)—N-((1s,4R)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1r,4S)-4-(cyanomethyl)-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((2-(2-fluoro-2-methylpropyl)-2-azabicyclo[2.1.1]hexan-4-yl)methyl)-4-azaspiro[2.5]octane-7-carboxamide;

(1R,3s,5S)—N-(4-amino-4-(trifluoromethyl)cyclohexyl)-8-(5-(5-fluoro-2-methoxypyridin-4-yl)-1H-pyrazole-3-carbonyl)-8-azabicyclo[3.2.1]octane-3-carboxamide;

(S)-4-(5-(5-fluoro-2-methoxypyridin-4-yl)-1H-pyrazole-3-carbonyl)-N-(2-(2-fluoro-2-methylpropyl)-2-azabicyclo[2.1.1]hexan-4-yl)-4-azaspiro[2.5]octane-7-carboxamide;

(S)-4-(5-(5-fluoro-2-methoxypyridin-4-yl)-1H-pyrazole-3-carbonyl)-N-((1-(trifluoromethyl)-2-oxabicyclo[2.1.1]hexan-4-yl)methyl)-4-azaspiro[2.5]octane-7-carboxamide;

5-(5-(5-fluoro-2-methoxypyridin-4-yl)-1H-pyrazole-3-carbonyl)-N-((1r,4r)-4-hydroxy-4-(trifluoromethyl)cyclohexyl)-2-oxa-5-azaspiro[3.5]nonane-8-carboxamide;

(S)-4-(5-(5-fluoro-2-methoxypyridin-4-yl)-1H-pyrazole-3-carbonyl)-N-(5-((R)-1-hydroxyethyl)pyrazolo[1,5-a]pyrimidin-3-yl)-4-azaspiro[2.5]octane-7-carboxamide;

(S)-4-(5-(5-fluoro-2-methoxypyridin-4-yl)-1H-pyrazole-3-carbonyl)-N-(5-((S)-1-hydroxyethyl)pyrazolo[1,5-a]pyrimidin-3-yl)-4-azaspiro[2.5]octane-7-carboxamide;

(S)—N-((3-chloro-5-(oxetan-3-yloxy)pyridin-2-yl)methyl)-4-(5-(5-fluoro-2-methoxypyridin-4-yl)-1H-pyrazole-3-carbonyl)-4-azaspiro[2.5]octane-7-carboxamide;

(7S)—N-((5-(3,5-dimethylpiperazin-1-yl)pyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)—N-(1-cyanocyclopropyl)-4-(5-(5-fluoro-2-methoxypyridin-4-yl)-1H-pyrazole-3-carbonyl)-4-azaspiro[2.5]octane-7-carboxamide;

(S)-4-(5-(2-methoxy-5-methylpyridin-4-yl)-1H-pyrazole-3-carbonyl)-N—((R)-1,6,6-trimethylpiperidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1,6,6-trimethylpiperidin-3-yl)-4-azaspiro[2.5]octane-7-carboxamide;

(S)—N—((S)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(1H-pyrazolo[3,4-b]pyridin-4-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3-chloro-6-methylpyrazin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(6-methylpyridazin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(6-methylpyridazin-4-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-(2-methylpyrimidin-5-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-(2-methylpyrimidin-5-yl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((R)-1-((3-hydroxyoxetan-3-yl)methyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N—((S)-1-((3-hydroxyoxetan-3-yl)methyl)pyrrolidin-3-yl)-4-azaspiro[2.5]octane-7-carboxamide;

(S)-4-(5-(5-fluoro-2-methoxypyridin-4-yl)-1H-pyrazole-3-carbonyl)-N-((5-methoxypyrimidin-2-yl)methyl)-4-azaspiro[2.5]octane-7-carboxamide;

(S)—N-((5-cyanopyrimidin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-(trifluoromethyl)pyrimidin-2-yl)methyl)-4-azaspiro[2.5]octane-7-carboxamide;

(S)—N-(1-(3,5-dichloropyridin-2-yl)cyclopropyl)-4-(5-(5-fluoro-2-methoxypyridin-4-yl)-1H-pyrazole-3-carbonyl)-4-azaspiro[2.5]octane-7-carboxamide;

(S)—N—((S)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(2,2-difluoro-3-hydroxypropyl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((1R,4S)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1 S,4R)-4-((3S,5R)-3,5-dimethylpiperazin-1-yl)cyclohexyl)-4-(5-(5-fluoro-2-methoxypyridin-4-yl)-1H-pyrazole-3-carbonyl)-4-azaspiro[2.5]octane-7-carboxamide;

(S)—N—((R)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((R)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((S)-1-oxa-6-azaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((5-((1R,4R)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1 S,4S)-2,5-diazabicyclo[2.2.1]heptan-2-yl)-3-chloropyridin-2-yl)methyl)-4-(3-(5-fluoro-2-methoxypyridin-4-yl)-1H-pyrazole-5-carbonyl)-4-azaspiro[2.5]octane-7-carboxamide;

(S)-4-(3-(5-fluoro-2-methoxypyridin-4-yl)-1H-pyrazole-5-carbonyl)-N-((3-hydroxyoxetan-3-yl)methyl)-4-azaspiro[2.5]octane-7-carboxamide;

(S)—N—((R)-1-((R)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((R)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-((S)-1-oxaspiro[3.3]heptan-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1,4,5-trimethyl-1H-imidazol-2-yl)methyl)-4-azaspiro[2.5]octane-7-carboxamide;

(S)—N-(5-((1 S,2S)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)—N-(5-((1R,2R)-2-cyanocyclopropyl)pyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(S)—N-((5-((1R,4R)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1 S,4S)-2,5-diazabicyclo[2.2.1]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(R)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide;

(S)-4-(5-(5-fluoro-2-methoxypyridin-4-yl)-1H-pyrazole-3-carbonyl)-N-(6-fluoropyrazolo[1,5-a]pyridin-7-yl)-4-azaspiro[2.5]octane-7-carboxamide;

(S)—N-((5-((1 S,6R)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N-((5-((1R,6S)-2,5-diazabicyclo[4.1.0]heptan-2-yl)pyrimidin-2-yl)methyl)-4-(3-(5-fluoro-2-methoxypyridin-4-yl)-1H-pyrazole-5-carbonyl)-4-azaspiro[2.5]octane-7-carboxamide;

(S)—N—((R)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide;

(S)—N—((S)-4,4-difluoro-1-((1-hydroxycyclopropyl)methyl)pyrrolidin-3-yl)-4-(3-(5-fluoro-2-methoxypyridin-4-yl)-1H-pyrazole-5-carbonyl)-4-azaspiro[2.5]octane-7-carboxamide;

(7S)-4-(5-(5-fluoro-2-methoxypyridin-4-yl)-1H-pyrazole-3-carbonyl)-N-(pyrrolidin-3-yl)-4-azaspiro[2.5]octane-7-carboxamide;

(S)—N—((R)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-(5-cyanopyrimidin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((1-isopropyl-3-methyl-1H-1,2,4-triazol-5-yl)methyl)-4-azaspiro[2.5]octane-7-carboxamide;

(S)—N-((1 S,3R,4S)-3,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1 S,3S,4R)-3,4-dihydroxy-4-(trifluoromethyl) cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,3R,4S)-3,4-dihydroxy-4-(trifluoromethyl) cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,3S,4R)-3,4-dihydroxy-4-(trifluoromethyl) cyclohexyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-1-(5-methyl-4,5,6,7-tetrahydro-pyrazolo[1,5-a]pyrazin-2-yl)ethyl)-4-azaspiro[2.5]octane-7-carboxamide;

(S)-4-(5-(5-fluoro-2-methoxypyridin-4-yl)-1H-pyrazole-3-carbonyl)-N—((R)-1-(5-methyl-4,5,6,7-tetrahydro-pyrazolo[1,5-a]pyrazin-2-yl)ethyl)-4-azaspiro[2.5]octane-7-carboxamide;

(S)-4-(3-(5-fluoro-2-methoxypyridin-4-yl)-1H-pyrazole-5-carbonyl)-N-((5-(trifluoromethyl)-1H-imidazol-2-yl) methyl)-4-azaspiro[2.5]octane-7-carboxamide;

4-(5-(2-acetyl-5-fluoropyridin-4-yl)-1H-pyrazole-3-carbonyl)-N-((3-chloro-5-fluoropyridin-2-yl)methyl)-4-azaspiro[2.5]octane-7-carboxamide;

(R)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-((S)-1-hydroxyethyl)pyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(5-fluoro-2-((R)-1-hydroxyethyl)pyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((R)-5,6,7,8-tetrahydroimidazo[1,2-a] pyridin-8-yl)-4-azaspiro[2.5]octane-7-carboxamide;

(S)-4-(5-(5-fluoro-2-methoxypyridin-4-yl)-1H-pyrazole-3-carbonyl)-N—((S)-5,6,7,8-tetrahydroimidazo[1,2-a] pyridin-8-yl)-4-azaspiro[2.5]octane-7-carboxamide;

(S)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(2-cyclopropyl-5-fluoropyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((3-((1 S,2S)-2-(hydroxymethyl)cyclopropyl)pyrazin-2-yl)methyl)-4-azaspiro[2.5]octane-7-carboxamide;

(S)-4-(5-(5-fluoro-2-methoxypyridin-4-yl)-1H-pyrazole-3-carbonyl)-N-((3-((1R,2R)-2-(hydroxymethyl)cyclopropyl)pyrazin-2-yl)methyl)-4-azaspiro[2.5]octane-7-carboxamide;

(S)—N-((2-((3S,5R)-3,5-dimethylpiperazin-1-yl)-5-(trifluoromethyl)oxazol-4-yl)methyl)-4-(5-(5-fluoro-2-methoxypyridin-4-yl)-1H-pyrazole-3-carbonyl)-4-azaspiro[2.5]octane-7-carboxamide;

(S)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide;

(R)—N-((3-chloro-5-fluoropyridin-2-yl)methyl)-4-(5-(2-ethyl-5-fluoropyridin-4-yl)-1H-pyrazole-3-carbonyl)-4-azaspiro[2.5]octane-7-carboxamide;

(S)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide;

(R)—N-((3-chloro-5-methoxypyridin-2-yl)methyl)-4-(5-(5-fluoro-2-methylpyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-((5-(trifluoromethyl)-2-((3S,5R)-3,4,5-trimethylpiperazin-1-yl)oxazol-4-yl)methyl)-4-azaspiro[2.5]octane-7-carboxamide;

(S)-5-(5-(5-fluoro-2-methoxypyridin-4-yl)-1H-pyrazole-3-carbonyl)-N-((1r,4S)-4-hydroxy-4-(trifluoromethyl) cyclohexyl)-5-azaspiro[3.5]nonane-8-carboxamide;

(R)-5-(5-(5-fluoro-2-methoxypyridin-4-yl)-1H-pyrazole-3-carbonyl)-N-((1r,4R)-4-hydroxy-4-(trifluoromethyl) cyclohexyl)-5-azaspiro[3.5]nonane-8-carboxamide;

(S)—N-(5-cyanopyrazolo[1,5-a]pyrimidin-3-yl)-4-(5-(5-fluoro-2-methoxypyridin-4-yl)-1H-pyrazole-3-carbonyl)-4-azaspiro[2.5]octane-7-carboxamide;

(7S)—N-(1-(6-cyanopyridin-3-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-1-(5-cyanopyridin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((S)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N—((R)-4,4-difluoro-1-(5-methylpyrazin-2-yl)pyrrolidin-3-yl)-4-(5-(5-fluoro-2-methoxypyridin-4-yl)-1H-pyrazole-3-carbonyl)-4-azaspiro[2.5]octane-7-carboxamide;

(S)—N-((3-chloro-5-isopropoxypyridin-2-yl)methyl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N—((S)-3-methyl-5,6,7,8-tetrahydro-[1,2,4]triazolo[4,3-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((R)-3-methyl-5,6,7,8-tetrahydro-[1,2,4]triazolo[4,3-a]pyridin-8-yl)-4-azaspiro[2.5]octane-7-carboxamide;

(R)-4-(5-(5-fluoro-2-methoxy-3-methylpyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;

(S)-4-(5-(5-fluoro-2-methoxy-3-methylpyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;

(S)—N-(6-acetylpyrazolo[1,5-a]pyridin-3-yl)-4-(5-(5-fluoro-2-methoxypyridin-4-yl)-1H-pyrazole-3-carbonyl)-4-azaspiro[2.5]octane-7-carboxamide;

(S)-4-(5-(5-fluoro-2-methoxypyridin-4-yl)-1H-pyrazole-3-carbonyl)-N-(6-((S)-1-hydroxyethyl)pyrazolo[1,5-a] pyridin-3-yl)-4-azaspiro[2.5]octane-7-carboxamide;

(S)-4-(5-(5-fluoro-2-methoxypyridin-4-yl)-1H-pyrazole-3-carbonyl)-N-(6-((R)-1-hydroxyethyl)pyrazolo[1,5-a]pyridin-3-yl)-4-azaspiro[2.5]octane-7-carboxamide;

(7S)—N-(7',8'-dihydro-6'H-spiro[oxetane-3,5'-quinolin]-8'-yl)-4-(5-(5-fluoro-2-methoxypyridin-4-yl)-1H-pyrazole-3-carbonyl)-4-azaspiro[2.5]octane-7-carboxamide;

(7S)—N-(5-ethyl-2-oxa-5-azaspiro[3.5]nonan-7-yl)-4-(5-(5-fluoro-2-methoxypyridin-4-yl)-1H-pyrazole-3-carbonyl)-4-azaspiro[2.5]octane-7-carboxamide;

(S)—N-(5,5-dimethyl-6,7-dihydro-5H-pyrazolo[5,1-b][1,3]oxazin-3-yl)-4-(5-(5-fluoro-2-methoxypyridin-4-yl)-1H-pyrazole-3-carbonyl)-4-azaspiro[2.5]octane-7-carboxamide;

(S)—N-((1-(aminomethyl)-2-oxabicyclo[2.1.1]hexan-4-yl)methyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((2-(trifluoromethyl)pyridin-3-yl)methyl)-4-azaspiro[2.5]octane-7-carboxamide;

(S)-4-(5-(5-fluoro-2-methoxypyridin-4-yl)-1H-pyrazole-3-carbonyl)-N-((1R,3R,4S)-3-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N-((1 S,3S,4R)-3-hydroxy-4-(trifluoromethyl)cyclohexyl)-4-azaspiro[2.5]octane-7-carboxamide;

(S)-4-(5-(5-fluoro-2-methoxypyridin-4-yl)-1H-pyrazole-3-carbonyl)-N—((S)-2-(trifluoromethyl)-5,6,7,8-tetrahydroimidazo[1,2-a]pyridin-8-yl)-4-azaspiro[2.5]octane-7-carboxamide;

(S)-4-(5-(5-fluoro-2-methoxypyridin-4-yl)-1H-pyrazole-3-carbonyl)-N—((R)-2-(trifluoromethyl)-5,6,7,8-tetrahydroimidazo[1,2-a]pyridin-8-yl)-4-azaspiro[2.5]octane-7-carboxamide;

(S)-4-(3-(5-fluoro-2-methoxypyridin-4-yl)-1H-pyrazole-5-carbonyl)-N-((4-(trifluoromethyl)-1H-imidazol-5-yl)methyl)-4-azaspiro[2.5]octane-7-carboxamide;

(S)—N-((1 S,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1 S,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2R,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2S,4S)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1 S,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1 S,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2R,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)—N-((1R,2S,4R)-2,4-dihydroxy-4-(trifluoromethyl)cyclohexyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)isoxazol-4-yl)methyl)-4-azaspiro[2.5]octane-7-carboxamide;

(S)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide;

(R)—N-((3-cyclopropylpyridin-2-yl)methyl)-4-(3-(5-fluoro-2-methylpyridin-4-yl)-1H-pyrazole-5-carbonyl)-4-azaspiro[2.5]octane-7-carboxamide;

(S)-4-(3-(5-fluoro-2-methoxypyridin-4-yl)-1H-pyrazole-5-carbonyl)-N-((1-methyl-4-(trifluoromethyl)-1H-pyrazol-5-yl)methyl)-4-azaspiro[2.5]octane-7-carboxamide;

(S)-4-(3-(5-fluoro-2-methoxypyridin-4-yl)-1H-pyrazole-5-carbonyl)-N-((1-methyl-5-(trifluoromethyl)-1H-1,2,3-triazol-4-yl)methyl)-4-azaspiro[2.5]octane-7-carboxamide;

(S)-4-(3-(5-fluoro-2-methoxypyridin-4-yl)-1H-pyrazole-5-carbonyl)-N-((1-methyl-3-(trifluoromethyl)-1H-pyrazol-4-yl)methyl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)pyridin-2-yl)methyl)-4-azaspiro[2.5]octane-7-carboxamide;

(S)—N—(((S)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide;

(S)—N—(((R)-3,3-difluoropiperidin-4-yl)methyl)-4-(5-(5-fluoro-2-methoxypyridin-4-yl)-1H-pyrazole-3-carbonyl)-4-azaspiro[2.5]octane-7-carboxamide;

(S)-4-(3-(5-fluoro-2-methoxypyridin-4-yl)-1H-pyrazole-5-carbonyl)-N-((5-fluoropyrimidin-2-yl)methyl)-4-azaspiro[2.5]octane-7-carboxamide;

(S)-4-(3-(5-fluoro-2-methoxypyridin-4-yl)-1H-pyrazole-5-carbonyl)-N-((2-(trifluoromethyl)pyridin-3-yl)methyl)-4-azaspiro[2.5]octane-7-carboxamide;

(S)-4-(5-(5-fluoro-2-methoxypyridin-4-yl)-1H-pyrazole-3-carbonyl)-N—((S)-5-hydroxy-4,5,6,7-tetrahydropyrazolo[1,5-a]pyridin-3-yl)-4-azaspiro[2.5]octane-7-carboxamide;

(S)-4-(5-(5-fluoro-2-methoxypyridin-4-yl)-1H-pyrazole-3-carbonyl)-N—((R)-5-hydroxy-4,5,6,7-tetrahydropyrazolo[1,5-a]pyridin-3-yl)-4-azaspiro[2.5]octane-7-carboxamide;

(S)-4-(3-(5-fluoro-2-methoxypyridin-4-yl)-1H-pyrazole-5-carbonyl)-N-((3-(trifluoromethyl)bicyclo[1.1.1]pentan-1-yl)methyl)-4-azaspiro[2.5]octane-7-carboxamide;

(S)-4-(5-(5-fluoro-2-methoxypyridin-4-yl)-1H-pyrazole-3-carbonyl)-N-((4-(trifluoromethyl)pyridin-3-yl)methyl)-4-azaspiro[2.5]octane-7-carboxamide;

(S)-4-(3-(5-fluoro-2-methoxypyridin-4-yl)-1H-pyrazole-5-carbonyl)-N-((2-methyl-4-(trifluoromethyl)thiazol-5-yl)methyl)-4-azaspiro[2.5]octane-7-carboxamide;

(S)-4-(5-(5-fluoro-2-methoxypyridin-4-yl)-1H-pyrazole-3-carbonyl)-N—((R)-1-(hydroxymethyl)-3-methyl-2-oxabicyclo[2.1.1]hexan-4-yl)-4-azaspiro[2.5]octane-7-carboxamide;

(S)-4-(5-(5-fluoro-2-methoxypyridin-4-yl)-1H-pyrazole-3-carbonyl)-N—((S)-1-(hydroxymethyl)-3-methyl-2-oxabicyclo[2.1.1]hexan-4-yl)-4-azaspiro[2.5]octane-7-carboxamide;
(S)-4-(3-(5-fluoro-2-methoxypyridin-4-yl)-1H-pyrazole-5-carbonyl)-N-((1-(trifluoromethyl)-1H-imidazol-2-yl)methyl)-4-azaspiro[2.5]octane-7-carboxamide;
(S)-4-(5-(5-fluoro-2-methoxypyridin-4-yl)-1H-pyrazole-3-carbonyl)-N-(1-(hydroxymethyl)-2-oxabicyclo[2.1.1]hexan-4-yl)-4-azaspiro[2.5]octane-7-carboxamide;
(S)—N-((3-chloro-5-(4-methylpiperazin-1-yl)pyridin-2-yl)methyl)-4-(5-(5-fluoro-2-methoxypyridin-4-yl)-1H-pyrazole-3-carbonyl)-4-azaspiro[2.5]octane-7-carboxamide;
(S)-4-(3-(5-fluoro-2-methoxypyridin-4-yl)-1H-pyrazole-5-carbonyl)-N-((1-hydroxy-3,3-dimethyl-1,3-dihydrobenzo[c][1,2]oxaborol-6-yl)methyl)-4-azaspiro[2.5]octane-7-carboxamide;
(S)-4-(3-(5-fluoro-2-methoxypyridin-4-yl)-1H-pyrazole-5-carbonyl)-N-(1-hydroxy-1,3-dihydrobenzo[c][1,2]oxaborol-5-yl)-4-azaspiro[2.5]octane-7-carboxamide;
(S)-4-(5-(5-fluoro-2-methoxypyridin-4-yl)-1H-pyrazole-3-carbonyl)-N-((1R,3S)-3-hydroxy-3-(trifluoromethyl)cyclohexyl)-4-azaspiro[2.5]octane-7-carboxamide;
(S)-4-(5-(5-fluoro-2-methoxypyridin-4-yl)-1H-pyrazole-3-carbonyl)-N-((1 S,3S)-3-hydroxy-3-(trifluoromethyl)cyclohexyl)-4-azaspiro[2.5]octane-7-carboxamide;
(S)-4-(5-(5-fluoro-2-methoxypyridin-4-yl)-1H-pyrazole-3-carbonyl)-N-((1R,3R)-3-hydroxy-3-(trifluoromethyl)cyclohexyl)-4-azaspiro[2.5]octane-7-carboxamide;
(S)-4-(5-(5-fluoro-2-methoxypyridin-4-yl)-1H-pyrazole-3-carbonyl)-N-((1 S,3R)-3-hydroxy-3-(trifluoromethyl)cyclohexyl)-4-azaspiro[2.5]octane-7-carboxamide;
(S)-4-(3-(5-fluoro-2-methoxypyridin-4-yl)-1H-pyrazole-5-carbonyl)-N-((3-(trifluoromethyl)pyridin-4-yl)methyl)-4-azaspiro[2.5]octane-7-carboxamide;
(S)—N-((5-chloro-1-methyl-3-(trifluoromethyl)-1H-pyrazol-4-yl)methyl)-4-(3-(5-fluoro-2-methoxypyridin-4-yl)-1H-pyrazole-5-carbonyl)-4-azaspiro[2.5]octane-7-carboxamide;
(S)-4-(5-(5-fluoro-2-methoxypyridin-4-yl)-1H-pyrazole-3-carbonyl)-N-((5-methoxy-3-(trifluoromethyl)pyridin-2-yl)methyl)-4-azaspiro[2.5]octane-7-carboxamide;
(R)-4-(5-(6-cyanopyrimidin-4-yl)-1H-pyrazole-3-carbonyl)-N-((1r,4R)-4-hydroxy-4-(trifluoromethyl)cyclohexyl)-4-azaspiro[2.5]octane-7-carboxamide;
(S)-4-(5-(6-cyanopyrimidin-4-yl)-1H-pyrazole-3-carbonyl)-N-((1r,4S)-4-hydroxy-4-(trifluoromethyl)cyclohexyl)-4-azaspiro[2.5]octane-7-carboxamide;
(S)-4-(5-(2-chloro-5-fluoropyridin-4-yl)-1H-pyrazole-3-carbonyl)-N-((1r,4S)-4-hydroxy-4-(trifluoromethyl)cyclohexyl)-4-azaspiro[2.5]octane-7-carboxamide;
(R)-4-(5-(2-chloro-5-fluoropyridin-4-yl)-1H-pyrazole-3-carbonyl)-N-((1r,4R)-4-hydroxy-4-(trifluoromethyl)cyclohexyl)-4-azaspiro[2.5]octane-7-carboxamide;
(S)-4-(5-(5-fluoro-2-methoxypyridin-4-yl)-1H-pyrazole-3-carbonyl)-N-((5-methoxy-3-(trifluoromethyl)pyrazin-2-yl)methyl)-4-azaspiro[2.5]octane-7-carboxamide;

and pharmaceutically acceptable salts thereof.

25. A pharmaceutical composition comprising at least one entity chosen from compounds of Formula (I) and pharmaceutically acceptable salts thereof according to claim 1.

26. The pharmaceutical composition according to claim 25, further comprising at least one pharmaceutically acceptable carrier.

27. The compound or pharmaceutically acceptable salt according to claim 1, wherein the m of $R^1$ is 0.

28. The compound or pharmaceutically acceptable salt thereof according to claim 1, wherein the compound is chosen from compounds of Formula (IIIB):

Formula (IIIB)

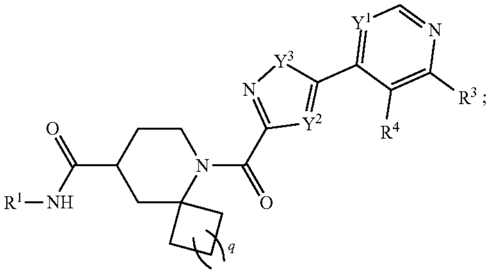

wherein q is 0 or 1.

29. A compound of Formula (III)

Formula (III)

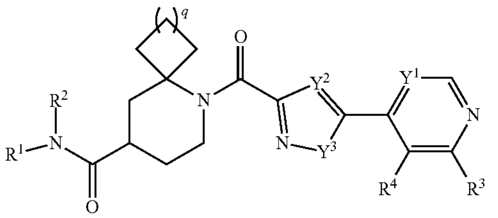

or a pharmaceutically acceptable salt thereof, wherein:

$Y^1$ is chosen from N and C—$X^1$ wherein $X^1$ is chosen from hydrogen, hydroxyl, halogen, and $C_1$-$C_4$ alkyl;

$R^3$ is chosen from hydrogen, optionally substituted alkyl, optionally substituted amine, halogen, cyano, and optionally substituted alkoxy;

$R^4$ is chosen from hydrogen and alkyl;

either $Y^2$ is chosen from C—$X^2$ and N and $Y^3$ is NH, or $Y^2$ is N and $Y^3$ is $C(X^2)_2$, wherein each $X^2$ is independently chosen from hydrogen and halogen;

q is 0 or 1;

$R^2$ is chosen from hydrogen and optionally substituted alkyl; and $R^1$ is chosen from —$(CHR^5)_k$—$(CR^6R^7)_n$—$(O)_m$-Ring B, wherein k is 0 or 1, n is 0 or 1, m is 0 or 1, $R^5$ is chosen from hydrogen and optionally substituted alkyl, $R^6$ is chosen from hydrogen and halogen,
$R^7$ chosen from hydrogen and halogen, and
Ring B is

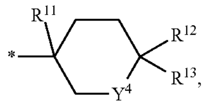

wherein
$Y^4$ is chosen from optionally substituted —$(CH_2)$—, optionally substituted —(NH)—, and —O—, and
$R^{11}$, $R^{12}$, and $R^{13}$ are each independently chosen from hydrogen, halogen, optionally substituted alkyl, hydroxyl, optionally substituted amine, and optionally substituted alkoxy.

30. The compound or pharmaceutically acceptable salt according to claim 29,
wherein Ring B is

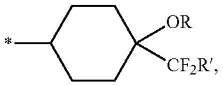

wherein
R is chosen from hydrogen, optionally substituted alkyl, and aryl; and
R' is chosen from hydrogen, optionally substituted alkyl, and halogen.

31. The compound or pharmaceutically acceptable salt thereof according to claim 30, wherein the compound is chosen from compounds of the following formula:

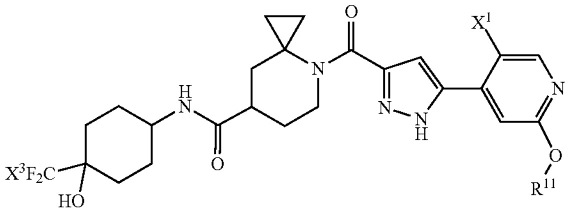

wherein
$X^1$ is chosen from hydrogen, hydroxyl, halogen, and $C_1$-$C_4$ alkyl;
$X^3$ is chosen from hydrogen and halogen; and
$R^{11}$ is independently chosen from hydrogen and $C_1$-$C_3$ alkyl.

32. A compound chosen from:

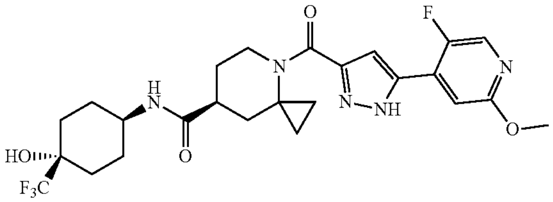 [SMILES: COc1cc(-c2cc(C(=O)N3CC[C@H](C(=O)N[C@H]4CC[C@@](O)(C(F)(F)F)CC4)CC34CC4)n[nH]2)c(F)cn1]

and pharmaceutically acceptable salts thereof.

33. A pharmaceutical composition comprising at least one entity chosen from

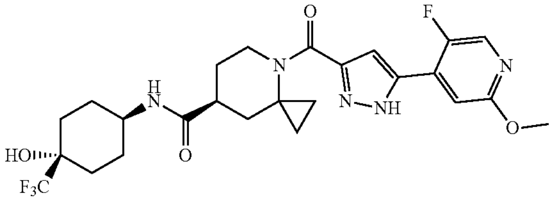 [SMILES: COc1cc(-c2cc(C(=O)N3CC[C@H](C(=O)N[C@H]4CC[C@@](O)(C(F)(F)F)CC4)CC34CC4)n[nH]2)c(F)cn1]

and pharmaceutically acceptable salts thereof according to claim 32.

34. The pharmaceutical composition according to claim 33, further comprising at least one pharmaceutically acceptable carrier.

* * * * *